United States Patent
Baruah et al.

(10) Patent No.: US 12,157,771 B2
(45) Date of Patent: Dec. 3, 2024

(54) PROTEINS BINDING NKG2D, CD16 AND CLEC12A

(71) Applicant: Dragonfly Therapeutics, Inc., Waltham, MA (US)

(72) Inventors: Hemanta Baruah, Euless, TX (US); Gregory P. Chang, Medford, MA (US); Ann F. Cheung, Lincoln, MA (US); Daniel Fallon, Winchester, MA (US); Asya Grinberg, Lexington, MA (US); Zong Sean Juo, Taipei (TW); Christopher Ryan Morgan, Southborough, MA (US)

(73) Assignee: Dragonfly Therapeutics, Inc., Waltham, MA (US)

( * ) Notice: Subject to any disclaimer, the term of this patent is extended or adjusted under 35 U.S.C. 154(b) by 568 days.

(21) Appl. No.: 17/308,691

(22) Filed: May 5, 2021

(65) Prior Publication Data
US 2022/0119534 A1 Apr. 21, 2022

Related U.S. Application Data

(60) Provisional application No. 63/020,798, filed on May 6, 2020.

(51) Int. Cl.
*C07K 16/00* (2006.01)
*A61P 35/02* (2006.01)
*C07K 16/28* (2006.01)

(52) U.S. Cl.
CPC .......... *C07K 16/2851* (2013.01); *A61P 35/02* (2018.01); *C07K 16/283* (2013.01); *C07K 2317/515* (2013.01); *C07K 2317/53* (2013.01); *C07K 2317/565* (2013.01); *C07K 2317/622* (2013.01)

(58) Field of Classification Search
CPC .............. C07K 16/2851; C07K 16/283; C07K 2317/515; C07K 2317/53; C07K 2317/565; C07K 2317/622; A61P 35/02
See application file for complete search history.

(56) References Cited

U.S. PATENT DOCUMENTS

| | | |
|---|---|---|
| 5,776,427 A | 7/1998 | Thorpe et al. |
| 5,807,706 A | 9/1998 | Carter et al. |
| 5,863,538 A | 1/1999 | Thorpe et al. |
| 5,959,084 A | 9/1999 | Ring et al. |
| 6,036,955 A | 3/2000 | Thorpe et al. |
| 6,129,914 A | 10/2000 | Weiner et al. |
| 6,210,670 B1 | 4/2001 | Berg |
| 6,294,167 B1 | 9/2001 | Lindhofer et al. |
| 6,572,856 B1 | 6/2003 | Taylor et al. |
| 6,737,056 B1 | 5/2004 | Presta |
| 7,112,324 B1 | 9/2006 | Dorken et al. |
| 7,235,641 B2 | 6/2007 | Kufer et al. |
| 7,575,923 B2 | 8/2009 | Dorken et al. |
| 7,635,472 B2 | 12/2009 | Kufer et al. |
| 7,642,228 B2 | 1/2010 | Carter et al. |
| 7,695,936 B2 | 4/2010 | Carter et al. |
| 7,820,166 B2 | 10/2010 | Lanzavecchia |
| 7,879,985 B2 | 2/2011 | Urso et al. |
| 7,951,917 B1 | 5/2011 | Arathoon et al. |
| 8,007,796 B2 | 8/2011 | Baeuerle et al. |
| 8,076,459 B2 | 12/2011 | Hofmeister et al. |
| 8,101,722 B2 | 1/2012 | Kufer et al. |
| 8,236,308 B2 | 8/2012 | Kischel et al. |
| 8,409,577 B2 | 4/2013 | Thompson et al. |
| 8,518,403 B2 | 8/2013 | Hoffmann et al. |
| 8,592,562 B2 | 11/2013 | Kannan et al. |
| 8,658,765 B2 | 2/2014 | Martin, Jr. et al. |
| 8,759,494 B2 | 6/2014 | Bachmann |
| 8,784,821 B1 | 7/2014 | Kufer et al. |
| 8,796,420 B2 | 8/2014 | Martin, Jr. et al. |
| 8,840,888 B2 | 9/2014 | Nagorsen et al. |
| 8,931,406 B2 | 1/2015 | Detloff et al. |
| 9,079,969 B2 | 7/2015 | Martin, Jr. et al. |
| 9,102,736 B2 | 8/2015 | Hofmeister et al. |
| 9,127,064 B2 | 9/2015 | Urso et al. |
| 9,150,656 B2 | 10/2015 | Johnson et al. |
| 9,150,663 B2 | 10/2015 | Labrijn et al. |
| 9,200,078 B2 | 12/2015 | Bachmann |
| 9,248,181 B2 | 2/2016 | De Kruif et al. |
| 9,248,182 B2 | 2/2016 | De Kruif et al. |
| 9,273,136 B2 | 3/2016 | Radar et al. |

(Continued)

FOREIGN PATENT DOCUMENTS

| | | |
|---|---|---|
| CA | 2990511 A1 | 12/2016 |
| CN | 102378768 A | 3/2012 |

(Continued)

OTHER PUBLICATIONS

Affimed, Affimed Enters Into Collaboration With Merck too Evaluate AFM13 in Combination With . . . Retreived < U RL: https ://www.affimed.com/affi med-enters-into-collaboration-with-merck-to-evaluate-afm 13-i n-combination-with-keytruda-pembrolizumab-for-patients-with-hodgkin-lymphoma/>[retrieved on Feb. 1, 2023] Jan. 25, 2016.

(Continued)

*Primary Examiner* — Lei Yao

(74) *Attorney, Agent, or Firm* — Goodwin Procter LLP

(57) ABSTRACT

Described herein are multispecific binding proteins that bind NKG2D receptor, CD16, and CLEC12A, pharmaceutical compositions comprising the multispecific binding proteins, and therapeutic methods useful for the treatment of cancer.

21 Claims, 483 Drawing Sheets

Specification includes a Sequence Listing.

(56) References Cited

U.S. PATENT DOCUMENTS

| | | |
|---|---|---|
| 9,334,331 B2 | 5/2016 | Igawa et al. |
| 9,447,185 B2 | 9/2016 | Romagne et al. |
| 9,493,578 B2 | 11/2016 | Lazar et al. |
| 9,562,109 B2 | 2/2017 | Von Kreudenstein et al. |
| 9,587,036 B2 | 3/2017 | Kufer et al. |
| 9,637,557 B2 | 5/2017 | Scheer et al. |
| 9,683,053 B2 | 6/2017 | Blein et al. |
| 9,690,969 B2 | 6/2017 | Okamoto |
| 9,718,893 B2 | 8/2017 | Jung et al. |
| 9,951,145 B2 | 4/2018 | Kim et al. |
| 9,963,513 B2 | 5/2018 | Vu et al. |
| 10,040,853 B2 | 8/2018 | Spies et al. |
| 10,047,167 B2 | 8/2018 | Demarest et al. |
| 10,059,765 B2 | 8/2018 | Velardi et al. |
| 10,377,827 B2 | 8/2019 | Swanson et al. |
| 10,421,807 B2 | 9/2019 | Gonzalez et al. |
| 10,526,409 B2 | 1/2020 | Urso et al. |
| 11,124,582 B2 | 9/2021 | Ambrogelly et al. |
| 11,787,864 B2 | 10/2023 | Cheung et al. |
| 11,834,506 B2 | 12/2023 | Chang et al. |
| 2002/0103345 A1 | 8/2002 | Zhu |
| 2002/0193569 A1 | 12/2002 | Hanna |
| 2003/0095965 A1 | 5/2003 | Van Beneden et al. |
| 2004/0038339 A1 | 2/2004 | Kufer et al. |
| 2004/0052783 A1 | 3/2004 | Weiner et al. |
| 2004/0115198 A1 | 6/2004 | Spies et al. |
| 2005/0037002 A1 | 2/2005 | Velardi et al. |
| 2005/0054019 A1 | 3/2005 | Michaud et al. |
| 2005/0058639 A1 | 3/2005 | Gudas et al. |
| 2005/0158307 A1 | 7/2005 | Spies et al. |
| 2005/0244416 A1 | 11/2005 | Jung |
| 2006/0018899 A1 | 1/2006 | Kao et al. |
| 2006/0235201 A1 | 10/2006 | Kischel |
| 2006/0246004 A1 | 11/2006 | Adams et al. |
| 2007/0004909 A1 | 1/2007 | Johnson et al. |
| 2007/0071759 A1 | 3/2007 | Shin et al. |
| 2007/0179086 A1 | 8/2007 | Gliniak et al. |
| 2007/0190063 A1 | 8/2007 | Bahjat et al. |
| 2008/0025975 A1 | 1/2008 | Weiner et al. |
| 2008/0299137 A1 | 12/2008 | Svendsen et al. |
| 2008/0305105 A1 | 12/2008 | Kufer et al. |
| 2009/0142352 A1 | 6/2009 | Jackson et al. |
| 2009/0175867 A1 | 7/2009 | Thompson et al. |
| 2009/0226442 A1 | 9/2009 | Huet et al. |
| 2009/0226466 A1 | 9/2009 | Fong et al. |
| 2009/0252729 A1 | 10/2009 | Farrington et al. |
| 2009/0304693 A1 | 12/2009 | Ghayur et al. |
| 2009/0304696 A1 | 12/2009 | Lawson et al. |
| 2010/0009866 A1 | 1/2010 | Prinz et al. |
| 2010/0055034 A1 | 3/2010 | Martin et al. |
| 2010/0056764 A1 | 3/2010 | Urso et al. |
| 2010/0174053 A1 | 7/2010 | Johnson et al. |
| 2010/0178298 A1 | 7/2010 | Lindhofer |
| 2010/0260765 A1 | 10/2010 | Barry et al. |
| 2010/0272718 A1 | 10/2010 | Urso et al. |
| 2010/0286374 A1 | 11/2010 | Kannan et al. |
| 2010/0291112 A1 | 11/2010 | Kellner et al. |
| 2010/0310463 A1 | 12/2010 | Cicortas Gunnarsson et al. |
| 2011/0008355 A1 | 1/2011 | Velardi et al. |
| 2011/0020273 A1 | 1/2011 | Chang et al. |
| 2011/0044980 A1 | 2/2011 | Ghayur et al. |
| 2011/0054151 A1 | 3/2011 | Lazar et al. |
| 2011/0150870 A1 | 6/2011 | Rader et al. |
| 2011/0311535 A1 | 12/2011 | Dranoff et al. |
| 2012/0014957 A1 | 1/2012 | Ghayur et al. |
| 2012/0058082 A1 | 3/2012 | Kaplan et al. |
| 2012/0058906 A1 | 3/2012 | Smider et al. |
| 2012/0093823 A1 | 4/2012 | Van Den Brink et al. |
| 2012/0149876 A1 | 6/2012 | Kreudenstein |
| 2012/0171173 A1 | 7/2012 | Ideno et al. |
| 2012/0195900 A1 | 8/2012 | Ghayur et al. |
| 2012/0263722 A1 | 10/2012 | Ghayur et al. |
| 2012/0269723 A1 | 10/2012 | Brinkmann et al. |
| 2012/0294796 A1 | 11/2012 | Johnson et al. |
| 2012/0294857 A1 | 11/2012 | Sentman et al. |
| 2012/0321626 A1 | 12/2012 | Zhou |
| 2012/0328619 A1 | 12/2012 | Fey et al. |
| 2013/0115208 A1 | 5/2013 | Ho et al. |
| 2013/0177555 A1 | 7/2013 | Wilkinson et al. |
| 2013/0209514 A1 | 8/2013 | Gilboa et al. |
| 2013/0216528 A1 | 8/2013 | Cheung et al. |
| 2013/0216544 A1 | 8/2013 | Bachmann |
| 2013/0295118 A1 | 11/2013 | Jiang et al. |
| 2013/0336977 A1 | 12/2013 | Thompson et al. |
| 2014/0044739 A1 | 2/2014 | Teng et al. |
| 2014/0072579 A1 | 3/2014 | De Kruif et al. |
| 2014/0072581 A1 | 3/2014 | Dixit et al. |
| 2014/0105889 A1 | 4/2014 | Igawa et al. |
| 2014/0112926 A1 | 4/2014 | Liu et al. |
| 2014/0120096 A1 | 5/2014 | Bakker et al. |
| 2014/0127203 A1 | 5/2014 | Thompson et al. |
| 2014/0140999 A1 | 5/2014 | De Kruif et al. |
| 2014/0141022 A1 | 5/2014 | Thompson et al. |
| 2014/0154250 A1 | 6/2014 | Thompson et al. |
| 2014/0154252 A1 | 6/2014 | Thompson et al. |
| 2014/0199294 A1 | 7/2014 | Mimoto et al. |
| 2014/0234342 A1 | 8/2014 | Narni-Mancinelli et al. |
| 2014/0242077 A1 | 8/2014 | Choi et al. |
| 2014/0271617 A1 | 9/2014 | Igawa et al. |
| 2014/0288275 A1 | 9/2014 | Moore et al. |
| 2014/0294827 A1 | 10/2014 | Gastwirt et al. |
| 2014/0302064 A1 | 10/2014 | Moore |
| 2014/0363426 A1 | 12/2014 | Moore et al. |
| 2014/0364340 A1 | 12/2014 | Vasquez et al. |
| 2015/0050269 A1 | 2/2015 | Igawa et al. |
| 2015/0056206 A1 | 2/2015 | Zhou |
| 2015/0079088 A1 | 3/2015 | Lowman et al. |
| 2015/0119555 A1 | 4/2015 | Jung et al. |
| 2015/0166636 A1 | 6/2015 | Igawa et al. |
| 2015/0166654 A1 | 6/2015 | Igawa et al. |
| 2015/0175697 A1 | 6/2015 | Bonvini et al. |
| 2015/0175700 A1 | 6/2015 | Lum et al. |
| 2015/0203591 A1 | 7/2015 | Yancopoulos et al. |
| 2015/0210765 A1 | 7/2015 | Roschke et al. |
| 2015/0259431 A1 | 9/2015 | Stemmer et al. |
| 2015/0259434 A1 | 9/2015 | Johnson et al. |
| 2015/0274838 A1 | 10/2015 | Johnson et al. |
| 2015/0299319 A1 | 10/2015 | Velardi et al. |
| 2015/0307617 A1 | 10/2015 | Du et al. |
| 2015/0307628 A1 | 10/2015 | Kim et al. |
| 2015/0329637 A1 | 11/2015 | Urech et al. |
| 2015/0353636 A1 | 12/2015 | Parren et al. |
| 2016/0017038 A1 | 1/2016 | Koenig |
| 2016/0024214 A1 | 1/2016 | Urso et al. |
| 2016/0032009 A1 | 2/2016 | Cheung et al. |
| 2016/0039942 A1 | 2/2016 | Cobbold et al. |
| 2016/0046727 A1 | 2/2016 | Labrijn et al. |
| 2016/0046730 A1 | 2/2016 | Ghayur et al. |
| 2016/0077105 A1 | 3/2016 | Bobrowicz et al. |
| 2016/0090426 A1 | 3/2016 | Zhou et al. |
| 2016/0096892 A1 | 4/2016 | Brogdon et al. |
| 2016/0122432 A1 | 5/2016 | Inserm et al. |
| 2016/0159882 A1 | 6/2016 | Landgraf et al. |
| 2016/0159924 A1 | 6/2016 | Padkjaer et al. |
| 2016/0176968 A1 | 6/2016 | Chang et al. |
| 2016/0289341 A1 | 10/2016 | Wu |
| 2016/0326249 A1 | 11/2016 | Ng et al. |
| 2016/0347849 A1 | 12/2016 | Cai et al. |
| 2016/0369002 A1 | 12/2016 | Gauthier et al. |
| 2017/0022291 A1 | 1/2017 | Baruah et al. |
| 2017/0029529 A1 | 2/2017 | Croasdale et al. |
| 2017/0066827 A1 | 3/2017 | Pule et al. |
| 2017/0114141 A1 | 4/2017 | Amann et al. |
| 2017/0233472 A1 | 8/2017 | Barat et al. |
| 2017/0291955 A1 | 10/2017 | Li et al. |
| 2017/0362321 A1 | 12/2017 | Campbell et al. |
| 2017/0368169 A1 | 12/2017 | Loew et al. |
| 2017/0369595 A1 | 12/2017 | Brinkmann et al. |
| 2018/0044415 A1 | 2/2018 | Escarpe et al. |
| 2018/0057608 A1 | 3/2018 | Jung et al. |
| 2018/0105594 A1 | 4/2018 | Urso et al. |
| 2018/0105599 A1 | 4/2018 | Cobbold et al. |
| 2018/0118851 A1 | 5/2018 | Comeau et al. |
| 2018/0237519 A1 | 8/2018 | Yu et al. |

(56) References Cited

U.S. PATENT DOCUMENTS

| | | |
|---|---|---|
| 2018/0237541 A1 | 8/2018 | Kim et al. |
| 2018/0273633 A1 | 9/2018 | Jiang et al. |
| 2018/0326027 A1 | 11/2018 | Cashman et al. |
| 2018/0346600 A1 | 12/2018 | Kim et al. |
| 2019/0048079 A1 | 2/2019 | Spies et al. |
| 2019/0225702 A1 | 7/2019 | Baeuerle et al. |
| 2019/0359716 A1 | 11/2019 | Chang et al. |
| 2019/0375838 A1 | 12/2019 | Chang et al. |
| 2020/0002436 A1 | 1/2020 | Chang et al. |
| 2020/0024353 A1 | 1/2020 | Chang et al. |
| 2020/0048347 A1 | 2/2020 | Miao et al. |
| 2020/0055939 A1 | 2/2020 | Lombana et al. |
| 2020/0095327 A1 | 3/2020 | Chang et al. |
| 2020/0157174 A1 | 5/2020 | Chang et al. |
| 2020/0157226 A1 | 5/2020 | Chang et al. |
| 2020/0157227 A1 | 5/2020 | Chang et al. |
| 2020/0165344 A1 | 5/2020 | Chang et al. |
| 2020/0216544 A1 | 7/2020 | Chang et al. |
| 2020/0231678 A1 | 7/2020 | Chang et al. |
| 2020/0231679 A1 | 7/2020 | Chang et al. |
| 2020/0231700 A1 | 7/2020 | Cheung et al. |
| 2020/0277383 A1 | 9/2020 | Chang et al. |
| 2020/0277384 A1* | 9/2020 | Chang .................. C07K 16/283 |
| 2020/0376034 A1 | 12/2020 | Chang et al. |
| 2021/0009718 A1 | 1/2021 | Ambrogelly et al. |
| 2021/0032349 A1 | 2/2021 | Dengl et al. |
| 2021/0054082 A1 | 2/2021 | Chang et al. |
| 2021/0070887 A1 | 3/2021 | Ambrogelly et al. |
| 2021/0079102 A1 | 3/2021 | Chang et al. |
| 2021/0101976 A1 | 4/2021 | Chang et al. |
| 2021/0130471 A1 | 5/2021 | Chang et al. |
| 2021/0130474 A1 | 5/2021 | Chang et al. |
| 2021/0130496 A1 | 5/2021 | Chang et al. |
| 2021/0198369 A1 | 7/2021 | Chang et al. |
| 2021/0206859 A1 | 7/2021 | Chang et al. |
| 2021/0214436 A1 | 7/2021 | Chang et al. |
| 2021/0221894 A1 | 7/2021 | Bigelow et al. |
| 2021/0238290 A1 | 8/2021 | Chang et al. |
| 2021/0261668 A1 | 8/2021 | Chang et al. |
| 2021/0292420 A1 | 9/2021 | Chang et al. |
| 2021/0363261 A1 | 11/2021 | Chang et al. |
| 2022/0025037 A1 | 1/2022 | Baruah et al. |
| 2022/0089760 A1 | 3/2022 | Begelow et al. |
| 2022/0119533 A1 | 4/2022 | Cheung et al. |
| 2022/0153848 A1 | 5/2022 | Chang et al. |
| 2022/0195065 A1 | 6/2022 | Chang et al. |
| 2023/0034186 A1 | 2/2023 | Cuillerot et al. |
| 2023/0203202 A1 | 6/2023 | Bigelow et al. |
| 2023/0227562 A1 | 7/2023 | Chang et al. |
| 2023/0250176 A1 | 8/2023 | Cheung et al. |
| 2023/0257467 A1 | 8/2023 | Cheung et al. |
| 2023/0272041 A1 | 8/2023 | Bigelow et al. |
| 2023/0303702 A1 | 9/2023 | Chang et al. |
| 2023/0357409 A1 | 11/2023 | Chang et al. |
| 2023/0391877 A1 | 12/2023 | Chang et al. |
| 2023/0416402 A1 | 12/2023 | Cuillerot et al. |

FOREIGN PATENT DOCUMENTS

| | | |
|---|---|---|
| CN | 105906722 A | 8/2016 |
| DE | 102013019352 A1 | 9/2015 |
| EP | 0627940 A1 | 12/1994 |
| EP | 0845998 A1 | 6/1998 |
| EP | 0871673 A1 | 10/1998 |
| EP | 1124568 A1 | 8/2001 |
| EP | 1769000 B1 | 4/2007 |
| EP | 2185595 A1 | 5/2010 |
| EP | 2222706 B2 | 9/2010 |
| EP | 2927321 A1 | 10/2015 |
| EP | 2930188 A1 | 10/2015 |
| EP | 2942629 A1 | 11/2015 |
| EP | 2982380 A1 | 2/2016 |
| EP | 2990416 A1 | 3/2016 |
| KR | 10-2013-0103325 | 9/2013 |
| KR | 10-2014-0067944 | 6/2014 |
| RU | 2588668 C2 | 7/2016 |
| RU | 2593720 C2 | 8/2016 |
| RU | 2608504 C2 | 1/2017 |
| WO | WO 1988/008854 A1 | 11/1988 |
| WO | WO 1989/006544 A1 | 7/1989 |
| WO | WO 1996/027011 | 9/1996 |
| WO | WO 2001/071005 A2 | 9/2001 |
| WO | WO 2004/056873 A1 | 7/2004 |
| WO | WO 2005/003172 | 1/2005 |
| WO | WO 2005/009465 | 2/2005 |
| WO | WO 2005/105849 | 11/2005 |
| WO | WO 2006/037960 A2 | 4/2006 |
| WO | WO 2007/002905 | 1/2007 |
| WO | WO 2007/042573 | 4/2007 |
| WO | WO 2007/055926 A1 | 5/2007 |
| WO | WO 2007/085815 A2 | 8/2007 |
| WO | WO 2007/097812 A2 | 8/2007 |
| WO | WO 2008/127735 A1 | 10/2008 |
| WO | WO 2009/007124 A1 | 1/2009 |
| WO | WO 2009/077483 A1 | 6/2009 |
| WO | WO 2009/089004 | 7/2009 |
| WO | WO 2010/017103 A2 | 2/2010 |
| WO | WO2010/080124 A2 | 7/2010 |
| WO | WO 2011/014659 | 2/2011 |
| WO | WO 2011/075636 A2 | 6/2011 |
| WO | WO 2011/076922 | 6/2011 |
| WO | WO 2011/109400 | 9/2011 |
| WO | WO 2011/131746 | 10/2011 |
| WO | WO 2011/143545 | 11/2011 |
| WO | WO 2012/006490 A2 | 1/2012 |
| WO | WO 2012/025530 | 3/2012 |
| WO | WO 2012/032080 | 3/2012 |
| WO | WO 2012/034039 A2 | 3/2012 |
| WO | WO 2012/045752 A1 | 4/2012 |
| WO | WO 2012/058768 | 5/2012 |
| WO | WO 2012/115241 | 8/2012 |
| WO | WO 2012/125850 A1 | 9/2012 |
| WO | WO 2012/158818 A2 | 11/2012 |
| WO | WO 2012/162482 A1 | 11/2012 |
| WO | WO 2013/013700 A1 | 1/2013 |
| WO | WO 2013/036799 A2 | 3/2013 |
| WO | WO 2013/092001 | 6/2013 |
| WO | WO 2013/113615 A1 | 8/2013 |
| WO | WO 2013/192594 A2 | 12/2013 |
| WO | WO 2014/001324 A1 | 1/2014 |
| WO | WO 2014/012085 | 1/2014 |
| WO | WO 2014/051433 A1 | 4/2014 |
| WO | WO 2014/079000 | 5/2014 |
| WO | WO 2014/084607 | 6/2014 |
| WO | WO 2014/110601 | 7/2014 |
| WO | WO 2014/124326 | 8/2014 |
| WO | WO 2014/131712 A1 | 9/2014 |
| WO | WO 2014/144763 A2 | 9/2014 |
| WO | WO 2014/145806 A2 | 9/2014 |
| WO | WO 2014/159940 A1 | 10/2014 |
| WO | WO 2014/165818 A2 | 10/2014 |
| WO | WO 2014/198748 A1 | 12/2014 |
| WO | WO 2015/009856 | 1/2015 |
| WO | WO 2015/036582 A2 | 3/2015 |
| WO | WO 2015/036606 | 3/2015 |
| WO | WO 2015/063187 A1 | 5/2015 |
| WO | WO 2015/070061 | 5/2015 |
| WO | WO 2015/089344 A1 | 6/2015 |
| WO | WO 2015/095412 A1 | 6/2015 |
| WO | WO 2015/095539 A1 | 6/2015 |
| WO | WO 2015/095972 | 7/2015 |
| WO | WO 2015/150447 | 10/2015 |
| WO | WO 2015/153765 A1 | 10/2015 |
| WO | WO 2015/153912 A1 | 10/2015 |
| WO | WO 2015/158636 A1 | 10/2015 |
| WO | WO 2015/169781 A1 | 11/2015 |
| WO | WO 2015/181282 A1 | 12/2015 |
| WO | WO 2015/184203 A1 | 12/2015 |
| WO | WO 2015/184207 A1 | 12/2015 |
| WO | WO 2015/197582 | 12/2015 |
| WO | WO 2015/197593 A1 | 12/2015 |
| WO | WO 2015/197598 | 12/2015 |
| WO | WO 2016/001810 | 1/2016 |
| WO | WO 2016/011571 | 1/2016 |

(56) References Cited

FOREIGN PATENT DOCUMENTS

| | | |
|---|---|---|
| WO | WO 2016/023909 A1 | 2/2016 |
| WO | WO 2016/025880 A1 | 2/2016 |
| WO | WO 2016/028672 A1 | 2/2016 |
| WO | WO 2016/032334 | 3/2016 |
| WO | WO 2016/070959 | 5/2016 |
| WO | WO 2016/090278 | 6/2016 |
| WO | WO 2016/097408 | 6/2016 |
| WO | WO 2016/100533 | 6/2016 |
| WO | WO 2016/109774 | 7/2016 |
| WO | WO 2016/115274 | 7/2016 |
| WO | WO 2016/122701 | 8/2016 |
| WO | WO 2016/134371 A2 | 8/2016 |
| WO | WO 2016/135041 | 9/2016 |
| WO | WO 2016/135066 A1 | 9/2016 |
| WO | WO 2016/142768 | 9/2016 |
| WO | WO 2016/146702 A1 | 9/2016 |
| WO | WO 2016/161390 A1 | 10/2016 |
| WO | WO 2016/164369 | 10/2016 |
| WO | WO 2016/164637 A1 | 10/2016 |
| WO | WO 2016/166629 A1 | 10/2016 |
| WO | WO 2016/184592 A1 | 11/2016 |
| WO | WO 2016/187220 | 11/2016 |
| WO | WO 2016/191305 A1 | 12/2016 |
| WO | WO 2016/196237 A1 | 12/2016 |
| WO | WO 2016/201300 A1 | 12/2016 |
| WO | WO 2016/201389 | 12/2016 |
| WO | WO 2016/207273 A2 | 12/2016 |
| WO | WO 2016/207278 A1 | 12/2016 |
| WO | WO 2017/005732 A1 | 1/2017 |
| WO | WO 2017/008169 | 1/2017 |
| WO | WO 2017/011342 A1 | 1/2017 |
| WO | WO 2017/021349 A1 | 2/2017 |
| WO | WO 2017/048824 A1 | 3/2017 |
| WO | WO 2017/075432 A2 | 5/2017 |
| WO | WO 2017/079694 | 5/2017 |
| WO | WO 2017/081190 | 5/2017 |
| WO | WO 2017/083545 | 5/2017 |
| WO | WO 2017/114694 | 7/2017 |
| WO | WO 2017/124002 A1 | 7/2017 |
| WO | WO 2017/125897 A1 | 7/2017 |
| WO | WO 2017/143406 A1 | 8/2017 |
| WO | WO 2017/165464 | 9/2017 |
| WO | WO 2017/165683 A1 | 9/2017 |
| WO | WO 2017/177337 A1 | 10/2017 |
| WO | WO 2017/180813 | 10/2017 |
| WO | WO 2017/211873 A1 | 12/2017 |
| WO | WO 2017/218707 A2 | 12/2017 |
| WO | WO 2018/045090 | 3/2018 |
| WO | WO 2018/057735 A1 | 3/2018 |
| WO | WO 2018/098365 A2 | 5/2018 |
| WO | WO 2018/119171 A1 | 6/2018 |
| WO | WO 2018/148445 | 8/2018 |
| WO | WO 2018/148447 | 8/2018 |
| WO | WO 2018/148566 | 8/2018 |
| WO | WO 2018/152518 | 8/2018 |
| WO | WO 2018/157147 A1 | 8/2018 |
| WO | WO 2018/201051 | 11/2018 |
| WO | WO 2019/028027 | 2/2019 |
| WO | WO 2019/035939 | 2/2019 |
| WO | WO 2019/051308 A1 | 3/2019 |
| WO | WO 2019055677 * | 3/2019 |
| WO | WO 2019/157332 | 8/2019 |
| WO | WO 2019/157366 | 8/2019 |
| WO | WO 2019/164929 | 8/2019 |
| WO | WO 2019/195408 | 10/2019 |
| WO | WO 2019/195409 | 10/2019 |
| WO | WO 2019/217332 | 11/2019 |
| WO | WO 2019/222449 | 11/2019 |
| WO | WO 2019/231920 | 12/2019 |
| WO | WO 2020/073131 | 4/2020 |
| WO | WO 2020/086758 | 4/2020 |
| WO | WO 2020/172189 | 8/2020 |
| WO | WO 2021/041878 | 3/2021 |
| WO | WO 2021/216916 | 10/2021 |
| WO | WO 2021/226193 | 11/2021 |
| WO | WO 2022/031965 | 2/2022 |
| WO | WO 2022/187539 | 9/2022 |
| WO | WO 2023/056252 | 4/2023 |
| WO | WO2023/107956 | 6/2023 |
| WO | WO 2023/154796 | 8/2023 |
| WO | WO 2023/168384 | 9/2023 |

OTHER PUBLICATIONS

Ahmad et al., 2012, "scFv antibody: principles and clinical application," Clinical and Developmental Immunology, 2012: 1-16.
Akbar et al., 2021, "A compact vocabulary of paratope-epitope interactions enables predictability of antibody-antigen binding," *Cell Reports*, 34:108856 21 pages.
Altshuler et al., 2010, "Generation of Recombinant Antibodies and Means for Increasing Their Affinity," *Biochemistry* (Moscow), 75(13):1584-1605.
Atwell et al., 1997, "Stable heterodimers from remodeling the domain interface of a homodimer using a phage display library", J. Mol. Biol., 270(1):26-35.
Averdam et al., 2009, "A novel system of polymorphic and diverse NK cell receptors in primates", PLOS Genetics, 5(10): e1000688.
Baek et al., 2014, "Construction of a large synthetic human Fab antibody library on yeast cell surface by optimized yeast mating", Journal of Microbiology and Biotechnology, 24(3):408-420.
Bendayan et al., 1995, "Possibilities of False Immunocytochemical Results Generated by The Use of Monoclonal Antibodies: The Example of the Anti-proinsulin Antibody," J. Histochem. Cytochem, 43:881-886.
Berenbaum, 1977, "Synergy, additivism and antagonism in immunosuppression," Clin. Exp. Immunol., 28:1-18.
Berenbaum, 1989, "What is Synergy?" Pharmacological Reviews, 41:93-141.
Boltz, 2011, "Bi-specific Aptamers mediating Tumour Cell Lysis," Dissertation, M.Sc. Molekulare Biotechnologie, Technische Universität Darmstadt, pp. 1-133.
Bost et al., 1988, "Antibodies Against a Peptide Sequence Within the HIV Envelope Protein Crossreacts with Human Interleukin-2," Immunological Investigations, 17(6&7): 577-586.
Bostrom, et al., 2009, "Improving Antibody Binding Affinity and Specificity for Therapeutic Development, " Methods and Protocols, 525:353-376.
Bowen et al., 2016, "Revisiting the Immunoglobulin Intramolecular Signaling Hypothesis," *Trends Immunol.*, 37(11):721-723.
Branca et al., 2018, "Nature Biotechnology's Academic Spinouts of 2017," Nature Biotechnology, 36(4): 297-306.
Brinkmann et al., 2017, "The making of bispecific antibodies," MABS, 9(2)182-212.
Brown, et al., 1996, "Tolerance of single, but not multiple, amino acid replacements in antibody VH CDR 2: a means of minimizing B cell wastage from somatic hypermutation?," Journal of Immunology, 156: 3285-3291.
Bruhns et al., 2009, "Specificity and affinity of human FCg receptors and their polymorphic variants for human IgG subclasses," *Blood*, 113(16):3716-3724.
Bryceson et al., 2006, "Synergy among receptors on resting NK cells for the activation of natural cytotoxicity and cytokine secretion," Blood, 107(1):159-166.
Busfield et al., 2014, "Targeting of acute myeloid leukemia in vitro and in vivo with an anti-CD 123 mAb engineered for optimal ADCC," Leukemia, 28 (11): 2213-2221.
Cai et al., 2014, "Autonomous stimulation of cancer cell plasticity by the human NKG2D lymphocyte receptor coexpressed with its ligands on cancer cells", PLOS One, 9(10):e108942.
Casset et al., 2003, "A peptide mimetic of an anti-CD4 monoclonal antibody by rational design," Biochemical and Biophysical Research Communications, 307:198-205.
Chan et al., 2010, "Therapeutic antibodies for autoimmunity and inflammation," Nature Reviews 10:301-316.
Chen et al., 1995, "Enhancement and destruction of antibody function by somatic mutation: unequal occurrence is controlled by V gene combinatorial associations," The EMBO Journal, 14(12):2784-2794.

(56) References Cited

OTHER PUBLICATIONS

Chen et al., 1999, "Selection and Analysis of an Optimized Anti-VEGF Antibody: Crystal Structure of an Affinity-matured Fab in Complex with Antigen," J. Mol. Biol., 293:865-881.
Chen et al., 2017, "Targeting FLT3 by chimeric antigen receptor T ccells for the treatment of acute myeloid leuikemia", Leukemia, 31(8): 1830-1834.
Chen et al., 2013, "Fusion protein linkers: property, design and functionality" Advanced Drug Delivery Reviews, 65(10):1357-1369.
Cho et al., 2010, "Delivery of NKG2D ligand using an anti-HER2 antibody-NKG2D ligand fusion protein results in an enhanced innate and adaptive antitumor response", Cancer Research, 70(24):10121-10130.
Choi et al., 2013, "A Heterodimeric Fc-Based Bispecific Antibody Simultaneously Targeting VEGFR-2 and Met Exhibits Potent Antitumor Activity," Mol Cancer Ther, 12(12):2748-2759.
Choi et al., 2015, "Engineering of immunoglobin Fc heterodimers using yeast surface-displayed combinatorial Fc library screening", PloS One, vol. 10, article No. 30145349:1-20.
Choi et al., 2015, "Crystal structures of immunoglobulin Fc heterodimers reveal the molecular basis for heterodimer formation," Molecular Immunology 65(2):377-83.
Chu et al., 2014, "Immunotherapy with Long-Lived Anti-CD123 x Anti-CD3 Bispecific Antibodies Stimulates Potent T Cell-Mediated Killing of Human AML Cell Lines and of CD123+ Cells in Monkeys: A Potential Therapy for Acute Myelogenous Leukemia 11," Blood, 124(21) (5 pages).
Colman, 1994, "Effects of amino acid sequence changes on antibody-antigen interactions" Research in Immunology, 145(1):33-36.
Cunningham et al., 1969, "Subgroups of Amino Acid Sequences in the Variable Regions of Immunoglobulin Heavy Chains," Proc Natl Acad Sci USA 64(3):997-1003.
Dahlberg et al., 2015, "Natural Killer Cell-Based Therapies Targeting Cancer: Possible Strategies to Gain and sustain Anti-Tumor Activity" Frontiers in Immunology 6(Article 605):19 pages.
Davis et al., 1999, "Therapy of B-Cell Lymphoma with Anti-CD20 Antibodies Can Result in the Loss of CD20 Antigen Expression," Clinical Cancer Research, 5:611-615.
Davis et al., 2010, "SEEDbodies: Fusion Proteins Based on Strand-Exchange Engineered Domain (SEED) CH3 Heterodimers in an Fc Analogue Platform for Asymmetric Binders or Immunofusions and Bispecific Antibodies," Protein Eng Des Sel 23(4):195-202.
De Pascalis et al., 2002, "Grafting of "Abbreviated" Complementarity-Determining Regions Containing Specificity-Determining Residues Essential for Ligand Contact to Engineer a Less Immunogenic Humanized Monoclonal Antibody," The Journal of Immunology, 169:3076-3084.
Dickopf et al., 2020, "Format and geometries matter: Structure-based design defines the functionality of bispecific antibodies," Computational and Structural Biotechnology Journal, 18:1221-1227.
Ding et al., 2018, "Fusion proteins of NKG2DL in cancer immunotherapy", International J of Molecular Sciences, 19(1):177.
Doppalapudi et al., 2010, "Chemical generation of bispecific antibodies," PNAS, 107(52):22611-22616.
Edwards et al., 2003, "The Remarkable Flexibility of the Human Antibody Repertoire; Isolation of Over One Thousand Different Antibodies to a Single Protein, BLyS," J. Mol. Biol., 334:103-118.
El-Amine et al., 2002, "In vivo induction of tolerance by an Ig peptide is not affected by the deletion of FcR or a mutated IgG Fc fragment," *International Immunology* , 14(7):761-766.
Elliott et al., 2014, "Antiparallel conformation of knob and hole aglycosylated half-antibody homodimers is mediated by a CH2-CH3 hydrophobic interaction", J. Mol. Biol., 426(9):1947-57.
Epling-Burnette et al., 2004, "Dysregulated NK receptor expression in patients with lymphoproliferative disease of granular lymphocytes", Blood, 13(9):3431-3439.
Extended European Search Report dated Mar. 18, 2021 for EP App. No. 18840650.8 (14247-472-227).

Farumashia, 2015, Journal of the Pharmaceutical Society of Japan, 51(5), pp. 424-428.
Felices et al., 2016, "Generation of BiKEs and TriKEs to Improve NK Cell-Mediated Targeting of Tumor Cells" Methods Mol. Biol., vol. 1441:333-346.
Feng et al., 2011, "Design, Expression and Characterization of a Soluble Single-Chain Functional Human Neonatal Fc Receptor," Protein Expr Purif 79(1):66-71.
Gantke et al., 2017, "Trispecific antibodies for CD16A-directed NK cell engagement and dual-targeting of tumor cells," Protein Engineering, Design & Selection, 38(9):673-684.
Gantke et al., 2016, Trispecific antibodies for selective CD16A-directed NK-cell engagement in multiple myeloma, Blood, 128(22):4513-4513 (abstract only).
Gauthier et al., 2019, "Multifunctional Natural Killer Cell Engagers Targeting NKp46 Trigger Protective Tumor Immunity," Cell, 177(7):1701-1713.
Germain et al., 2005, "MHC class I-related chain A conjugated to antitumor antibodies can sensitize tumor cells to specific lysis by natural killer cells", Clinical Cancer Research, Amer. Assoc. for Cancer Research, 11(20):7516-7522.
Germain et al., 2008, "Redirecting NK cells mediated tumor cell lysis by a new recombinant bifunctional protein," *Protein Engineering, Design & Selection* , 21(11):665-672.
Glas et al., 1997, "Analysis of rearranged immunoglobulin heavy chain variable region genes obtained from a bone marrow transplant (BMT) recipient," Clinical & Experimental Immunology, 107(2):372-380.
Gleason et al., 2014, "CD16xCD33 bispecific killer cell engager (BiKE) activates NK cells against primary MDS and MDSC CD33+ targets." Blood, The Journal of the American Society of Hematology, 123.19: 3016-3026.
Gleason et al., 2012, "Bispecific and Trispecific Killer Cell Engagers Directly Activate Human NK Cells through CD16 Signaling and Induce Cytotoxicity and Cytokine Production," Molecular Cancer Therapeutics, 11 (12): 2674-2684.
Goel et al., 2004, "Plasticity Within the Antigen-Combining Site May Manifest as Molecular Mimicry in the Humoral Immune Response," Journal of Immunology, 173:7358-7367.
Gonzales et al., 2005, "Minimizing the Immunogenicity of Antibodies for Clinical Application," Tumour Biol., 26(1):31-43.
Gooden et al., 2012, "Infiltrating CTLs are bothered by HLA-E on tumors," OncoImmunology, 1(1):92-93.
Gunasekaran et al., 2010, "Enhancing Antibody Fc Heterodimer Formation through Electrostatic Steering Effects: Applications to Bispecific Molecules and Monovalent lgG," J Biol Chem 285(25):19637-46.
Ha et al., 2016, "Immunoglobin Fc heterodimer platform technology: from design to applications in therapeutic antibodies and proteins", Frontiers in Immunology, 7(394):1-16.
Hasegawa et al., 2017, "Single amino acid substitution in LC-CDR1 induces Russell body phenotype that attenuates cellular protein synthesis through elF2a phosphorylation and thereby downregulates IgG secretion despite operational secretory pathway traffic," *MABS* , 9(5):854-873.
Henry et al., 2004, "A Prostate-Specific Membrane Antigen-Targeted Monoclonal Antibody-Chemotherapeutic Conjugate Designed for the Treatment of Prostate Cancer," Cancer Research, 64:7995-8001.
Henry et al., 2017, "Stability-Diversity Tradeoffs Impose Fundamental Constraints on Selection of Synthetic Human VH/VL Single-Domain Antibodies from In Vitro Display Libraries," Frontiers in Immunology, 8:1-15.
Hezareh et al., 2001, "Effector Function Activities of a Panel of Mutants of a Broadly Neutralizing Antibody against Human Immunodeficiency Virus Type 1," Journal of Virology, 75 (24):12161-12168.
Hlavacek et al., 1999, "Steric Effects on Multivalent Ligand-Receptor Binding: Exclusion of Ligand Sites by Bound Cell Surface Receptors," Biophysical Journal, 76(6): 3031-3043.
Holliger et al., 2005, "Engineered antibody fragments and the rise of single domains," Nat Biotechnol 23(9): 1126-36.

(56) References Cited

OTHER PUBLICATIONS

Hoseini et al., 2017, "Acute myeloid leukemia targets for bispecific antibodies," Blood Cancer Journal, 7(2):e522-e522.
International Search Report and Written Opinion dated Mar. 21, 2019 for PCT/US2018/050916.
Jachimowicz et al., 2011, "Induction of In Vitro and In Vivo NK Cell Cytotoxicity Using High-Avidity Immunoligands Targeting Prostate-Specific Membrane Antigen in Prostate Carcinoma," Mol Cancer Thera, 10(6): 1036-1045.
Janeway et al., 1997, "Immunology Third Edition," Garland Publishing, Inc. Ch. 3, Structure of the Antibody Molecule and Immunoglobulin Genes, 3:1-11.
Jonnalagadda et al., 2015, "Chimeric Antigen Receptors With Mutated IgG4 Fc Spacer Avoid Fc Receptor Binding and Improve T Cell Persistence and Antitumor Efficacy," *Molecular Therapy*, 23(4):757-768.
Junttila et al., 2014, "Antitumor Efficacy of a Bispecific Antibody That Targets HER2 and Activates T Cells," Cancer Research, 74(19):5561-5571.
Kanyavuz et al., 2019, "Breaking the Law: Unconventional Strategies for Antibody Diversification," Nature Review, 19:355-368.
Kaur et al., 2015, "Applications of In Vitro- In Vivo Correlations in Generic Drug Development: Case Studies," *The AAPS Journal* , 17(4):1035-1039; doi: 10.1208/s12248-015-9765-1.
Kellner et al., 2012, "Fusion proteins between ligands for NKG2D and CD20-directed single-chain variable fragments sensitize lymphoma cells for natural killer cell-mediated lysis and enhance antibody-dependent cellular cytotoxicity," Leukemia, 26:830-834.
Kellner et al., 2013, "Promoting natural killer cell functions by recombinant immunoligands mimicking an induced self phenotype", OncoImmunology, 2(6):e24481.
Kellner et al., 2016, "Enhancing natural killer cell-mediated lysis of lymphoma cells by combining therapeutic antibodies with CD20-specific immunoligands engaging NKG2D or NKp30," OncoImmunology, 5 (1): e1058459.
Kennedy et al., 2002, "Incidence and nature of CD20-negative relapses following rituximab therapy in aggressive B-cell non-Hodgkin's lymphoma: a retrospective review," British Journal of Haematology, 119:412-416.
Kijanka et al., 2013, "Rapid optical imaging of human breast tumour xenografts using anti-HER2 VHHs site-directly conjugated to IRDye 800CW for image-guided surgery," Eur J Nucl Med Mol Imaging, 40:1718-1729.
Kim et al., 2014, "Mutational approaches to improve the biophysical properties of human singledomain antibodies," Biochimica et Biophysica Acta, 1844:1983-2001.
Kjellev et al., 2007, "Inhibition of NKG2D receptor function by antibody therapy attenuates transfer-induced colitis in SCID mice," *Eur. J. Immunol.* , 37:1397-1406.
Klein et al., 2012, "Progress in overcoming the chain association issue in bispecific; heterodimeric IgG antibodies," MaBs 4(6):653-663.
Kluge et al., 2017, "EGFR/CD16A TandAbs are efficacious NK-cell engagers with favorable biological properties which potently kill EGFR(+) tumors with and without Ras mutation," Cancer Research, 77(13 Suppl.):Abstract 3641.
Koerner et al., 2015, "Induction of NK and T Cell Immune Responses Against Leukemia Cells By Bispecific NKG2D-CD16 and -CD3 Fusion Proteins," Blood 126(23):2558, Abstract 606.
Kranz et al., 1981, "Restricted reassociation of heavy and light chains from hapten-specific monoclonal antibodies." Proceedings of the National Academy of Sciences, 78.9: 5807-5811.
Krieg et al., 2005, "Functional Analysis of B and T Lymphocyte Attenuator Engagement on CD4+ and CD8+ T Cells," The Journal of Immunology, 175(10):6420-6427.
Kunik et al., 2012, "Structural consensus among antibodies defines the antigen binding site," PLoS Comput Biol., 8(2):e1002388. Epub Feb. 23, 2012.

Kwong et al., 2008, "Generation, affinity maturation, and characterization of a human anti-human NKG2D monoclonal antibody with dual antagonistic and agonistic activity," Journal of Molecular Biology, 384 (5): 1143-1156.
Laborda, et al., 2017, "Development of A Chimeric Antigen Receptor Targeting C-Type Letin-Like Molecule-1 for Human Acute Myeloid Leukemia," International Journal of Molecular Sciences, 18(2259).
Lamminmaki et al., 2001, "Crystal structure of a recombinant anti-estradiol Fab fragment in complex with 17β-estradiol." Journal of Biological Chemistry, 276.39: 36687-36694.
Lewis et al., 2014, "Generation of bispecific IgG antibodies by structure-based design of an orthogonal Fab interface", Nat. Biotechnol., 32(2):198-198.
Lin et al., 2011, "Improved affinity of a chicken single-chain antibody to avian infectious bronchitis virus by site-directed mutagenesis of complementarity-determining region H3," African Journal of Biotechnology, 10(79):18294-18302.
Lin et al., 2013, "CD4(+) NKG2D(+) T cells induce NKG2D down-regulation in natural killer cells in CD86-RAE-1ε transgenic mice", Immunology, 141(3):401-415.
Lippow et al., 2007, "Computational design of antibody-affinity improvement beyond in vivo maturation," *Nature Biotechnology* , 25(10):1171-1176.
Liu et al., 2017, "Fc engineering for Developing Therapeutic Bispecific Antibodies and Novel Scaffolds," Frontiers in Immunology, 8, 38: 1-15.
Lloyd et al., 2009, "Modelling the human immune response: performance of a 1011 human antibody repertoire against a broad panel of therapeutically relevant antigens," Protein Engineering, Design and Selection, 22(3):159-168.
Lo et al., 2021 "Conformational epitope matching and prediction based on protein surface spiral features," *BMC Genomics* , 22(Suppl 2):116 16 pages.
Lund et al., 1996, "Multiple interactions of IgG with its core oligosaccharide can modulate recognition by complement and human Fc gamma receptor I and influence the synthesis of its oligosaccharide chains," J. Immunol, 157:4963-4969.
MacCallum et al., 1996, "Antibody-antigen Interactions: Contact Analysis and Binding Site Topography, " J. Mol. Biol., 262:732-745.
Madlener et al., 2010, "A Bispecific Protein Targeting the NKG2D Receptor on Natural Killer Cells: In Vitro and In Vivo activity of ULBP2-CEA," Blood, 116(21):2095.
Maeda et al., 2015, "New antibody modification technology and its application to antibody drugs," Farumashia, 51(5):424-428.
Maeda et al., 1997, "Engineering of Functional Chimeric Protein G-Vargula Luciferase" Analytical biochemistry, 249(2):147-152.
Maelig et al., 2016, "NK cells and cancer: you can teach innate cells new tricks", Nature Reviews Cancer, 16(1):7-19.
Mandelboim et al., 1999, "Human CD16 as a lysis receptor mediating direct natural killer cell cytotoxicity," *PNAS USA* , 96(10):5640-5644; doi: 10.1073/pnas.96.10.5640.
Mariuzza et al., 1987, "The Structural Basis of Antigen-Antibody Recognition," Ann. Rev. Biophys. Chem., 16:139:59.
Marks et al., 2020, "How repertoire data are changing antibody science," *J. Biol. Chem.*, 295(29):9823-9837.
McCarthy et al., 2001, "Altering the fine specificity of an anti-Legionella single chain antibody by a single amino acid insertion," Journal of Immunological Methods 251:137-149.
McWilliams et al., 2015, "Targeting the Tumor Evasion Interaction of NKG2A and Its Ligand HLA-E Increases Natural-Killer Cell Activity in Chronic Lymphocytic Leukemia," Blood 126 (23):1289.
Merchant et al., 1998, "An efficient route to human bispecific IgG," Nature Biotechnology 16, 677-681 doi : 10.1038/nbt0798-677.
Miller et al., 2003, "Design, Construction, and in Vitro Analyses of Multivalent Antibodies," J Immunol 170(9):4854-61.
Mimoto et al., 2014, "Crystal structure of a novel asymmetrically engineered Fc variant with improved affinity for FcγRs", Mol. Immunol., 58(1):132-138.
Moore et al., 2011, "A novel bispecific antibody format enables simultaneous bivalent and monovalent co-engagement of distinct

(56) References Cited

OTHER PUBLICATIONS target antigens, " mAbs 3:6, 546-557; Nov./Dec. 2011, Landes Bioscience, DOI: 10.4161/mabs.3.6.18123.
Morris, 1996, "Epitope Mapping of Protein Antigens by Competition ELISA," The Protein Protocols Handbook, Totowa, NJ, Humana Press, 595-600.
Morvan et al., 2016, "NK cells and cancer: you can teach innate cells new tricks" Nat Rev Cancer, 16(1):7-19.
Muda et al., 2011, "Therapeutic assessment of SEED: a new engineered antibody platform designed to generate mono- and bispecific antibodies", Protein Eng. Des. Sel., 24(5):447-454.
Muller et al., 2015, "Trastuzumab emtansine (T-DM1) renders HER2+ breast cancer highly susceptible to CTLA-4/PD-1 blockade," Sci. Transl. Med., 7(315):1-14.
Muntasell et al., 2017, "Targeting NK-cell checkpoints for cancer immunotherapy," Current Opinion in Immunology 45:73-81.
Myers et al., 2021, "Exploring the NK cell platform for cancer immunotherapy," Nature Reviews Clinical Oncology 18(2):85-100.
Nagasaki et al., 2013, "Interleukin-6 released by colon cancer-associated fibroblasts is critical for tumour angiogenesis: anti-interleukin-6 receptor antibody suppressed angiogenesis and inhibited tumour-stroma interaction", British Journal of Cancer, 110(2):469-478.
Nie et al., 2020, "Biology drives the discovery of bispecific antibodies as innovative therapeutics," Antibody Therapeutics 3(1):18-62.
Notice of Opposition for Colombia Patent Application No. NC2020/0010345 dated Dec. 16, 2020.
Padlan et al., 1989, "Structure of an antibody-antigen complex: Crystal structure of the HyHEL-10 Fab-lysozyme complex," Pro. Natl. Acad. Sci. USA 86:5938-5942.
Pakula et al., 1989, "Genetic analysis of protein stability and function." Annual review of genetics 23.1: 289-310.
Parsons et al., 2016, "NKG2D Acts as a Co-Receptor for Natural Killer Cell-Mediated Anti-HIV-1 Antibody-Dependent Cellular Cytotoxicity," AIDS Research and Human Retroviruses 32(10-11) 1089-1096.
Paul et al., 1993, "Fundamental Immunology," (textbook) 292-295.
Petricevic et al., 2013, "Trastuzumab mediates antibody-dependent cell-mediated cytotoxicity and phagocytosis to the same extent in both adjuvant and metastatic HER2/neu breast cancer patients," Journal of Translational Medicine 11 (307).
Piche-Nicholas et al., 2018, "Changes in complementarity-determining regions significantly alter IgG binding to the neonatal Fc receptor (FcRn) and pharmacokinetics," mAbs 10(1): 81-94.
Portolano et al., 1993, "Lack of promiscuity in autoantigen-specific H and L chain combinations as revealed by human H and L chain 'roulette'," J. Immunol. 15(30):880-887.
Powers et al., 2016, "Abstract 1407: FPA 144, a therapeutic monoclonal antibody targeting the FGFR2b receptor, promotes antibody dependent cell-mediated cytotoxicity and stimulates sensitivity to PD-1 in the 4T1 syngeneic tumor model," Cancer Research 4 pages.
Raab et al., 2014, "Fc-Optimized NKG2D-Fc Constructs Induce NK Cell Antibody-Dependent Cellular Cytotoxicity Against Breast Cancer Cells Independently of HER2/neu Expession Status," Journal of Immunology 193(8): 4261-72.
Rabia et al., 2018, "Understanding and overcoming trade-offs between antibody affinity, specificity, stability and solubility" Biochem Eng J., 137:365-374.
Raulet, 2003, "Roles of the NKG2D immunoreceptor and its ligands," *Nature: Reviews Immunology*, 3:781-790; doi: 10.1038/nri1199.
Ridgway et al., 1996, "'Knobs-into-Holes' engineering of antibody Ch3 domains for heavy chain heterodimerization," Protein Engineering 9(7):617-21.
Roda-Navarro et al., 2020, "Understanding the Spatial Topology of Artificial Immunological Synapses Assembled in T Cell-Redirecting Strategies: A Major Issue in Cancer Immunotherapy," Frontiers in Cell and Developmental Biology 7:1-5.

Roell et al., 2017, "An Introduction to Terminology and Methoodology of Chemical Synergy—Perspectives from Across Disciplines," *Frontiers in Pharmacology: Cancer Molecular Targets and Therapeutics*, 8:1-11.
Romee et al., 2013, "NK cell CD16 surface expression and function is regulated by a disintegrin and metalloprotease-17 (ADAM17)," Blood 121(18): 3599-608.
Rosano et al., 2014, "Recombinant protein expression in *Escherichia coli*: advances and challenges" Frontiers in Microbiology, 5(172):17 pages.
Roskopf, et al., 2016, "Dual-targeting triplebody 33-3-19 mediates selective lyssi of biphenotypic CD19+ CD33+ leukemia cells," Oncotarget, 7(6): 22579-22589.
Rothe et al., 2013, "The Bispecific Immunoligand ULBP2-aCEA Redirects Natural Killer Cells to Tumor Cells and Reveals Potent Anti-Tumor Activity Against Colon Carcinoma," Int. J. Cancer 134(12):2829-2840.
Rudikoff et al., 1982, "Single amino acid substitution altering antigen-binding specificity," Pro. Natl. Acad. Sci USA 79:1979-1983.
Safdari et al., 2013, "Antibody humanization methods-a review and update" Biotechnology and Genetic Engineering Reviews, 29(2):175-186.
Sazinsky et al., 2008, "Aglycosylated immunoglobulin $G_1$ variants productively engage activating Fc receptors," *Proceedings of the National Academy of Sciences*, 105(51)20167-20172.
Schroeder et al., 2010, "Structure and Function of Immunoglobulins," J Allergy Clin Immunol, 125:S41-S52.
Schmitz et al., 2001, "Pharmacogenomics: implications for laboratory medicine," Clinica Chimica Acta 308:43-53.
Schuster et al., 2015, "Immunotherapy with the trifunctional anti-CD20 x anti-CD3 antibody FBTA05 (Lymphomun) in paediatric high-risk patients with recurrent CD20-positive B cell malignancies," British Journal of Haematology, 169 (1):90-102.
Shen et al., 2006, "Single variable domain-IgG fusion: a novel recombinant approach to Fc domain-containing bispecific antibodies" Journal of Biological Chemistry, 281(16):10706-10714.
Shum et al., 2002, "Conservation and Variation in Human and Common Chimpanzee CD94 and NKG2 Genes," The Journal of Immunology, 168:240-252.
Singer et al., 1998, "Genes and Genomes," Moscow, "Mir" 1:63-64.
Smits et al., 2016, "Designing multivalent proteins based on natural killer cell receptors and their ligands as immunotherapy for cancer", Expert Opinion on Biological Therapy, 16(9):1105-1112.
Sondermann et al., 2000, "The 3.2-Åcrystal structure of the human IgG1 Fc fragment-FcγRIII complex," Nature, 406(6793):267-273.
Spear et al., 2013, "NKG2D ligands as therapeutic targets", Cancer Immunology, 13(8): 14 pages.
Stamova et al., 2011, "Simultaneous engagement of the activatory receptors NKG2D and CD3 for retargeting of effector cells to CD33-positive malignant cells," Leukemia, 25:1053-1056.
Steigerwald et al., 2009, "Human lgG1 antibodies antagonizing activating receptor NKG2D on natural killer cells," mAbs 1(2): 115-127.
Steimer et al., 2001, "Pharmacogenetics: a new diagnostic tool in the management of antidepressive drug therapy," Clinica Chimica Acta, 308:33-41.
Stein et al., 2012, "Natural Killer (NK)- and T-Cell Engaging Antibody-Derived Therapeutics," Antibodies 1:88-123.
Steinbacher et al., 2014, "An Fc-optimized NKG2D-immunoglobulin G fusion protein for induction of natural killer cell reactivity against leukemia," International Journal of Cancer, 136(5):1073-1084.
Strong, 2002, "Asymmetric ligand recognition by the activating natural killer cell receptor NKG2D, a symmetric homodimer," Molecular Immunology, 38 (14):1029-1037.
Strop et al., 2012, "Generating Bispecific Human lgG1 and lgG2 Antibodies from Any Antibody Pair," J Mol Biol 420:204-19.
Sulea et al., 2018, "Application of Assisted Design of Antibody and Protein Therapeutics (ADAPT) improves efficacy of a *Clostridium difficile* toxin A single-domain antibody," 8:2260, 11 pages.
Tallarida, 2000, "Drug Synergism and Dose Effect Analysis," Ed. Chapman & Hall pp. 1-71.

(56) References Cited

OTHER PUBLICATIONS

Tashiro, et al., 2017 "Treatment of Acute Myeloid Leukemia with T Cellls Expressing Chimeric Antigen Receptors Directed to C-Type Lectin-like Molecule 1," Molecular Therapy, 25(9):2202-2213.
Tay et al., 2016, "TriKEs and BiKEs join CARs on the cancer immunotherapy highway", Human Vaccines and Immunotherapeutics, 12(11):2790-2796.
Teplyakov A. et al., 2014, "Antibody modeling assessment II. Structures and models" Proteins: Structure, Function, and Bioinformatics, 82(8):1563-1582.
Thakur et al., 2018, "Bispecific antibody based therapeutics: Strengths and challenges," Blood Review, 32:339-347.
Torres et al., 2008, "The immunoglobulin constant region contributes to affinity and specificity" Trends in Immunology, 29(2):91-97.
Vajda et al., 2021, "Progress toward improved understanding of antibody maturation," *Current Opinion in Structural Biology*, 67:226-231.
Vajdos et al., 2002, "Comprehensive Functional Maps of the Antigen-binding Site of an Anti-ErbB2 Antibody Obtained with Shotgun Scanning Mutagenesis," J. Mol. Biol., 320:415-428.
Vaks et al., 2018, "Design Principles for Bispecific lgGs, Opportunities and Pitfalls of Artificial Disulfide Bonds," Antibodies, 7(3): 1-28.
Vallera et al., 2016, "IL 15 Trispecific Killer Engagers (TriKE) Make Natural Killer Cells Specific to CD33+ Targets While Also Inducing Persistence, In Vivo Expansion, and Enhanced Function," Clin Cancer Res, 22(14):3440-50.
Van Rhenen et al., 2007, "The novel AML stem cell associated antigen CLL-1 aids in discrimination between normal and leukemic stem cells," Blood, American Society of Hematology, 110(7):2659-2666.
Vidarsson et al., 2014, "IgG subclasses and allotypes: from structure to effector functions," Front. Immunol. 5:520.
Von Kreudenstein et al., 2013, "Improving Biophysical Properties of a Bispecific Antibody Scaffold to Aid Developability: Quality by Molecular Design," mAbs 5(5):646-54.
Von Kreudenstein et al., 2014, "Protein Engineering and the Use of Molecular Modeling and Simulation: The Case of Heterodimeric Fc Engineering, " Methods 65(1):77-94.
Von Strandmann, 2006, "A novel bispecific protein (ULBP2-BB4) targeting the NKG2D receptor on natural killer (NK) cells and CD138 activates NK cells and has potent antitumor activity against human multiple myeloma in vitro and in vivo," Blood, 107(5): 1955-1962.
Vyas et al., 2016, "Mono- and dual-targeting triplebodies activate natural killer cells and have anti-tumor activity in vitro and in vivo against chronic lymphocytic leukemia," Oncoimmunology, 5(9):p.e1211220.
Wang et al., 2018, "IgG Fc engineering to modulate antibody effector functions," Protein Cell, 9(1):63-73.
Wang et al., 2016, "A bispecific protein rG7S-MICA recruits natural killer cells and enhances NKG2D-mediated immunosurveillance against hepatocellular carcinoma," Cancer Letters, 372:166-178.
Ward et al., 1989, "Binding activities of a epertoire of single immunoglobulin variable domains secreted from *Escherichia coli,*" *Nature*, 341:544-546.
Wark et al., 2006, "Latest technologies for the enhancement of antibody affinity", *Advanced Drug Delivery Reviews*, 58(5-6):657-670.
Weiss-Steider et al., 2011, "Expression of Mica, Micb and NKG2D in human leukemic myelomonocytic and cervical cancer cells," Journal of Experimental & Clinical Cancer Research, 30(1):37.
Wensveen et al., 2018, "NKG2D: A master regulator of immune cell responsiveness," Frontiers in Immunology, 9:441.
Wikipedia: "Trifunctional antibody Feb. 1, 2018",, Jan. 2, 2018 (Jan. 2, 2018), pp. 1-4, XP093016568, Retrieved from the Internet: URL:https://en.wikipedia.org/w/index.php?title=Trifunctional antibody8 oldid=818265015.
Wranik et al., 2012, "LUZ-Y, a novel platform for the mammalian cell production of full-length IgG-bispecific antibodies", J. Biol. Chem., 287:43331-43339.
Written Opinion for International Application No. PCT/US2018/017470 dated Apr. 24, 2018.
Written Opinion for International Application No. PCT/US2018/050916 dated Dec. 4, 2018.
Written Opinion for International Application No. PCT/US2019/017330 dated Jun. 11, 2019.
Written Opinion for International Application No. PCT/US2019/018751 dated Jul. 1, 2019.
Wu et al., 1999, "Humanization of a Murine Monoclonal Antibody by Simultaneous Optimization of Framework and CDR Residues," J. Mol. Biol., 294:151-162.
Xie et al., 2005, "A new format of bispecific antibody: highly efficient heterodimerization, expression and tumor cell lysis," J Immunol Methods 296(1):95-101.
Xu et al., 2014, "Production of bispecific antibodies in "knobs-into-holes" using a cell-free expression system," mAbs, 7(1)231-242.
Xu et al., 2019, "A VEGFR2-MICA bispecific antibody activates tumor-infiltrating lymphocytes and exhibits potent anti-tumor efficacy in mice," Cancer Immunology Immunotherapy, 68(9): 1429-1441.
Yan et al., 2014, "Construction of a synthetic phage-displayed Nanobody library with CDR3 regions randomized by trinucleotide cassettes for diagnostic applications." Journal of Translational Medicine, 12.1 : 1-12.
Yao et al., 2019, "A VEGFR2-MICA bispecific antibody activates tumor-infiltrating lymphocytes and exhibits potent anti-tumor efficacy in mice," Cancer Immunology Immunotherapy, Springer, Berlin/Heidelberg 68 (9):1429-1441.
Yeap et al., 2016, "CD16 is indispensable for antibodydependent cellular cytotoxicity by human monocytes," Scientific Reports, 6:34310.
Young et al., 1995, "Thermal stabilization of a single-chain Fv antibody fragment by introduction of a disulphide bond," FEBS Letters, 377 (2): 135-139.
Zhang et al., 2021, "Bispecific antibody-mediated redirection of NKG2D-CAR natural killer cells facilitates dual targeting and enhances antitumor activity." Journal for Immunotherapy of Cancer, 9.10.
Zhao et al., 2009, "Targeting C-type lectin-like molecule-1 for antibody-mediated immunotherapy in acute myeloid leukemia," Haematologica, 95(1):71-78.
Zhou et al., 1995, "Characterization of human homologue of 4-1BB and its ligand," Immunology Letters 45:67-73.
Bogen et al., 2021, "Design of a Trispecific Checkpoint Inhibitor and Natural Killer Cell Engager Based on a 2+1 Common Light Chain Antibody Architecture," Frontiers in Immunology 12:16 pages.
Briney et al., 2019, "Commonality despite exceptional diversity in the baseline human antibody repertoire," Nature 566:393 (19 pages).
Dasgupta et al., 2005, "Inhibition of NK Cell Activity through TGF-b1 by Down-Regulation of NKG2D in a Murine Model of Head and Neck Cancer," J Immunol 175(8):5541-5550.
Demaria et al., 2021, "Natural killer cell engagers in cancer immunotherapy: Next generation of immuno-oncology treatments," Eur. J. Immunol. 51:1934-1942.
Feng et al., 2020, "NKG2D-Fc fusion protein promotes antitumor immunity through the depletion of immunosuppressive cells," Cancer Immunol. Immunother. 69(10):2147-2155.
Giuliani et al., 2017, "Activation of NK cells and disruption of PD-L1/PD-1 axis: two different ways for lenalidomide to block myeloma progression," Oncotarget 8(14):24031-24044.
Hilpert et al., 2012, "Comprehensive analysis of NKG2D ligand expression and release in leukemia: implications for NKG2D-mediated NK cell responses," J. Immunol., 189(3):1360-1371.
Katano et al., 2015, "Predominant Development of Mature and Functional Human NK Cells in a Novel Human IL-2-Producing Transgenic NOG Mouse" J. Immunol. 194(7):3513-3525.
Khan et al., 2014, "Adjustable Locks and Flexible Keys: Plasticity of Epitope-Paratope Interactions in Germline Antibodies," J. Immunol 192:5398-5405.

(56) References Cited

OTHER PUBLICATIONS

Mendoza Rincón, 2014, "The NKG2D receptor in the border of immune surveillance and carcinogenesis," Publicación Científica en Ciencias Biomédicas 2(21):37-43. (English Abstract).
Miller et al., 2018, "Annual Review of Cancer Biology Natural Killer Cells in Cancer Immunotherapy," Annu. Rev. Cancer Biol. 8(3):77-103.
Miller et al,. 2019, "Natural Killer Cells in Cancer Immunotherapy," Ann. Rev. Cancer Biol. 3:77-103.
Poosaria et al., 2017, "Computational de novo Design of Antibodies binding to a Peptide with High Affinity," 114(6):1331-1342.
Spiess et al., 2015, "Alternative molecular formats and therapeutic applications for bispecific antibodies," Molecular Immunology 67:95-106.
Watanabe et al., 2014, NKG2D functions as an activating receptor on natural killer cells in the common marmoset (*Callithrix jacchus*), Int. Immunol., 26(11): 597-606.
Watzl et al., 2010, "Signal Transduction During Activation and Inhibition of Natural Killer Cells", Curr Protoc Immunol., 90(1):11.9B1-11.9B.17.
Whalen et al., 2023, "Engaging natural killer cells for cancer therapy via NKG2D, CD16A and other receptors," 15(1) 15 pages.
Xie et al., 2015, "VEGFR2 targeted antibody fused with MICA stimultes NKG2D mediated immunosurveillance and exhibits potent anti-tumor activity against breast cancer," Oncotarget 7(13):16455-16471.
Yang et al., 2016, "Bispecific Antibodies as a Development Platform for New Concepts and Treatment Strategies" Int. J. Mol. Sci. 18(48) 21 pages.
Yang et al., 2017, "Enhancing NK cell-mediated cytotoxicity to cisplatin-resistant lung cancer cells via MEK/Erk signaling inhibition," Nature Scientific Reports, 7:7958 (13 pages).

\* cited by examiner

Tumor-associated antigen binding arms

NKG2D arm

Tumor-associated antigen binding arms

NKG2D arm

NK cell targeting Fab fragment

Tumor cell targeting scFv

Binders

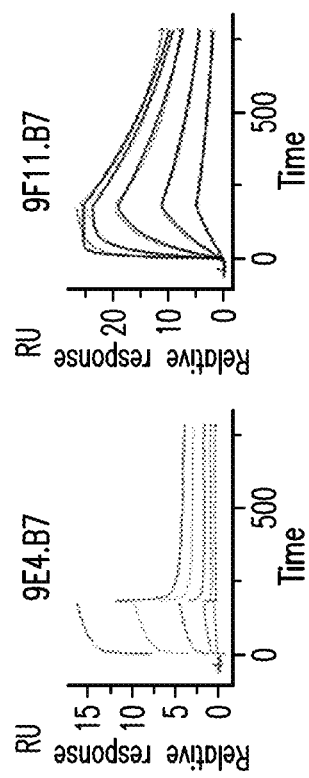
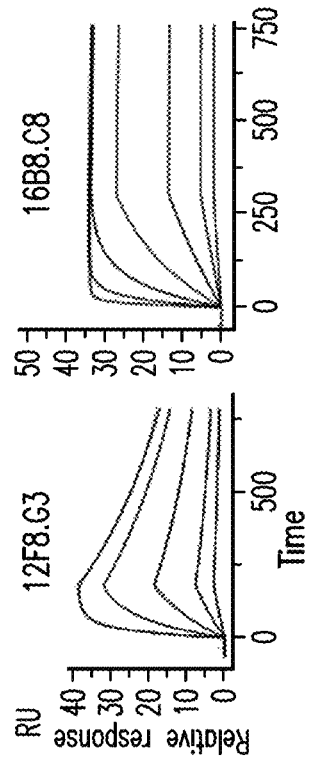
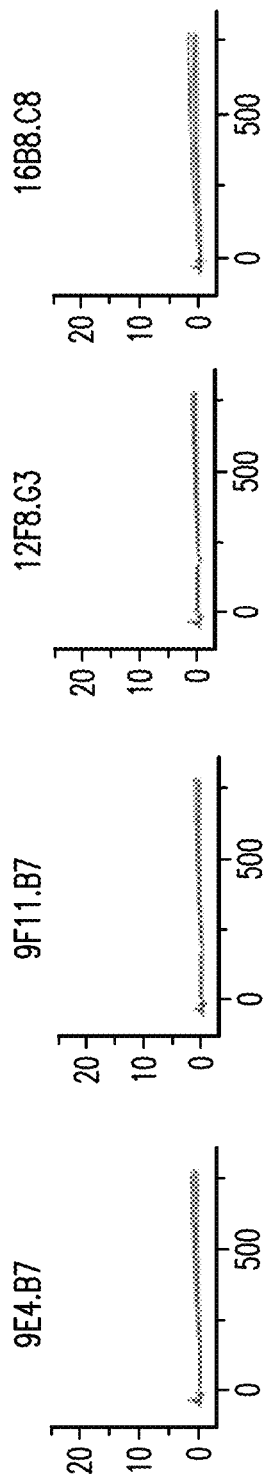
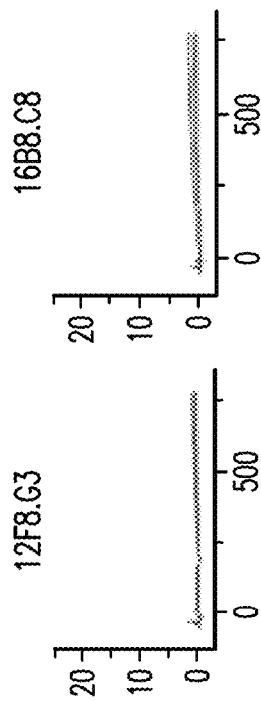
FIG. 19A  FIG. 19B  FIG. 19C  FIG. 19D
FIG. 19E  FIG. 19F  FIG. 19G  FIG. 19H

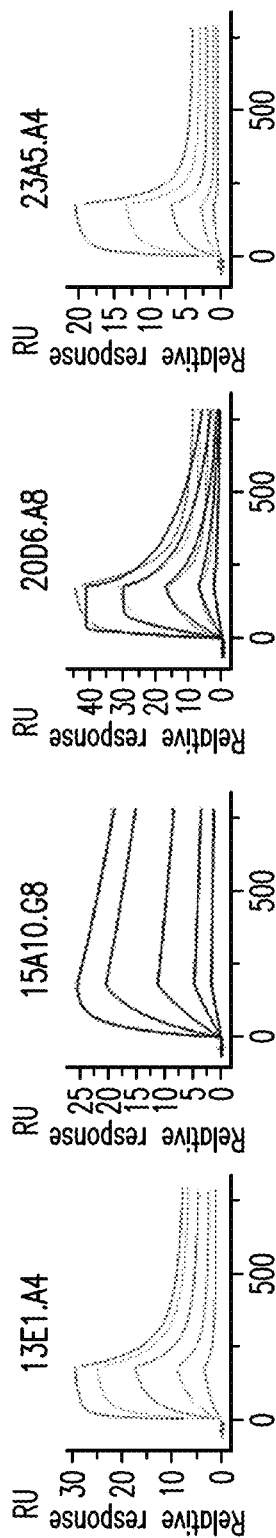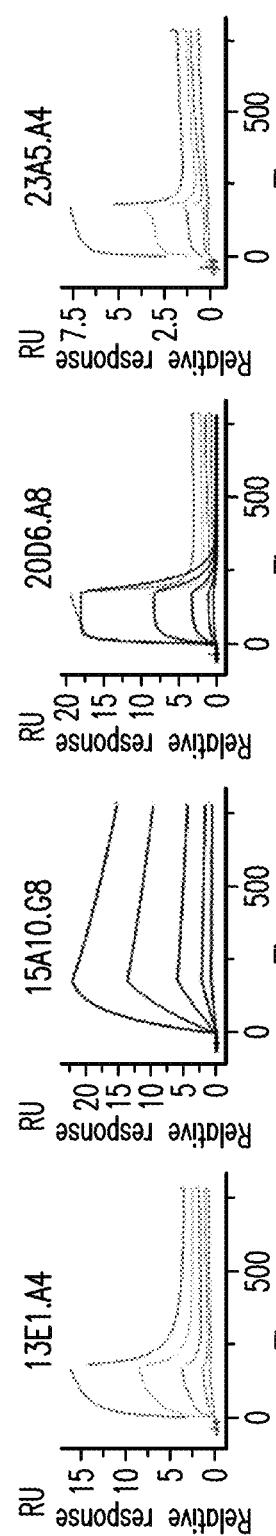
FIG. 19I  FIG. 19J  FIG. 19K  FIG. 19L
FIG. 19M  FIG. 19N  FIG. 19O  FIG. 19P Group 5
hCLEC12A-Factor Xa-His; 1294+854+424

Group 4
hCLEC12A-his; hF3'_A49-M-I-YA.SJ81B-HL_REC_H85-YB; 1:1 binding

Group 7
hCLEC12A-his; hF3'_A49-M-I-YA.SJ84B-HL_REV_L70-YB; 1:1 binding

Group 8
hCLEC12A-his; hF3'_A49-M-I-YA.SJ85B-HL_REV_H83-YB; 1:1 binding

Group 9
hCLEC12A-Factor Xa-His; 1302+854+424

Group 10
hCLEC12A-FActor Xa-His; 1303+854+424

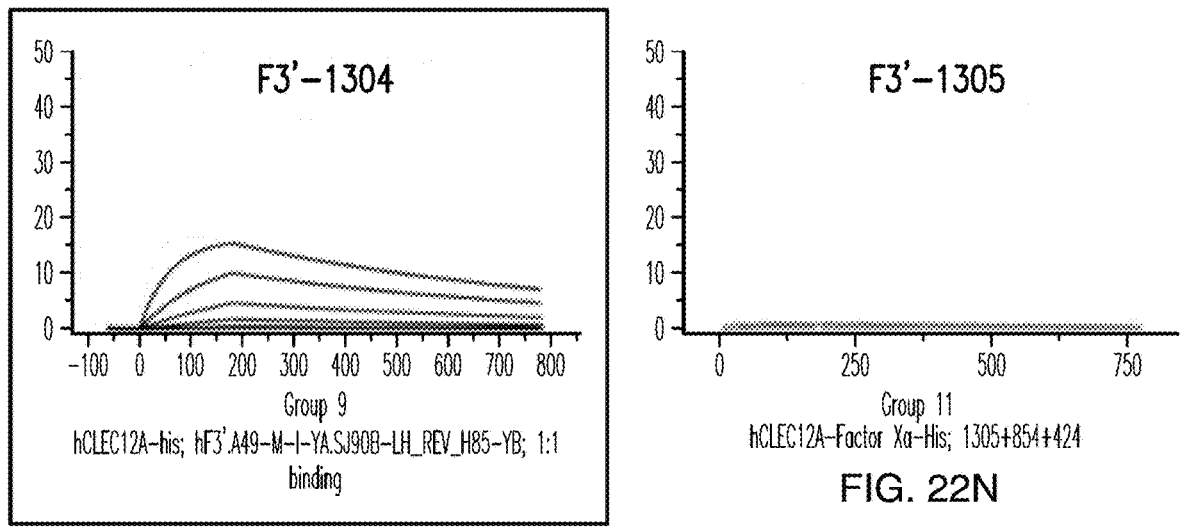
FIG. 22M
FIG. 22N
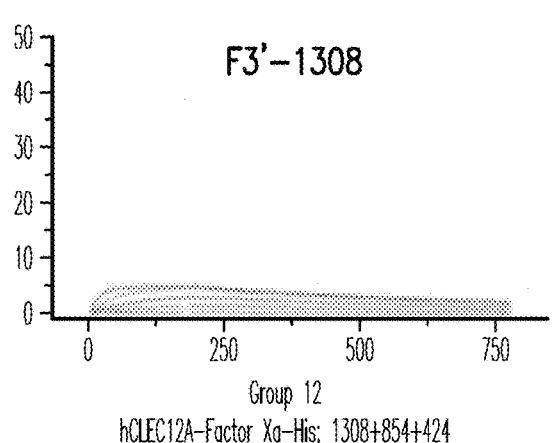
FIG. 22O
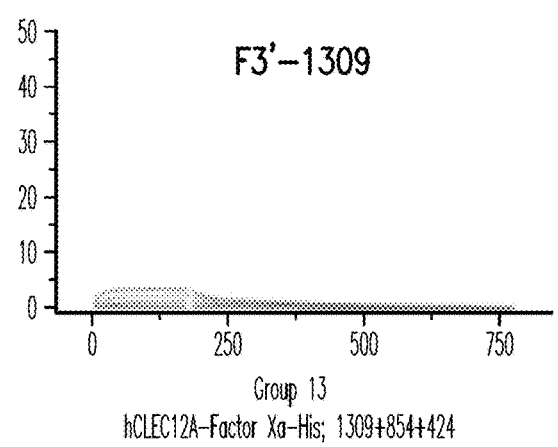
FIG. 22P

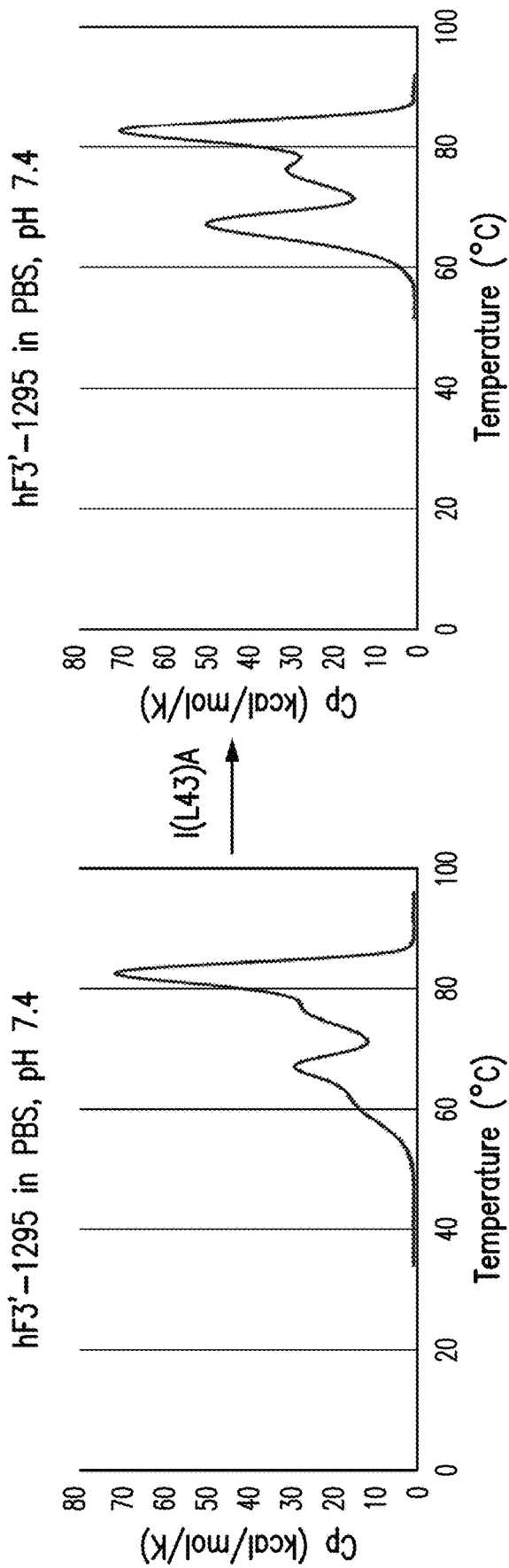

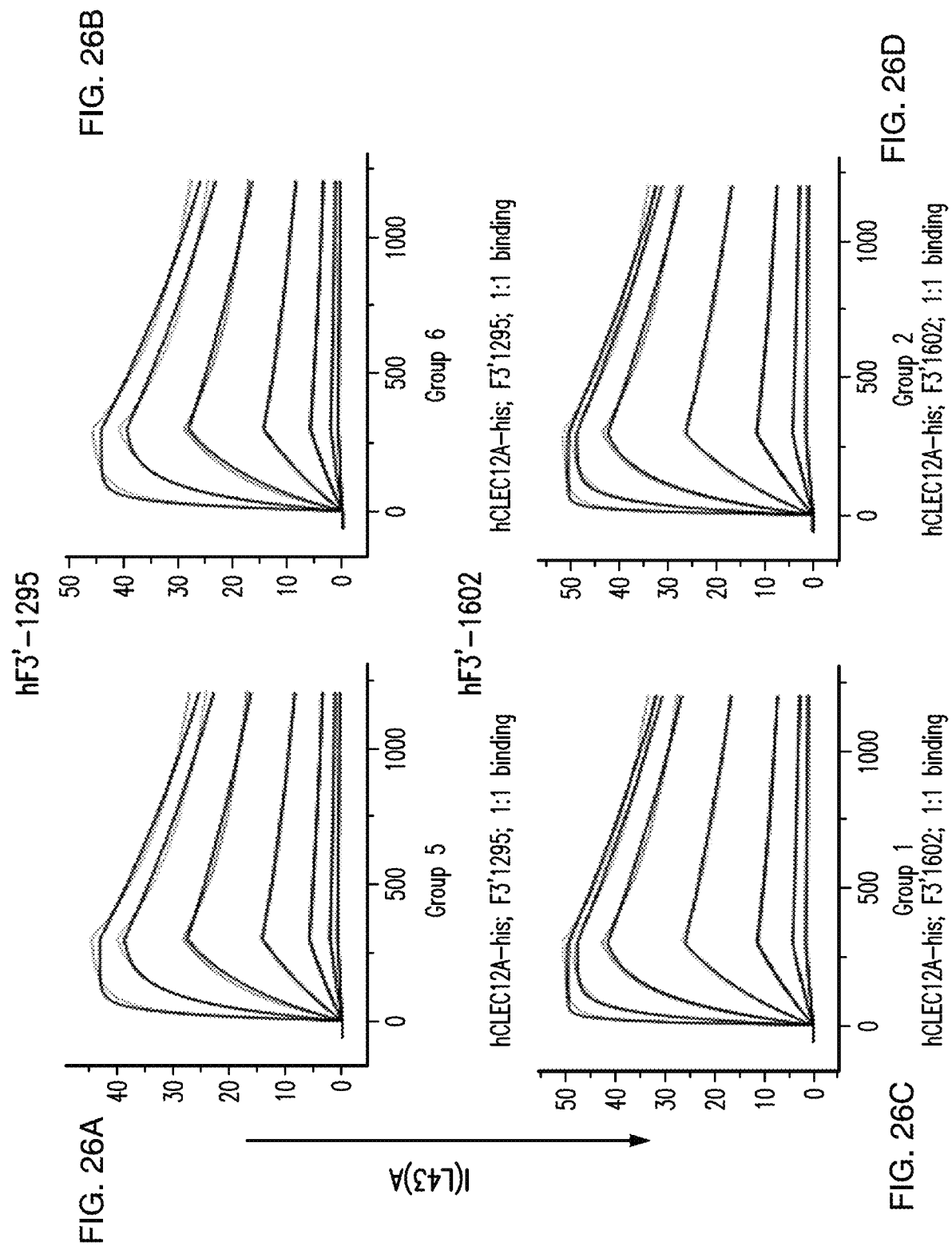

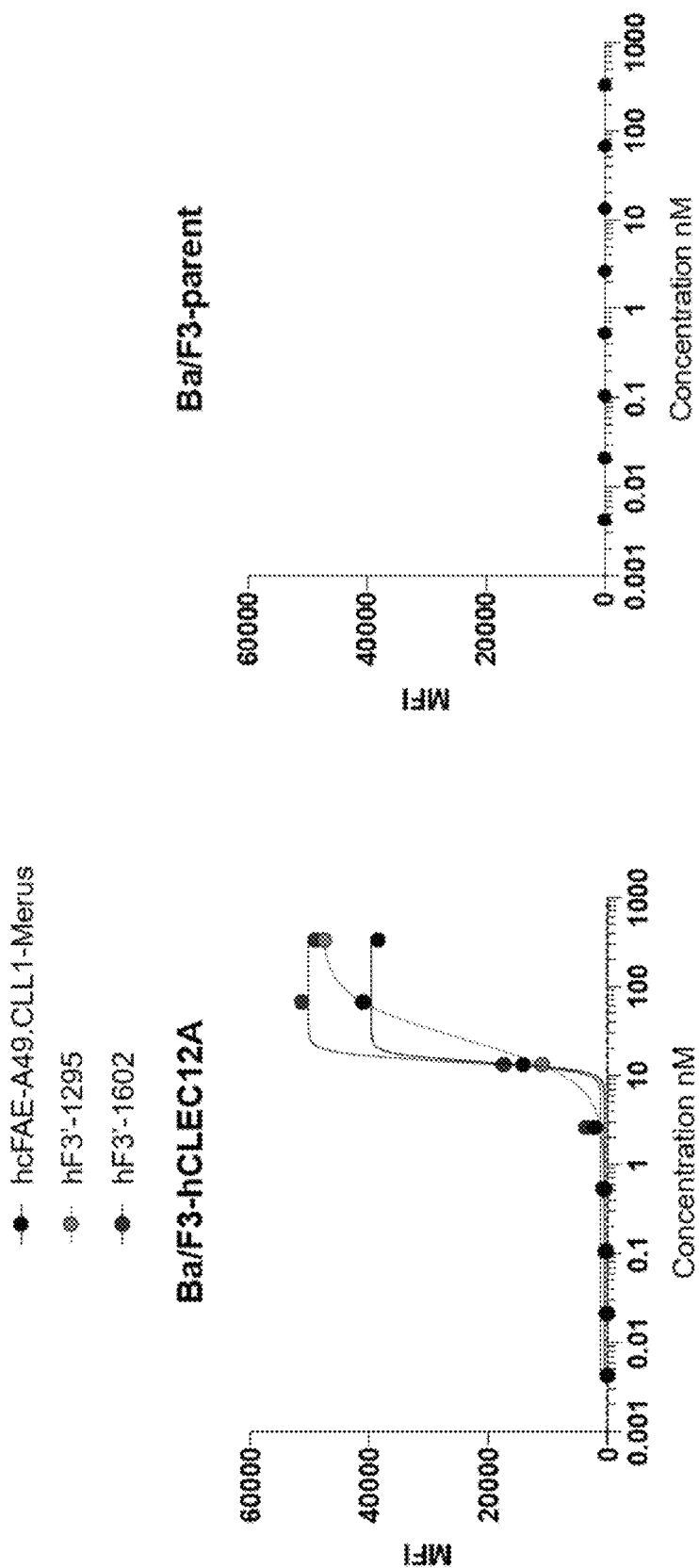

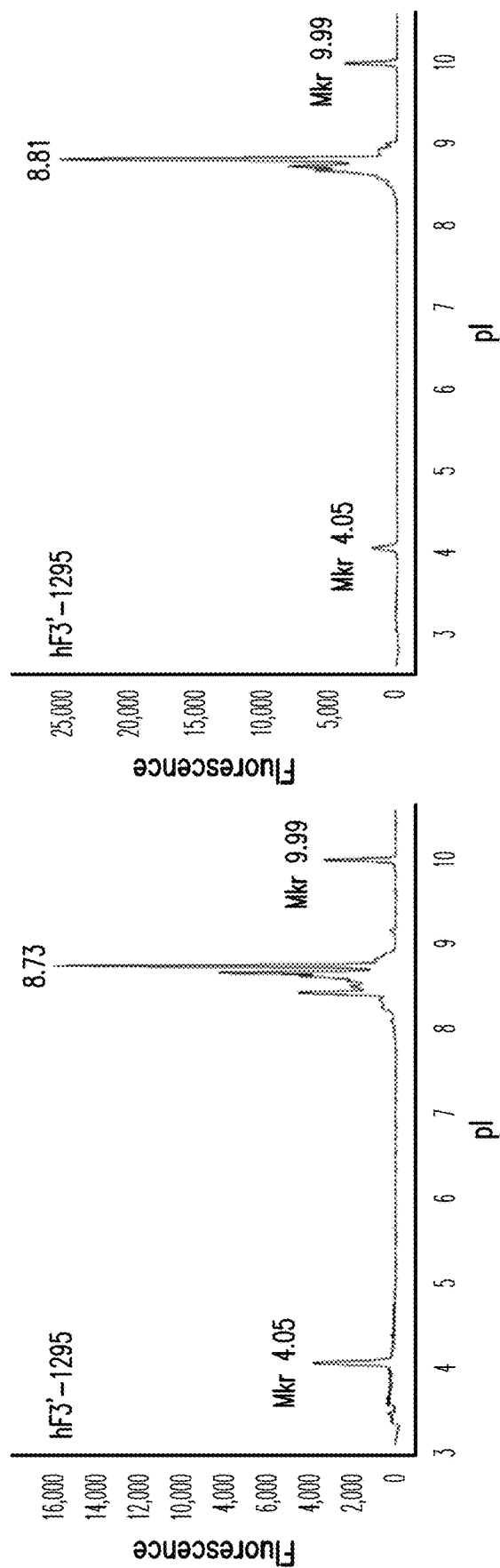

PSR=poly specificity reagent
SA-PE=Streptavidin phycoerythrin

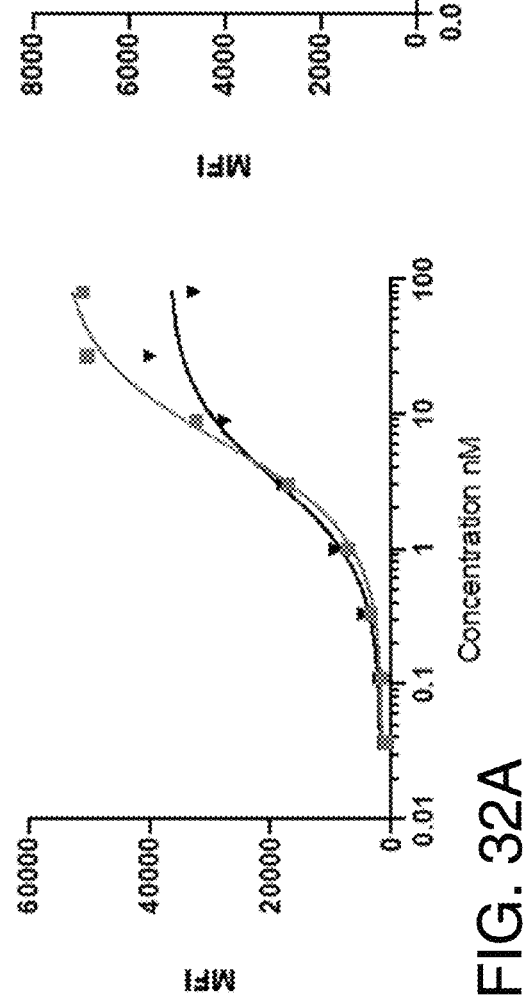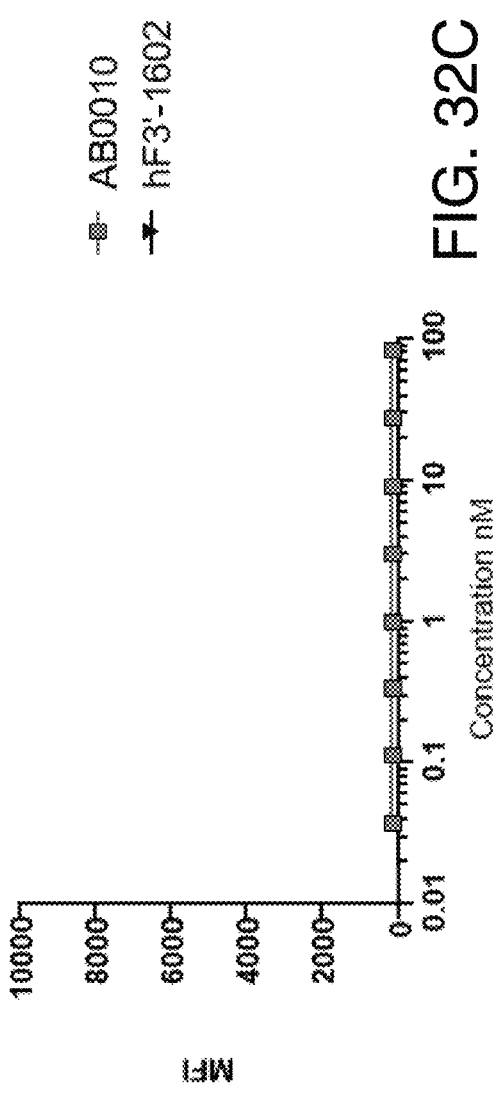

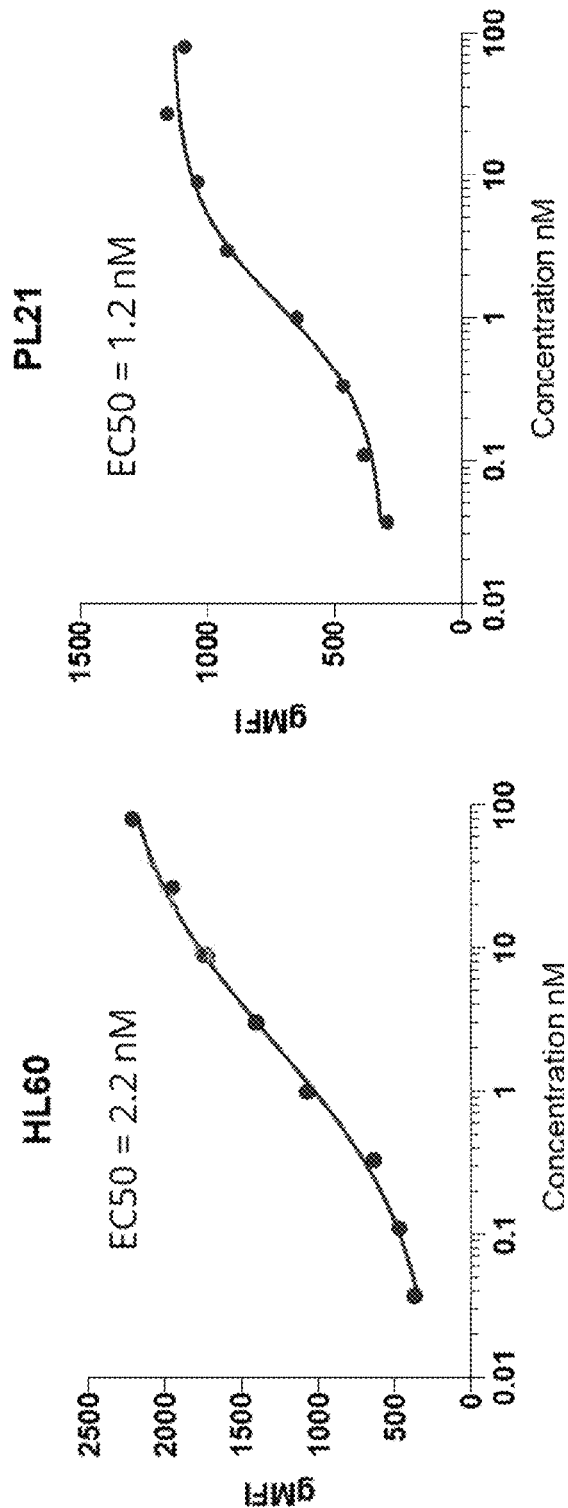

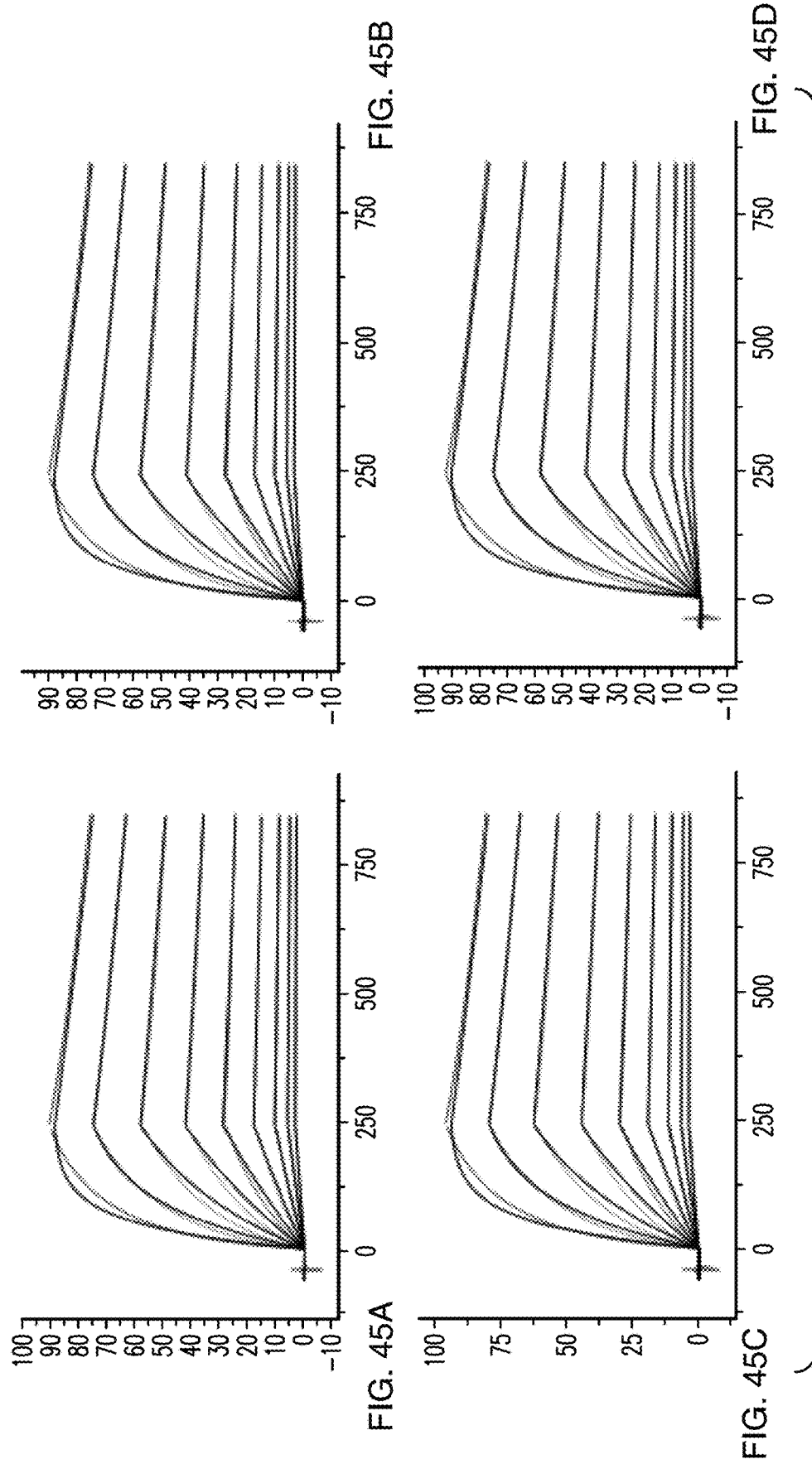

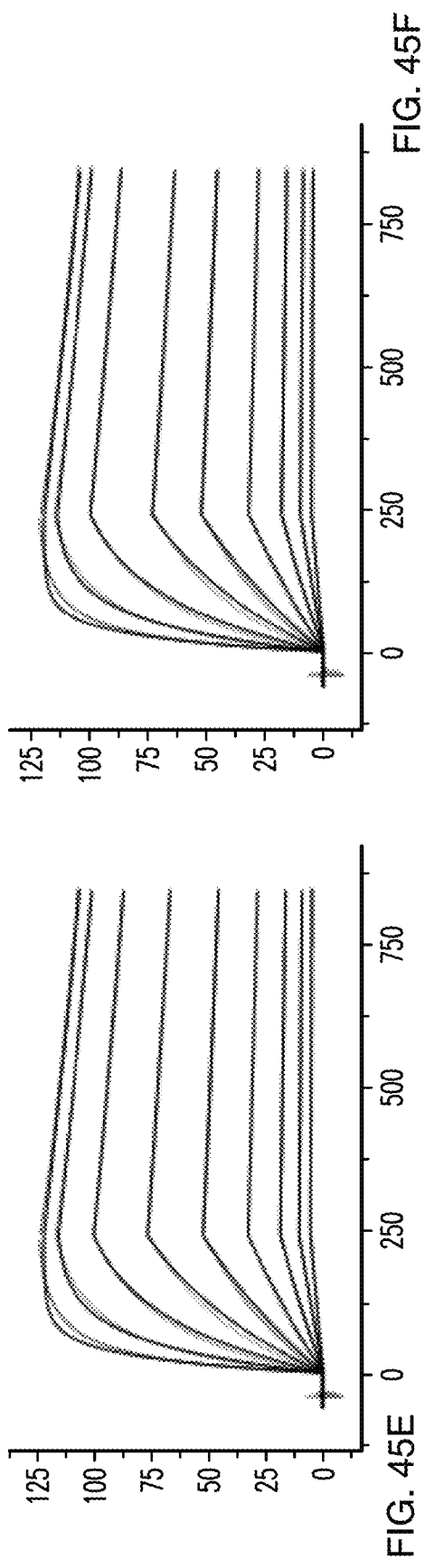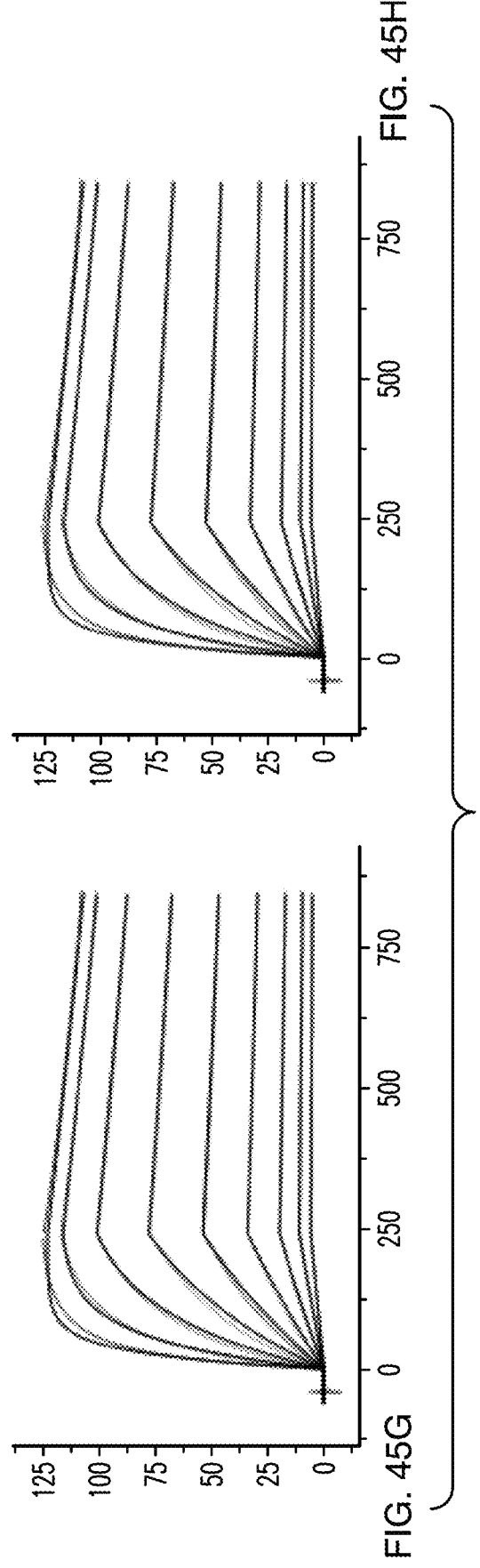

hF3'-1602
$K_D = 864.0 \pm 39.0$ nM
$(0.9 \pm 0.0 \ \mu M)$ trastuzumab
$K_D = 1140.0 \pm 60.0$ nM
$(1.1 \pm 0.1\ \mu M)$ hF3'-1602
$K_D = 1380.0 \pm 220.0$ nM
$(1.4 \pm 0.2 \, \mu M)$ trastuzmab
$K_D = 1690.0 \pm 170.0$ nM
$(1.7 \pm 0.2\ \mu M)$

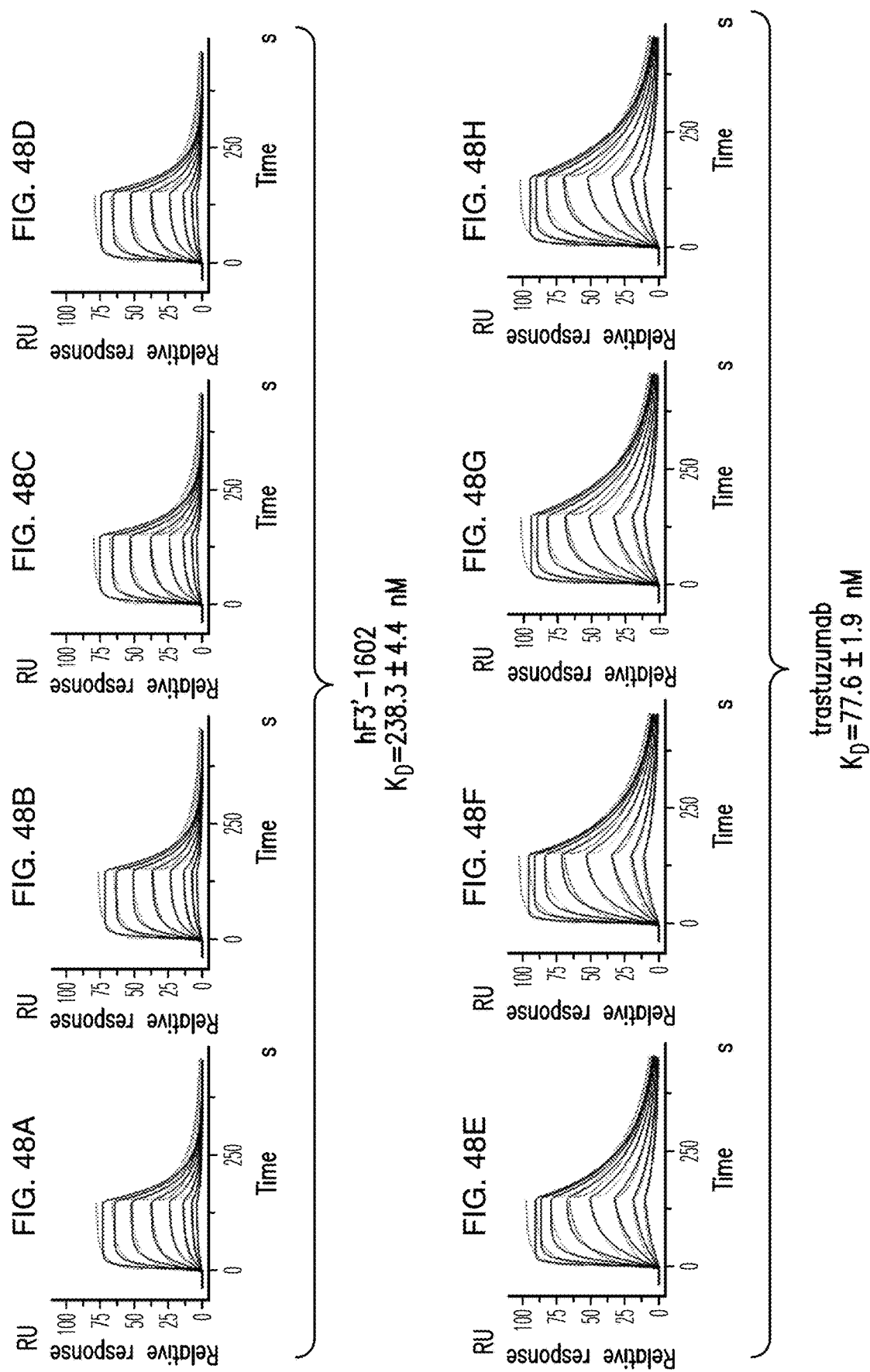

hF3'-1602
$K_D = 1107.5 \pm 20.6$ nM trastuzumab
$K_D = 439.8 \pm 8.3$ nM hF3'-1602
$K_D = 6560.0 \pm 560.0$ nM
($6.6 \pm 0.8$ μM)

trastuzumab
$K_D = 6880.0 \pm 270.0$ nM
($6.9 \pm 0.3$ μM)

hF3'-1602
$K_D = 7460.0 \pm 840.0$ nM
($7.5 \pm 0.8$ $\mu$M)

trastuzumab
$K_D = 4200.0 \pm 430.0$ nM
($4.2 \pm 0.4$ $\mu$M)

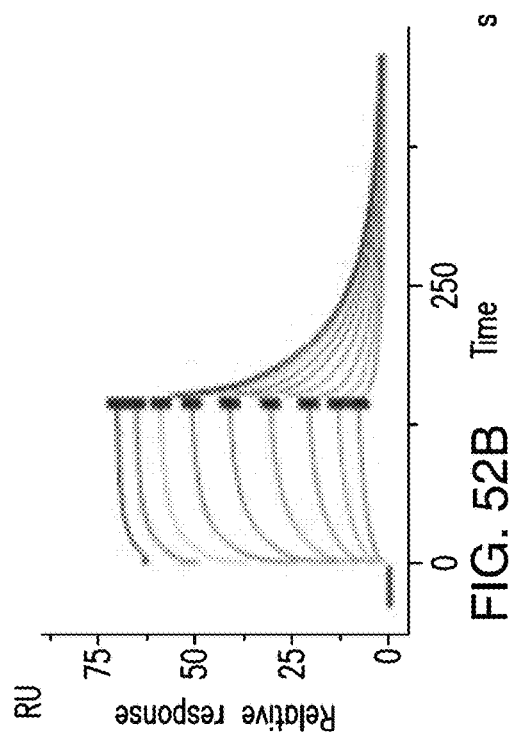
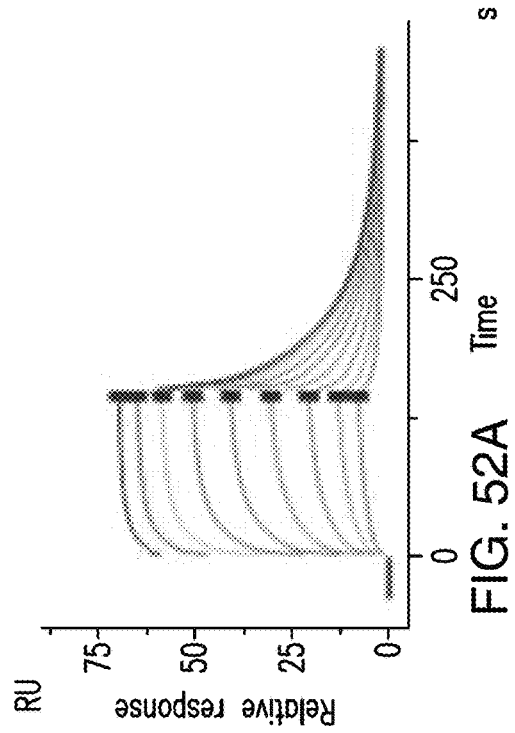
FIG. 52A, FIG. 52B, FIG. 52C, FIG. 52D
hF3'-1602
$K_D = 306.5 \pm 10.3$ nM

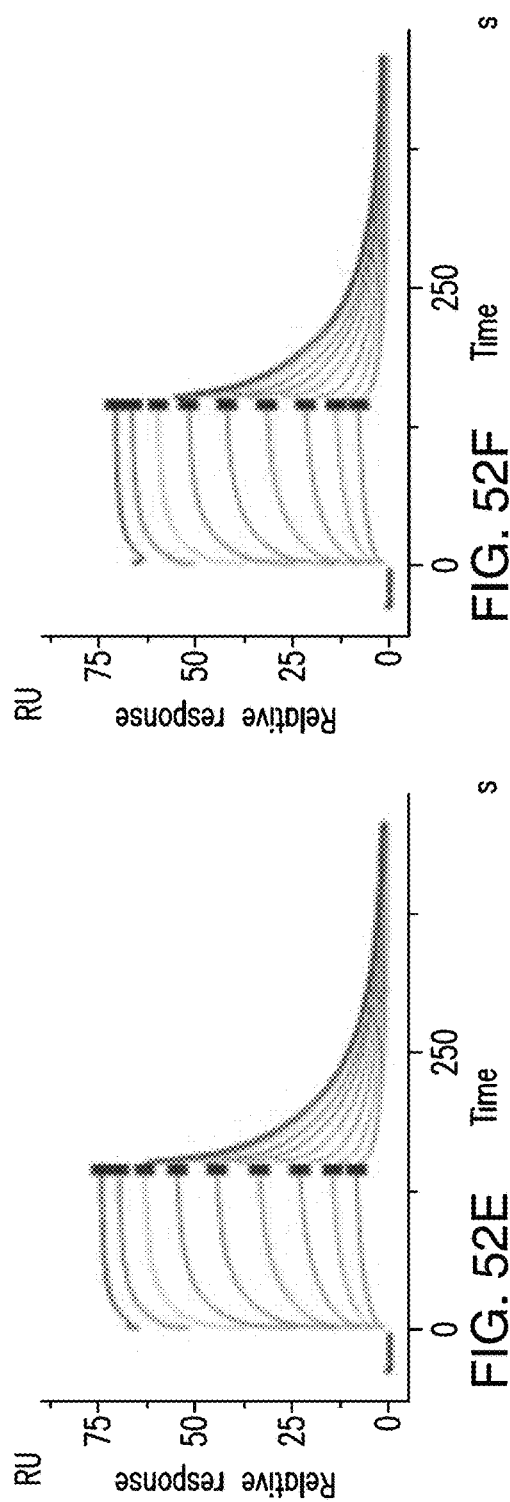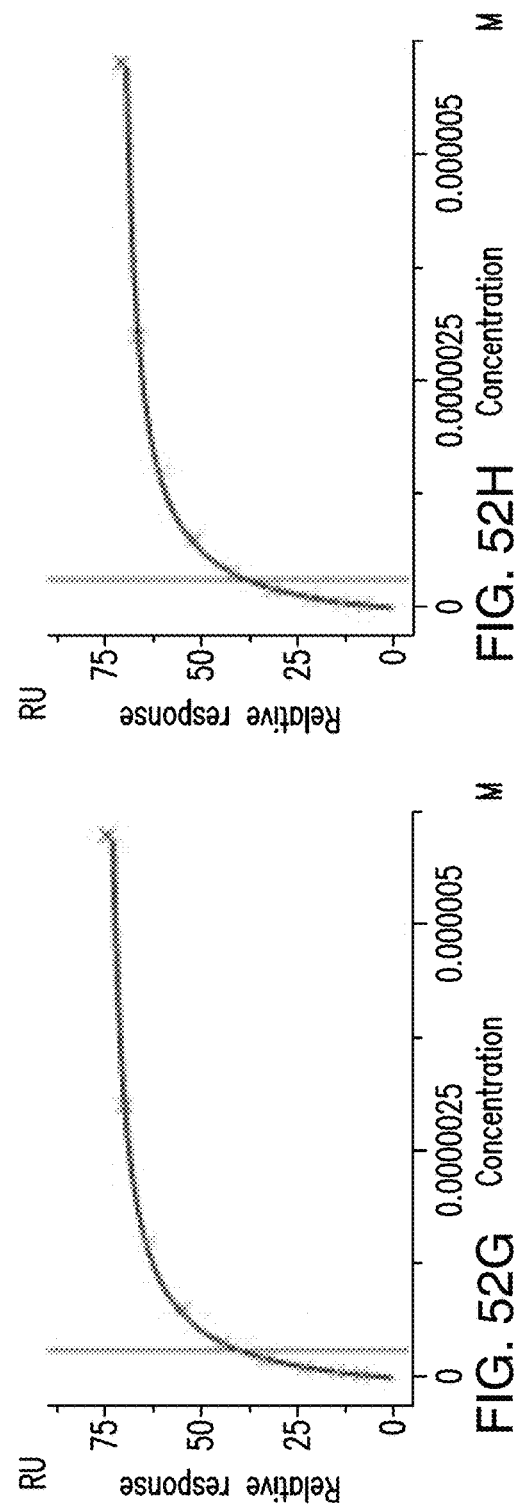

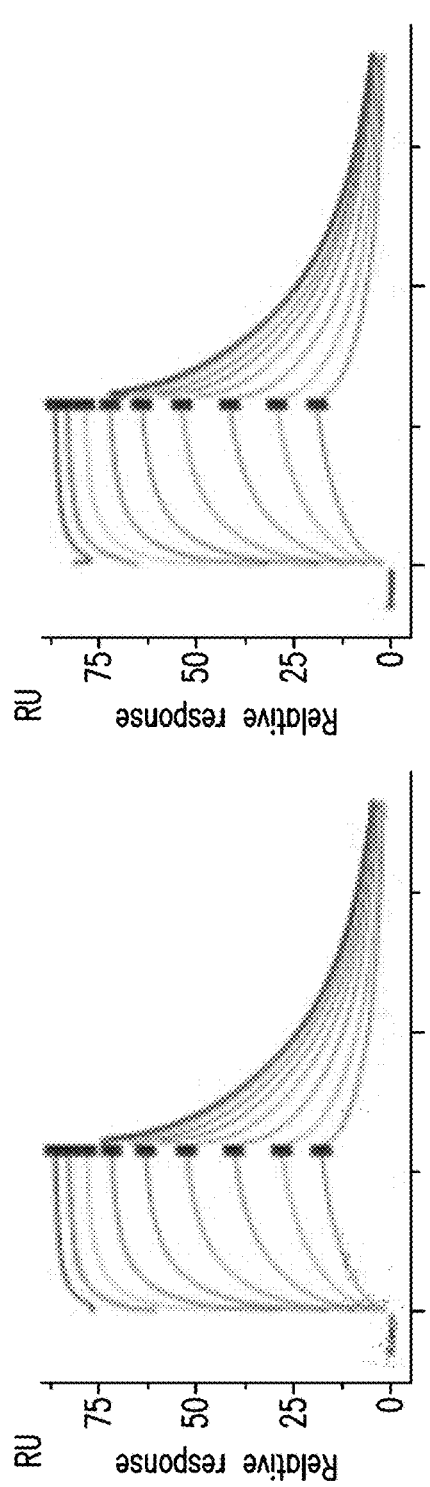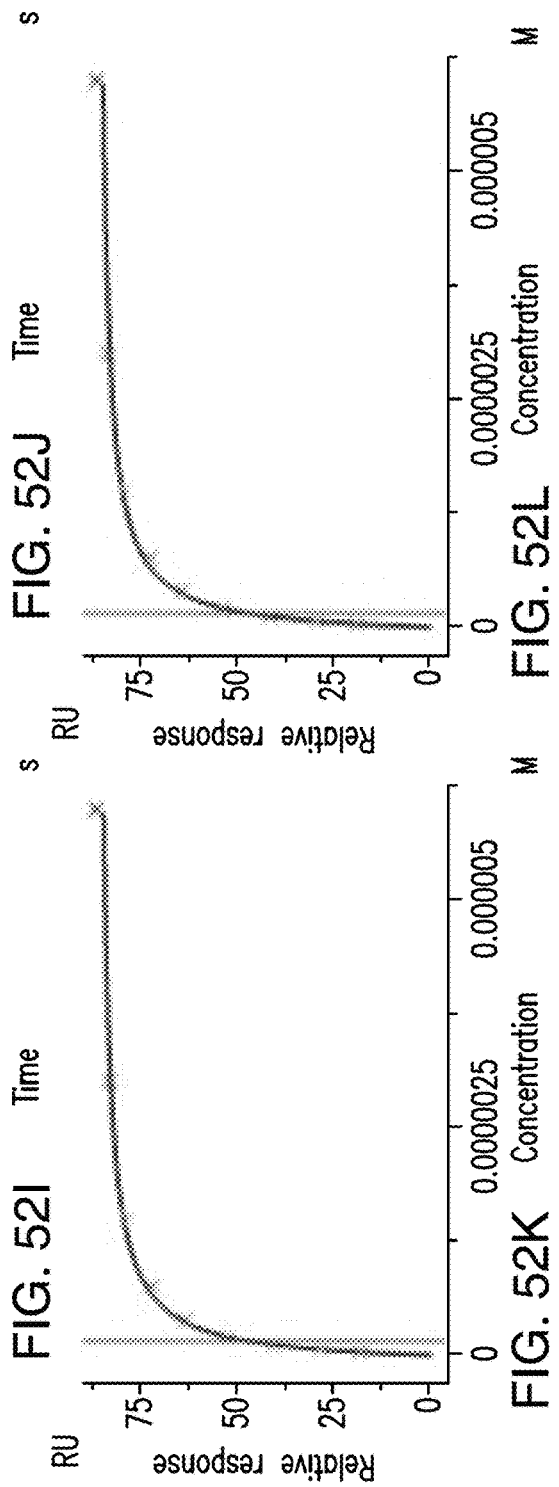

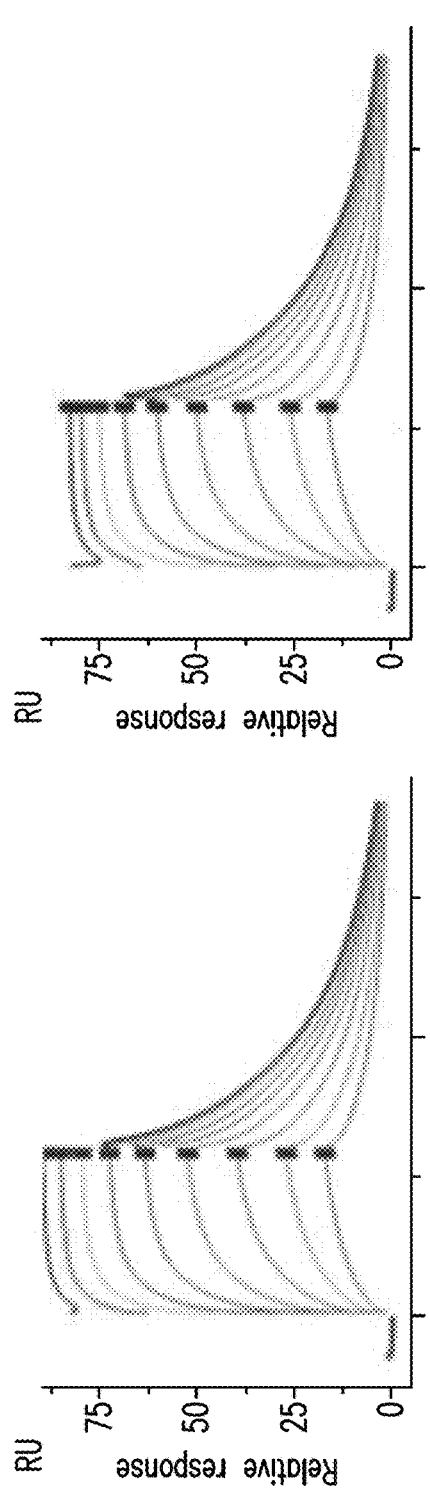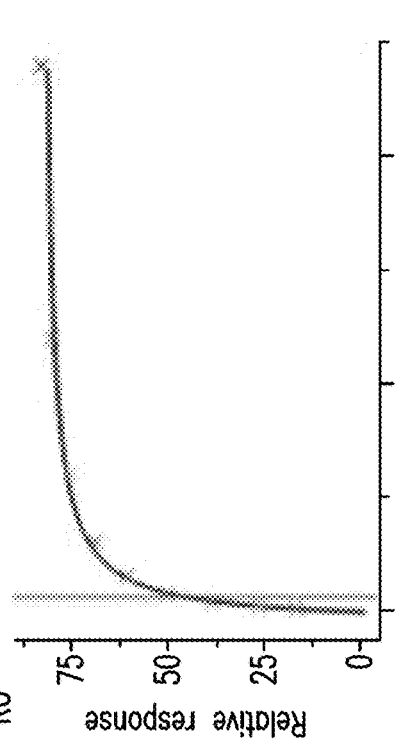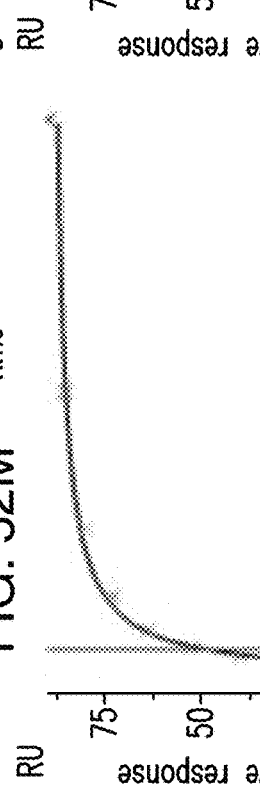
FIG. 52M  FIG. 52N  FIG. 52O  FIG. 52P
trastuzumab
$K_D = 150.5 \pm 9.7$ nM

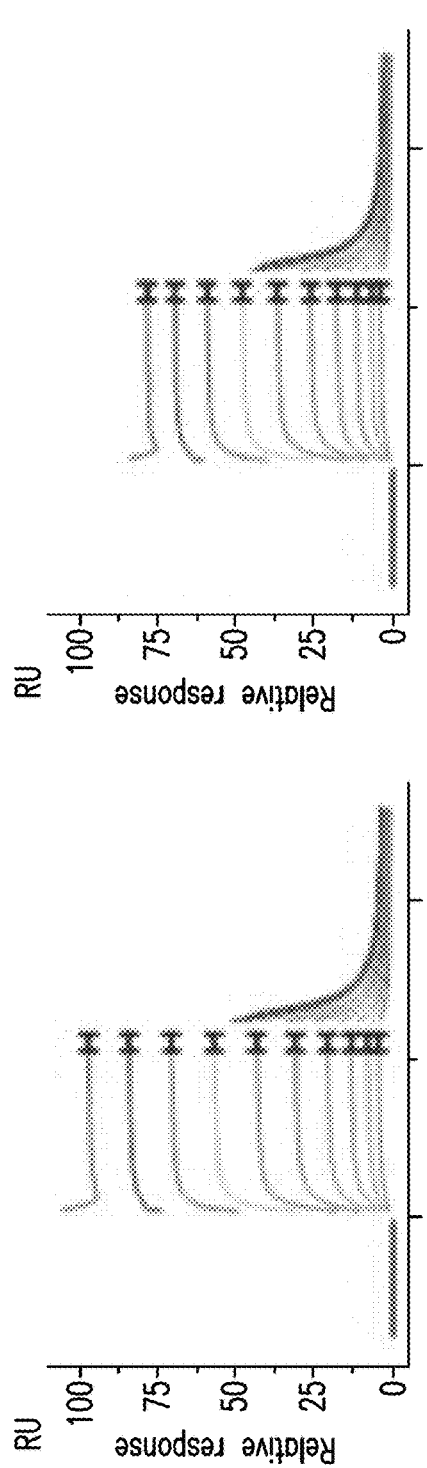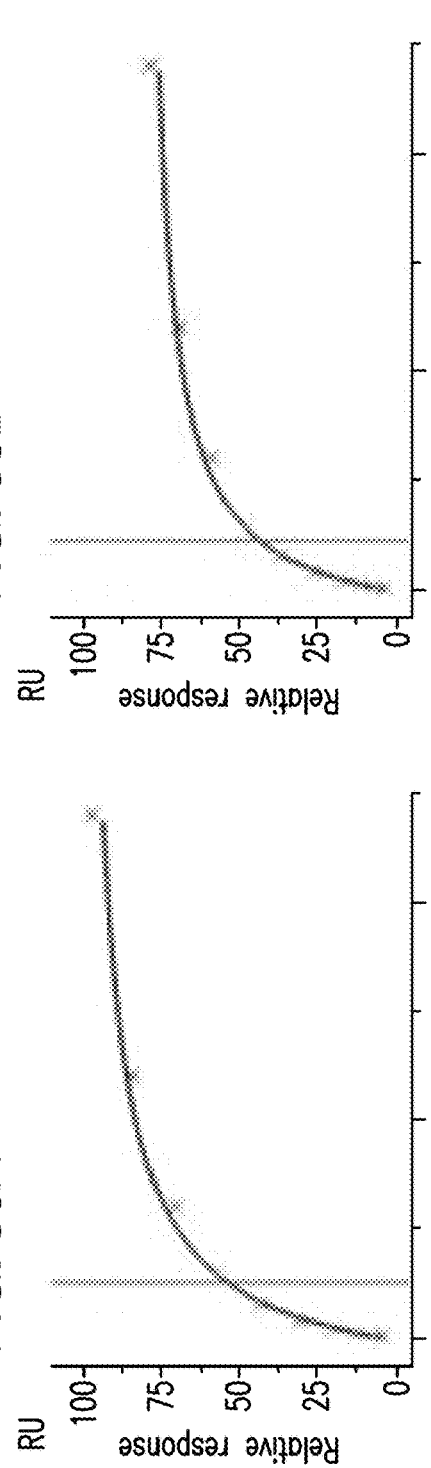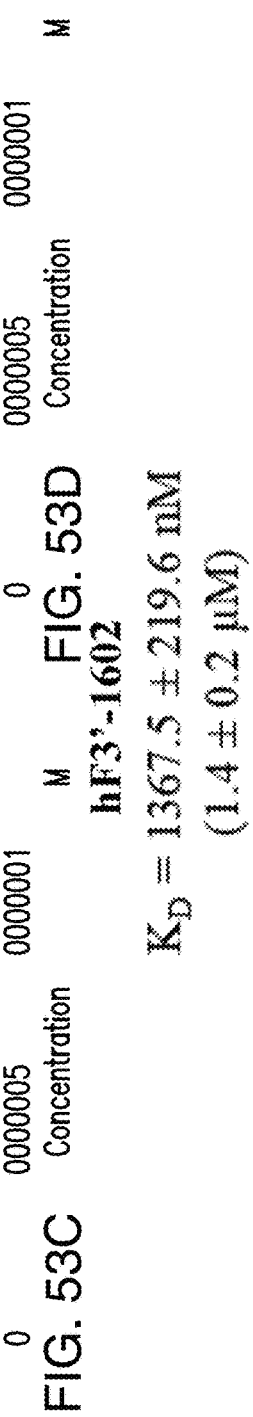
FIG. 53A  FIG. 53B  FIG. 53C  FIG. 53D
hF3'-1602
$K_D = 1367.5 \pm 219.6$ nM
$(1.4 \pm 0.2$ μM$)$

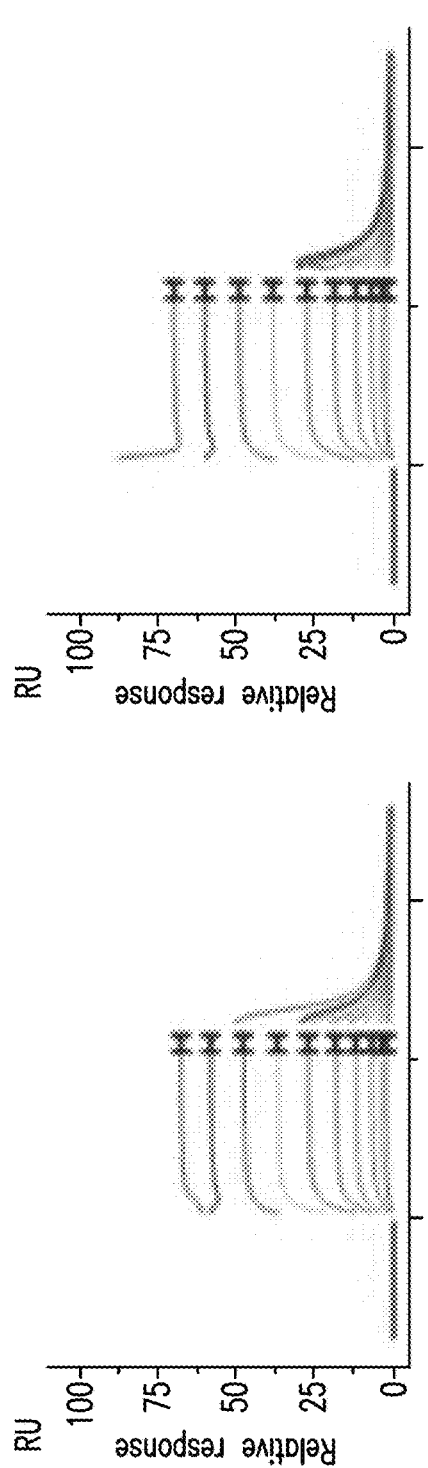
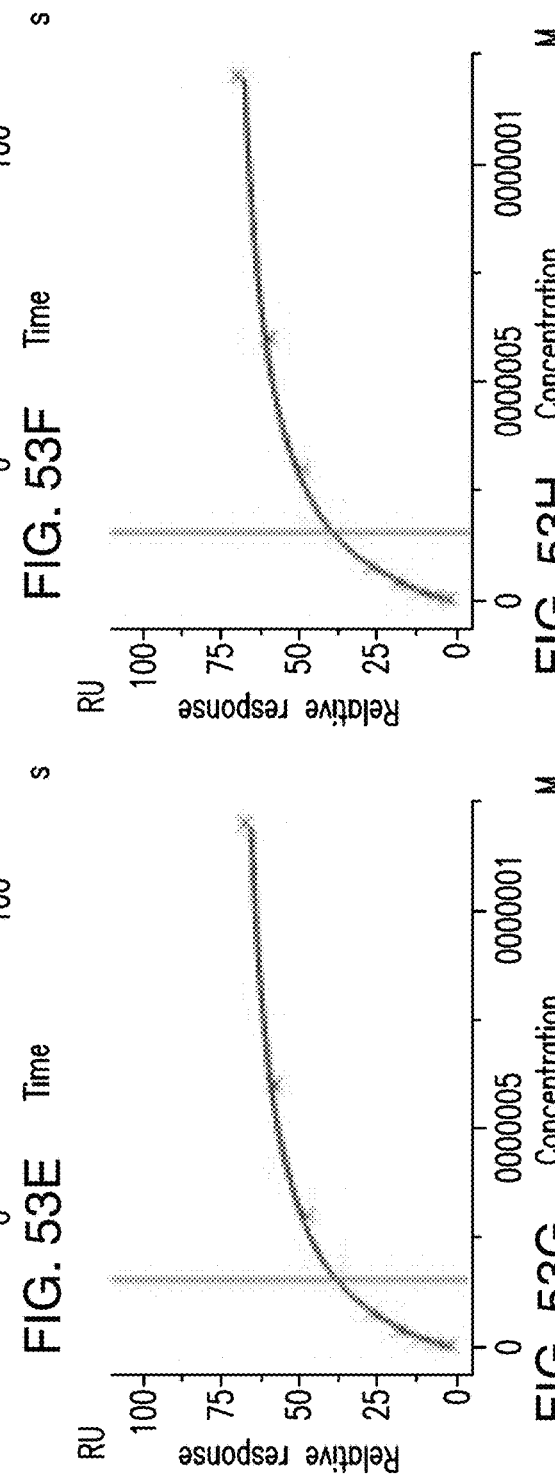
FIG. 53E  FIG. 53F  FIG. 53G  FIG. 53H hF3'-1602 $K_D = 1367.5 \pm 219.6$ nM ($1.4 \pm 0.2$ μM)

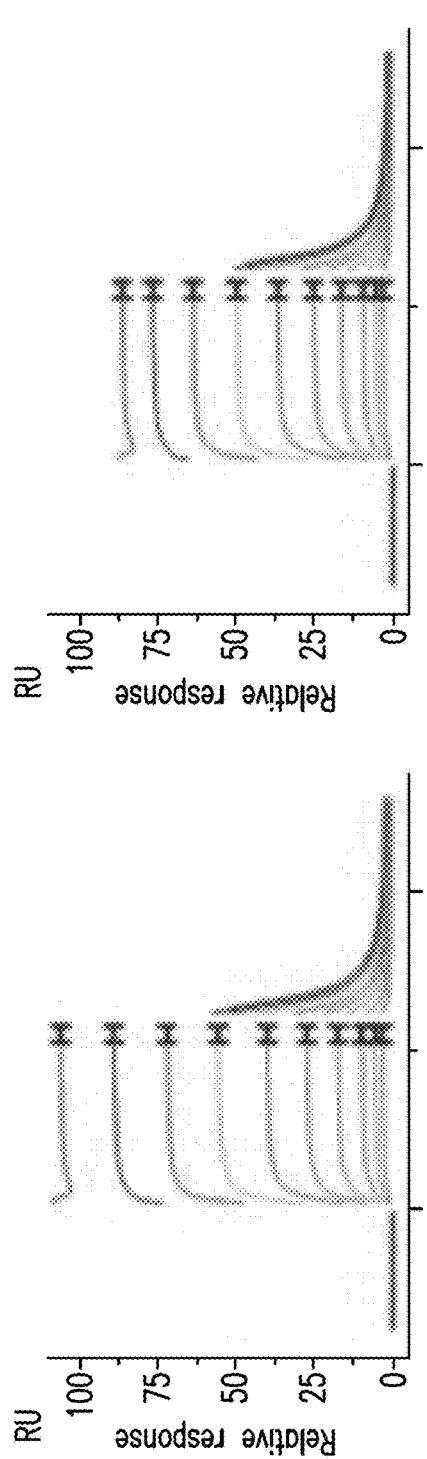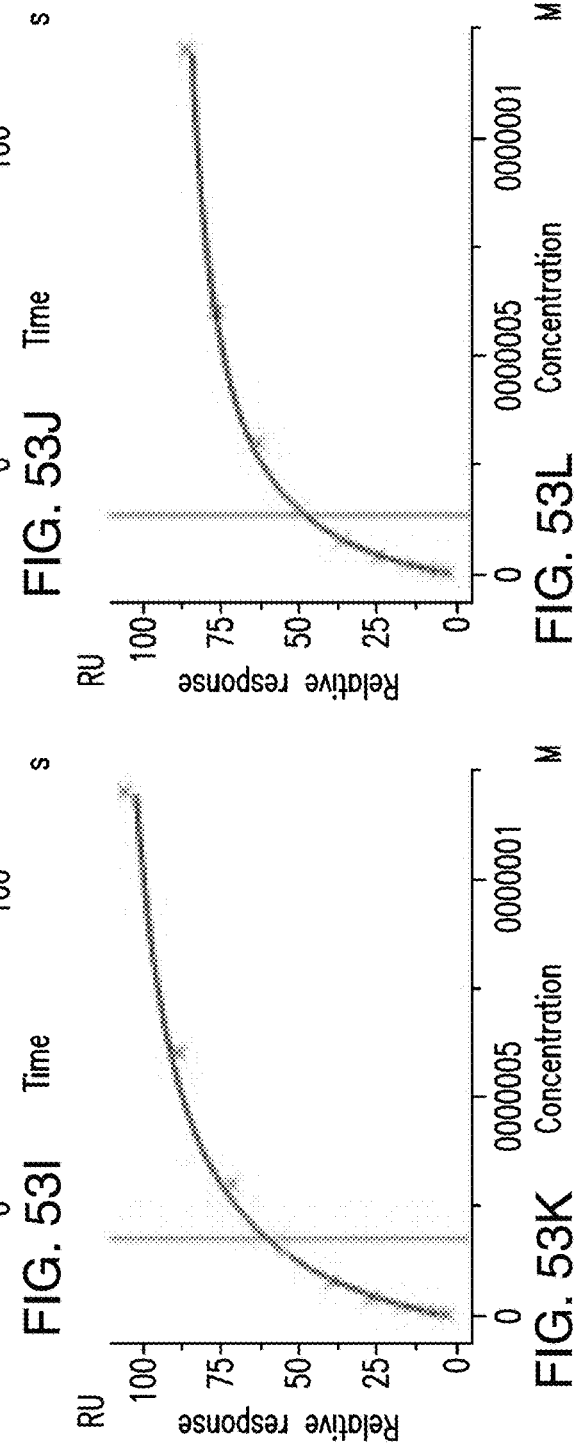
FIG. 53I  FIG. 53J  FIG. 53K  FIG. 53L trastuzumab $K_D = 1402.5 \pm 238.2$ nM ($1.4 \pm 0.2$ μM)

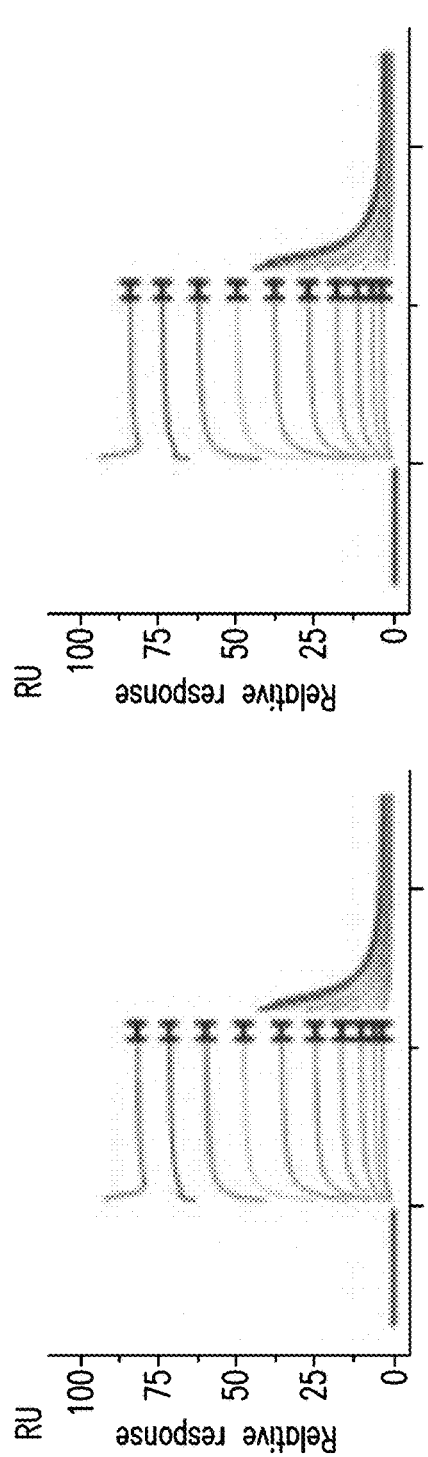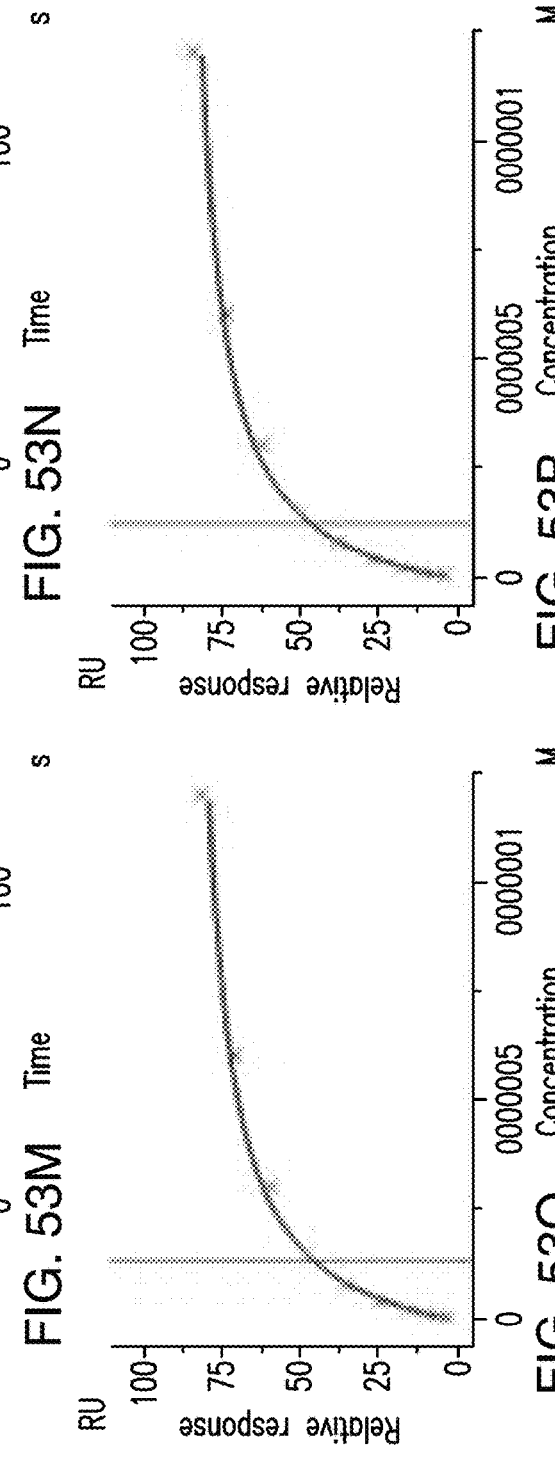

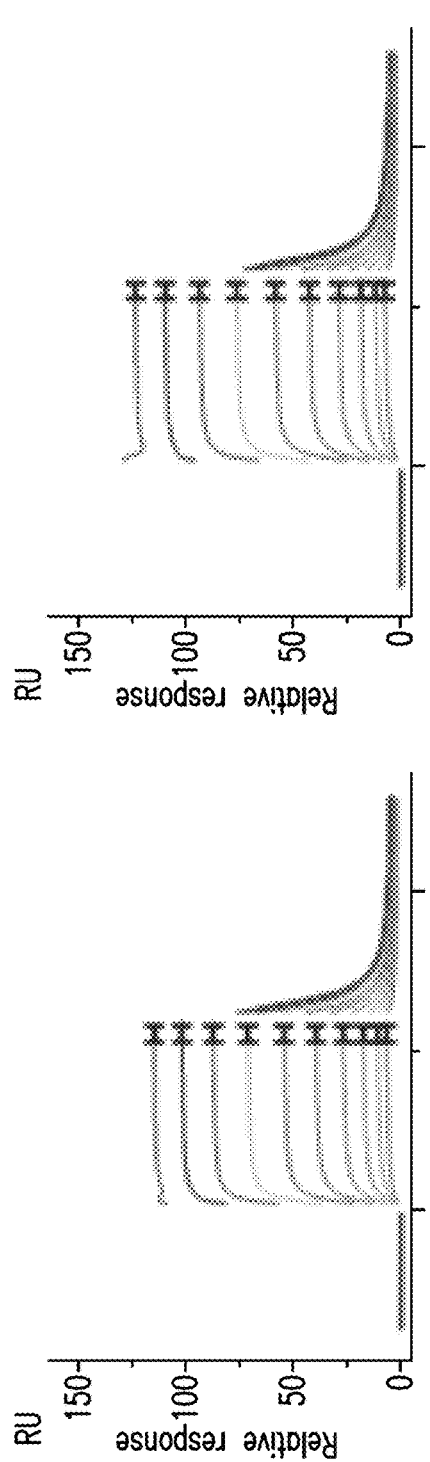
FIG. 54A
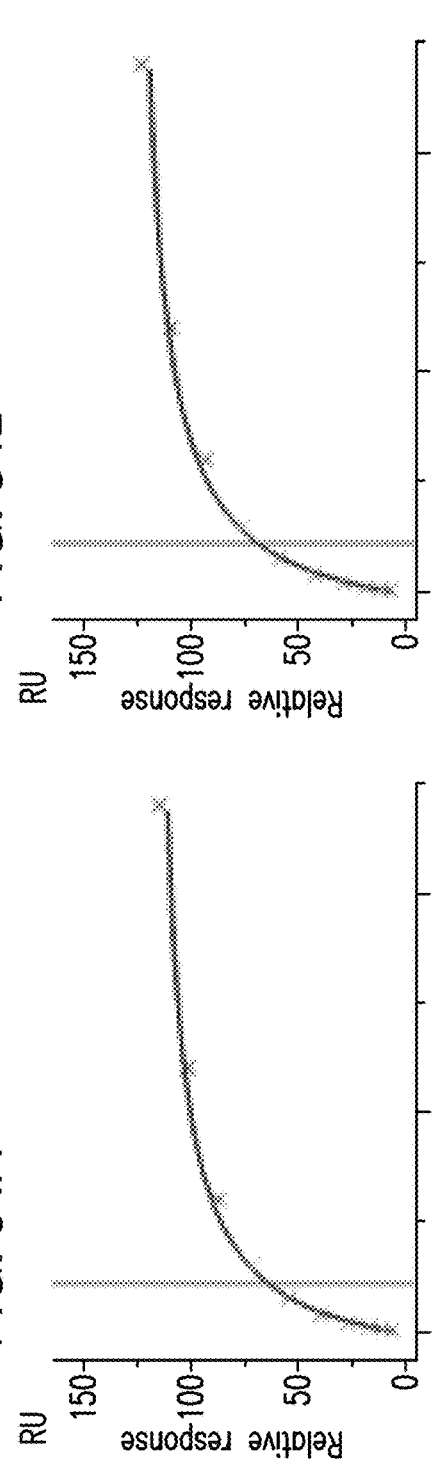
FIG. 54B
FIG. 54C
FIG. 54D
hF3'-1602
$K_D = 1270.0 \pm 214.0$ nM
$(1.3 \pm 0.2\ \mu M)$

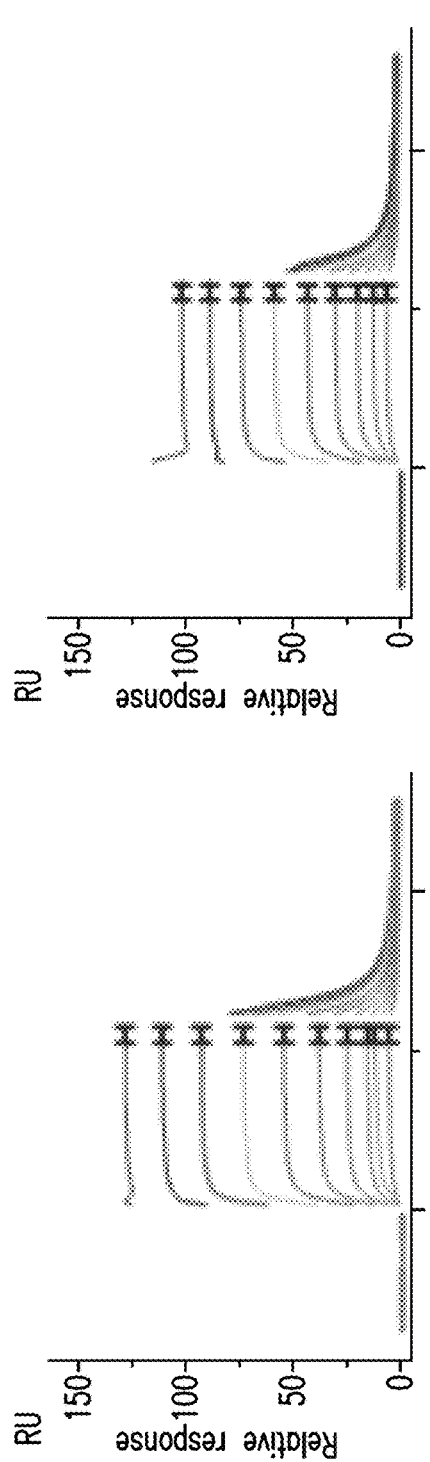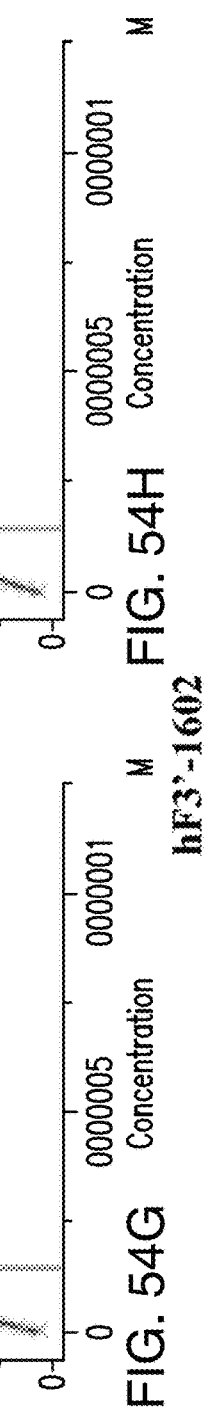
FIG. 54E
FIG. 54F
FIG. 54G
FIG. 54H
hF3'-1602
$K_D = 1270.0 \pm 214.0$ nM
$(1.3 \pm 0.2\ \mu M)$

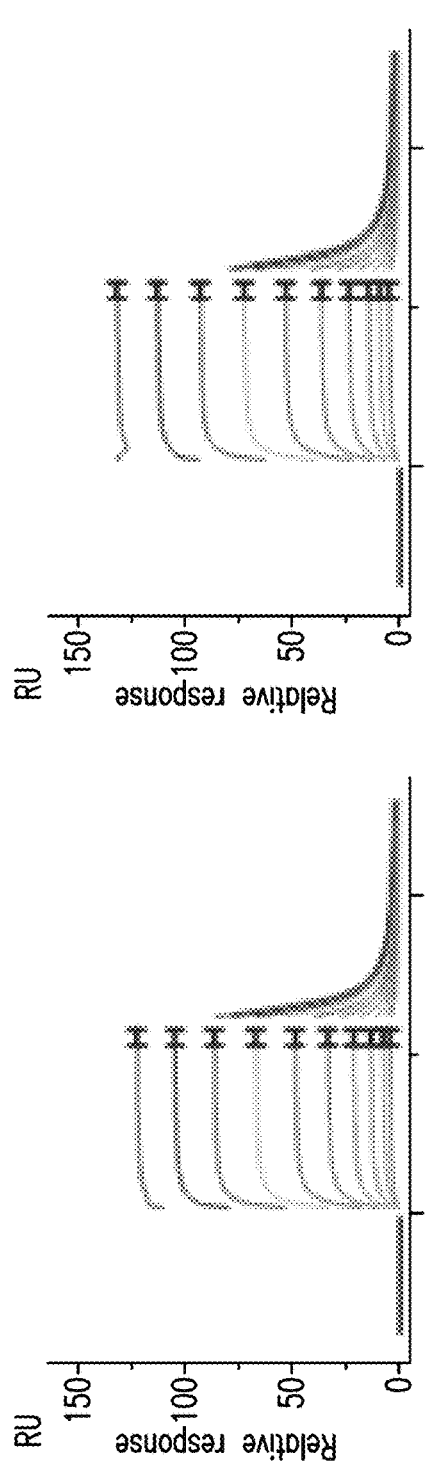
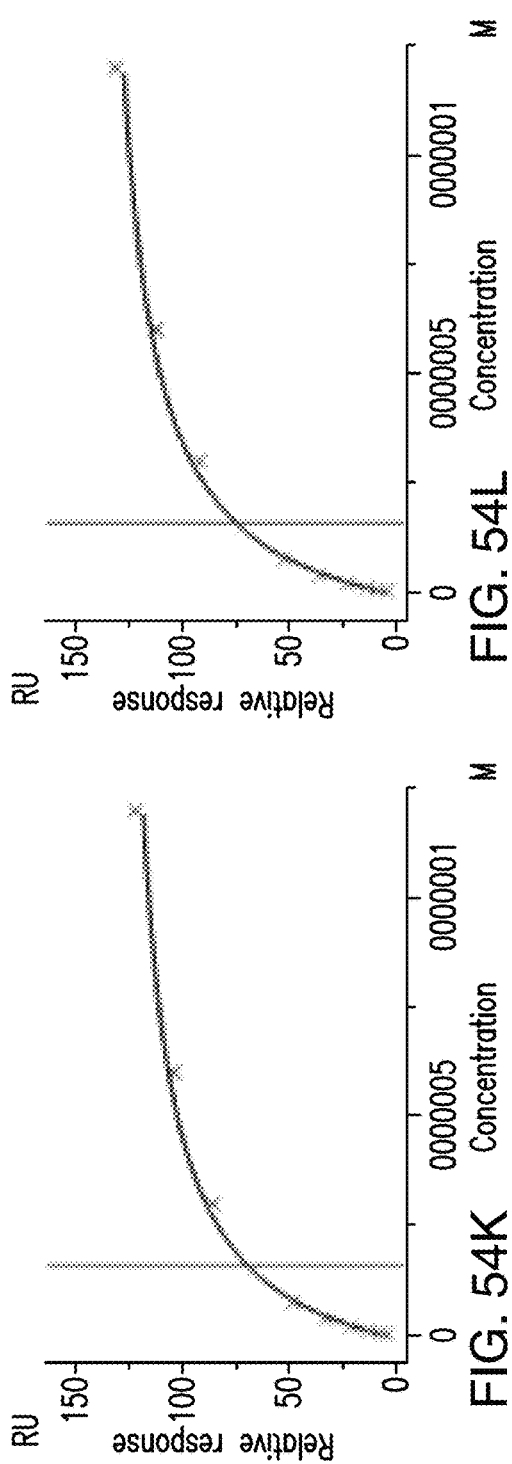

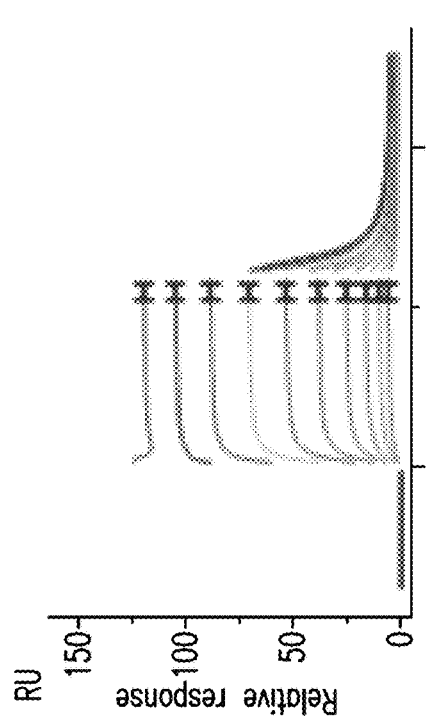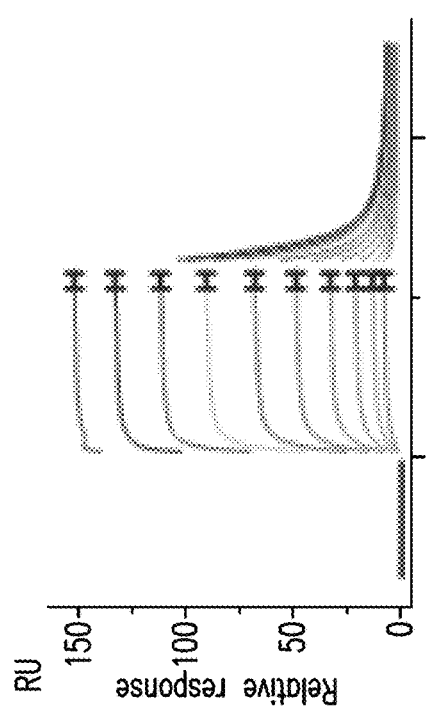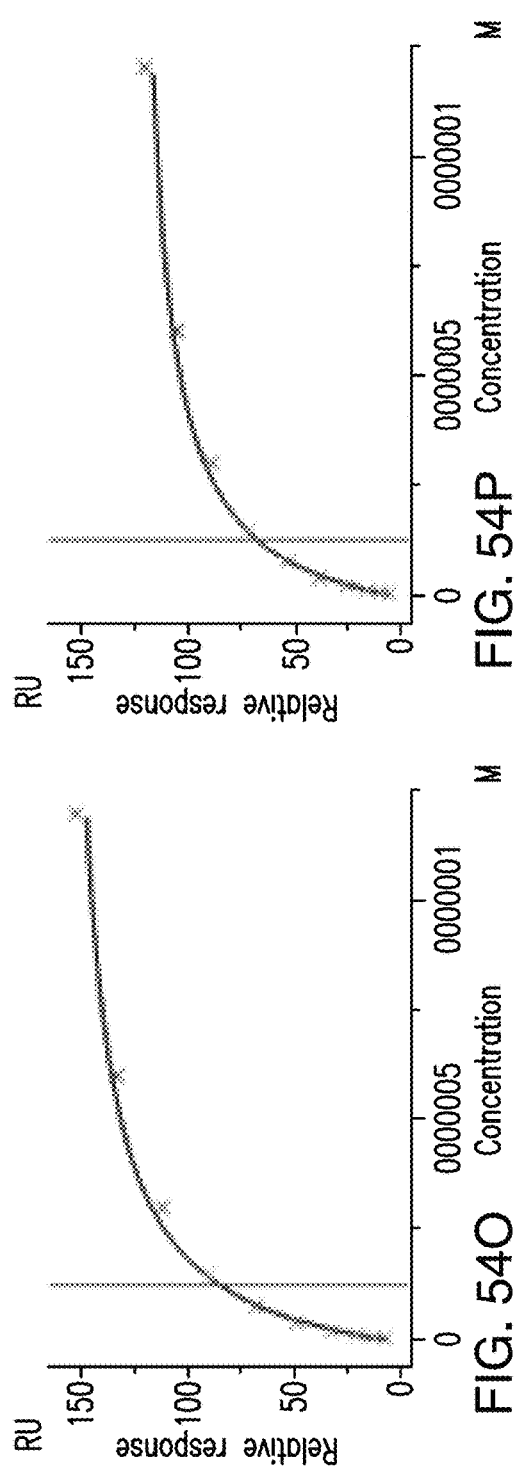
FIG. 54M  FIG. 54N  FIG. 54O  FIG. 54P
trastuzumab
$K_D = 1415.0 \pm 196.4$ nM
$(1.4 \pm 0.2$ μM$)$ Group 1
hCLEC12A-his; F3'1602; 1:1 binding Group 2
hCLEC12A-his; F3'1602; 1:1 binding Group 3
hCLEC12A-his; F3'1602; 1:1 binding Group 4
hCLEC12A-his; F3'1602; 1:1 binding

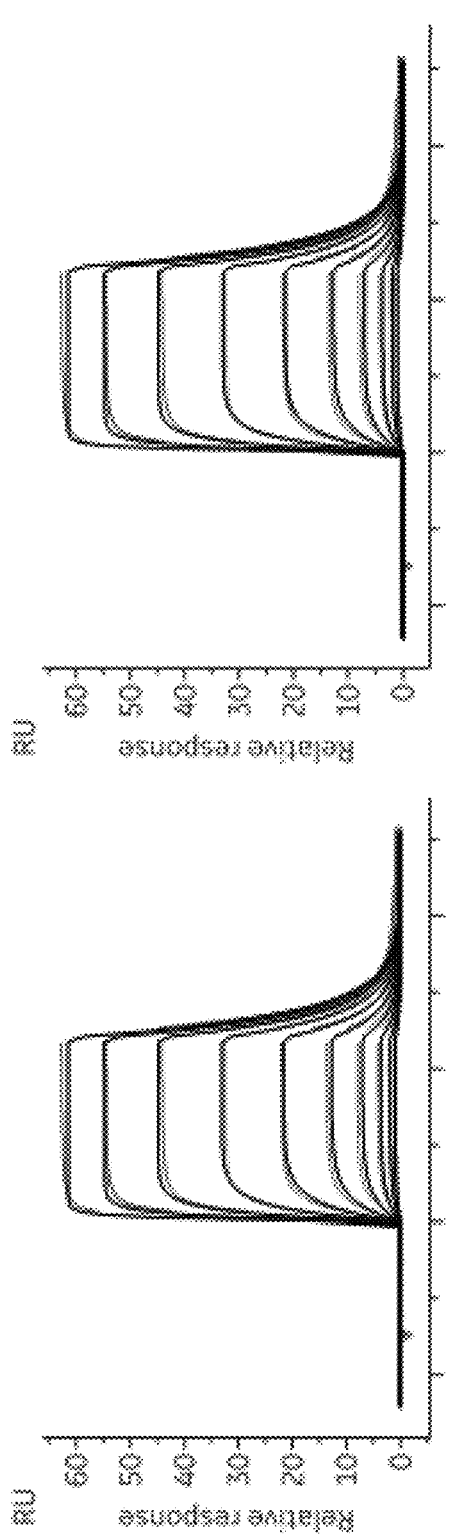
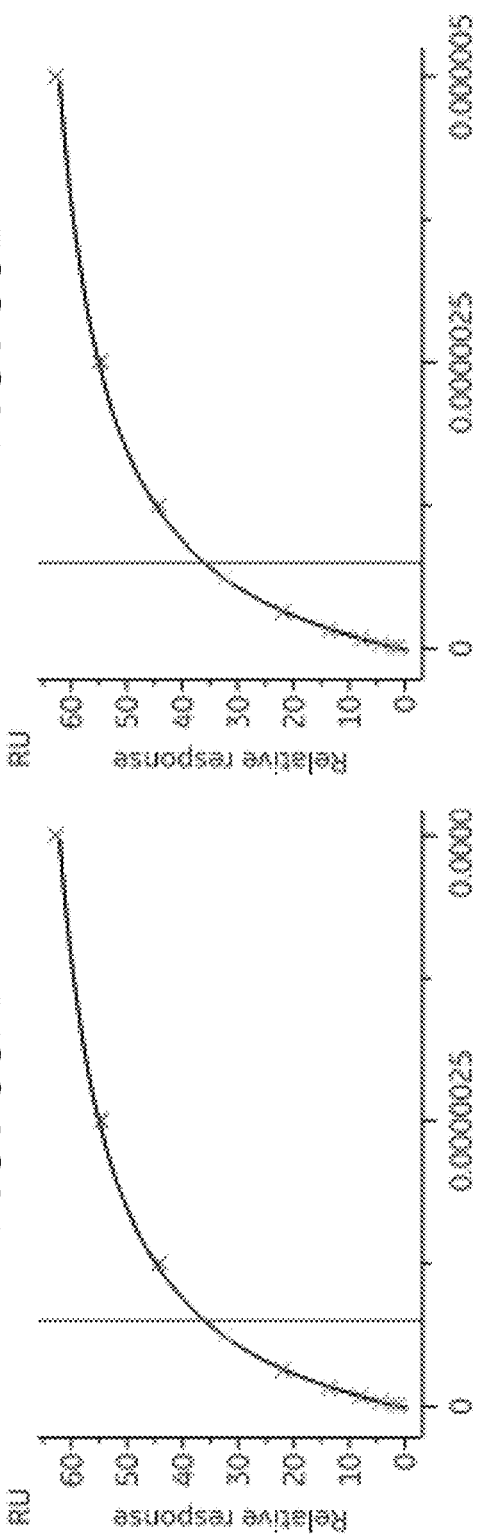
FIG. 56A
FIG. 56B
FIG. 56C
FIG. 56D

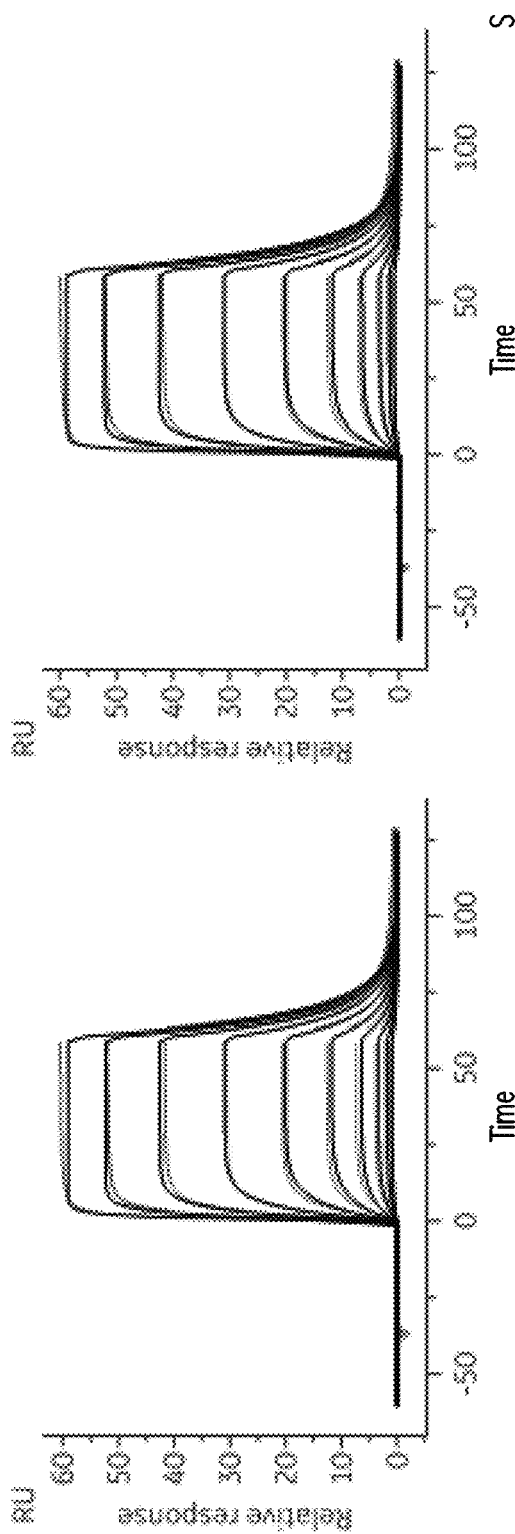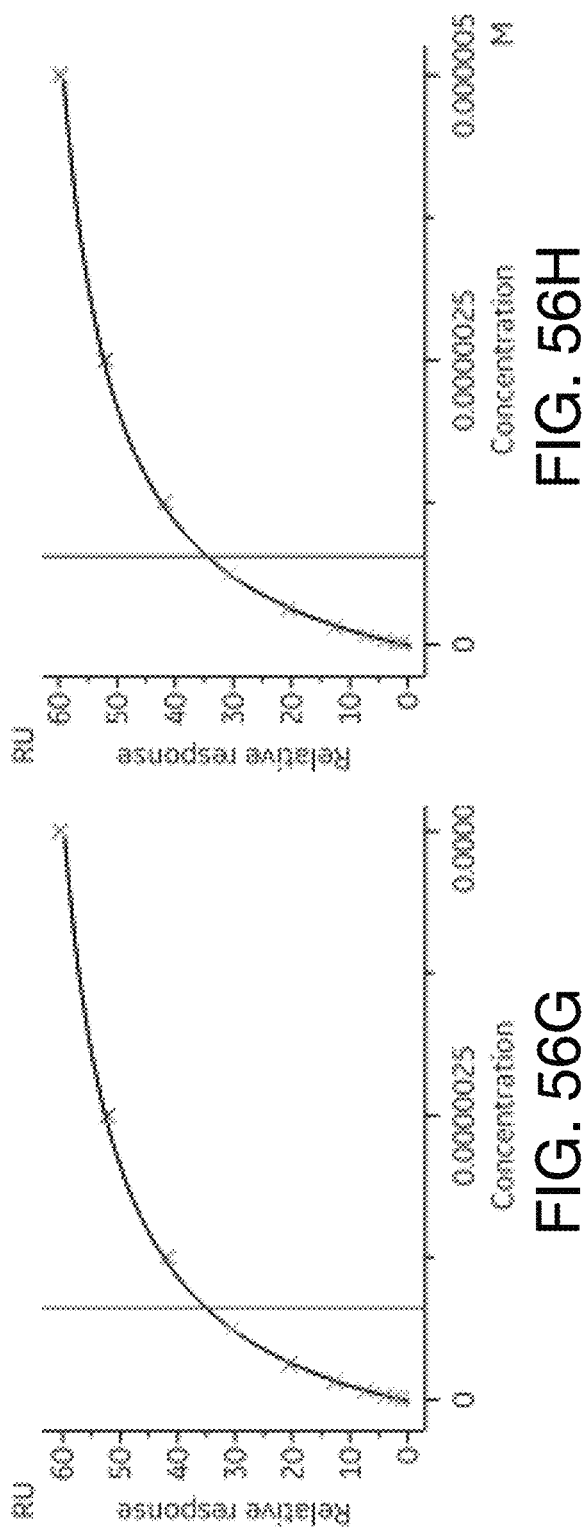

No fill = hIgG1 isotype
Black fill= hF3'-1602

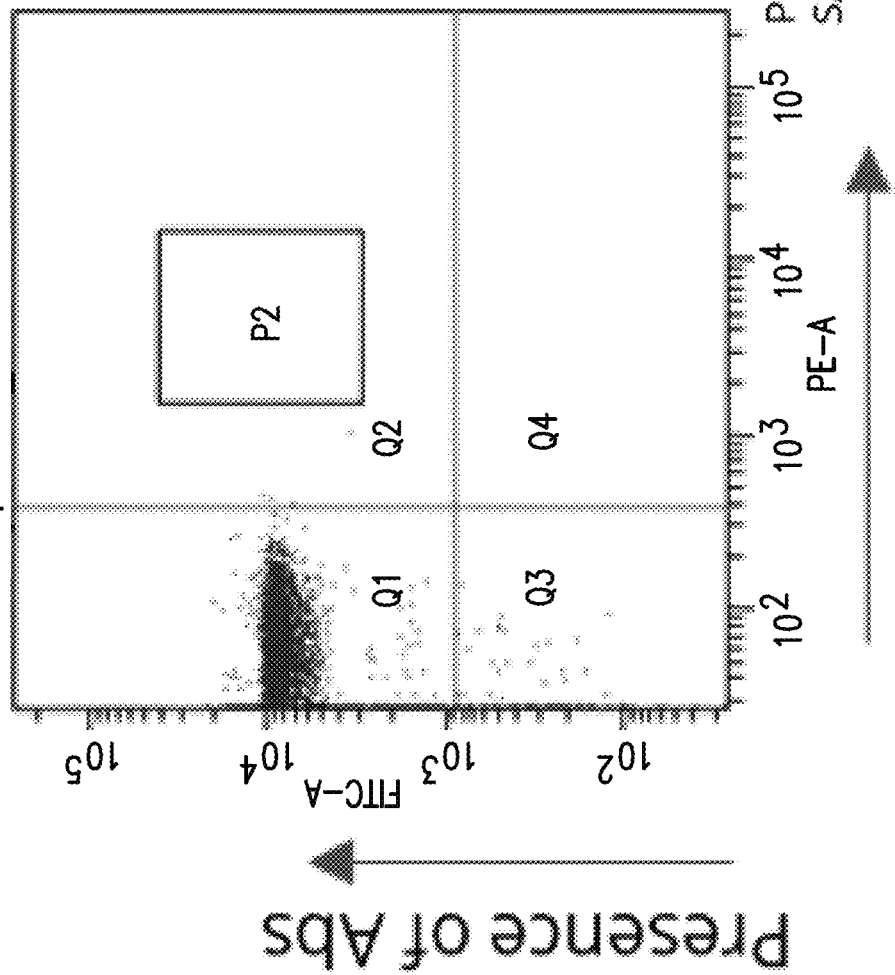

 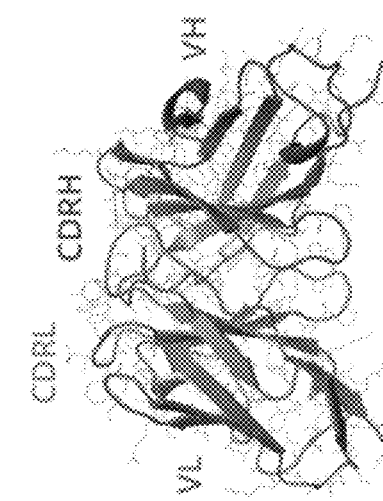 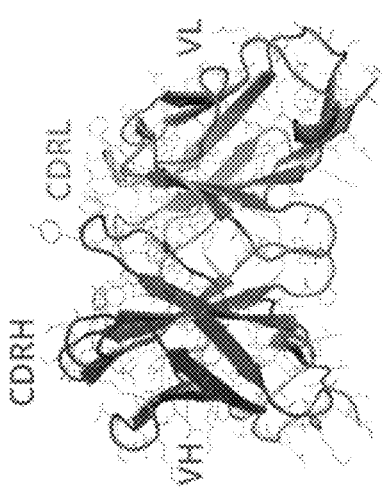
FIG. 63A  FIG. 63B  FIG. 63C
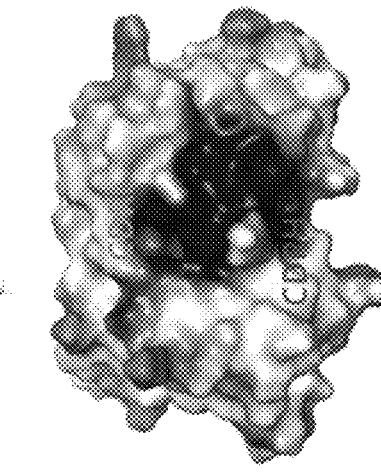 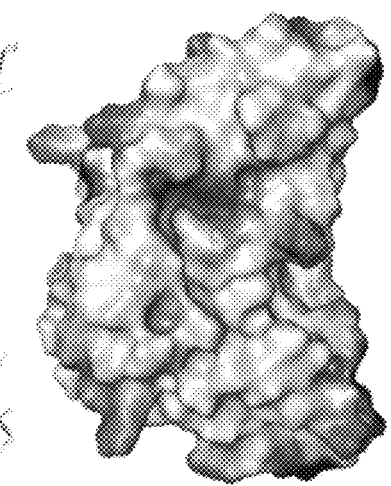 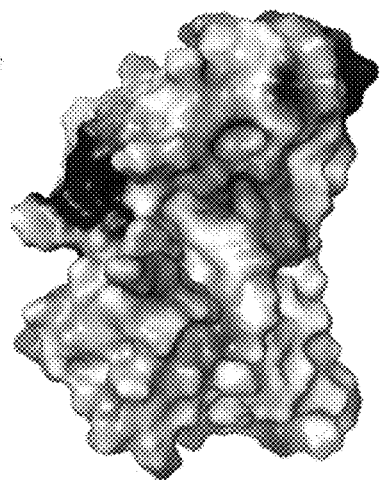
■: negatively charged  ▨: positively charged  □: hydrophobic

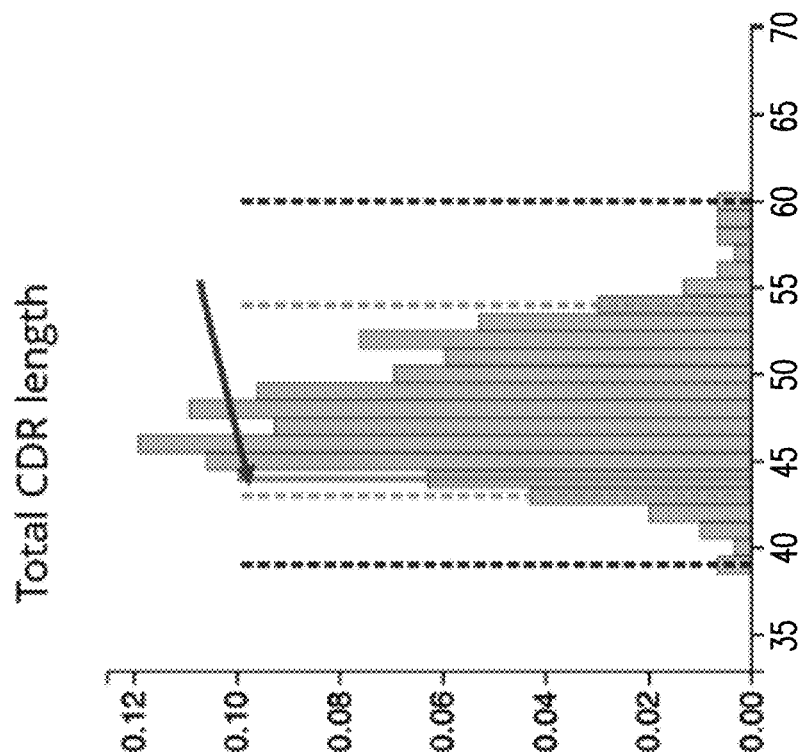
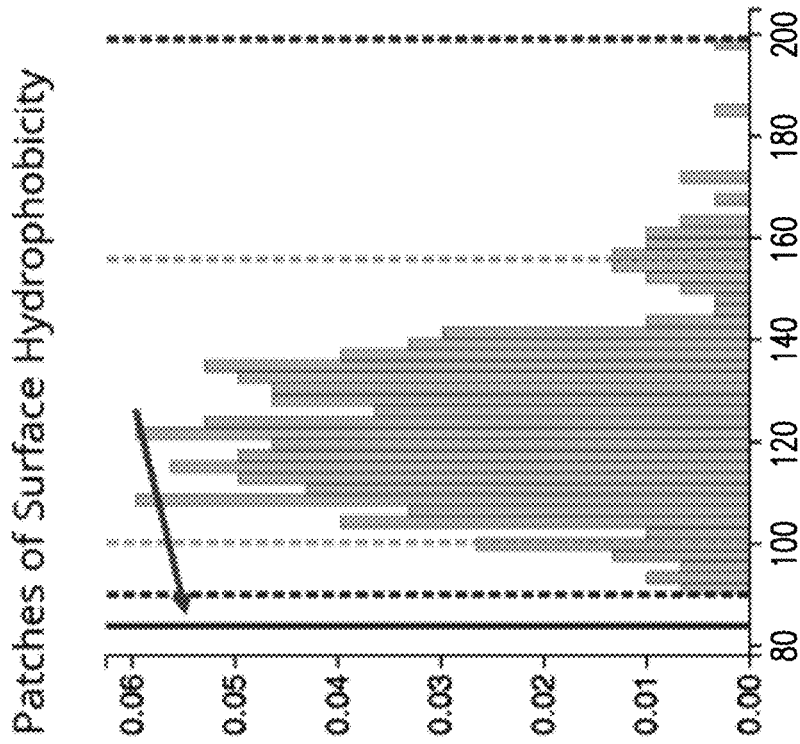
FIG. 64B
FIG. 64A

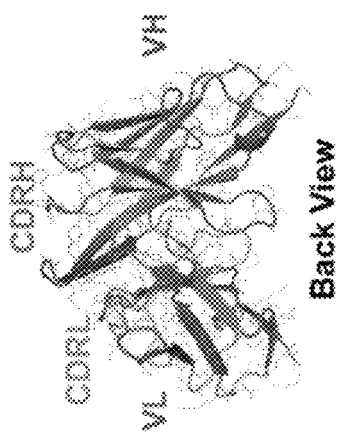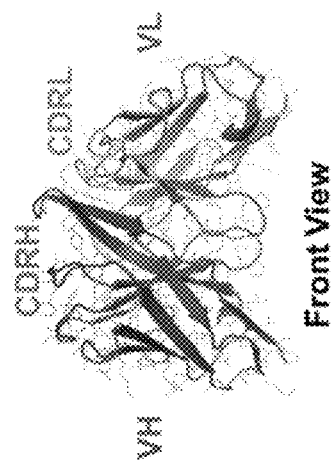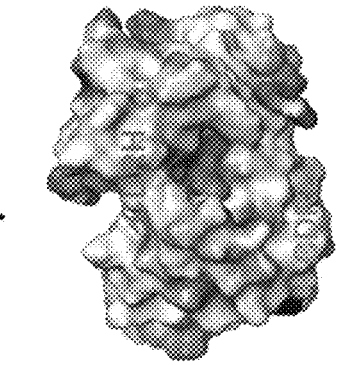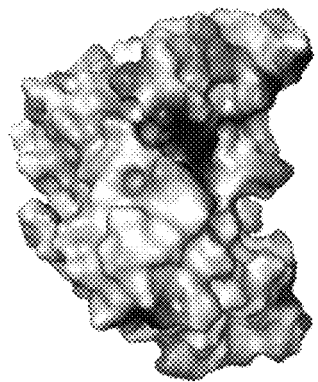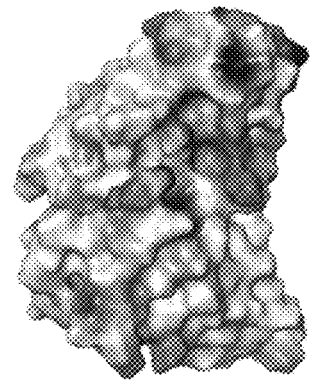

Starting library and parent control

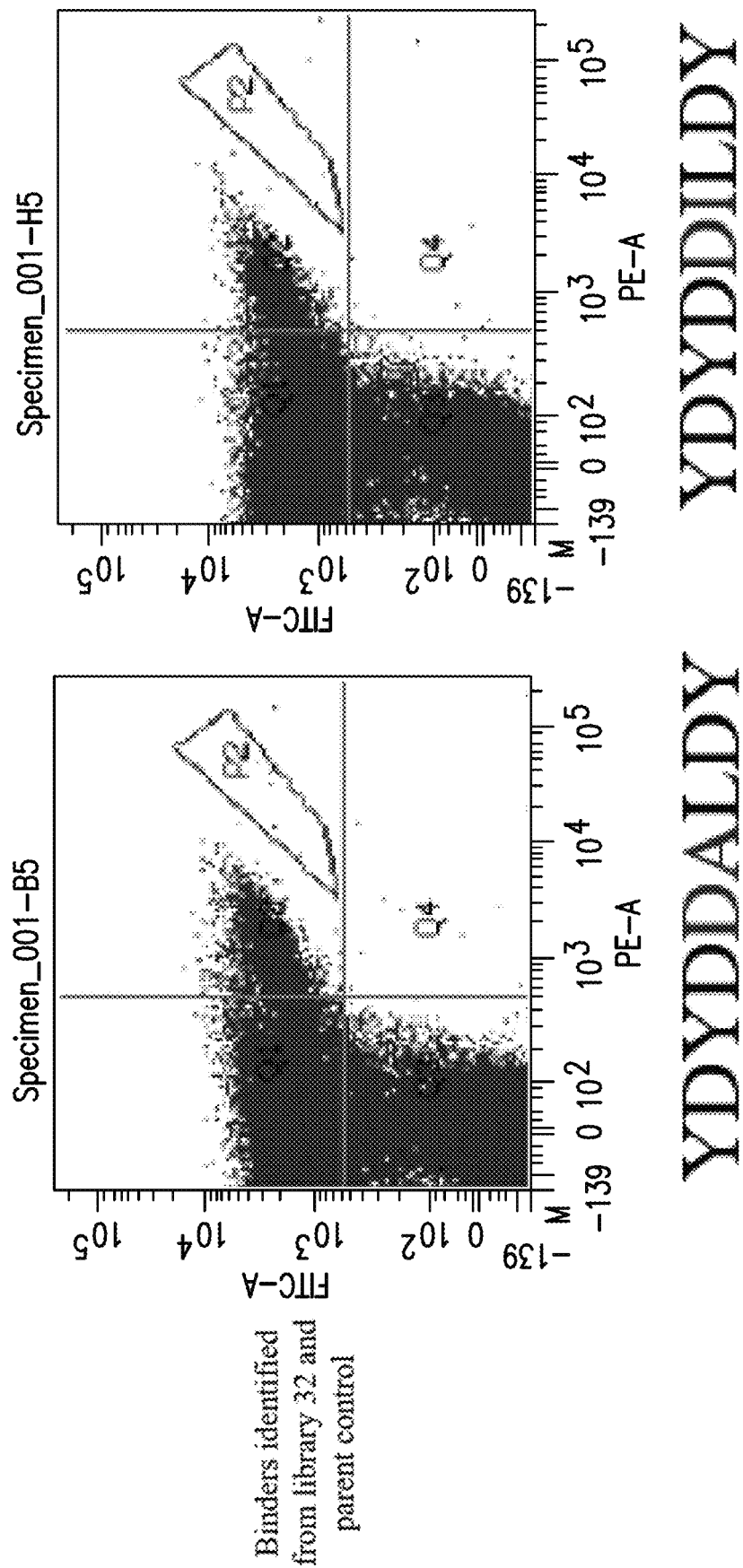

YDYDDSLDY

YDYDDLLDY

Binders identified from library 32 and parent control

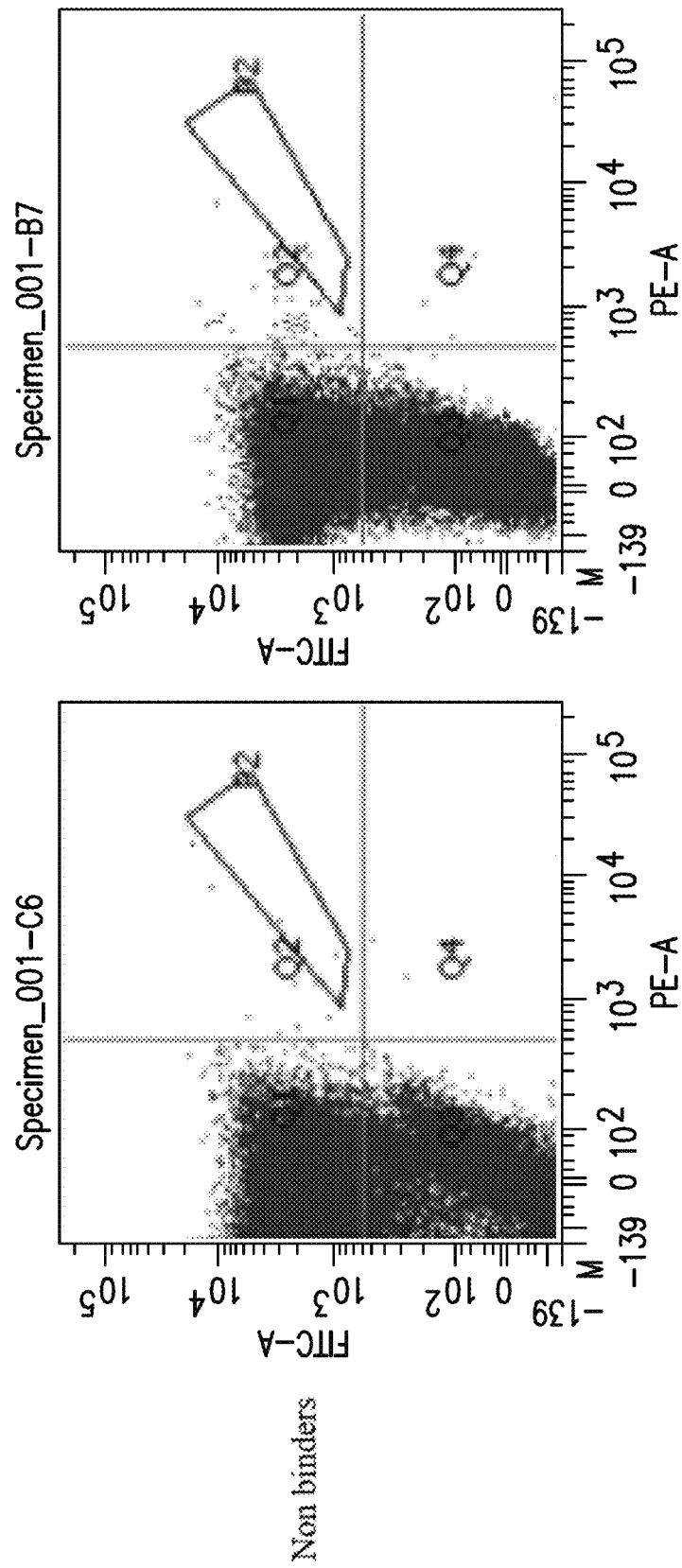
FIG. 69H YDYDDTLDY
FIG. 69G YDYDDVLDY
Non binders

Group 5
40C Control; mFc-hNKG2D; Steady state affinity

Group 1
NaCl 40C 4 Wks; mFc-hNKG2D; Steady state affinity

Group 15
1602 pH 8 2 Weeks; mFc-hNKG2D; 1:1 binding

Group 15
1602 pH 8 2 Weeks; mFc-hNKG2D; Steady state affinity

Group 4
Oxidation Control; mFc-hNKG2D; 1:1 binding

Group 4
Oxidation Control; mFc-hNKG2D; Steady state affinity

Group 1
Forced Oxidized; mFc-hNKG2D; 1:1 binding

Group 1
Forced Oxidized; mFc-hNKG2D; Steady state affinity

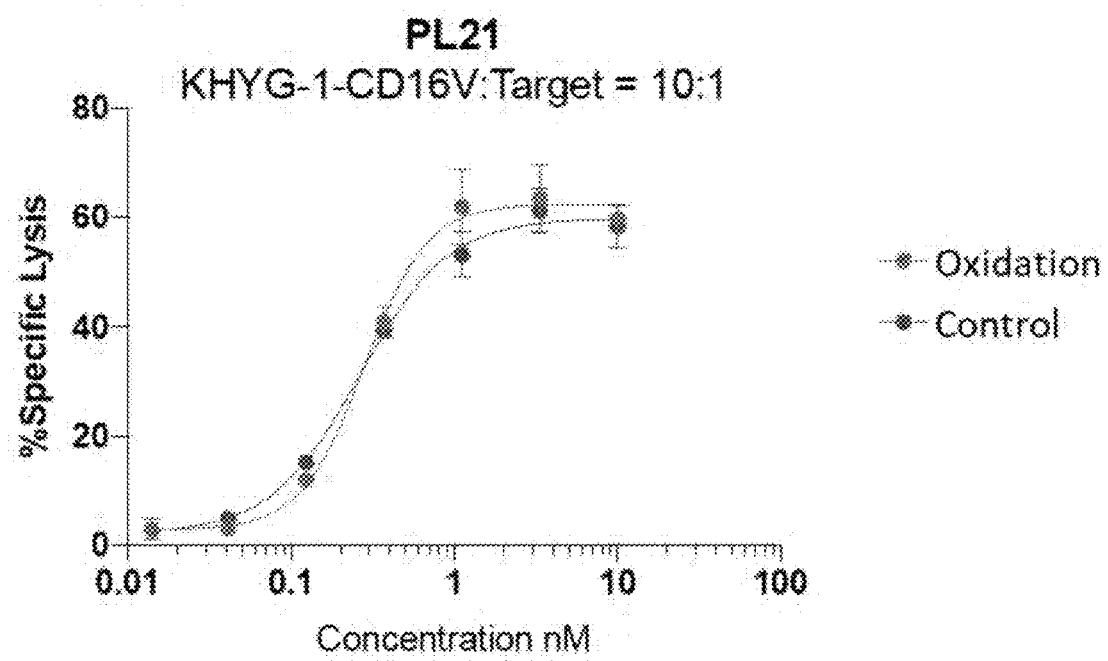

Group 11
Low pH Control; mFc-hNKG2D; 1:1 binding

Group 11
Low pH Control; mFc-hNKG2D; Steady state affinity

Group 8
Low pH; mFc-hNKG2D; 1:1 binding

Group 8
Low pH; mFc-hNKG2D; Steady state affinity

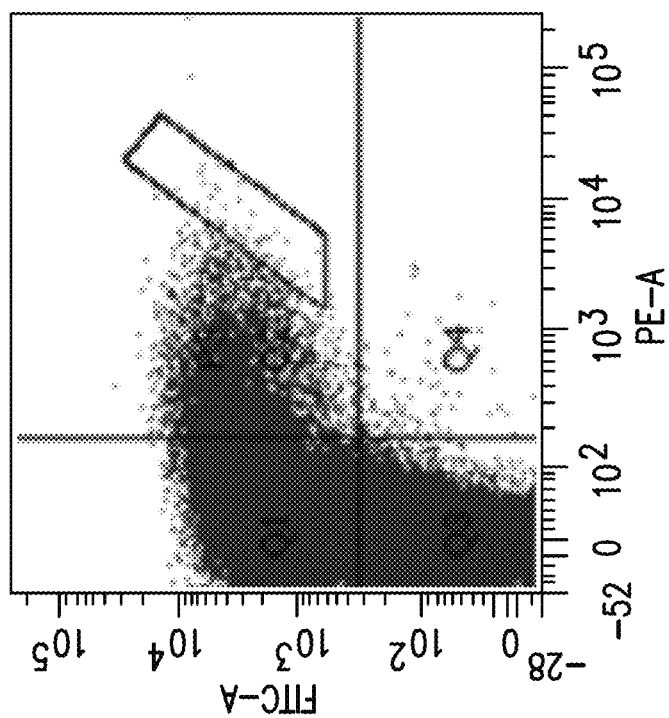
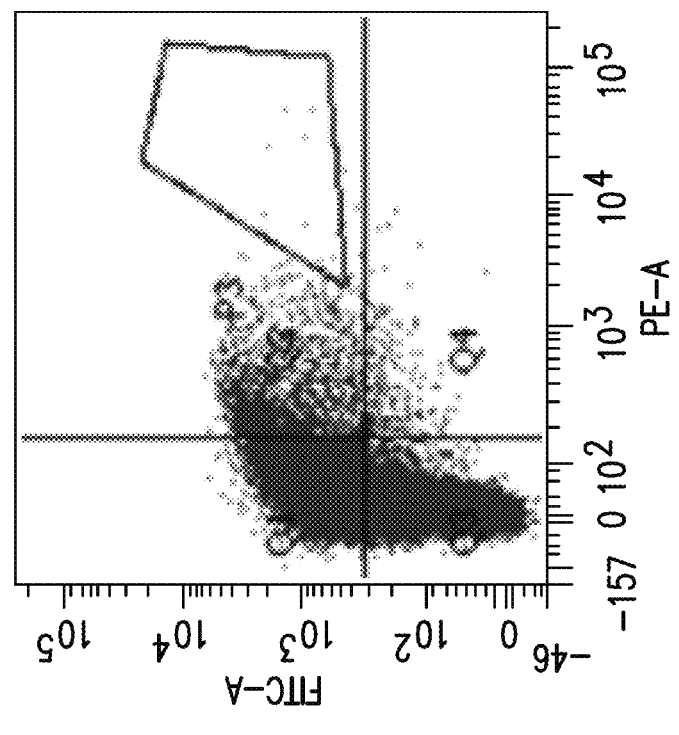
FIG. 105A
FIG. 105B

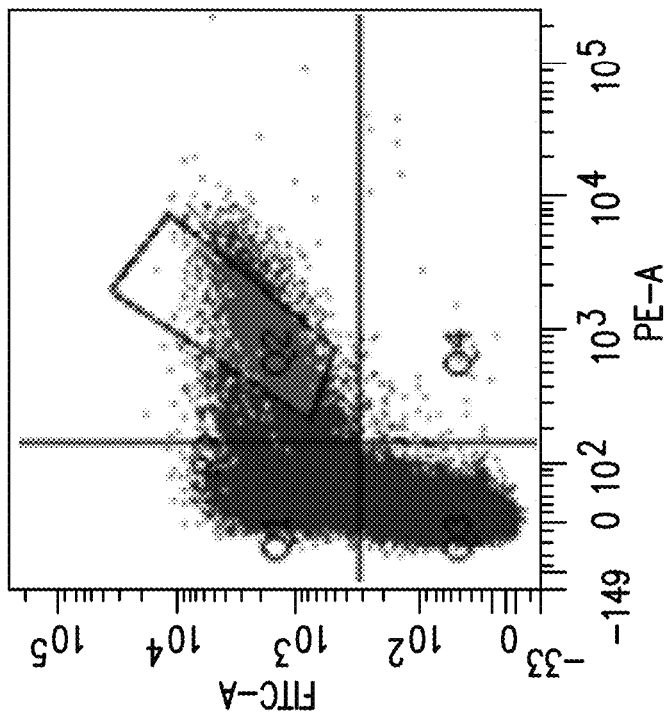
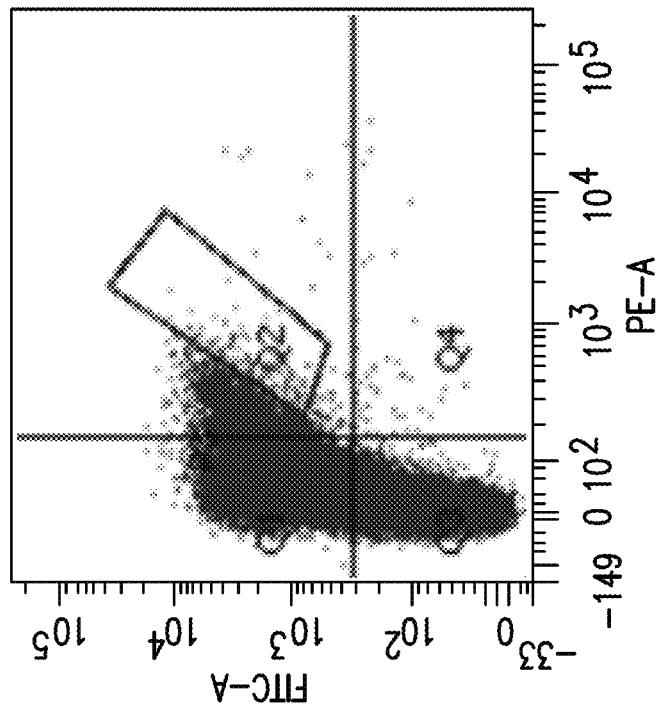
FIG. 105C
FIG. 105D

|  | CDRH1 | CDRH2 | CDRH3 |
|---|---|---|---|
| pET1596 | GFSLTNY | WSGGK | YDYDDSLDY |
| Improved affinity clone | GFSLTNY | WVGGA | GDYGDSLDY |
| AB0237 | GFSLTNY | WSGGK | YDYDDSLDY |

FIG. 107D

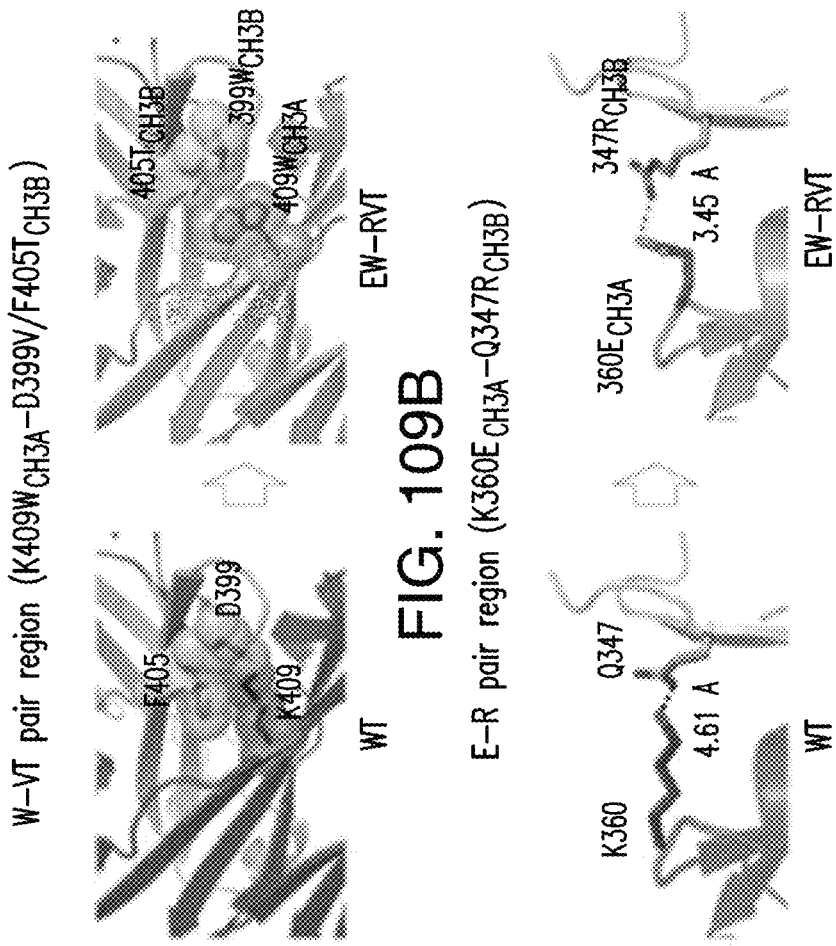
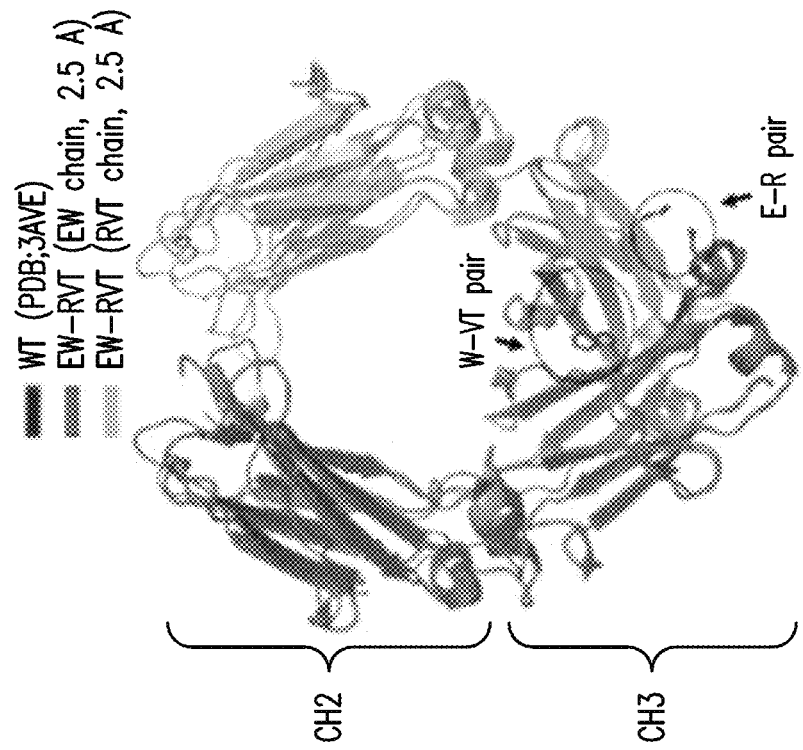
FIG. 109B
FIG. 109C
FIG. 109A

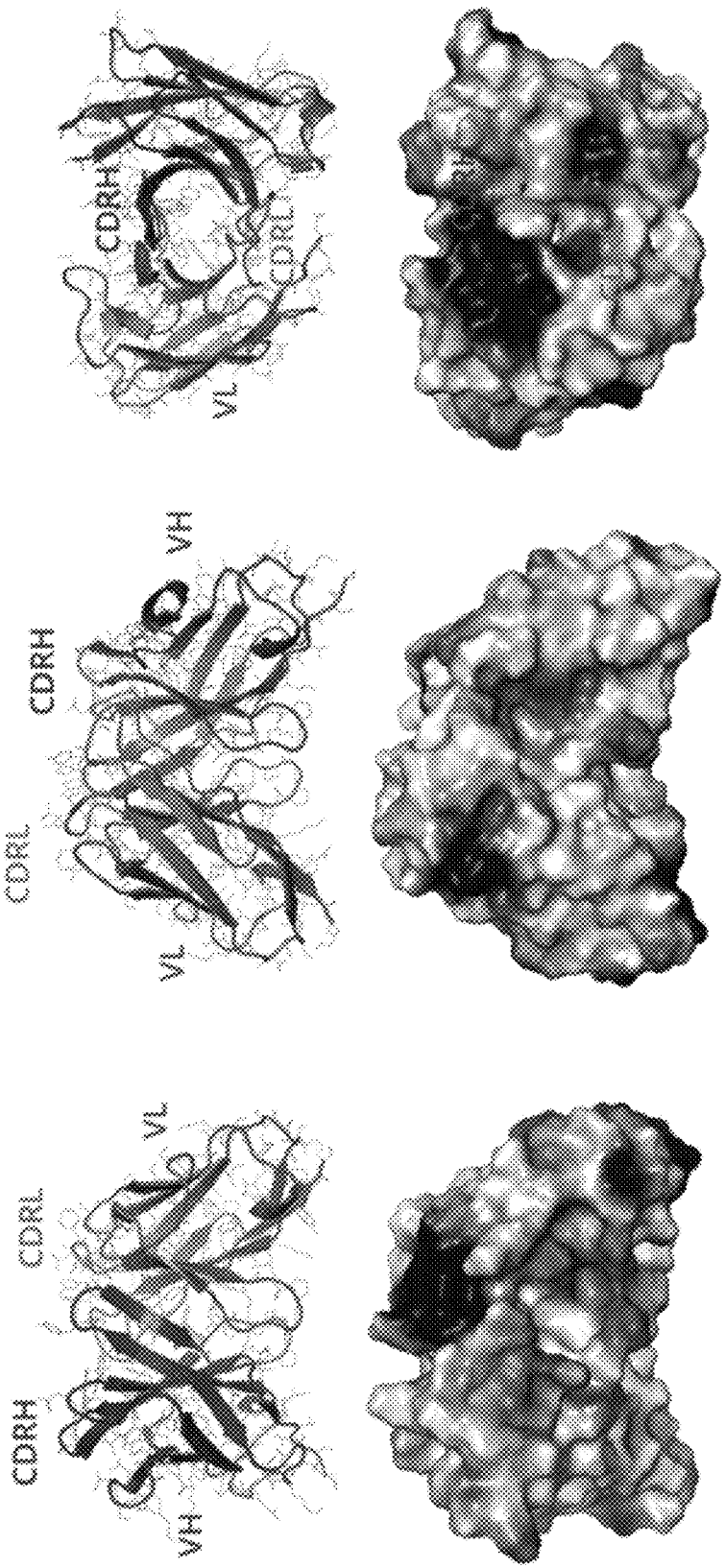

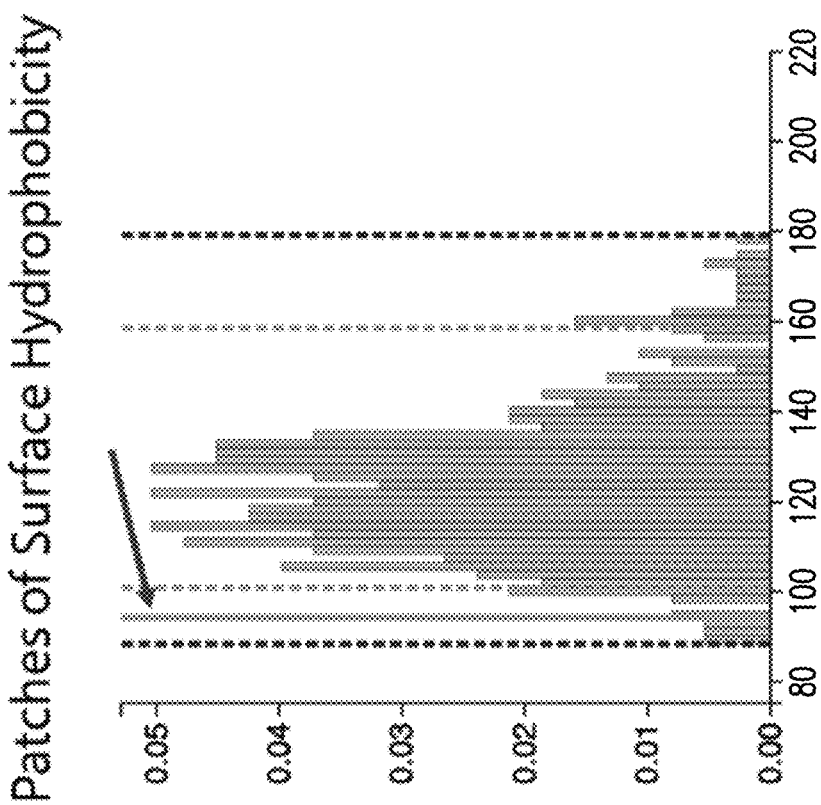
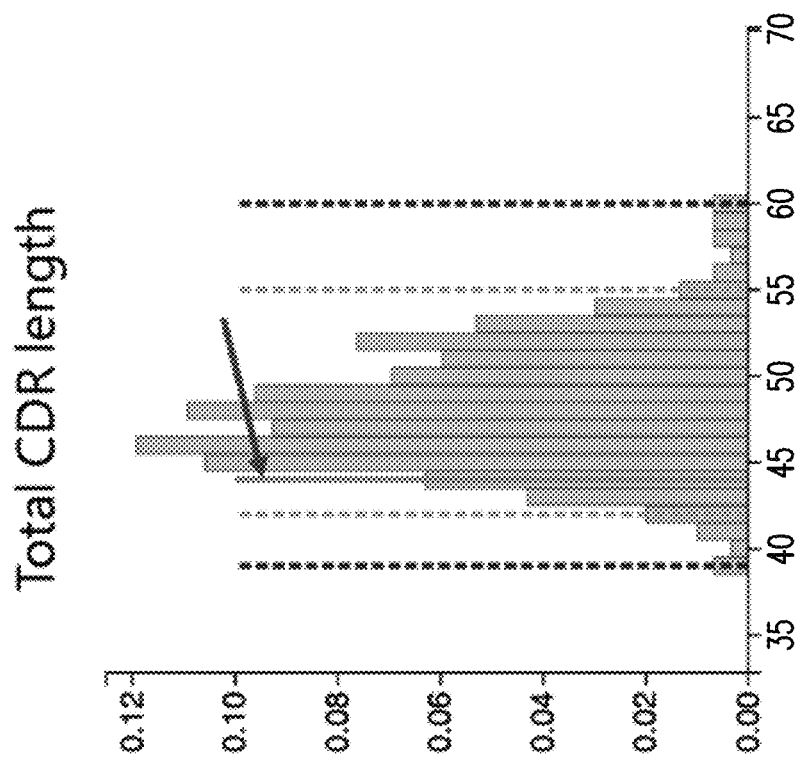
FIG. 112A
FIG. 112B

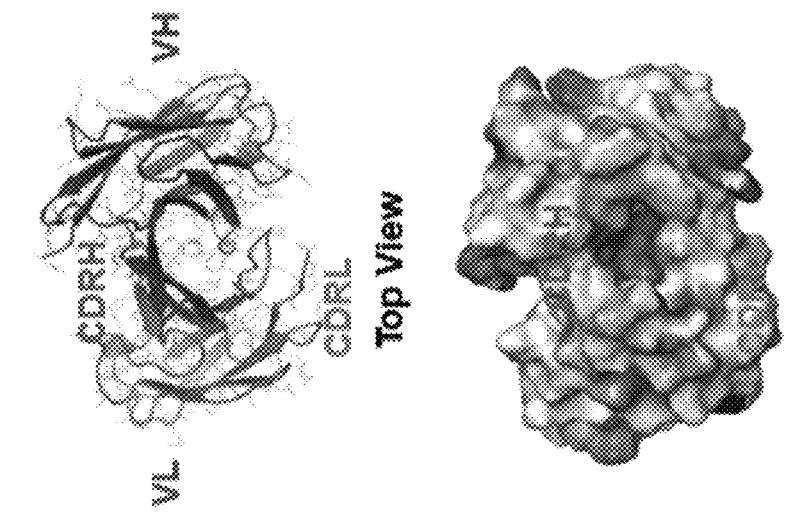
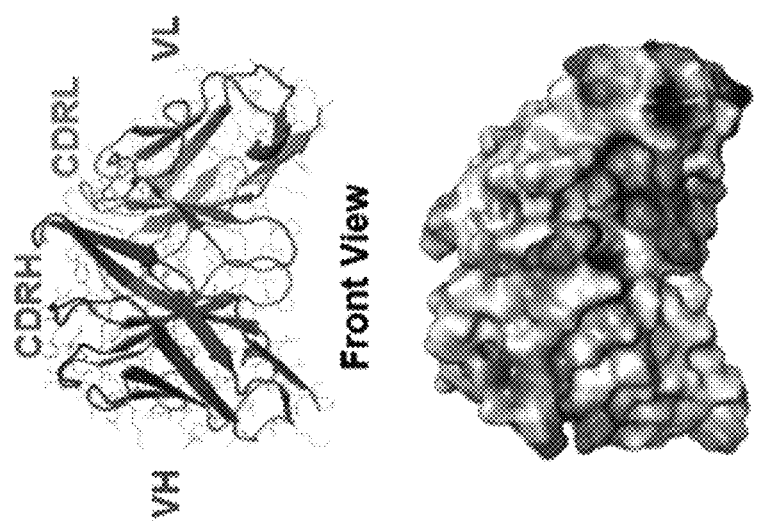
FIG. 114A  FIG. 114B  FIG. 114C

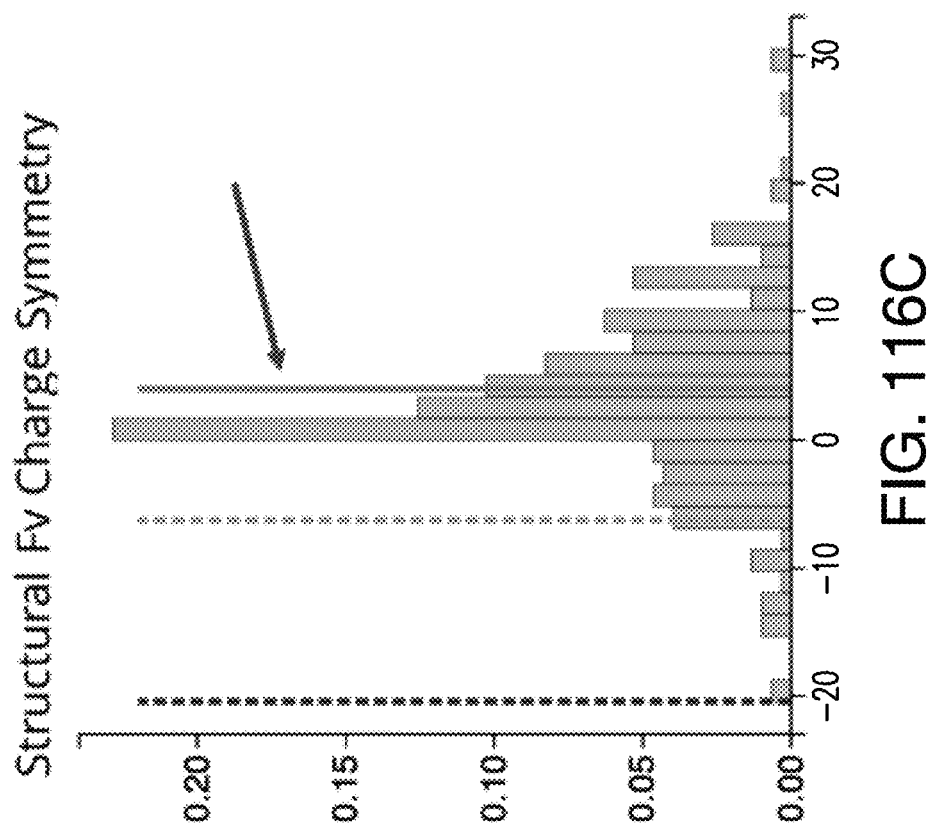

Humanized anti-CLEC12A arm

Fully human anti-NKG2D arm

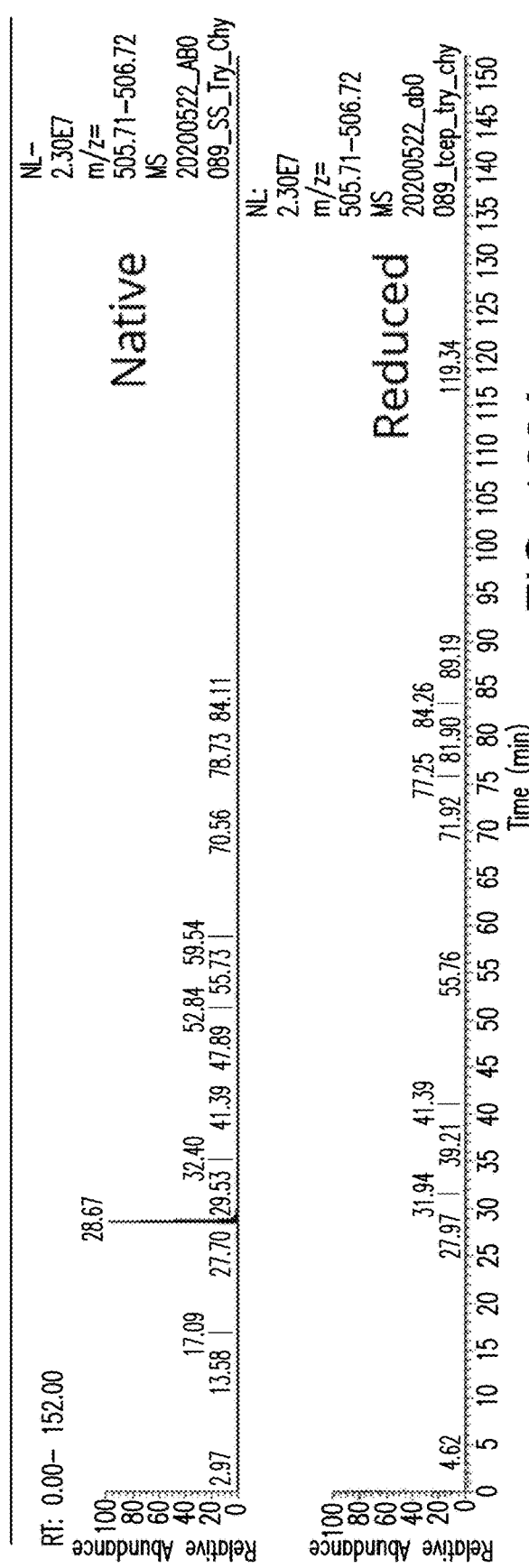
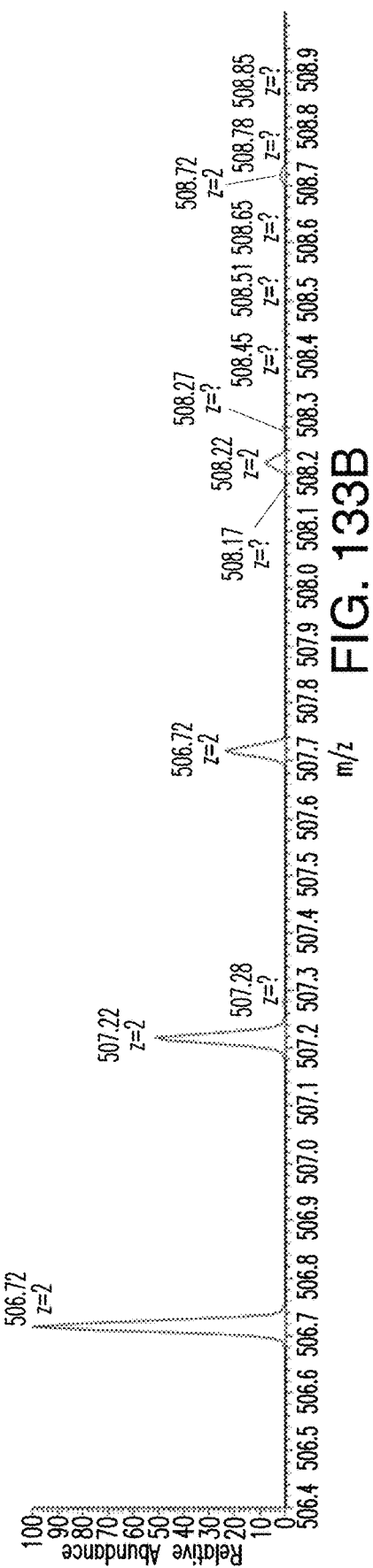
FIG. 133A
FIG. 133B

Group 3
hCLEC12A-His; AB0089-002; Two state reaction

Group 4
hCLEC12A-His; AB0089-002; Two state reaction

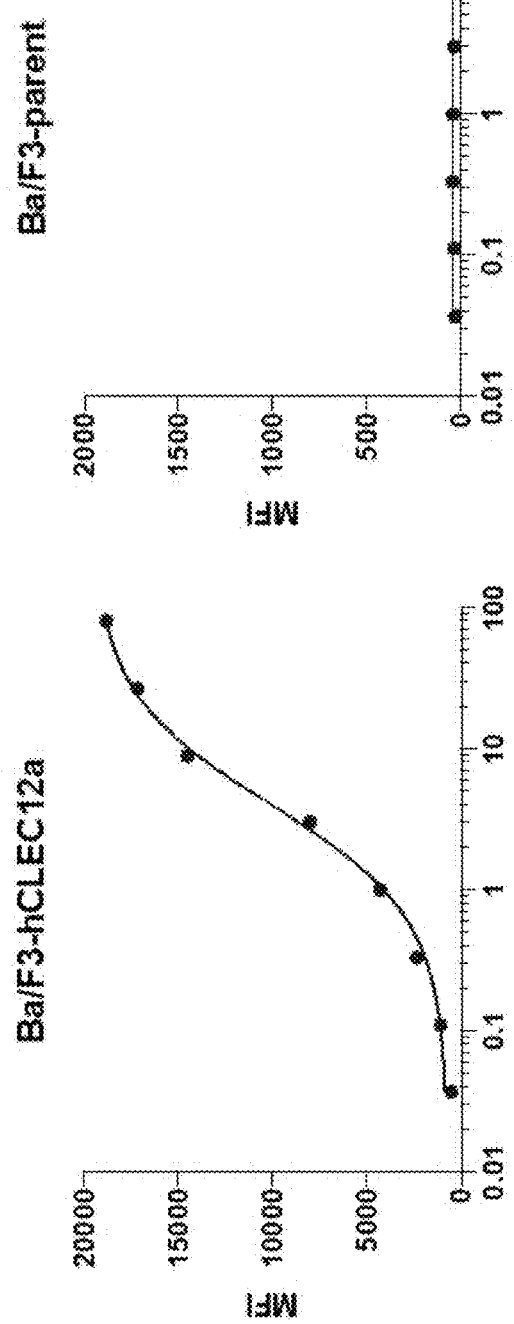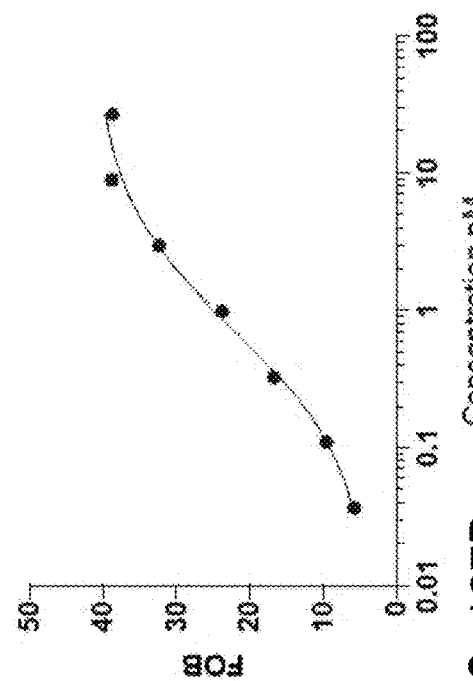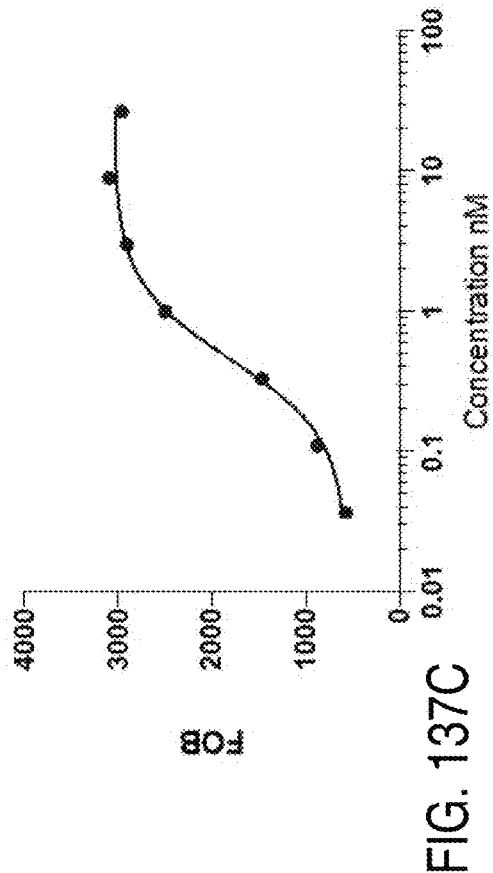
FIG. 137A  FIG. 137B  FIG. 137C  FIG. 137D

Group 16
AB0089-002; mFc-hNKG2D; 1:1 binding

Group 17
AB0089-002; mFc-hNKG2D; 1:1 binding

Group 18
AB0089-002; mFc-hNKG2D; 1:1 binding

Group 16
AB0089-002; mFc-hNKG2D; Steady state affinity

Group 17
AB0089-002; mFc-hNKG2D; Steady state affinity

Group 18
AB0089-002; mFc-hNKG2D; Steady state affinity

AB0089

$K_D = 5.1 \pm 1.0$ nM

AB0089

$K_D = 5.1 \pm 1.0$ nM trastuzumab
$K_D = 2.9 \pm 0.4$ nM trastuzumab
$K_D = 2.9 \pm 0.4\,nM$

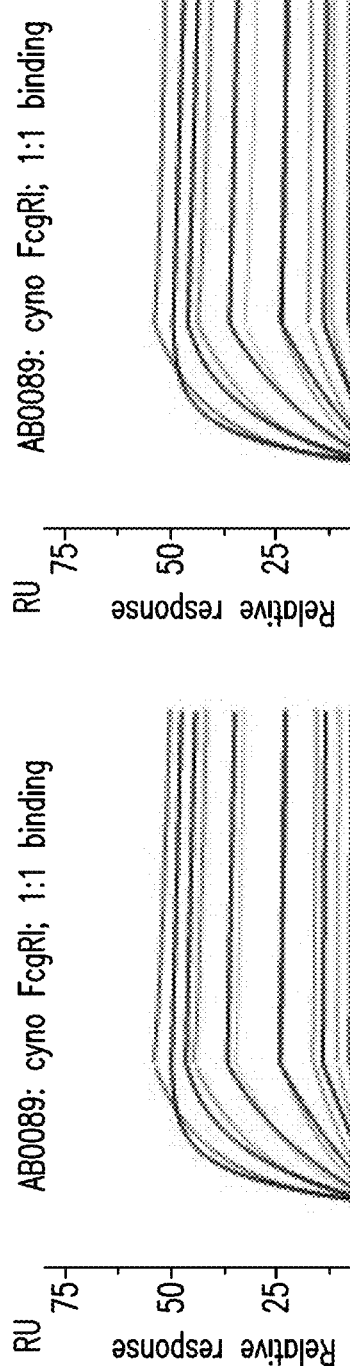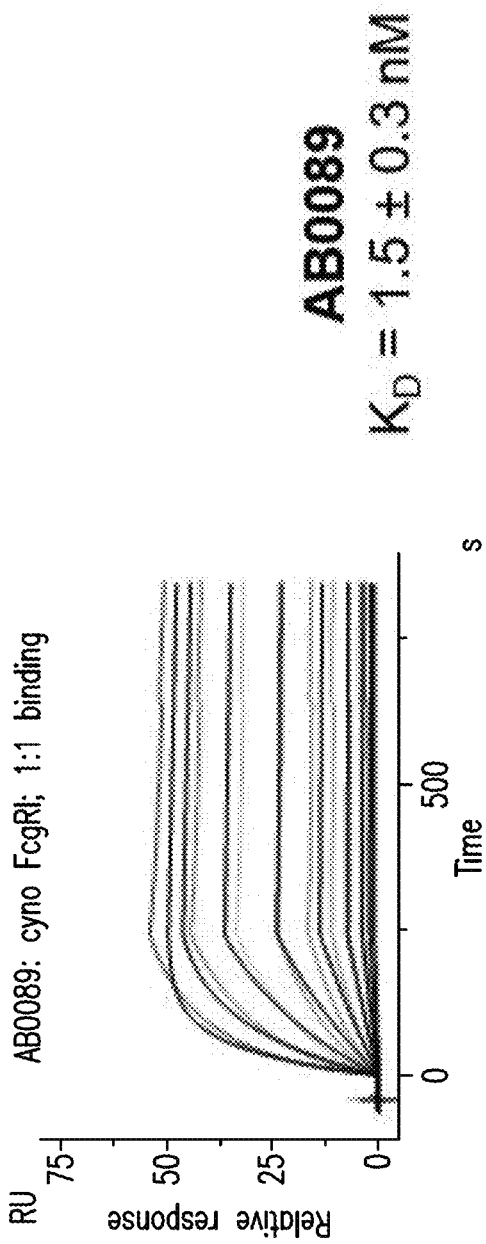
FIG. 143A
FIG. 143B
FIG. 143C
AB0089
$K_D = 1.5 \pm 0.3$ nM

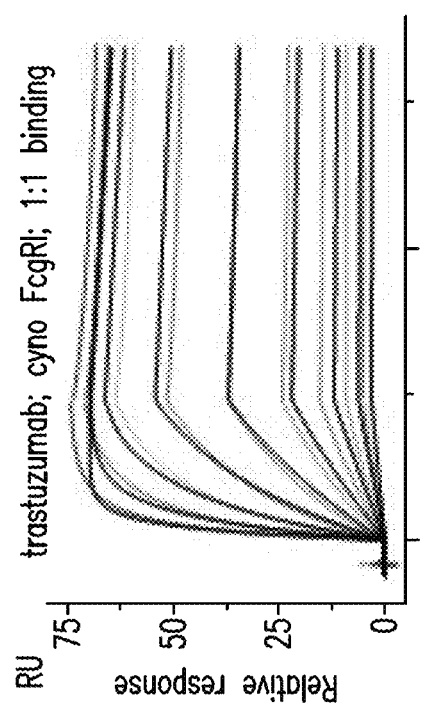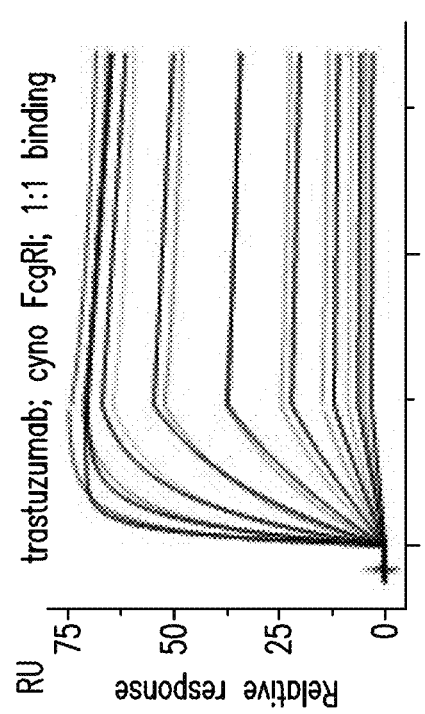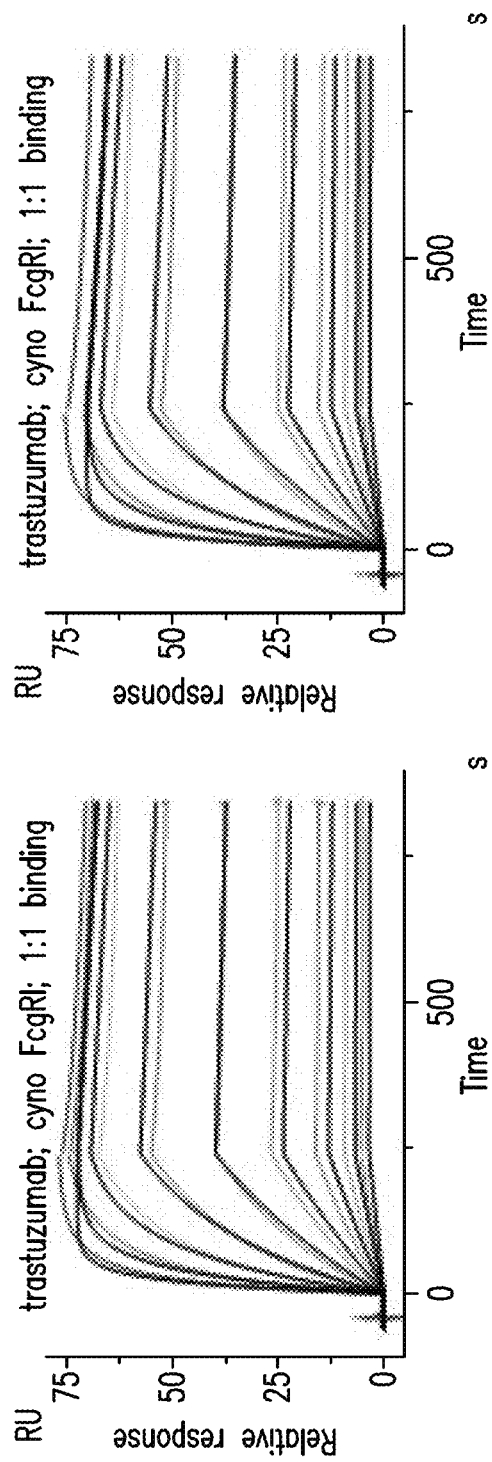
FIG. 143D
FIG. 143E
FIG. 143F
FIG. 143G
trastuzumab
$K_D = 1.0 \pm 0.1$ nM

AB0089
$K_D = 900.4 \pm 57.1$ nM

FIG. 144E

FIG. 144F
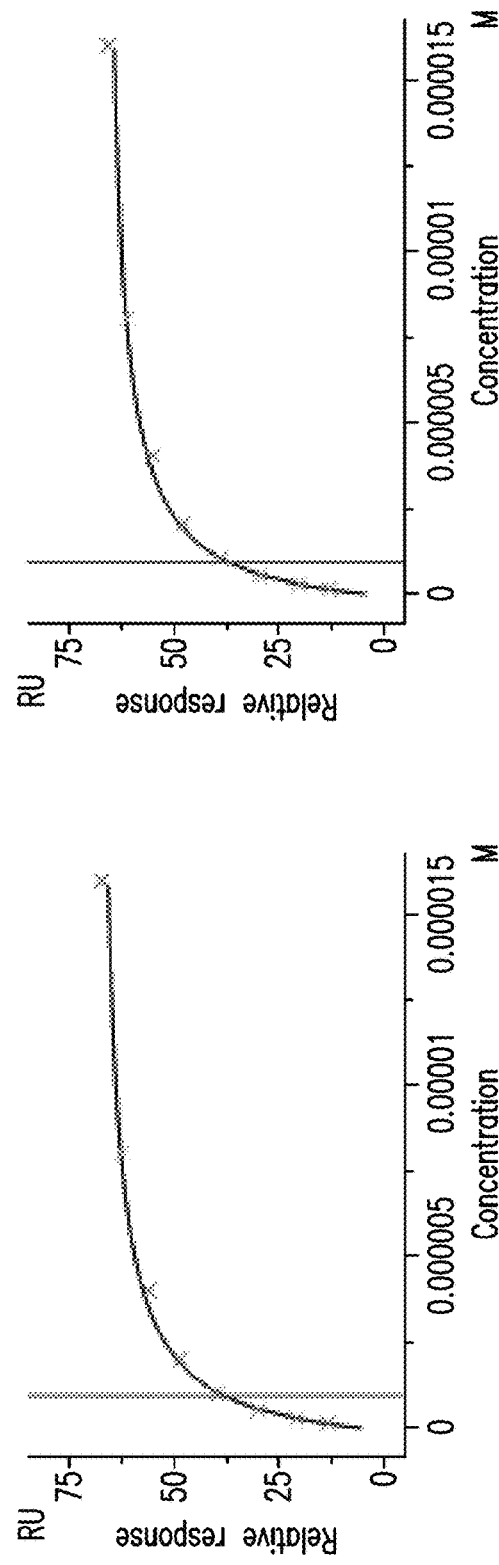
FIG. 144G
FIG. 144H
AB0089
$K_D = 900.4 \pm 57.1$ nM

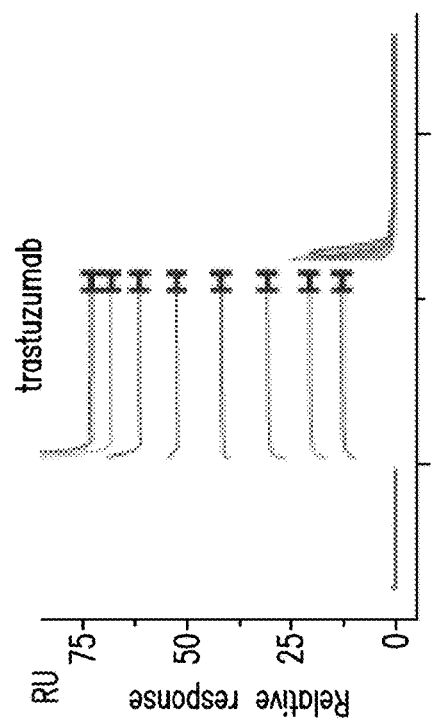
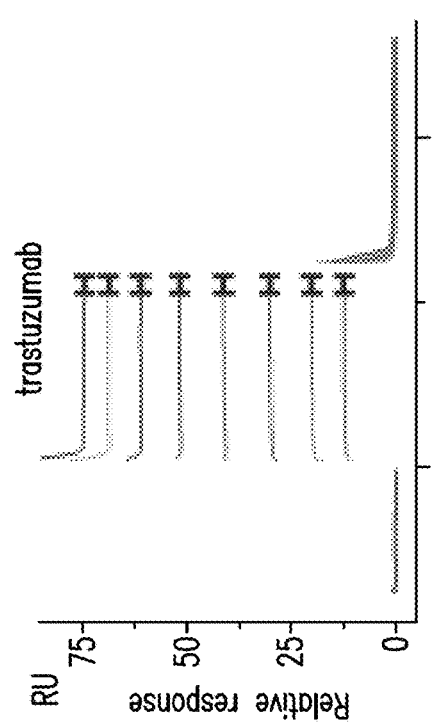
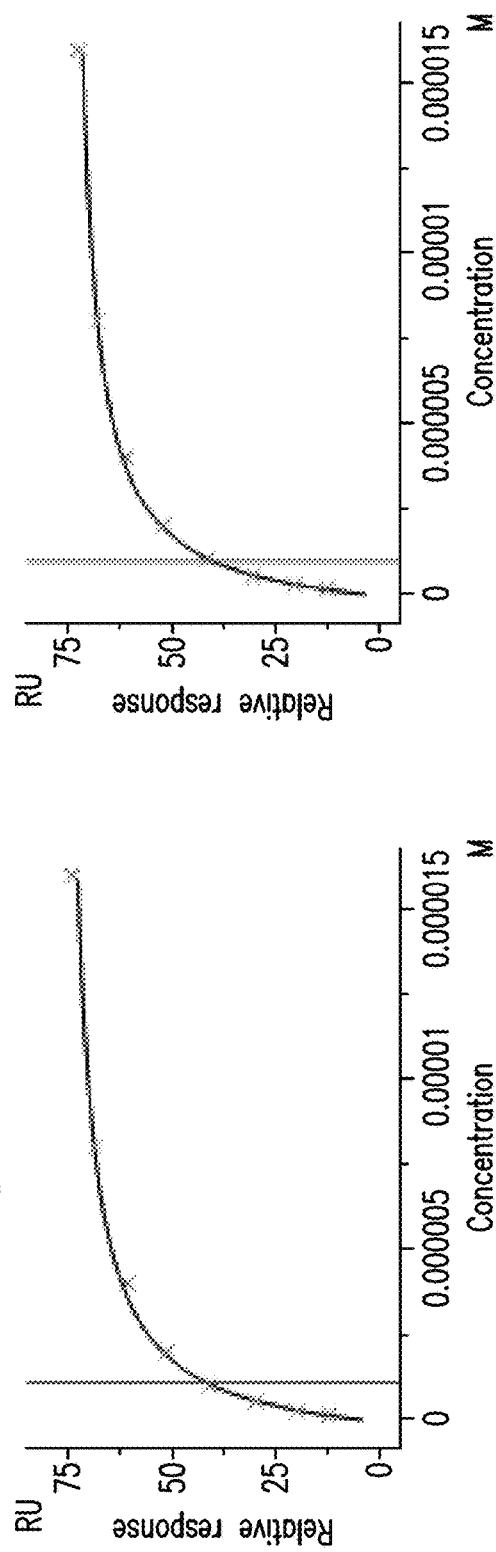
FIG. 144I    FIG. 144J
FIG. 144K    FIG. 144L
trastuzumab
$K_D = 1045.1 \pm 62.2$ nM

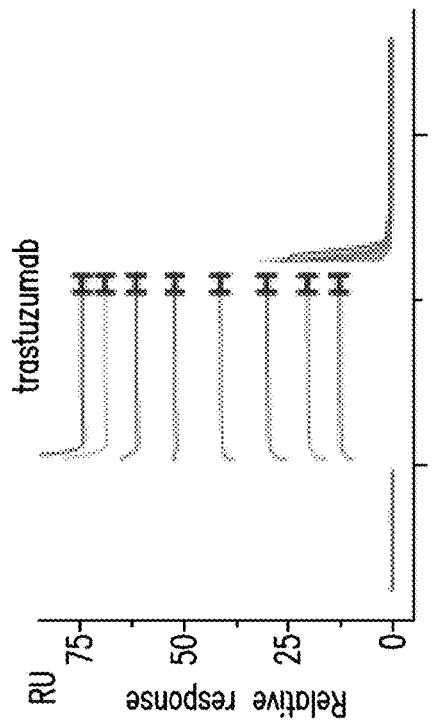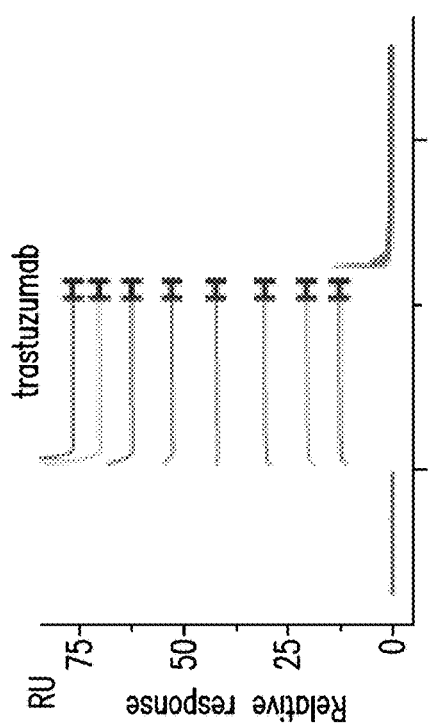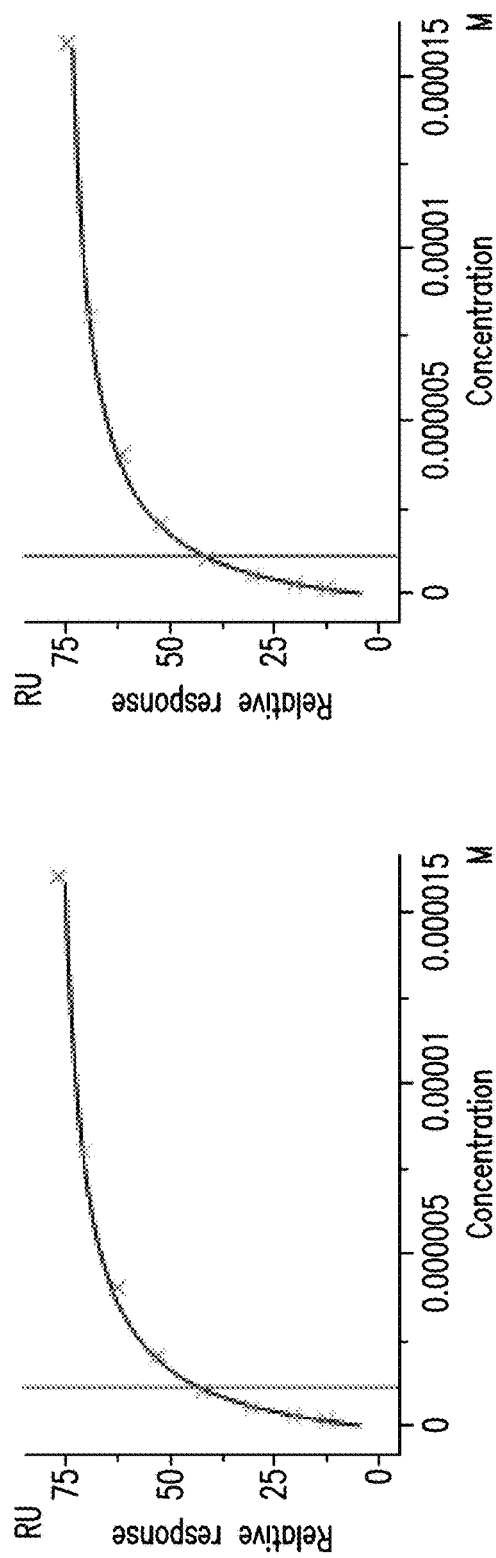
FIG. 144M  FIG. 144N  FIG. 144O  FIG. 144P
trastuzumab
$K_D = 1045.1 \pm 62.2$ nM

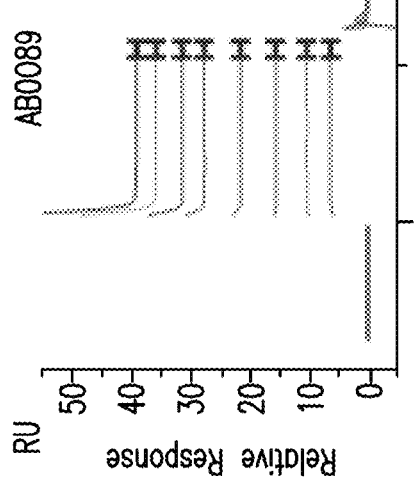
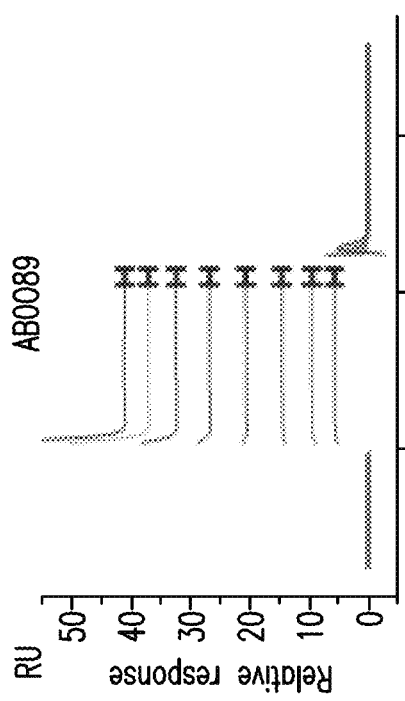
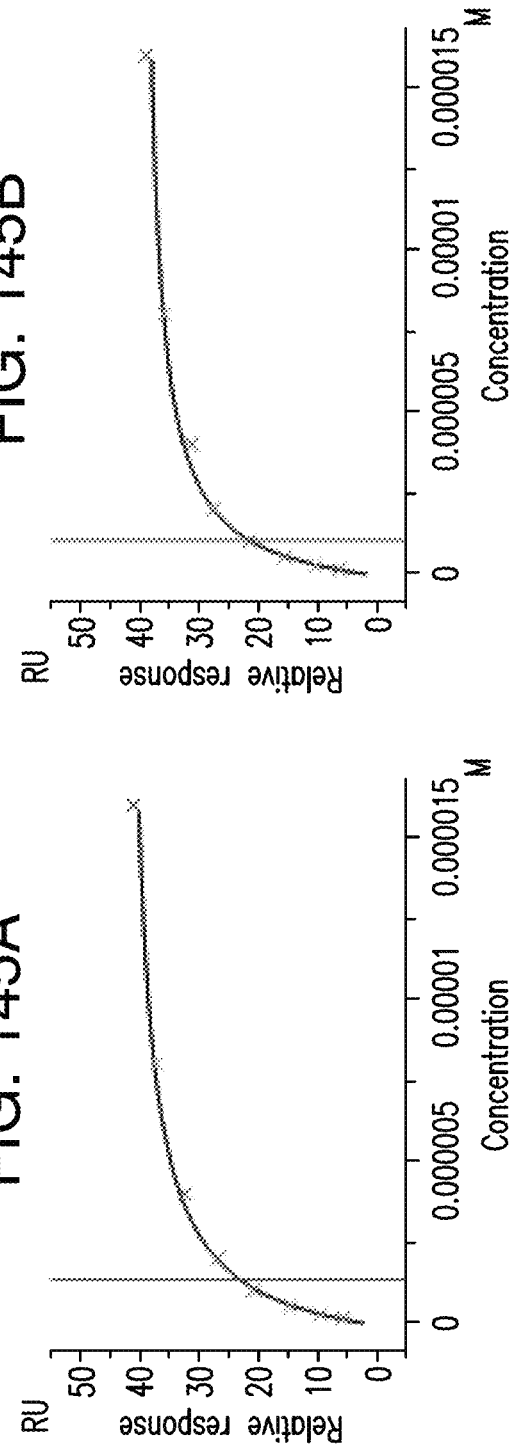
FIG. 145A
FIG. 145B
FIG. 145C
FIG. 145D
AB0089
$K_D = 1253.3 \pm 269.2$ nM

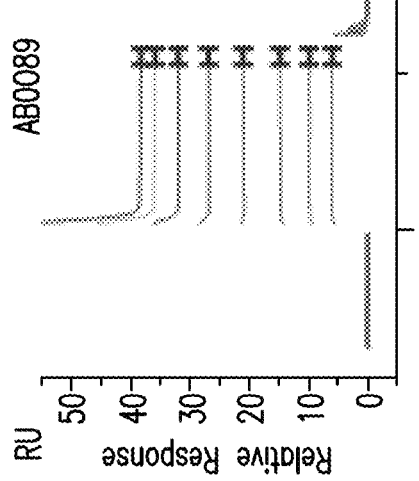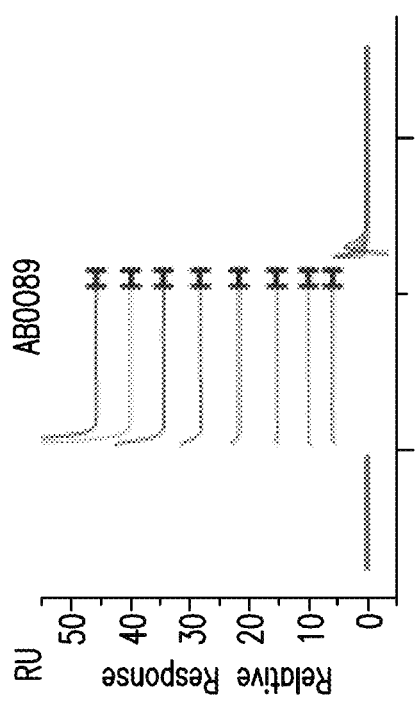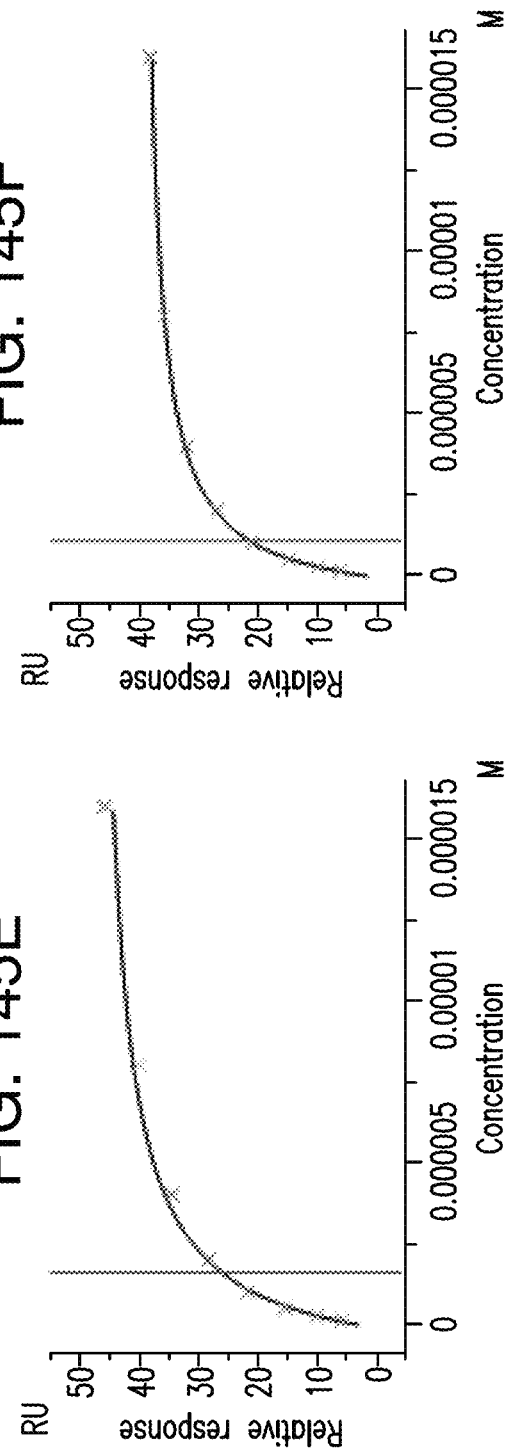
FIG. 145E  FIG. 145F  FIG. 145G  FIG. 145H
AB0089  $K_D = 1253.3 \pm 269.2$ nM

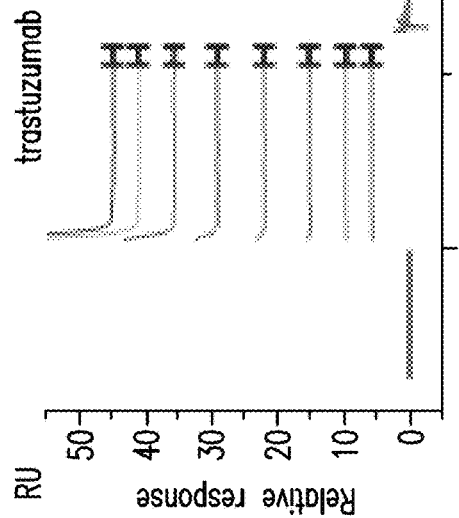
FIG. 145I
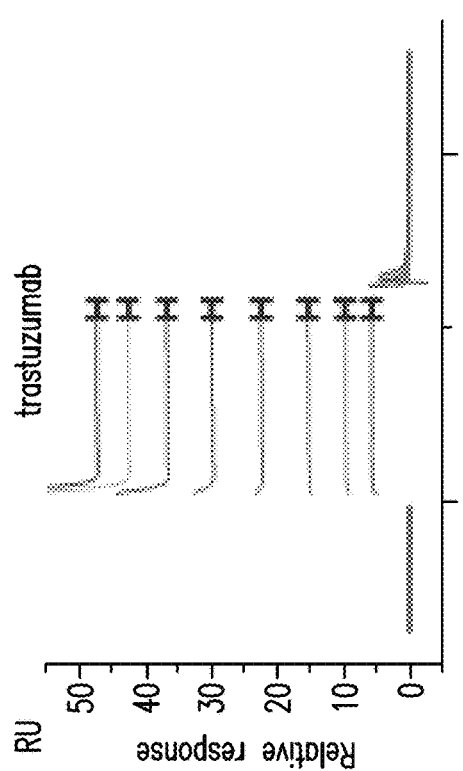
FIG. 145K
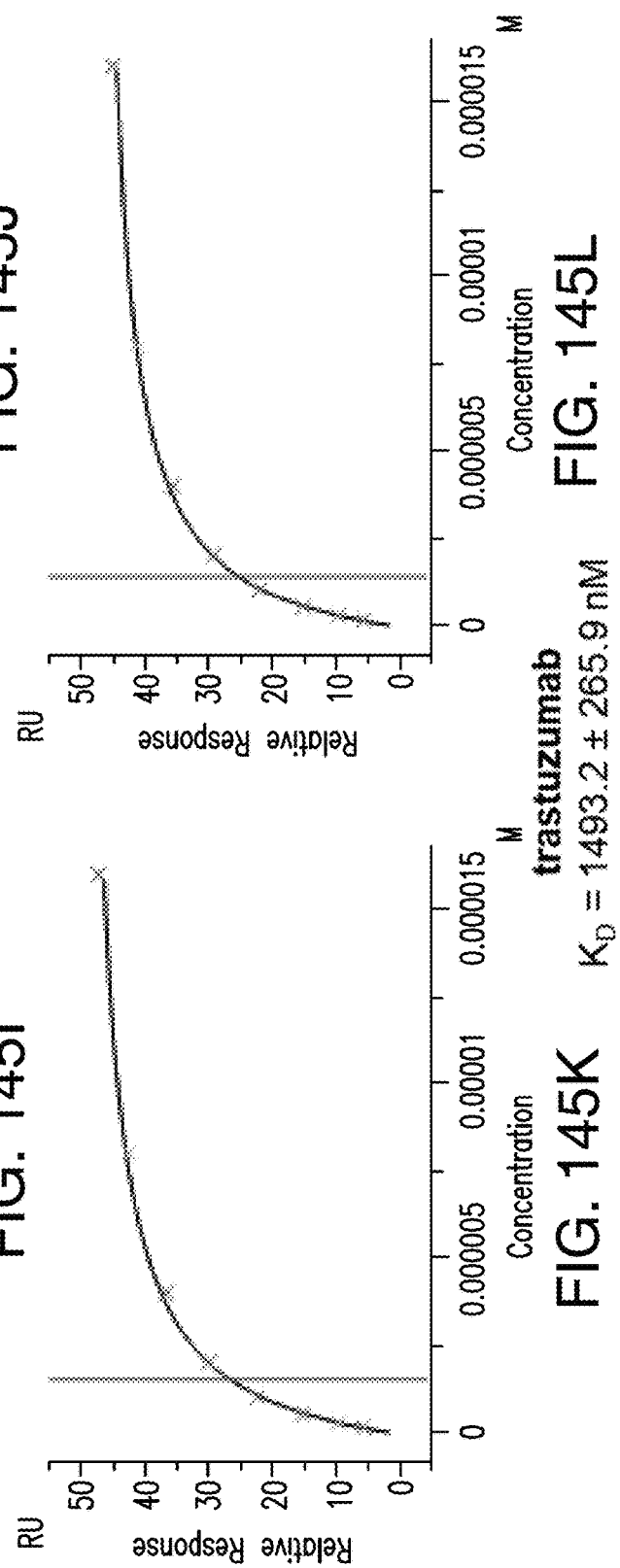
FIG. 145J
FIG. 145L
trastuzumab
$K_D = 1493.2 \pm 265.9$ nM

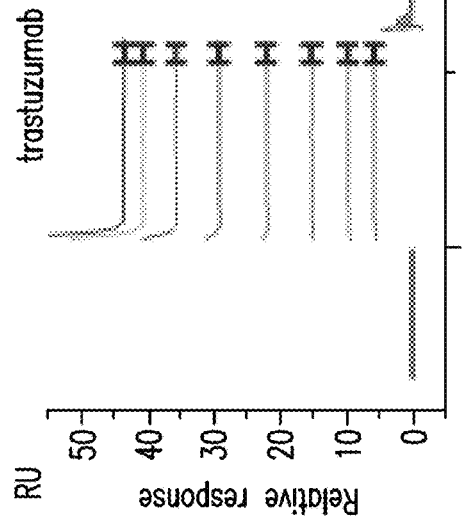
FIG. 145N
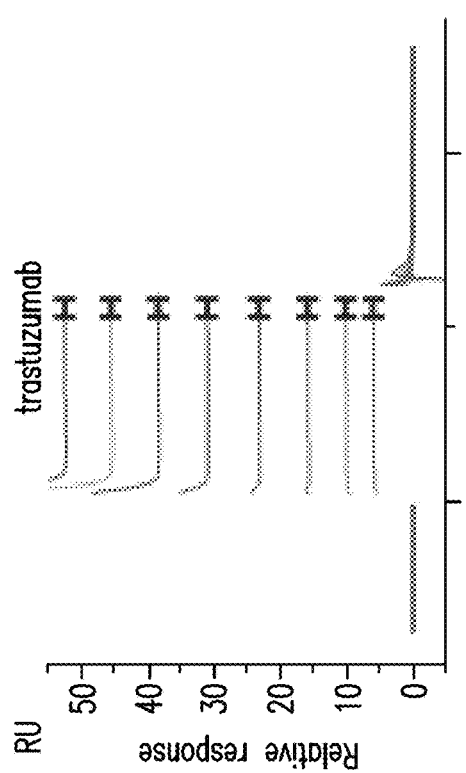
FIG. 145M

FIG. 145P
FIG. 145O
trastuzumab
$K_D = 1493.2 \pm 265.9$ nM

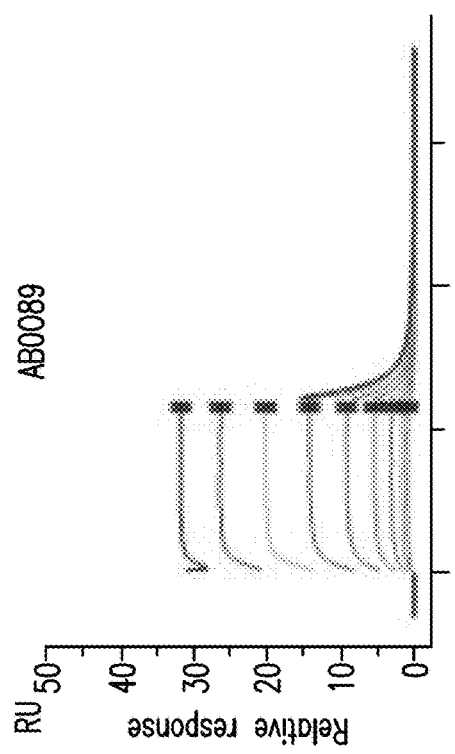
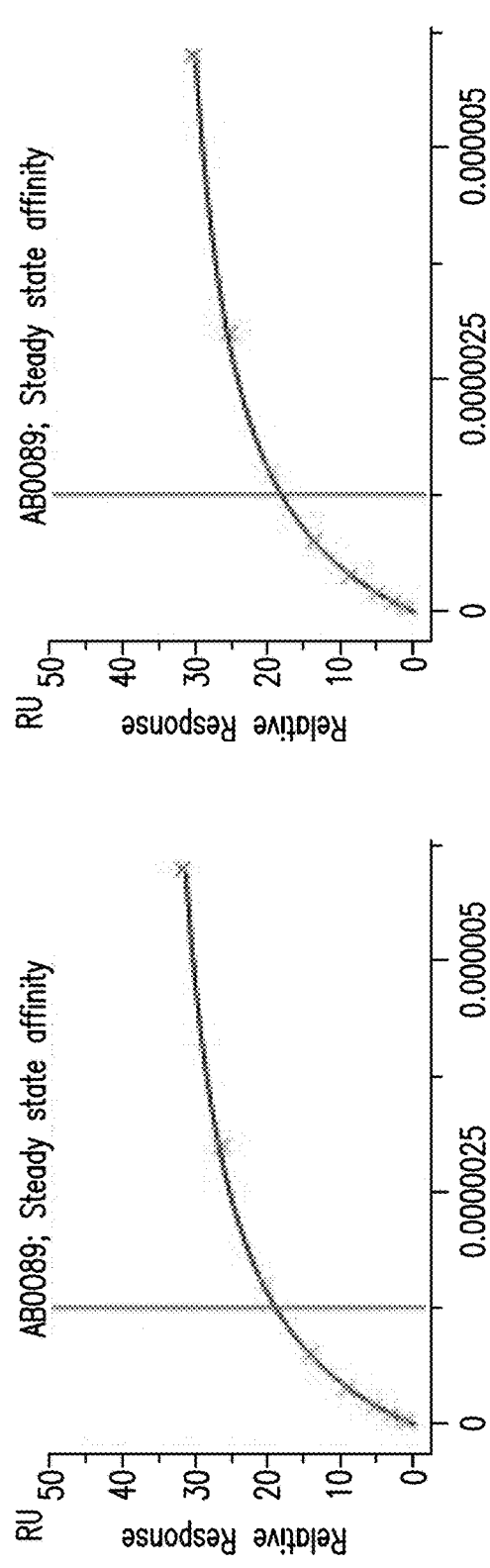
FIG. 146A
FIG. 146B
FIG. 146C  AB0089  $K_D = 1271.0 \pm 24.6$ nM
FIG. 146D

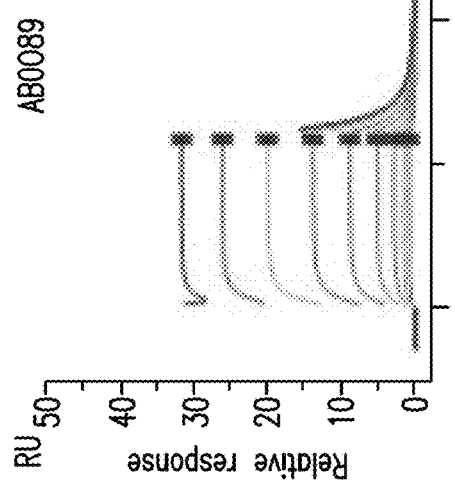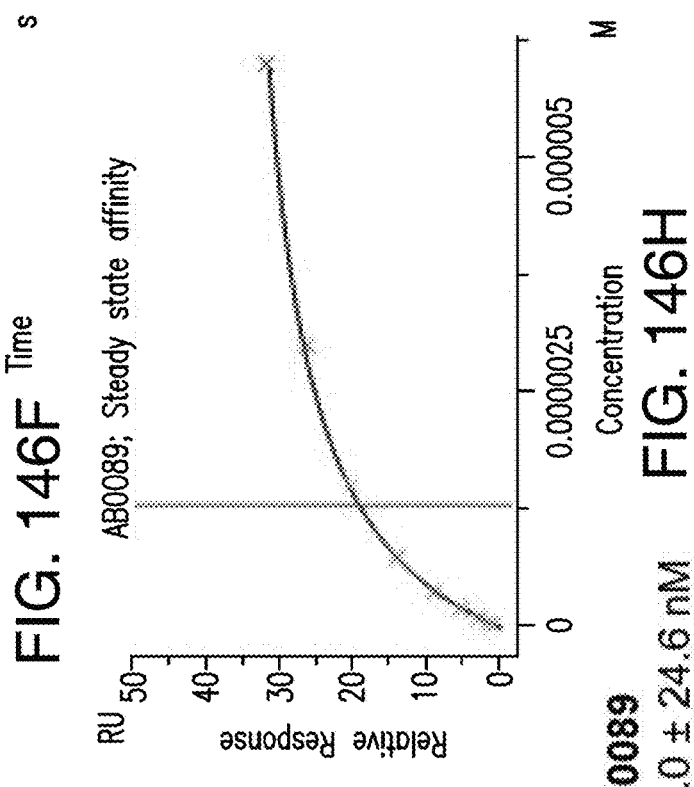
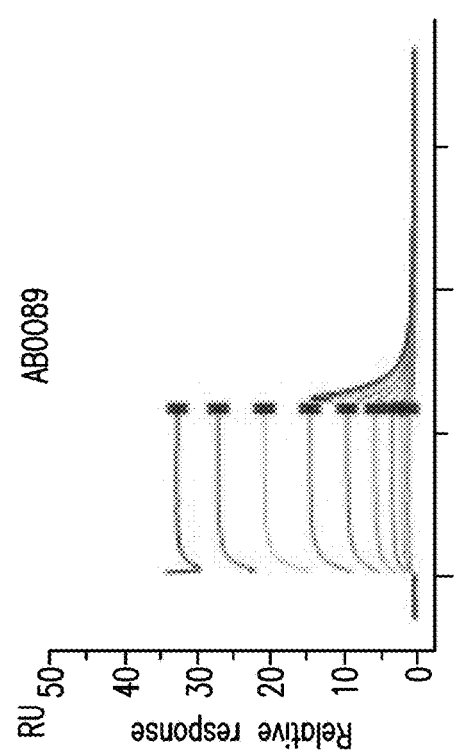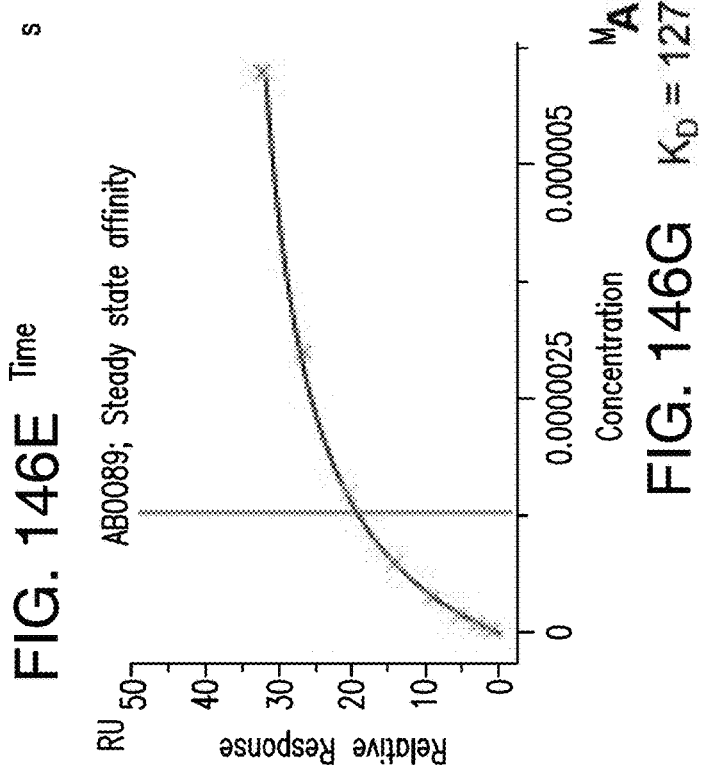
FIG. 146E
FIG. 146F
FIG. 146G  $K_D = 1271.0 \pm 24.6$ nM
FIG. 146H

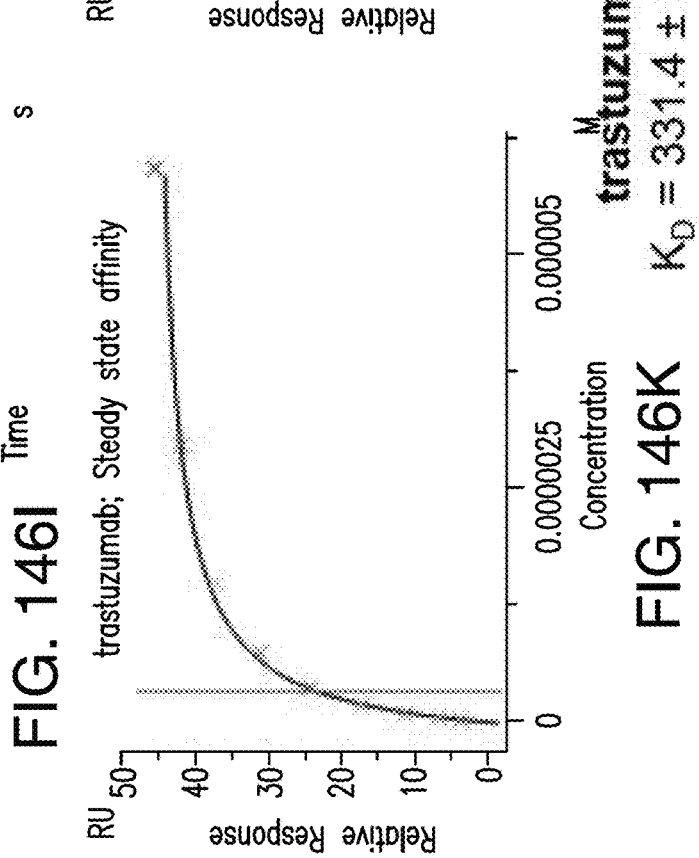
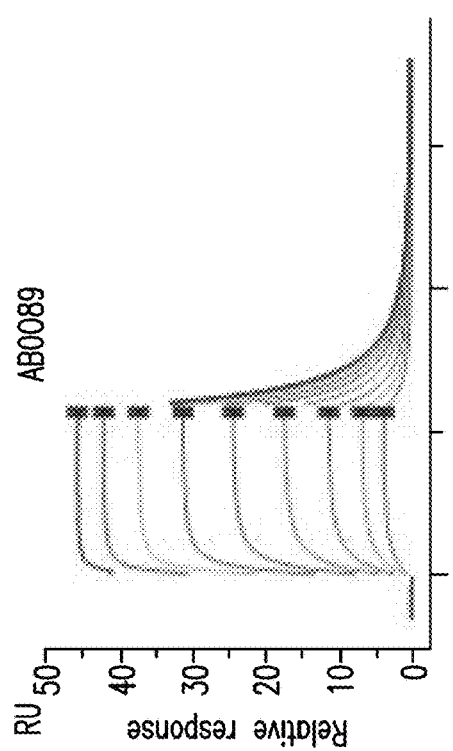

FIG. 146I  FIG. 146J  FIG. 146K  FIG. 146L
trastuzumab  $K_D = 331.4 \pm 3.3$ nM

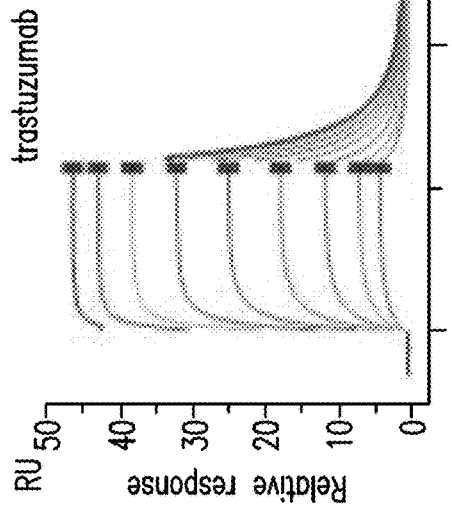
FIG. 146M
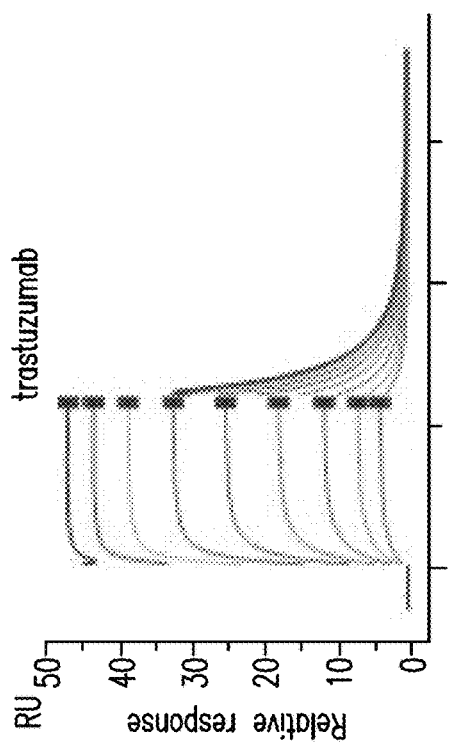
FIG. 146N
FIG. 146O
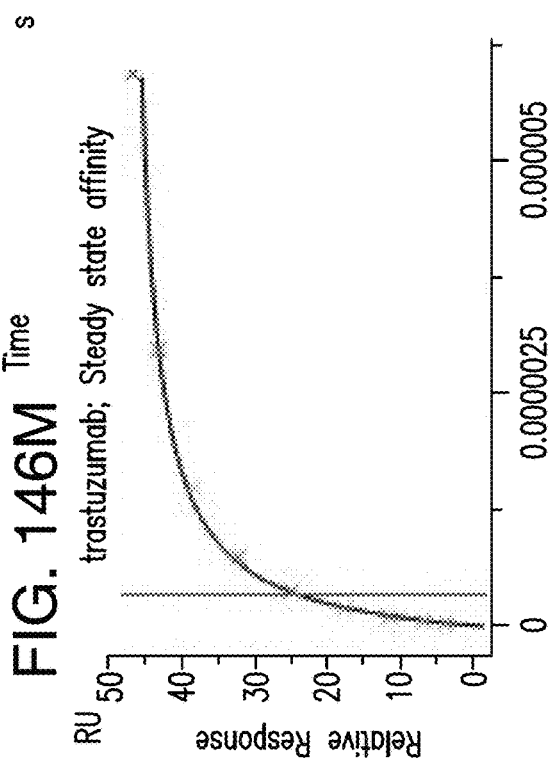
FIG. 146P
trastuzumab
$K_D = 331.4 \pm 3.3$ nM

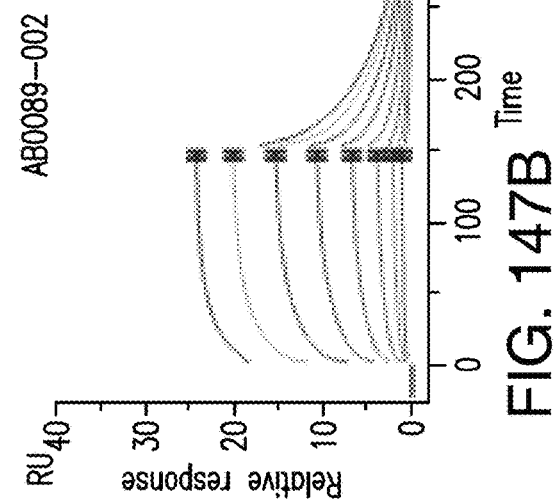
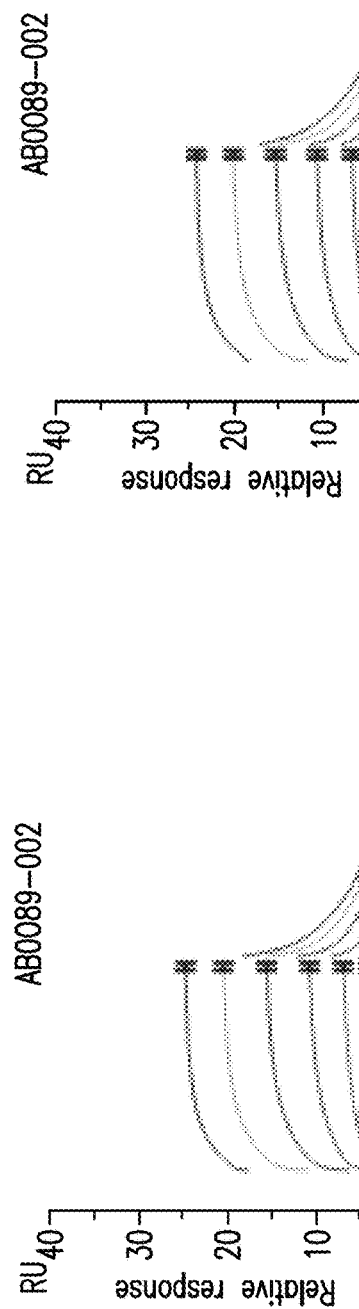
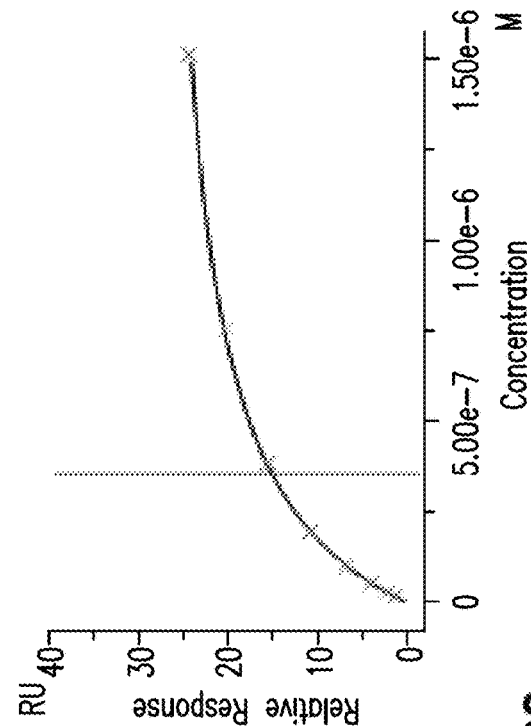
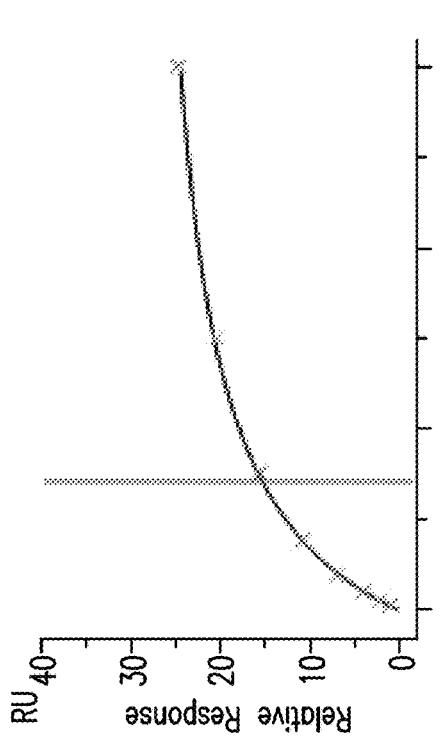
FIG. 147A
FIG. 147B
FIG. 147C
FIG. 147D
AB0089 $K_D = 348.8 \pm 2.4$ nM

AB0089

$K_D = 348.8 \pm 2.4$ nM

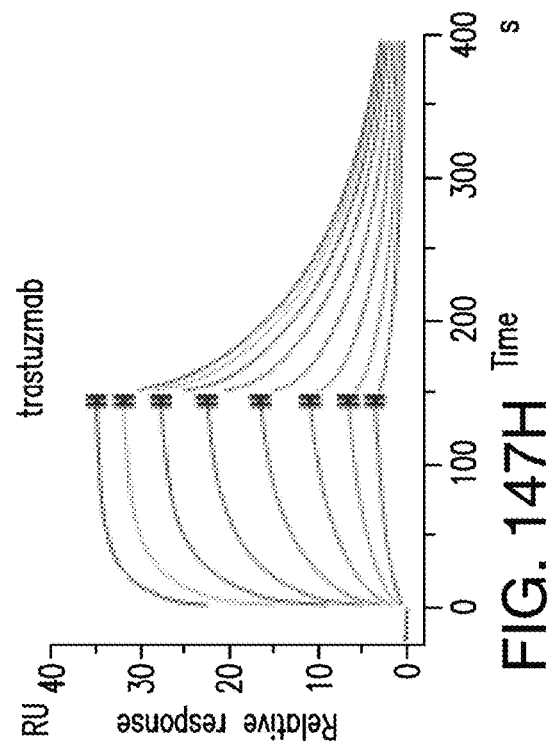
FIG. 147G
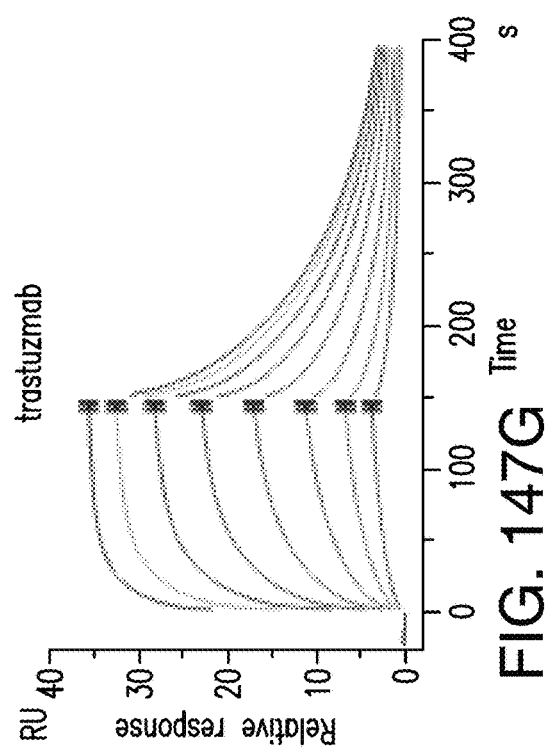
FIG. 147H
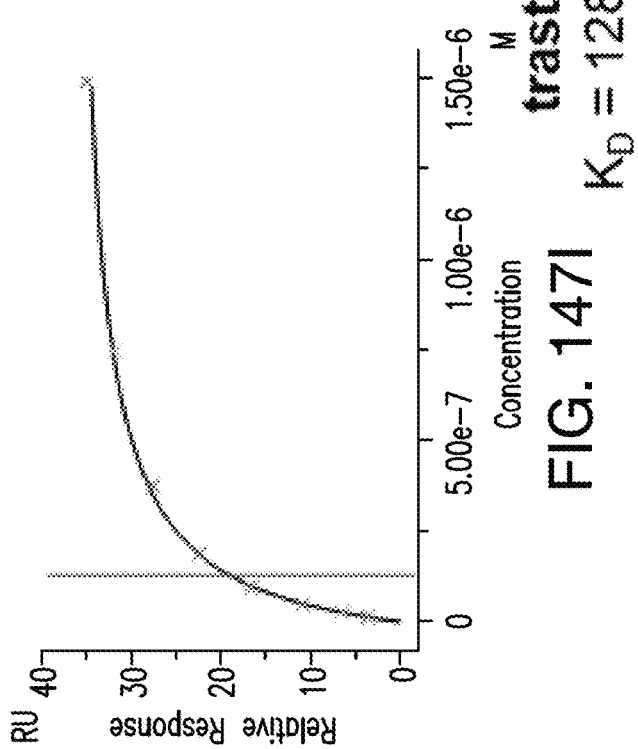
FIG. 147I
FIG. 147J
trastuzumab
$K_D = 128.8 \pm 2.1$ nM trastuzumab
$K_D = 128.8 \pm 2.1$ nM

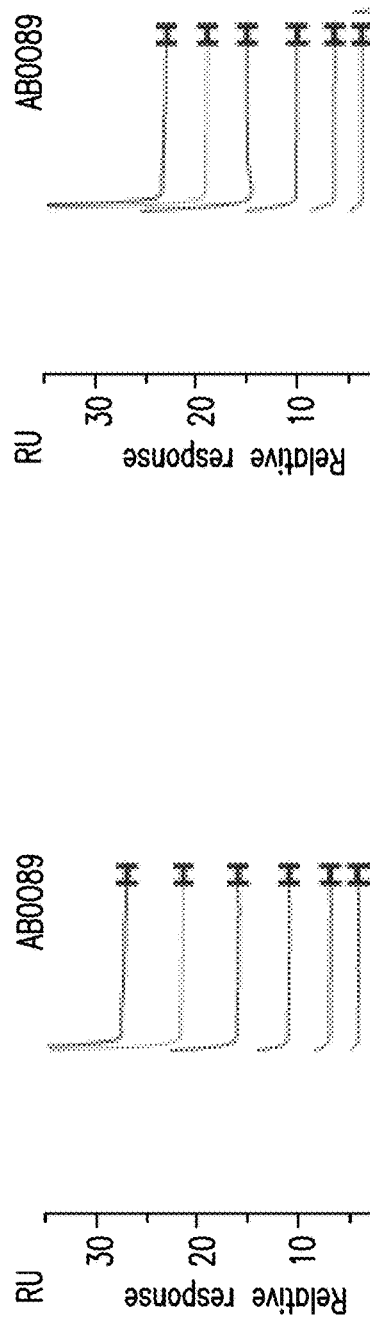
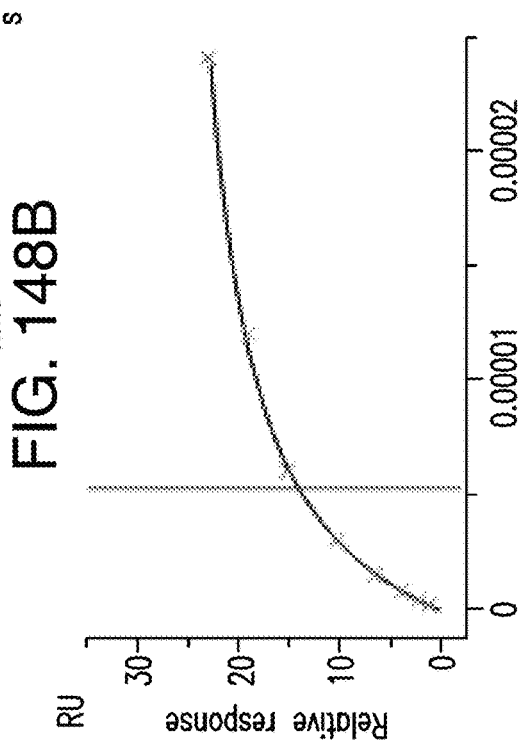
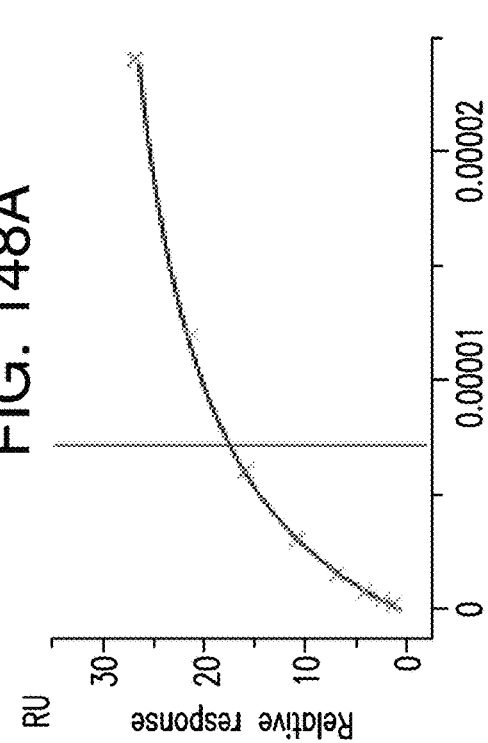
FIG. 148A  FIG. 148B  FIG. 148C  FIG. 148D
AB0089 $K_D = 6.3 \pm 1.2 \, \mu M$

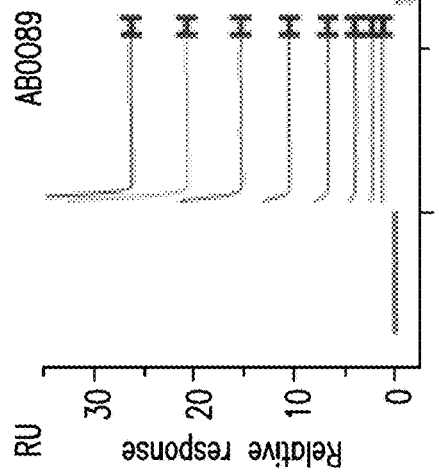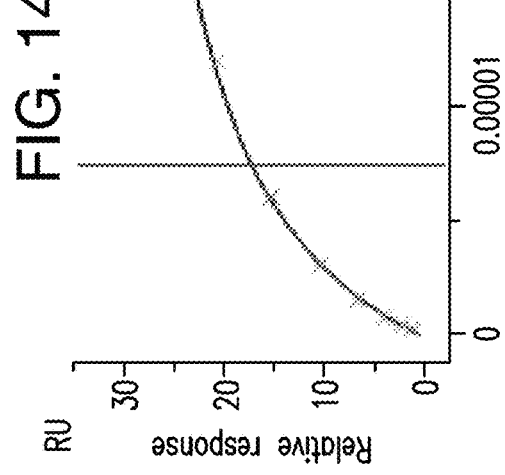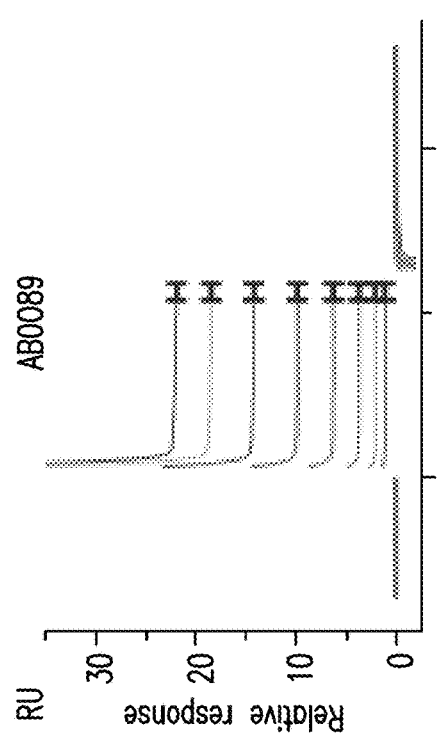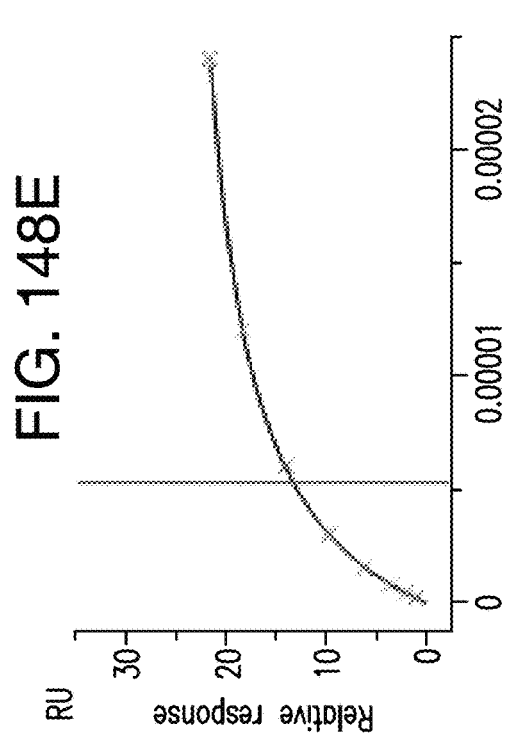
FIG. 148E
FIG. 148F
FIG. 148G
FIG. 148H
AB0089 $K_D = 6.3 \pm 1.2 \, \mu M$ trastuzumab
$K_D = 6.3 \pm 1.0\ \mu M$

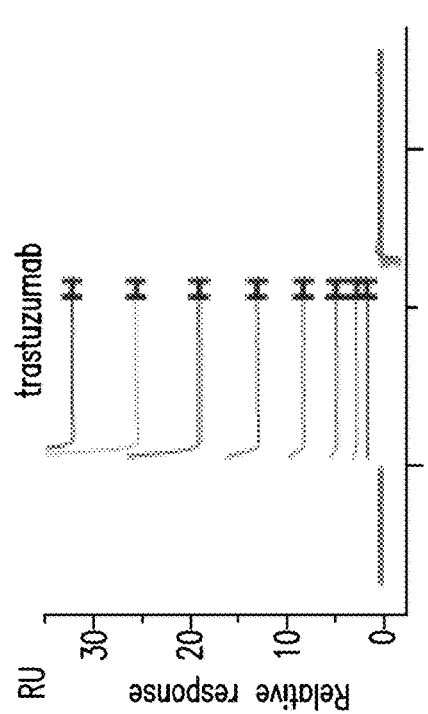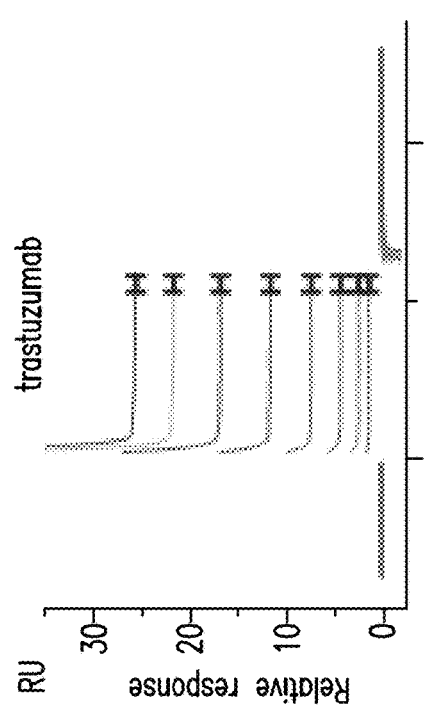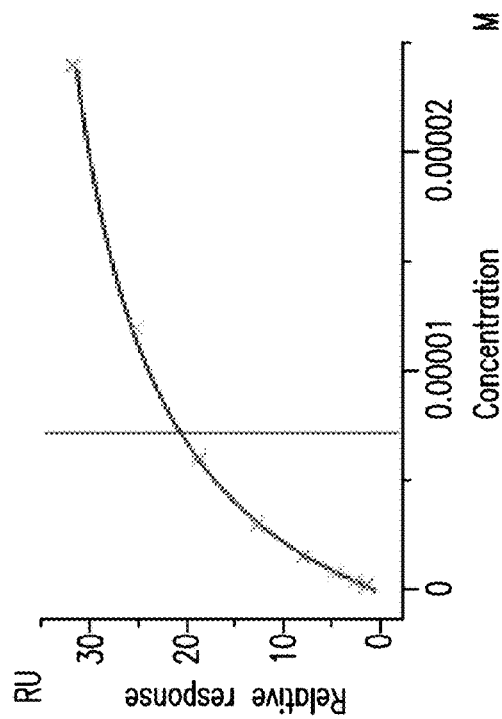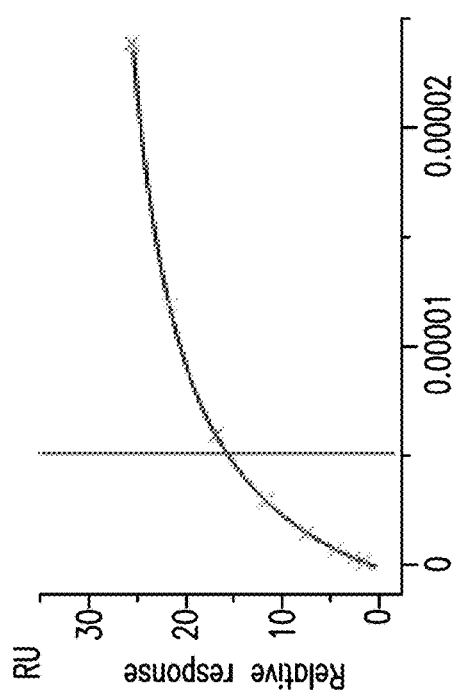

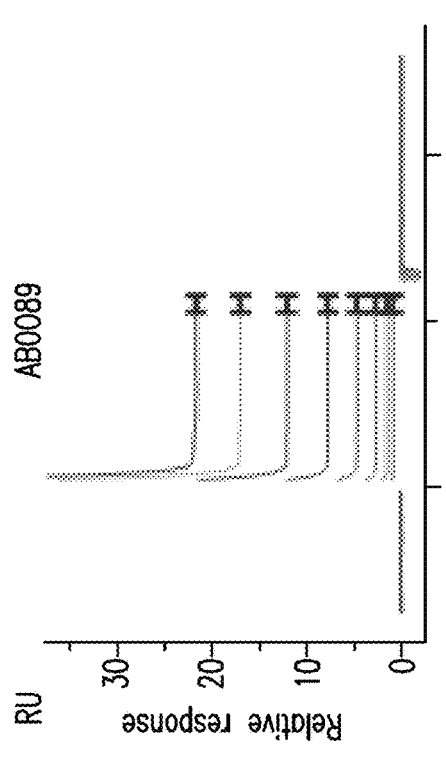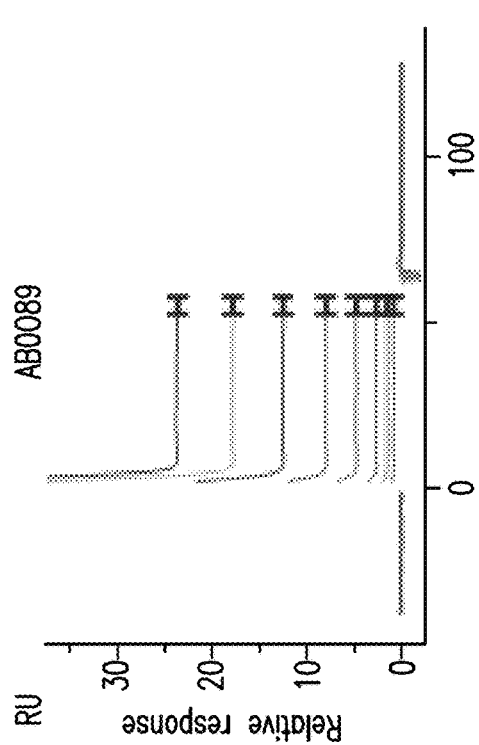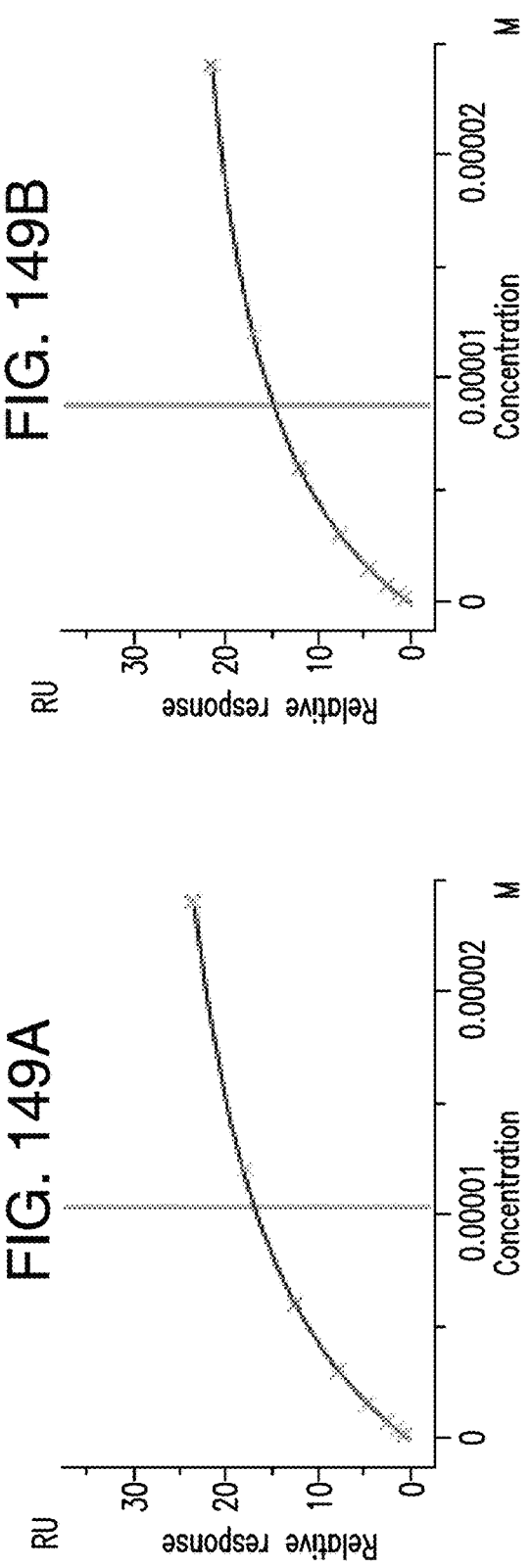
FIG. 149A
FIG. 149B
FIG. 149C
FIG. 149D
AB0089
$K_D = 8.9 \pm 1.5 \mu M$

AB0089

$K_D = 8.9 \pm 1.5 \mu M$ trastuzumab $K_D = 3.9 \pm 0.5\ \mu M$ trastuzumab
$K_D = 3.9 \pm 0.5 \mu M$

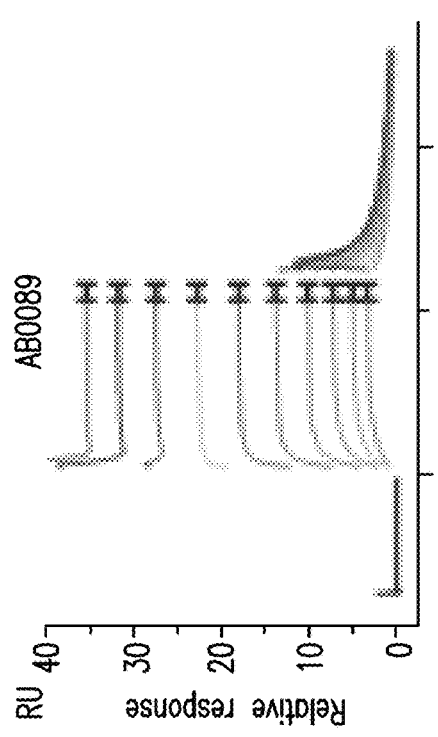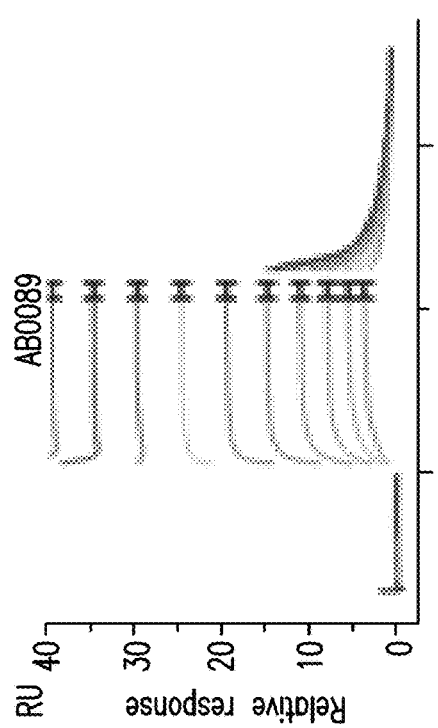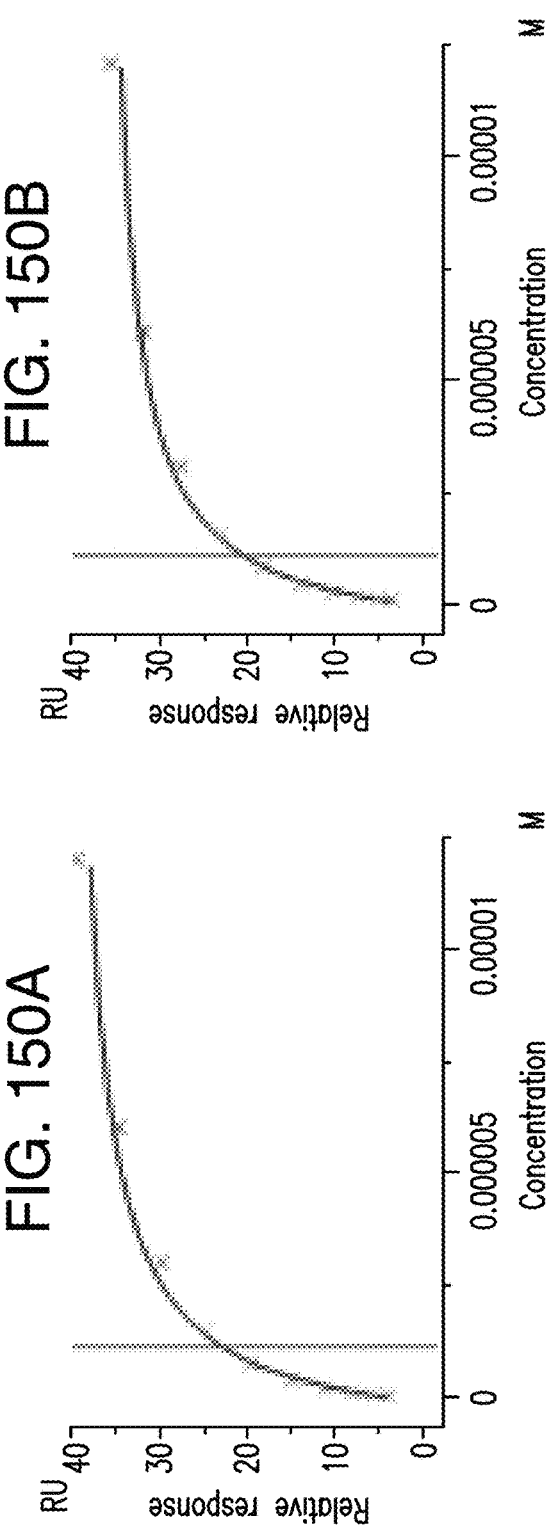
FIG. 150A  FIG. 150B  FIG. 150C  FIG. 150D
AB0089
$K_D = 1.1 \pm 0.1\ \mu M$

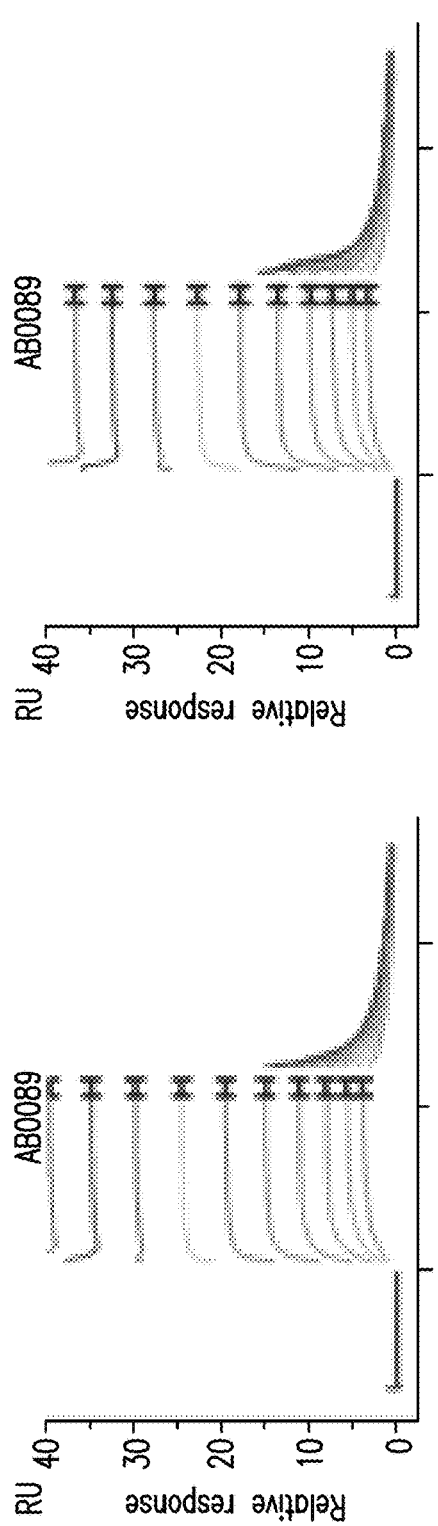
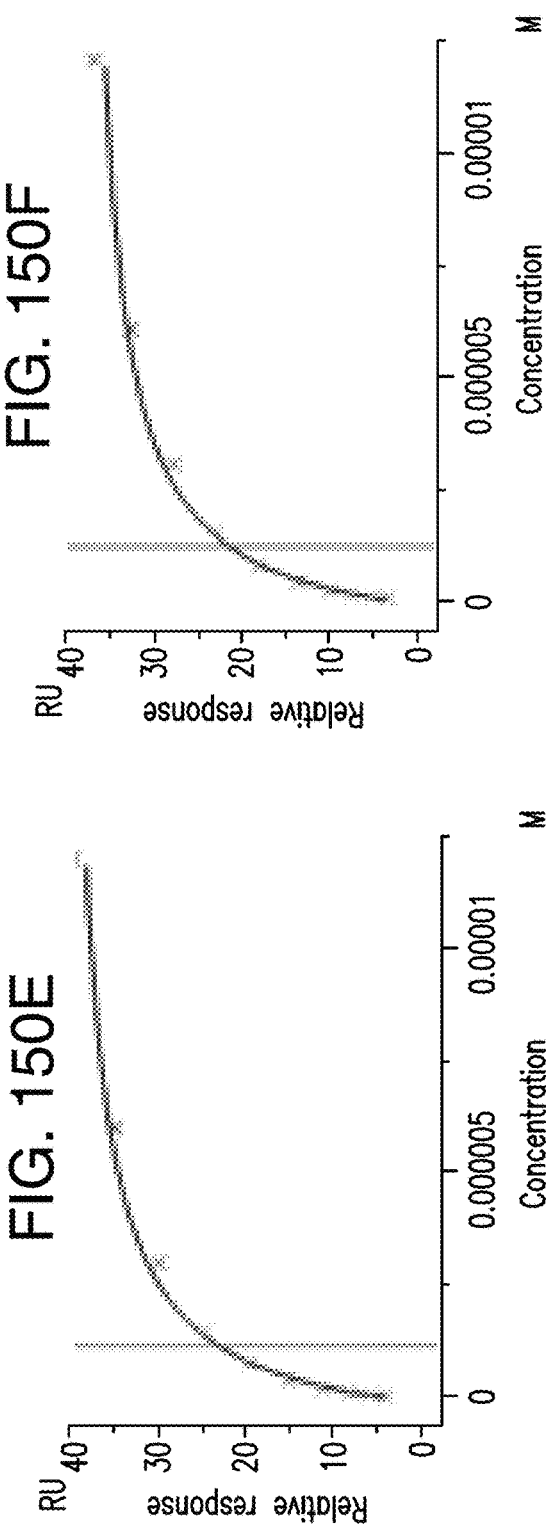
FIG. 150E
FIG. 150F
FIG. 150G
FIG. 150H
AB0089
$K_D = 1.1 \pm 0.1 \, \mu M$

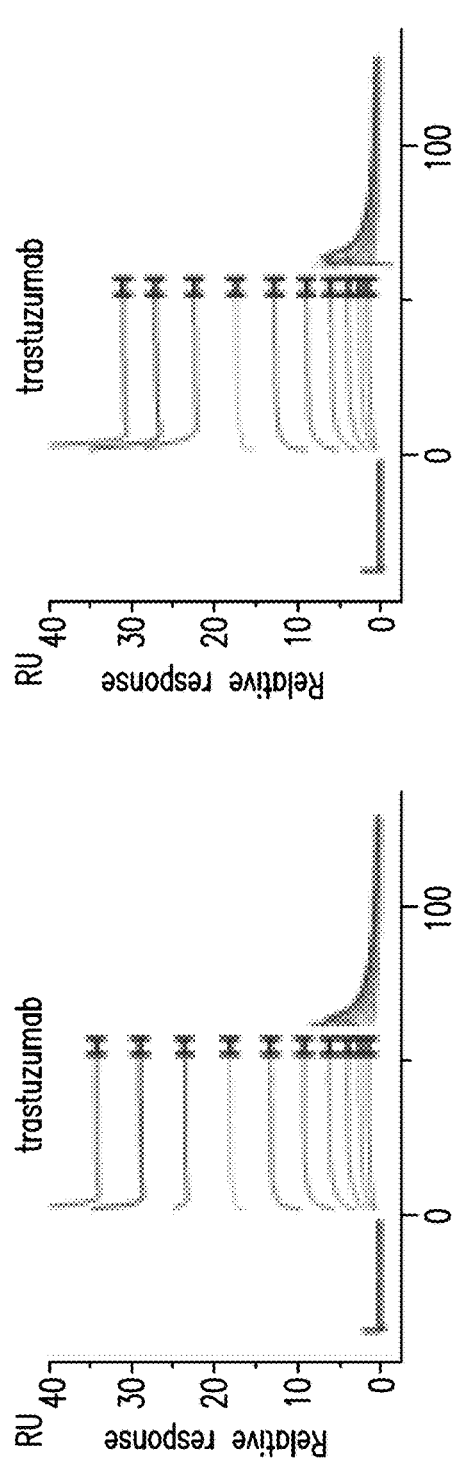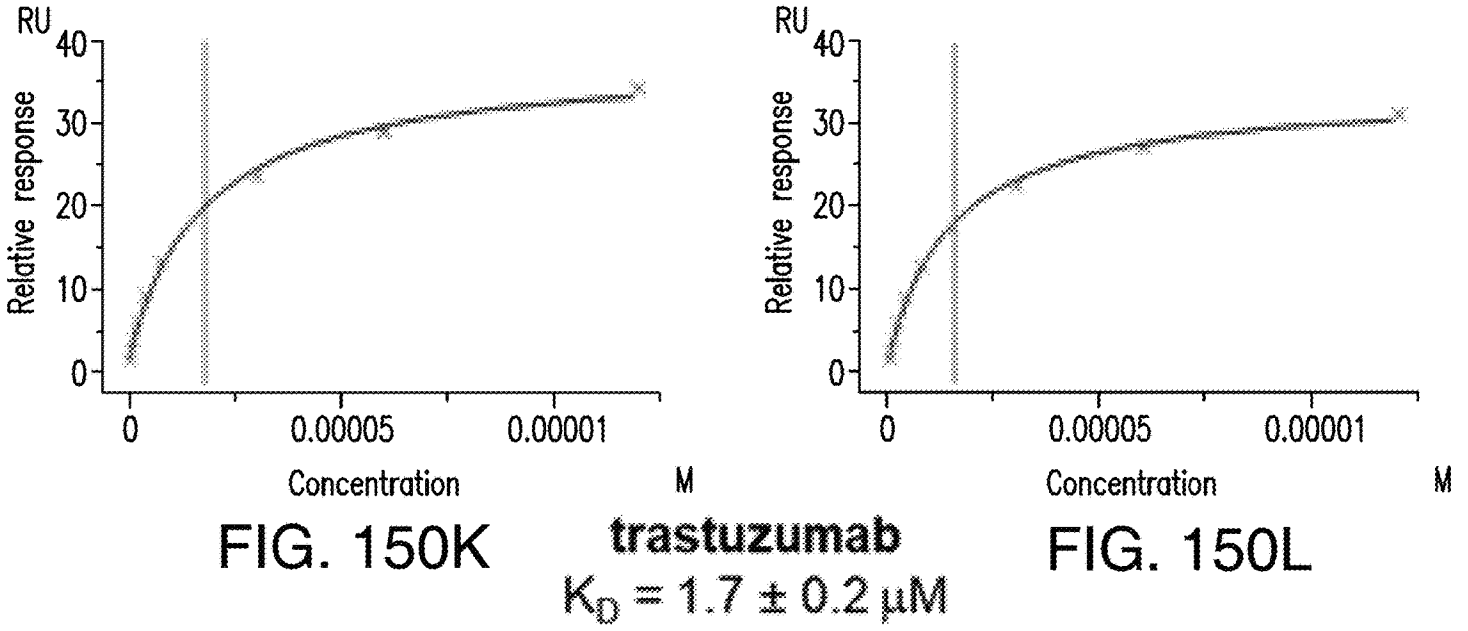
FIG. 150I  FIG. 150J  FIG. 150K  FIG. 150L
trastuzumab
$K_D = 1.7 \pm 0.2 \ \mu M$

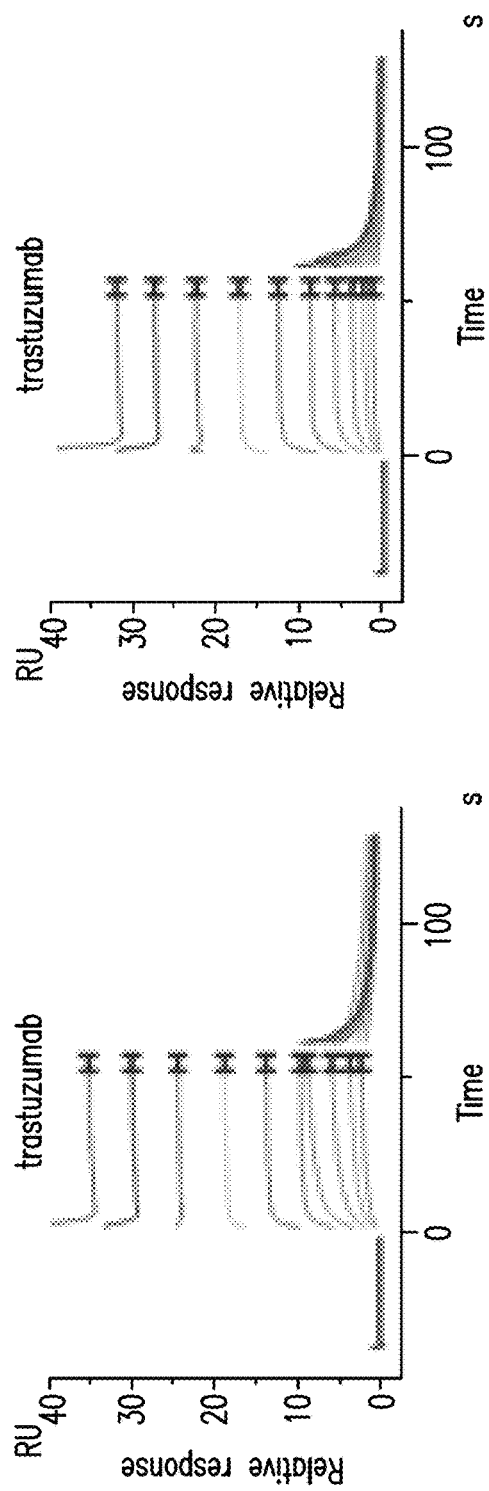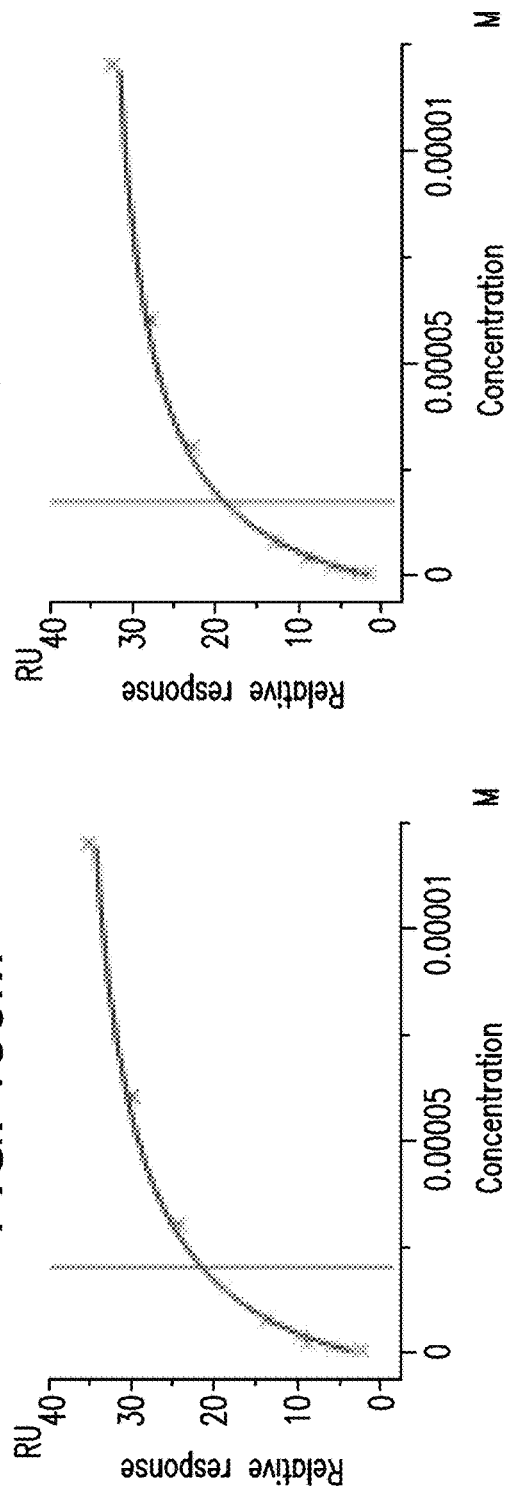

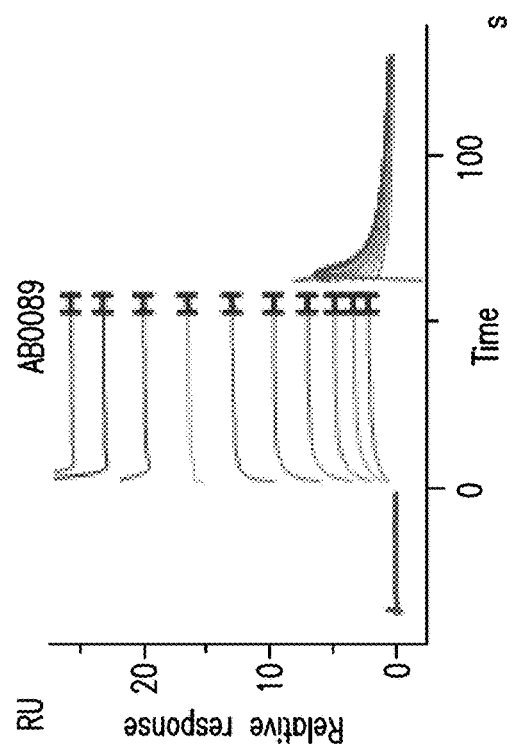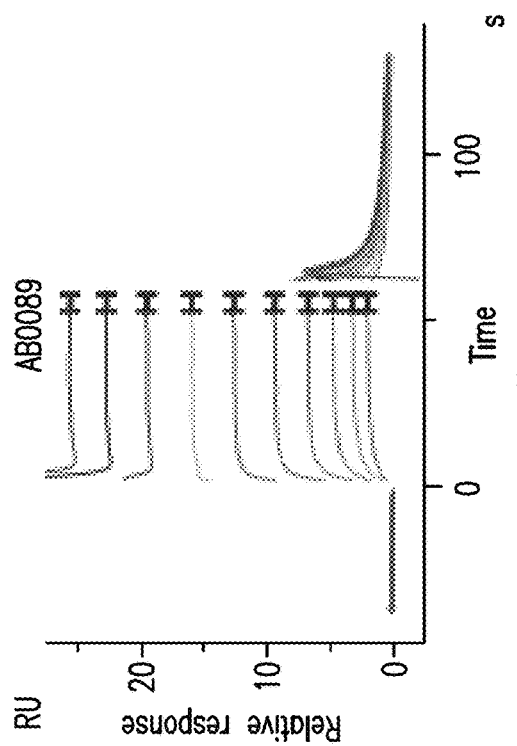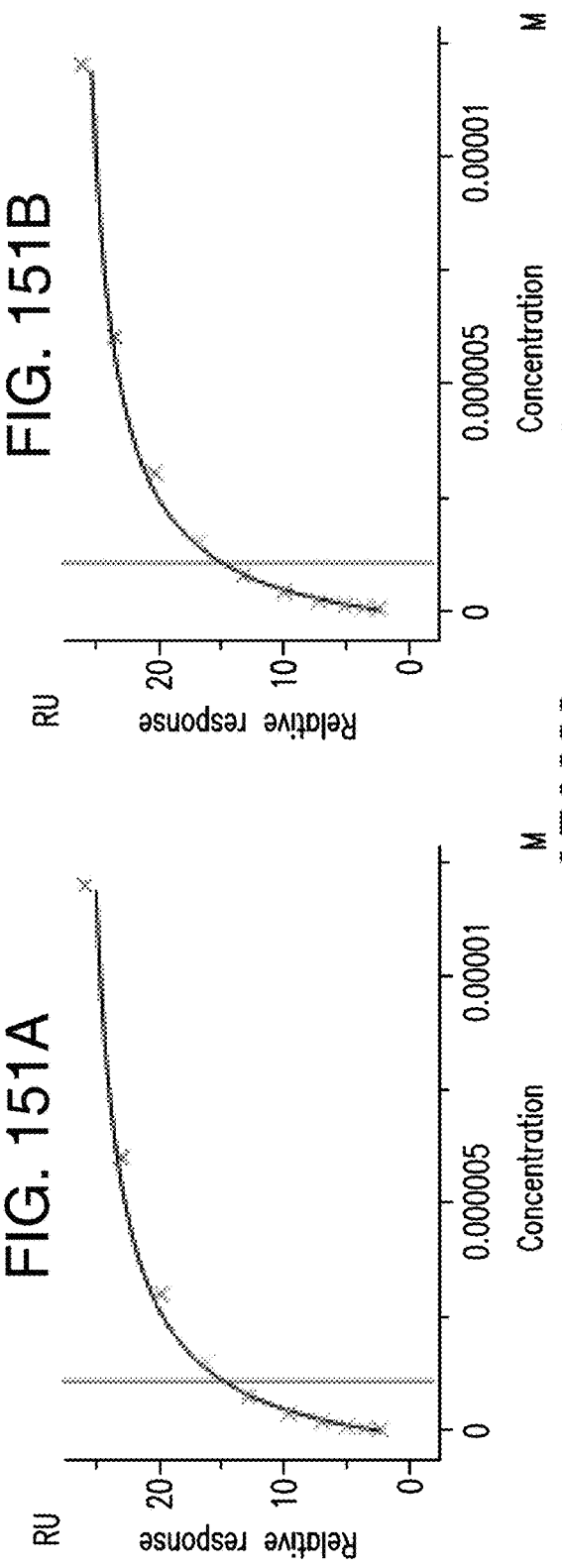

AB0089
$K_D = 1.0 \pm 0.1 \, \mu M$

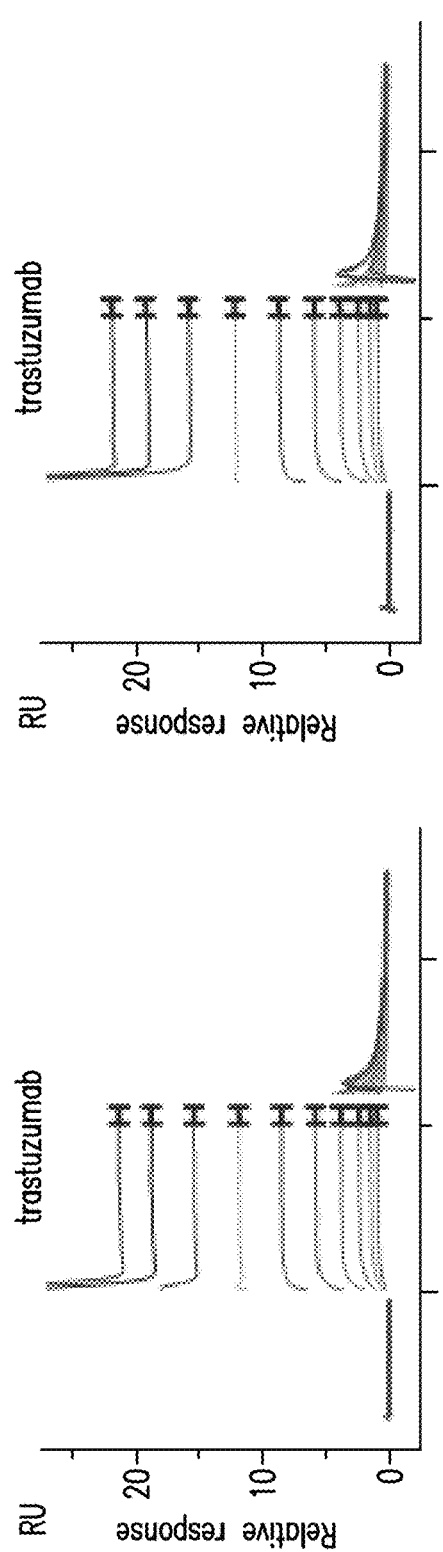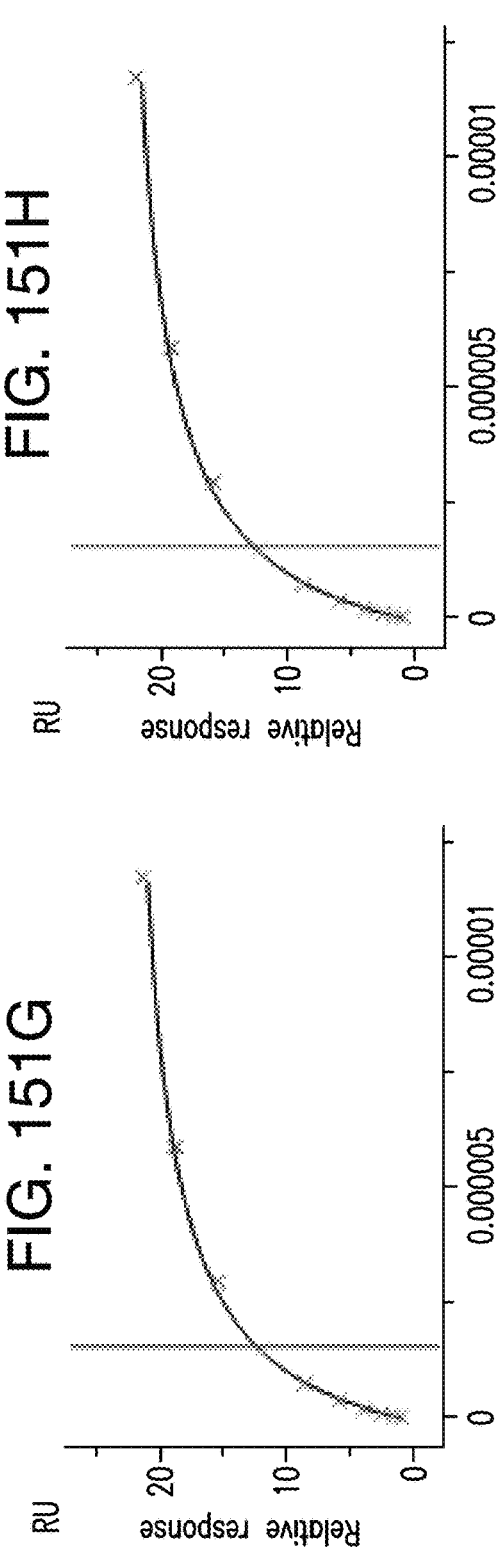

trastuzumab

$K_D = 1.5 \pm 0.2\ \mu M$

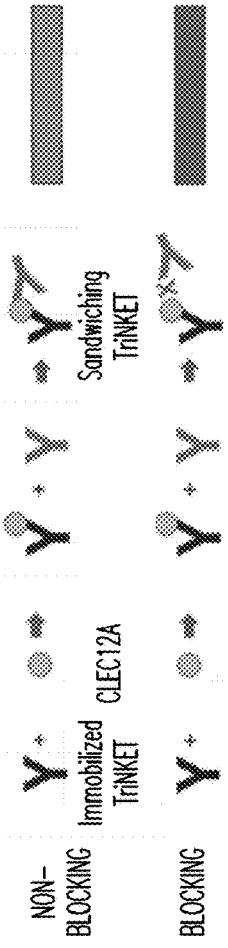
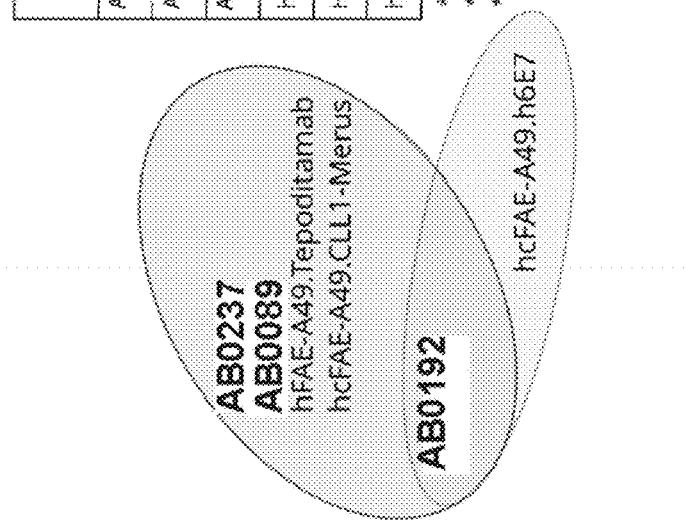
FIG. 154

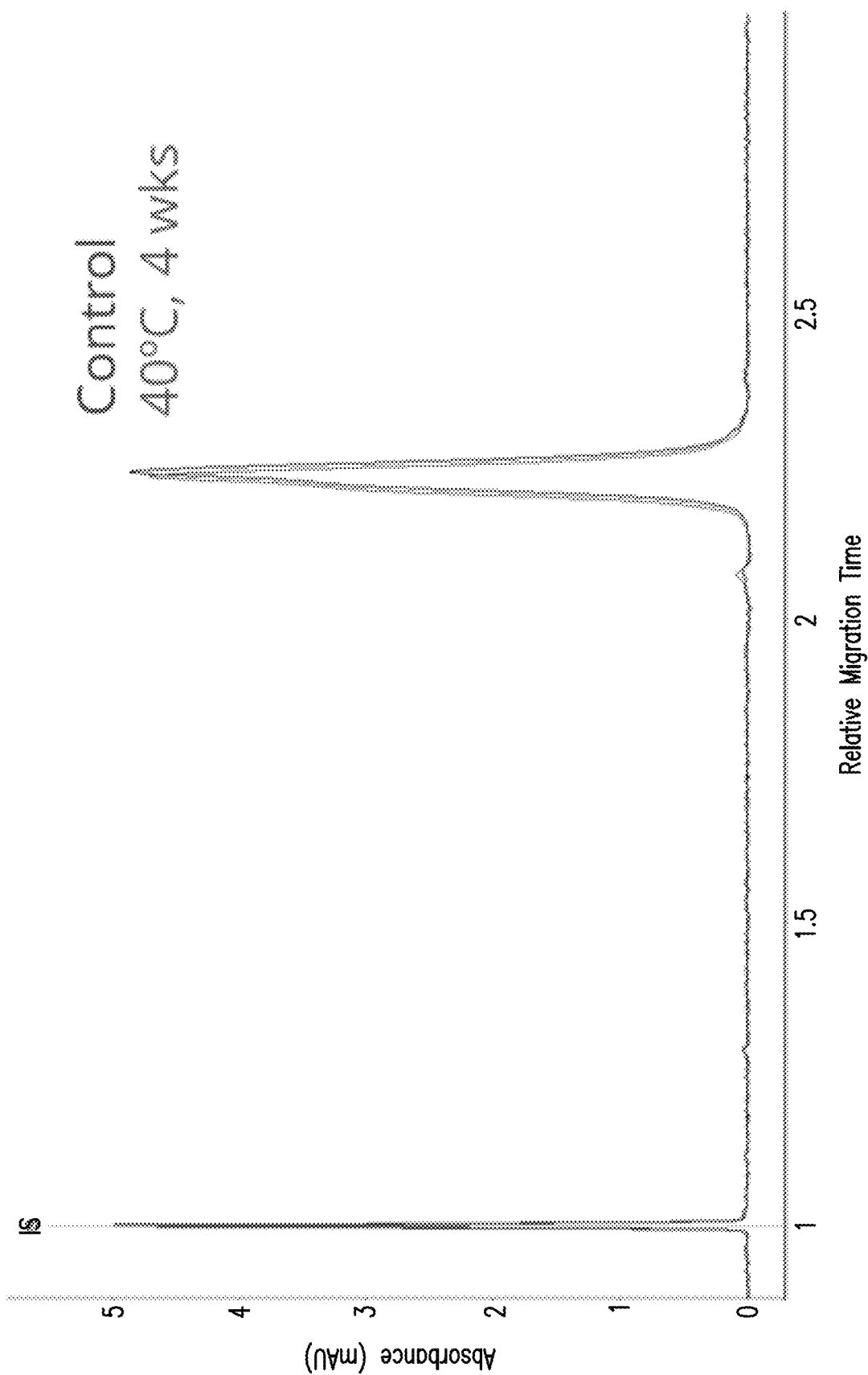

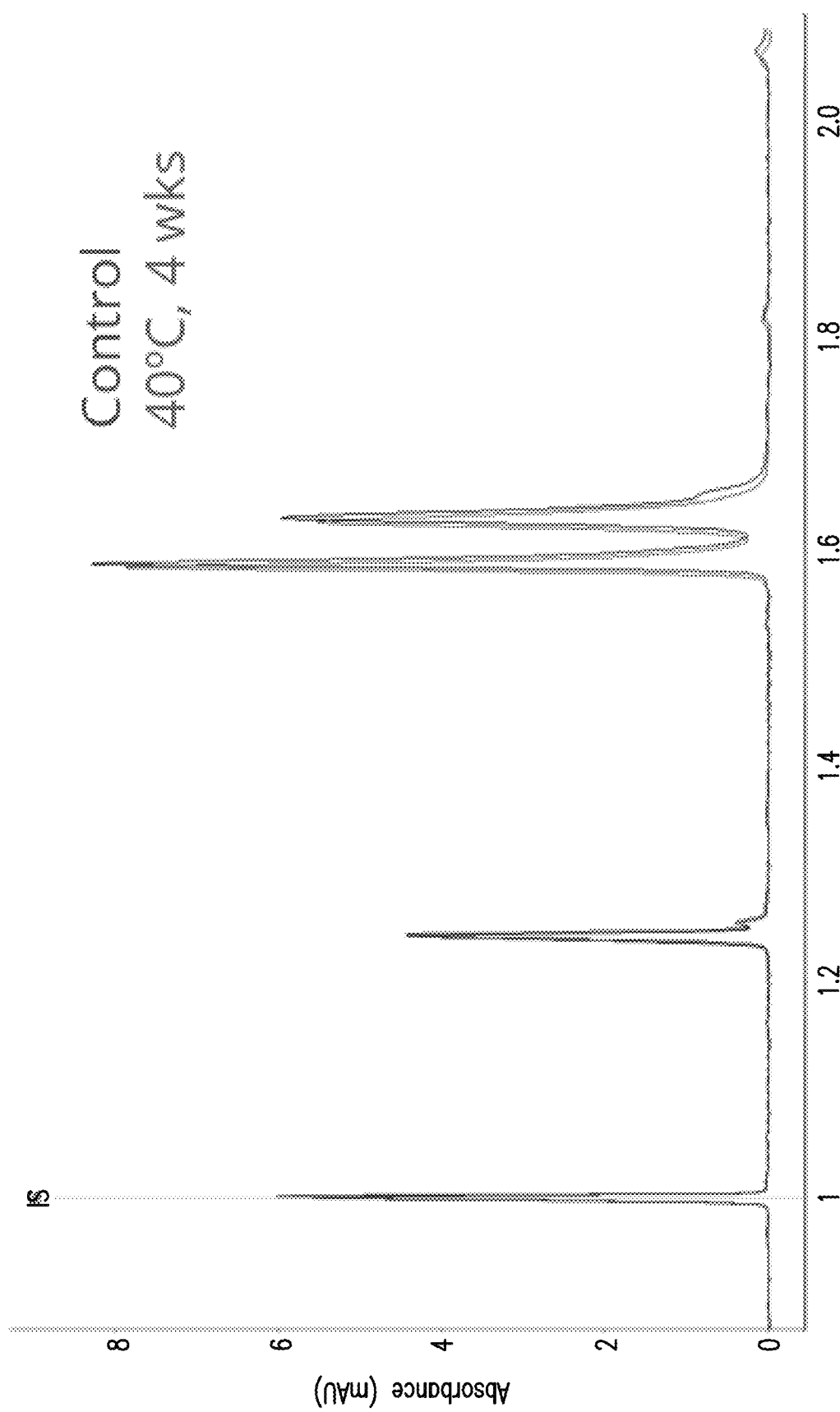

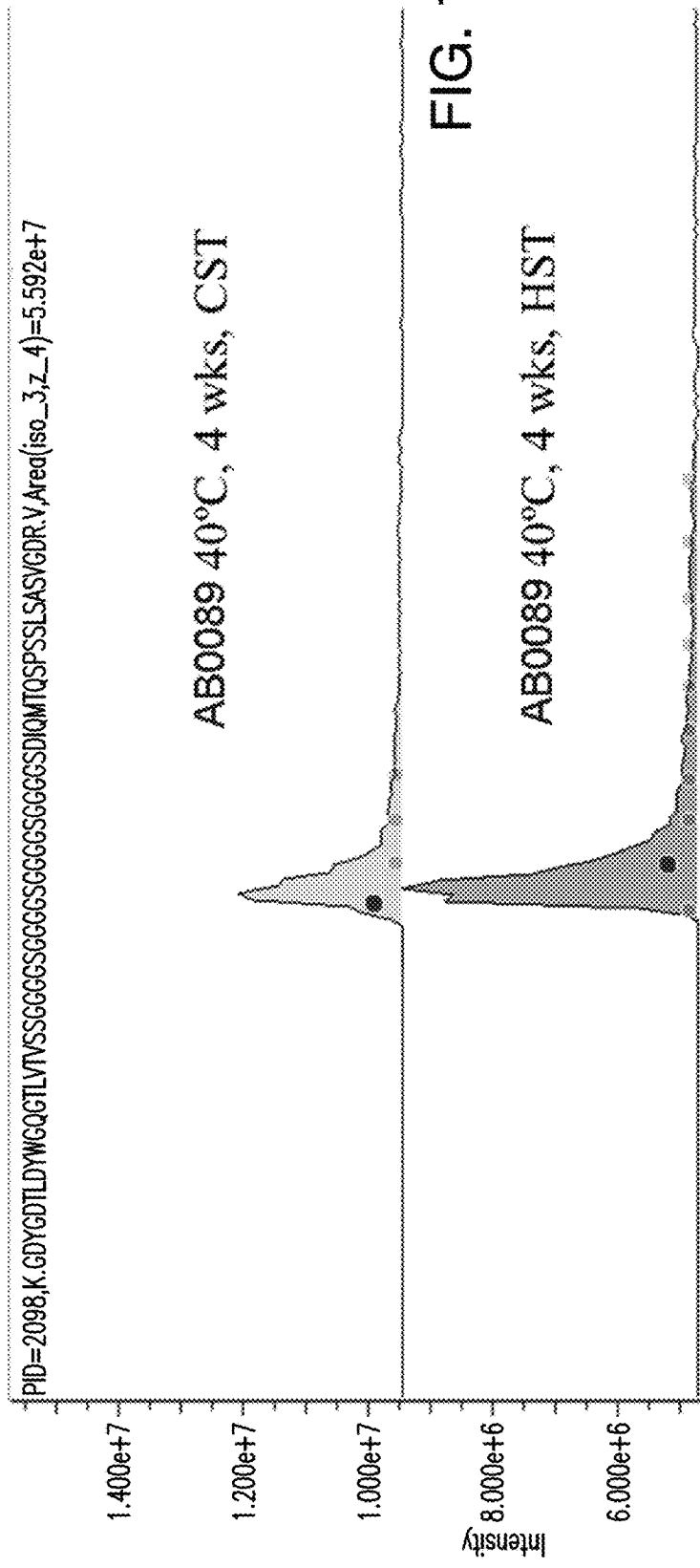
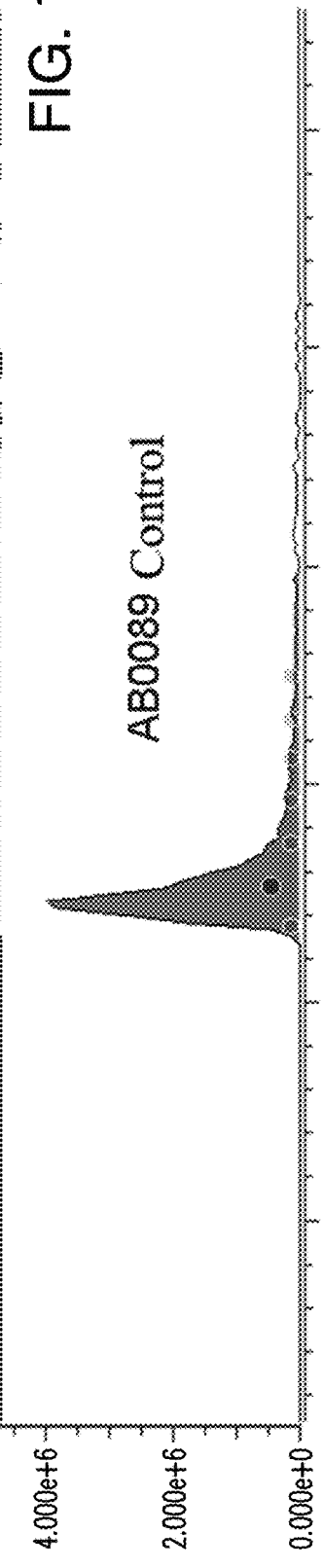
FIG. 167A
FIG. 167B
FIG. 167C

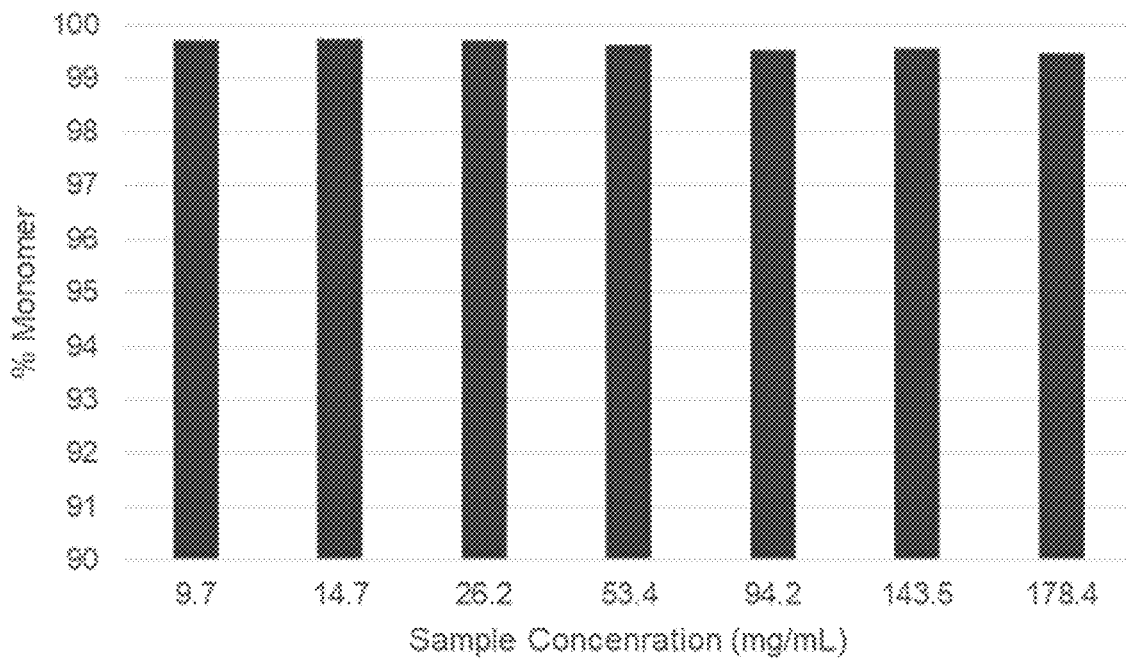
FIG. 187
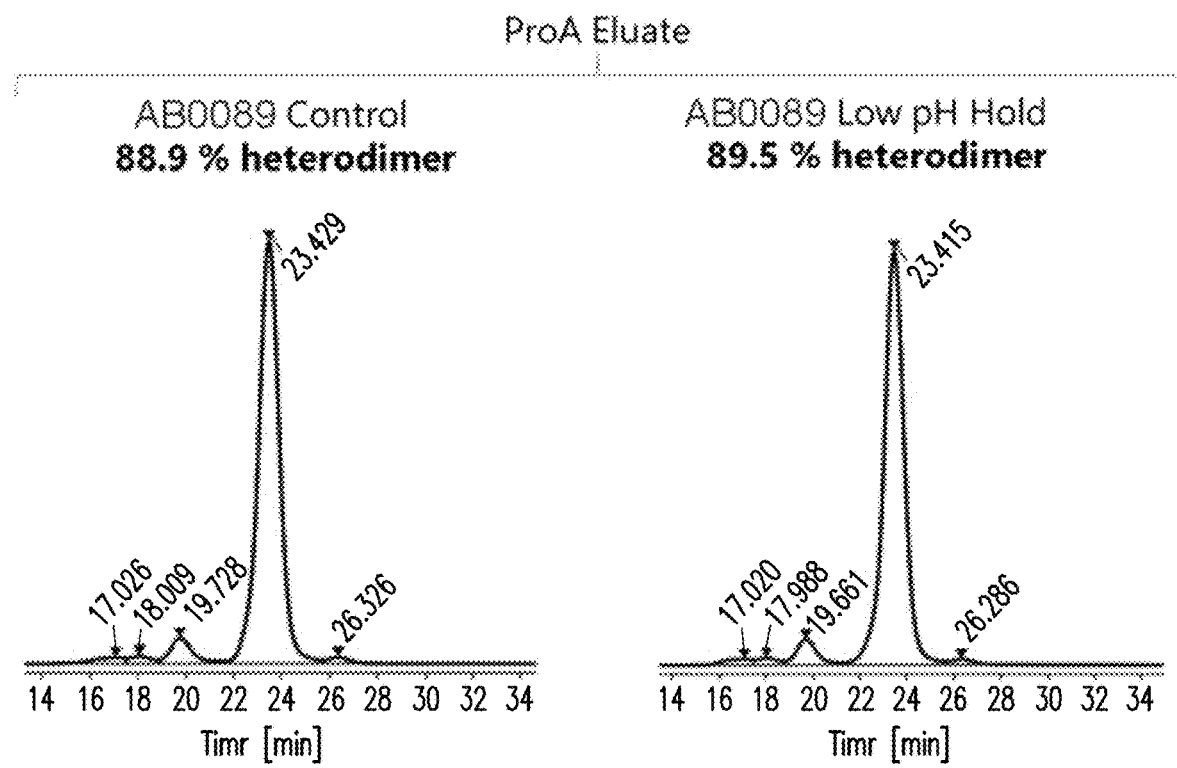
FIG. 188A
FIG. 188B

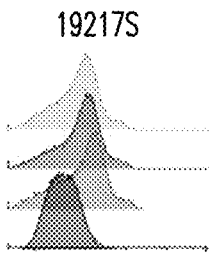
FIG. 206A 19217S
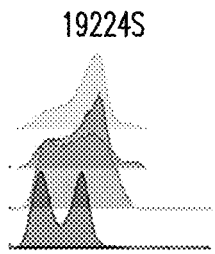
FIG. 206B 19224S
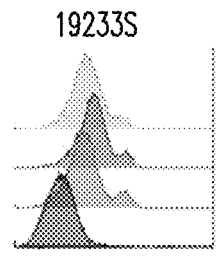
FIG. 206C 19233S
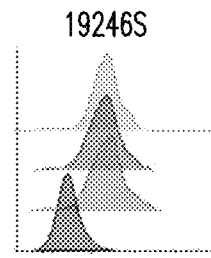
FIG. 206D 19246S
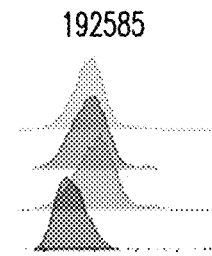
FIG. 206E 19258S
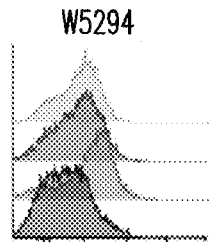
FIG. 206F W5294
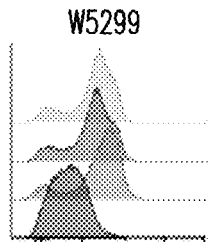
FIG. 206G W5299
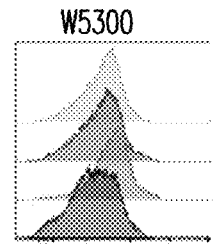
FIG. 206H W5300
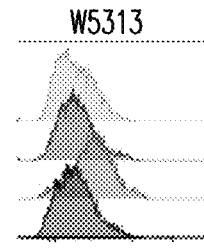
FIG. 206I W5313
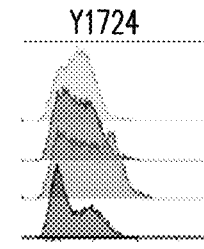
FIG. 206J Y1724
FIG. 207A 19217S
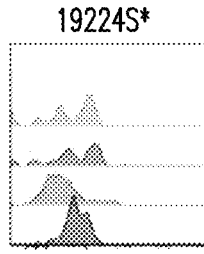
FIG. 207B 19224S*
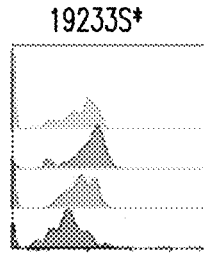
FIG. 207C 19233S*
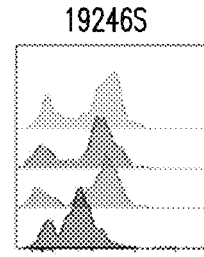
FIG. 207D 19246S
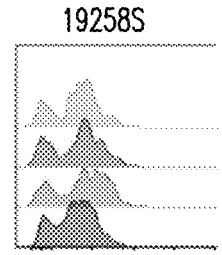
FIG. 207E 19258S
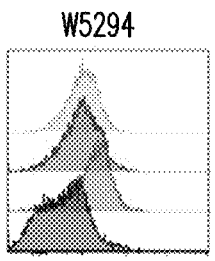
FIG. 207F W5294
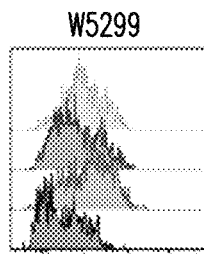
FIG. 207G W5299
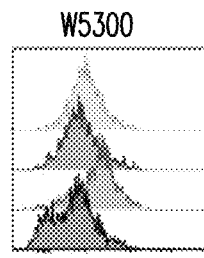
FIG. 207H W5300
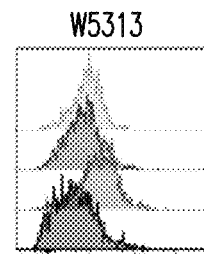
FIG. 207I W5313
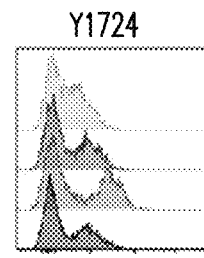
FIG. 207J Y1724

FIG. 210

Chain S: anti-CLEC12A scFv-CH2-CH3 (humanized sequence, CDRs are bold and not underlined, back mutations are bold and underlined, engineered scFv disulfide in italic and bold, and Fc mutations for heterodimerization and the engineered CH3 disulfide are underlined and not bold).

EVQLVESGGGVVQPGGSLRLSCAASGFTFNAFGMHWVRQAPGK*C*LEWVAFISSGSTSIYYANT
VKGRFTISRDNSKNTLYLQMNSLRAEDTAVYYCARDGYPTGGAMDYWGQGTSVTVSSGGGGS
GGGGSGGGGSGGGGSDIQMTQSPSSLSASVGDRVTITCKASQDIYNYLSWFQQKPGKAPKPLIY
RANILVSGVPSRFSGSGSGQDYTFTISSLQPEDIATYYCLQFDAFPFTF*G*CGTKLEIKGSDKTHTC
PPCPAPELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPRVYTLPPCR
DELTKNQVSLTCLVKGFYPSDIAVEWESNGQPENNYKTTPPVLSDGSFTLYSKLTVDKSRWQQ
GNVFSCSVMHEALHNHYTQKSLSLSPG (SEQ ID NO:278)

Chain H: anti-NKGD VH-CH1-CH2-CH3 (fully human, CDRs are bold and not underlined, Fc mutations for heterodimerization and the engineered CH3 disulfide are underlined and not bold)

EVQLVESGGGLVKPGGSLRLSCAASGFTFSSYSMNWVRQAPGKGLEWVSSISSSSSYIYYADSVK
GRFTISRDNAKNSLYLQMNSLRAEDTAVYYCARGAPIGAAAGWFDPWGQGTLVTVSSASTKGP
SVFPLAPSSKSTSGGTAALGCLVKDYFPEPVTVSWNSGALTSGVHTFPAVLQSSGLYSLSSVVTVP
SSSLGTQTYICNVNHKPSNTKVDKKVEPKSCDKTHTCPPCPAPELLGGPSVFLFPPKPKDTLMISRT
PEVTCVVVDVSHEDPEVKFNWYVDGVEVHNAKTKPREEQYNSTYRVVSVLTVLHQDWLNGKE
YKCKVSNKALPAPIEKTISKAKGQPREPQVCTLPPSRDELTENQVSLTCLVKGFYPSDIAVEWESN
GQPENNYKTTPPVLDSDGSFFLYSWLTVDKSRWQQGNVFSCSVMHEALHNHYTQKSLSLSPG
(SEQ ID NO:260)

Chain L: anti-NKGD VL-CL (fully human, CDRs are bold and not underlined)

DIQMTQSPSSVSASVGDRVTITCRASQGISSWLAWYQQKPGKAPKLLIYAASSLQSGVPSRFSGS
GSGTDFTLTISSLQPEDFATYYCQQGVSFPRTFGGGTKVEIKRTVAAPSVFIFPPSDEQLKSGTAS
VVCLLNNFYPREAKVQWKVDNALQSGNSQESVTEQDSKDSTYSLSSTLTLSKADYEKHKVYAC
EVTHQGLSSPVTKSFNRGEC (SEQ ID NO:261)

■: negatively charged  ■: positively charged  □: hydrophobic

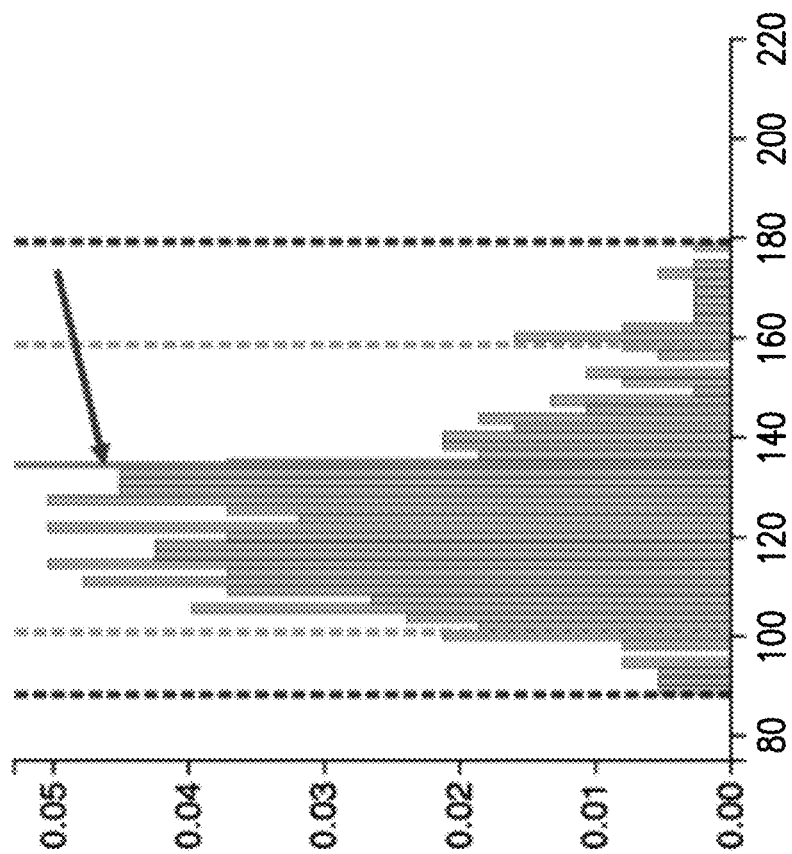
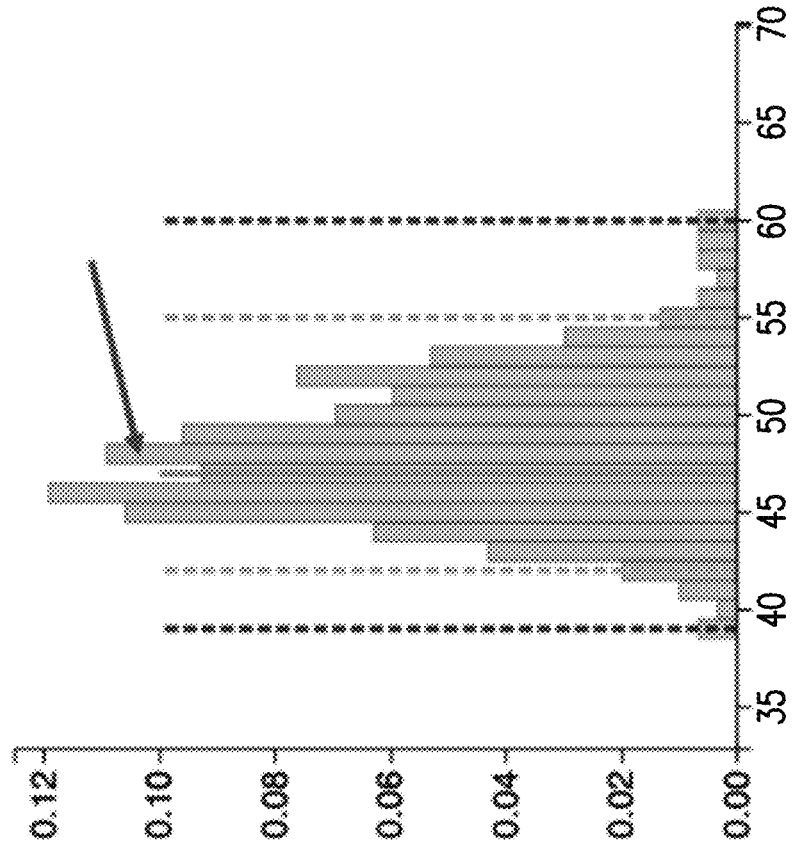
FIG. 213A
FIG. 213B

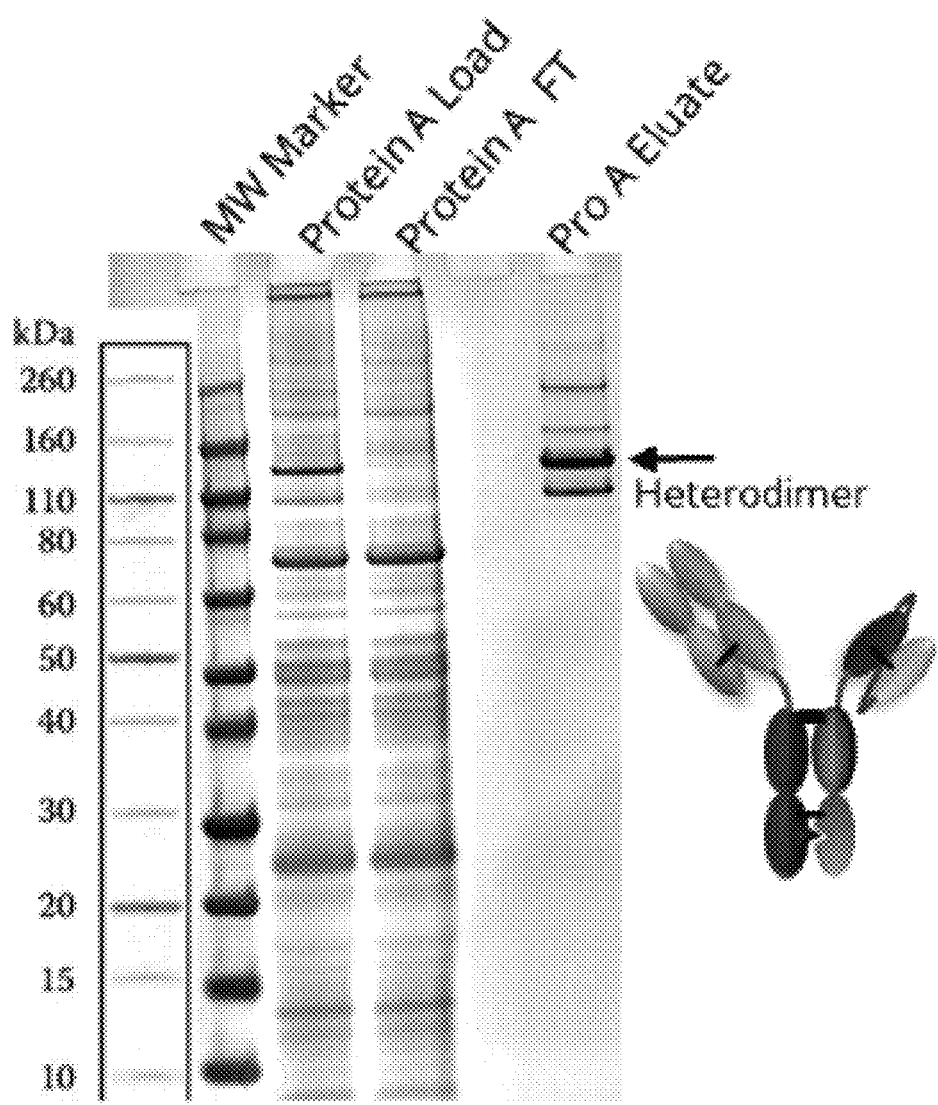
Plasmid ratio unoptimized.
FIG. 219A

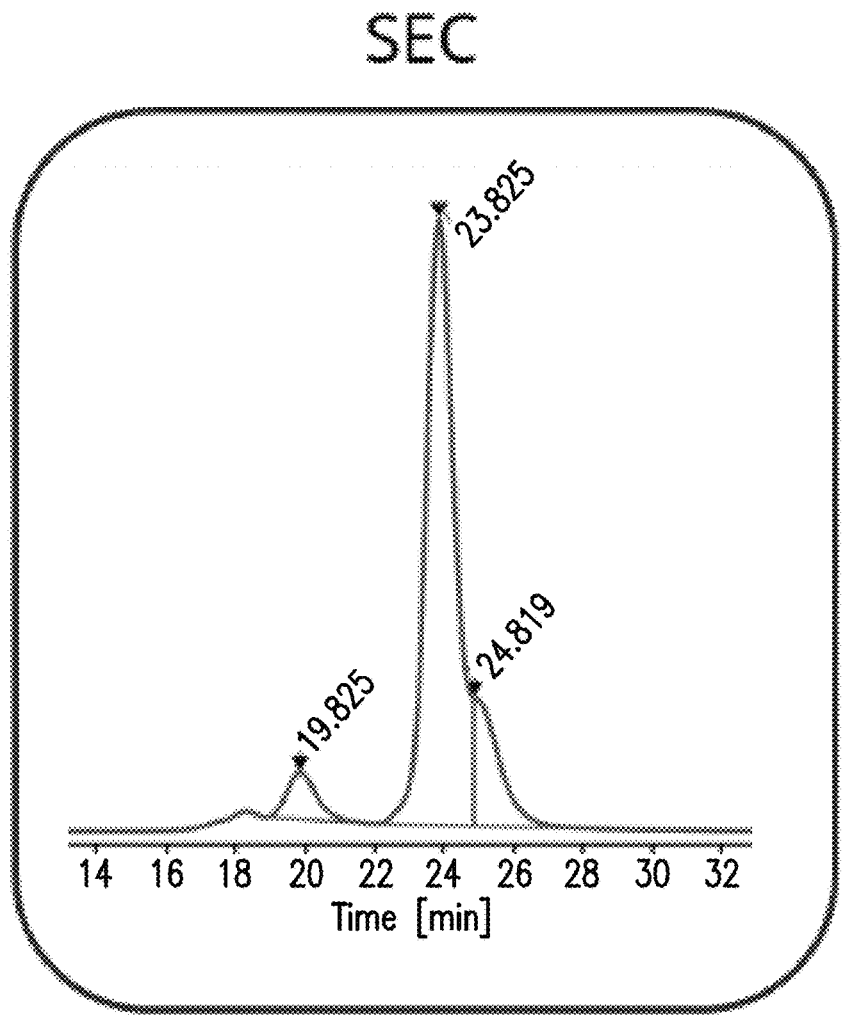
ProA Eluate:
~79% F3' heterodimer
FIG. 219B
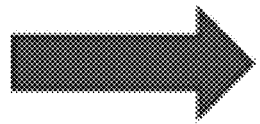

CEX Chromatography

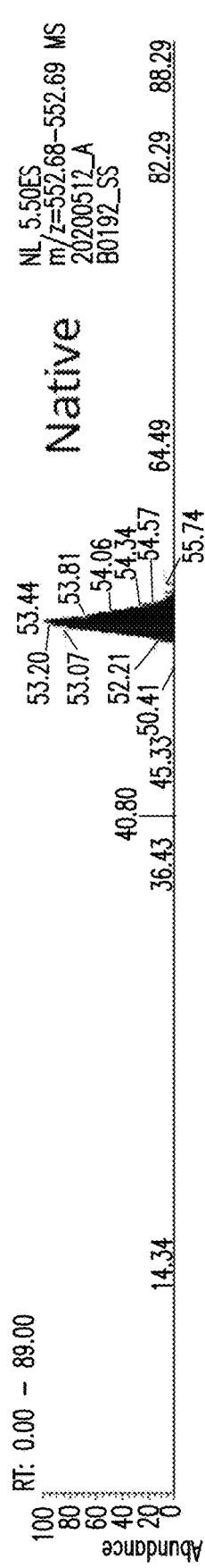
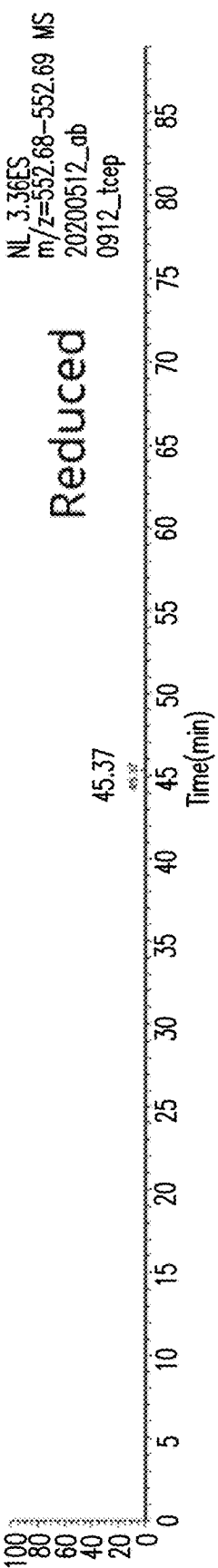
FIG. 228A
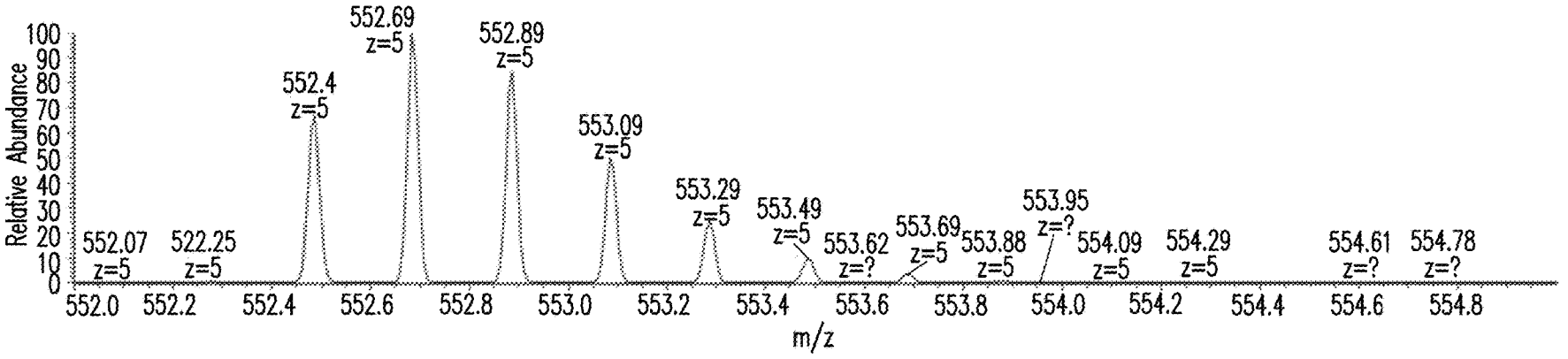
FIG. 228B

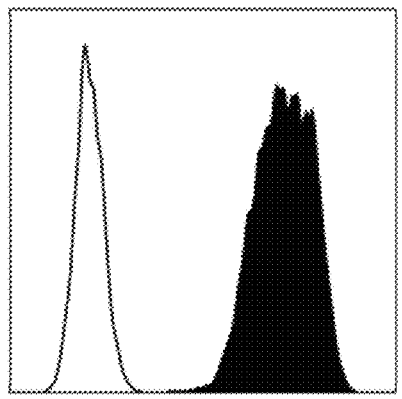
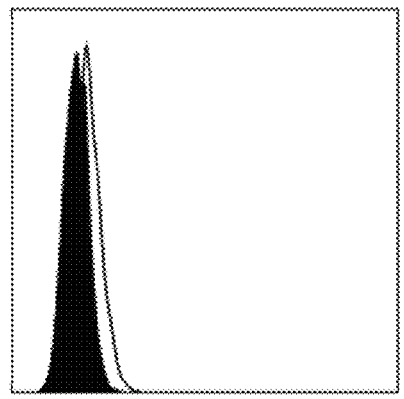
No fill = hIgG1 isotype
Black fill = AB0192
FIG. 232A
FIG. 232B
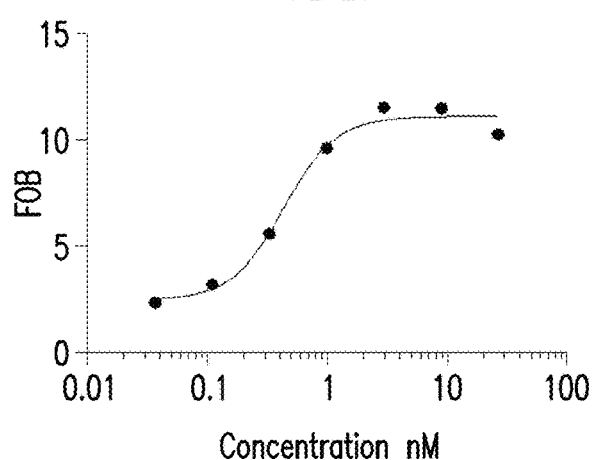
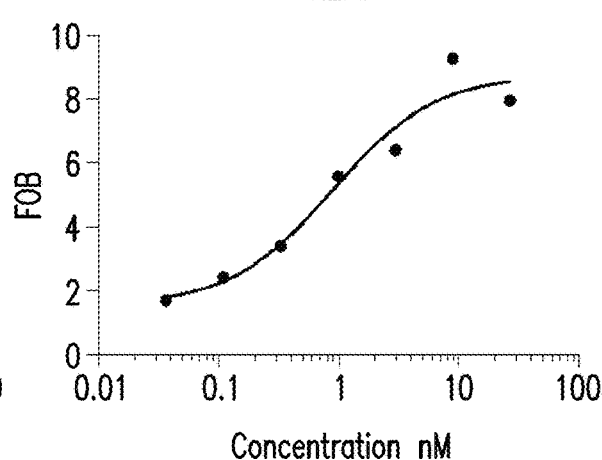
FIG. 232C
FIG. 232D Group 7
AB0192-005; mFc-cNKG2D; Steady state affinity Group 8
AB0192-005; mFc-cNKG2D; Steady state affinity Group 9
AB0192-005; mFc-cNKG2D; Steady state affinity Group 15
AB0192-005; 1:1 binding Group 25
trastuzumab; 1:1 binding Group 26
trastuzumab; 1:1 binding Group 27
trastuzumab; 1:1 binding

AB0192

$K_D = 5.2 \pm 1.2$ nM

AB0192

$K_D = 5.2 \pm 1.2$ nM trastuzumab
$K_D = 2.9 \pm 0.4\,nM$ trastuzumab
$K_D = 2.9 \pm 0.4 \, nM$

AB0192

$K_D = 1.9 \pm 0.3 \text{ nM}$

AB0192

$K_D = 1.9 \pm 0.3\,nM$ trastuzumab
$K_D = 1.0 \pm 0.1$ nM trastuzumab
$K_D = 1.0 \pm 0.1$ nM

AB0192  $K_D = 1011.3 \pm 63.3$ nM

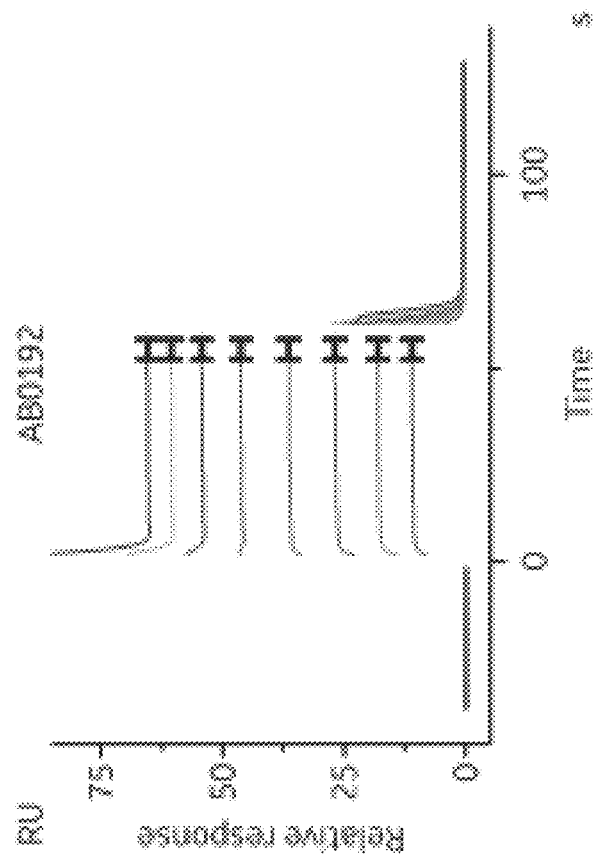
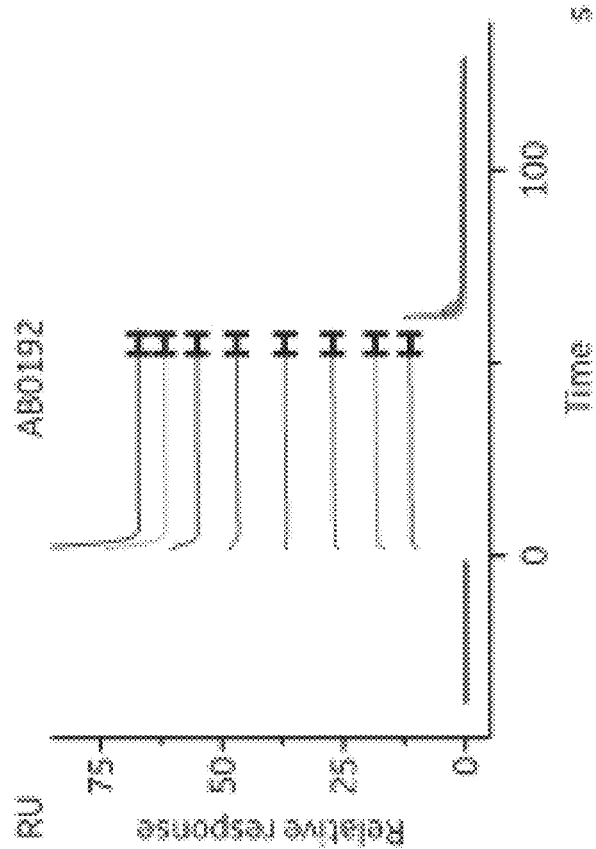
AB0192
$K_D = 1011.3 \pm 63.3$ nM
FIG. 239C
FIG. 239D AB0192  $K_D = 1011.3 \pm 63.3$ nM

AB0192

$K_D = 1011.3 \pm 63.3$ nM trastuzumab
$K_D = 1045.1 \pm 62.2$ nM trastuzumab $K_D = 1045.1 \pm 62.2$ nM

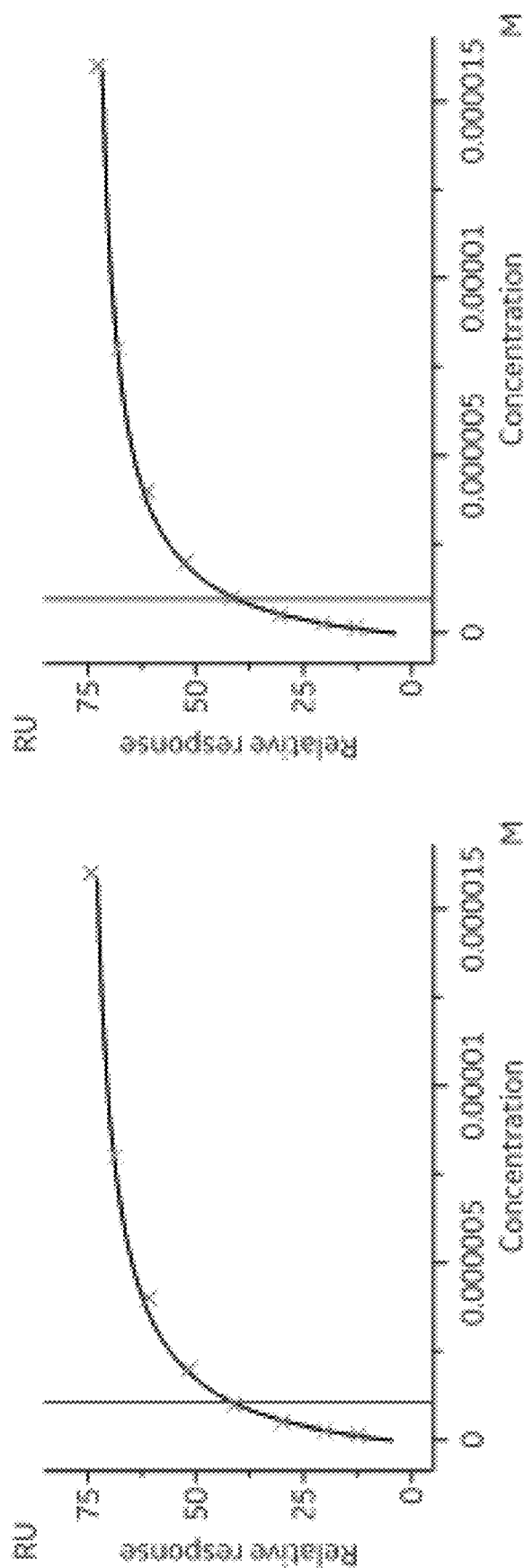

trastuzumab

$K_D = 1045.1 \pm 62.2$ nM

AB0192
$K_D = 1398.8 \pm 286.1$ nM

AB0192
$K_D = 1398.8 \pm 286.1$ nM

AB0192
$K_D = 1398.8 \pm 286.1$ nM

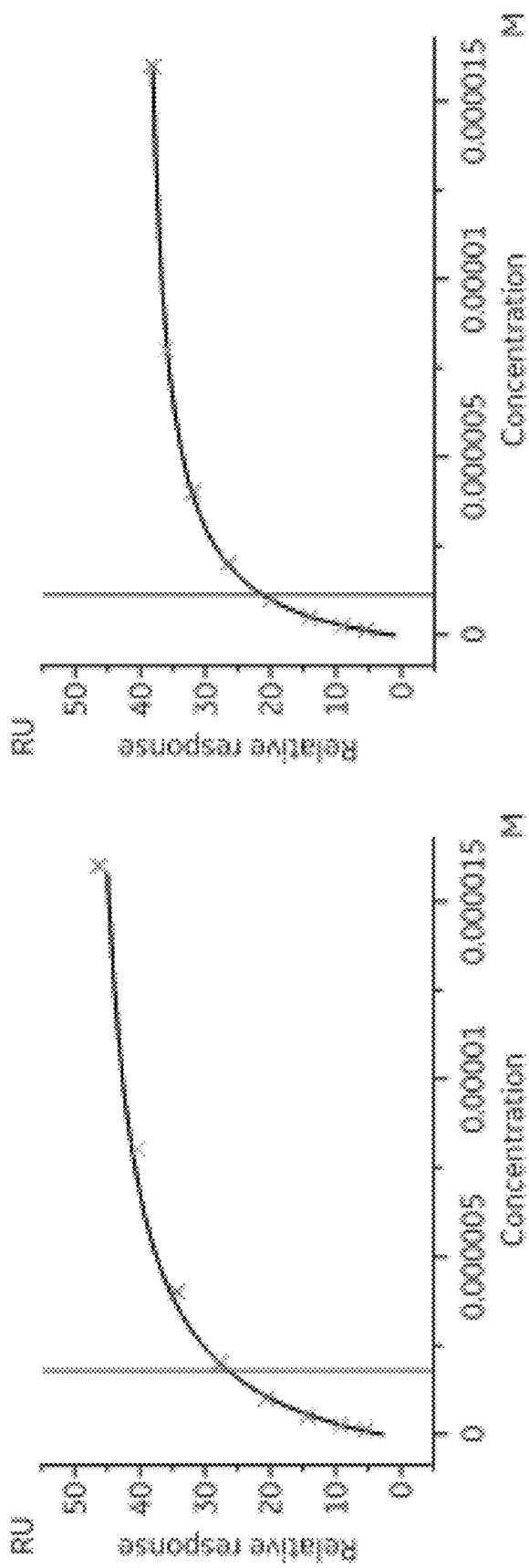
FIG. 240G  FIG. 240H  AB0192  $K_D = 1398.8 \pm 286.1$ nM trastuzumab
$K_D = 1493.2 \pm 265.9$ nM trastuzumab
$K_D = 1493.2 \pm 265.9$ nM

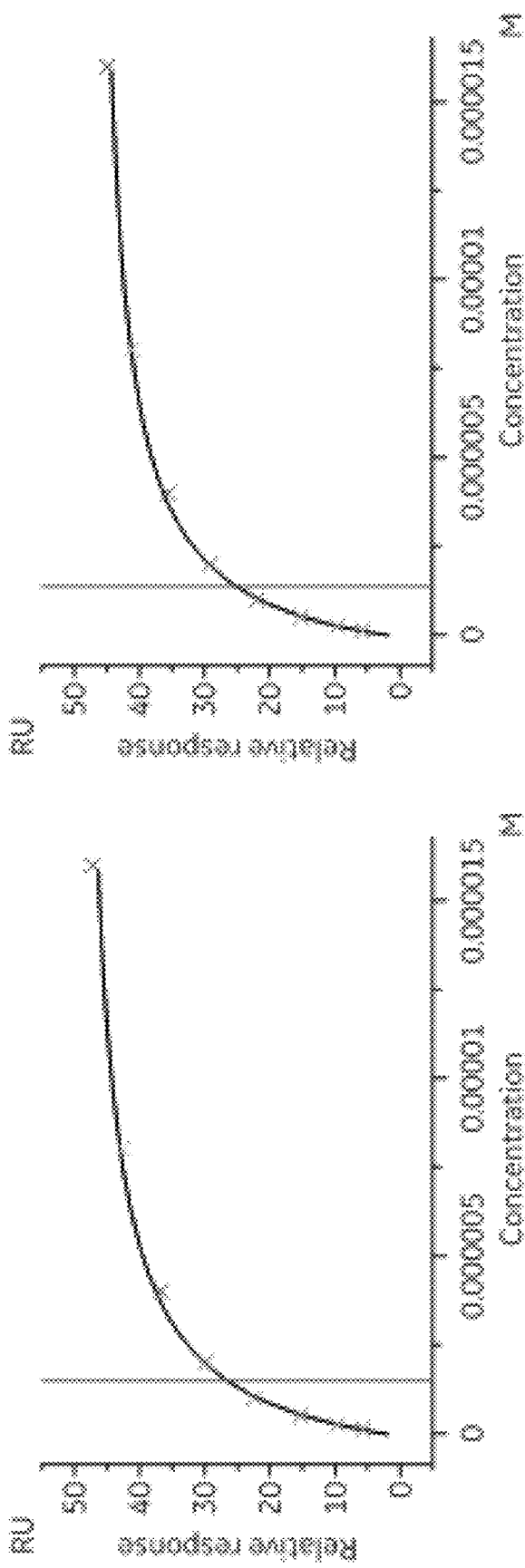
FIG. 240M  FIG. 240N  trastuzumab  $K_D = 1493.2 \pm 265.9$ nM

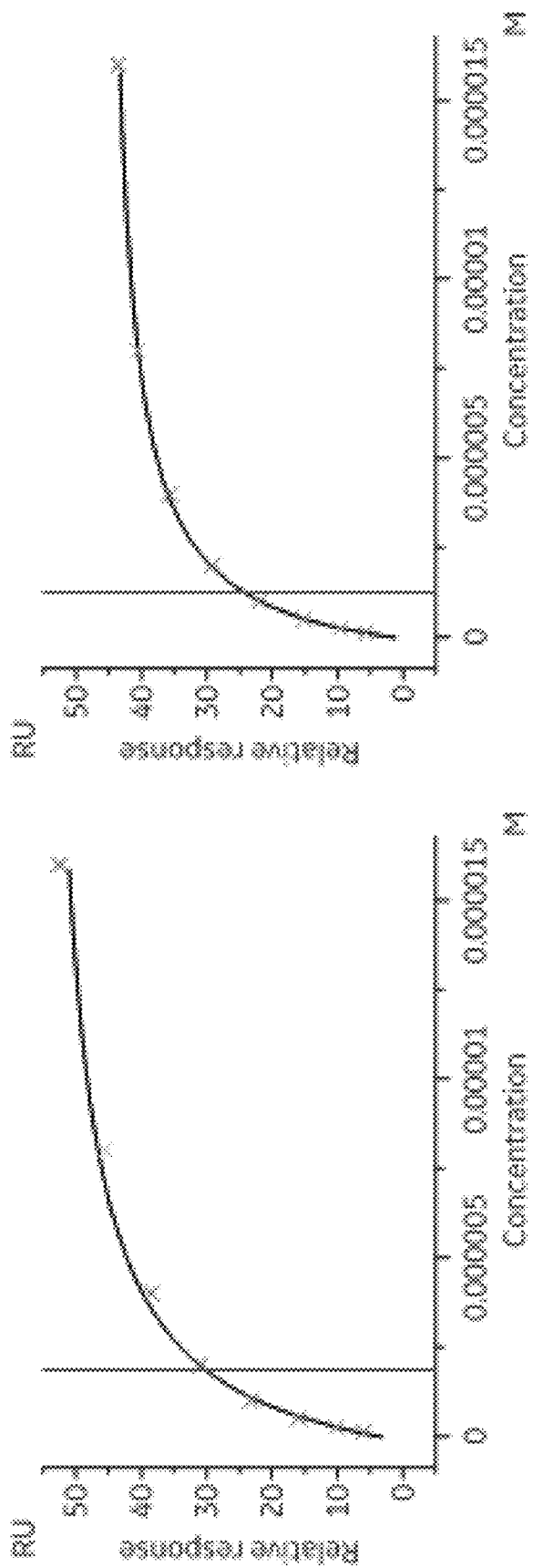

AB0192
$K_D = 680.0 \pm 69.6$ nM

AB0192
$K_D = 680.0 \pm 69.6$ nM

AB0192

$K_D = 680.0 \pm 69.6$ nM

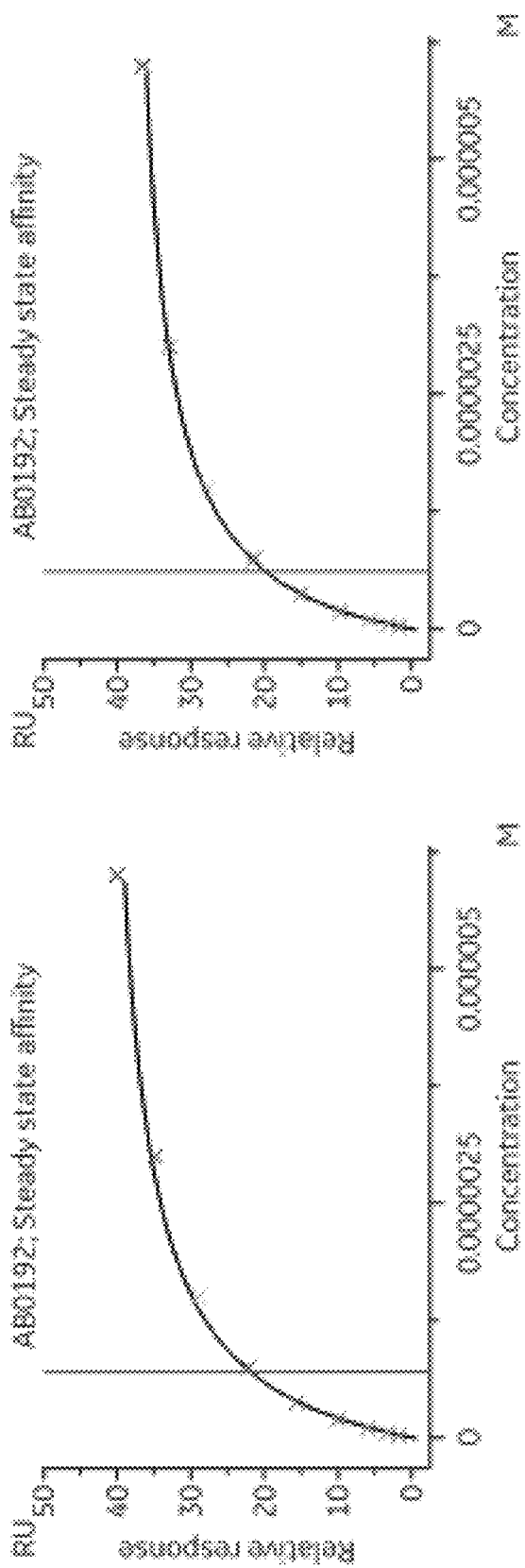

trastuzumab
$K_D = 331.4 \pm 3.3$ nM trastuzumab
$K_D = 331.4 \pm 3.3$ nM trastuzumab
$K_D = 331.4 \pm 3.3$ nM trastuzumab
$K_D = 331.4 \pm 3.3$ nM

AB0192
$K_D = 203.8 \pm 1.0$ nM

AB0192
$K_D = 203.8 \pm 1.0$ nM trastuzumab
$K_D = 128.8 \pm 2.1$ nM trastuzumab
$K_D = 128.8 \pm 2.1$ nM

AB0192
$K_D = 6.1 \pm 0.8\ \mu M$

AB0192
$K_D = 6.1 \pm 0.8\ \mu M$

AB0192

$K_D = 6.1 \pm 0.8\ \mu M$

AB0192
$K_D = 6.1 \pm 0.8 \, \mu M$ trastuzumab
$K_D = 6.3 \pm 1.0\ \mu M$ trastuzumab
$K_D = 6.3 \pm 1.0\ \mu M$ trastuzumab
$K_D = 6.3 \pm 1.0\ \mu M$

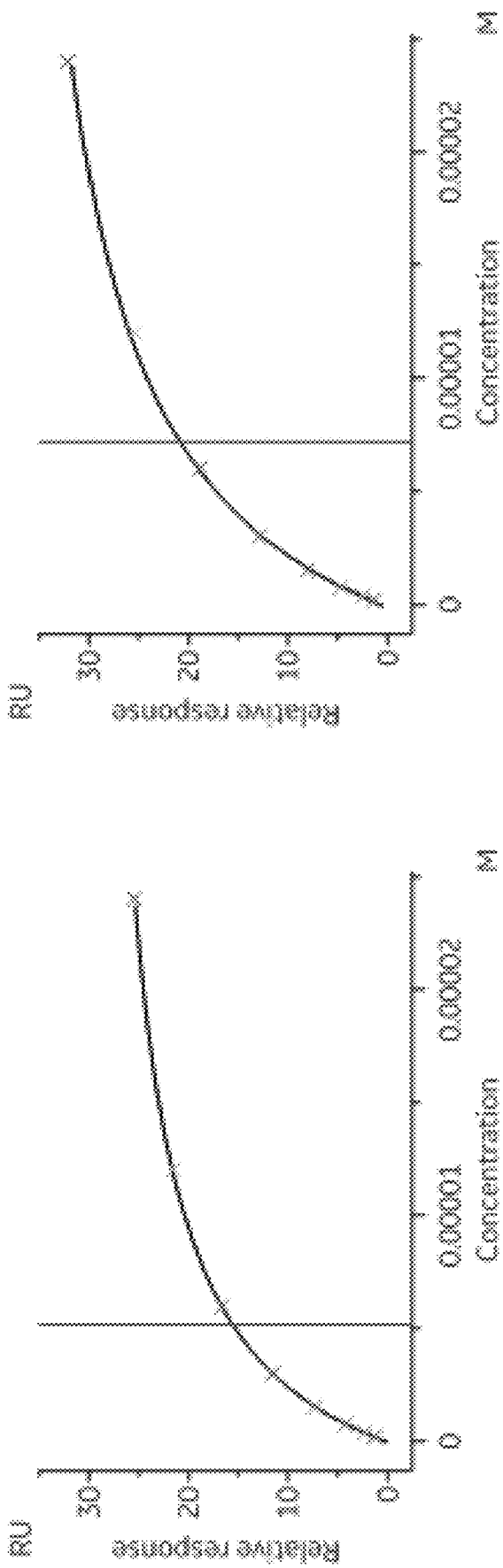
FIG. 243O   FIG. 243P   trastuzumab $K_D = 6.3 \pm 1.0\ \mu M$

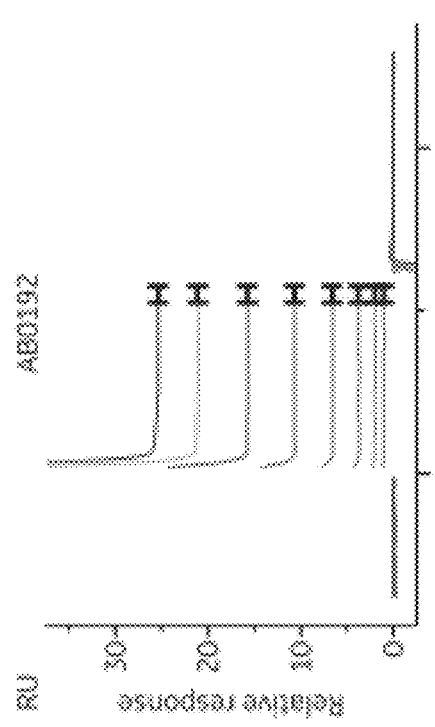
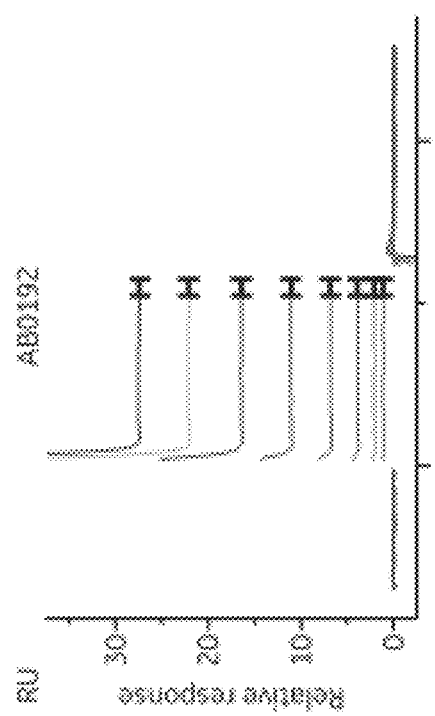
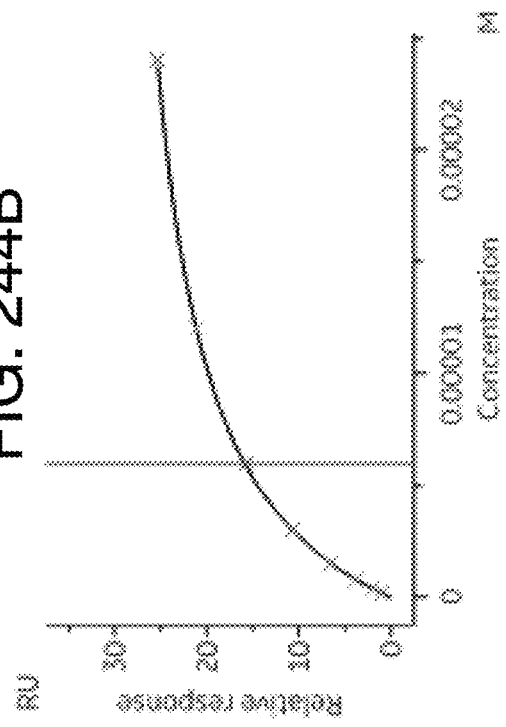
FIG. 244A
FIG. 244B
FIG. 244C
FIG. 244D
AB0192
$K_D = 6.0 \pm 0.7\ \mu M$

AB0192

$K_D = 6.0 \pm 0.7 \, \mu M$

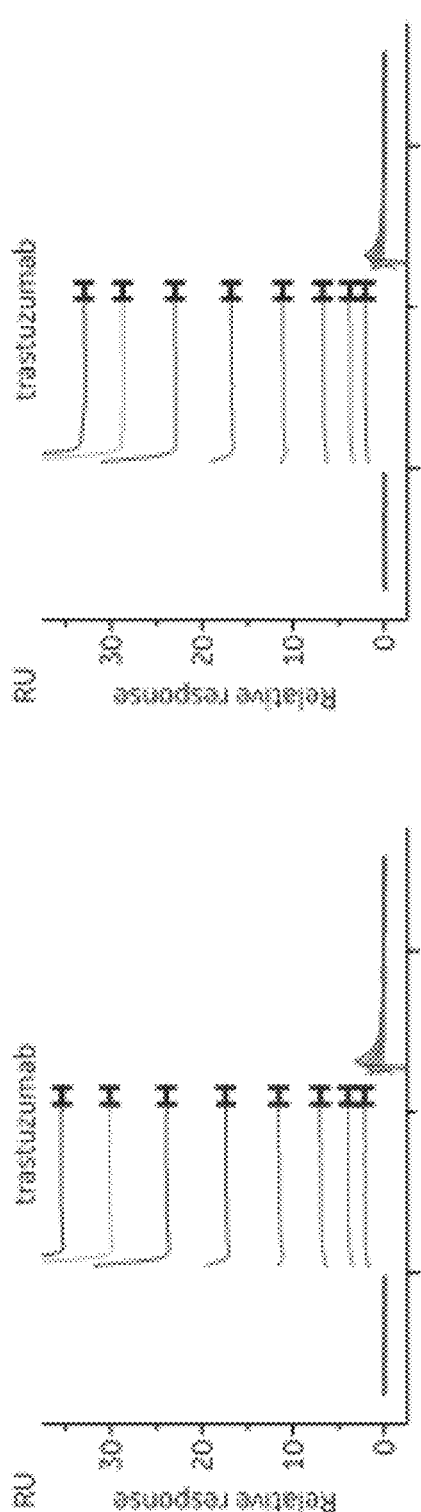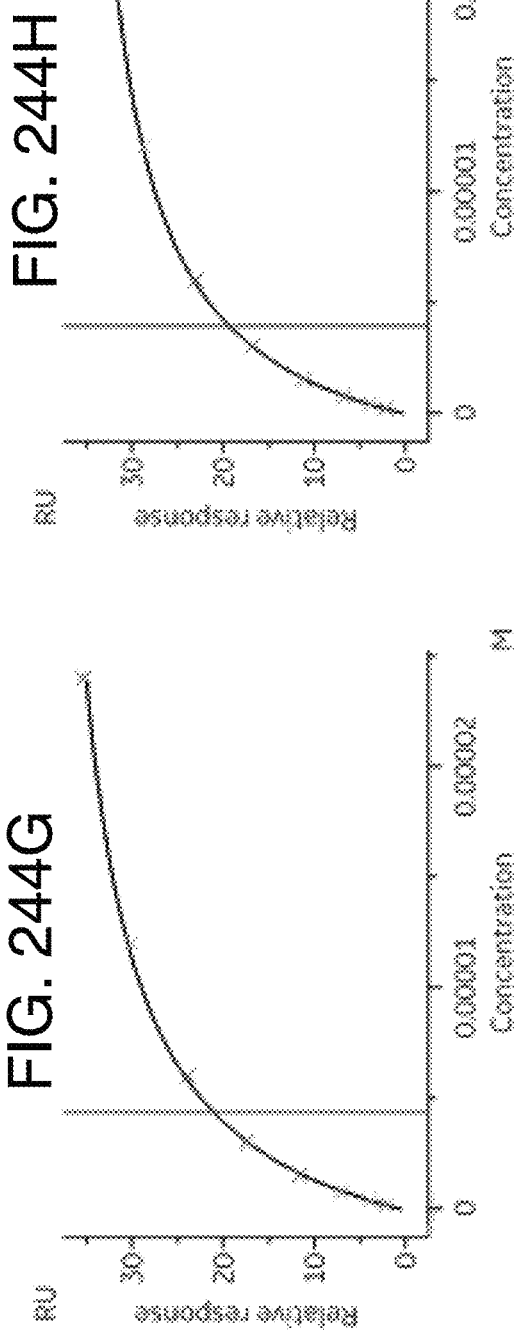
FIG. 244G  FIG. 244H  FIG. 244I  FIG. 244J  trastuzumab  $K_D = 3.9 \pm 0.5\ \mu M$ trastuzumab
$K_D = 3.9 \pm 0.5 \, \mu M$

AB0192
$K_D = 1.5 \pm 0.1\ \mu M$

AB0192
$K_D = 1.5 \pm 0.1\ \mu M$

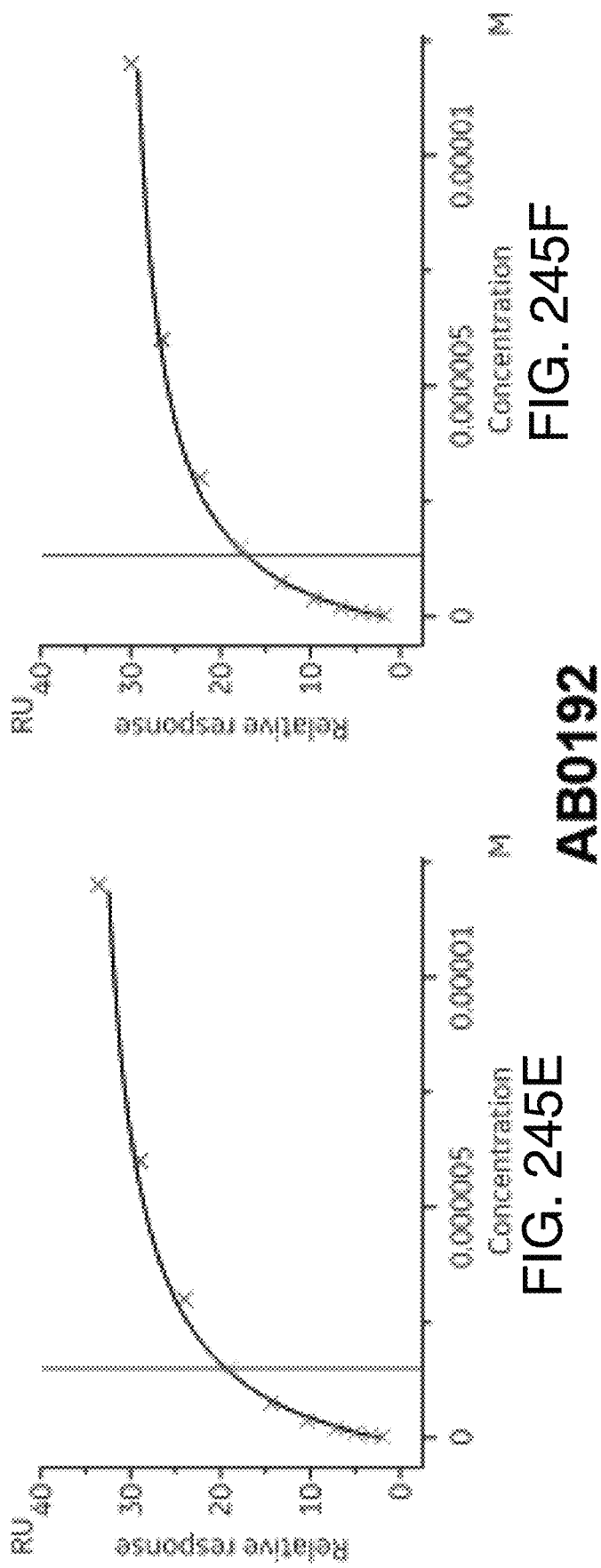

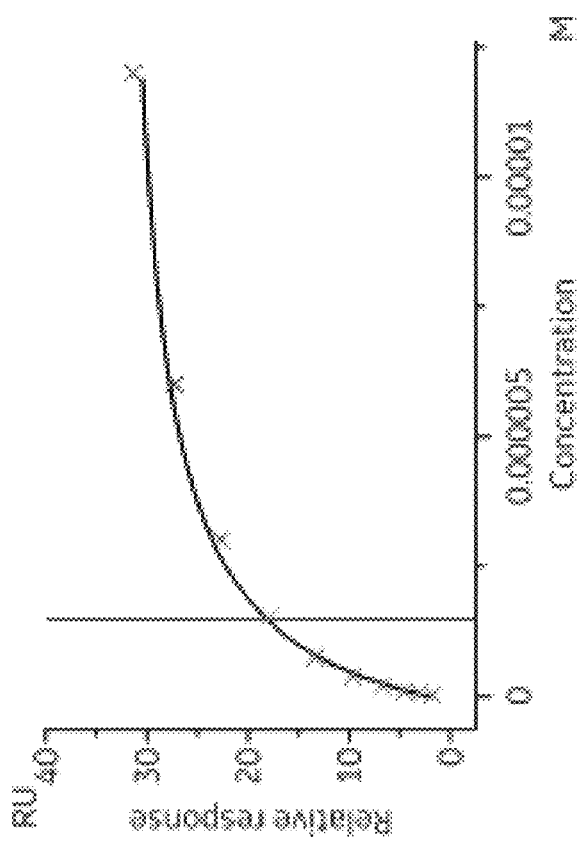
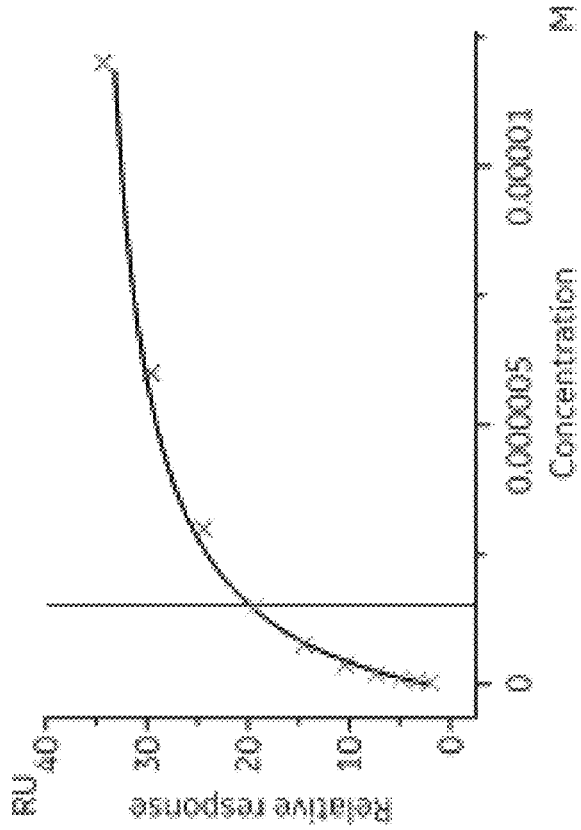
AB0192
$K_D = 1.5 \pm 0.1 \ \mu M$
FIG. 245G
FIG. 245H trastuzumab
$K_D = 1.7 \pm 0.2\ \mu M$ trastuzumab
$K_D = 1.7 \pm 0.2\ \mu M$ trastuzumab
$K_D = 1.7 \pm 0.2\ \mu M$ trastuzumab
$K_D = 1.7 \pm 0.2\ \mu M$

AB0192
$K_D = 1.4 \pm 0.1\ \mu M$

AB0192

$K_D = 1.4 \pm 0.1\ \mu M$

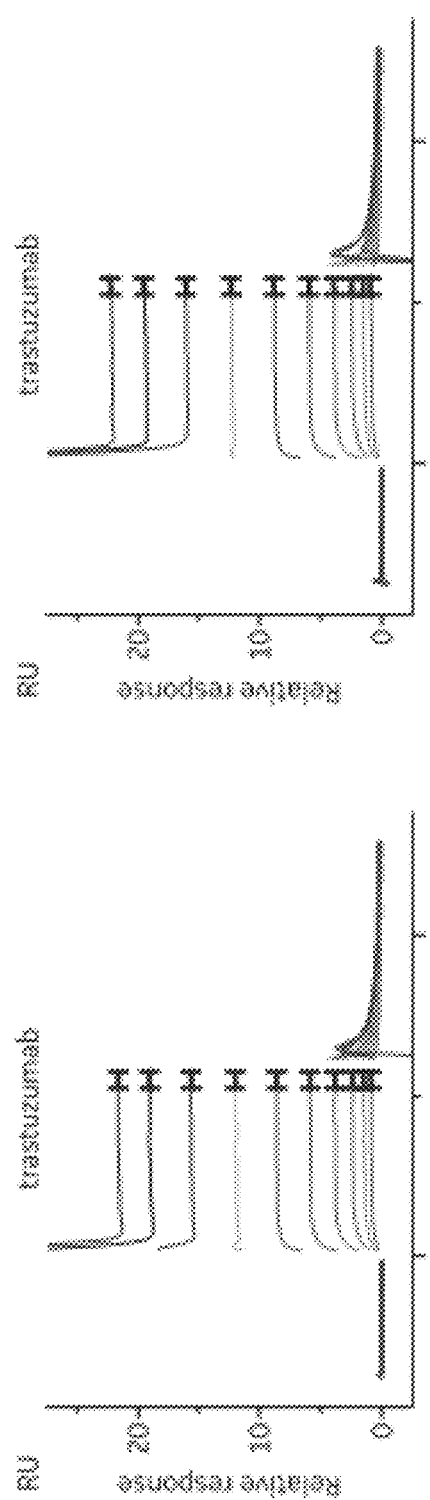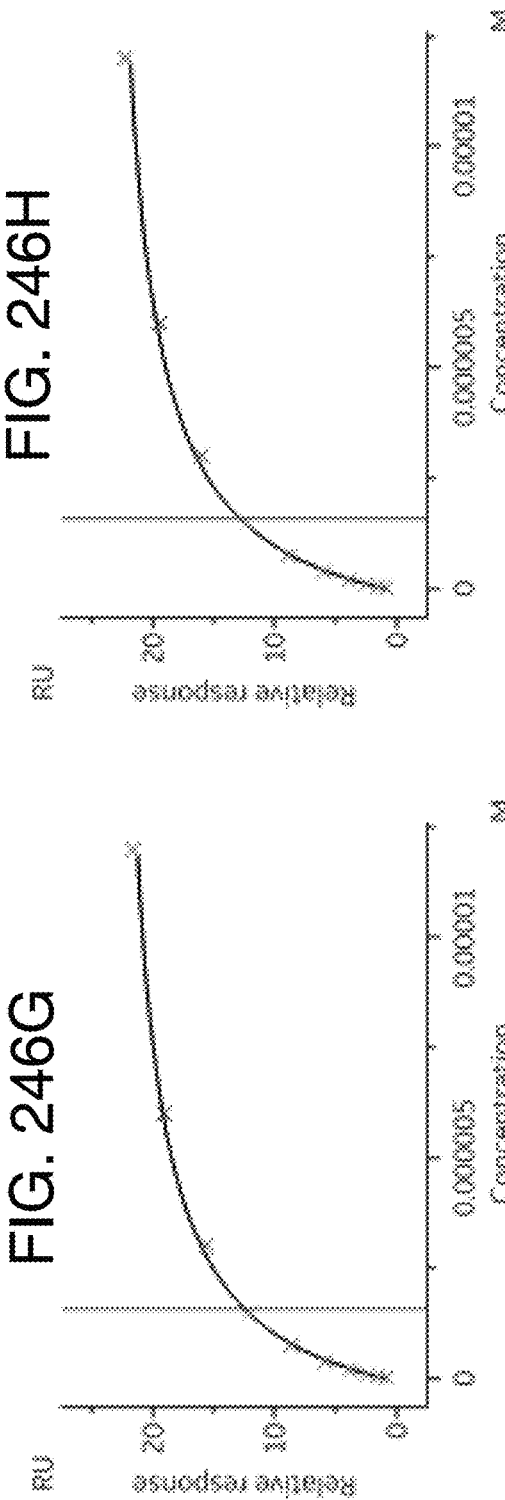
FIG. 246G, FIG. 246H, FIG. 246I, FIG. 246J
trastuzumab $K_D = 1.5 \pm 0.1 \, \mu M$ trastuzumab
$K_D = 1.5 \pm 0.1\ \mu M$

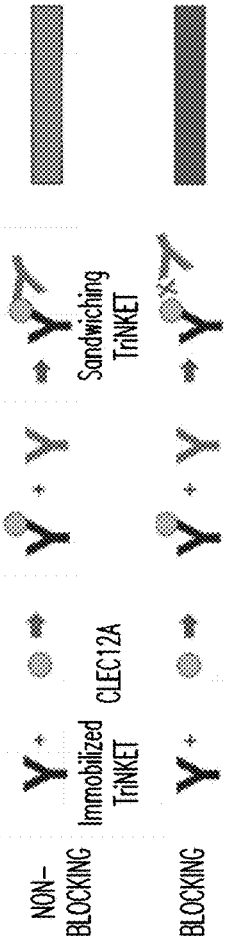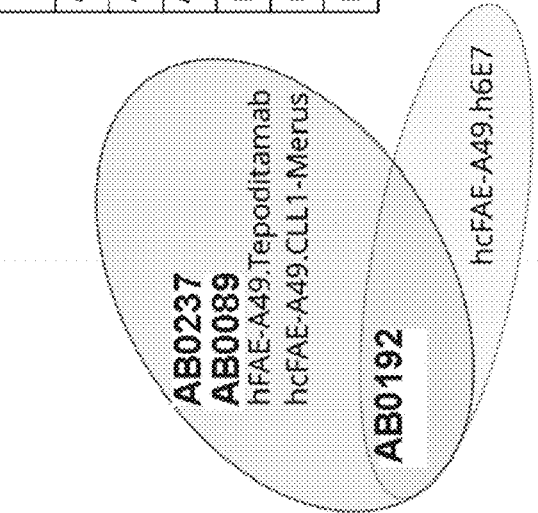
FIG. 247

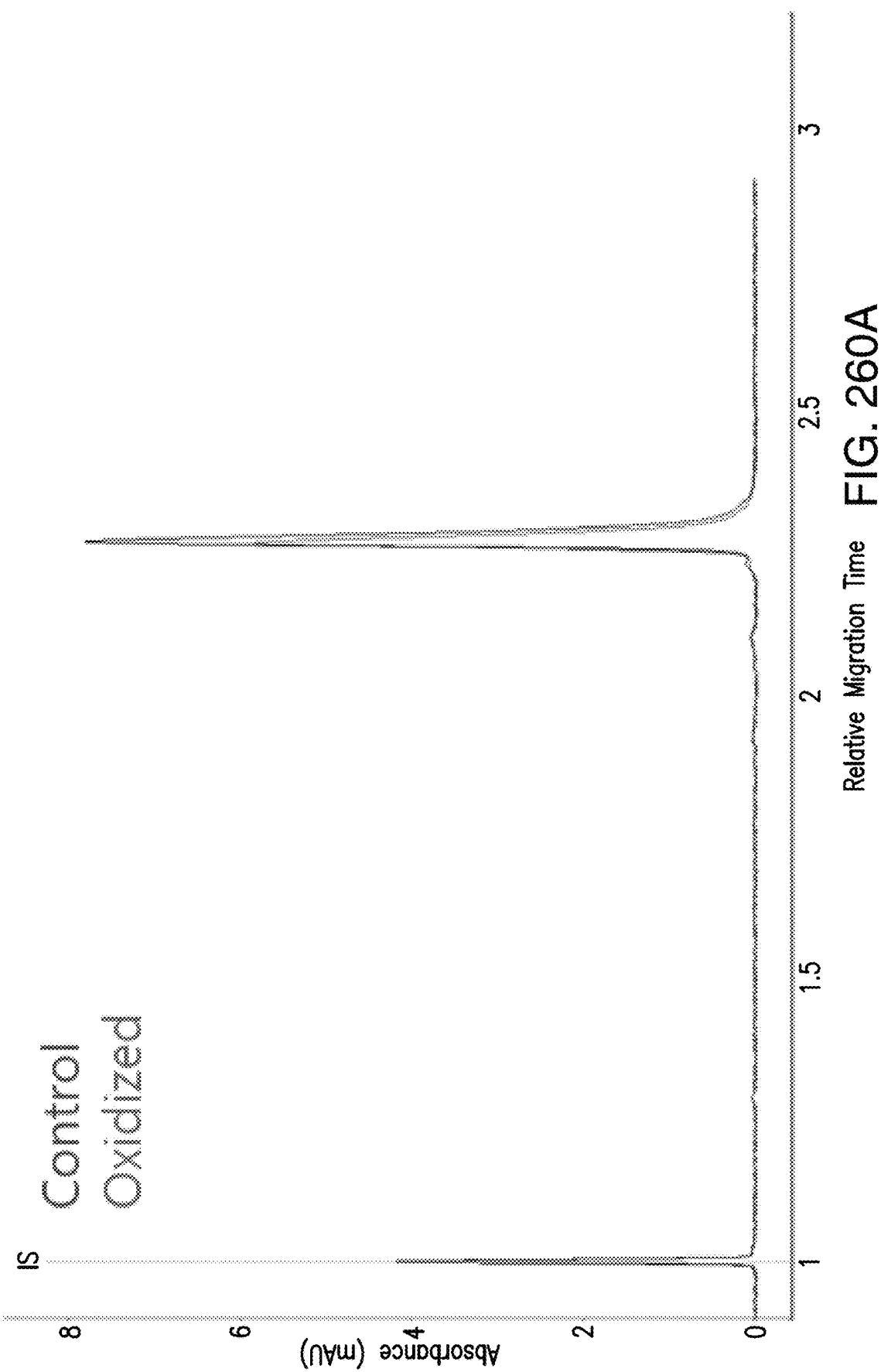

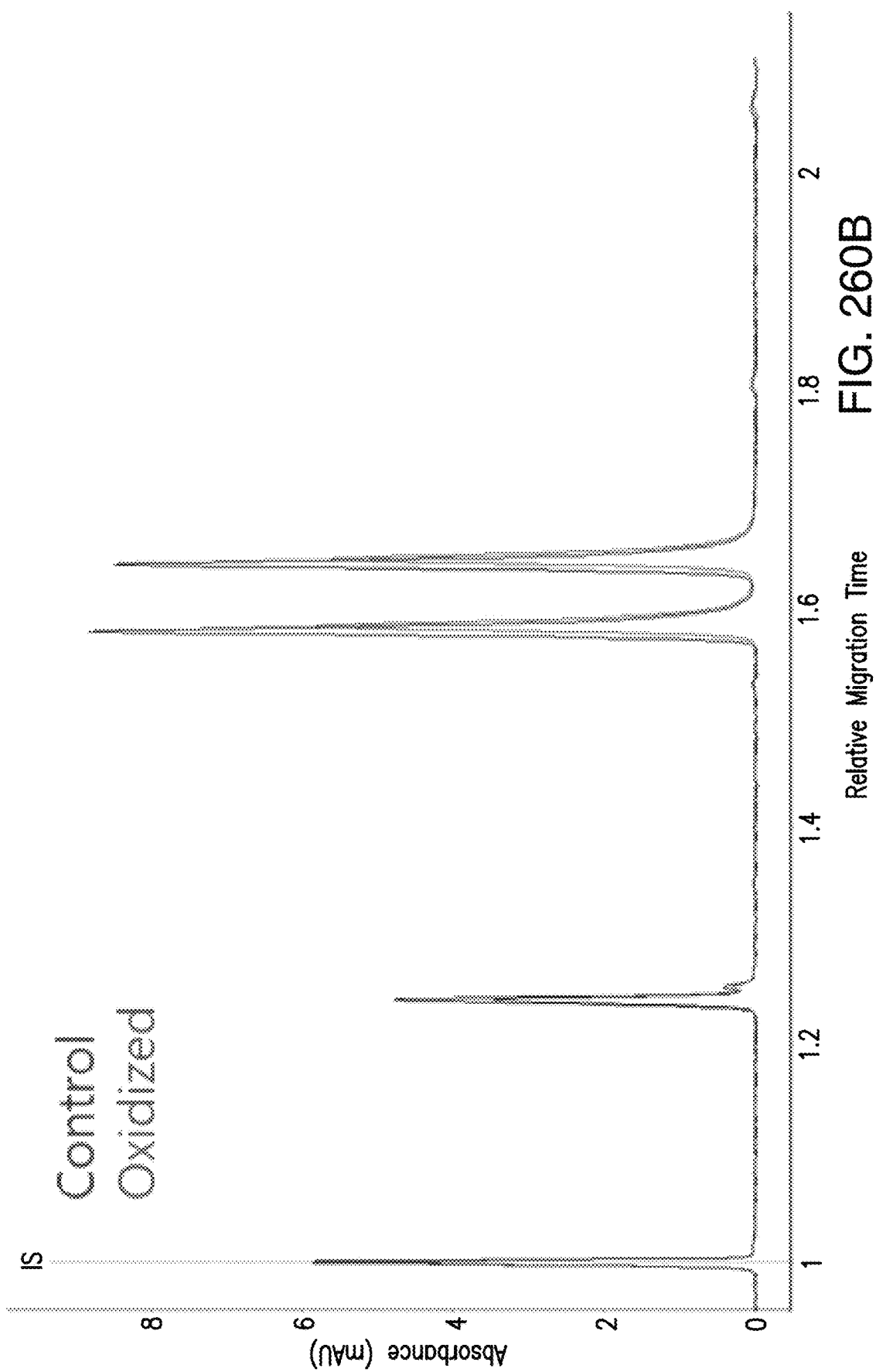

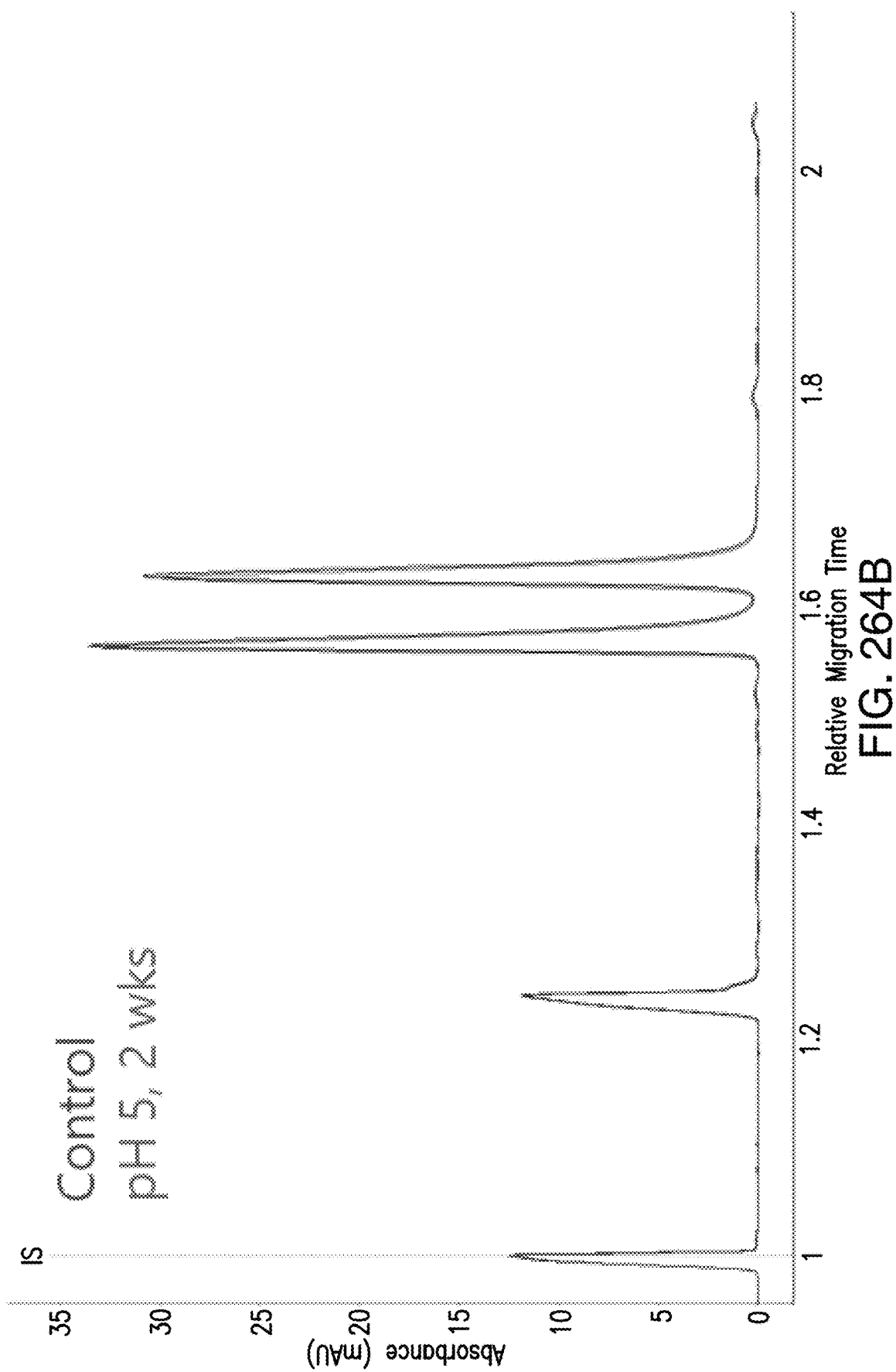

SEQUENCE LISTING

<160> NUMBER OF SEQ ID NOS: 342

<210> SEQ ID NO 1
<211> LENGTH: 117
<212> TYPE: PRT
<213> ORGANISM: Artificial Sequence
<220> FEATURE:
<223> OTHER INFORMATION: VH of ADI-27705, 27724, 27740 [A40], 27741,
      27743, 28154, 28226, 29399, 29401, 29403, 29405, 29407, 29419,
      29421, 29424, 29425, 29426, 29429, 29404[F04] and 29447[F47]

<400> SEQUENCE: 1

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 2
<211> LENGTH: 9
<212> TYPE: PRT
<213> ORGANISM: Artificial Sequence
<220> FEATURE:
<223> OTHER INFORMATION: ADI-27705 VH CDR1

<400> SEQUENCE: 2

Gly Ser Phe Ser Gly Tyr Tyr Trp Ser
1               5

```
<210> SEQ ID NO 3
<211> LENGTH: 16
<212> TYPE: PRT
<213> ORGANISM: Artificial Sequence
<220> FEATURE:
<223> OTHER INFORMATION: ADI-27705 VH CDR2

<400> SEQUENCE: 3

Glu Ile Asp His Ser Gly Ser Thr Asn Tyr Asn Pro Ser Leu Lys Ser
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: ADI-27705 VH CDR3

<400> SEQUENCE: 4

Ala Arg Ala Arg Gly Pro Trp Ser Phe Asp Pro
1               5                   10

<210> SEQ ID NO 5
<211> LENGTH: 107
<212> TYPE: PRT
<213> ORGANISM: Artificial Sequence
<220> FEATURE:
<223> OTHER INFORMATION: VL of ADI-27705

<400> SEQUENCE: 5

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Ile
                85                  90                  95

Thr Phe Gly Gly Gly Thr Lys Val Glu Ile Lys
            100                 105

<210> SEQ ID NO 6
<211> LENGTH: 108
<212> TYPE: PRT
<213> ORGANISM: Artificial Sequence
<220> FEATURE:
<223> OTHER INFORMATION: VL of ADI-27724

<400> SEQUENCE: 6

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60
```

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gly Gly Thr Lys Val Glu Ile Lys
            100                 105

<210> SEQ ID NO 7
<211> LENGTH: 106
<212> TYPE: PRT
<213> ORGANISM: Artificial Sequence
<220> FEATURE:
<223> OTHER INFORMATION: VL of ADI-27740 [A40]

<400> SEQUENCE: 7

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr His Ser Phe Tyr Thr
                85                  90                  95

Phe Gly Gly Gly Thr Lys Val Glu Ile Lys
            100                 105

<210> SEQ ID NO 8
<211> LENGTH: 106
<212> TYPE: PRT
<213> ORGANISM: Artificial Sequence
<220> FEATURE:
<223> OTHER INFORMATION: VL of ADI-27741

<400> SEQUENCE: 8

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Asn Ser Tyr Tyr Thr
                85                  90                  95

Phe Gly Gly Gly Thr Lys Val Glu Ile Lys
            100                 105

<210> SEQ ID NO 9
<211> LENGTH: 106
<212> TYPE: PRT
<213> ORGANISM: Artificial Sequence
<220> FEATURE:
<223> OTHER INFORMATION: VL of ADI-27743

```
<400> SEQUENCE: 9

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Thr
                85                  90                  95

Phe Gly Gly Gly Thr Lys Val Glu Ile Lys
            100                 105

<210> SEQ ID NO 10
<211> LENGTH: 117
<212> TYPE: PRT
<213> ORGANISM: Artificial Sequence
<220> FEATURE:
<223> OTHER INFORMATION: VH of ADI-28153

<400> SEQUENCE: 10

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Gly Phe Asp Pro Trp Gly Gln Gly Thr Leu
            100                 105                 110

Val Thr Val Ser Ser
        115

<210> SEQ ID NO 11
<211> LENGTH: 107
<212> TYPE: PRT
<213> ORGANISM: Artificial Sequence
<220> FEATURE:
<223> OTHER INFORMATION: VL of ADI-28153

<400> SEQUENCE: 11

Glu Leu Gln Met Thr Gln Ser Pro Ser Ser Leu Ser Ala Ser Val Gly
1               5                   10                  15

Asp Arg Val Thr Ile Thr Cys Thr Ser Gln Ser Ile Ser Ser Tyr
            20                  25                  30

Leu Asn Trp Tyr Gln Gln Lys Pro Gly Gln Pro Pro Lys Leu Leu Ile
        35                  40                  45

Tyr Trp Ala Ser Thr Arg Glu Ser Gly Val Pro Asp Arg Phe Ser Gly
50                  55                  60
```

```
Ser Gly Ser Gly Thr Asp Phe Thr Leu Thr Ile Ser Ser Leu Gln Pro
 65                  70                  75                  80

Glu Asp Ser Ala Thr Tyr Tyr Cys Gln Gln Ser Tyr Asp Ile Pro Tyr
                 85                  90                  95

Thr Phe Gly Gln Gly Thr Lys Leu Glu Ile Lys
            100                 105

<210> SEQ ID NO 12
<211> LENGTH: 107
<212> TYPE: PRT
<213> ORGANISM: Artificial Sequence
<220> FEATURE:
<223> OTHER INFORMATION: VL of ADI-28226 [C26]

<400> SEQUENCE: 12

Asp Ile Gln Met Thr Gln Ser Pro Ser Thr Leu Ser Ala Ser Val Gly
  1               5                  10                  15

Asp Arg Val Thr Ile Thr Cys Arg Ala Ser Gln Ser Ile Ser Ser Trp
                 20                  25                  30

Leu Ala Trp Tyr Gln Gln Lys Pro Gly Lys Ala Pro Lys Leu Leu Ile
             35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Gly Ser Phe Pro Ile
                 85                  90                  95

Thr Phe Gly Gly Gly Thr Lys Val Glu Ile Lys
            100                 105

<210> SEQ ID NO 13
<211> LENGTH: 107
<212> TYPE: PRT
<213> ORGANISM: Artificial Sequence
<220> FEATURE:
<223> OTHER INFORMATION: VL of ADI-28154

<400> SEQUENCE: 13

Asp Ile Gln Met Thr Gln Ser Pro Ser Thr Leu Ser Ala Ser Val Gly
  1               5                  10                  15

Asp Arg Val Thr Ile Thr Cys Arg Ala Ser Gln Ser Ile Ser Ser Trp
                 20                  25                  30

Leu Ala Trp Tyr Gln Gln Lys Pro Gly Lys Ala Pro Lys Leu Leu Ile
             35                  40                  45

Tyr Lys Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Asp Asp Phe Ala Thr Tyr Tyr Cys Gln Gln Ser Lys Glu Val Pro Trp
                 85                  90                  95

Thr Phe Gly Gln Gly Thr Lys Val Glu Ile Lys
            100                 105

<210> SEQ ID NO 14
<211> LENGTH: 106
<212> TYPE: PRT
<213> ORGANISM: Artificial Sequence
<220> FEATURE:
<223> OTHER INFORMATION: VL of ADI-29399
```

<400> SEQUENCE: 14

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Phe Pro Thr
                85                  90                  95

Phe Gly Gly Gly Thr Lys Val Glu Ile Lys
            100                 105

<210> SEQ ID NO 15
<211> LENGTH: 106
<212> TYPE: PRT
<213> ORGANISM: Artificial Sequence
<220> FEATURE:
<223> OTHER INFORMATION: VL of ADI-29401

<400> SEQUENCE: 15

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ile Tyr Pro Thr
                85                  90                  95

Phe Gly Gly Gly Thr Lys Val Glu Ile Lys
            100                 105

<210> SEQ ID NO 16
<211> LENGTH: 106
<212> TYPE: PRT
<213> ORGANISM: Artificial Sequence
<220> FEATURE:
<223> OTHER INFORMATION: VL of ADI-29403

<400> SEQUENCE: 16

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

```
Asp Asp Phe Ala Thr Tyr Tyr Cys Gln Gln Tyr Asp Ser Tyr Pro Thr
                85                  90                  95

Phe Gly Gly Gly Thr Lys Val Glu Ile Lys
            100                 105
```

<210> SEQ ID NO 17
<211> LENGTH: 106
<212> TYPE: PRT
<213> ORGANISM: Artificial Sequence
<220> FEATURE:
<223> OTHER INFORMATION: VL of ADI-29405

<400> SEQUENCE: 17

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
                35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gly Ser Phe Pro Thr
                85                  90                  95

Phe Gly Gly Gly Thr Lys Val Glu Ile Lys
            100                 105
```

<210> SEQ ID NO 18
<211> LENGTH: 106
<212> TYPE: PRT
<213> ORGANISM: Artificial Sequence
<220> FEATURE:
<223> OTHER INFORMATION: VL of ADI-29407

<400> SEQUENCE: 18

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
                35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gln Ser Phe Pro Thr
                85                  90                  95

Phe Gly Gly Gly Thr Lys Val Glu Ile Lys
            100                 105
```

<210> SEQ ID NO 19
<211> LENGTH: 106
<212> TYPE: PRT
<213> ORGANISM: Artificial Sequence
<220> FEATURE:
<223> OTHER INFORMATION: VL of ADI-29419

<400> SEQUENCE: 19

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Phe Ser Thr
                85                  90                  95

Phe Gly Gly Gly Thr Lys Val Glu Ile Lys
            100                 105

<210> SEQ ID NO 20
<211> LENGTH: 106
<212> TYPE: PRT
<213> ORGANISM: Artificial Sequence
<220> FEATURE:
<223> OTHER INFORMATION: VL of ADI-29421

<400> SEQUENCE: 20

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Glu Ser Tyr Ser Thr
                85                  90                  95

Phe Gly Gly Gly Thr Lys Val Glu Ile Lys
            100                 105

<210> SEQ ID NO 21
<211> LENGTH: 106
<212> TYPE: PRT
<213> ORGANISM: Artificial Sequence
<220> FEATURE:
<223> OTHER INFORMATION: VL of ADI-29424

<400> SEQUENCE: 21

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Phe Ile Thr
                85                  90                  95

```
Phe Gly Gly Gly Thr Lys Val Glu Ile Lys
            100                 105

<210> SEQ ID NO 22
<211> LENGTH: 106
<212> TYPE: PRT
<213> ORGANISM: Artificial Sequence
<220> FEATURE:
<223> OTHER INFORMATION: VL of ADI-29425

<400> SEQUENCE: 22

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gln Ser Tyr Pro Thr
                85                  90                  95

Phe Gly Gly Gly Thr Lys Val Glu Ile Lys
            100                 105

<210> SEQ ID NO 23
<211> LENGTH: 106
<212> TYPE: PRT
<213> ORGANISM: Artificial Sequence
<220> FEATURE:
<223> OTHER INFORMATION: VL of ADI-29426

<400> SEQUENCE: 23

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr His Ser Phe Pro Thr
                85                  90                  95

Phe Gly Gly Gly Thr Lys Val Glu Ile Lys
            100                 105

<210> SEQ ID NO 24
<211> LENGTH: 107
<212> TYPE: PRT
<213> ORGANISM: Artificial Sequence
<220> FEATURE:
<223> OTHER INFORMATION: VL of ADI-29429

<400> SEQUENCE: 24

Asp Ile Gln Met Thr Gln Ser Pro Ser Thr Leu Ser Ala Ser Val Gly
1               5                   10                  15
```

Asp Arg Val Thr Ile Thr Cys Arg Ala Ser Gln Ser Ile Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Glu Leu Tyr Ser Tyr
                85                  90                  95

Thr Phe Gly Gly Gly Thr Lys Val Glu Ile Lys
            100                 105

<210> SEQ ID NO 25
<211> LENGTH: 106
<212> TYPE: PRT
<213> ORGANISM: Artificial Sequence
<220> FEATURE:
<223> OTHER INFORMATION: VL of ADI-29447 [F47]

<400> SEQUENCE: 25

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Phe Ile Thr
                85                  90                  95

Phe Gly Gly Gly Thr Lys Val Glu Ile Lys
            100                 105

<210> SEQ ID NO 26
<211> LENGTH: 125
<212> TYPE: PRT
<213> ORGANISM: Artificial Sequence
<220> FEATURE:
<223> OTHER INFORMATION: VH of ADI-27727

<400> SEQUENCE: 26

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Ser Ser Ile Arg His Ala Tyr Tyr Tyr Gly Met
            100                 105                 110

```
Asp Val Trp Gly Gln Gly Thr Thr Val Thr Val Ser Ser
        115                 120                 125

<210> SEQ ID NO 27
<211> LENGTH: 9
<212> TYPE: PRT
<213> ORGANISM: Artificial Sequence
<220> FEATURE:
<223> OTHER INFORMATION: ADI-27727 and ADI-28200 VH CDR1

<400> SEQUENCE: 27

Gly Thr Phe Ser Ser Tyr Ala Ile Ser
1               5

<210> SEQ ID NO 28
<211> LENGTH: 5
<212> TYPE: PRT
<213> ORGANISM: Artificial Sequence
<220> FEATURE:
<223> OTHER INFORMATION: ADI-27727 VH CDR1

<400> SEQUENCE: 28

Ser Tyr Ala Ile Ser
1               5

<210> SEQ ID NO 29
<211> LENGTH: 17
<212> TYPE: PRT
<213> ORGANISM: Artificial Sequence
<220> FEATURE:
<223> OTHER INFORMATION: ADI-27727 and ADI-28200 VH CDR2

<400> SEQUENCE: 29

Gly Ile Ile Pro Ile Phe Gly Thr Ala Asn Tyr Ala Gln Lys Phe Gln
1               5                   10                  15

Gly

<210> SEQ ID NO 30
<211> LENGTH: 18
<212> TYPE: PRT
<213> ORGANISM: Artificial Sequence
<220> FEATURE:
<223> OTHER INFORMATION: ADI-27727 VH CDR3

<400> SEQUENCE: 30

Ala Arg Gly Asp Ser Ser Ile Arg His Ala Tyr Tyr Tyr Tyr Gly Met
1               5                   10                  15

Asp Val

<210> SEQ ID NO 31
<211> LENGTH: 16
<212> TYPE: PRT
<213> ORGANISM: Artificial Sequence
<220> FEATURE:
<223> OTHER INFORMATION: ADI-27727 VH CDR3

<400> SEQUENCE: 31

Gly Asp Ser Ser Ile Arg His Ala Tyr Tyr Tyr Tyr Gly Met Asp Val
1               5                   10                  15

<210> SEQ ID NO 32
<211> LENGTH: 113
<212> TYPE: PRT
<213> ORGANISM: Artificial Sequence
<220> FEATURE:
```

<223> OTHER INFORMATION: VL of ADI-27727

<400> SEQUENCE: 32

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Ile Thr Phe Gly Gly Gly Thr Lys Val Glu Ile
            100                 105                 110

Lys

<210> SEQ ID NO 33
<211> LENGTH: 17
<212> TYPE: PRT
<213> ORGANISM: Artificial Sequence
<220> FEATURE:
<223> OTHER INFORMATION: VL of ADI-27727 CDR1

<400> SEQUENCE: 33

Lys Ser Ser Gln Ser Val Leu Tyr Ser Ser Asn Asn Lys Asn Tyr Leu
1               5                   10                  15

Ala

<210> SEQ ID NO 34
<211> LENGTH: 7
<212> TYPE: PRT
<213> ORGANISM: Artificial Sequence
<220> FEATURE:
<223> OTHER INFORMATION: VL of ADI-27727 and 28200 CDR2

<400> SEQUENCE: 34

Trp Ala Ser Thr Arg Glu Ser
1               5

<210> SEQ ID NO 35
<211> LENGTH: 9
<212> TYPE: PRT
<213> ORGANISM: Artificial Sequence
<220> FEATURE:
<223> OTHER INFORMATION: VL of ADI-27727 CDR3

<400> SEQUENCE: 35

Gln Gln Tyr Tyr Ser Thr Pro Ile Thr
1               5

<210> SEQ ID NO 36
<211> LENGTH: 121
<212> TYPE: PRT
<213> ORGANISM: Artificial Sequence
<220> FEATURE:
<223> OTHER INFORMATION: ADI-29443 [F43] VH

<400> SEQUENCE: 36

Gln Leu Gln Leu Gln Glu Ser Gly Pro Gly Leu Val Lys Pro Ser Glu

```
                1               5                  10                  15
            Thr Leu Ser Leu Thr Cys Thr Val Ser Gly Gly Ser Ile Ser Ser Ser
                        20                  25                  30

Ser Tyr Tyr Trp Gly Trp Ile Arg Gln Pro Pro Gly Lys Gly Leu Glu
                        35                  40                  45

Trp Ile Gly Ser Ile Tyr Tyr Ser Gly Ser Thr Tyr Tyr Asn Pro Ser
                        50                  55                  60

Leu Lys Ser Arg Val Thr Ile Ser Val Asp Thr Ser Lys Asn Gln Phe
            65                  70                  75                  80

Ser Leu Lys Leu Ser Ser Val Thr Ala Ala Asp Thr Ala Val Tyr Tyr
                        85                  90                  95

Cys Ala Arg Gly Ser Asp Arg Phe His Pro Tyr Phe Asp Tyr Trp Gly
                        100                 105                 110

Gln Gly Thr Leu Val Thr Val Ser Ser
                        115                 120
```

<210> SEQ ID NO 37
<211> LENGTH: 11
<212> TYPE: PRT
<213> ORGANISM: Artificial Sequence
<220> FEATURE:
<223> OTHER INFORMATION: ADI-29443 [F43] VH CDR1

<400> SEQUENCE: 37

```
            Gly Ser Ile Ser Ser Ser Tyr Tyr Trp Gly
            1               5                   10
```

<210> SEQ ID NO 38
<211> LENGTH: 7
<212> TYPE: PRT
<213> ORGANISM: Artificial Sequence
<220> FEATURE:
<223> OTHER INFORMATION: ADI-29443 [F43] VH CDR1

<400> SEQUENCE: 38

```
            Ser Ser Ser Tyr Tyr Trp Gly
            1               5
```

<210> SEQ ID NO 39
<211> LENGTH: 16
<212> TYPE: PRT
<213> ORGANISM: Artificial Sequence
<220> FEATURE:
<223> OTHER INFORMATION: ADI-29443 [F43] VH CDR2

<400> SEQUENCE: 39

```
            Ser Ile Tyr Tyr Ser Gly Ser Thr Tyr Tyr Asn Pro Ser Leu Lys Ser
            1               5                   10                  15
```

<210> SEQ ID NO 40
<211> LENGTH: 13
<212> TYPE: PRT
<213> ORGANISM: Artificial Sequence
<220> FEATURE:
<223> OTHER INFORMATION: ADI-29443 [F43] VH CDR3

<400> SEQUENCE: 40

```
            Ala Arg Gly Ser Asp Arg Phe His Pro Tyr Phe Asp Tyr
            1               5                   10
```

<210> SEQ ID NO 41
<211> LENGTH: 11
<212> TYPE: PRT

```
<213> ORGANISM: Artificial Sequence
<220> FEATURE:
<223> OTHER INFORMATION: ADI-29443 [F43] VH CDR3

<400> SEQUENCE: 41

Gly Ser Asp Arg Phe His Pro Tyr Phe Asp Tyr
1               5                   10

<210> SEQ ID NO 42
<211> LENGTH: 107
<212> TYPE: PRT
<213> ORGANISM: Artificial Sequence
<220> FEATURE:
<223> OTHER INFORMATION: VL of ADI-29443 [F43]

<400> SEQUENCE: 42

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Asp Thr Trp Pro Pro
                85                  90                  95

Thr Phe Gly Gly Gly Thr Lys Val Glu Ile Lys
            100                 105

<210> SEQ ID NO 43
<211> LENGTH: 11
<212> TYPE: PRT
<213> ORGANISM: Artificial Sequence
<220> FEATURE:
<223> OTHER INFORMATION: VL of ADI-29443 [F43] CDR1

<400> SEQUENCE: 43

Arg Ala Ser Gln Ser Val Ser Arg Tyr Leu Ala
1               5                   10

<210> SEQ ID NO 44
<211> LENGTH: 7
<212> TYPE: PRT
<213> ORGANISM: Artificial Sequence
<220> FEATURE:
<223> OTHER INFORMATION: VL of ADI-29378[E78] and 29443[F43] CDR2

<400> SEQUENCE: 44

Asp Ala Ser Asn Arg Ala Thr
1               5

<210> SEQ ID NO 45
<211> LENGTH: 9
<212> TYPE: PRT
<213> ORGANISM: Artificial Sequence
<220> FEATURE:
<223> OTHER INFORMATION: VL of ADI-29443 [F43] CDR3

<400> SEQUENCE: 45

Gln Gln Phe Asp Thr Trp Pro Pro Thr
1               5
```

<210> SEQ ID NO 46
<211> LENGTH: 106
<212> TYPE: PRT
<213> ORGANISM: Artificial Sequence
<220> FEATURE:
<223> OTHER INFORMATION: VL of ADI-29404 [F04]

<400> SEQUENCE: 46

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Glu Gln Tyr Asp Ser Tyr Pro Thr
                85                  90                  95

Phe Gly Gly Gly Thr Lys Val Glu Ile Lys
            100                 105

<210> SEQ ID NO 47
<211> LENGTH: 126
<212> TYPE: PRT
<213> ORGANISM: Artificial Sequence
<220> FEATURE:
<223> OTHER INFORMATION: ADI-28200 VH

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Arg Lys Ala Ser Gly Ser Phe Tyr Tyr Tyr Tyr Gly
            100                 105                 110

Met Asp Val Trp Gly Gln Gly Thr Thr Val Thr Val Ser Ser
        115                 120                 125

<210> SEQ ID NO 48
<211> LENGTH: 19
<212> TYPE: PRT
<213> ORGANISM: Artificial Sequence
<220> FEATURE:
<223> OTHER INFORMATION: ADI-28200 VH CDR3

<400> SEQUENCE: 48

Ala Arg Arg Gly Arg Lys Ala Ser Gly Ser Phe Tyr Tyr Tyr Tyr Gly
1               5                   10                  15

Met Asp Val

<210> SEQ ID NO 49
<211> LENGTH: 113
<212> TYPE: PRT
<213> ORGANISM: Artificial Sequence
<220> FEATURE:
<223> OTHER INFORMATION: VL of ADI-28200

<400> SEQUENCE: 49

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Pro Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 50
<211> LENGTH: 17
<212> TYPE: PRT
<213> ORGANISM: Artificial Sequence
<220> FEATURE:
<223> OTHER INFORMATION: VL of ADI-28200 CDR1

<400> SEQUENCE: 50

Glu Ser Ser Gln Ser Leu Leu Asn Ser Gly Asn Gln Lys Asn Tyr Leu
1               5                   10                  15

Thr

<210> SEQ ID NO 51
<211> LENGTH: 9
<212> TYPE: PRT
<213> ORGANISM: Artificial Sequence
<220> FEATURE:
<223> OTHER INFORMATION: VL of ADI-28200 CDR3

<400> SEQUENCE: 51

Gln Asn Asp Tyr Ser Tyr Pro Tyr Thr
1               5

<210> SEQ ID NO 52
<211> LENGTH: 126
<212> TYPE: PRT
<213> ORGANISM: Artificial Sequence
<220> FEATURE:
<223> OTHER INFORMATION: ADI-29379 [E79] VH

<400> SEQUENCE: 52

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met

```
                    35                  40                  45
Gly Ile Ile Asn Pro Ser Gly Gly Ser Thr Ser Tyr Ala Gln Lys Phe
         50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Ala Pro Asn Tyr Gly Asp Thr His Asp Tyr Tyr Tyr
            100                 105                 110

Met Asp Val Trp Gly Lys Gly Thr Thr Val Thr Val Ser Ser
        115                 120                 125

<210> SEQ ID NO 53
<211> LENGTH: 9
<212> TYPE: PRT
<213> ORGANISM: Artificial Sequence
<220> FEATURE:
<223> OTHER INFORMATION: ADI-29378[78] and ADI-29379[E79] VH CDR1

<400> SEQUENCE: 53

Tyr Thr Phe Thr Ser Tyr Tyr Met His
1               5

<210> SEQ ID NO 54
<211> LENGTH: 5
<212> TYPE: PRT
<213> ORGANISM: Artificial Sequence
<220> FEATURE:
<223> OTHER INFORMATION: ADI-29378[78] and ADI-29379[E79] VH CDR1

<400> SEQUENCE: 54

Ser Tyr Tyr Met His
1               5

<210> SEQ ID NO 55
<211> LENGTH: 17
<212> TYPE: PRT
<213> ORGANISM: Artificial Sequence
<220> FEATURE:
<223> OTHER INFORMATION: ADI-29378[78] and ADI-29379[E79] VH CDR2

<400> SEQUENCE: 55

Ile Ile Asn Pro Ser Gly Gly Ser Thr Ser Tyr Ala Gln Lys Phe Gln
1               5                   10                  15

Gly

<210> SEQ ID NO 56
<211> LENGTH: 19
<212> TYPE: PRT
<213> ORGANISM: Artificial Sequence
<220> FEATURE:
<223> OTHER INFORMATION: ADI-29379[E79] VH CDR3-

<400> SEQUENCE: 56

Ala Arg Gly Ala Pro Asn Tyr Gly Asp Thr His Asp Tyr Tyr Tyr
1               5                   10                  15

Met Asp Val

<210> SEQ ID NO 57
<211> LENGTH: 17
<212> TYPE: PRT
<213> ORGANISM: Artificial Sequence
<220> FEATURE:
```

<223> OTHER INFORMATION: ADI-29379[E79] VH CDR3-

<400> SEQUENCE: 57

Gly Ala Pro Asn Tyr Gly Asp Thr Thr His Asp Tyr Tyr Tyr Met Asp
1               5                   10                  15
Val

<210> SEQ ID NO 58
<211> LENGTH: 107
<212> TYPE: PRT
<213> ORGANISM: Artificial Sequence
<220> FEATURE:
<223> OTHER INFORMATION: VL of ADI-29379 [E79]

<400> SEQUENCE: 58

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Asp Trp Pro Phe
                85                  90                  95

Thr Phe Gly Gly Gly Thr Lys Val Glu Ile Lys
            100                 105

<210> SEQ ID NO 59
<211> LENGTH: 11
<212> TYPE: PRT
<213> ORGANISM: Artificial Sequence
<220> FEATURE:
<223> OTHER INFORMATION: VL of ADI-29379 [E79] and 29463[F63] CDR1

<400> SEQUENCE: 59

Arg Ala Ser Gln Ser Val Ser Ser Asn Leu Ala
1               5                   10

<210> SEQ ID NO 60
<211> LENGTH: 7
<212> TYPE: PRT
<213> ORGANISM: Artificial Sequence
<220> FEATURE:
<223> OTHER INFORMATION: VL of ADI-29379 [E79] and 29463[F63] CDR2

<400> SEQUENCE: 60

Gly Ala Ser Thr Arg Ala Thr
1               5

<210> SEQ ID NO 61
<211> LENGTH: 9
<212> TYPE: PRT
<213> ORGANISM: Artificial Sequence
<220> FEATURE:
<223> OTHER INFORMATION: VL of ADI-29379 [E79] CDR3

<400> SEQUENCE: 61

Gln Gln Tyr Asp Asp Trp Pro Phe Thr
1               5

<210> SEQ ID NO 62
<211> LENGTH: 124
<212> TYPE: PRT
<213> ORGANISM: Artificial Sequence
<220> FEATURE:
<223> OTHER INFORMATION: ADI-29463[F63] VH

<400> SEQUENCE: 62

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Gly Glu Tyr Tyr Asp Thr Asp His Gly Met Asp
            100                 105                 110

Val Trp Gly Gln Gly Thr Thr Val Thr Val Ser Ser
        115                 120

<210> SEQ ID NO 63
<211> LENGTH: 9
<212> TYPE: PRT
<213> ORGANISM: Artificial Sequence
<220> FEATURE:
<223> OTHER INFORMATION: ADI-29379 [E79] VH CDR3

<400> SEQUENCE: 63

Tyr Thr Phe Thr Gly Tyr Tyr Met His
1               5

<210> SEQ ID NO 64
<211> LENGTH: 5
<212> TYPE: PRT
<213> ORGANISM: Artificial Sequence
<220> FEATURE:
<223> OTHER INFORMATION: ADI-29463[F63] VH CDR1-

<400> SEQUENCE: 64

Gly Tyr Tyr Met His
1               5

<210> SEQ ID NO 65
<211> LENGTH: 17
<212> TYPE: PRT
<213> ORGANISM: Artificial Sequence
<220> FEATURE:
<223> OTHER INFORMATION: ADI-29463[F63] VH CDR2

<400> SEQUENCE: 65

Trp Ile Asn Pro Asn Ser Gly Gly Thr Asn Tyr Ala Gln Lys Phe Gln
1               5                   10                  15

Gly

<210> SEQ ID NO 66
<211> LENGTH: 17
<212> TYPE: PRT

<213> ORGANISM: Artificial Sequence
<220> FEATURE:
<223> OTHER INFORMATION: ADI-29463[F63] VH CDR3

<400> SEQUENCE: 66

Ala Arg Asp Thr Gly Glu Tyr Tyr Asp Thr Asp Asp His Gly Met Asp
1               5                   10                  15
Val

<210> SEQ ID NO 67
<211> LENGTH: 15
<212> TYPE: PRT
<213> ORGANISM: Artificial Sequence
<220> FEATURE:
<223> OTHER INFORMATION: ADI-29463[F63] VH CDR3-

<400> SEQUENCE: 67

Asp Thr Gly Glu Tyr Tyr Asp Thr Asp Asp His Gly Met Asp Val
1               5                   10                  15

<210> SEQ ID NO 68
<211> LENGTH: 107
<212> TYPE: PRT
<213> ORGANISM: Artificial Sequence
<220> FEATURE:
<223> OTHER INFORMATION: VL of ADI-29463[F63]

<400> SEQUENCE: 68

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asp Asp Tyr Trp Pro Pro
                85                  90                  95

Thr Phe Gly Gly Gly Thr Lys Val Glu Ile Lys
            100                 105

<210> SEQ ID NO 69
<211> LENGTH: 9
<212> TYPE: PRT
<213> ORGANISM: Artificial Sequence
<220> FEATURE:
<223> OTHER INFORMATION: VL of ADI-29463[F63] CDR3

<400> SEQUENCE: 69

Gln Gln Asp Asp Tyr Trp Pro Pro Thr
1               5

<210> SEQ ID NO 70
<211> LENGTH: 121
<212> TYPE: PRT
<213> ORGANISM: Artificial Sequence
<220> FEATURE:
<223> OTHER INFORMATION: ADI-27744[A44] VH

<400> SEQUENCE: 70

Glu Val Gln Leu Leu Glu Ser Gly Gly Gly Leu Val Gln Pro Gly Gly

```
                1               5                      10                      15
Ser Leu Arg Leu Ser Cys Ala Ala Ser Gly Phe Thr Phe Ser Ser Tyr
                    20                      25                      30

Ala Met Ser Trp Val Arg Gln Ala Pro Gly Lys Gly Leu Glu Trp Val
                    35                      40                      45

Ser Ala Ile Ser Gly Ser Gly Gly Ser Thr Tyr Tyr Ala Asp Ser Val
                    50                      55                      60

Lys Gly Arg Phe Thr Ile Ser Arg Asp Asn Ser Lys Asn Thr Leu Tyr
65                          70                      75                      80

Leu Gln Met Asn Ser Leu Arg Ala Glu Asp Thr Ala Val Tyr Tyr Cys
                    85                      90                      95

Ala Lys Asp Gly Gly Tyr Tyr Asp Ser Gly Ala Gly Asp Tyr Trp Gly
                    100                     105                     110

Gln Gly Thr Leu Val Thr Val Ser Ser
            115                     120

<210> SEQ ID NO 71
<211> LENGTH: 9
<212> TYPE: PRT
<213> ORGANISM: Artificial Sequence
<220> FEATURE:
<223> OTHER INFORMATION: ADI-27744[A44] VH CDR1

<400> SEQUENCE: 71

Phe Thr Phe Ser Ser Tyr Ala Met Ser
1               5

<210> SEQ ID NO 72
<211> LENGTH: 17
<212> TYPE: PRT
<213> ORGANISM: Artificial Sequence
<220> FEATURE:
<223> OTHER INFORMATION: ADI-27744[A44] VH CDR2

<400> SEQUENCE: 72

Ala Ile Ser Gly Ser Gly Gly Ser Thr Tyr Tyr Ala Asp Ser Val Lys
1               5                       10                      15

Gly

<210> SEQ ID NO 73
<211> LENGTH: 14
<212> TYPE: PRT
<213> ORGANISM: Artificial Sequence
<220> FEATURE:
<223> OTHER INFORMATION: ADI-27744[A44] VH CDR3

<400> SEQUENCE: 73

Ala Lys Asp Gly Gly Tyr Tyr Asp Ser Gly Ala Gly Asp Tyr
1               5                       10

<210> SEQ ID NO 74
<211> LENGTH: 12
<212> TYPE: PRT
<213> ORGANISM: Artificial Sequence
<220> FEATURE:
<223> OTHER INFORMATION: ADI-27744[A44] VH CDR3

<400> SEQUENCE: 74

Asp Gly Gly Tyr Tyr Asp Ser Gly Ala Gly Asp Tyr
1               5                       10

<210> SEQ ID NO 75
```

<210> SEQ ID NO 75
<211> LENGTH: 107
<212> TYPE: PRT
<213> ORGANISM: Artificial Sequence
<220> FEATURE:
<223> OTHER INFORMATION: VL of ADI-27744[A44]

<400> SEQUENCE: 75

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Tyr Pro Arg
                85                  90                  95

Thr Phe Gly Gly Gly Thr Lys Val Glu Ile Lys
            100                 105
```

<210> SEQ ID NO 76
<211> LENGTH: 11
<212> TYPE: PRT
<213> ORGANISM: Artificial Sequence
<220> FEATURE:
<223> OTHER INFORMATION: VL of ADI-27744[A44] CDR1

<400> SEQUENCE: 76

```
Arg Ala Ser Gln Gly Ile Asp Ser Trp Leu Ala
1               5                   10
```

<210> SEQ ID NO 77
<211> LENGTH: 7
<212> TYPE: PRT
<213> ORGANISM: Artificial Sequence
<220> FEATURE:
<223> OTHER INFORMATION: VL of ADI-27744[A44], 27749[A49], A49MI, A49MQ,
      A49ML, A49MF, A49MV and A49-consensus CDR2

<400> SEQUENCE: 77

```
Ala Ala Ser Ser Leu Gln Ser
1               5
```

<210> SEQ ID NO 78
<211> LENGTH: 9
<212> TYPE: PRT
<213> ORGANISM: Artificial Sequence
<220> FEATURE:
<223> OTHER INFORMATION: VL of ADI-27744 [A44] CDR3

<400> SEQUENCE: 78

```
Gln Gln Gly Val Ser Tyr Pro Arg Thr
1               5
```

<210> SEQ ID NO 79
<211> LENGTH: 122
<212> TYPE: PRT
<213> ORGANISM: Artificial Sequence
<220> FEATURE:
<223> OTHER INFORMATION: ADI-27749 [A49] VH

<400> SEQUENCE: 79

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Met Gly Ala Ala Ala Gly Trp Phe Asp Pro Trp
            100                 105                 110

Gly Gln Gly Thr Leu Val Thr Val Ser Ser
            115                 120
```

<210> SEQ ID NO 80
<211> LENGTH: 9
<212> TYPE: PRT
<213> ORGANISM: Artificial Sequence
<220> FEATURE:
<223> OTHER INFORMATION: ADI-27749[A49], A49MI, A49MQ, A49ML, A49MF, A49MV and A49-consensus VH CDR1

<400> SEQUENCE: 80

```
Phe Thr Phe Ser Ser Tyr Ser Met Asn
1               5
```

<210> SEQ ID NO 81
<211> LENGTH: 5
<212> TYPE: PRT
<213> ORGANISM: Artificial Sequence
<220> FEATURE:
<223> OTHER INFORMATION: ADI-27749[A49], A49MI, A49MQ, A49ML, A49MF, A49MV and A49-consensus VH CDR1

<400> SEQUENCE: 81

```
Ser Tyr Ser Met Asn
1               5
```

<210> SEQ ID NO 82
<211> LENGTH: 17
<212> TYPE: PRT
<213> ORGANISM: Artificial Sequence
<220> FEATURE:
<223> OTHER INFORMATION: ADI-27749[A49], A49MI, A49MQ, A49ML, A49MF, A49MV and A49-consensus VH CDR2

<400> SEQUENCE: 82

```
Ser Ile Ser Ser Ser Ser Tyr Ile Tyr Tyr Ala Asp Ser Val Lys
1               5                   10                  15

Gly
```

<210> SEQ ID NO 83
<211> LENGTH: 15
<212> TYPE: PRT
<213> ORGANISM: Artificial Sequence
<220> FEATURE:
<223> OTHER INFORMATION: ADI-27749 [A49] VH CDR3

<400> SEQUENCE: 83

```
Ala Arg Gly Ala Pro Met Gly Ala Ala Ala Gly Trp Phe Asp Pro
```

<210> SEQ ID NO 84
<211> LENGTH: 13
<212> TYPE: PRT
<213> ORGANISM: Artificial Sequence
<220> FEATURE:
<223> OTHER INFORMATION: ADI-27749 [A49] VH CDR3

<400> SEQUENCE: 84

Gly Ala Pro Met Gly Ala Ala Ala Gly Trp Phe Asp Pro
1               5                   10

<210> SEQ ID NO 85
<211> LENGTH: 107
<212> TYPE: PRT
<213> ORGANISM: Artificial Sequence
<220> FEATURE:
<223> OTHER INFORMATION: ADI-27749[A49], A49MI, A49MQ, A49ML, A49MF,
      A49MV and A49-consensus VL

<400> SEQUENCE: 85

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Phe Pro Arg
                85                  90                  95

Thr Phe Gly Gly Gly Thr Lys Val Glu Ile Lys
            100                 105

<210> SEQ ID NO 86
<211> LENGTH: 11
<212> TYPE: PRT
<213> ORGANISM: Artificial Sequence
<220> FEATURE:
<223> OTHER INFORMATION: ADI-27749[A49], A49MI, A49MQ, A49ML, A49MF,
      A49MV and A49-consensus VL CDR1

<400> SEQUENCE: 86

Arg Ala Ser Gln Gly Ile Ser Ser Trp Leu Ala
1               5                   10

<210> SEQ ID NO 87
<211> LENGTH: 9
<212> TYPE: PRT
<213> ORGANISM: Artificial Sequence
<220> FEATURE:
<223> OTHER INFORMATION: ADI-27749[A49], A49MI, A49MQ, A49ML, A49MF,
      A49MV and A49-consensus VL CDR3

<400> SEQUENCE: 87

Gln Gln Gly Val Ser Phe Pro Arg Thr
1               5

<210> SEQ ID NO 88
<211> LENGTH: 249
<212> TYPE: PRT

-continued

<213> ORGANISM: Artificial Sequence
<220> FEATURE:
<223> OTHER INFORMATION: ADI-27749 [A49]-scFv (VL-VH) with Q44C in VH
      and G100C in VL

<400> SEQUENCE: 88

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Phe Pro Arg
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Glu
        115                 120                 125

Val Gln Leu Val Glu Ser Gly Gly Gly Leu Val Lys Pro Gly Gly Ser
130                 135                 140

Leu Arg Leu Ser Cys Ala Ala Ser Gly Phe Thr Phe Ser Ser Tyr Ser
145                 150                 155                 160

Met Asn Trp Val Arg Gln Ala Pro Gly Lys Cys Leu Glu Trp Val Ser
                165                 170                 175

Ser Ile Ser Ser Ser Ser Ser Tyr Ile Tyr Tyr Ala Asp Ser Val Lys
            180                 185                 190

Gly Arg Phe Thr Ile Ser Arg Asp Asn Ala Lys Asn Ser Leu Tyr Leu
        195                 200                 205

Gln Met Asn Ser Leu Arg Ala Glu Asp Thr Ala Val Tyr Tyr Cys Ala
    210                 215                 220

Arg Gly Ala Pro Met Gly Ala Ala Ala Gly Trp Phe Asp Pro Trp Gly
225                 230                 235                 240

Gln Gly Thr Leu Val Thr Val Ser Ser
                245

<210> SEQ ID NO 89
<211> LENGTH: 125
<212> TYPE: PRT
<213> ORGANISM: Artificial Sequence
<220> FEATURE:
<223> OTHER INFORMATION: ADI-29378 [E78] VH

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

```
Met Glu Leu Ser Ser Leu Arg Ser Glu Asp Thr Ala Val Tyr Tyr Cys
            85                  90                  95

Ala Arg Glu Gly Ala Gly Phe Ala Tyr Gly Met Asp Tyr Tyr Tyr Met
            100                 105                 110

Asp Val Trp Gly Lys Gly Thr Thr Val Thr Val Ser Ser
        115                 120                 125

<210> SEQ ID NO 90
<211> LENGTH: 18
<212> TYPE: PRT
<213> ORGANISM: Artificial Sequence
<220> FEATURE:
<223> OTHER INFORMATION: ADI-29378 [E78] VH CDR3

<400> SEQUENCE: 90

Ala Arg Glu Gly Ala Gly Phe Ala Tyr Gly Met Asp Tyr Tyr Tyr Met
1               5                   10                  15

Asp Val

<210> SEQ ID NO 91
<211> LENGTH: 16
<212> TYPE: PRT
<213> ORGANISM: Artificial Sequence
<220> FEATURE:
<223> OTHER INFORMATION: ADI-29378 [E78] VH CDR3

<400> SEQUENCE: 91

Glu Gly Ala Gly Phe Ala Tyr Gly Met Asp Tyr Tyr Tyr Met Asp Val
1               5                   10                  15

<210> SEQ ID NO 92
<211> LENGTH: 107
<212> TYPE: PRT
<213> ORGANISM: Artificial Sequence
<220> FEATURE:
<223> OTHER INFORMATION: VL of ADI-29378 [E78]

<400> SEQUENCE: 92

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Asn Trp Pro Phe
                85                  90                  95

Thr Phe Gly Gly Gly Thr Lys Val Glu Ile Lys
            100                 105

<210> SEQ ID NO 93
<211> LENGTH: 11
<212> TYPE: PRT
<213> ORGANISM: Artificial Sequence
<220> FEATURE:
<223> OTHER INFORMATION: VL of ADI-29378 [E78] CDR1

<400> SEQUENCE: 93
```

```
Arg Ala Ser Gln Ser Val Ser Ser Tyr Leu Ala
1               5                   10

<210> SEQ ID NO 94
<211> LENGTH: 9
<212> TYPE: PRT
<213> ORGANISM: Artificial Sequence
<220> FEATURE:
<223> OTHER INFORMATION: VL of ADI-29378 [E78] CDR3

<400> SEQUENCE: 94

Gln Gln Ser Asp Asn Trp Pro Phe Thr
1               5

<210> SEQ ID NO 95
<211> LENGTH: 122
<212> TYPE: PRT
<213> ORGANISM: Artificial Sequence
<220> FEATURE:
<223> OTHER INFORMATION: A49MI VH

<400> SEQUENCE: 95

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Ile Gly Ala Ala Ala Gly Trp Phe Asp Pro Trp
            100                 105                 110

Gly Gln Gly Thr Leu Val Thr Val Ser Ser
        115                 120

<210> SEQ ID NO 96
<211> LENGTH: 15
<212> TYPE: PRT
<213> ORGANISM: Artificial Sequence
<220> FEATURE:
<223> OTHER INFORMATION: A49MI VH CDR3

<400> SEQUENCE: 96

Ala Arg Gly Ala Pro Ile Gly Ala Ala Ala Gly Trp Phe Asp Pro
1               5                   10                  15

<210> SEQ ID NO 97
<211> LENGTH: 13
<212> TYPE: PRT
<213> ORGANISM: Artificial Sequence
<220> FEATURE:
<223> OTHER INFORMATION: A49MI VH CDR3

<400> SEQUENCE: 97

Gly Ala Pro Ile Gly Ala Ala Ala Gly Trp Phe Asp Pro
1               5                   10

<210> SEQ ID NO 98
<211> LENGTH: 122
```

```
<212> TYPE: PRT
<213> ORGANISM: Artificial Sequence
<220> FEATURE:
<223> OTHER INFORMATION: A49MQ VH

<400> SEQUENCE: 98

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Gln Gly Ala Ala Gly Trp Phe Asp Pro Trp
            100                 105                 110

Gly Gln Gly Thr Leu Val Thr Val Ser Ser
        115                 120

<210> SEQ ID NO 99
<211> LENGTH: 15
<212> TYPE: PRT
<213> ORGANISM: Artificial Sequence
<220> FEATURE:
<223> OTHER INFORMATION: A49MQ VH CDR3

<400> SEQUENCE: 99

Ala Arg Gly Ala Pro Gln Gly Ala Ala Ala Gly Trp Phe Asp Pro
1               5                   10                  15

<210> SEQ ID NO 100
<211> LENGTH: 13
<212> TYPE: PRT
<213> ORGANISM: Artificial Sequence
<220> FEATURE:
<223> OTHER INFORMATION: A49MQ VH CDR3

<400> SEQUENCE: 100

Gly Ala Pro Gln Gly Ala Ala Ala Gly Trp Phe Asp Pro
1               5                   10

<210> SEQ ID NO 101
<211> LENGTH: 122
<212> TYPE: PRT
<213> ORGANISM: Artificial Sequence
<220> FEATURE:
<223> OTHER INFORMATION: A49ML VH

<400> SEQUENCE: 101

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ala Pro Leu Gly Ala Ala Ala Gly Trp Phe Asp Pro Trp
            100                 105                 110

Gly Gln Gly Thr Leu Val Thr Val Ser Ser
            115                 120

<210> SEQ ID NO 102
<211> LENGTH: 15
<212> TYPE: PRT
<213> ORGANISM: Artificial Sequence
<220> FEATURE:
<223> OTHER INFORMATION: A49ML VH CDR3

<400> SEQUENCE: 102

Ala Arg Gly Ala Pro Leu Gly Ala Ala Ala Gly Trp Phe Asp Pro
 1               5                  10                  15

<210> SEQ ID NO 103
<211> LENGTH: 13
<212> TYPE: PRT
<213> ORGANISM: Artificial Sequence
<220> FEATURE:
<223> OTHER INFORMATION: A49ML VH CDR3

<400> SEQUENCE: 103

Gly Ala Pro Leu Gly Ala Ala Ala Gly Trp Phe Asp Pro
 1               5                  10

<210> SEQ ID NO 104
<211> LENGTH: 122
<212> TYPE: PRT
<213> ORGANISM: Artificial Sequence
<220> FEATURE:
<223> OTHER INFORMATION: A49MF VH

<400> SEQUENCE: 104

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
             35                  40                  45

Ser Ser Ile Ser Ser Ser Ser Tyr Ile Tyr Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ala Pro Phe Gly Ala Ala Ala Gly Trp Phe Asp Pro Trp
            100                 105                 110

Gly Gln Gly Thr Leu Val Thr Val Ser Ser
            115                 120

<210> SEQ ID NO 105
<211> LENGTH: 15
<212> TYPE: PRT
<213> ORGANISM: Artificial Sequence
<220> FEATURE:
<223> OTHER INFORMATION: A49MF VH CDR3
```

<400> SEQUENCE: 105

Ala Arg Gly Ala Pro Phe Gly Ala Ala Ala Gly Trp Phe Asp Pro
1               5                   10                  15

<210> SEQ ID NO 106
<211> LENGTH: 13
<212> TYPE: PRT
<213> ORGANISM: Artificial Sequence
<220> FEATURE:
<223> OTHER INFORMATION: A49MF VH CDR3

<400> SEQUENCE: 106

Gly Ala Pro Phe Gly Ala Ala Ala Gly Trp Phe Asp Pro
1               5                   10

<210> SEQ ID NO 107
<211> LENGTH: 122
<212> TYPE: PRT
<213> ORGANISM: Artificial Sequence
<220> FEATURE:
<223> OTHER INFORMATION: A49MV VH

<400> SEQUENCE: 107

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Val Gly Ala Ala Ala Gly Trp Phe Asp Pro Trp
            100                 105                 110

Gly Gln Gly Thr Leu Val Thr Val Ser Ser
        115                 120

<210> SEQ ID NO 108
<211> LENGTH: 15
<212> TYPE: PRT
<213> ORGANISM: Artificial Sequence
<220> FEATURE:
<223> OTHER INFORMATION: A49MV VH CDR3

<400> SEQUENCE: 108

Ala Arg Gly Ala Pro Val Gly Ala Ala Ala Gly Trp Phe Asp Pro
1               5                   10                  15

<210> SEQ ID NO 109
<211> LENGTH: 13
<212> TYPE: PRT
<213> ORGANISM: Artificial Sequence
<220> FEATURE:
<223> OTHER INFORMATION: A49MV VH CDR3

<400> SEQUENCE: 109

Gly Ala Pro Val Gly Ala Ala Ala Gly Trp Phe Asp Pro
1               5                   10

<210> SEQ ID NO 110
<211> LENGTH: 122
<212> TYPE: PRT
<213> ORGANISM: Artificial Sequence
<220> FEATURE:
<223> OTHER INFORMATION: A49-consensus VH
<220> FEATURE:
<221> NAME/KEY: misc_feature
<222> LOCATION: (102)..(102)
<223> OTHER INFORMATION: Xaa can be Met, Leu, Ile, Val, Gln or Phe

<400> SEQUENCE: 110

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Xaa Gly Ala Ala Ala Gly Trp Phe Asp Pro Trp
            100                 105                 110

Gly Gln Gly Thr Leu Val Thr Val Ser Ser
        115                 120

<210> SEQ ID NO 111
<211> LENGTH: 15
<212> TYPE: PRT
<213> ORGANISM: Artificial Sequence
<220> FEATURE:
<223> OTHER INFORMATION: A49-consensus VH CDR3
<220> FEATURE:
<221> NAME/KEY: misc_feature
<222> LOCATION: (6)..(6)
<223> OTHER INFORMATION: Xaa can be Met, Leu, Ile, Val, Gln or Phe

<400> SEQUENCE: 111

Ala Arg Gly Ala Pro Xaa Gly Ala Ala Ala Gly Trp Phe Asp Pro
1               5                   10                  15

<210> SEQ ID NO 112
<211> LENGTH: 13
<212> TYPE: PRT
<213> ORGANISM: Artificial Sequence
<220> FEATURE:
<223> OTHER INFORMATION: A49-consensus VH CDR3
<220> FEATURE:
<221> NAME/KEY: misc_feature
<222> LOCATION: (4)..(4)
<223> OTHER INFORMATION: Xaa can be Met, Leu, Ile, Val, Gln or Phe

<400> SEQUENCE: 112

Gly Ala Pro Xaa Gly Ala Ala Ala Gly Trp Phe Asp Pro
1               5                   10

<210> SEQ ID NO 113
<211> LENGTH: 121
<212> TYPE: PRT
<213> ORGANISM: Artificial Sequence
<220> FEATURE:
<223> OTHER INFORMATION: NKG2D binder in US 9,273,136

<400> SEQUENCE: 113

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Leu Gly Asp Gly Thr Tyr Phe Asp Tyr Trp Gly
            100                 105                 110

Gln Gly Thr Thr Val Thr Val Ser Ser
        115                 120

<210> SEQ ID NO 114
<211> LENGTH: 110
<212> TYPE: PRT
<213> ORGANISM: Artificial Sequence
<220> FEATURE:
<223> OTHER INFORMATION: NKG2D binder in US 9,273,136

<400> SEQUENCE: 114

Gln Ser Ala Leu Thr Gln Pro Ala Ser Val Ser Gly Ser Pro Gly Gln
1               5                   10                  15

Ser Ile Thr Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Ala Phe Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110

<210> SEQ ID NO 115
<211> LENGTH: 5
<212> TYPE: PRT
<213> ORGANISM: Artificial Sequence
<220> FEATURE:
<223> OTHER INFORMATION: ADI-27744 [A44] VH CDR1

<400> SEQUENCE: 115

Ser Tyr Ala Met Ser
1               5

<210> SEQ ID NO 116
<211> LENGTH: 115
<212> TYPE: PRT
<213> ORGANISM: Artificial Sequence
<220> FEATURE:
<223> OTHER INFORMATION: NKG2D binder in US 7,879,985

```
<400> SEQUENCE: 116

Gln Val His Leu Gln Glu Ser Gly Pro Gly Leu Val Lys Pro Ser Glu
1               5                   10                  15

Thr Leu Ser Leu Thr Cys Thr Val Ser Asp Asp Ser Ile Ser Ser Tyr
            20                  25                  30

Tyr Trp Ser Trp Ile Arg Gln Pro Pro Gly Lys Gly Leu Glu Trp Ile
        35                  40                  45

Gly His Ile Ser Tyr Ser Gly Ser Ala Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Asn Trp Asp Asp Ala Phe Asn Ile Trp Gly Gln Gly Thr Met Val Thr
            100                 105                 110

Val Ser Ser
        115

<210> SEQ ID NO 117
<211> LENGTH: 108
<212> TYPE: PRT
<213> ORGANISM: Artificial Sequence
<220> FEATURE:
<223> OTHER INFORMATION: NKG2D binder in US 7,879,985

<400> SEQUENCE: 117

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 118
<211> LENGTH: 226
<212> TYPE: PRT
<213> ORGANISM: Homo sapiens
<220> FEATURE:
<223> OTHER INFORMATION: wild-type human IgG1 Fc sequence

<400> SEQUENCE: 118

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60
```

```
His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 119
<211> LENGTH: 20
<212> TYPE: PRT
<213> ORGANISM: Artificial Sequence
<220> FEATURE:
<223> OTHER INFORMATION: Linker sequence

<400> SEQUENCE: 119

Gly Gly Gly Gly Ser Gly Gly Gly Ser Gly Gly Gly Ser Gly
1               5                   10                  15

Gly Gly Gly Ser
            20

<210> SEQ ID NO 120
<211> LENGTH: 2
<212> TYPE: PRT
<213> ORGANISM: Artificial Sequence
<220> FEATURE:
<223> OTHER INFORMATION: Linker sequence
<220> FEATURE:
<221> NAME/KEY: REPEAT
<222> LOCATION: (1)..(2)
<223> OTHER INFORMATION: sequence can be repeated 1, 2, 3, 4, 5, 6, 7,
      8, 9, 10, 11, 12, 13, 14, 15, 16, 17, 18, 19, or 20 times

<400> SEQUENCE: 120

Gly Ser
1

<210> SEQ ID NO 121
<211> LENGTH: 3
<212> TYPE: PRT
<213> ORGANISM: Artificial Sequence
<220> FEATURE:
<223> OTHER INFORMATION: Linker sequence
<220> FEATURE:
<221> NAME/KEY: REPEAT
<222> LOCATION: (1)..(3)
<223> OTHER INFORMATION: sequence can be repeated 1, 2, 3, 4, 5, 6, 7,
      8, 9, 10, 11, 12, 13, 14, 15, 16, 17, 18, 19, or 20 times
```

```
<400> SEQUENCE: 121

Gly Gly Ser
1

<210> SEQ ID NO 122
<211> LENGTH: 4
<212> TYPE: PRT
<213> ORGANISM: Artificial Sequence
<220> FEATURE:
<223> OTHER INFORMATION: Linker sequence
<220> FEATURE:
<221> NAME/KEY: REPEAT
<222> LOCATION: (1)..(4)
<223> OTHER INFORMATION: sequence can be repeated 1, 2, 3, 4, 5, 6, 7,
      8, 9, 10, 11, 12, 13, 14, 15, 16, 17, 18, 19, or 20 times

<400> SEQUENCE: 122

Gly Gly Gly Ser
1

<210> SEQ ID NO 123
<211> LENGTH: 4
<212> TYPE: PRT
<213> ORGANISM: Artificial Sequence
<220> FEATURE:
<223> OTHER INFORMATION: Linker sequence
<220> FEATURE:
<221> NAME/KEY: REPEAT
<222> LOCATION: (1)..(4)
<223> OTHER INFORMATION: sequence can be repeated 1, 2, 3, 4, 5, 6, 7,
      8, 9, 10, 11, 12, 13, 14, 15, 16, 17, 18, 19, or 20 times

<400> SEQUENCE: 123

Gly Gly Ser Gly
1

<210> SEQ ID NO 124
<211> LENGTH: 5
<212> TYPE: PRT
<213> ORGANISM: Artificial Sequence
<220> FEATURE:
<223> OTHER INFORMATION: Linker sequence
<220> FEATURE:
<221> NAME/KEY: REPEAT
<222> LOCATION: (1)..(5)
<223> OTHER INFORMATION: sequence can be repeated 1, 2, 3, 4, 5, 6, 7,
      8, 9, 10, 11, 12, 13, 14, 15, 16, 17, 18, 19, or 20 times

<400> SEQUENCE: 124

Gly Gly Ser Gly Gly
1               5

<210> SEQ ID NO 125
<211> LENGTH: 5
<212> TYPE: PRT
<213> ORGANISM: Artificial Sequence
<220> FEATURE:
<223> OTHER INFORMATION: Linker sequence
<220> FEATURE:
<221> NAME/KEY: REPEAT
<222> LOCATION: (1)..(5)
<223> OTHER INFORMATION: sequence can be repeated 1, 2, 3, 4, 5, 6, 7,
      8, 9, 10, 11, 12, 13, 14, 15, 16, 17, 18, 19, or 20 times

<400> SEQUENCE: 125

Gly Gly Gly Gly Ser
1               5
```

```
<210> SEQ ID NO 126
<211> LENGTH: 20
<212> TYPE: PRT
<213> ORGANISM: Artificial Sequence
<220> FEATURE:
<223> OTHER INFORMATION: Linker sequence

<400> SEQUENCE: 126

Gly Ser Gly Ser Gly Ser Gly Ser Gly Ser Gly Ser Gly Ser Gly Ser
1               5                   10                  15

Gly Ser Gly Ser
            20

<210> SEQ ID NO 127
<211> LENGTH: 30
<212> TYPE: PRT
<213> ORGANISM: Artificial Sequence
<220> FEATURE:
<223> OTHER INFORMATION: Linker sequence

<400> SEQUENCE: 127

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser
            20                  25                  30

<210> SEQ ID NO 128
<211> LENGTH: 40
<212> TYPE: PRT
<213> ORGANISM: Artificial Sequence
<220> FEATURE:
<223> OTHER INFORMATION: Linker sequence

<400> SEQUENCE: 128

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 129
<211> LENGTH: 40
<212> TYPE: PRT
<213> ORGANISM: Artificial Sequence
<220> FEATURE:
<223> OTHER INFORMATION: Linker sequence

<400> SEQUENCE: 129

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly
        35                  40

<210> SEQ ID NO 130
<211> LENGTH: 50
<212> TYPE: PRT
<213> ORGANISM: Artificial Sequence
<220> FEATURE:
<223> OTHER INFORMATION: Linker sequence

<400> SEQUENCE: 130
```

Gly Gly Ser Gly Gly Gly Ser Gly Gly Gly Ser Gly Gly Gly
1               5                   10                  15

Gly Ser Gly Gly Gly Ser Gly Gly Gly Ser Gly Gly Gly
        20                  25                  30

Ser Gly Gly Gly Ser Gly Gly Gly Ser Gly Gly Gly Ser
        35                  40                  45

Gly Gly
    50

<210> SEQ ID NO 131
<211> LENGTH: 50
<212> TYPE: PRT
<213> ORGANISM: Artificial Sequence
<220> FEATURE:
<223> OTHER INFORMATION: Linker sequence

<400> SEQUENCE: 131

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly
            20                  25                  30

Gly Gly Ser Gly Gly Gly Ser Gly Gly Gly Ser Gly Gly
        35                  40                  45

Gly Ser
    50

<210> SEQ ID NO 132
<211> LENGTH: 15
<212> TYPE: PRT
<213> ORGANISM: Artificial Sequence
<220> FEATURE:
<223> OTHER INFORMATION: Linker sequence

<400> SEQUENCE: 132

Gly Gly Gly Gly Ser Gly Gly Gly Gly Ser Gly Gly Gly Gly Ser
1               5                   10                  15

<210> SEQ ID NO 133
<211> LENGTH: 100
<212> TYPE: PRT
<213> ORGANISM: Artificial Sequence
<220> FEATURE:
<223> OTHER INFORMATION: Linker sequence

<400> SEQUENCE: 133

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Gly Ser Gly Gly Gly Ser Gly Gly
        35                  40                  45

Gly Ser Gly Gly Gly Gly Ser Gly Gly Gly Ser Gly Gly Gly
    50                  55                  60

Ser Gly Gly Gly Ser Gly Gly Gly Ser Gly Gly Gly Ser
65                  70                  75              80

Gly Gly Gly Gly Ser Gly Gly Gly Ser Gly Gly Gly Ser Gly
                85                  90                  95

Gly Gly Gly Ser
            100

-continued

```
<210> SEQ ID NO 134
<211> LENGTH: 100
<212> TYPE: PRT
<213> ORGANISM: Artificial Sequence
<220> FEATURE:
<223> OTHER INFORMATION: Linker sequence

<400> SEQUENCE: 134

Gly Gly Ser Gly Gly Gly Ser Gly Gly Gly Ser Gly Gly Gly
1               5                   10                  15

Gly Ser Gly Gly Gly Ser Gly Gly Gly Ser Gly Gly Gly Gly
                20                  25                  30

Ser Gly Gly Gly Ser Gly Gly Gly Ser Gly Gly Gly Gly Ser
        35                  40                  45

Gly Gly Gly Ser Gly Gly Gly Ser Gly Gly Gly Ser Gly
            50                  55                  60

Gly Gly Gly Ser Gly Gly Gly Ser Gly Gly Gly Ser Gly Gly
65                  70                  75                  80

Gly Gly Ser Gly Gly Gly Ser Gly Gly Gly Ser Gly Gly Gly
                85                  90                  95

Gly Ser Gly Gly
            100

<210> SEQ ID NO 135
<211> LENGTH: 117
<212> TYPE: PRT
<213> ORGANISM: Artificial Sequence
<220> FEATURE:
<223> OTHER INFORMATION: VH of 16B8.C8

<400> SEQUENCE: 135

Glu Val Gln Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Leu His Trp Val Arg Gln Ser Pro Gly Lys Gly Leu Glu Trp Leu
        35                  40                  45

Gly Val Ile Trp Ser Gly Gly Lys Thr Asp Tyr Asn Thr Pro Phe Lys
    50                  55                  60

Ser Arg Leu Ser Ile Ser Lys Asp Ile Ser Lys Asn Gln Val Phe Phe
65                  70                  75                  80

Lys Met Asn Ser Leu Gln Pro Asn Asp Thr Ala Ile Tyr Phe Cys Ala
                85                  90                  95

Lys Tyr Asp Tyr Asp Asp Ser Leu Asp Tyr Trp Gly Gln Gly Thr Ser
            100                 105                 110

Val Thr Val Ser Ser
        115

<210> SEQ ID NO 136
<211> LENGTH: 107
<212> TYPE: PRT
<213> ORGANISM: Artificial Sequence
<220> FEATURE:
<223> OTHER INFORMATION: VL of 16B8.C8

<400> SEQUENCE: 136

Asp Ile Gln Met Asn Gln Ser Pro Ser Ser Leu Ser Ala Ser Leu Gly
1               5                   10                  15

Asp Thr Ile Ala Ile Thr Cys His Ala Ser Gln Asn Ile Asn Phe Trp
            20                  25                  30
```

```
Leu Ser Trp Tyr Gln Gln Lys Pro Gly Asn Ile Pro Lys Leu Leu Ile
        35                  40                  45

Tyr Glu Ala Ser Asn Leu His Thr Gly Val Pro Ser Arg Phe Ser Gly
    50                  55                  60

Ser Gly Ser Gly Thr Arg Phe Thr Leu Thr Ile Ser Ser Leu Gln Pro
65                  70                  75                  80

Glu Asp Ile Ala Thr Tyr Tyr Cys Gln Gln Ser His Ser Tyr Pro Leu
                85                  90                  95

Thr Phe Gly Gln Gly Thr Lys Leu Glu Ile Lys
            100                 105

<210> SEQ ID NO 137
<211> LENGTH: 7
<212> TYPE: PRT
<213> ORGANISM: Artificial Sequence
<220> FEATURE:
<223> OTHER INFORMATION: Humanized 16B8.C8 - VH CDR1

<400> SEQUENCE: 137

Gly Phe Ser Leu Thr Asn Tyr
1               5

<210> SEQ ID NO 138
<211> LENGTH: 5
<212> TYPE: PRT
<213> ORGANISM: Artificial Sequence
<220> FEATURE:
<223> OTHER INFORMATION: Humanized 16B8.C8 - VH CDR2

<400> SEQUENCE: 138

Trp Ser Gly Gly Lys
1               5

<210> SEQ ID NO 139
<211> LENGTH: 9
<212> TYPE: PRT
<213> ORGANISM: Artificial Sequence
<220> FEATURE:
<223> OTHER INFORMATION: Humanized 16B8.C8 - VH CDR3

<400> SEQUENCE: 139

Tyr Asp Tyr Asp Asp Ser Leu Asp Tyr
1               5

<210> SEQ ID NO 140
<211> LENGTH: 11
<212> TYPE: PRT
<213> ORGANISM: Artificial Sequence
<220> FEATURE:
<223> OTHER INFORMATION: Humanized 16B8.C8 - VL CDR1

<400> SEQUENCE: 140

His Ala Ser Gln Asn Ile Asn Phe Trp Leu Ser
1               5                   10

<210> SEQ ID NO 141
<211> LENGTH: 7
<212> TYPE: PRT
<213> ORGANISM: Artificial Sequence
<220> FEATURE:
<223> OTHER INFORMATION: Humanized 16B8.C8 - VL CDR2

<400> SEQUENCE: 141

Glu Ala Ser Asn Leu His Thr
```

<210> SEQ ID NO 142
<211> LENGTH: 9
<212> TYPE: PRT
<213> ORGANISM: Artificial Sequence
<220> FEATURE:
<223> OTHER INFORMATION: Humanized 16B8.C8 - VL CDR3

<400> SEQUENCE: 142

Gln Gln Ser His Ser Tyr Pro Leu Thr
1               5

<210> SEQ ID NO 143
<211> LENGTH: 117
<212> TYPE: PRT
<213> ORGANISM: Artificial Sequence
<220> FEATURE:
<223> OTHER INFORMATION: Humanized 16B8.C8 in scFv-1292/scFv-1301,
    scFv-1297/scFv-1306, scFv-1298/scFv-1307 and scFv-1299/scFv-1308 -
    VH

<400> SEQUENCE: 143

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Leu His Trp Ile Arg Gln Pro Pro Gly Lys Gly Leu Glu Trp Ile
        35                  40                  45

Gly Val Ile Trp Ser Gly Gly Lys Thr Asp Tyr Asn Pro Ser Leu Lys
    50                  55                  60

Ser Arg Val Thr Ile Ser Lys Asp Thr Ser Lys Asn Gln Phe Ser Leu
65                  70                  75                  80

Lys Leu Ser Ser Val Gln Ala Asn Asp Thr Ala Val Tyr Tyr Cys Ala
                85                  90                  95

Lys Tyr Asp Tyr Asp Asp Ser Leu Asp Tyr Trp Gly Gln Gly Thr Leu
            100                 105                 110

Val Thr Val Ser Ser
        115

<210> SEQ ID NO 144
<211> LENGTH: 107
<212> TYPE: PRT
<213> ORGANISM: Artificial Sequence
<220> FEATURE:
<223> OTHER INFORMATION: Humanized 16B8.C8 in scFv-1293/scFv-1302,
    scFv-1294/scFv-1303, scFv-1295/scFv-1304 and scFv-1296/scFv-1305
    VL

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Phe Trp
            20                  25                  30

Leu Ser Trp Tyr Gln Gln Lys Pro Gly Lys Ile Pro Lys Leu Leu Ile
        35                  40                  45

Tyr Glu Ala Ser Asn Leu His Thr Gly Val Pro Ser Arg Phe Ser Gly
    50                  55                  60

Ser Gly Ser Gly Thr Arg Phe Thr Leu Thr Ile Ser Ser Leu Gln Pro
65                  70                  75                  80

Glu Asp Ile Ala Thr Tyr Tyr Cys Gln Gln Ser His Ser Tyr Pro Leu

```
                85                  90                  95
Thr Phe Gly Gln Gly Thr Lys Leu Glu Ile Lys
            100                 105

<210> SEQ ID NO 145
<211> LENGTH: 244
<212> TYPE: PRT
<213> ORGANISM: Artificial Sequence
<220> FEATURE:
<223> OTHER INFORMATION: humanized 16B8.C8 of scFv -1292 [VH-VL]:

<400> SEQUENCE: 145

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Leu His Trp Ile Arg Gln Pro Pro Gly Lys Cys Leu Glu Trp Ile
        35                  40                  45

Gly Val Ile Trp Ser Gly Gly Lys Thr Asp Tyr Asn Pro Ser Leu Lys
    50                  55                  60

Ser Arg Val Thr Ile Ser Lys Asp Thr Ser Lys Asn Gln Phe Ser Leu
65                  70                  75                  80

Lys Leu Ser Ser Val Gln Ala Asn Asp Thr Ala Val Tyr Tyr Cys Ala
                85                  90                  95

Lys Tyr Asp Tyr Asp Asp Ser Leu Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Ser Gly Gly Gly Ser Asp Ile Gln Met Thr Gln Ser
130                 135                 140

Pro Ser Ser Leu Ser Ala Ser Val Gly Asp Arg Val Thr Ile Thr Cys
145                 150                 155                 160

His Ala Ser Gln Asn Ile Asn Phe Trp Leu Ser Trp Tyr Gln Gln Lys
                165                 170                 175

Pro Gly Lys Ile Pro Lys Leu Leu Ile Tyr Glu Ala Ser Asn Leu His
            180                 185                 190

Thr Gly Val Pro Ser Arg Phe Ser Gly Ser Gly Ser Gly Thr Arg Phe
        195                 200                 205

Thr Leu Thr Ile Ser Ser Leu Gln Pro Glu Asp Ile Ala Thr Tyr Tyr
    210                 215                 220

Cys Gln Gln Ser His Ser Tyr Pro Leu Thr Phe Gly Cys Gly Thr Lys
225                 230                 235                 240

Leu Glu Ile Lys

<210> SEQ ID NO 146
<211> LENGTH: 244
<212> TYPE: PRT
<213> ORGANISM: Artificial Sequence
<220> FEATURE:
<223> OTHER INFORMATION: humanized 16B8.C8 of scFv -1301 [VL-VH]:

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Phe Trp
            20                  25                  30

Leu Ser Trp Tyr Gln Gln Lys Pro Gly Lys Ile Pro Lys Leu Leu Ile
```

```
                35                  40                  45
Tyr Glu Ala Ser Asn Leu His Thr Gly Val Pro Ser Arg Phe Ser Gly
 50                  55                  60

Ser Gly Ser Gly Thr Arg Phe Thr Leu Thr Ile Ser Ser Leu Gln Pro
 65                  70                  75                  80

Glu Asp Ile Ala Thr Tyr Tyr Cys Gln Gln Ser His Ser Tyr Pro Leu
                 85                  90                  95

Thr Phe Gly Cys Gly Thr Lys Leu Glu Ile Lys Gly Gly Gly Gly Ser
                100                 105                 110

Gly Gly Gly Gly Ser Gly Gly Gly Ser Gly Gly Gly Ser Gln
                115                 120                 125

Leu Gln Leu Gln Glu Ser Gly Pro Gly Leu Val Lys Pro Ser Glu Thr
130                 135                 140

Leu Ser Leu Thr Cys Thr Val Ser Gly Phe Ser Leu Thr Asn Tyr Gly
145                 150                 155                 160

Leu His Trp Ile Arg Gln Pro Pro Gly Lys Cys Leu Glu Trp Ile Gly
                165                 170                 175

Val Ile Trp Ser Gly Gly Lys Thr Asp Tyr Asn Pro Ser Leu Lys Ser
                180                 185                 190

Arg Val Thr Ile Ser Lys Asp Thr Ser Lys Asn Gln Phe Ser Leu Lys
                195                 200                 205

Leu Ser Ser Val Gln Ala Asn Asp Thr Ala Val Tyr Tyr Cys Ala Lys
210                 215                 220

Tyr Asp Tyr Asp Asp Ser Leu Asp Tyr Trp Gly Gln Gly Thr Leu Val
225                 230                 235                 240

Thr Val Ser Ser

<210> SEQ ID NO 147
<211> LENGTH: 117
<212> TYPE: PRT
<213> ORGANISM: Artificial Sequence
<220> FEATURE:
<223> OTHER INFORMATION: Humanized 16B8.C8 in scFv-1293/scFv-1302 VH

<400> SEQUENCE: 147

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Asn Tyr
                20                  25                  30

Gly Leu His Trp Ile Arg Gln Pro Pro Gly Lys Gly Leu Glu Trp Ile
            35                  40                  45

Gly Val Ile Trp Ser Gly Gly Lys Thr Asp Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Gln Ala Asn Asp Thr Ala Val Tyr Tyr Cys Ala
                 85                  90                  95

Lys Tyr Asp Tyr Asp Asp Ser Leu Asp Tyr Trp Gly Gln Gly Thr Leu
                100                 105                 110

Val Thr Val Ser Ser
        115

<210> SEQ ID NO 148
<211> LENGTH: 120
<212> TYPE: PRT
<213> ORGANISM: Artificial Sequence
```

```
<220> FEATURE:
<223> OTHER INFORMATION: Humanized 9F11.B7 in AB0192/AB0186 and
      AB0195/AB0189 VH

<400> SEQUENCE: 148
```

| | | | | | | | | | | | | | | | |
|---|---|---|---|---|---|---|---|---|---|---|---|---|---|---|---|
|Glu|Val|Gln|Leu|Val|Glu|Ser|Gly|Gly|Val|Val|Gln|Pro|Gly|Gly| |
|1| | | |5| | | | |10| | | | |15| |

Ser Leu Arg Leu Ser Cys Ala Ala Ser Gly Phe Thr Phe Asn Ala Phe
            20                  25                  30

Gly Met His Trp Val Arg Gln Ala Pro Gly Lys Gly Leu Glu Trp Val
        35                  40                  45

Ala Phe Ile Ser Ser Gly Ser Thr Ser Ile Tyr Tyr Ala Asn Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Tyr Pro Thr Gly Gly Ala Met Asp Tyr Trp Gly Gln
            100                 105                 110

Gly Thr Ser Val Thr Val Ser Ser
        115                 120

```
<210> SEQ ID NO 149
<211> LENGTH: 244
<212> TYPE: PRT
<213> ORGANISM: Artificial Sequence
<220> FEATURE:
<223> OTHER INFORMATION: humanized 16B8.C8 of scFv -1293 [VH-VL]

<400> SEQUENCE: 149
```

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Leu His Trp Ile Arg Gln Pro Pro Gly Lys Cys Leu Glu Trp Ile
        35                  40                  45

Gly Val Ile Trp Ser Gly Gly Lys Thr Asp Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Gln Ala Asn Asp Thr Ala Val Tyr Tyr Cys Ala
                85                  90                  95

Lys Tyr Asp Tyr Asp Asp Ser Leu Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Ser Gly Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

His Ala Ser Gln Asn Ile Asn Phe Trp Leu Ser Trp Tyr Gln Gln Lys
                165                 170                 175

Pro Gly Lys Ile Pro Lys Leu Leu Ile Tyr Glu Ala Ser Asn Leu His
            180                 185                 190

Thr Gly Val Pro Ser Arg Phe Ser Gly Ser Gly Ser Gly Thr Arg Phe
        195                 200                 205

Thr Leu Thr Ile Ser Ser Leu Gln Pro Glu Asp Ile Ala Thr Tyr Tyr
210                 215                 220

Cys Gln Gln Ser His Ser Tyr Pro Leu Thr Phe Gly Cys Gly Thr Lys
225                 230                 235                 240

Leu Glu Ile Lys

<210> SEQ ID NO 150
<211> LENGTH: 244
<212> TYPE: PRT
<213> ORGANISM: Artificial Sequence
<220> FEATURE:
<223> OTHER INFORMATION: humanized 16B8.C8 of scFv -1302 [VL-VH]

<400> SEQUENCE: 150

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Phe Trp
                20                  25                  30

Leu Ser Trp Tyr Gln Gln Lys Pro Gly Lys Ile Pro Lys Leu Leu Ile
            35                  40                  45

Tyr Glu Ala Ser Asn Leu His Thr Gly Val Pro Ser Arg Phe Ser Gly
50                  55                  60

Ser Gly Ser Gly Thr Arg Phe Thr Leu Thr Ile Ser Ser Leu Gln Pro
65                  70                  75                  80

Glu Asp Ile Ala Thr Tyr Tyr Cys Gln Gln Ser His Ser Tyr Pro Leu
                85                  90                  95

Thr Phe Gly Cys Gly Thr Lys Leu Glu Ile Lys Gly Gly Gly Gly Ser
            100                 105                 110

Gly Gly Gly Gly Ser Gly Gly Gly Ser Gly Gly Gly Gly Ser Gln
            115                 120                 125

Leu Gln Leu Gln Glu Ser Gly Pro Gly Leu Val Lys Pro Ser Glu Thr
130                 135                 140

Leu Ser Leu Thr Cys Thr Val Ser Gly Phe Ser Leu Thr Asn Tyr Gly
145                 150                 155                 160

Leu His Trp Ile Arg Gln Pro Pro Gly Lys Cys Leu Glu Trp Ile Gly
                165                 170                 175

Val Ile Trp Ser Gly Gly Lys Thr Asp Tyr Asn Pro Ser Leu Lys Ser
            180                 185                 190

Arg Val Thr Ile Ser Val Asp Thr Ser Lys Asn Gln Phe Ser Leu Lys
        195                 200                 205

Leu Ser Ser Val Gln Ala Asn Asp Thr Ala Val Tyr Tyr Cys Ala Lys
210                 215                 220

Tyr Asp Tyr Asp Asp Ser Leu Asp Tyr Trp Gly Gln Gly Thr Leu Val
225                 230                 235                 240

Thr Val Ser Ser

<210> SEQ ID NO 151
<211> LENGTH: 107
<212> TYPE: PRT
<213> ORGANISM: Artificial Sequence
<220> FEATURE:
<223> OTHER INFORMATION: Humanized 16B8.C8 consensus
<220> FEATURE:
<221> NAME/KEY: misc_feature
<222> LOCATION: (43)..(43)
<223> OTHER INFORMATION: Xaa can be Ala or Ile
<220> FEATURE:
<221> NAME/KEY: misc_feature
<222> LOCATION: (70)..(70)

<223> OTHER INFORMATION: Xaa can be Asp or Arg
<220> FEATURE:
<221> NAME/KEY: misc_feature
<222> LOCATION: (83)..(83)
<223> OTHER INFORMATION: Xaa can be Phe or Ile
<220> FEATURE:
<221> NAME/KEY: misc_feature
<222> LOCATION: (100)..(100)
<223> OTHER INFORMATION: Xaa can be Gln or Gly

<400> SEQUENCE: 151

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Phe Trp
            20                  25                  30

Leu Ser Trp Tyr Gln Gln Lys Pro Gly Lys Xaa Pro Lys Leu Leu Ile
        35                  40                  45

Tyr Glu Ala Ser Asn Leu His Thr Gly Val Pro Ser Arg Phe Ser Gly
50                  55                  60

Ser Gly Ser Gly Thr Xaa Phe Thr Leu Thr Ile Ser Ser Leu Gln Pro
65                  70                  75                  80

Glu Asp Xaa Ala Thr Tyr Tyr Cys Gln Gln Ser His Ser Tyr Pro Leu
            85                  90                  95

Thr Phe Gly Xaa Gly Thr Lys Leu Glu Ile Lys
            100                 105

<210> SEQ ID NO 152
<211> LENGTH: 17
<212> TYPE: PRT
<213> ORGANISM: Artificial Sequence
<220> FEATURE:
<223> OTHER INFORMATION: 20D6.H8 VL CDR1

<400> SEQUENCE: 152

Lys Ser Ser Gln Ser Leu Leu Trp Asn Val Asn Gln Asn Asn Tyr Leu
1               5                   10                  15

Val

<210> SEQ ID NO 153
<211> LENGTH: 244
<212> TYPE: PRT
<213> ORGANISM: Artificial Sequence
<220> FEATURE:
<223> OTHER INFORMATION: humanized 16B8.C8 of scFv -1294 [VH-VL]

<400> SEQUENCE: 153

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Leu His Trp Ile Arg Gln Pro Pro Gly Lys Cys Leu Glu Trp Ile
        35                  40                  45

Gly Val Ile Trp Ser Gly Gly Lys Thr Asp Tyr Asn Pro Ser Leu Lys
50                  55                  60

Ser Arg Val Thr Ile Ser Lys Asp Thr Ser Lys Asn Gln Phe Ser Leu
65                  70                  75                  80

Lys Leu Ser Ser Val Thr Ala Asn Asp Thr Ala Val Tyr Tyr Cys Ala
            85                  90                  95

Lys Tyr Asp Tyr Asp Asp Ser Leu Asp Tyr Trp Gly Gln Gly Thr Leu
            100                 105                 110

```
Val Thr Val Ser Ser Gly Gly Gly Ser Gly Gly Gly Ser Gly
        115                 120                 125

Gly Gly Gly Ser Gly Gly Gly Ser Asp Ile Gln Met Thr Gln Ser
        130                 135                 140

Pro Ser Ser Leu Ser Ala Ser Val Gly Asp Arg Val Thr Ile Thr Cys
145                 150                     155                 160

His Ala Ser Gln Asn Ile Asn Phe Trp Leu Ser Trp Tyr Gln Lys
                165                 170                 175

Pro Gly Lys Ile Pro Lys Leu Leu Ile Tyr Glu Ala Ser Asn Leu His
                180                 185                 190

Thr Gly Val Pro Ser Arg Phe Ser Gly Ser Gly Ser Thr Arg Phe
                195                 200                 205

Thr Leu Thr Ile Ser Ser Leu Gln Pro Glu Asp Ile Ala Thr Tyr Tyr
        210                 215                 220

Cys Gln Gln Ser His Ser Tyr Pro Leu Thr Phe Gly Cys Gly Thr Lys
225                 230                 235                 240

Leu Glu Ile Lys
```

<210> SEQ ID NO 154
<211> LENGTH: 244
<212> TYPE: PRT
<213> ORGANISM: Artificial Sequence
<220> FEATURE:
<223> OTHER INFORMATION: humanized 16B8.C8 of scFv -1303 [VL-VH]

<400> SEQUENCE: 154

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Phe Trp
            20                  25                  30

Leu Ser Trp Tyr Gln Lys Pro Gly Lys Ile Pro Lys Leu Leu Ile
        35                  40                  45

Tyr Glu Ala Ser Asn Leu His Thr Gly Val Pro Ser Arg Phe Ser Gly
50                  55                  60

Ser Gly Ser Gly Thr Arg Phe Thr Leu Thr Ile Ser Ser Leu Gln Pro
65                  70                  75                  80

Glu Asp Ile Ala Thr Tyr Tyr Cys Gln Gln Ser His Ser Tyr Pro Leu
                85                  90                  95

Thr Phe Gly Cys Gly Thr Lys Leu Glu Ile Lys Gly Gly Gly Gly Ser
            100                 105                 110

Gly Gly Gly Gly Ser Gly Gly Gly Gly Ser Gly Gly Gly Gly Ser Gln
        115                 120                 125

Leu Gln Leu Gln Glu Ser Gly Pro Gly Leu Val Lys Pro Ser Glu Thr
    130                 135                 140

Leu Ser Leu Thr Cys Thr Val Ser Gly Phe Ser Leu Thr Asn Tyr Gly
145                 150                 155                 160

Leu His Trp Ile Arg Gln Pro Pro Gly Lys Cys Leu Glu Trp Ile Gly
                165                 170                 175

Val Ile Trp Ser Gly Gly Lys Thr Asp Tyr Asn Pro Ser Leu Lys Ser
                180                 185                 190

Arg Val Thr Ile Ser Lys Asp Thr Ser Lys Asn Gln Phe Ser Leu Lys
                195                 200                 205

Leu Ser Ser Val Thr Ala Asn Asp Thr Ala Val Tyr Tyr Cys Ala Lys
        210                 215                 220

Tyr Asp Tyr Asp Asp Ser Leu Asp Tyr Trp Gly Gln Gly Thr Leu Val
```

```
                225                 230                 235                 240
Thr Val Ser Ser

<210> SEQ ID NO 155
<211> LENGTH: 119
<212> TYPE: PRT
<213> ORGANISM: Artificial Sequence
<220> FEATURE:
<223> OTHER INFORMATION: 15A10.G8 VH

<400> SEQUENCE: 155

Glu Val Gln Leu Gln Glu Ser Gly Ala Glu Leu Val Arg Ser Gly Ala
1               5                   10                  15

Ser Ile Lys Leu Ser Cys Ala Ala Ser Ala Phe Asn Ile Lys Asp Tyr
            20                  25                  30

Phe Ile His Trp Val Arg Gln Arg Pro Asp Gln Gly Leu Glu Trp Ile
        35                  40                  45

Gly Trp Ile Asp Pro Glu Asn Asp Asp Thr Glu Tyr Ala Pro Lys Phe
    50                  55                  60

Gln Asp Lys Ala Thr Met Thr Ala Asp Thr Ser Ser Asn Thr Ala Tyr
65                  70                  75                  80

Leu Gln Leu Ser Ser Leu Thr Ser Ala Asp Thr Ala Val Tyr Tyr Cys
                85                  90                  95

Asn Ala Leu Trp Ser Arg Gly Gly Tyr Phe Asp Tyr Trp Gly Gln Gly
            100                 105                 110

Thr Thr Leu Thr Val Ser Ser
        115

<210> SEQ ID NO 156
<211> LENGTH: 244
<212> TYPE: PRT
<213> ORGANISM: Artificial Sequence
<220> FEATURE:
<223> OTHER INFORMATION: humanized 16B8.C8 of scFv -1295 [VH-VL]

<400> SEQUENCE: 156

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Leu His Trp Ile Arg Gln Pro Pro Gly Lys Cys Leu Glu Trp Ile
        35                  40                  45

Gly Val Ile Trp Ser Gly Gly Lys Thr Asp Tyr Asn Pro Ser Leu Lys
    50                  55                  60

Ser Arg Val Thr Ile Ser Lys Asp Thr Ser Lys Asn Gln Phe Ser Leu
65                  70                  75                  80

Lys Leu Ser Ser Val Gln Ala Ala Asp Thr Ala Val Tyr Tyr Cys Ala
                85                  90                  95

Lys Tyr Asp Tyr Asp Asp Ser Leu Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Gly Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

His Ala Ser Gln Asn Ile Asn Phe Trp Leu Ser Trp Tyr Gln Gln Lys
```

```
                  165                 170                 175
Pro Gly Lys Ile Pro Lys Leu Leu Ile Tyr Glu Ala Ser Asn Leu His
              180                 185                 190

Thr Gly Val Pro Ser Arg Phe Ser Gly Ser Gly Ser Gly Thr Arg Phe
          195                 200                 205

Thr Leu Thr Ile Ser Ser Leu Gln Pro Glu Asp Ile Ala Thr Tyr Tyr
      210                 215                 220

Cys Gln Gln Ser His Ser Tyr Pro Leu Thr Phe Gly Cys Gly Thr Lys
225                 230                 235                 240

Leu Glu Ile Lys

<210> SEQ ID NO 157
<211> LENGTH: 244
<212> TYPE: PRT
<213> ORGANISM: Artificial Sequence
<220> FEATURE:
<223> OTHER INFORMATION: humanized 16B8.C8 of scFv -1304 [VL-VH]

<400> SEQUENCE: 157

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Phe Trp
                20                  25                  30

Leu Ser Trp Tyr Gln Gln Lys Pro Gly Lys Ile Pro Lys Leu Leu Ile
            35                  40                  45

Tyr Glu Ala Ser Asn Leu His Thr Gly Val Pro Ser Arg Phe Ser Gly
        50                  55                  60

Ser Gly Ser Gly Thr Arg Phe Thr Leu Thr Ile Ser Ser Leu Gln Pro
65                  70                  75                  80

Glu Asp Ile Ala Thr Tyr Tyr Cys Gln Gln Ser His Ser Tyr Pro Leu
                85                  90                  95

Thr Phe Gly Cys Gly Thr Lys Leu Glu Ile Lys Gly Gly Gly Gly Ser
            100                 105                 110

Gly Gly Gly Gly Ser Gly Gly Gly Ser Gly Gly Gly Gly Ser Gln
        115                 120                 125

Leu Gln Leu Gln Glu Ser Gly Pro Gly Leu Val Lys Pro Ser Glu Thr
    130                 135                 140

Leu Ser Leu Thr Cys Thr Val Ser Gly Phe Ser Leu Thr Asn Tyr Gly
145                 150                 155                 160

Leu His Trp Ile Arg Gln Pro Pro Gly Lys Cys Leu Glu Trp Ile Gly
                165                 170                 175

Val Ile Trp Ser Gly Gly Lys Thr Asp Tyr Asn Pro Ser Leu Lys Ser
            180                 185                 190

Arg Val Thr Ile Ser Lys Asp Thr Ser Lys Asn Gln Phe Ser Leu Lys
        195                 200                 205

Leu Ser Ser Val Gln Ala Ala Asp Thr Ala Val Tyr Tyr Cys Ala Lys
    210                 215                 220

Tyr Asp Tyr Asp Asp Ser Leu Asp Tyr Trp Gly Gln Gly Thr Leu Val
225                 230                 235                 240

Thr Val Ser Ser

<210> SEQ ID NO 158
<211> LENGTH: 106
<212> TYPE: PRT
<213> ORGANISM: Artificial Sequence
<220> FEATURE:
```

<223> OTHER INFORMATION: 15A10.G8 VL

<400> SEQUENCE: 158

Glu Val Leu Leu Thr Gln Ser Pro Ala Ile Ile Ala Ser Pro Gly
1               5                   10                  15

Glu Lys Val Thr Ile Thr Cys Ser Ala Arg Ser Ser Val Ser Tyr Met
            20                  25                  30

Ser Trp Tyr Gln Gln Lys Pro Gly Ser Ser Pro Lys Ile Trp Ile Tyr
        35                  40                  45

Gly Ile Ser Lys Leu Ala Ser Gly Val Pro Ala Arg Phe Ser Gly Ser
    50                  55                  60

Gly Ser Gly Thr Tyr Phe Ser Phe Thr Ile Asn Asn Leu Glu Ala Glu
65                  70                  75                  80

Asp Val Ala Thr Tyr Tyr Cys Gln Gln Arg Ser Tyr Tyr Pro Phe Thr
                85                  90                  95

Phe Gly Ser Gly Thr Lys Leu Glu Ile Lys
            100                 105

<210> SEQ ID NO 159
<211> LENGTH: 7
<212> TYPE: PRT
<213> ORGANISM: Artificial Sequence
<220> FEATURE:
<223> OTHER INFORMATION: 15A10.G8 VH CDR1

<400> SEQUENCE: 159

Ala Phe Asn Ile Lys Asp Tyr
1               5

<210> SEQ ID NO 160
<211> LENGTH: 244
<212> TYPE: PRT
<213> ORGANISM: Artificial Sequence
<220> FEATURE:
<223> OTHER INFORMATION: humanized 16B8.C8 of scFv -1296 [VH-VL]

<400> SEQUENCE: 160

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Leu His Trp Ile Arg Gln Pro Pro Gly Lys Cys Leu Glu Trp Ile
        35                  40                  45

Gly Val Ile Trp Ser Gly Gly Lys Thr Asp Tyr Asn Pro Ser Leu Lys
    50                  55                  60

Ser Arg Val Thr Ile Ser Lys Asp Thr Ser Lys Asn Gln Phe Ser Leu
65                  70                  75                  80

Lys Leu Ser Ser Val Gln Ala Asn Asp Thr Ala Val Tyr Tyr Cys Ala
                85                  90                  95

Arg Tyr Asp Tyr Asp Asp Ser Leu Asp Tyr Trp Gly Gln Gly Thr Leu
            100                 105                 110

Val Thr Val Ser Ser Gly Gly Gly Ser Gly Gly Gly Ser Gly
            115                 120                 125

Gly Gly Gly Ser Gly Gly Gly Ser Asp Ile Gln Met Thr Gln Ser
        130                 135                 140

Pro Ser Ser Leu Ser Ala Ser Val Gly Asp Arg Val Thr Ile Thr Cys
145                 150                 155                 160

His Ala Ser Gln Asn Ile Asn Phe Trp Leu Ser Trp Tyr Gln Gln Lys

```
                    165                 170                 175
Pro Gly Lys Ile Pro Lys Leu Leu Ile Tyr Glu Ala Ser Asn Leu His
            180                 185                 190

Thr Gly Val Pro Ser Arg Phe Ser Gly Ser Gly Ser Gly Thr Arg Phe
        195                 200                 205

Thr Leu Thr Ile Ser Ser Leu Gln Pro Glu Asp Ile Ala Thr Tyr Tyr
    210                 215                 220

Cys Gln Gln Ser His Ser Tyr Pro Leu Thr Phe Gly Cys Gly Thr Lys
225                 230                 235                 240

Leu Glu Ile Lys

<210> SEQ ID NO 161
<211> LENGTH: 244
<212> TYPE: PRT
<213> ORGANISM: Artificial Sequence
<220> FEATURE:
<223> OTHER INFORMATION: humanized 16B8.C8 of scFv -1305 [VL-VH]

<400> SEQUENCE: 161

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Phe Trp
            20                  25                  30

Leu Ser Trp Tyr Gln Gln Lys Pro Gly Lys Ile Pro Lys Leu Leu Ile
        35                  40                  45

Tyr Glu Ala Ser Asn Leu His Thr Gly Val Pro Ser Arg Phe Ser Gly
    50                  55                  60

Ser Gly Ser Gly Thr Arg Phe Thr Leu Thr Ile Ser Ser Leu Gln Pro
65                  70                  75                  80

Glu Asp Ile Ala Thr Tyr Tyr Cys Gln Gln Ser His Ser Tyr Pro Leu
                85                  90                  95

Thr Phe Gly Cys Gly Thr Lys Leu Glu Ile Lys Gly Gly Gly Gly Ser
            100                 105                 110

Gly Gly Gly Gly Ser Gly Gly Gly Ser Gly Gly Gly Gly Ser Gln
        115                 120                 125

Leu Gln Leu Gln Glu Ser Gly Pro Gly Leu Val Lys Pro Ser Glu Thr
    130                 135                 140

Leu Ser Leu Thr Cys Thr Val Ser Gly Phe Ser Leu Thr Asn Tyr Gly
145                 150                 155                 160

Leu His Trp Ile Arg Gln Pro Pro Gly Lys Cys Leu Glu Trp Ile Gly
                165                 170                 175

Val Ile Trp Ser Gly Gly Lys Thr Asp Tyr Asn Pro Ser Leu Lys Ser
            180                 185                 190

Arg Val Thr Ile Ser Lys Asp Thr Ser Lys Asn Gln Phe Ser Leu Lys
        195                 200                 205

Leu Ser Ser Val Gln Ala Asn Asp Thr Ala Val Tyr Tyr Cys Ala Arg
    210                 215                 220

Tyr Asp Tyr Asp Asp Ser Leu Asp Tyr Trp Gly Gln Gly Thr Leu Val
225                 230                 235                 240

Thr Val Ser Ser

<210> SEQ ID NO 162
<211> LENGTH: 120
<212> TYPE: PRT
<213> ORGANISM: Artificial Sequence
<220> FEATURE:
```

<223> OTHER INFORMATION: Humanized 9F11.B7 in AB0191/AB0185 and
       AB0194/AB0188 VH

<400> SEQUENCE: 162

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Asn Ser
            20                  25                  30

Gly Met His Trp Val Arg Gln Ala Pro Gly Lys Gly Leu Glu Trp Val
        35                  40                  45

Ala Phe Ile Ser Ser Gly Ser Thr Ser Ile Tyr Tyr Ala Asn Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Tyr Pro Thr Gly Gly Ala Met Asp Tyr Trp Gly Gln
            100                 105                 110

Gly Thr Ser Val Thr Val Ser Ser
        115                 120

<210> SEQ ID NO 163
<211> LENGTH: 107
<212> TYPE: PRT
<213> ORGANISM: Artificial Sequence
<220> FEATURE:
<223> OTHER INFORMATION: Humanized 16B8.C8 in scFv-1297 / scFv-1306 VL

<400> SEQUENCE: 163

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Phe Trp
            20                  25                  30

Leu Ser Trp Tyr Gln Gln Lys Pro Gly Lys Ala Pro Lys Leu Leu Ile
        35                  40                  45

Tyr Glu Ala Ser Asn Leu His Thr Gly Val Pro Ser Arg Phe Ser Gly
    50                  55                  60

Ser Gly Ser Gly Thr Arg Phe Thr Leu Thr Ile Ser Ser Leu Gln Pro
65                  70                  75                  80

Glu Asp Ile Ala Thr Tyr Tyr Cys Gln Gln Ser His Ser Tyr Pro Leu
                85                  90                  95

Thr Phe Gly Gln Gly Thr Lys Leu Glu Ile Lys
            100                 105

<210> SEQ ID NO 164
<211> LENGTH: 244
<212> TYPE: PRT
<213> ORGANISM: Artificial Sequence
<220> FEATURE:
<223> OTHER INFORMATION: humanized 16B8.C8 of scFv -1297 [VH-VL]

<400> SEQUENCE: 164

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Leu His Trp Ile Arg Gln Pro Pro Gly Lys Cys Leu Glu Trp Ile
        35                  40                  45

-continued

```
Gly Val Ile Trp Ser Gly Gly Lys Thr Asp Tyr Asn Pro Ser Leu Lys
 50                  55                  60
Ser Arg Val Thr Ile Ser Lys Asp Thr Ser Lys Asn Gln Phe Ser Leu
 65                  70                  75                  80
Lys Leu Ser Ser Val Gln Ala Asn Asp Thr Ala Val Tyr Tyr Cys Ala
                 85                  90                  95
Lys Tyr Asp Tyr Asp Asp Ser Leu Asp Tyr Trp Gly Gln Gly Thr Leu
                100                 105                 110
Val Thr Val Ser Ser Gly Gly Gly Gly Ser Gly Gly Gly Gly Ser Gly
                115                 120                 125
Gly Gly Ser Gly Gly Gly Ser Asp Ile Gln Met Thr Gln Ser
 130                 135                 140
Pro Ser Leu Ser Ala Ser Val Gly Asp Arg Val Thr Ile Thr Cys
 145                 150                 155                 160
His Ala Ser Gln Asn Ile Asn Phe Trp Leu Ser Trp Tyr Gln Gln Lys
                165                 170                 175
Pro Gly Lys Ala Pro Lys Leu Leu Ile Tyr Glu Ala Ser Asn Leu His
                180                 185                 190
Thr Gly Val Pro Ser Arg Phe Ser Gly Ser Gly Ser Gly Thr Arg Phe
                195                 200                 205
Thr Leu Thr Ile Ser Ser Leu Gln Pro Glu Asp Ile Ala Thr Tyr Tyr
 210                 215                 220
Cys Gln Gln Ser His Ser Tyr Pro Leu Thr Phe Gly Cys Gly Thr Lys
 225                 230                 235                 240
Leu Glu Ile Lys

<210> SEQ ID NO 165
<211> LENGTH: 244
<212> TYPE: PRT
<213> ORGANISM: Artificial Sequence
<220> FEATURE:
<223> OTHER INFORMATION: humanized 16B8.C8 of scFv -1306 [VL-VH]

<400> SEQUENCE: 165

Asp Ile Gln Met Thr Gln Ser Pro Ser Ser Leu Ser Ala Ser Val Gly
 1               5                  10                  15
Asp Arg Val Thr Ile Thr Cys His Ala Ser Gln Asn Ile Asn Phe Trp
                 20                  25                  30
Leu Ser Trp Tyr Gln Gln Lys Pro Gly Lys Ala Pro Lys Leu Leu Ile
             35                  40                  45
Tyr Glu Ala Ser Asn Leu His Thr Gly Val Pro Ser Arg Phe Ser Gly
 50                  55                  60
Ser Gly Ser Gly Thr Arg Phe Thr Leu Thr Ile Ser Ser Leu Gln Pro
 65                  70                  75                  80
Glu Asp Ile Ala Thr Tyr Tyr Cys Gln Gln Ser His Ser Tyr Pro Leu
                 85                  90                  95
Thr Phe Gly Cys Gly Thr Lys Leu Glu Ile Lys Gly Gly Gly Gly Ser
                100                 105                 110
Gly Gly Gly Gly Ser Gly Gly Gly Gly Ser Gly Gly Gly Gly Ser Gln
                115                 120                 125
Leu Gln Leu Gln Glu Ser Gly Pro Gly Leu Val Lys Pro Ser Glu Thr
 130                 135                 140
Leu Ser Leu Thr Cys Thr Val Ser Gly Phe Ser Leu Thr Asn Tyr Gly
 145                 150                 155                 160
Leu His Trp Ile Arg Gln Pro Pro Gly Lys Cys Leu Glu Trp Ile Gly
```

165                 170                 175

Val Ile Trp Ser Gly Gly Lys Thr Asp Tyr Asn Pro Ser Leu Lys Ser
                180                 185                 190

Arg Val Thr Ile Ser Lys Asp Thr Ser Lys Asn Gln Phe Ser Leu Lys
            195                 200                 205

Leu Ser Ser Val Gln Ala Asn Asp Thr Ala Val Tyr Tyr Cys Ala Lys
        210                 215                 220

Tyr Asp Tyr Asp Asp Ser Leu Asp Tyr Trp Gly Gln Gly Thr Leu Val
225                 230                 235                 240

Thr Val Ser Ser

<210> SEQ ID NO 166
<211> LENGTH: 5
<212> TYPE: PRT
<213> ORGANISM: Artificial Sequence
<220> FEATURE:
<223> OTHER INFORMATION: 23A5.H8 and 30A9.E9 VH CDR2

<400> SEQUENCE: 166

Trp Ser Gly Gly Ser
1               5

<210> SEQ ID NO 167
<211> LENGTH: 107
<212> TYPE: PRT
<213> ORGANISM: Artificial Sequence
<220> FEATURE:
<223> OTHER INFORMATION: Humanized 16B8.C8 in scFv-1298 / scFv-1307 VL

<400> SEQUENCE: 167

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Phe Trp
                20                  25                  30

Leu Ser Trp Tyr Gln Gln Lys Pro Gly Lys Ile Pro Lys Leu Leu Ile
            35                  40                  45

Tyr Glu Ala Ser Asn Leu His Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Ser His Ser Tyr Pro Leu
                85                  90                  95

Thr Phe Gly Gln Gly Thr Lys Leu Glu Ile Lys
            100                 105

<210> SEQ ID NO 168
<211> LENGTH: 244
<212> TYPE: PRT
<213> ORGANISM: Artificial Sequence
<220> FEATURE:
<223> OTHER INFORMATION: humanized 16B8.C8 of scFv -1298 [VH-VL]

<400> SEQUENCE: 168

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
                20                  25                  30

Gly Leu His Trp Ile Arg Gln Pro Pro Gly Lys Cys Leu Glu Trp Ile
            35                  40                  45

Gly Val Ile Trp Ser Gly Gly Lys Thr Asp Tyr Asn Pro Ser Leu Lys
50                  55                  60

Ser Arg Val Thr Ile Ser Lys Asp Thr Ser Lys Asn Gln Phe Ser Leu
65                  70                  75                  80

Lys Leu Ser Ser Val Gln Ala Asn Asp Thr Ala Val Tyr Tyr Cys Ala
                85                  90                  95

Lys Tyr Asp Tyr Asp Asp Ser Leu Asp Tyr Trp Gly Gln Gly Thr Leu
                100                 105                 110

Val Thr Val Ser Ser Gly Gly Gly Gly Ser Gly Gly Gly Gly Ser Gly
                115                 120                 125

Gly Gly Ser Gly Gly Gly Gly Ser Asp Ile Gln Met Thr Gln Ser
130                 135                 140

Pro Ser Leu Ser Ala Ser Val Gly Asp Arg Val Thr Ile Thr Cys
145                 150                 155                 160

His Ala Ser Gln Asn Ile Asn Phe Trp Leu Ser Trp Tyr Gln Gln Lys
                165                 170                 175

Pro Gly Lys Ile Pro Lys Leu Leu Ile Tyr Glu Ala Ser Asn Leu His
                180                 185                 190

Thr Gly Val Pro Ser Arg Phe Ser Gly Ser Gly Ser Gly Thr Asp Phe
                195                 200                 205

Thr Leu Thr Ile Ser Ser Leu Gln Pro Glu Asp Ile Ala Thr Tyr Tyr
210                 215                 220

Cys Gln Gln Ser His Ser Tyr Pro Leu Thr Phe Gly Cys Gly Thr Lys
225                 230                 235                 240

Leu Glu Ile Lys

<210> SEQ ID NO 169
<211> LENGTH: 244
<212> TYPE: PRT
<213> ORGANISM: Artificial Sequence
<220> FEATURE:
<223> OTHER INFORMATION: humanized 16B8.C8 of scFv -1307 [VL-VH]

<400> SEQUENCE: 169

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Phe Trp
                20                  25                  30

Leu Ser Trp Tyr Gln Gln Lys Pro Gly Lys Ile Pro Lys Leu Leu Ile
                35                  40                  45

Tyr Glu Ala Ser Asn Leu His Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Ser His Ser Tyr Pro Leu
                85                  90                  95

Thr Phe Gly Cys Gly Thr Lys Leu Glu Ile Lys Gly Gly Gly Gly Ser
                100                 105                 110

Gly Gly Gly Gly Ser Gly Gly Gly Ser Gly Gly Gly Gly Ser Gln
                115                 120                 125

Leu Gln Leu Gln Glu Ser Gly Pro Gly Leu Val Lys Pro Ser Glu Thr
130                 135                 140

Leu Ser Leu Thr Cys Thr Val Ser Gly Phe Ser Leu Thr Asn Tyr Gly
145                 150                 155                 160

Leu His Trp Ile Arg Gln Pro Pro Gly Lys Cys Leu Glu Trp Ile Gly

```
                    165                 170                 175
Val Ile Trp Ser Gly Gly Lys Thr Asp Tyr Asn Pro Ser Leu Lys Ser
            180                 185                 190

Arg Val Thr Ile Ser Lys Asp Thr Ser Lys Asn Gln Phe Ser Leu Lys
        195                 200                 205

Leu Ser Ser Val Gln Ala Asn Asp Thr Ala Val Tyr Tyr Cys Ala Lys
    210                 215                 220

Tyr Asp Tyr Asp Asp Ser Leu Asp Tyr Trp Gly Gln Gly Thr Leu Val
225                 230                 235                 240

Thr Val Ser Ser

<210> SEQ ID NO 170
<211> LENGTH: 6
<212> TYPE: PRT
<213> ORGANISM: Artificial Sequence
<220> FEATURE:
<223> OTHER INFORMATION: 15A10.G8 VH CDR2

<400> SEQUENCE: 170

Asp Pro Glu Asn Asp Asp
1               5

<210> SEQ ID NO 171
<211> LENGTH: 107
<212> TYPE: PRT
<213> ORGANISM: Artificial Sequence
<220> FEATURE:
<223> OTHER INFORMATION: Humanized 16B8.C8 in scFv-1299 / scFv-1308

<400> SEQUENCE: 171

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Phe Trp
            20                  25                  30

Leu Ser Trp Tyr Gln Gln Lys Pro Gly Lys Ile Pro Lys Leu Leu Ile
        35                  40                  45

Tyr Glu Ala Ser Asn Leu His Thr Gly Val Pro Ser Arg Phe Ser Gly
    50                  55                  60

Ser Gly Ser Gly Thr Arg Phe Thr Leu Thr Ile Ser Ser Leu Gln Pro
65                  70                  75                  80

Glu Asp Phe Ala Thr Tyr Tyr Cys Gln Gln Ser His Ser Tyr Pro Leu
                85                  90                  95

Thr Phe Gly Gln Gly Thr Lys Leu Glu Ile Lys
            100                 105

<210> SEQ ID NO 172
<211> LENGTH: 244
<212> TYPE: PRT
<213> ORGANISM: Artificial Sequence
<220> FEATURE:
<223> OTHER INFORMATION: humanized 16B8.C8 of scFv -1299 [VH-VL]

<400> SEQUENCE: 172

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Leu His Trp Ile Arg Gln Pro Pro Gly Lys Cys Leu Glu Trp Ile
        35                  40                  45
```

Gly Val Ile Trp Ser Gly Gly Lys Thr Asp Tyr Asn Pro Ser Leu Lys
            50                  55                  60

Ser Arg Val Thr Ile Ser Lys Asp Thr Ser Lys Asn Gln Phe Ser Leu
 65                  70                  75                  80

Lys Leu Ser Ser Val Gln Ala Asn Asp Thr Ala Val Tyr Tyr Cys Ala
                 85                  90                  95

Lys Tyr Asp Tyr Asp Asp Ser Leu Asp Tyr Trp Gly Gln Gly Thr Leu
                100                 105                 110

Val Thr Val Ser Ser Gly Gly Gly Gly Ser Gly Gly Gly Gly Ser Gly
            115                 120                 125

Gly Gly Ser Gly Gly Gly Gly Ser Asp Ile Gln Met Thr Gln Ser
 130                 135                 140

Pro Ser Leu Ser Ala Ser Val Gly Asp Arg Val Thr Ile Thr Cys
145                 150                 155                 160

His Ala Ser Gln Asn Ile Asn Phe Trp Leu Ser Trp Tyr Gln Gln Lys
                165                 170                 175

Pro Gly Lys Ile Pro Lys Leu Leu Ile Tyr Glu Ala Ser Asn Leu His
                180                 185                 190

Thr Gly Val Pro Ser Arg Phe Ser Gly Ser Gly Ser Gly Thr Arg Phe
                195                 200                 205

Thr Leu Thr Ile Ser Ser Leu Gln Pro Glu Asp Phe Ala Thr Tyr Tyr
                210                 215                 220

Cys Gln Gln Ser His Ser Tyr Pro Leu Thr Phe Gly Cys Gly Thr Lys
225                 230                 235                 240

Leu Glu Ile Lys

<210> SEQ ID NO 173
<211> LENGTH: 244
<212> TYPE: PRT
<213> ORGANISM: Artificial Sequence
<220> FEATURE:
<223> OTHER INFORMATION: humanized 16B8.C8 of scFv -1308 [VL-VH]

<400> SEQUENCE: 173

Asp Ile Gln Met Thr Gln Ser Pro Ser Ser Leu Ser Ala Ser Val Gly
 1               5                  10                  15

Asp Arg Val Thr Ile Thr Cys His Ala Ser Gln Asn Ile Asn Phe Trp
                 20                  25                  30

Leu Ser Trp Tyr Gln Gln Lys Pro Gly Lys Ile Pro Lys Leu Leu Ile
             35                  40                  45

Tyr Glu Ala Ser Asn Leu His Thr Gly Val Pro Ser Arg Phe Ser Gly
 50                  55                  60

Ser Gly Ser Gly Thr Arg Phe Thr Leu Thr Ile Ser Ser Leu Gln Pro
 65                  70                  75                  80

Glu Asp Phe Ala Thr Tyr Tyr Cys Gln Gln Ser His Ser Tyr Pro Leu
                 85                  90                  95

Thr Phe Gly Cys Gly Thr Lys Leu Glu Ile Lys Gly Gly Gly Gly Ser
                100                 105                 110

Gly Gly Gly Gly Ser Gly Gly Gly Ser Gly Gly Gly Gly Ser Gln
             115                 120                 125

Leu Gln Leu Gln Glu Ser Gly Pro Gly Leu Val Lys Pro Ser Glu Thr
130                 135                 140

Leu Ser Leu Thr Cys Thr Val Ser Gly Phe Ser Leu Thr Asn Tyr Gly
145                 150                 155                 160

Leu His Trp Ile Arg Gln Pro Pro Gly Lys Cys Leu Glu Trp Ile Gly 165                 170                 175

Val Ile Trp Ser Gly Gly Lys Thr Asp Tyr Asn Pro Ser Leu Lys Ser
            180                 185                 190

Arg Val Thr Ile Ser Lys Asp Thr Ser Lys Asn Gln Phe Ser Leu Lys
        195                 200                 205

Leu Ser Ser Val Gln Ala Asn Asp Thr Ala Val Tyr Tyr Cys Ala Lys
    210                 215                 220

Tyr Asp Tyr Asp Asp Ser Leu Asp Tyr Trp Gly Gln Gly Thr Leu Val
225                 230                 235                 240

Thr Val Ser Ser

<210> SEQ ID NO 174
<211> LENGTH: 117
<212> TYPE: PRT
<213> ORGANISM: Artificial Sequence
<220> FEATURE:
<223> OTHER INFORMATION: Humanized 16B8.C8 in scFv-1300/ scFv-1309 - VH

<400> SEQUENCE: 174

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Leu His Trp Ile Arg Gln Pro Pro Gly Lys Gly Leu Glu Trp Ile
        35                  40                  45

Gly Val Ile Trp Ser Gly Gly Lys Thr Asp Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Tyr Asp Tyr Asp Asp Ser Leu Asp Tyr Trp Gly Gln Gly Thr Leu
            100                 105                 110

Val Thr Val Ser Ser
        115

<210> SEQ ID NO 175
<211> LENGTH: 107
<212> TYPE: PRT
<213> ORGANISM: Artificial Sequence
<220> FEATURE:
<223> OTHER INFORMATION: Humanized 16B8.C8 in scFv-1300/ scFv-1309

<400> SEQUENCE: 175

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Phe Trp
            20                  25                  30

Leu Ser Trp Tyr Gln Gln Lys Pro Gly Lys Ala Pro Lys Leu Leu Ile
        35                  40                  45

Tyr Glu Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Ser Tyr Pro Leu
                85                  90                  95

Thr Phe Gly Gln Gly Thr Lys Leu Glu Ile Lys 100                     105

<210> SEQ ID NO 176
<211> LENGTH: 244
<212> TYPE: PRT
<213> ORGANISM: Artificial Sequence
<220> FEATURE:
<223> OTHER INFORMATION: humanized 16B8.C8 of scFv -1300 [VH-VL]

<400> SEQUENCE: 176

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Leu His Trp Ile Arg Gln Pro Pro Gly Lys Cys Leu Glu Trp Ile
        35                  40                  45

Gly Val Ile Trp Ser Gly Gly Lys Thr Asp Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Tyr Asp Tyr Asp Asp Ser Leu Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Ser Gly Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

His Ala Ser Gln Asn Ile Asn Phe Trp Leu Ser Trp Tyr Gln Gln Lys
                165                 170                 175

Pro Gly Lys Ala Pro Lys Leu Leu Ile Tyr Glu Ala Ser Asn Leu His
            180                 185                 190

Thr Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Ser His Ser Tyr Pro Leu Thr Phe Gly Cys Gly Thr Lys
225                 230                 235                 240

Leu Glu Ile Lys

<210> SEQ ID NO 177
<211> LENGTH: 244
<212> TYPE: PRT
<213> ORGANISM: Artificial Sequence
<220> FEATURE:
<223> OTHER INFORMATION: humanized 16B8.C8 of scFv -1309 [VL-VH]

<400> SEQUENCE: 177

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Phe Trp
            20                  25                  30

Leu Ser Trp Tyr Gln Gln Lys Pro Gly Lys Ala Pro Lys Leu Leu Ile
        35                  40                  45

Tyr Glu Ala Ser Asn Leu His Thr Gly Val Pro Ser Arg Phe Ser Gly

```
                50             55             60
Ser Gly Ser Gly Thr Asp Phe Thr Leu Thr Ile Ser Ser Leu Gln Pro
 65                 70                 75                 80

Glu Asp Phe Ala Thr Tyr Tyr Cys Gln Gln Ser His Ser Tyr Pro Leu
                85                 90                 95

Thr Phe Gly Cys Gly Thr Lys Leu Glu Ile Lys Gly Gly Gly Gly Ser
            100                105                110

Gly Gly Gly Gly Ser Gly Gly Gly Gly Ser Gly Gly Gly Gly Ser Gln
        115                120                125

Leu Gln Leu Gln Glu Ser Gly Pro Gly Leu Val Lys Pro Ser Glu Thr
    130                135                140

Leu Ser Leu Thr Cys Thr Val Ser Gly Phe Ser Leu Thr Asn Tyr Gly
145                150                155                160

Leu His Trp Ile Arg Gln Pro Pro Gly Lys Cys Leu Glu Trp Ile Gly
                165                170                175

Val Ile Trp Ser Gly Gly Lys Thr Asp Tyr Asn Pro Ser Leu Lys Ser
            180                185                190

Arg Val Thr Ile Ser Val Asp Thr Ser Lys Asn Gln Phe Ser Leu Lys
        195                200                205

Leu Ser Ser Val Thr Ala Ala Asp Thr Ala Val Tyr Tyr Cys Ala Arg
    210                215                220

Tyr Asp Tyr Asp Asp Ser Leu Asp Tyr Trp Gly Gln Gly Thr Leu Val
225                230                235                240

Thr Val Ser Ser
```

<210> SEQ ID NO 178
<211> LENGTH: 117
<212> TYPE: PRT
<213> ORGANISM: Artificial Sequence
<220> FEATURE:
<223> OTHER INFORMATION: Humanized 16B8.C8 in scFv-1295/scFv-1304 and
      scFv-1602/scFv-2061 VH

<400> SEQUENCE: 178

```
Gln Leu Gln Leu Gln Glu Ser Gly Pro Gly Leu Val Lys Pro Ser Glu
 1               5                  10                 15

Thr Leu Ser Leu Thr Cys Thr Val Ser Gly Phe Ser Leu Thr Asn Tyr
            20                 25                 30

Gly Leu His Trp Ile Arg Gln Pro Pro Gly Lys Gly Leu Glu Trp Ile
        35                 40                 45

Gly Val Ile Trp Ser Gly Gly Lys Thr Asp Tyr Asn Pro Ser Leu Lys
 50                 55                 60

Ser Arg Val Thr Ile Ser Lys Asp Thr Ser Lys Asn Gln Phe Ser Leu
 65                 70                 75                 80

Lys Leu Ser Ser Val Gln Ala Ala Asp Thr Ala Val Tyr Tyr Cys Ala
                85                 90                 95

Lys Tyr Asp Tyr Asp Asp Ser Leu Asp Tyr Trp Gly Gln Gly Thr Leu
            100                105                110

Val Thr Val Ser Ser
        115
```

<210> SEQ ID NO 179
<211> LENGTH: 11
<212> TYPE: PRT
<213> ORGANISM: Artificial Sequence
<220> FEATURE:
<223> OTHER INFORMATION: 20D6.H8, 23A5.H8 and 30A9.E9 VL CDR3

<400> SEQUENCE: 179

Gln His Asn His Gly Ser Phe Leu Pro Tyr Thr
1               5                   10

<210> SEQ ID NO 180
<211> LENGTH: 244
<212> TYPE: PRT
<213> ORGANISM: Artificial Sequence
<220> FEATURE:
<223> OTHER INFORMATION: humanized 16B8.C8 of scFv -1602 [VH-VL]

<400> SEQUENCE: 180

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Leu His Trp Ile Arg Gln Pro Pro Gly Lys Cys Leu Glu Trp Ile
        35                  40                  45

Gly Val Ile Trp Ser Gly Gly Lys Thr Asp Tyr Asn Pro Ser Leu Lys
    50                  55                  60

Ser Arg Val Thr Ile Ser Lys Asp Thr Ser Lys Asn Gln Phe Ser Leu
65                  70                  75                  80

Lys Leu Ser Ser Val Gln Ala Ala Asp Thr Ala Val Tyr Tyr Cys Ala
                85                  90                  95

Lys Tyr Asp Tyr Asp Asp Ser Leu Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Gly Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

His Ala Ser Gln Asn Ile Asn Phe Trp Leu Ser Trp Tyr Gln Gln Lys
                165                 170                 175

Pro Gly Lys Ala Pro Lys Leu Leu Ile Tyr Glu Ala Ser Asn Leu His
            180                 185                 190

Thr Gly Val Pro Ser Arg Phe Ser Gly Ser Gly Ser Gly Thr Arg Phe
        195                 200                 205

Thr Leu Thr Ile Ser Ser Leu Gln Pro Glu Asp Ile Ala Thr Tyr Tyr
    210                 215                 220

Cys Gln Gln Ser His Ser Tyr Pro Leu Thr Phe Gly Cys Gly Thr Lys
225                 230                 235                 240

Leu Glu Ile Lys

<210> SEQ ID NO 181
<211> LENGTH: 244
<212> TYPE: PRT
<213> ORGANISM: Artificial Sequence
<220> FEATURE:
<223> OTHER INFORMATION: humanized 16B8.C8 of scFv-2061 [VL-VH]

<400> SEQUENCE: 181

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Phe Trp
            20                  25                  30

```
Leu Ser Trp Tyr Gln Gln Lys Pro Gly Lys Ala Pro Lys Leu Leu Ile
             35                  40                  45

Tyr Glu Ala Ser Asn Leu His Thr Gly Val Pro Ser Arg Phe Ser Gly
 50                  55                  60

Ser Gly Ser Gly Thr Arg Phe Thr Leu Thr Ile Ser Ser Leu Gln Pro
 65                  70                  75                  80

Glu Asp Ile Ala Thr Tyr Tyr Cys Gln Gln Ser His Ser Tyr Pro Leu
                 85                  90                  95

Thr Phe Gly Cys Gly Thr Lys Leu Glu Ile Lys Gly Gly Gly Gly Ser
                100                 105                 110

Gly Gly Gly Gly Ser Gly Gly Gly Ser Gly Gly Gly Gly Ser Gly Gln
            115                 120                 125

Leu Gln Leu Gln Glu Ser Gly Pro Gly Leu Val Lys Pro Ser Glu Thr
        130                 135                 140

Leu Ser Leu Thr Cys Thr Val Ser Gly Phe Ser Leu Thr Asn Tyr Gly
145                 150                 155                 160

Leu His Trp Ile Arg Gln Pro Pro Gly Lys Cys Leu Glu Trp Ile Gly
                165                 170                 175

Val Ile Trp Ser Gly Gly Lys Thr Asp Tyr Asn Pro Ser Leu Lys Ser
            180                 185                 190

Arg Val Thr Ile Ser Lys Asp Thr Ser Lys Asn Gln Phe Ser Leu Lys
        195                 200                 205

Leu Ser Ser Val Gln Ala Ala Asp Thr Ala Val Tyr Tyr Cys Ala Lys
    210                 215                 220

Tyr Asp Tyr Asp Asp Ser Leu Asp Tyr Trp Gly Gln Gly Thr Leu Val
225                 230                 235                 240

Thr Val Ser Ser

<210> SEQ ID NO 182
<211> LENGTH: 117
<212> TYPE: PRT
<213> ORGANISM: Artificial Sequence
<220> FEATURE:
<223> OTHER INFORMATION: Humanized 16B8.C8 consensus - VH
<220> FEATURE:
<221> NAME/KEY: misc_feature
<222> LOCATION: (71)..(71)
<223> OTHER INFORMATION: Xaa can be Val or Lys
<220> FEATURE:
<221> NAME/KEY: misc_feature
<222> LOCATION: (86)..(86)
<223> OTHER INFORMATION: Xaa can be Thr or Gln
<220> FEATURE:
<221> NAME/KEY: misc_feature
<222> LOCATION: (88)..(88)
<223> OTHER INFORMATION: Xaa can be Ala or Asn
<220> FEATURE:
<221> NAME/KEY: misc_feature
<222> LOCATION: (97)..(97)
<223> OTHER INFORMATION: Xaa can be Arg or Lys

<400> SEQUENCE: 182

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Asn Tyr
             20                  25                  30

Gly Leu His Trp Ile Arg Gln Pro Pro Gly Lys Gly Leu Glu Trp Ile
         35                  40                  45

Gly Val Ile Trp Ser Gly Gly Lys Thr Asp Tyr Asn Pro Ser Leu Lys
     50                  55                  60
```

```
Ser Arg Val Thr Ile Ser Xaa Asp Thr Ser Lys Asn Gln Phe Ser Leu
 65                  70                  75                  80

Lys Leu Ser Ser Val Xaa Ala Xaa Asp Thr Ala Val Tyr Tyr Cys Ala
                 85                  90                  95

Xaa Tyr Asp Tyr Asp Asp Ser Leu Asp Tyr Trp Gly Gln Gly Thr Leu
            100                 105                 110

Val Thr Val Ser Ser
            115

<210> SEQ ID NO 183
<211> LENGTH: 10
<212> TYPE: PRT
<213> ORGANISM: Artificial Sequence
<220> FEATURE:
<223> OTHER INFORMATION: 15A10.G8 VH CDR3

<400> SEQUENCE: 183

Leu Trp Ser Arg Gly Gly Tyr Phe Asp Tyr
 1               5                   10

<210> SEQ ID NO 184
<211> LENGTH: 247
<212> TYPE: PRT
<213> ORGANISM: Artificial Sequence
<220> FEATURE:
<223> OTHER INFORMATION: scFv of humanized 9F11.B7 of AB0191 [VH-VL]

<400> SEQUENCE: 184

Glu Val Gln Leu Val Glu Ser Gly Gly Gly Val Val Gln Pro Gly Gly
 1               5                   10                  15

Ser Leu Arg Leu Ser Cys Ala Ala Ser Gly Phe Thr Phe Asn Ser Phe
                 20                  25                  30

Gly Met His Trp Val Arg Gln Ala Pro Gly Lys Cys Leu Glu Trp Val
             35                  40                  45

Ala Phe Ile Ser Ser Gly Ser Thr Ser Ile Tyr Tyr Ala Asn Thr Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Tyr Pro Thr Gly Gly Ala Met Asp Tyr Trp Gly Gln
            100                 105                 110

Gly Thr Ser Val Thr Val Ser Ser Gly Gly Gly Gly Ser Gly Gly Gly
            115                 120                 125

Gly Ser Gly Gly Gly Gly Ser Gly Gly Gly Gly Ser Asp Ile Gln Met
        130                 135                 140

Thr Gln Ser Pro Ser Ser Leu Ser Ala Ser Val Gly Asp Arg Val Thr
145                 150                 155                 160

Ile Thr Cys Lys Ala Ser Gln Asp Ile Tyr Asn Tyr Leu Ser Trp Phe
                165                 170                 175

Gln Gln Lys Pro Gly Lys Ala Pro Lys Pro Leu Ile Tyr Arg Ala Asn
            180                 185                 190

Ile Leu Val Ser Gly Val Pro Ser Arg Phe Ser Gly Ser Gly Ser Gly
        195                 200                 205

Gln Asp Tyr Thr Phe Thr Ile Ser Ser Leu Gln Pro Glu Asp Ile Ala
    210                 215                 220

Thr Tyr Tyr Cys Leu Gln Phe Asp Ala Phe Pro Phe Thr Phe Gly Cys
225                 230                 235                 240
```

Gly Thr Lys Leu Glu Ile Lys
            245

<210> SEQ ID NO 185
<211> LENGTH: 247
<212> TYPE: PRT
<213> ORGANISM: Artificial Sequence
<220> FEATURE:
<223> OTHER INFORMATION: scFv of humanized 9F11.B7 of AB0185 [VL-VH]

<400> SEQUENCE: 185

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Tyr Asn Tyr
            20                  25                  30

Leu Ser Trp Phe Gln Gln Lys Pro Gly Lys Ala Pro Lys Pro Leu Ile
        35                  40                  45

Tyr Arg Ala Asn Ile Leu Val Ser Gly Val Pro Ser Arg Phe Ser Gly
    50                  55                  60

Ser Gly Ser Gly Gln Asp Tyr Thr Phe Thr Ile Ser Ser Leu Gln Pro
65                  70                  75                  80

Glu Asp Ile Ala Thr Tyr Tyr Cys Leu Gln Phe Asp Ala Phe Pro Phe
                85                  90                  95

Thr Phe Gly Cys Gly Thr Lys Leu Glu Ile Lys Gly Gly Gly Gly Ser
            100                 105                 110

Gly Gly Gly Gly Ser Gly Gly Gly Ser Gly Gly Gly Gly Ser Glu
        115                 120                 125

Val Gln Leu Val Glu Ser Gly Gly Val Val Gln Pro Gly Gly Ser
    130                 135                 140

Leu Arg Leu Ser Cys Ala Ala Ser Gly Phe Thr Phe Asn Ser Phe Gly
145                 150                 155                 160

Met His Trp Val Arg Gln Ala Pro Gly Lys Cys Leu Glu Trp Val Ala
                165                 170                 175

Phe Ile Ser Ser Gly Ser Thr Ser Ile Tyr Tyr Ala Asn Thr Val Lys
            180                 185                 190

Gly Arg Phe Thr Ile Ser Arg Asp Asn Ser Lys Asn Thr Leu Tyr Leu
        195                 200                 205

Gln Met Asn Ser Leu Arg Ala Glu Asp Thr Ala Val Tyr Tyr Cys Ala
    210                 215                 220

Arg Asp Gly Tyr Pro Thr Gly Gly Ala Met Asp Tyr Trp Gly Gln Gly
225                 230                 235                 240

Thr Ser Val Thr Val Ser Ser
            245

<210> SEQ ID NO 186
<211> LENGTH: 10
<212> TYPE: PRT
<213> ORGANISM: Artificial Sequence
<220> FEATURE:
<223> OTHER INFORMATION: 15A10.G8 VL CDR1

<400> SEQUENCE: 186

Ser Ala Arg Ser Ser Val Ser Tyr Met Ser
1               5                   10

<210> SEQ ID NO 187
<211> LENGTH: 11
<212> TYPE: PRT

<213> ORGANISM: Artificial Sequence
<220> FEATURE:
<223> OTHER INFORMATION: Humanized 9F11.B7 VH CDR3

<400> SEQUENCE: 187

Asp Gly Tyr Pro Thr Gly Gly Ala Met Asp Tyr
1               5                   10

<210> SEQ ID NO 188
<211> LENGTH: 7
<212> TYPE: PRT
<213> ORGANISM: Artificial Sequence
<220> FEATURE:
<223> OTHER INFORMATION: 15A10.G8 VL CDR2

<400> SEQUENCE: 188

Gly Ile Ser Lys Leu Ala Ser
1               5

<210> SEQ ID NO 189
<211> LENGTH: 9
<212> TYPE: PRT
<213> ORGANISM: Artificial Sequence
<220> FEATURE:
<223> OTHER INFORMATION: 15A10.G8 VL CDR3

<400> SEQUENCE: 189

Gln Gln Arg Ser Tyr Tyr Pro Phe Thr
1               5

<210> SEQ ID NO 190
<211> LENGTH: 120
<212> TYPE: PRT
<213> ORGANISM: Artificial Sequence
<220> FEATURE:
<223> OTHER INFORMATION: 13E1.A4 VH

<400> SEQUENCE: 190

Glu Val Gln Leu Gln Glu Ser Gly Pro Glu Leu Glu Lys Pro Gly Ala
1               5                   10                  15

Ser Val Arg Ile Ser Cys Lys Ala Ser Gly Tyr Ser Phe Thr Ala Tyr
            20                  25                  30

Asn Met Asn Trp Val Lys Gln Ser Asn Gly Lys Ser Leu Glu Trp Ile
        35                  40                  45

Gly Asn Ile Asp Pro Ser Tyr Gly Asp Ala Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Asp Asn Tyr Tyr Gly Ser Gly Tyr Phe Asp Tyr Trp Gly Gln
            100                 105                 110

Gly Thr Thr Leu Thr Val Ser Ser
        115                 120

<210> SEQ ID NO 191
<211> LENGTH: 112
<212> TYPE: PRT
<213> ORGANISM: Artificial Sequence
<220> FEATURE:
<223> OTHER INFORMATION: 13E1.A4 VL

<400> SEQUENCE: 191

```
Ser Val Leu Met Thr Gln Thr Pro Leu Ser Leu Pro Val Ser Leu Gly
1               5                   10                  15

Asp Arg Ala Ser Ile Ser Cys Arg Ser Ser Gln Gly Ile Val His Ile
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110
```

<210> SEQ ID NO 192
<211> LENGTH: 7
<212> TYPE: PRT
<213> ORGANISM: Artificial Sequence
<220> FEATURE:
<223> OTHER INFORMATION: Humanized 9F11.B7, AB0193/AB0187 and
      AB0196/AB0190 VH CDR1

<400> SEQUENCE: 192

```
Gly Phe Thr Phe Asn Ser Phe
1               5
```

<210> SEQ ID NO 193
<211> LENGTH: 120
<212> TYPE: PRT
<213> ORGANISM: Artificial Sequence
<220> FEATURE:
<223> OTHER INFORMATION: 9F11.B7 VH

<400> SEQUENCE: 193

```
Glu Val Gln Leu Gln Glu Ser Gly Gly Gly Leu Val Gln Pro Gly Gly
1               5                   10                  15

Ser Arg Lys Leu Ser Cys Ala Ala Ser Gly Phe Thr Phe Asn Ser Phe
            20                  25                  30

Gly Met His Trp Val Arg Gln Ala Pro Glu Lys Gly Leu Glu Trp Val
        35                  40                  45

Ala Phe Ile Ser Ser Gly Ser Thr Ser Ile Tyr Tyr Ala Asn Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Asp Gly Tyr Pro Thr Gly Gly Ala Met Asp Tyr Trp Gly Gln
            100                 105                 110

Gly Thr Ser Val Thr Val Ser Ser
        115                 120
```

<210> SEQ ID NO 194
<211> LENGTH: 107
<212> TYPE: PRT
<213> ORGANISM: Artificial Sequence
<220> FEATURE:
<223> OTHER INFORMATION: 9F11.B7 VL

<400> SEQUENCE: 194

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Tyr Asn Tyr
            20                  25                  30

Leu Ser Trp Phe Gln Leu Lys Pro Gly Lys Ser Pro Arg Pro Leu Ile
            35                  40                  45

Tyr Arg Ala Asn Ile Leu Val Ser Gly Val Pro Ser Lys Phe Ser Gly
50                  55                  60

Ser Gly Ser Gly Gln Asp Tyr Ser Leu Thr Ile Asn Ser Leu Glu Tyr
65                  70                  75                  80

Glu Asp Leu Gly Ile Tyr Tyr Cys Leu Gln Phe Asp Ala Phe Pro Phe
                85                  90                  95

Thr Phe Gly Ser Gly Thr Lys Leu Glu Ile Lys
            100                 105

<210> SEQ ID NO 195
<211> LENGTH: 7
<212> TYPE: PRT
<213> ORGANISM: Artificial Sequence
<220> FEATURE:
<223> OTHER INFORMATION: Humanized 9F11.B7 in AB0192/AB0186,
      AB0195/AB0189 VH CDR1

<400> SEQUENCE: 195

Gly Phe Thr Phe Asn Ala Phe
1               5

<210> SEQ ID NO 196
<211> LENGTH: 6
<212> TYPE: PRT
<213> ORGANISM: Artificial Sequence
<220> FEATURE:
<223> OTHER INFORMATION: Humanized 9F11.B7, AB0193/AB0187,
      AB0195/AB0189, in AB0192/AB0186, AB0196/AB0190 and 9F11.B7
      consensus VH CDR2

<400> SEQUENCE: 196

Ser Ser Gly Ser Thr Ser
1               5

<210> SEQ ID NO 197
<211> LENGTH: 7
<212> TYPE: PRT
<213> ORGANISM: Artificial Sequence
<220> FEATURE:
<223> OTHER INFORMATION: 13E1.A4 VH CDR1

<400> SEQUENCE: 197

Gly Tyr Ser Phe Thr Ala Tyr
1               5

<210> SEQ ID NO 198
<211> LENGTH: 11
<212> TYPE: PRT
<213> ORGANISM: Artificial Sequence
<220> FEATURE:
<223> OTHER INFORMATION: 9F11.B7 VL CDR1

<400> SEQUENCE: 198

Lys Ala Ser Gln Asp Ile Tyr Asn Tyr Leu Ser
1               5                   10

<210> SEQ ID NO 199
<211> LENGTH: 7
```

```
<212> TYPE: PRT
<213> ORGANISM: Artificial Sequence
<220> FEATURE:
<223> OTHER INFORMATION: 9F11.B7 VL CDR2

<400> SEQUENCE: 199

Arg Ala Asn Ile Leu Val Ser
1               5

<210> SEQ ID NO 200
<211> LENGTH: 244
<212> TYPE: PRT
<213> ORGANISM: Artificial Sequence
<220> FEATURE:
<223> OTHER INFORMATION: scFv of humanized 16B8.C8 of AB7410 [VL-VH]

<400> SEQUENCE: 200

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Phe Trp
                20                  25                  30

Leu Ser Trp Tyr Gln Gln Lys Pro Gly Lys Ala Pro Lys Leu Leu Ile
            35                  40                  45

Tyr Glu Ala Ser Asn Leu His Thr Gly Val Pro Ser Arg Phe Ser Gly
        50                  55                  60

Ser Gly Ser Gly Thr Arg Phe Thr Leu Thr Ile Ser Ser Leu Gln Pro
65                  70                  75                  80

Glu Asp Ile Ala Thr Tyr Tyr Cys Gln Gln Ser His Ser Tyr Pro Leu
                85                  90                  95

Thr Phe Gly Cys Gly Thr Lys Leu Glu Ile Lys Gly Gly Gly Gly Ser
            100                 105                 110

Gly Gly Gly Gly Ser Gly Gly Gly Ser Gly Gly Gly Gly Ser Gln
        115                 120                 125

Leu Gln Leu Gln Glu Ser Gly Pro Gly Leu Val Lys Pro Ser Glu Thr
    130                 135                 140

Leu Ser Leu Thr Cys Thr Val Ser Gly Phe Ser Leu Thr Asn Tyr Gly
145                 150                 155                 160

Leu His Trp Ile Arg Gln Pro Pro Gly Lys Cys Leu Glu Trp Ile Gly
                165                 170                 175

Val Ile Leu Ser Gly Gly Trp Thr Asp Tyr Asn Pro Ser Leu Lys Ser
            180                 185                 190

Arg Val Thr Ile Ser Lys Asp Thr Ser Lys Asn Gln Phe Ser Leu Lys
        195                 200                 205

Leu Ser Ser Val Gln Ala Ala Asp Thr Ala Val Tyr Tyr Cys Ala Lys
    210                 215                 220

Gly Asp Tyr Gly Asp Ala Leu Asp Tyr Trp Gly Gln Gly Thr Leu Val
225                 230                 235                 240

Thr Val Ser Ser

<210> SEQ ID NO 201
<211> LENGTH: 9
<212> TYPE: PRT
<213> ORGANISM: Artificial Sequence
<220> FEATURE:
<223> OTHER INFORMATION: 9F11.B7 VL CDR3

<400> SEQUENCE: 201

Leu Gln Phe Asp Ala Phe Pro Phe Thr
1               5
```

<210> SEQ ID NO 202
<211> LENGTH: 6
<212> TYPE: PRT
<213> ORGANISM: Artificial Sequence
<220> FEATURE:
<223> OTHER INFORMATION: 13E1.A4 VH CDR2

<400> SEQUENCE: 202

Asp Pro Ser Tyr Gly Asp
1               5

<210> SEQ ID NO 203
<211> LENGTH: 107
<212> TYPE: PRT
<213> ORGANISM: Artificial Sequence
<220> FEATURE:
<223> OTHER INFORMATION: Humanized 9F11.B7 in AB0191/AB0185,
    AB0192/AB0186, AB0193/AB0187 VL

<400> SEQUENCE: 203

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Tyr Asn Tyr
            20                  25                  30

Leu Ser Trp Phe Gln Gln Lys Pro Gly Lys Ala Pro Lys Pro Leu Ile
        35                  40                  45

Tyr Arg Ala Asn Ile Leu Val Ser Gly Val Pro Ser Arg Phe Ser Gly
    50                  55                  60

Ser Gly Ser Gly Gln Asp Tyr Thr Phe Thr Ile Ser Ser Leu Gln Pro
65                  70                  75                  80

Glu Asp Ile Ala Thr Tyr Tyr Cys Leu Gln Phe Asp Ala Phe Pro Phe
                85                  90                  95

Thr Phe Gly Ser Gly Thr Lys Leu Glu Ile Lys
            100                 105

<210> SEQ ID NO 204
<211> LENGTH: 247
<212> TYPE: PRT
<213> ORGANISM: Artificial Sequence
<220> FEATURE:
<223> OTHER INFORMATION: scFv of humanized 9F11.B7 of AB0192 [VH-VL]

<400> SEQUENCE: 204

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Asn Ala Phe
            20                  25                  30

Gly Met His Trp Val Arg Gln Ala Pro Gly Lys Cys Leu Glu Trp Val
        35                  40                  45

Ala Phe Ile Ser Ser Gly Ser Thr Ser Ile Tyr Tyr Ala Asn Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Tyr Pro Thr Gly Gly Ala Met Asp Tyr Trp Gly Gln
            100                 105                 110

Gly Thr Ser Val Thr Val Ser Ser Gly Gly Gly Gly Ser Gly Gly Gly
        115                 120                 125

```
Gly Ser Gly Gly Gly Ser Gly Gly Gly Ser Asp Ile Gln Met
        130                 135                 140

Thr Gln Ser Pro Ser Ser Leu Ser Ala Ser Val Gly Asp Arg Val Thr
145                 150                 155                 160

Ile Thr Cys Lys Ala Ser Gln Asp Ile Tyr Asn Tyr Leu Ser Trp Phe
                165                 170                 175

Gln Gln Lys Pro Gly Lys Ala Pro Lys Pro Leu Ile Tyr Arg Ala Asn
                180                 185                 190

Ile Leu Val Ser Gly Val Pro Ser Arg Phe Ser Gly Ser Gly Ser Gly
            195                 200                 205

Gln Asp Tyr Thr Phe Thr Ile Ser Ser Leu Gln Pro Glu Asp Ile Ala
        210                 215                 220

Thr Tyr Tyr Cys Leu Gln Phe Asp Ala Phe Pro Phe Thr Phe Gly Cys
225                 230                 235                 240

Gly Thr Lys Leu Glu Ile Lys
                245

<210> SEQ ID NO 205
<211> LENGTH: 247
<212> TYPE: PRT
<213> ORGANISM: Artificial Sequence
<220> FEATURE:
<223> OTHER INFORMATION: scFv of humanized 9F11.B7 of AB0186 [VL-VH]

<400> SEQUENCE: 205

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Tyr Asn Tyr
                20                  25                  30

Leu Ser Trp Phe Gln Gln Lys Pro Gly Lys Ala Pro Lys Pro Leu Ile
            35                  40                  45

Tyr Arg Ala Asn Ile Leu Val Ser Gly Val Pro Ser Arg Phe Ser Gly
        50                  55                  60

Ser Gly Ser Gly Gln Asp Tyr Thr Phe Thr Ile Ser Ser Leu Gln Pro
65                  70                  75                  80

Glu Asp Ile Ala Thr Tyr Tyr Cys Leu Gln Phe Asp Ala Phe Pro Phe
                85                  90                  95

Thr Phe Gly Cys Gly Thr Lys Leu Glu Ile Lys Gly Gly Gly Gly Ser
                100                 105                 110

Gly Gly Gly Gly Ser Gly Gly Gly Ser Gly Gly Gly Gly Ser Glu
            115                 120                 125

Val Gln Leu Val Glu Ser Gly Gly Val Val Gln Pro Gly Gly Ser
        130                 135                 140

Leu Arg Leu Ser Cys Ala Ala Ser Gly Phe Thr Phe Asn Ala Phe Gly
145                 150                 155                 160

Met His Trp Val Arg Gln Ala Pro Gly Lys Cys Leu Glu Trp Val Ala
                165                 170                 175

Phe Ile Ser Ser Gly Ser Thr Ser Ile Tyr Tyr Ala Asn Thr Val Lys
                180                 185                 190

Gly Arg Phe Thr Ile Ser Arg Asp Asn Ser Lys Asn Thr Leu Tyr Leu
            195                 200                 205

Gln Met Asn Ser Leu Arg Ala Glu Asp Thr Ala Val Tyr Tyr Cys Ala
        210                 215                 220

Arg Asp Gly Tyr Pro Thr Gly Gly Ala Met Asp Tyr Trp Gly Gln Gly
225                 230                 235                 240
```

Thr Ser Val Thr Val Ser Ser
            245

<210> SEQ ID NO 206
<211> LENGTH: 7
<212> TYPE: PRT
<213> ORGANISM: Artificial Sequence
<220> FEATURE:
<223> OTHER INFORMATION: 23A5.H8 VH CDR1

<400> SEQUENCE: 206

Gly Phe Ser Leu Thr Ser Tyr
1               5

<210> SEQ ID NO 207
<211> LENGTH: 11
<212> TYPE: PRT
<213> ORGANISM: Artificial Sequence
<220> FEATURE:
<223> OTHER INFORMATION: 13E1.A4 VH CDR3

<400> SEQUENCE: 207

Asp Asn Tyr Tyr Gly Ser Gly Tyr Phe Asp Tyr
1               5                   10

<210> SEQ ID NO 208
<211> LENGTH: 247
<212> TYPE: PRT
<213> ORGANISM: Artificial Sequence
<220> FEATURE:
<223> OTHER INFORMATION: scFv of humanized 9F11.B7 of AB0193 [VH-VL]:

<400> SEQUENCE: 208

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Asn Ser Phe
            20                  25                  30

Gly Met His Trp Val Arg Gln Ala Pro Gly Lys Cys Leu Glu Trp Val
        35                  40                  45

Ala Phe Ile Ser Ser Gly Ser Thr Ser Ile Tyr Tyr Ala Asn Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Pro Thr Gly Gly Ala Met Asp Tyr Trp Gly Gln
            100                 105                 110

Gly Thr Ser Val Thr Val Ser Ser Gly Gly Gly Gly Ser Gly Gly Gly
        115                 120                 125

Gly Ser Gly Gly Gly Gly Ser Gly Gly Gly Gly Ser Asp Ile Gln Met
    130                 135                 140

Thr Gln Ser Pro Ser Ser Leu Ser Ala Ser Val Gly Asp Arg Val Thr
145                 150                 155                 160

Ile Thr Cys Lys Ala Ser Gln Asp Ile Tyr Asn Tyr Leu Ser Trp Phe
                165                 170                 175

Gln Gln Lys Pro Gly Lys Ala Pro Lys Pro Leu Ile Tyr Arg Ala Asn
            180                 185                 190

Ile Leu Val Ser Gly Val Pro Ser Arg Phe Ser Gly Ser Gly Ser Gly
        195                 200                 205

Gln Asp Tyr Thr Phe Thr Ile Ser Ser Leu Gln Pro Glu Asp Ile Ala
            210                 215                 220

Thr Tyr Tyr Cys Leu Gln Phe Asp Ala Phe Pro Phe Thr Phe Gly Cys
225                 230                 235                 240

Gly Thr Lys Leu Glu Ile Lys
            245

<210> SEQ ID NO 209
<211> LENGTH: 247
<212> TYPE: PRT
<213> ORGANISM: Artificial Sequence
<220> FEATURE:
<223> OTHER INFORMATION: scFv of humanized 9F11.B7 of AB0187 [VL-VH]

<400> SEQUENCE: 209

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Tyr Asn Tyr
            20                  25                  30

Leu Ser Trp Phe Gln Gln Lys Pro Gly Lys Ala Pro Lys Pro Leu Ile
        35                  40                  45

Tyr Arg Ala Asn Ile Leu Val Ser Gly Val Pro Ser Arg Phe Ser Gly
    50                  55                  60

Ser Gly Ser Gly Gln Asp Tyr Thr Phe Thr Ile Ser Ser Leu Gln Pro
65                  70                  75                  80

Glu Asp Ile Ala Thr Tyr Tyr Cys Leu Gln Phe Asp Ala Phe Pro Phe
                85                  90                  95

Thr Phe Gly Cys Gly Thr Lys Leu Glu Ile Lys Gly Gly Gly Gly Ser
            100                 105                 110

Gly Gly Gly Gly Ser Gly Gly Gly Ser Gly Gly Gly Gly Gly Ser Glu
        115                 120                 125

Val Gln Leu Val Glu Ser Gly Gly Val Val Gln Pro Gly Gly Ser
130                 135                 140

Leu Arg Leu Ser Cys Ala Ala Ser Gly Phe Thr Phe Asn Ser Phe Gly
145                 150                 155                 160

Met His Trp Val Arg Gln Ala Pro Gly Lys Cys Leu Glu Trp Val Ala
                165                 170                 175

Phe Ile Ser Ser Gly Ser Thr Ser Ile Tyr Tyr Ala Asn Thr Val Lys
            180                 185                 190

Gly Arg Phe Thr Ile Ser Arg Asp Asn Ser Lys Asn Thr Leu Tyr Leu
        195                 200                 205

Gln Met Asn Ser Leu Arg Ala Glu Asp Thr Ala Val Tyr Tyr Cys Ala
    210                 215                 220

Arg Ser Gly Tyr Pro Thr Gly Gly Ala Met Asp Tyr Trp Gly Gln Gly
225                 230                 235                 240

Thr Ser Val Thr Val Ser Ser
            245

<210> SEQ ID NO 210
<211> LENGTH: 120
<212> TYPE: PRT
<213> ORGANISM: Artificial Sequence
<220> FEATURE:
<223> OTHER INFORMATION: Humanized 9F11.B7 in AB0193/AB0187 and
      AB0196/AB0190 VH

<400> SEQUENCE: 210

Glu Val Gln Leu Val Glu Ser Gly Gly Gly Val Val Gln Pro Gly Gly

```
                1               5                   10                  15
            Ser Leu Arg Leu Ser Cys Ala Ala Ser Gly Phe Thr Phe Asn Ser Phe
                        20                  25                  30

Gly Met His Trp Val Arg Gln Ala Pro Gly Lys Gly Leu Glu Trp Val
                        35                  40                  45

Ala Phe Ile Ser Ser Gly Ser Thr Ser Ile Tyr Tyr Ala Asn Thr Val
                        50                  55                  60

Lys Gly Arg Phe Thr Ile Ser Arg Asp Asn Ser Lys Asn Thr Leu Tyr
             65                 70                  75                  80

Leu Gln Met Asn Ser Leu Arg Ala Glu Asp Thr Ala Val Tyr Tyr Cys
                            85                  90                  95

Ala Arg Ser Gly Tyr Pro Thr Gly Gly Ala Met Asp Tyr Trp Gly Gln
                        100                 105                 110

Gly Thr Ser Val Thr Val Ser Ser
                        115                 120
```

<210> SEQ ID NO 211
<211> LENGTH: 16
<212> TYPE: PRT
<213> ORGANISM: Artificial Sequence
<220> FEATURE:
<223> OTHER INFORMATION: 13E1.A4 VL CDR1

<400> SEQUENCE: 211

```
            Arg Ser Ser Gln Gly Ile Val His Ile Asn Gly Asn Thr Tyr Leu Glu
             1               5                   10                  15
```

<210> SEQ ID NO 212
<211> LENGTH: 7
<212> TYPE: PRT
<213> ORGANISM: Artificial Sequence
<220> FEATURE:
<223> OTHER INFORMATION: 13E1.A4 VL CDR2

<400> SEQUENCE: 212

```
            Lys Val Ser Asn Arg Phe Ser
             1               5
```

<210> SEQ ID NO 213
<211> LENGTH: 11
<212> TYPE: PRT
<213> ORGANISM: Artificial Sequence
<220> FEATURE:
<223> OTHER INFORMATION: Humanized 9F11.B7 in AB0193/AB0187 and
      AB0196/AB0190 VH CDR3

<400> SEQUENCE: 213

```
            Ser Gly Tyr Pro Thr Gly Gly Ala Met Asp Tyr
             1               5                   10
```

<210> SEQ ID NO 214
<211> LENGTH: 9
<212> TYPE: PRT
<213> ORGANISM: Artificial Sequence
<220> FEATURE:
<223> OTHER INFORMATION: 13E1.A4 VL CDR3

<400> SEQUENCE: 214

```
            Phe Gln Gly Ser His Val Pro Trp Thr
             1               5
```

<210> SEQ ID NO 215
<211> LENGTH: 247

<212> TYPE: PRT
<213> ORGANISM: Artificial Sequence
<220> FEATURE:
<223> OTHER INFORMATION: scFv of humanized 9F11.B7 of AB0194 [VH-VL]

<400> SEQUENCE: 215

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Asn Ser Phe
            20                  25                  30

Gly Met His Trp Val Arg Gln Ala Pro Gly Lys Cys Leu Glu Trp Val
        35                  40                  45

Ala Phe Ile Ser Ser Gly Ser Thr Ser Ile Tyr Tyr Ala Asn Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Gly Tyr Pro Thr Gly Gly Ala Met Asp Tyr Trp Gly Gln
        100                 105                 110

Gly Thr Ser Val Thr Val Ser Ser Gly Gly Gly Ser Gly Gly Gly
    115                 120                 125

Gly Ser Gly Gly Gly Ser Gly Gly Gly Ser Asp Ile Lys Met
    130                 135                 140

Thr Gln Ser Pro Ser Ser Leu Ser Ala Ser Val Gly Asp Arg Val Thr
145                 150                 155                 160

Ile Thr Cys Lys Ala Ser Gln Asp Ile Tyr Asn Tyr Leu Ser Trp Phe
            165                 170                 175

Gln Gln Lys Pro Gly Lys Ala Pro Lys Pro Leu Ile Tyr Arg Ala Asn
        180                 185                 190

Ile Leu Val Ser Gly Val Pro Ser Arg Phe Ser Gly Ser Gly Ser Gly
    195                 200                 205

Gln Asp Tyr Thr Leu Thr Ile Ser Ser Leu Gln Pro Glu Asp Ile Ala
    210                 215                 220

Thr Tyr Tyr Cys Leu Gln Phe Asp Ala Phe Pro Phe Thr Phe Gly Cys
225                 230                 235                 240

Gly Thr Lys Leu Glu Ile Lys
            245

<210> SEQ ID NO 216
<211> LENGTH: 247
<212> TYPE: PRT
<213> ORGANISM: Artificial Sequence
<220> FEATURE:
<223> OTHER INFORMATION: scFv of humanized 9F11.B7 of AB0188 [VL-VH]

<400> SEQUENCE: 216

Asp Ile Lys Met Thr Gln Ser Pro Ser Ser Leu Ser Ala Ser Val Gly
1               5                   10                  15

Asp Arg Val Thr Ile Thr Cys Lys Ala Ser Gln Asp Ile Tyr Asn Tyr
            20                  25                  30

Leu Ser Trp Phe Gln Gln Lys Pro Gly Lys Ala Pro Lys Pro Leu Ile
        35                  40                  45

Tyr Arg Ala Asn Ile Leu Val Ser Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

```
Glu Asp Ile Ala Thr Tyr Tyr Cys Leu Gln Phe Asp Ala Phe Pro Phe
                85                  90                  95

Thr Phe Gly Cys Gly Thr Lys Leu Glu Ile Lys Gly Gly Gly Gly Ser
            100                 105                 110

Gly Gly Gly Gly Ser Gly Gly Gly Ser Gly Gly Gly Gly Ser Glu
        115                 120                 125

Val Gln Leu Val Glu Ser Gly Gly Val Val Gln Pro Gly Gly Ser
130                 135                 140

Leu Arg Leu Ser Cys Ala Ala Ser Gly Phe Thr Phe Asn Ser Phe Gly
145                 150                 155                 160

Met His Trp Val Arg Gln Ala Pro Gly Lys Cys Leu Glu Trp Val Ala
                165                 170                 175

Phe Ile Ser Ser Gly Ser Thr Ser Ile Tyr Tyr Ala Asn Thr Val Lys
                180                 185                 190

Gly Arg Phe Thr Ile Ser Arg Asp Asn Ser Lys Asn Thr Leu Tyr Leu
                195                 200                 205

Gln Met Asn Ser Leu Arg Ala Glu Asp Thr Ala Val Tyr Tyr Cys Ala
            210                 215                 220

Arg Asp Gly Tyr Pro Thr Gly Gly Ala Met Asp Tyr Trp Gly Gln Gly
225                 230                 235                 240

Thr Ser Val Thr Val Ser Ser
            245
```

<210> SEQ ID NO 217
<211> LENGTH: 121
<212> TYPE: PRT
<213> ORGANISM: Artificial Sequence
<220> FEATURE:
<223> OTHER INFORMATION: 12F8.H7 VH

<400> SEQUENCE: 217

```
Glu Val Gln Leu Gln Glu Ser Gly Ala Glu Leu Val Arg Ser Gly Ala
1               5                   10                  15

Ser Val Lys Leu Ser Cys Thr Val Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Asn Val Pro Lys Phe
    50                  55                  60

Gln Gly Lys Ala Thr Met Thr Ala Asp Thr Ser Ser Asn Thr Ala Tyr
65                  70                  75                  80

Leu Gln Leu Arg Ser Leu Thr Ser Glu Asp Thr Ala Val Tyr Tyr Cys
                85                  90                  95

Lys Ser Tyr Tyr Tyr Asp Ser Ser Arg Tyr Val Asp Val Trp Gly
            100                 105                 110

Ala Gly Thr Thr Val Thr Val Ser Ser
        115                 120
```

<210> SEQ ID NO 218
<211> LENGTH: 107
<212> TYPE: PRT
<213> ORGANISM: Artificial Sequence
<220> FEATURE:
<223> OTHER INFORMATION: Humanized 9F11.B7 in AB0194/AB0188,
      AB0195/AB0189 and AB0196/AB0190 VL

<400> SEQUENCE: 218

```
Asp Ile Lys Met Thr Gln Ser Pro Ser Ser Leu Ser Ala Ser Val Gly
1               5                   10                  15

Asp Arg Val Thr Ile Thr Cys Lys Ala Ser Gln Asp Ile Tyr Asn Tyr
                20                  25                  30

Leu Ser Trp Phe Gln Gln Lys Pro Gly Lys Ala Pro Lys Pro Leu Ile
            35                  40                  45

Tyr Arg Ala Asn Ile Leu Val Ser Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Ile Ala Thr Tyr Tyr Cys Leu Gln Phe Asp Ala Phe Pro Phe
                85                  90                  95

Thr Phe Gly Ser Gly Thr Lys Leu Glu Ile Lys
            100                 105
```

<210> SEQ ID NO 219
<211> LENGTH: 112
<212> TYPE: PRT
<213> ORGANISM: Artificial Sequence
<220> FEATURE:
<223> OTHER INFORMATION: 12F8.H7 VL

<400> SEQUENCE: 219

```
Gly Ile Val Met Thr Gln Ala Pro Leu Thr Leu Ser Val Thr Ile Gly
1               5                   10                  15

Gln Pro Ala Ser Ile Ser Cys Lys Ser Ser Gln Ser Leu Leu Asp Ser
                20                  25                  30

Asp Gly Lys Thr Phe Leu Asn Trp Phe Leu Gln Arg Pro Gly Gln Ser
            35                  40                  45

Pro Lys Arg Leu Ile Ser Leu Val Ser Lys Leu Asp Ser Gly Val Pro
    50                  55                  60

Asp Arg Phe Thr Gly Ser Gly Ser Gly Thr Asp Phe Thr Leu Lys Leu
65                  70                  75                  80

Ser Arg Val Glu Pro Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110
```

<210> SEQ ID NO 220
<211> LENGTH: 7
<212> TYPE: PRT
<213> ORGANISM: Artificial Sequence
<220> FEATURE:
<223> OTHER INFORMATION: 12F8.H7 VH CDR1

<400> SEQUENCE: 220

```
Gly Phe Asn Ile Lys Asp Tyr
1               5
```

<210> SEQ ID NO 221
<211> LENGTH: 7
<212> TYPE: PRT
<213> ORGANISM: Artificial Sequence
<220> FEATURE:
<223> OTHER INFORMATION: 20D6.H8 and 30A9.E9 VH CDR1

<400> SEQUENCE: 221

```
Gly Phe Ser Leu Thr Ser Phe
1               5
```

```
<210> SEQ ID NO 222
<211> LENGTH: 6
<212> TYPE: PRT
<213> ORGANISM: Artificial Sequence
<220> FEATURE:
<223> OTHER INFORMATION: 12F8.H7 VH CDR2

<400> SEQUENCE: 222

Asp Pro Glu Asn Gly Asp
1               5

<210> SEQ ID NO 223
<211> LENGTH: 7
<212> TYPE: PRT
<213> ORGANISM: Artificial Sequence
<220> FEATURE:
<223> OTHER INFORMATION: 20D6.H8 and 30A9.E9 VH CDR3

<400> SEQUENCE: 223

Ser Tyr Phe Ala Met Asp Tyr
1               5

<210> SEQ ID NO 224
<211> LENGTH: 16
<212> TYPE: PRT
<213> ORGANISM: Artificial Sequence
<220> FEATURE:
<223> OTHER INFORMATION: 12F8.H7 VL CDR1

<400> SEQUENCE: 224

Lys Ser Ser Gln Ser Leu Leu Asp Ser Asp Gly Lys Thr Phe Leu Asn
1               5                   10                  15

<210> SEQ ID NO 225
<211> LENGTH: 7
<212> TYPE: PRT
<213> ORGANISM: Artificial Sequence
<220> FEATURE:
<223> OTHER INFORMATION: 12F8.H7 VL CDR2

<400> SEQUENCE: 225

Leu Val Ser Lys Leu Asp Ser
1               5

<210> SEQ ID NO 226
<211> LENGTH: 7
<212> TYPE: PRT
<213> ORGANISM: Artificial Sequence
<220> FEATURE:
<223> OTHER INFORMATION: 20D6.H8 and 30A9.E9 VL CDR2

<400> SEQUENCE: 226

Gly Ala Ser Ile Arg Glu Ser
1               5

<210> SEQ ID NO 227
<211> LENGTH: 9
<212> TYPE: PRT
<213> ORGANISM: Artificial Sequence
<220> FEATURE:
<223> OTHER INFORMATION: 12F8.H7 VL CDR3

<400> SEQUENCE: 227

Trp Gln Gly Thr His Phe Pro Tyr Thr
1               5

<210> SEQ ID NO 228
```

```
<211> LENGTH: 119
<212> TYPE: PRT
<213> ORGANISM: Artificial Sequence
<220> FEATURE:
<223> OTHER INFORMATION: 9E4.B7 VH

<400> SEQUENCE: 228

Glu Val Gln Leu Gln Glu Ser Gly Ala Glu Leu Met Lys Pro Gly Ala
1               5                   10                  15

Ser Val Lys Ile Ser Cys Arg Thr Thr Gly Tyr Thr Phe Ser Thr Tyr
            20                  25                  30

Trp Ile Glu Trp Val Lys Gln Arg Pro Gly Arg Gly Pro Glu Trp Ile
        35                  40                  45

Gly Glu Leu Phe Pro Gly Asn Ser Asp Thr Thr Leu Asn Glu Lys Phe
    50                  55                  60

Thr Gly Lys Ala Thr Phe Thr Ala Asp Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Gly Tyr Tyr Gly Ser Ser Leu Asp Tyr Trp Gly Gln Gly
            100                 105                 110

Thr Thr Leu Thr Val Ser Ser
        115

<210> SEQ ID NO 229
<211> LENGTH: 107
<212> TYPE: PRT
<213> ORGANISM: Artificial Sequence
<220> FEATURE:
<223> OTHER INFORMATION: 9E4.B7 VL

<400> SEQUENCE: 229

Gly Ile Val Met Thr Gln Ser Pro Ala Ser Leu Ser Ala Ser Val Gly
1               5                   10                  15

Glu Thr Val Thr Ile Thr Cys Arg Ala Gly Glu Asn Ile His Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Arg
                85                  90                  95

Thr Phe Gly Gly Gly Thr Lys Leu Glu Ile Lys
            100                 105

<210> SEQ ID NO 230
<211> LENGTH: 7
<212> TYPE: PRT
<213> ORGANISM: Artificial Sequence
<220> FEATURE:
<223> OTHER INFORMATION: 9E4.B7 VH CDR1

<400> SEQUENCE: 230

Gly Tyr Thr Phe Ser Thr Tyr
1               5

<210> SEQ ID NO 231
<211> LENGTH: 6
```

```
<212> TYPE: PRT
<213> ORGANISM: Artificial Sequence
<220> FEATURE:
<223> OTHER INFORMATION: 9E4.B7 VH CDR2

<400> SEQUENCE: 231

Phe Pro Gly Asn Ser Asp
1               5

<210> SEQ ID NO 232
<211> LENGTH: 10
<212> TYPE: PRT
<213> ORGANISM: Artificial Sequence
<220> FEATURE:
<223> OTHER INFORMATION: 9E4.B7 VH CDR3

<400> SEQUENCE: 232

Ser Gly Tyr Tyr Gly Ser Ser Leu Asp Tyr
1               5                   10

<210> SEQ ID NO 233
<211> LENGTH: 11
<212> TYPE: PRT
<213> ORGANISM: Artificial Sequence
<220> FEATURE:
<223> OTHER INFORMATION: 9E4.B7 VL CDR1

<400> SEQUENCE: 233

Arg Ala Gly Glu Asn Ile His Ser Tyr Leu Ala
1               5                   10

<210> SEQ ID NO 234
<211> LENGTH: 7
<212> TYPE: PRT
<213> ORGANISM: Artificial Sequence
<220> FEATURE:
<223> OTHER INFORMATION: 9E4.B7 VL CDR2

<400> SEQUENCE: 234

Asn Ala Lys Thr Leu Ala Glu
1               5

<210> SEQ ID NO 235
<211> LENGTH: 9
<212> TYPE: PRT
<213> ORGANISM: Artificial Sequence
<220> FEATURE:
<223> OTHER INFORMATION: 9E4.B7 VL CDR3

<400> SEQUENCE: 235

Gln His His Tyr Gly Thr Pro Arg Thr
1               5

<210> SEQ ID NO 236
<211> LENGTH: 5
<212> TYPE: PRT
<213> ORGANISM: Artificial Sequence
<220> FEATURE:
<223> OTHER INFORMATION: 20D6.H8 VH CDR2

<400> SEQUENCE: 236

Trp Ser Gly Gly Asn
1               5

<210> SEQ ID NO 237
<211> LENGTH: 115
<212> TYPE: PRT
```

<213> ORGANISM: Artificial Sequence
<220> FEATURE:
<223> OTHER INFORMATION: 20D6.H8 VL

<400> SEQUENCE: 237

Gly Ile Val Met Thr Gln Ser Pro Ser Leu Ala Val Thr Ala Gly
1               5                   10                  15

Glu Lys Val Thr Met Arg Cys Lys Ser Ser Gln Ser Leu Leu Trp Asn
            20                  25                  30

Val Asn Gln Asn Asn Tyr Leu Val Trp Tyr Gln Gln Lys Gln Gly Gln
        35                  40                  45

Pro Pro Lys Leu Leu Ile Tyr Gly Ala Ser Ile Arg Glu Ser Trp Val
50                  55                  60

Pro Asp Arg Phe Thr Gly Ser Gly Ser Gly Thr Asp Phe Thr Leu Thr
65                  70                  75                  80

Ile Ser Asn Val His Ala Glu Asp Leu Ala Val Tyr Tyr Cys Gln His
                85                  90                  95

Asn His Gly Ser Phe Leu Pro Tyr Thr Phe Gly Gly Gly Thr Lys Leu
            100                 105                 110

Glu Ile Lys
        115

<210> SEQ ID NO 238
<211> LENGTH: 115
<212> TYPE: PRT
<213> ORGANISM: Artificial Sequence
<220> FEATURE:
<223> OTHER INFORMATION: 20D6.H8 VH

<400> SEQUENCE: 238

Glu Val Gln Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Ser Phe
            20                  25                  30

Gly Ile His Trp Val Arg Gln Ser Pro Gly Lys Gly Leu Glu Trp Leu
        35                  40                  45

Gly Val Ile Trp Ser Gly Gly Asn Thr Asp Ser Asn Ala Ala Phe Ile
50                  55                  60

Ser Arg Leu Ser Ile Thr Lys Asp Ile Ser Lys Ser Gln Val Phe Phe
65                  70                  75                  80

Lys Met Asn Ser Leu Gln Val Thr Asp Thr Ala Ile Tyr Tyr Cys Ala
                85                  90                  95

Arg Ser Tyr Phe Ala Met Asp Tyr Trp Gly Gln Gly Thr Ser Val Thr
            100                 105                 110

Val Ser Ser
        115

<210> SEQ ID NO 239
<211> LENGTH: 7
<212> TYPE: PRT
<213> ORGANISM: Artificial Sequence
<220> FEATURE:
<223> OTHER INFORMATION: 23A5.H8 VL CDR2

<400> SEQUENCE: 239

Gly Ala Ser Ile Arg Gln Ser
1               5

<210> SEQ ID NO 240

```
<211> LENGTH: 17
<212> TYPE: PRT
<213> ORGANISM: Artificial Sequence
<220> FEATURE:
<223> OTHER INFORMATION: 30A9.E9 VL CDR1

<400> SEQUENCE: 240

Lys Ser Ser Gln Ser Leu Leu Trp Asn Val Asn Gln Asn Asn Tyr Leu
1               5                   10                  15

Leu

<210> SEQ ID NO 241
<211> LENGTH: 7
<212> TYPE: PRT
<213> ORGANISM: Artificial Sequence
<220> FEATURE:
<223> OTHER INFORMATION: 23A5.H8 VH CDR3

<400> SEQUENCE: 241

Thr His Phe Gly Met Asp Tyr
1               5

<210> SEQ ID NO 242
<211> LENGTH: 115
<212> TYPE: PRT
<213> ORGANISM: Artificial Sequence
<220> FEATURE:
<223> OTHER INFORMATION: 23A5.H8 VH

<400> SEQUENCE: 242

Gln Val Gln Leu Arg Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
                20                  25                  30

Gly Val His Trp Val Arg Gln Ser Pro Gly Lys Gly Leu Glu Trp Leu
            35                  40                  45

Gly Val Met Trp Ser Gly Gly Ser Thr Asp Tyr Asn Ala Ala Phe Met
        50                  55                  60

Ser Arg Leu Ser Ile Ser Lys Asp Asn Ser Lys Ser Gln Val Phe Phe
65                  70                  75                  80

Thr Met Asn Ser Leu Gln Ala Asp Asp Thr Ala Ile Tyr Tyr Cys Ala
                85                  90                  95

Arg Thr His Phe Gly Met Asp Tyr Trp Gly Gln Gly Thr Pro Val Thr
            100                 105                 110

Val Ser Ser
        115

<210> SEQ ID NO 243
<211> LENGTH: 115
<212> TYPE: PRT
<213> ORGANISM: Artificial Sequence
<220> FEATURE:
<223> OTHER INFORMATION: 23A5.H8 VL

<400> SEQUENCE: 243

Gly Ile Val Met Thr Gln Ser Pro Ser Ser Leu Ala Val Thr Ala Gly
1               5                   10                  15

Glu Lys Val Thr Met Arg Cys Lys Ser Ser Gln Ser Leu Leu Trp Ser
                20                  25                  30

Val Asn Gln Asn Asn Tyr Leu Leu Trp Tyr Gln Gln Lys Gln Gly Gln
            35                  40                  45
```

Pro Pro Lys Leu Leu Ile Tyr Gly Ala Ser Ile Arg Gln Ser Trp Val
    50                  55                  60

Pro Asp Arg Phe Thr Gly Ser Gly Ser Gly Thr Asp Phe Thr Leu Ser
65                  70                  75                  80

Ile Ser Asn Val His Ala Glu Asp Leu Ala Val Tyr Tyr Cys Gln His
                85                  90                  95

Asn His Gly Ser Phe Leu Pro Tyr Thr Phe Gly Gly Gly Thr Lys Leu
            100                 105                 110

Glu Ile Lys
        115

<210> SEQ ID NO 244
<211> LENGTH: 117
<212> TYPE: PRT
<213> ORGANISM: Artificial Sequence
<220> FEATURE:
<223> OTHER INFORMATION: Humanized 16B8.C8 in scFv-1294 / scFv-1303 VH

<400> SEQUENCE: 244

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Leu His Trp Ile Arg Gln Pro Pro Gly Lys Gly Leu Glu Trp Ile
        35                  40                  45

Gly Val Ile Trp Ser Gly Gly Lys Thr Asp Tyr Asn Pro Ser Leu Lys
    50                  55                  60

Ser Arg Val Thr Ile Ser Lys Asp Thr Ser Lys Asn Gln Phe Ser Leu
65                  70                  75                  80

Lys Leu Ser Ser Val Thr Ala Asn Asp Thr Ala Val Tyr Tyr Cys Ala
                85                  90                  95

Lys Tyr Asp Tyr Asp Asp Ser Leu Asp Tyr Trp Gly Gln Gly Thr Leu
            100                 105                 110

Val Thr Val Ser Ser
        115

<210> SEQ ID NO 245
<211> LENGTH: 17
<212> TYPE: PRT
<213> ORGANISM: Artificial Sequence
<220> FEATURE:
<223> OTHER INFORMATION: 23A5.H8 VL CDR1

<400> SEQUENCE: 245

Lys Ser Ser Gln Ser Leu Leu Trp Ser Val Asn Gln Asn Asn Tyr Leu
1               5                   10                  15

Leu

<210> SEQ ID NO 246
<211> LENGTH: 11
<212> TYPE: PRT
<213> ORGANISM: Artificial Sequence
<220> FEATURE:
<223> OTHER INFORMATION: Humanized 9F11.B7 consensus VH CDR3
<220> FEATURE:
<221> NAME/KEY: misc_feature
<222> LOCATION: (1)..(1)
<223> OTHER INFORMATION: Xaa can be Asp or Ser

<400> SEQUENCE: 246

Xaa Gly Tyr Pro Thr Gly Gly Ala Met Asp Tyr

<210> SEQ ID NO 247
<211> LENGTH: 115
<212> TYPE: PRT
<213> ORGANISM: Artificial Sequence
<220> FEATURE:
<223> OTHER INFORMATION: 30A9.E9 VH

<400> SEQUENCE: 247

Glu Val Gln Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Ser Phe
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Ser Asn Ala Ala Phe Ile
    50                  55                  60

Ser Arg Leu Thr Ile Thr Lys Asp Asn Ser Lys Ser Gln Val Phe Phe
65                  70                  75                  80

Lys Met Asn Ser Leu Gln Ala Thr Asp Thr Ala Ile Tyr Tyr Cys Ala
                85                  90                  95

Arg Ser Tyr Phe Ala Met Asp Tyr Trp Gly Gln Gly Thr Ser Val Ser
            100                 105                 110

Val Ser Ser
        115

<210> SEQ ID NO 248
<211> LENGTH: 115
<212> TYPE: PRT
<213> ORGANISM: Artificial Sequence
<220> FEATURE:
<223> OTHER INFORMATION: 30A9.E9 VL

<400> SEQUENCE: 248

Asp Ile Val Met Thr Gln Ser Pro Ser Ser Leu Ala Val Thr Ala Gly
1               5                   10                  15

Glu Lys Val Thr Met Arg Cys Lys Ser Ser Gln Ser Leu Leu Trp Asn
            20                  25                  30

Val Asn Gln Asn Asn Tyr Leu Leu Trp Tyr Gln Gln Lys Gln Gly Gln
        35                  40                  45

Pro Pro Lys Leu Leu Ile Tyr Gly Ala Ser Ile Arg Glu Ser Trp Val
    50                  55                  60

Pro Asp Arg Phe Thr Gly Ser Gly Ser Gly Thr Asp Phe Thr Leu Thr
65                  70                  75                  80

Ile Ser Asn Val His Val Glu Asp Leu Ala Val Tyr Tyr Cys Gln His
                85                  90                  95

Asn His Gly Ser Phe Leu Pro Tyr Thr Phe Gly Gly Gly Thr Lys Leu
            100                 105                 110

Glu Ile Lys
        115

<210> SEQ ID NO 249
<211> LENGTH: 120
<212> TYPE: PRT
<213> ORGANISM: Artificial Sequence
<220> FEATURE:
<223> OTHER INFORMATION: Humanized 9F11.B7 consensus - VH
<220> FEATURE:
<221> NAME/KEY: misc_feature

```
<222> LOCATION: (31)..(31)
<223> OTHER INFORMATION: Xaa can be Ser or Ala
<220> FEATURE:
<221> NAME/KEY: misc_feature
<222> LOCATION: (99)..(99)
<223> OTHER INFORMATION: Xaa can be Asp or Ser

<400> SEQUENCE: 249
```

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Asn Xaa Phe
            20                  25                  30

Gly Met His Trp Val Arg Gln Ala Pro Gly Lys Gly Leu Glu Trp Val
        35                  40                  45

Ala Phe Ile Ser Ser Gly Ser Thr Ser Ile Tyr Tyr Ala Asn Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Xaa Gly Tyr Pro Thr Gly Gly Ala Met Asp Tyr Trp Gly Gln
            100                 105                 110

Gly Thr Ser Val Thr Val Ser Ser
        115                 120

```
<210> SEQ ID NO 250
<211> LENGTH: 114
<212> TYPE: PRT
<213> ORGANISM: Artificial Sequence
<220> FEATURE:
<223> OTHER INFORMATION: Humanized 9F11.B7 consensus
<220> FEATURE:
<221> NAME/KEY: misc_feature
<222> LOCATION: (3)..(3)
<223> OTHER INFORMATION: Xaa can be Gln or Lys
<220> FEATURE:
<221> NAME/KEY: misc_feature
<222> LOCATION: (73)..(73)
<223> OTHER INFORMATION: Xaa can be Phe or Leu

<400> SEQUENCE: 250
```

Asp Ile Xaa Met Thr Gln Ser Pro Ser Ser Leu Ser Ala Ser Val Gly
1               5                   10                  15

Asp Arg Val Thr Ile Thr Cys Lys Ala Ser Gln Asp Ile Tyr Asn Tyr
            20                  25                  30

Leu Ser Trp Phe Gln Gln Lys Pro Gly Lys Ala Pro Lys Pro Leu Ile
        35                  40                  45

Tyr Arg Ala Asn Ile Leu Val Ser Gly Val Pro Ser Arg Phe Ser Gly
    50                  55                  60

Ser Gly Ser Gly Gln Asp Tyr Thr Xaa Thr Ile Ser Ser Leu Gln Pro
65                  70                  75                  80

Glu Asp Ile Ala Thr Tyr Tyr Cys Leu Gln Phe Asp Ala Phe Pro Phe
                85                  90                  95

Thr Phe Gly Ser Gly Thr Lys Leu Glu Ile Lys Trp His Glu Arg Glu
            100                 105                 110

Ile Asn

```
<210> SEQ ID NO 251
<211> LENGTH: 7
<212> TYPE: PRT
<213> ORGANISM: Artificial Sequence
```

```
<220> FEATURE:
<223> OTHER INFORMATION: Humanized 9F11.B7 consensus VH CDR1
<220> FEATURE:
<221> NAME/KEY: misc_feature
<222> LOCATION: (6)..(6)
<223> OTHER INFORMATION: Xaa can be Ser or Ala

<400> SEQUENCE: 251

Gly Phe Thr Phe Asn Xaa Phe
1               5

<210> SEQ ID NO 252
<211> LENGTH: 247
<212> TYPE: PRT
<213> ORGANISM: Artificial Sequence
<220> FEATURE:
<223> OTHER INFORMATION: scFv of humanized 9F11.B7 of AB0195 [VH-VL]

<400> SEQUENCE: 252

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Asn Ala Phe
            20                  25                  30

Gly Met His Trp Val Arg Gln Ala Pro Gly Lys Cys Leu Glu Trp Val
        35                  40                  45

Ala Phe Ile Ser Ser Gly Ser Thr Ser Ile Tyr Tyr Ala Asn Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Tyr Pro Thr Gly Gly Ala Met Asp Tyr Trp Gly Gln
            100                 105                 110

Gly Thr Ser Val Thr Val Ser Ser Gly Gly Gly Ser Gly Gly Gly
        115                 120                 125

Gly Ser Gly Gly Gly Ser Gly Gly Gly Ser Asp Ile Lys Met
        130                 135                 140

Thr Gln Ser Pro Ser Ser Leu Ser Ala Ser Val Gly Asp Arg Val Thr
145                 150                 155                 160

Ile Thr Cys Lys Ala Ser Gln Asp Ile Tyr Asn Tyr Leu Ser Trp Phe
                165                 170                 175

Gln Gln Lys Pro Gly Lys Ala Pro Lys Pro Leu Ile Tyr Arg Ala Asn
            180                 185                 190

Ile Leu Val Ser Gly Val Pro Ser Arg Phe Ser Gly Ser Gly Ser Gly
        195                 200                 205

Gln Asp Tyr Thr Leu Thr Ile Ser Ser Leu Gln Pro Glu Asp Ile Ala
    210                 215                 220

Thr Tyr Tyr Cys Leu Gln Phe Asp Ala Phe Pro Phe Thr Phe Gly Cys
225                 230                 235                 240

Gly Thr Lys Leu Glu Ile Lys
                245

<210> SEQ ID NO 253
<211> LENGTH: 247
<212> TYPE: PRT
<213> ORGANISM: Artificial Sequence
<220> FEATURE:
<223> OTHER INFORMATION: scFv of humanized 9F11.B7 of AB0189 [VL-VH]

<400> SEQUENCE: 253
```

```
Asp Ile Lys Met Thr Gln Ser Pro Ser Ser Leu Ser Ala Ser Val Gly
1               5                   10                  15

Asp Arg Val Thr Ile Thr Cys Lys Ala Ser Gln Asp Ile Tyr Asn Tyr
            20                  25                  30

Leu Ser Trp Phe Gln Lys Pro Gly Lys Ala Pro Lys Pro Leu Ile
        35                  40                  45

Tyr Arg Ala Asn Ile Leu Val Ser Gly Val Pro Ser Arg Phe Ser Gly
    50                  55                  60

Ser Gly Ser Gly Gln Asp Tyr Thr Leu Thr Ile Ser Ser Leu Gln Pro
65              70                  75                  80

Glu Asp Ile Ala Thr Tyr Tyr Cys Leu Gln Phe Asp Ala Phe Pro Phe
                85                  90                  95

Thr Phe Gly Cys Gly Thr Lys Leu Glu Ile Lys Gly Gly Gly Gly Ser
            100                 105                 110

Gly Gly Gly Gly Ser Gly Gly Gly Ser Gly Gly Gly Ser Glu
            115                 120                 125

Val Gln Leu Val Glu Ser Gly Gly Val Val Gln Pro Gly Gly Ser
        130                 135                 140

Leu Arg Leu Ser Cys Ala Ala Ser Gly Phe Thr Phe Asn Ala Phe Gly
145                 150                 155                 160

Met His Trp Val Arg Gln Ala Pro Gly Lys Cys Leu Glu Trp Val Ala
                165                 170                 175

Phe Ile Ser Ser Gly Ser Thr Ser Ile Tyr Tyr Ala Asn Thr Val Lys
            180                 185                 190

Gly Arg Phe Thr Ile Ser Arg Asp Asn Ser Lys Asn Thr Leu Tyr Leu
            195                 200                 205

Gln Met Asn Ser Leu Arg Ala Glu Asp Thr Ala Val Tyr Tyr Cys Ala
        210                 215                 220

Arg Asp Gly Tyr Pro Thr Gly Gly Ala Met Asp Tyr Trp Gly Gln Gly
225                 230                 235                 240

Thr Ser Val Thr Val Ser Ser
                245

<210> SEQ ID NO 254
<211> LENGTH: 247
<212> TYPE: PRT
<213> ORGANISM: Artificial Sequence
<220> FEATURE:
<223> OTHER INFORMATION: scFv of humanized 9F11.B7 of AB0196 [VH-VL]

<400> SEQUENCE: 254

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Asn Ser Phe
            20                  25                  30

Gly Met His Trp Val Arg Gln Ala Pro Gly Lys Cys Leu Glu Trp Val
        35                  40                  45

Ala Phe Ile Ser Ser Gly Ser Thr Ser Ile Tyr Tyr Ala Asn Thr Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Arg Ser Gly Tyr Pro Thr Gly Gly Ala Met Asp Tyr Trp Gly Gln
            100                 105                 110
```

```
Gly Thr Ser Val Thr Val Ser Ser Gly Gly Gly Ser Gly Gly
            115                 120                 125

Gly Ser Gly Gly Gly Ser Gly Gly Gly Ser Asp Ile Lys Met
        130                 135                 140

Thr Gln Ser Pro Ser Ser Leu Ser Ala Ser Val Gly Asp Arg Val Thr
145                 150                 155                 160

Ile Thr Cys Lys Ala Ser Gln Asp Ile Tyr Asn Tyr Leu Ser Trp Phe
                165                 170                 175

Gln Gln Lys Pro Gly Lys Ala Pro Lys Pro Leu Ile Tyr Arg Ala Asn
            180                 185                 190

Ile Leu Val Ser Gly Val Pro Ser Arg Phe Ser Gly Ser Gly
        195                 200                 205

Gln Asp Tyr Thr Leu Thr Ile Ser Ser Leu Gln Pro Glu Asp Ile Ala
    210                 215                 220

Thr Tyr Tyr Cys Leu Gln Phe Asp Ala Phe Pro Phe Thr Phe Gly Cys
225                 230                 235                 240

Gly Thr Lys Leu Glu Ile Lys
            245

<210> SEQ ID NO 255
<211> LENGTH: 247
<212> TYPE: PRT
<213> ORGANISM: Artificial Sequence
<220> FEATURE:
<223> OTHER INFORMATION: scFv of humanized 9F11.B7 of AB0190 [VL-VH]

<400> SEQUENCE: 255

Asp Ile Lys Met Thr Gln Ser Pro Ser Ser Leu Ser Ala Ser Val Gly
1               5                   10                  15

Asp Arg Val Thr Ile Thr Cys Lys Ala Ser Gln Asp Ile Tyr Asn Tyr
            20                  25                  30

Leu Ser Trp Phe Gln Gln Lys Pro Gly Lys Ala Pro Lys Pro Leu Ile
        35                  40                  45

Tyr Arg Ala Asn Ile Leu Val Ser Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Ile Ala Thr Tyr Tyr Cys Leu Gln Phe Asp Ala Phe Pro Phe
                85                  90                  95

Thr Phe Gly Cys Gly Thr Lys Leu Glu Ile Lys Gly Gly Gly Gly Ser
            100                 105                 110

Gly Gly Gly Gly Ser Gly Gly Gly Ser Gly Gly Gly Ser Glu
        115                 120                 125

Val Gln Leu Val Glu Ser Gly Gly Val Gln Pro Gly Gly Ser
    130                 135                 140

Leu Arg Leu Ser Cys Ala Ala Ser Gly Phe Thr Phe Asn Ser Phe Gly
145                 150                 155                 160

Met His Trp Val Arg Gln Ala Pro Gly Lys Cys Leu Glu Trp Val Ala
                165                 170                 175

Phe Ile Ser Ser Gly Ser Thr Ser Ile Tyr Tyr Ala Asn Thr Val Lys
            180                 185                 190

Gly Arg Phe Thr Ile Ser Arg Asp Asn Ser Lys Asn Thr Leu Tyr Leu
        195                 200                 205

Gln Met Asn Ser Leu Arg Ala Glu Asp Thr Ala Val Tyr Tyr Cys Ala
    210                 215                 220
```

Arg Ser Gly Tyr Pro Thr Gly Gly Ala Met Asp Tyr Trp Gly Gln Gly
225                 230                 235                 240

Thr Ser Val Thr Val Ser Ser
            245

<210> SEQ ID NO 256
<211> LENGTH: 117
<212> TYPE: PRT
<213> ORGANISM: Artificial Sequence
<220> FEATURE:
<223> OTHER INFORMATION: Humanized 16B8.C8 in scFv-1296/scFv-1305,
      scFv-1297/scFv-1306 -VH

<400> SEQUENCE: 256

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Leu His Trp Ile Arg Gln Pro Pro Gly Lys Gly Leu Glu Trp Ile
        35                  40                  45

Gly Val Ile Trp Ser Gly Gly Lys Thr Asp Tyr Asn Pro Ser Leu Lys
    50                  55                  60

Ser Arg Val Thr Ile Ser Lys Asp Thr Ser Lys Asn Gln Phe Ser Leu
65                  70                  75                  80

Lys Leu Ser Ser Val Gln Ala Asn Asp Thr Ala Val Tyr Tyr Cys Ala
                85                  90                  95

Arg Tyr Asp Tyr Asp Asp Ser Leu Asp Tyr Trp Gly Gln Gly Thr Leu
            100                 105                 110

Val Thr Val Ser Ser
        115

<210> SEQ ID NO 257
<211> LENGTH: 12
<212> TYPE: PRT
<213> ORGANISM: Artificial Sequence
<220> FEATURE:
<223> OTHER INFORMATION: 12F8.H7 VH CDR3

<400> SEQUENCE: 257

Tyr Tyr Tyr Asp Ser Ser Ser Arg Tyr Val Asp Val
1               5                   10

<210> SEQ ID NO 258
<211> LENGTH: 265
<212> TYPE: PRT
<213> ORGANISM: Artificial Sequence
<220> FEATURE:
<223> OTHER INFORMATION: Uniprot ID No. Q5QGZ9

<400> SEQUENCE: 258

Met Ser Glu Glu Val Thr Tyr Ala Asp Leu Gln Phe Gln Asn Ser Ser
1               5                   10                  15

Glu Met Glu Lys Ile Pro Glu Ile Gly Lys Phe Gly Glu Lys Ala Pro
            20                  25                  30

Pro Ala Pro Ser His Val Trp Arg Pro Ala Ala Leu Phe Leu Thr Leu
        35                  40                  45

Leu Cys Leu Leu Leu Leu Ile Gly Leu Gly Val Leu Ala Ser Met Phe
    50                  55                  60

His Val Thr Leu Lys Ile Glu Met Lys Lys Met Asn Lys Leu Gln Asn
65                  70                  75                  80

```
Ile Ser Glu Glu Leu Gln Arg Asn Ile Ser Leu Gln Leu Met Ser Asn
                85                  90                  95

Met Asn Ile Ser Asn Lys Ile Arg Asn Leu Ser Thr Thr Leu Gln Thr
            100                 105                 110

Ile Ala Thr Lys Leu Cys Arg Glu Leu Tyr Ser Lys Glu Gln Glu His
            115                 120                 125

Lys Cys Lys Pro Cys Pro Arg Arg Trp Ile Trp His Lys Asp Ser Cys
130                 135                 140

Tyr Phe Leu Ser Asp Asp Val Gln Thr Trp Gln Glu Ser Lys Met Ala
145                 150                 155                 160

Cys Ala Ala Gln Asn Ala Ser Leu Leu Lys Ile Asn Asn Lys Asn Ala
                165                 170                 175

Leu Glu Phe Ile Lys Ser Gln Ser Arg Ser Tyr Asp Tyr Trp Leu Gly
            180                 185                 190

Leu Ser Pro Glu Glu Asp Ser Thr Arg Gly Met Arg Val Asp Asn Ile
            195                 200                 205

Ile Asn Ser Ser Ala Trp Val Ile Arg Asn Ala Pro Asp Leu Asn Asn
210                 215                 220

Met Tyr Cys Gly Tyr Ile Asn Arg Leu Tyr Val Gln Tyr Tyr His Cys
225                 230                 235                 240

Thr Tyr Lys Lys Arg Met Ile Cys Glu Lys Met Ala Asn Pro Val Gln
                245                 250                 255

Leu Gly Ser Thr Tyr Phe Arg Glu Ala
            260                 265

<210> SEQ ID NO 259
<211> LENGTH: 472
<212> TYPE: PRT
<213> ORGANISM: Artificial Sequence
<220> FEATURE:
<223> OTHER INFORMATION: scFv-1602-VH-VL-Fc [Chain S]

<400> SEQUENCE: 259

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Leu His Trp Ile Arg Gln Pro Pro Gly Lys Cys Leu Glu Trp Ile
        35                  40                  45

Gly Val Ile Trp Ser Gly Gly Lys Thr Asp Tyr Asn Pro Ser Leu Lys
    50                  55                  60

Ser Arg Val Thr Ile Ser Lys Asp Thr Ser Lys Asn Gln Phe Ser Leu
65                  70                  75                  80

Lys Leu Ser Ser Val Gln Ala Ala Asp Thr Ala Val Tyr Tyr Cys Ala
                85                  90                  95

Lys Tyr Asp Tyr Asp Asp Ser Leu Asp Tyr Trp Gly Gln Gly Thr Leu
            100                 105                 110

Val Thr Val Ser Ser Gly Gly Gly Gly Ser Gly Gly Gly Gly Ser Gly
            115                 120                 125

Gly Gly Gly Ser Gly Gly Gly Ser Asp Ile Gln Met Thr Gln Ser
130                 135                 140

Pro Ser Ser Leu Ser Ala Ser Val Gly Asp Arg Val Thr Ile Thr Cys
145                 150                 155                 160

His Ala Ser Gln Asn Ile Asn Phe Trp Leu Ser Trp Tyr Gln Gln Lys
                165                 170                 175
```

-continued

Pro Gly Lys Ala Pro Lys Leu Leu Ile Tyr Glu Ala Ser Asn Leu His
            180                 185                 190

Thr Gly Val Pro Ser Arg Phe Ser Gly Ser Gly Ser Gly Thr Arg Phe
            195                 200                 205

Thr Leu Thr Ile Ser Ser Leu Gln Pro Glu Asp Ile Ala Thr Tyr Tyr
            210                 215                 220

Cys Gln Gln Ser His Ser Tyr Pro Leu Thr Phe Gly Cys Gly Thr Lys
225                 230                 235                 240

Leu Glu Ile Lys Gly Ser Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
            325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Arg Val Tyr Thr Leu Pro Pro Cys Arg Asp Glu Leu
            370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
            405                 410                 415

Tyr Lys Thr Thr Pro Pro Val Leu Val Ser Asp Gly Ser Phe Thr Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
450                 455                 460

Lys Ser Leu Ser Leu Ser Pro Gly
465                 470

<210> SEQ ID NO 260
<211> LENGTH: 451
<212> TYPE: PRT
<213> ORGANISM: Artificial Sequence
<220> FEATURE:
<223> OTHER INFORMATION: A49MI-VH-CH1-Fc [Chain H]

<400> SEQUENCE: 260

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ala Pro Ile Gly Ala Ala Gly Trp Phe Asp Pro Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Cys Thr Leu Pro Pro Ser Arg Asp Glu Leu Thr Glu Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Trp Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly
    450

<210> SEQ ID NO 261
<211> LENGTH: 214
```

<212> TYPE: PRT
<213> ORGANISM: Artificial Sequence
<220> FEATURE:
<223> OTHER INFORMATION: A49MI-VL-CL [Chain L]

<400> SEQUENCE: 261

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Phe Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 262
<211> LENGTH: 472
<212> TYPE: PRT
<213> ORGANISM: Artificial Sequence
<220> FEATURE:
<223> OTHER INFORMATION: scFv-2061-VL-VH-Fc

<400> SEQUENCE: 262

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Phe Trp
            20                  25                  30

Leu Ser Trp Tyr Gln Gln Lys Pro Gly Lys Ala Pro Lys Leu Leu Ile
        35                  40                  45

Tyr Glu Ala Ser Asn Leu His Thr Gly Val Pro Ser Arg Phe Ser Gly
    50                  55                  60

Ser Gly Ser Gly Thr Arg Phe Thr Leu Thr Ile Ser Ser Leu Gln Pro
65                  70                  75                  80

Glu Asp Ile Ala Thr Tyr Tyr Cys Gln Gln Ser His Ser Tyr Pro Leu
                85                  90                  95

Thr Phe Gly Cys Gly Thr Lys Leu Glu Ile Lys Gly Gly Gly Gly Ser
            100                 105                 110

Gly Gly Gly Gly Ser Gly Gly Gly Ser Gly Gly Gly Ser Gln
            115                 120                 125
Leu Gln Leu Gln Glu Ser Gly Pro Gly Leu Val Lys Pro Ser Glu Thr
130                 135                 140
Leu Ser Leu Thr Cys Thr Val Ser Gly Phe Ser Leu Thr Asn Tyr Gly
145                 150                 155                 160
Leu His Trp Ile Arg Gln Pro Pro Gly Lys Cys Leu Glu Trp Ile Gly
                165                 170                 175
Val Ile Trp Ser Gly Gly Lys Thr Asp Tyr Asn Pro Ser Leu Lys Ser
            180                 185                 190
Arg Val Thr Ile Ser Lys Asp Thr Ser Lys Asn Gln Phe Ser Leu Lys
        195                 200                 205
Leu Ser Ser Val Gln Ala Ala Asp Thr Ala Val Tyr Tyr Cys Ala Lys
210                 215                 220
Tyr Asp Tyr Asp Asp Ser Leu Asp Tyr Trp Gly Gln Gly Thr Leu Val
225                 230                 235                 240
Thr Val Ser Ser Gly Ser Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
        355                 360                 365
Pro Arg Glu Pro Arg Val Tyr Thr Leu Pro Pro Cys Arg Asp Glu Leu
370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Val Ser Asp Gly Ser Phe Thr Leu
            420                 425                 430
Tyr Ser Lys Leu Thr Val Asp Lys Ser Arg Trp Gln Gln Gly Asn Val
        435                 440                 445
Phe Ser Cys Ser Val Met His Glu Ala Leu His Asn His Tyr Thr Gln
450                 455                 460
Lys Ser Leu Ser Leu Ser Pro Gly
465                 470

<210> SEQ ID NO 263
<211> LENGTH: 118
<212> TYPE: PRT
<213> ORGANISM: Artificial Sequence
<220> FEATURE:
<223> OTHER INFORMATION: Anti-CLEC12A mAb Merus-CLL1 -VH

<400> SEQUENCE: 263

```
Glu Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asn Tyr Gly Asp Glu Phe Asp Tyr Trp Gly Gln Gly Thr
            100                 105                 110

Leu Val Thr Val Ser Ser
            115
```

```
<210> SEQ ID NO 264
<211> LENGTH: 107
<212> TYPE: PRT
<213> ORGANISM: Artificial Sequence
<220> FEATURE:
<223> OTHER INFORMATION: Anti-CLEC12A mAb Merus-CLL1 - VL

<400> SEQUENCE: 264

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
            100                 105
```

```
<210> SEQ ID NO 265
<211> LENGTH: 111
<212> TYPE: PRT
<213> ORGANISM: Artificial Sequence
<220> FEATURE:
<223> OTHER INFORMATION: Anti-CLEC12A mAb Genentech-h6E7 - VH

<400> SEQUENCE: 265

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Thr Ser
            20                  25                  30

Ser Tyr Asn Tyr Met His Trp Tyr Gln Gln Lys Pro Gly Lys Pro Pro
        35                  40                  45

Lys Leu Leu Ile Lys Tyr Ala Ser Asn Leu Glu Ser Gly Val Pro Ser
    50                  55                  60

Arg Phe Ser Gly Ser Gly Ser Gly Thr Asp Phe Thr Leu Thr Ile Ser
```

```
                65                  70                  75                  80
Ser Leu Gln Pro Glu Asp Phe Ala Thr Tyr Tyr Cys Gln His Ser Trp
                        85                  90                  95

Glu Ile Pro Leu Thr Phe Gly Gln Gly Thr Lys Val Glu Ile Lys
                100                 105                 110

<210> SEQ ID NO 266
<211> LENGTH: 122
<212> TYPE: PRT
<213> ORGANISM: Artificial Sequence
<220> FEATURE:
<223> OTHER INFORMATION: Anti-CLEC12A mAb Genentech-h6E7 - VL

<400> SEQUENCE: 266

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
                20                  25                  30

Tyr Met His Trp Val Arg Gln Ala Pro Gly Gln Gly Leu Glu Trp Ile
            35                  40                  45

Gly Arg Ile Asn Pro Tyr Asn Gly Ala Ala Phe Tyr Ser Gln Asn Phe
    50                  55                  60

Lys Asp Arg Val Thr Leu Thr Val Asp Thr Ser Ser Thr Ala Tyr
65                  70                  75                  80

Leu Glu Leu Ser Ser Leu Arg Ser Glu Asp Thr Ala Val Tyr Tyr Cys
                85                  90                  95

Ala Ile Glu Arg Gly Ala Asp Leu Glu Gly Tyr Ala Met Asp Tyr Trp
                100                 105                 110

Gly Gln Gly Thr Leu Val Thr Val Ser Ser
            115                 120

<210> SEQ ID NO 267
<211> LENGTH: 1485
<212> TYPE: DNA
<213> ORGANISM: Artificial Sequence
<220> FEATURE:
<223> OTHER INFORMATION: scFv-1602-VH-VL-Fc

<400> SEQUENCE: 267
atggacatga gggtaccagc tcagctgctg ggcctgctgc tgctttggct tcctggcgct      60
agatgccaat tgcagctgca agaatccgga ccagggctcg taaaaccttc tgaaaccctc     120
tccctcactt gcactgtgtc tggattctct ctcacgaact acgggttgca ttggatccga     180
cagccgcctg gcaagtgtct tgagtggatt ggcgttatct ggtcaggagg aagacggat      240 tataatccaa gtctgaaatc cagagtgaca atttctaagg acacgtccaa aaatcagttt     300
agcctcaaac tttcctcagt tcaggctgct gatacagcgg tgtactattg cgcaaagtac     360
gactatgatg acagtttgga ctactgggga caggtacac tggtaacagt gagttctgga     420
ggcggcggta gtggaggcgg gggaagtggt ggcgagggga gtgaggaggg ggcagtgat     480 attcaaatga cgcagagccc cagttccctt tcagctagcg ttggcgacag agtaacgata     540
acgtgtcacg cttcccagaa cattaatttt tggcttagct ggtatcaaca gaaaccggga     600
aaagcaccca agctgcttat ctatgaagcg tccaatctcc acacgggtgt cccatcaaga     660
ttttctggat caggcagtgg cacacgattc acactgacca ttagttcctt gcagcccgag     720
gatatcgcaa cttactactg tcagcaaagt cactcttacc cgttgacatt cggatgtgga     780
actaaactgg agattaaggg atccgataag acccacacct gtcctccatg tcctgctcca     840
```

```
gaactgctcg gcggaccttc cgtgttcctg tttcctccaa agcctaagga caccctgatg    900
atcagcagga cccctgaagt gacctgcgtg gtggtggatg tgtctcacga ggacccagaa    960
gtgaagttca attggtacgt ggacggcgtg gaagtgcaca acgccaagac caagcctaga   1020
gaggaacagt acaacagcac ctacagagtg gtgtccgtgc tgaccgtgct gcaccaggat   1080
tggctgaacg gcaaagagta caagtgcaag gtgtccaaca aggccctgcc tgctcctatc   1140
gagaaaacca tcagcaaggc caagggccag cctcgcgagc ctagagtgta taccttgcct   1200
ccatgccggg acgagctgac caagaatcag gtgtccctga cctgcctggt caagggcttc   1260
tacccttccg atatcgccgt ggaatgggag agcaatggcc agccagagaa caactacaag   1320
accacacctc ctgtgctggt gtccgacggc agctttaccc tgtacagcaa gctgacagtg   1380
gacaagagca gatggcagca gggcaacgtg ttctcctgca gcgtgatgca cgaggccctg   1440
cacaaccact acacccagaa aagcctgagc ctgtctcctg gctaa                   1485

<210> SEQ ID NO 268
<211> LENGTH: 1413
<212> TYPE: DNA
<213> ORGANISM: Artificial Sequence
<220> FEATURE:
<223> OTHER INFORMATION: A49MI-VH-CH1-Fc

<400> SEQUENCE: 268
atgggctggt cctgcatcat cctgtttctg gtggccacag ccacaggcgt gcactctgag     60
gtgcagctgg ttgaatctgg cggcggactt gtgaagcctg gcggatctct gagactgagc    120
tgtgccgcca gcggcttcac ctttagcagc tacagcatga actgggtccg acaggcccct    180
ggcaaaggcc ttgaatgggt gtccagcatc agcagcagct ccagctacat ctactacgcc    240
gacagcgtga agggcagatt caccatcagc cgggacaacg ccaagaacag cctgtacctg    300
cagatgaact ccctgagagc cgaggacacc gccgtgtact attgtgctag aggcgcccct    360
attggagccg ccgctggatg gttcgatcct tggggacagg gaaccctggt caccgtttct    420
tctgcctcta caagggcccc cagcgttttt ccactggctc ctagcagcaa gagcacaagc    480
ggaggaacag ctgccctggg ctgtctggtc aaggactact tcctgagcc tgtgaccgtg    540 tcctggaaca gcggagcact gactagcggc gtgcacacat tccagccgt gctgcaaagc    600 agcggcctgt actctctgag cagcgtcgtg acagtgccta gcagctctct gggcacccag    660
acctacatct gcaatgtgaa ccacaagcct agcaacacca aggtggacaa gaaggtggaa    720
cccaagagct gcgacaagac ccacacctgt cctccatgtc ctgctccaga actgctcggc    780
ggaccttccg tgttcctgtt tcctccaaag cctaaggaca cctgatgat cagcagaacc    840 cctgaagtga cctgcgtggt ggtggatgtg tctcacgagg accccgaagt gaagttcaat    900
tggtacgtgg acggcgtgga agtgcacaac gccaagacca gcctagaga ggaacagtac    960 aacagcacct acagagtggt gtccgtgctg acagtgctgc accaggattg gctgaacggc   1020
aaagagtaca agtgcaaggt gtccaacaag gccctgcctg ctcctatcga gaaaaccatc   1080
agcaaggcca agggccagcc tcgcgaacct caagtctgta cactgcctcc tagccgggat   1140
gagctgaccg agaatcaggt gtccctgacc tgtctcgtga agggcttcta ccctccgat   1200 atcgccgtgg aatgggagag caatggccag ccagagaaca actacaagac aaccctcct   1260 gtgctggaca gcgacggctc attcttcctg tacagctggc tgaccgtgga caagtccaga   1320
tggcagcagg gcaacgtgtt ctcctgcagc gtgatgcacg aggccctgca caaccactac   1380
```

```
                                                       -continued
acccagaagt ccctgtctct gagcccaggc taa                              1413
```

<210> SEQ ID NO 269
<211> LENGTH: 711
<212> TYPE: DNA
<213> ORGANISM: Artificial Sequence
<220> FEATURE:
<223> OTHER INFORMATION: A49MI-VL-CL

<400> SEQUENCE: 269

```
atggacatga gagttccagc tcagctgctg ggcctgctgc tgctttggct tcctggcgct    60
agatgcgaca tccagatgac acagagcccc agctccgtgt ctgcctctgt gggagacaga   120
gtgaccatca cctgtagagc cagccagggc atctcttctt ggctggcctg gtatcagcag   180
aagcctggca aggcccctaa gctgctgatc tatgccgcta gctctctgca gtctggcgtg   240
ccctctagat tttctggcag cggctctggc accgacttca ccctgaccat atctagcctg   300
cagcctgagg acttcgccac ctactattgt cagcagggcg tgtcctttcc acggaccttt   360
ggcggcggaa caaaggtgga aatcaagcgg acagtggccg ctcctagcgt gttcatcttt   420
ccacctagcg acgagcagct gaagtccggc acagcctctg ttgtgtgcct gctgaacaac   480
ttctacccca gagaagccaa ggtgcagtgg aaggtggaca tgccctgca gagcggcaac   540
agccaagaga gcgtgacaga gcaggacagc aaggactcca cctacagcct gagcagcacc   600
ctgacactga gcaaggccga ctacgagaag cacaaagtgt acgcctgcga agtgaccccac   660
cagggccttt ctagccctgt gaccaagagc ttcaaccggg gcgagtgttg a           711
```

<210> SEQ ID NO 270
<211> LENGTH: 117
<212> TYPE: PRT
<213> ORGANISM: Artificial Sequence
<220> FEATURE:
<223> OTHER INFORMATION: Humanized 16B8.C8 in AB0305/AB5030 - VH

<400> SEQUENCE: 270

```
Gln Leu Gln Leu Gln Glu Ser Gly Pro Gly Leu Val Lys Pro Ser Glu
1               5                   10                  15
Thr Leu Ser Leu Thr Cys Thr Val Ser Gly Phe Ser Leu Thr Asn Tyr
            20                  25                  30
Gly Leu His Trp Ile Arg Gln Pro Pro Gly Lys Gly Leu Glu Trp Ile
        35                  40                  45
Gly Val Ile Trp Val Gly Gly Ala Thr Asp Tyr Asn Pro Ser Leu Lys
    50                  55                  60
Ser Arg Val Thr Ile Ser Val Asp Thr Ser Lys Asn Gln Phe Ser Leu
65                  70                  75                  80
Lys Leu Ser Ser Val Gln Ala Ala Asp Thr Ala Val Tyr Tyr Cys Ala
                85                  90                  95
Lys Gly Asp Tyr Gly Asp Thr Leu Asp Tyr Trp Gly Gln Gly Thr Leu
            100                 105                 110
Val Thr Val Ser Ser
        115
```

<210> SEQ ID NO 271
<211> LENGTH: 107
<212> TYPE: PRT
<213> ORGANISM: Artificial Sequence
<220> FEATURE:
<223> OTHER INFORMATION: Humanized 16B8.C8 in AB0305/AB5030

<400> SEQUENCE: 271

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Phe Trp
                20                  25                  30

Leu Ser Trp Tyr Gln Gln Lys Pro Gly Lys Ala Pro Lys Leu Leu Ile
            35                  40                  45

Tyr Glu Ala Ser Asn Leu His Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Ser Tyr Pro Leu
                85                  90                  95

Thr Phe Gly Ser Gly Thr Lys Leu Glu Ile Lys
            100                 105
```

<210> SEQ ID NO 272
<211> LENGTH: 5
<212> TYPE: PRT
<213> ORGANISM: Artificial Sequence
<220> FEATURE:
<223> OTHER INFORMATION: Humanized 16B8.C8 in AB0305/AB5030 VH - CDR2

<400> SEQUENCE: 272

```
Trp Val Gly Gly Ala
1               5
```

<210> SEQ ID NO 273
<211> LENGTH: 9
<212> TYPE: PRT
<213> ORGANISM: Artificial Sequence
<220> FEATURE:
<223> OTHER INFORMATION: Humanized 16B8.C8 in AB0305/AB5030 VH - CDR3

<400> SEQUENCE: 273

```
Gly Asp Tyr Gly Asp Thr Leu Asp Tyr
1               5
```

<210> SEQ ID NO 274
<211> LENGTH: 244
<212> TYPE: PRT
<213> ORGANISM: Artificial Sequence
<220> FEATURE:
<223> OTHER INFORMATION: scFv of humanized 16B8.C8 of AB0305 [VH-VL]

<400> SEQUENCE: 274

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
                20                  25                  30

Gly Leu His Trp Ile Arg Gln Pro Pro Gly Lys Cys Leu Glu Trp Ile
            35                  40                  45

Gly Val Ile Trp Val Gly Gly Ala Thr Asp Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Gln Ala Ala Asp Thr Ala Val Tyr Tyr Cys Ala
                85                  90                  95

Lys Gly Asp Tyr Gly Asp Thr Leu Asp Tyr Trp Gly Gln Gly Thr Leu
            100                 105                 110
```

```
Val Thr Val Ser Ser Gly Gly Gly Ser Gly Gly Gly Ser Gly
        115                 120                 125

Gly Gly Gly Ser Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

His Ala Ser Gln Asn Ile Asn Phe Trp Leu Ser Trp Tyr Gln Gln Lys
                165                 170                 175

Pro Gly Lys Ala Pro Lys Leu Leu Ile Tyr Glu Ala Ser Asn Leu His
                180                 185                 190

Thr Gly Val Pro Ser Arg Phe Ser Gly Ser Gly Ser Gly Thr Asp Phe
                195                 200                 205

Thr Leu Thr Ile Ser Ser Leu Gln Pro Glu Asp Phe Ala Thr Tyr Tyr
    210                 215                 220

Cys Gln Gln Ser His Ser Tyr Pro Leu Thr Phe Gly Cys Gly Thr Lys
225                 230                 235                 240

Leu Glu Ile Lys

<210> SEQ ID NO 275
<211> LENGTH: 244
<212> TYPE: PRT
<213> ORGANISM: Artificial Sequence
<220> FEATURE:
<223> OTHER INFORMATION: scFv of humanized 16B8.C8 of AB5030 [VL-VH]

<400> SEQUENCE: 275

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Phe Trp
            20                  25                  30

Leu Ser Trp Tyr Gln Gln Lys Pro Gly Lys Ala Pro Lys Leu Leu Ile
        35                  40                  45

Tyr Glu Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Ser Tyr Pro Leu
                85                  90                  95

Thr Phe Gly Cys Gly Thr Lys Leu Glu Ile Lys Gly Gly Gly Gly Ser
                100                 105                 110

Gly Gly Gly Gly Ser Gly Gly Gly Ser Gly Gly Gly Ser Gln
                115                 120                 125

Leu Gln Leu Gln Glu Ser Gly Pro Gly Leu Val Lys Pro Ser Glu Thr
    130                 135                 140

Leu Ser Leu Thr Cys Thr Val Ser Gly Phe Ser Leu Thr Asn Tyr Gly
145                 150                 155                 160

Leu His Trp Ile Arg Gln Pro Pro Gly Lys Cys Leu Glu Trp Ile Gly
                165                 170                 175

Val Ile Trp Val Gly Gly Ala Thr Asp Tyr Asn Pro Ser Leu Lys Ser
                180                 185                 190

Arg Val Thr Ile Ser Val Asp Thr Ser Lys Asn Gln Phe Ser Leu Lys
            195                 200                 205

Leu Ser Ser Val Gln Ala Ala Asp Thr Ala Val Tyr Tyr Cys Ala Lys
    210                 215                 220

Gly Asp Tyr Gly Asp Thr Leu Asp Tyr Trp Gly Gln Gly Thr Leu Val
```

Thr Val Ser Ser

<210> SEQ ID NO 276
<211> LENGTH: 472
<212> TYPE: PRT
<213> ORGANISM: Artificial Sequence
<220> FEATURE:
<223> OTHER INFORMATION: AB0305-VH-VL-Fc

<400> SEQUENCE: 276

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Leu His Trp Ile Arg Gln Pro Pro Gly Lys Cys Leu Glu Trp Ile
        35                  40                  45

Gly Val Ile Trp Val Gly Gly Ala Thr Asp Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Gln Ala Ala Asp Thr Ala Val Tyr Tyr Cys Ala
                85                  90                  95

Lys Gly Asp Tyr Gly Asp Thr Leu Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Ser Gly Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

His Ala Ser Gln Asn Ile Asn Phe Trp Leu Ser Trp Tyr Gln Gln Lys
                165                 170                 175

Pro Gly Lys Ala Pro Lys Leu Leu Ile Tyr Glu Ala Ser Asn Leu His
            180                 185                 190

Thr Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Ser His Ser Tyr Pro Leu Thr Phe Gly Cys Gly Thr Lys
225                 230                 235                 240

Leu Glu Ile Lys Gly Ser Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

```
Ala Leu Pro Ala Pro Ile Glu Lys Thr Ile Ser Lys Ala Lys Gly Gln
            355                 360                 365

Pro Arg Glu Pro Arg Val Tyr Thr Leu Pro Pro Cys Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Val Ser Asp Gly Ser Phe Thr Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
    450                 455                 460

Lys Ser Leu Ser Leu Ser Pro Gly
465                 470

<210> SEQ ID NO 277
<211> LENGTH: 472
<212> TYPE: PRT
<213> ORGANISM: Artificial Sequence
<220> FEATURE:
<223> OTHER INFORMATION: AB0304-VH-VL-Fc

<400> SEQUENCE: 277

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Leu His Trp Ile Arg Gln Pro Pro Gly Lys Cys Leu Glu Trp Ile
        35                  40                  45

Gly Val Ile Leu Ser Gly Gly Trp Thr Asp Tyr Asn Pro Ser Leu Lys
    50                  55                  60

Ser Arg Val Thr Ile Ser Lys Asp Thr Ser Lys Asn Gln Phe Ser Leu
65                  70                  75                  80

Lys Leu Ser Ser Val Gln Ala Ala Asp Thr Ala Val Tyr Tyr Cys Ala
                85                  90                  95

Lys Gly Asp Tyr Gly Asp Ala Leu Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Ser Gly Gly Gly Gly Ser Asp Ile Gln Met Thr Gln Ser
        130                 135                 140

Pro Ser Ser Leu Ser Ala Ser Val Gly Asp Arg Val Thr Ile Thr Cys
145                 150                 155                 160

His Ala Ser Gln Asn Ile Asn Phe Trp Leu Ser Trp Tyr Gln Gln Lys
                165                 170                 175

Pro Gly Lys Ala Pro Lys Leu Leu Ile Tyr Glu Ala Ser Asn Leu His
            180                 185                 190

Thr Gly Val Pro Ser Arg Phe Ser Gly Ser Gly Ser Gly Thr Arg Phe
        195                 200                 205

Thr Leu Thr Ile Ser Ser Leu Gln Pro Glu Asp Ile Ala Thr Tyr Tyr
    210                 215                 220

Cys Gln Gln Ser His Ser Tyr Pro Leu Thr Phe Gly Cys Gly Thr Lys
225                 230                 235                 240
```

Leu Glu Ile Lys Gly Ser Asp Lys Thr His Thr Cys Pro Pro Cys Pro
             245                 250                 255

Ala Pro Glu Leu Leu Gly Gly Pro Ser Val Phe Leu Phe Pro Pro Lys
         260                 265                 270

Pro Lys Asp Thr Leu Met Ile Ser Arg Thr Pro Glu Val Thr Cys Val
     275                 280                 285

Val Val Asp Val Ser His Glu Asp Pro Glu Val Lys Phe Asn Trp Tyr
 290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
             325                 330                 335

Gln Asp Trp Leu Asn Gly Lys Glu Tyr Lys Cys Lys Val Ser Asn Lys
         340                 345                 350

Ala Leu Pro Ala Pro Ile Glu Lys Thr Ile Ser Lys Ala Lys Gly Gln
     355                 360                 365

Pro Arg Glu Pro Arg Val Tyr Thr Leu Pro Pro Cys Arg Asp Glu Leu
 370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
             405                 410                 415

Tyr Lys Thr Thr Pro Pro Val Leu Val Ser Asp Gly Ser Phe Thr Leu
         420                 425                 430

Tyr Ser Lys Leu Thr Val Asp Lys Ser Arg Trp Gln Gln Gly Asn Val
     435                 440                 445

Phe Ser Cys Ser Val Met His Glu Ala Leu His Asn His Tyr Thr Gln
 450                 455                 460

Lys Ser Leu Ser Leu Ser Pro Gly
465                 470

<210> SEQ ID NO 278
<211> LENGTH: 475
<212> TYPE: PRT
<213> ORGANISM: Artificial Sequence
<220> FEATURE:
<223> OTHER INFORMATION: AB0192-VH-VL-Fc

<400> SEQUENCE: 278

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Asn Ala Phe
             20                  25                  30

Gly Met His Trp Val Arg Gln Ala Pro Gly Lys Cys Leu Glu Trp Val
         35                  40                  45

Ala Phe Ile Ser Ser Gly Ser Thr Ser Ile Tyr Tyr Ala Asn Thr Val
     50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
             85                  90                  95

Ala Arg Asp Gly Tyr Pro Thr Gly Gly Ala Met Asp Tyr Trp Gly Gln
         100                 105                 110

Gly Thr Ser Val Thr Val Ser Ser Gly Gly Gly Gly Ser Gly Gly Gly
     115                 120                 125

```
Gly Ser Gly Gly Gly Ser Gly Gly Gly Ser Asp Ile Gln Met
        130                 135                 140

Thr Gln Ser Pro Ser Ser Leu Ser Ala Ser Val Gly Asp Arg Val Thr
145                 150                 155                 160

Ile Thr Cys Lys Ala Ser Gln Asp Ile Tyr Asn Tyr Leu Ser Trp Phe
                165                 170                 175

Gln Gln Lys Pro Gly Lys Ala Pro Lys Pro Leu Ile Tyr Arg Ala Asn
                180                 185                 190

Ile Leu Val Ser Gly Val Pro Ser Arg Phe Ser Gly Ser Gly Ser Gly
                195                 200                 205

Gln Asp Tyr Thr Phe Thr Ile Ser Ser Leu Gln Pro Glu Asp Ile Ala
210                 215                 220

Thr Tyr Tyr Cys Leu Gln Phe Asp Ala Phe Pro Phe Thr Phe Gly Cys
225                 230                 235                 240

Gly Thr Lys Leu Glu Ile Lys Gly Ser Asp Lys Thr His Thr Cys Pro
                245                 250                 255

Pro Cys Pro Ala Pro Glu Leu Leu Gly Gly Pro Ser Val Phe Leu Phe
                260                 265                 270

Pro Pro Lys Pro Lys Asp Thr Leu Met Ile Ser Arg Thr Pro Glu Val
                275                 280                 285

Thr Cys Val Val Val Asp Val Ser His Glu Asp Pro Glu Val Lys Phe
290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
                340                 345                 350

Ser Asn Lys Ala Leu Pro Ala Pro Ile Glu Lys Thr Ile Ser Lys Ala
                355                 360                 365

Lys Gly Gln Pro Arg Glu Pro Arg Val Tyr Thr Leu Pro Pro Cys Arg
                370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Val Ser Asp Gly Ser
                420                 425                 430

Phe Thr Leu Tyr Ser Lys Leu Thr Val Asp Lys Ser Arg Trp Gln Gln
                435                 440                 445

Gly Asn Val Phe Ser Cys Ser Val Met His Glu Ala Leu His Asn His
                450                 455                 460

Tyr Thr Gln Lys Ser Leu Ser Leu Ser Pro Gly
465                 470                 475

<210> SEQ ID NO 279
<211> LENGTH: 9
<212> TYPE: PRT
<213> ORGANISM: Artificial Sequence
<220> FEATURE:
<223> OTHER INFORMATION: Humanized 16B8.C8 in AB0147/AB7410 VH CDR3

<400> SEQUENCE: 279

Gly Asp Tyr Gly Asp Ala Leu Asp Tyr
1               5
```

<210> SEQ ID NO 280
<211> LENGTH: 244
<212> TYPE: PRT
<213> ORGANISM: Artificial Sequence
<220> FEATURE:
<223> OTHER INFORMATION: scFv of humanized 16B8.C8 of AB0147[VH-VL]

<400> SEQUENCE: 280

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Leu His Trp Ile Arg Gln Pro Pro Gly Lys Cys Leu Glu Trp Ile
        35                  40                  45

Gly Val Ile Leu Ser Gly Gly Trp Thr Asp Tyr Asn Pro Ser Leu Lys
    50                  55                  60

Ser Arg Val Thr Ile Ser Lys Asp Thr Ser Lys Asn Gln Phe Ser Leu
65                  70                  75                  80

Lys Leu Ser Ser Val Gln Ala Ala Asp Thr Ala Val Tyr Tyr Cys Ala
                85                  90                  95

Lys Gly Asp Tyr Gly Asp Ala Leu Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Ser Gly Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

His Ala Ser Gln Asn Ile Asn Phe Trp Leu Ser Trp Tyr Gln Gln Lys
                165                 170                 175

Pro Gly Lys Ala Pro Lys Leu Leu Ile Tyr Glu Ala Ser Asn Leu His
            180                 185                 190

Thr Gly Val Pro Ser Arg Phe Ser Gly Ser Gly Ser Gly Thr Arg Phe
        195                 200                 205

Thr Leu Thr Ile Ser Ser Leu Gln Pro Glu Asp Ile Ala Thr Tyr Tyr
    210                 215                 220

Cys Gln Gln Ser His Ser Tyr Pro Leu Thr Phe Gly Cys Gly Thr Lys
225                 230                 235                 240

Leu Glu Ile Lys
```

<210> SEQ ID NO 281
<211> LENGTH: 472
<212> TYPE: PRT
<213> ORGANISM: Artificial Sequence
<220> FEATURE:
<223> OTHER INFORMATION: scFv-1295-VH-VL-Fc

<400> SEQUENCE: 281

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Leu His Trp Ile Arg Gln Pro Pro Gly Lys Cys Leu Glu Trp Ile
        35                  40                  45

Gly Val Ile Trp Ser Gly Gly Lys Thr Asp Tyr Asn Pro Ser Leu Lys
    50                  55                  60
```

Ser Arg Val Thr Ile Ser Lys Asp Thr Ser Lys Asn Gln Phe Ser Leu
 65                  70                  75                  80

Lys Leu Ser Ser Val Gln Ala Ala Asp Thr Ala Val Tyr Tyr Cys Ala
             85                  90                  95

Lys Tyr Asp Tyr Asp Asp Ser Leu Asp Tyr Trp Gly Gln Gly Thr Leu
            100                 105                 110

Val Thr Val Ser Ser Gly Gly Gly Ser Gly Gly Gly Ser Gly
            115                 120                 125

Gly Gly Gly Ser Gly Gly Gly Ser Asp Ile Gln Met Thr Gln Ser
130                 135                 140

Pro Ser Ser Leu Ser Ala Ser Val Gly Asp Arg Val Thr Ile Thr Cys
145                 150                 155                 160

His Ala Ser Gln Asn Ile Asn Phe Trp Leu Ser Trp Tyr Gln Gln Lys
                165                 170                 175

Pro Gly Lys Ile Pro Lys Leu Leu Ile Tyr Glu Ala Ser Asn Leu His
            180                 185                 190

Thr Gly Val Pro Ser Arg Phe Ser Gly Ser Gly Ser Gly Thr Arg Phe
            195                 200                 205

Thr Leu Thr Ile Ser Ser Leu Gln Pro Glu Asp Ile Ala Thr Tyr Tyr
210                 215                 220

Cys Gln Gln Ser His Ser Tyr Pro Leu Thr Phe Gly Cys Gly Thr Lys
225                 230                 235                 240

Leu Glu Ile Lys Gly Ser Asp Lys Thr His Thr Cys Pro Pro Cys Pro
            245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
            325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Arg Val Tyr Thr Leu Pro Pro Cys Arg Asp Glu Leu
            370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
            405                 410                 415

Tyr Lys Thr Thr Pro Pro Val Leu Val Ser Asp Gly Ser Phe Thr Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
            450                 455                 460

Lys Ser Leu Ser Leu Ser Pro Gly
465                 470

<210> SEQ ID NO 282
<211> LENGTH: 106
<212> TYPE: PRT
<213> ORGANISM: Artificial Sequence
<220> FEATURE:
<223> OTHER INFORMATION: TriNKET variants of A49-mutation

<400> SEQUENCE: 282

Asp Ile Gln Met Thr Gln Ser Pro Ser Thr Leu Ser Ala Ser Val Gly
1               5                   10                  15

Asp Arg Val Thr Ile Thr Cys Arg Ala Ser Asn Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Thr Lys Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Asp Leu Pro Thr
                85                  90                  95

Phe Gly Gly Gly Thr Lys Val Glu Ile Lys
            100                 105

<210> SEQ ID NO 283
<211> LENGTH: 9
<212> TYPE: PRT
<213> ORGANISM: Artificial Sequence
<220> FEATURE:
<223> OTHER INFORMATION: Variant of motif without the DS site in CDRH3 -
      binding analysis to hCLEC12A - AB0053

<400> SEQUENCE: 283

Tyr Asp Tyr Asp Asp Ala Leu Asp Tyr
1               5

<210> SEQ ID NO 284
<211> LENGTH: 9
<212> TYPE: PRT
<213> ORGANISM: Artificial Sequence
<220> FEATURE:
<223> OTHER INFORMATION: Variant of motif without the DS site in CDRH3 -
      binding analysis to hCLEC12A - AB0085

<400> SEQUENCE: 284

Tyr Asp Tyr Asp Asp Ile Leu Asp Tyr
1               5

<210> SEQ ID NO 285
<211> LENGTH: 9
<212> TYPE: PRT
<213> ORGANISM: Artificial Sequence
<220> FEATURE:
<223> OTHER INFORMATION: Variant of motif without the DS site in CDRH3

<400> SEQUENCE: 285

Tyr Asp Tyr Asp Asp Leu Leu Asp Tyr
1               5

<210> SEQ ID NO 286
<211> LENGTH: 477
<212> TYPE: PRT
<213> ORGANISM: Artificial Sequence
<220> FEATURE:
<223> OTHER INFORMATION: scFv-A49MI-VH-VL-Fc

<400> SEQUENCE: 286

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Phe Pro Arg
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Glu
            115                 120                 125

Val Gln Leu Val Glu Ser Gly Gly Gly Leu Val Lys Pro Gly Gly Ser
    130                 135                 140

Leu Arg Leu Ser Cys Ala Ala Ser Gly Phe Thr Phe Ser Ser Tyr Ser
145                 150                 155                 160

Met Asn Trp Val Arg Gln Ala Pro Gly Lys Gly Leu Glu Trp Val Ser
                165                 170                 175

Ser Ile Ser Ser Ser Ser Ser Tyr Ile Tyr Tyr Ala Asp Ser Val Lys
            180                 185                 190

Gly Arg Phe Thr Ile Ser Arg Asp Asn Ala Lys Asn Ser Leu Tyr Leu
        195                 200                 205

Gln Met Asn Ser Leu Arg Ala Glu Asp Thr Ala Val Tyr Tyr Cys Ala
    210                 215                 220

Arg Gly Ala Pro Ile Gly Ala Ala Gly Trp Phe Asp Pro Trp Gly
225                 230                 235                 240

Gln Gly Thr Leu Val Thr Val Ser Ser Gly Ser Asp Lys Thr His Thr
                245                 250                 255

Cys Pro Pro Cys Pro Ala Pro Glu Leu Leu Gly Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
        355                 360                 365

Lys Ala Lys Gly Gln Pro Arg Glu Pro Arg Val Tyr Thr Leu Pro Pro
    370                 375                 380

Cys Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
```

```
                        405                 410                 415
Gln Pro Glu Asn Asn Tyr Lys Thr Thr Pro Pro Val Leu Val Ser Asp
                420                 425                 430

Gly Ser Phe Thr Leu Tyr Ser Lys Leu Thr Val Asp Lys Ser Arg Trp
            435                 440                 445

Gln Gln Gly Asn Val Phe Ser Cys Ser Val Met His Glu Ala Leu His
        450                 455                 460

Asn His Tyr Thr Gln Lys Ser Leu Ser Leu Ser Pro Gly
465                 470                 475

<210> SEQ ID NO 287
<211> LENGTH: 446
<212> TYPE: PRT
<213> ORGANISM: Artificial Sequence
<220> FEATURE:
<223> OTHER INFORMATION: 1602-VH-CH1-Fc

<400> SEQUENCE: 287

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Leu His Trp Ile Arg Gln Pro Pro Gly Lys Gly Leu Glu Trp Ile
        35                  40                  45

Gly Val Ile Trp Ser Gly Gly Lys Thr Asp Tyr Asn Pro Ser Leu Lys
    50                  55                  60

Ser Arg Val Thr Ile Ser Lys Asp Thr Ser Lys Asn Gln Phe Ser Leu
65                  70                  75                  80

Lys Leu Ser Ser Val Gln Ala Ala Asp Thr Ala Val Tyr Tyr Cys Ala
                85                  90                  95

Lys Tyr Asp Tyr Asp Asp Ser Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
```

```
            290                 295                 300
Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Cys Thr Leu Pro
                340                 345                 350

Pro Ser Arg Asp Glu Leu Thr Glu Asn Gln Val Ser Leu Thr Cys Leu
                355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Trp Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly
            435                 440                 445

<210> SEQ ID NO 288
<211> LENGTH: 214
<212> TYPE: PRT
<213> ORGANISM: Artificial Sequence
<220> FEATURE:
<223> OTHER INFORMATION: 1602-VL-CL

<400> SEQUENCE: 288

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Phe Trp
                20                  25                  30

Leu Ser Trp Tyr Gln Gln Lys Pro Gly Lys Ala Pro Lys Leu Leu Ile
            35                  40                  45

Tyr Glu Ala Ser Asn Leu His Thr Gly Val Pro Ser Arg Phe Ser Gly
        50                  55                  60

Ser Gly Ser Gly Thr Arg Phe Thr Leu Thr Ile Ser Ser Leu Gln Pro
65                  70                  75                  80

Glu Asp Ile Ala Thr Tyr Tyr Cys Gln Gln Ser His Ser Tyr Pro Leu
                85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
```

```
              210

<210> SEQ ID NO 289
<211> LENGTH: 107
<212> TYPE: PRT
<213> ORGANISM: Artificial Sequence
<220> FEATURE:
<223> OTHER INFORMATION: Humanized 16B8.C8 in scFv-1602/ scFv-2061

<400> SEQUENCE: 289

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Phe Trp
            20                  25                  30

Leu Ser Trp Tyr Gln Gln Lys Pro Gly Lys Ala Pro Lys Leu Leu Ile
        35                  40                  45

Tyr Glu Ala Ser Asn Leu His Thr Gly Val Pro Ser Arg Phe Ser Gly
    50                  55                  60

Ser Gly Ser Gly Thr Arg Phe Thr Leu Thr Ile Ser Ser Leu Gln Pro
65                  70                  75                  80

Glu Asp Ile Ala Thr Tyr Tyr Cys Gln Gln Ser His Ser Tyr Pro Leu
                85                  90                  95

Thr Phe Gly Gly Gly Thr Lys Leu Glu Ile Lys
            100                 105

<210> SEQ ID NO 290
<211> LENGTH: 9
<212> TYPE: PRT
<213> ORGANISM: Artificial Sequence
<220> FEATURE:
<223> OTHER INFORMATION: Variant for binding analysis to hCLEC12A

<400> SEQUENCE: 290

Tyr Asp Tyr Asp Asp Val Leu Asp Tyr
1               5

<210> SEQ ID NO 291
<211> LENGTH: 9
<212> TYPE: PRT
<213> ORGANISM: Artificial Sequence
<220> FEATURE:
<223> OTHER INFORMATION: Variant for binding analysis to hCLEC12A

<400> SEQUENCE: 291

Tyr Asp Tyr Asp Asp Thr Leu Asp Tyr
1               5

<210> SEQ ID NO 292
<211> LENGTH: 9
<212> TYPE: PRT
<213> ORGANISM: Artificial Sequence
<220> FEATURE:
<223> OTHER INFORMATION: Variant for binding analysis to hCLEC12A

<400> SEQUENCE: 292

Tyr Asp Tyr Asp Glu Ser Leu Asp Tyr
1               5

<210> SEQ ID NO 293
<211> LENGTH: 8
<212> TYPE: PRT
<213> ORGANISM: Artificial Sequence
<220> FEATURE:
<223> OTHER INFORMATION: scFv VH
```

<400> SEQUENCE: 293

Asp Tyr Asp Asp Ser Leu Asp Tyr
1               5

<210> SEQ ID NO 294
<211> LENGTH: 117
<212> TYPE: PRT
<213> ORGANISM: Artificial Sequence
<220> FEATURE:
<223> OTHER INFORMATION: Humanized 16B8.C8 in AB0147/AB7410

<400> SEQUENCE: 294

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Leu His Trp Ile Arg Gln Pro Pro Gly Lys Gly Leu Glu Trp Ile
        35                  40                  45

Gly Val Ile Leu Ser Gly Gly Trp Thr Asp Tyr Asn Pro Ser Leu Lys
    50                  55                  60

Ser Arg Val Thr Ile Ser Lys Asp Thr Ser Lys Asn Gln Phe Ser Leu
65                  70                  75                  80

Lys Leu Ser Ser Val Gln Ala Ala Asp Thr Ala Val Tyr Tyr Cys Ala
                85                  90                  95

Lys Gly Asp Tyr Gly Asp Ala Leu Asp Tyr Trp Gly Gln Gly Thr Leu
            100                 105                 110

Val Thr Val Ser Ser
        115

<210> SEQ ID NO 295
<211> LENGTH: 107
<212> TYPE: PRT
<213> ORGANISM: Artificial Sequence
<220> FEATURE:
<223> OTHER INFORMATION: Humanized 16B8.C8 in AB0147/ AB7410

<400> SEQUENCE: 295

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Phe Trp
            20                  25                  30

Leu Ser Trp Tyr Gln Gln Lys Pro Gly Lys Ala Pro Lys Leu Leu Ile
        35                  40                  45

Tyr Glu Ala Ser Asn Leu His Thr Gly Val Pro Ser Arg Phe Ser Gly
    50                  55                  60

Ser Gly Ser Gly Thr Arg Phe Thr Leu Thr Ile Ser Ser Leu Gln Pro
65                  70                  75                  80

Glu Asp Ile Ala Thr Tyr Tyr Cys Gln Gln Ser His Ser Tyr Pro Leu
                85                  90                  95

Thr Phe Gly Ser Gly Thr Lys Leu Glu Ile Lys
            100                 105

<210> SEQ ID NO 296
<211> LENGTH: 5
<212> TYPE: PRT
<213> ORGANISM: Artificial Sequence
<220> FEATURE:
<223> OTHER INFORMATION: Humanized 16B8.C8 in AB0147/AB7410 VH CDR2

```
<400> SEQUENCE: 296

Leu Ser Gly Gly Trp
1               5

<210> SEQ ID NO 297
<211> LENGTH: 7
<212> TYPE: PRT
<213> ORGANISM: Artificial Sequence
<220> FEATURE:
<223> OTHER INFORMATION: F3'-1602 CDR H1- Chothia

<400> SEQUENCE: 297

Gly Phe Thr Phe Ser Ser Tyr
1               5

<210> SEQ ID NO 298
<211> LENGTH: 6
<212> TYPE: PRT
<213> ORGANISM: Artificial Sequence
<220> FEATURE:
<223> OTHER INFORMATION: F3'-1602 CDR H2- Chothia

<400> SEQUENCE: 298

Ser Ser Ser Ser Ser Tyr
1               5

<210> SEQ ID NO 299
<211> LENGTH: 19
<212> TYPE: PRT
<213> ORGANISM: Artificial Sequence
<220> FEATURE:
<223> OTHER INFORMATION: found in chain H of F3'-1602

<400> SEQUENCE: 299

Leu Ser Cys Ala Ala Ser Gly Phe Thr Phe Ser Ser Tyr Ser Met Asn
1               5                   10                  15

Trp Val Arg

<210> SEQ ID NO 300
<211> LENGTH: 11
<212> TYPE: PRT
<213> ORGANISM: Artificial Sequence
<220> FEATURE:
<223> OTHER INFORMATION: found in chain H of F3'-1602

<400> SEQUENCE: 300

Asn Ser Leu Tyr Leu Gln Met Asn Ser Leu Arg
1               5                   10

<210> SEQ ID NO 301
<211> LENGTH: 7
<212> TYPE: PRT
<213> ORGANISM: Artificial Sequence
<220> FEATURE:
<223> OTHER INFORMATION: found in chain H and S of F3'-1602

<400> SEQUENCE: 301

Asp Thr Leu Met Ile Ser Arg
1               5

<210> SEQ ID NO 302
<211> LENGTH: 23
<212> TYPE: PRT
<213> ORGANISM: Artificial Sequence
<220> FEATURE:
<223> OTHER INFORMATION: found in chain H and S of F3'-1602
```

<400> SEQUENCE: 302

Trp Gln Gln Gly Asn Val Phe Ser Cys Ser Val Met His Glu Ala Leu
1               5                   10                  15

His Asn His Tyr Thr Gln Lys
            20

<210> SEQ ID NO 303
<211> LENGTH: 18
<212> TYPE: PRT
<213> ORGANISM: Artificial Sequence
<220> FEATURE:
<223> OTHER INFORMATION: found in chain L of F3'-1602

<400> SEQUENCE: 303

Asp Ile Gln Met Thr Gln Ser Pro Ser Ser Val Ser Ala Ser Val Gly
1               5                   10                  15

Asp Arg

<210> SEQ ID NO 304
<211> LENGTH: 85
<212> TYPE: PRT
<213> ORGANISM: Artificial Sequence
<220> FEATURE:
<223> OTHER INFORMATION: found in chain S of F3'-1602

<400> SEQUENCE: 304

Tyr Asp Tyr Asp Asp Ser Leu Asp Tyr Trp Gly Gln Gly Thr Leu Val
1               5                   10                  15

Thr Val Ser Ser Gly Gly Gly Gly Ser Gly Gly Gly Gly Ser Gly Gly
            20                  25                  30

Gly Gly Ser Gly Gly Gly Ser Asp Ile Gln Met Thr Gln Ser Pro
        35                  40                  45

Ser Ser Leu Ser Ala Ser Val Gly Asp Arg Val Thr Ile Thr Cys His
    50                  55                  60

Ala Ser Gln Asn Ile Asn Phe Trp Leu Ser Trp Tyr Gln Gln Lys Pro
65                  70                  75                  80

Gly Lys Ala Pro Lys
            85

<210> SEQ ID NO 305
<211> LENGTH: 9
<212> TYPE: PRT
<213> ORGANISM: Artificial Sequence
<220> FEATURE:
<223> OTHER INFORMATION: CDRH3 library (Library 17)
<220> FEATURE:
<221> NAME/KEY: misc_feature
<222> LOCATION: (1)..(1)
<223> OTHER INFORMATION: Xaa can be any naturally occurring amino acid

<400> SEQUENCE: 305

Xaa Asp Tyr Asp Asp Ser Leu Asp Tyr
1               5

<210> SEQ ID NO 306
<211> LENGTH: 9
<212> TYPE: PRT
<213> ORGANISM: Artificial Sequence
<220> FEATURE:
<223> OTHER INFORMATION: CDRH3 library(Library 17)
<220> FEATURE:
<221> NAME/KEY: misc_feature
<222> LOCATION: (2)..(2)

<223> OTHER INFORMATION: Xaa can be any naturally occurring amino acid

<400> SEQUENCE: 306

Tyr Xaa Tyr Asp Asp Ser Leu Asp Tyr
1               5

<210> SEQ ID NO 307
<211> LENGTH: 9
<212> TYPE: PRT
<213> ORGANISM: Artificial Sequence
<220> FEATURE:
<223> OTHER INFORMATION: CDRH3 library(Library 17)
<220> FEATURE:
<221> NAME/KEY: misc_feature
<222> LOCATION: (3)..(3)
<223> OTHER INFORMATION: Xaa can be any naturally occurring amino acid

<400> SEQUENCE: 307

Tyr Asp Xaa Asp Asp Ser Leu Asp Tyr
1               5

<210> SEQ ID NO 308
<211> LENGTH: 9
<212> TYPE: PRT
<213> ORGANISM: Artificial Sequence
<220> FEATURE:
<223> OTHER INFORMATION: CDRH3 library(Library 17)
<220> FEATURE:
<221> NAME/KEY: misc_feature
<222> LOCATION: (4)..(4)
<223> OTHER INFORMATION: Xaa can be any naturally occurring amino acid

<400> SEQUENCE: 308

Tyr Asp Tyr Xaa Asp Ser Leu Asp Tyr
1               5

<210> SEQ ID NO 309
<211> LENGTH: 9
<212> TYPE: PRT
<213> ORGANISM: Artificial Sequence
<220> FEATURE:
<223> OTHER INFORMATION: CDRH3 library(Library 17)
<220> FEATURE:
<221> NAME/KEY: misc_feature
<222> LOCATION: (5)..(5)
<223> OTHER INFORMATION: Xaa can be any naturally occurring amino acid

<400> SEQUENCE: 309

Tyr Asp Tyr Asp Xaa Ser Leu Asp Tyr
1               5

<210> SEQ ID NO 310
<211> LENGTH: 9
<212> TYPE: PRT
<213> ORGANISM: Artificial Sequence
<220> FEATURE:
<223> OTHER INFORMATION: CDRH3 library(Library 17)
<220> FEATURE:
<221> NAME/KEY: misc_feature
<222> LOCATION: (6)..(6)
<223> OTHER INFORMATION: Xaa can be any naturally occurring amino acid

<400> SEQUENCE: 310

Tyr Asp Tyr Asp Asp Xaa Leu Asp Tyr
1               5

<210> SEQ ID NO 311
<211> LENGTH: 9
<212> TYPE: PRT

```
<213> ORGANISM: Artificial Sequence
<220> FEATURE:
<223> OTHER INFORMATION: CDRH3 library(Library 17)
<220> FEATURE:
<221> NAME/KEY: misc_feature
<222> LOCATION: (7)..(7)
<223> OTHER INFORMATION: Xaa can be any naturally occurring amino acid

<400> SEQUENCE: 311

Tyr Asp Tyr Asp Asp Ser Xaa Asp Tyr
1               5

<210> SEQ ID NO 312
<211> LENGTH: 9
<212> TYPE: PRT
<213> ORGANISM: Artificial Sequence
<220> FEATURE:
<223> OTHER INFORMATION: CDRH3 library(Library 17)
<220> FEATURE:
<221> NAME/KEY: misc_feature
<222> LOCATION: (8)..(8)
<223> OTHER INFORMATION: Xaa can be any naturally occurring amino acid

<400> SEQUENCE: 312

Tyr Asp Tyr Asp Asp Ser Leu Xaa Tyr
1               5

<210> SEQ ID NO 313
<211> LENGTH: 9
<212> TYPE: PRT
<213> ORGANISM: Artificial Sequence
<220> FEATURE:
<223> OTHER INFORMATION: CDRH3 library(Library 17)
<220> FEATURE:
<221> NAME/KEY: misc_feature
<222> LOCATION: (9)..(9)
<223> OTHER INFORMATION: Xaa can be any naturally occurring amino acid

<400> SEQUENCE: 313

Tyr Asp Tyr Asp Asp Ser Leu Asp Xaa
1               5

<210> SEQ ID NO 314
<211> LENGTH: 9
<212> TYPE: PRT
<213> ORGANISM: Artificial Sequence
<220> FEATURE:
<223> OTHER INFORMATION: CDRH3 library(Library 17)
<220> FEATURE:
<221> NAME/KEY: misc_feature
<222> LOCATION: (1)..(2)
<223> OTHER INFORMATION: Xaa can be any naturally occurring amino acid

<400> SEQUENCE: 314

Xaa Xaa Tyr Asp Asp Ser Leu Asp Tyr
1               5

<210> SEQ ID NO 315
<211> LENGTH: 9
<212> TYPE: PRT
<213> ORGANISM: Artificial Sequence
<220> FEATURE:
<223> OTHER INFORMATION: CDRH3 library(Library 17)
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
```

```
<400> SEQUENCE: 315

Xaa Asp Xaa Asp Asp Ser Leu Asp Tyr
1               5

<210> SEQ ID NO 316
<211> LENGTH: 9
<212> TYPE: PRT
<213> ORGANISM: Artificial Sequence
<220> FEATURE:
<223> OTHER INFORMATION: CDRH3 library(Library 17)
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 316

Xaa Asp Tyr Xaa Asp Ser Leu Asp Tyr
1               5

<210> SEQ ID NO 317
<211> LENGTH: 9
<212> TYPE: PRT
<213> ORGANISM: Artificial Sequence
<220> FEATURE:
<223> OTHER INFORMATION: CDRH3 library(Library 17)
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 317

Xaa Asp Tyr Asp Xaa Ser Leu Asp Tyr
1               5

<210> SEQ ID NO 318
<211> LENGTH: 9
<212> TYPE: PRT
<213> ORGANISM: Artificial Sequence
<220> FEATURE:
<223> OTHER INFORMATION: CDRH3 library(Library 17)
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 318

Xaa Asp Tyr Asp Asp Xaa Leu Asp Tyr
1               5

<210> SEQ ID NO 319
<211> LENGTH: 9
<212> TYPE: PRT
<213> ORGANISM: Artificial Sequence
<220> FEATURE:
<223> OTHER INFORMATION: CDRH3 library(Library 17)
<220> FEATURE:
<221> NAME/KEY: misc_feature
<222> LOCATION: (1)..(1)
```

```
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 319

Xaa Asp Tyr Asp Asp Ser Xaa Asp Tyr
1               5

<210> SEQ ID NO 320
<211> LENGTH: 9
<212> TYPE: PRT
<213> ORGANISM: Artificial Sequence
<220> FEATURE:
<223> OTHER INFORMATION: CDRH3 library(Library 17)
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 320

Xaa Asp Tyr Asp Asp Ser Leu Xaa Tyr
1               5

<210> SEQ ID NO 321
<211> LENGTH: 9
<212> TYPE: PRT
<213> ORGANISM: Artificial Sequence
<220> FEATURE:
<223> OTHER INFORMATION: CDRH3 library(Library 17)
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 321

Xaa Asp Tyr Asp Asp Ser Leu Asp Xaa
1               5

<210> SEQ ID NO 322
<211> LENGTH: 9
<212> TYPE: PRT
<213> ORGANISM: Artificial Sequence
<220> FEATURE:
<223> OTHER INFORMATION: CDRH3

<400> SEQUENCE: 322

Gly Asp Tyr Gly Asp Ser Leu Asp Tyr
1               5

<210> SEQ ID NO 323
<211> LENGTH: 5
<212> TYPE: PRT
<213> ORGANISM: Artificial Sequence
<220> FEATURE:
<223> OTHER INFORMATION: CDRH3 library(Library 30)
<220> FEATURE:
<221> NAME/KEY: misc_feature
<222> LOCATION: (1)..(1)
<223> OTHER INFORMATION: Xaa can be any naturally occurring amino acid

<400> SEQUENCE: 323
```

```
Xaa Ser Gly Gly Lys
1               5

<210> SEQ ID NO 324
<211> LENGTH: 5
<212> TYPE: PRT
<213> ORGANISM: Artificial Sequence
<220> FEATURE:
<223> OTHER INFORMATION: CDRH3 library(Library 30)
<220> FEATURE:
<221> NAME/KEY: misc_feature
<222> LOCATION: (2)..(2)
<223> OTHER INFORMATION: Xaa can be any naturally occurring amino acid

<400> SEQUENCE: 324

Trp Xaa Gly Gly Lys
1               5

<210> SEQ ID NO 325
<211> LENGTH: 5
<212> TYPE: PRT
<213> ORGANISM: Artificial Sequence
<220> FEATURE:
<223> OTHER INFORMATION: CDRH3 library(Library 30)
<220> FEATURE:
<221> NAME/KEY: misc_feature
<222> LOCATION: (3)..(3)
<223> OTHER INFORMATION: Xaa can be any naturally occurring amino acid

<400> SEQUENCE: 325

Trp Ser Xaa Gly Lys
1               5

<210> SEQ ID NO 326
<211> LENGTH: 5
<212> TYPE: PRT
<213> ORGANISM: Artificial Sequence
<220> FEATURE:
<223> OTHER INFORMATION: CDRH3 library(Library 30)
<220> FEATURE:
<221> NAME/KEY: misc_feature
<222> LOCATION: (4)..(4)
<223> OTHER INFORMATION: Xaa can be any naturally occurring amino acid

<400> SEQUENCE: 326

Trp Ser Gly Xaa Lys
1               5

<210> SEQ ID NO 327
<211> LENGTH: 5
<212> TYPE: PRT
<213> ORGANISM: Artificial Sequence
<220> FEATURE:
<223> OTHER INFORMATION: CDRH3 library(Library 30)
<220> FEATURE:
<221> NAME/KEY: misc_feature
<222> LOCATION: (5)..(5)
<223> OTHER INFORMATION: Xaa can be any naturally occurring amino acid

<400> SEQUENCE: 327

Trp Ser Gly Gly Xaa
1               5

<210> SEQ ID NO 328
<211> LENGTH: 5
<212> TYPE: PRT
<213> ORGANISM: Artificial Sequence
<220> FEATURE:
<223> OTHER INFORMATION: CDRH3 library(Library 30)
```

```
<220> FEATURE:
<221> NAME/KEY: misc_feature
<222> LOCATION: (1)..(2)
<223> OTHER INFORMATION: Xaa can be any naturally occurring amino acid

<400> SEQUENCE: 328

Xaa Xaa Gly Gly Lys
1               5

<210> SEQ ID NO 329
<211> LENGTH: 5
<212> TYPE: PRT
<213> ORGANISM: Artificial Sequence
<220> FEATURE:
<223> OTHER INFORMATION: CDRH3 library(Library 30)
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 329

Xaa Ser Xaa Gly Lys
1               5

<210> SEQ ID NO 330
<211> LENGTH: 5
<212> TYPE: PRT
<213> ORGANISM: Artificial Sequence
<220> FEATURE:
<223> OTHER INFORMATION: CDRH3 library(Library 30)
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 330

Xaa Ser Gly Xaa Lys
1               5

<210> SEQ ID NO 331
<211> LENGTH: 5
<212> TYPE: PRT
<213> ORGANISM: Artificial Sequence
<220> FEATURE:
<223> OTHER INFORMATION: CDRH3 library(Library 30)
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 331

Xaa Ser Gly Gly Xaa
1               5

<210> SEQ ID NO 332
<211> LENGTH: 5
<212> TYPE: PRT
<213> ORGANISM: Artificial Sequence
<220> FEATURE:
```

```
<223> OTHER INFORMATION: CDRH3 library(Library 30)
<220> FEATURE:
<221> NAME/KEY: misc_feature
<222> LOCATION: (2)..(3)
<223> OTHER INFORMATION: Xaa can be any naturally occurring amino acid

<400> SEQUENCE: 332

Trp Xaa Xaa Gly Lys
1               5

<210> SEQ ID NO 333
<211> LENGTH: 5
<212> TYPE: PRT
<213> ORGANISM: Artificial Sequence
<220> FEATURE:
<223> OTHER INFORMATION: CDRH3 library(Library 30)
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 333

Trp Xaa Gly Xaa Lys
1               5

<210> SEQ ID NO 334
<211> LENGTH: 5
<212> TYPE: PRT
<213> ORGANISM: Artificial Sequence
<220> FEATURE:
<223> OTHER INFORMATION: CDRH3 library(Library 30)
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 334

Trp Xaa Gly Gly Xaa
1               5

<210> SEQ ID NO 335
<211> LENGTH: 117
<212> TYPE: PRT
<213> ORGANISM: Artificial Sequence
<220> FEATURE:
<223> OTHER INFORMATION: Humanized 16B8.C8 in AB0305/ AB5030 VH with
      G44C mutation

<400> SEQUENCE: 335

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Leu His Trp Ile Arg Gln Pro Pro Gly Lys Cys Leu Glu Trp Ile
        35                  40                  45

Gly Val Ile Trp Val Gly Gly Ala Thr Asp Tyr Asn Pro Ser Leu Lys
    50                  55                  60

Ser Arg Val Thr Ile Ser Val Asp Thr Ser Lys Asn Gln Phe Ser Leu
65                  70                  75                  80
```

-continued

```
Lys Leu Ser Ser Val Gln Ala Ala Asp Thr Ala Val Tyr Tyr Cys Ala
                85                  90                  95

Lys Gly Asp Tyr Gly Asp Thr Leu Asp Tyr Trp Gly Gln Gly Thr Leu
            100                 105                 110

Val Thr Val Ser Ser
        115

<210> SEQ ID NO 336
<211> LENGTH: 107
<212> TYPE: PRT
<213> ORGANISM: Artificial Sequence
<220> FEATURE:
<223> OTHER INFORMATION: Humanized 16B8.C8 in AB0305/ AB5030 VL with
      S100C mutation

<400> SEQUENCE: 336

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Phe Trp
            20                  25                  30

Leu Ser Trp Tyr Gln Gln Lys Pro Gly Lys Ala Pro Lys Leu Leu Ile
        35                  40                  45

Tyr Glu Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Ser Tyr Pro Leu
                85                  90                  95

Thr Phe Gly Cys Gly Thr Lys Leu Glu Ile Lys
            100                 105

<210> SEQ ID NO 337
<211> LENGTH: 10
<212> TYPE: PRT
<213> ORGANISM: Artificial Sequence
<220> FEATURE:
<223> OTHER INFORMATION: AB0192 Chain L VL CDR1

<400> SEQUENCE: 337

Arg Ala Ser Gln Gly Ile Ser Ser Trp Ala
1               5                   10

<210> SEQ ID NO 338
<211> LENGTH: 5
<212> TYPE: PRT
<213> ORGANISM: Artificial Sequence
<220> FEATURE:
<223> OTHER INFORMATION: AB0192 Chain H VH CDR2

<400> SEQUENCE: 338

Ser Ser Ser Ser Tyr
1               5

<210> SEQ ID NO 339
<211> LENGTH: 14
<212> TYPE: PRT
<213> ORGANISM: Artificial Sequence
<220> FEATURE:
<223> OTHER INFORMATION: AB0192 Chain H VH CDR3

<400> SEQUENCE: 339

Gly Ala Pro Met Ile Gly Ala Ala Ala Gly Trp Phe Asp Pro
1               5                   10
```

```
<210> SEQ ID NO 340
<211> LENGTH: 19
<212> TYPE: PRT
<213> ORGANISM: Artificial Sequence
<220> FEATURE:
<223> OTHER INFORMATION: found in AB0192 Chain S

<400> SEQUENCE: 340

Leu Ser Cys Ala Ala Ser Gly Phe Thr Phe Asn Ala Phe Gly Met His
1               5                   10                  15

Trp Val Arg

<210> SEQ ID NO 341
<211> LENGTH: 11
<212> TYPE: PRT
<213> ORGANISM: Artificial Sequence
<220> FEATURE:
<223> OTHER INFORMATION: found in AB0192 Chain S

<400> SEQUENCE: 341

Asn Thr Leu Tyr Leu Gln Met Asn Ser Leu Arg
1               5                   10

<210> SEQ ID NO 342
<211> LENGTH: 60
<212> TYPE: PRT
<213> ORGANISM: Artificial Sequence
<220> FEATURE:
<223> OTHER INFORMATION: found in AB0192 Chain S

<400> SEQUENCE: 342

Asp Gly Tyr Pro Thr Gly Gly Ala Met Asp Tyr Trp Gly Gln Gly Thr
1               5                   10                  15

Ser Val Thr Val Ser Ser Gly Gly Gly Ser Gly Gly Gly Gly Ser
            20                  25                  30

Gly Gly Gly Gly Ser Gly Gly Gly Gly Ser Asp Ile Gln Met Thr Gln
        35                  40                  45

Ser Pro Ser Ser Leu Ser Ala Ser Val Gly Asp Arg
    50                  55                  60
```

PROTEINS BINDING NKG2D, CD16 AND CLEC12A

This application claims priority to U.S. Provisional Application No. 63/020,798, filed on May 6, 2020, the entirety of which is incorporated herein by reference.

SEQUENCE LISTING

This application incorporates by reference in its entirety the Computer Readable Form (CRF) of a Sequence Listing in ASCII text format. The Sequence Listing text file is entitled "14247-540-999_SEQ_LISTING," was created on May 3, 2021, and is 291,326 bytes in size.

FIELD OF THE INVENTION

The present application relates to multispecific binding proteins that bind NKG2D, CD16 and CLEC12A on a cell, pharmaceutical compositions comprising such proteins, and therapeutic methods using such proteins and pharmaceutical compositions, including for the treatment of cancer.

BACKGROUND

Despite substantial research efforts, cancer continues to be a significant clinical and financial burden in countries across the globe. According to the World Health Organization (WHO), it is the second leading cause of death. Surgery, radiation therapy, chemotherapy, biological therapy, immunotherapy, hormone therapy, stem-cell transplantation, and precision medicine are among the existing treatment modalities. Despite extensive research in these areas, a highly effective, curative solution, particularly for the most aggressive cancers, has yet to be identified. Furthermore, many of the existing anti-cancer treatment modalities have substantial adverse side effects.

Cancer immunotherapies are desirable because they are highly specific and can facilitate destruction of cancer cells using the patient's own immune system. Fusion proteins such as bi-specific T-cell engagers are cancer immunotherapies described in the literature that bind to tumor cells and T-cells to facilitate destruction of tumor cells. Antibodies that bind to certain tumor-associated antigens have been described in the literature. See, e.g., WO 2016/134371 and WO 2015/095412.

Natural killer (NK) cells are a component of the innate immune system and make up approximately 15% of circulating lymphocytes. NK cells infiltrate virtually all tissues and were originally characterized by their ability to kill tumor cells effectively without the need for prior sensitization. Activated NK cells kill target cells by means similar to cytotoxic T cells—i.e., via cytolytic granules that contain perforin and granzymes as well as via death receptor pathways. Activated NK cells also secrete inflammatory cytokines such as IFN-γ and chemokines that promote the recruitment of other leukocytes to the target tissue.

NK cells respond to signals through a variety of activating and inhibitory receptors on their surface. For example, when NK cells encounter healthy self-cells, their activity is inhibited through activation of the killer-cell immunoglobulin-like receptors (KIRs). Alternatively, when NK cells encounter foreign cells or cancer cells, they are activated via their activating receptors (e.g., NKG2D, NCRs, DNAM1). NK cells are also activated by the constant region of some immunoglobulins through CD16 receptors on their surface. The overall sensitivity of NK cells to activation depends on the sum of stimulatory and inhibitory signals. NKG2D is a type-II transmembrane protein that is expressed by essentially all natural killer cells where NKG2D serves as an activating receptor. NKG2D is also be found on T cells where it acts as a costimulatory receptor. The ability to modulate NK cell function via NKG2D is useful in various therapeutic contexts including malignancy.

C-type lectin domain family 12 member A (CLEC12A), also known as C-type lectin-like molecule-1 (CLL-1) or myeloid inhibitory C-type lectin-like receptor (MICL), is a member of the C-type lectin/C-type lectin-like domain (CTL/CTLD) superfamily. Members of this family share a common protein fold and have diverse functions, such as cell adhesion, cell-cell signaling, glycoprotein turnover, and roles in inflammation and immune response. CLEC12A, a type II transmembrane glycoprotein, is overexpressed in over 90% of acute myeloid leukemia patient on leukemic stem cells, but not on normal haematopoietic cells.

Despite many efforts undertaken by several biotech and pharma companies, development of specific CLEC12A targeted biologics is hindered by the absence of antibodies with good developability characteristics. The challenges in discovering CLEC12A antibodies may be attributed to the complexity of the antigen. CLEC12A is a monomeric heavily glycosylated protein with six potential N-glycosylation sites within an extracellular domain having 201 amino acids. Four out of six N-glycosylation sites are clustered in the membrane proximal domain of the molecule and are likely to be involved in presentation of the target on the cell surface. Variations in the glycosylation status of CLEC12A on the surface of different cell types has been reported (Marshall et al., (2006) *Eur J Immunol.* 36(8):2159-69).

Therefore, there remains a need in the field for new and useful proteins that bind CLEC12A for use in treatment of cancer.

SUMMARY

The present application provides multispecific binding proteins that bind to the NKG2D receptor and CD16 receptor on natural killer cells, and CLEC12A. Such proteins can engage more than one kind of NK-activating receptor, and may block the binding of natural ligands to NKG2D. In certain embodiments, the proteins can agonize NK cells in humans. In some embodiments, the proteins can agonize NK cells in humans and in other species such as rodents and cynomolgus monkeys. Formulations containing any one of the proteins disclosed herein; cells containing one or more nucleic acids expressing the proteins, and methods of enhancing tumor cell death using the proteins are also provided.

Accordingly, in one aspect, the present application provides a protein comprising:

(a) a first antigen-binding site that binds NKG2D;

(b) a second antigen-binding site that binds CLEC12A; and (c) an antibody Fc domain or a portion thereof sufficient to bind CD16, or a third antigen-binding site that binds CD16;

wherein the second antigen-binding site that binds CLEC12A comprises:

(i) a heavy chain variable domain (VH) comprising complementarity-determining region 1 (CDR1), complementarity-determining region 2 (CDR2), and complementarity-determining region 3 (CDR3) comprising the amino acid sequences of SEQ ID NOs: 137, 272, and 273, respectively; and a light chain variable domain (VL) comprising CDR1, CDR2, and CDR3 comprising the amino acid sequences of SEQ ID NOs: 140, 141, and 142, respectively;

(ii) a VH comprising CDR1, CDR2, and CDR3 comprising the amino acid sequences of SEQ ID NOs: 137, 138, and 139, respectively; and a VL comprising CDR1, CDR2, and CDR3 comprising the amino acid sequences of SEQ ID NOs: 140, 141, and 142, respectively;

(iii) a VH comprising CDR1, CDR2, and CDR3 comprising the amino acid sequences of SEQ ID NOs: 251, 196, and 246, respectively; and a VL comprising CDR1, CDR2, and CDR3 comprising the amino acid sequences of SEQ ID NOs: 198, 199, and 201, respectively;

(v) a VH comprising CDR1, CDR2, and CDR3 comprising the amino acid sequences of SEQ ID NOs: 221, 166, and 223, respectively; and a VL comprising CDR1, CDR2, and CDR3 comprising the amino acid sequences of SEQ ID NOs: 240, 226, and 179, respectively;

(v) a VH comprising CDR1, CDR2, and CDR3 comprising the amino acid sequences of SEQ ID NOs: 206, 166, and 241, respectively; and a VL comprising CDR1, CDR2, and CDR3 comprising the amino acid sequences of SEQ ID NOs: 245, 239, and 179, respectively;

(vi) a VH comprising CDR1, CDR2, and CDR3 comprising the amino acid sequences of SEQ ID NOs: 221, 236, and 223, respectively; and a VL comprising CDR1, CDR2, and CDR3 comprising the amino acid sequences of SEQ ID NOs: 152, 226, and 179, respectively;

(vii) a VH comprising CDR1, CDR2, and CDR3 comprising the amino acid sequences of SEQ ID NOs: 159, 170, and 183, respectively; and a VL comprising CDR1, CDR2, and CDR3 comprising the amino acid sequences of SEQ ID NOs: 186, 188, and 189, respectively;

(viii) a VH comprising CDR1, CDR2, and CDR3 comprising the amino acid sequences of SEQ ID NOs: 197, 202, and 207, respectively; and a VL comprising CDR1, CDR2, and CDR3 comprising the amino acid sequences of SEQ ID NOs: 211, 212, and 214, respectively;

(ix) a VH comprising CDR1, CDR2, and CDR3 comprising the amino acid sequences of SEQ ID NOs: 220, 222, and 257, respectively; and a VL comprising CDR1, CDR2, and CDR3 comprising the amino acid sequences of SEQ ID NOs: 224, 225, and 227, respectively; or (x) a VH comprising CDR1, CDR2, and CDR3 comprising the amino acid sequences of SEQ ID NOs: 230, 231, and 232, respectively; and a VL comprising CDR1, CDR2, and CDR3 comprising the amino acid sequences of SEQ ID NOs: 233, 234, and 235, respectively.

In some embodiments, the second antigen-binding site that binds CLEC12A comprises a VH comprising CDR1, CDR2, and CDR3 comprising the amino acid sequences of SEQ ID NOs: 137, 272, and 273, respectively; and a VL comprising CDR1, CDR2, and CDR3 comprising the amino acid sequences of SEQ ID NOs: 140, 141, and 142, respectively. In some embodiments, the second antigen-binding site that binds CLEC12A comprises a VH comprising CDR1, CDR2, and CDR3 comprising the amino acid sequences of SEQ ID NOs: 137, 138, and 139, respectively; and a VL comprising CDR1, CDR2, and CDR3 comprising the amino acid sequences of SEQ ID NOs: 140, 141, and 142, respectively.

In certain embodiments, the VH comprises an amino acid sequence at least 90% identical to SEQ ID NO:335, and the VL comprises an amino acid sequence at least 90% identical to SEQ ID NO:336. In certain embodiments, the VH comprises an amino acid sequence at least 90% identical to SEQ ID NO:270, and the VL comprises an amino acid sequence at least 90% identical to SEQ ID NO:271. In certain embodiments, the VH comprises an amino acid sequence at least 90% identical to SEQ ID NO:178, and the VL comprises an amino acid sequence at least 90% identical to SEQ ID NO:289. In certain embodiments, the VH comprises the amino acid sequence of SEQ ID NO:335, and the VL comprises the amino acid sequence of SEQ ID NO:336. In certain embodiments, the VH comprises the amino acid sequence of SEQ ID NO:270, and the VL comprises the amino acid sequence of SEQ ID NO:271. In certain embodiments, the VH comprises the amino acid sequence of SEQ ID NO:178, and the VL comprises the amino acid sequence of SEQ ID NO:289. In certain embodiments, the VH and the VL comprise the amino acid sequences of SEQ ID NOs: 143 and 144; 147 and 144; 244 and 144; 178 and 144; 256 and 144; 143 and 163; 143 and 167; 143 and 171; or 174 and 175, respectively.

In some embodiments, the second antigen-binding site is present as a single-chain fragment variable (scFv), and wherein the scFv comprises an amino acid sequence selected from SEQ ID NOs: 274, 145, 146, 149, 150, 153, 154, 156, 157, 160, 161, 164, 165, 168, 169, 172, 173, 176, 177, 180, and 181. In certain embodiments, the scFv comprises the amino acid sequence of SEQ ID NO:274. In certain embodiments, the scFv comprises the amino acid sequence of SEQ ID NO:180.

In some embodiments, the second antigen-binding site that binds CLEC12A comprises a VH comprising CDR1, CDR2, and CDR3 comprising the amino acid sequences of SEQ ID NOs: 251, 196, and 246, respectively; and a VL comprising CDR1, CDR2, and CDR3 comprising the amino acid sequences of SEQ ID NOs: 198, 199, and 201, respectively.

In certain embodiments, the second antigen-binding site that binds CLEC12A comprises:

(i) a VH comprising CDR1, CDR2, and CDR3 comprising the amino acid sequences of SEQ ID NOs: 195, 196, 187, respectively; and a VL comprising CDR1, CDR2, and CDR3 comprising the amino acid sequences of SEQ ID NOs: 198, 199, 201, respectively;

(ii) a VH comprising CDR1, CDR2, and CDR3 comprising the amino acid sequences of SEQ ID NOs: 192, 196, and 187, respectively; and a VL comprising CDR1, CDR2, and CDR3 comprising the amino acid sequences of SEQ ID NOs: 198, 199, and 201, respectively; or (iii) a VH comprising CDR1, CDR2, and CDR3 comprising the amino acid sequences of SEQ ID NOs: 192, 196, and 213, respectively; and a VL comprising CDR1, CDR2, and CDR3 comprising the amino acid sequences of SEQ ID NOs: 198, 199, and 201, respectively.

In certain embodiments, the VH comprises an amino acid sequence at least 90% identical to SEQ ID NO:148, and the VL comprises an amino acid sequence at least 90% identical to SEQ ID NO:203.

In certain embodiments, the VH comprises the amino acid sequence of SEQ ID NO:148, and the VL comprises the amino acid sequence of SEQ ID NO:203. In certain embodiments, the VH and the VL comprise the amino acid sequences of SEQ ID NOs: 162 and 203; 210 and 203; 162 and 218; 148 and 218; or 210 and 218, respectively. In some embodiments, second the antigen-binding site is present as an scFv, and wherein the scFv comprises an amino acid sequence selected from SEQ ID NOs: 184, 185, 204, 205, 208, 209, 215, 216, 252, 253, 254, and 255. In certain embodiments, the scFv comprises the amino acid sequence of SEQ ID NO:204.

In certain embodiments, the second antigen-binding site of a preceding embodiment binds CLEC12A in a glycosylation independent manner.

In another aspect, the present application provides a protein comprising:

(a) a first antigen-binding site that binds NKG2D;
(b) a second antigen-binding site that binds CLEC12A; and
(c) an antibody Fc domain or a portion thereof sufficient to bind CD16, or a third antigen-binding site that binds CD16;

wherein the second antigen-binding site binds CLEC12A in a glycosylation independent manner.

In some embodiments of a protein disclosed herein, the second antigen-binding site binds human CLEC12A with a dissociation constant ($K_D$) smaller than or equal to 20 nM as measured by surface plasmon resonance (SPR). In certain embodiments, the second antigen-binding site binds human CLEC12A with a $K_D$ smaller than or equal to 1 nM as measured by SPR. In certain embodiments, the second antigen-binding site binds human CLEC12A comprising a K244Q substitution.

In some embodiments of a protein disclosed herein, the protein comprises an antibody Fc domain or a portion thereof sufficient to bind CD16.

In some embodiments of a protein disclosed herein, the first antigen-binding site that binds NKG2D is a Fab fragment, and the second antigen-binding site that binds CLEC12A is an scFv.

In some embodiments of a protein disclosed herein, the first antigen-binding site that binds NKG2D is an scFv, and the second antigen-binding site that binds CLEC12A is a Fab fragment.

In some embodiments of a protein disclosed herein, the protein further comprises an additional antigen-binding site that binds CLEC12A. In certain embodiments, the first antigen-binding site that binds NKG2D is an scFv, and the second and the additional antigen-binding sites that bind CLEC12A are each a Fab fragment. In certain embodiments, the first antigen-binding site that binds NKG2D is an scFv, and the second and the additional antigen-binding sites that bind CLEC12A are each an scFv. In certain embodiments, the amino acid sequences of the second and the additional antigen-binding sites are identical. In certain embodiments, the amino acid sequences of the second and the additional antigen-binding sites are different.

In another aspect, the present application provides a protein comprising:

(a) a first antigen-binding site that binds NKG2D;
(b) a second antigen-binding site that binds CLEC12A; and
(c) an antibody Fc domain or a portion thereof sufficient to bind CD16, or a third antigen-binding site that binds CD16;

wherein the first antigen-binding site that binds NKG2D is a Fab fragment, and the second antigen-binding site that binds CLEC12A is an scFv.

In some embodiments of a protein disclosed herein, the scFv that binds NKG2D is linked to an antibody constant domain or a portion thereof sufficient to bind CD16, via a hinge comprising Ala-Ser or Gly-Ser. In certain embodiments, the hinge further comprises an amino acid sequence Thr-Lys-Gly.

In some embodiments of a protein disclosed herein, each scFv that binds CLEC12A is linked to an antibody constant domain or a portion thereof sufficient to bind CD16, via a hinge comprising Ala-Ser or Gly-Ser. In certain embodiments, the hinge further comprises an amino acid sequence Thr-Lys-Gly.

In some embodiments of a protein disclosed herein, within the scFv that binds NKG2D, the heavy chain variable domain of the scFv forms a disulfide bridge with the light chain variable domain of the scFv. In certain embodiments, the disulfide bridge is formed between C44 of the heavy chain variable domain and C100 of the light chain variable domain, numbered under the Kabat numbering scheme In some embodiments of a protein disclosed herein, within each scFv that binds CLEC12A, the heavy chain variable domain of the scFv forms a disulfide bridge with the light chain variable domain of the scFv. In certain embodiments, the disulfide bridge is formed between C44 of the heavy chain variable domain and C100 of the light chain variable domain, numbered under the Kabat numbering scheme.

In some embodiments of a protein disclosed herein, within the scFv that binds NKG2D, the heavy chain variable domain is linked to the light chain variable domain via a flexible linker. In certain embodiments, the flexible linker comprises $(G_4S)_4$.

In some embodiments of a protein disclosed herein, within each scFv that binds CLEC12A, the heavy chain variable domain is linked to the light chain variable domain via a flexible linker. In certain embodiments, the flexible linker comprises $(G_4S)_4$.

In some embodiments of a protein disclosed herein, within the scFv that binds NKG2D, the heavy chain variable domain is positioned at the C-terminus of the light chain variable domain.

In some embodiments of a protein disclosed herein, within each scFv that binds CLEC12A, the heavy chain variable domain is positioned at the C-terminus of the light chain variable domain.

In some embodiments of a protein disclosed herein, within the scFv that binds NKG2D, the heavy chain variable domain is positioned at the N-terminus of the light chain variable domain.

In some embodiments of a protein disclosed herein, within each scFv that binds CLEC12A, the heavy chain variable domain is positioned at the N-terminus of the light chain variable domain.

In some embodiments of a protein disclosed herein, the Fab fragment that binds NKG2D is not positioned between an antigen-binding site and the Fc or the portion thereof.

In some embodiments of a protein disclosed herein, no Fab fragment that binds CLEC12A is positioned between an antigen-binding site and the Fc or the portion thereof.

In some embodiments of a protein disclosed herein, the first antigen-binding site that binds NKG2D comprises a VH comprising CDR1, CDR2, and CDR3 comprising the amino acid sequences of SEQ ID NOs: 81, 82, and 112, respectively; and a VL comprising CDR1, CDR2, and CDR3 comprising the amino acid sequences of SEQ ID NOs: 86, 77, and 87, respectively. In certain embodiments, the first antigen-binding site that binds NKG2D comprises:

(i) a VH comprising CDR1, CDR2, and CDR3 comprising the amino acid sequences of SEQ ID NOs: 81, 82, and 97, respectively; and a VL comprising CDR1, CDR2, and CDR3 comprising the amino acid sequences of SEQ ID NOs: 86, 77, and 87, respectively; or (ii) a VH comprising CDR1, CDR2, and CDR3 comprising the amino acid sequences of SEQ ID NOs: 81, 82, and 84, respectively; and a VL comprising CDR1, CDR2, and CDR3 comprising the amino acid sequences of SEQ ID NOs: 86, 77, and 87, respectively.

In some embodiments of a protein disclosed herein, the VH of the first antigen-binding site comprises an amino acid sequence at least 90% identical to SEQ ID NO:95, and the VL of the first antigen-binding site comprises an amino acid sequence at least 90% identical to SEQ ID NO:85. In certain embodiments, the VH of the first antigen-binding site comprises the amino acid sequence of SEQ ID NO:95, and the VL of the first antigen-binding site comprises the amino acid sequence of SEQ ID NO:85.

In some embodiments of a protein disclosed herein, the antibody Fc domain is a human IgG1 antibody Fc domain. In some embodiments, the antibody Fc domain or the portion thereof comprises an amino acid sequence at least 90% identical to SEQ ID NO:118. In certain embodiments, at least one polypeptide chain of the antibody Fc domain comprises one or more mutations, relative to SEQ ID NO:118, at one or more positions selected from Q347, Y349, L351, S354, E356, E357, K360, Q362, S364, T366, L368, K370, N390, K392, T394, D399, S400, D401, F405, Y407, K409, T411, and K439, numbered according to the EU numbering system. In certain embodiments, at least one polypeptide chain of the antibody Fc domain comprises one or more mutations, relative to SEQ ID NO:118, selected from Q347E, Q347R, Y349S, Y349K, Y349T, Y349D, Y349E, Y349C, L351K, L351D, L351Y, S354C, E356K, E357Q, E357L, E357W, K360E, K360W, Q362E, S364K, S364E, S364H, S364D, T366V, T366I, T366L, T366M, T366K, T366W, T366S, L368E, L368A, L368D, K370S, N390D, N390E, K392L, K392M, K392V, K392F, K392D, K392E, T394F, D399R, D399K, D399V, S400K, S400R, D401K, F405A, F405T, Y407A, Y407I, Y407V, K409F, K409W, K409D, T411D, T411E, K439D, and K439E, numbered according to the EU numbering system. In certain embodiments, one polypeptide chain of the antibody heavy chain constant region comprises one or more mutations, relative to SEQ ID NO:118, at one or more positions selected from Q347, Y349, L351, S354, E356, E357, K360, Q362, S364, T366, L368, K370, K392, T394, D399, S400, D401, F405, Y407, K409, T411 and K439; and the other polypeptide chain of the antibody heavy chain constant region comprises one or more mutations, relative to SEQ ID NO:136, at one or more positions selected from Q347, Y349, L351, S354, E356, E357, S364, T366, L368, K370, N390, K392, T394, D399, D401, F405, Y407, K409, T411, and K439, numbered according to the EU numbering system. In certain embodiments, one polypeptide chain of the antibody heavy chain constant region comprises K360E and K409W substitutions relative to SEQ ID NO:118; and the other polypeptide chain of the antibody heavy chain constant region comprises Q347R, D399V and F405T substitutions relative to SEQ ID NO:136, numbered according to the EU numbering system. In certain embodiments, one polypeptide chain of the antibody heavy chain constant region comprises a Y349C substitution relative to SEQ ID NO:118; and the other polypeptide chain of the antibody heavy chain constant region comprises an S354C substitution relative to SEQ ID NO:136, numbered according to the EU numbering system.

In another aspect, the present application provides a protein comprising:
(a) a first polypeptide comprising the amino acid sequence of SEQ ID NO:259;
(b) a second polypeptide comprising the amino acid sequence of SEQ ID NO:260; and
(c) a third polypeptide comprising the amino acid sequence of SEQ ID NO:261.

In another aspect, the present application provides a protein comprising:
(a) a first polypeptide comprising the amino acid sequence of SEQ ID NO:276;
(b) a second polypeptide comprising the amino acid sequence of SEQ ID NO:260; and
(c) a third polypeptide comprising the amino acid sequence of SEQ ID NO:261.

In another aspect, the present application provides a pharmaceutical composition comprising a protein disclosed herein and a pharmaceutically acceptable carrier.

In another aspect, the present application provides a pharmaceutical formulation comprising a protein disclosed herein and a buffer at pH 7.0 or higher. In some embodiments, the pH of the formulation is between 7.0 and 8.0. In some embodiments, the buffer comprises citrate. In certain embodiments, the concentration of citrate is 10 to 20 mM. In some embodiments, the buffer further comprises phosphate. In some embodiments, the buffer further comprises a sugar or sugar alcohol. In certain embodiments, the sugar or sugar alcohol is a disaccharide. In certain embodiments, the disaccharide is sucrose. In some embodiments, the concentration of the sugar or sugar alcohol in the pharmaceutical formulation is 200 to 300 mM. In certain embodiments, the concentration of the sugar or sugar alcohol in the pharmaceutical formulation is about 250 mM. In some embodiments, the buffer further comprises a nonionic surfactant. In certain embodiments, the nonionic surfactant comprises a polysorbate. In certain embodiments, the polysorbate is polysorbate 80. In some embodiments, the concentration of polysorbate 80 in the pharmaceutical formulation is 0.005% to 0.05%. In certain embodiments, the concentration of polysorbate 80 in the pharmaceutical formulation is about 0.01%. In some embodiments, the concentration of NaCl, if any, is about 1 mM or lower in the pharmaceutical formulation. In some embodiments, the concentration of the protein is 10 to 200 mg/mL. In certain embodiments, the concentration of the protein is about 20 mg/mL.

In some embodiments, the pharmaceutical formulation comprises about 20 mM citrate, about 250 mM sucrose, and about 0.01% polysorbate 80, at pH 7.0. In certain embodiments, the pharmaceutical formulation comprises about 20 mg/mL of the protein, about 20 mM potassium phosphate, about 10 mM sodium citrate, and about 125 mM sodium chloride, at pH 7.8.

In another aspect, the present application provides a cell comprising one or more nucleic acids encoding a protein disclosed herein.

In another aspect, the present application provides a method of enhancing tumor cell death, the method comprising exposing the tumor cell and a natural killer cell to an effective amount of a protein, a pharmaceutical composition, or a pharmaceutical formulation disclosed herein.

In another aspect, the present application provides a method of treating cancer, the method comprising administering to a subject in need thereof an effective amount of a protein, a pharmaceutical composition, or a pharmaceutical formulation disclosed herein. In some embodiments, the cancer is a hematologic malignancy. In certain embodiments, the hematologic malignancy is selected from the group consisting of acute myeloid leukemia (AML), myelodysplastic syndrome (MDS), acute lymphoblastic leukemia (ALL), myeloproliferative neoplasms (MPNs), lymphoma, non-Hodgkin lymphomas, and classical Hodgkin lymphoma.

In some embodiments, the AML is selected from undifferentiated acute myeloblastic leukemia, acute myeloblastic leukemia with minimal maturation, acute myeloblastic leukemia with maturation, acute promyelocytic leukemia (APL), acute myelomonocytic leukemia, acute myelomonocytic leukemia with eosinophilia, acute monocytic leukemia, acute erythroid leukemia, acute megakaryoblastic leukemia (AMKL), acute basophilic leukemia, acute panmyelosis with fibrosis, and blastic plasmacytoid dendritic cell neoplasm (BPDCN). In certain embodiments, the AML is characterized by expression of CLL-1 on the AML leukemia stem cells (LSCs). In certain embodiments, the LSCs further express a membrane marker selected from CD34, CD38, CD123, TIM3, CD25, CD32, and CD96.

In some embodiments, the AML is a minimal residual disease (MRD). In certain embodiments, the MRD is characterized by the presence or absence of a mutation selected from FLT3-ITD ((Fms-like tyrosine kinase 3)-internal tandem duplications (ITD)), NPM1 (Nucleophosmin 1), DNMT3A (DNA methyltransferase gene DNMT3A), and IDH (Isocitrate dehydrogenase 1 and 2 (IDH1 and IDH2)).

In certain embodiments, the MDS is selected from MDS with multilineage dysplasia (MDS-MLD), MDS with single lineage dysplasia (MDS-SLD), MDS with ring sideroblasts (MDS-RS), MDS with excess blasts (MDS-EB), MDS with isolated del(5q), and MDS, unclassified (MDS-U). In certain embodiments, the MDS is a primary MDS or a secondary MDS.

In some embodiments, the ALL is selected from B-cell acute lymphoblastic leukemia (B-ALL) and T-cell acute lymphoblastic leukemia (T-ALL). In some embodiments, the MPN is selected from polycythaemia vera, essential thrombocythemia (ET), and myelofibrosis. In some embodiments, the non-Hodgkin lymphoma is selected from B-cell lymphoma and T-cell lymphoma. In some embodiments, the lymphoma is selected from chronic lymphocytic leukemia (CLL), lymphoblastic lymphoma (LPL), diffuse large B-cell lymphoma (DLBCL), Burkitt lymphoma (BL), primary mediastinal large B-cell lymphoma (PMBL), follicular lymphoma, mantle cell lymphoma, hairy cell leukemia, plasma cell myeloma (PCM) or multiple myeloma (MM), mature T/NK neoplasms, and histiocytic neoplasms. In certain embodiments, the cancer expresses CLEC12A.

BRIEF DESCRIPTION OF THE DRAWINGS

As shown in FIG. 2A, either the NKG2D-binding domain or the tumor-associated antigen binding domain can take the scFv format (left arm). An antibody that contains a NKG2D-targeting scFv, a tumor-associated antigen targeting Fab fragment, and a heterodimerized antibody constant region is referred herein as the F3-TriNKET. An antibody that contains a tumor-associated antigen targeting scFv, a NKG2D-targeting Fab fragment, and a heterodimerized antibody constant region/domain that binds CD16 is referred herein as the F3'-TriNKET (FIG. 2E). As shown in FIG. 2B, both the NKG2D-binding domain and tumor-associated antigen binding domain can take the scFv format. FIGS. 2C to 2D are illustrations of an antibody with three antigen-binding sites, including two antigen-binding sites that bind the tumor-associated antigen, and the NKG2D-binding site fused to the heterodimerized antibody constant region. These antibody formats are referred herein as F4-TriNKET. FIG. 2C illustrates that the two tumor-associated antigen binding sites are in the Fab fragment format, and the NKG2D binding site in the scFv format. FIG. 2D illustrates that the tumor-associated antigen binding sites are in the scFv format, and the NKG2D binding site is in the scFv format. FIG. 2E represents a trispecific antibody (TriNKET) that contains a tumor-targeting scFv, a NKG2D-targeting Fab fragment, and a heterodimerized antibody constant region/domain ("CD domain") that binds CD16. The antibody format is referred herein as F3'-TriNKET. In certain exemplary multispecific binding proteins, heterodimerization mutations on the antibody constant region include K360E and K409W on one constant domain; and Q347R, D399V and F405T on the opposite constant domain (shown as a triangular lock-and-key shape in the CD domains). The bold bar between the heavy and the light chain variable domains of the Fab fragments represents a disulfide bond.

FIG. 13A is an exemplary representation of one form of a κλ-Body; FIG. 13B is an exemplary representation of another κλ-Body.

FIG. 19A-FIG. 19P are a set of sensorgrams showing SPR profiles of antibodies collected from the murine mAb subclones binding to hCLEC12A (FIG. 19A-FIG. 19D, and FIG. 19I-FIG. 19L) and cCLEC12A (FIG. 19E-FIG. 19H, and FIG. 19M-FIG. 19P).

FIG. 25A-FIG. 25B are line graphs showing differential scanning colorimetry (DSC) analysis of TriNKETs F3'-129.

FIG. 26A-FIG. 26H are a set of sensorgrams showing SPR profiles of TriNKETs F3'-1295 (FIGS. 26A, 26B, 26E, and 26F) and F3'-1602 (FIGS. 26C, 26D, 26G, and 26H).

FIG. 27A-FIG. 27D are line graphs showing binding of hCLEC12A-targeting TriNKETs F3'-1295, F3'-1602, and a control CLEC12A-TriNKET to hCLEC12A-expressing cell line Ba/F3 (FIG. 27A), wild-type Ba/F3 (FIG. 27B), cancer line HL60 (FIG. 27C), and cancer line PL21 (FIG. 27D).

FIG. 29A-FIG. 29B are line graphs showing isoelectric point (pI) determined by capillary isoelectric focusing (cIEF) of F3'-1295 (FIG. 29A) and F3'-1602 (FIG. 29B).

FIG. 32A-FIG. 32C are line graphs showing binding of hF3'-1602 TriNKET and F3-TriNKET AB0010 to Ba/F3 expressing hCLEC12A (FIG. 32A), cancer line HL60 (FIG. 32B), and wild-type Ba/F3 (FIG. 32C).

FIG. 38A-FIG. 38B are line graphs showing binding of hF3'-1602 TriNKET to cancer cell line HL60 (FIG. 38A) and PL21 (FIG. 38B).

FIG. 45A-FIG. 45H are a set of sensorgrams showing SPR profiles of hF3'-1602 TriNKET (FIG. 45A-FIG. 45D) and trastuzumab control (FIG. 45E-FIG. 45H) binding to recombinant human CD64.

FIG. 48A-FIG. 48H are a set of sensorgrams showing SPR profiles of hF3'-1602 TriNKET (FIG. 48A-FIG. 48D) and trastuzumab control (FIG. 48E-FIG. 48H) binding to human CD16a high affinity allele V158 (FcγRIIIa V158).

FIG. 52A-FIG. 52P are a set of sensorgrams showing SPR profiles of hF3'-1602 TriNKET (FIG. 52A-FIG. 52H) and trastuzumab control (FIG. 52I-FIG. 52P) binding to cynomolgus (cyno) CD16.

FIG. 53A-FIG. 53P are a set of sensorgrams showing SPR profiles of hF3'-1602 TriNKET (FIG. 53A-FIG. 53H) and trastuzumab control (FIG. 53I-FIG. 53P) binding to human FcRn as measured at pH 6.0.

FIG. 54A-FIG. 54P are a set of sensorgrams showing SPR profiles of hF3'-1602 TriNKET (FIG. 54A-FIG. 54H) and trastuzumab control (FIG. 54I-FIG. 54P) binding to cyno FcRn as measured at pH 6.0.

FIG. 56A-FIG. 56H are a set of sensorgrams showing SPR profiles of hF3'-1602 TriNKET binding to human NKG2D.

FIG. 61A-FIG. 61C shows flow cytometry based polyspecificity reagent (PSR) analysis of Rituximab (FIG. 61A), Trastuzumab (FIG. 61B), and F3'-1602 TriNKET (FIG. 61C).

FIG. 63A-FIG. 63C show models of hydrophobicity patches in hF3'-1602 TriNKET CLEC12A-binding arm.

FIG. 64A-FIG. 64E are bar graphs based on models of CDR-length (FIG. 64A), surface hydrophobicity (FIG. 64B), and surface charge (FIG. 64C-FIG. 64E) in hF3'-1602 TriNKET CLEC12A-binding arm.

FIG. 65A-FIG. 65C show models of hydrophobicity patches in hF3'-1602 TriNKET NKG2D-binding arm.

FIG. 69A-FIG. 69I are a set of flow cytometry plots demonstrating sequence liability-remediated variants of hF3'-1602 binding to hCLEC12A.

FIG. 72A and FIG. 72B represent the raw data of F3'-1602 injected over captured mFc-hNKG2D (9.77 nM to 5 μM). The black overlays represent the 1:1 kinetic fit of the raw data. FIG. 72C and FIG. 72D represent steady state response measurements plotted against the corresponding analyte concentrations. The vertical lines represent the steady state $K_D$ value.

FIGS. 77A and 77B represent the raw data of F3'-1602 injected over captured mFc-hNKG2D (9.77 nM to 5 μM). The black overlays represent the 1:1 kinetic fit of the raw data. FIGS. 77C and 77D represent steady state response measurements plotted against the corresponding analyte concentrations. The vertical lines represent the steady state $K_D$ value.

FIGS. 82A and 82B represent the raw data of F3'-1602 injected over captured mFc-hNKG2D (9.77 nM to 5 μM). The black overlays represent the 1:1 kinetic fit of the raw data. FIGS. 82C and 82D represent steady state response measurements plotted against the corresponding analyte concentrations. The vertical lines represent the steady state $K_D$ value.

FIG. 89A and FIG. 89B represent the raw data of F3'-1602 injected over captured mFc-hNKG2D (9.77 nM to 5 μM). The black overlays represent the 1:1 kinetic fit of the raw data. FIGS. 89C and 89D represent steady state response measurements plotted against the corresponding analyte concentrations. The vertical lines represent the steady state $K_D$ value.

FIGS. 90A and 90C represent the raw data of F3'-1602 injected over captured mFc-hNKG2D (9.77 nM to 5 μM). The black overlays represent the 1:1 kinetic fit of the raw data. FIGS. 90B and 90D represent steady state response measurements plotted against the corresponding analyte concentrations. The vertical lines represent the steady state $K_D$ value.

FIG. 94A and FIG. 94C represent the raw data of F3'-1602 injected over captured mFc-hNKG2D (9.77 nM to 5 μM). The black overlays represent the 1:1 kinetic fit of the raw data. FIG. 94B and FIG. 94D represent steady state response measurements plotted against the corresponding analyte concentrations. The vertical lines represent the steady state $K_D$ value.

FIG. 95 is a graph showing the percentage lysis of PL21 cells by NKG2D- and CD16a-expressing KHYG-1-CD16a cells in the presence of F3'-1602 after forced oxidation stress.

FIG. 97A and FIG. 97C represent the raw data of F3'-1602 injected over captured mFc-hNKG2D (9.77 nM to 5 μM). The black overlays represent the 1:1 kinetic fit of the raw data. FIG. 97B and FIG. 97D represent steady state response measurements plotted against the corresponding analyte concentrations. The vertical lines represent the steady state $K_D$ value.

FIG. 103A: Substitution of pET1596 scFv CDRH3 with BamHI restriction enzyme site. FIG. 103B: Insertion of CDRH3 mutated library oligos at the previously introduced BamHI restriction site. FIG. 103C: Electroporation of BamHI linearized plasmid and library oligos into yeast followed by homologous recombination in yeast.

FIG. 104A-FIG. 104D represent results of CLEC12A binding by surface plasmon resonance (SPR). FIG. 104E-FIG. 104H represent binding to CLEC12A+ PL-21 AML cancer cells. Binding affinities and EC50 for each variant are indicated. BM, backmutation.

FIG. 105A-FIG. 105E shows FACS analysis of CDRH3 yeast library 17. First round of selection of affinity maturating yeast display library sorted at 1 nM CLEC12A-His (FIG. 105A). Second round of selection sorted at 1 nM CLEC12A-His (FIG. 105B). Third round of selection sorted at 0.1 nM CLEC12A-His (FIG. 105C). Binding of library 17-R3 displayed on yeast cells to 1 nM CLEC12A (FIG. 105D). Binding of original clone pET1596 displayed on yeast cells at 10 nM CLEC12A (FIG. 105E).

FIG. 107A-FIG. 107D is a comparison of the improved affinity clone (FIGS. 107A and 107D) identified from Library 30 to pET1596 (FIGS. 107B and 107D) and AB0237 (FIGS. 107C and 107D).

FIG. 109A-FIG. 109C is an X-ray crystal structure of EW-RVT Fc heterodimer. Superposition of the overall structure of the EW-RVT Fc heterodimer with the human wild-type (WT) IgG1 Fc homodimer (PDB ID: 3AVE) (FIG. 109A). Close-up view of W-VT interaction pair regions (FIG. 109B). Close-up view of the E-R interaction pair regions (FIG. 109C).

FIG. 111A-FIG. 111C show a ribbon diagram model of the CLEC12A binding scFv in three different orientations (upper panel) and their corresponding surface charge distribution of the same orientation (lower panel). Three orientations are shown: both façades (FIG. 111A: front view; FIG. 111B: back view) and the antigen-engaging surface (FIG. 111C: top view).

FIG. 112A-FIG. 112B show the analyses of CDR length (FIG. 112A) and surface hydrophobicity patches (FIG. 112B) of the CLEC12A-targeting arm of AB0089. The arrow points to the line where CLEC12A targeting scFv of AB0089 stands in reference to advanced clinical stage mAbs. The two inner dotted lines indicate 2 SD (>95% of reference molecules within this region). The two outer most dotted lines indicate 3 SD (>99.7% of reference molecules within this region).

FIG. 114A-FIG. 114C show NKG2D-binding Fab with ribbon diagrams of three different orientations: both façades (FIG. 114A: front view; FIG. 114B: back view) and the antigen-engaging surface (FIG. 114C: top view).

FIG. 116A-FIG. 116C show the analyses of the CDR length (FIG. 116A) patches of surface hydrophobicity (FIG. 116B) and patches of negative charge (FIG. 116C) of NKG2D targeting arm of AB0089. The arrows indicate the position of the NKG2D targeting arm of AB0089 in reference to a database of 377 late-stage therapeutic antibodies. In each plot, there are two dashed lines—one closer and the other further to the solid line. The dashed line closer to the solid line indicates 2 SD (>95% of reference molecules within this region), whereas the dashed line further to the solid line indicates 3 SD (>99.7% of reference molecules within this region).

FIG. 121 shows a SEC analysis of Protein A eluate, pH-adjusted and filtered for IEX loading.

Figure 122:
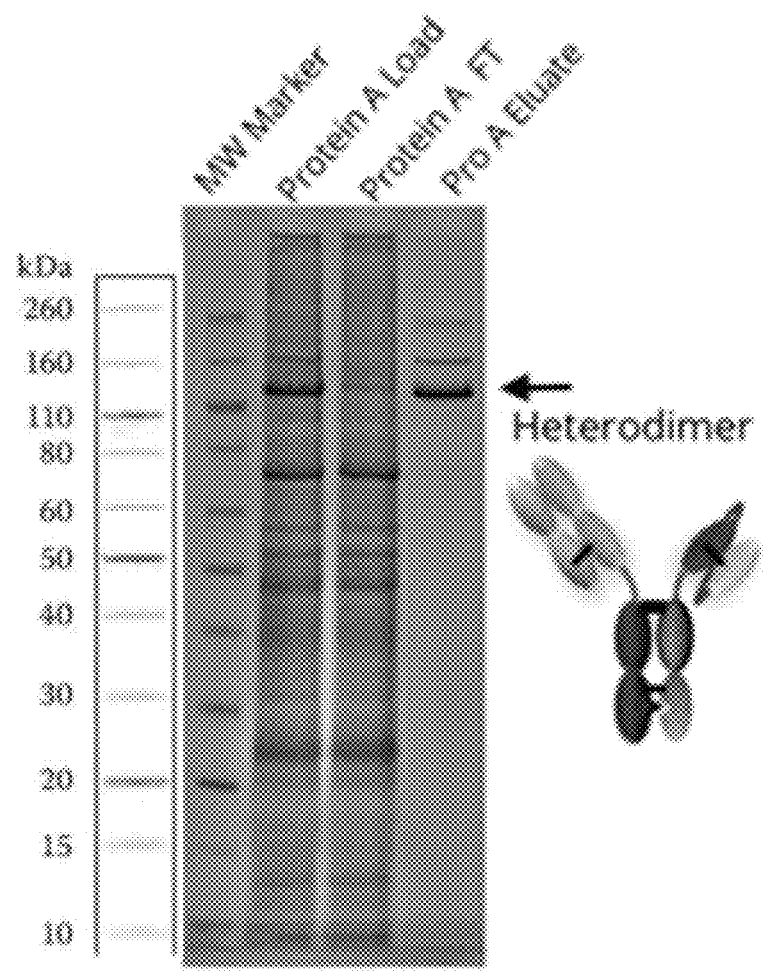

FIG. 122 shows a SDS-PAGE analysis of AB0089 Protein A load, flow through, and eluate. Based on absorbance readings, 15 μl was loaded in the "Protein A load" and "Protein A FT" lanes, 2 μg was loaded in the "Protein A Eluate lane". The major band at ~120 kDa corresponds to AB0089.

Figure 123:
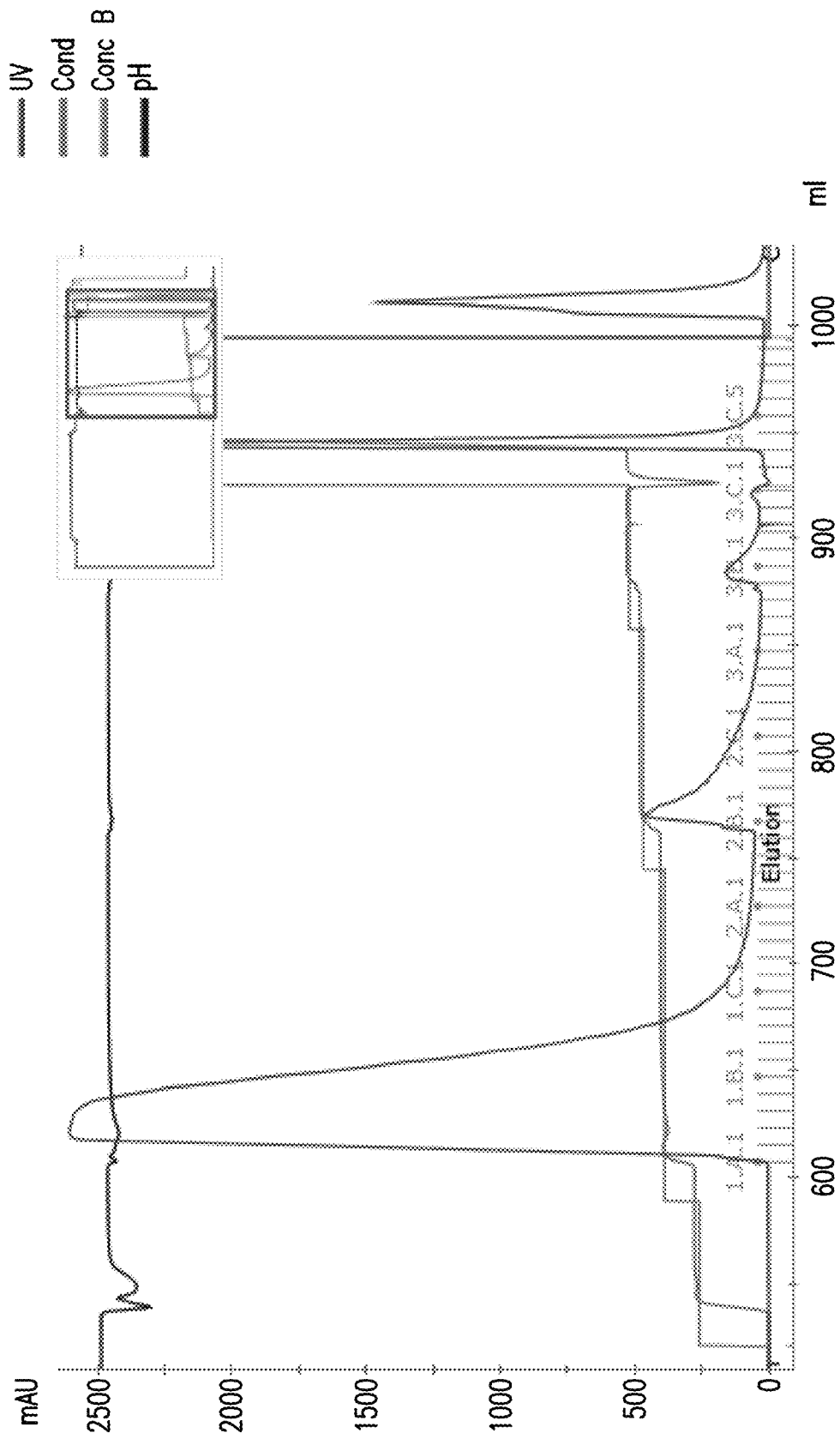

FIG. 123 shows a Poros XS cation exchange chromatogram.

Figure 124:
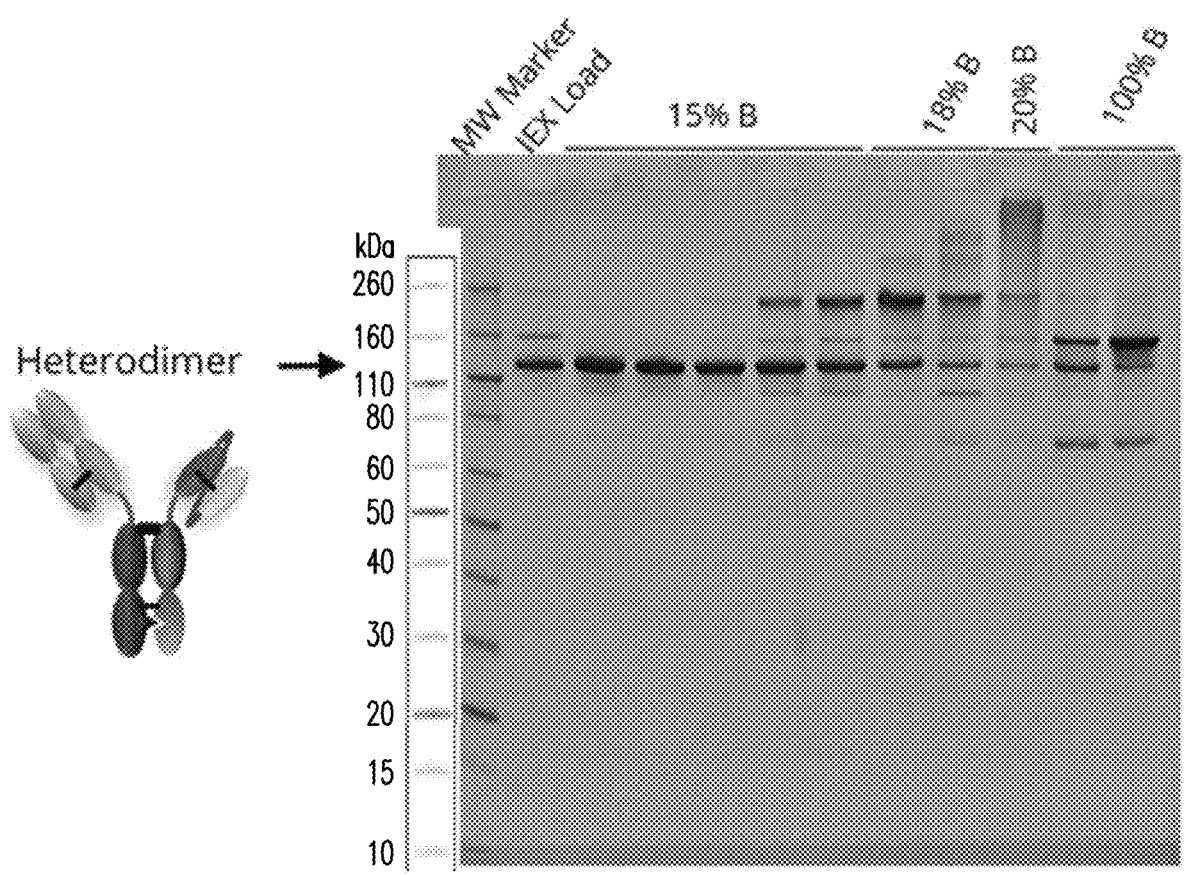

FIG. 124 shows a SDS-PAGE analysis of AB0089 CIEX load and elution fractions. Based on absorbance readings, lanes contain ~2.0 μg of protein. The major band at ~120 kDa is AB0089.

Figure 125:
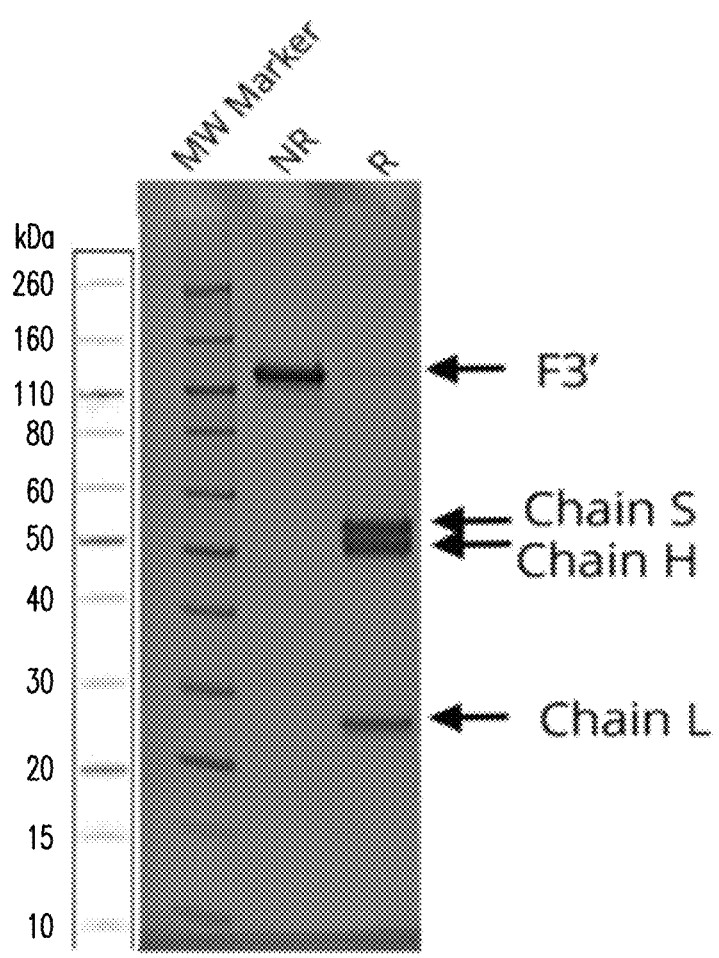

FIG. 125 shows reduced ("R") and non-reduced ("NR") SDS-PAGE of AB0089 Lot AB0089-002. The three chains (S, H, and L) of the molecule are labeled in the R lane. F3' in the NR lane refers to AB0089.

Figure 126:
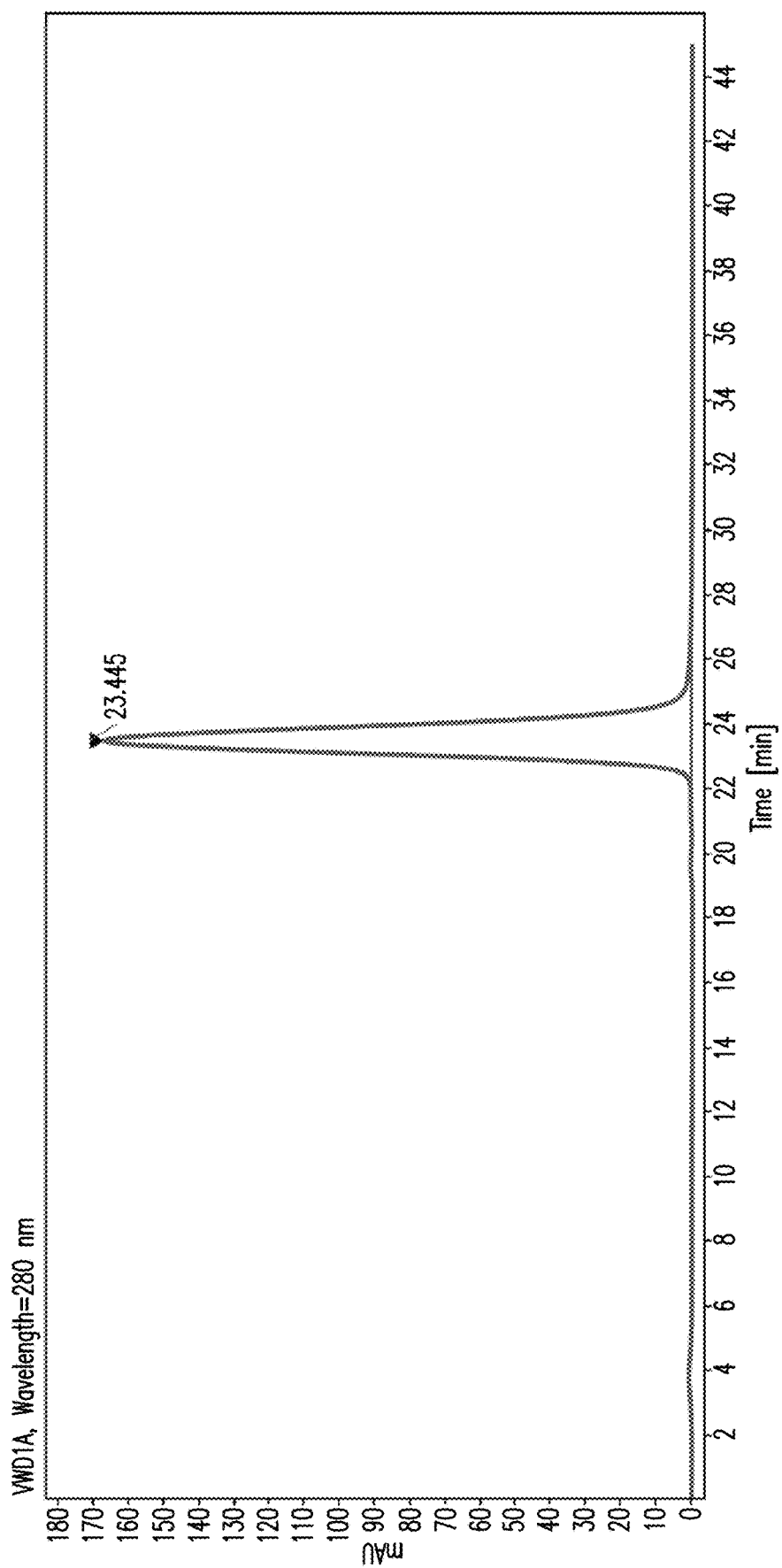

FIG. 126 shows SEC analysis of purified AB0089 lot AB0089-002 and indicates 100% monomer as determined by integrated peak area.

Figure 127:
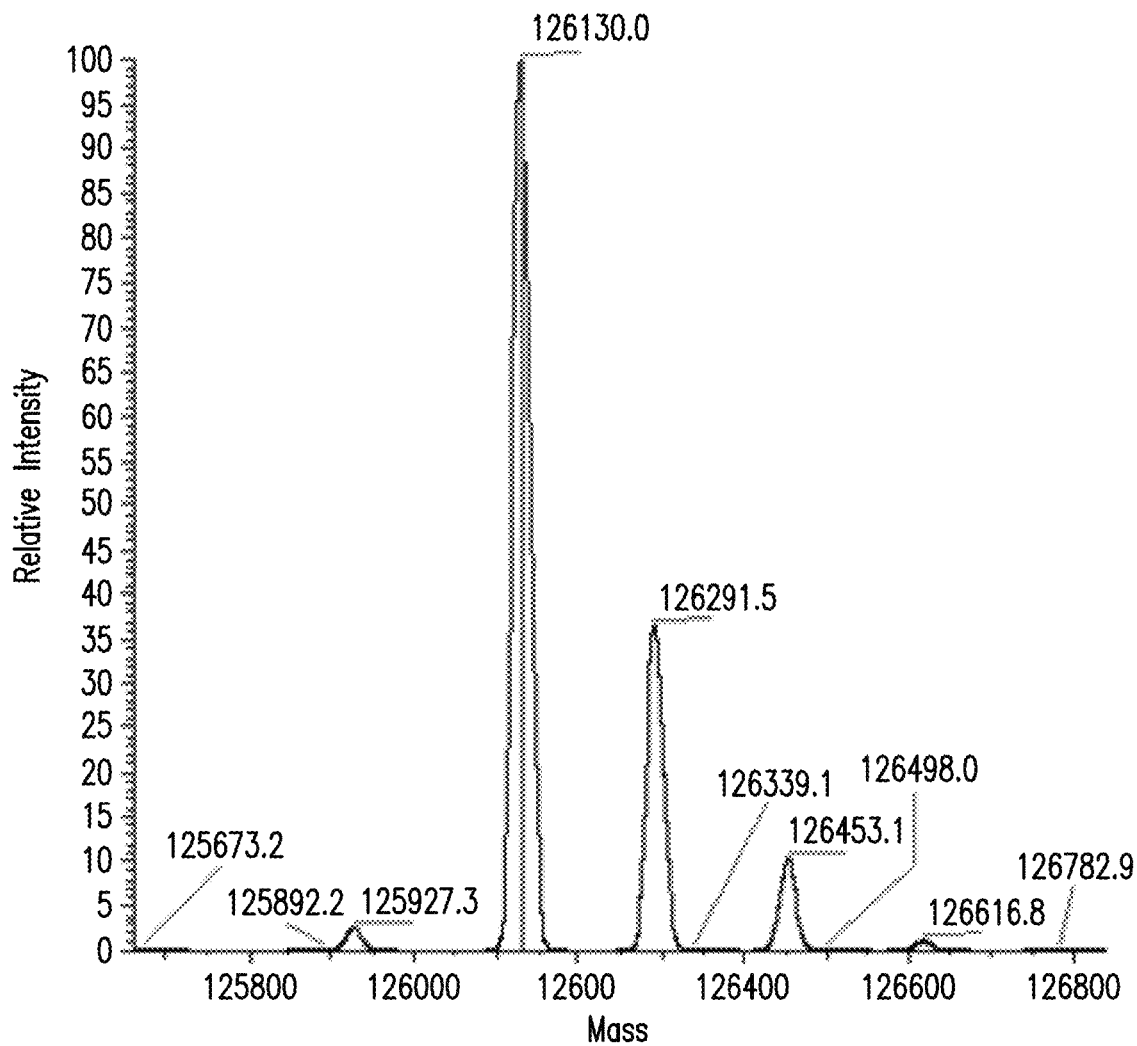

FIG. 127 shows intact mass spectrometry analysis of AB0089 lot AB0089-002. LC-MS analysis of the intact AB0089 showed an observed mass (126,130.0 Da) that agrees well with the theoretical mass of 126,129.1 Da.

Figure 128A:
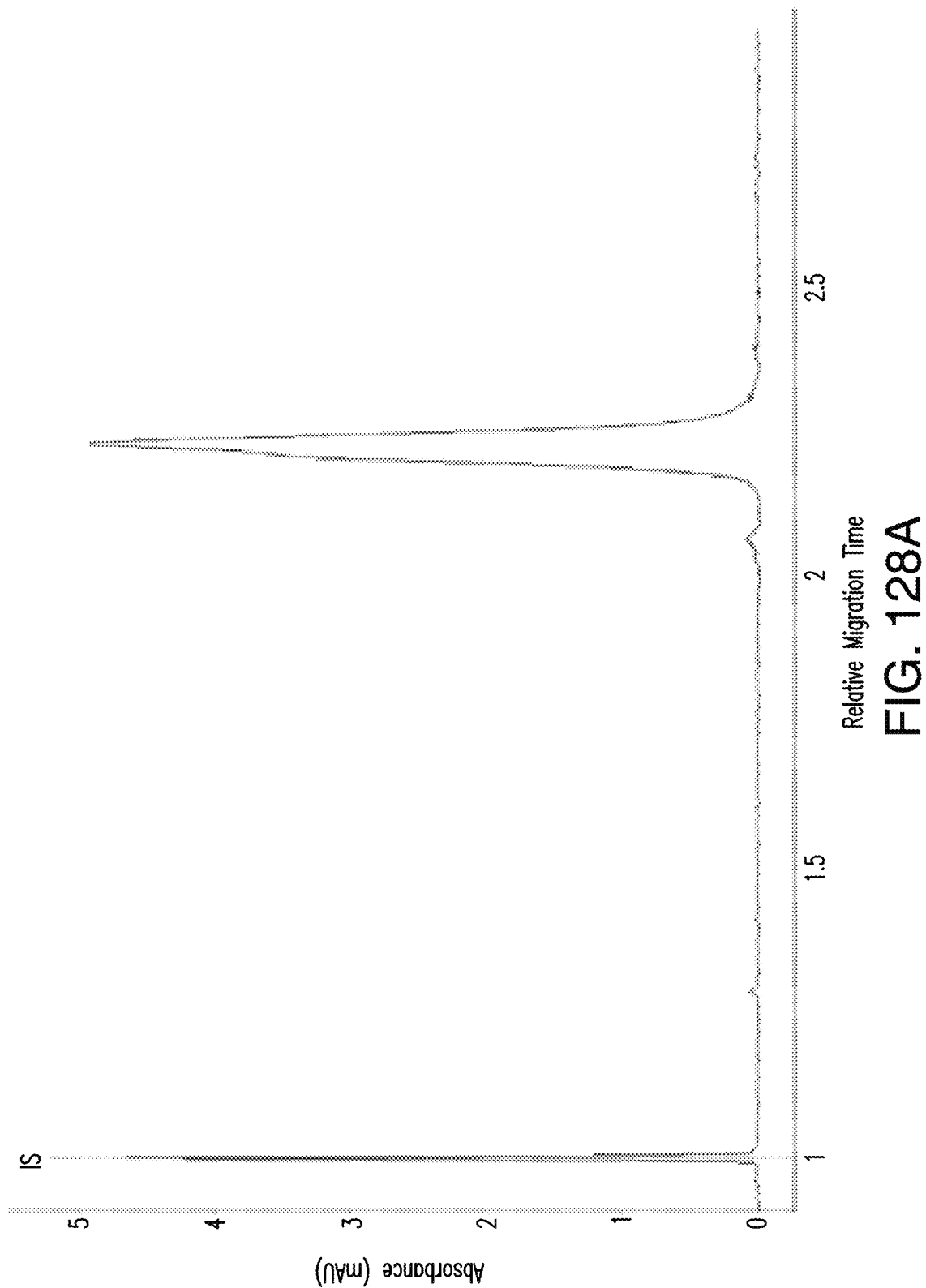
Figure 128B:
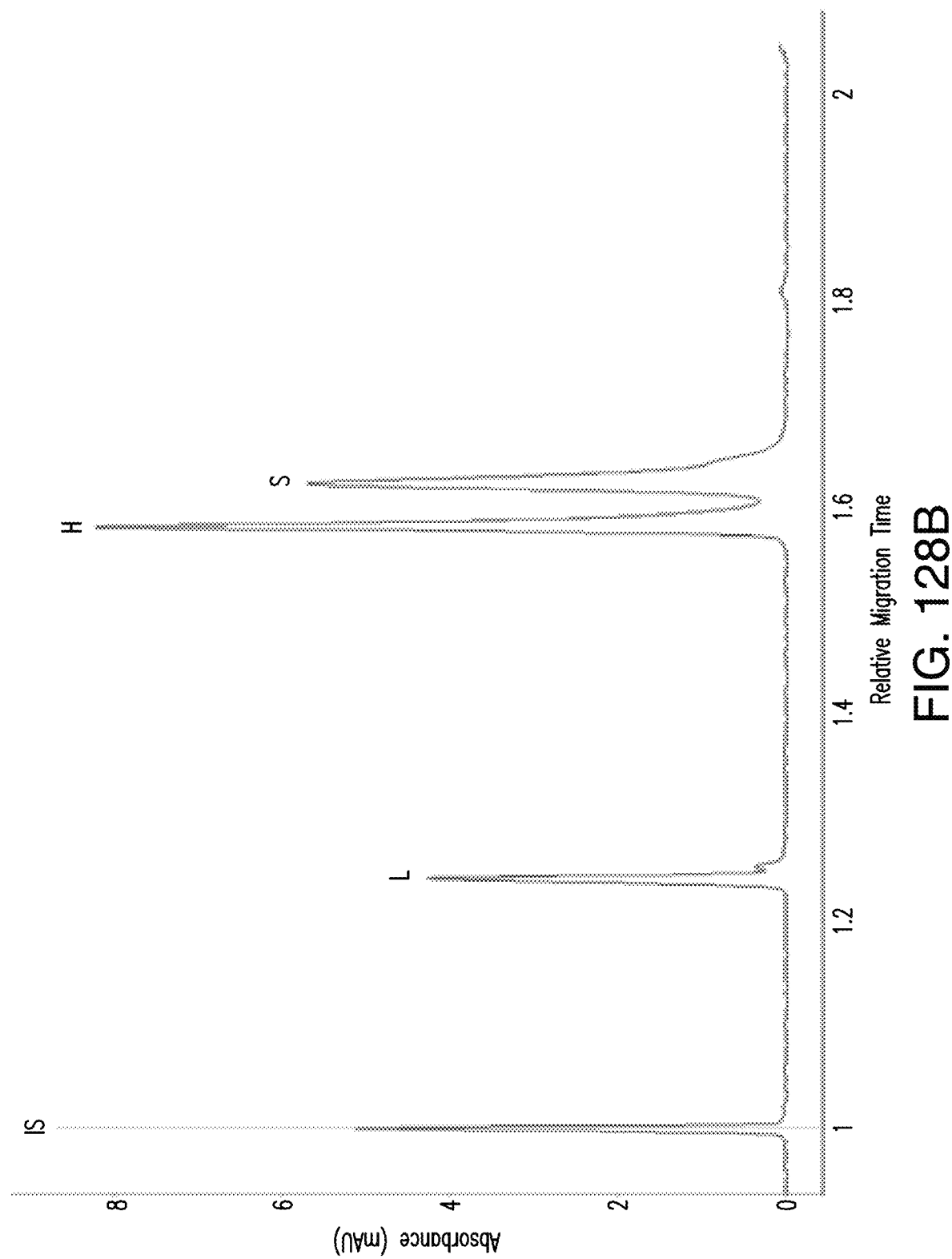

FIG. 128A-FIG. 128B show CE-SDS analysis of AB0089, R (FIG. 128A) and NR (FIG. 128B) CE-SDS analysis of AB0089.

Figure 129:
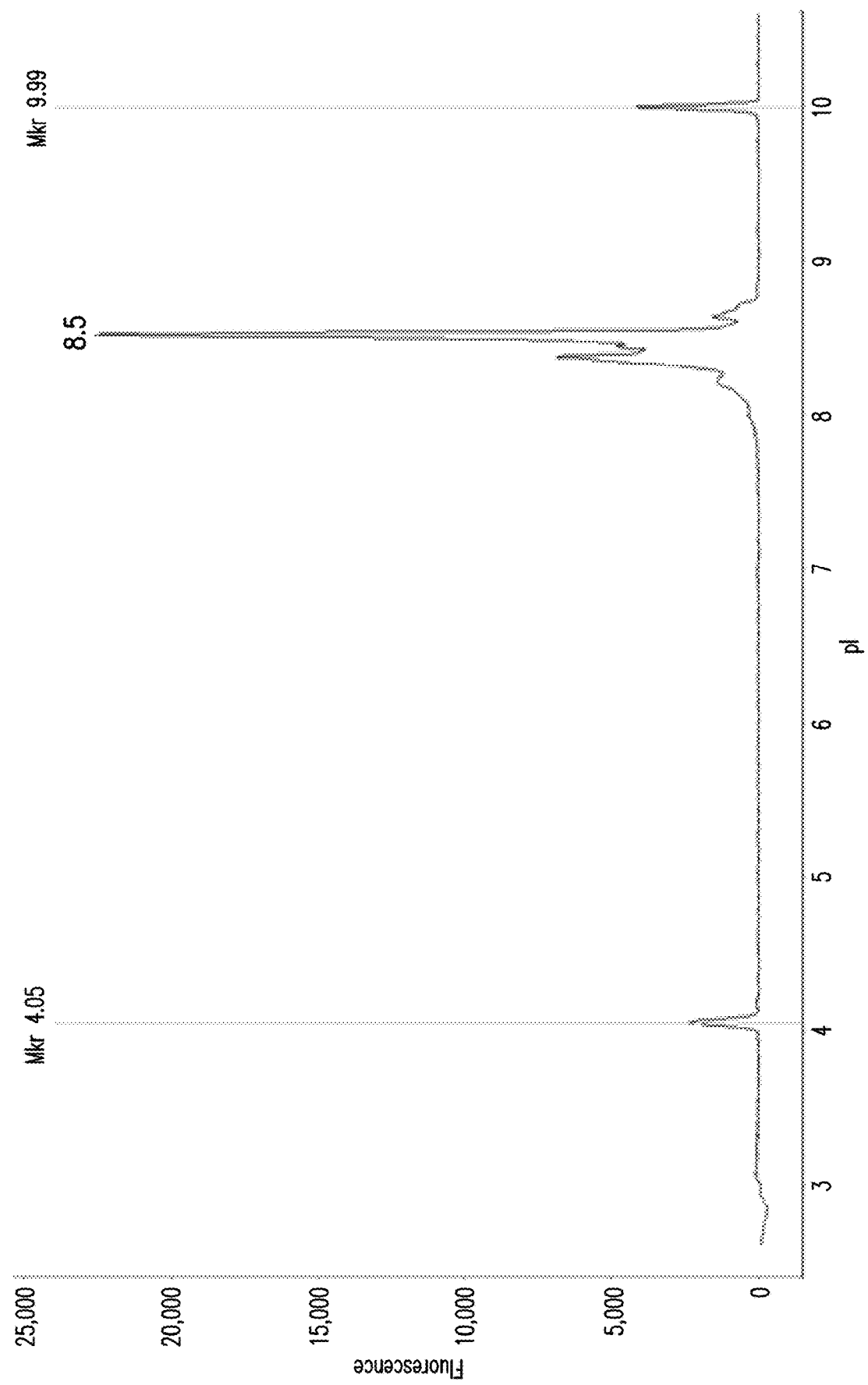

FIG. 129 shows a charge profile of AB0089 by cIEF, indicating that AB0089 showed a major peak at a pI of 8.52±0.0

Figure 130:
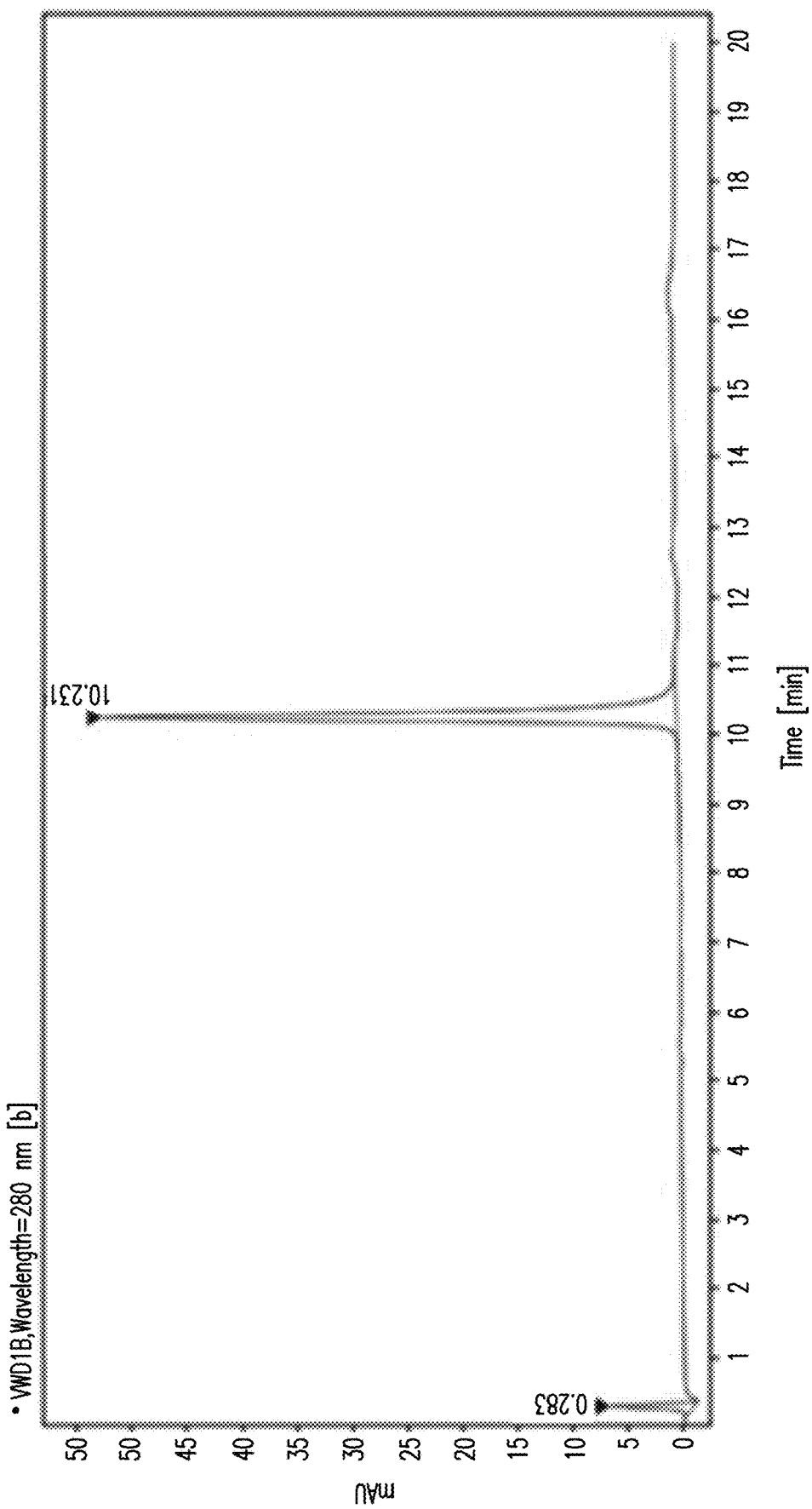

FIG. 130 shows a chromatogram of the hydrophobicity analysis of AB0089 by HIC, indicating that AB0089 is highly pure and homogenous.

Figure 131A:
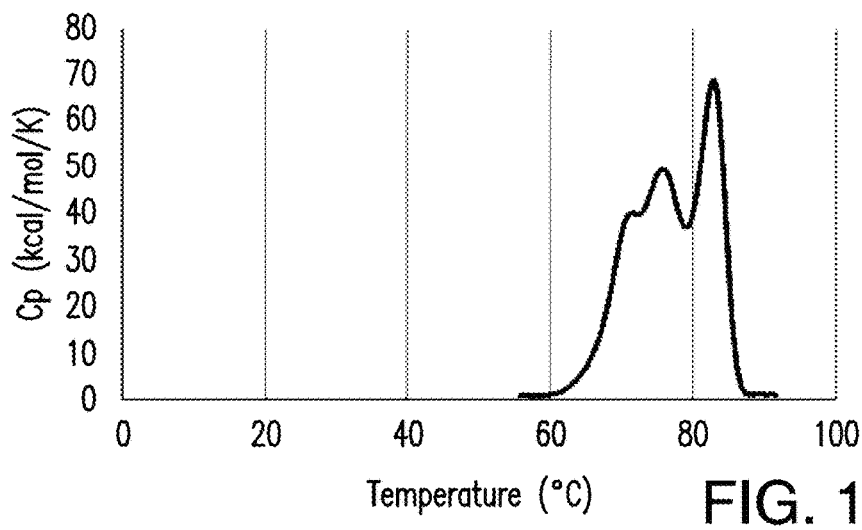
Figure 131B:
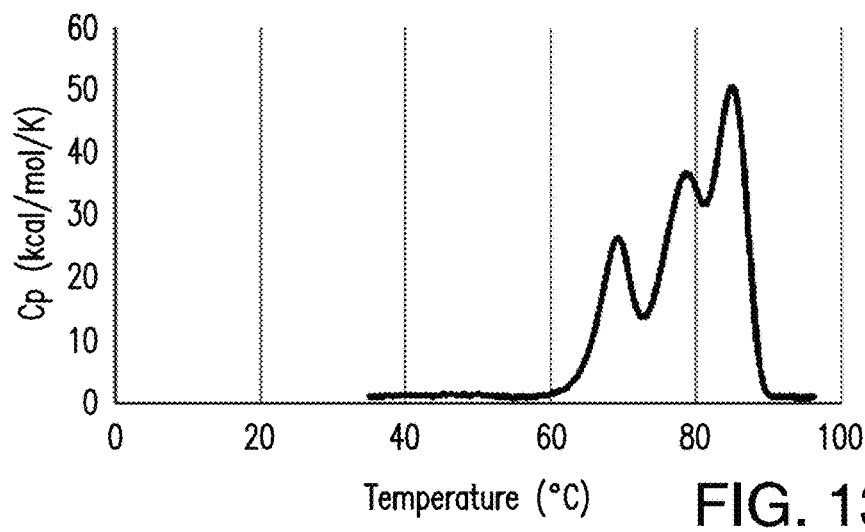
Figure 131C:
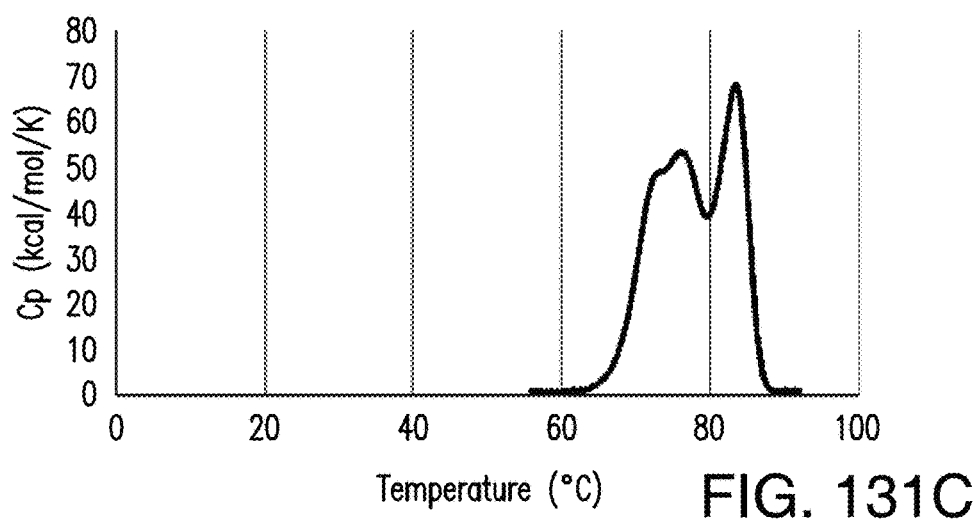

FIG. 131A-FIG. 131C shows the thermal stability of AB0089 as assessed by DSC analysis in three different formulations: PBS pH 7.4 (FIG. 131A), HST pH 6.0 (FIG. 131B), and CST, pH 7.0 (FIG. 131C).

Figure 132:
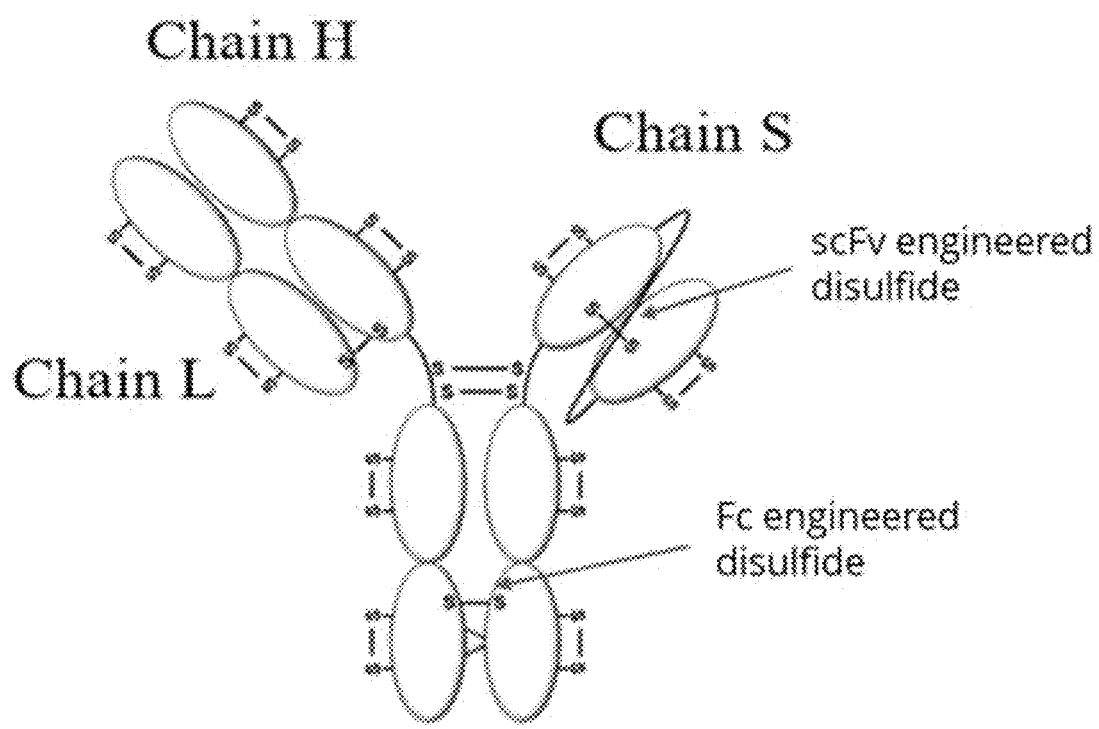

FIG. 132 shows a predicted disulfide map of AB0089.

FIG. 133A-FIG. 133B show the extracted ion chromatogram (XICs) for the engineered disulfide pair in the scFv (non-reduced and reduced; FIG. 133A) and the most intense charge state for that peptide pair (FIG. 133B).

Figure 134A:
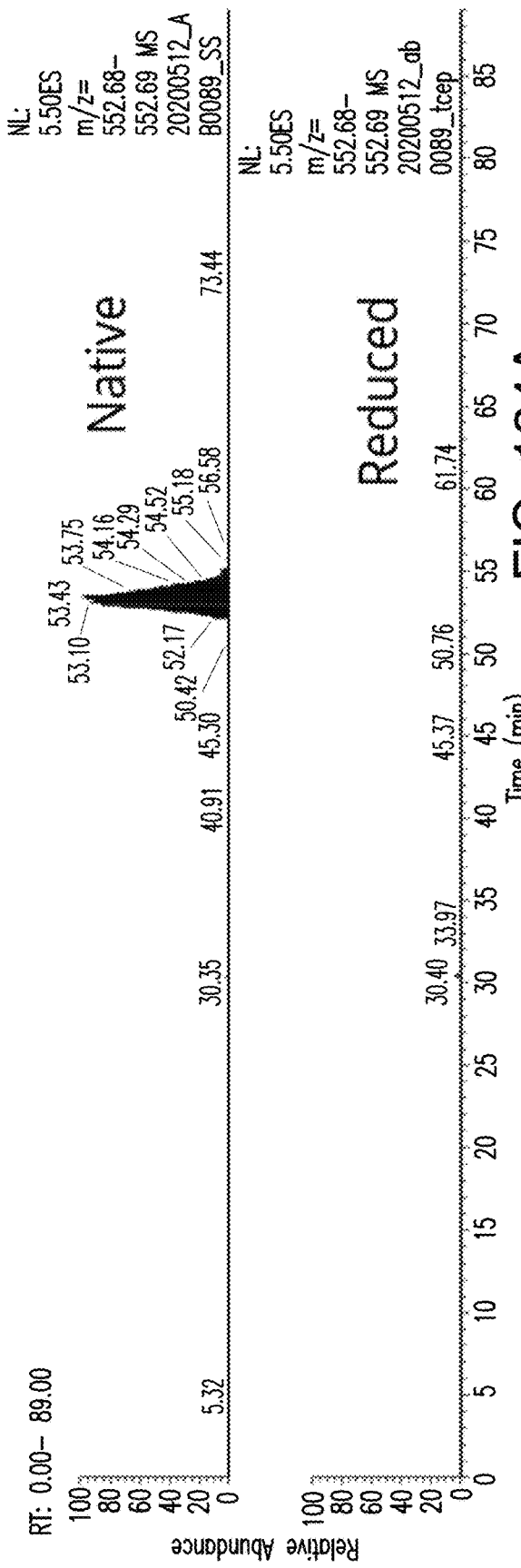
Figure 134B:
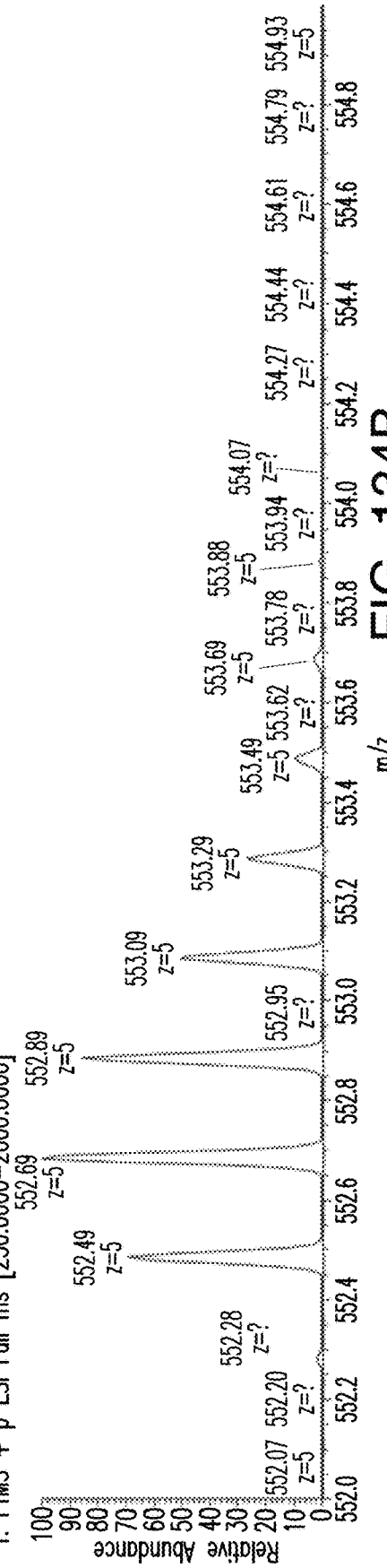
Figure 135A:
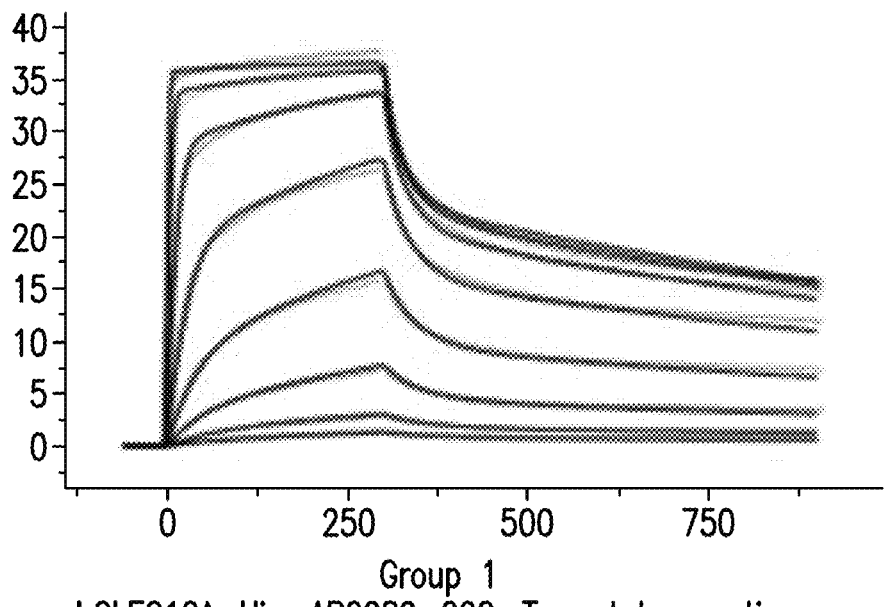
Figure 135B:
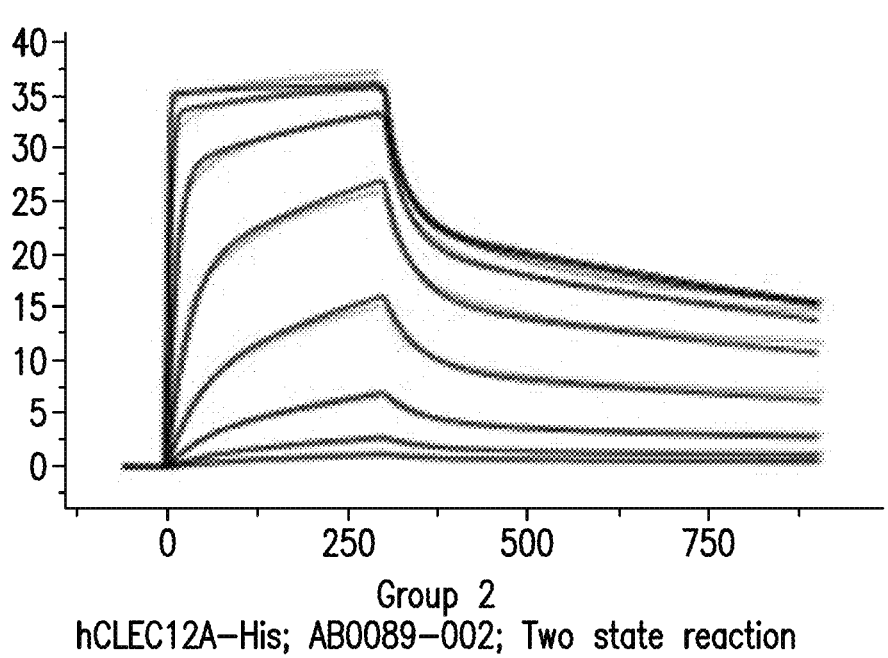
Figure 135C:
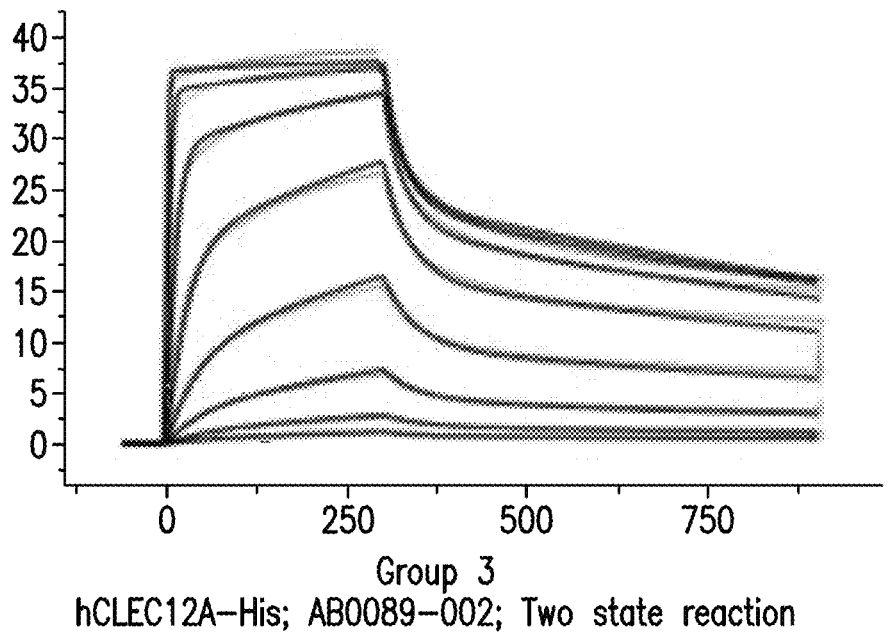
Figure 135D:
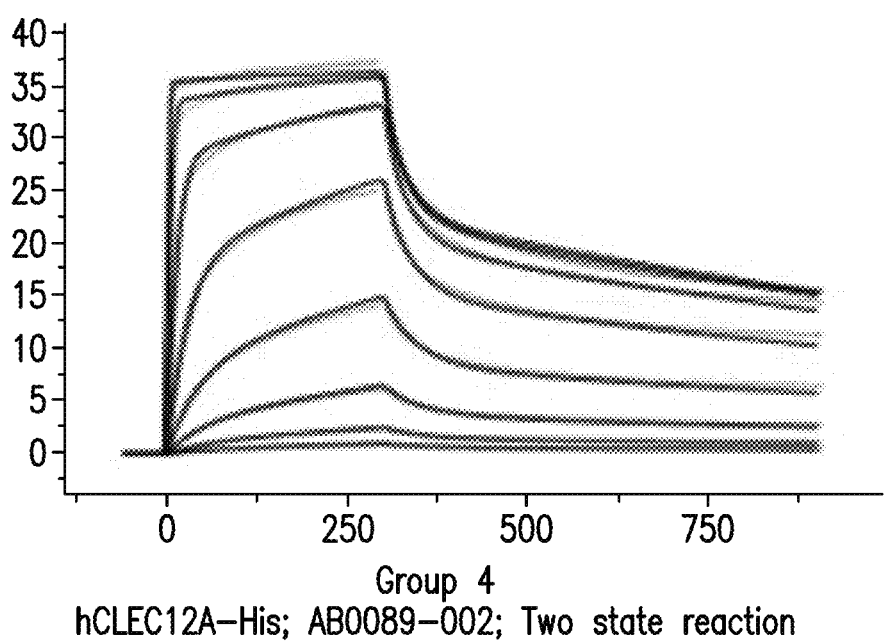

FIG. 134A-FIG. 134B show identification of CH3-CH3 intermolecular Fc engineered disulfide.

FIG. 135A-FIG. 135D show binding of human CLEC12A to AB0089 tested by SPR.

Figure 136B:
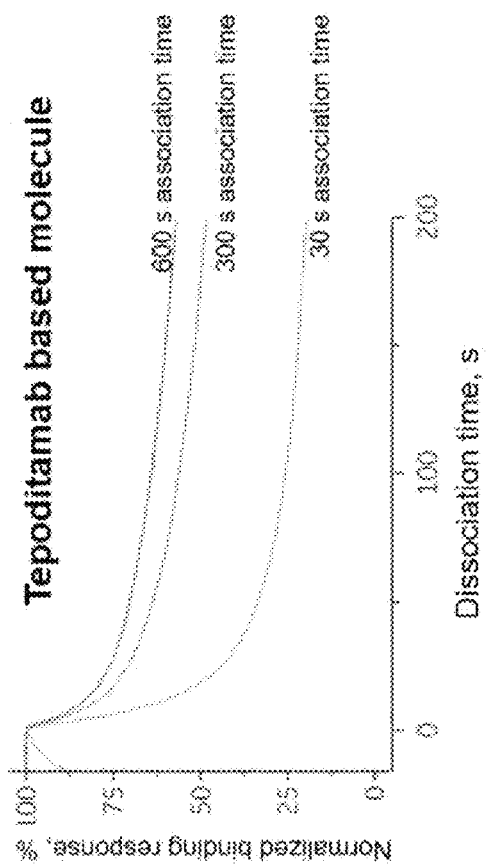
Figure 136A:
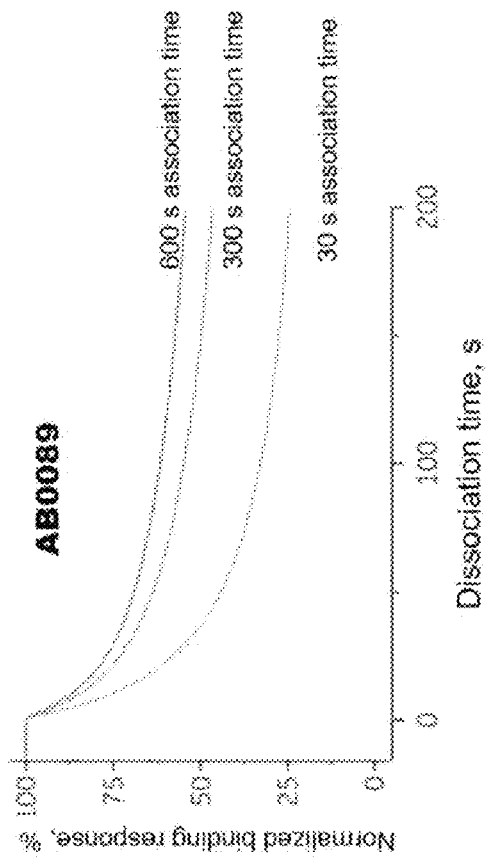

FIG. 136A-FIG. 136B show that AB0089 (FIG. 136A) and tepoditamab (FIG. 136B) based molecule binding of CLEC12A conforms to a two-state model.

FIG. 137A-FIG. 137D show FACS assessment of AB0089 binding to isogenic cell lines expressing CLEC12A, and AML cancer cell lines (PL-21 and HL-60).

Figure 138A:
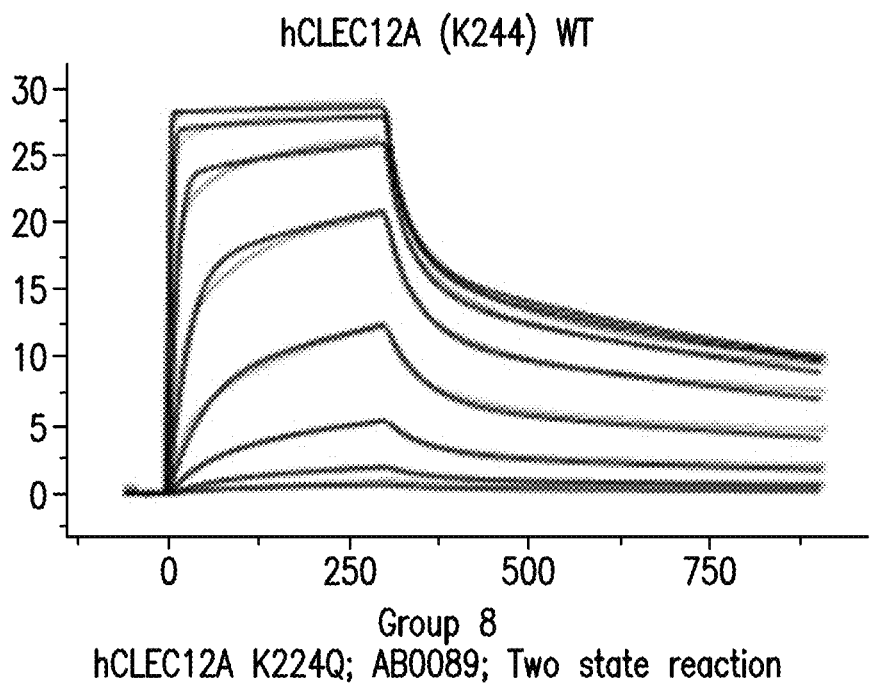
Figure 138B:
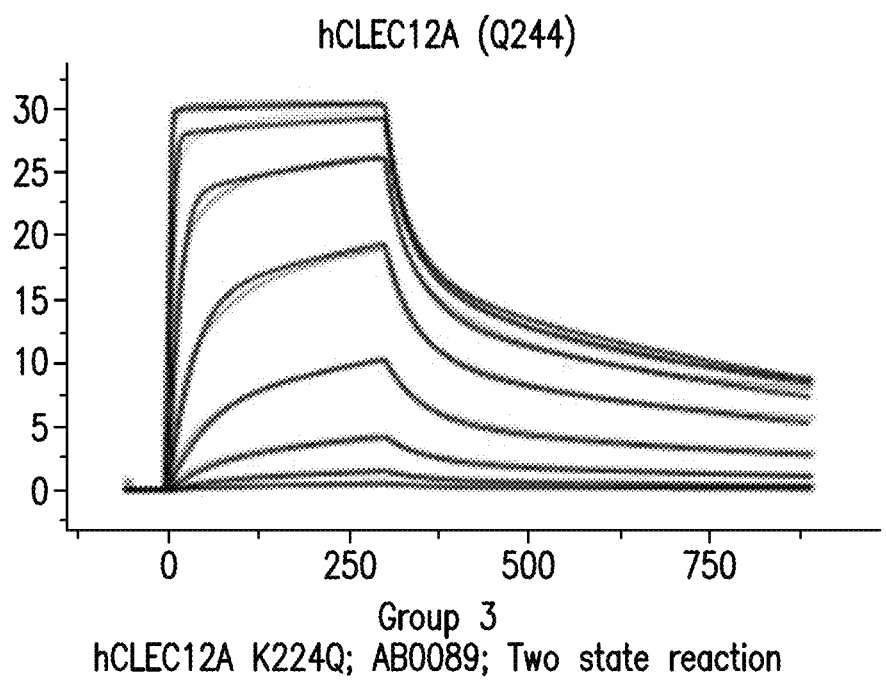
Figure 138C:
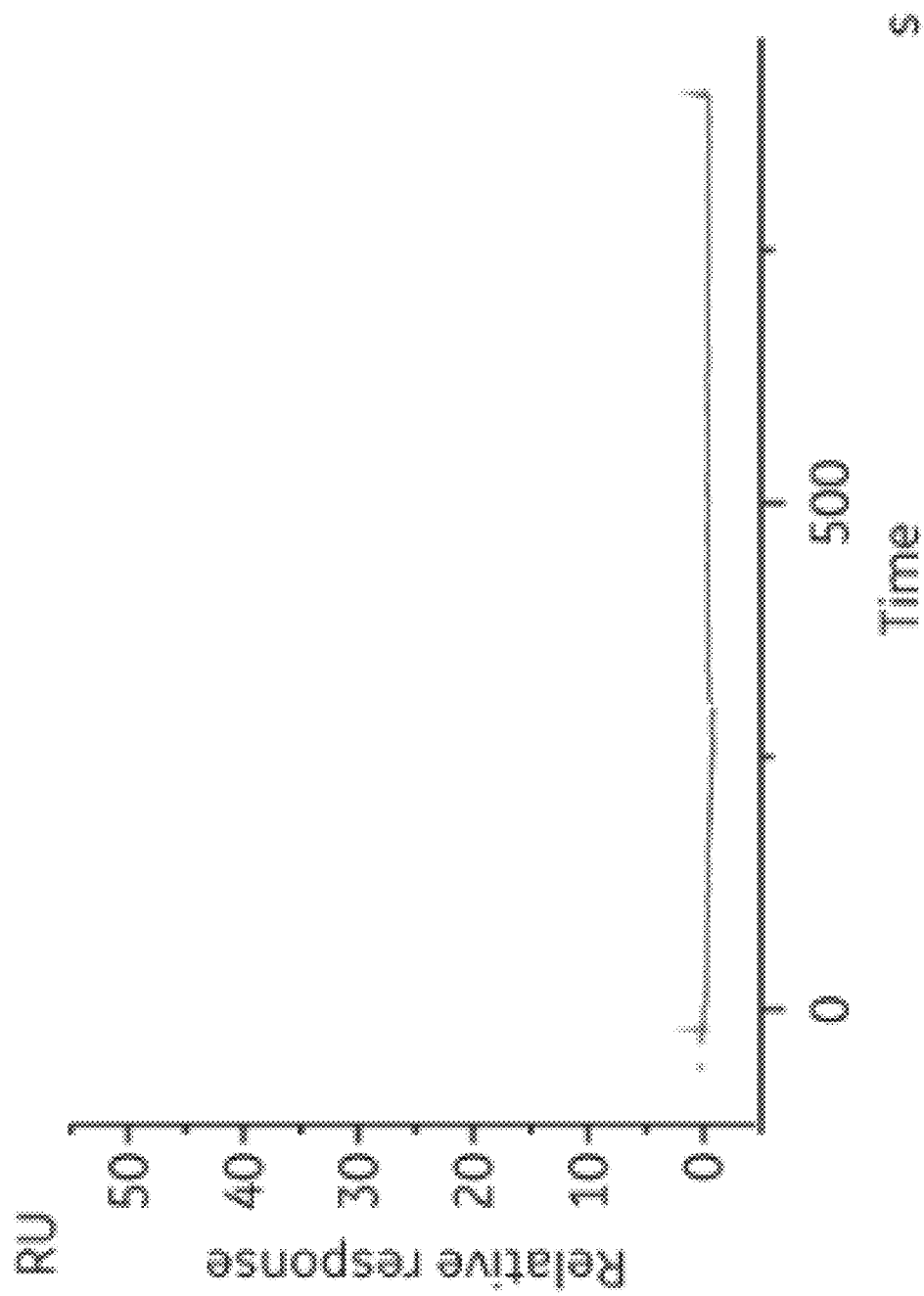

FIG. 138A-FIG. 138C show binding of AB0089 to a genetic variant CLEC12A (Q244) (FIG. 138B) compared to CLEC12A (K244) WT (FIG. 138A) and cyno CLEC12A (cCLEC12A) (FIG. 138C).

Figure 139A:
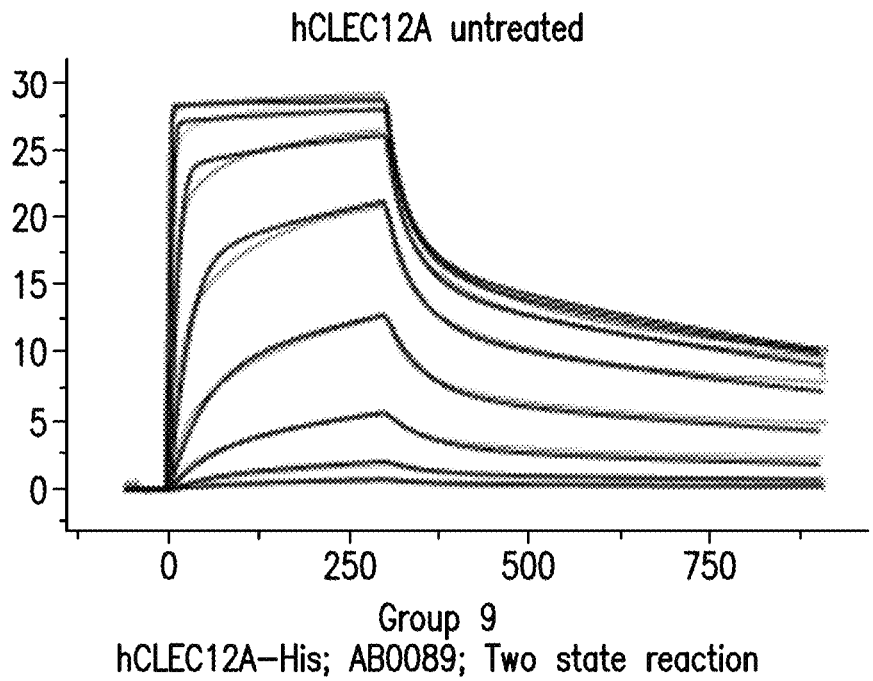
Figure 139B:
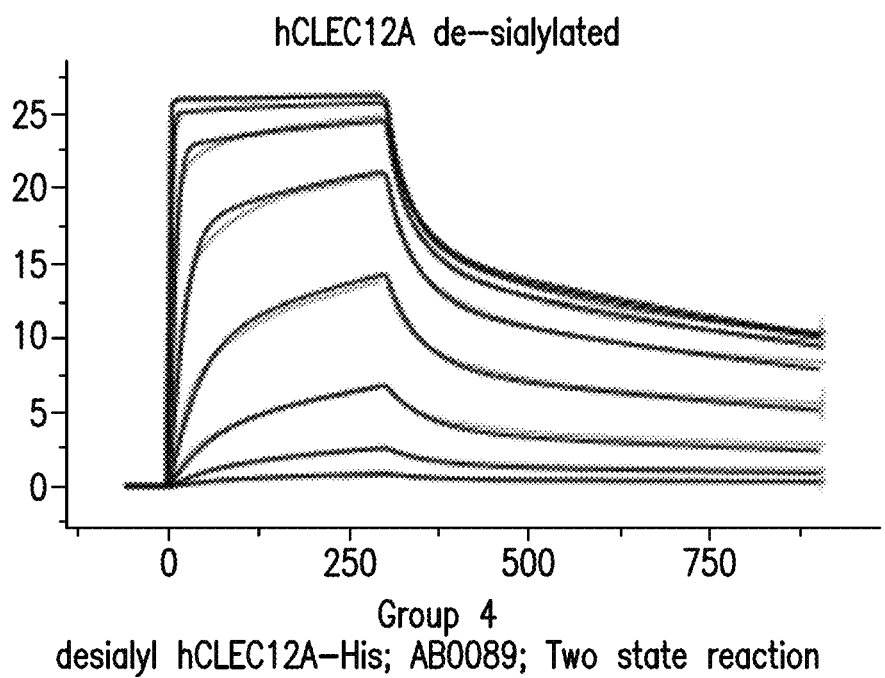
Figure 139C:
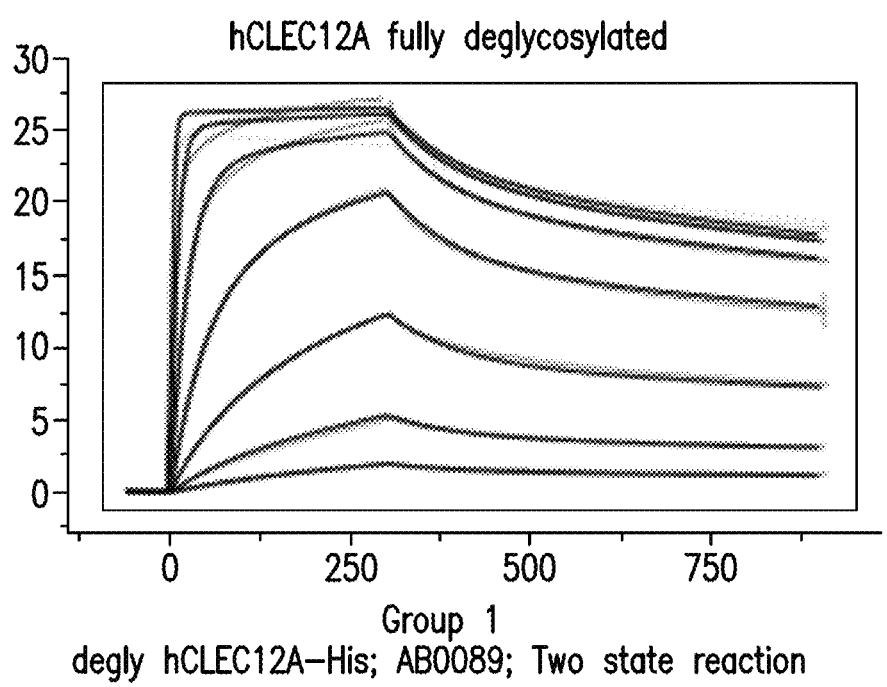

FIG. 139A-FIG. 139C show AB0089 binding to differentially glycosylated CLEC12A: hCLEC12A untreated (FIG. 139A), hCLEC12A de-sialylated (FIG. 139B) and hCLEC12A fully deglycosylated (FIG. 139C).

Figure 140A:
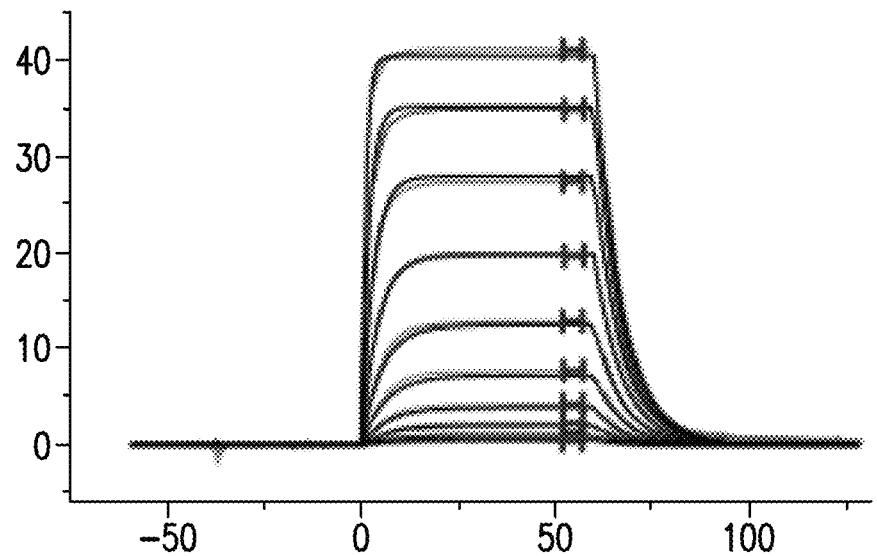
Figure 140B:
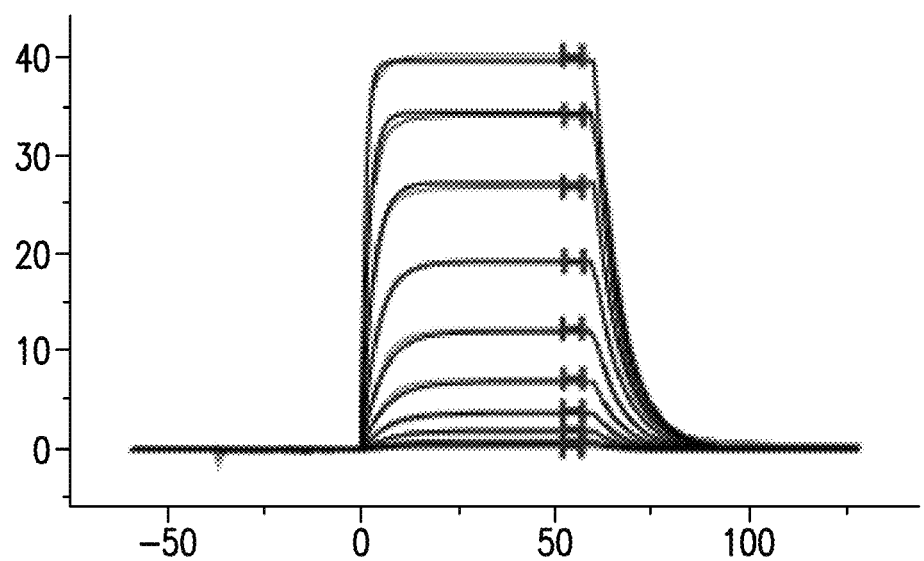
Figure 140C:
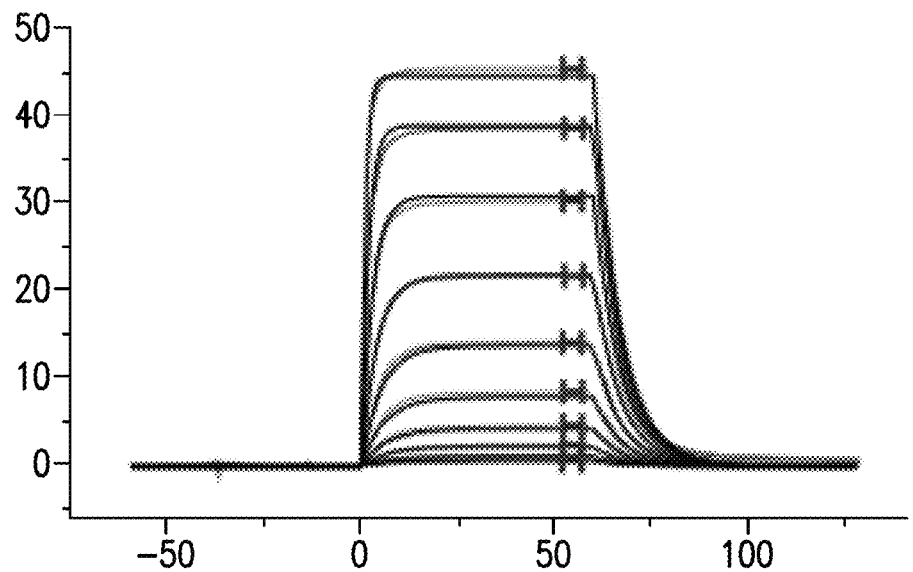
Figure 140D:
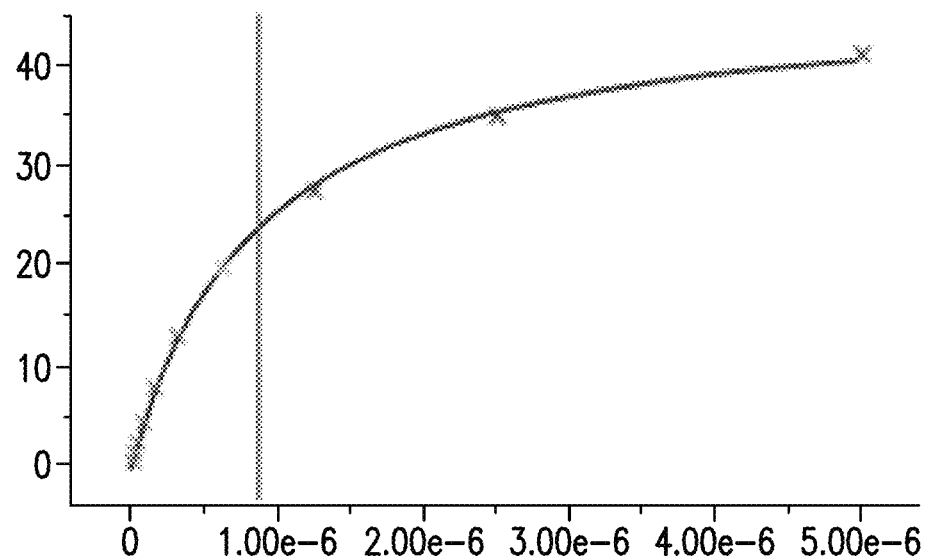
Figure 140E:
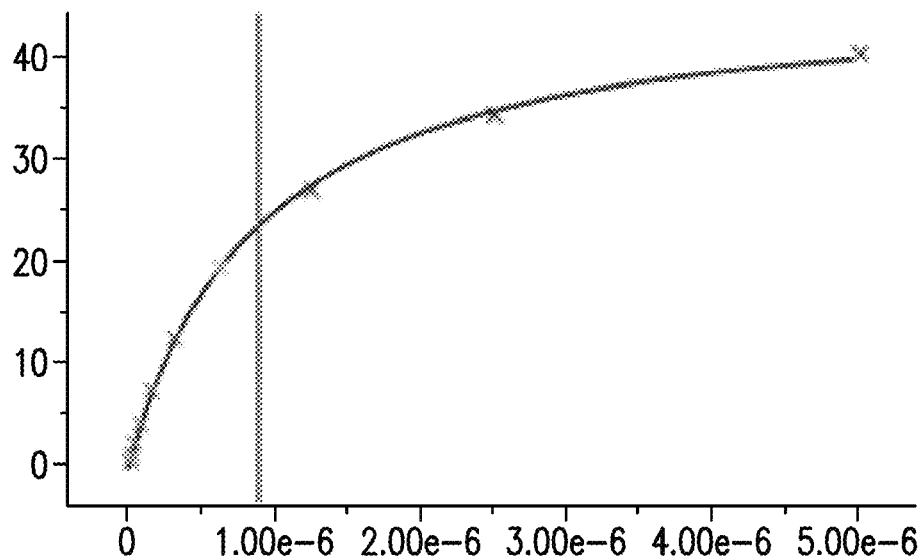
Figure 140F:
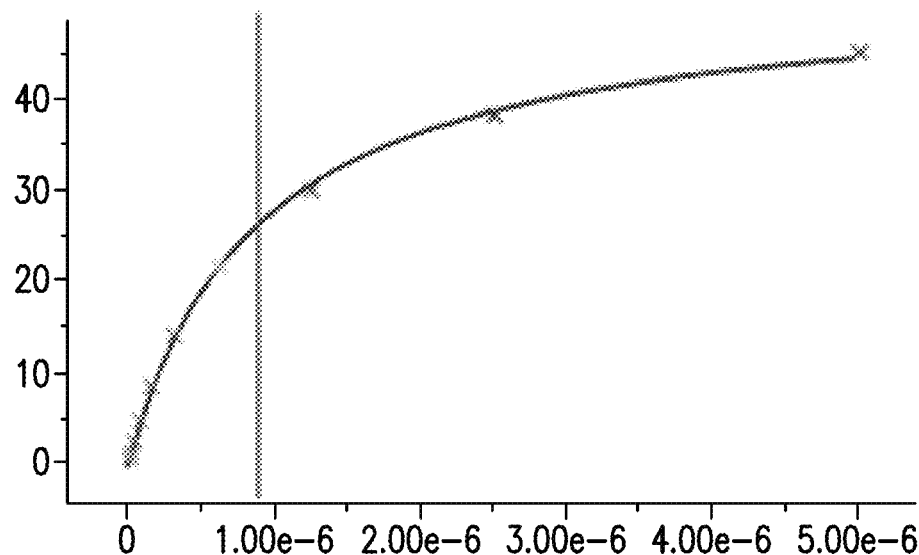
Figure 141A:
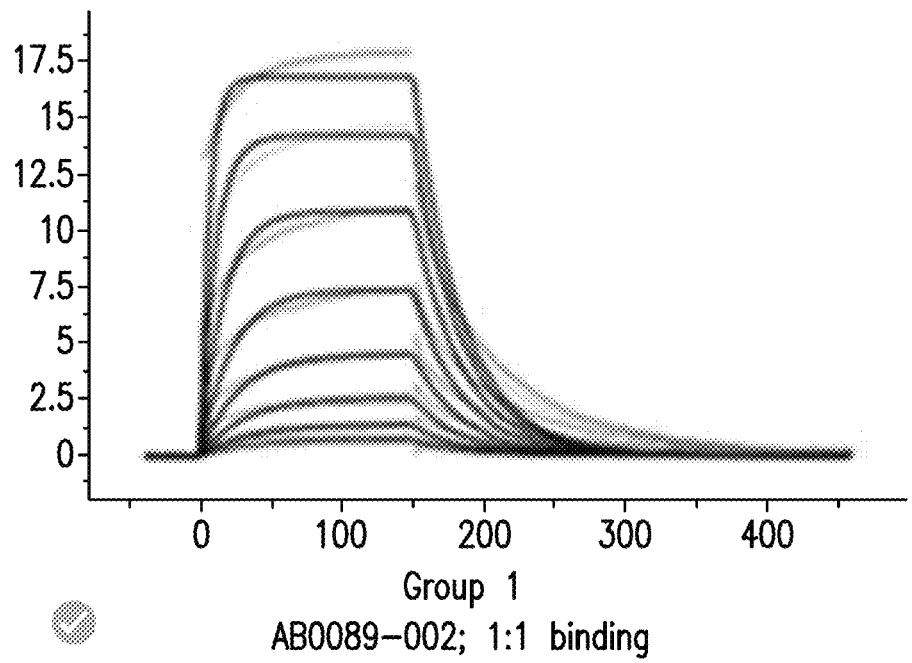
Figure 141B:
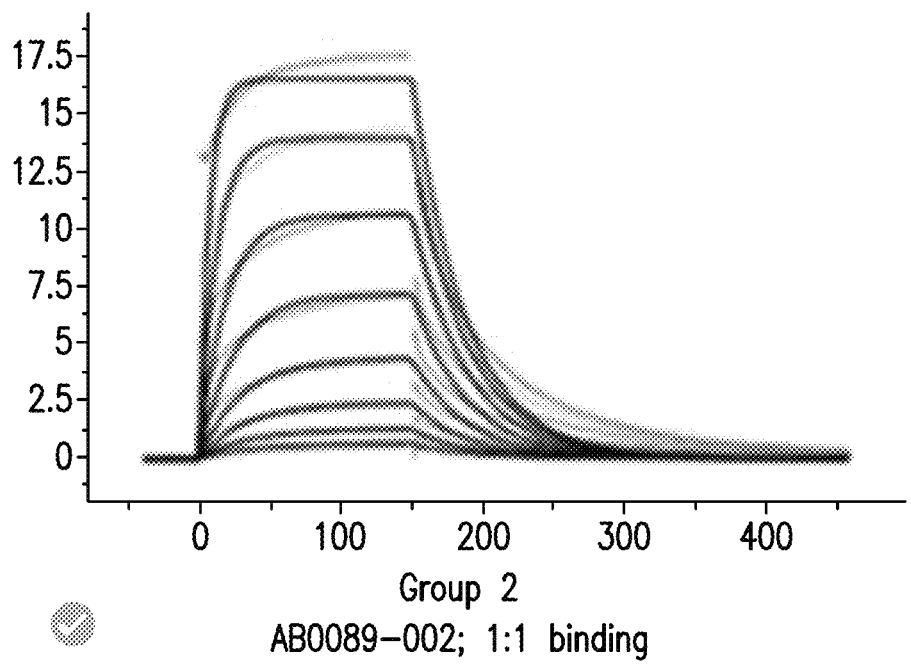
Figure 141C:
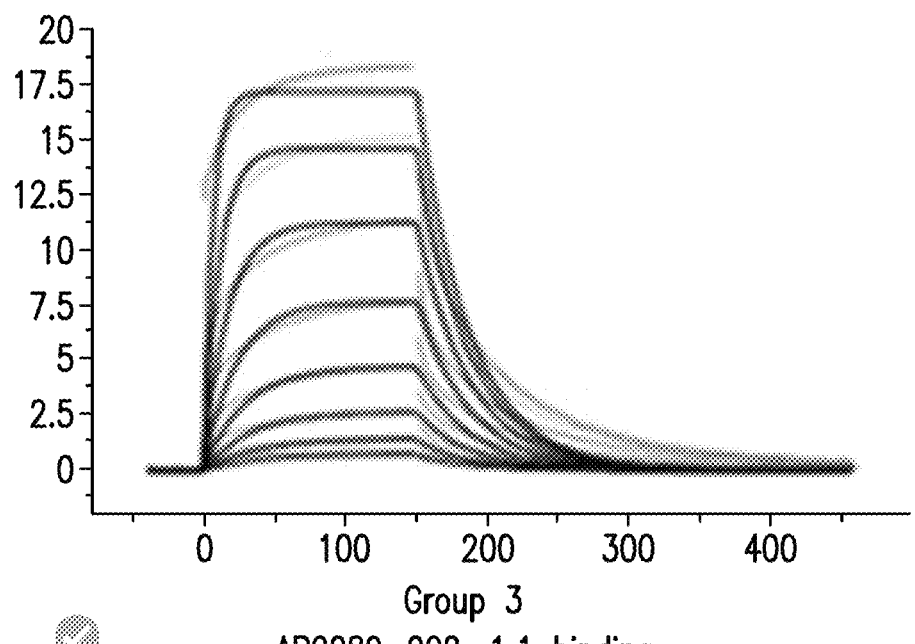
Figure 141D:
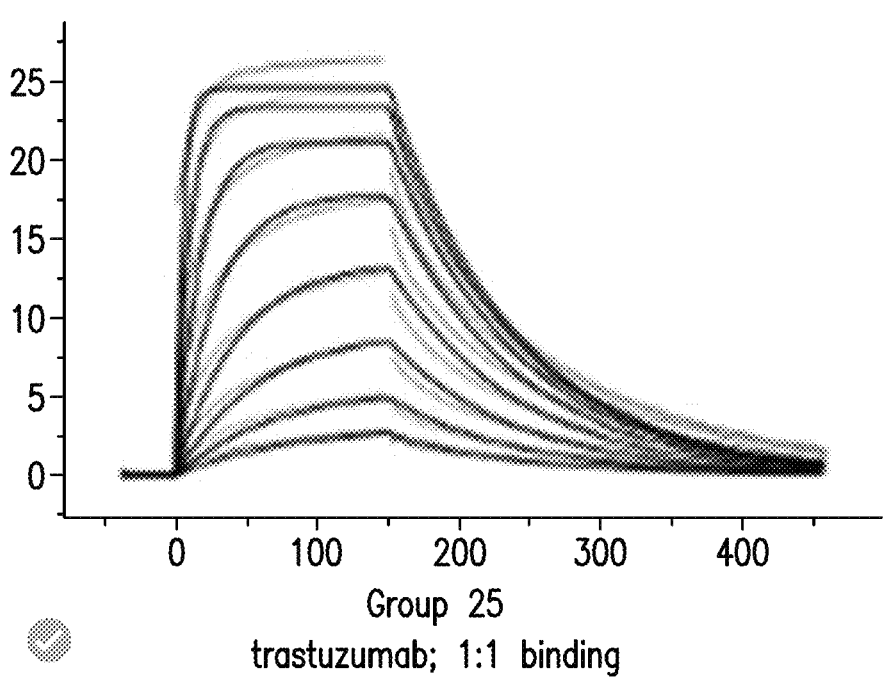
Figure 141E:
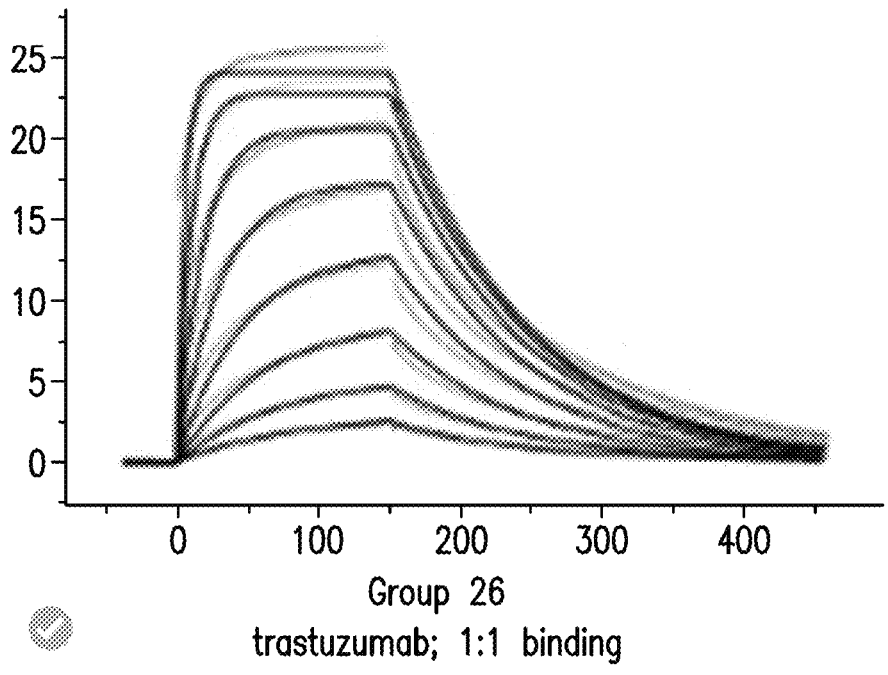
Figure 141F:
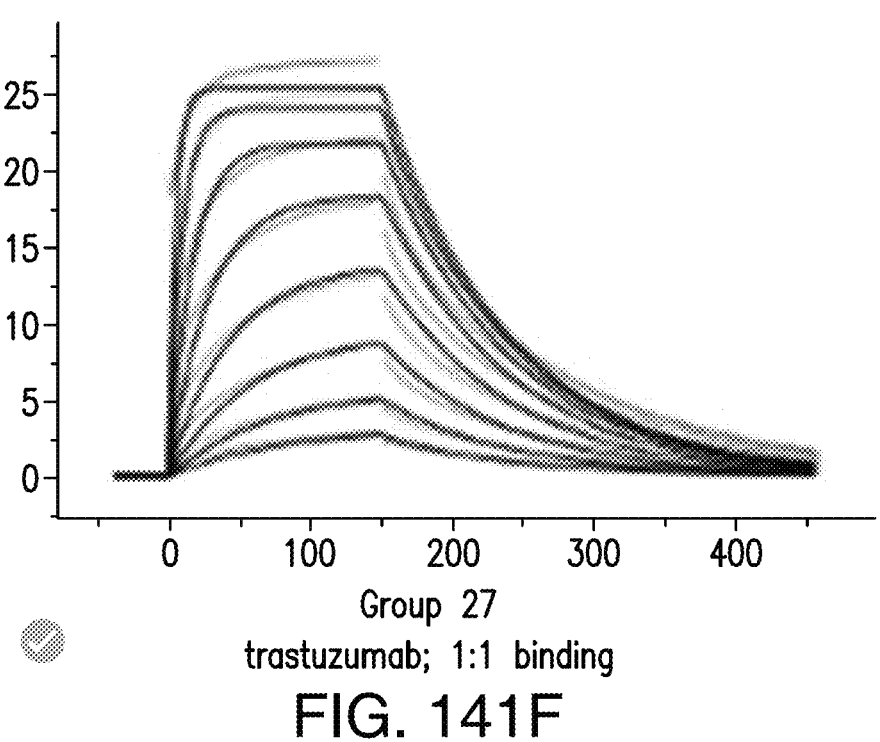
Figure 142A:
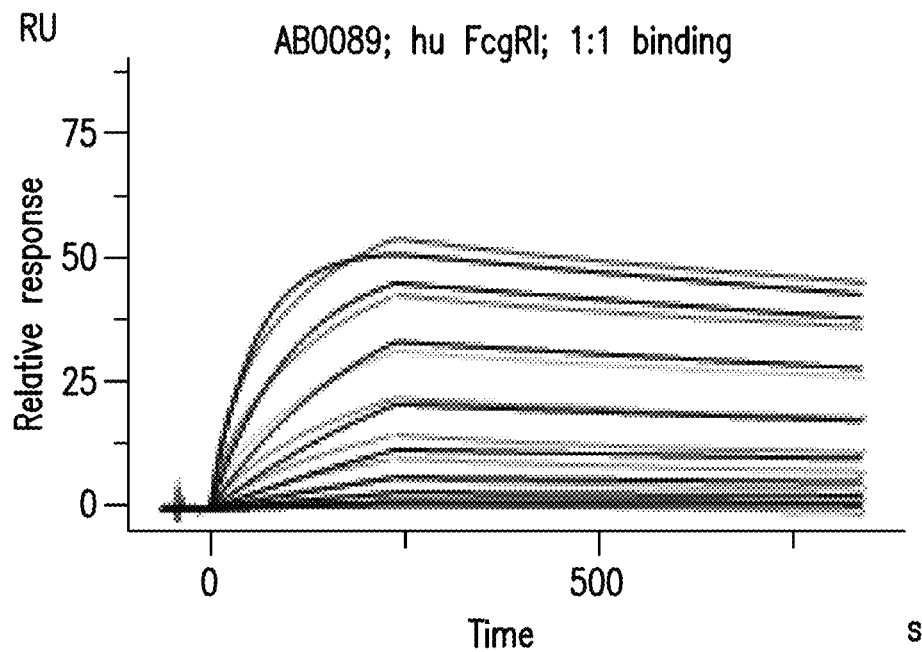
Figure 142B:
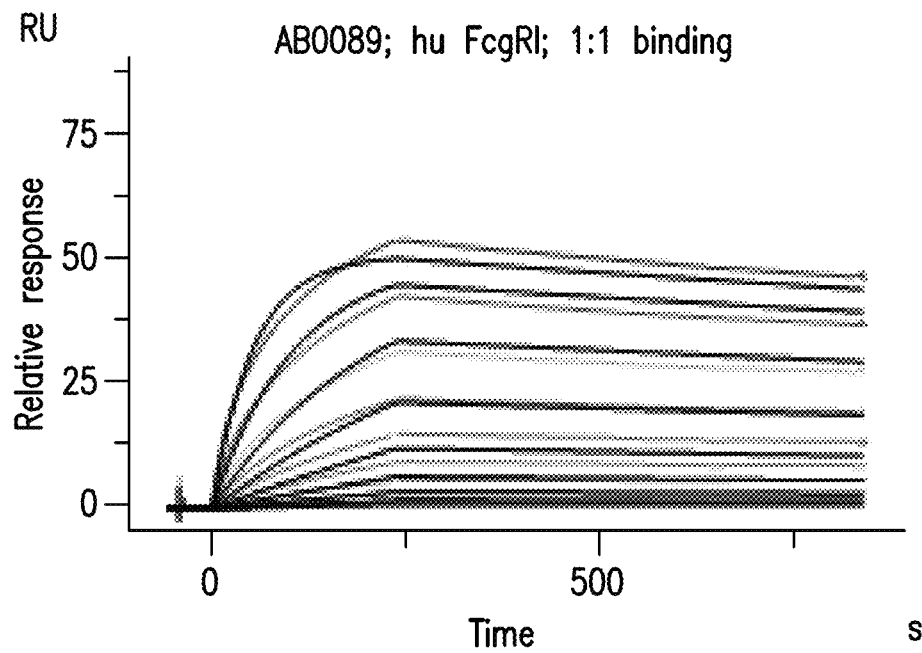
Figure 142C:
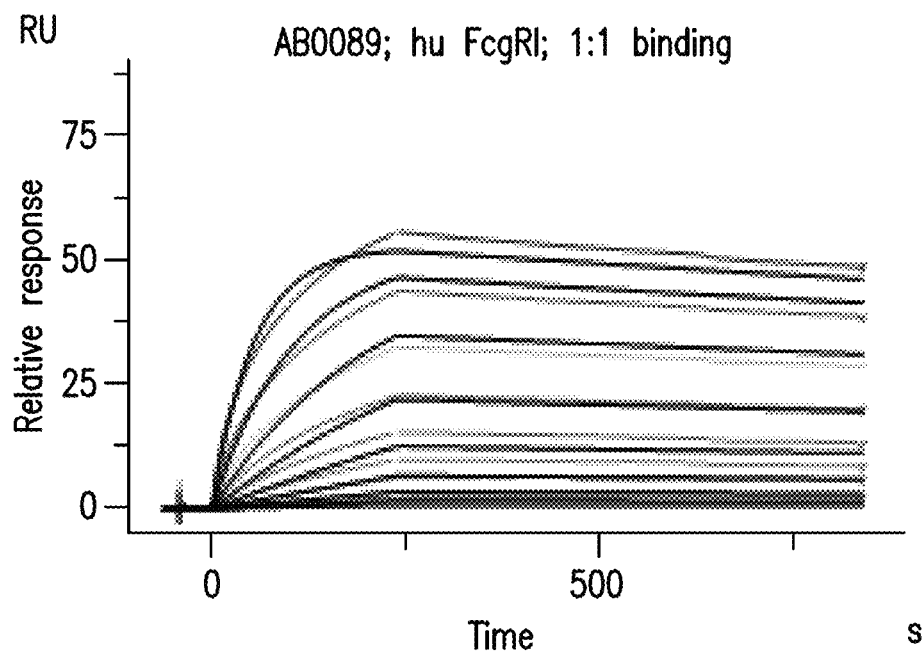
Figure 142D:
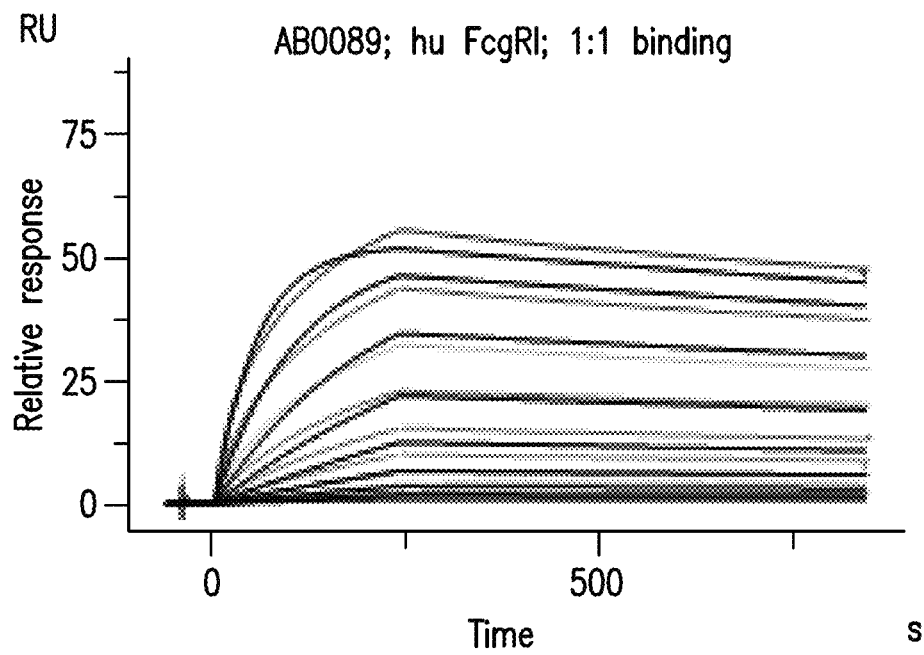
Figure 142E:
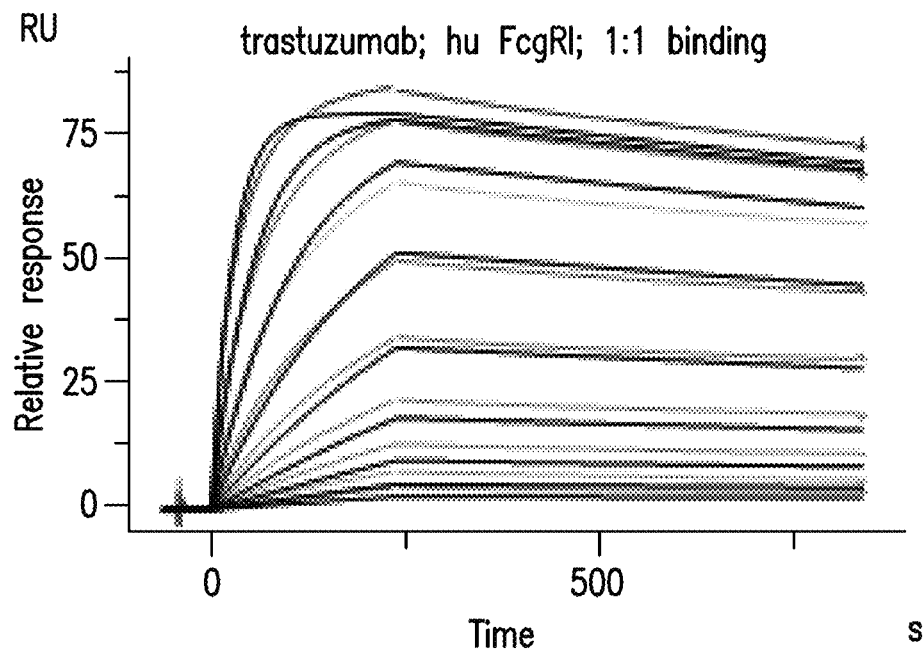
Figure 142F:
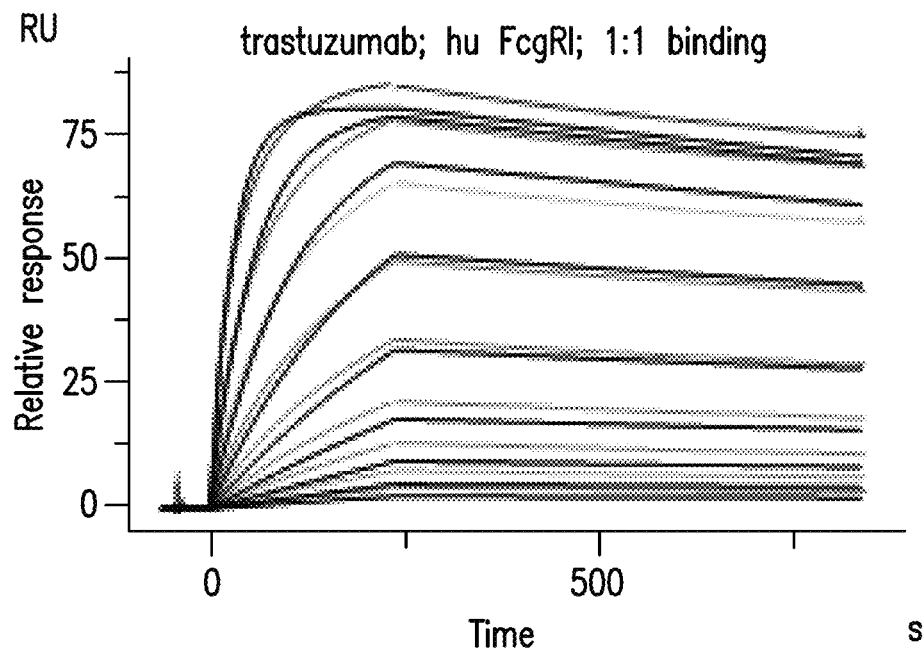
Figure 142G:
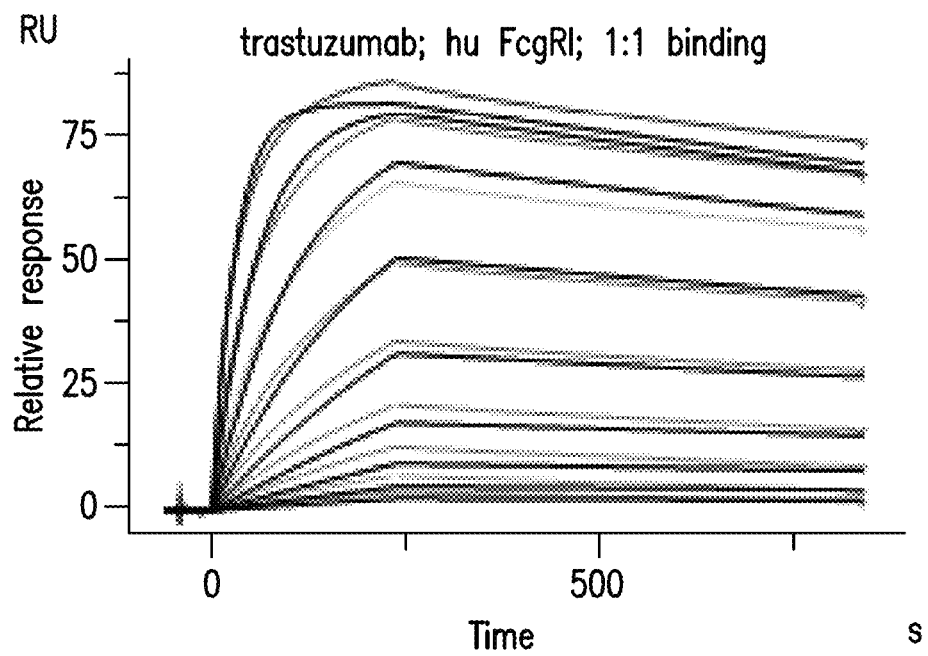
Figure 142H:
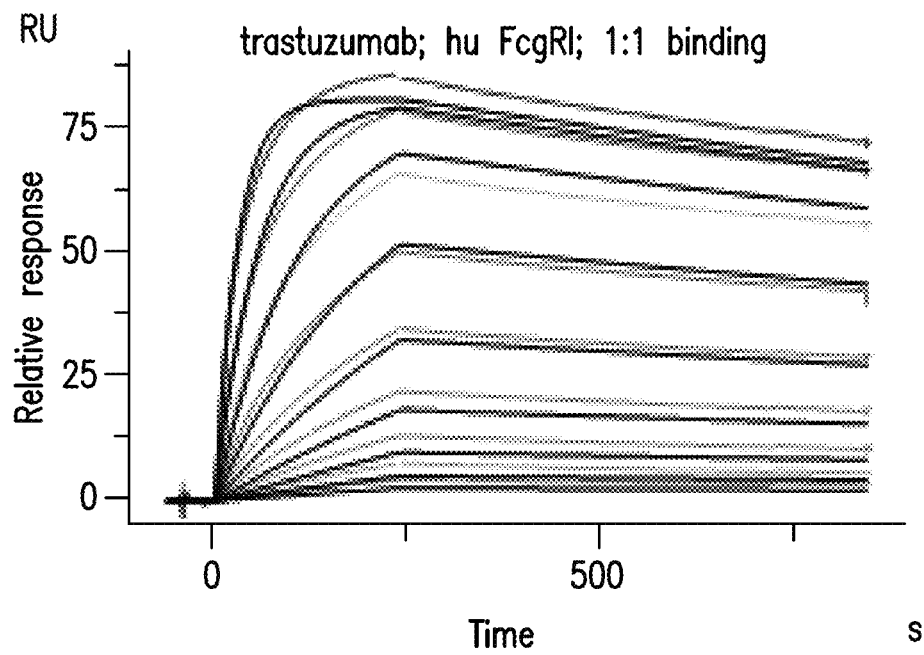

FIG. 140A-FIG. 140F show binding of AB0089 to human NKG2D tested by SPR. FIG. 140A-FIG. 140C sensorgrams represent raw data. Black overlays represent the 1:1 kinetic fit. FIG. 140D-FIG. 140F state affinity fit. Data from four independent Biacore channels are shown. The line represents the steady state KD value.

FIG. 141A-FIG. 141F show binding of AB0089 and trastuzumab to recombinant human CD16a (V158).

FIG. 142A-FIG. 142H show binding of AB0089 and trastuzumab to recombinant human CD64 (FcγRI).

FIG. 143A-FIG. 143G show binding of AB0089 and trastuzumab to cynomolgus CD64 (FcγRI).

Figure 144A:
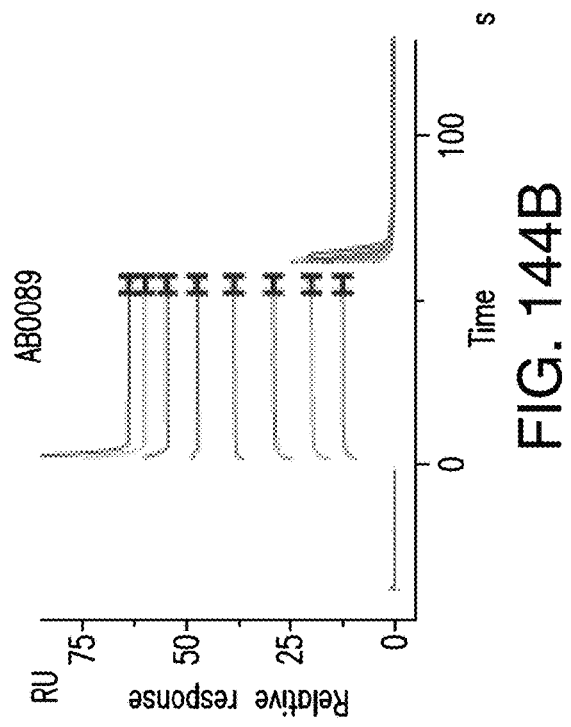
Figure 144B:
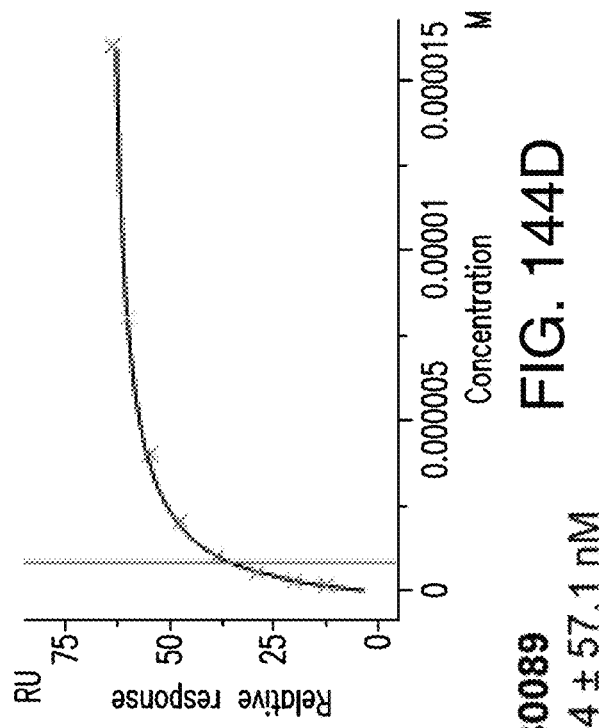
Figure 144C:
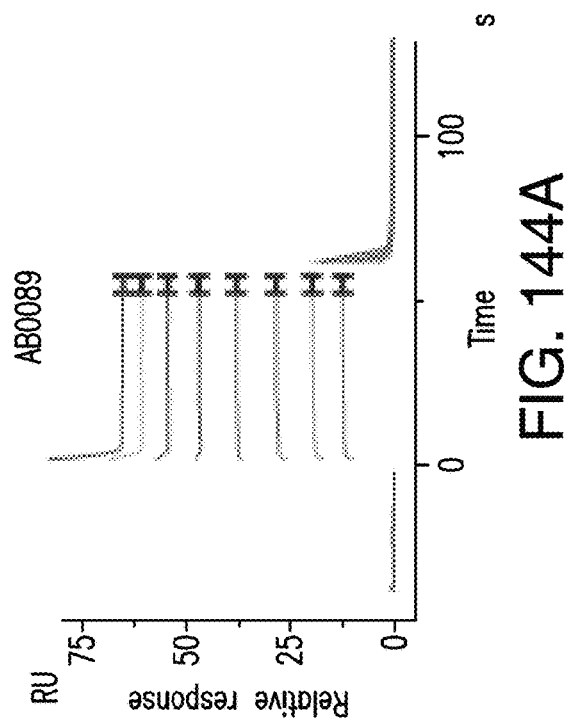
Figure 144D:
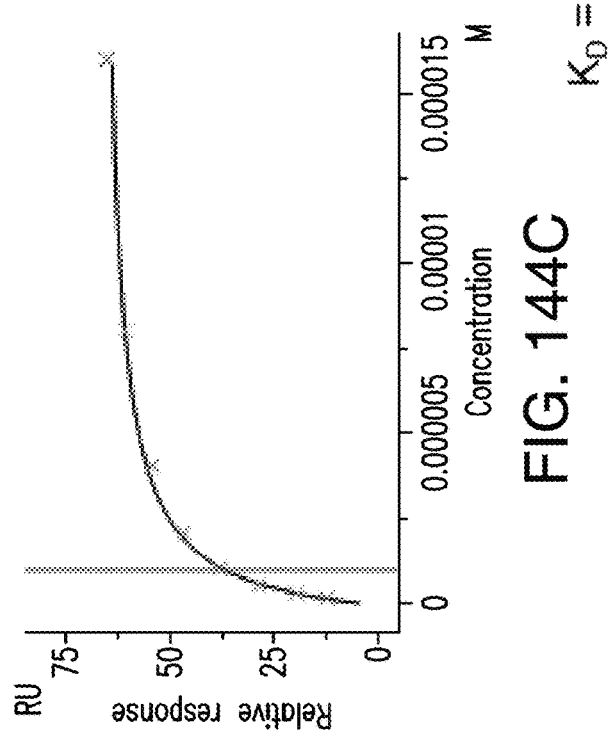
Figure 147E:
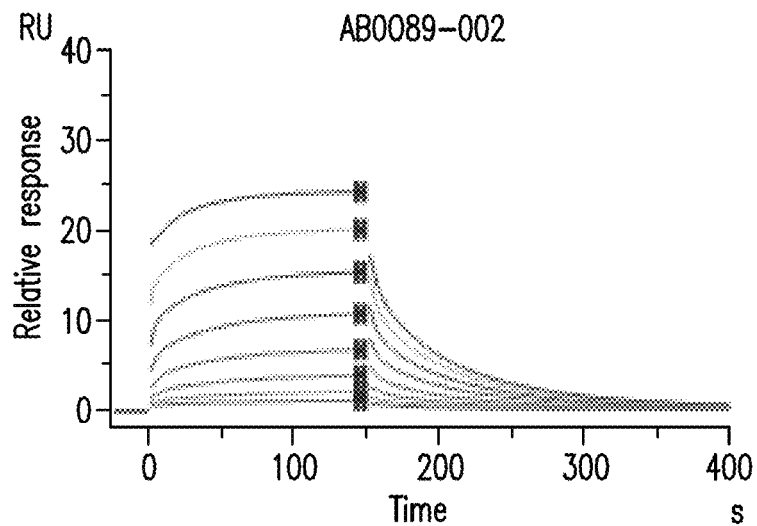
Figure 147F:
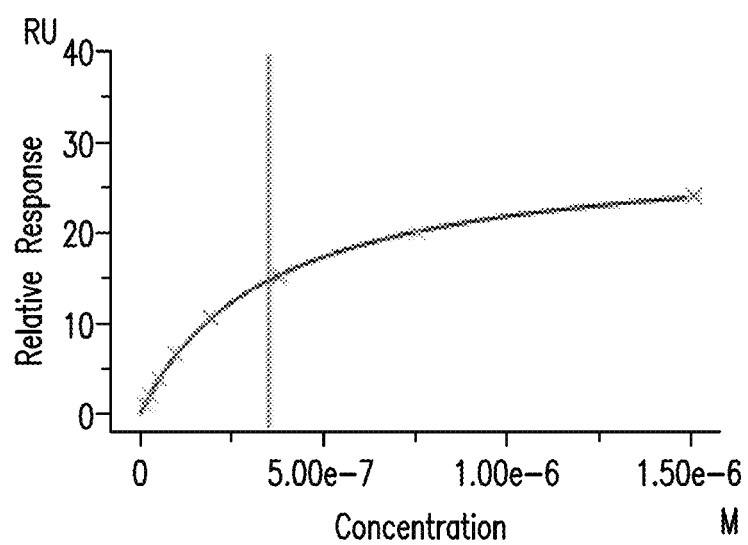
Figure 147K:
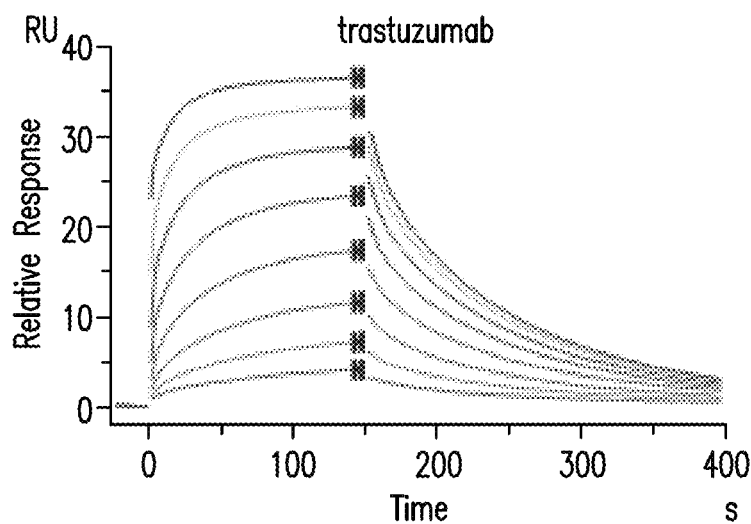
Figure 147L:
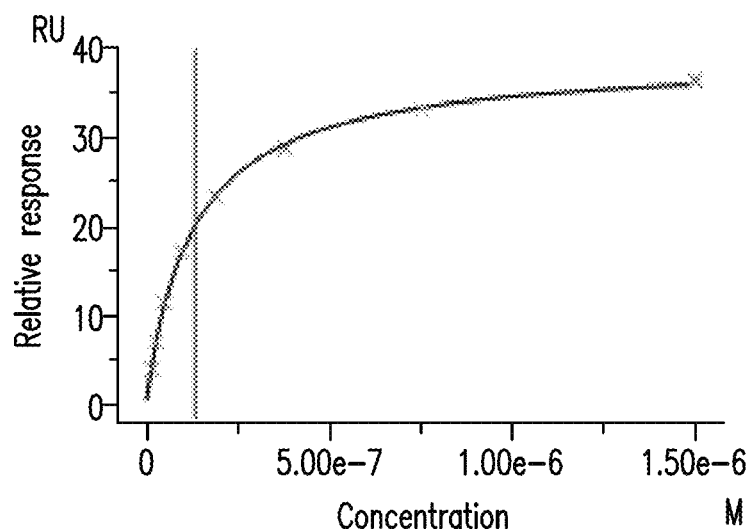

FIG. 144A-FIG. 144P show binding of AB0089 and trastuzumab to human CD32a H131 (FcγRIIa H131).

FIG. 145A-FIG. 145P show binding of AB0089 and trastuzumab to human CD32a R131 (FcγRIIa R131).

FIG. 146A-FIG. 146P show binding of AB0089 and trastuzumab to recombinant human CD16a F158 (FcγRIIIa F158).

FIG. 147A-FIG. 147L show binding of AB0089 and trastuzumab to recombinant cynomolgus CD16 (FcγRIII).

Figure 148I:
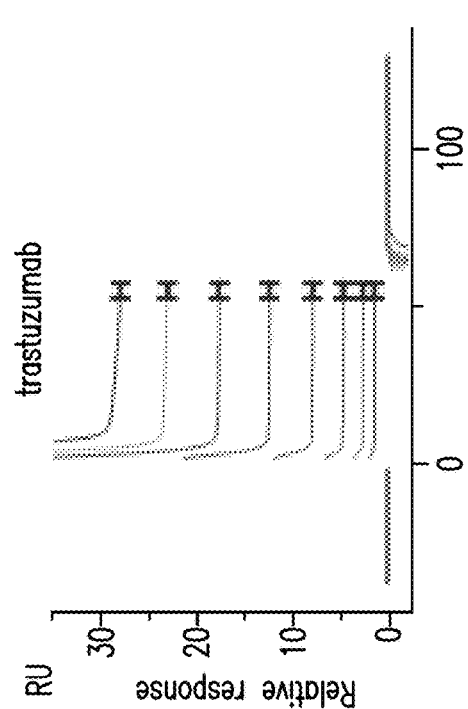
Figure 148J:
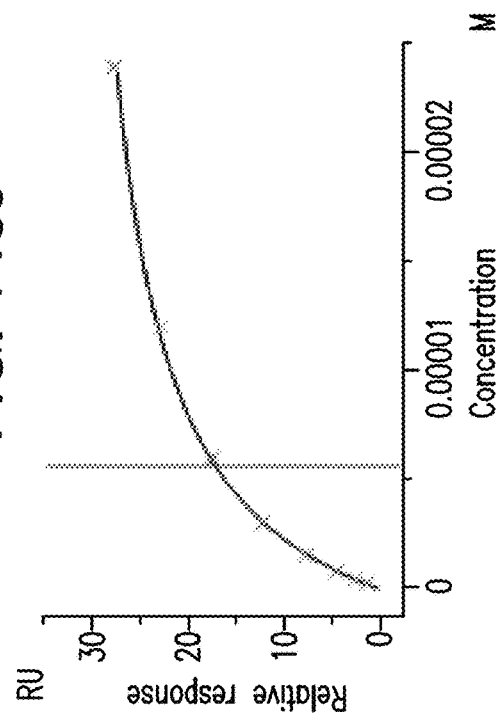
Figure 148K:
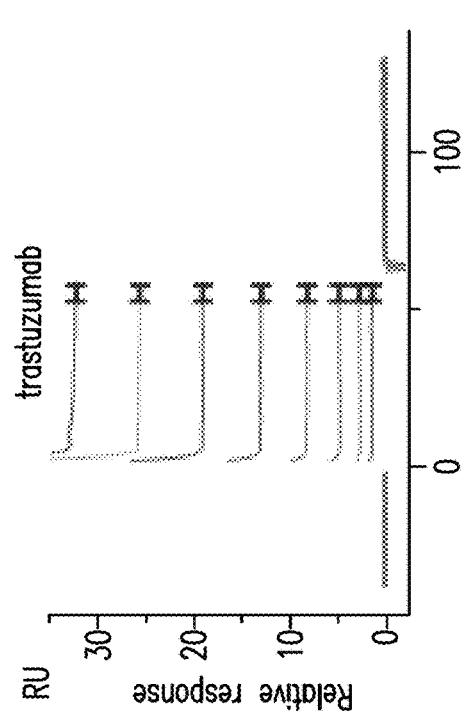
Figure 148L:
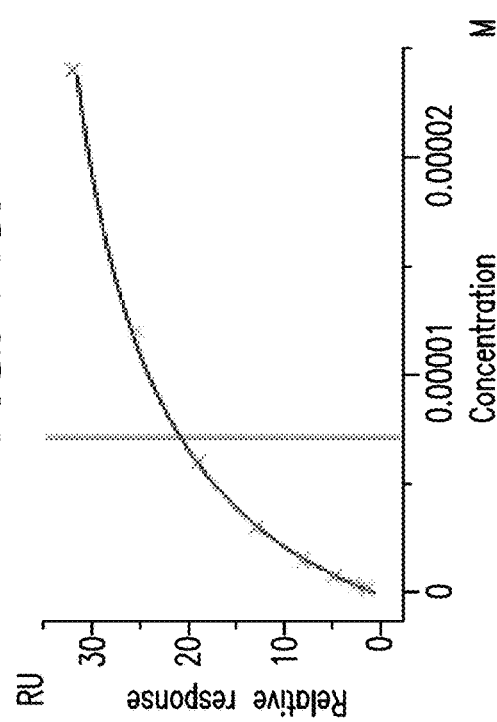
Figure 149E:
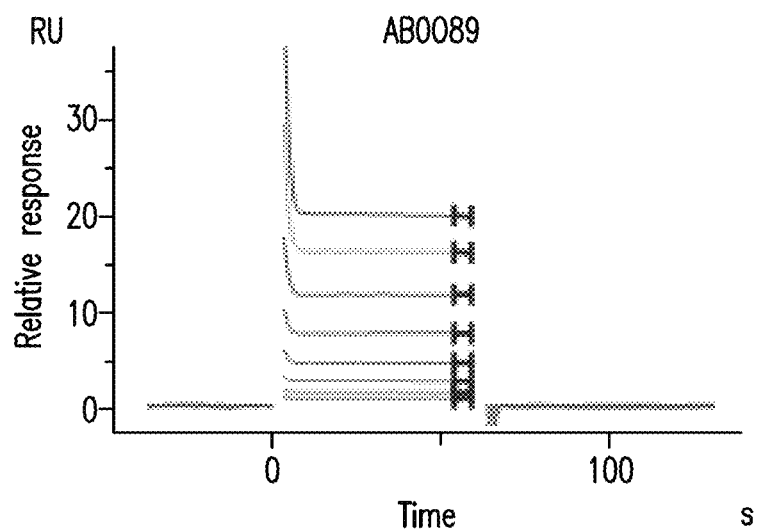
Figure 149F:
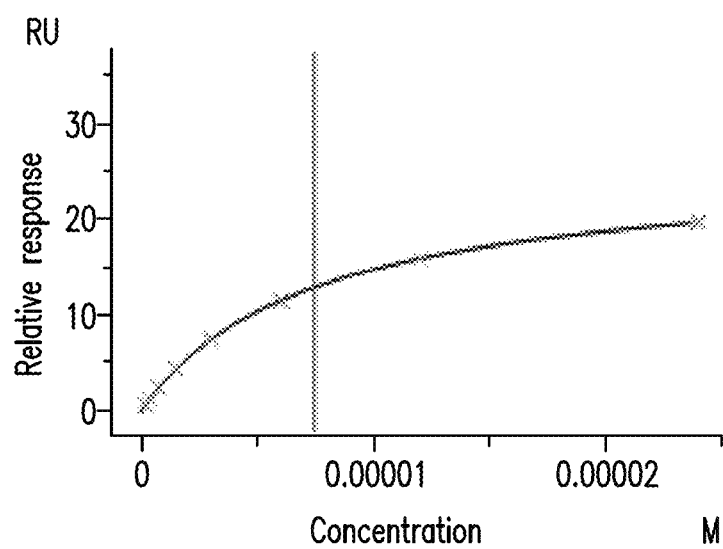
Figure 149G:
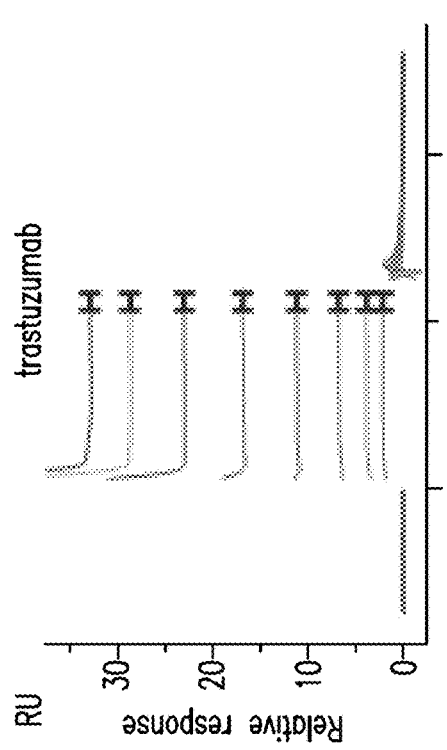
Figure 149H:
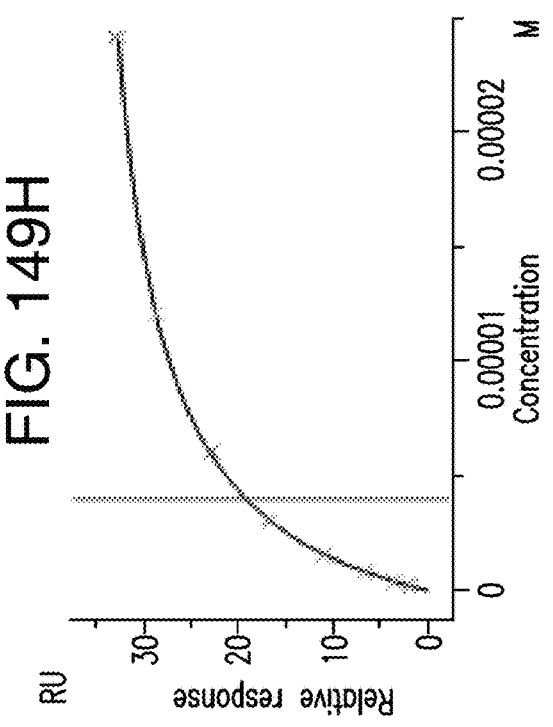
Figure 149I:
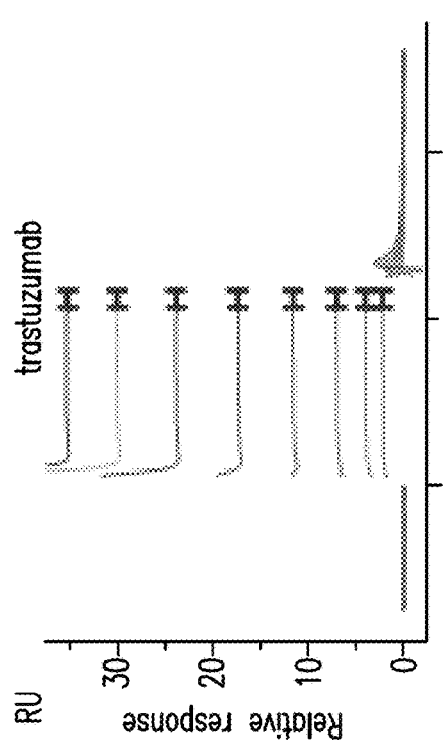
Figure 149J:
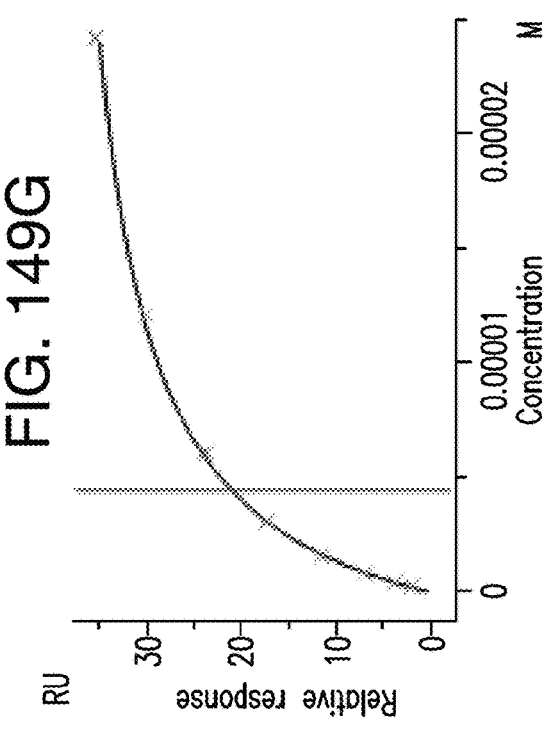
Figure 149K:
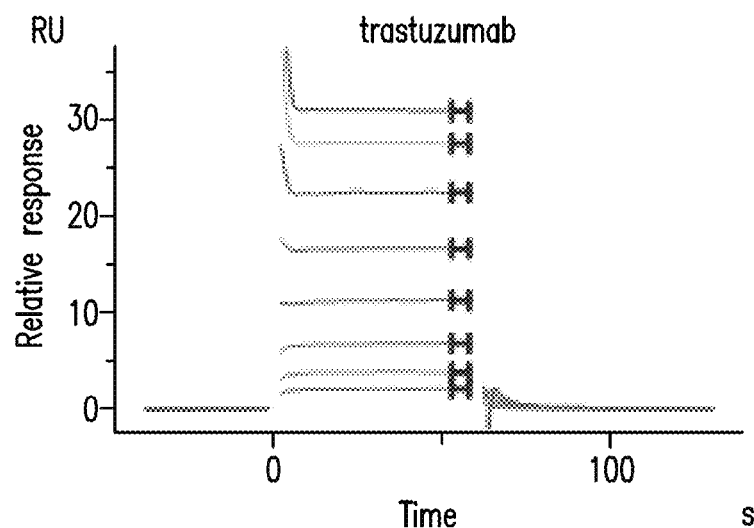
Figure 149L:
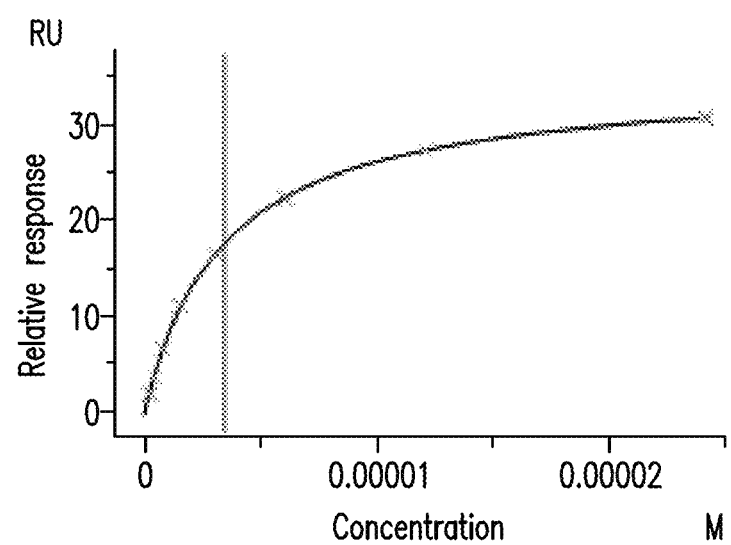
Figure 151E:
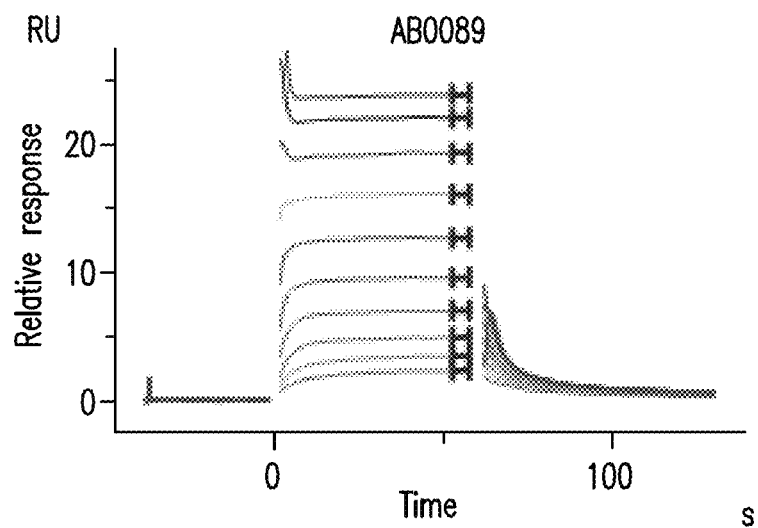
Figure 151F:
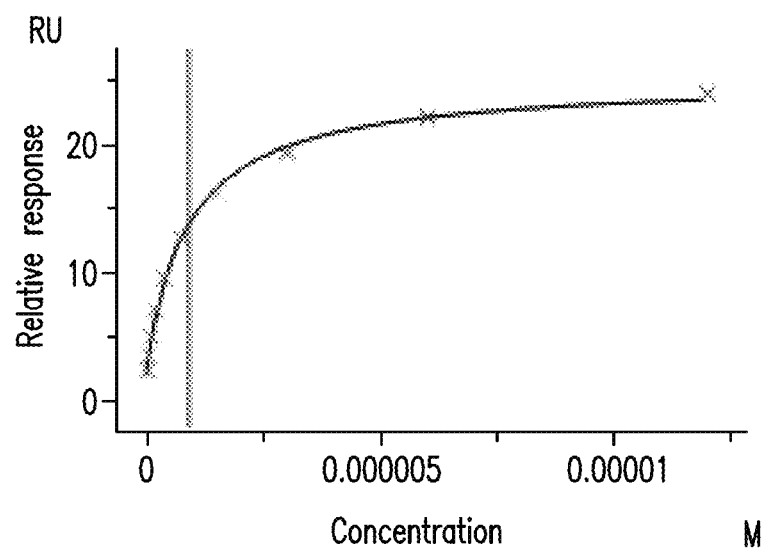
Figure 151K:
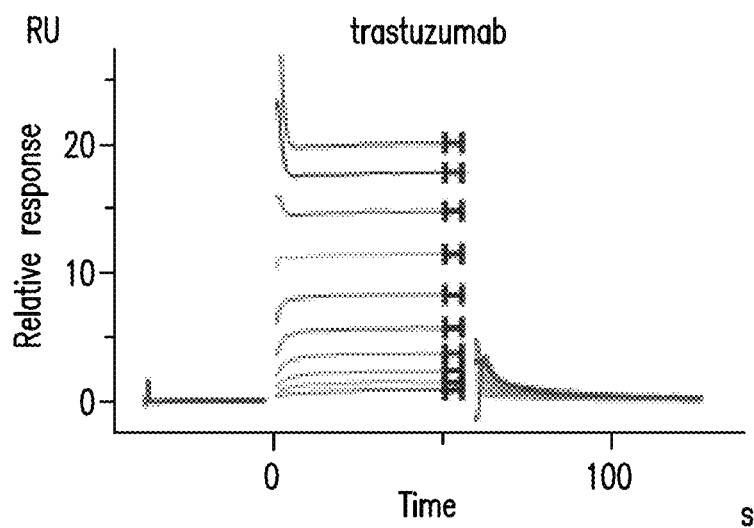
Figure 151L:
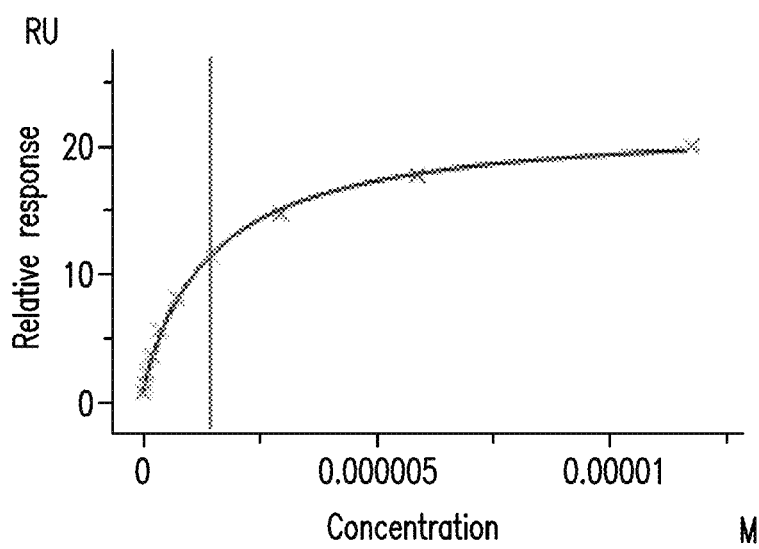

FIG. 148A-FIG. 148P show binding of AB0089 and trastuzumab to recombinant human CD32b (FcγRII).

FIG. 149A-FIG. 149L show binding of AB0089 and trastuzumab to recombinant human CD16b (FcγRIIIb).

FIG. 150A-FIG. 150P show binding of AB0089 and trastuzumab to recombinant human FcRn.

FIG. 151A-FIG. 151L show binding of AB0089 and trastuzumab to recombinant cynomolgus FcRn.

Figure 152:
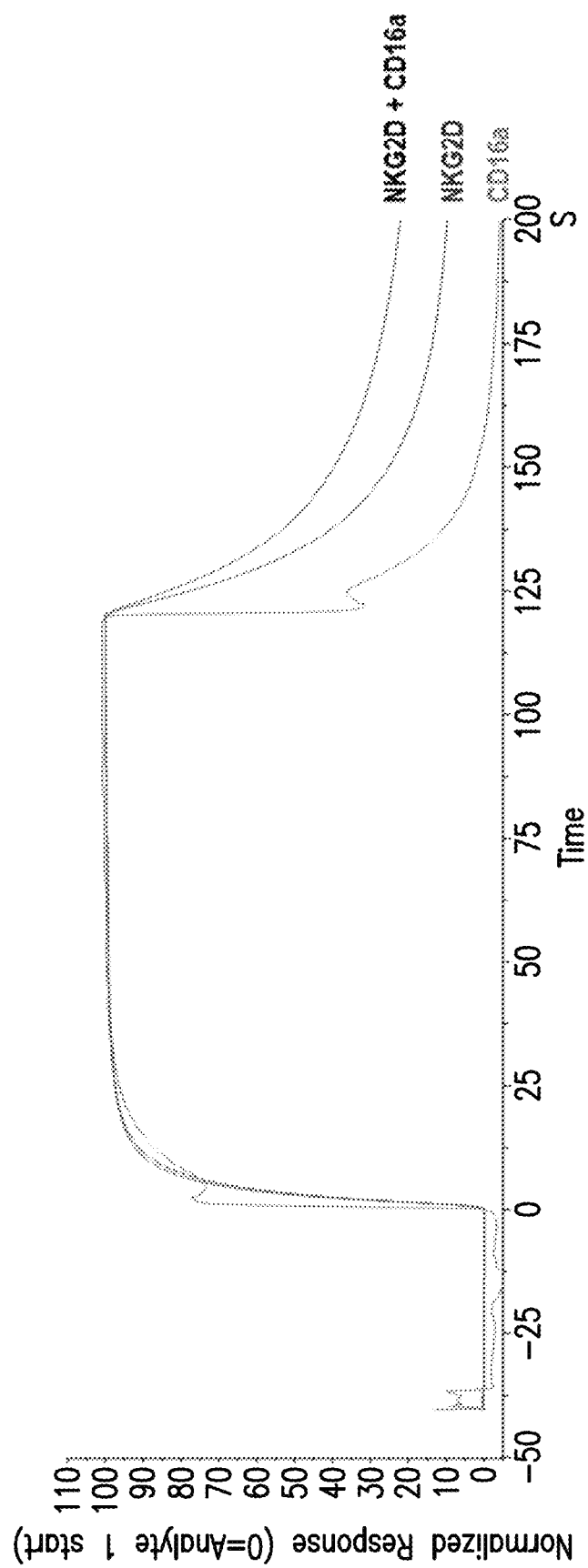

FIG. 152 shows that simultaneous engagement of AB0089 to CD16a and NKG2D results in avid binding.

Figure 153A:
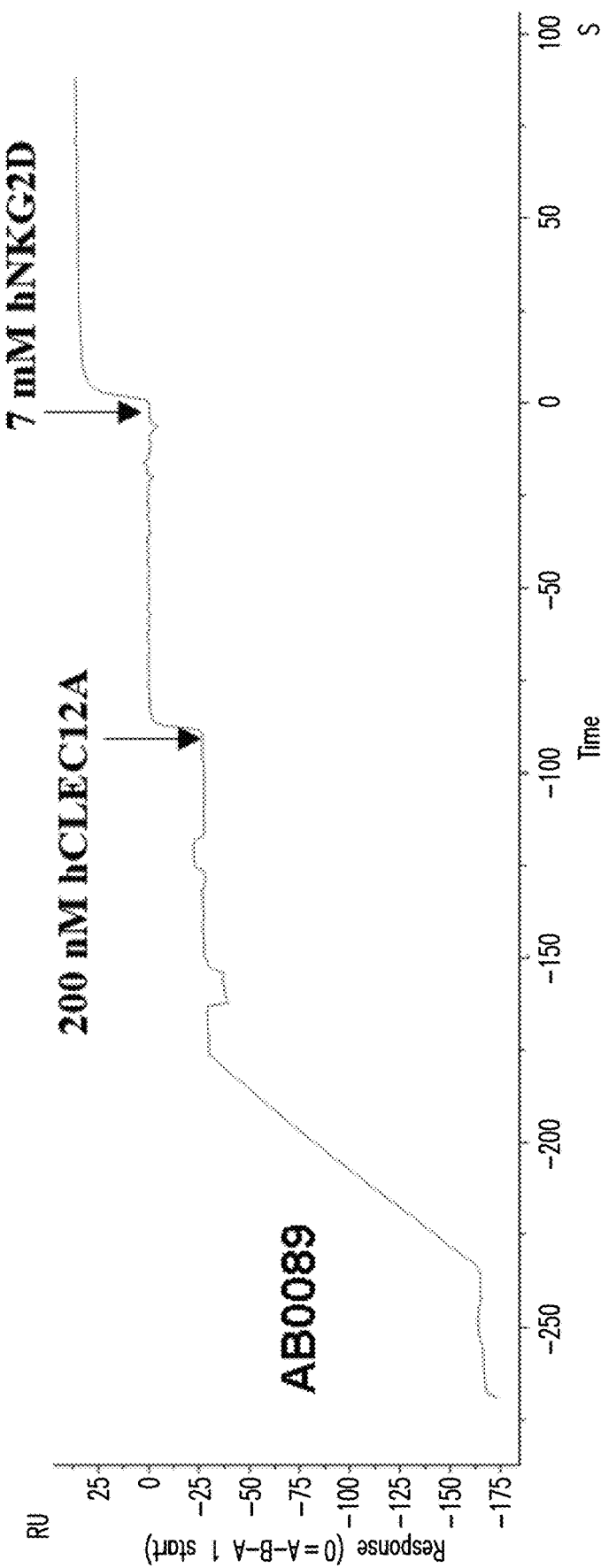
Figure 153B:
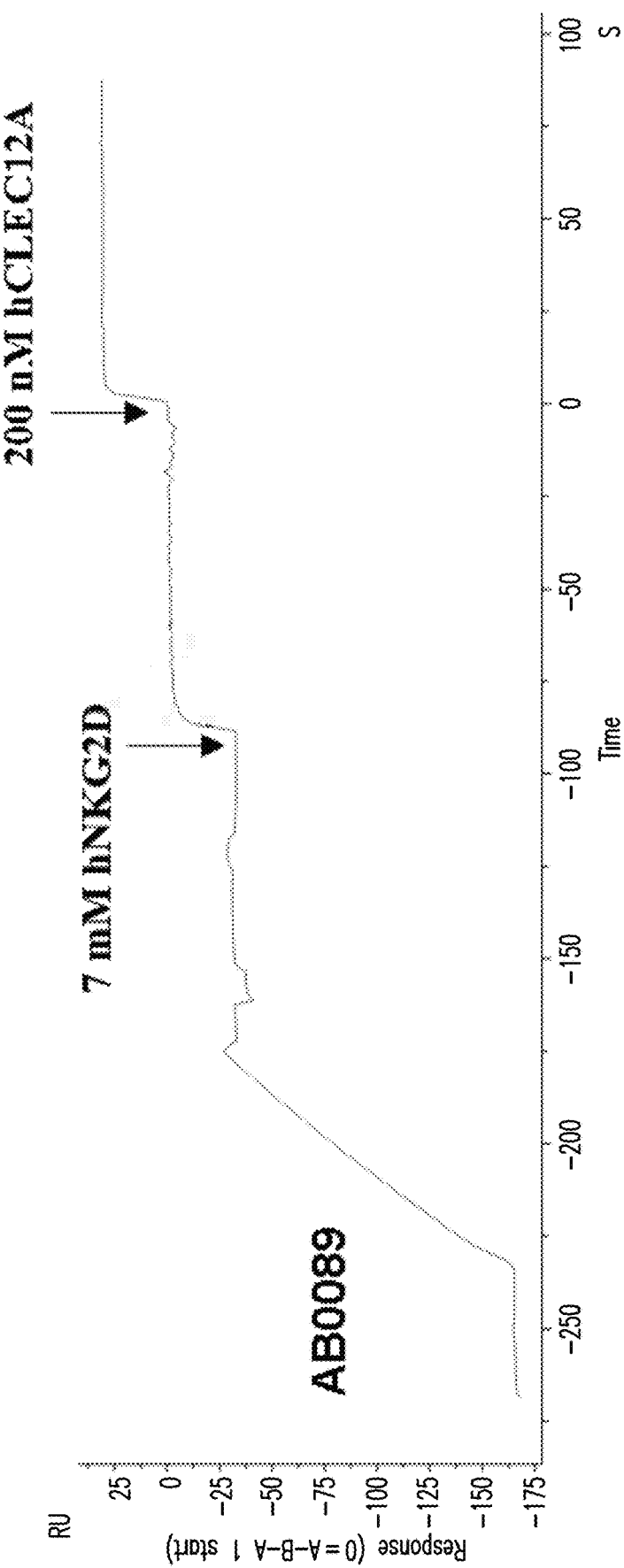

FIG. 153A-FIG. 153B show AB0089 simultaneous co-engagement of CLEC12A and NKG2D binding arms.

FIG. 154 is a summary of a comparison of the binding epitope of AB0089 in relation to AB0237, AB0192 and three CLEC12A binding reference TriNKETs by SPR. AB0089 interaction with hCLEC12A was blocked by AB0237, and two control molecules, cFAE-A49 CLL1-Merus and cFAE-A49 Tepoditamab, but not by Genentech-h6E7 based molecule, and illustrates that AB0089 binding epitope overlaps with Merus-CLL1 and tepoditamab.

Figures 155A, 155B:
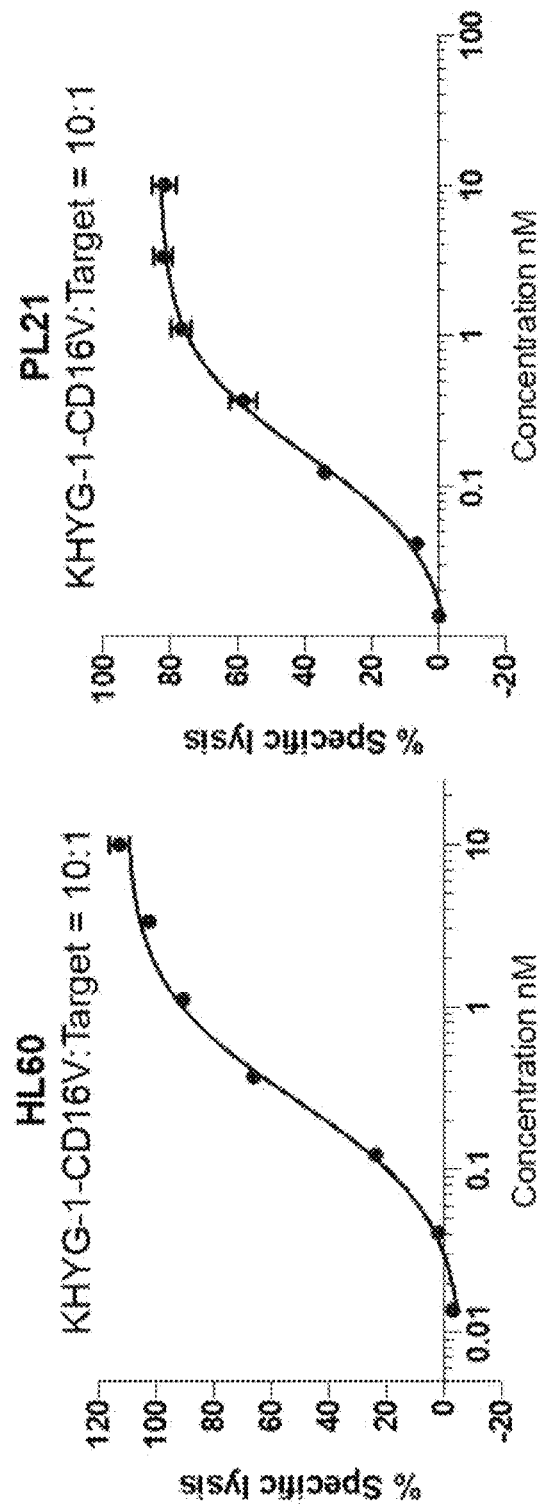

FIG. 155A-FIG. 155B show potency of AB0089 in KHYG-1-CD16aV mediated cytotoxicity assay with HL60 and PL21 cells.

Figure 156:
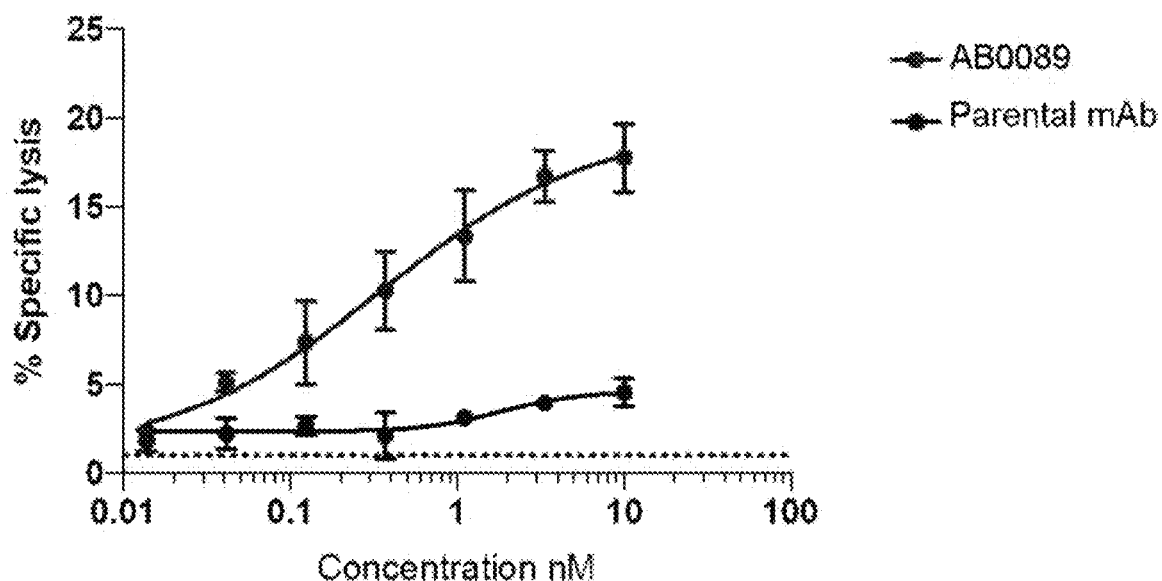

FIG. 156 shows that AB0089 potently enhances primary NK mediated cell lysis of cancer cells, outperforming parental mAb.

Figure 157A:
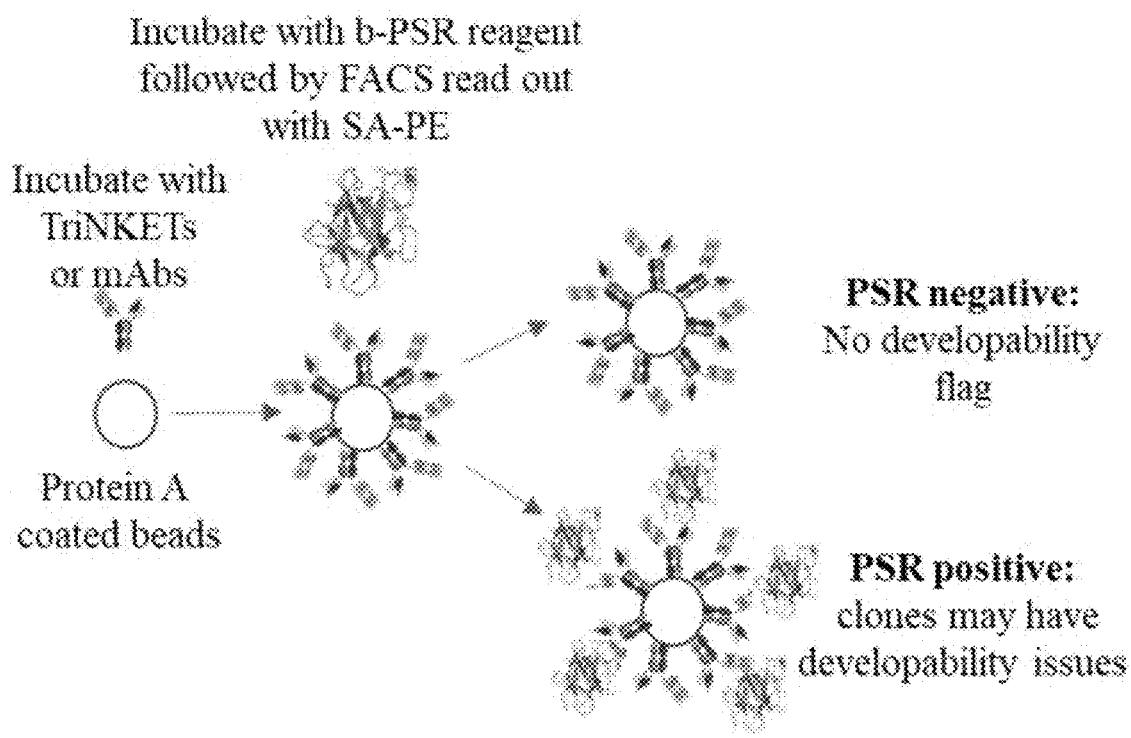
Figures 157B, 157C:
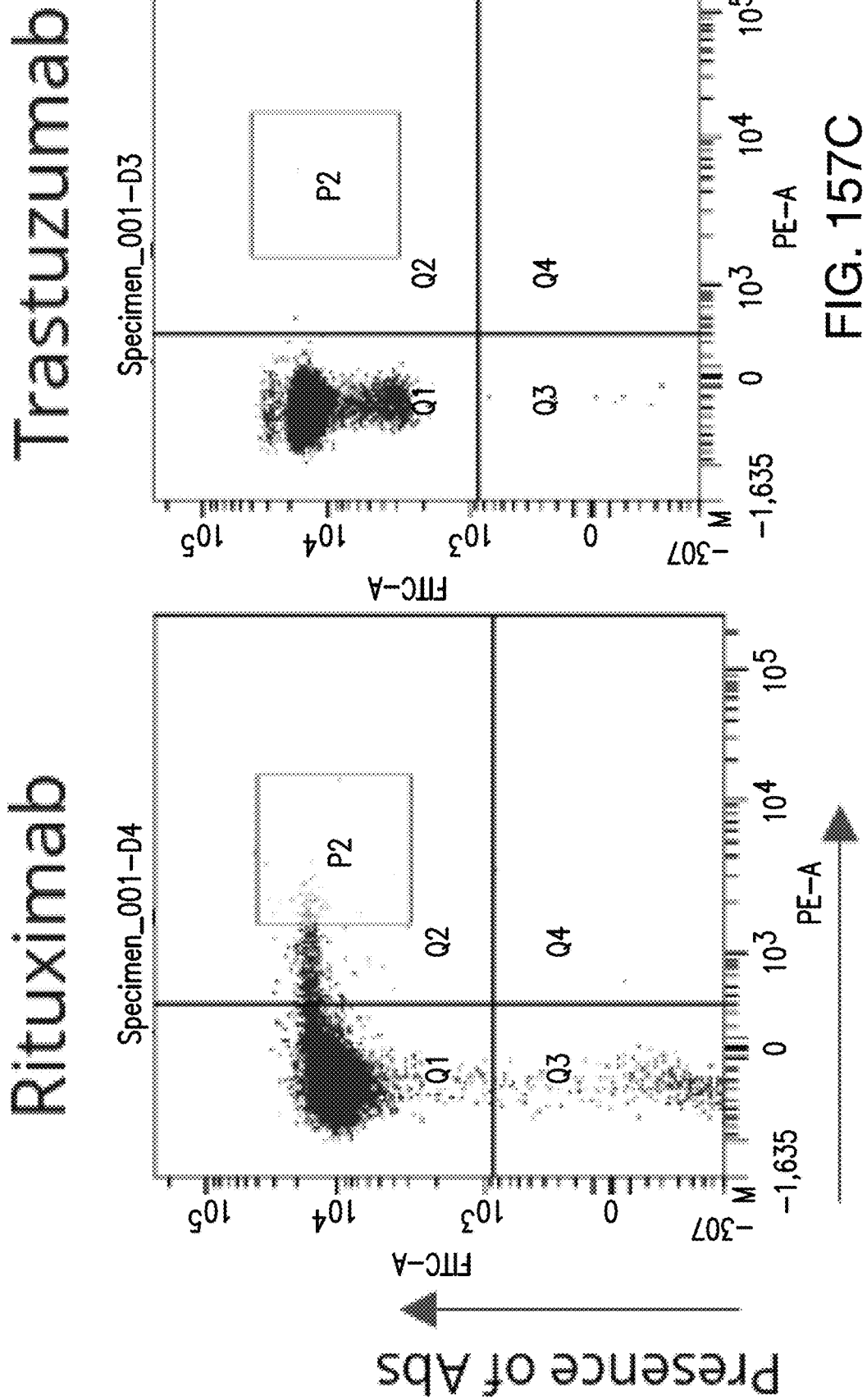
Figure 157D:
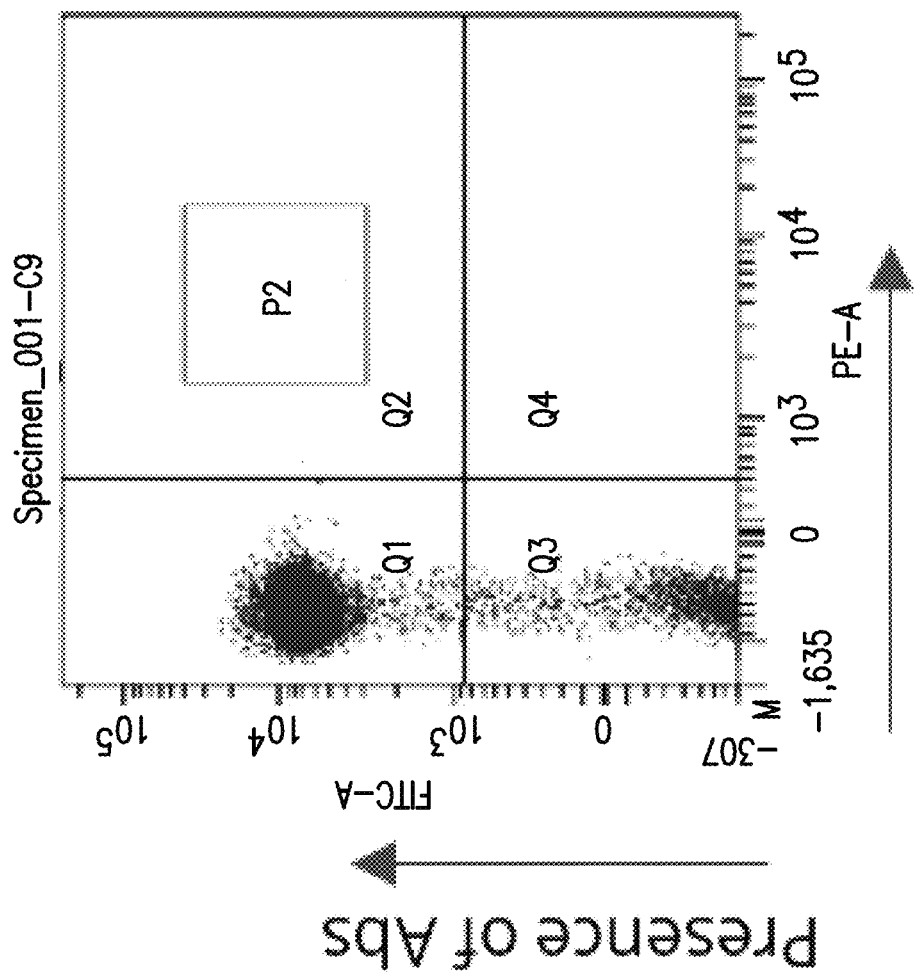

FIG. 157A-FIG. 157D shows a schematic representation of a PSR assay (FIG. 157A), and PSR binding AB0089 (FIG. 157D) in comparison with antibodies with known PSR binding (Rituximab; FIG. 157B) and an antibody with no known non-specificity (Trastuzumab) (FIG. 157C).

Figure 158:
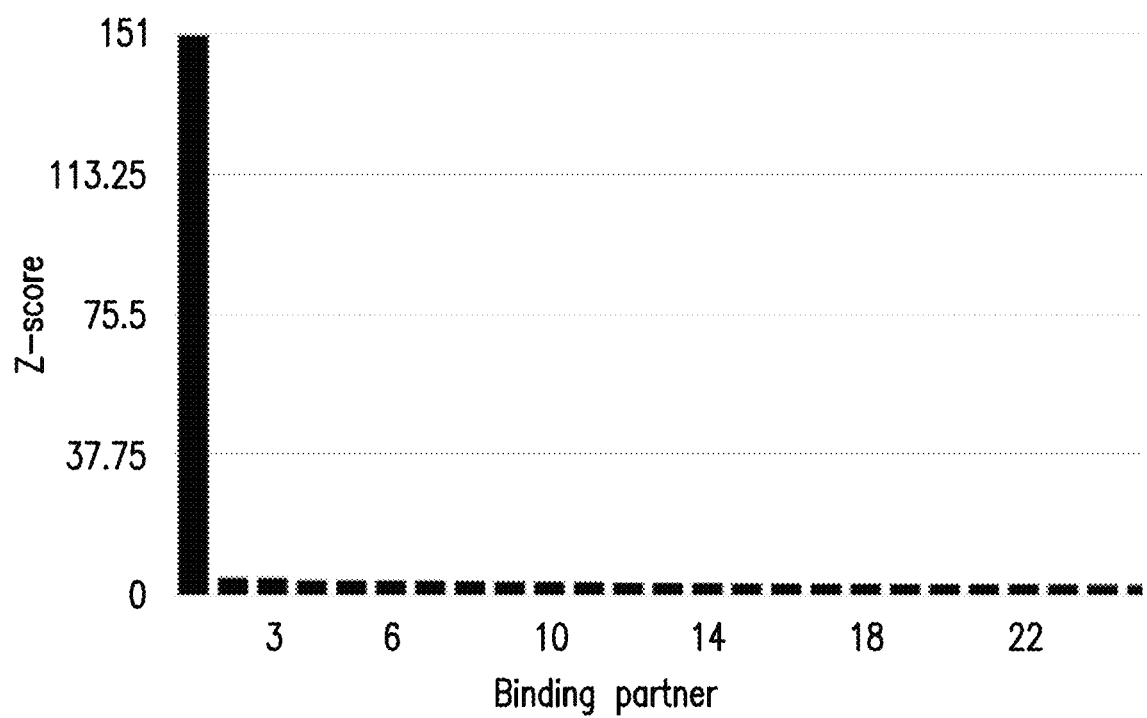

FIG. 158 shows the relative binding (Z score) of AB0089 at 1 μg/ml to human CLEC12A in comparison to the entire human proteome microarray. Plot depicting the relative binding Z-score (y-axis) vs. the top 24 identified binding partners of AB0089 (x-axis). hCLEC12a is plotted at position 1 with a Z-score of 150.61.

Figure 159:
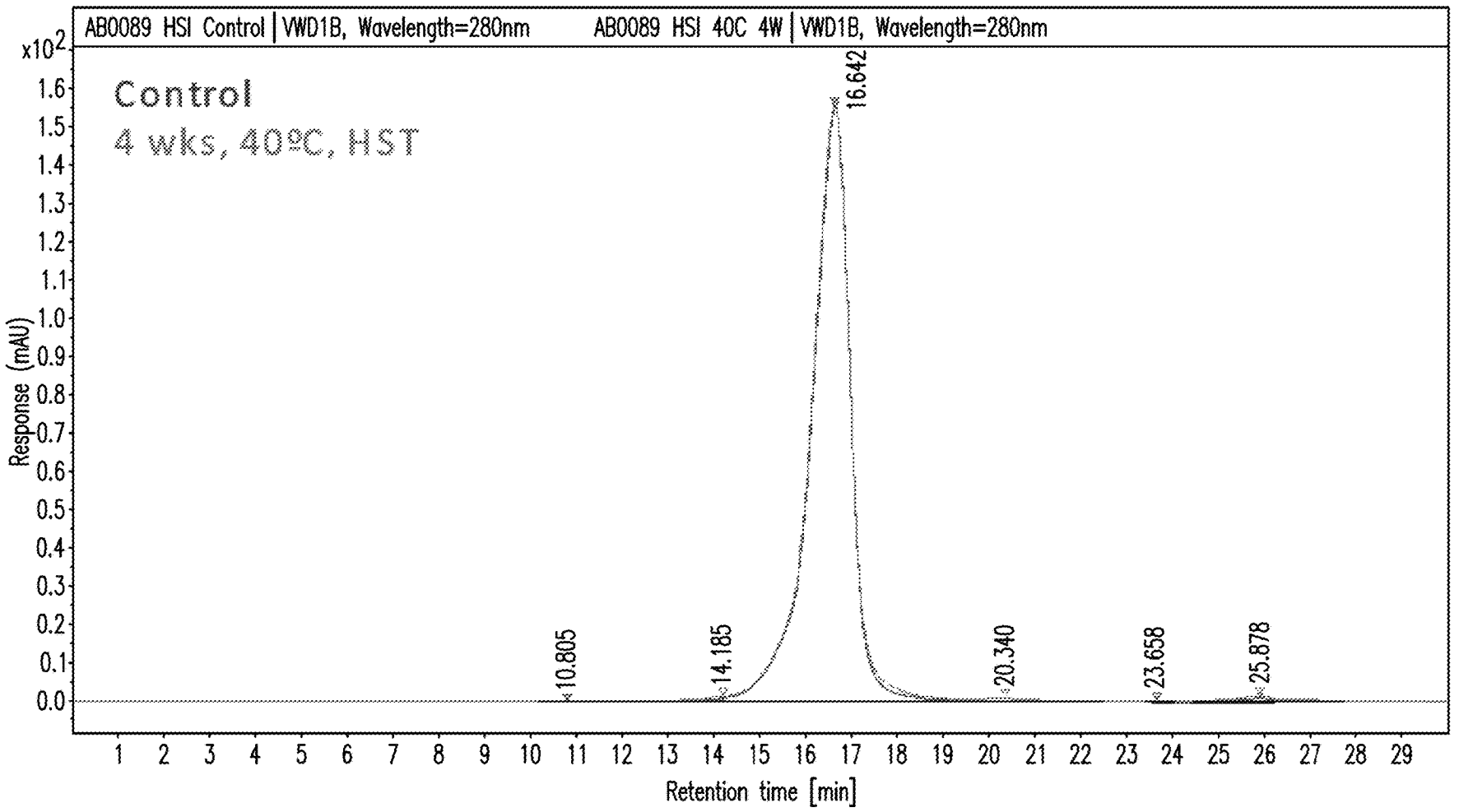

FIG. 159 shows SEC analysis of AB0089 after 4 weeks at 40° C. in HST, pH 6.0 compared to control sample, demonstrating that AB0089 exhibited high stability.

FIG. 160A-FIG. 160B shows CE-SDS analysis of AB0089 after 4 weeks at 40° C. in HST, pH 6.0, compared to control. Non-reduced (NR) (FIG. 160A) and reduced (R) (FIG. 160B).

Figure 161A:
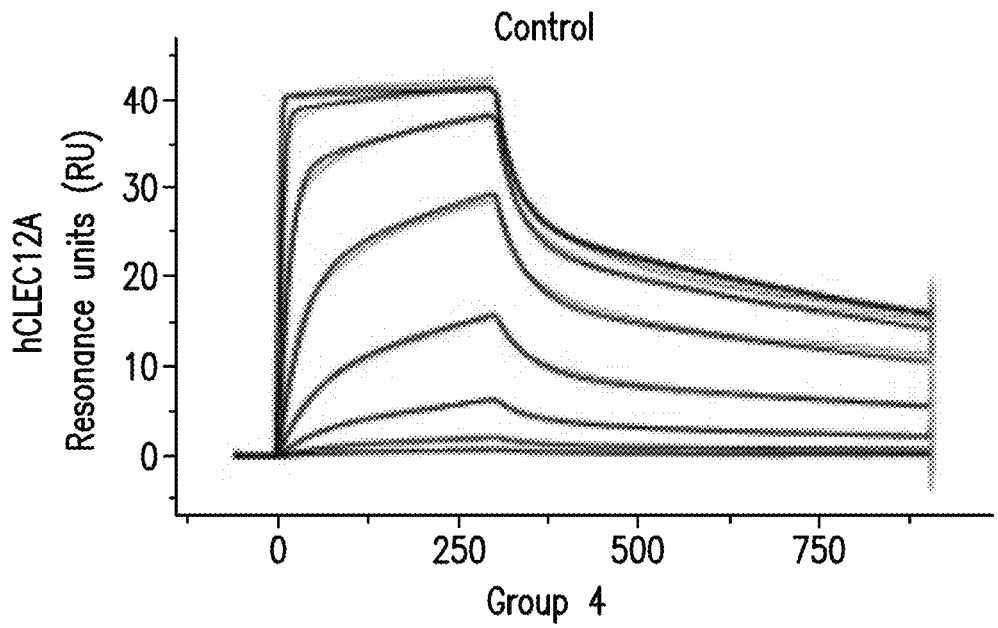
Figure 161B:
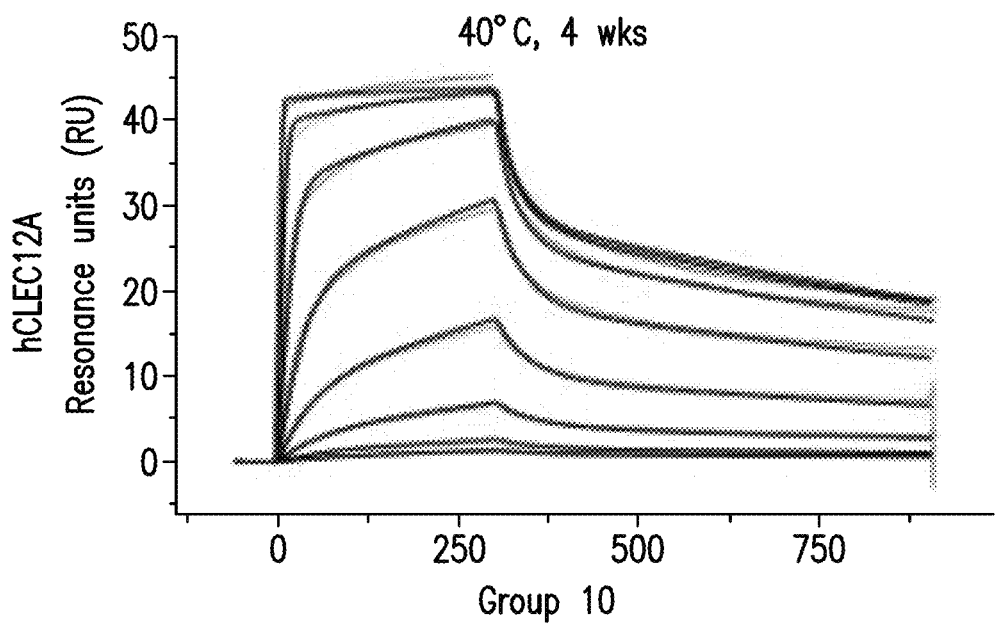
Figure 161C:
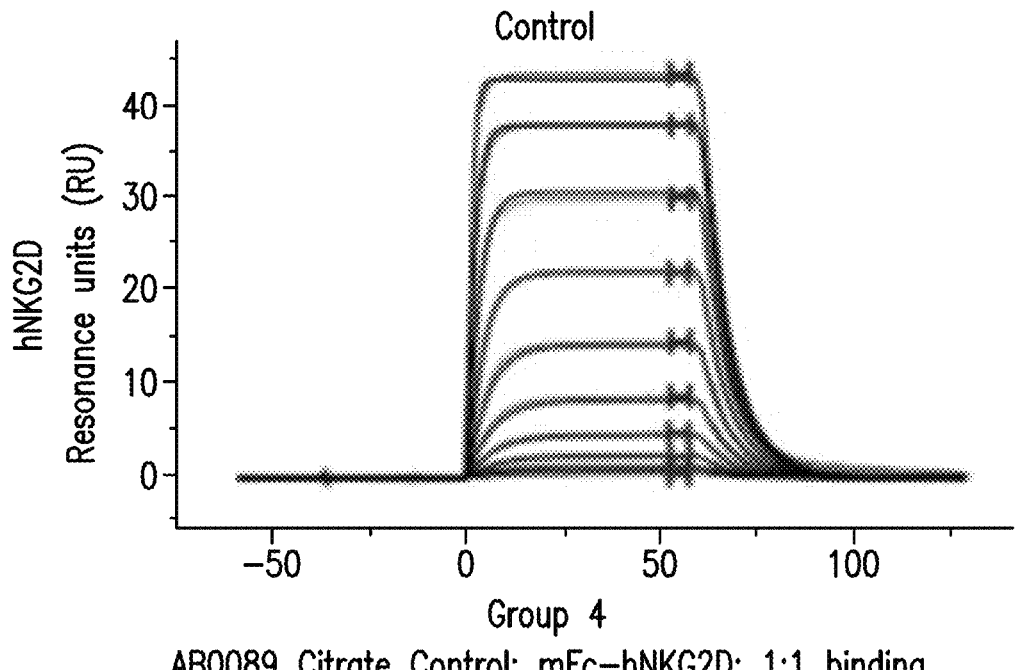
Figure 161D:
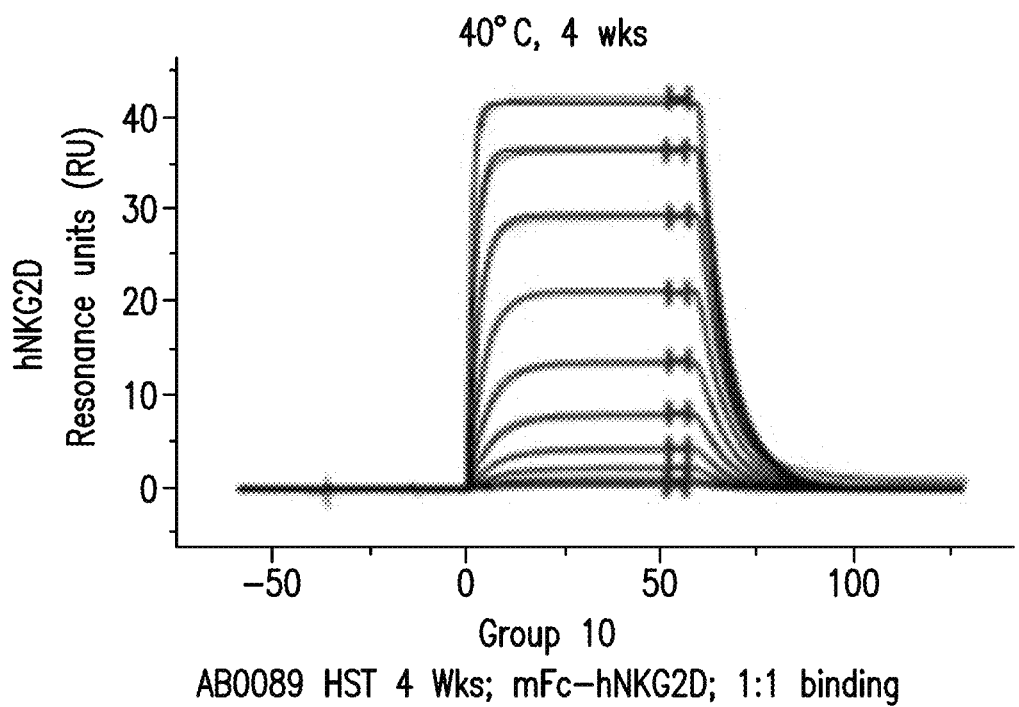
Figure 161E:
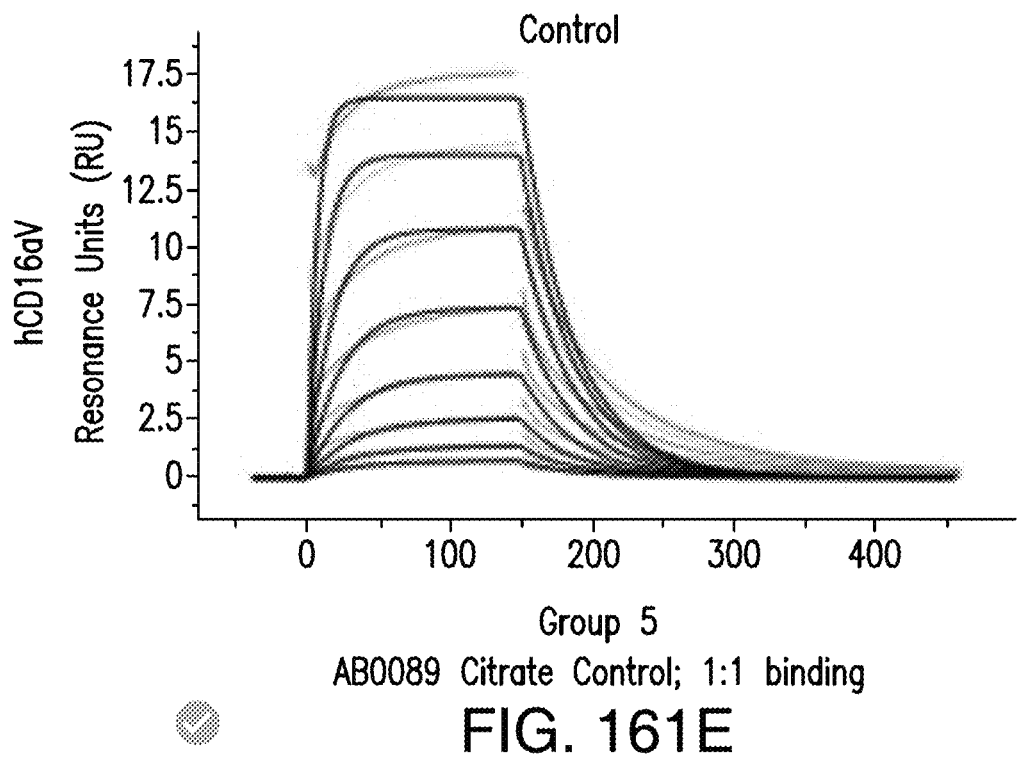
Figure 161F:
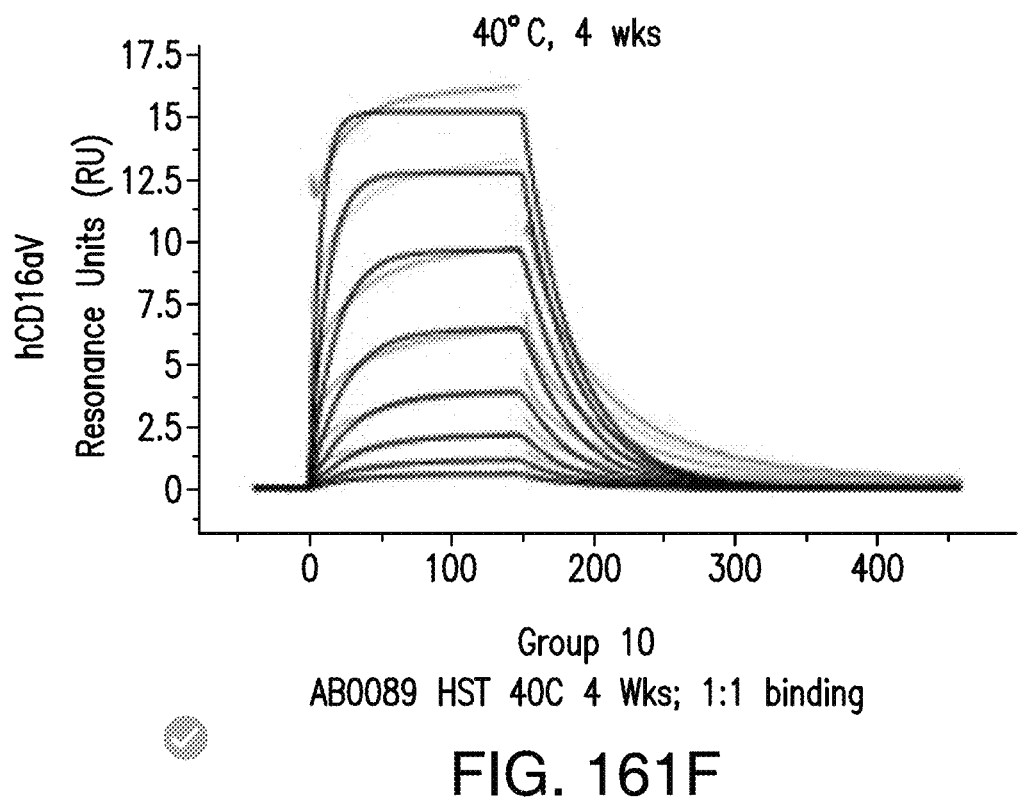

FIG. 161A-FIG. 161F shows that AB0089 is stable after 4 weeks at 40° C. in HST, pH 6.0 with no effect on binding to hCLEC12A (FIG. 161A and FIG. 161B), hNKG2D (FIGS. 161C and 161D), or hCD16aV (FIG. 161E and FIG. 161F).

Figure 162:
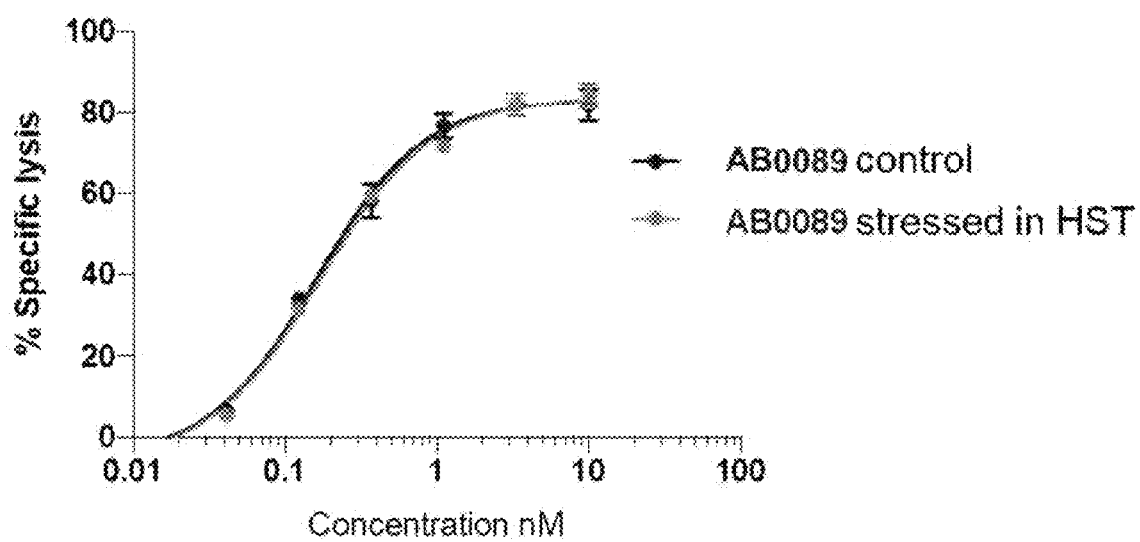

FIG. 162 shows AB0089 potency after 4 weeks at 40° C. in HST, pH 6.0.

Figure 163:
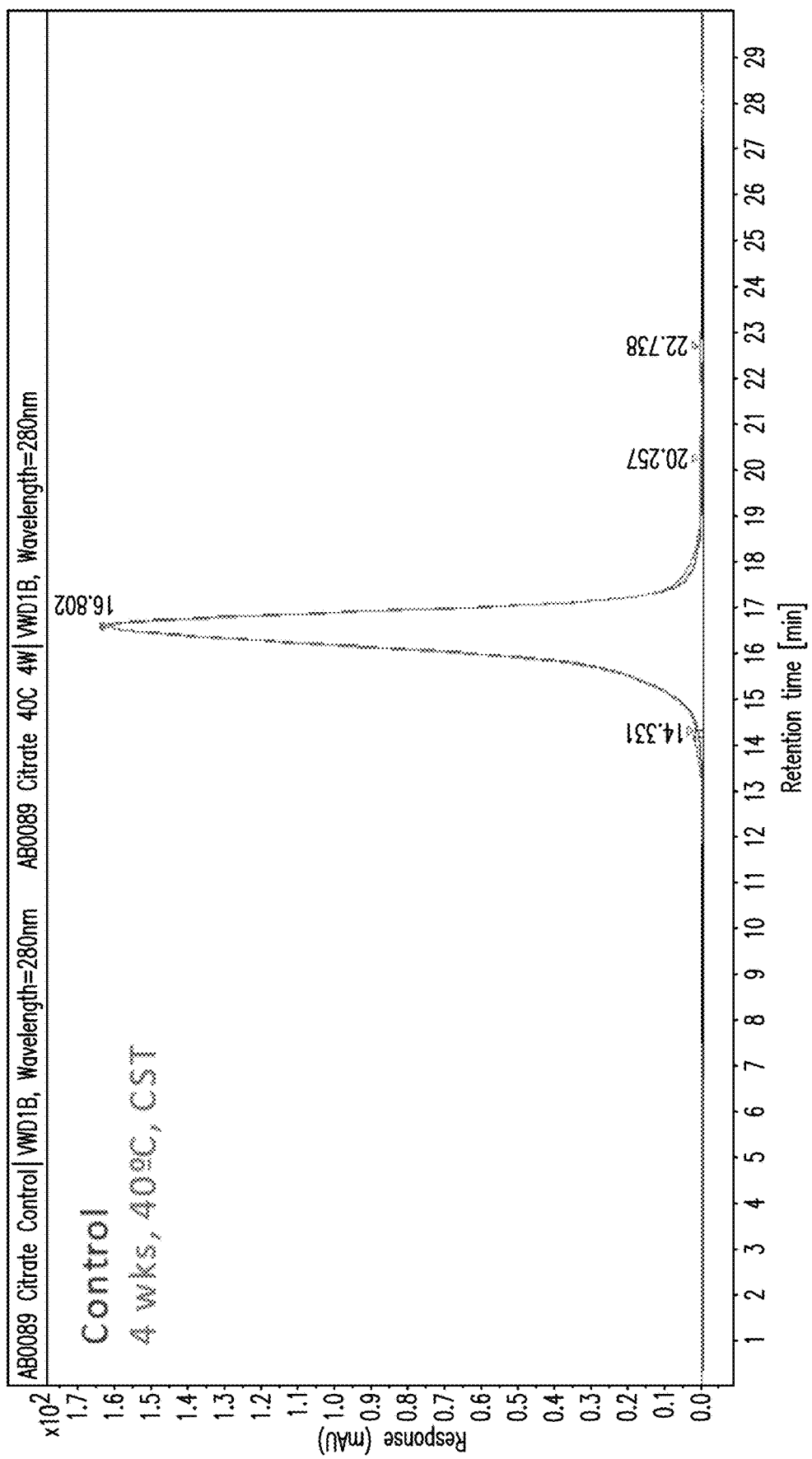

FIG. 163 shows that AB0089 demonstrated high stability after 4 weeks of incubation in CST, pH 7.0, at 40° C., compared to control sample as measured by SEC analysis.

Figure 164A:
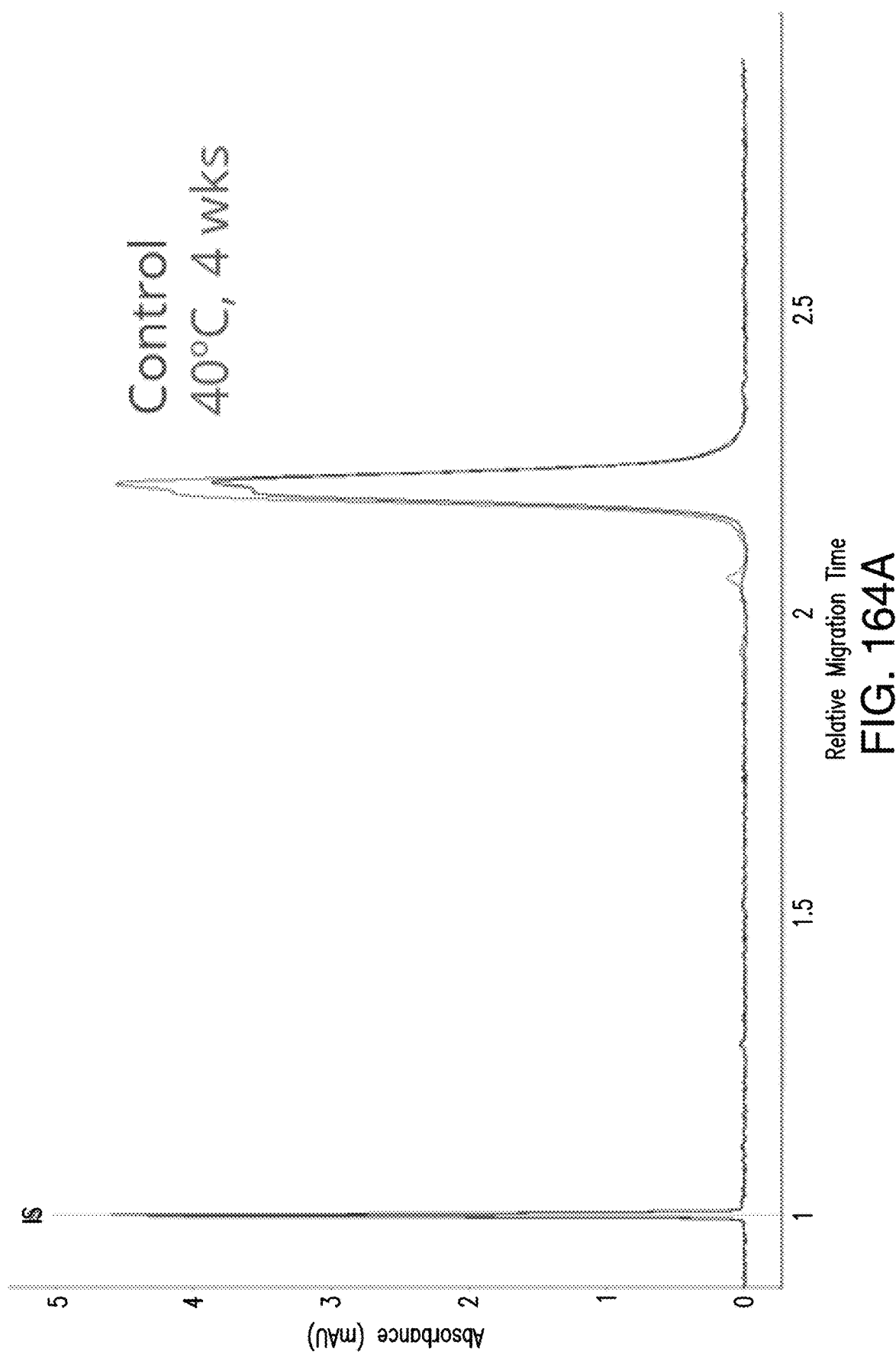
Figure 164B:
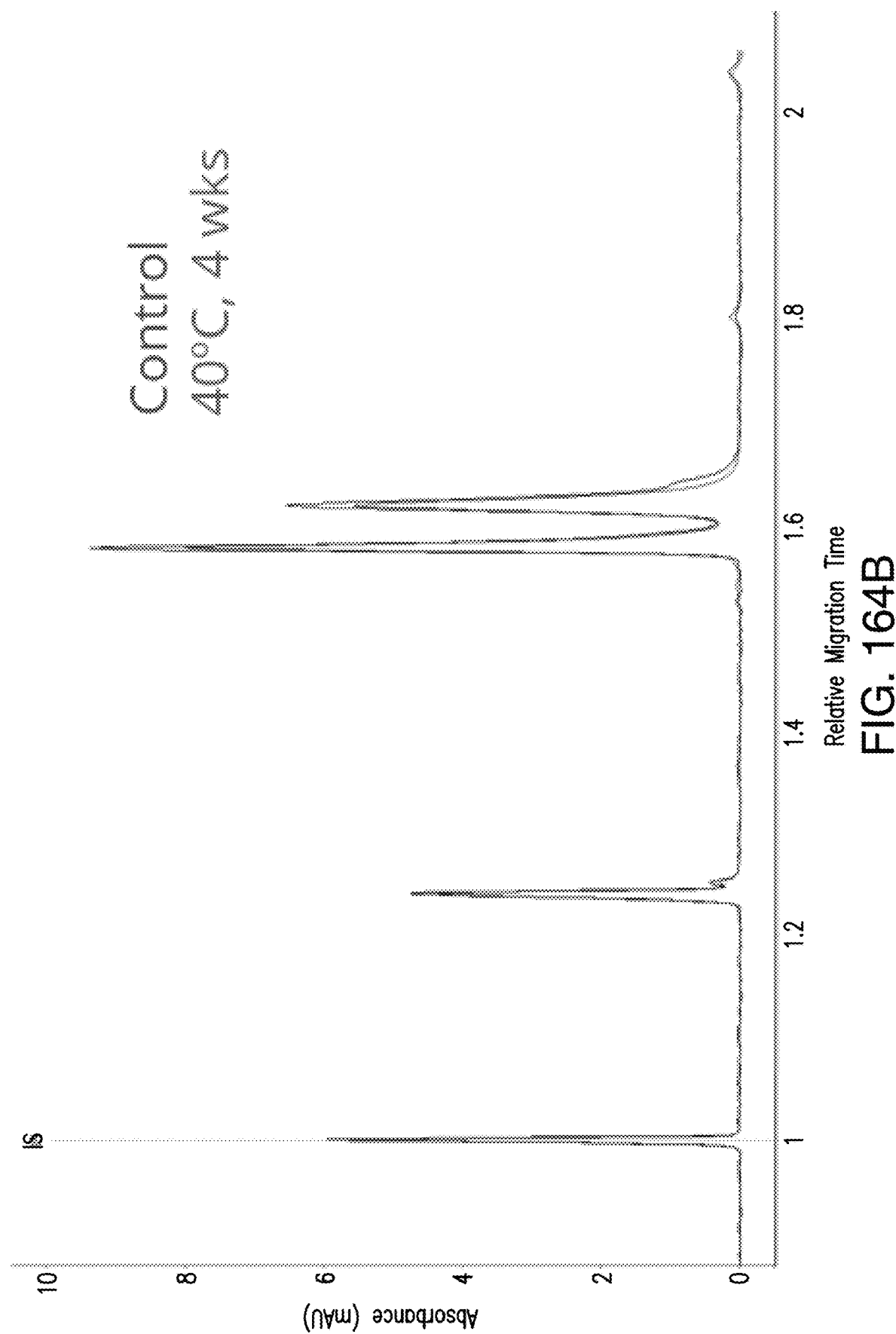

FIG. 164A-FIG. 164B show that no fragmentation of AB0089 was observed by CE-SDS after 4 weeks at 40° C. in CST, pH 7.0 compared to control sample. NR (FIG. 164A) and R (FIG. 164B).

Figure 165A:
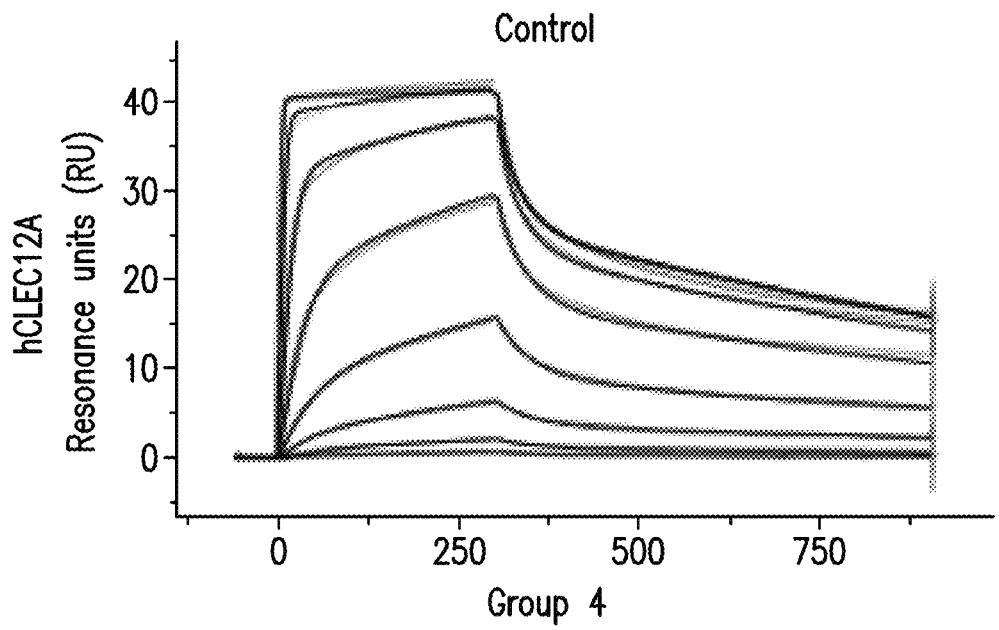
Figure 165B:
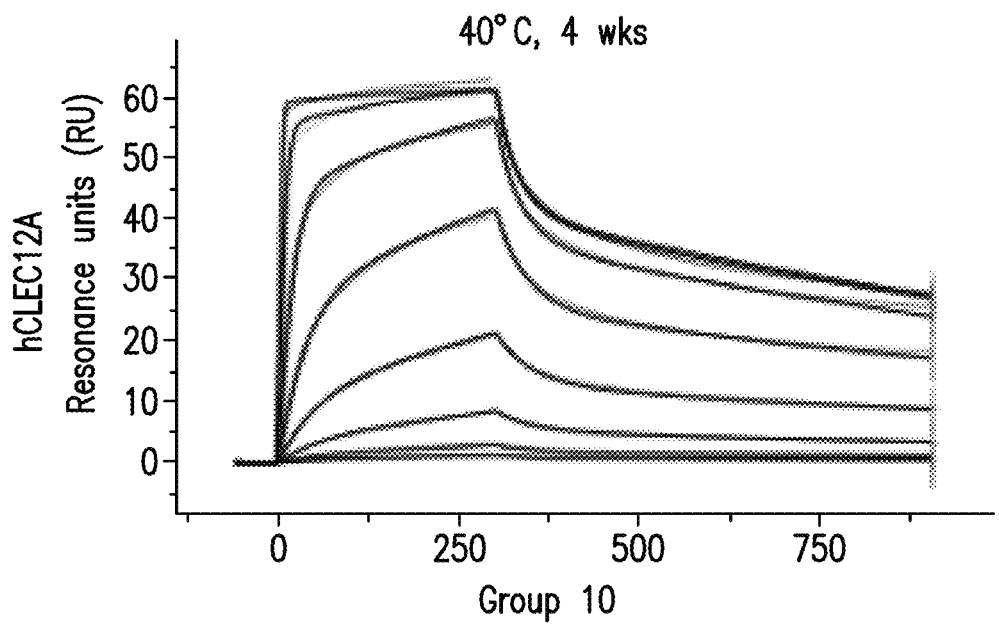
Figure 165C:
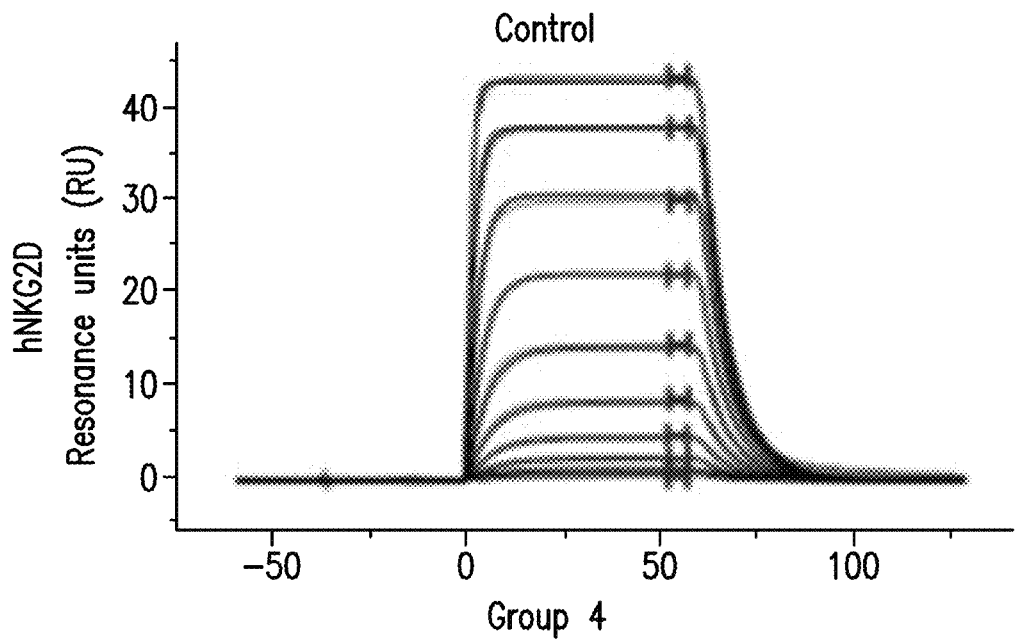
Figure 165D:
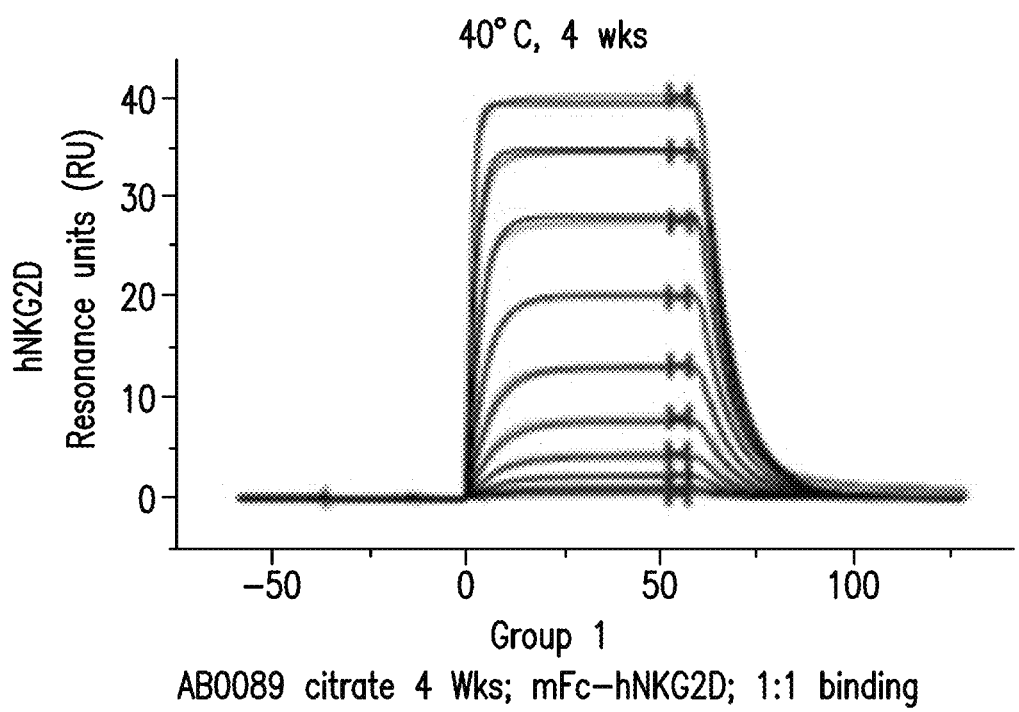
Figure 165E:
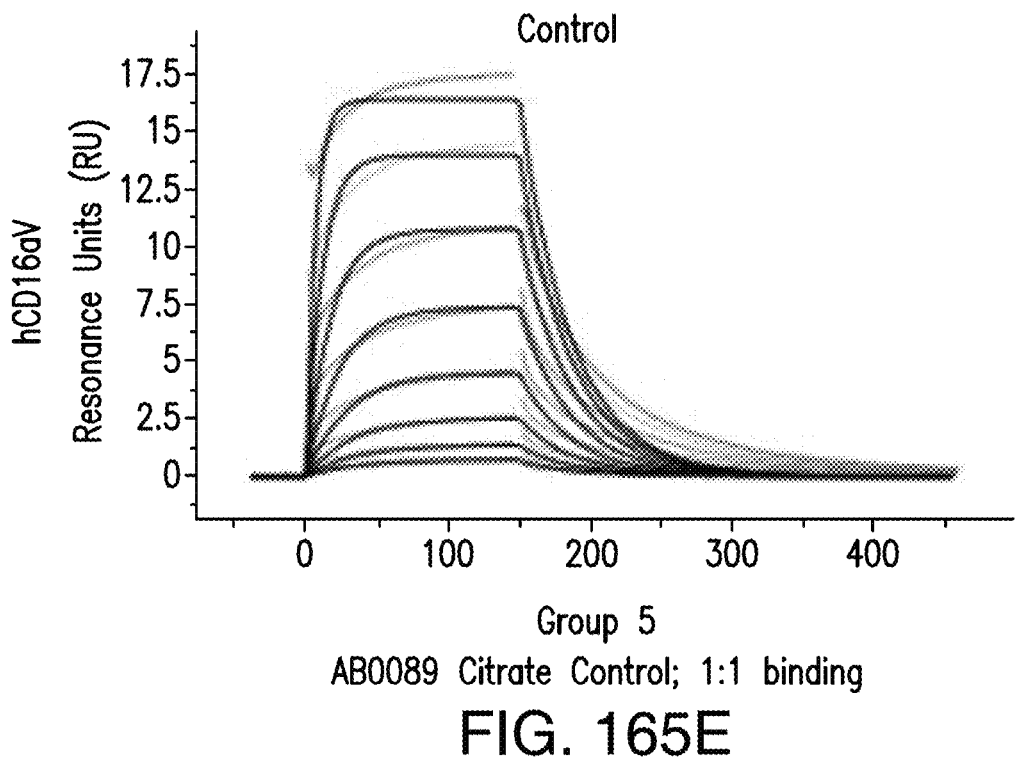
Figure 165F:
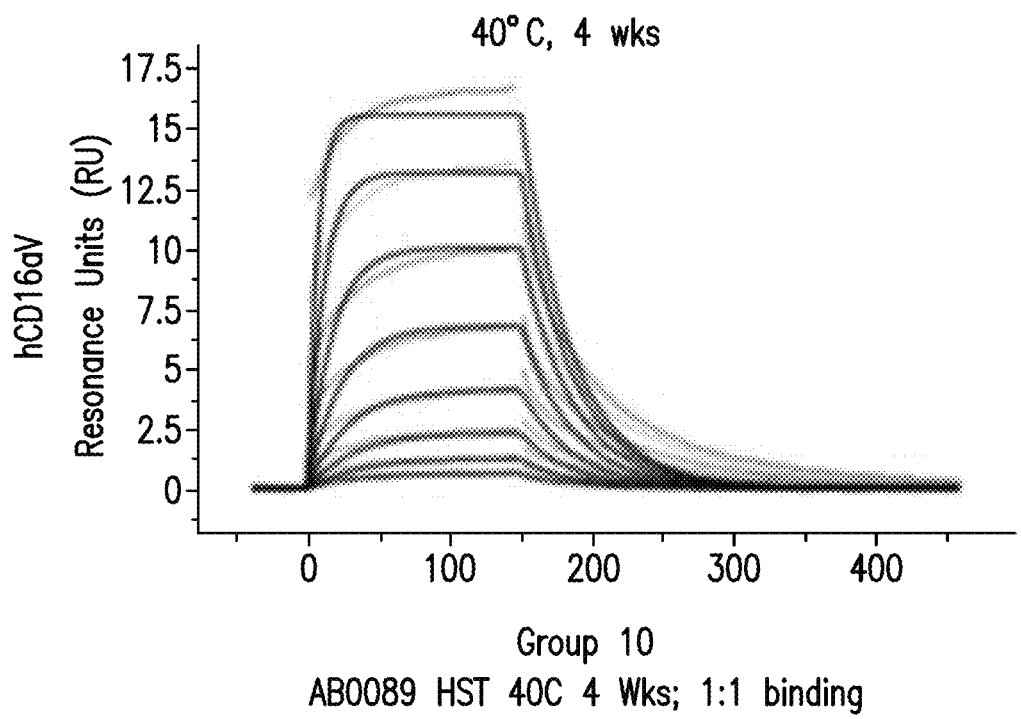

FIG. 165A-FIG. 165F shows that AB0089 is stable after 4 weeks at 40° C. in CST, pH 7.0, with no effect on binding to hCLEC12A (FIG. 165A and FIG. 165B), hNKG2D (FIG. 165C and FIG. 165D), or hCD16aV (FIG. 165E and FIG. 165F).

Figure 166:
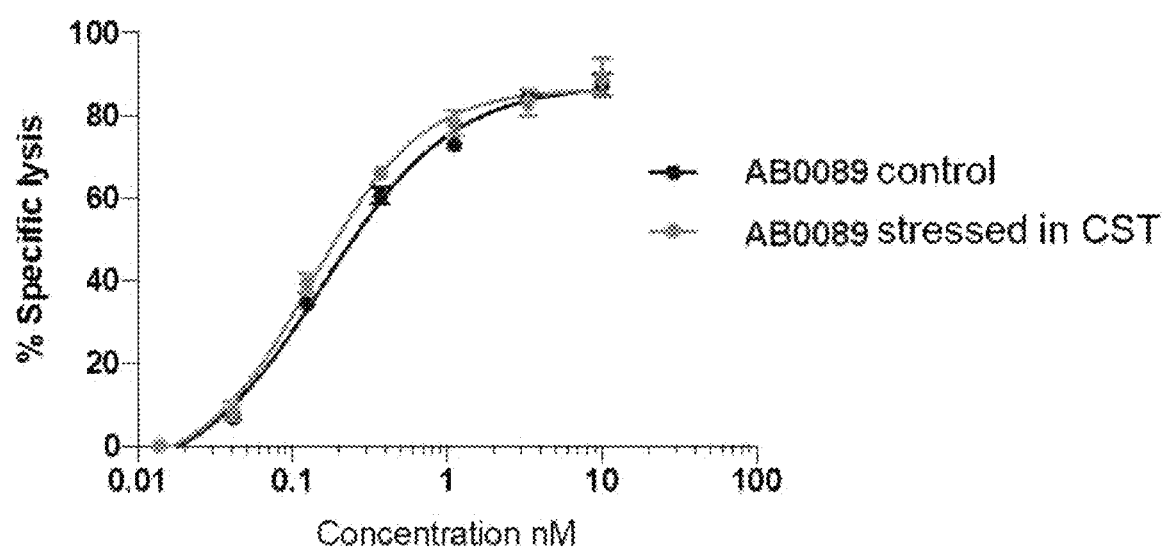

FIG. 166 shows that long term thermal stress did not affect potency of AB0089 after 4 weeks at 40° C. in CST, pH 7.0 compared to control.

FIG. 167A-FIG. 167C are a set of extracted ion chromatograms of the tryptic peptide encompassing CDRH3 of CLEC12a targeting arm of AB0089, which showed no evidence of aspartic acid isomerization in the peptide encompassing the CLEC12A binding CDRH3 was observed, based on manual inspection of peak shape.

Figure 168:
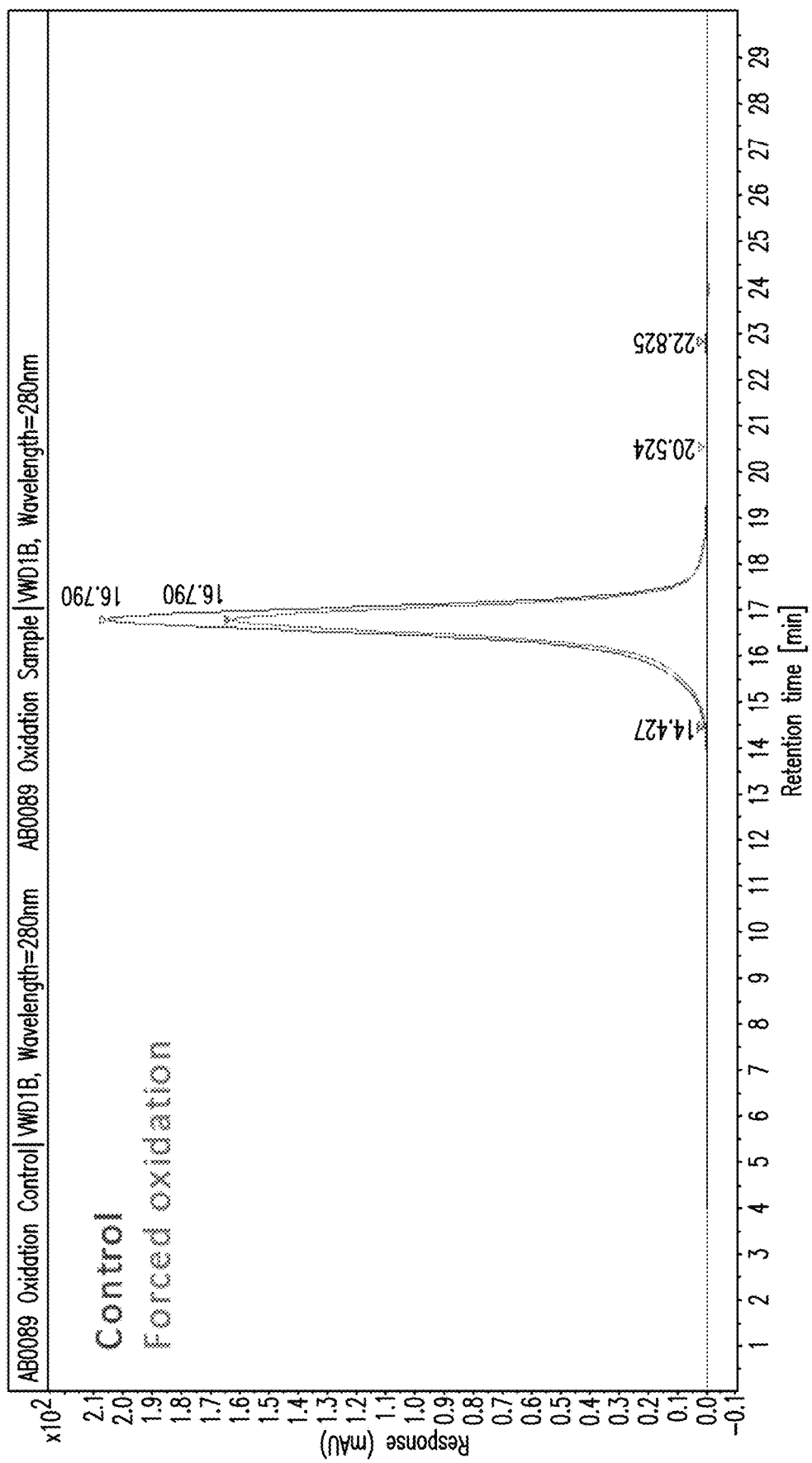

FIG. 168 is an SEC analysis showing that there is no difference in monomer content between oxidized AB0089 and control sample after forced oxidation.

Figure 169A:
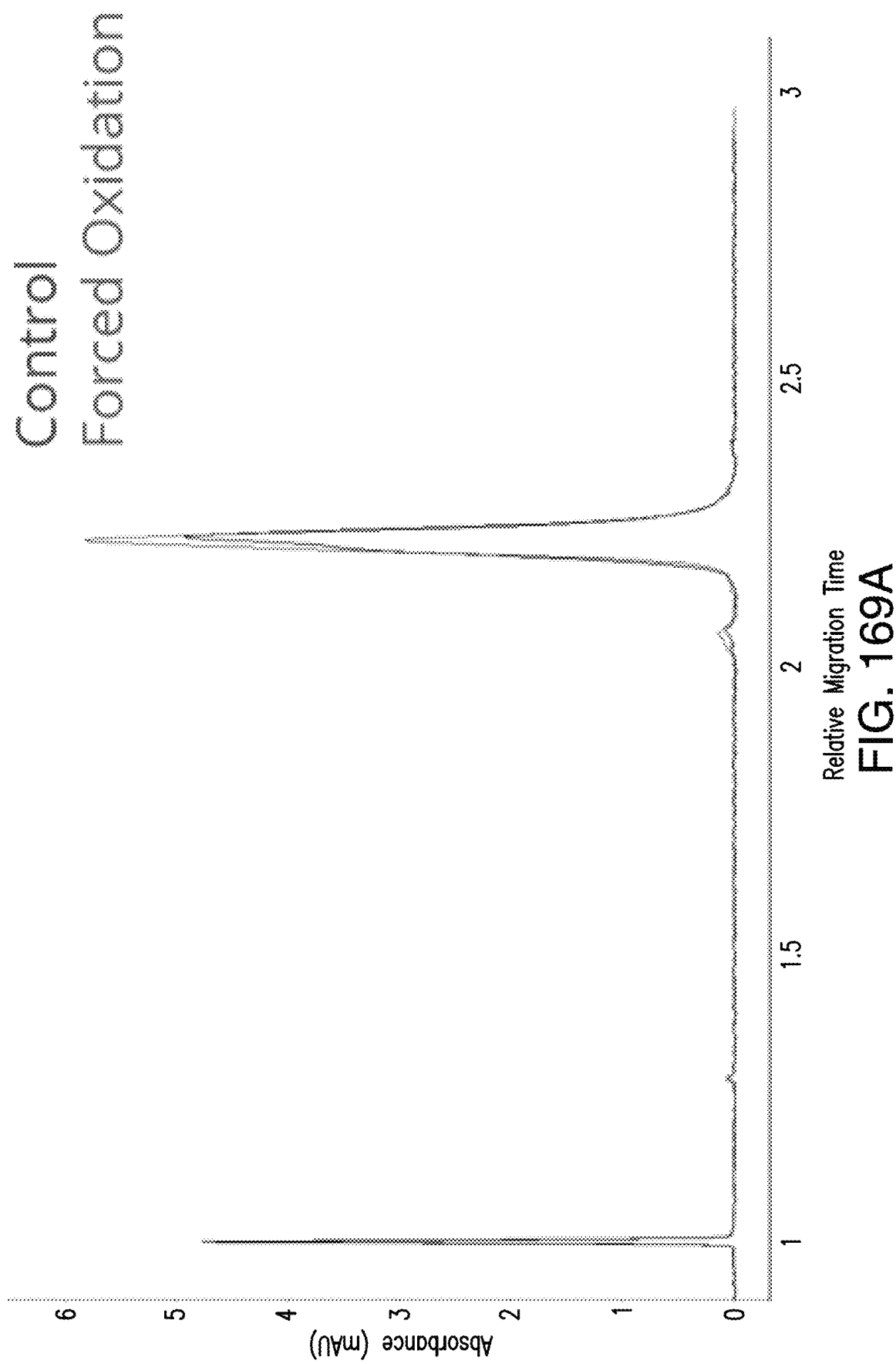
Figure 169B:
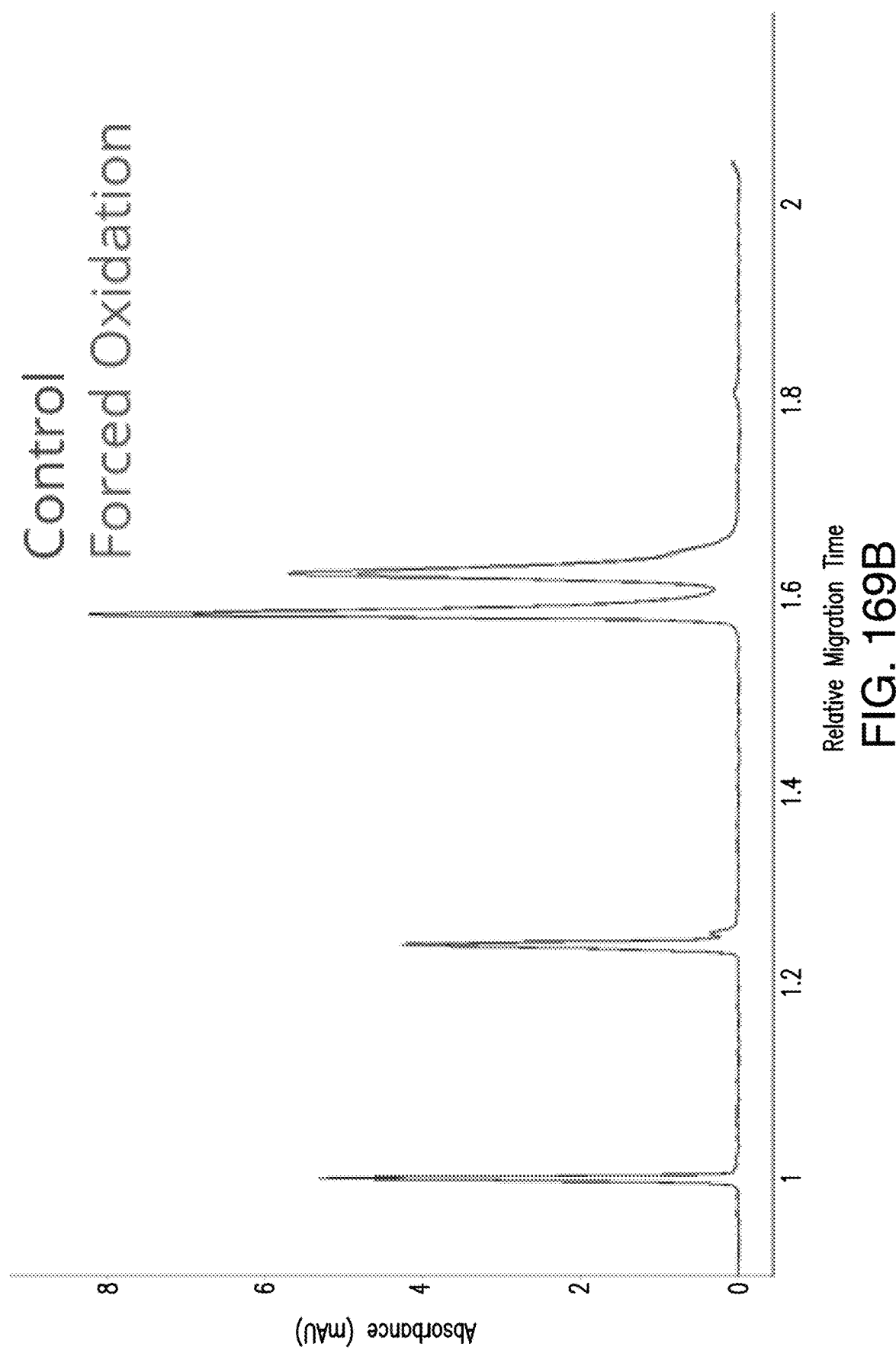

FIG. 169A-FIG. 169B show that no fragmentation of AB0089 was observed by CE-SDS after forced oxidation compared to control sample. NR (FIG. 169A) and R (FIG. 169B).

Figure 170A:
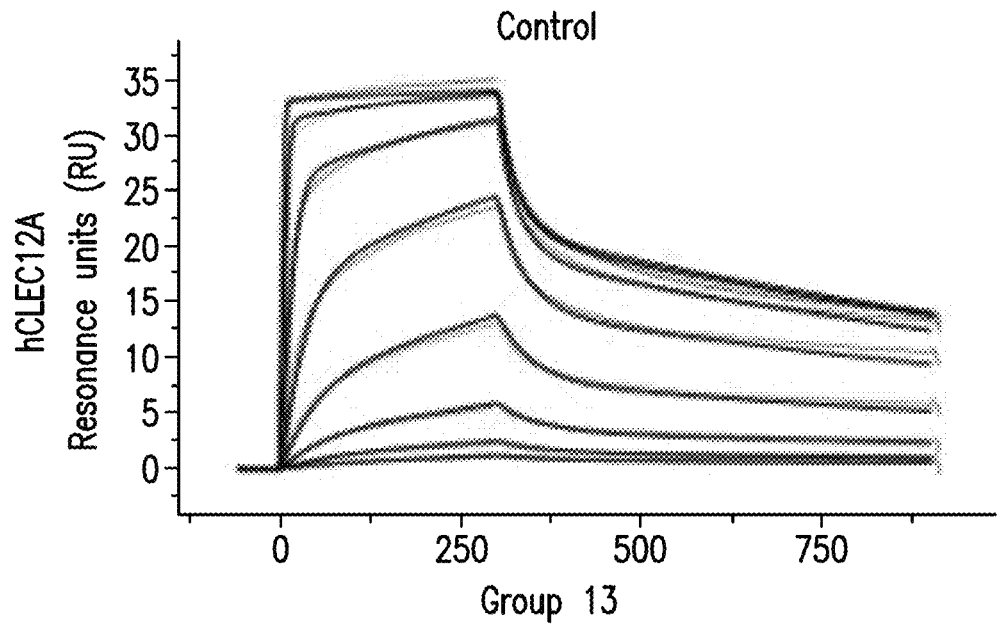
Figure 170B:
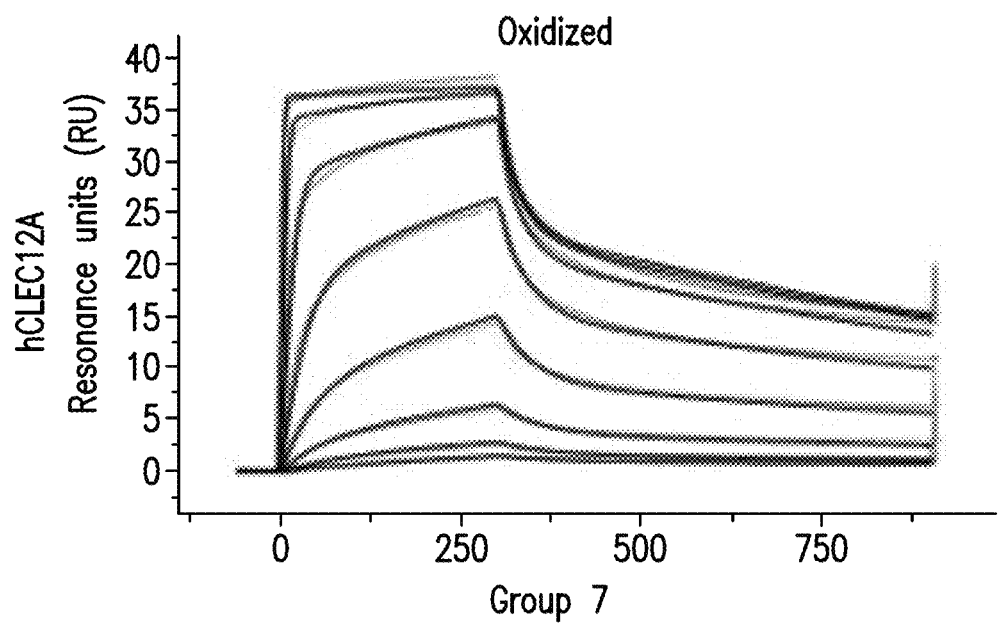
Figure 170C:
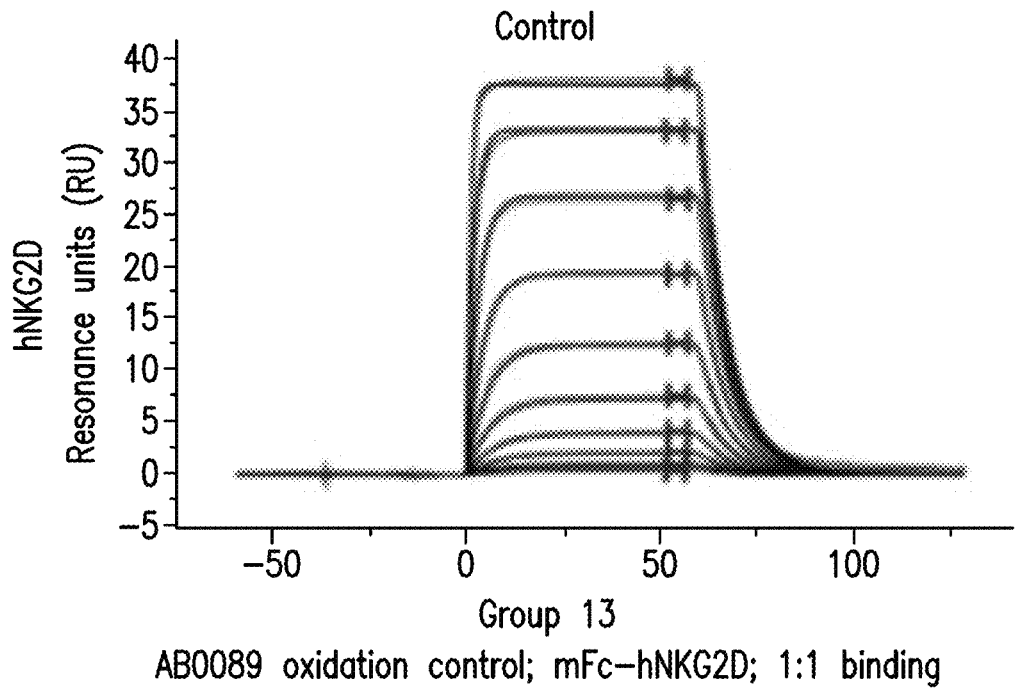
Figure 170D:
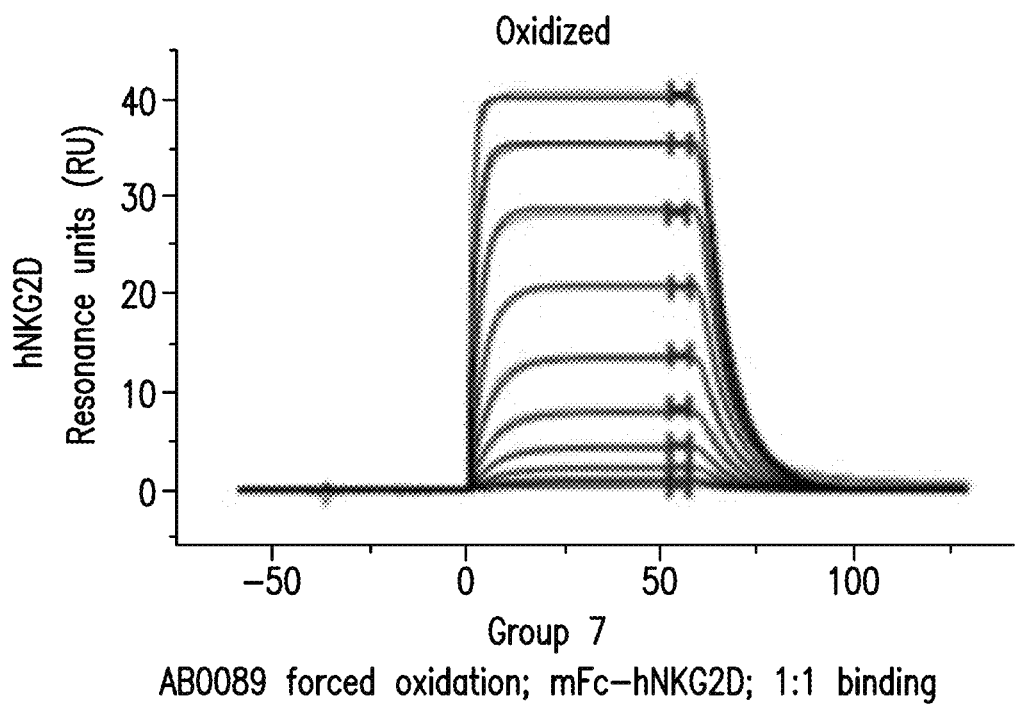
Figure 170E:
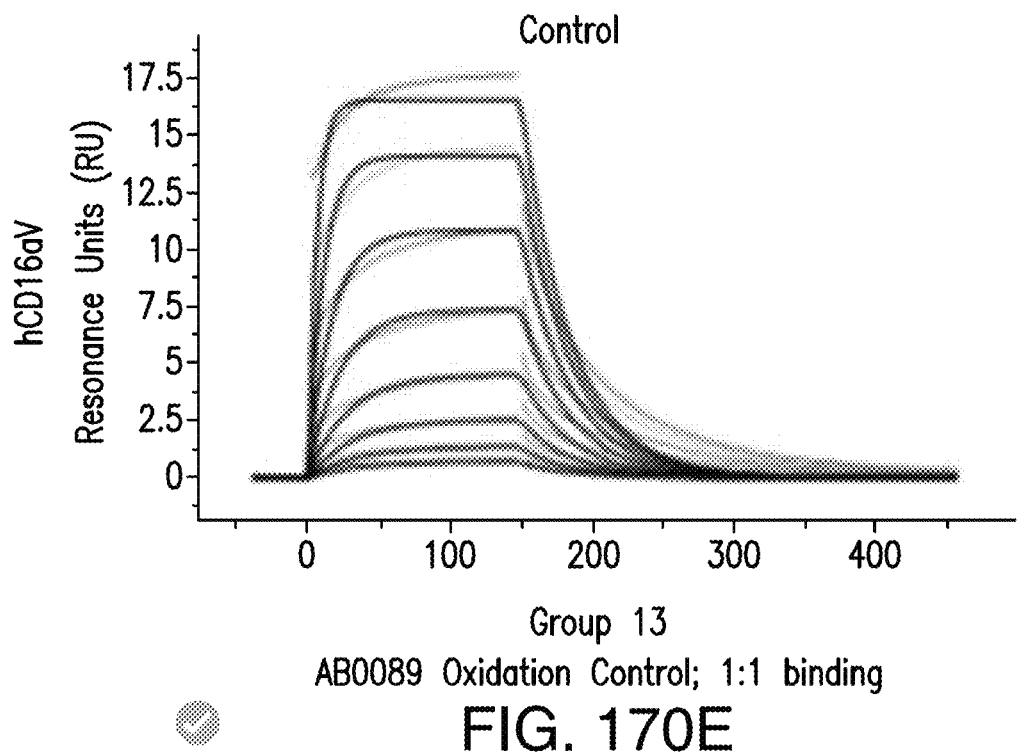
Figure 170F:
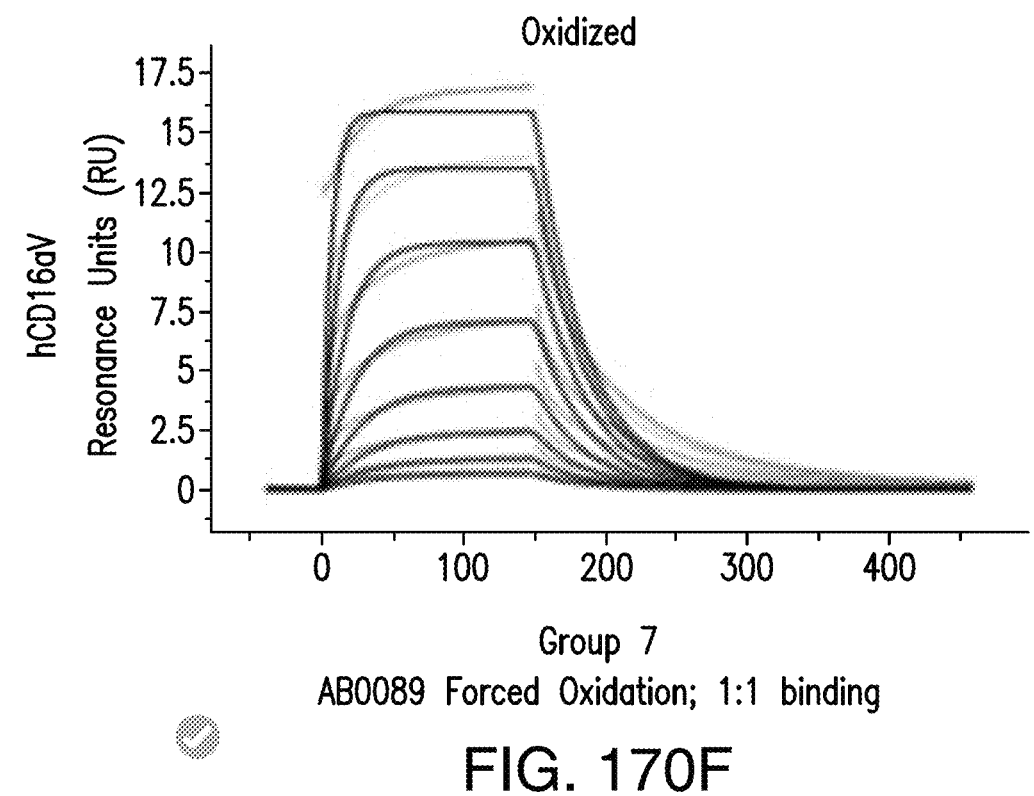

FIG. 170A-FIG. 170F show that oxidative stress had no significant effect on the active protein content or on the affinities for hCLEC12A (FIG. 170A and 170B), hNKG2D (FIGS. 170C and 170D), and hCD16aV (FIGS. 170E and 170F).

Figure 171:
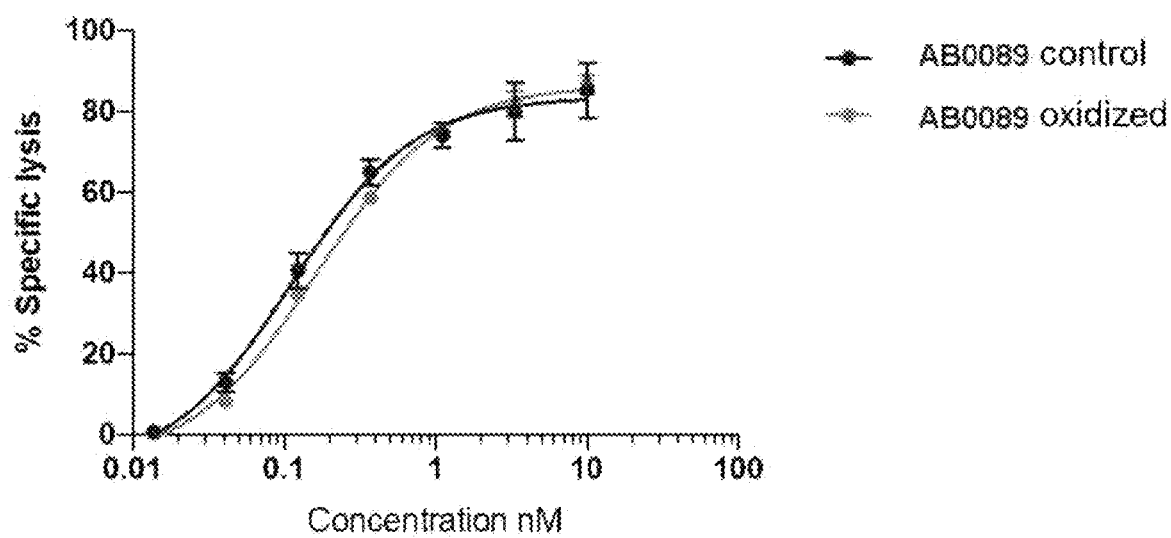

FIG. 171 shows that AB0089 is stable in forced oxidation.

Figure 172:
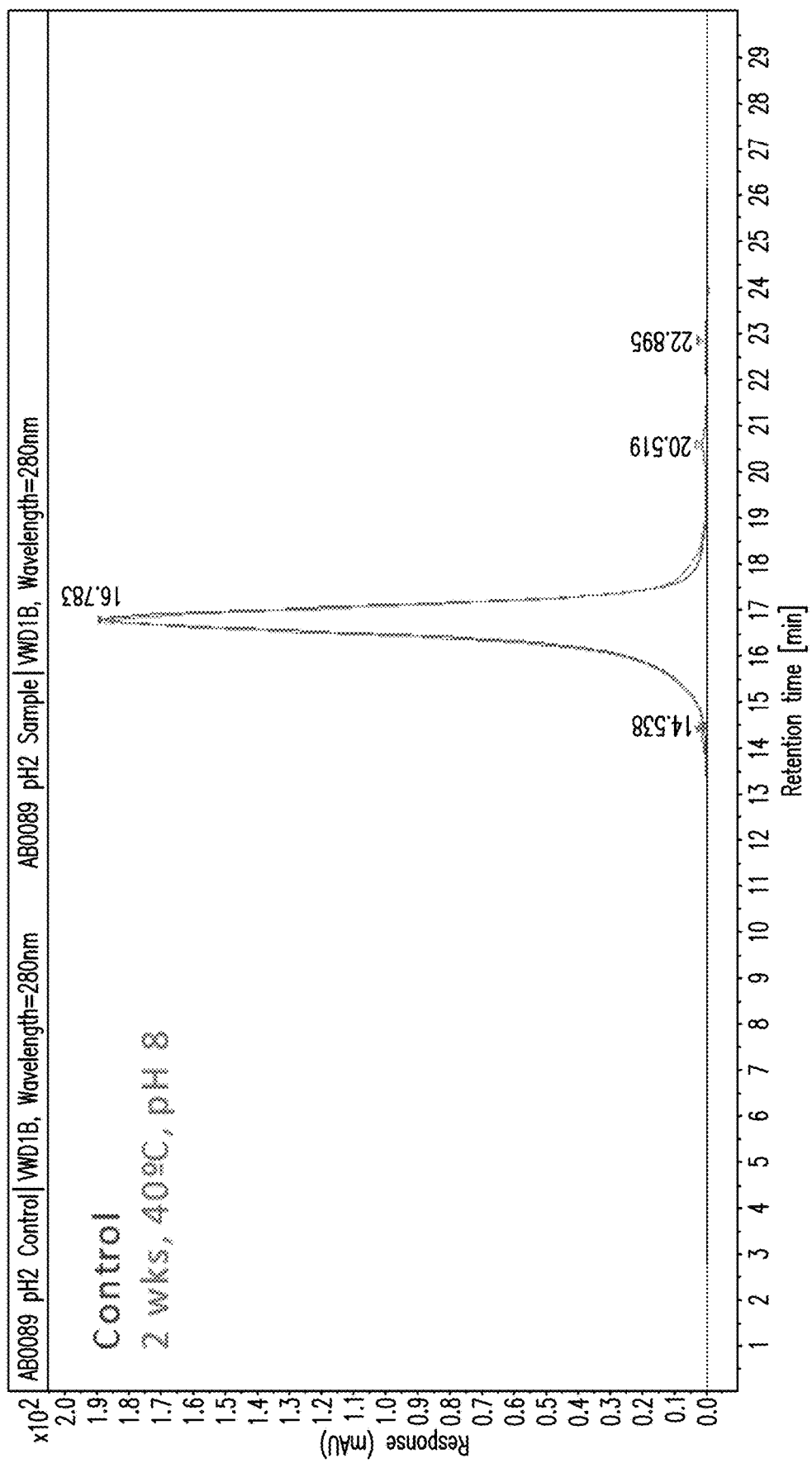

FIG. 172 is an SEC analysis showing that AB0089 is stable under high pH stress (pH 8.0, 40° C., 2 weeks).

Figure 173A:
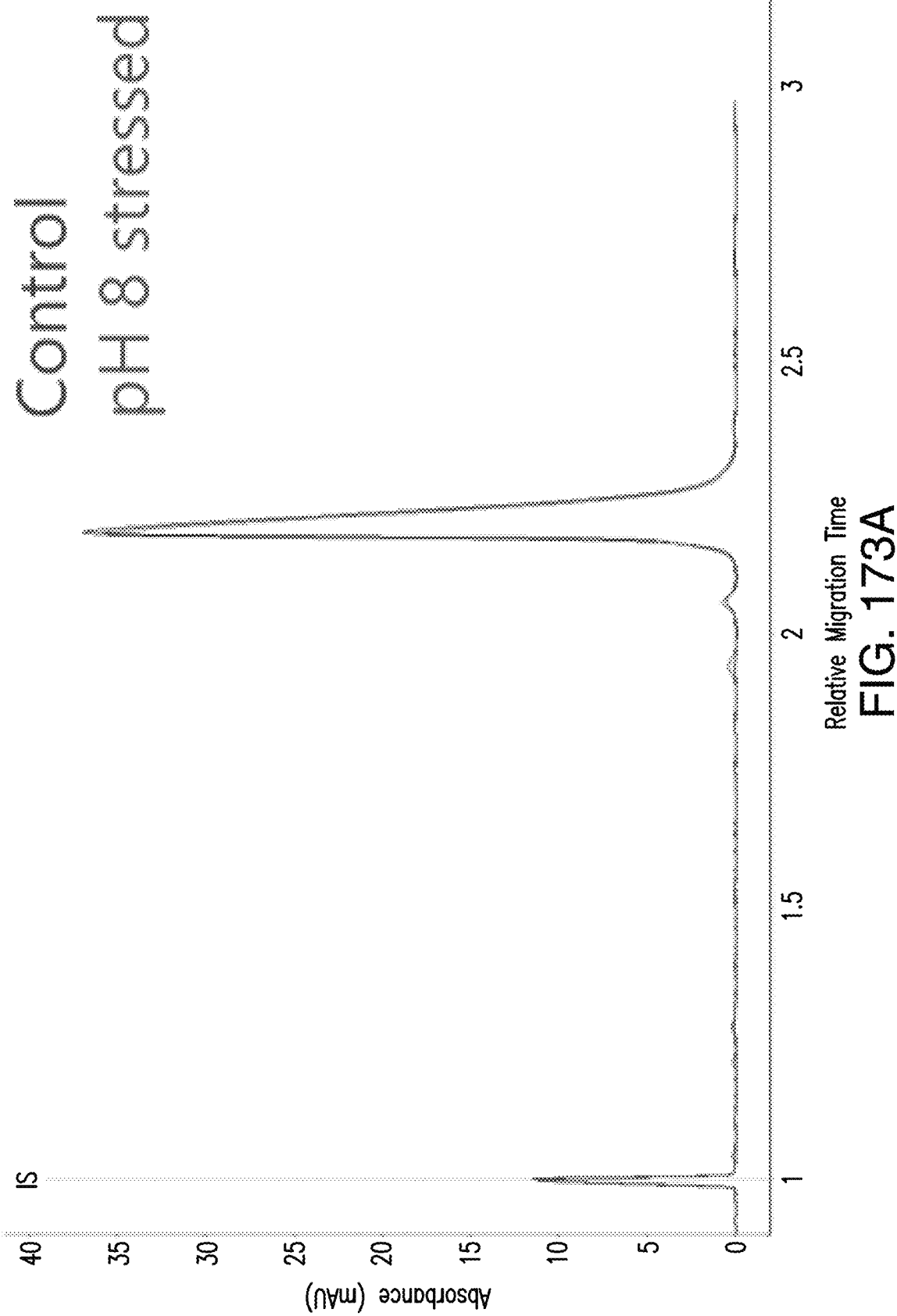
Figure 173B:
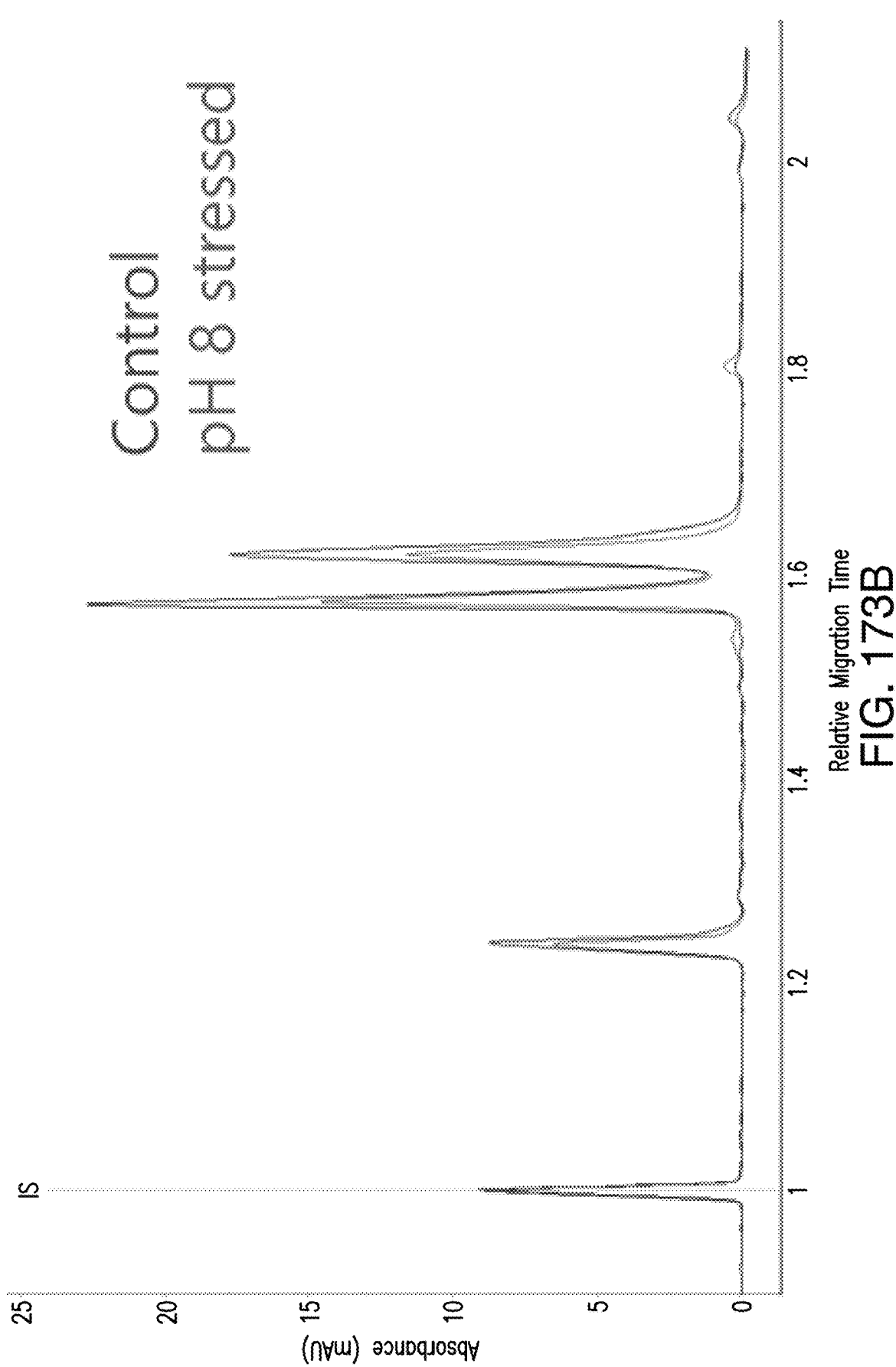

FIG. 173A-FIG. 173B is an CE-SDS analysis showing that AB0089 exhibited low levels of degradation AB0089 after long term high pH stress (pH 8, 40° C., 2 weeks). NR (FIG. 173A) and R (FIG. 173B).

Figure 174:
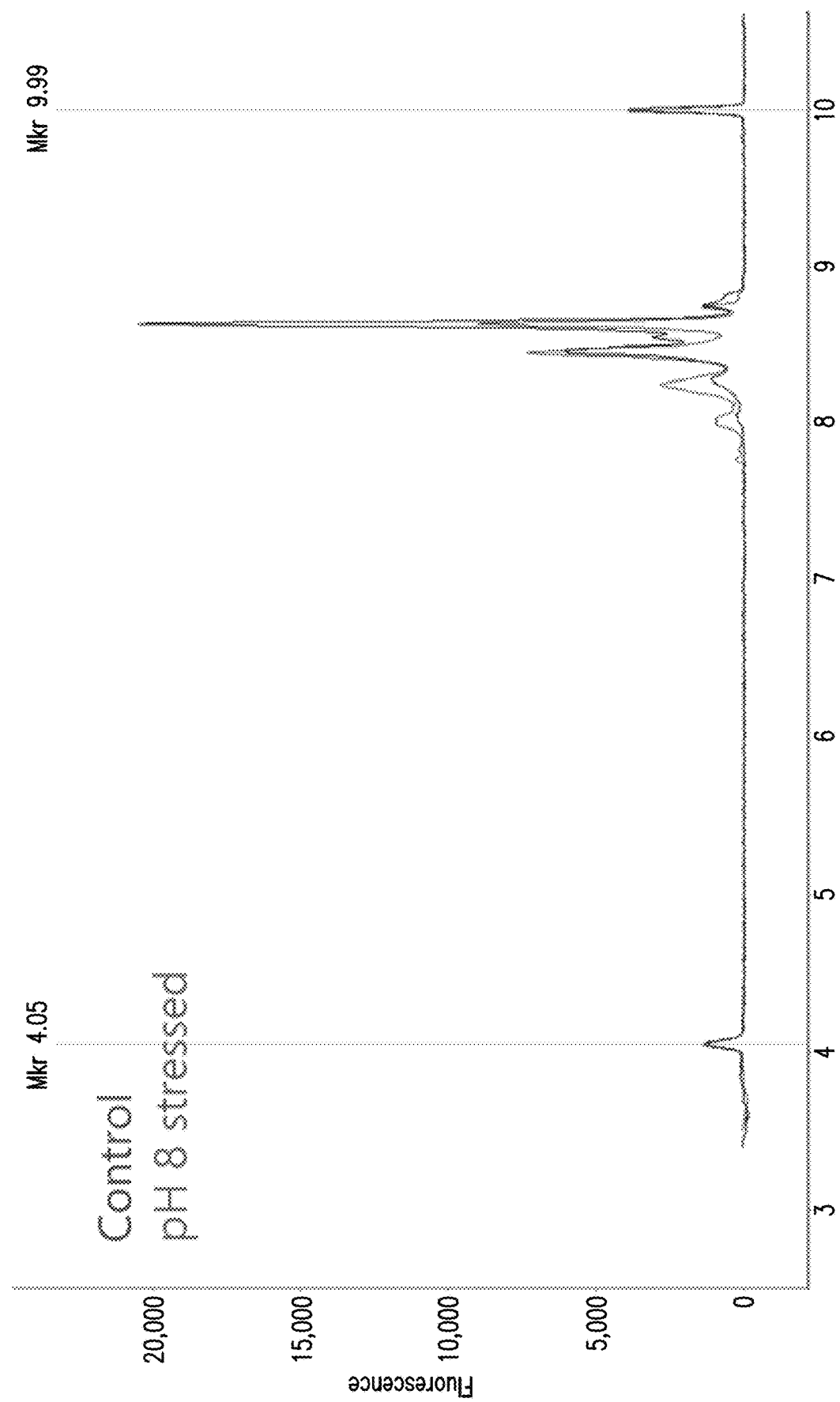
Figure 175A:
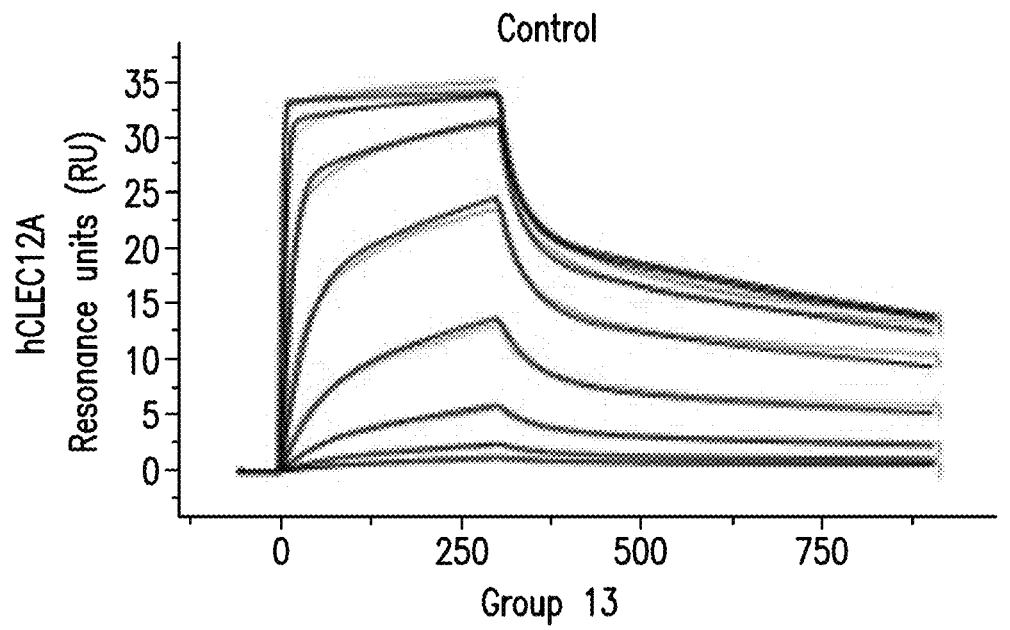
Figure 175B:
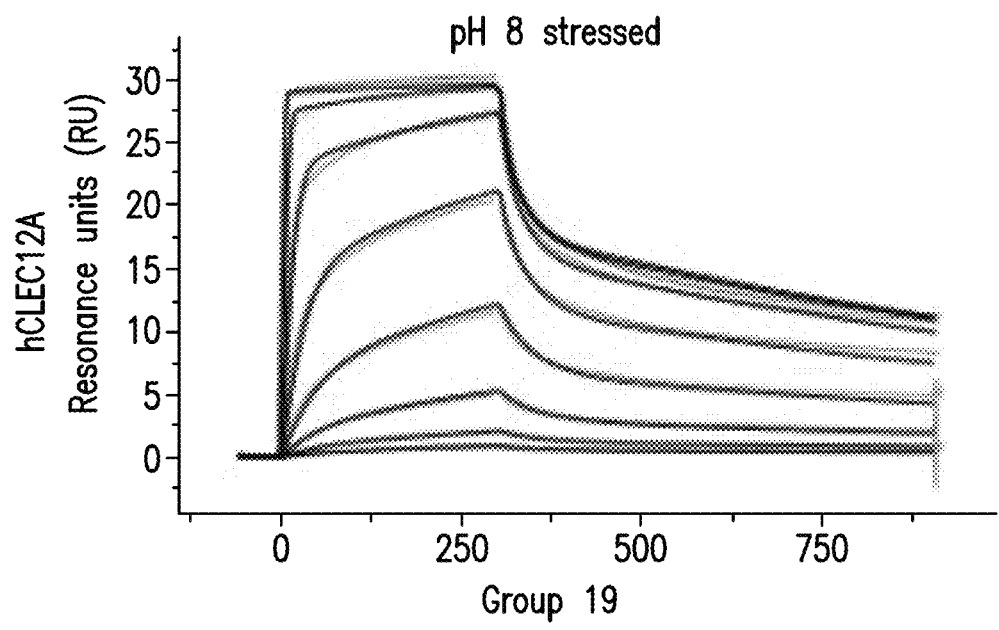
Figure 175C:
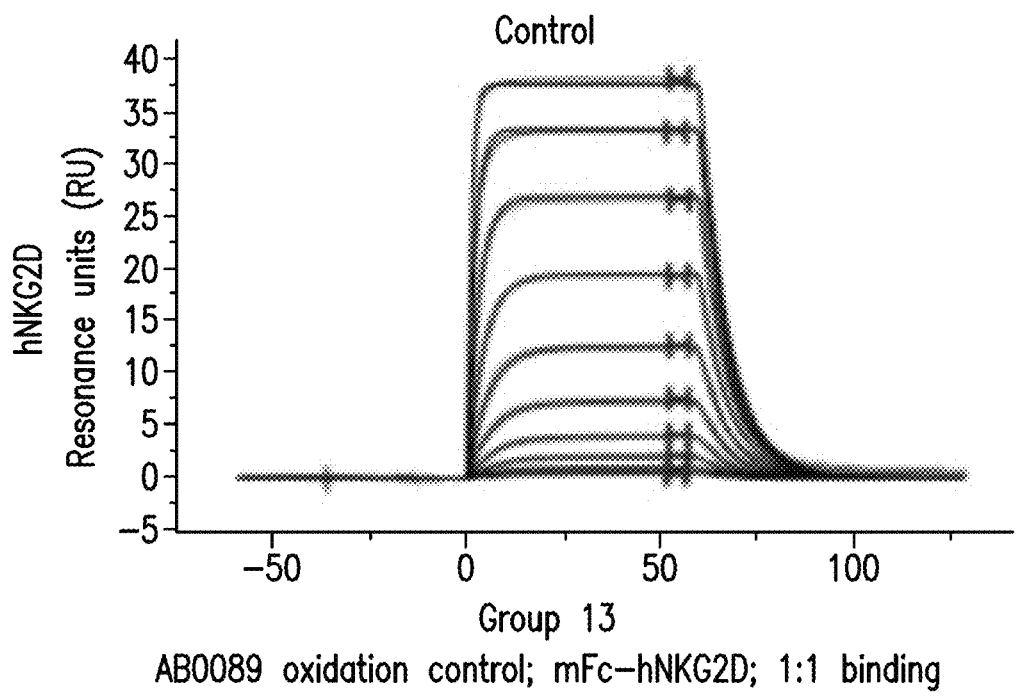
Figure 175D:
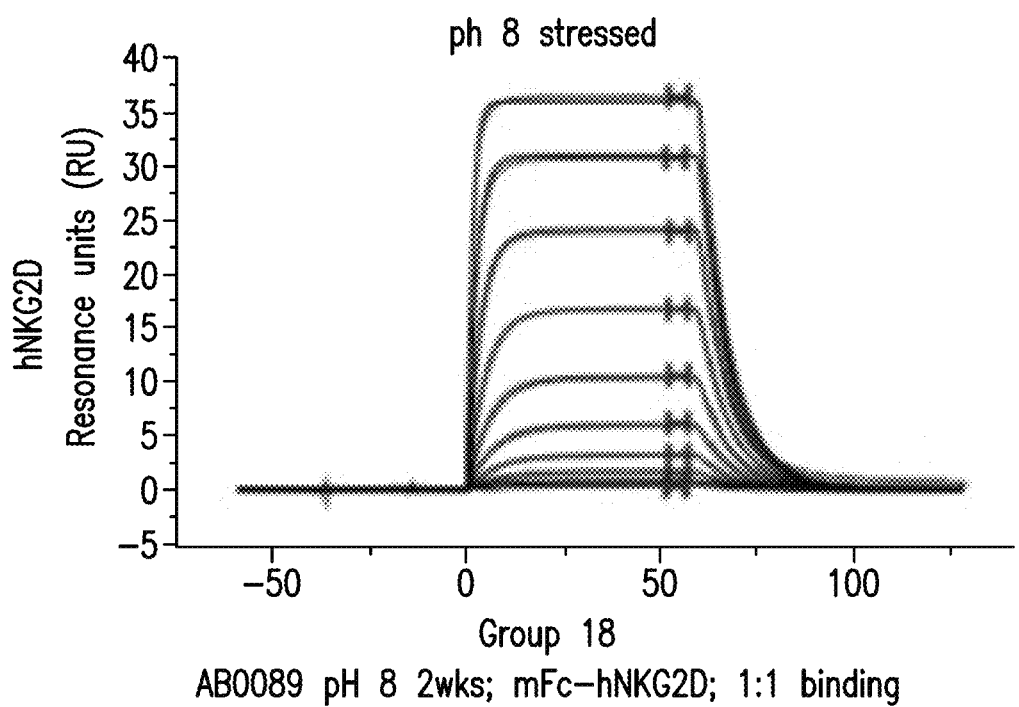
Figure 175E:
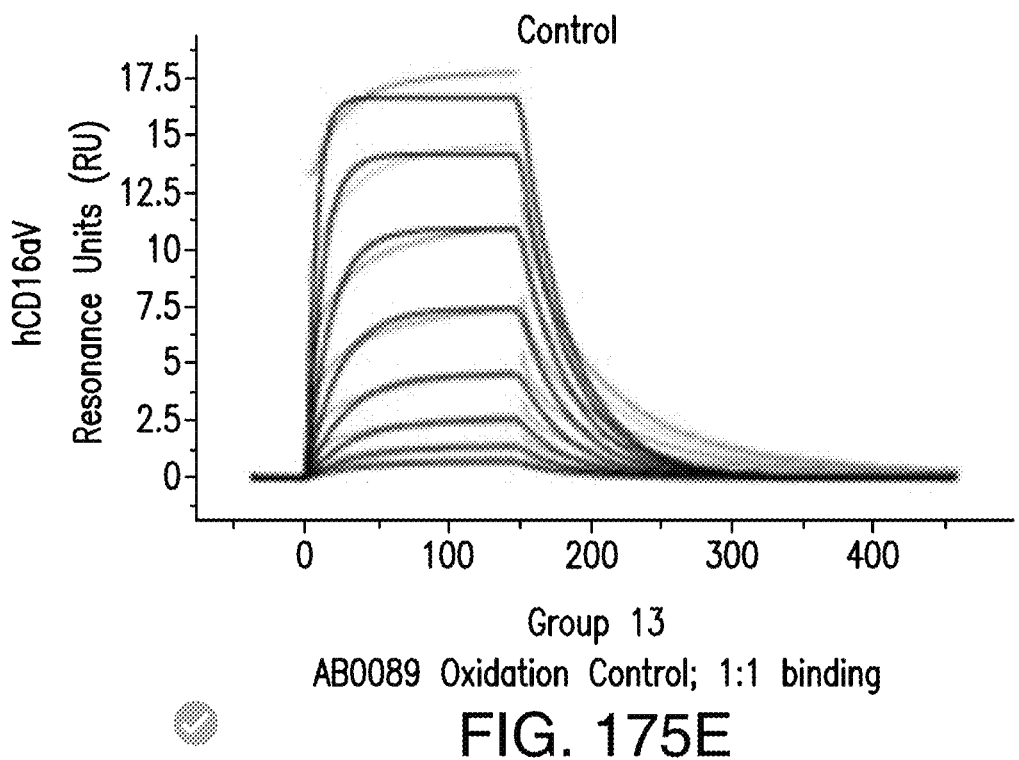
Figure 175F:
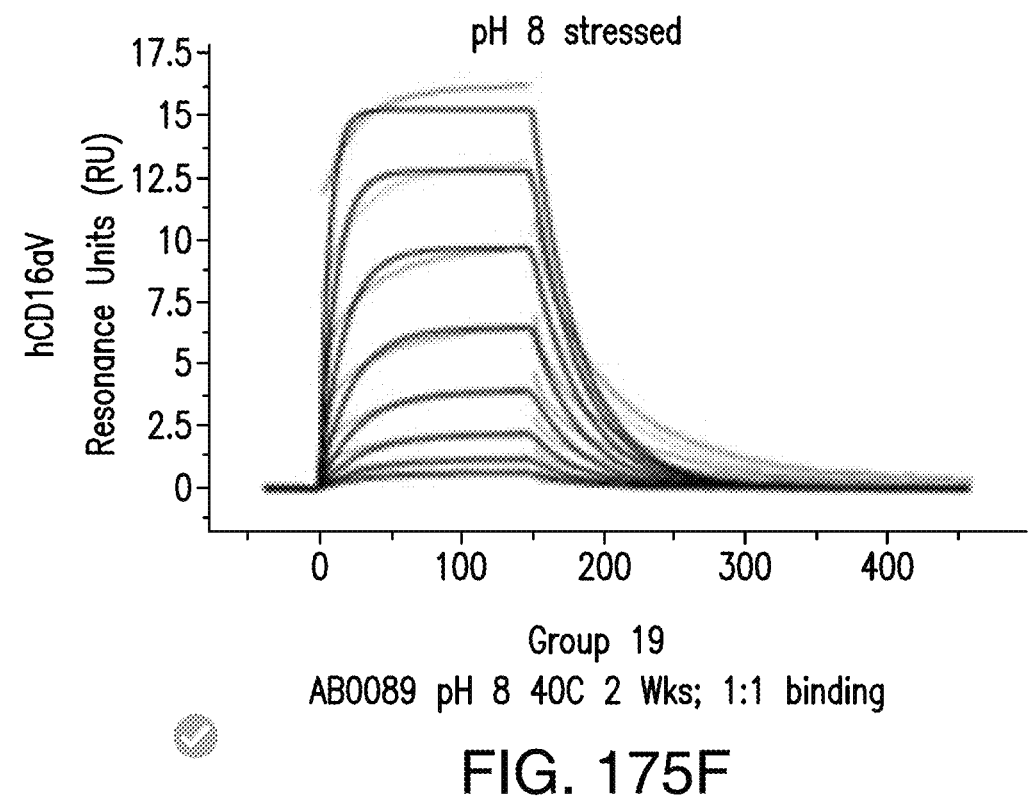

FIG. 174 is a cIEF showing that AB0089 exhibited an acidic shift after long term high pH exposure (pH 8, 40° C., 2 weeks).

FIG. 175A-FIG. 175F show that there was no meaningful difference in the amount of active protein or in the affinities for hCLEC12A (FIGS. 175A and 175B), hNKG2D (FIGS. 175C and 175D), or hCD16aV (FIGS. 175E and 175F) between stressed and control samples after long term high pH 8.0 stress (pH 8, 40° C., 2 weeks).

Figure 176:
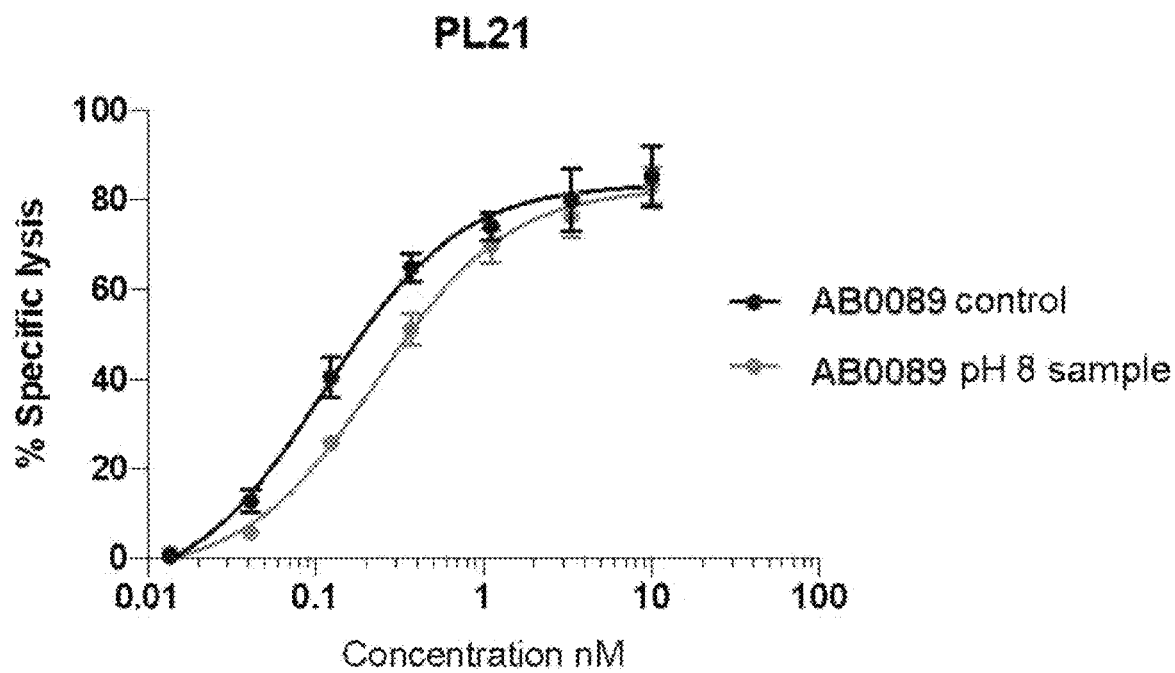

FIG. 176 shows that the potency of AB0089 was reduced approximately 2-fold after long term high pH stress (pH 8, 40° C., 2 weeks).

Figure 177:
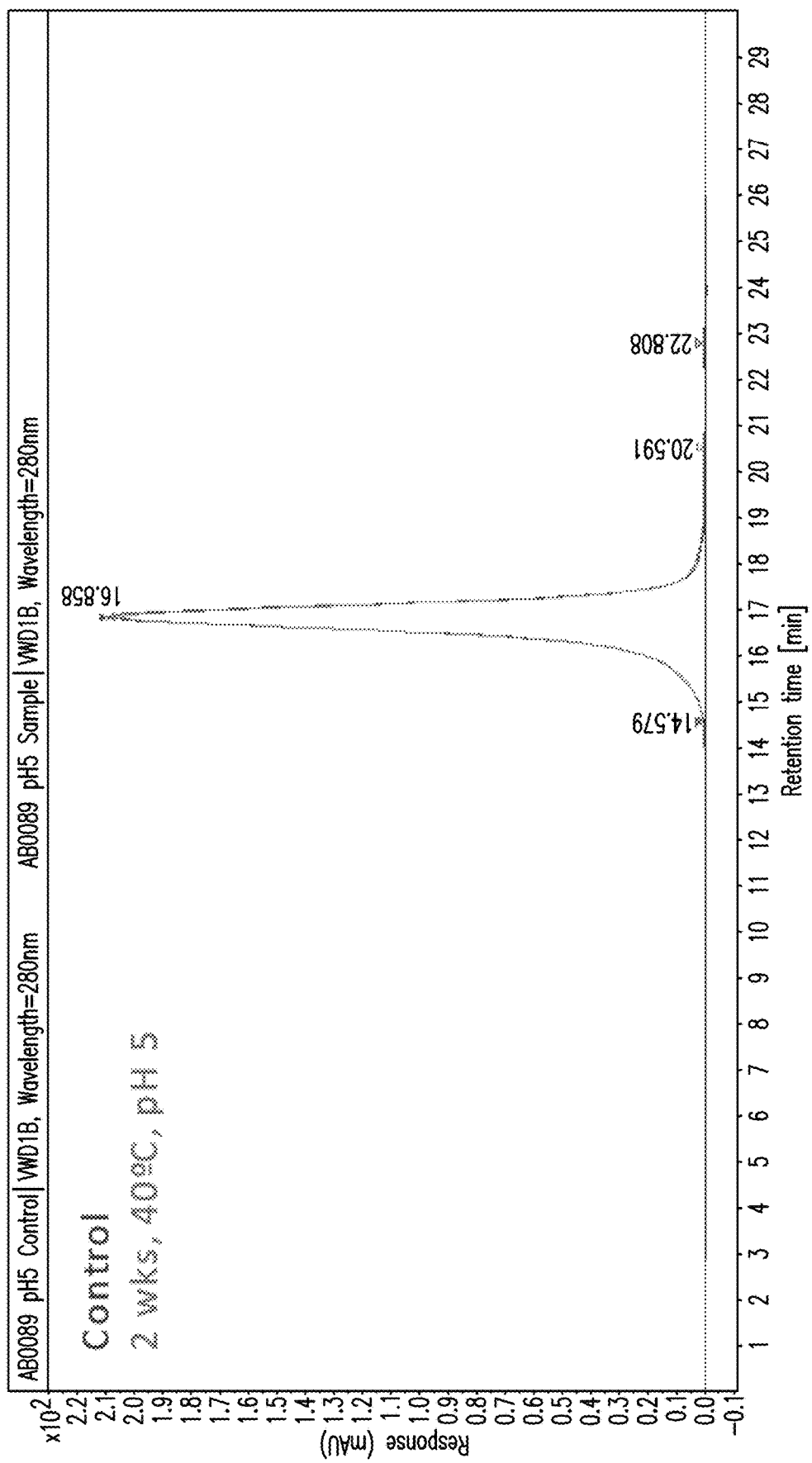

FIG. 177 is an SEC analysis showing that AB0089 is highly stable under low pH stress (pH 5.0, 40° C., 2 weeks).

Figure 178A:
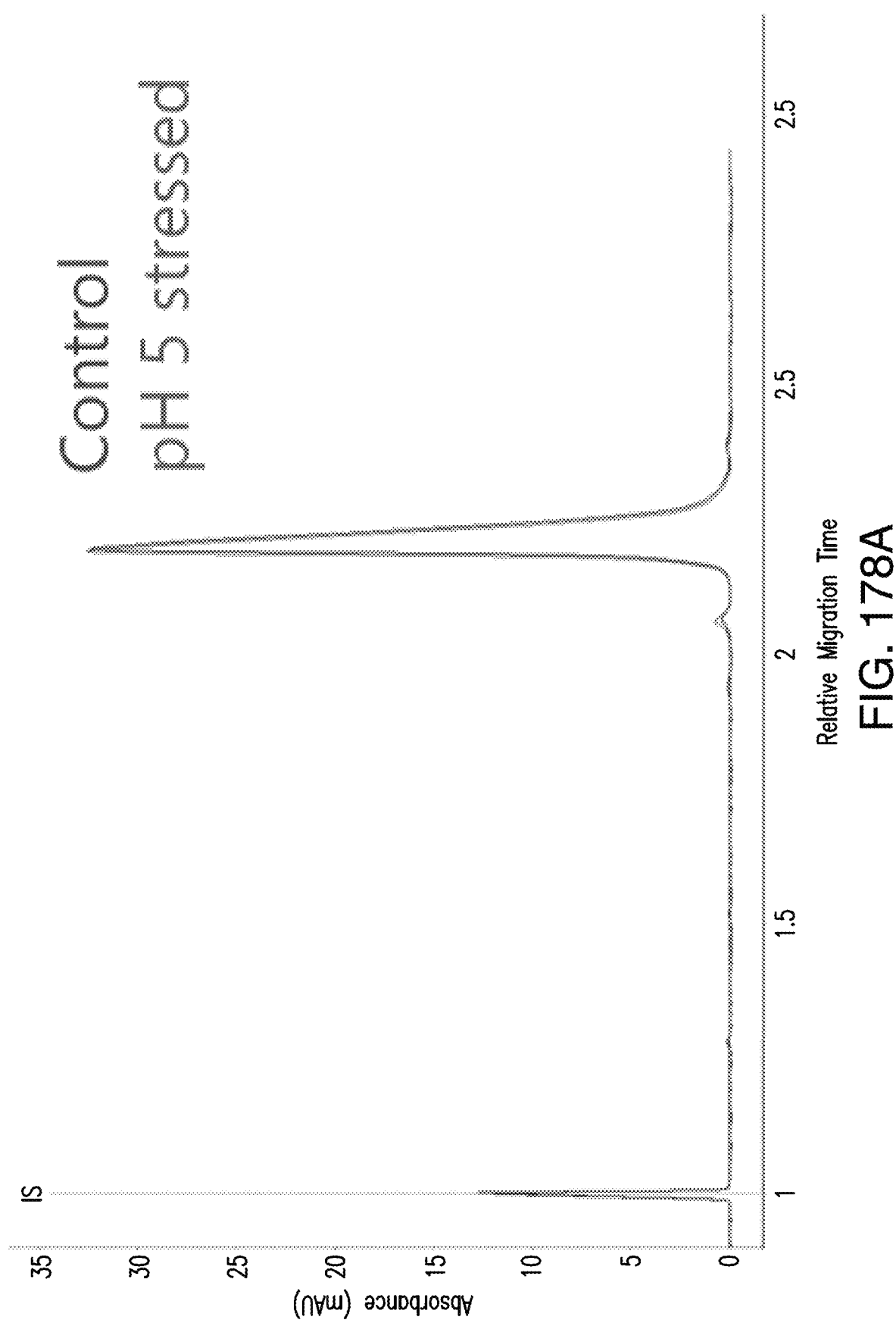
Figure 178B:
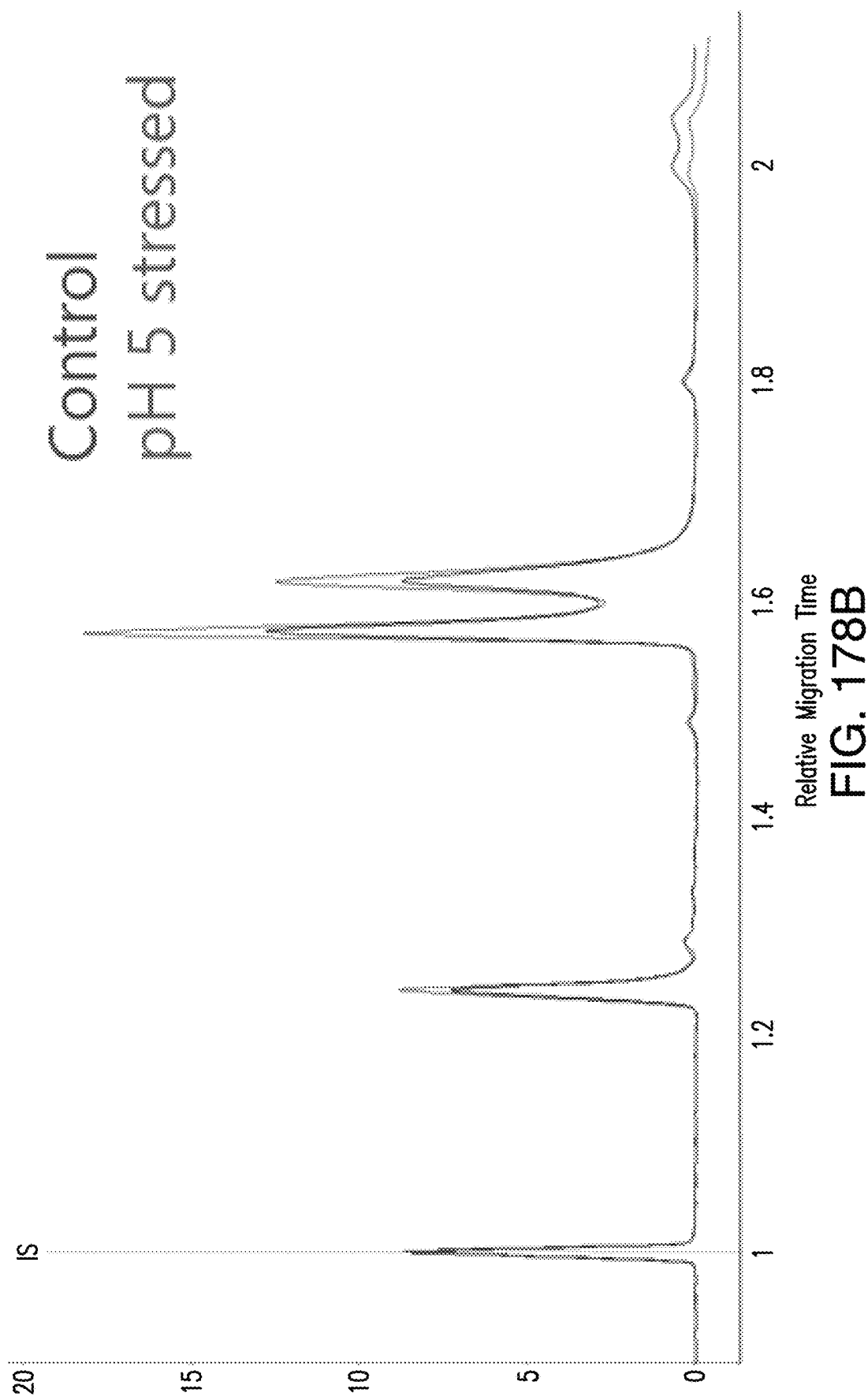

FIG. 178A-FIG. 178B is a CE-SDS analysis of AB0089 after long term low pH stress (pH 5.0 40° C., 2 weeks) showing that low levels of AB0089 degradation were detected by non-reduced (FIG. 178A) and reduced (FIG. 178B) CE-SDS.

Figure 179:
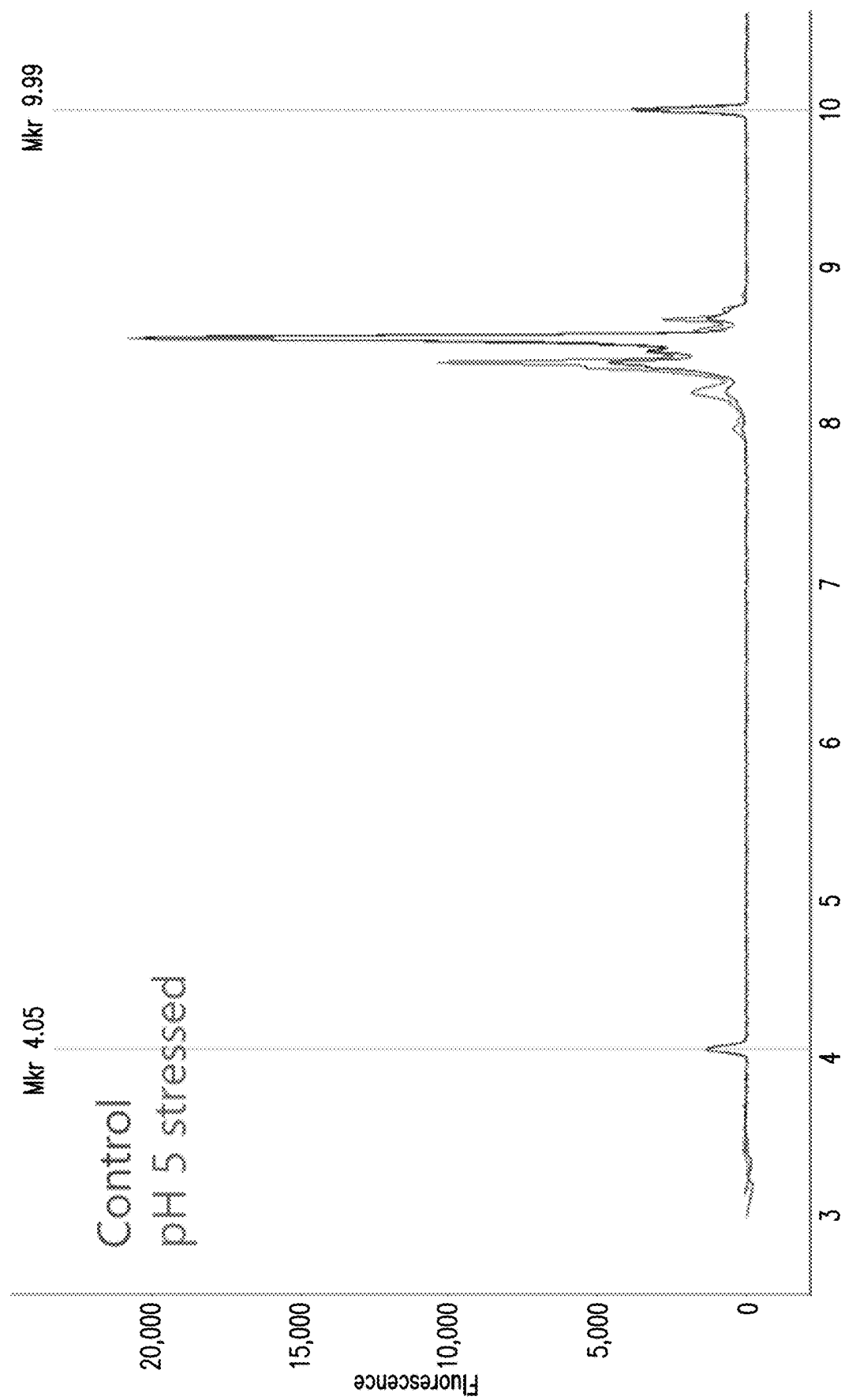
Figure 180A:
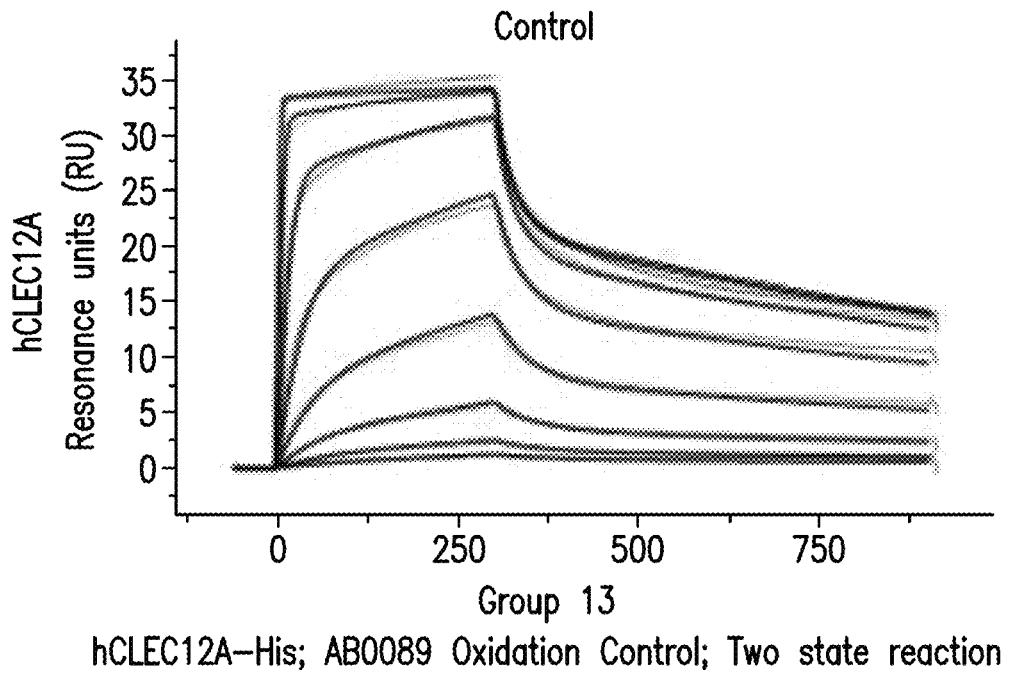
Figure 180B:
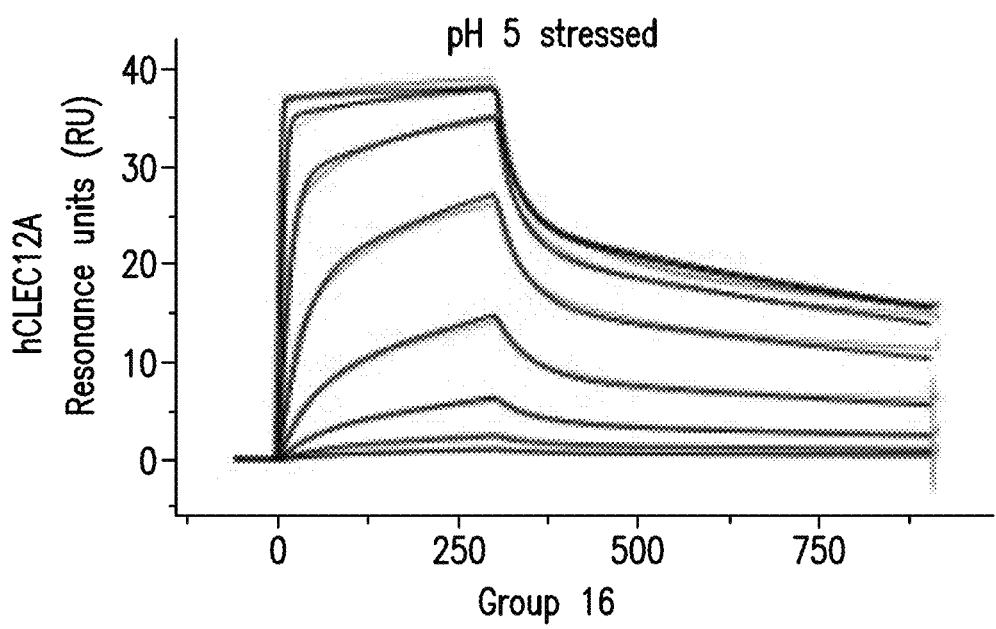
Figure 180C:
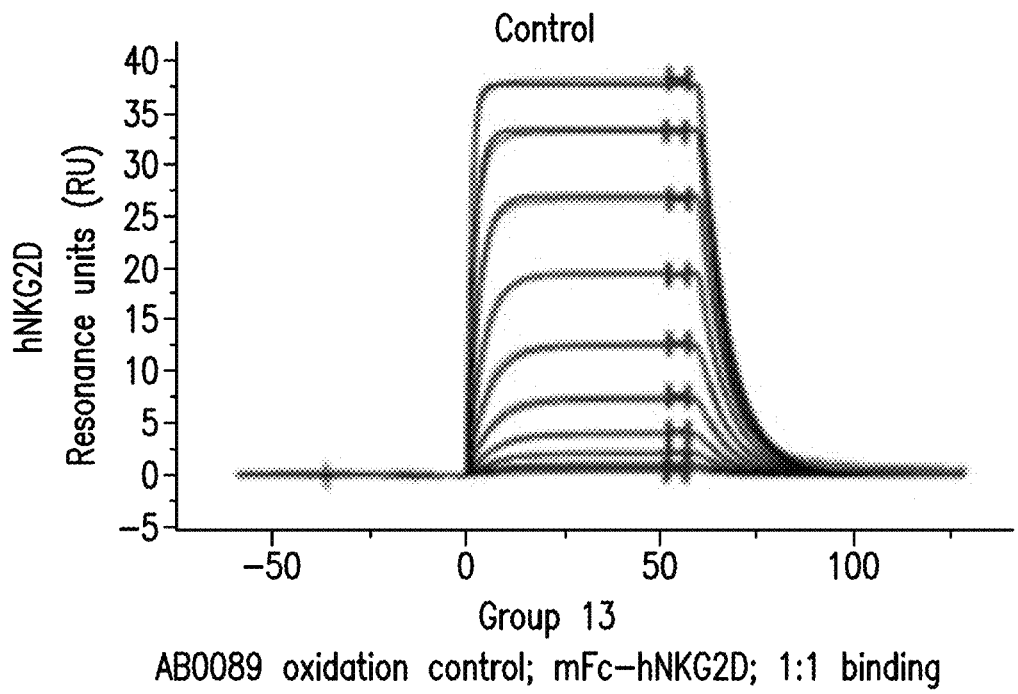
Figure 180D:
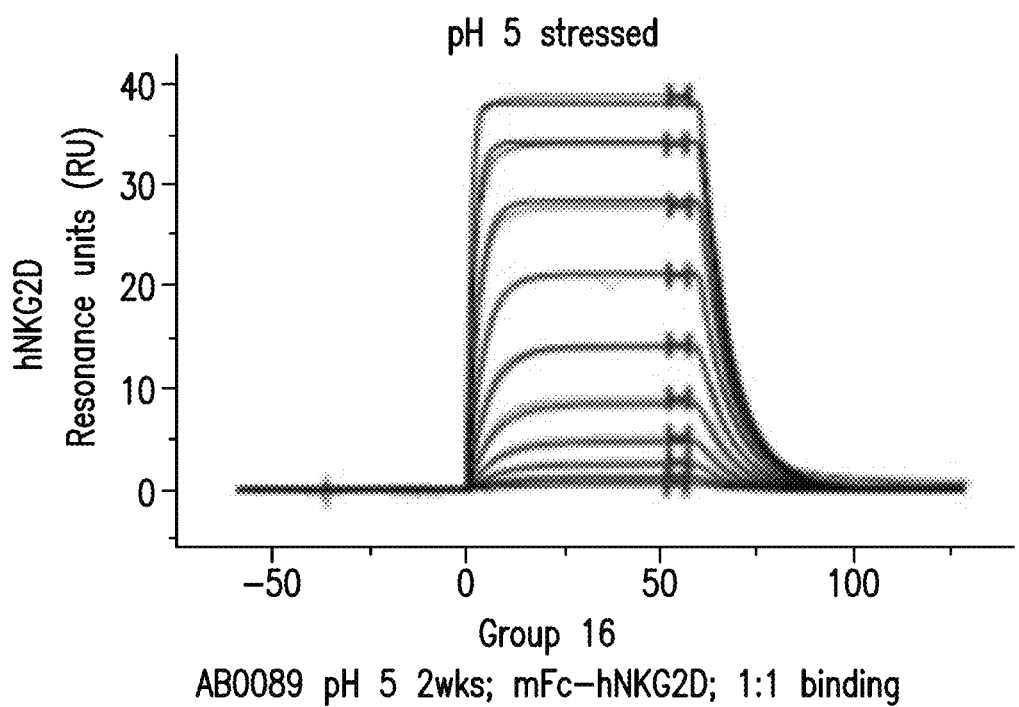
Figure 180E:
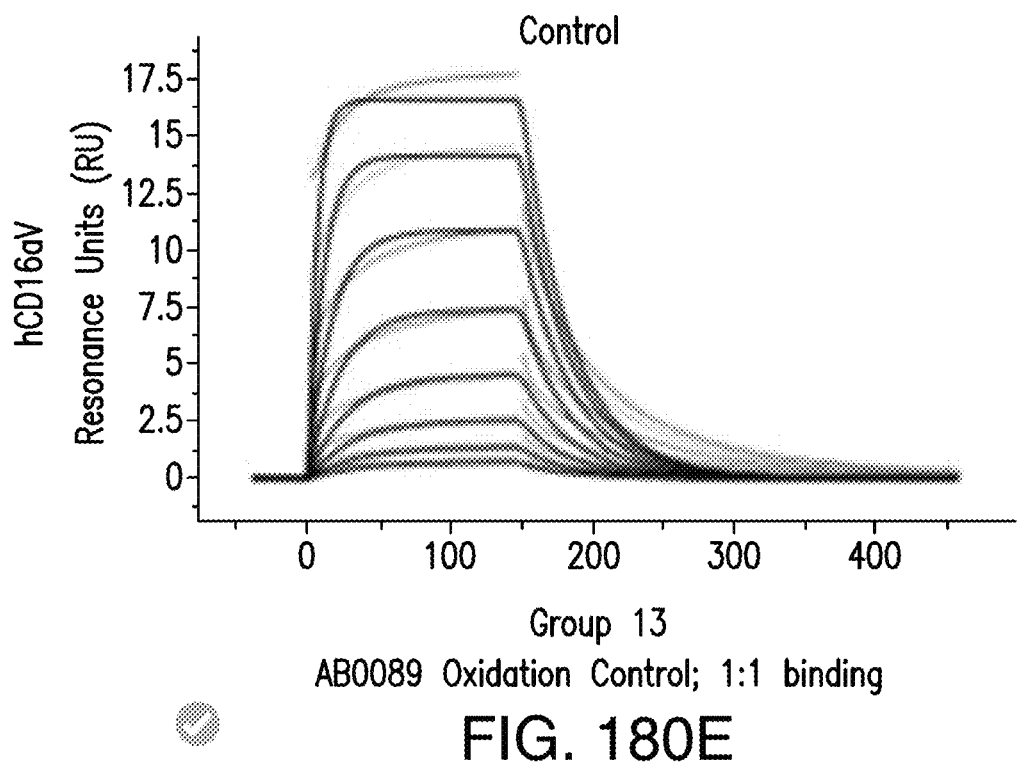
Figure 180F:
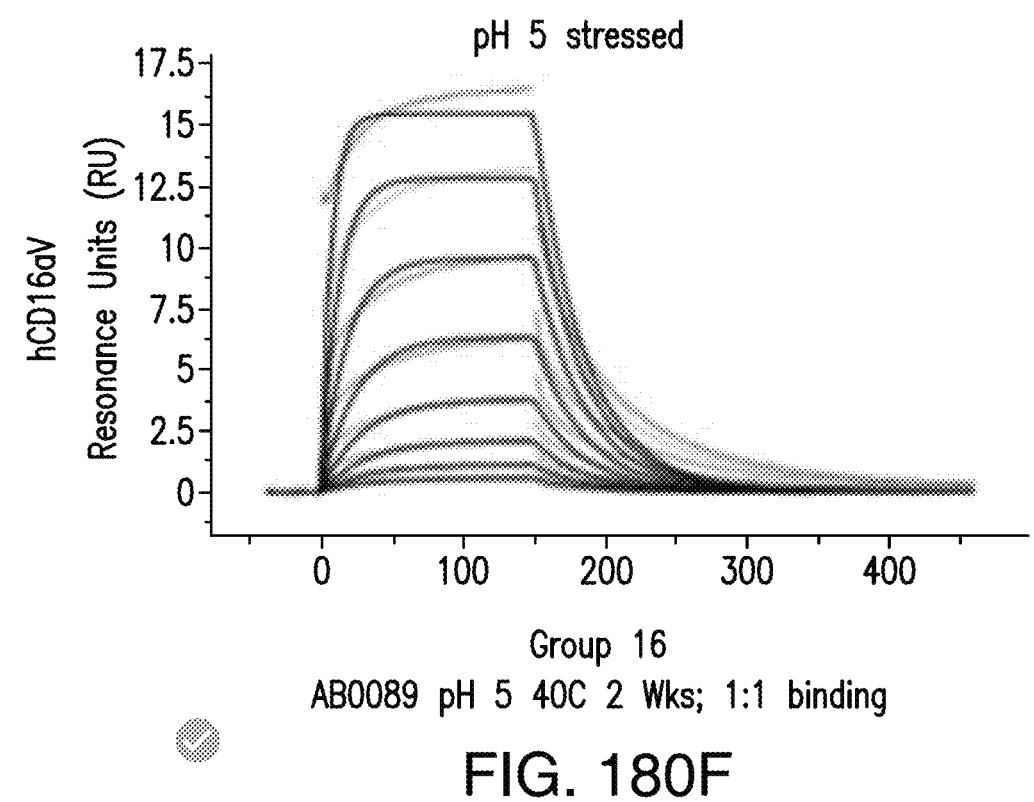
Figure 181:
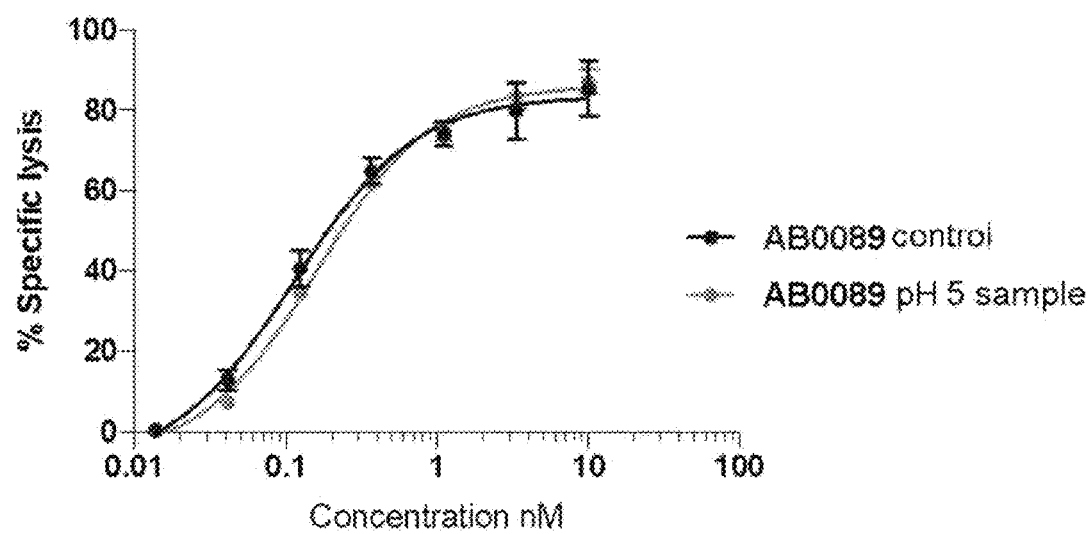

FIG. 179 is a cIEF analysis showing that AB0089 exposed to low pH stress shows slight acidic shift in charge profile.

FIG. 180A-FIG. 180F shows that there was no meaningful difference in active protein content or in AB0089 affinities for hCLEC12A (FIGS. 180A and 180B), hNKG2D (FIGS. 180C and 180D), or hCD16aV (FIGS. 180E and 180F) after long term low pH stress (pH 5.0, 40° C., 2 weeks).

Figure 18A:
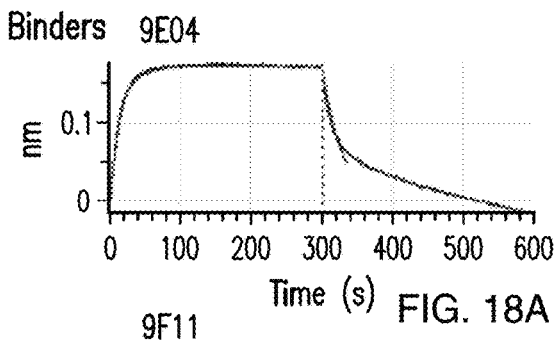
FIG. 18A-FIG. 18P are a set of traces showing Bio-Layer Interferometry (BLI) profiles of antibodies collected from the murine hybridomas supernatants binding to hCLEC12A. Antibodies include 9E04 (FIG. 18A), 9F11 (FIG. 18B), 11E02 (FIG. 18C), 12F08 (FIG. 18D), 13E01 (FIG. 18E), 15A10 (FIG. 18F), 15D11 (FIG. 18G), 16B08 (FIG. 18H), 23D06 (FIG. 18I), 23A05 (FIG. 18J), 30A09 (FIG. 18K), 6D07 (FIG. 18L), 12B06 (FIG. 18M), 20G10 (FIG. 18N), 30H07 (FIG. 18O), and 32A03 (FIG. 18P).
Figure 18B:
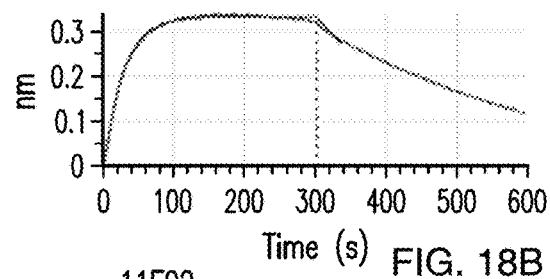
Figure 18C:
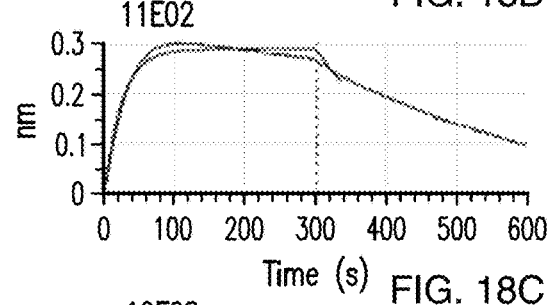
Figure 18D:

Figure 18E:

Figure 18F:
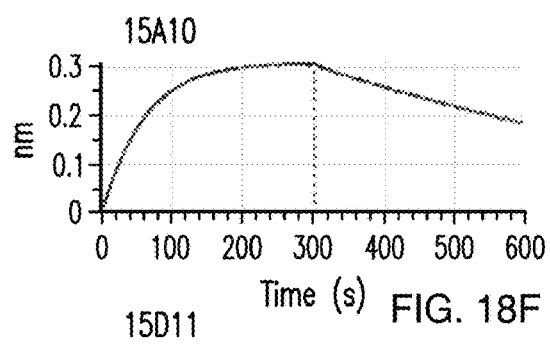
Figure 18G:
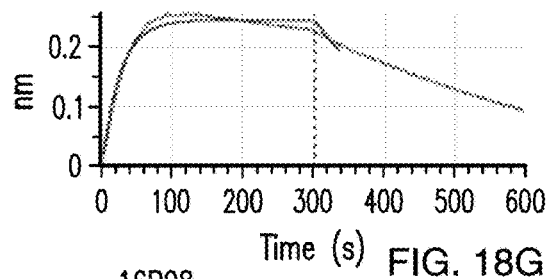
Figure 18H:
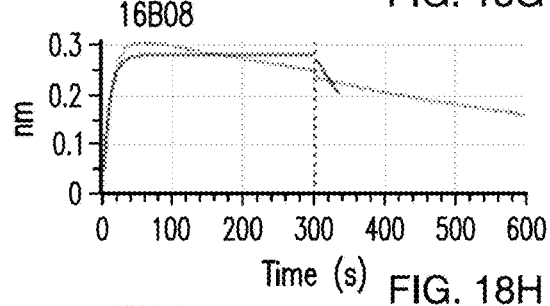
Figure 18I:
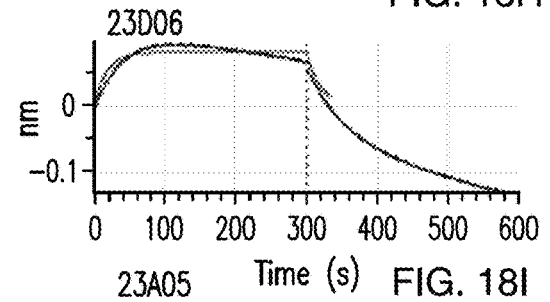
Figure 18J:
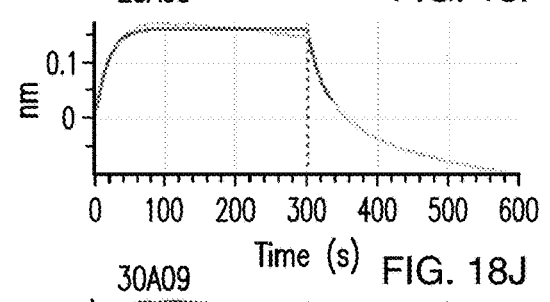
Figure 18K:
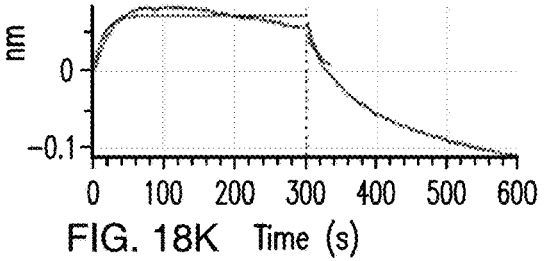
Figure 18L:
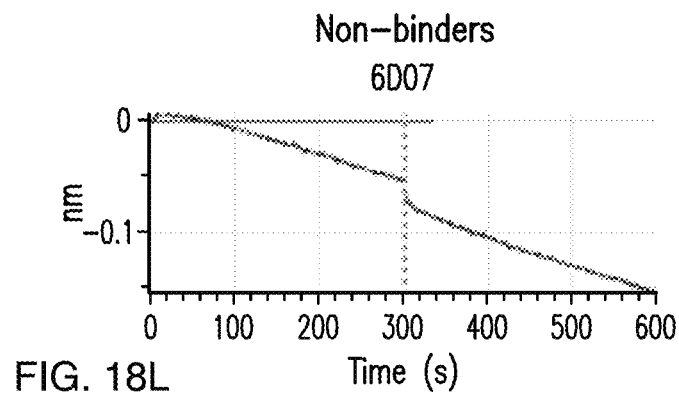
Figure 18M:
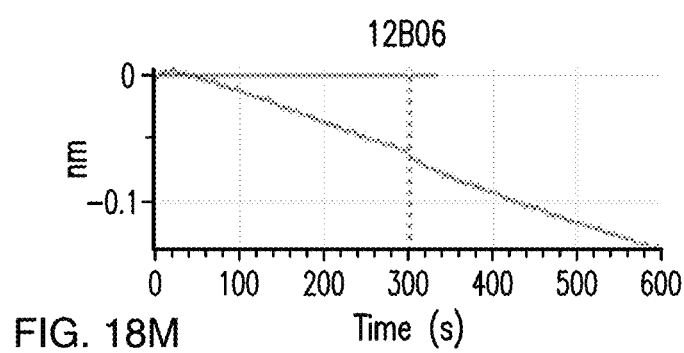
Figure 18N:

Figure 18O:

FIG. 18I shows that the potency of AB0089 remained similar to potency of the control sample after long term low pH stress (pH 5.0 40° C., 2 weeks).

Figures 182A, 182B:
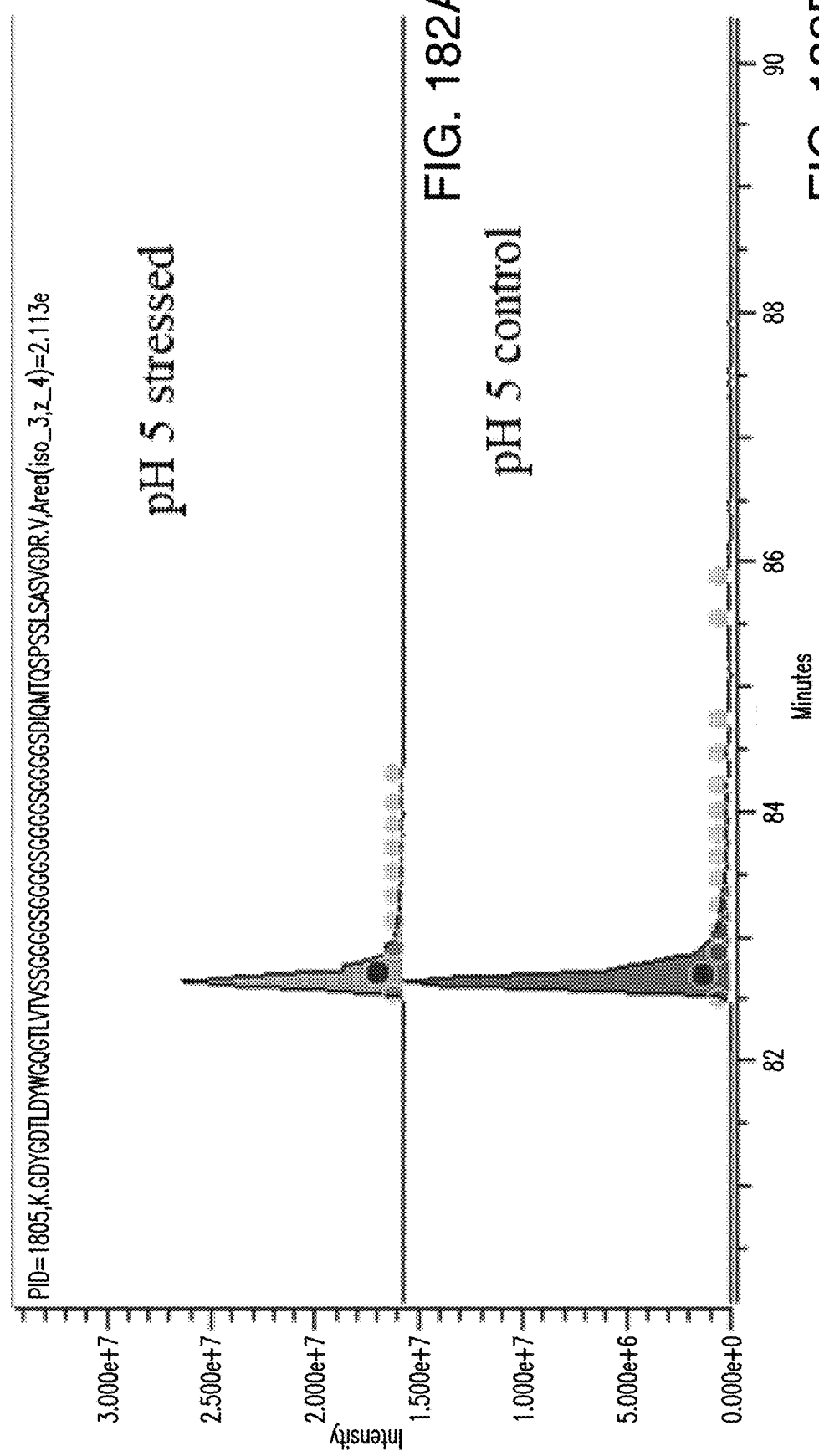

FIGS. 182A and 182B show an extracted ion chromatogram of the tryptic peptide encompassing CDRH3 of CLEC12A targeting arm of AB0089, which showed no evidence of aspartic acid isomerization in the peptide encompassing the CLEC12A binding CDRH3 after long term exposure to low pH (pH 5.0), based on manual inspection of peak shape.

Figure 183:
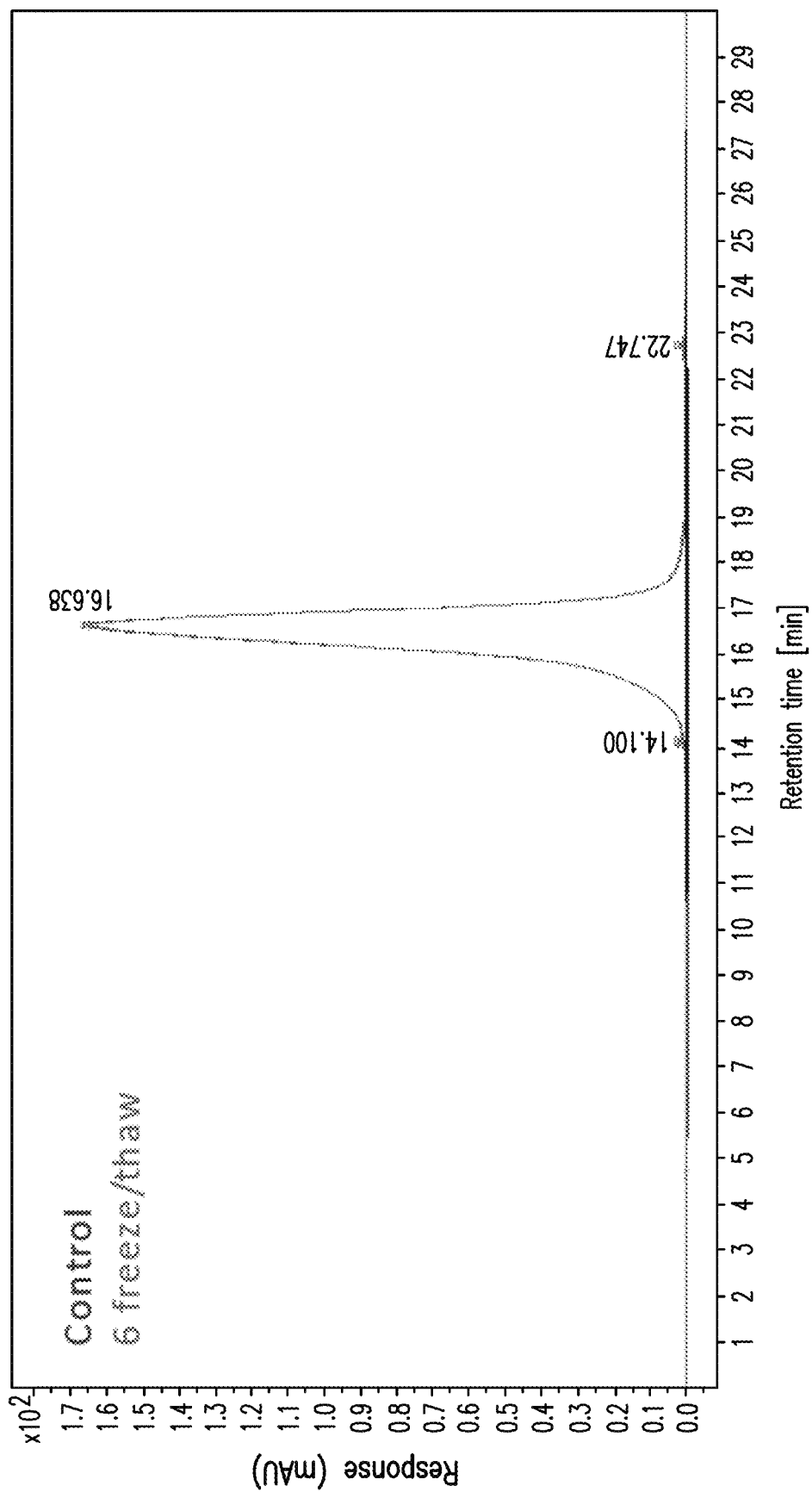

FIG. 183 is an SEC analysis showing that AB0089 is stable after six cycles of freeze/thaw.

Figure 184A:
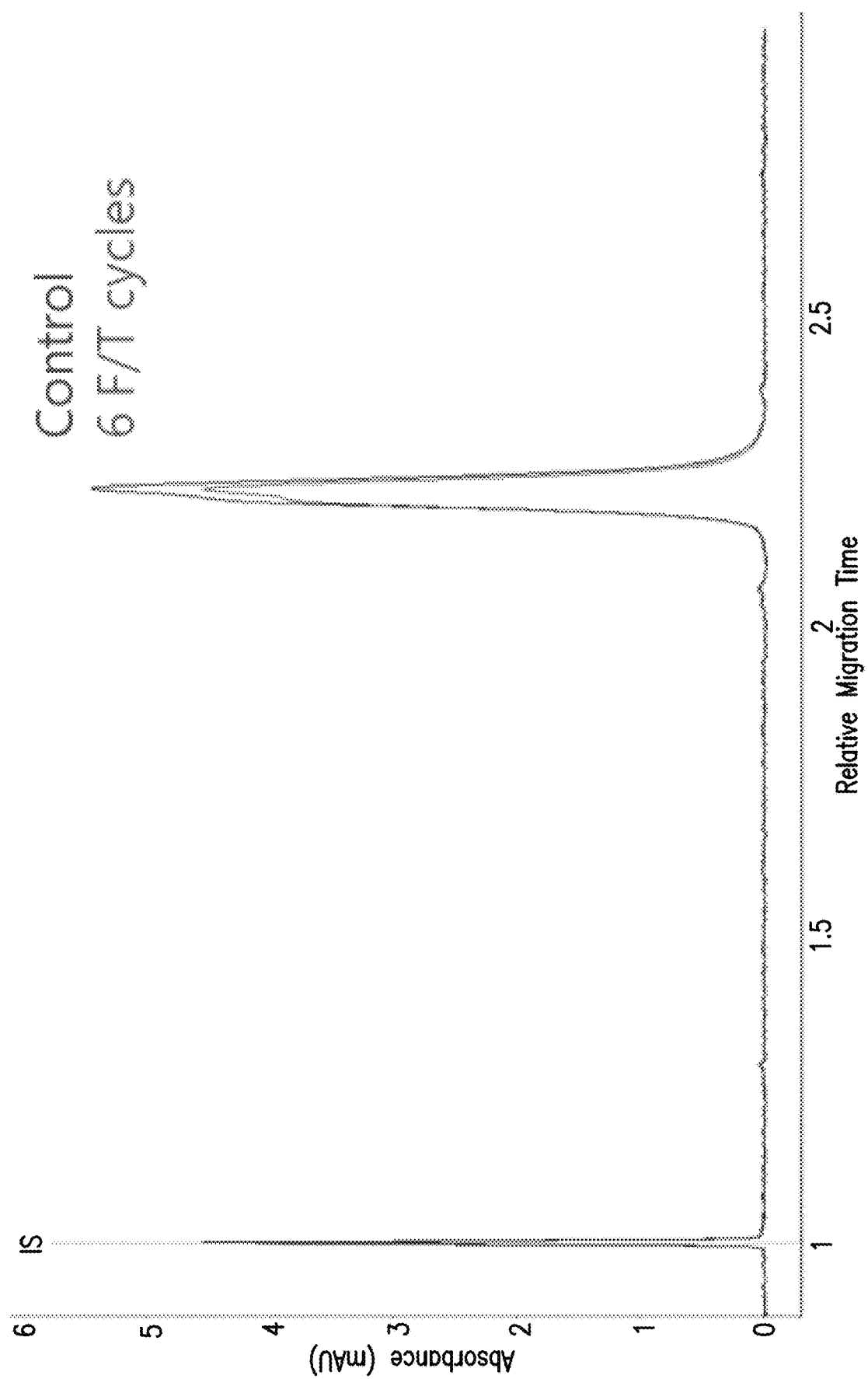
Figure 184B:
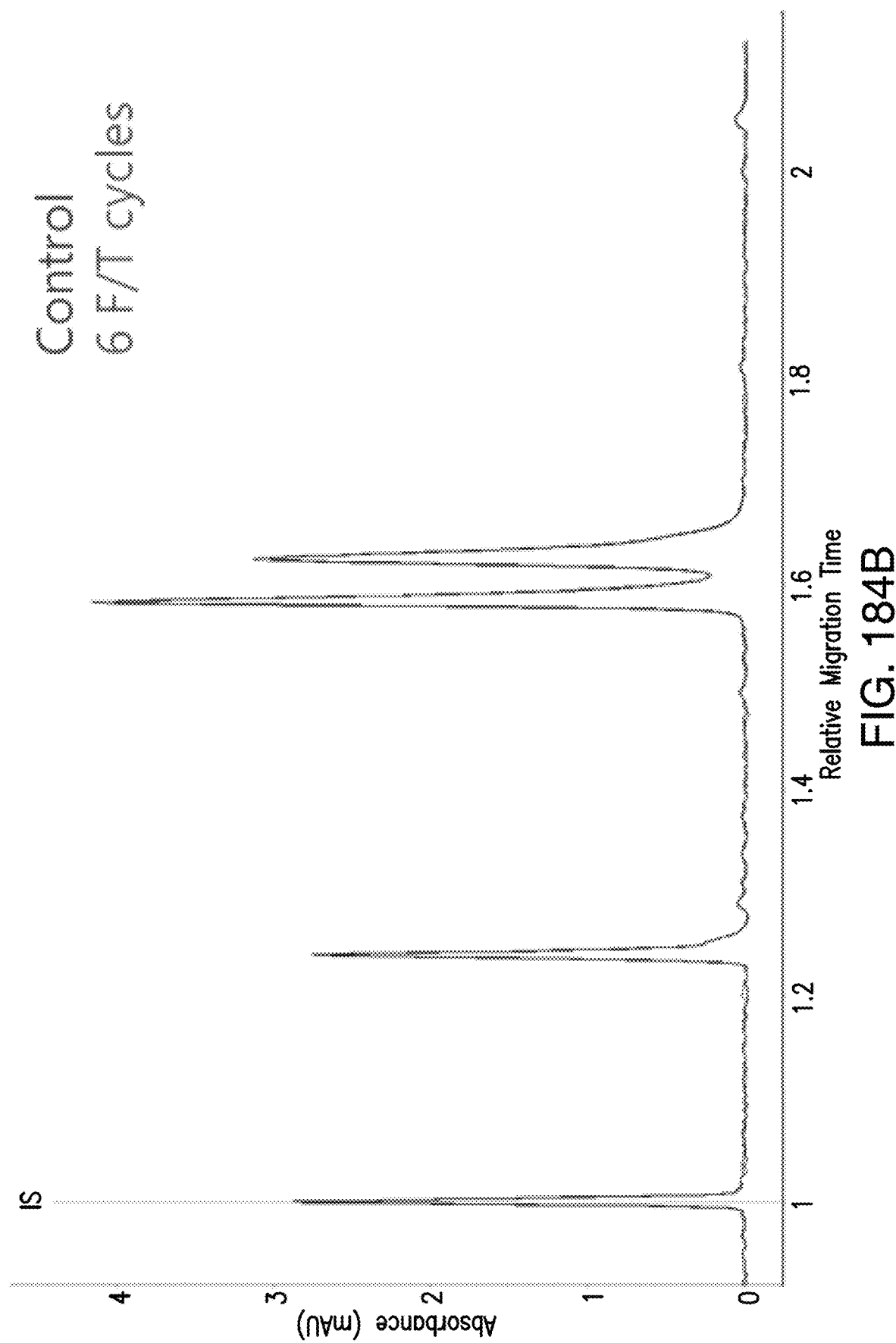

FIG. 184A-FIG. 184B show a CE-SDS analysis of AB0089 after six freeze/thaw cycles showing that no loss of purity was detected by reduced (FIG. 184A) or non-reduced CE-SDS (FIG. 184B).

Figure 185A:
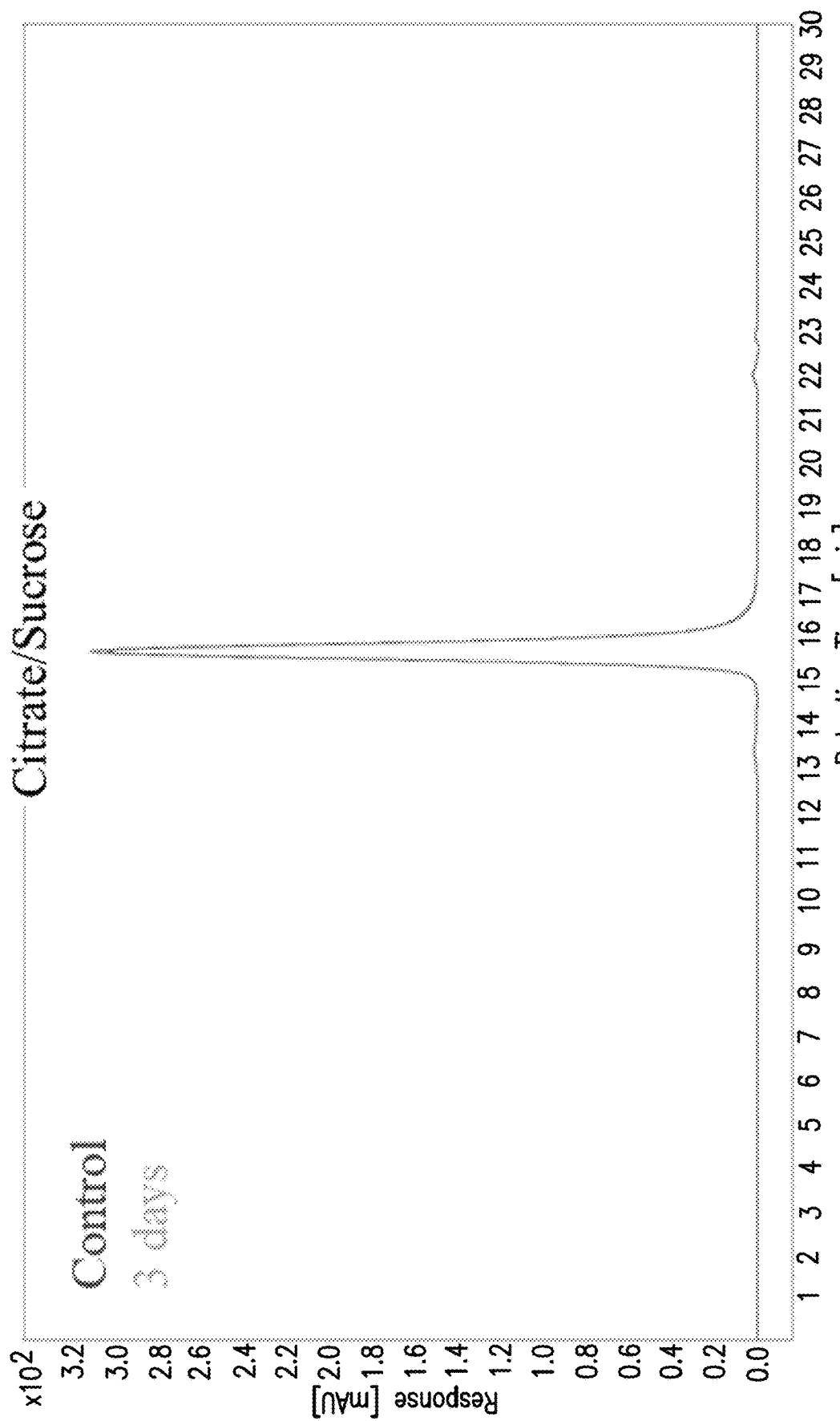
Figure 185B:
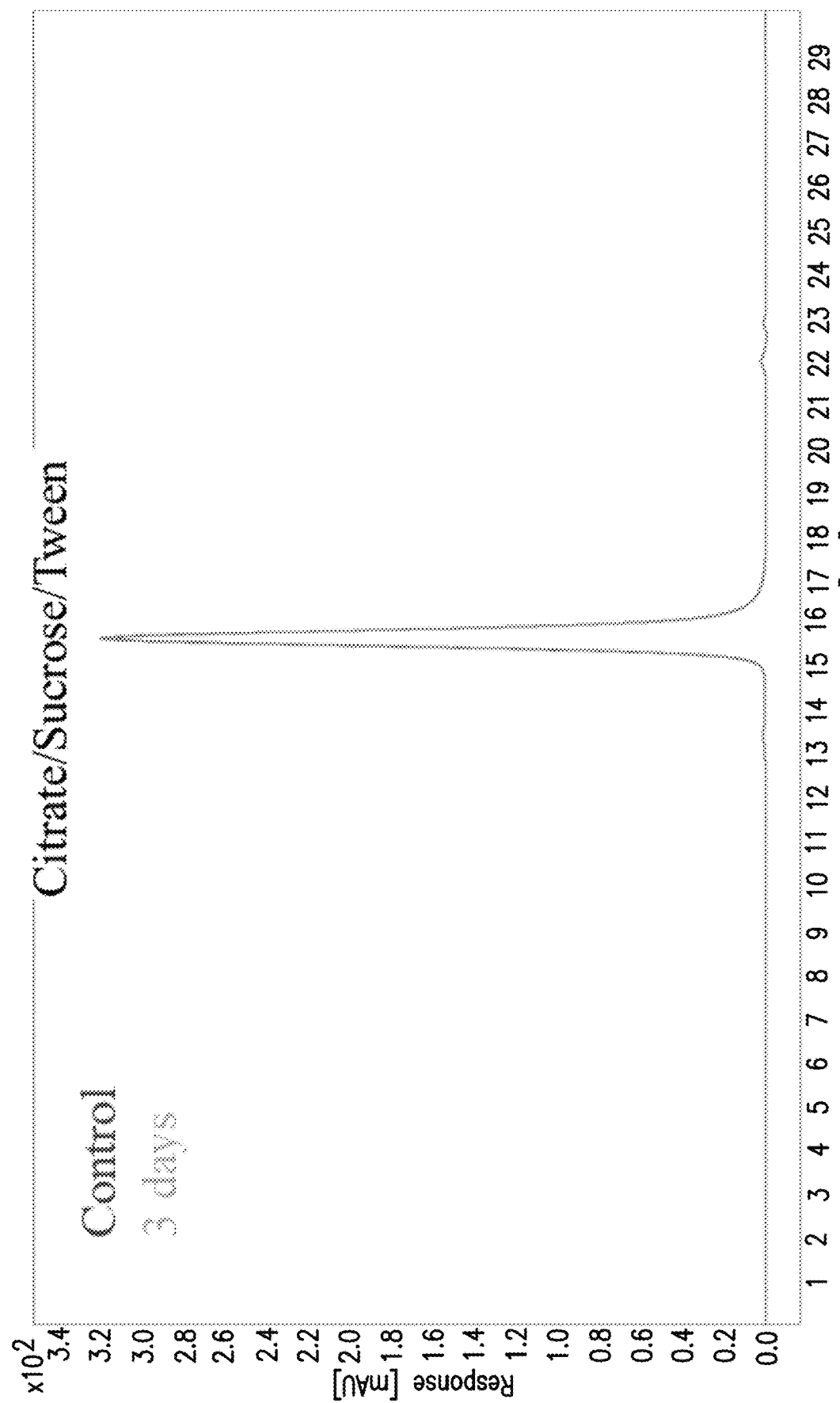

FIG. 185A-FIG. 185B show an SEC analysis showing that AB0089 is stable after agitation stress (300 rpm at room temperature in a deep well plate for 3 days).

Figure 186A:
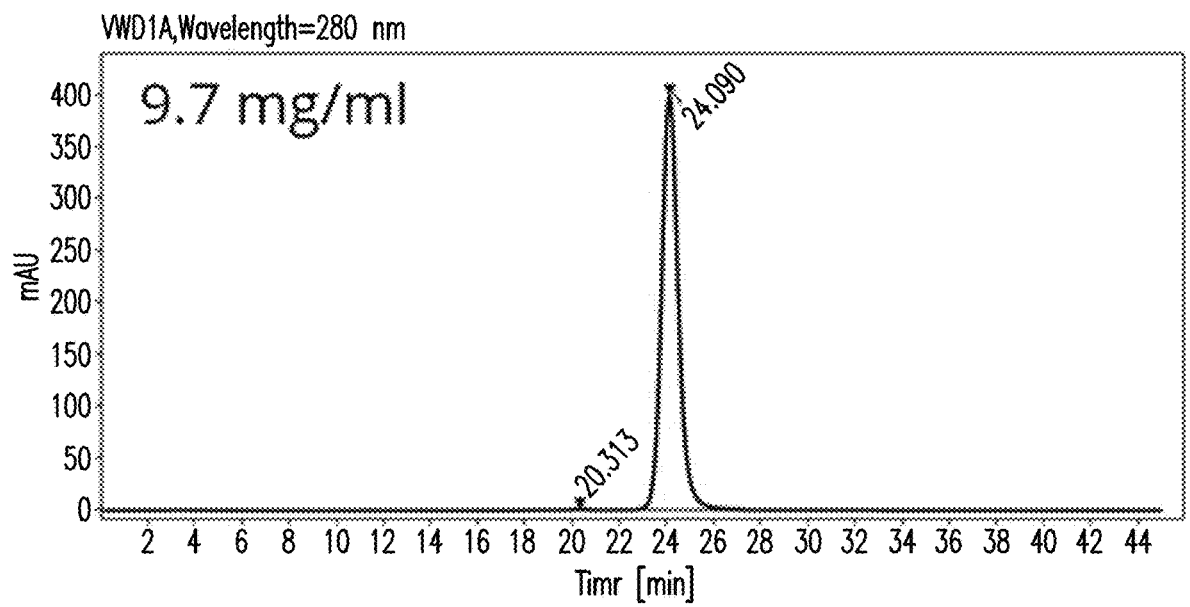
Figure 186B:
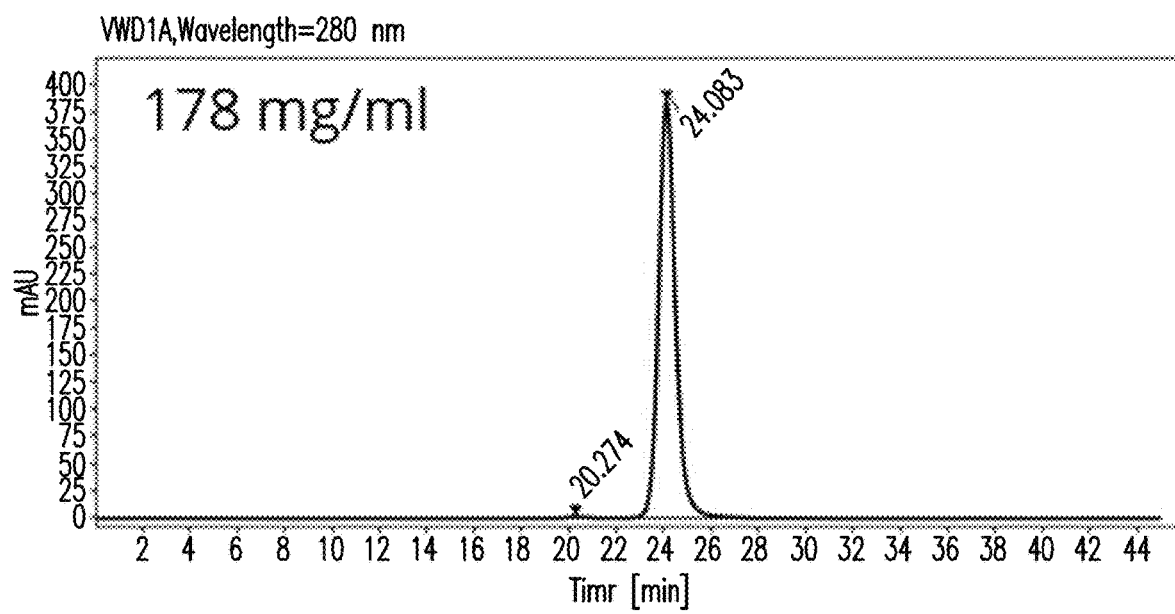

FIG. 186A-FIG. 186B show an SEC analysis showing that AB0089 was able to be concentrated to >175 mg/ml with minimal loss in percent monomer.

FIG. 187 is a graph showing that AB0089 is amendable to concentration (up to 178 mg/ml) without loss of monomer.

FIG. 188A-FIG. 188B show an SEC analysis of Protein A eluate pre- and post-low pH hold showing that AB0089 is highly stable during low pH hold/viral inactivation conditions used in biologics manufacturing.

Figure 189:
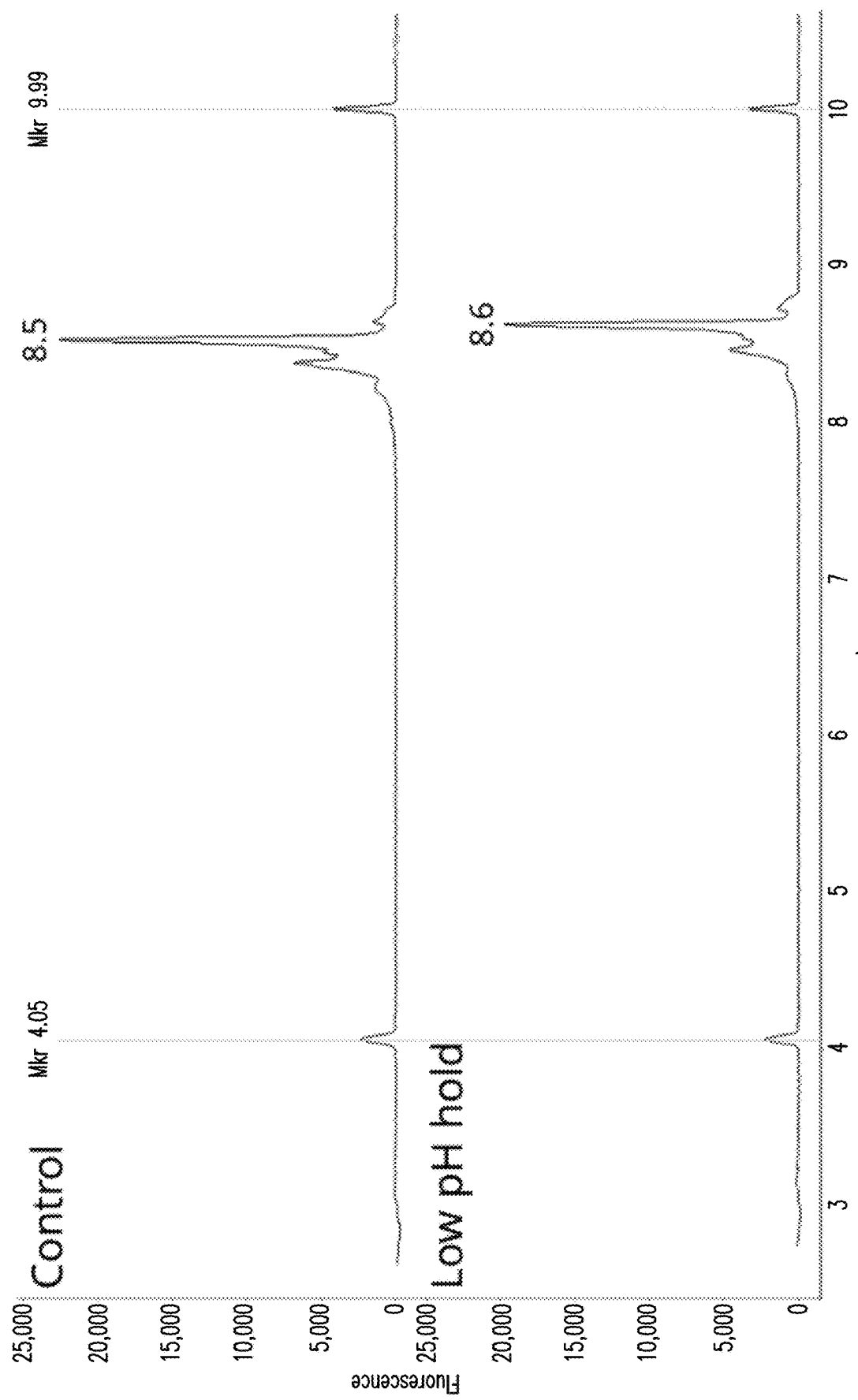
Figure 190A:
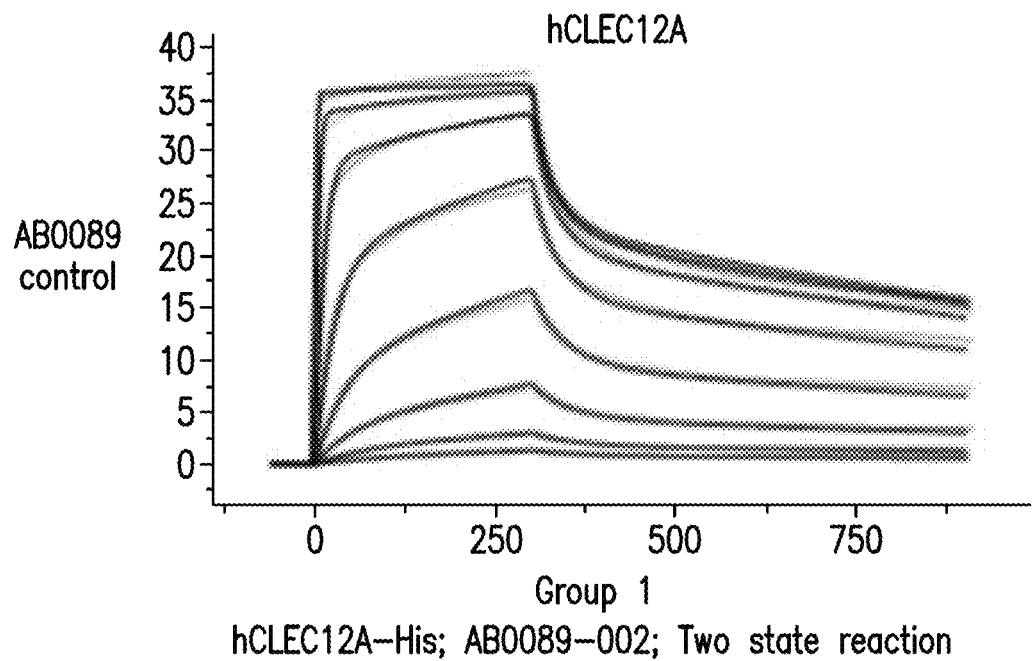
Figure 190B:
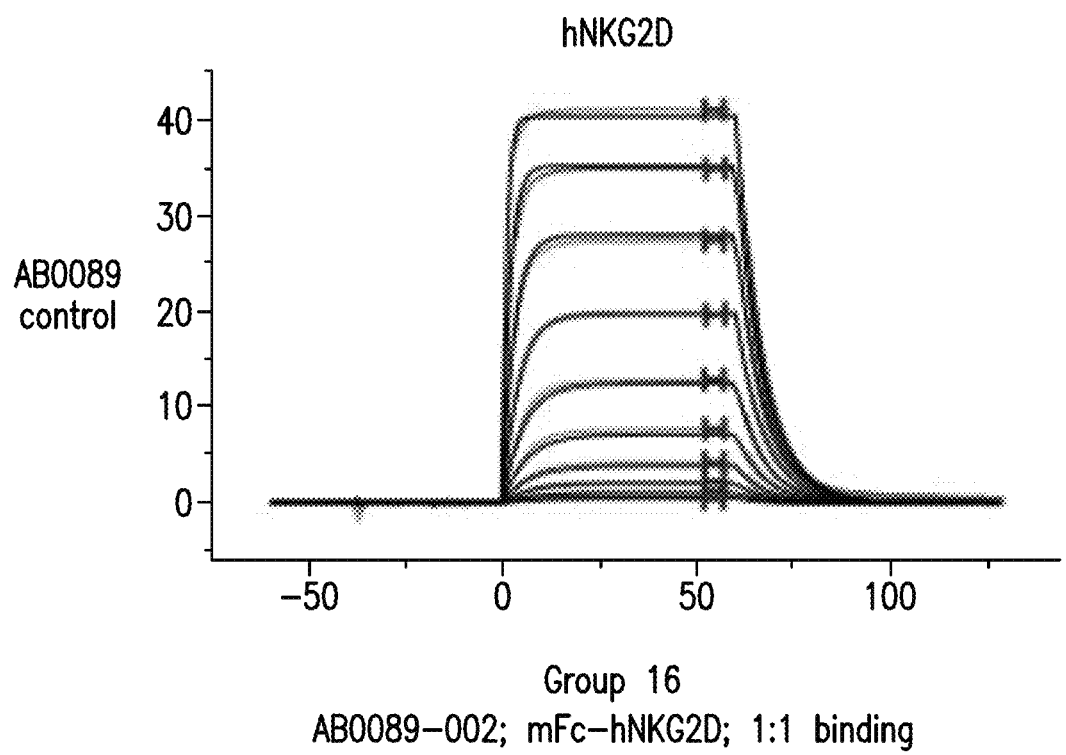
Figure 190C:
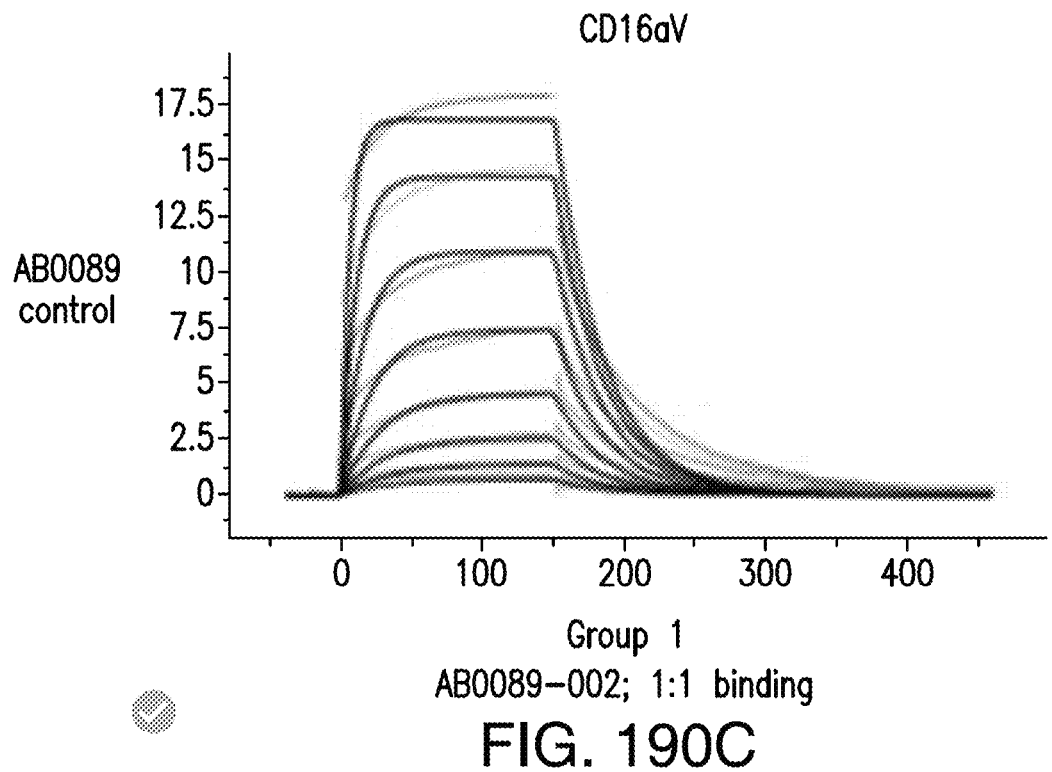
Figure 190D:
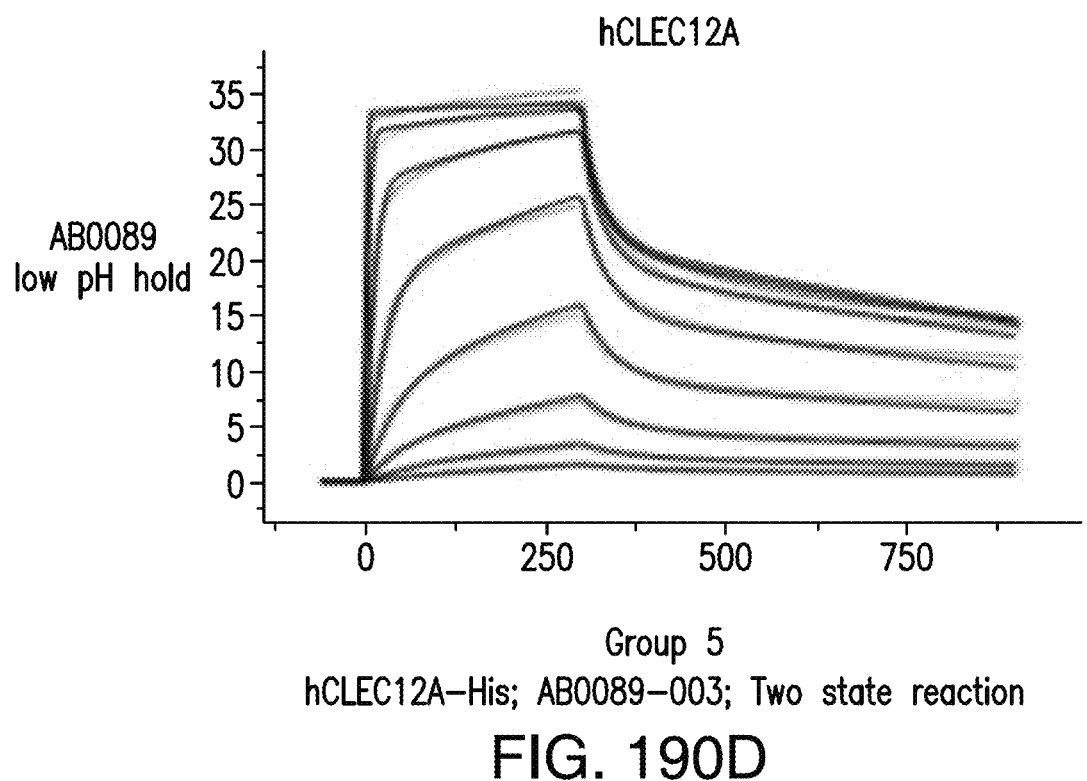
Figure 190E:
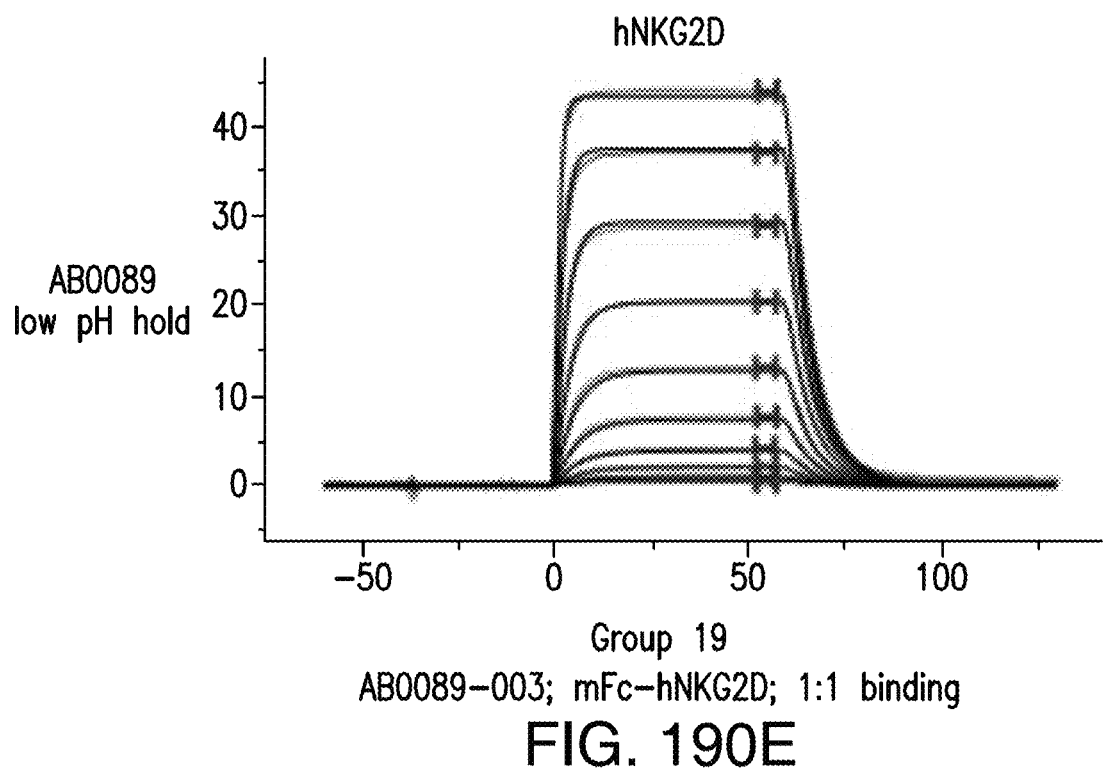
Figure 190F:
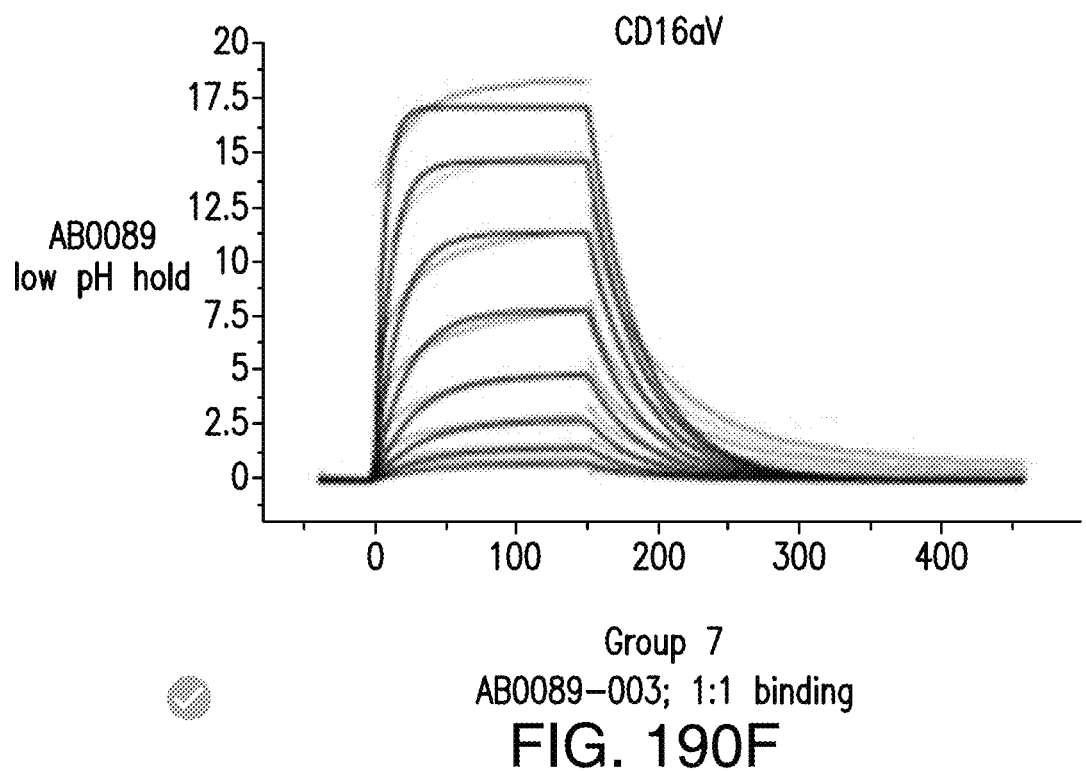
Figure 191:
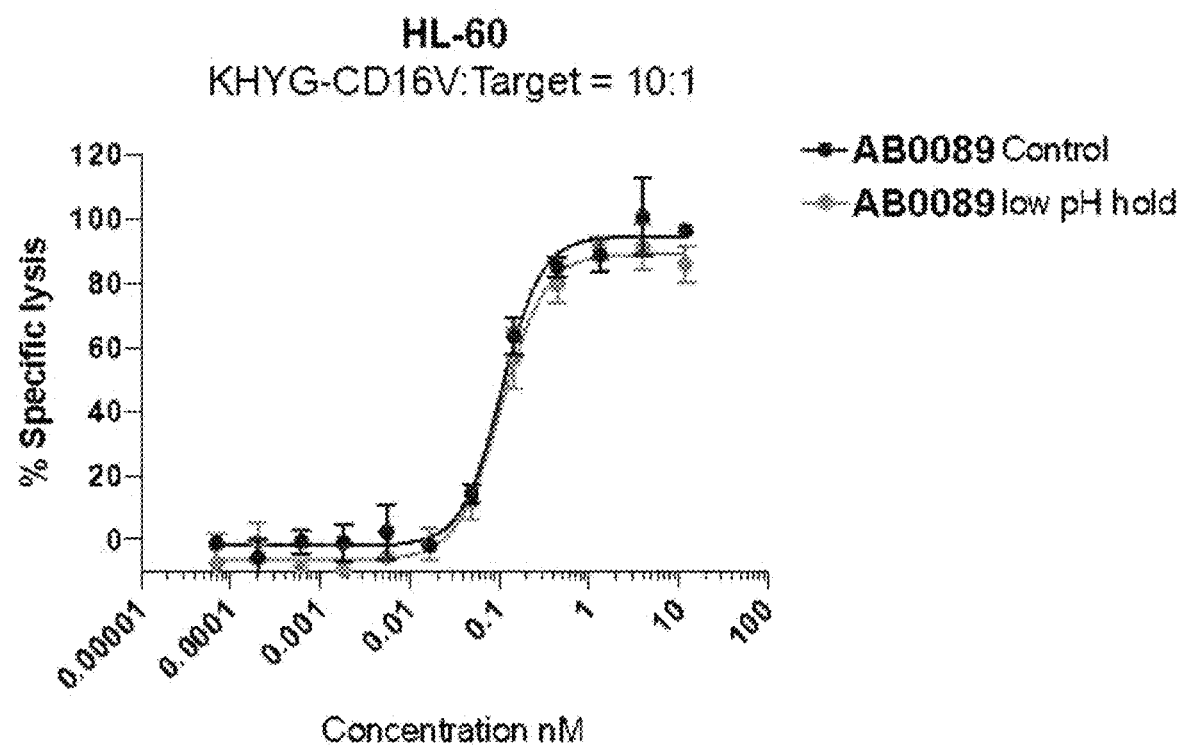

FIG. 189 shows that AB0089 charge profile remains unaltered after low pH hold.

FIG. 190A-FIG. 190F show that the affinities of AB0089 for hCLEC12a, hNKG2D, and CD16aV were not affected by low pH hold.

FIG. 19I shows that the potency of AB0089 was unaltered after the low pH hold step.

Figure 192A:
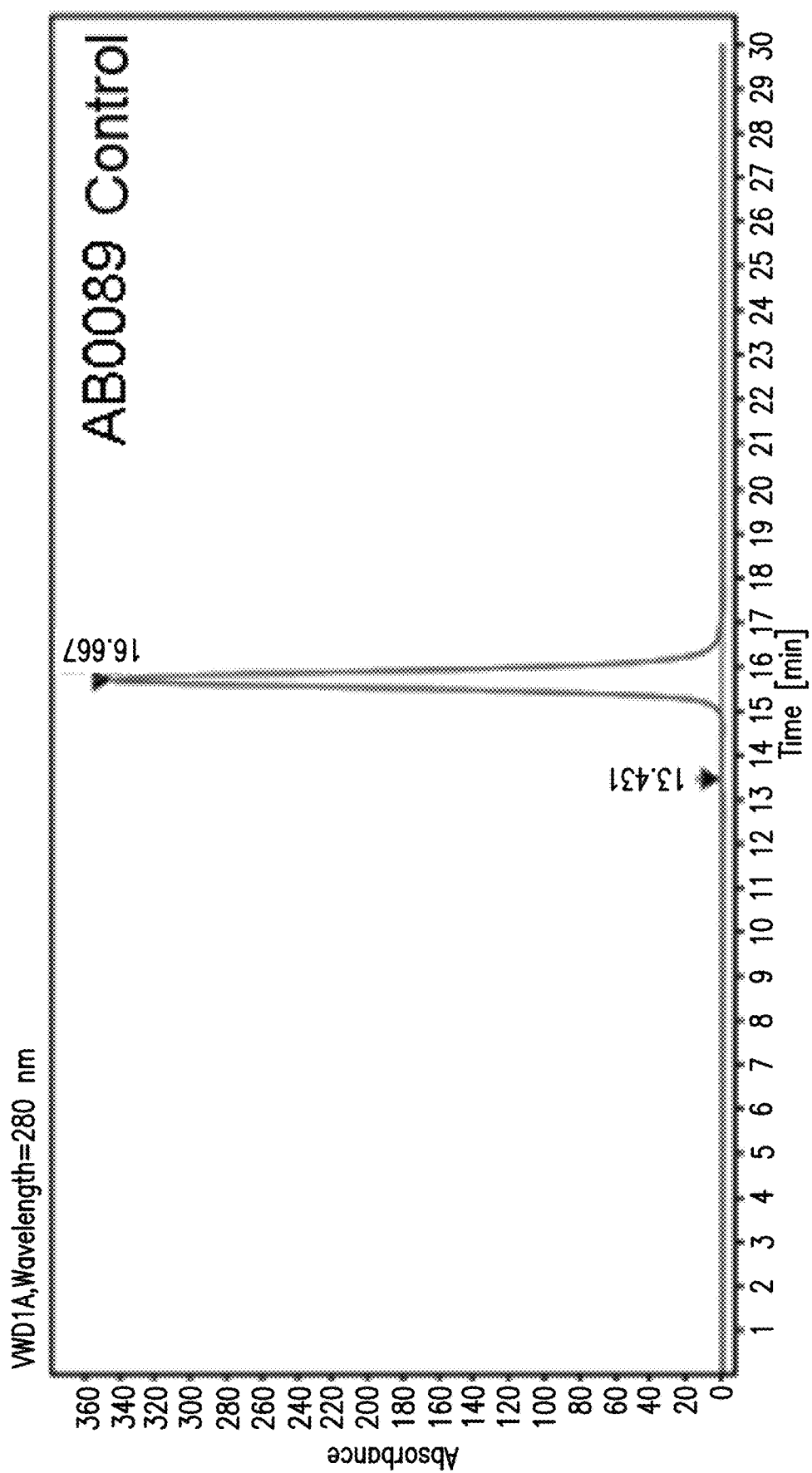
Figure 192B:
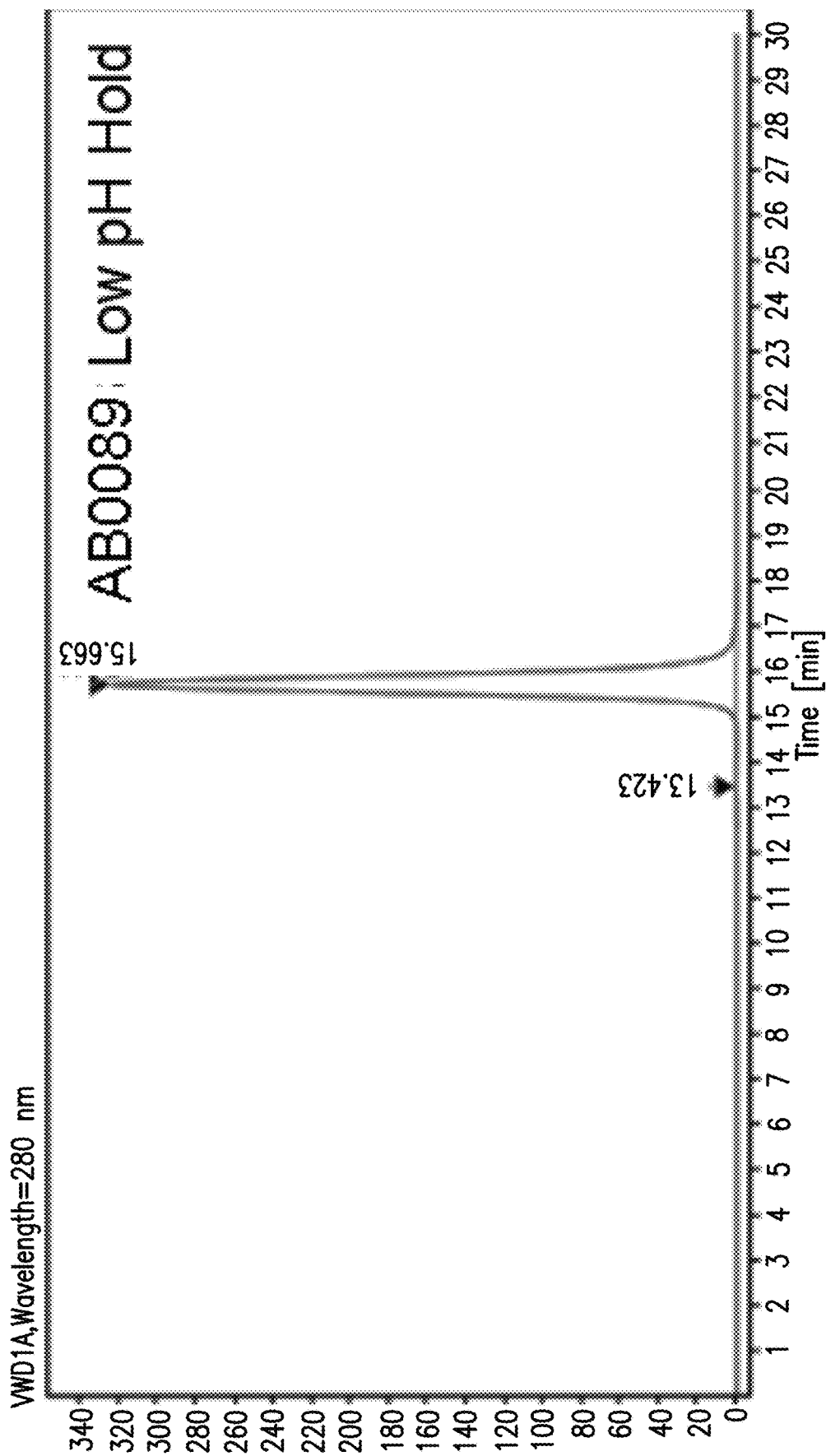

FIG. 192A-FIG. 192B show an SEC analysis showing that there was no change in profile of percent monomer was observed after the low pH hold.

Figure 193:
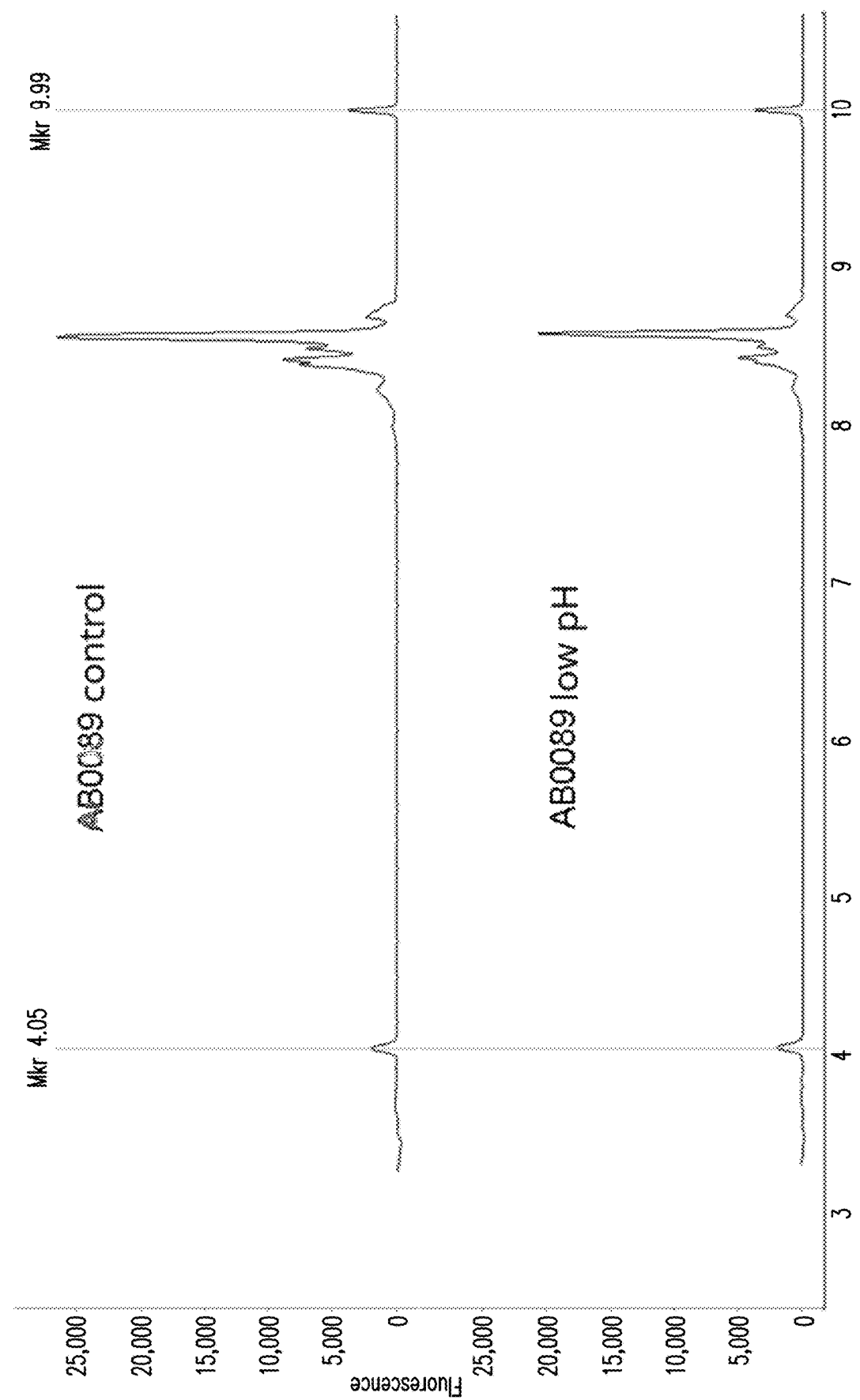

FIG. 193 shows that low pH hold did not have a significant effect on the charge profile of AB0089.

Figure 194:
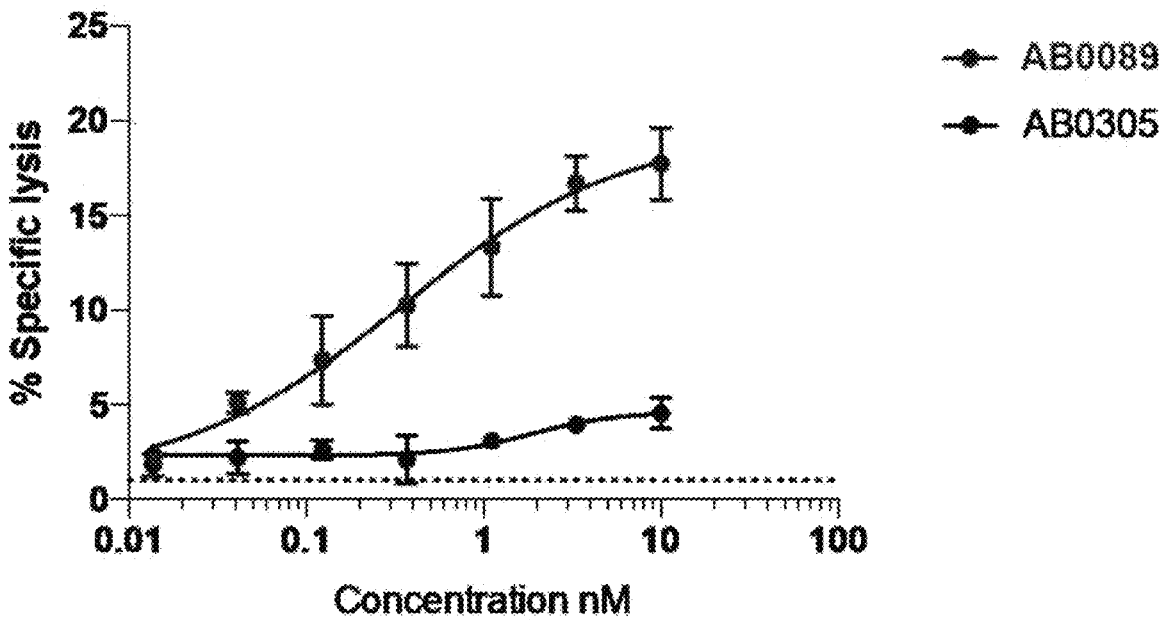

FIG. 194 shows that AB0089 strongly enhances human NK cytotoxicity of PL21 AML cells. Purified human NK cells were rested overnight and, the following day, were co-cultured with labeled PL21 target cells for DELFIA assay. Dose-titrations of CLEC12A TriNKET AB0089 or parental mAb AB0305 were prepared starting at 10 nM and added to the co-cultures. Assays were performed with a total of six healthy NK cell donors; shown is a representative result. Specific lysis was plotted against test article concentration, and data were fit to a 4-parameter non-linear regression model to generate potency values. Data points represent mean±standard deviation.

Figure 195:
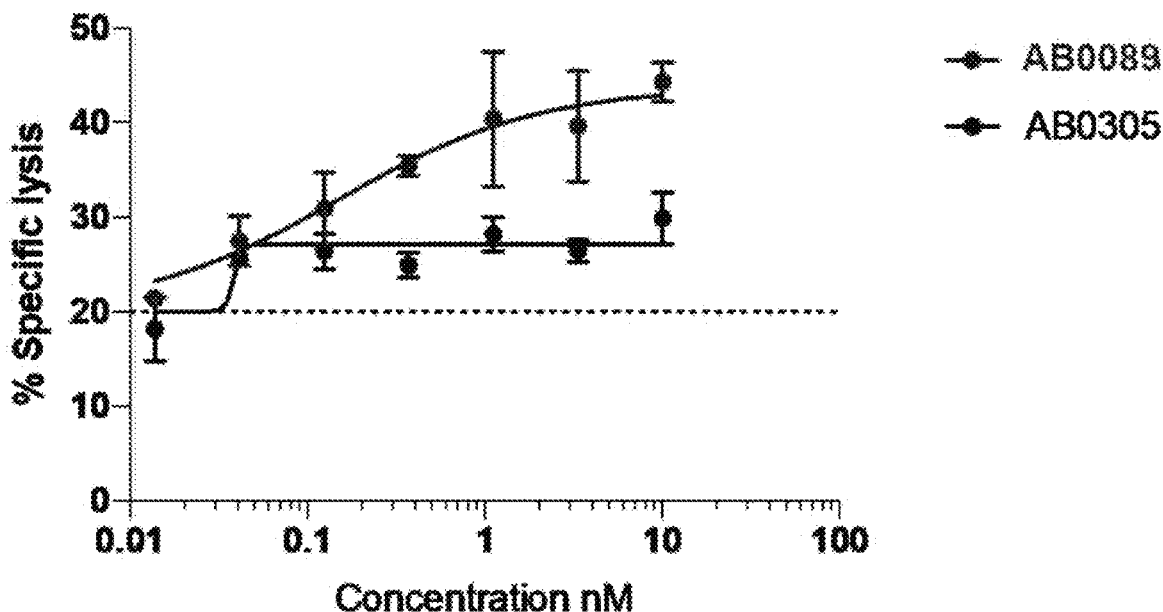

FIG. 195 shows that AB0192 strongly enhances human NK cytotoxicity of HL60 AML cells. Purified human NK cells were rested overnight and, the following day, were co-cultured with labeled HL60 target cells for DELFIA assay. Dose-titrations of CLEC12A TriNKET AB0089 or parental mAb AB0305 were prepared starting at 10 nM and added to the co-cultures. Assays were performed with a total of four healthy NK cell donors; shown is a representative result. Specific lysis was plotted against test article concentration, and data were fit to a 4-parameter non-linear regression model to generate potency values. Data points represent mean±standard deviation.

Figure 196:
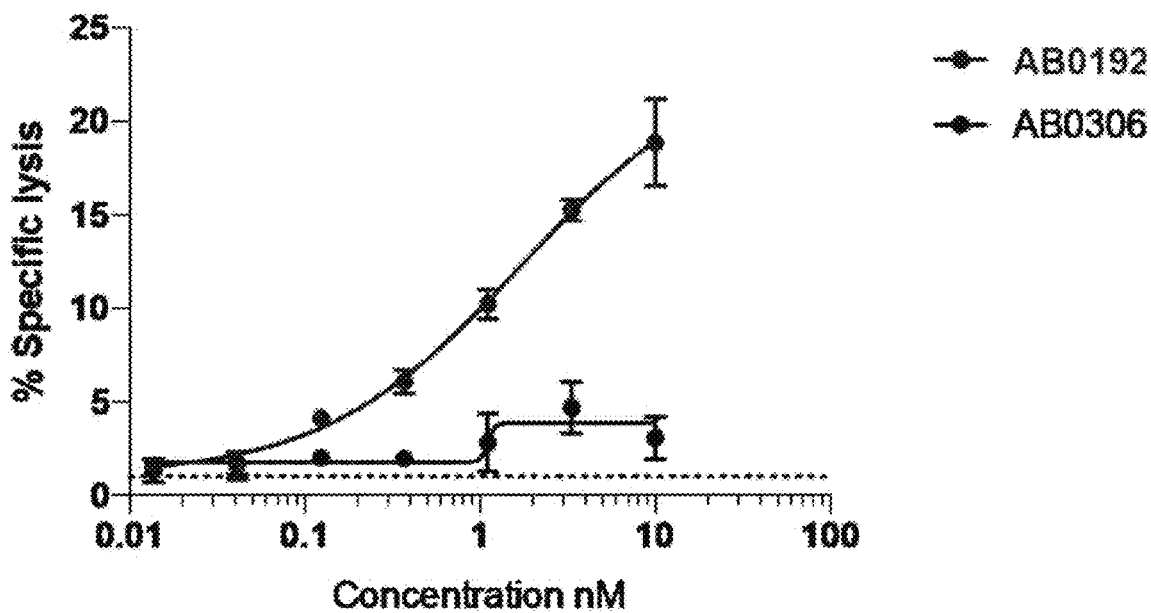

FIG. 196 shows that AB0192 strongly enhances human NK cytotoxicity of PL21 AML cells. Purified human NK cells were rested overnight and, the following day, were co-cultured with labeled PL21 target cells for DELFIA assay. Dose-titrations of CLEC12A TriNKET AB0192 or parental mAb AB0306 were prepared starting at 10 nM and added to the co-cultures. Assays were performed with a total of six healthy NK cell donors; shown is a representative result. Specific lysis was plotted against test article concentration, and data were fit to a 4-parameter non-linear regression model to generate potency values. Data points represent mean±standard deviation.

Figure 197:
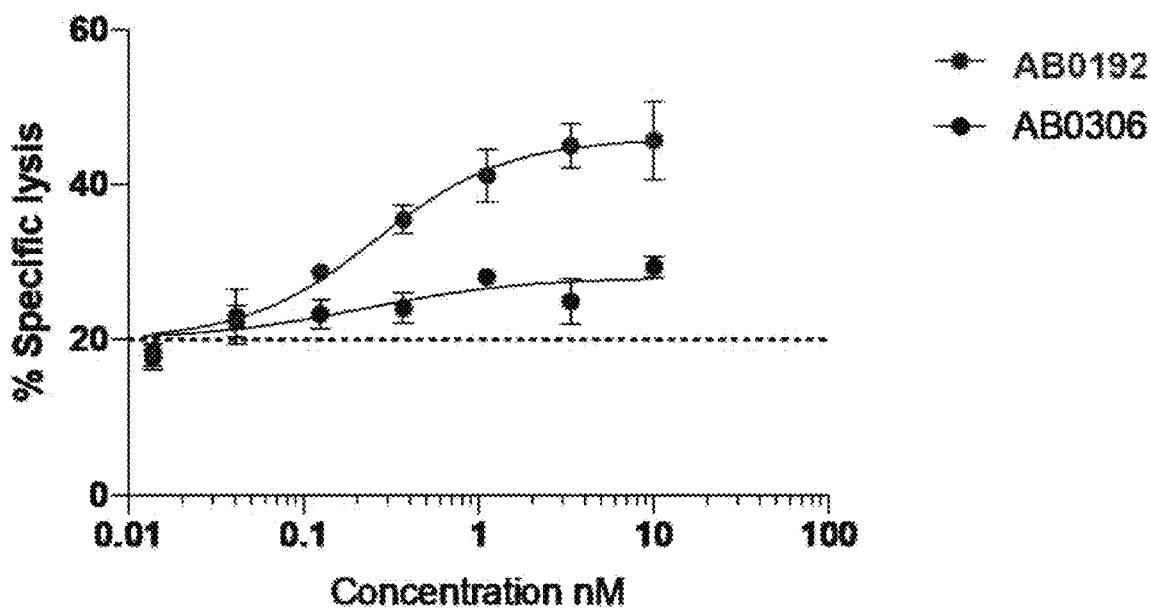

FIG. 197 shows that AB0192 strongly enhances human NK cytotoxicity of HL60 AML cells. Purified human NK cells were rested overnight and, the following day, were co-cultured with labeled HL60 target cells for DELFIA assay. Dose-titrations of CLEC12A TriNKET AB0192 or parental mAb AB0306 were prepared starting at 10 nM and added to the co-cultures. Assays were performed with a total of four healthy NK cell donors; shown is a representative result. Specific lysis was plotted against test article concentration, and data were fit to a 4-parameter non-linear regression model to generate potency values. Data points represent mean±standard deviation.

Figure 198:
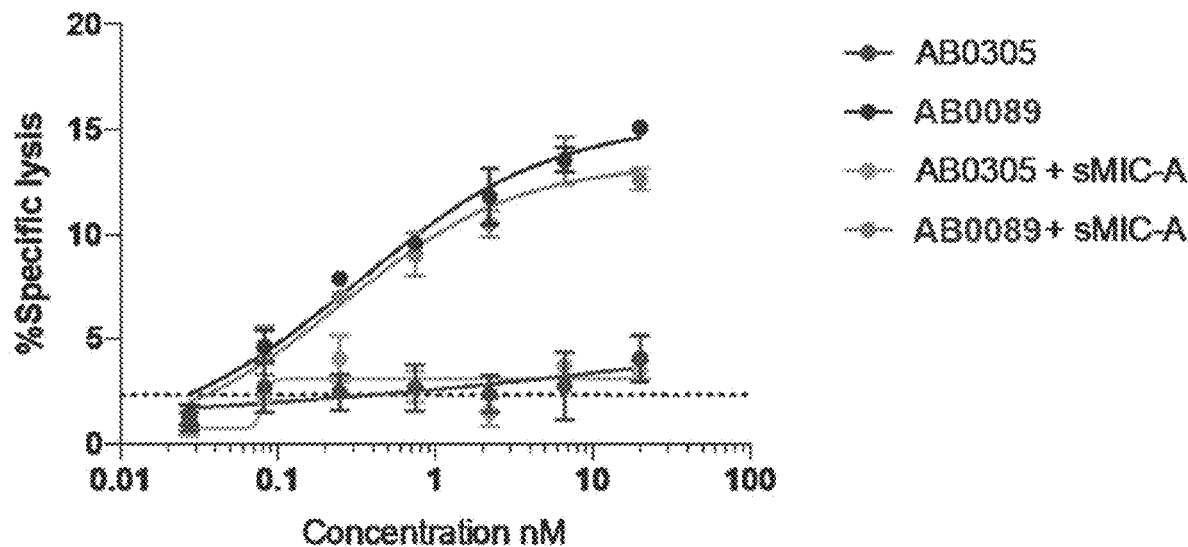

FIG. 198 shows that AB0089 activity is not influenced by the presence of soluble MIC-A. Purified human NK cells were rested overnight and, the following day, were set up in co-culture wells with DELFIA labeled PL21 target cells. Dose-titrations of AB0089 and AB0305 were prepared, and soluble MIC-A-Fc was added to 20 ng/mL into a titration series of each test article. Dose-titrations were fit to a 4-parameter non-linear regression model. Data points represent mean±standard deviation.

Figure 199:
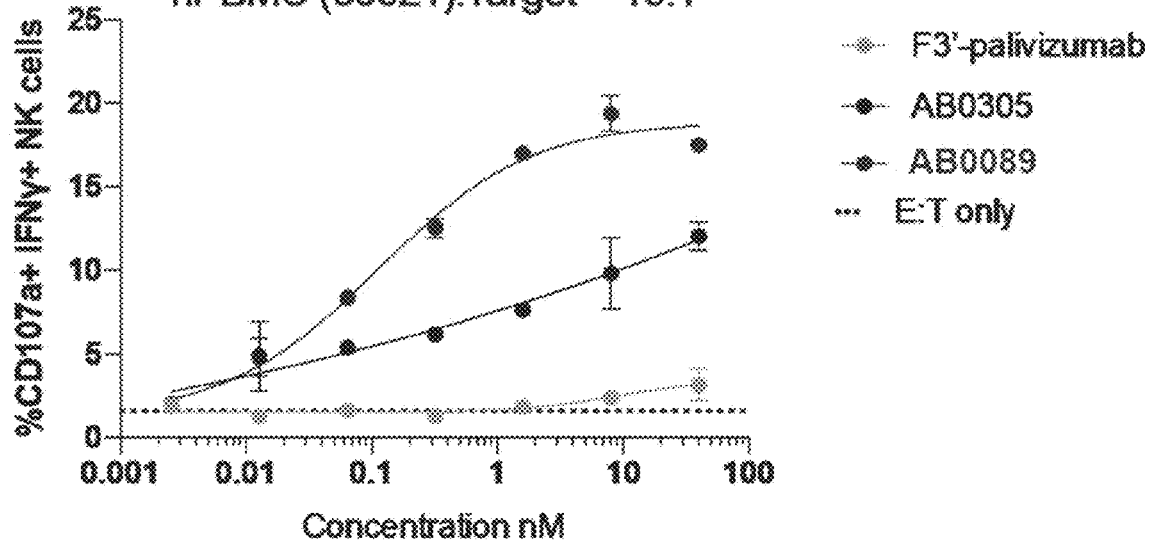

FIG. 199 shows that AB0089 induces IFNγ production and degranulation by human NK cells against PL21 AML cells. Frozen PBMCs were thawed and co-cultured with PL21 target cells in the presence of a dose-titration of AB0089, AB0305 or F3'-palivizumab. After incubation, cells were prepared for FACS analysis of CD107a degranulation and intracellular accumulation of IFNγ. The figure shown is representative of the three PBMC donors tested. The percentage of IFNγ+CD107+ NK cells induced was plotted against concentration, and data were fit to a 4-parameter non-linear regression model to generate potency values. Data points represent mean±standard deviation.

Figure 200:
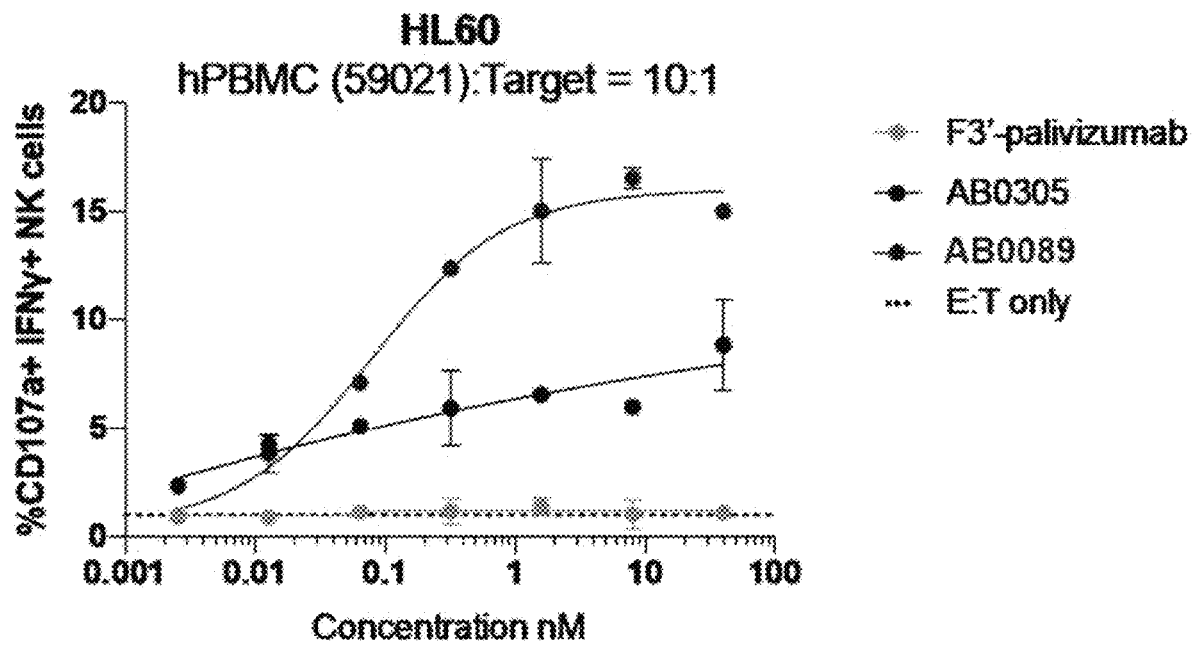

FIG. 200 shows that AB0089 induces IFNγ production and degranulation by human NK cells against HL60 AML cells. Frozen PBMCs were thawed and co-cultured with HL60 target cells in the presence of a dose-titration of AB0089, AB0305 or F3'-palivizumab. After incubation, cells were prepared for FACS analysis of CD107a degranulation and intracellular accumulation of IFNγ. The figure shown is representative of the three PBMC donors tested. The percentage of IFNγ+CD107+ NK cells induced was plotted against concentration, and data were fit to a 4-parameter non-linear regression model to generate potency values. Data points represent mean±standard deviation.

Figure 201:
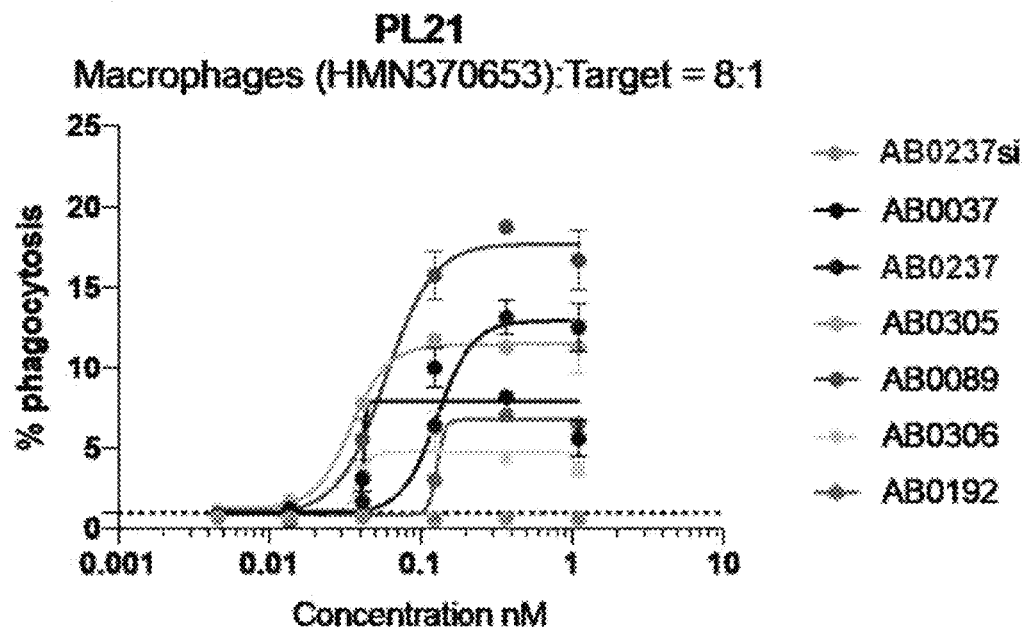

FIG. 201 shows that CLEC12A TriNKETs induce M0-macrophage ADCP activity against PL21 AML cells. In vitro generated M0 macrophages were labeled with Cell Trace Violet and co-cultured with Cell Trace CFSE-labeled PL21 target cells at an 8:1 E:T ratio. After two-hours, cells were prepared for flow cytometry analysis. Double-positive Cell Trace Violet/CFSE cells were considered phagocytic events. Assays were conducted with macrophages derived from three independent donors with the figure shown being a representative result. Percentage phagocytosis of target cells was plotted against test article concentration, and data were fit to a 4-parameter non-linear regression model to generate potency values. Data points represent mean±standard deviation.

Figure 202:
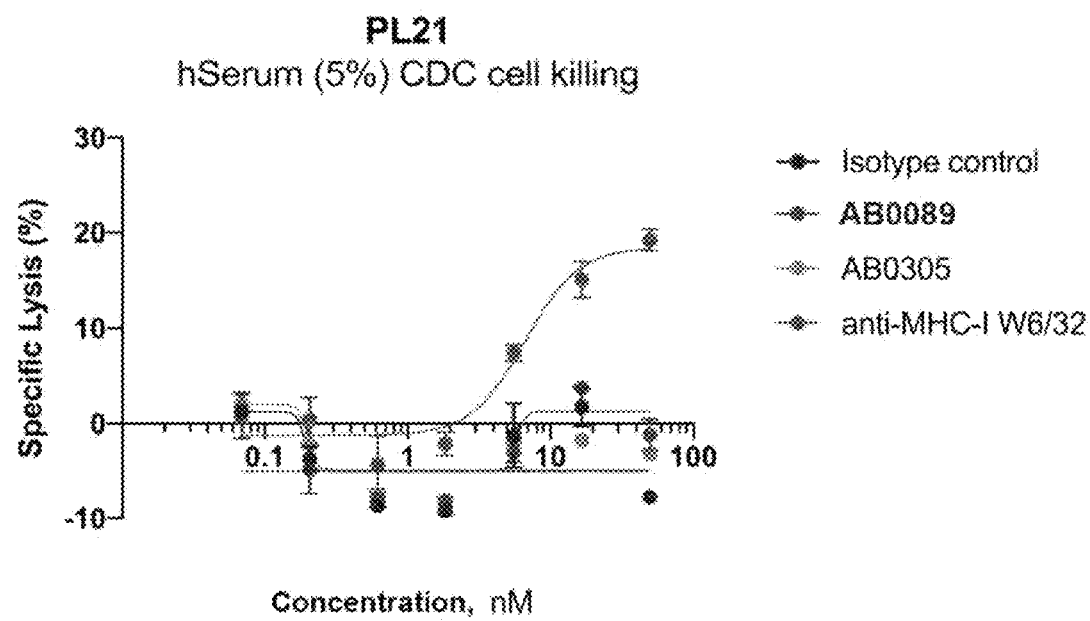

FIG. 202 shows that AB0089 does not stimulate CDC against PL21 AML cells. AB0089 was incubated with BATDA-labeled PL21 cells in cell culture media containing 5% human serum for 60 minutes. Human IgG1 isotype control served as a negative control, while anti-MHC class I clone W6/32 was used as a positive control. Specific lysis of target cells was plotted against concentration, and data were fit to a 4-parameter non-linear regression model to generate potency values. Data points represent mean±standard deviation.

Figure 203A:
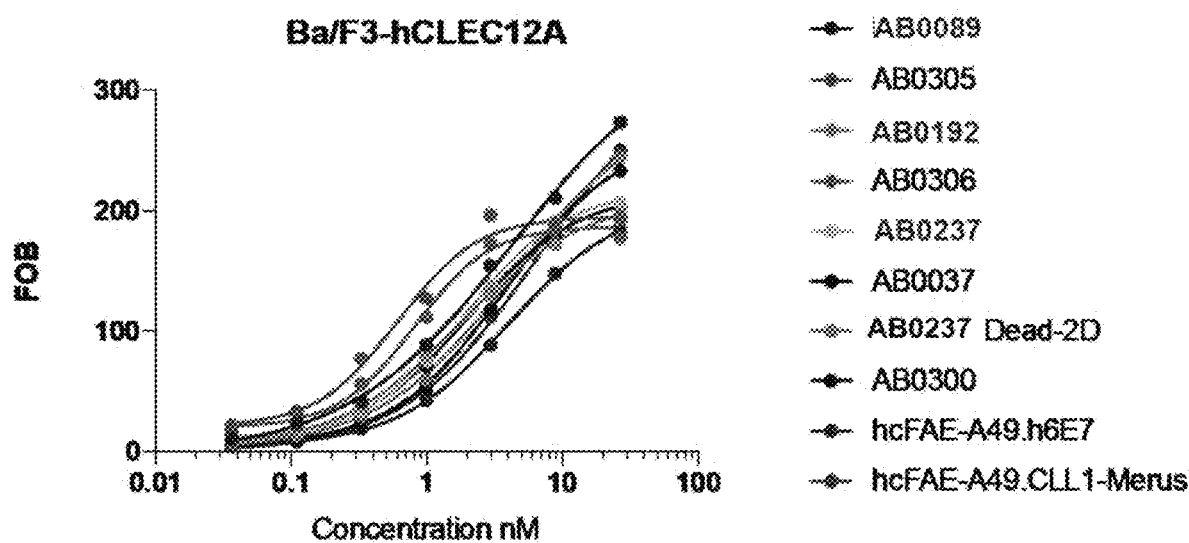
Figure 203B:
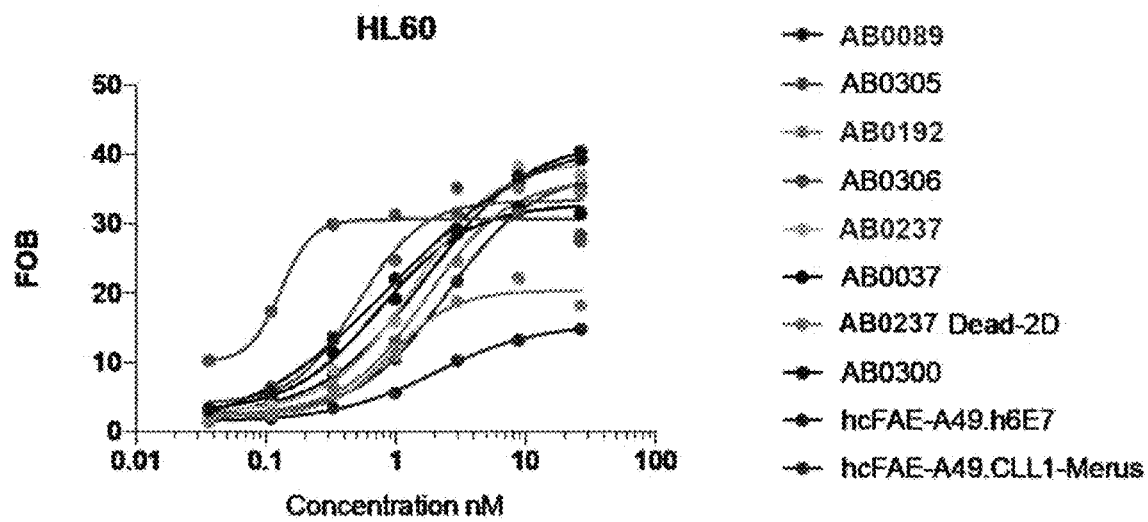
Figure 203C:
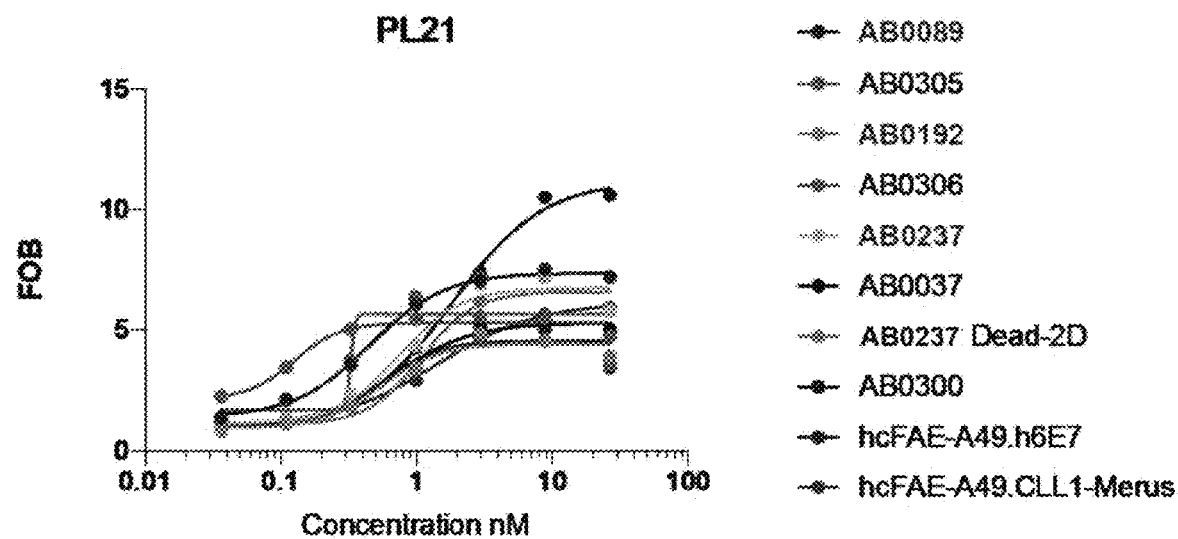

FIG. 203A-FIG. 203C show binding of CLEC12A-TriNKETs to cell lines expressing CLEC12A. Dose-response binding of CLEC12A TriNKETs and their parental mAbs were analyzed on (FIG. 203A) Ba/F3 cells overexpressing human CLEC12A. The human cancer cell lines (FIG. 203B) HL60 and (FIG. 203C) PL21 with endogenous expression of CLEC12A were used to corroborate results with the transfected cell line. Figures shown are representative of results from three independent experiments, which are summarized in Table 201.

Figure 204A:
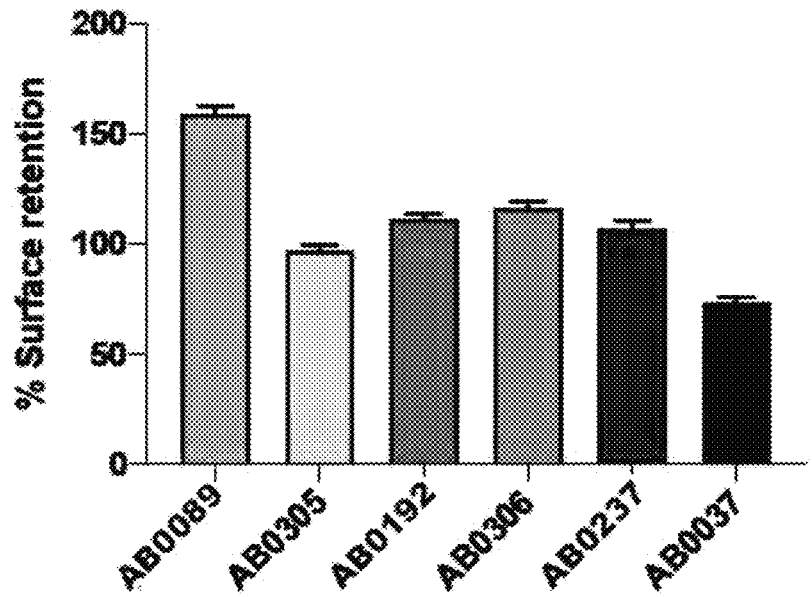
Figure 204B:
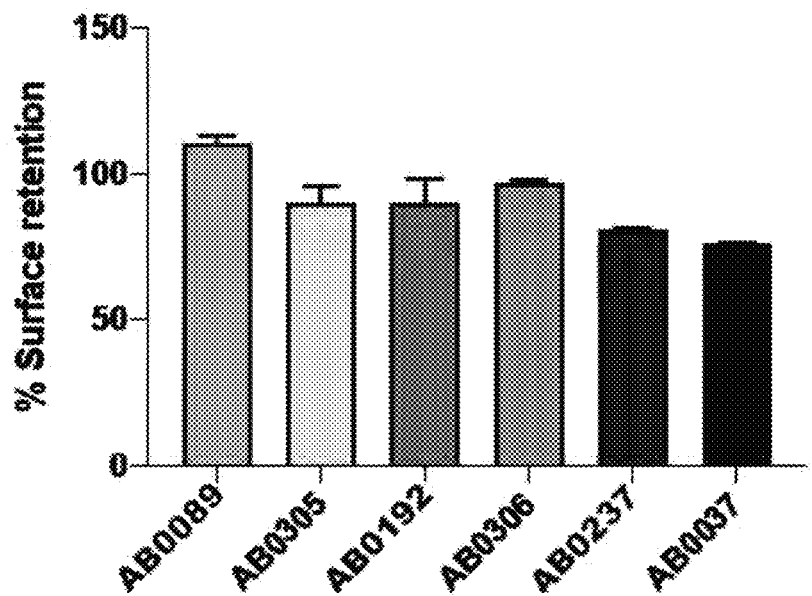

FIG. 204A-FIG. 204B show CLEC12A surface retention on AML cell lines exposed to CLEC12A TriNKETs. CLEC12A surface retention on (FIG. 204A) HL60 and (FIG. 204B) PL21 cells was measured after exposure to test articles at 40 nM for two hours at 37° C. Test articles were used at saturation concentrations and detected using a human IgG Fc-specific secondary antibody. Staining intensity after two hours at 37° C. was normalized to staining intensity of the same test article on cells incubated for two hours on ice to derive the percentage of CLEC12A retained on cell surfaces. Data bars represent the average of duplicate wells and error bars represent standard deviation. Figures shown are representative of results from three independent experiments, which are summarized in Table 202.

Figure 205:
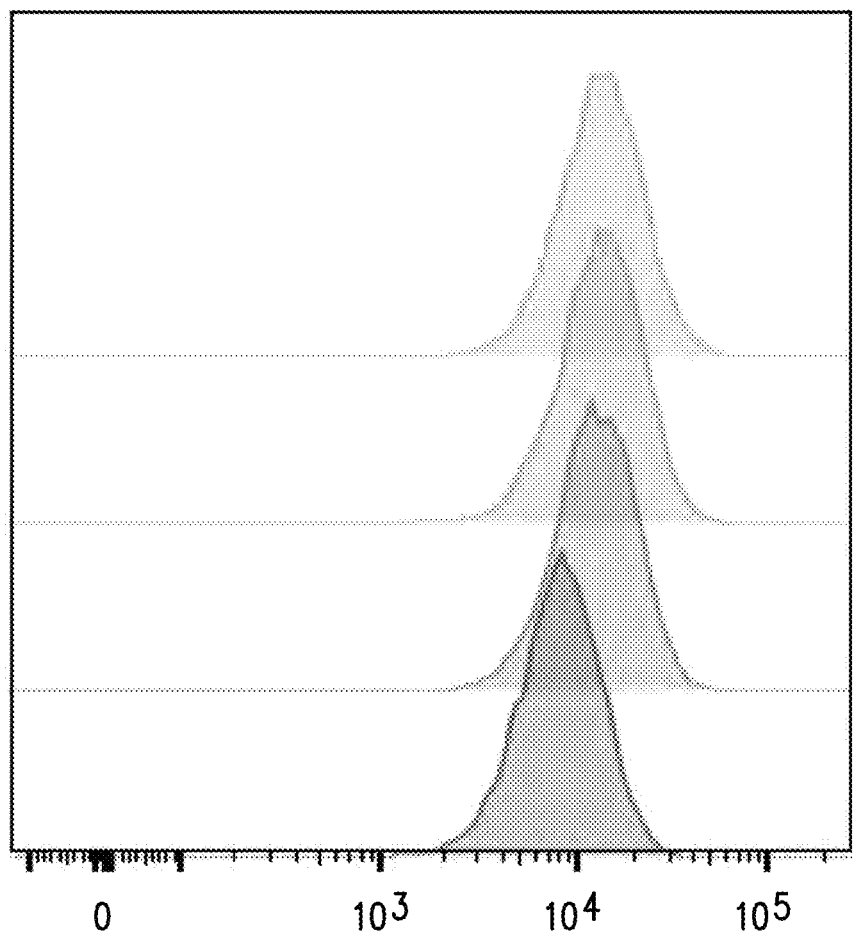
Figure 208A:
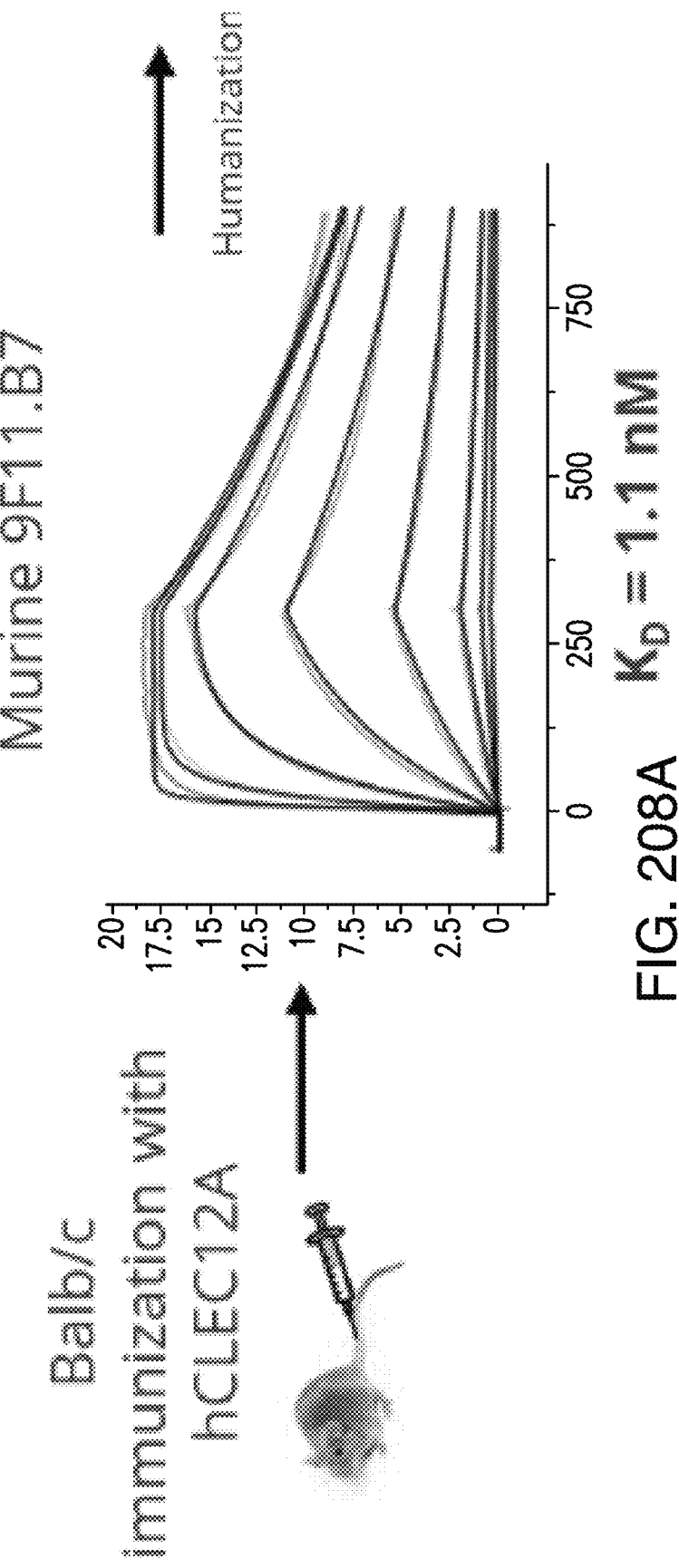
Figure 208B:
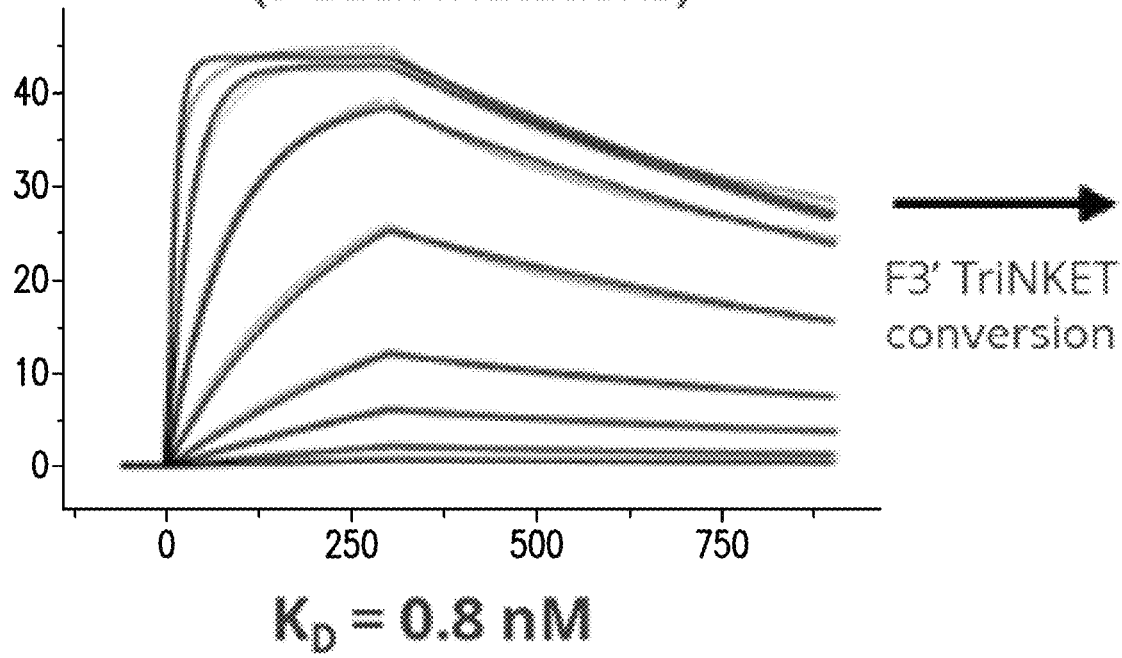
Figure 208C:
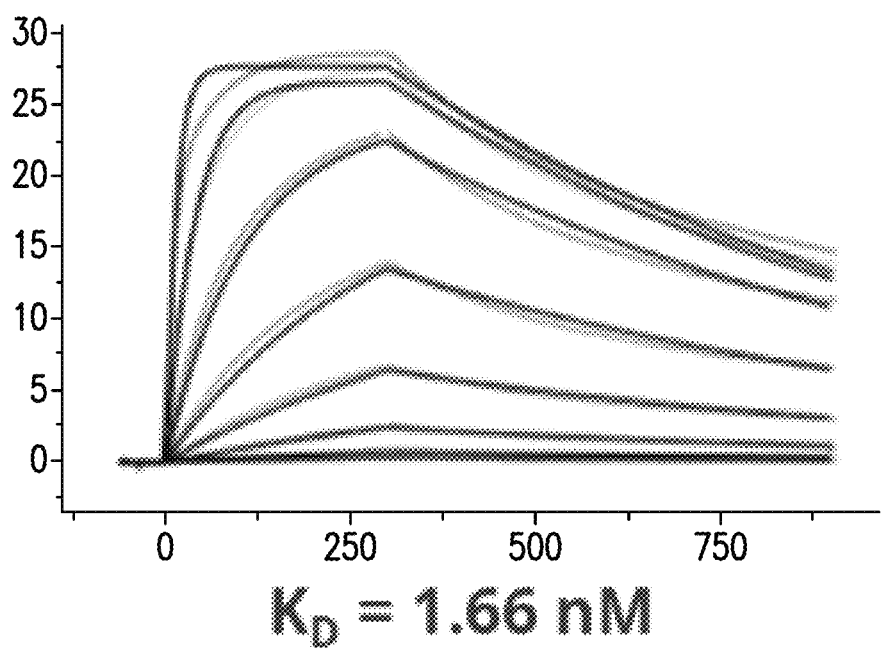
Figure 208D:
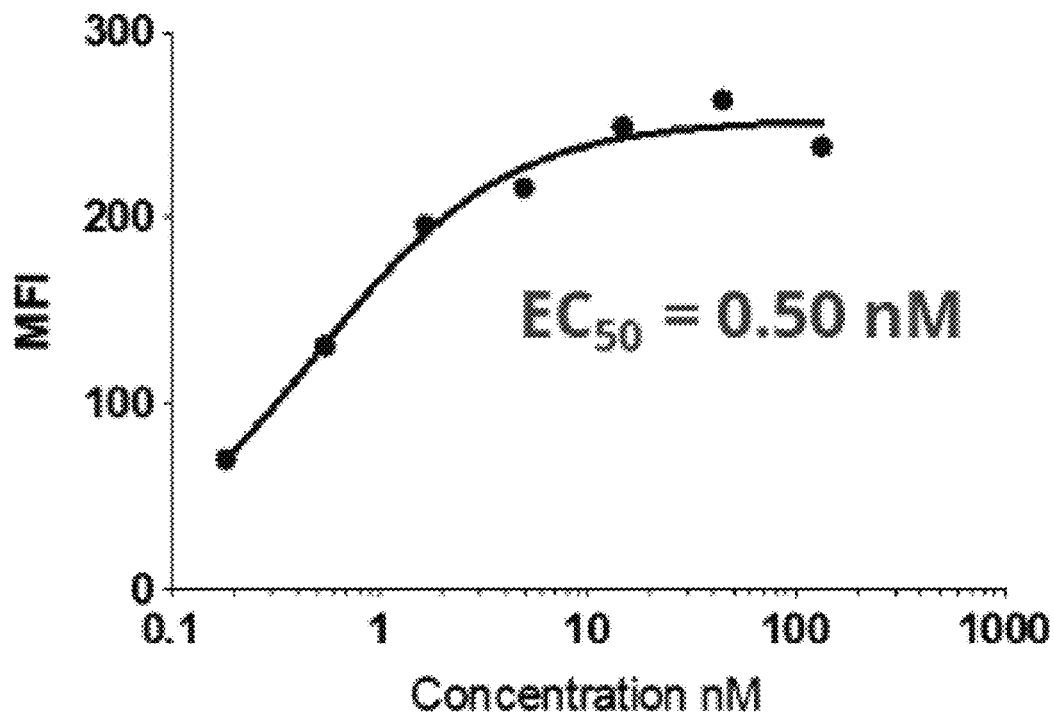
Figure 208E:
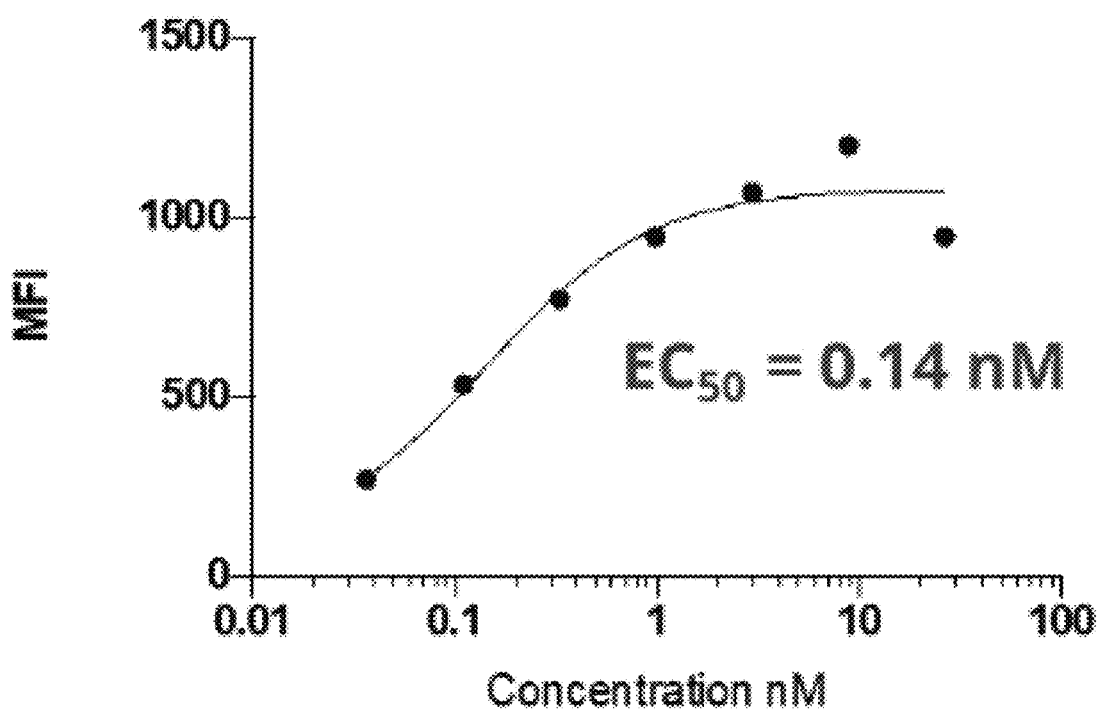
Figure 208F:
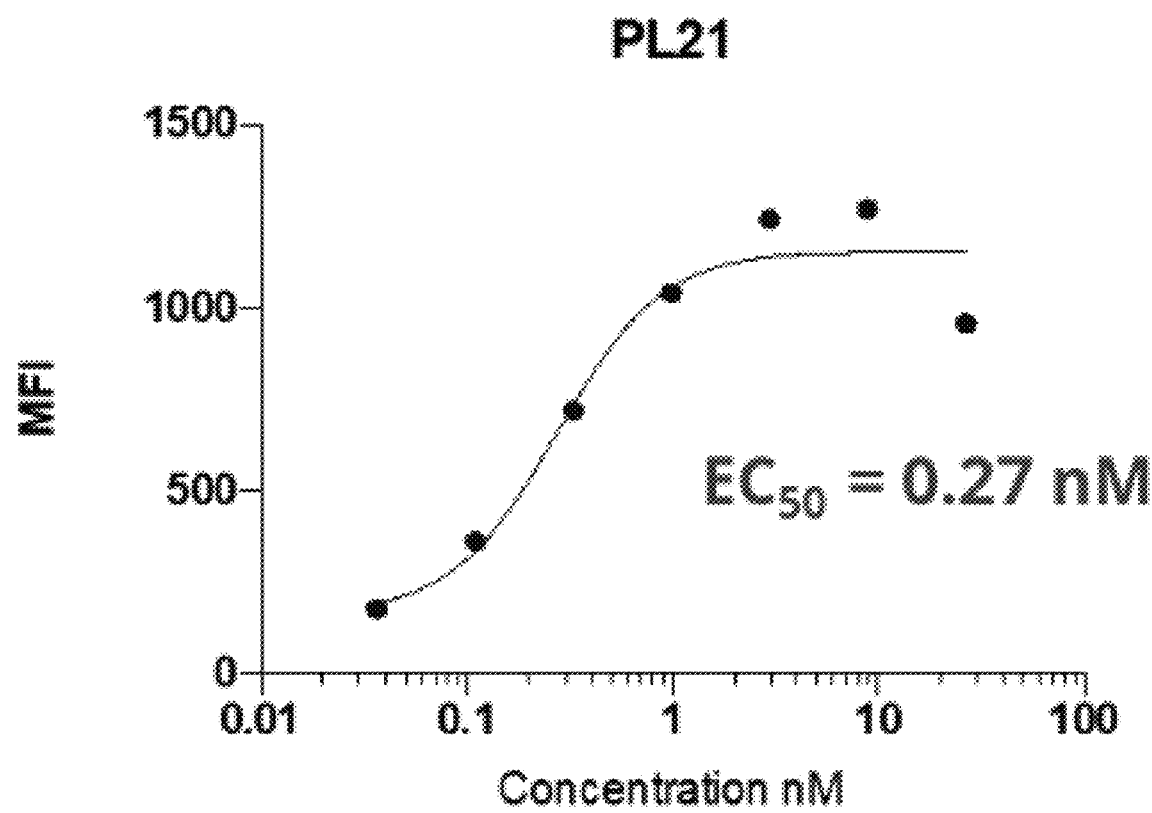

FIG. 205 shows AB0089 binding normalized to AB0237 after two hours at 37° C. AB0089 and AB0237 binding were compared on HL60 cells after a two-hour incubation on ice or at 37° C. Histograms represent the following: (1st from top to bottom) AB0237 two-hours 37° C., (2nd from top to bottom) AB0237 two-hour on ice, (3rd from top to bottom) AB0089 two-hours at 37° C., (4th from top to bottom) AB0089 two-hours on ice. Binding of all test articles was detected with an anti-human IgG Fc fluorophore-conjugated antibody.

FIG. 206A-FIG. 206J show AB0089 binds CLEC12A+ blasts across 10 primary AML patient samples. Primary AML bone marrow and PBMC samples were obtained from commercial vendors, see Table 3. Samples were prepared for flow cytometry analysis according to the antibody panel in Table 1. Histograms represent staining on AML blasts as follows: 4th from top to bottom=hIgG1 isotype control, 3rd from top to bottom=AB0305-CF568, 2nd from top to bottom=AB0089-CF568, 1st from top to bottom=anti-CLEC12 50C1-CF568.

FIG. 207A-FIG. 207J show AB0089 binds CLEC12A+ CD34+CD38− cells across 10 primary AML patient samples. Primary AML bone marrow and PBMC samples were obtained from commercial vendors, see Table 200. Samples were prepared for flow cytometry analysis according to the antibody panel in Table 298. Samples were further gated on CD34+CD38− subpopulation to enrich for leukemic stem cells. Histograms represent staining on CD34+ CD38− blasts as follows: 4th from top to bottom=hIgG1 isotype control, 3rd from top to bottom=AB0305-CF568, 2nd from top to bottom=AB0089-CF568, 1st from top to bottom=anti-CLEC12 50C1-CF568.

FIG. 208A-FIG. 208F show the path from immunization to AB0192. Upper panel represents results of CLEC12A binding by SPR. Lower panel shows binding to CLEC12A+ PL-21 AML cancer cells.

Figure 209:
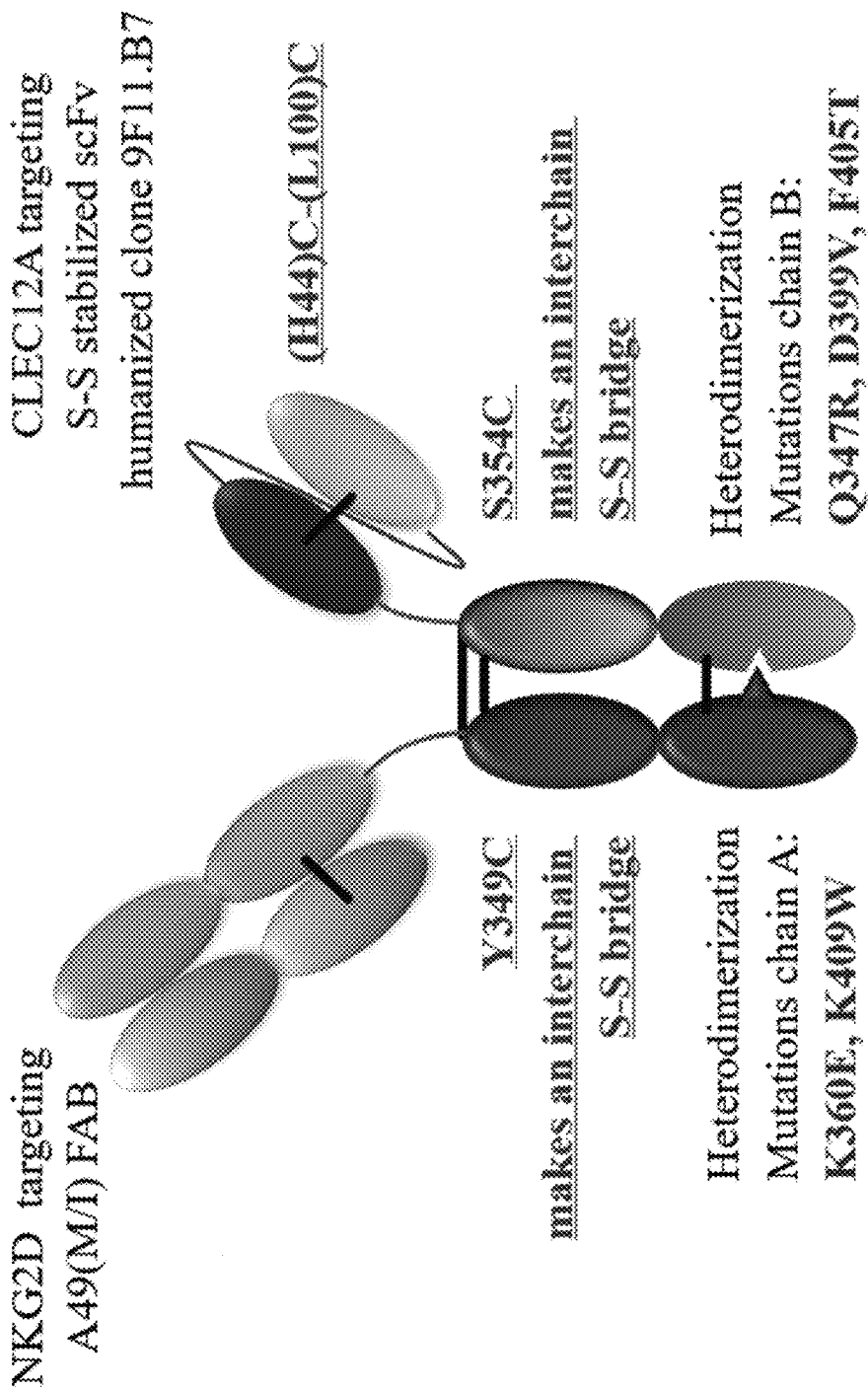
Figure 211A:
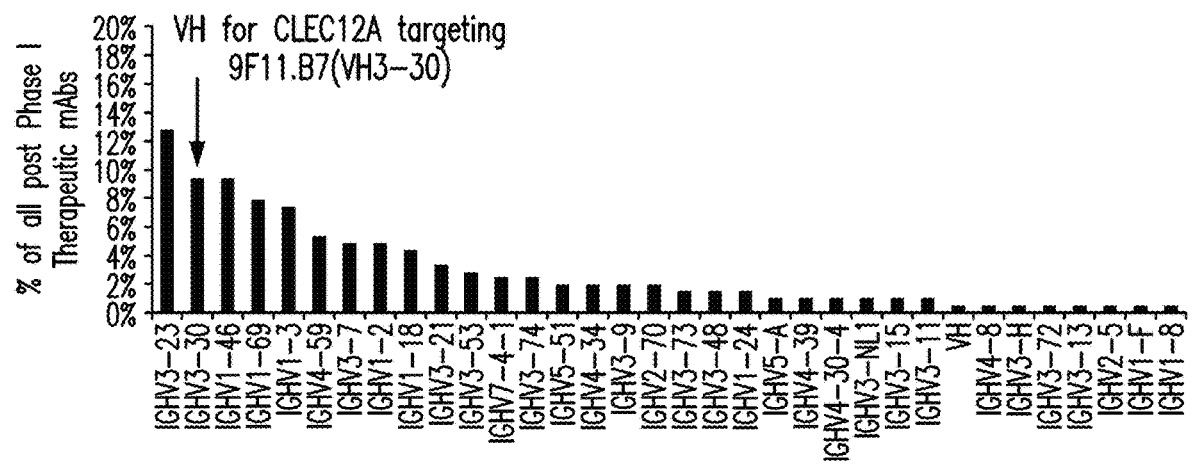
Figure 211B:
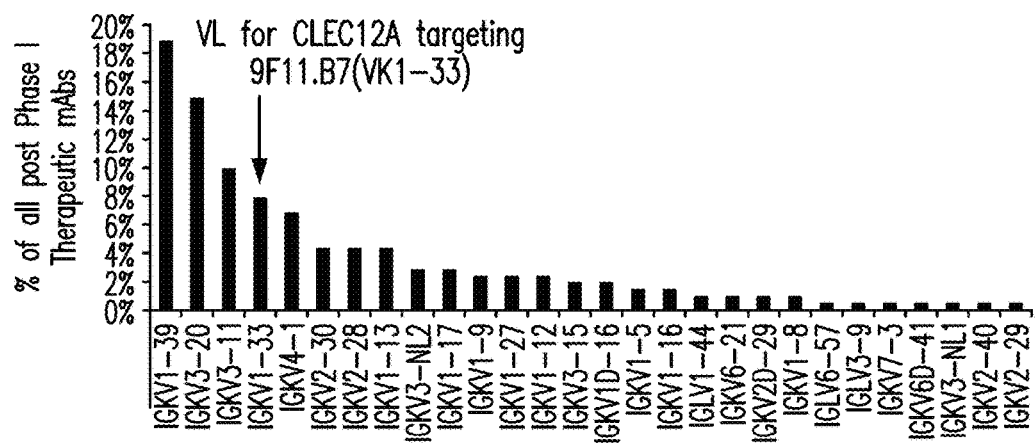
Figure 211C:
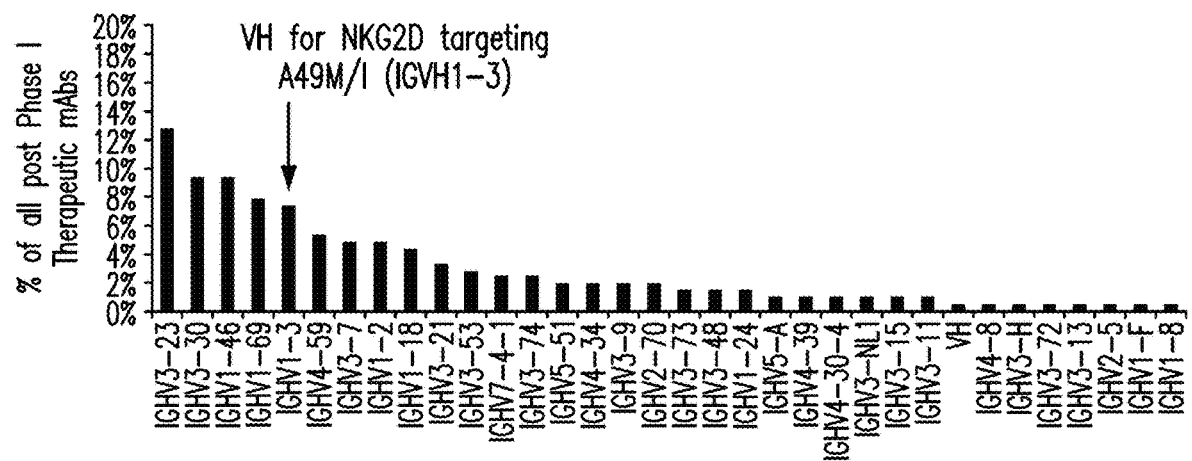
Figure 211D:
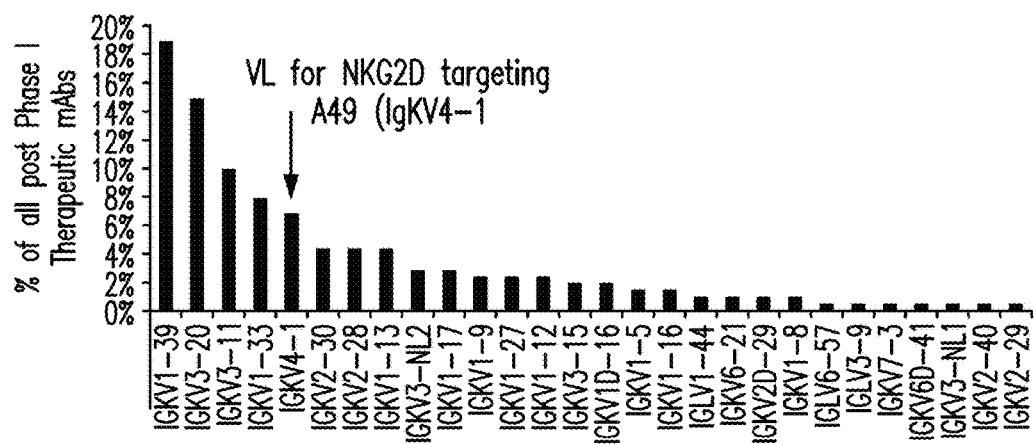

FIG. 209 shows a schematic representation of AB0192. Proprietary heterodimerization mutations and an engineered interchain disulfide bridge ensure efficient chain pairing of the IgG1 Fc. The scFv is derived from the humanized and sequence liability corrected CLEC12A mAb 9F11.B7. The scFv is stabilized by an engineered disulfide bridge between VH and VL.

FIG. 210 shows the amino acid sequences of the three polypeptide chains that make up AB0192. Chain S: anti-CLEC12A scFv-CH2-CH3 (humanized sequence, CDRs are bold not underlined, back mutations bold and underlined, engineered scFv disulfide in italic and bold, and Fc mutations for heterodimerization and the engineered CH3 disulfide are underlined not bold). Chain H: anti-NKGD VH-CH1-CH2-CH3 (fully human, CDRs are bold not underlined, Fc mutations for heterodimerization and the engineered CH3 disulfide are underlined not bold). Chain L: anti-NKGD VL-CL (fully human, CDRs are bold not underlined).

FIG. 211A-FIG. 211D show human acceptor frameworks used in AB0192 compared to other clinical stage therapeutic mAbs. Benchmarking of frameworks used in AB0192 against human germlines frequently used in clinical stage antibodies database containing 400+ mAbs from phase I+.

Figure 212C:
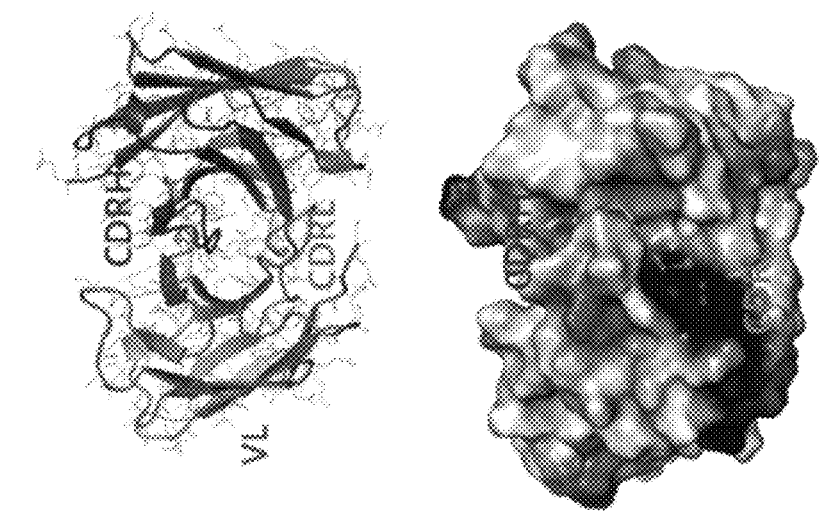
Figure 212B:
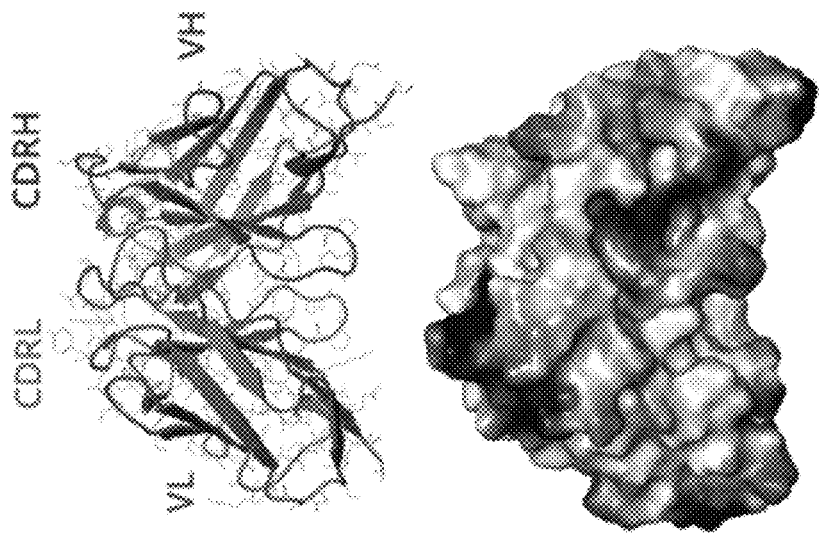
Figure 212A:
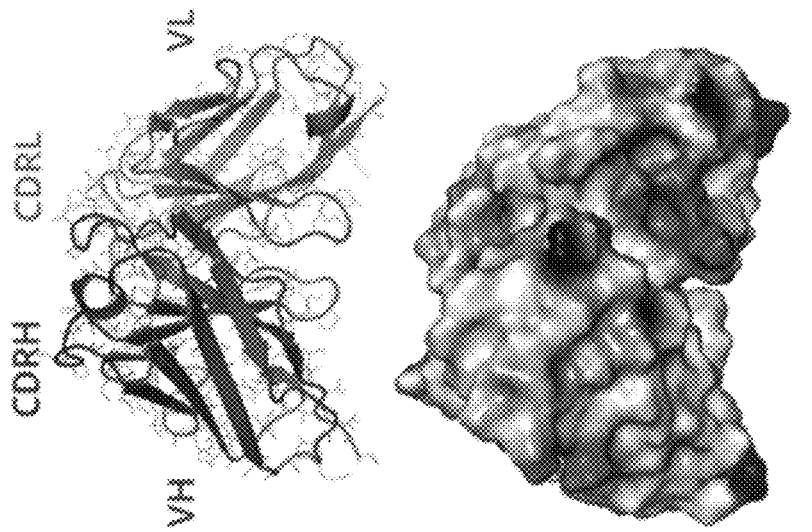

FIG. 212A-FIG. 212C show a ribbon diagram model of the CLEC12A binding scFv in three different orientations (upper panel) and their corresponding surface charge distribution of the same orientation (lower panel). The charge distribution of anti-FIG. CLEC12A scFv is polarized ("top view", lower panel), with negatively-charged residues populated predominately within CDRH3 and CDRL2. Three orientations are shown: both façades (FIG. 212A: front view; FIG. 212B: back view) and the antigen-engaging surface (FIG. 212C: top view).

FIG. 213A-FIG. 213B show the analysis of CDR length and surface hydrophobicity patches of the CLEC12A-targeting arm of AB0192. The arrow indicates where CLEC12A targeting scFv of AB0192 stands in reference to advanced clinical stage mAbs. The inner dotted lines indicate 2 SD (>95% of reference molecules within this region). The outermost dotted lines indicate 3 SD (>99.7% of reference molecules within this region).

Figure 214B:
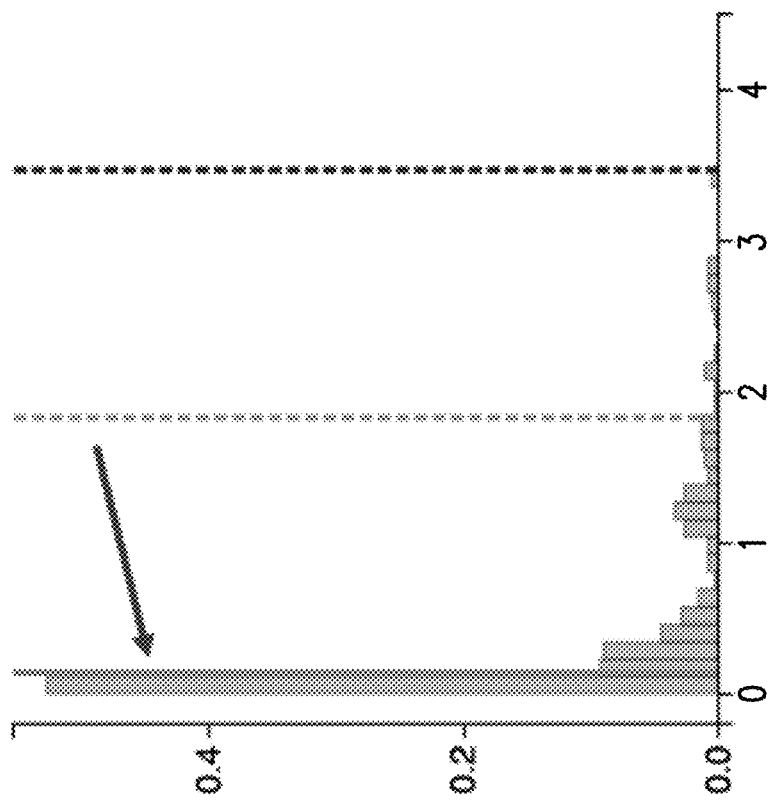
Figure 214A:
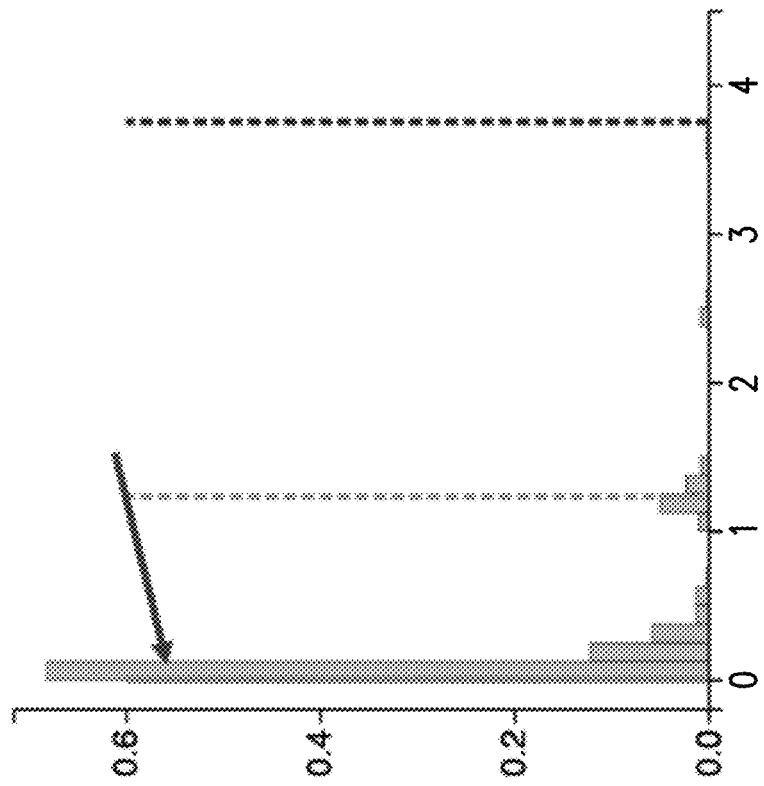
Figure 214C:
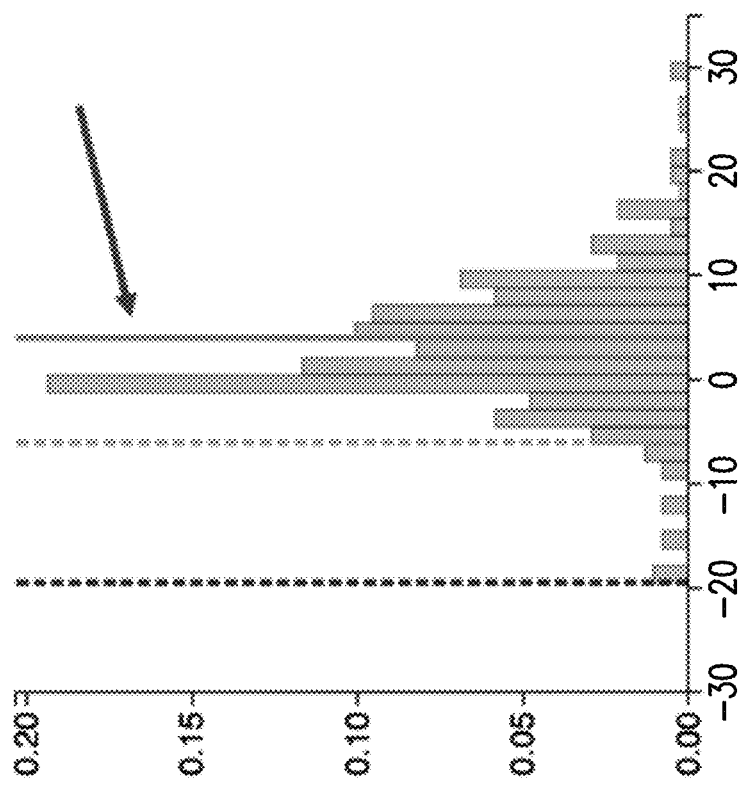

FIG. 214A-FIG. 214C show the analysis of patches containing positive and negative charges, as well as the symmetry of these charges around the CDR regions. The arrow indicates where CLEC12A targeting scFv of AB0192 stands in reference to advanced clinical stage mAbs. In each plot, there are two dashed lines—one closer and the other further to the solid line. The dashed line closer to the solid line indicates 2 SD (>95% of reference molecules within this region), whereas the dashed line further to the solid line indicates 3 SD (>99.7% of reference molecules within this region).

Figure 215C:
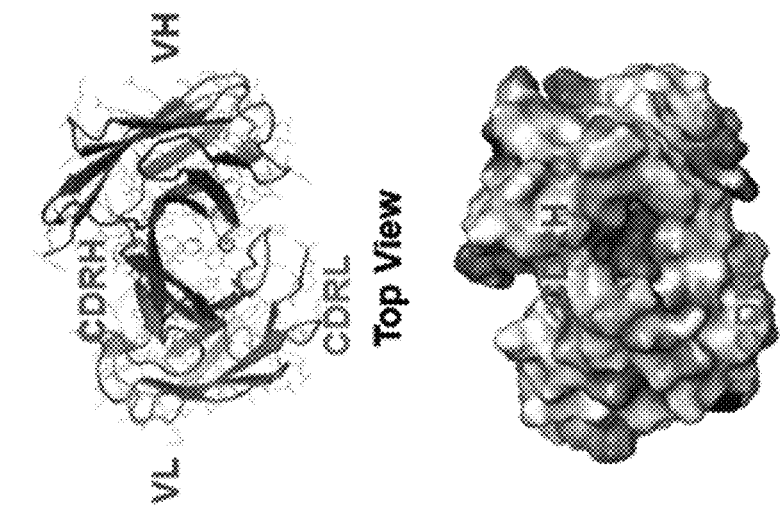
Figure 215B:
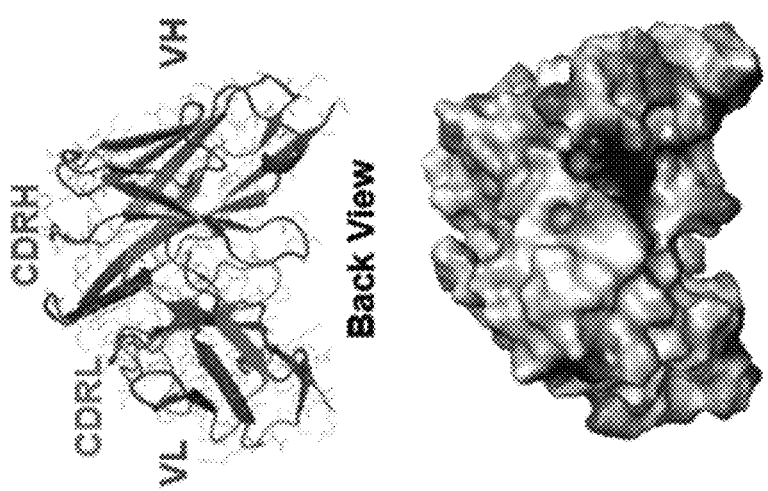
Figure 215A:
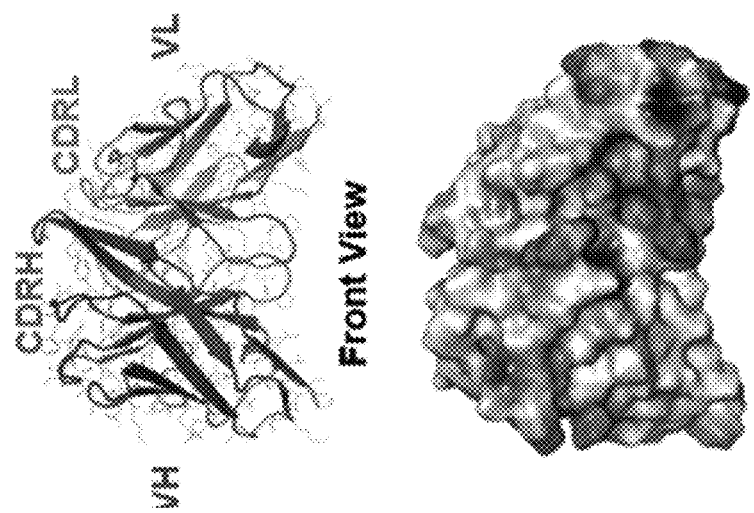

FIG. 215A-FIG. 215C show a ribbon diagrams with three different orientations of the NKG2D-binding Fab arm (upper panel) and their corresponding surface charge distribution of the same orientation (lower panel). Three orientations are shown: both façades (FIG. 215A: front view; FIG. 215B: back view) and the antigen-engaging surface (FIG. 215C: top view).

Figure 216A:
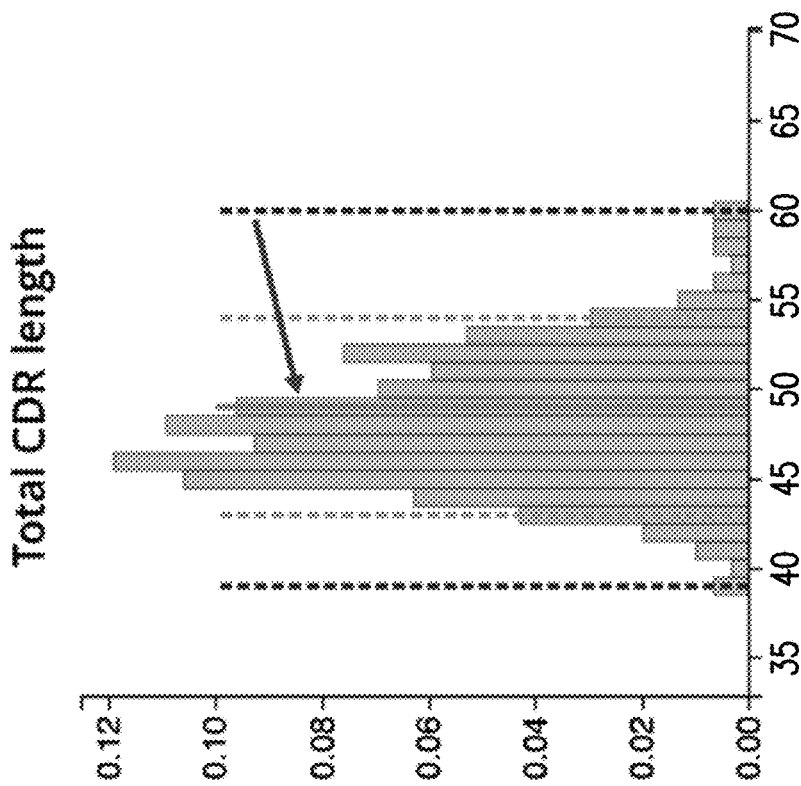
Figure 216B:
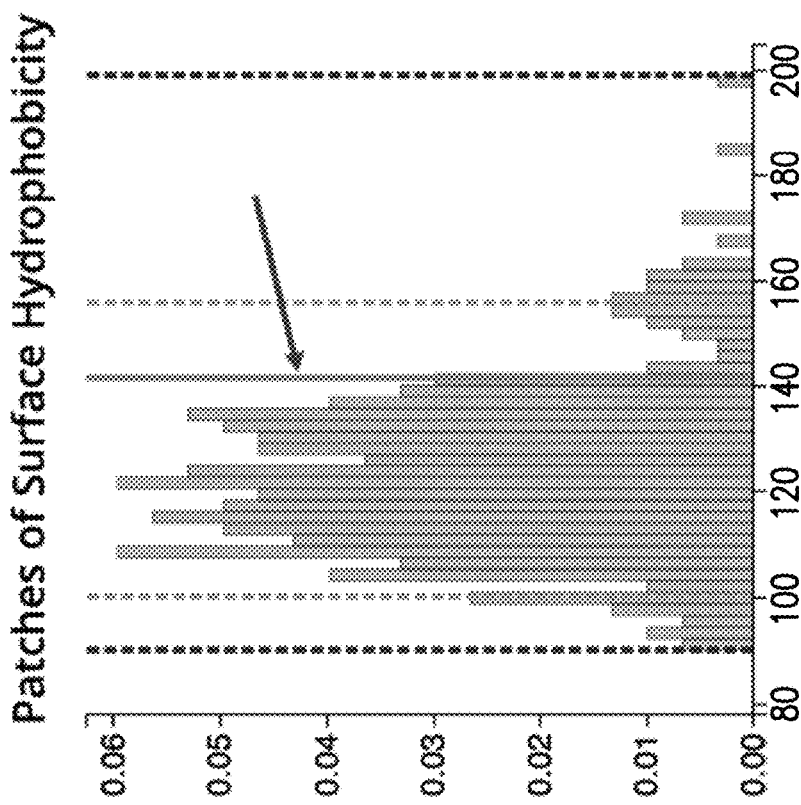

FIG. 216A-FIG. 216B show the CDR length (FIG. 216A) and patches of surface hydrophobicity (FIG. 216B) analyses of NKG2D-targeting arm of AB0192. The arrow indicates where NKG2D targeting Fab of AB0192 stands in reference to advanced clinical stage mAbs. The inner dotted lines indicate 2 SD (>95% of reference molecules within this region). The outermost dotted lines indicate 3 SD (>99.7% of reference molecules within this region).

Figure 217B:
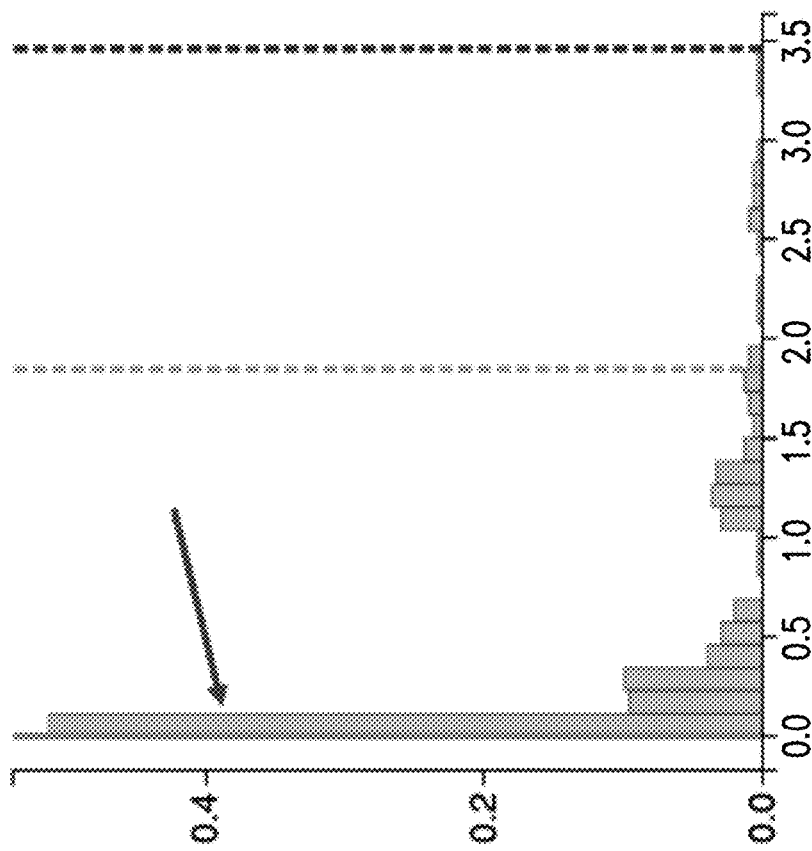
Figure 217A:
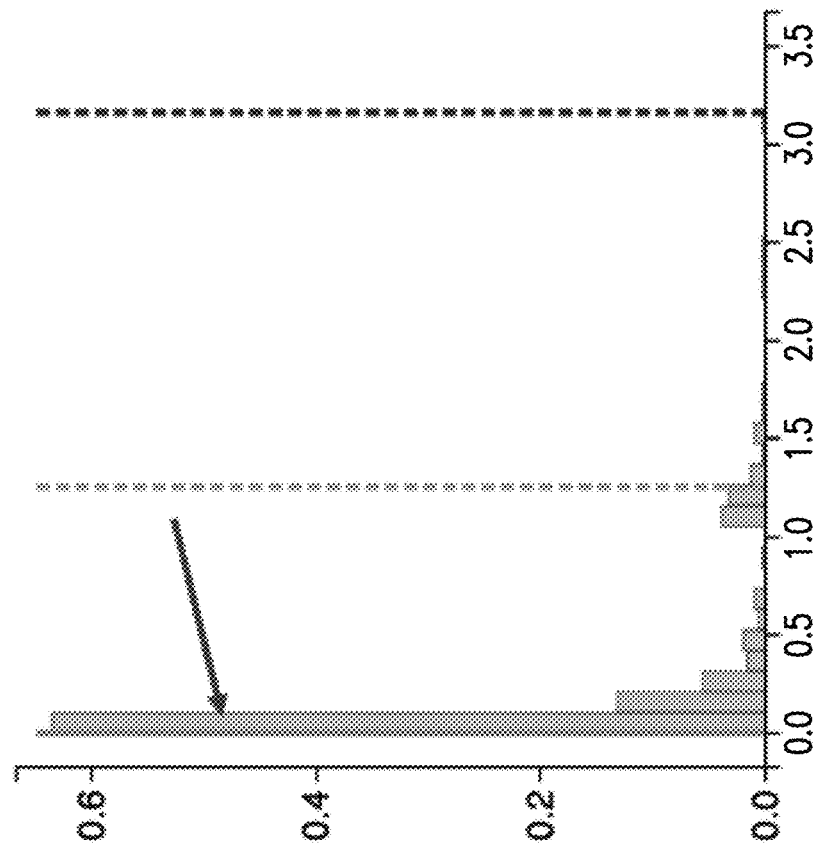
Figure 217C:
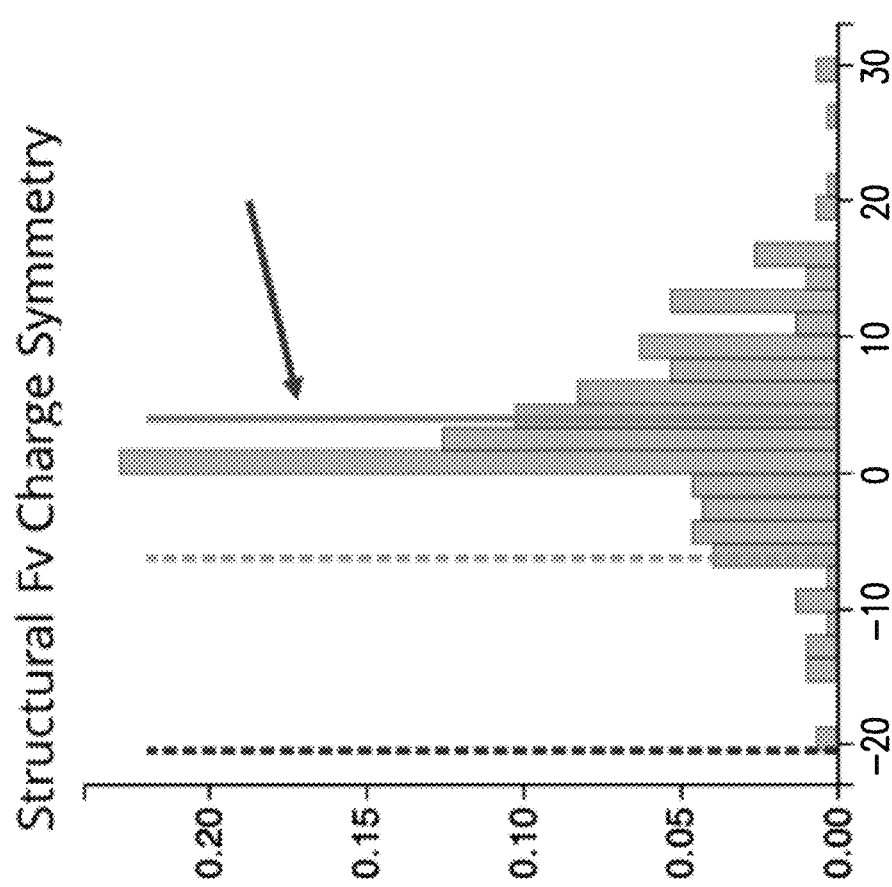

FIG. 217A-FIG. 217C shows the analyses of patches containing positive (FIG. 217A) and negative charges (FIG. 217B), as well as the symmetry of these charges around the CDR regions (FIG. 217C). The arrows indicate the position of the NKG2D targeting Fab of AB0192 stands in reference to a database of 377 late-stage therapeutic antibodies. In each plot, there are two dashed lines—one closer and the other further to the solid line. The dashed line closer to the solid line indicates 2 SD (>95% of reference molecules within this region), whereas the dashed line further to the solid line indicates 3 SD (>99.7% of reference molecules within this region).

Figure 218A:
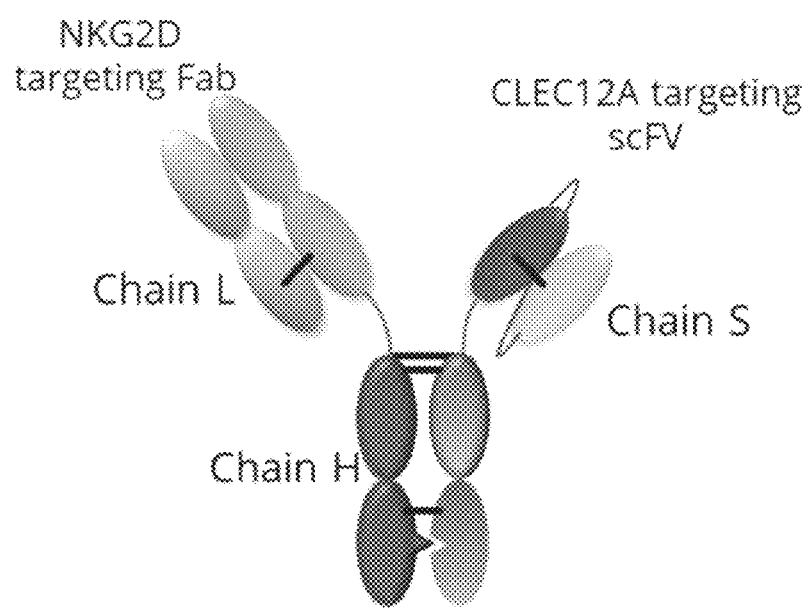
Figure 218B:
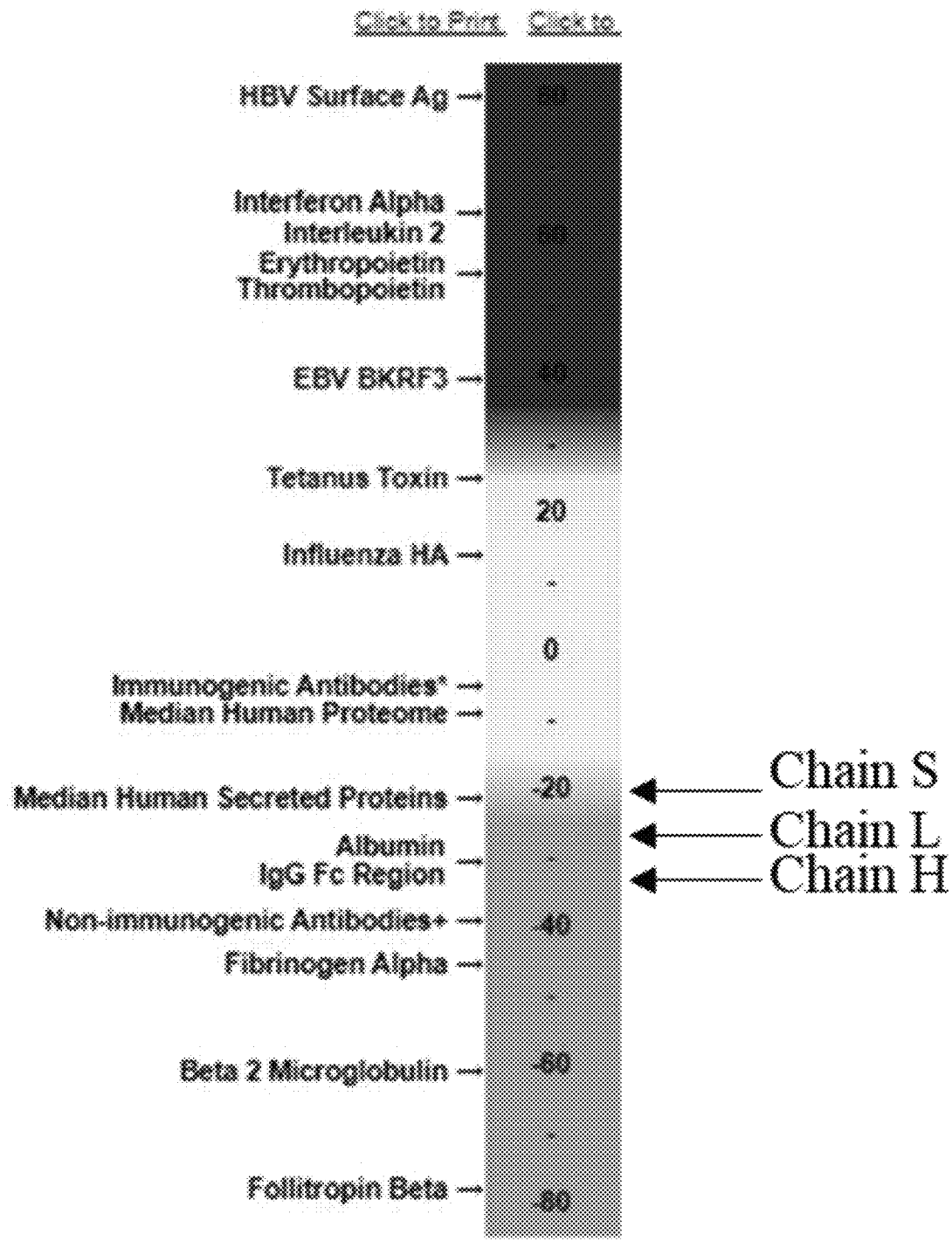

FIG. 218A-FIG. 218B show the position of AB0192 chains on the Treg-adjusted EpiMatrix protein immunogenicity scale. FIG. 218A shows a cartoon representation of AB0192; FIG. 218B shows positions of chain H, S, and L of AB0192 on Treg-Adjusted Immunogenicity Protein Scale.

Figure 219C:
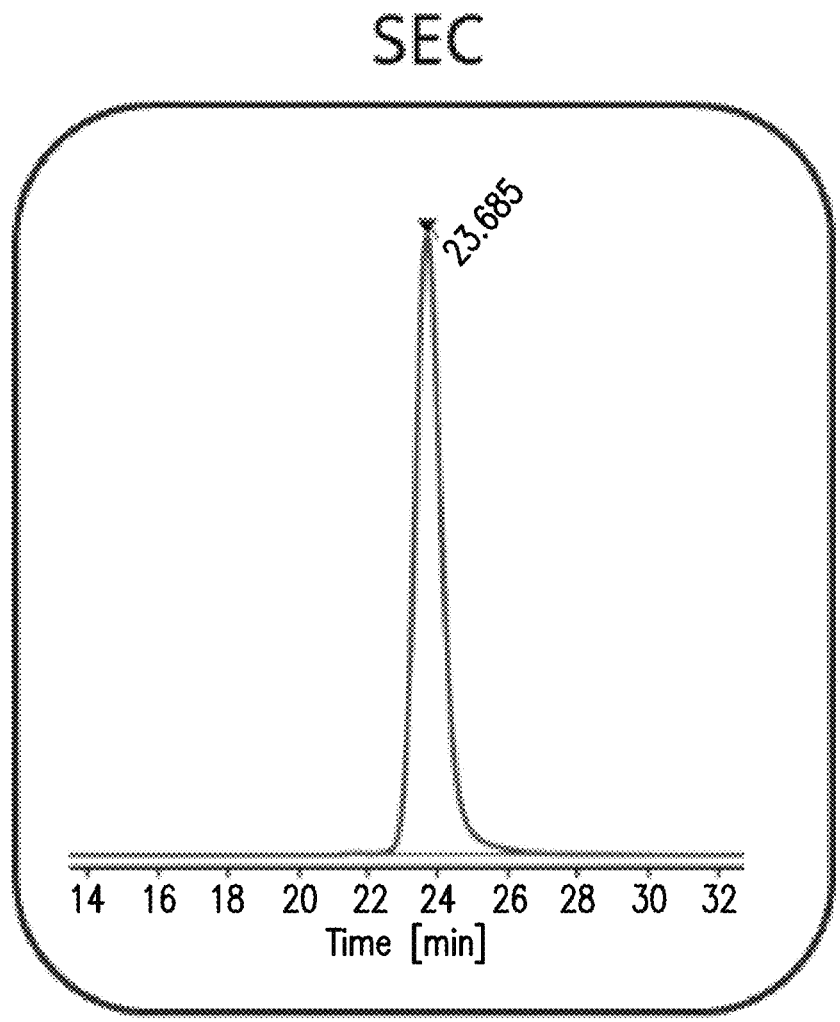
Figure 219D:
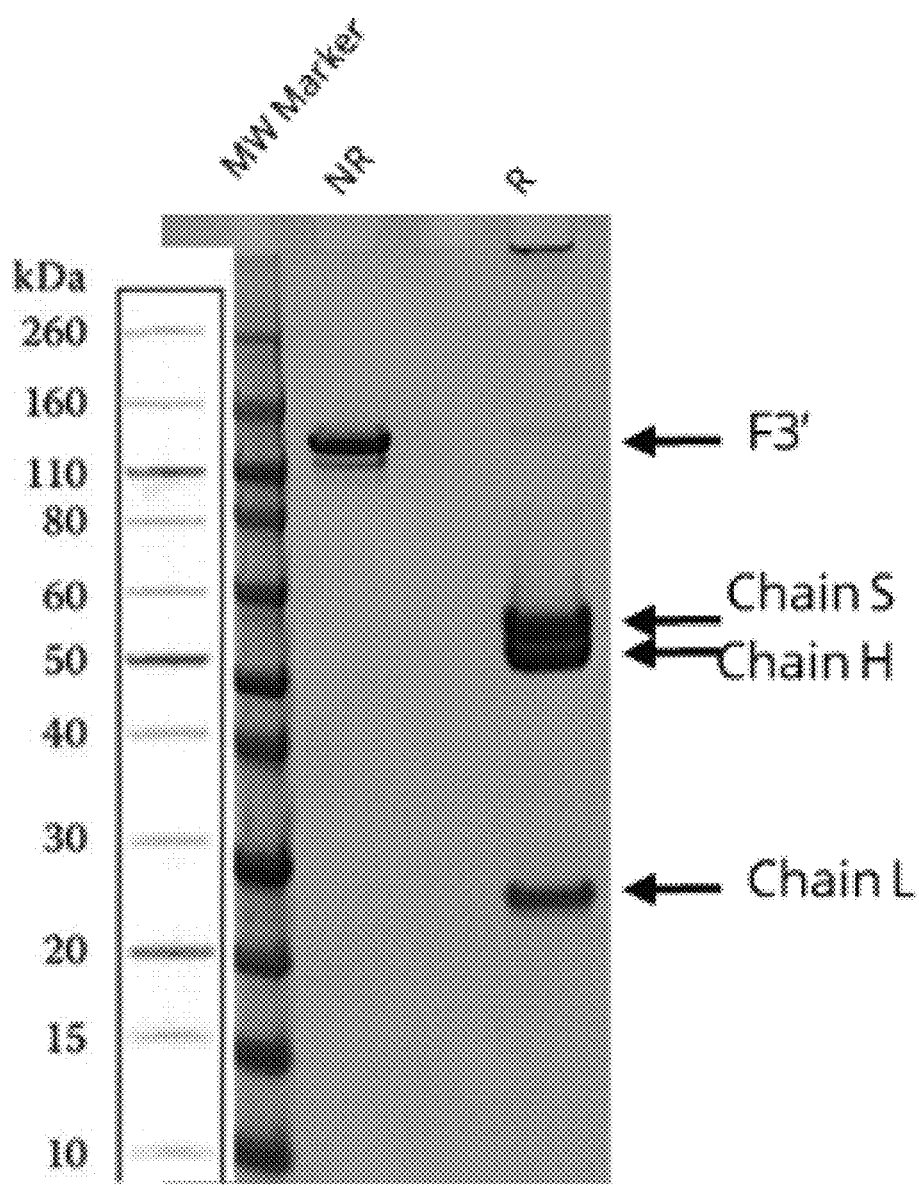

FIG. 219A-FIG. 219D show a schematic representation of the AB0192 2 step platform purification. FIG. 219A and FIG. 219B: SDS-PAGE analysis of AB0192 before and after first step of purification process (Protein A capture). FIG. 219C: SEC analysis of AB0192 after protein A step and after cIEX step. FIG. 219D: Reduced and non-reduced SDS-PAGE of purified AB0192.

Figure 220:
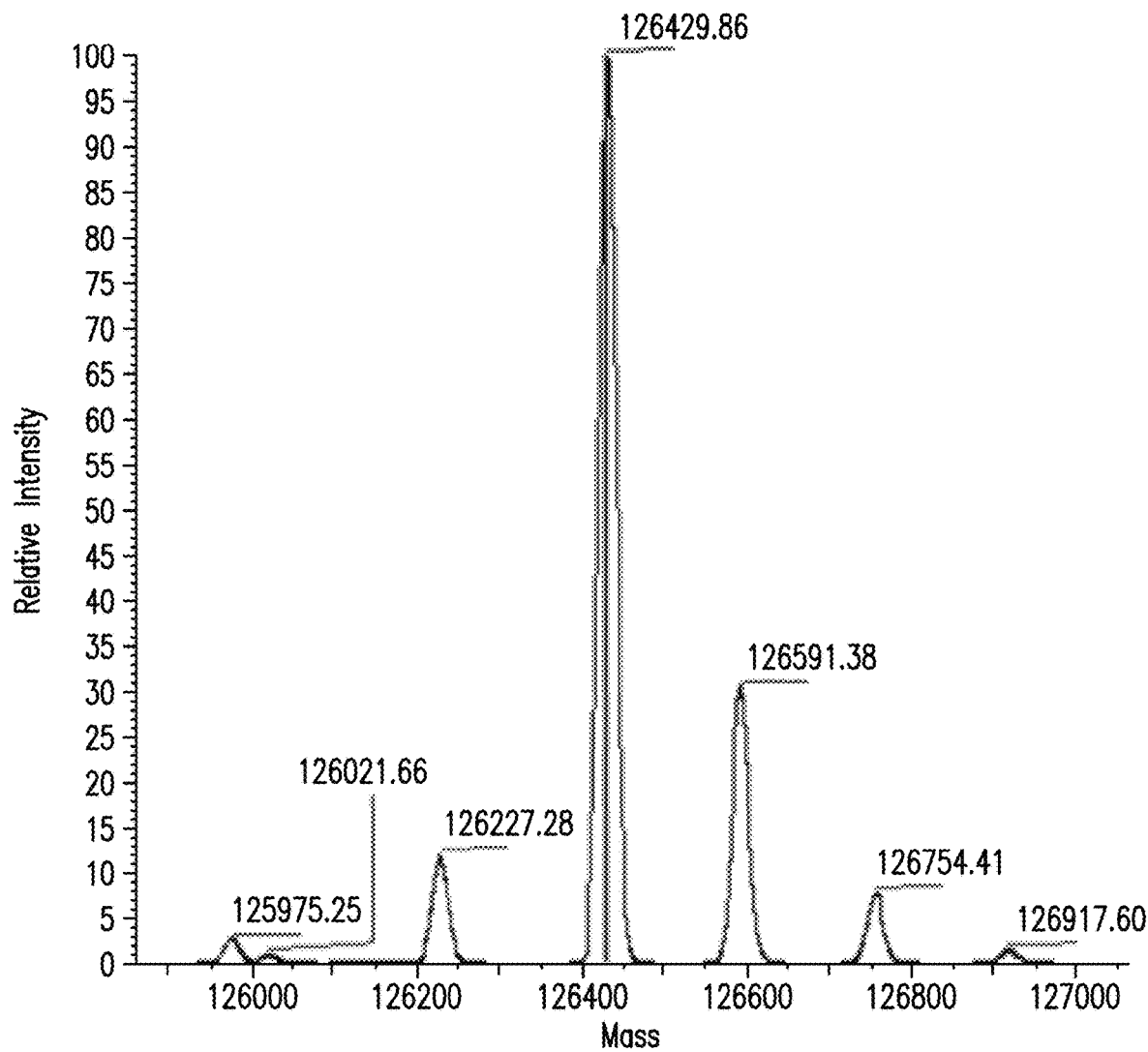

FIG. 220 shows the intact mass analysis of AB0192 (lot AB0192-005) using LC-MS analysis. AB0192 theoretical mass=126,429.5 Da. AB0192 Lot AB0192-005 observed mass=126,429.9 Da.

Figure 221:
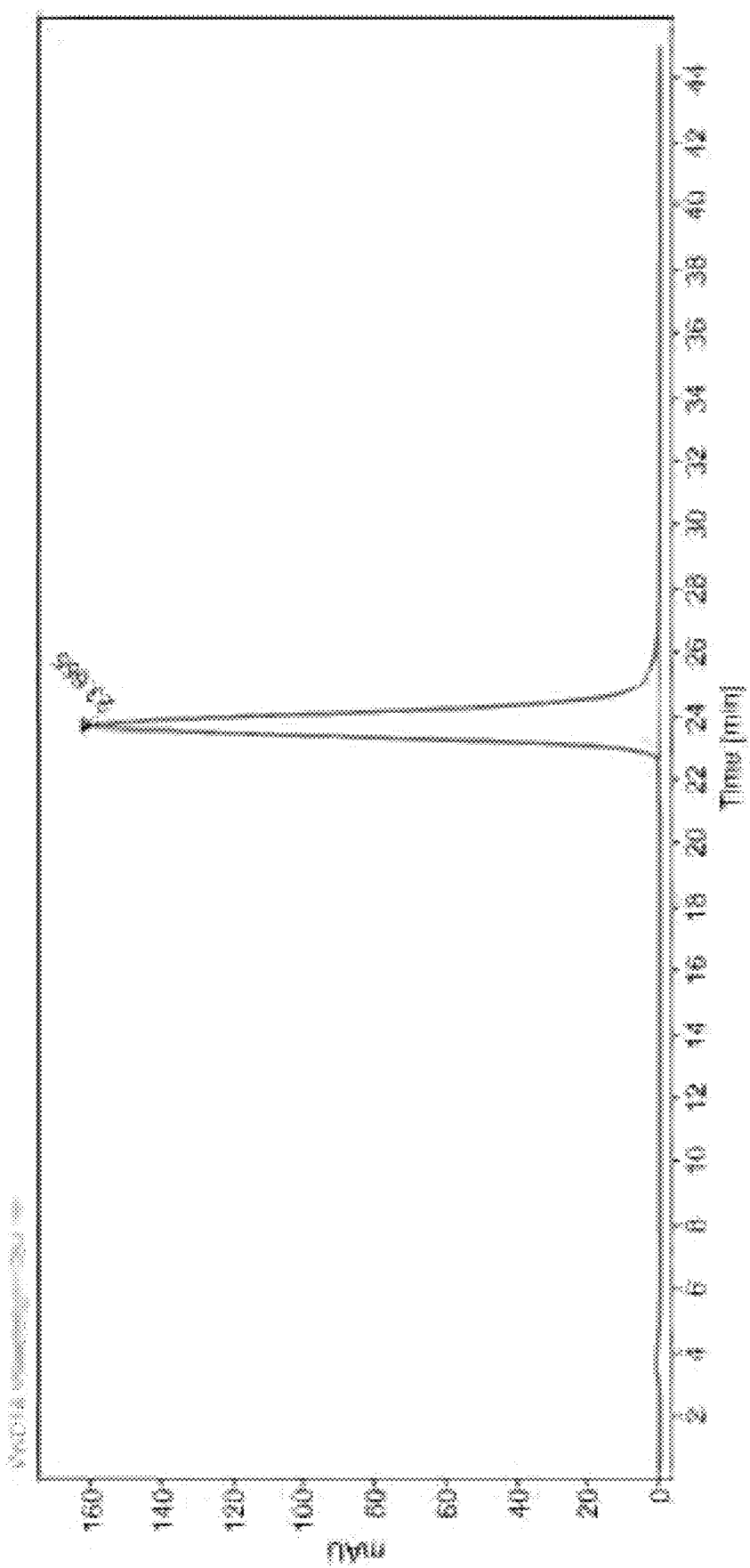

FIG. 221 shows a SEC (Superdex 200) analysis of purified AB0192 (lot AB0192-005), which showed >99% monomer as determined by integrated peak area.

Figure 222A:
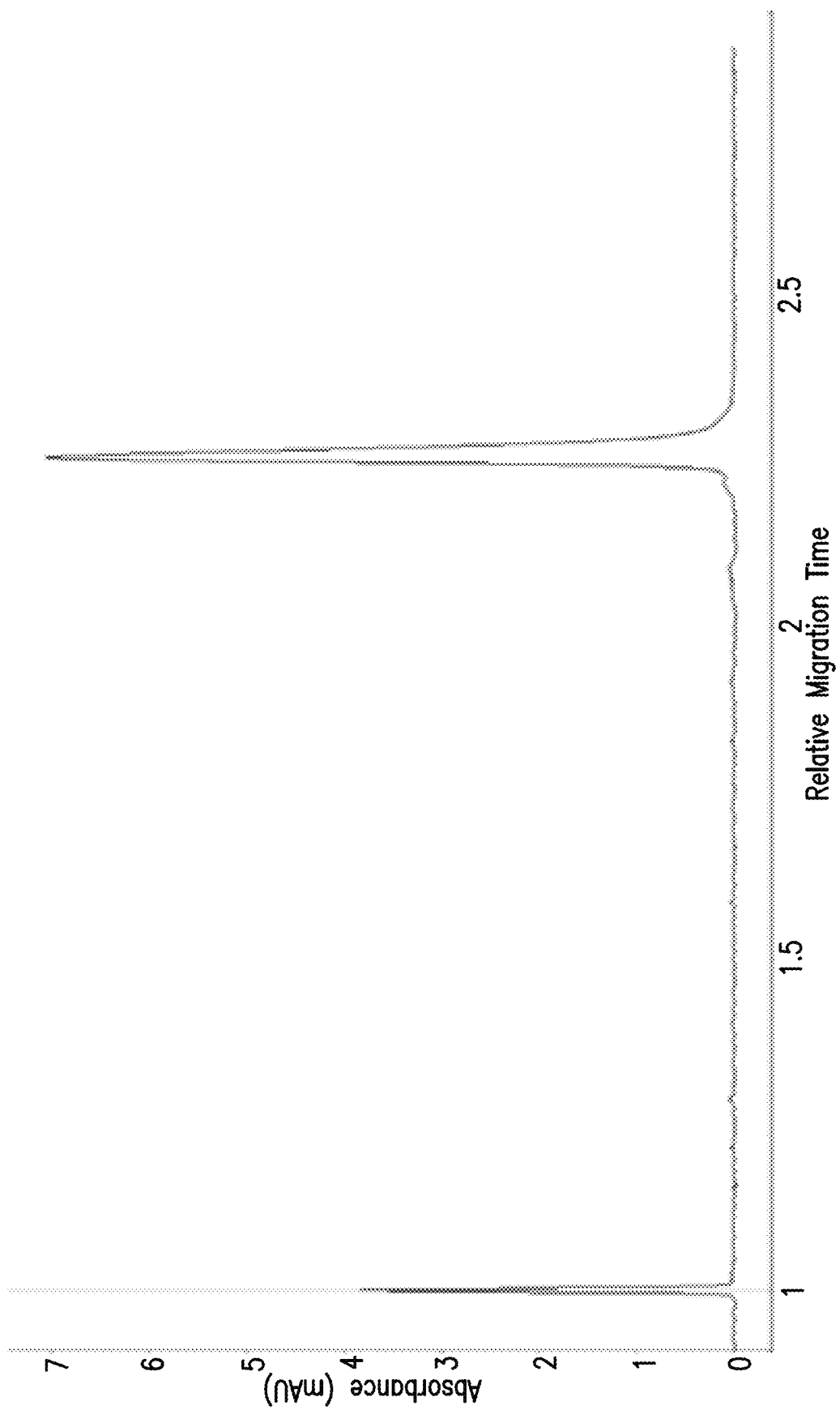
Figure 222B:
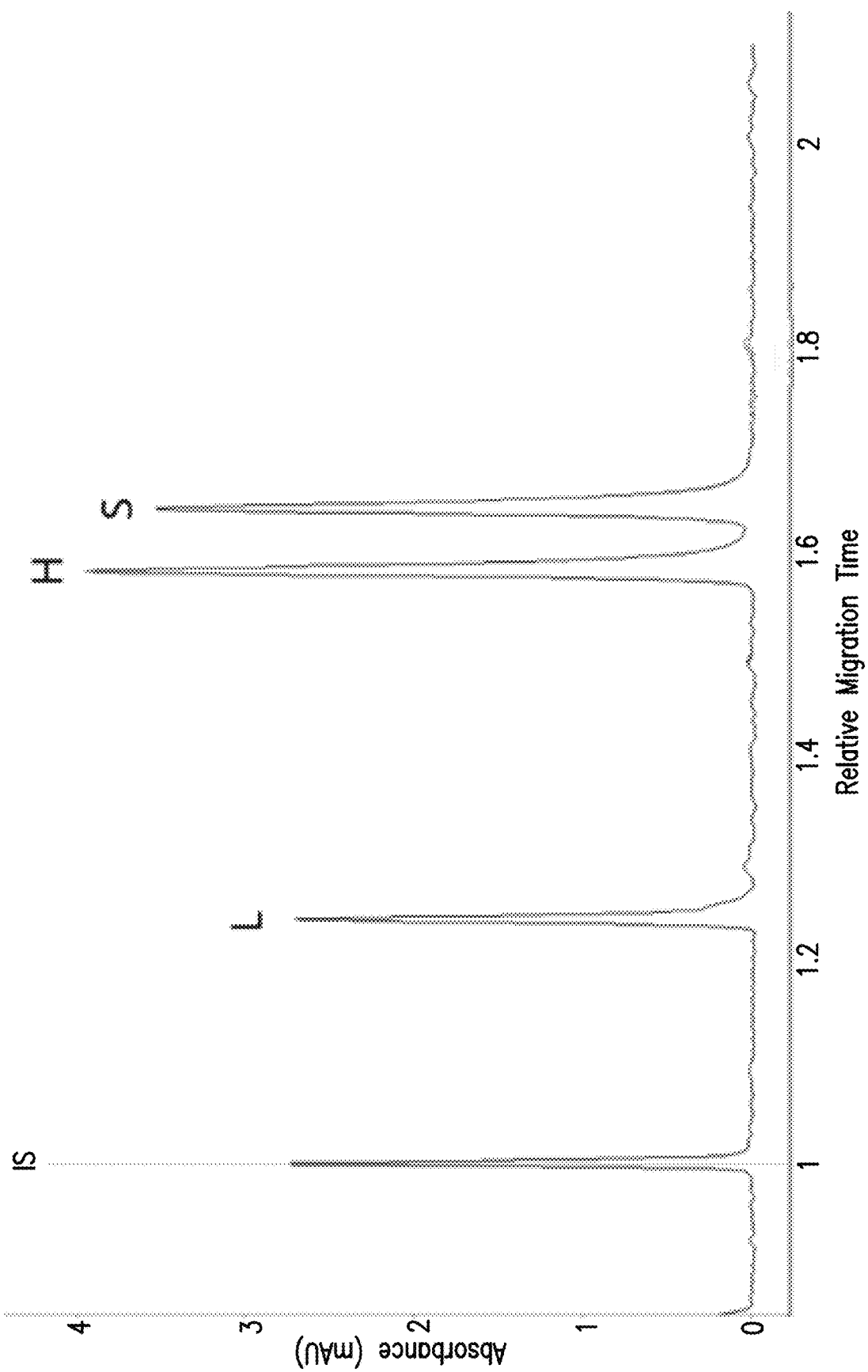

FIG. 222A-FIG. 222B show the purity of AB0192 (lot AB0192-005) by non-reduced conditions ("NR"; FIG. 222A) and reduced conditions ("R"; FIG. 222B) by CE-SDS.

Figure 223:
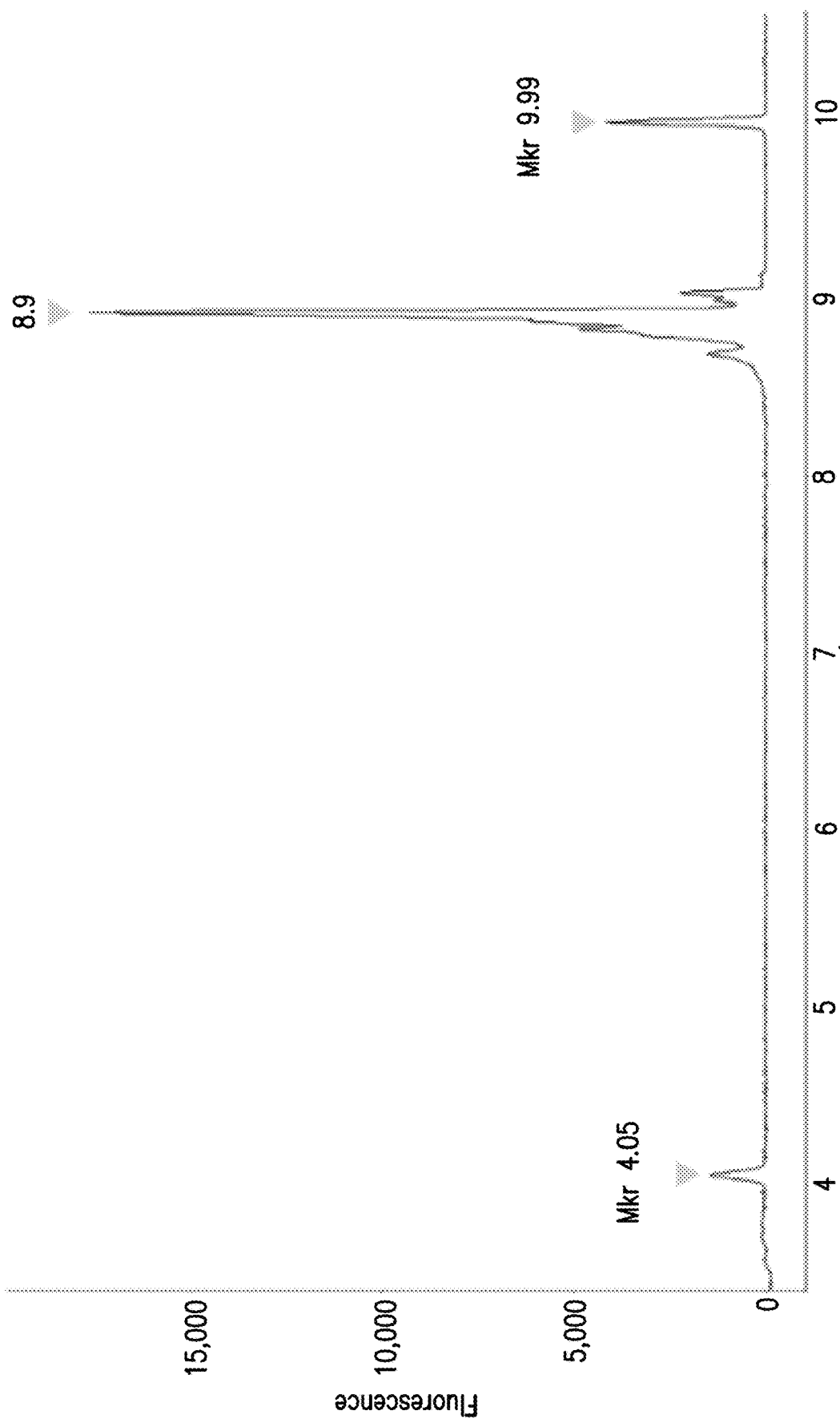

FIG. 223 shows the cIEF profile of AB0192 (lot AB0192-005).

Figure 224:
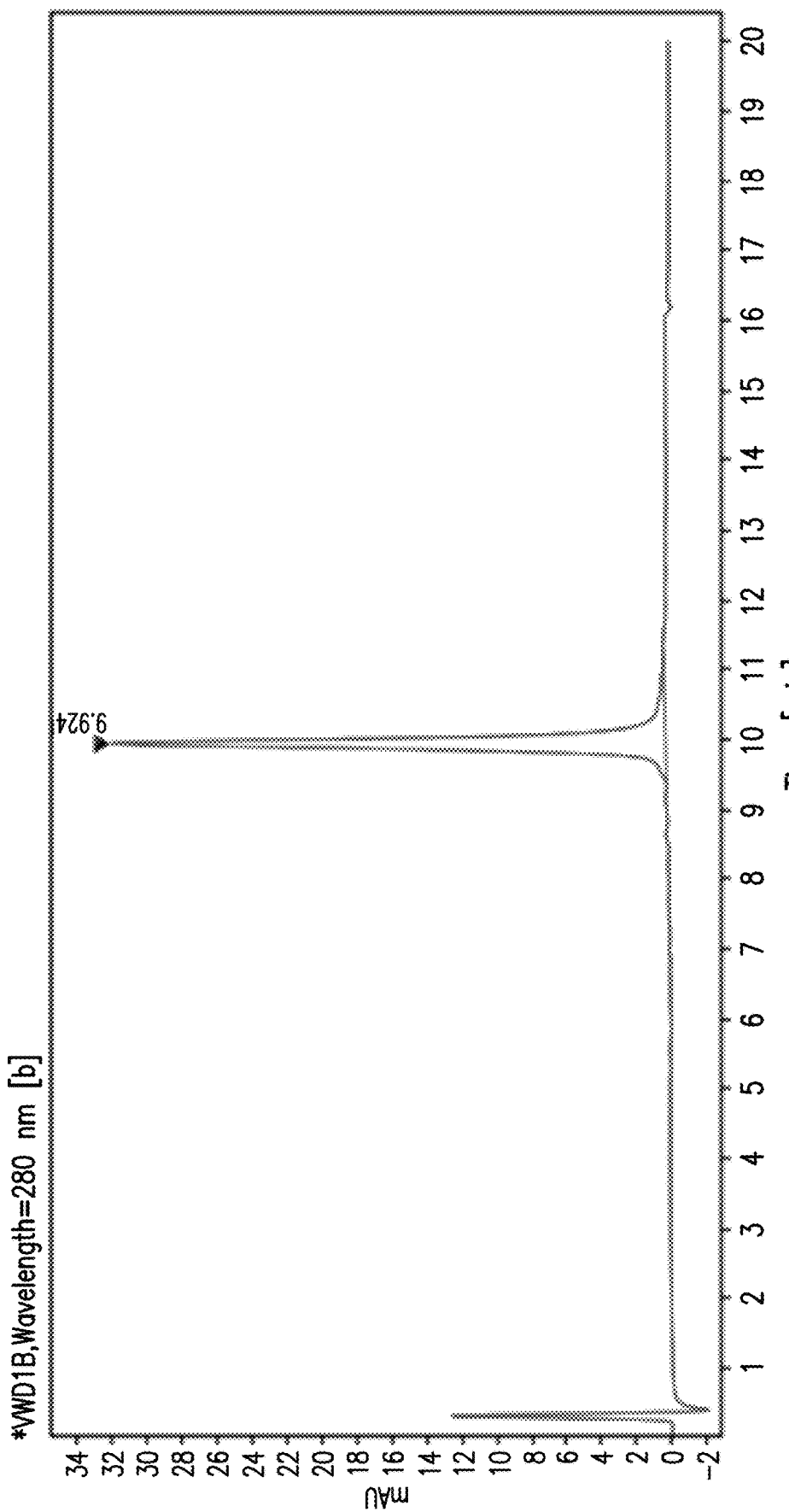

FIG. 224 shows the hydrophobicity analysis of AB0192 by HIC.

Figure 225A:
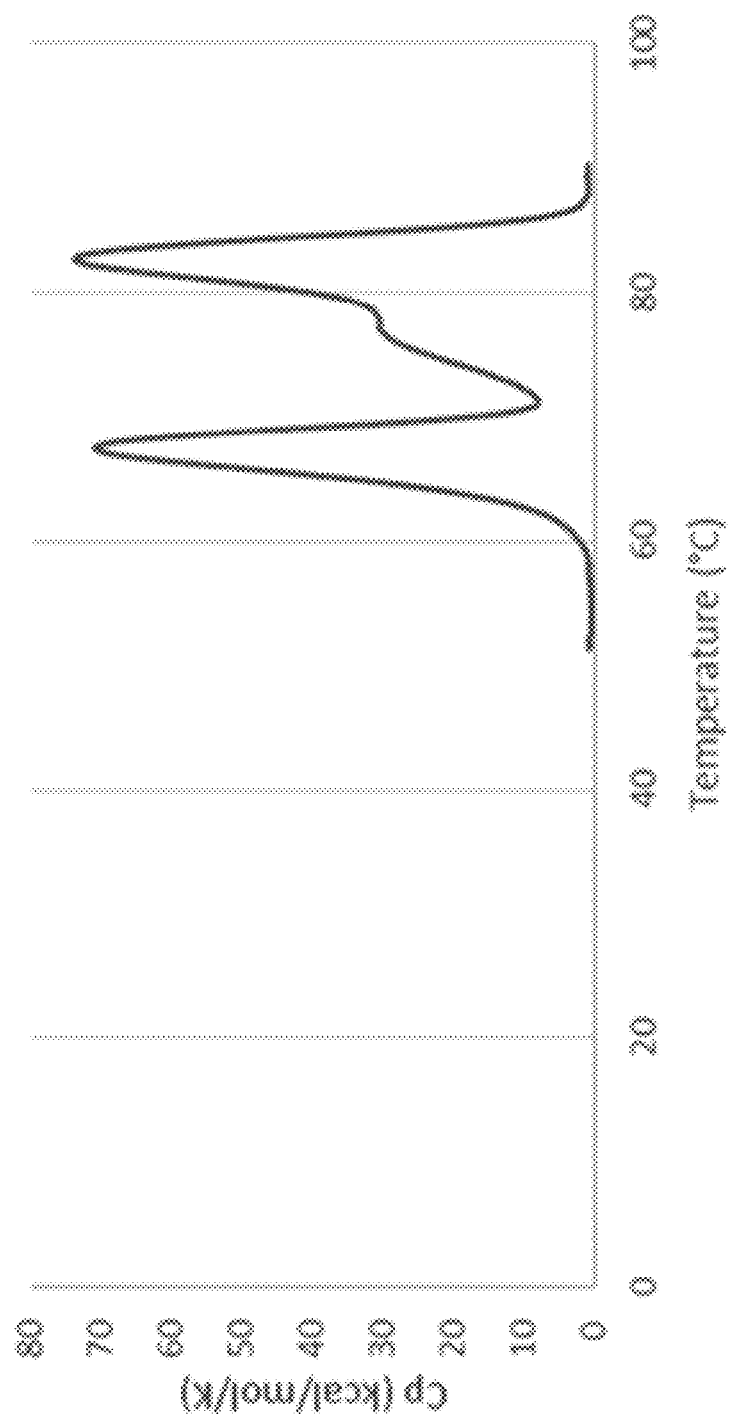
Figure 225B:
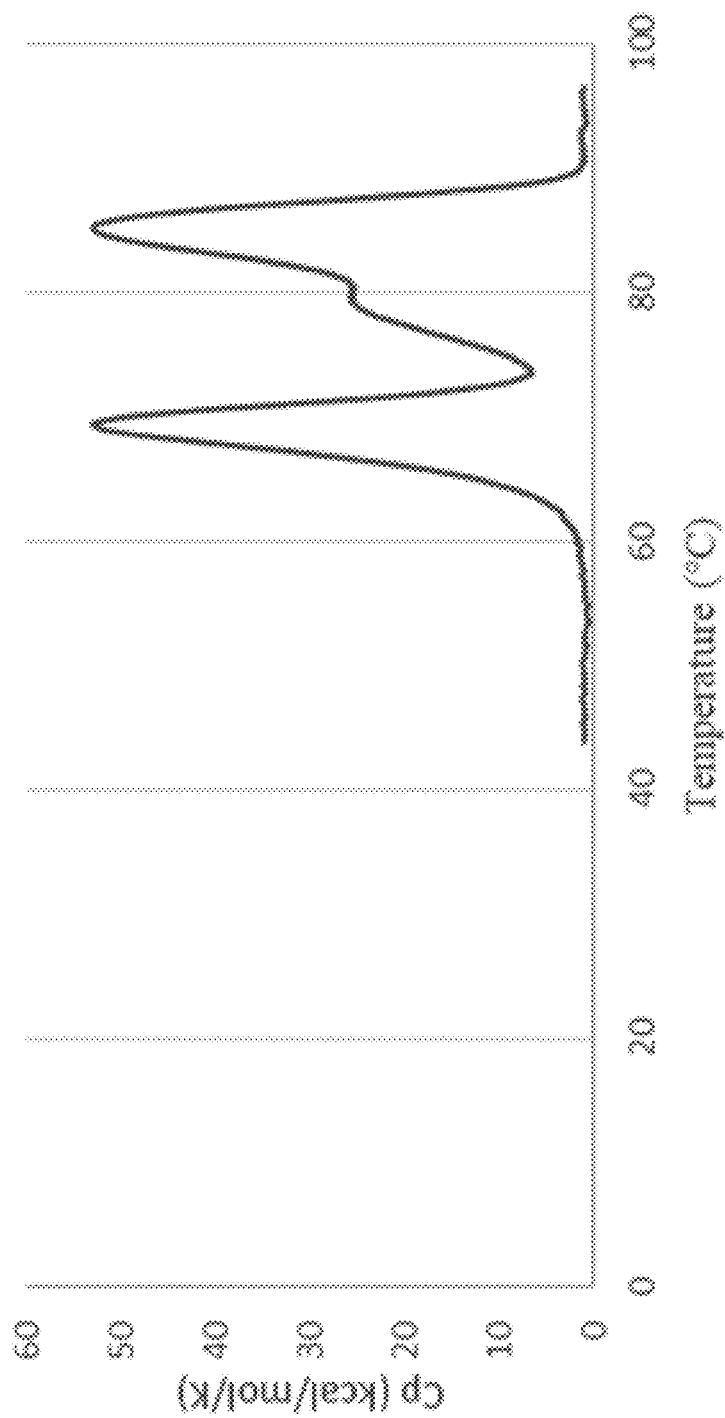
Figure 225C:
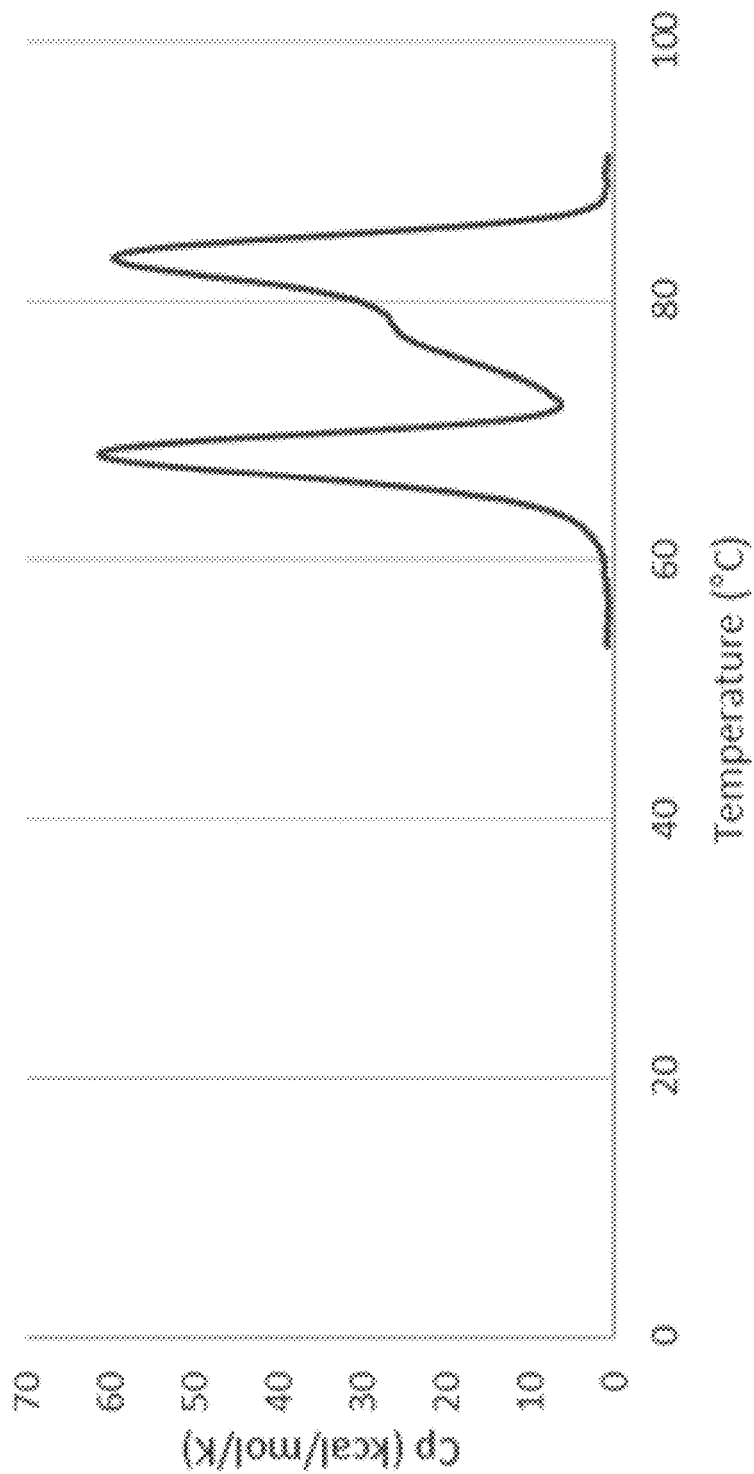

FIG. 225A-FIG. 225C show DSC analysis of AB0192 in three different buffer systems. PBS pH 7.4 (FIG. 225A), HST, pH 6.0 (FIG. 225B) and CST, pH 7.0 (FIG. 225C).

Figure 226:
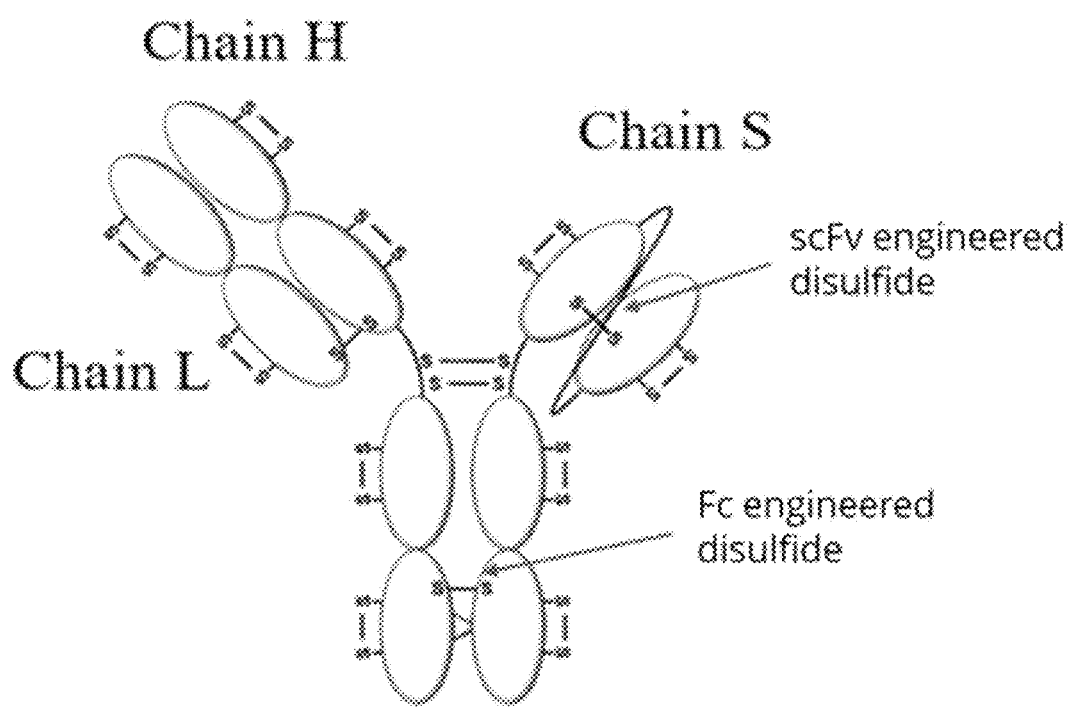

FIG. 226 shows the predicted disulfide map for AB0192.

Figure 227A:
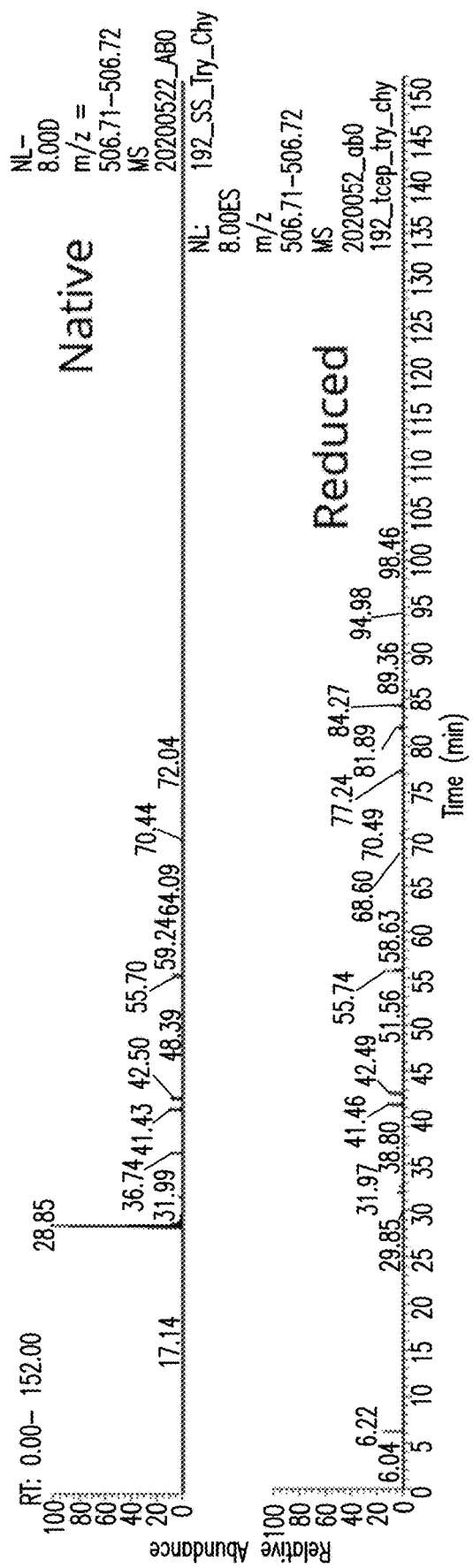
Figure 227B:
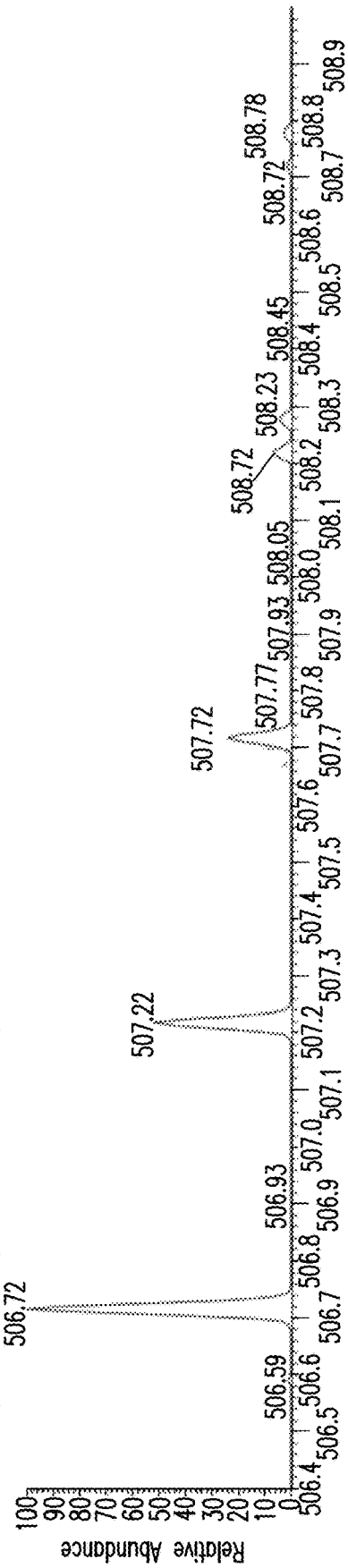

FIG. 227A-FIG. 227B show the extracted ion chromatogram (XICs) for the engineered disulfide pair in the scFv (non-reduced and reduced; FIG. 227A) and the most intense charge state for that peptide pair (FIG. 227B).

FIG. 228A-FIG. 228B show the existence of the CH3-CH3 intermolecular Fc engineered disulfide.

Figure 229A:
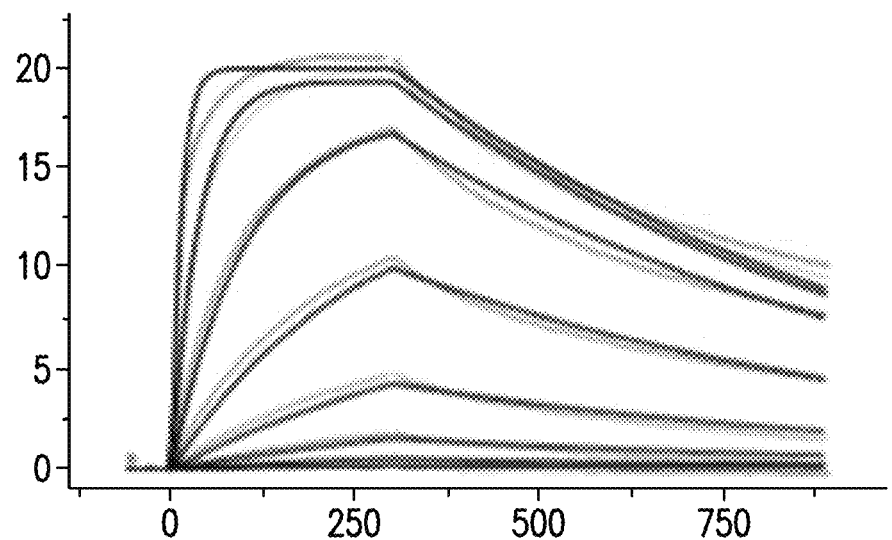
Figure 229B:
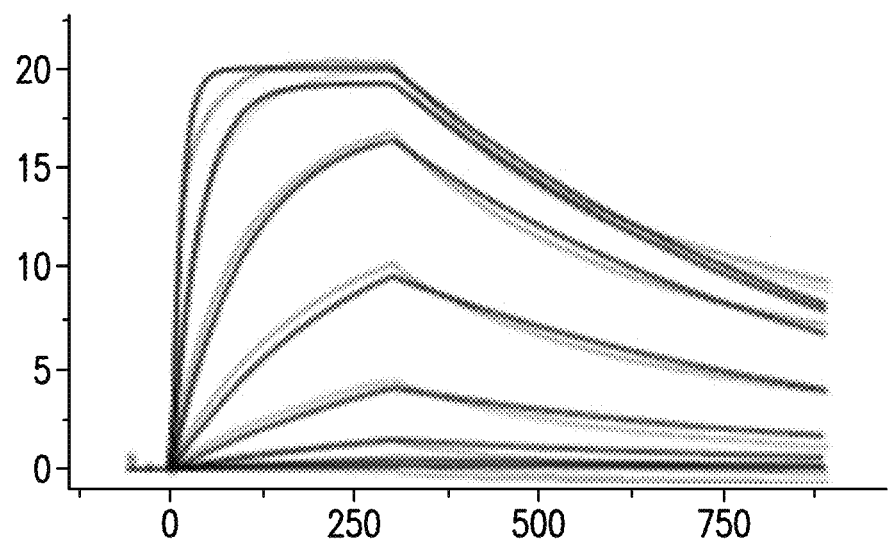
Figure 229C:
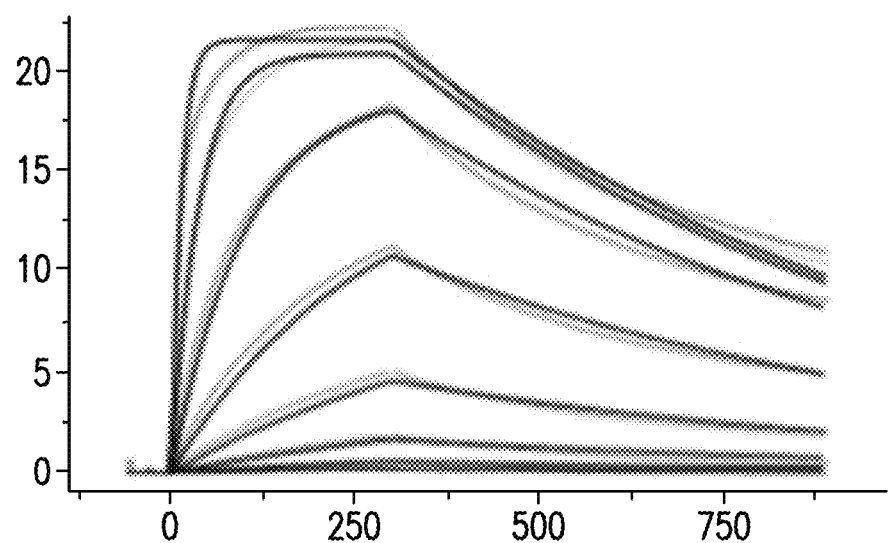

FIG. 229A-FIG. 229C show binding of AB0192 to human CLEC12A tested by SPR.

Figure 230A:
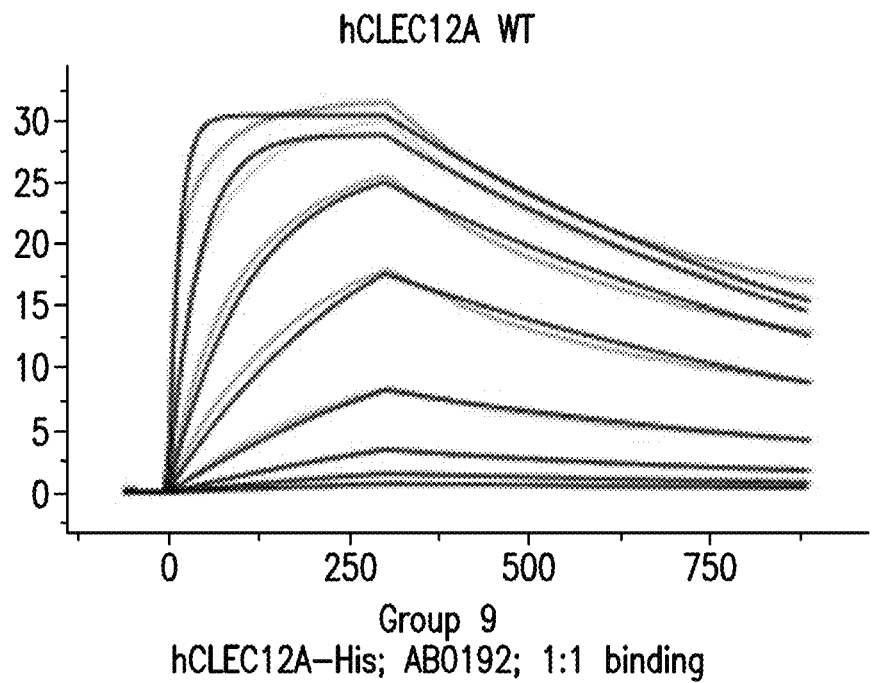
Figure 230B:
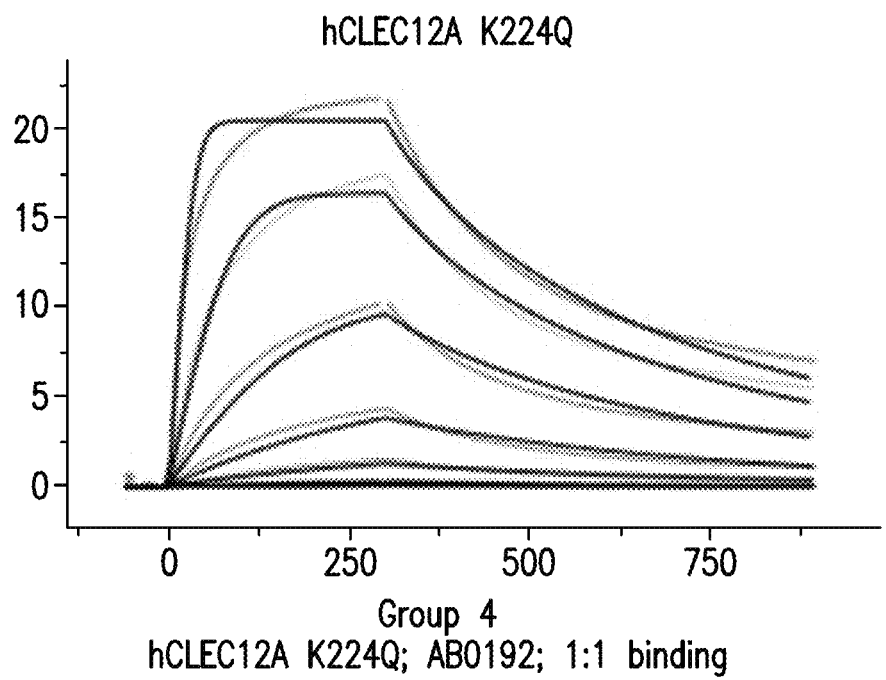
Figure 230C:
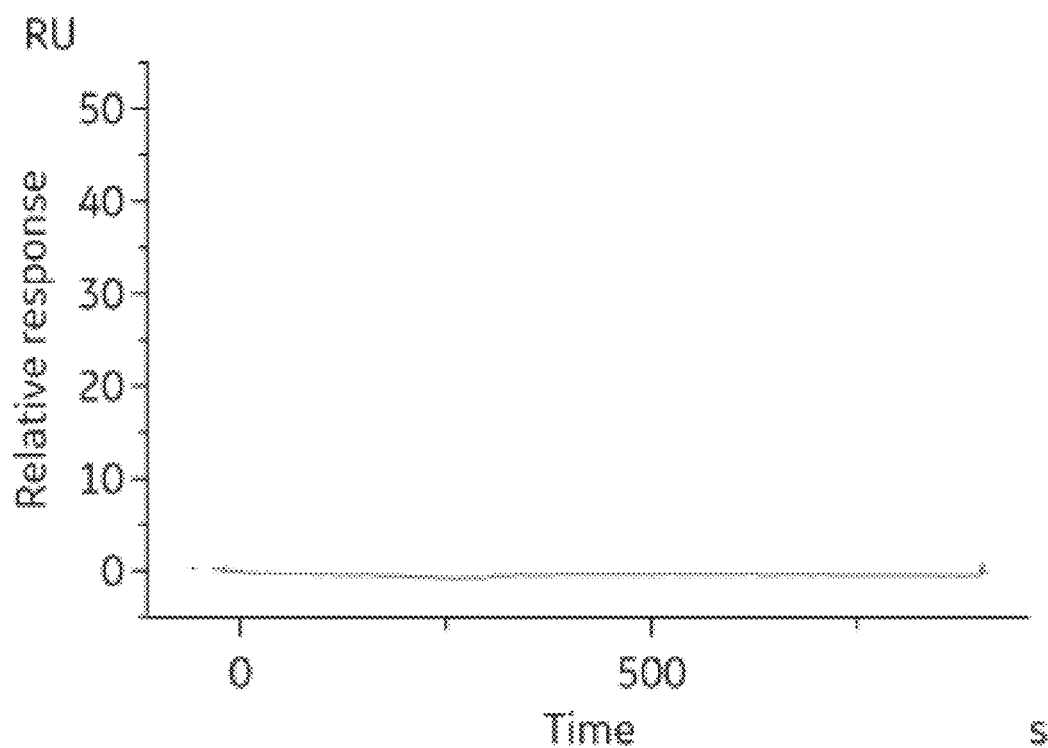

FIG. 230A-FIG. 230C show binding of AB0192 to a genetic variant of human CLEC12A (Q244) (FIG. 230B) compared to CLEC12A (K244) WT (FIG. 230A) and cyno CLEC12A tested by SPR (FIG. 230C).

Figure 231A:
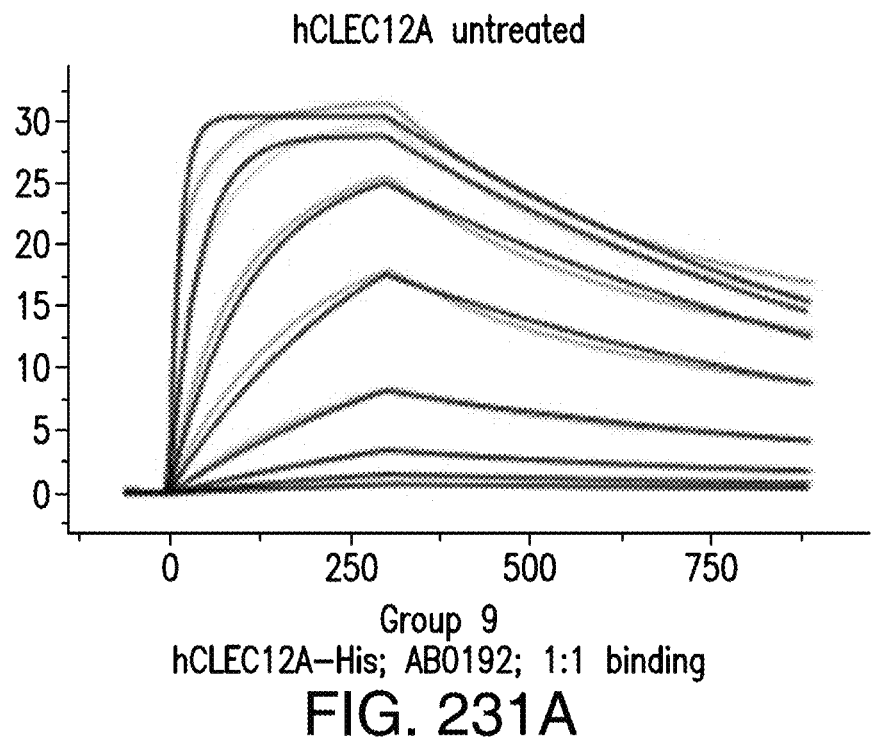
Figure 231B:
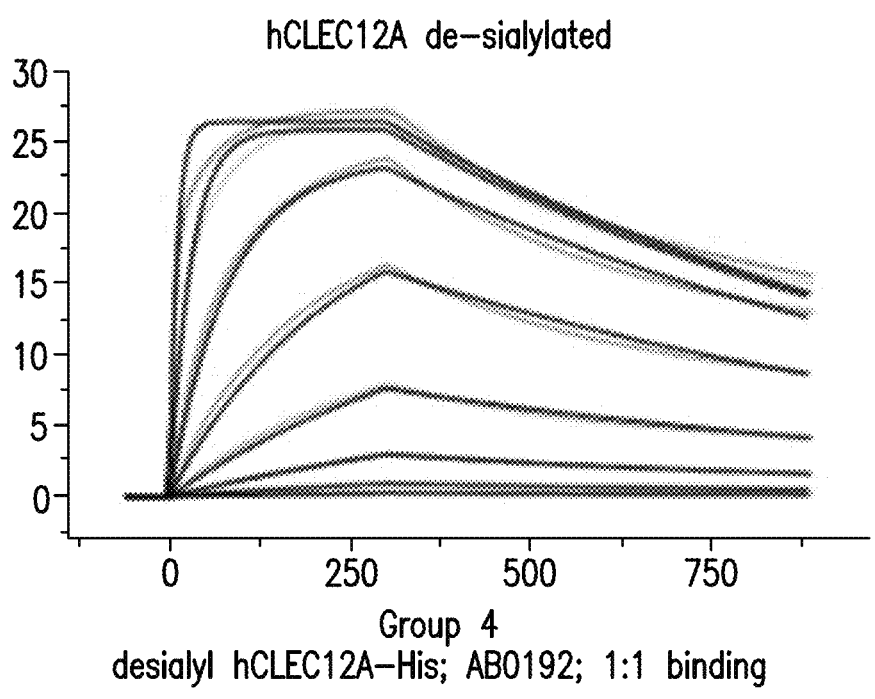
Figure 231C:
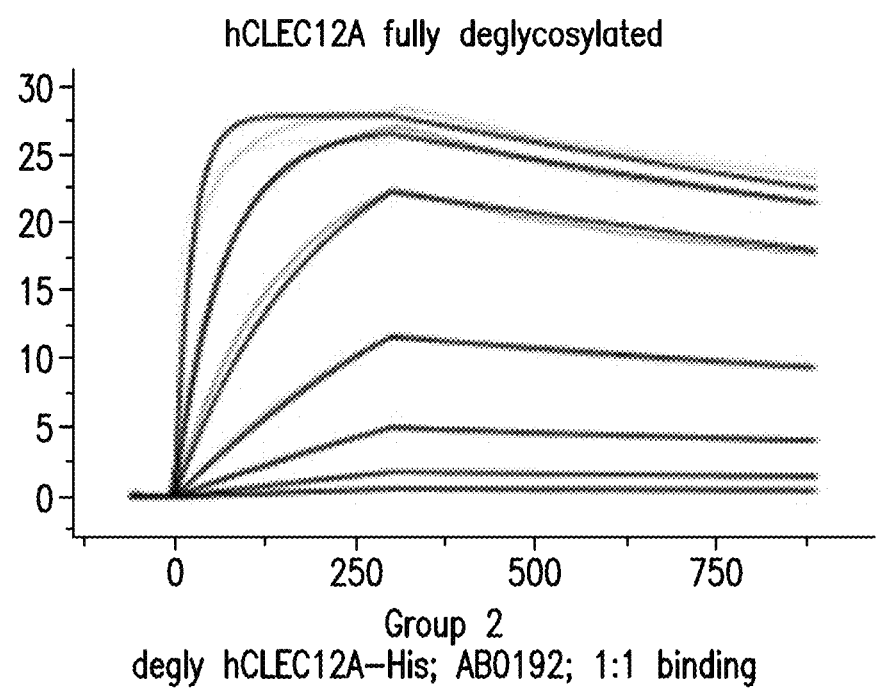
Figure 233A:
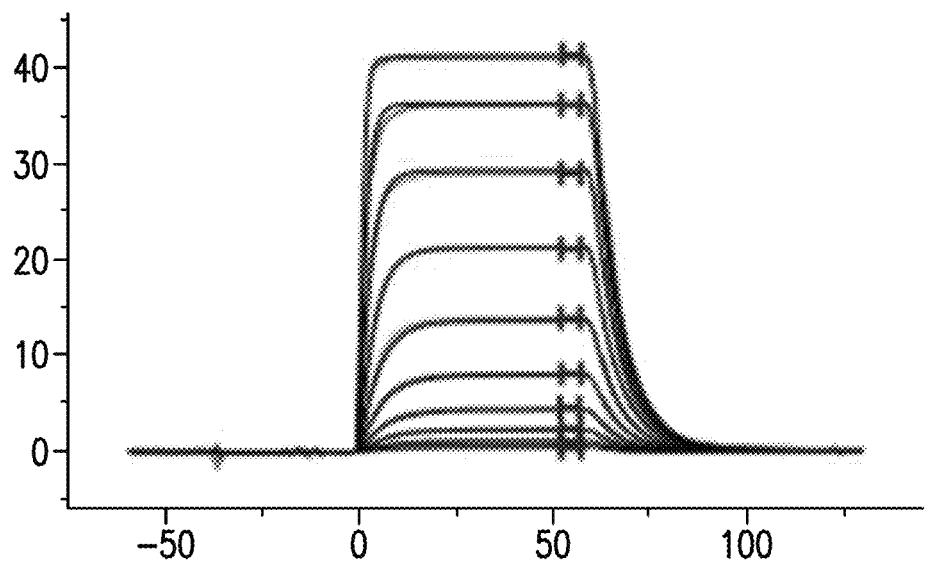
Figure 233B:
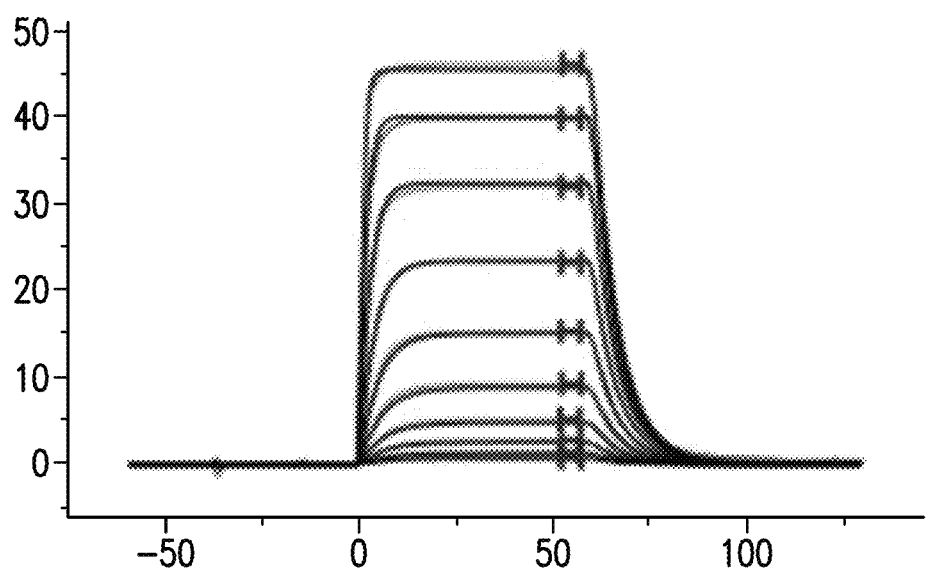
Figure 233C:
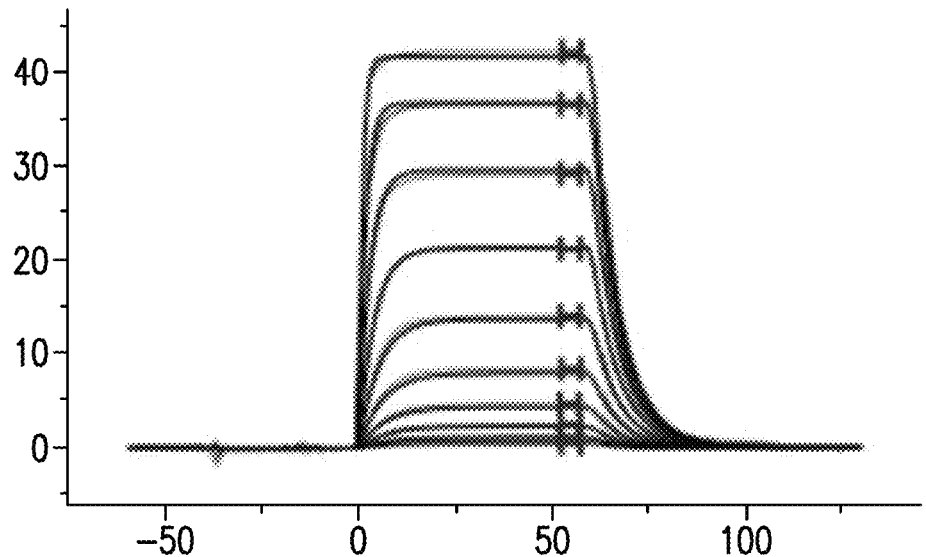
Figure 233D:
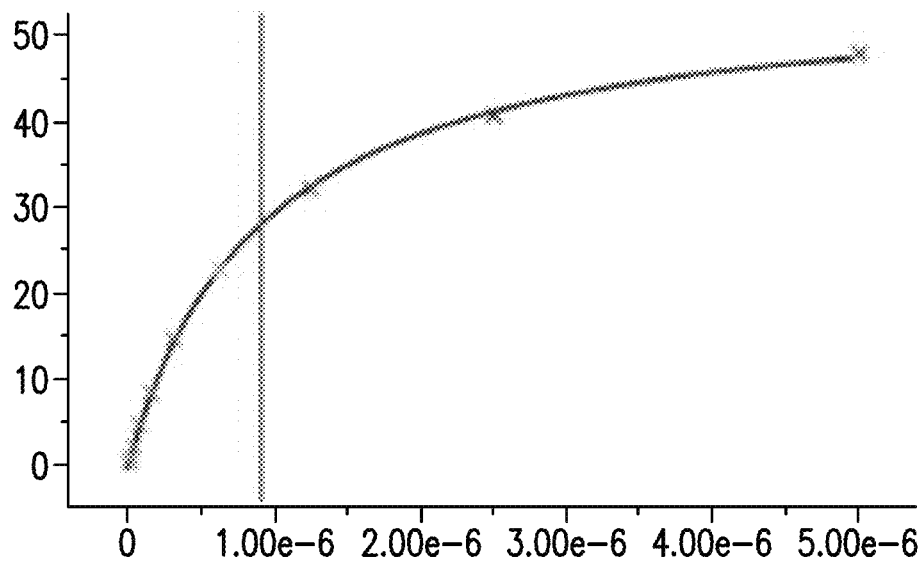
Figure 233E:
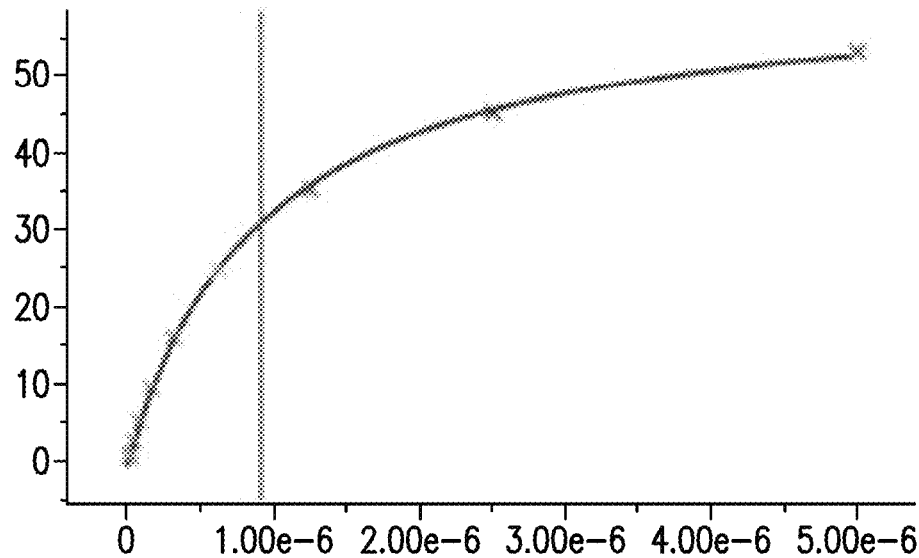
Figure 233F:
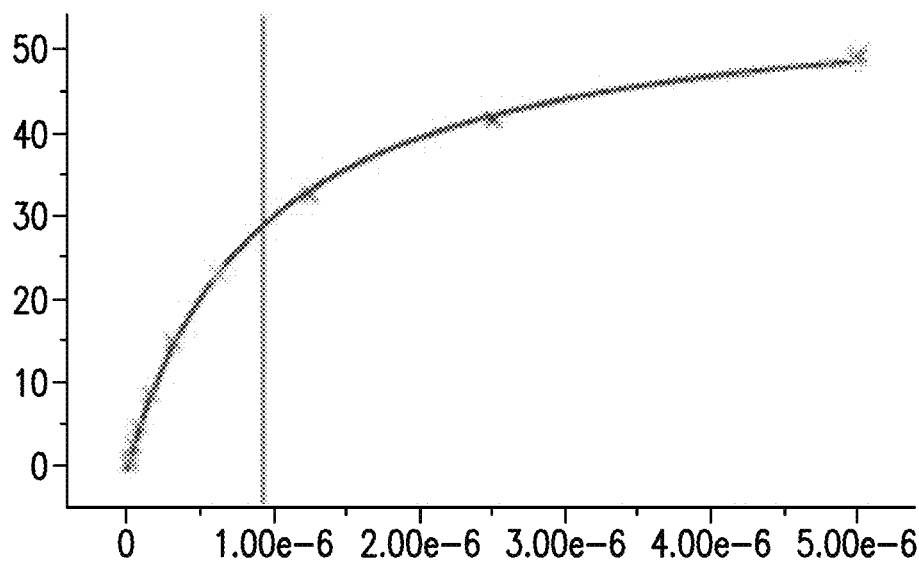
Figure 234A:
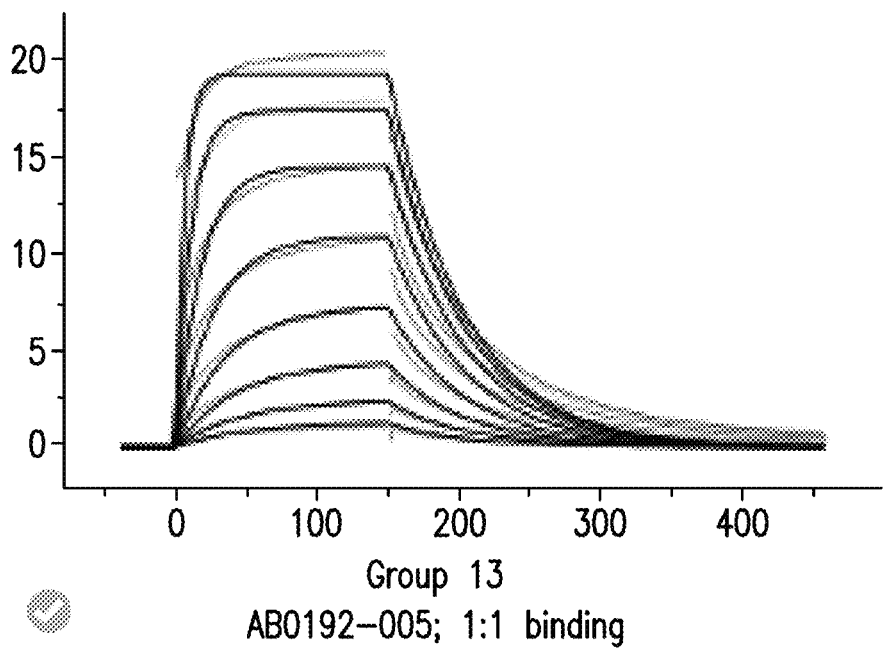
Figure 234B:
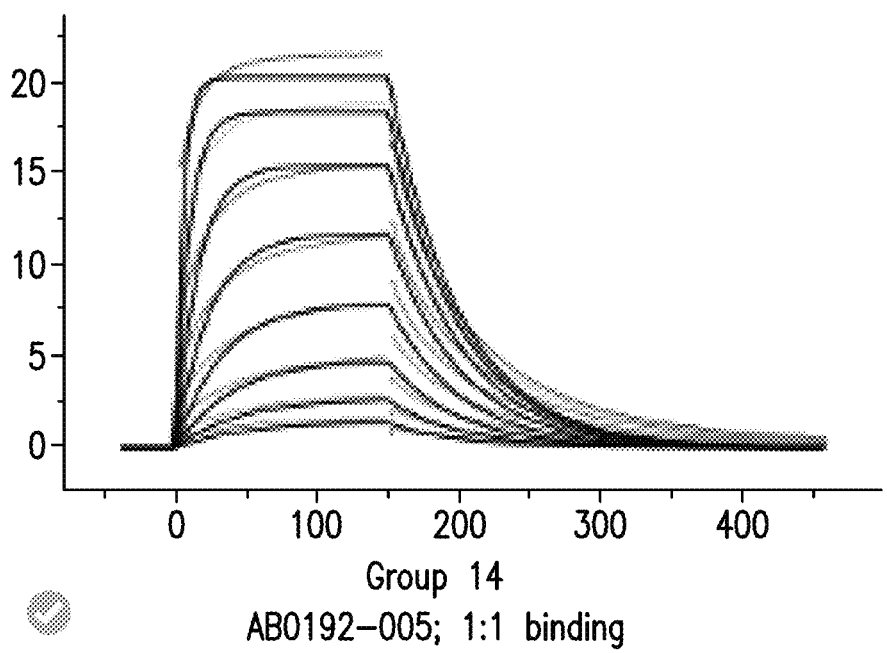
Figure 234C:

Figure 234D:
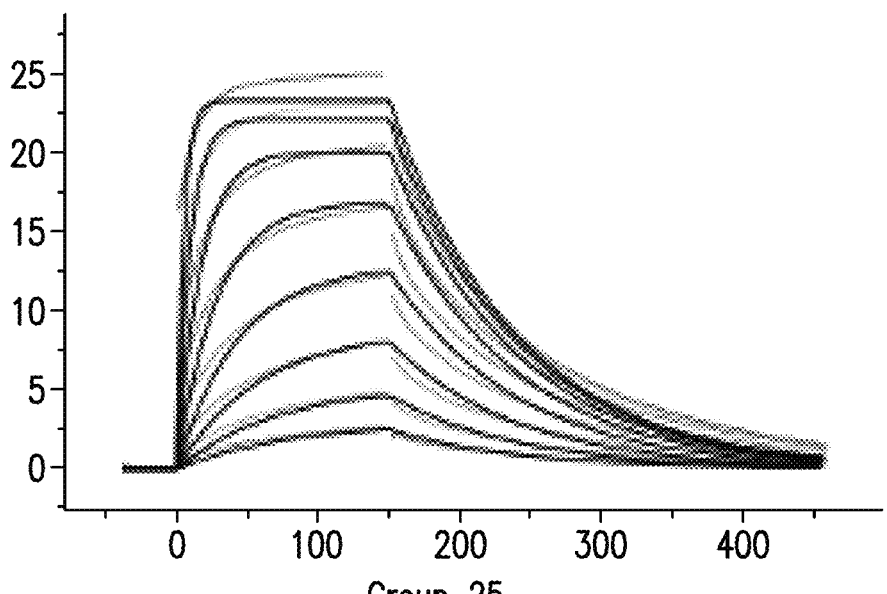
Figure 234E:
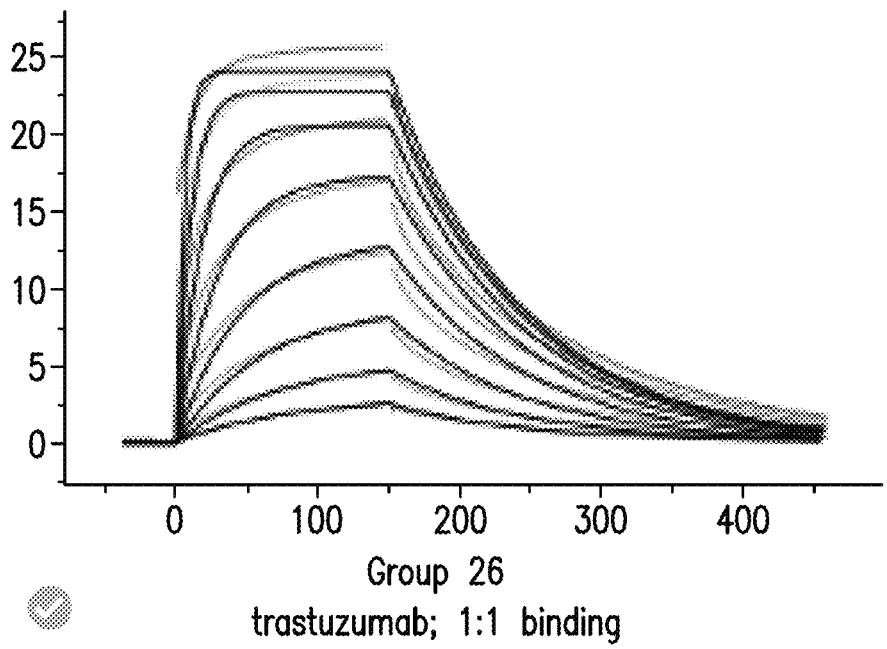
Figure 234F:
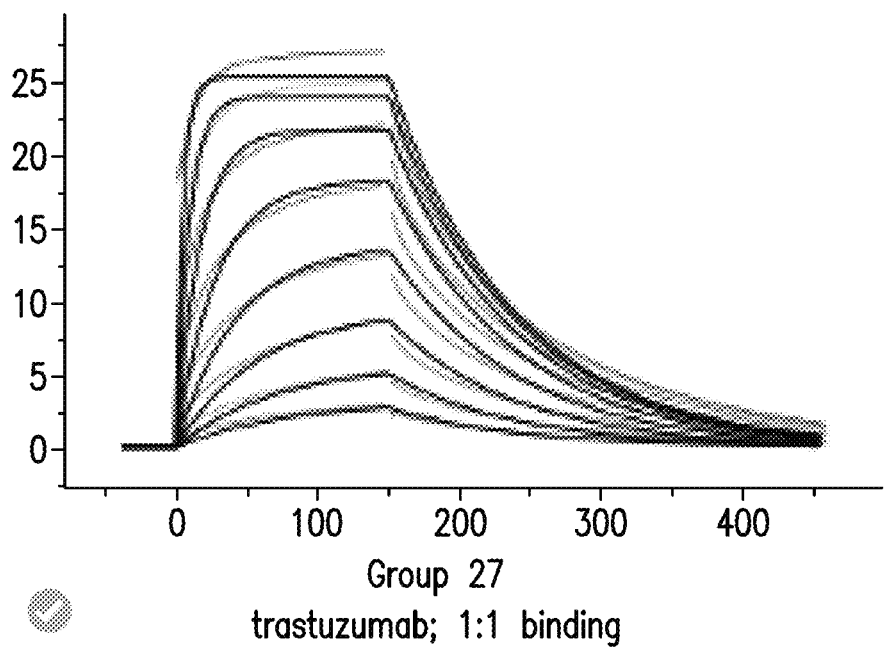

FIG. 231A-FIG. 231C show binding of AB0192 to differentially glycosylated CLEC12A tested by SPR.

FIG. 232A-FIG. 232D show binding of AB0192 to CLEC12A+ isogenic and HL60 and PL21 AML cells.

FIG. 233A-FIG. 233F show binding of AB0192 to human NKG2D tested by SPR.

FIG. 234A-FIG. 234F show binding of AB0192 to hCD16a V158 allele.

Figure 235:
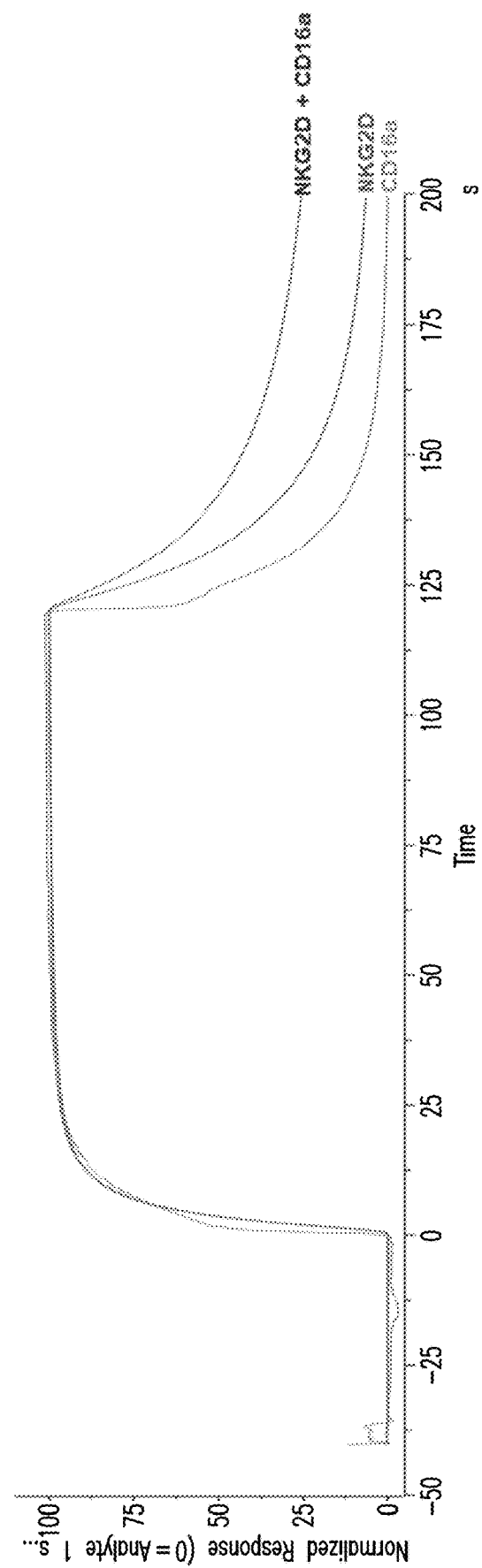

FIG. 235 shows simultaneous binding of AB0192 to CD16a and NKG2D results in avid binding. AB0192 injected over NKG2D (middle line, as indicated on right side of graph), CD16a (bottom line, as indicated on right side of graph) or mixed, CD16a and NKG2D, (top line, as indicated on right side of graph) surfaces. Note that the surface has not been optimized for a maximum avidity effect.

Figure 236A:
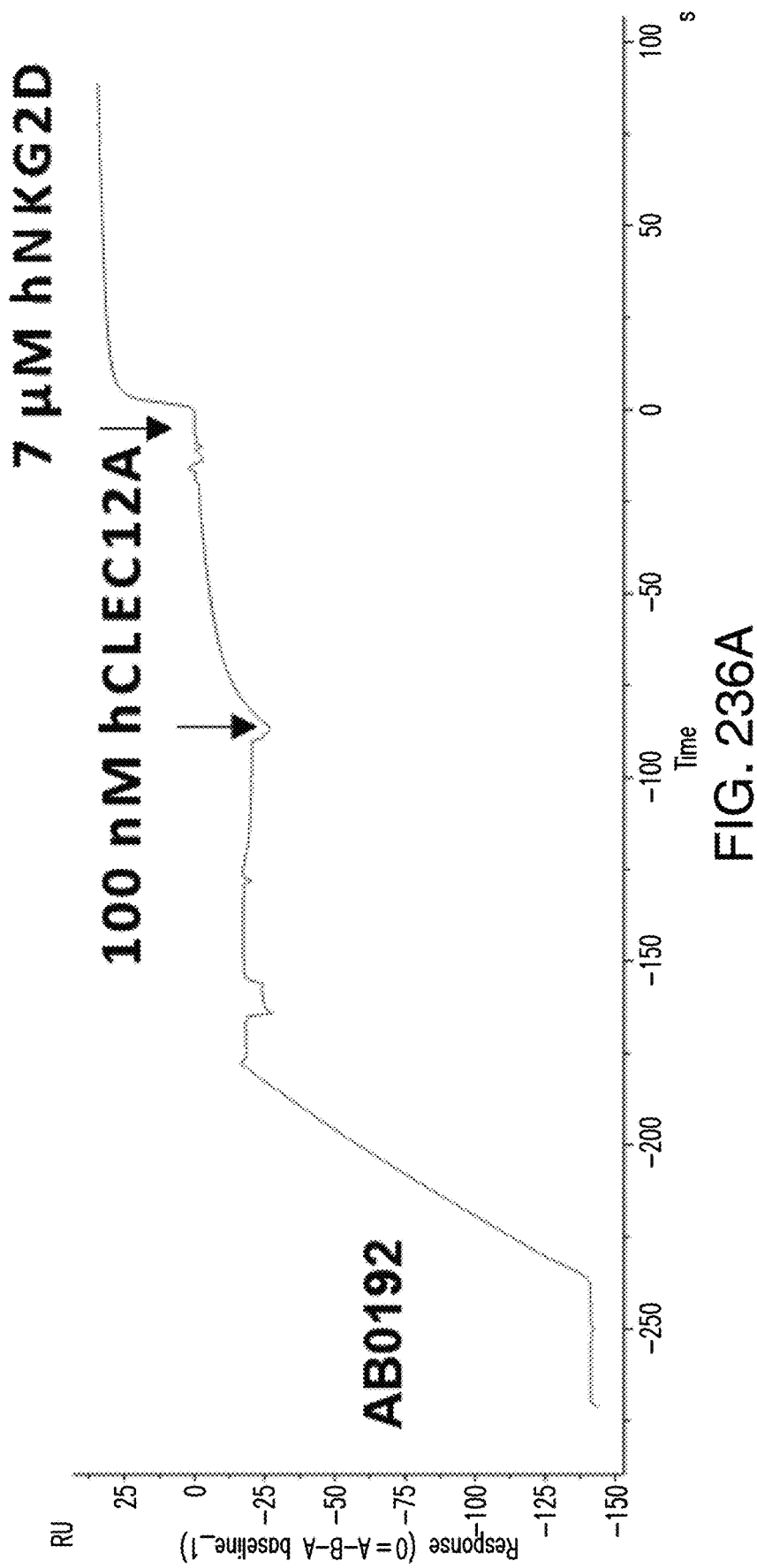
Figure 236B:
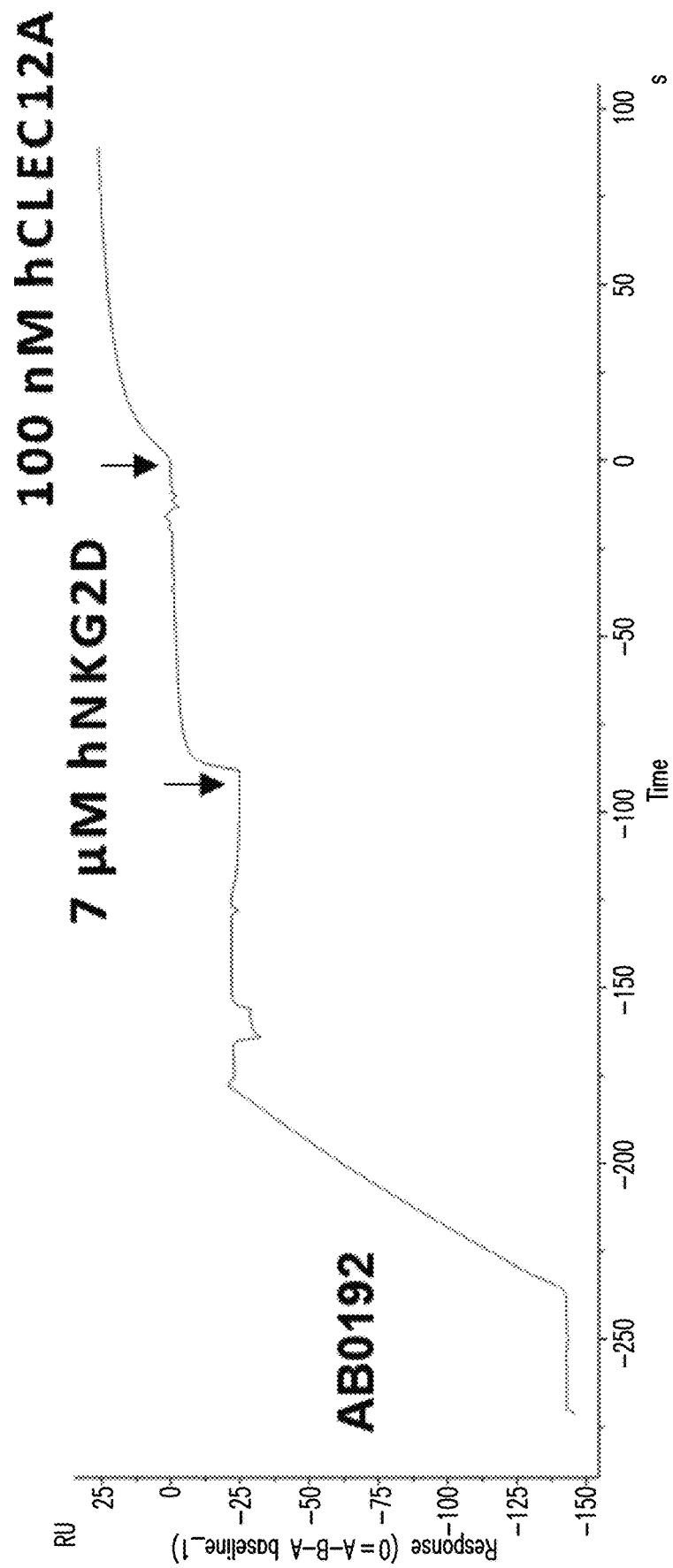
Figure 237A:
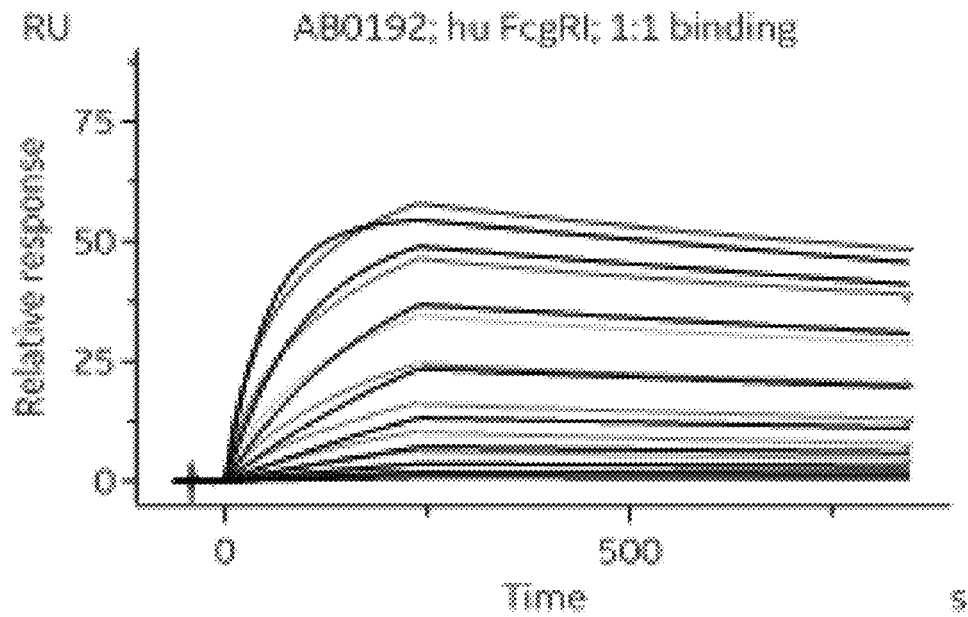
Figure 237B:
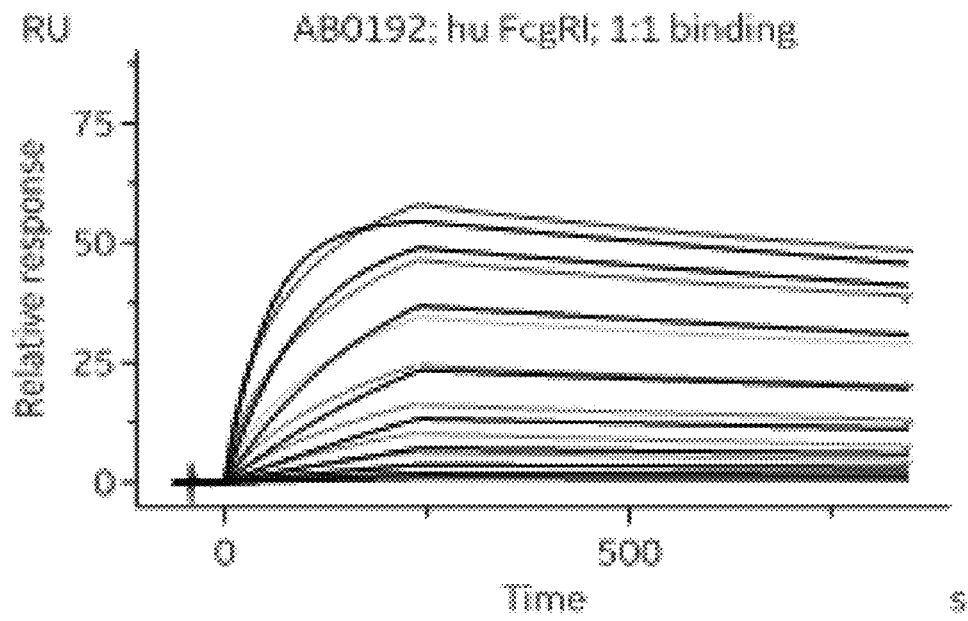
Figure 237C:
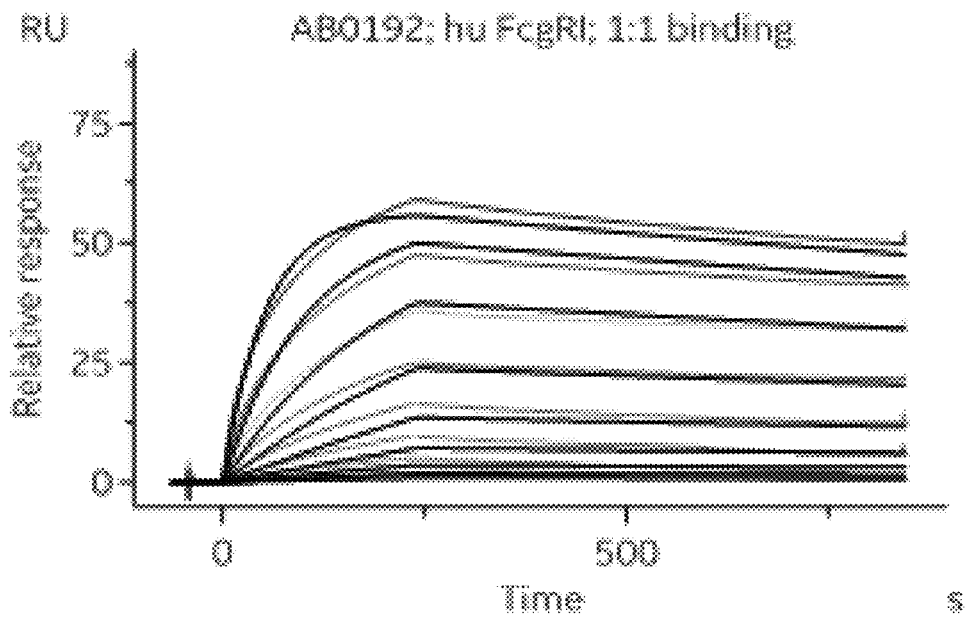
Figure 237D:
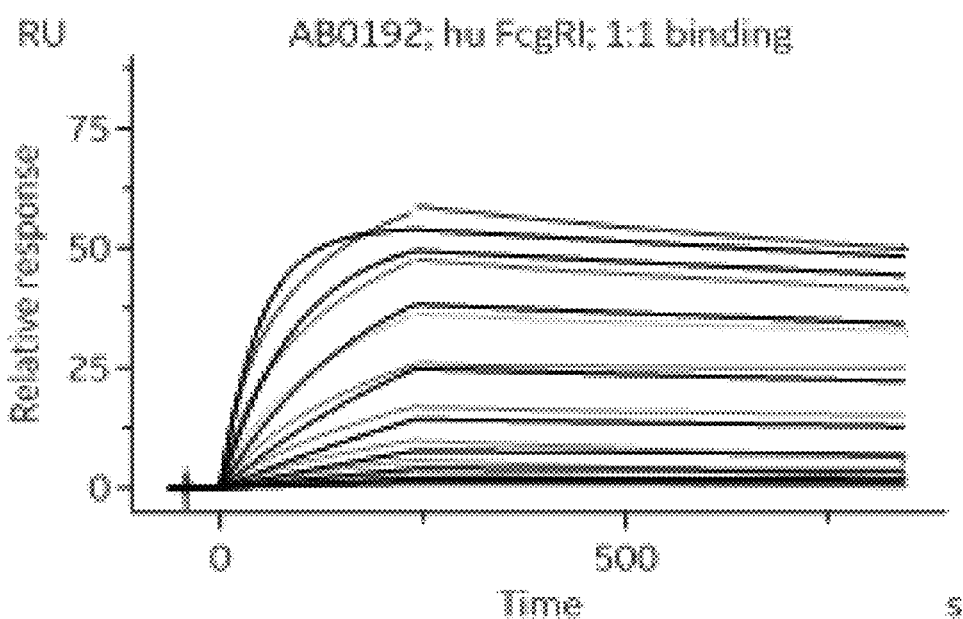
Figure 237E:
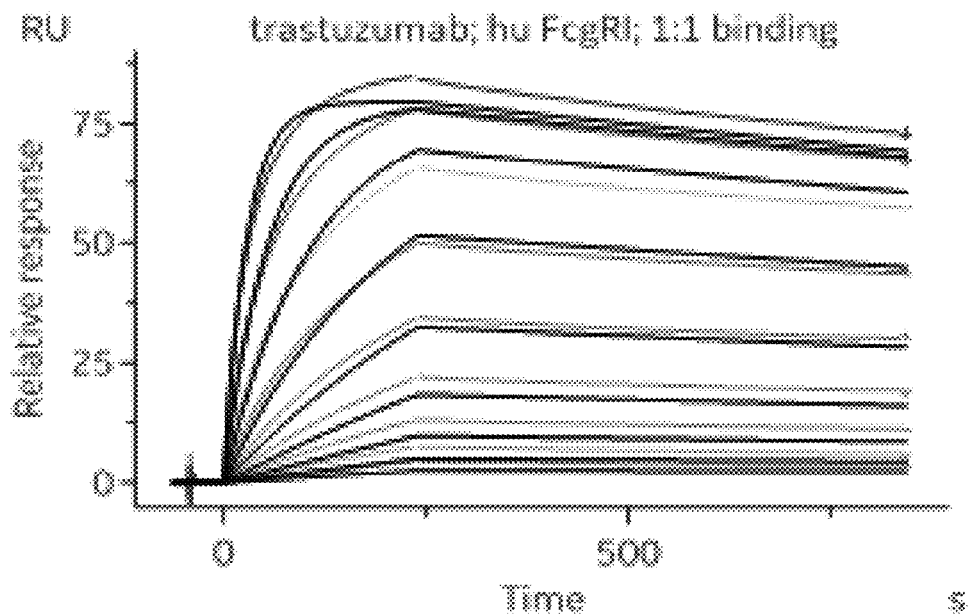
Figure 237F:
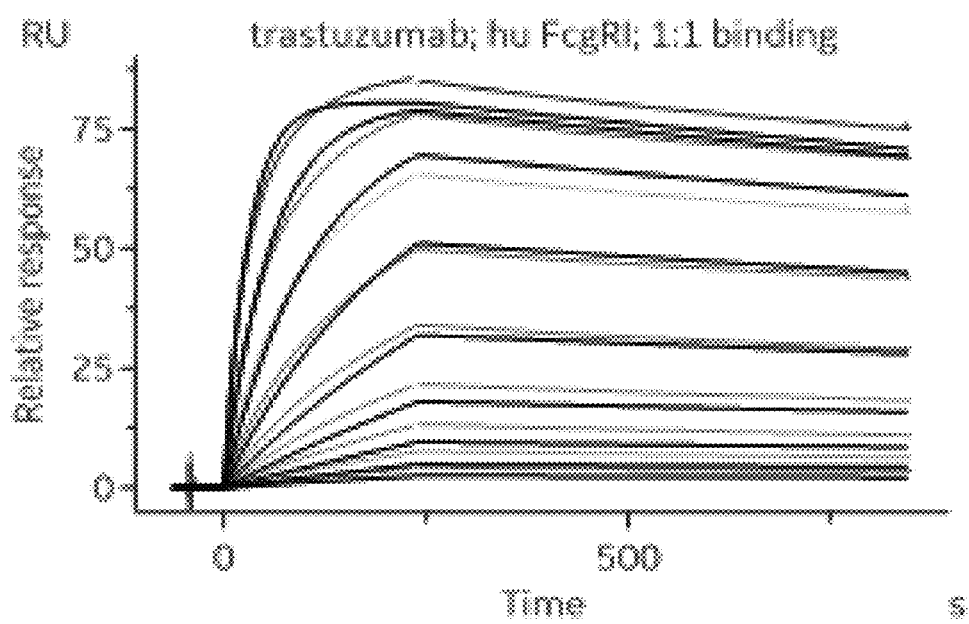
Figure 237G:
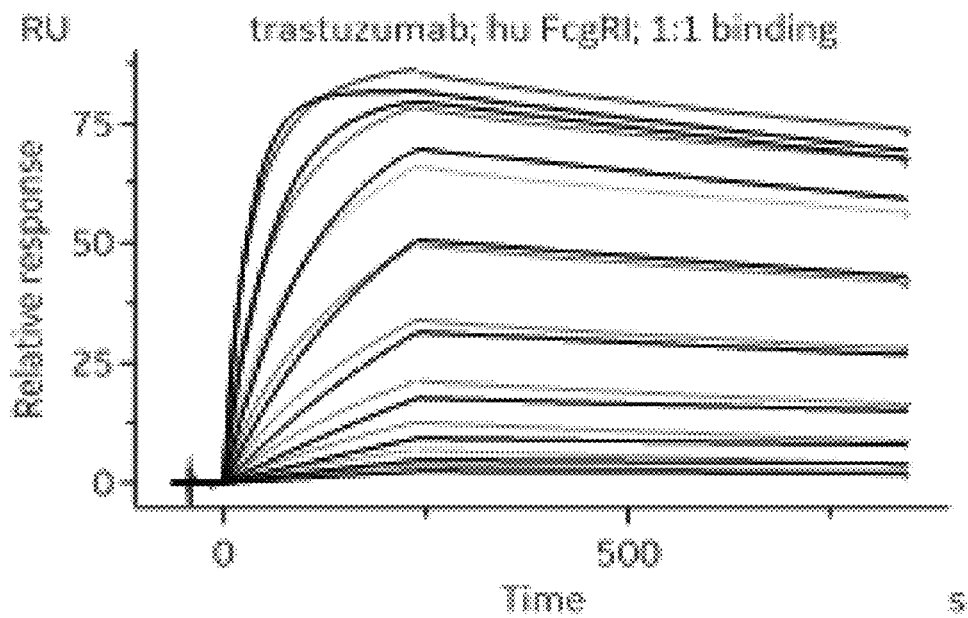
Figure 237H:
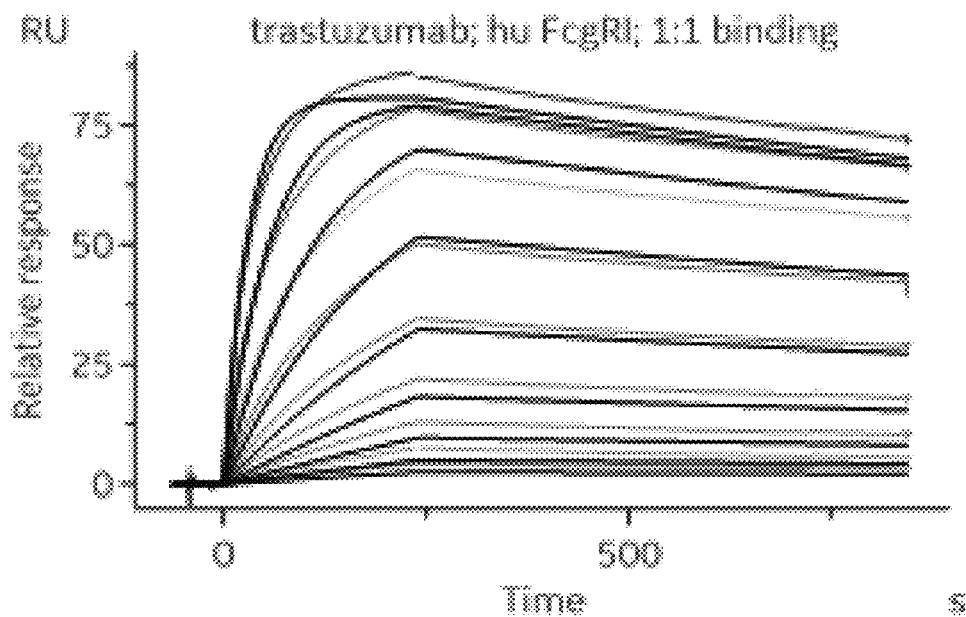
Figure 238A:
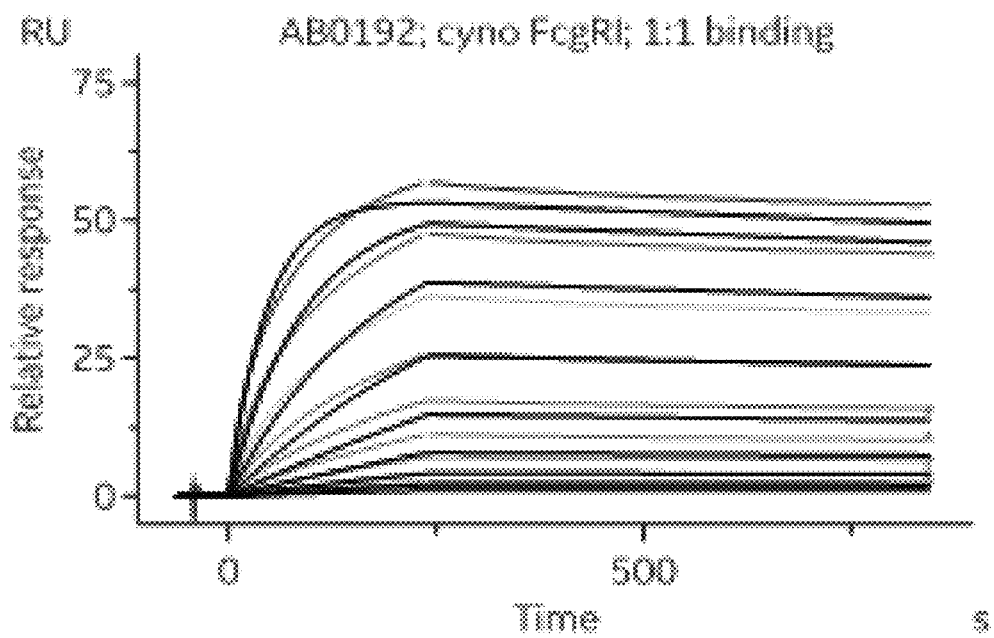
Figure 238B:
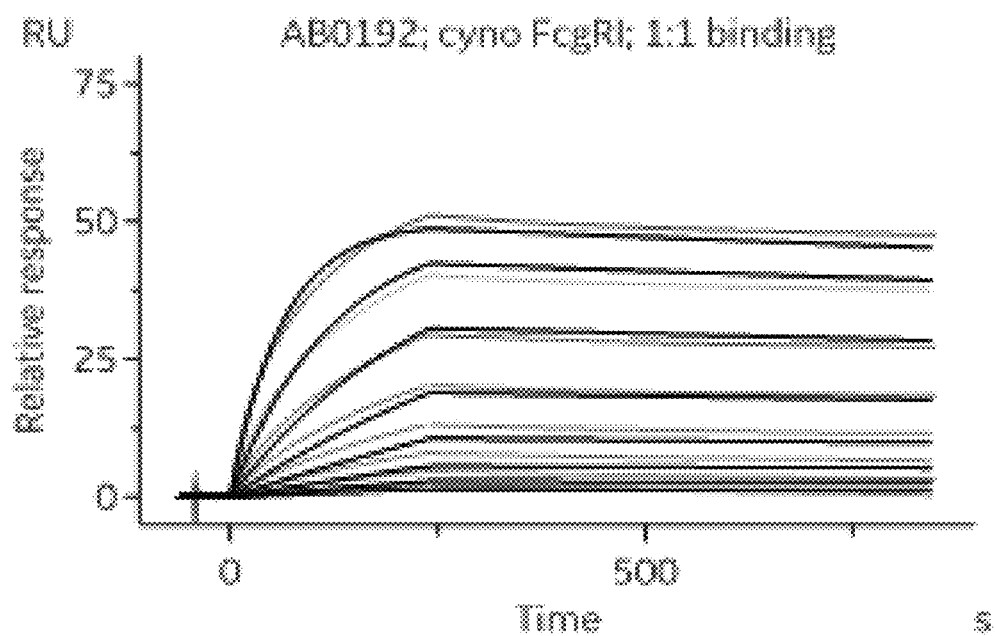
Figure 238C:
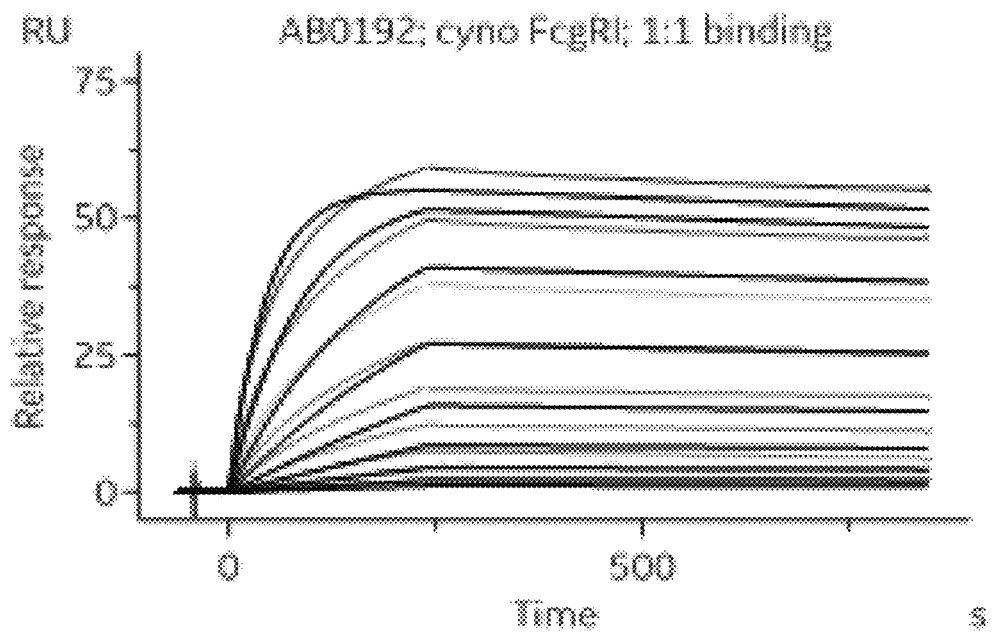
Figure 238D:
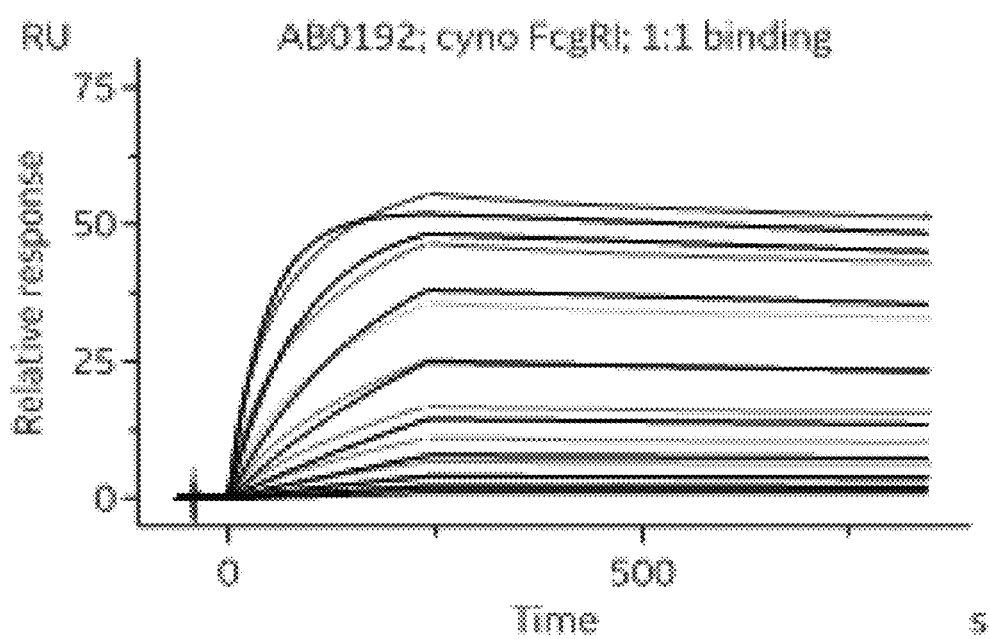
Figure 238E:
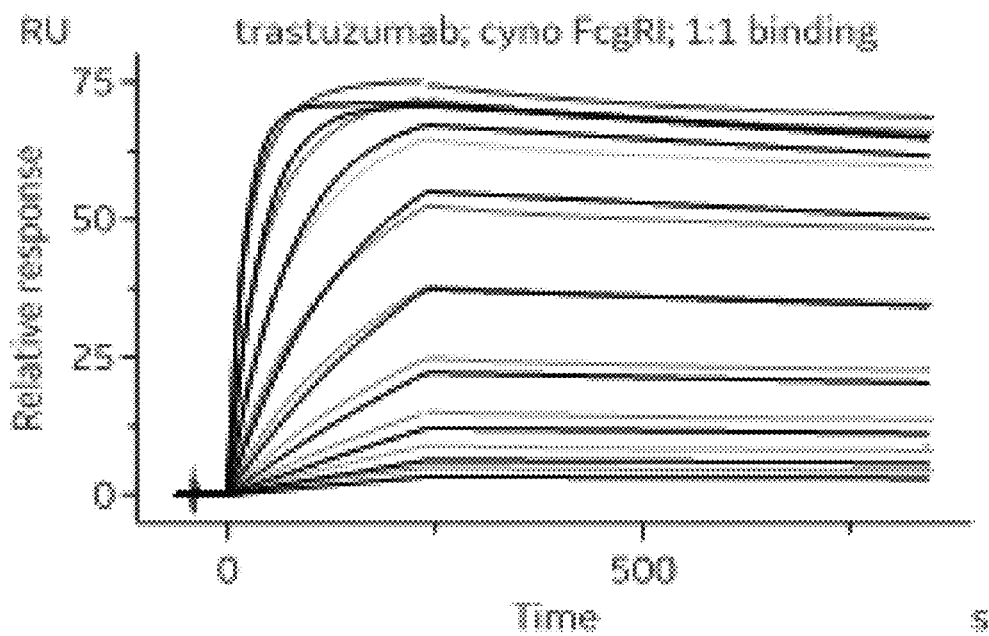
Figure 238F:
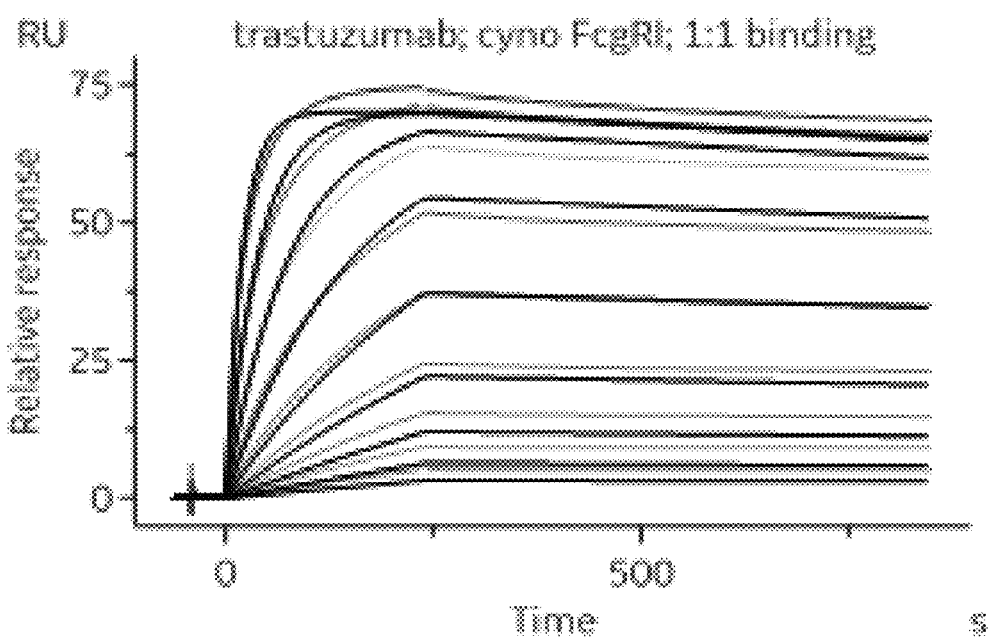
Figure 238G:
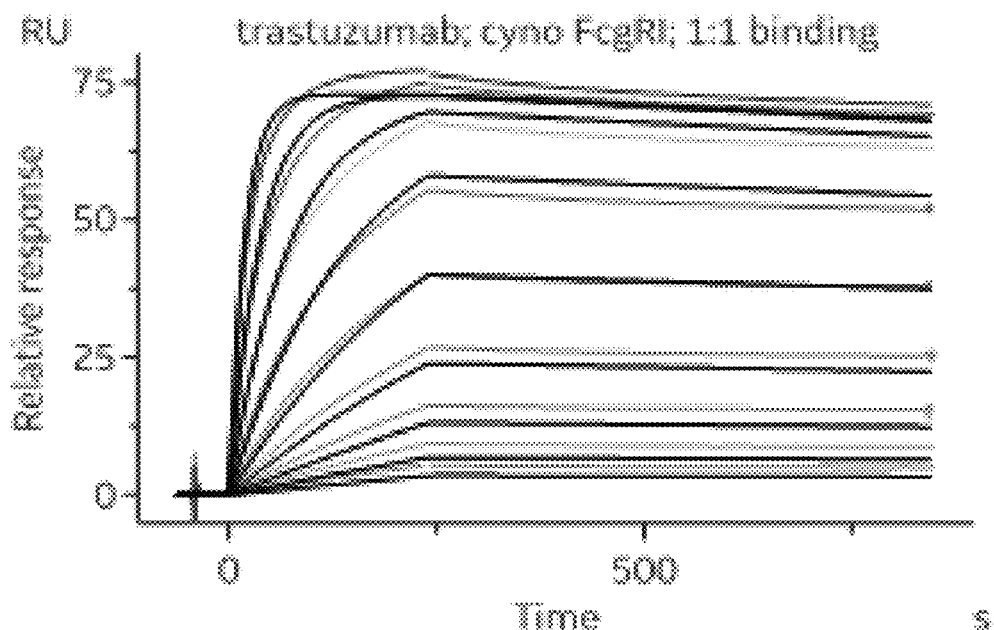
Figure 238H:
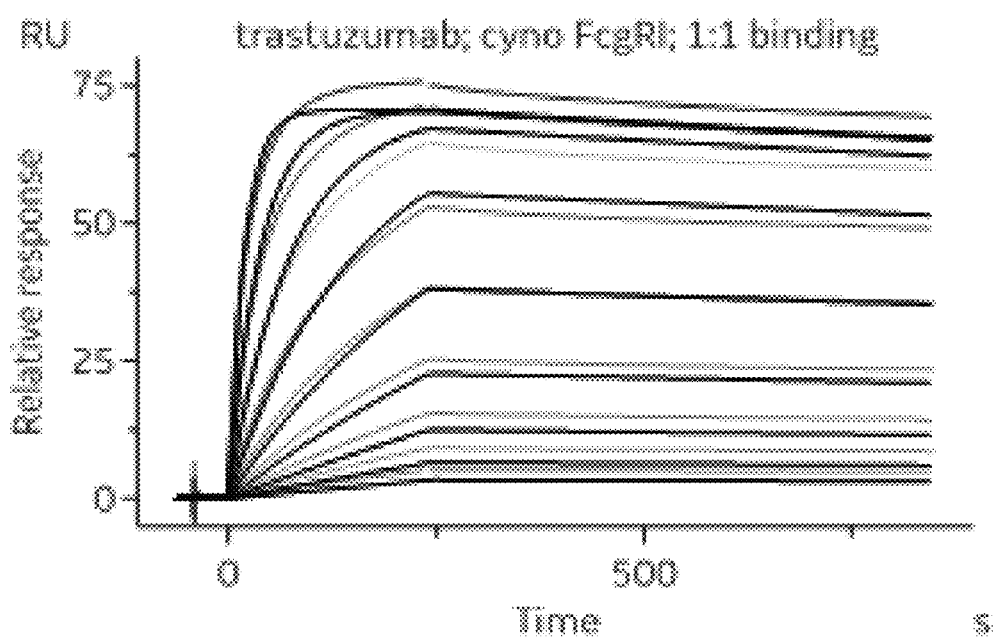

FIG. 236A-FIG. 236B show sequential saturation of captured AB0192 with hCLEC12A and hNKG2D. Targets were sequentially injected over AB0192 captured on a Biacore chip. FIG. 236A represents binding of hCLEC12A (100 nM) followed by binding of hNKG2D (7 µM) to captured AB0192. FIG. 236B depicts the reverse order of target binding (human NKG2D binding followed by hCLEC12A). Relative binding stoichiometries (relative to binding of each target to unoccupied captured AB0192) are shown in Table 218.

FIG. 237A-FIG. 237H show binding of AB0192 and trastuzumab to recombinant human CD64 (FcγRI). A difference in apparent maximum binding responses between the molecules is due to their difference in molecular weight.

Figures 239A, 239B:
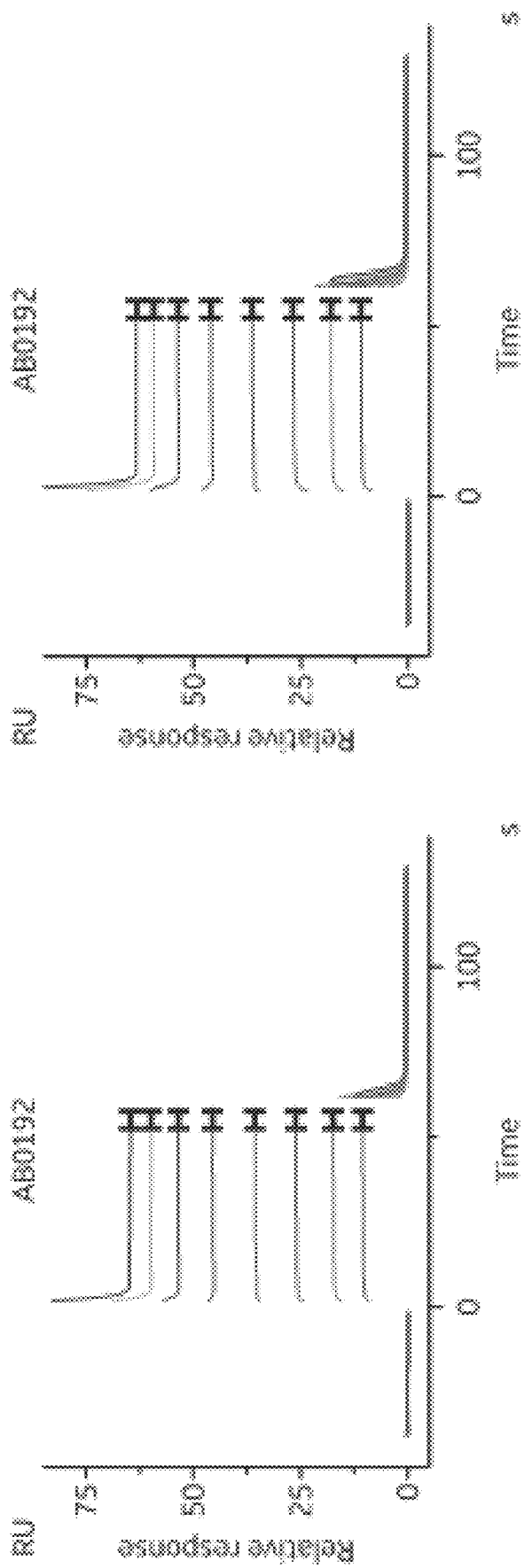
Figures 239E, 239F:
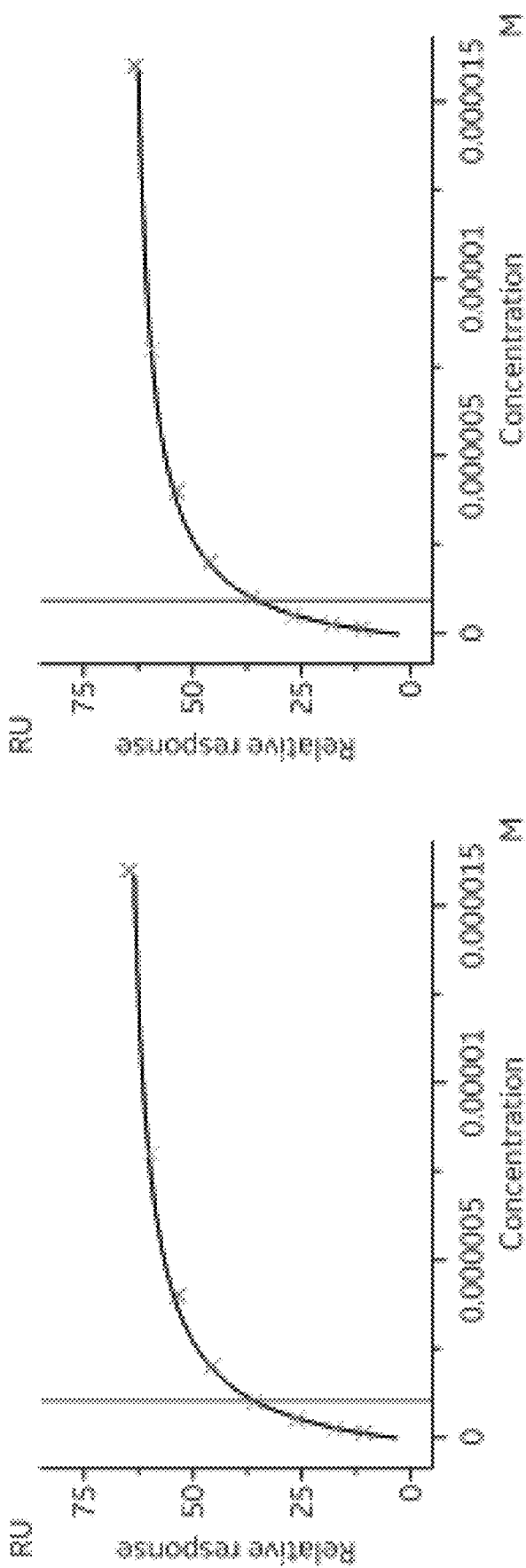
Figures 239G, 239H:
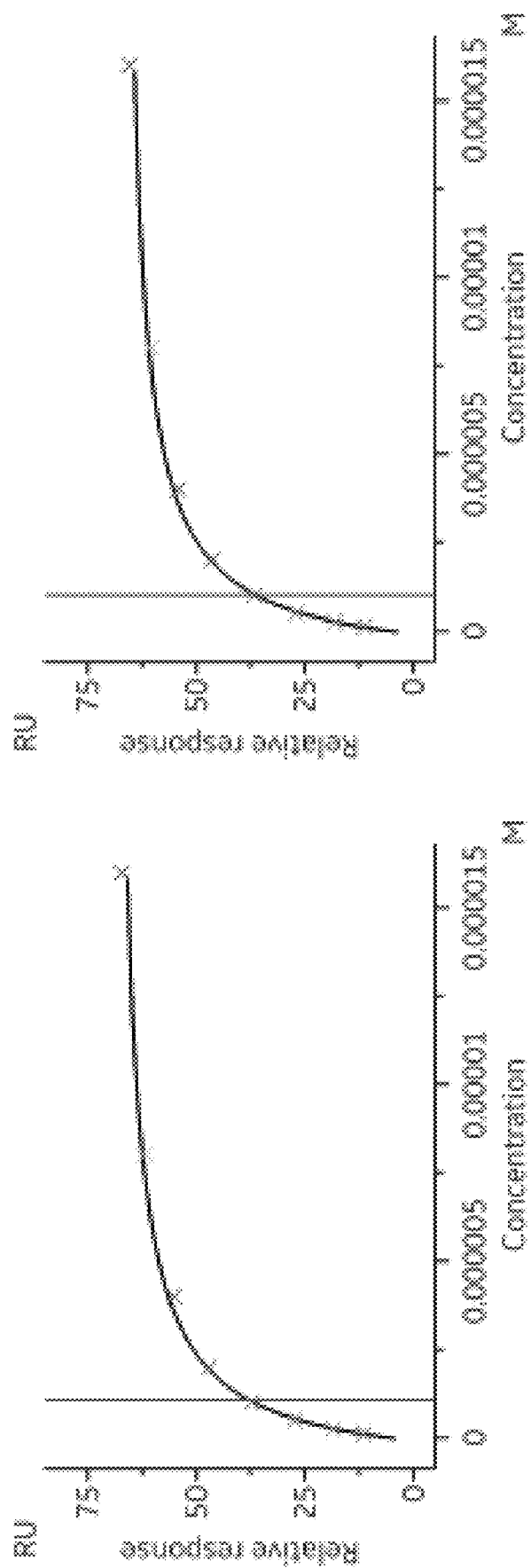
Figures 239I, 239J:
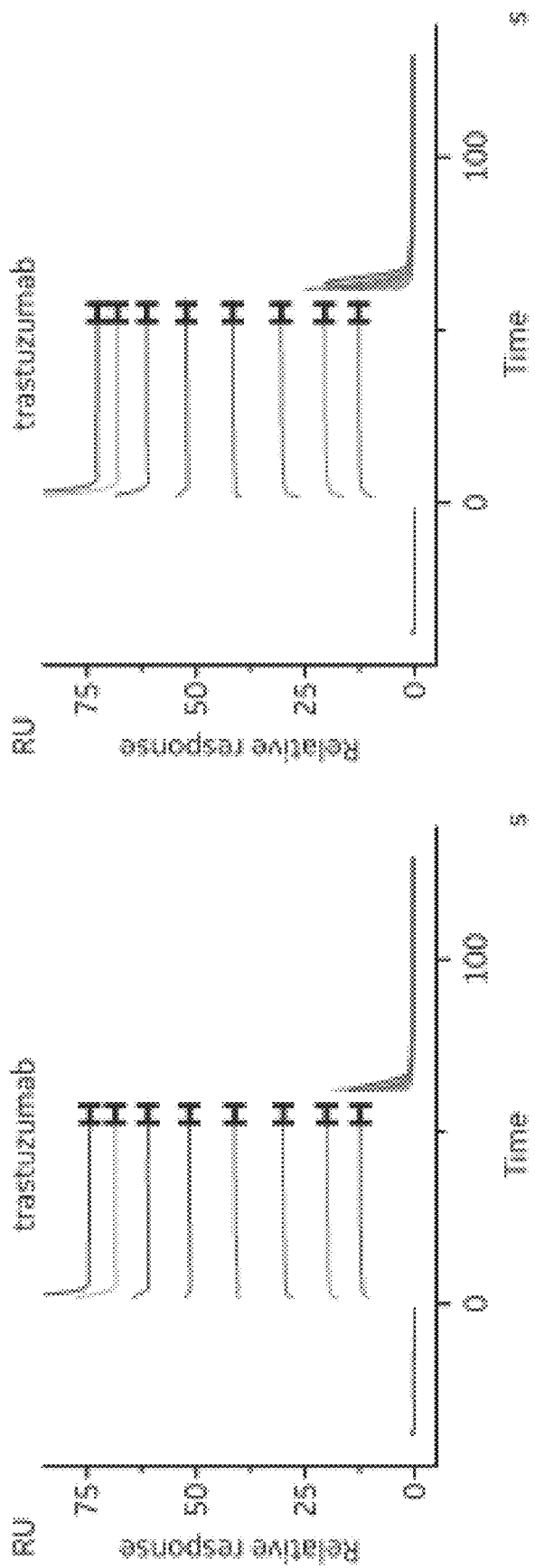
Figures 239K, 239L:
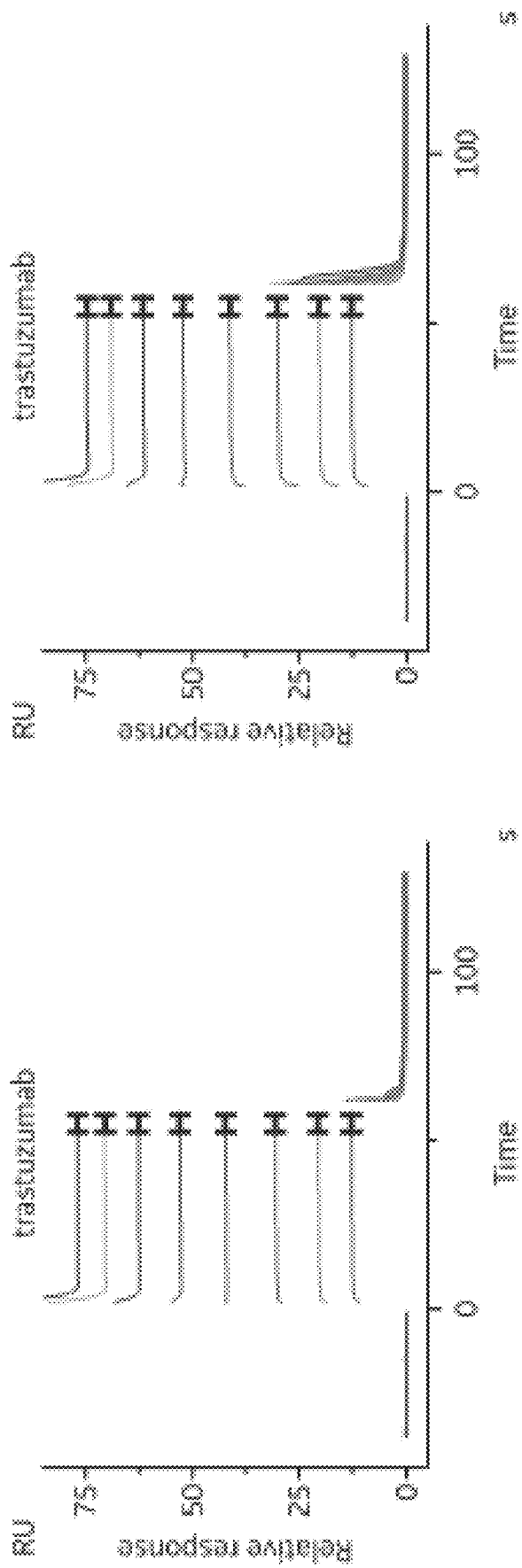
Figure 239O:
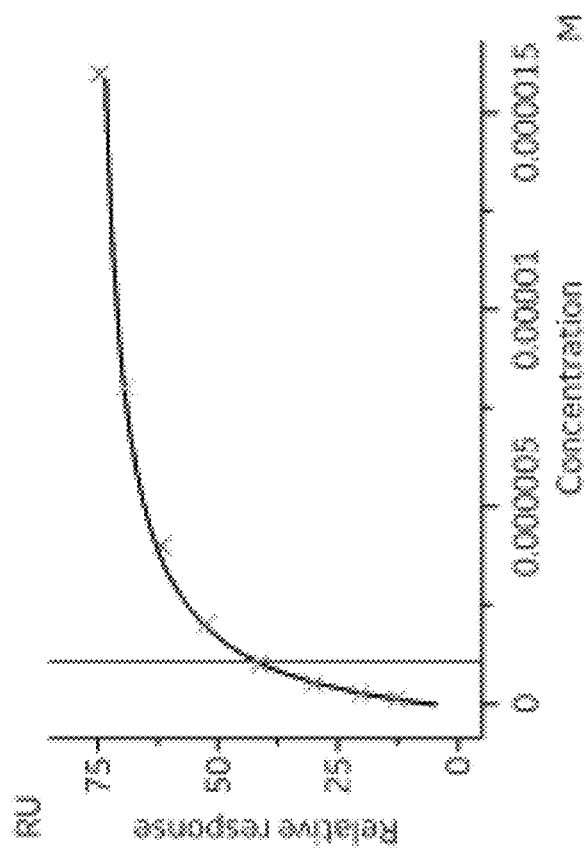
Figure 239P:
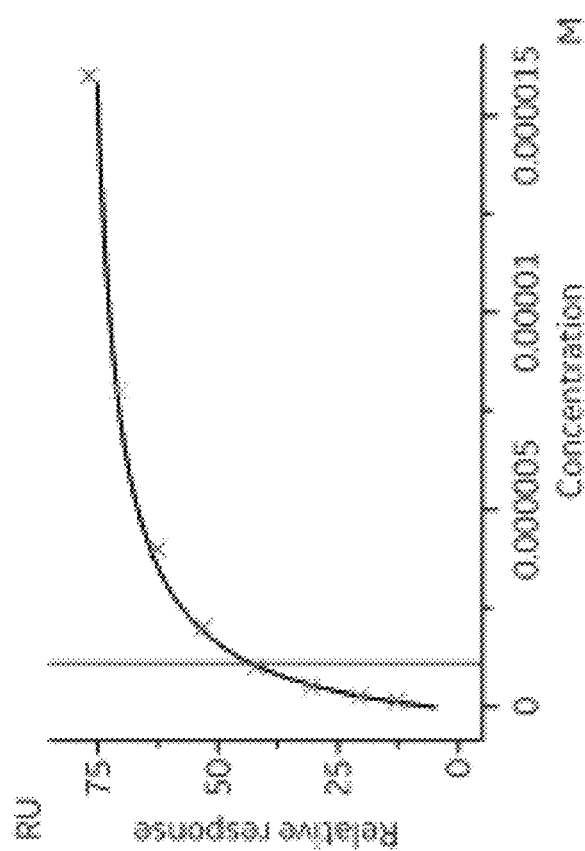

FIG. 238A-FIG. 238H show binding of AB0192 and trastuzumab to recombinant human CD64 (FcγRI). A difference in apparent maximum binding responses between the molecules is due to their difference in molecular weight FIG. 239A-FIG. 239P show binding of AB0192 and trastuzumab to recombinant human CD32a (FcγRIIa) H131 allele. FIG. 239A-FIG. 239D and FIG. 239I-FIG. 239H and FIG. 239M-FIG. 239P for each molecule represent raw binding sensorgrams while FIG. 239E-FIG. 239H and FIG. 239M-FIG. 239P represent fitting to a steady state affinity model. A difference in apparent maximum binding responses between the molecules is due to a difference in molecular weight.

Figure 240A:
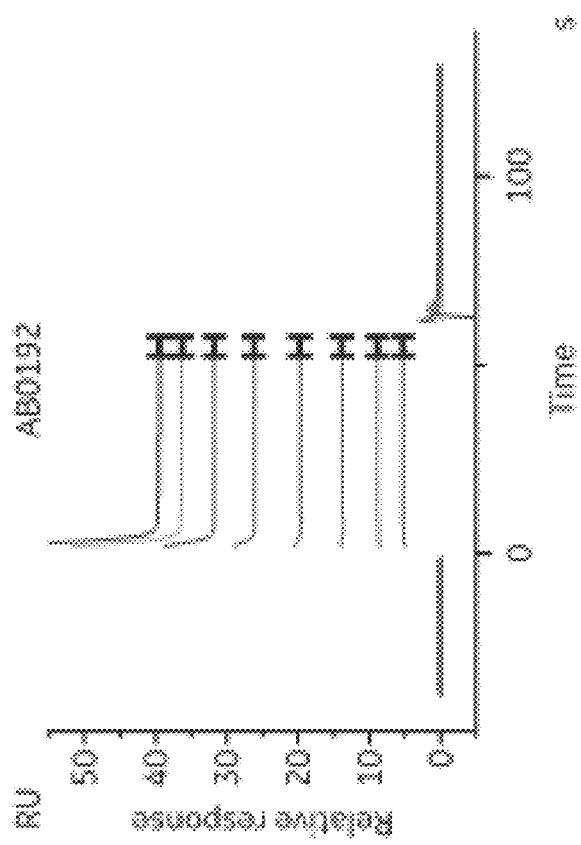
Figure 240B:
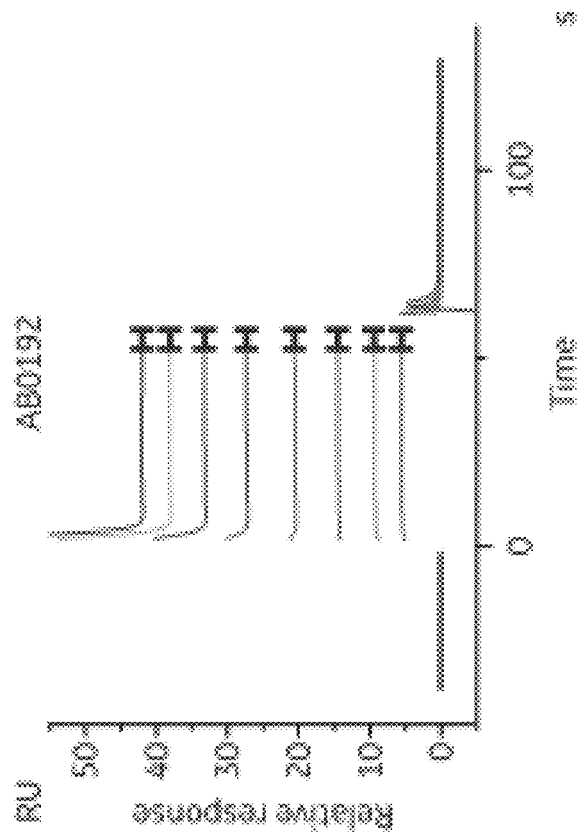
Figures 240C, 240D:
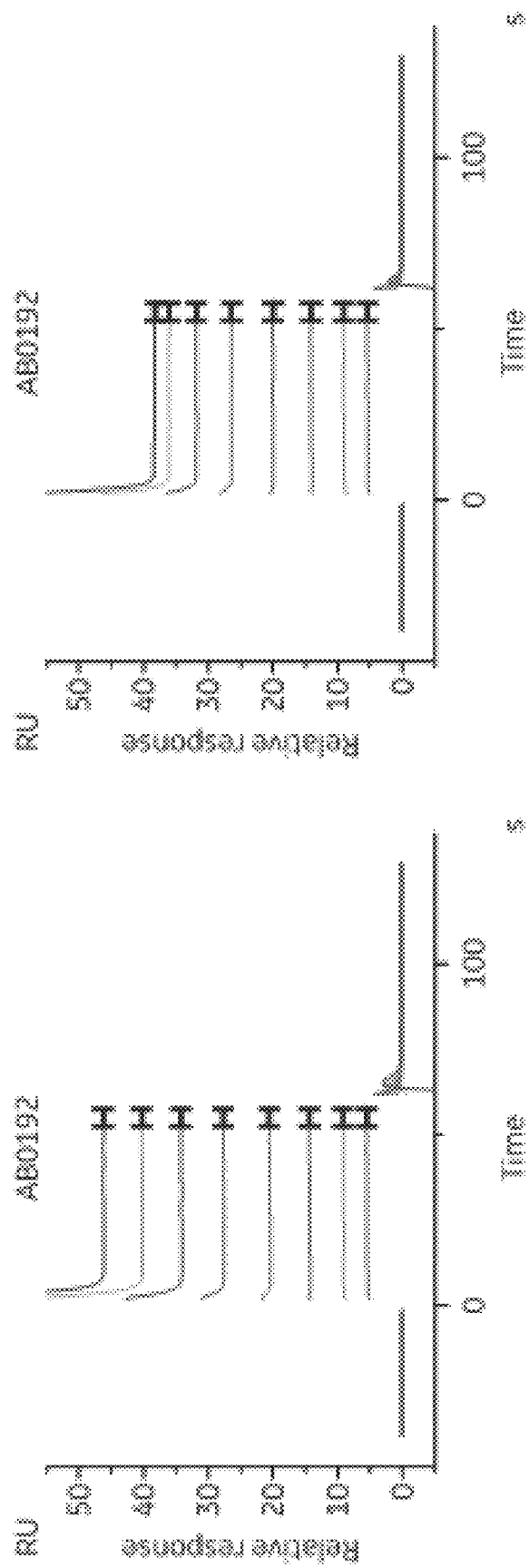
Figures 240E, 240F:
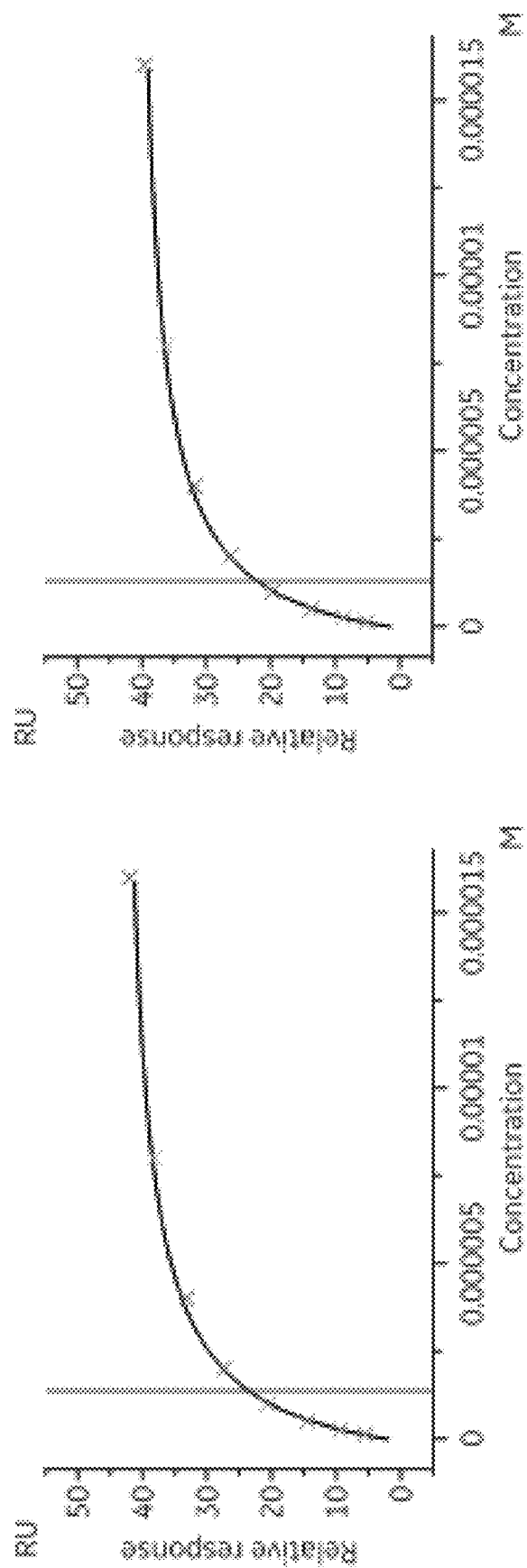
Figures 240I, 240J:
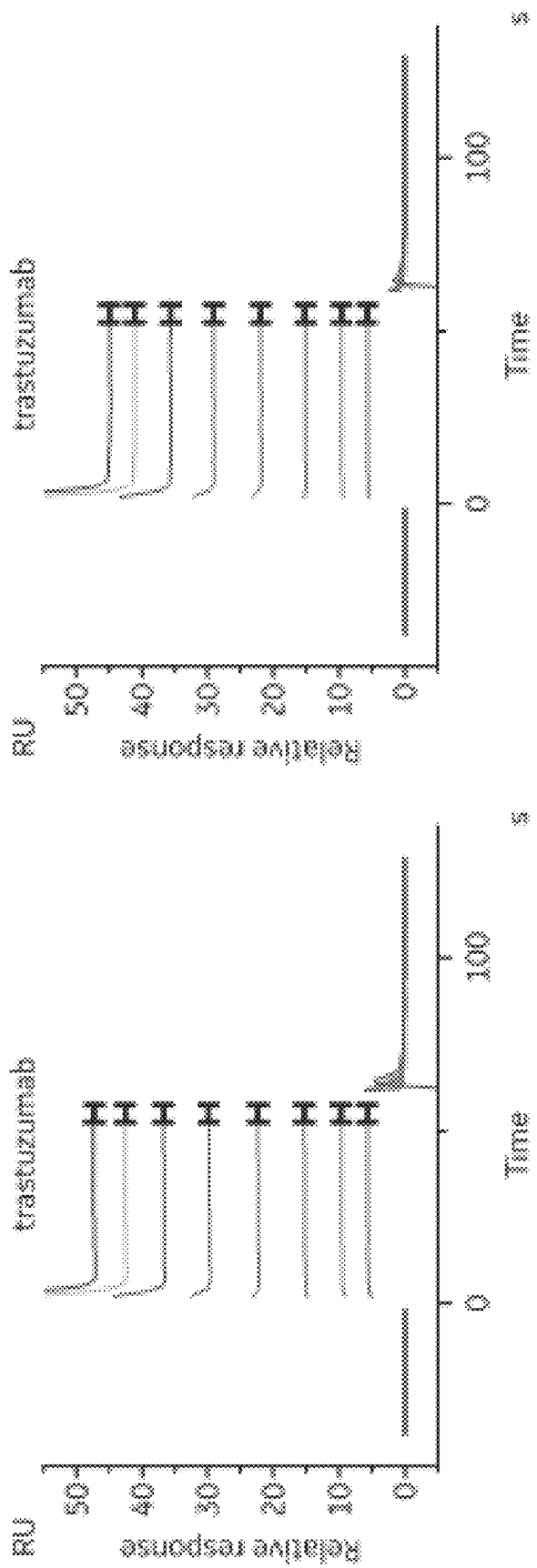
Figures 240K, 240L:
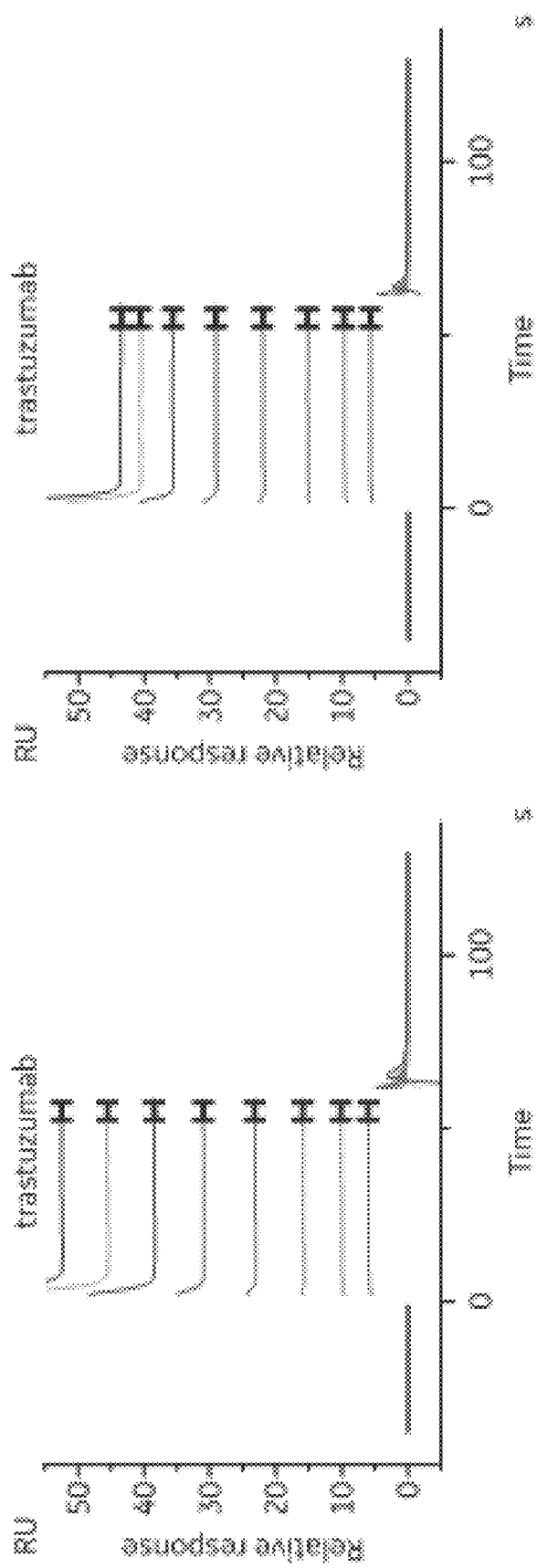

FIG. 240A-FIG. 240P show binding of AB0192 and trastuzumab to recombinant human CD32a (FcγRIIa) R131 allele. Top panel for each molecule represent raw binding sensorgrams while the bottom panels represent fitting to a steady state affinity model. A difference in apparent maximum binding responses between the molecules is due to a difference in molecular weight.

Figure 241A:
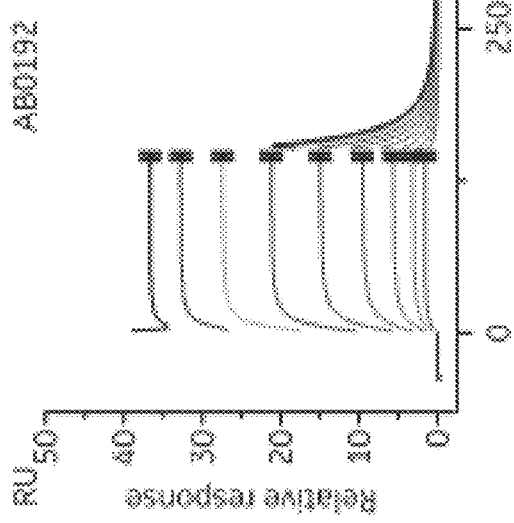
Figure 241B:
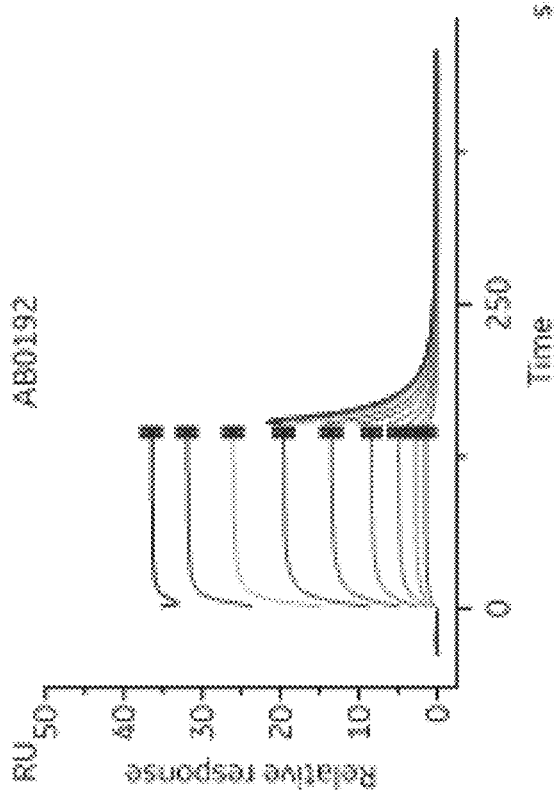
Figure 241C:
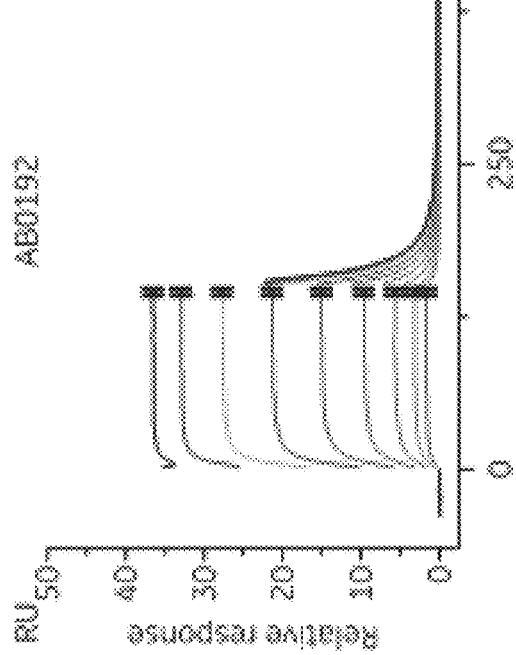
Figure 241D:
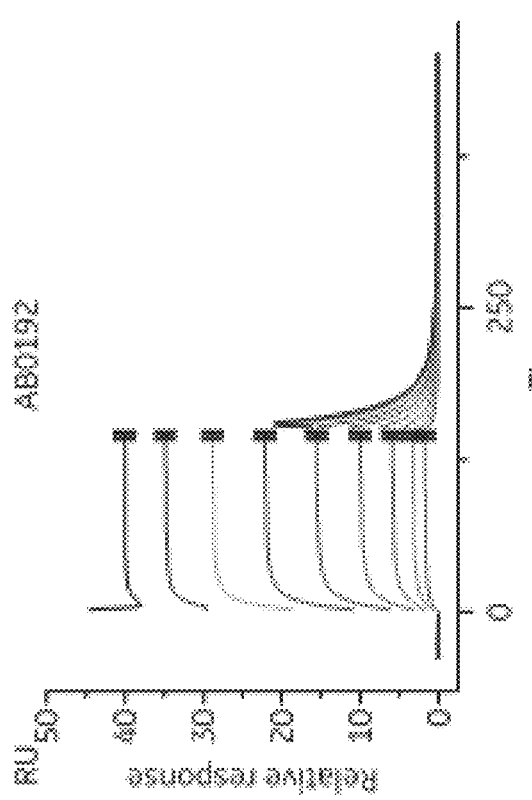
Figures 241E, 241F:
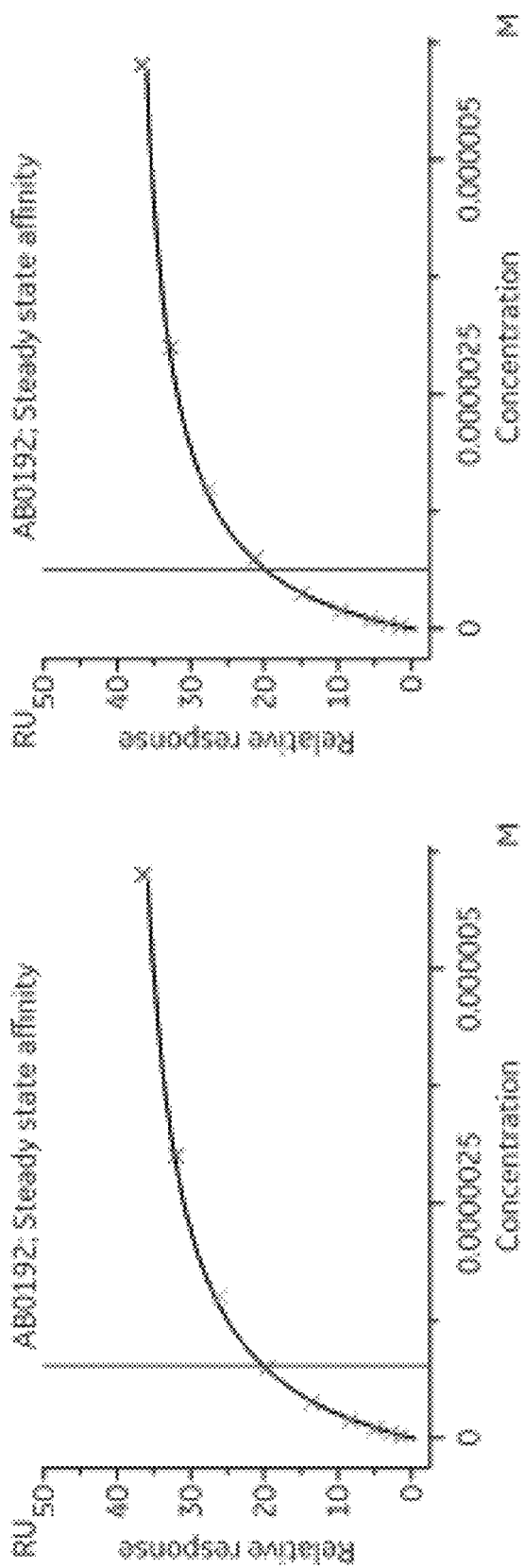
Figure 241I:
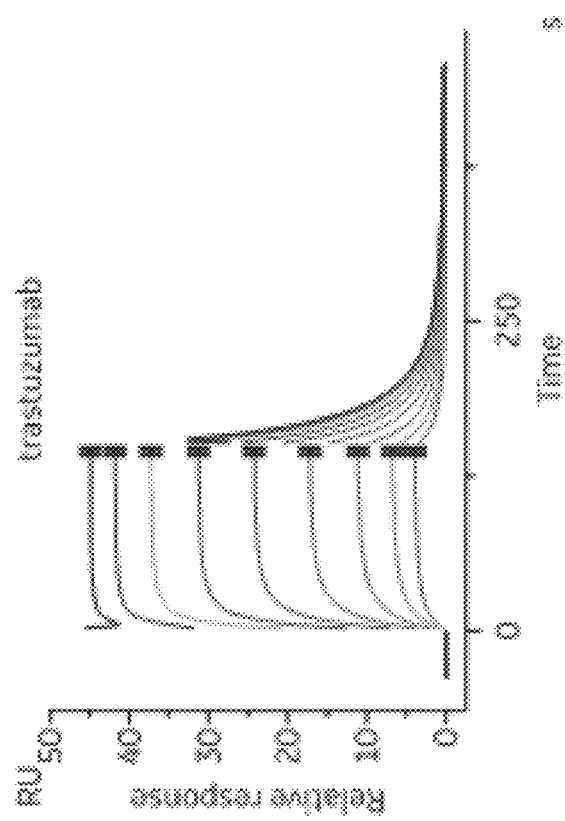
Figure 241J:
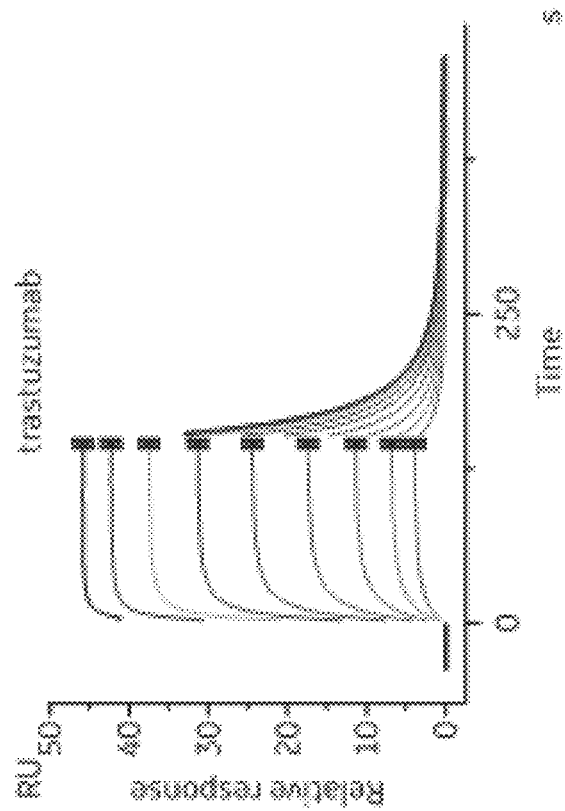
Figure 241K:
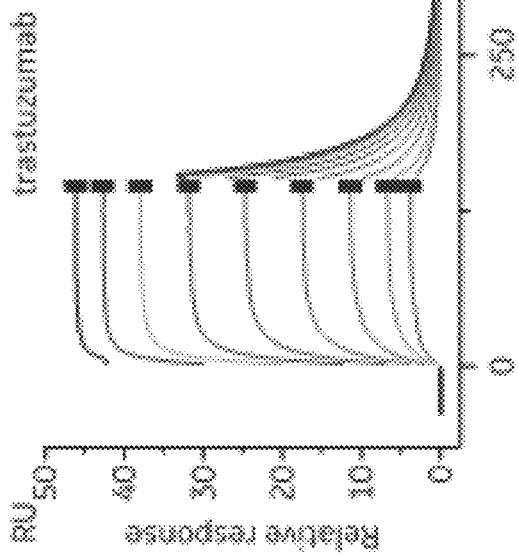
Figure 241L:
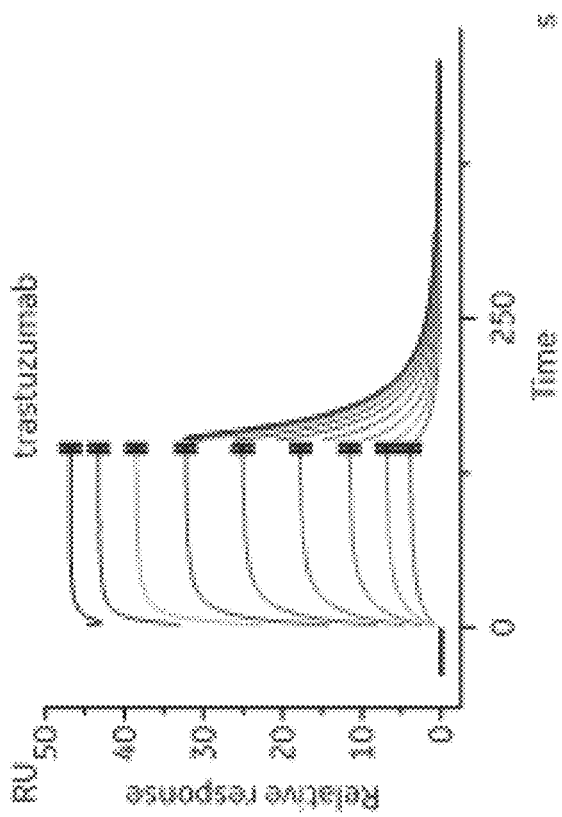
Figures 241M, 241N:
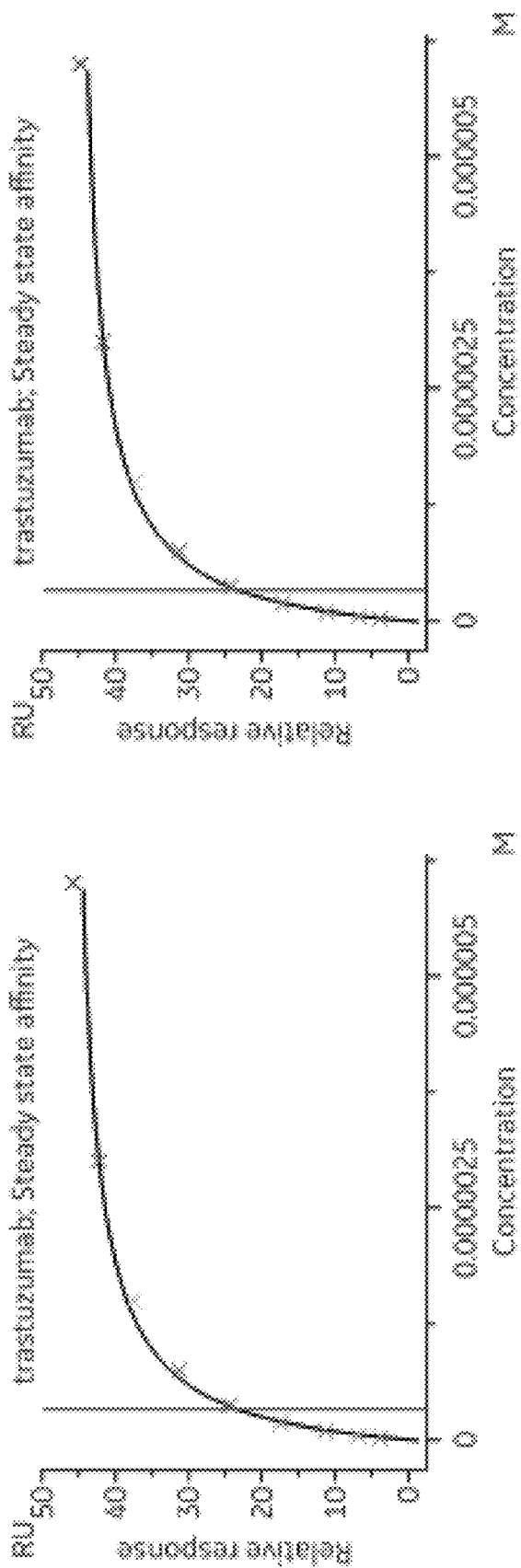
Figures 241O, 241P:
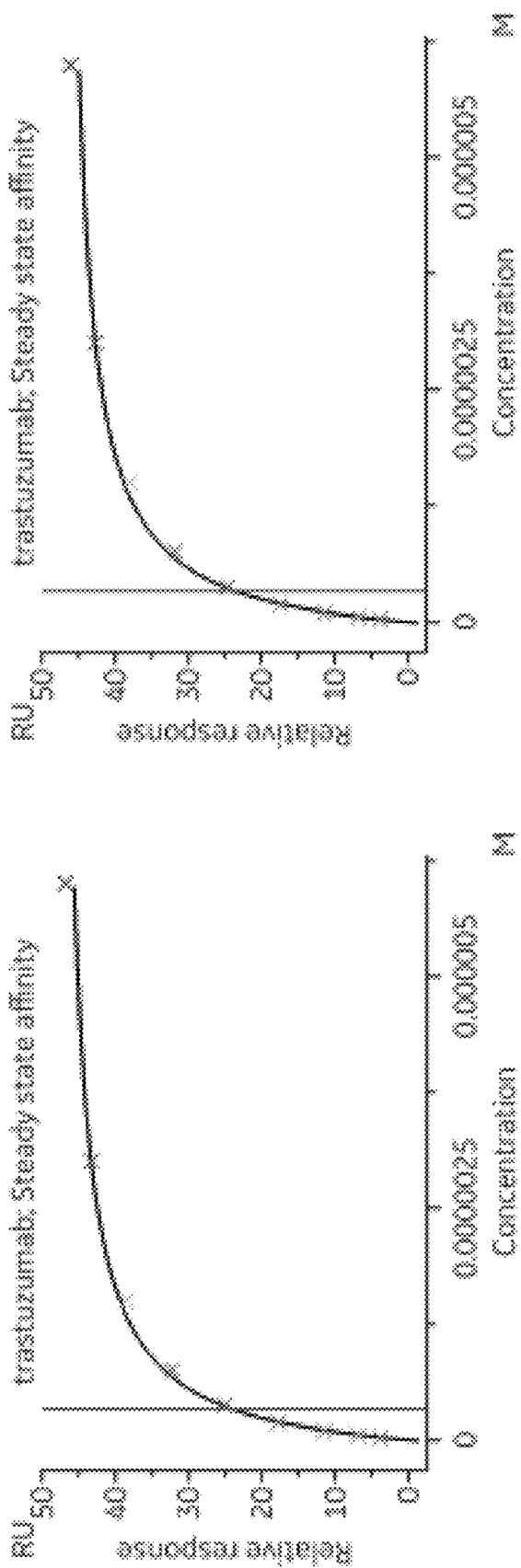
Figure 242A:
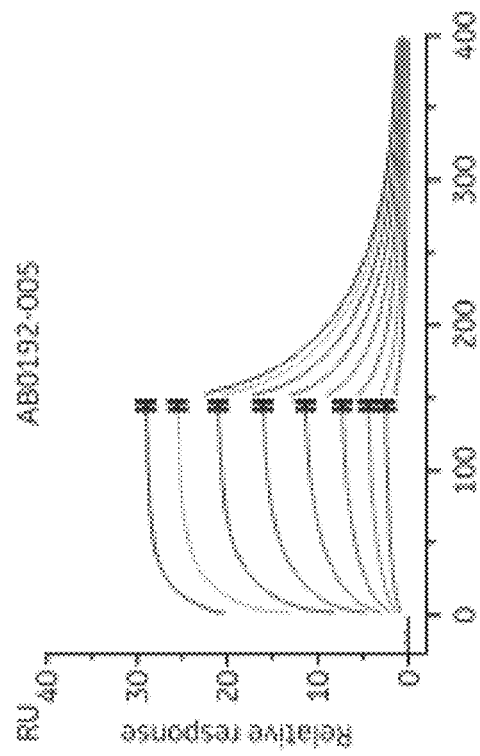
Figure 242B:
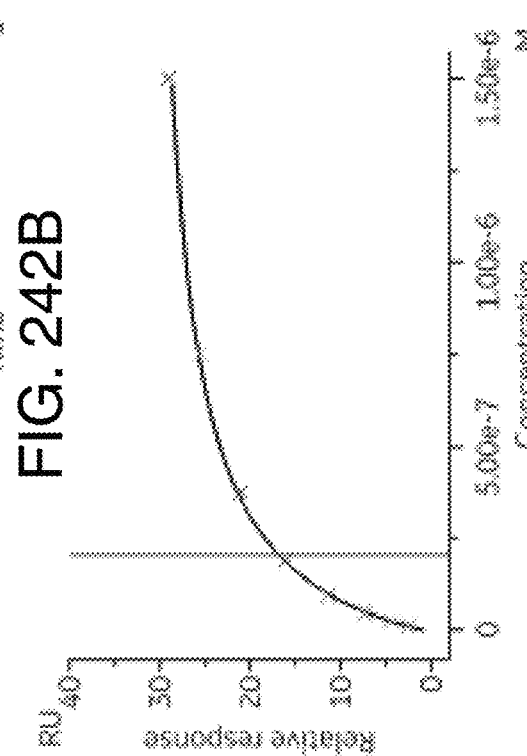
Figure 242C:
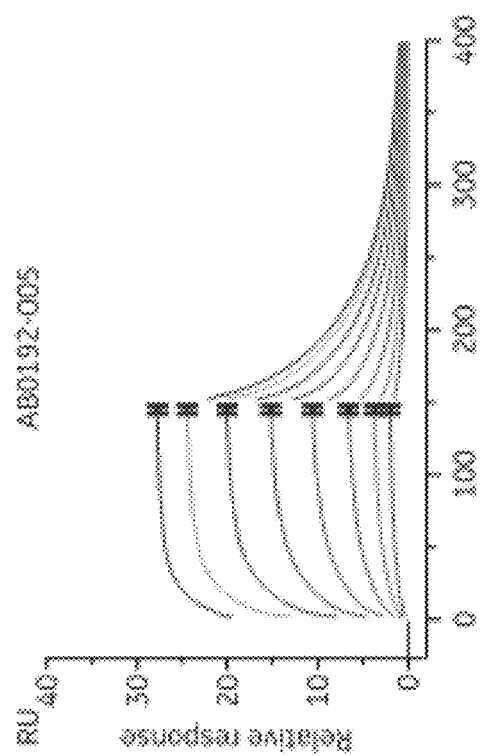
Figure 242D:
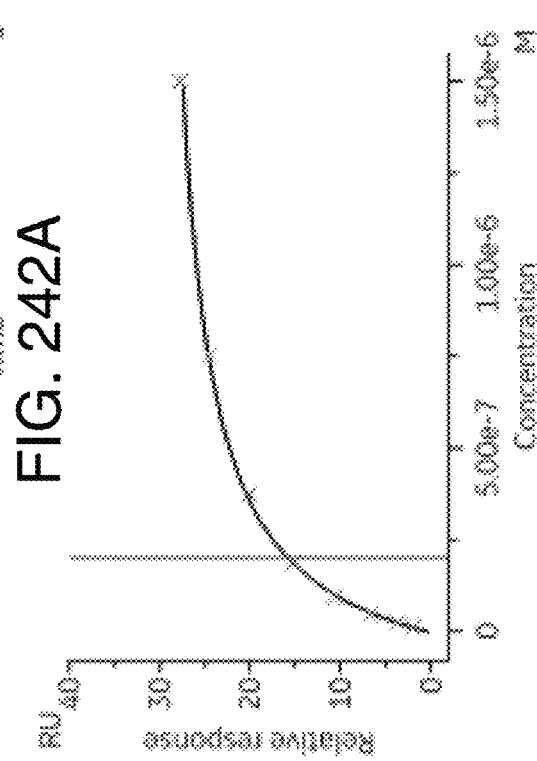
Figure 242E:
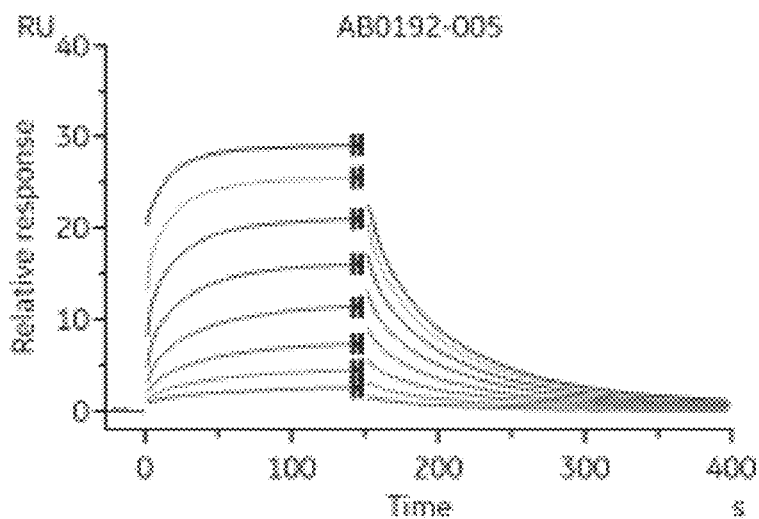
Figure 242F:
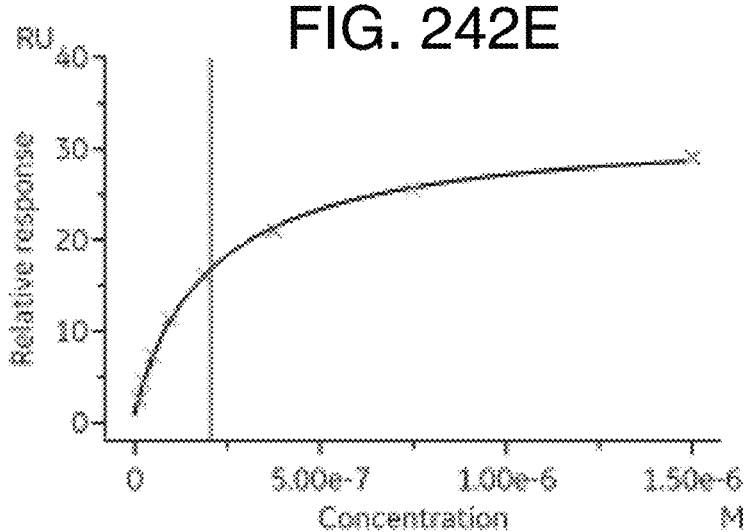
Figure 242G:
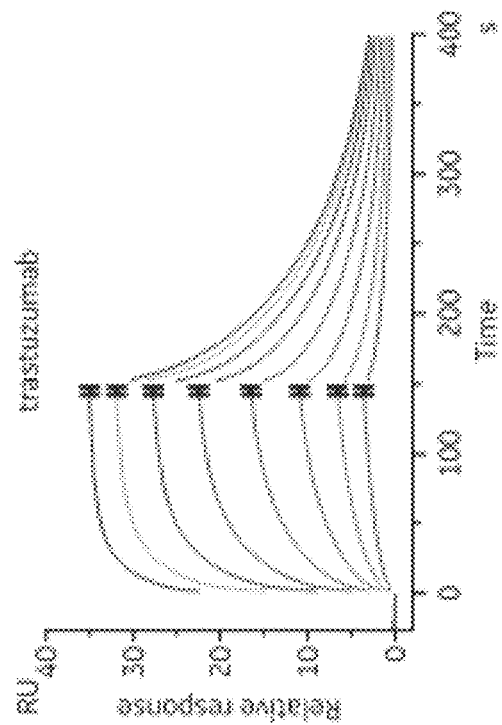
Figure 242H:
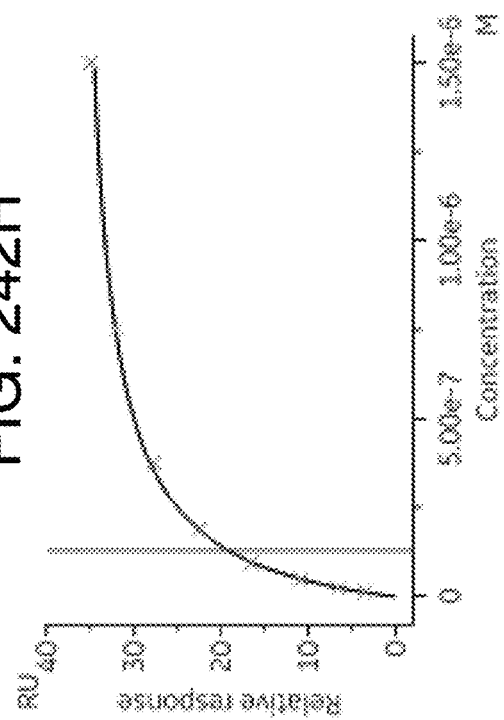
Figure 242I:
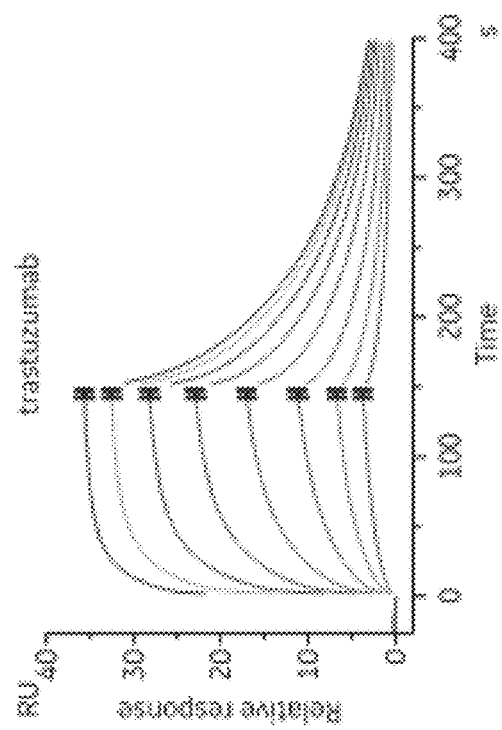
Figure 242J:
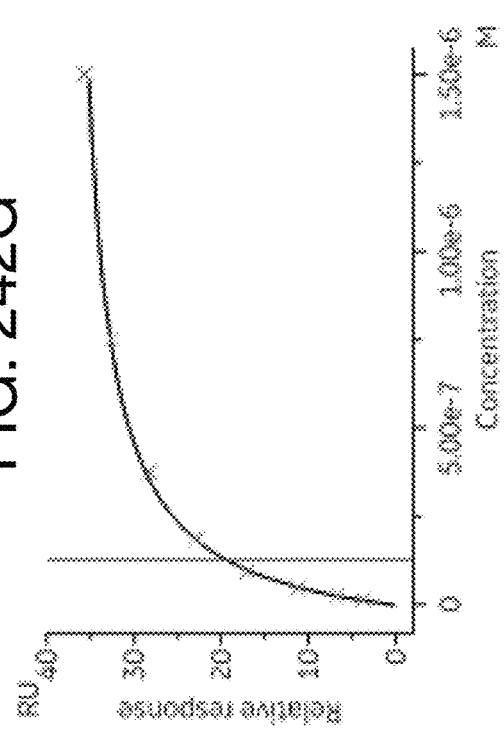
Figure 242K:
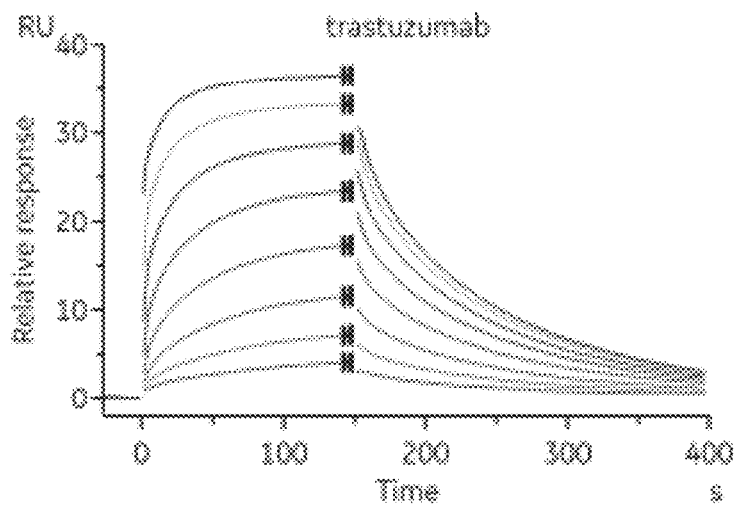
Figure 242L:
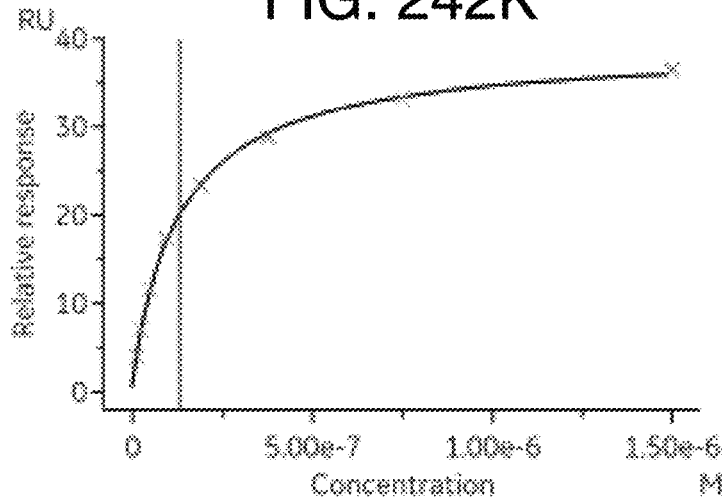

FIG. 241A-FIG. 241P show binding of AB0192 and trastuzumab to recombinant human CD16a (FcγRIIIa) F158 allele. FIG. 241A-FIGS. 241D and 241I-FIG. 241L for each molecule represent raw binding sensorgrams while FIG. 241E-FIG. 241H and FIG. 241M-FIG. 241P represent fitting to a steady state affinity model. A difference in apparent maximum binding responses between the molecules is due to a difference in molecular weight.

FIG. 242A-FIG. 242L show binding of AB0192 and trastuzumab to recombinant cynomolgus CD16 (FcγRIII). FIGS. 242A, 242B, 242E, 242G, 242H, and 242K for each molecule represent raw binding sensorgrams while FIG. 242C, FIG. 242D, FIG. 242F, FIG. 242I, FIG. 242J, and FIG. 242L represent fitting to a steady state affinity model. A difference in apparent maximum binding responses between the molecules is due to a difference in molecular weight.

Figure 243A:
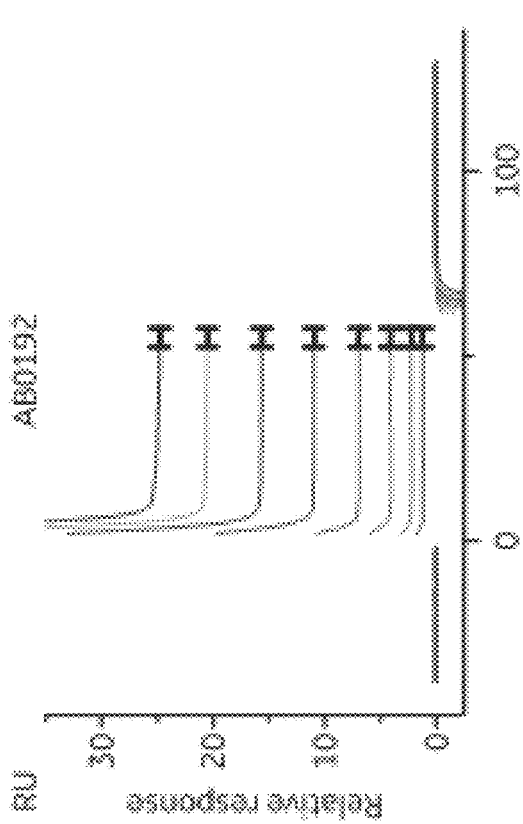
Figure 243B:
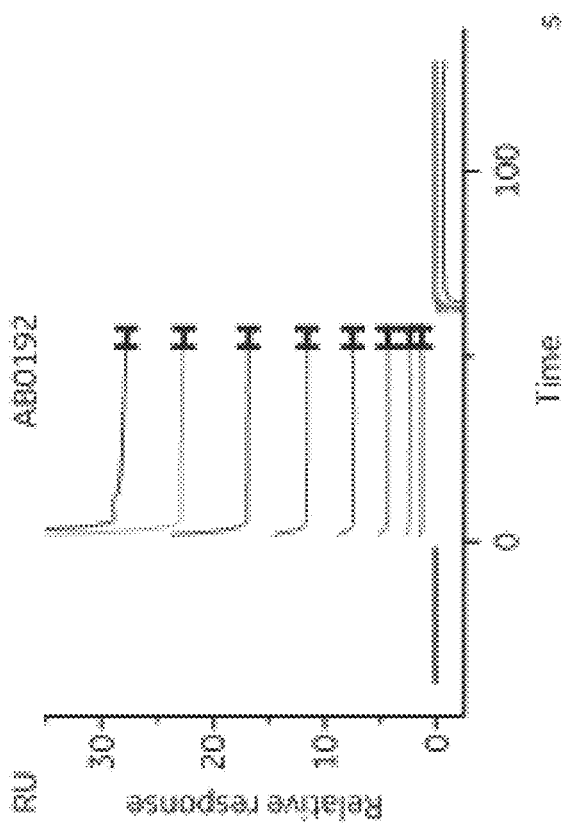
Figure 243D:
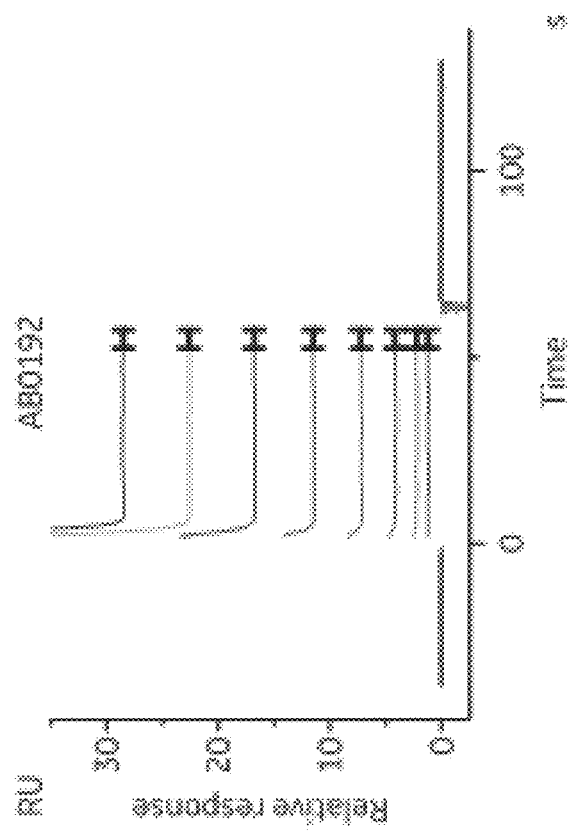
Figure 243C:
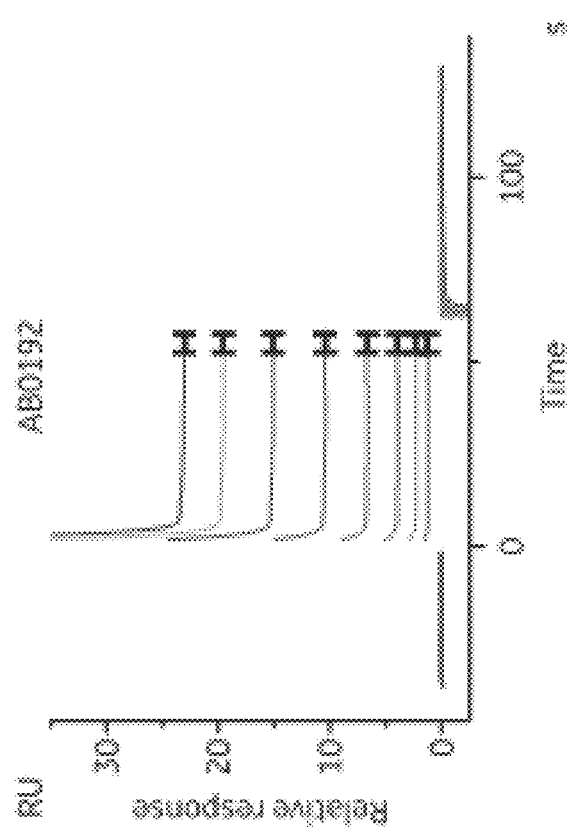
Figure 243F:
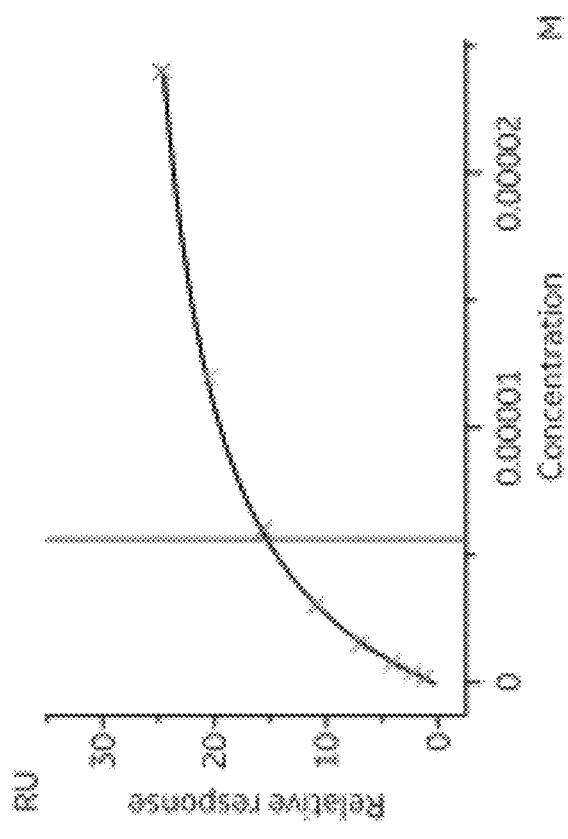
Figure 243E:
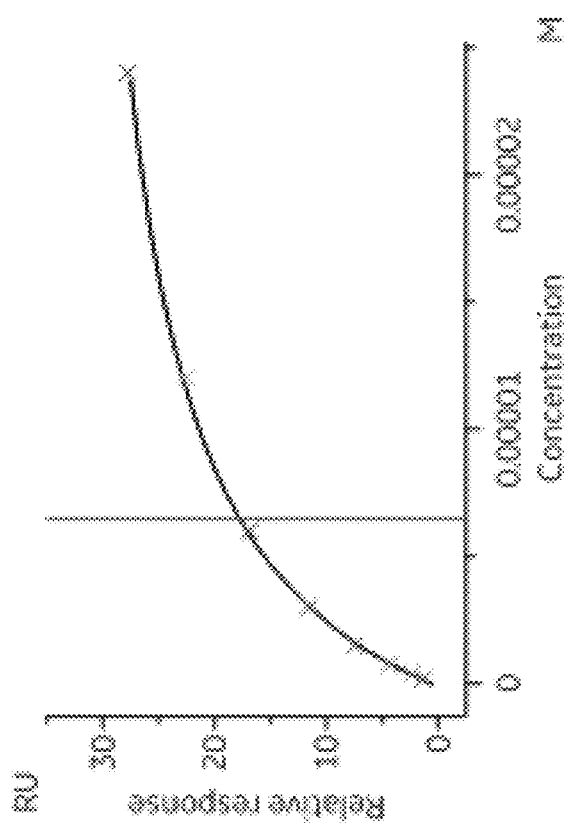
Figures 243G, 243H:
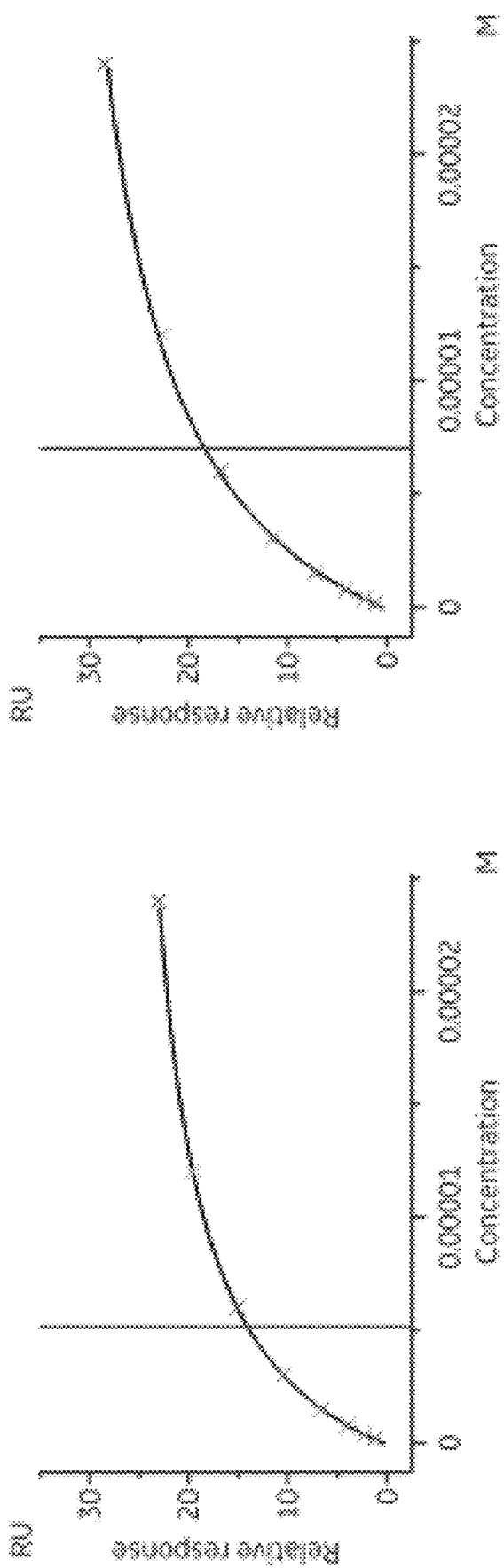
Figure 243J:
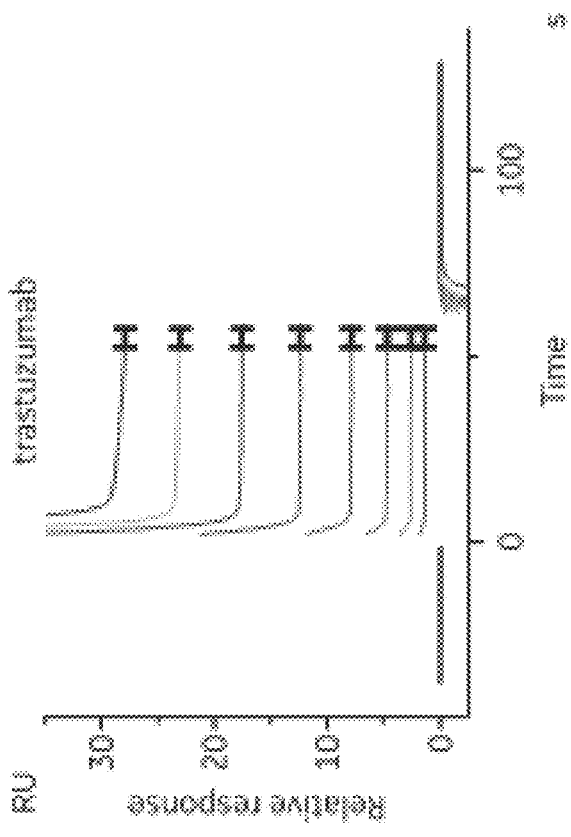
Figure 243I:
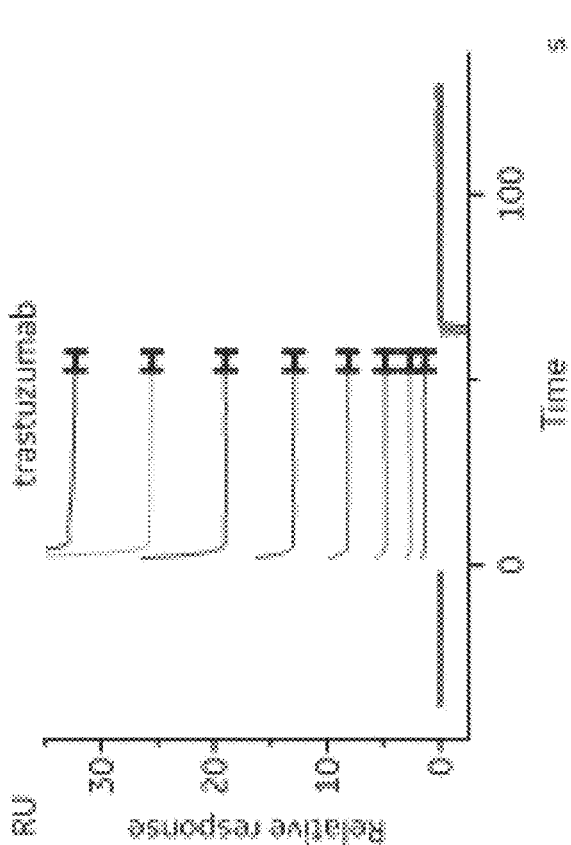
Figures 243K, 243L:
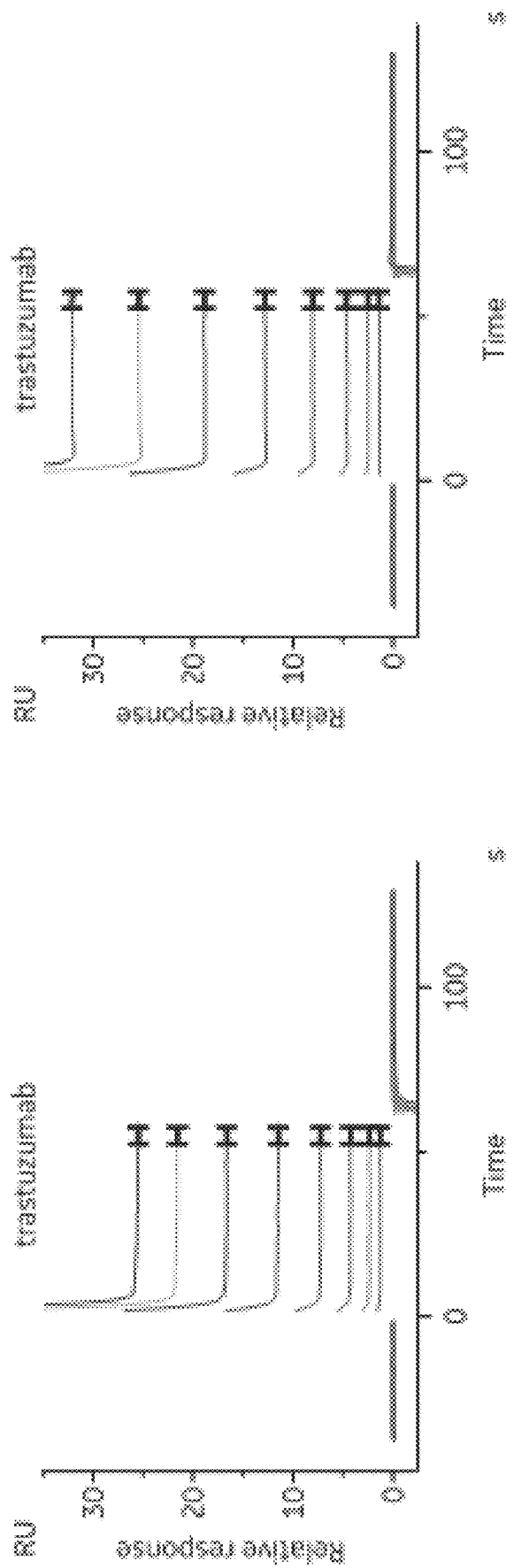
Figures 243M, 243N:

Figure 244E:
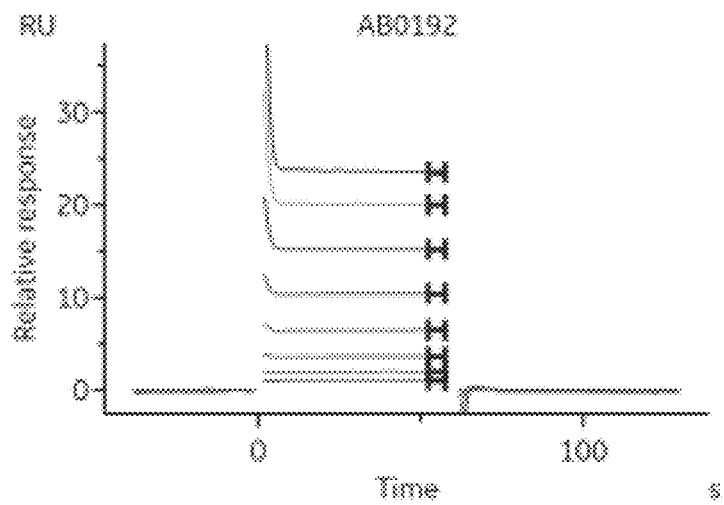
Figure 244F:
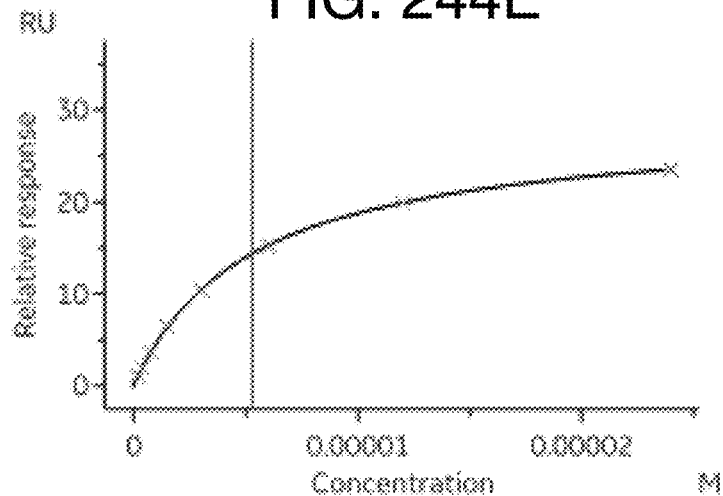
Figure 244K:
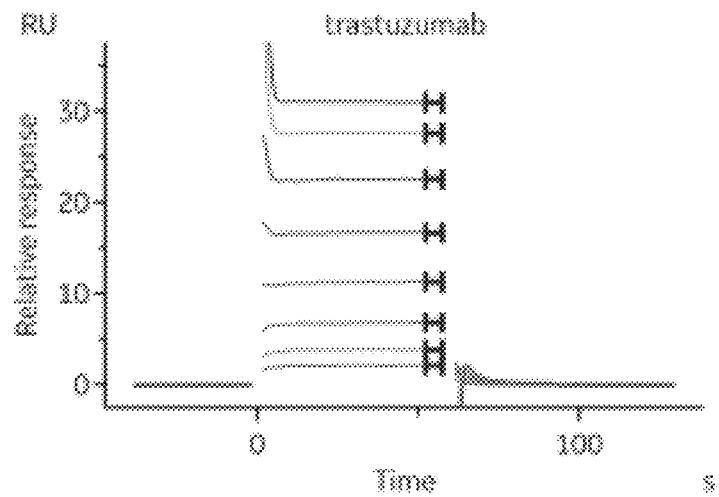
Figure 244L:
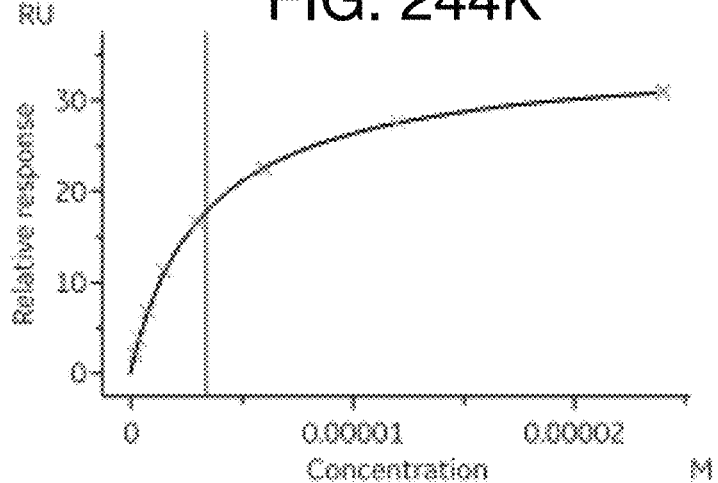

FIG. 243A-FIG. 243P show binding of AB0192 and trastuzumab to recombinant human CD32b (FcγRIIb). FIG. 243A-FIG. 243D and FIG. 243I-FIG. 243L for each molecule represent raw binding sensorgrams while FIG. 243E-FIG. 243H and FIG. 243M-FIG. 243P represent fitting to a steady state affinity model. A difference in apparent maximum binding responses between the molecules is due to a difference in molecular weight.

FIG. 244A-FIG. 244L show binding of AB0192 and trastuzumab to recombinant human CD16b (FcγRIIIb). FIGS. 244A, 244B, 244E, 244G, 244H and 244K for each molecule represent raw binding sensorgrams while FIG. 244C, FIG. 244D, FIG. 244F, FIG. 244I, FIG. 244J, and FIG. 244L represent fitting to a steady state affinity model. A difference in apparent maximum binding responses between the molecules is due to a difference in molecular weight.

Figure 245A:
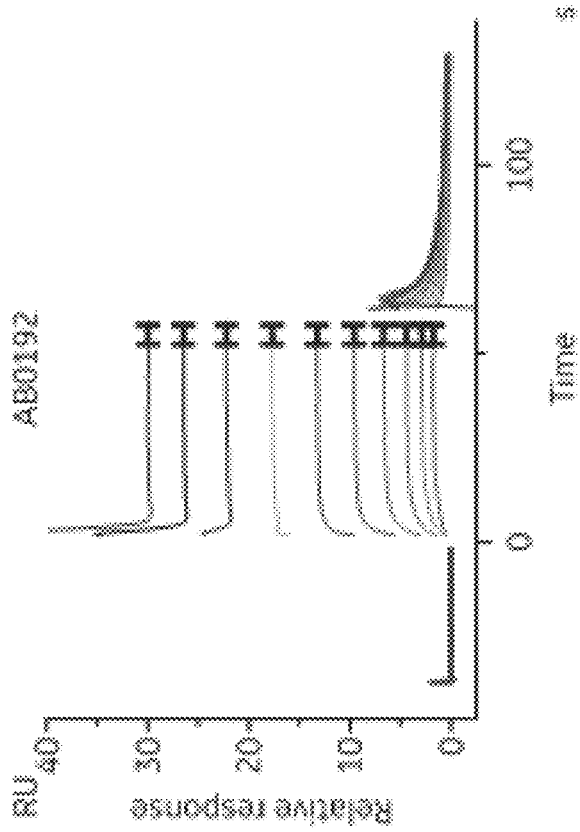
Figure 245B:
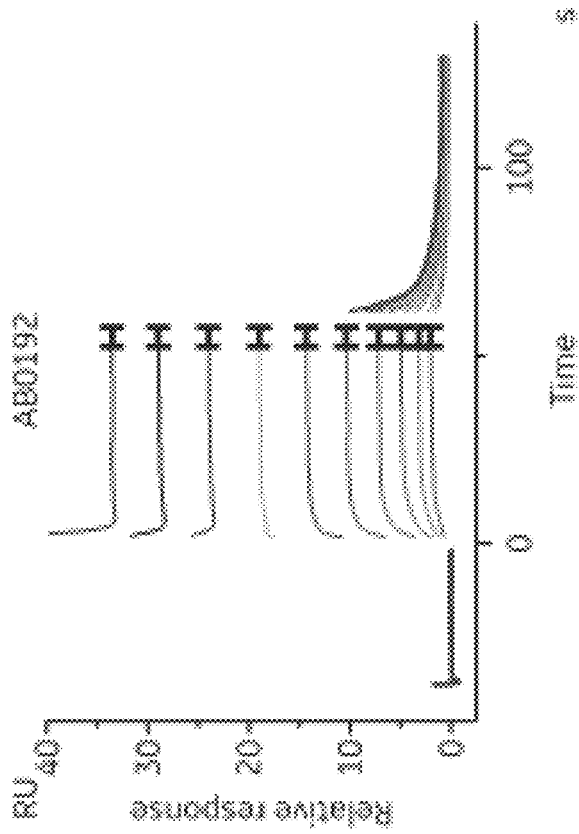
Figure 245C:
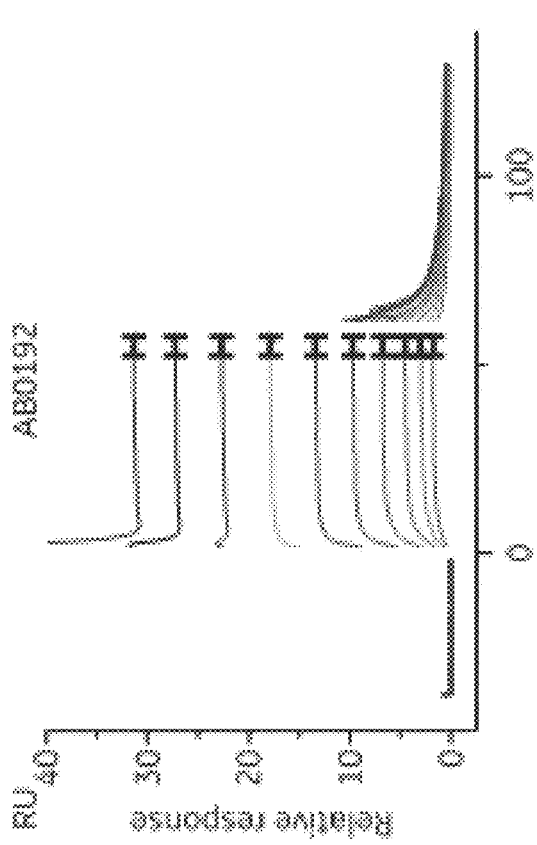
Figure 245D:

Figure 245I:
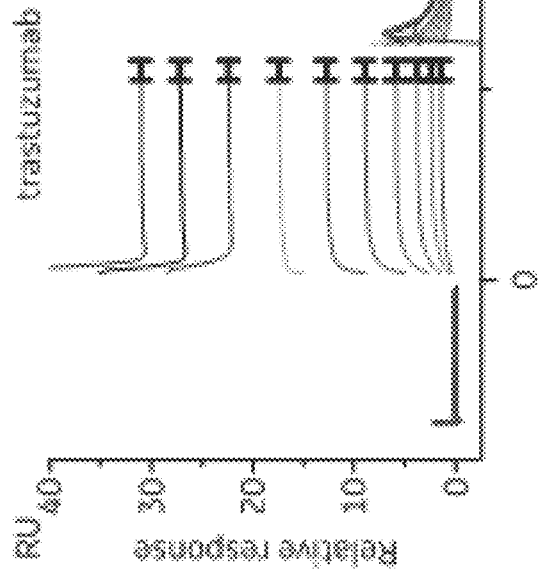
Figure 245J:
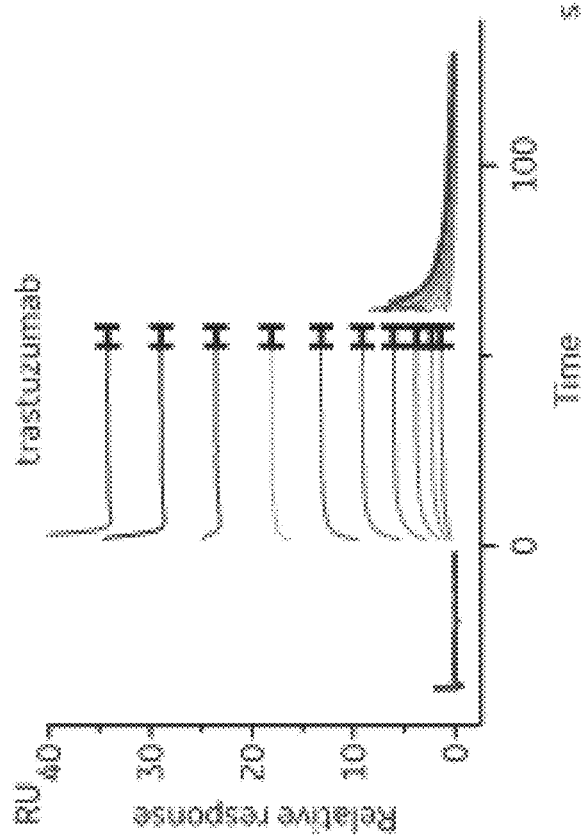
Figure 245K:
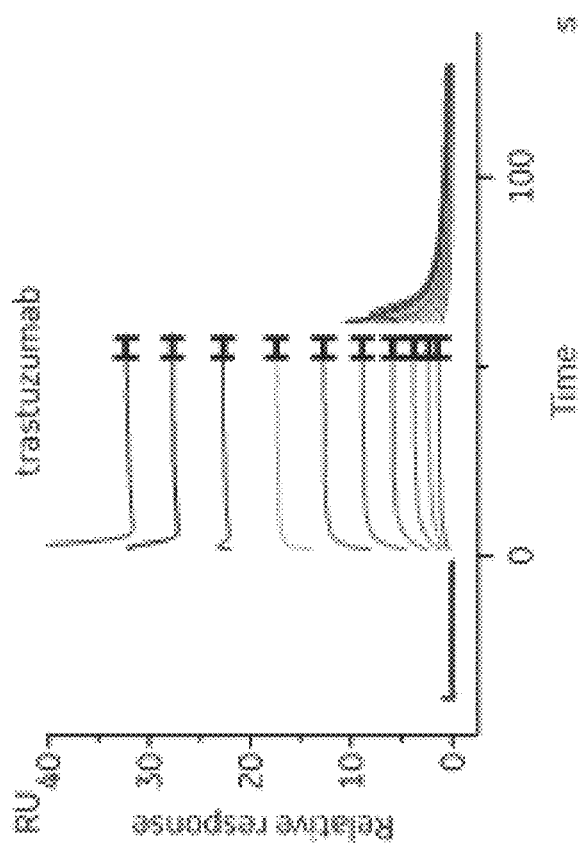
Figure 245L:
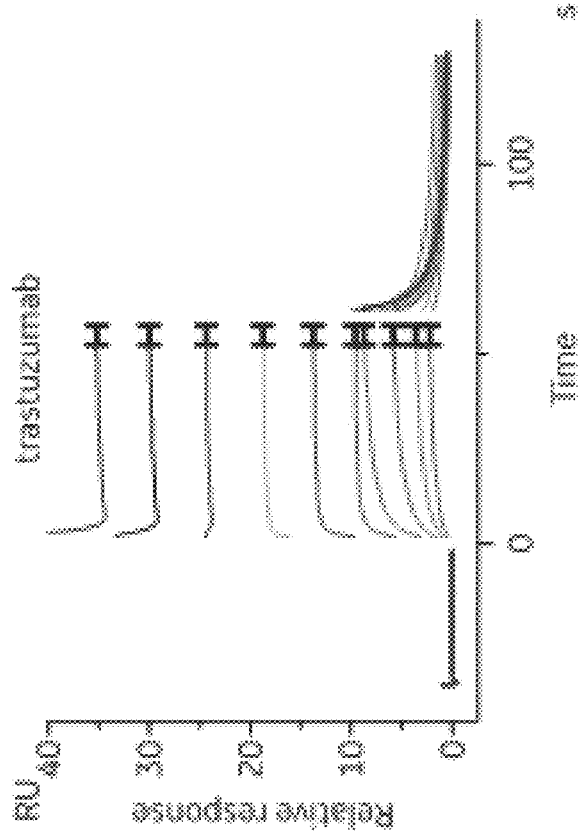
Figure 245M:
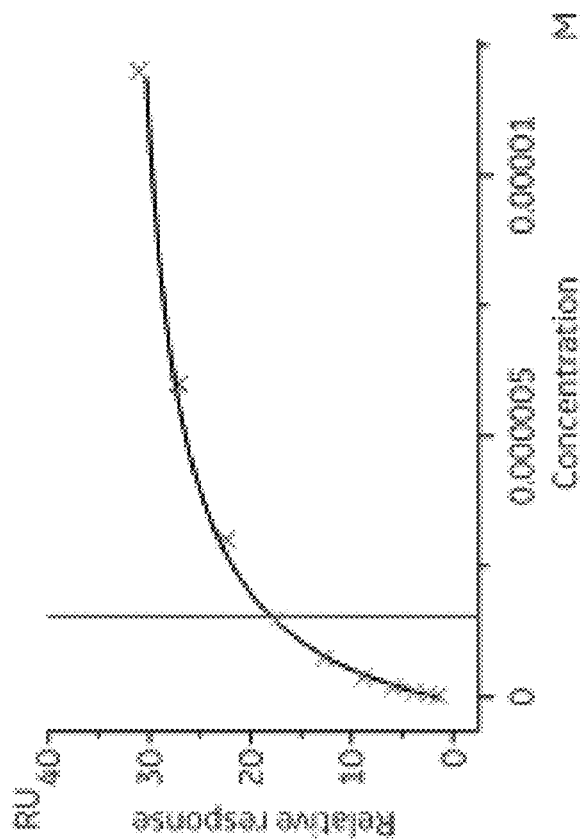
Figure 245N:
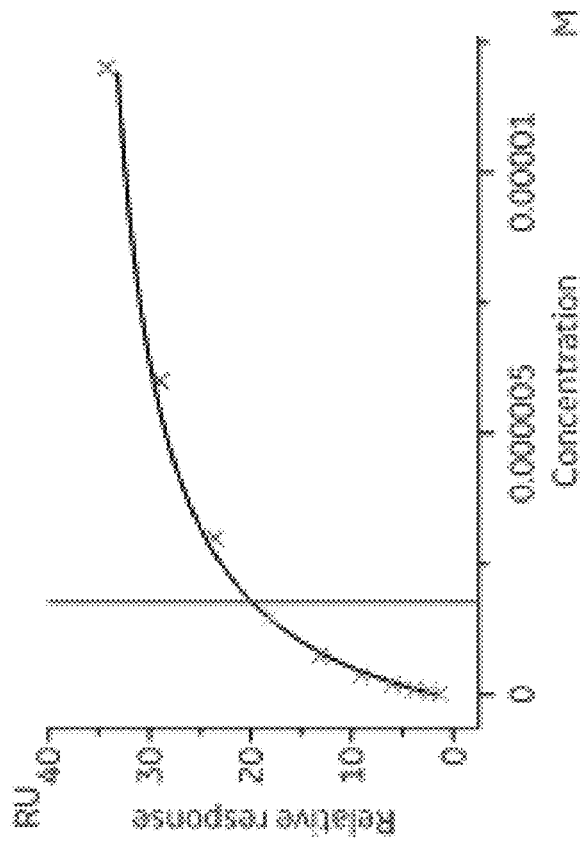
Figure 245O:
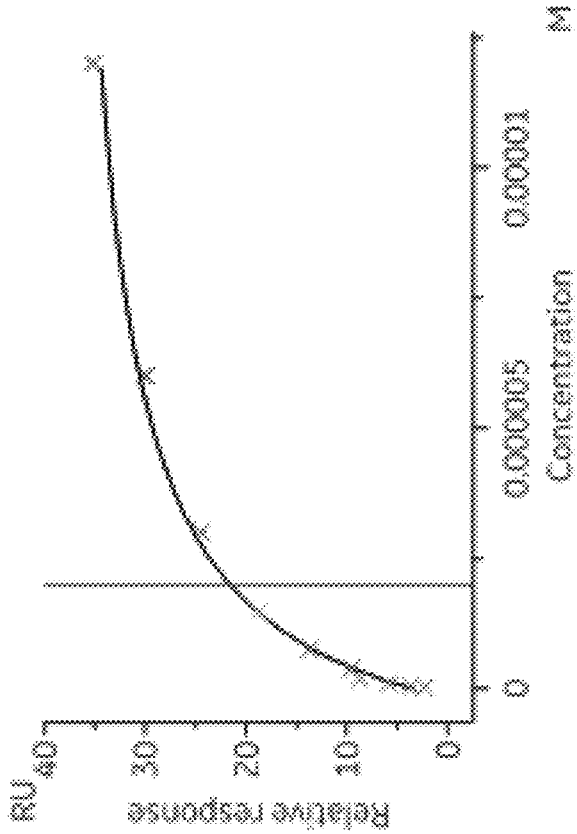
Figure 245P:
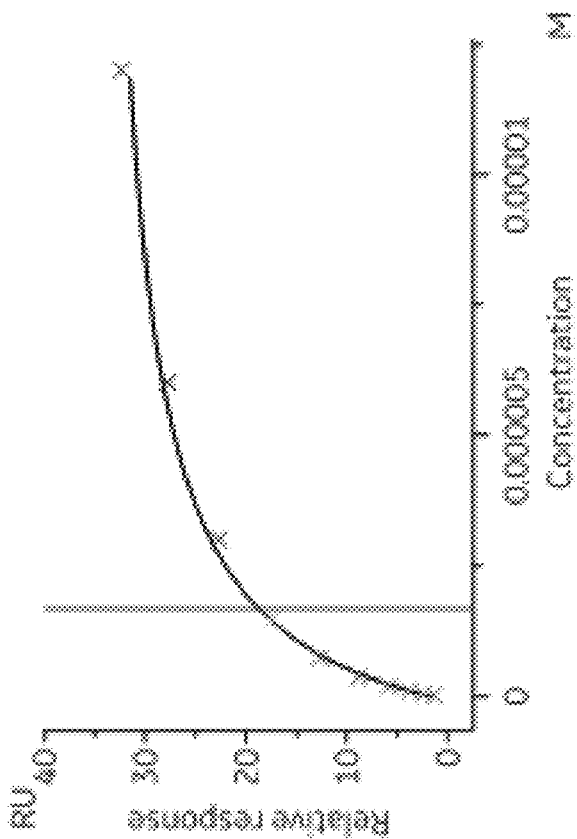
Figure 246A:
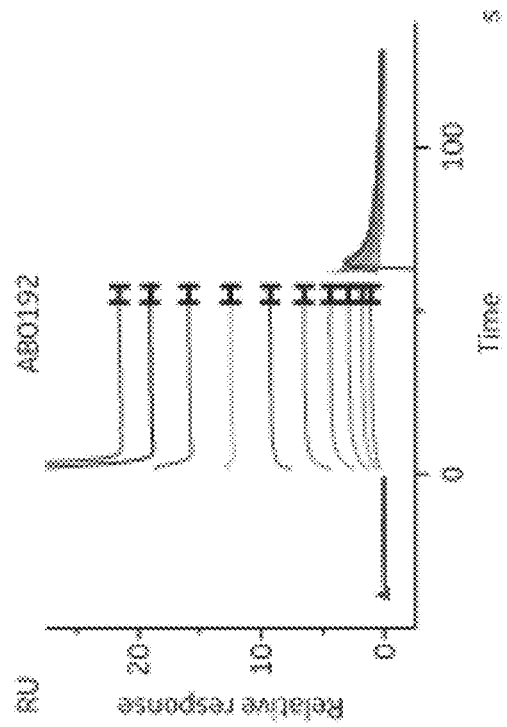
Figure 246B:
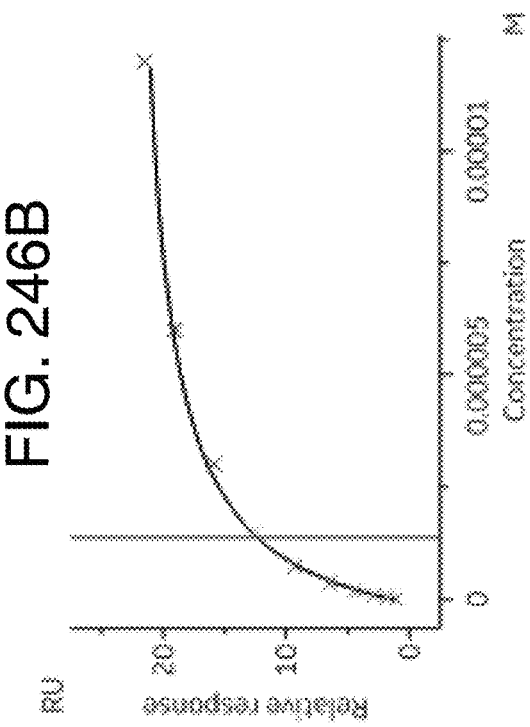
Figure 246C:
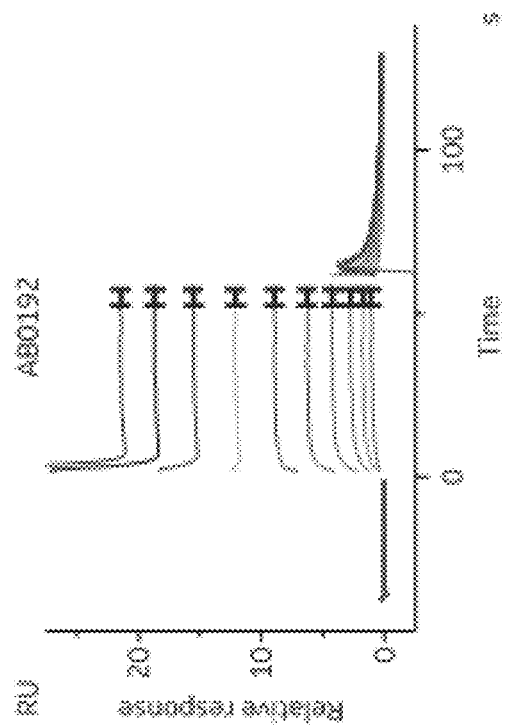
Figure 246D:
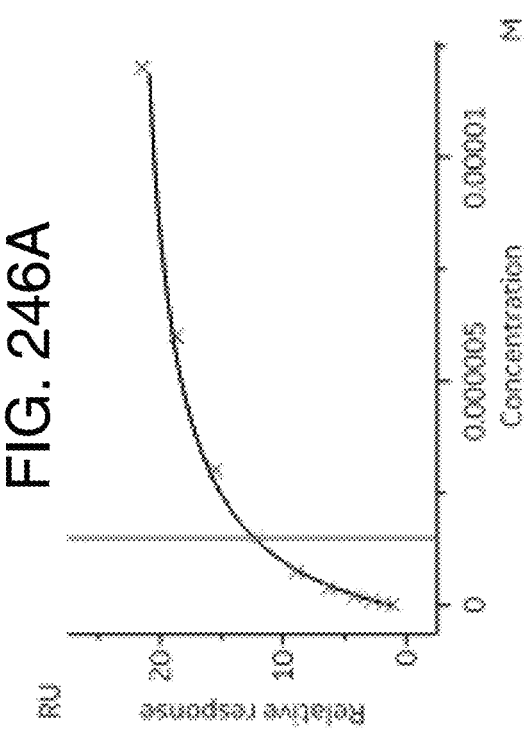
Figure 246E:
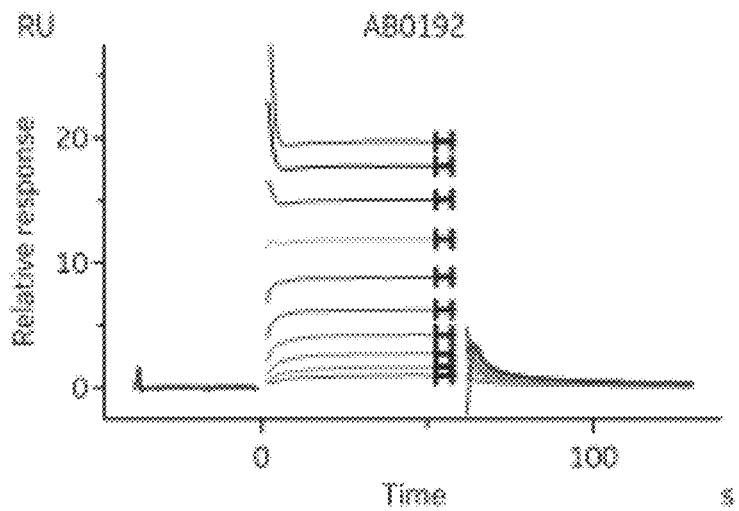
Figure 246F:
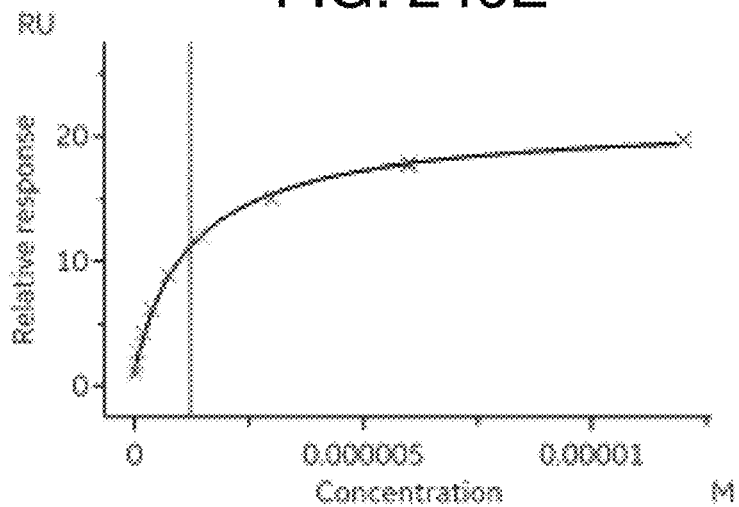
Figure 246K:
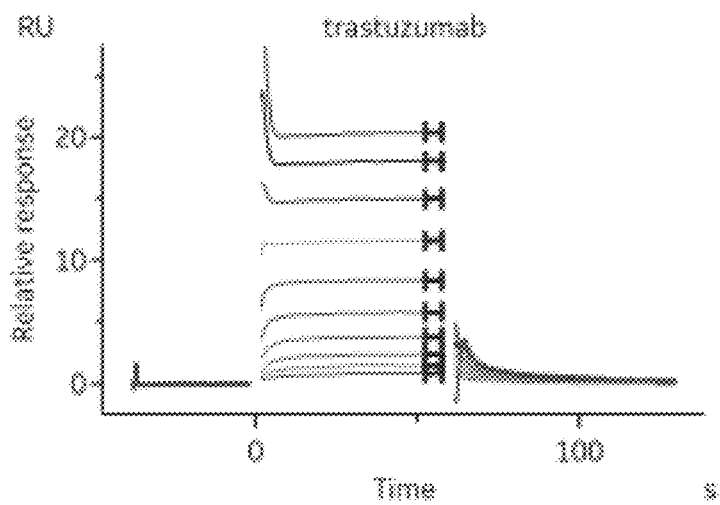
Figure 246L:
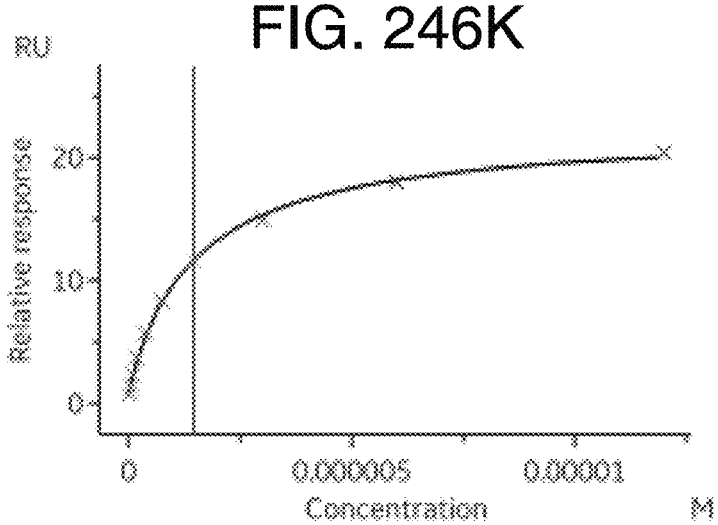

FIG. 245A-FIG. 245P show binding of AB0192 and trastuzumab to recombinant human FcRn. FIG. 245A-FIG. 245D and FIG. 245I-FIG. 245L for each molecule represent raw binding sensorgrams while FIG. 245E-FIG. 245H and FIG. 245M-FIG. 245P represent fitting to a steady state affinity model. A difference in apparent maximum binding responses between the molecules is due to a difference in molecular weight.

FIG. 246A-FIG. 246L show binding of AB0192 and trastuzumab to recombinant cynomolgus FcRn. FIGS. 246A, 246B, 246E, 246G, 246H, and 246K for each molecule represent raw binding sensorgrams while FIG. 242C, FIG. 242D, FIG. 242F, FIG. 242I, FIG. 242J, and FIG. 242L represent fitting to a steady state affinity model. A difference in apparent maximum binding responses between the molecules is due to a difference in molecular weight.

FIG. 247 shows Epitope binning of AB0192 against other CLEC12A binding TriNKETs.

Figure 248:
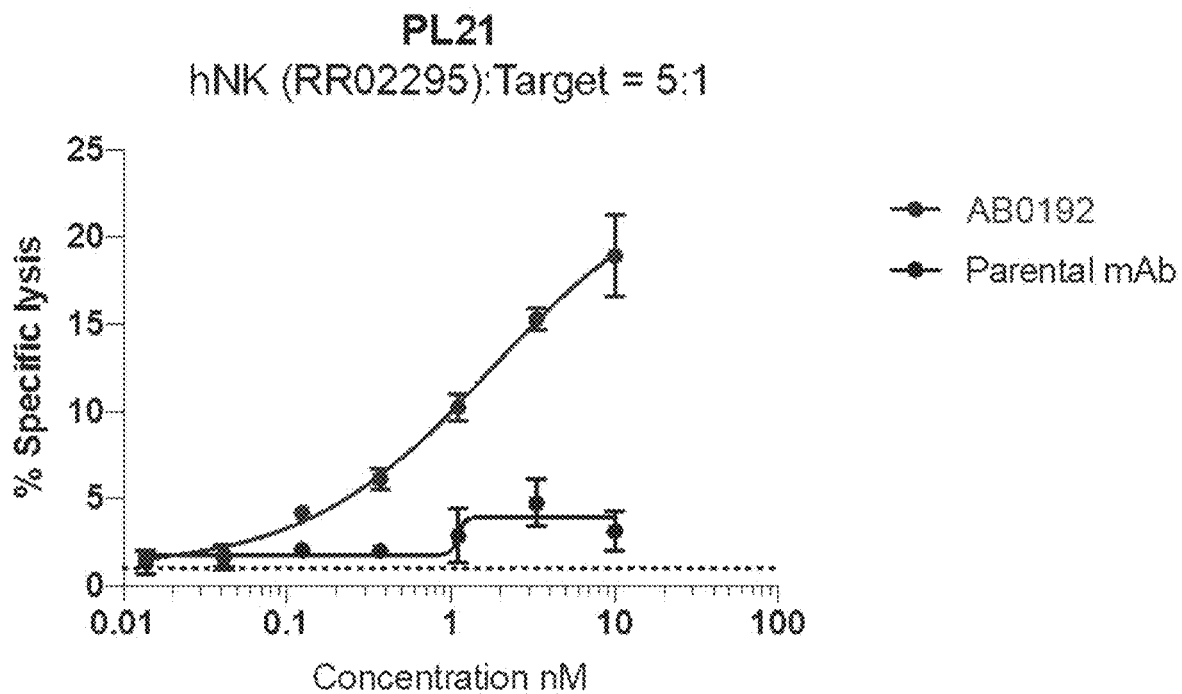

FIG. 248 shows potency of AB0192 in primary NK mediated cytotoxicity assay compared to corresponding mAb control.

Figure 249A:
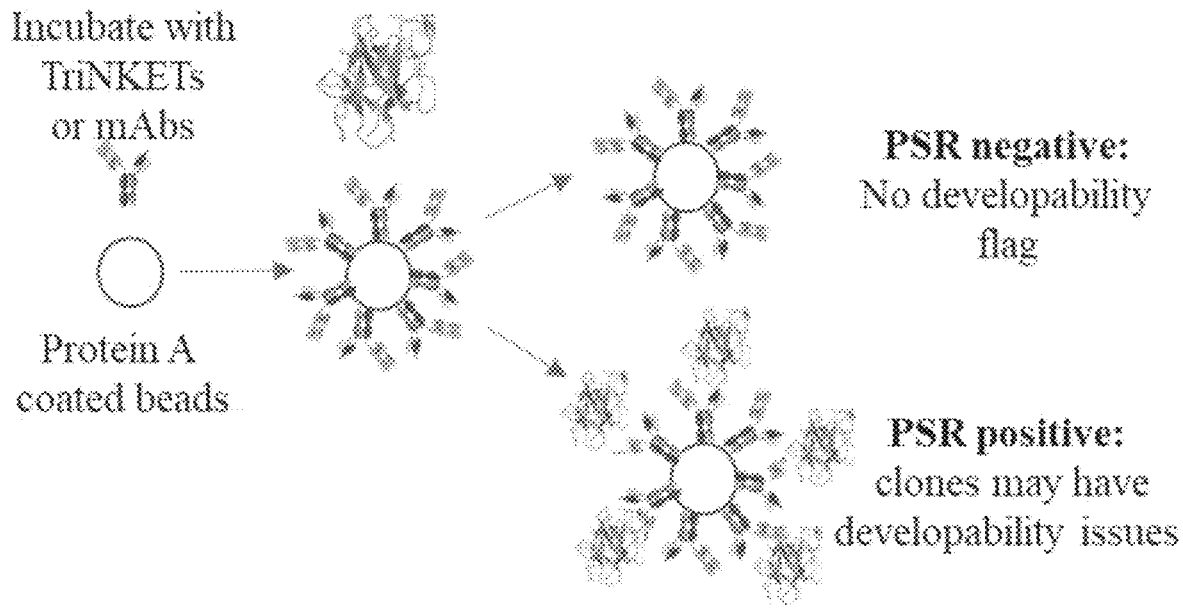
Figure 249C:
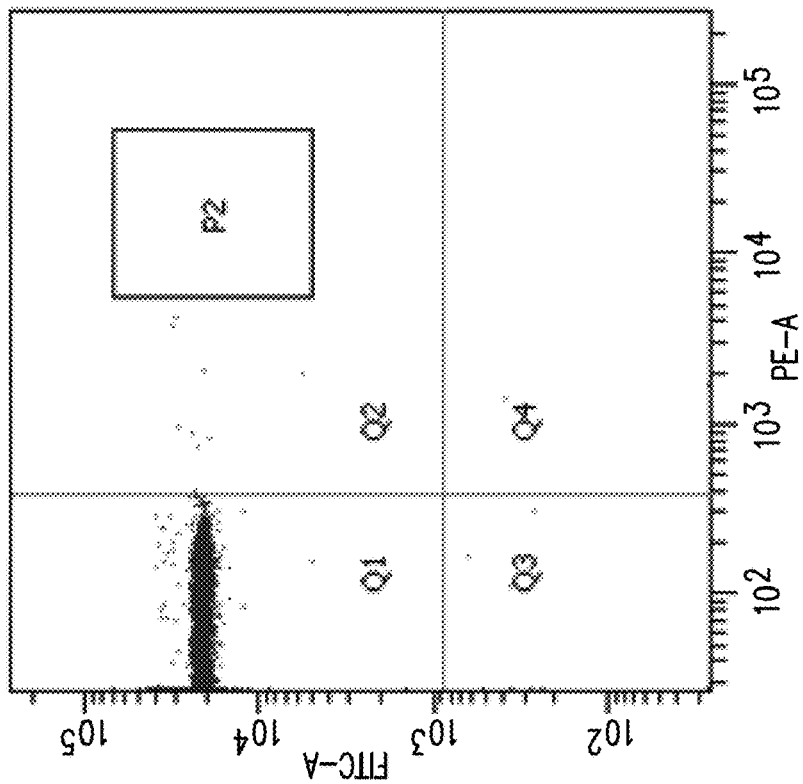
Figure 249B:
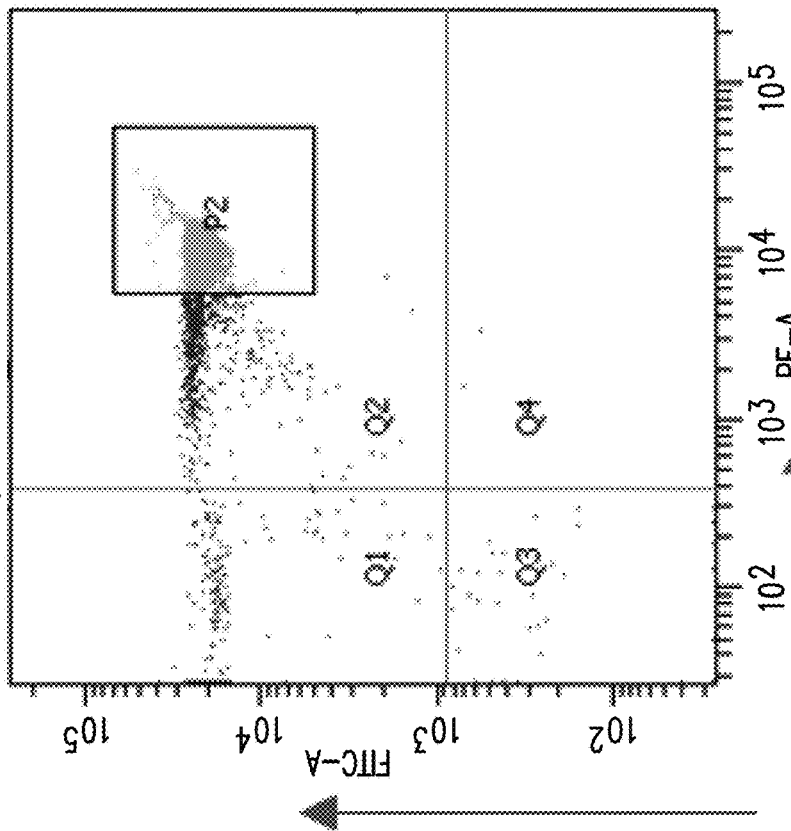
Figure 249D:
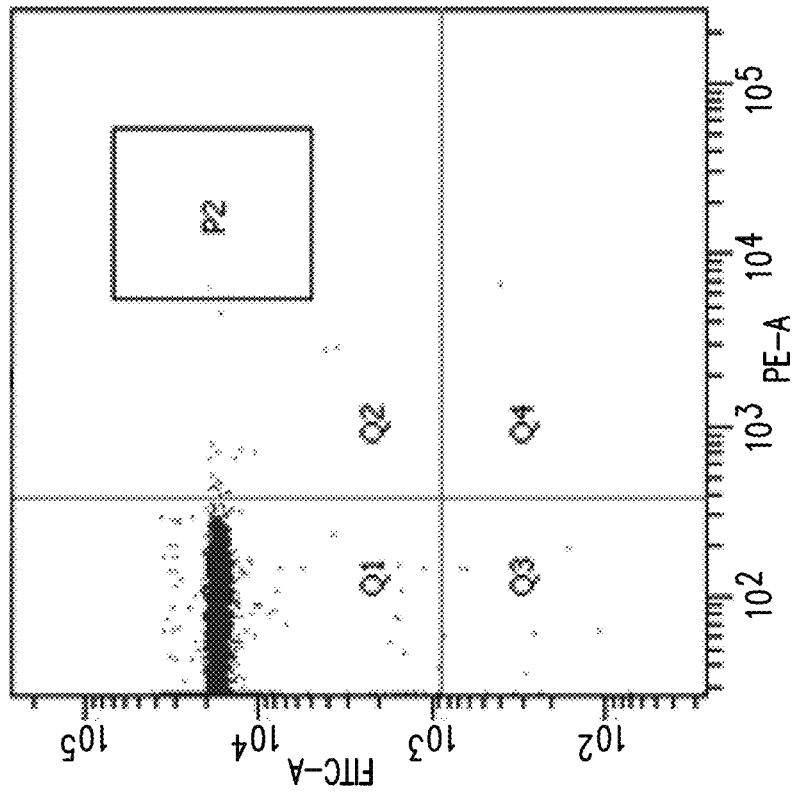

FIG. 249A and FIG. 249B show non-specificity analysis of AB0192 in PSR assay. FIG. 249A: schematic representation of a PSR assay; FIG. 249B: PSR binding AB0089 (FIG. 249D) in comparison with antibodies with known PSR binding (Ixekizumab; FIG. 249B) and an antibody with no known non-specificity (Trastuzumab; FIG. 249C).

Figure 250:
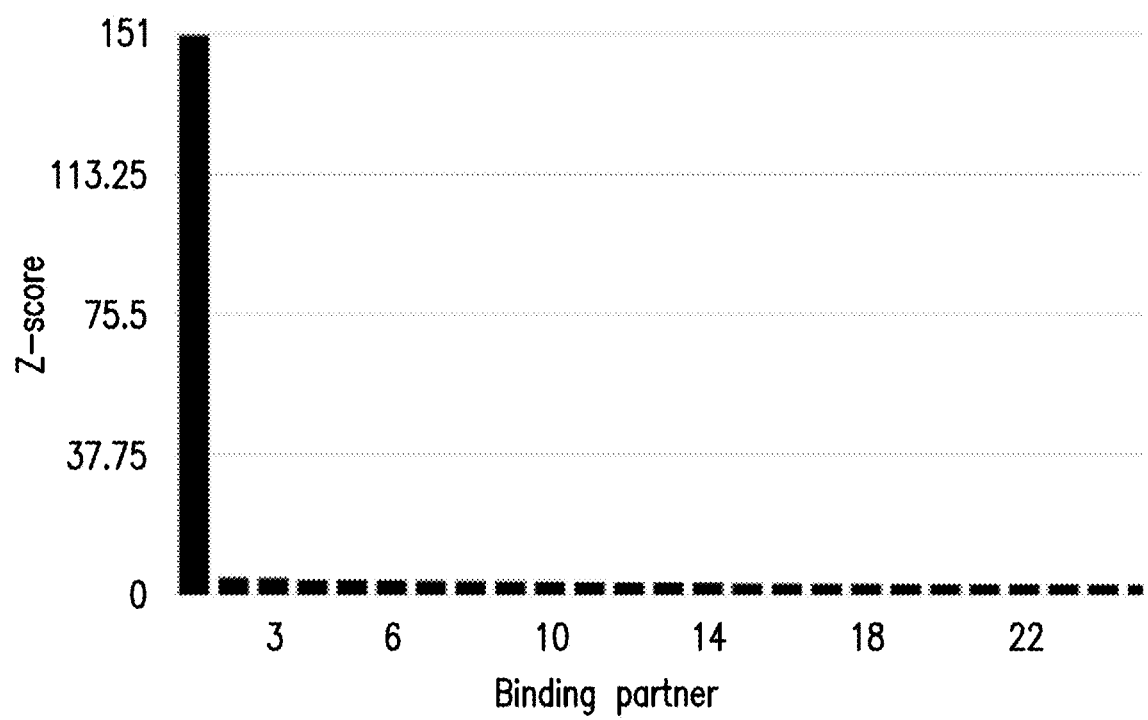

FIG. 250 shows the relative Z score of AB0089 in HuProt™ human proteome microarray assay. Plot depicting the relative binding Z-score (y-axis) vs. the top 24 identified binding partners of AB0192 (x-axis). hCLEC12a is plotted at position 1 with a Z-score of 150.06.

Figure 251A:
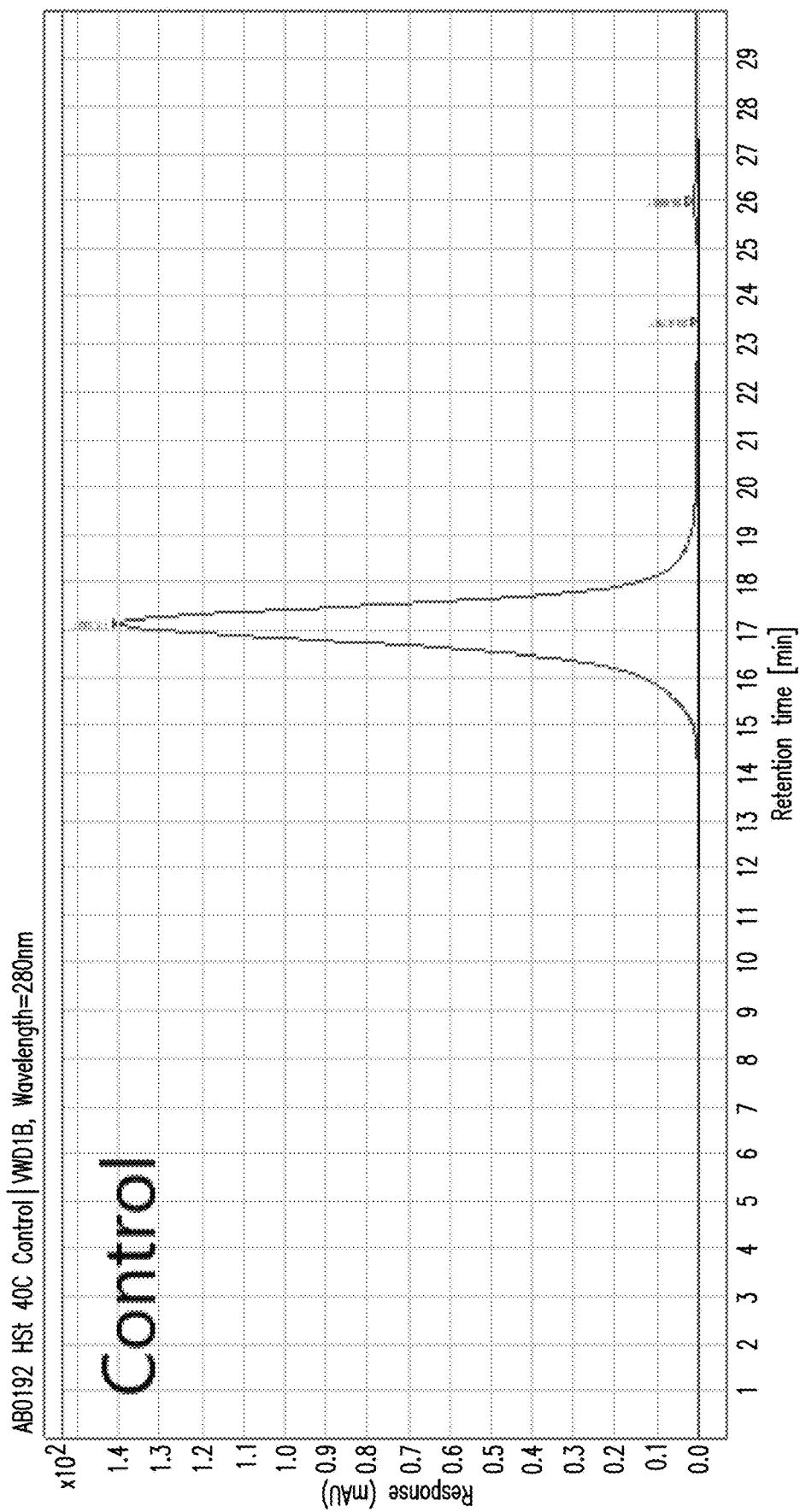
Figure 251B:
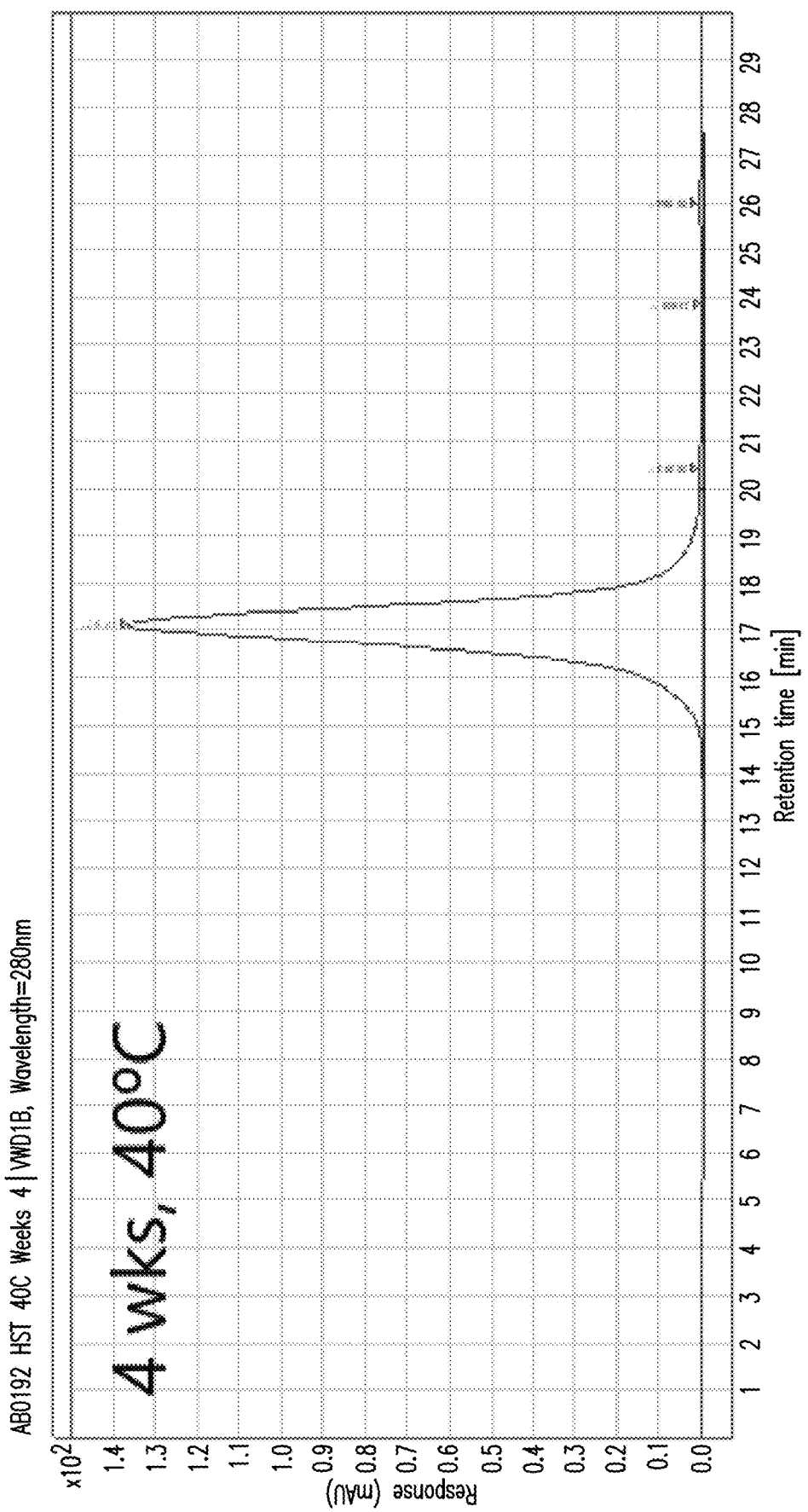

FIG. 251A-FIG. 251B show an SEC analysis of AB0192 after 4 weeks at 40° C. in HST, pH6.0, compared to control.

Figure 252A:
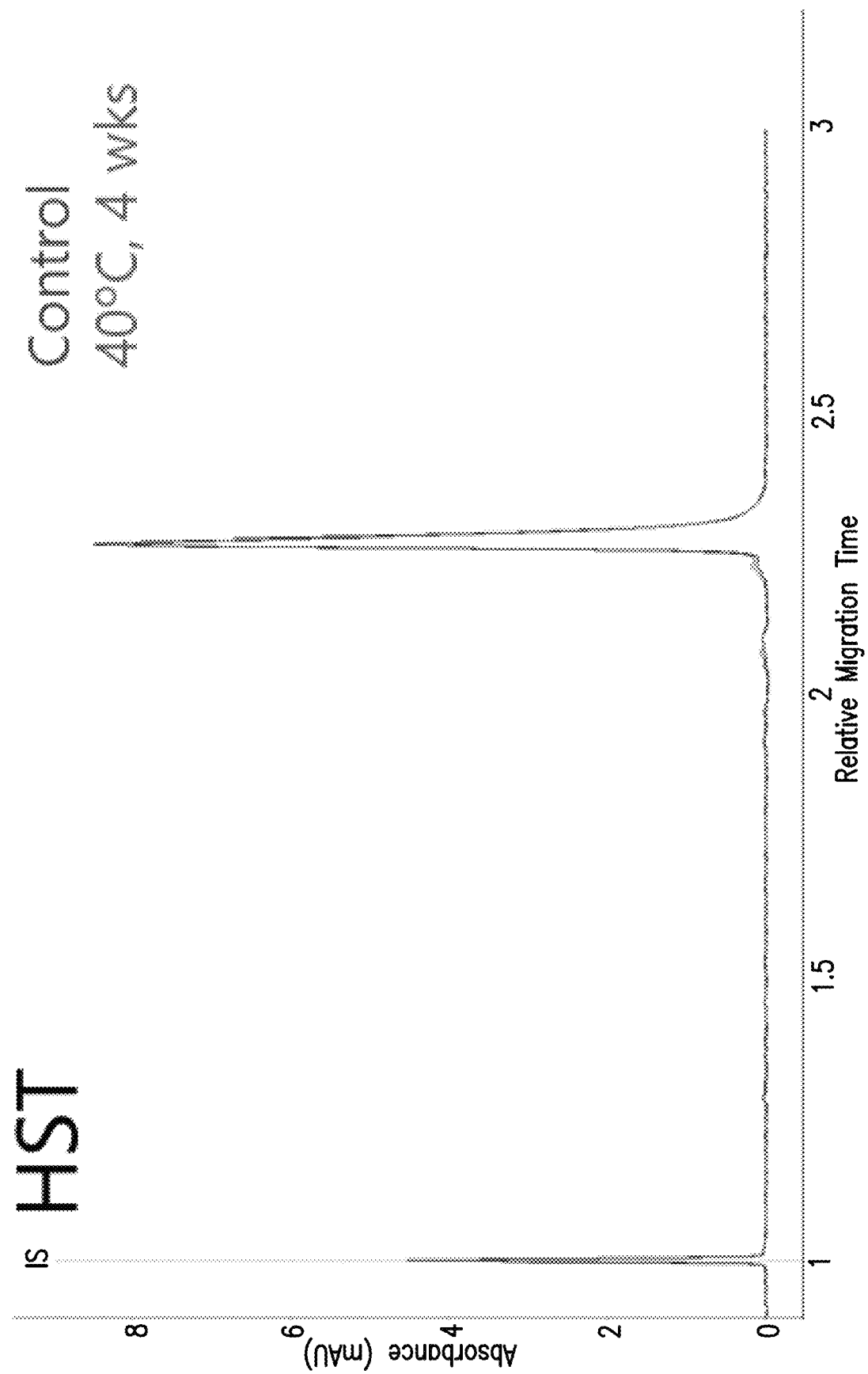
Figure 252B:
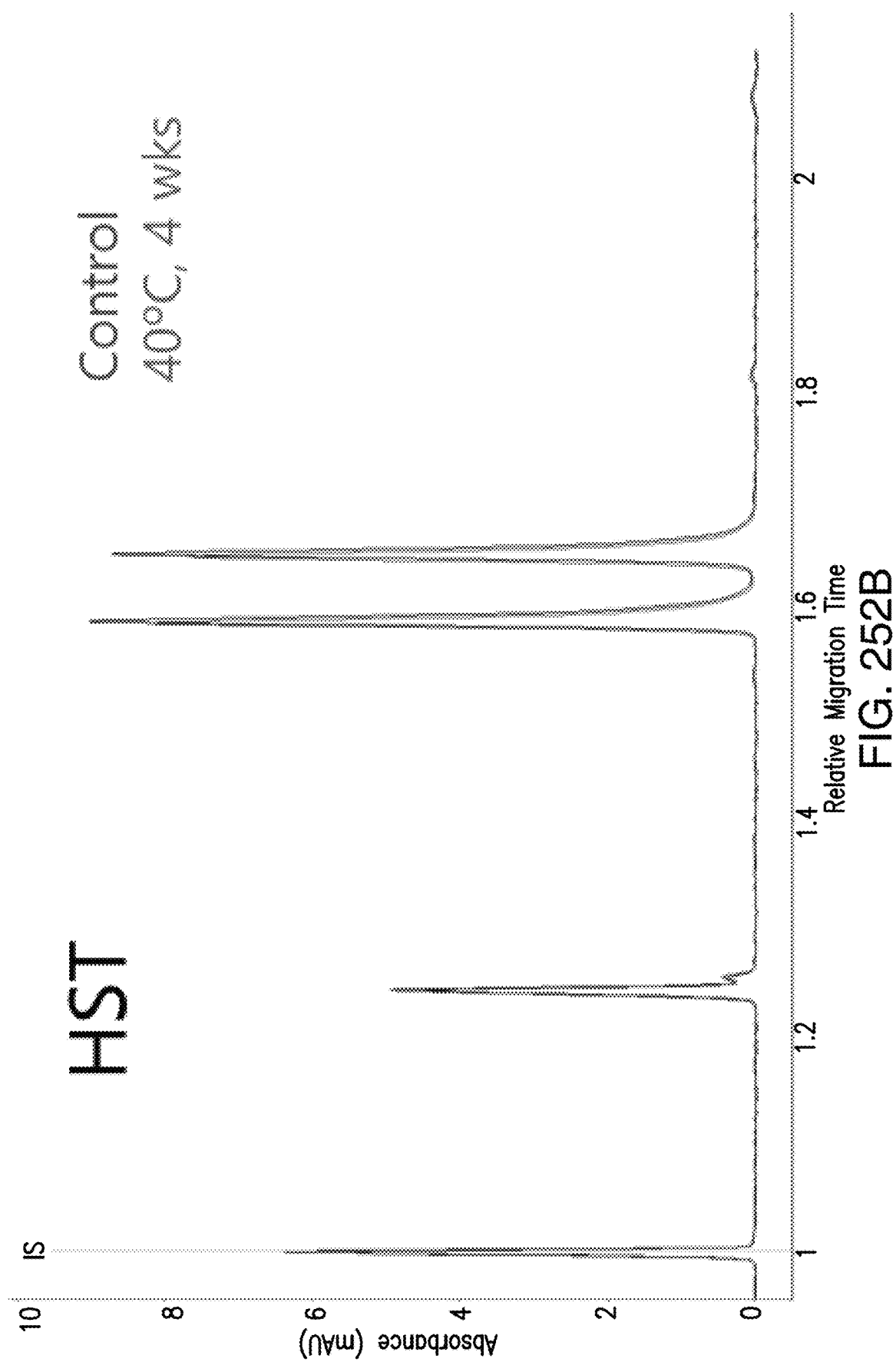
Figure 253A:
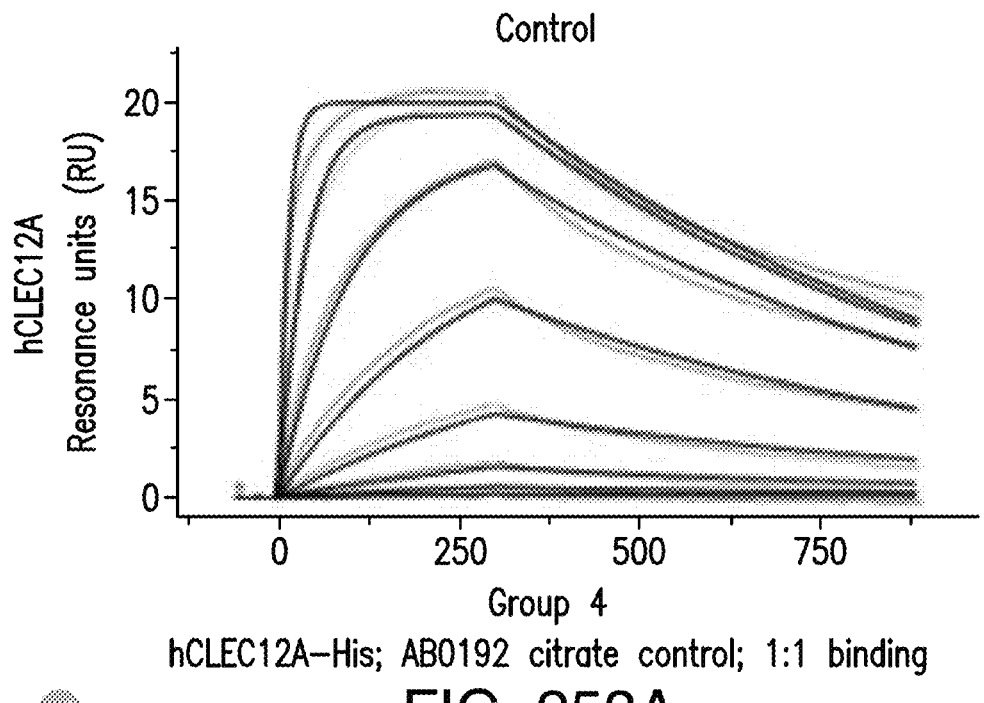
Figure 253B:
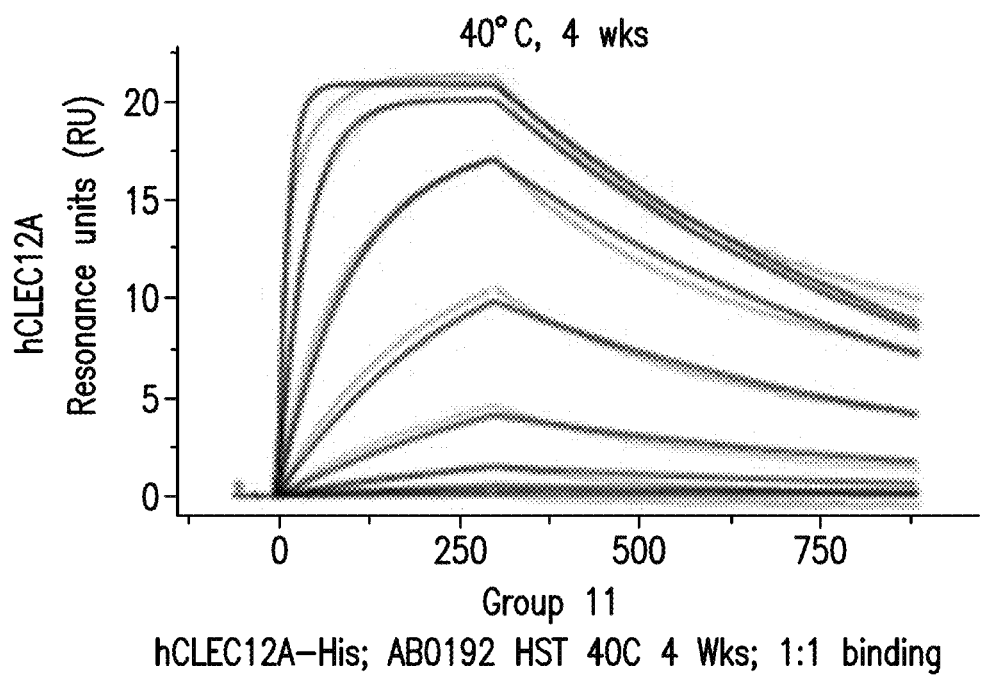
Figure 253C:
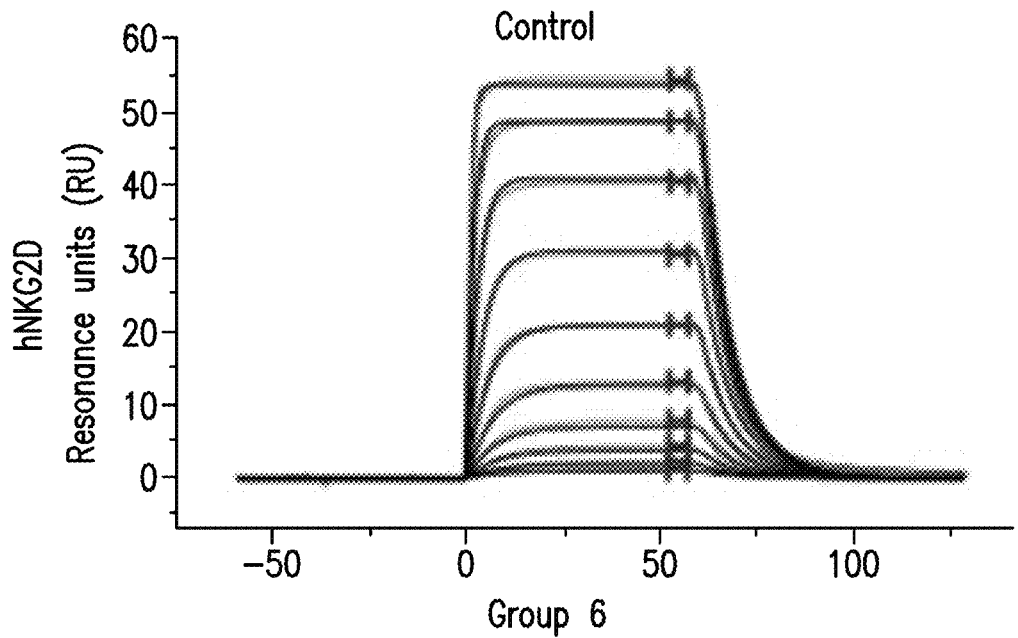
Figure 253D:
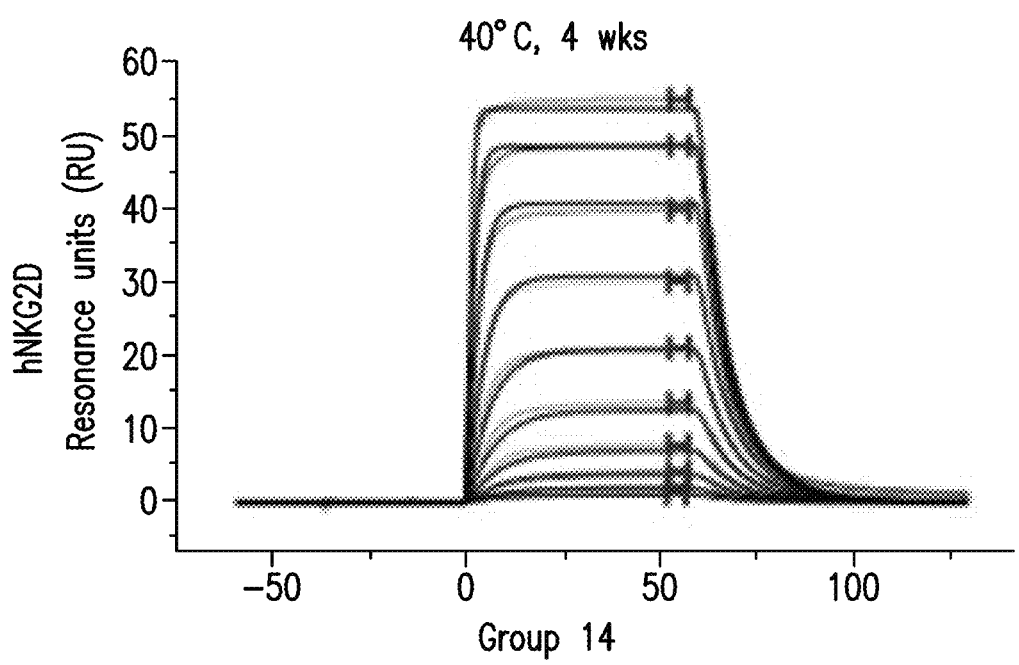
Figure 253E:
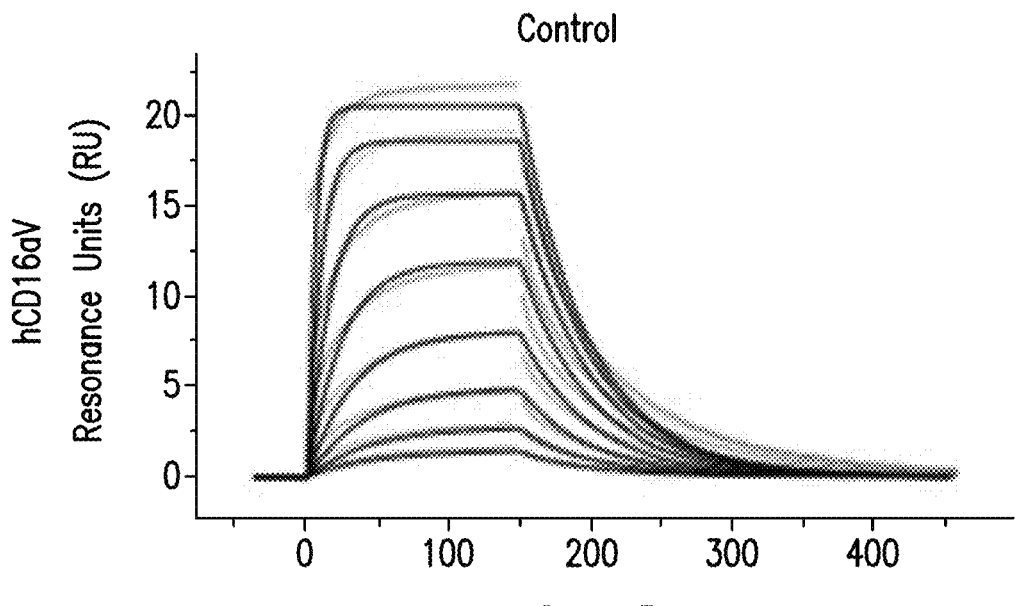
Figure 253F:
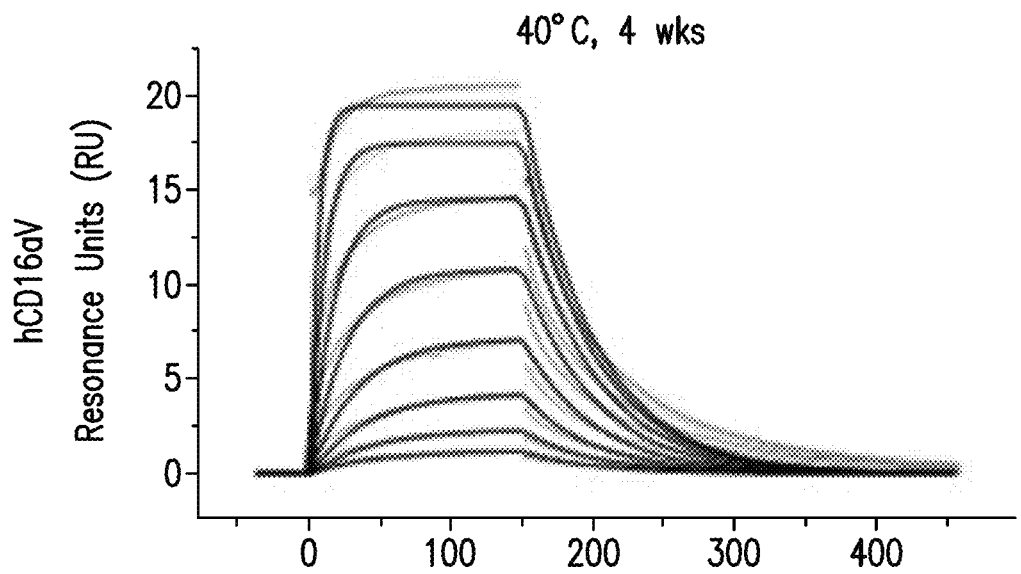

FIG. 252A-FIG. 252B show a CE-SDS analysis of AB0192 after 4 weeks at 40° C. in HST, pH 6.0, compared to control. Non-reduced conditions are shown in FIG. 252A. Reduced conditions are shown in FIG. 252B.

FIG. 253A-FIG. 253F show that AB0192 is stable after 4 weeks 40° C. stress in HST, pH 6.0: no effect on CLEC12A, NKG2D or CD16a binding.

Figure 254:
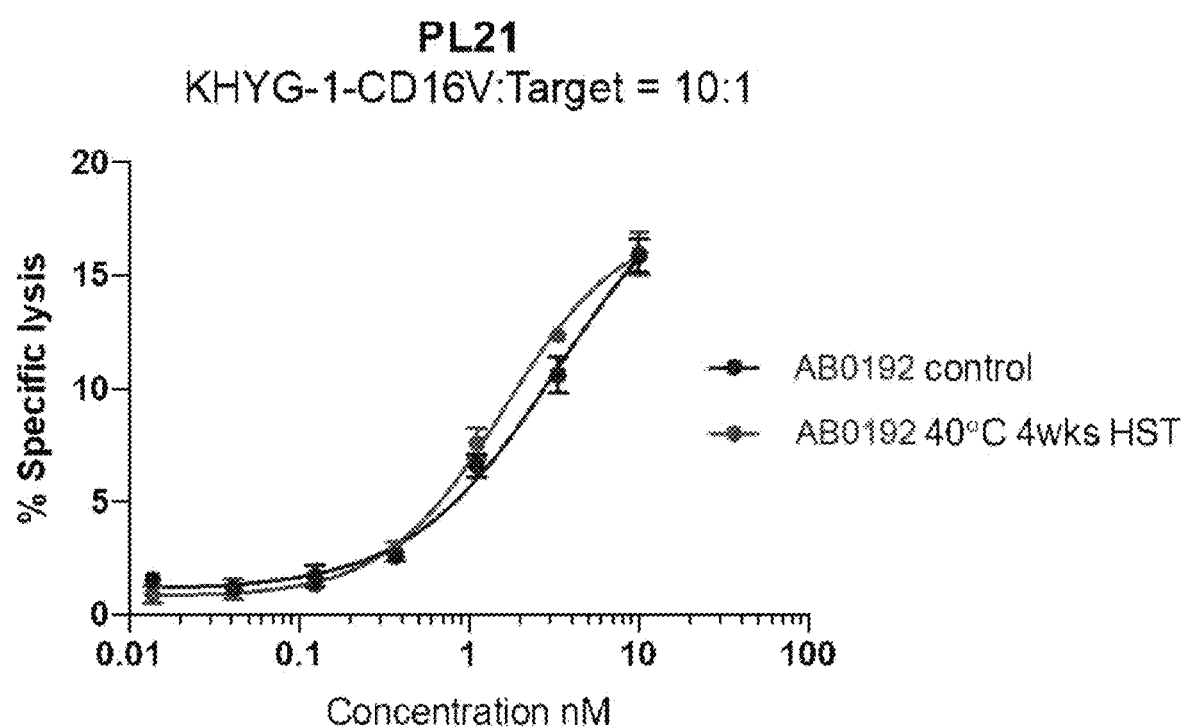

FIG. 254 shows that there was no difference in potency between the control and stressed samples of AB0192 after 4 weeks at 40° C. in HST, pH 6.0 in KHYG-1-CD16a mediated cytotoxicity assay.

Figure 255A:
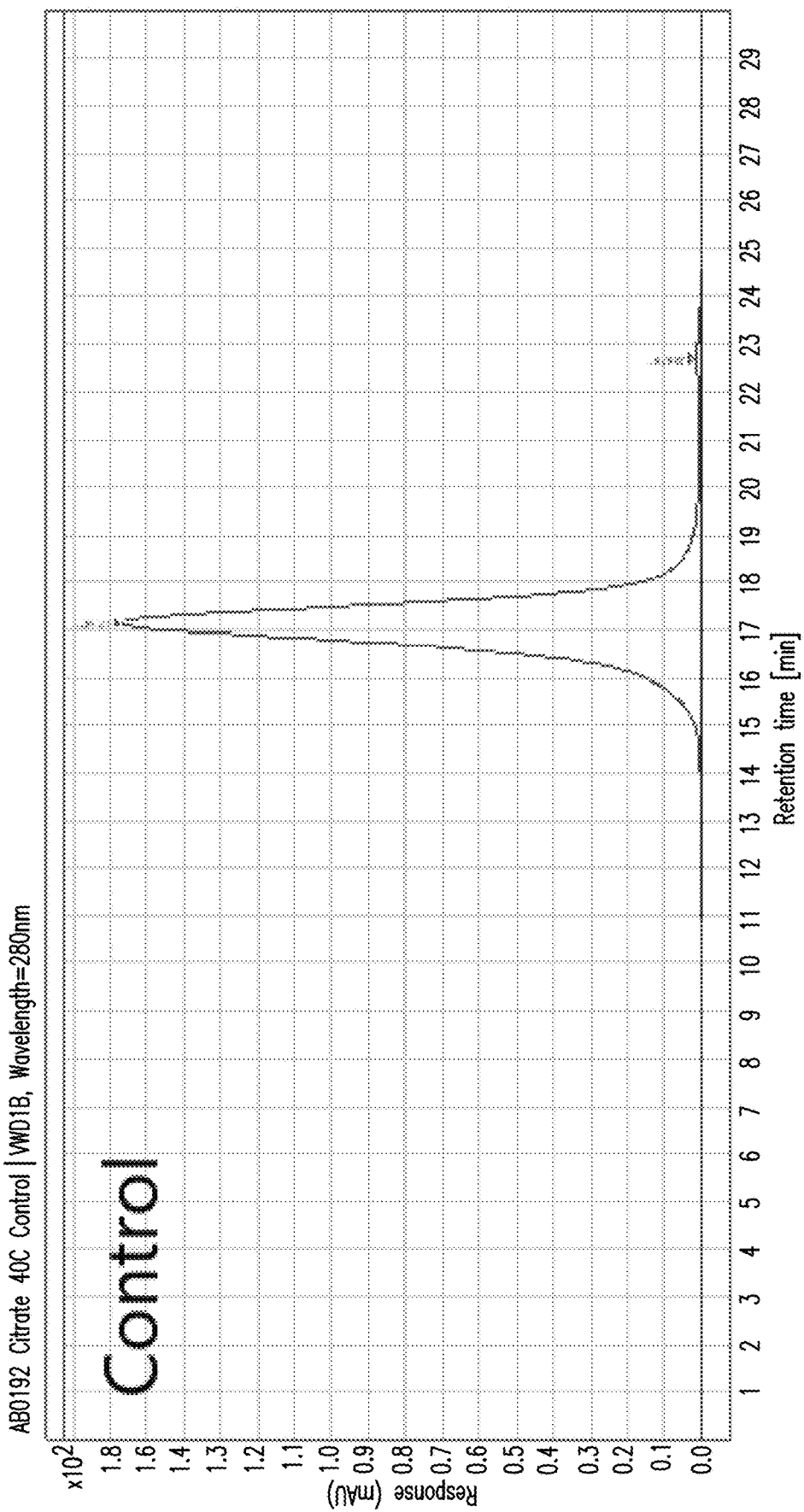
Figure 255B:
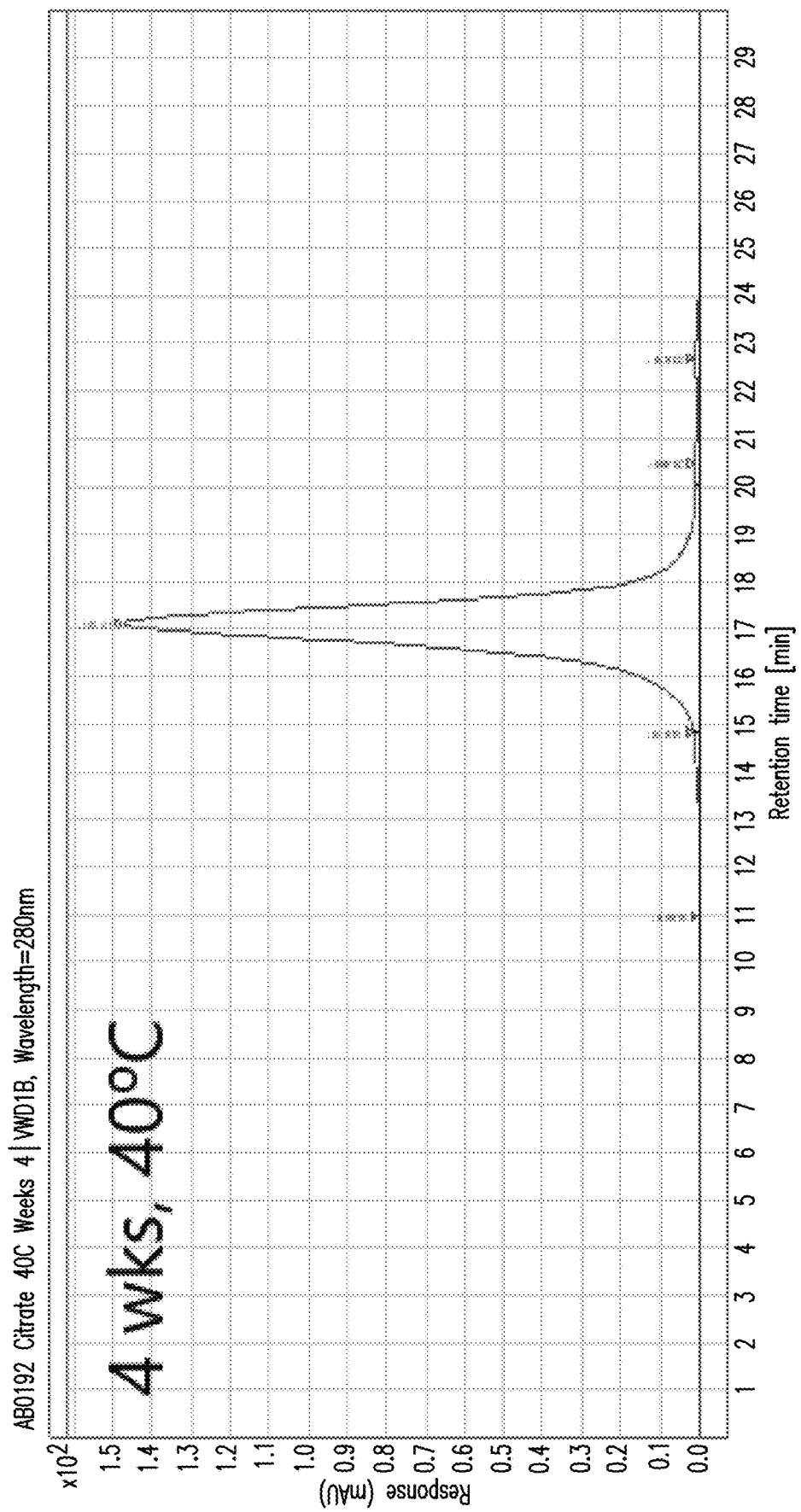

FIG. 255A-FIG. 255B show minimal aggregation of AB0192 after 4 weeks at 40° C. in CST, pH 7.0, as measured by SEC analysis.

Figure 256A:
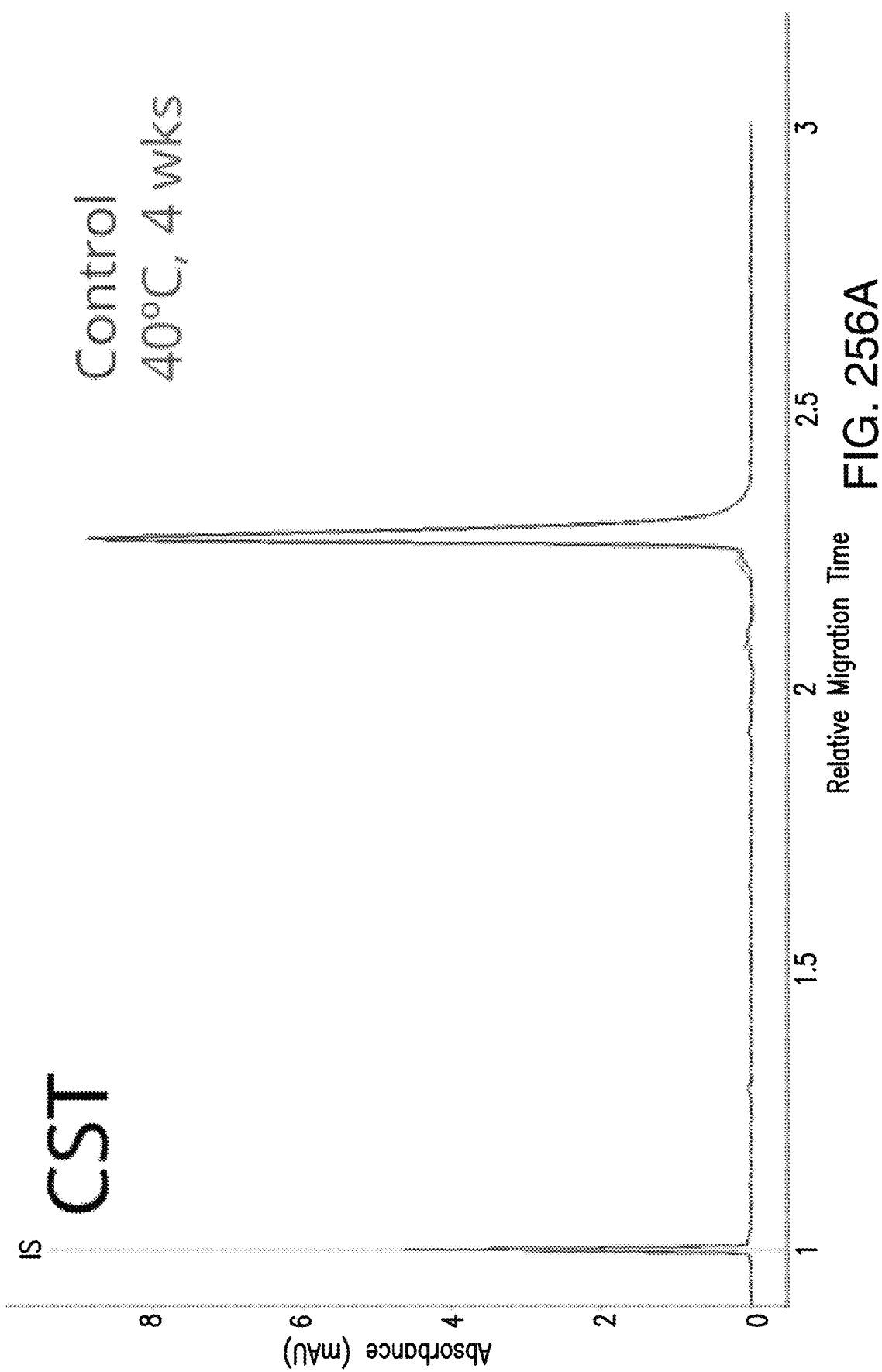
Figure 256B:
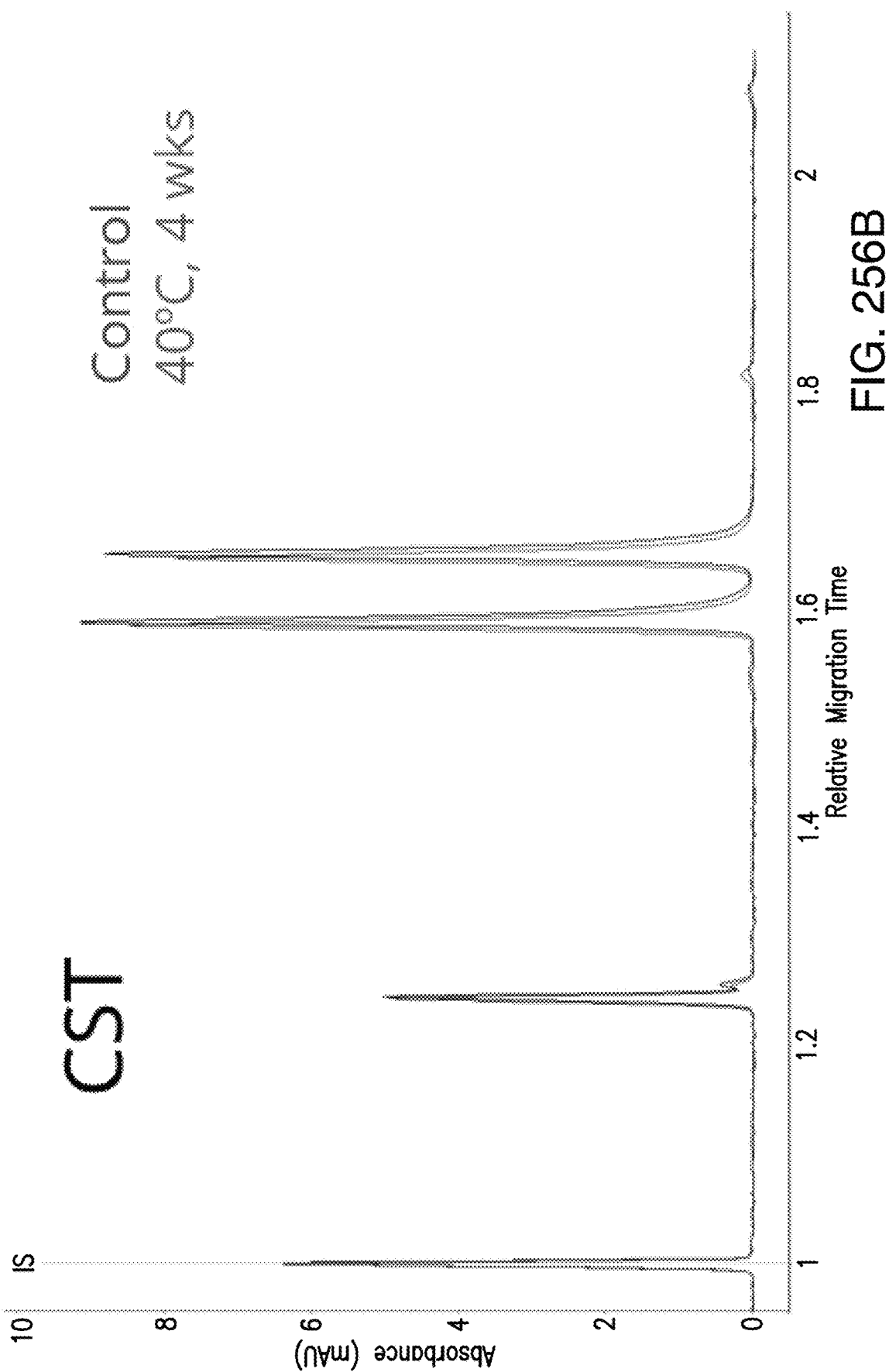
Figure 257A:
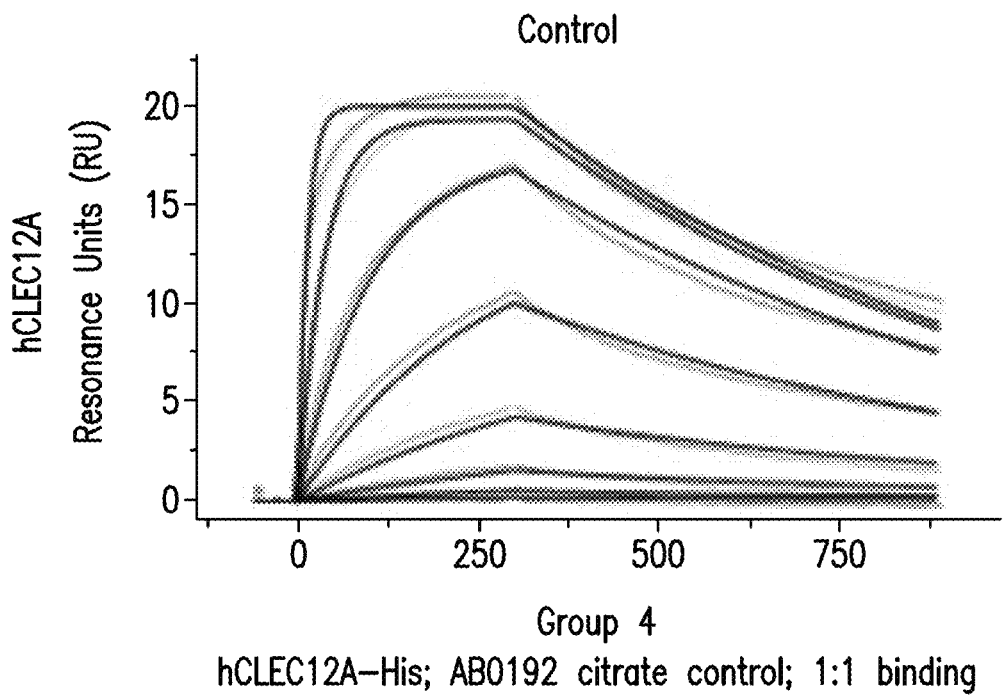
Figure 257B:
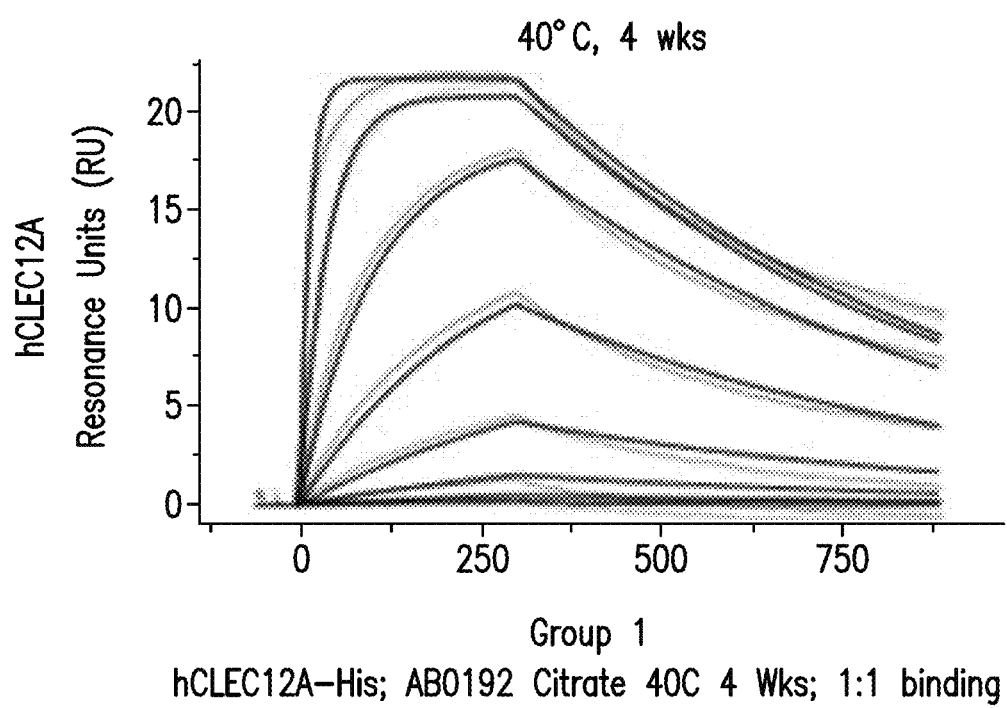
Figure 257C:
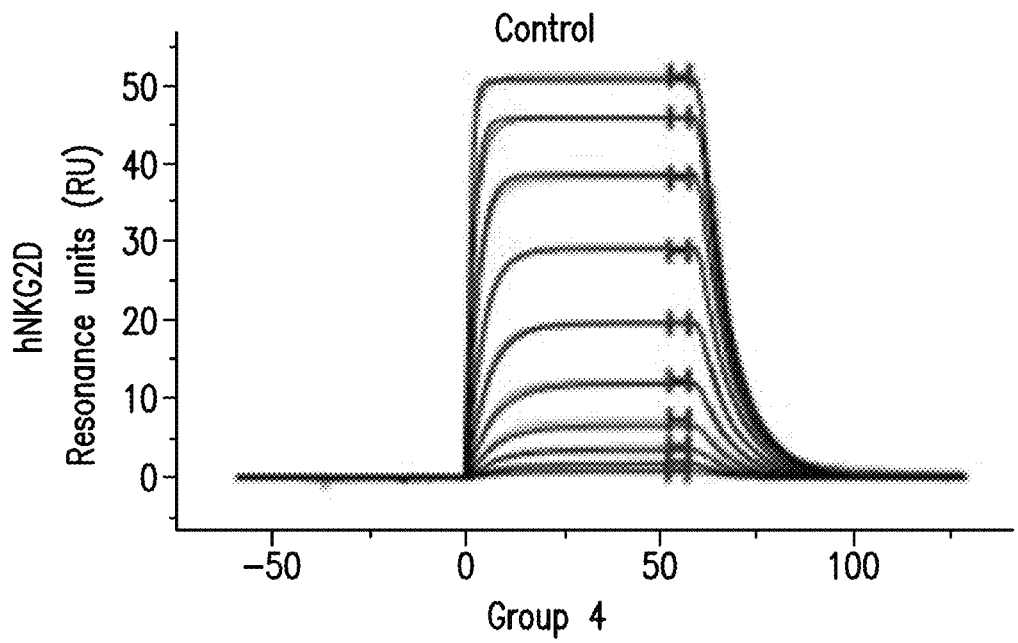
Figure 257D:
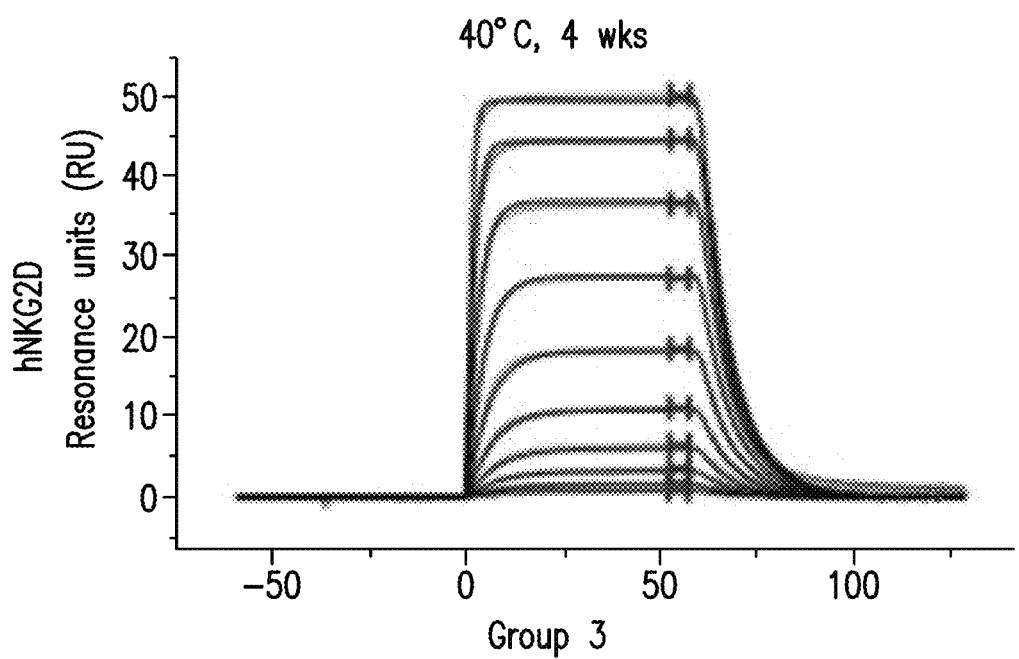
Figure 257E:
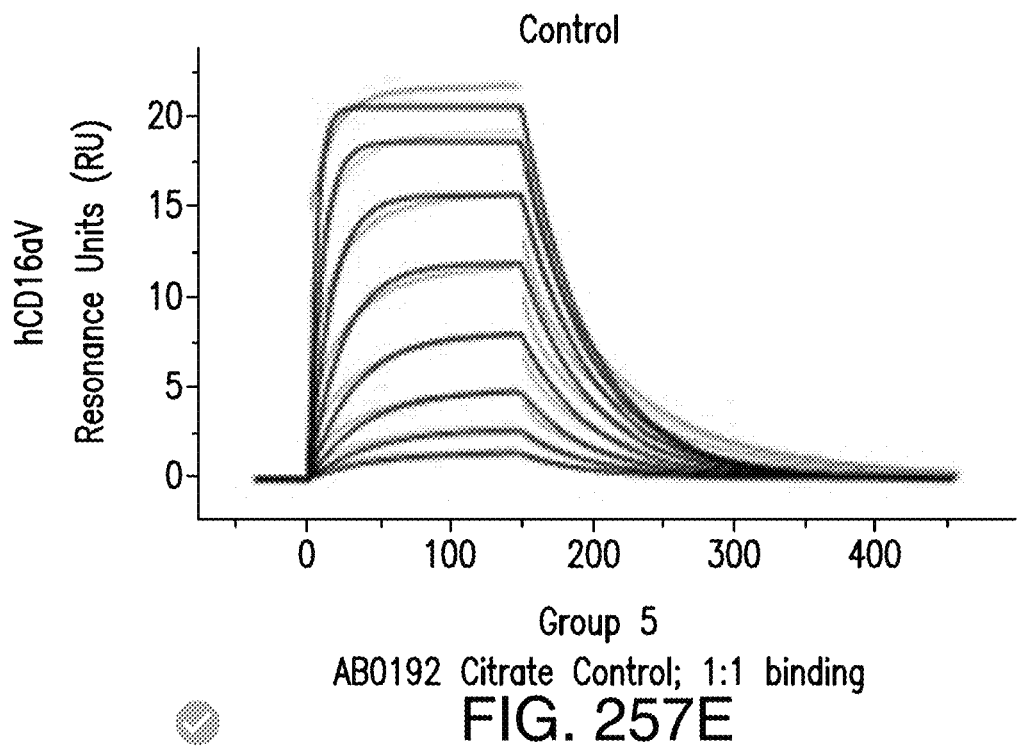
Figure 257F:
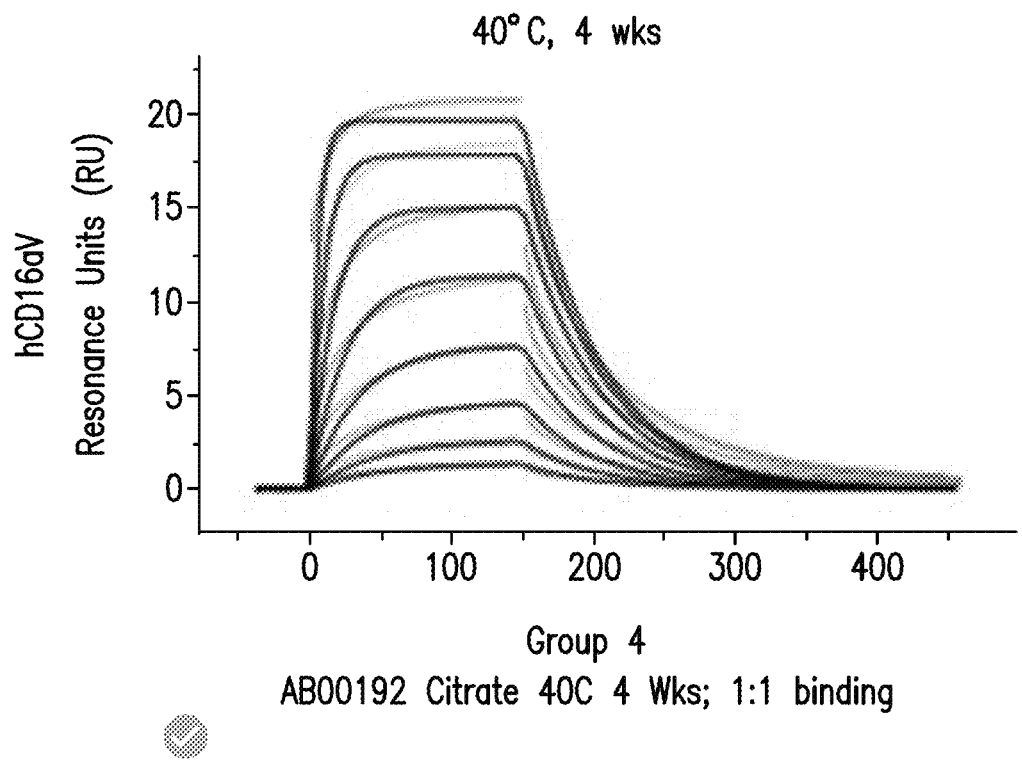

FIG. 256A-FIG. 256B show minimal fragmentation of AB0192 after 4 weeks at 40° C. in CST, pH 7.0 compared to control, as measured by CE-SDS analysis.

FIG. 257A-FIG. 257F show that AB0192 is stable after 4 weeks 40° C. stress in CST, pH 7.0: no effect on CLEC12A, NKG2D or CD16a binding.

Figure 258:
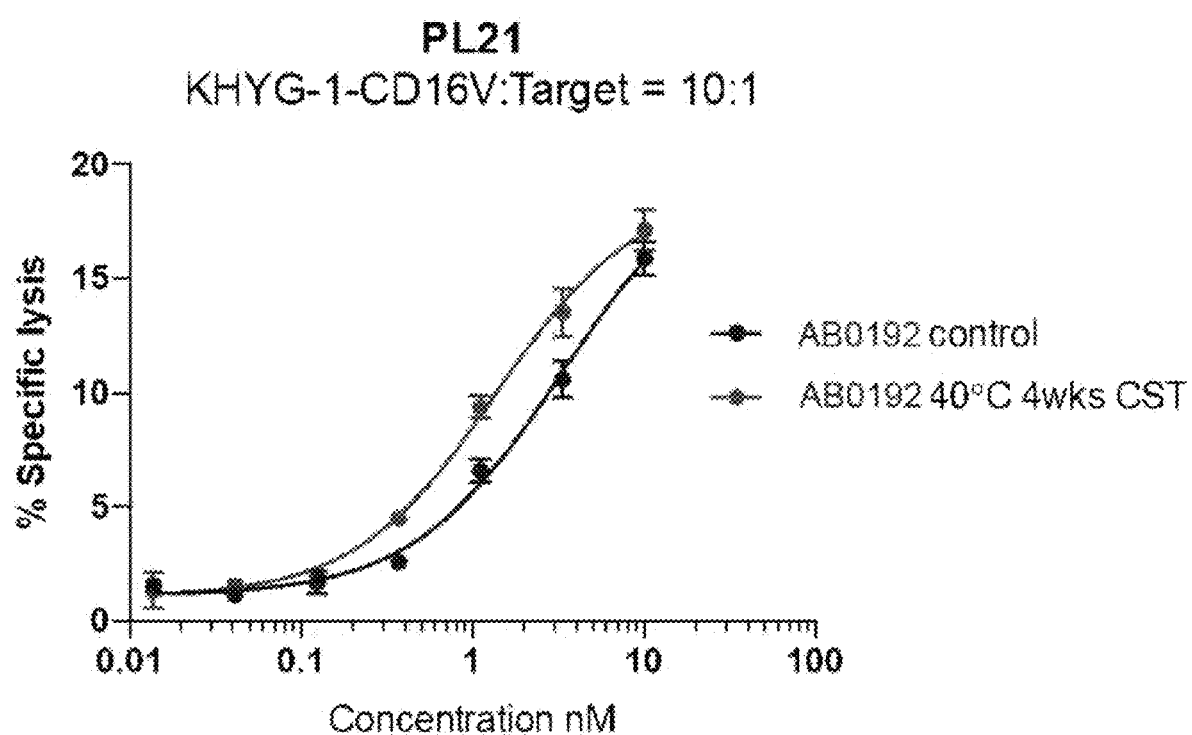

FIG. 258 shows that there was no difference in potency between the control and stressed samples of AB0192 after 4 weeks at 40° C. in CST, pH 7.0, in KHYG-1-CD16a cytotoxicity assay.

Figure 259A:
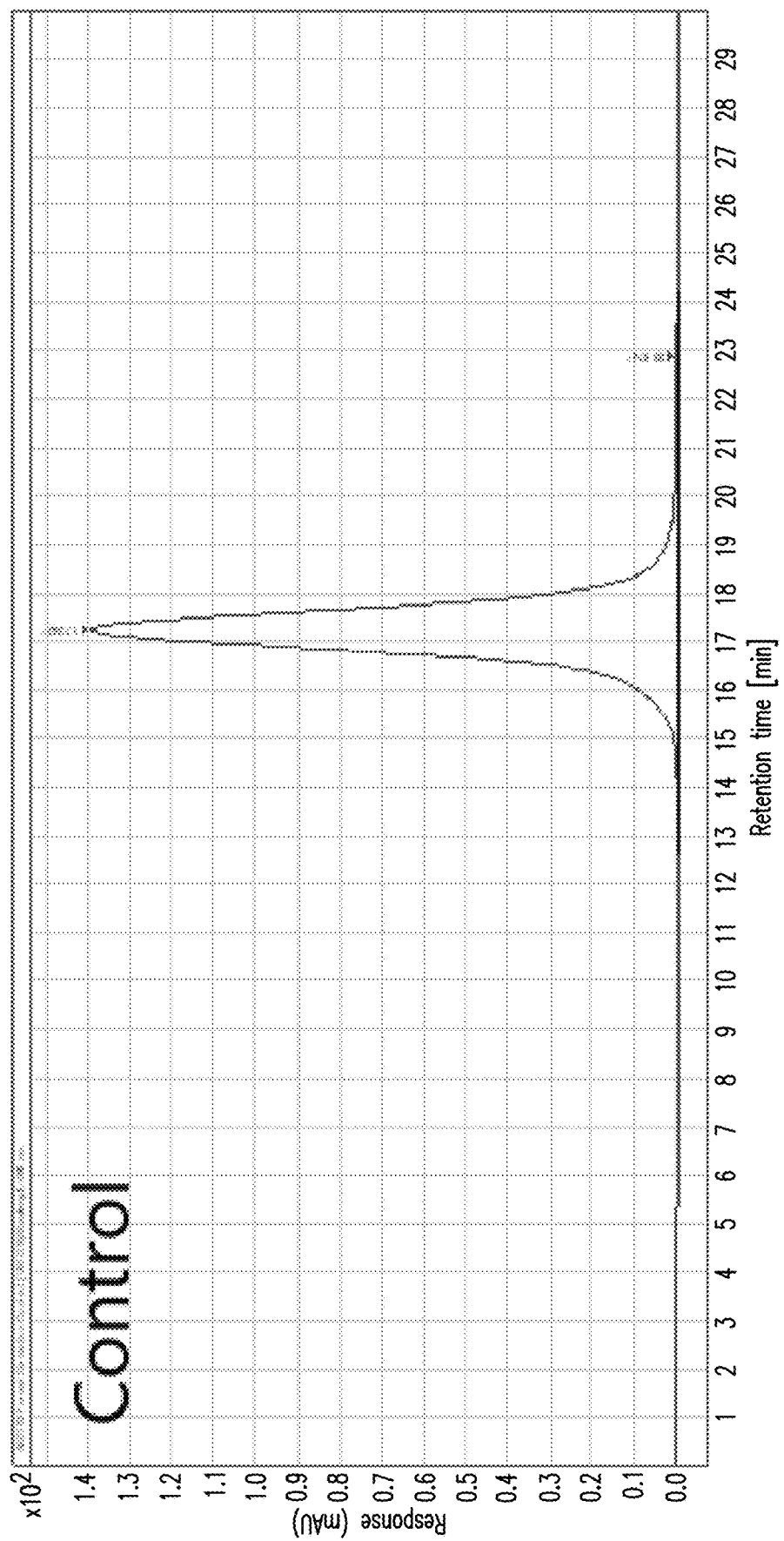
Figure 259B:
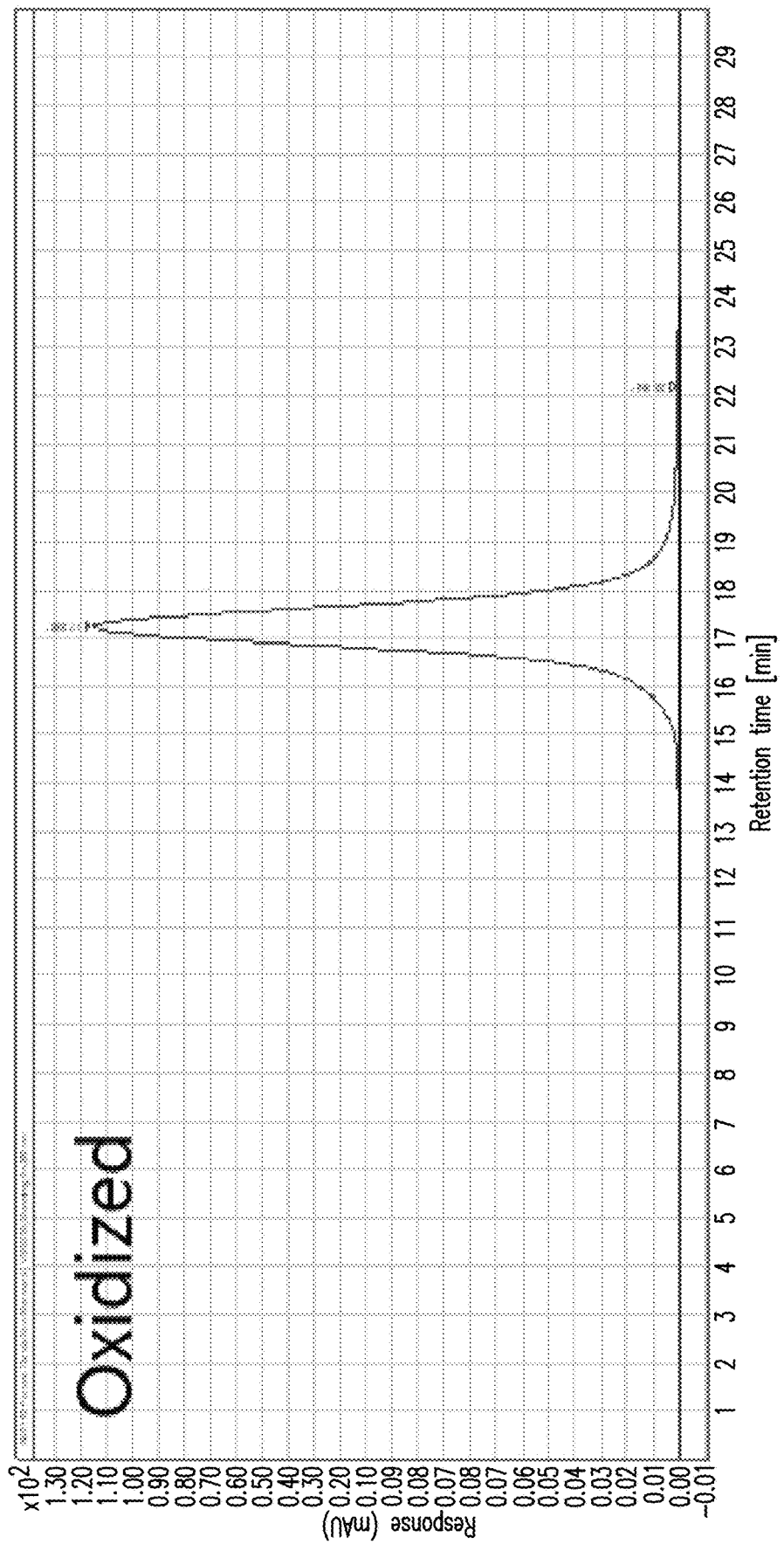
Figure 261A:
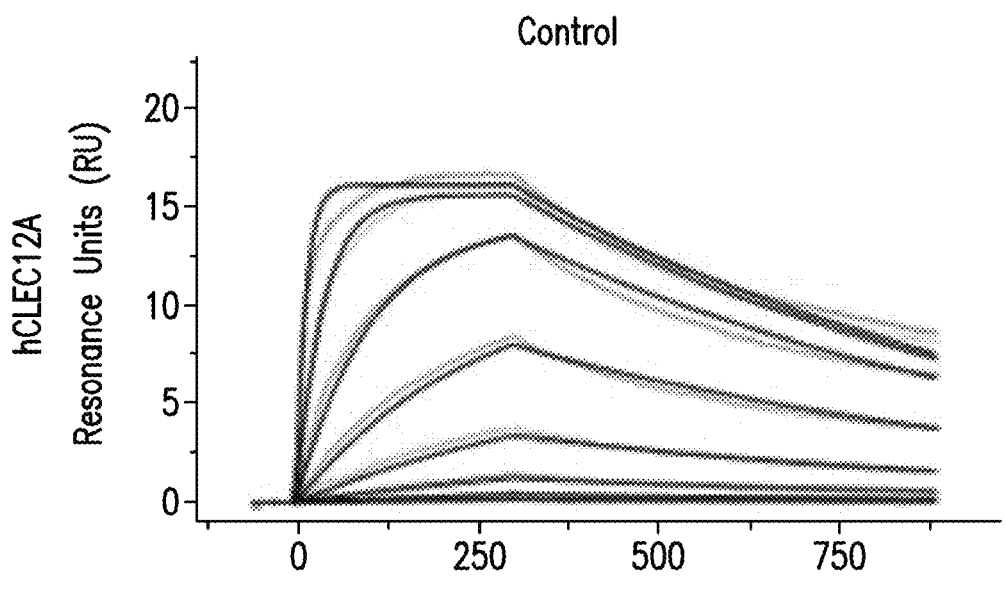
Figure 261B:
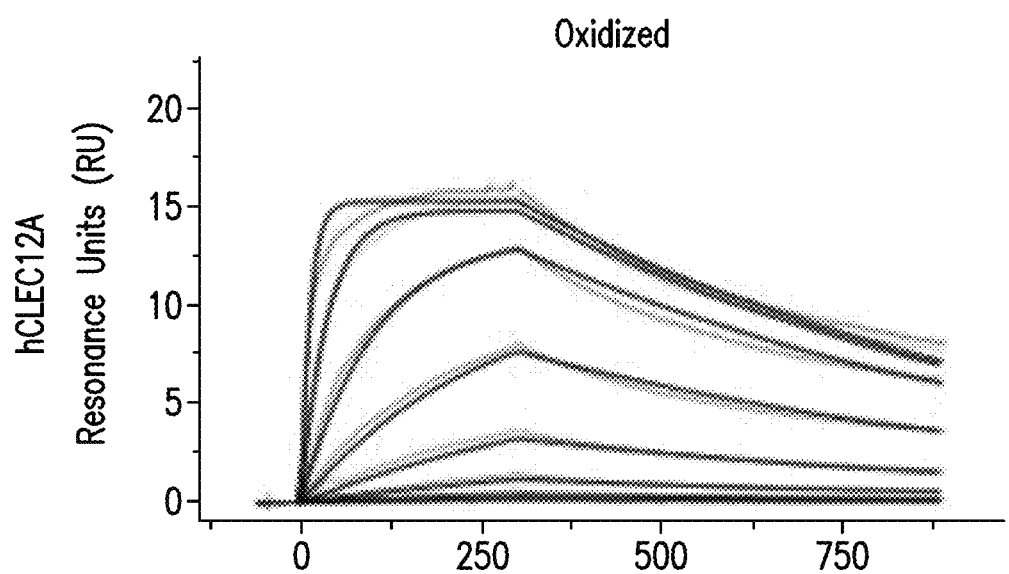
Figure 261C:
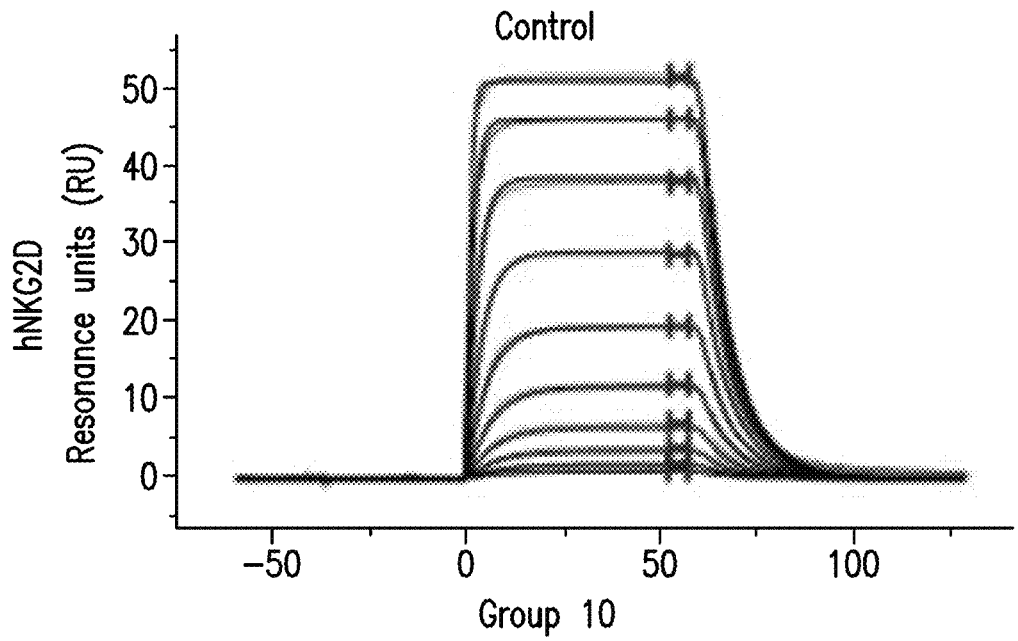
Figure 261D:
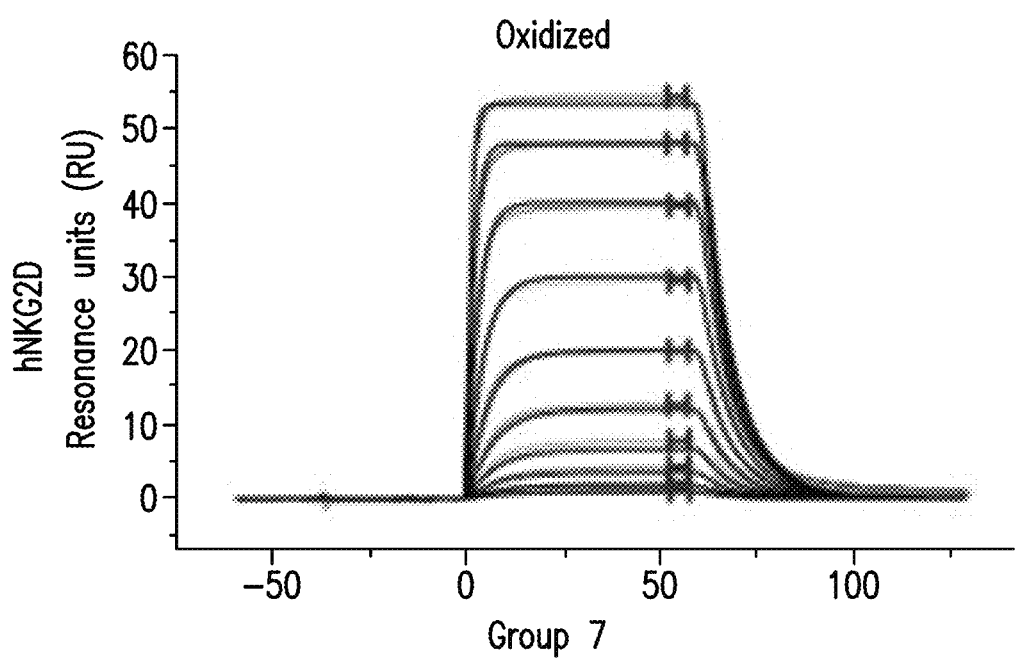
Figure 261E:
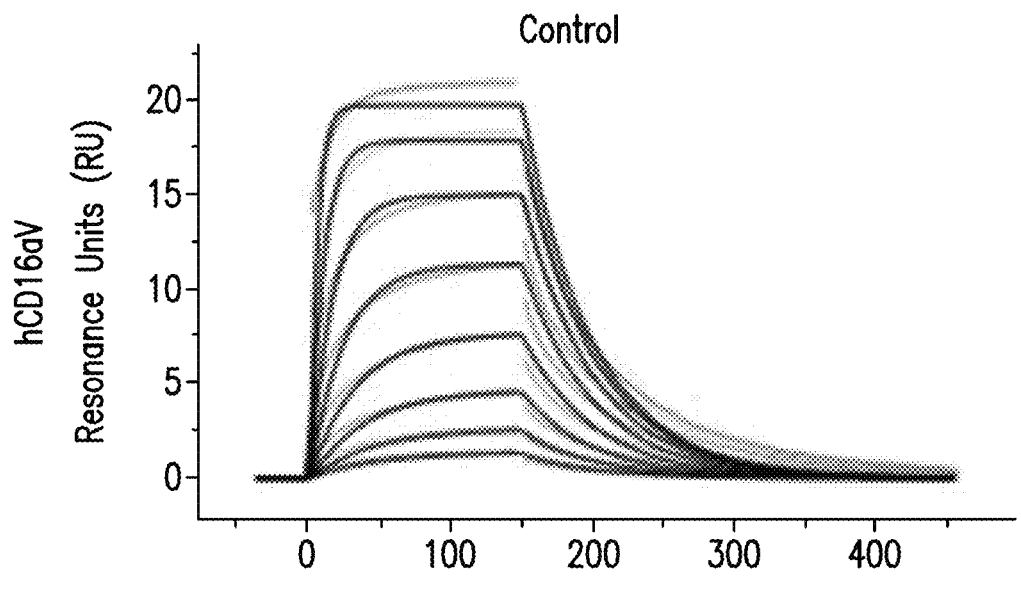
Figure 261F:
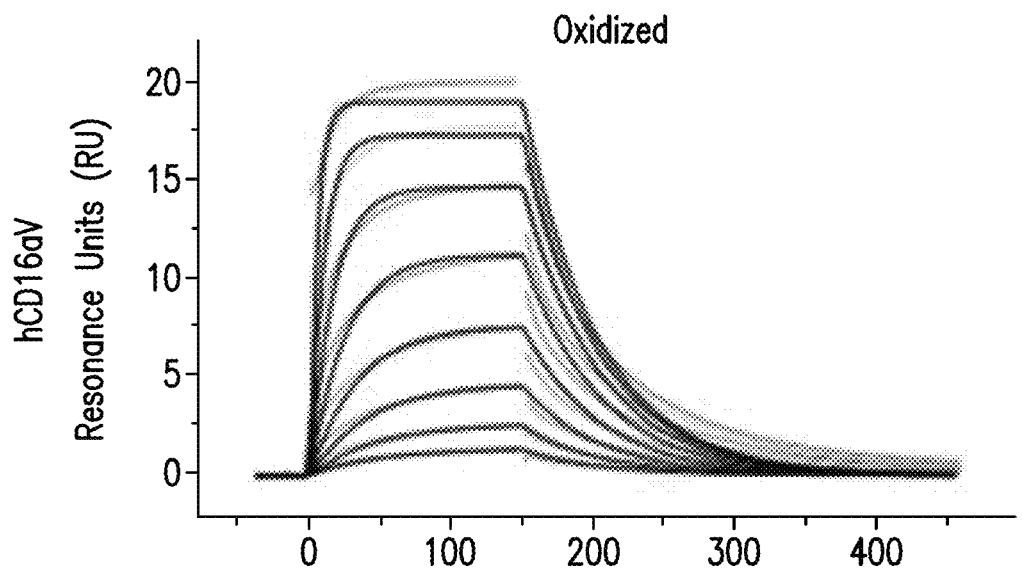

FIG. 259A-FIG. 259B show an SEC analysis of AB0192 after forced oxidation stress compared to control, and indicated no significant decrease in monomer content.

FIG. 260A-FIG. 260B show a CE-SDS analysis of AB0192 after forced oxidation compared to control, and indicated that purity remained high.

FIG. 261A-FIG. 261F show that AB0192 is stable after oxidation stress (pH 5.0, 40° C., 14 days): no effect on CLEC12A, NKG2D or CD16a binding. Slight differences in the maximum binding signal reflect differences in capture levels.

Figure 262:
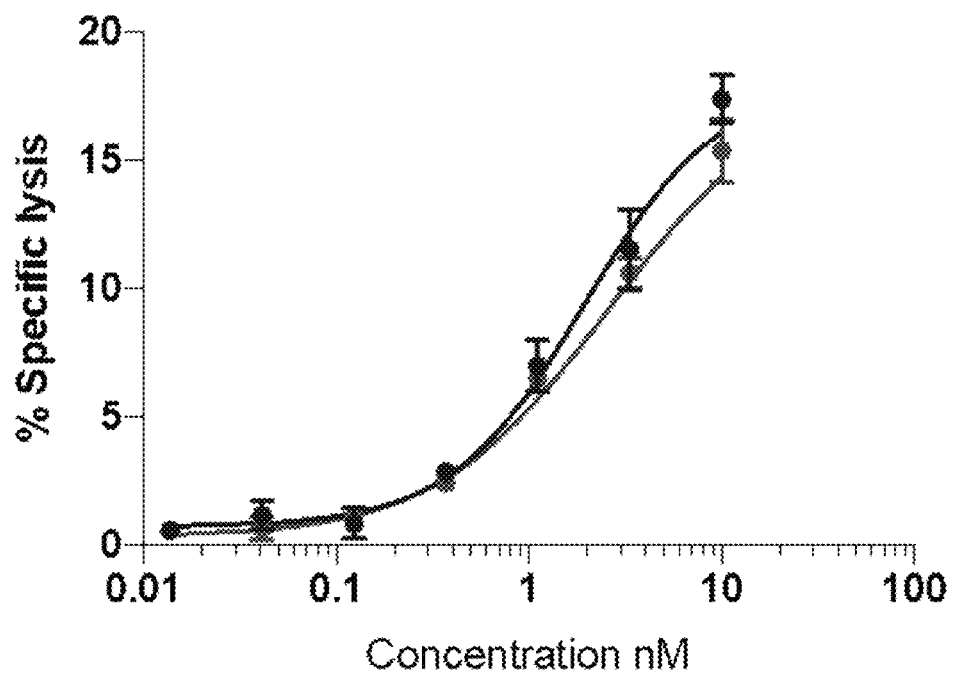

FIG. 262 shows that the potency of AB0192 after forced oxidation in KHYG-1-CD16a mediated cytotoxicity assay was similar to the control sample.

Figure 263A:
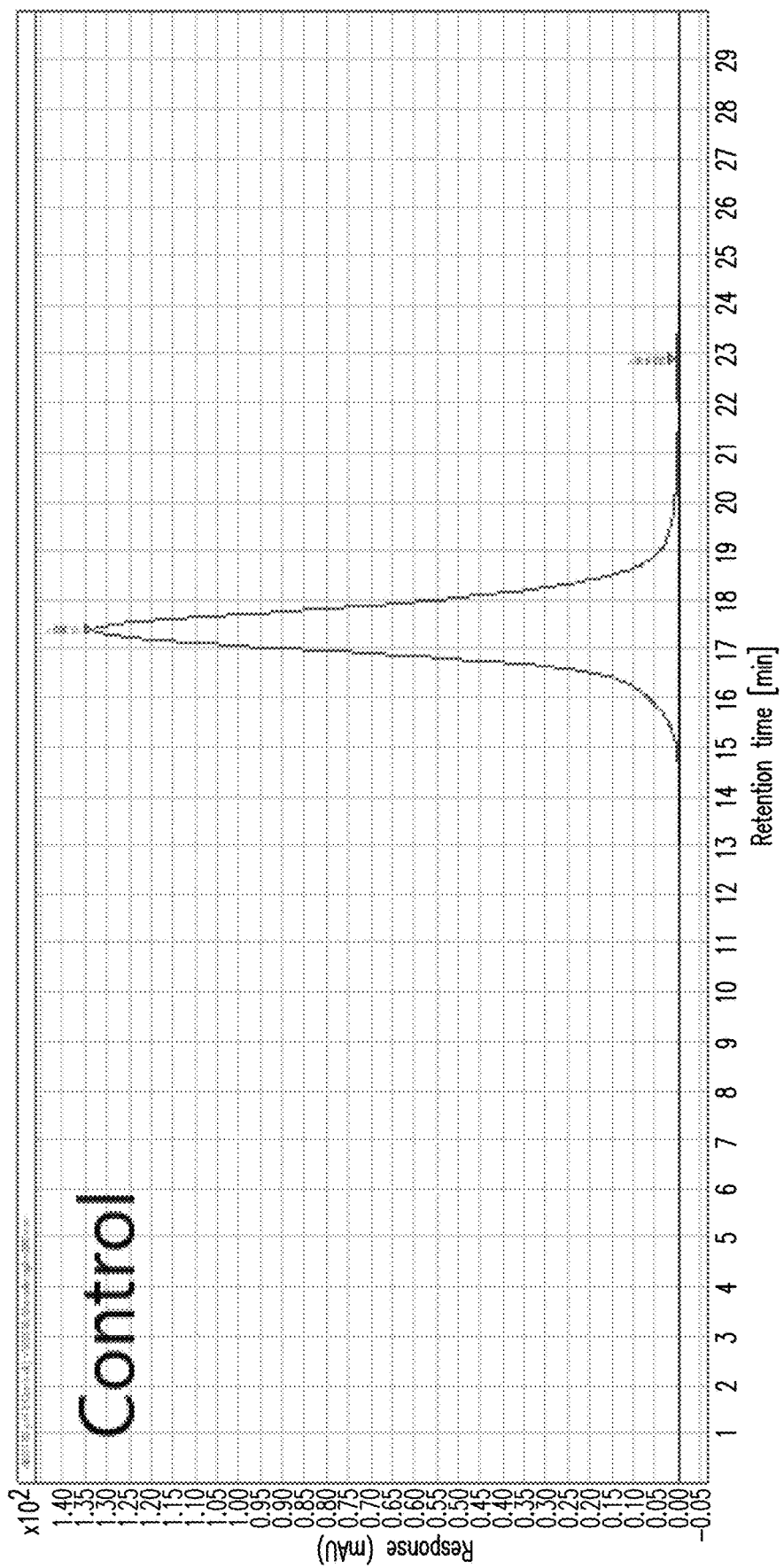
Figure 263B:
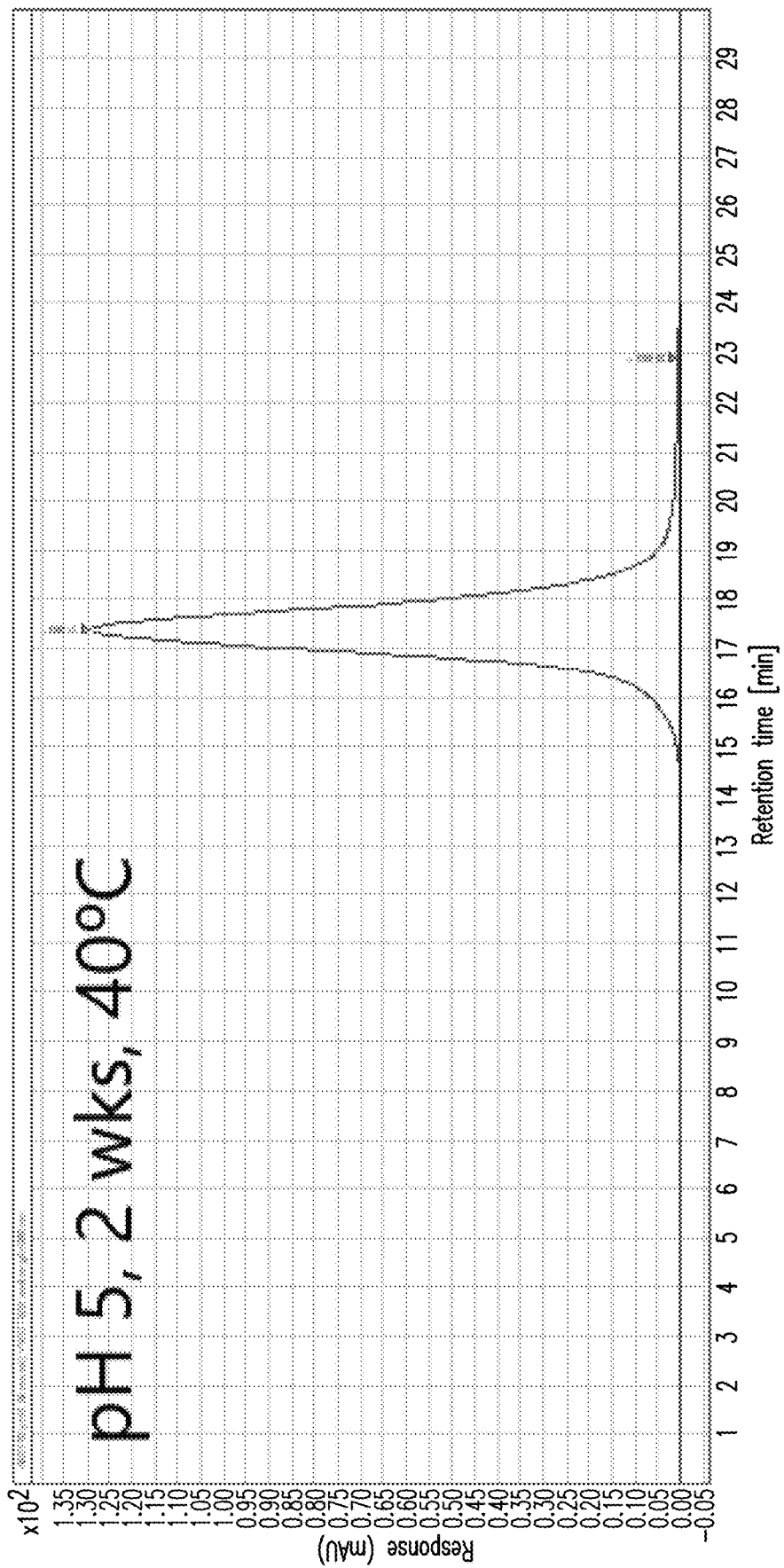

FIG. 263A-FIG. 263B show an SEC analysis of AB0192 after long term low pH exposure (pH 5.0, 40° C., 14 days), and indicated no loss of monomer.

Figure 264A:
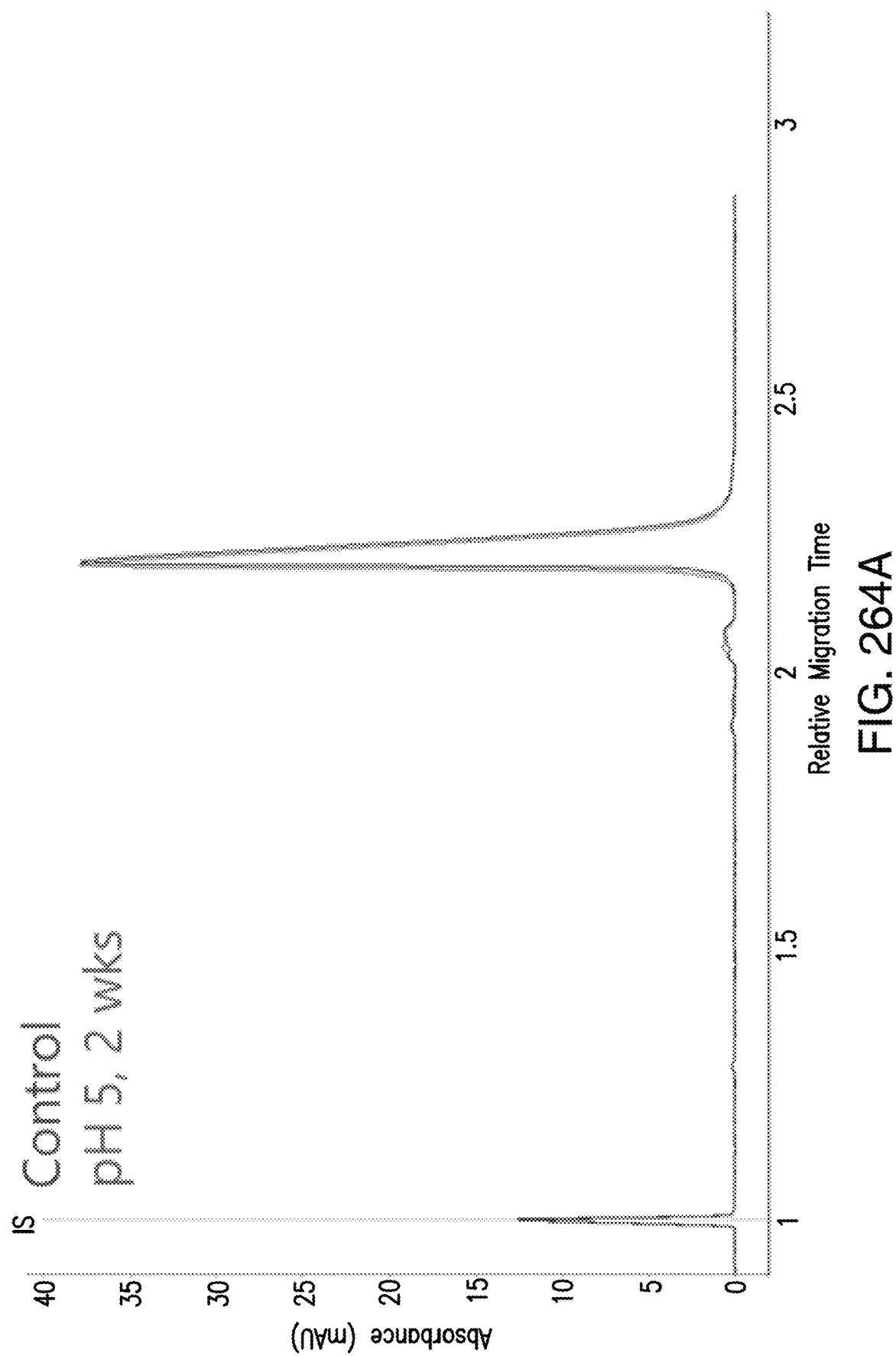
Figure 265A:
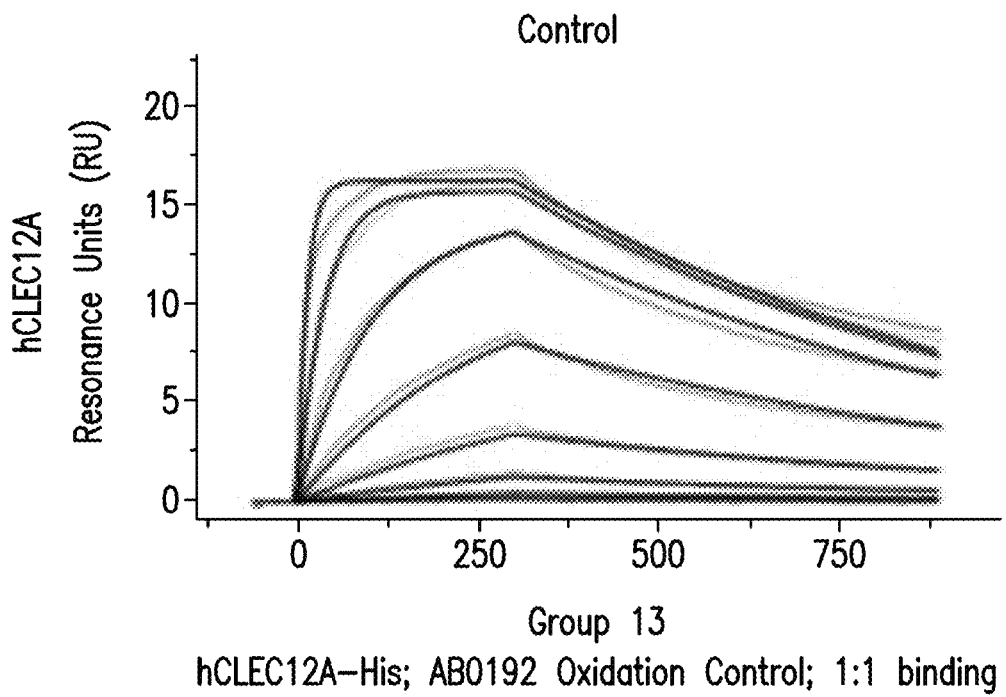
Figure 265B:
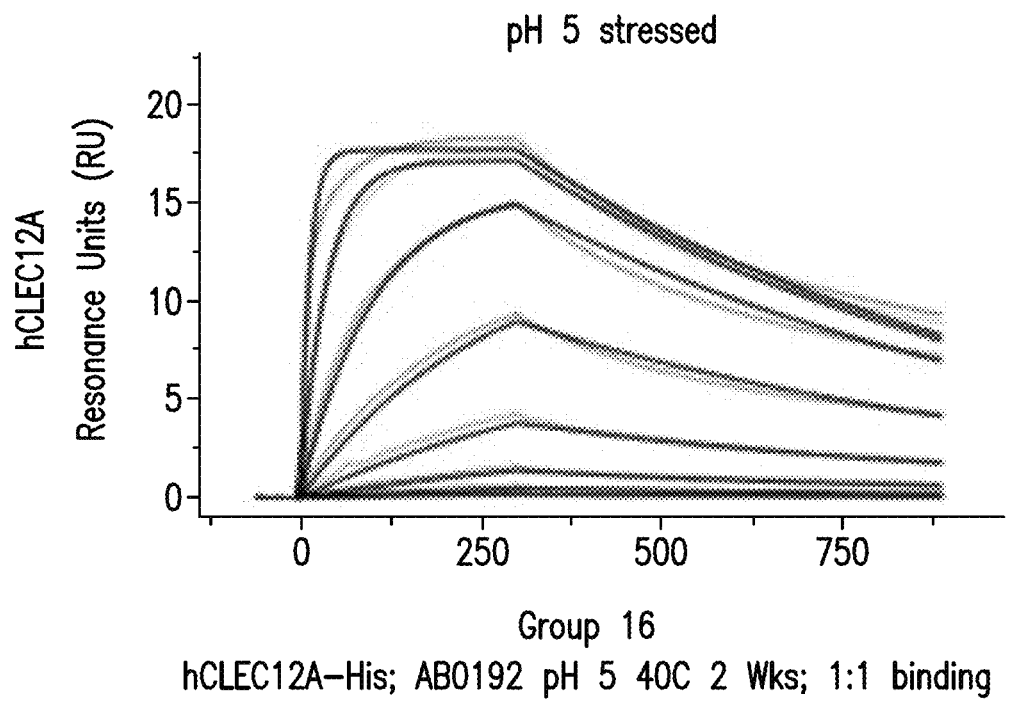
Figure 265C:
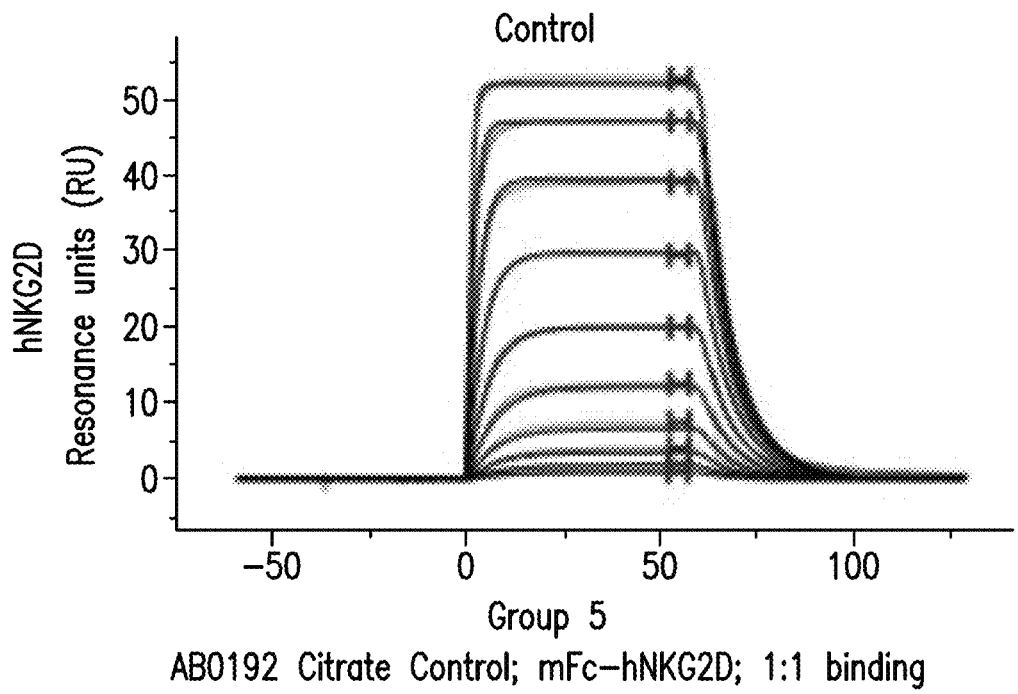
Figure 265D:
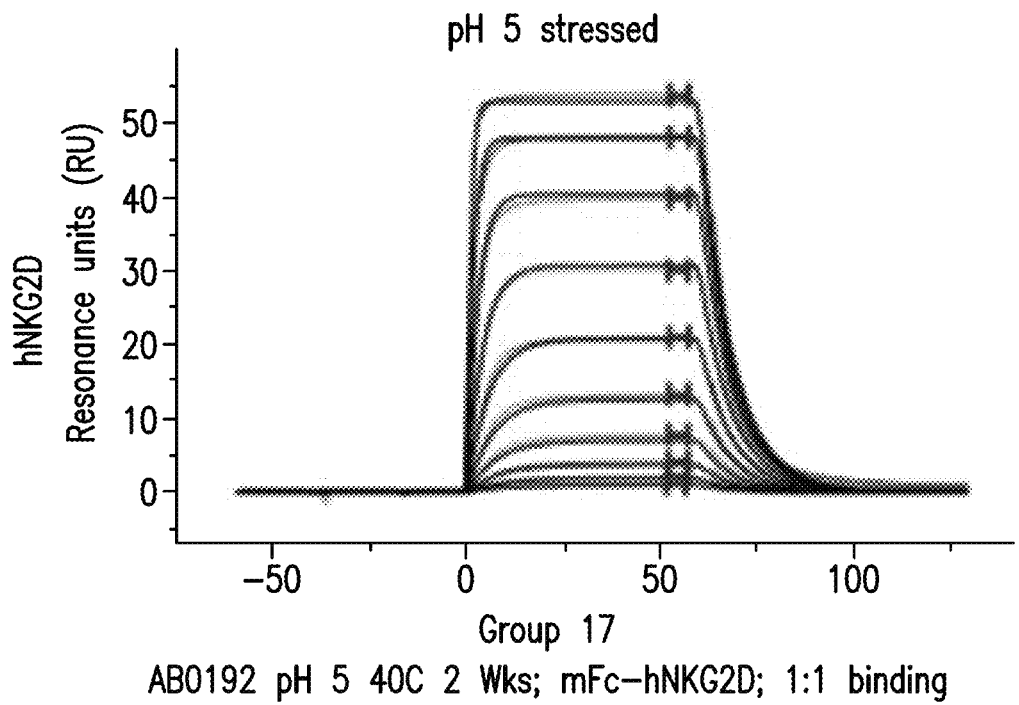
Figure 265E:
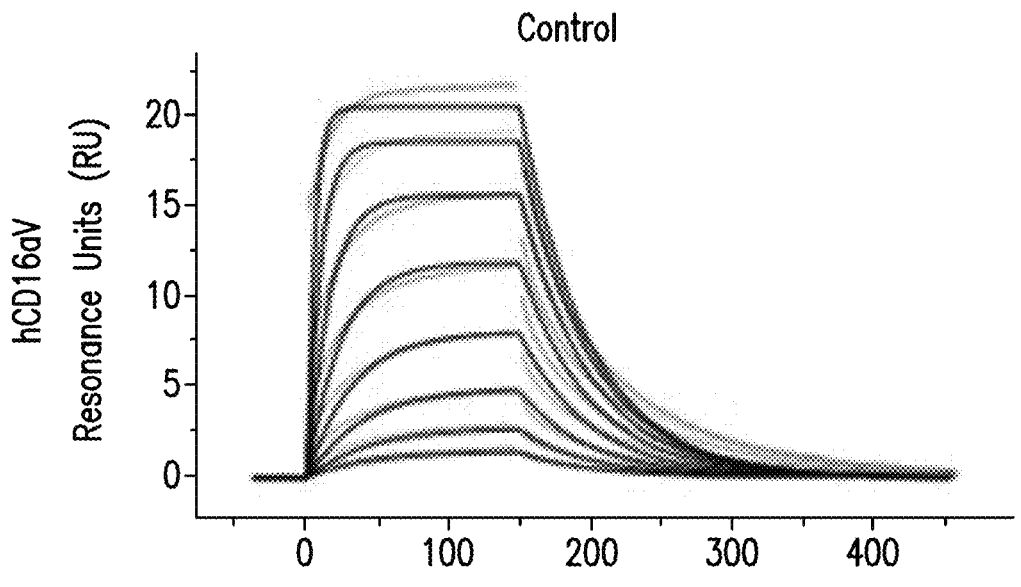
Figure 265F:
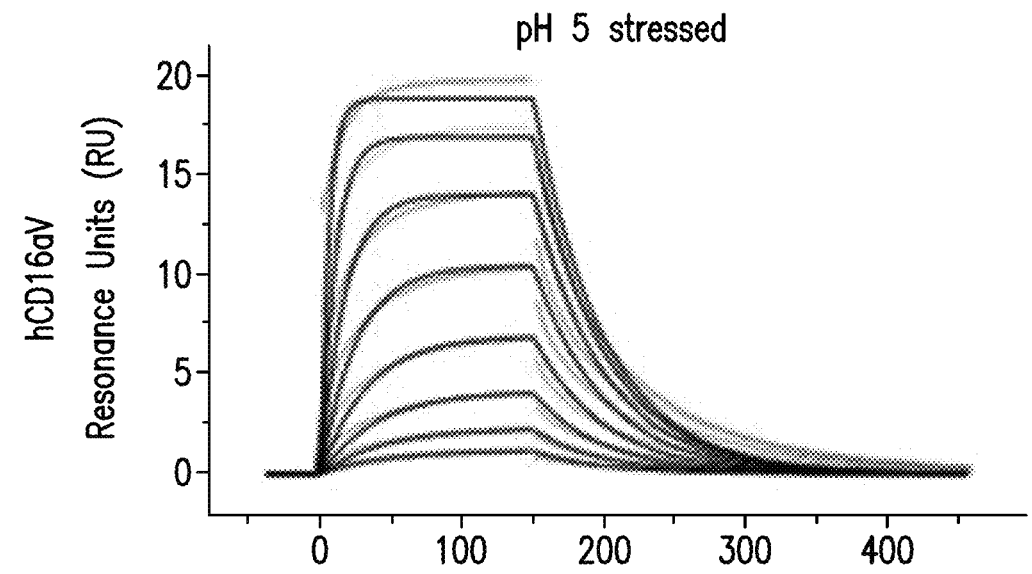

FIG. 264A-FIG. 264B show a CE-SDS analysis of AB0192 after long term low pH stress (pH 5.0, 40° C., 14 days), and indicated that the differences in purity detected by non-reduced and reduced CE-SDS were less than 1%. Non-reduced conditions are shown in FIG. 264A. Reduced conditions are shown in FIG. 264B.

FIG. 265A-FIG. 265F show that AB0192 is stable after low pH stress (pH 5.0, 40° C., 14 days): no effect on CLEC12A, NKG2D or CD16a binding.

Figure 266:
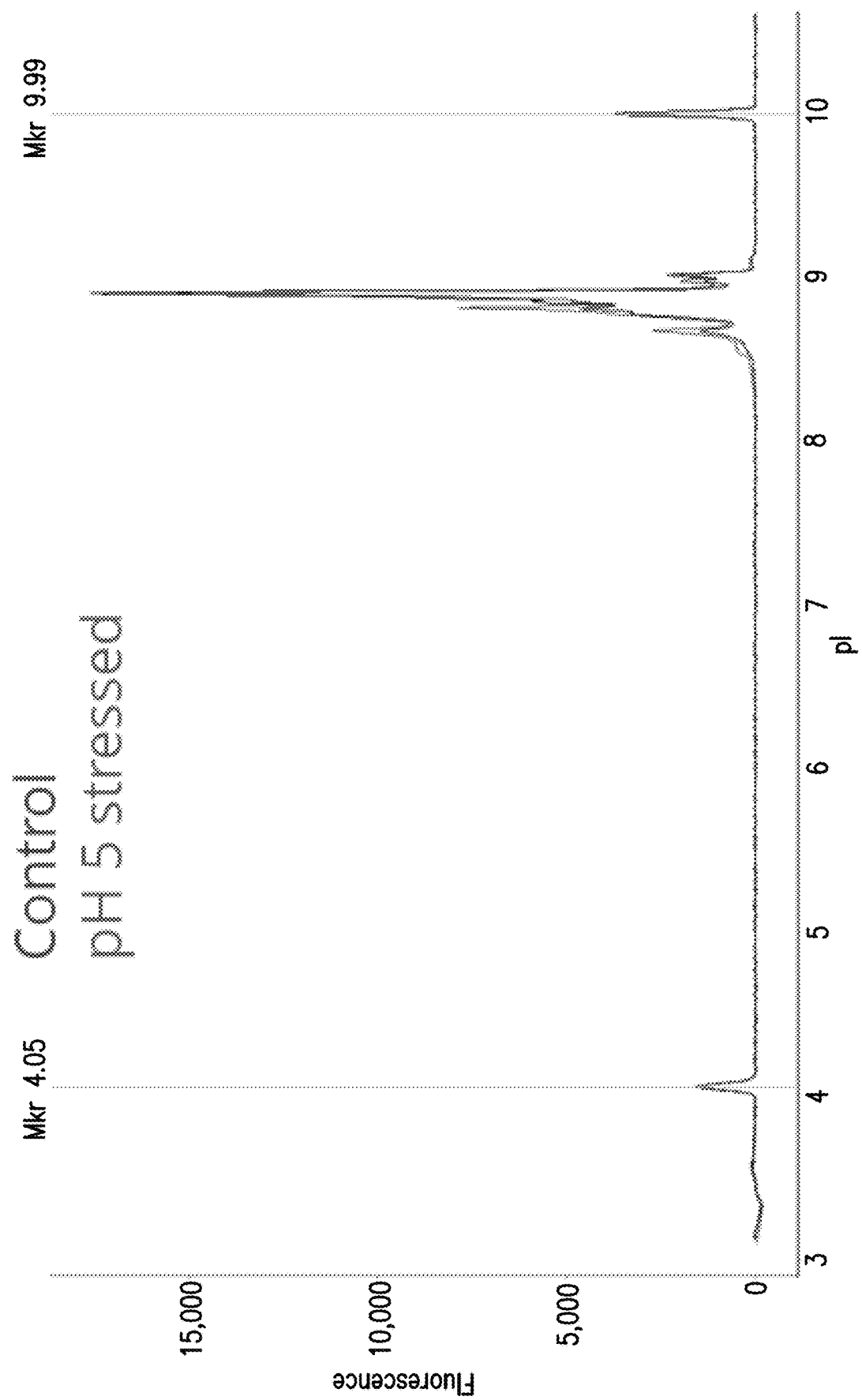

FIG. 266 shows a charge analysis of AB0192 after long term low pH stress (pH 5.0, 40° C., 14 days) by cIEF, with control and pH 5 stressed samples showing no difference.

Figure 267:
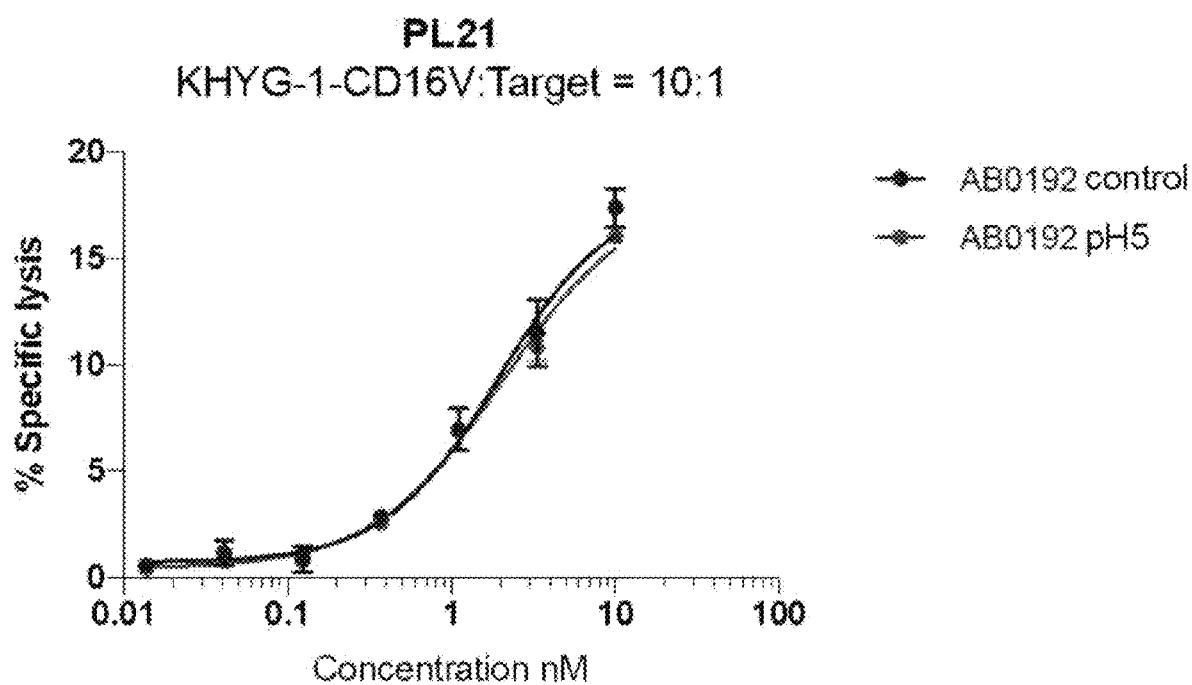

FIG. 267 shows that the potency of AB0192 after long term pH 5.0 stress was unchanged relative to control in KHYG-1-CD16a cytotoxicity assay.

Figure 268A:
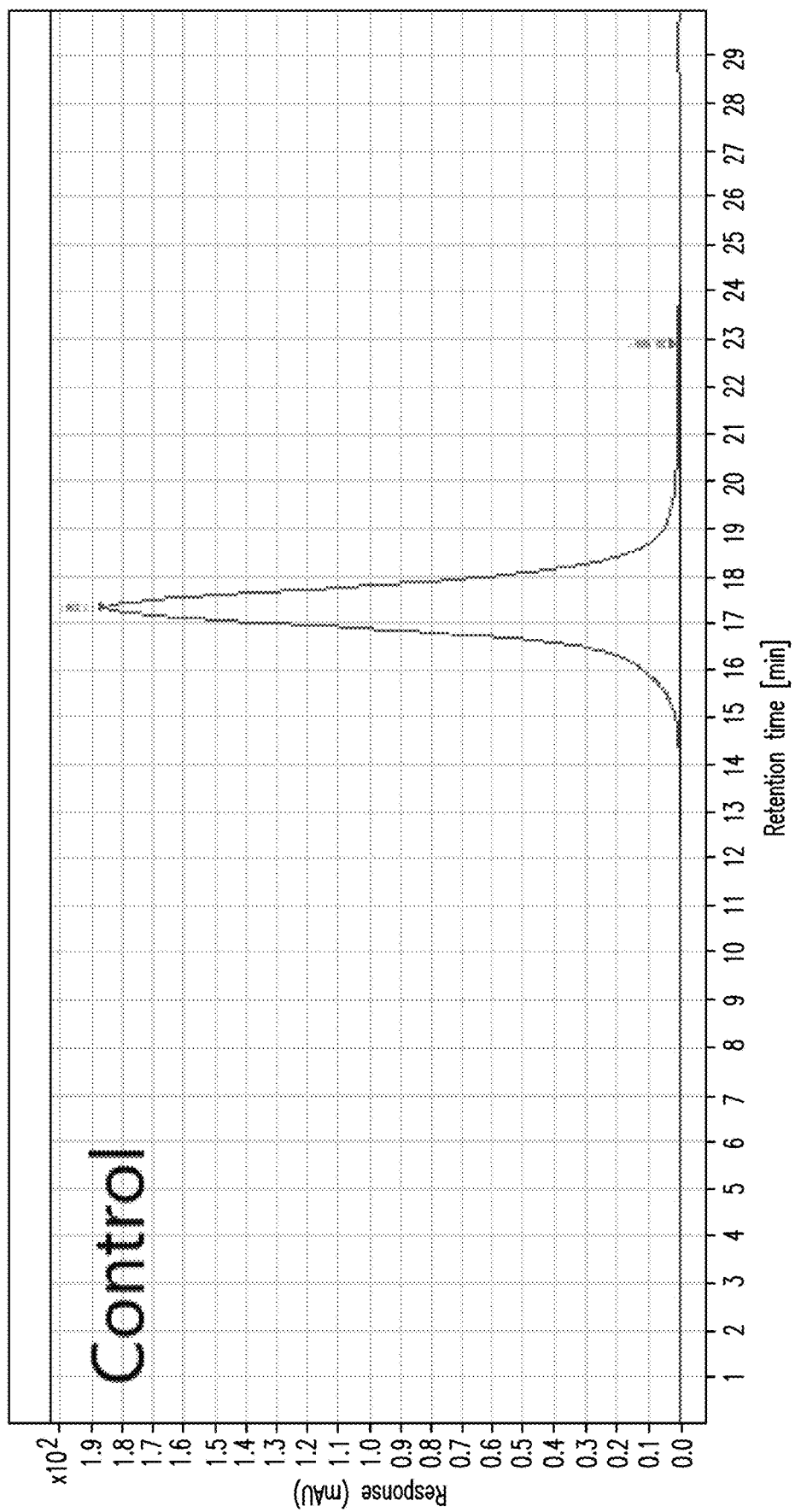
Figure 268B:
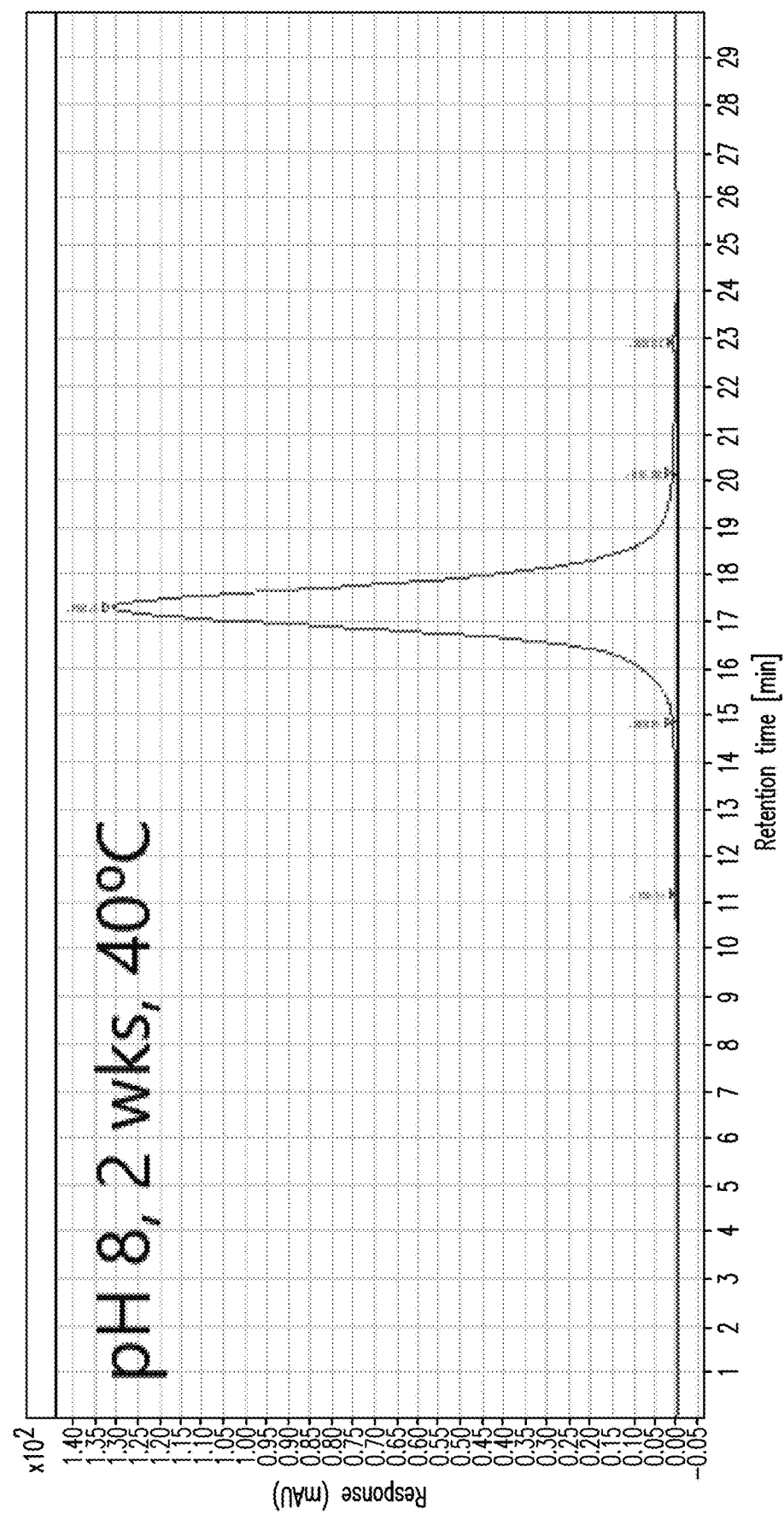

FIG. 268A-FIG. 268B show an SEC analysis of AB0192 after long term high pH stress (pH 8.0, 40° C., 14 days), which indicated that there was a 1.6% loss of monomer.

Figure 269A:
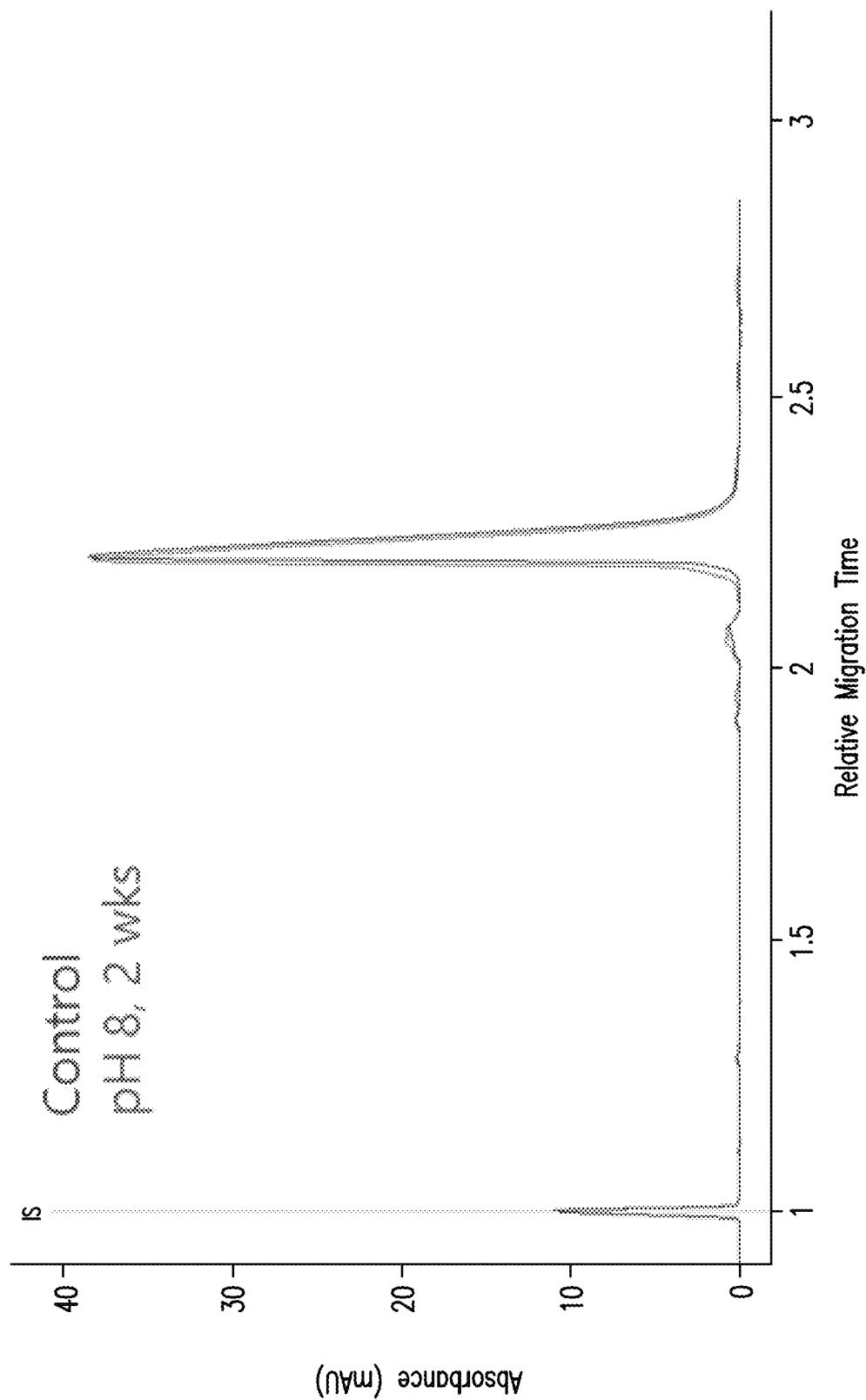
Figure 269B:
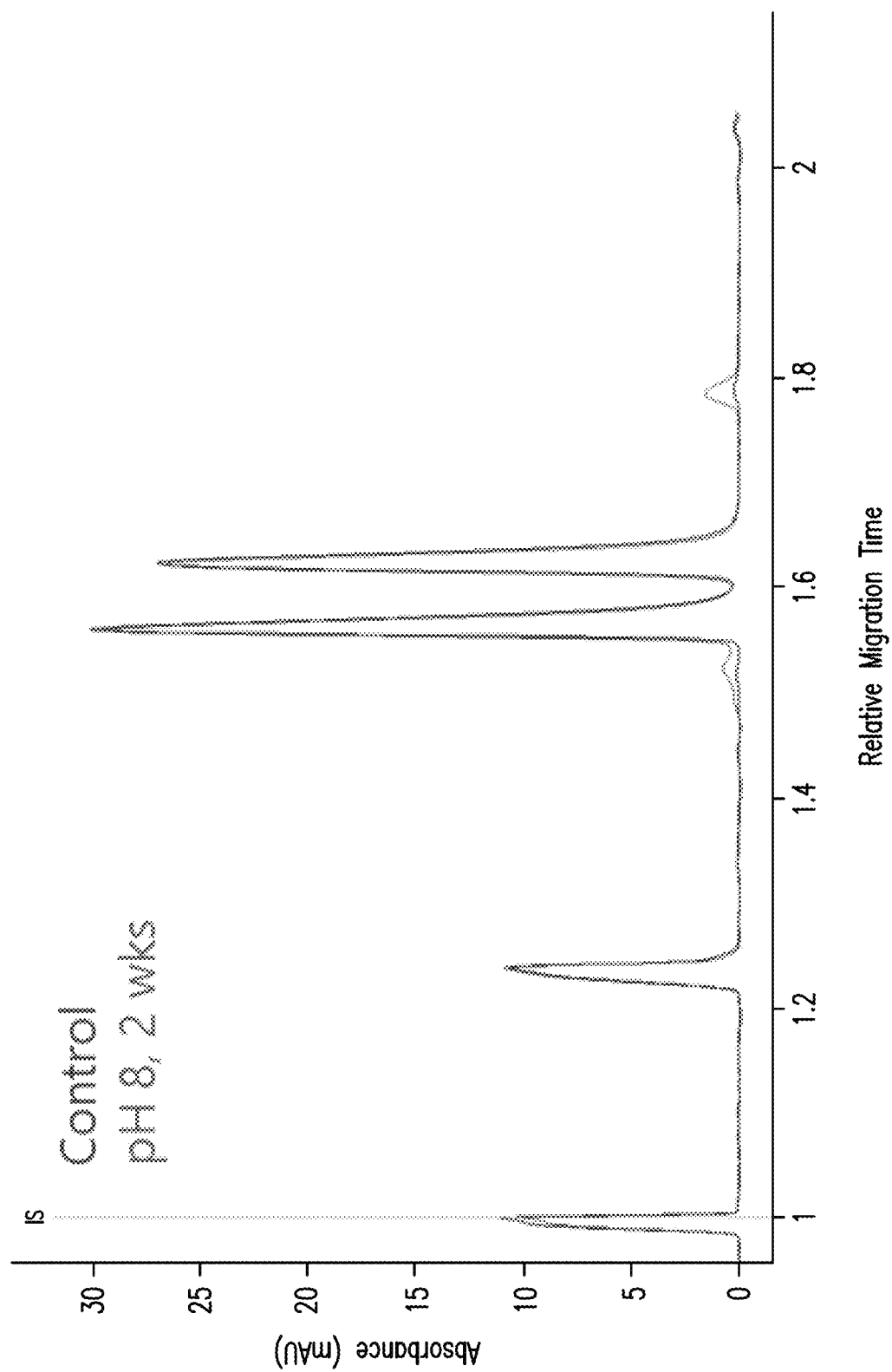
Figure 270A:
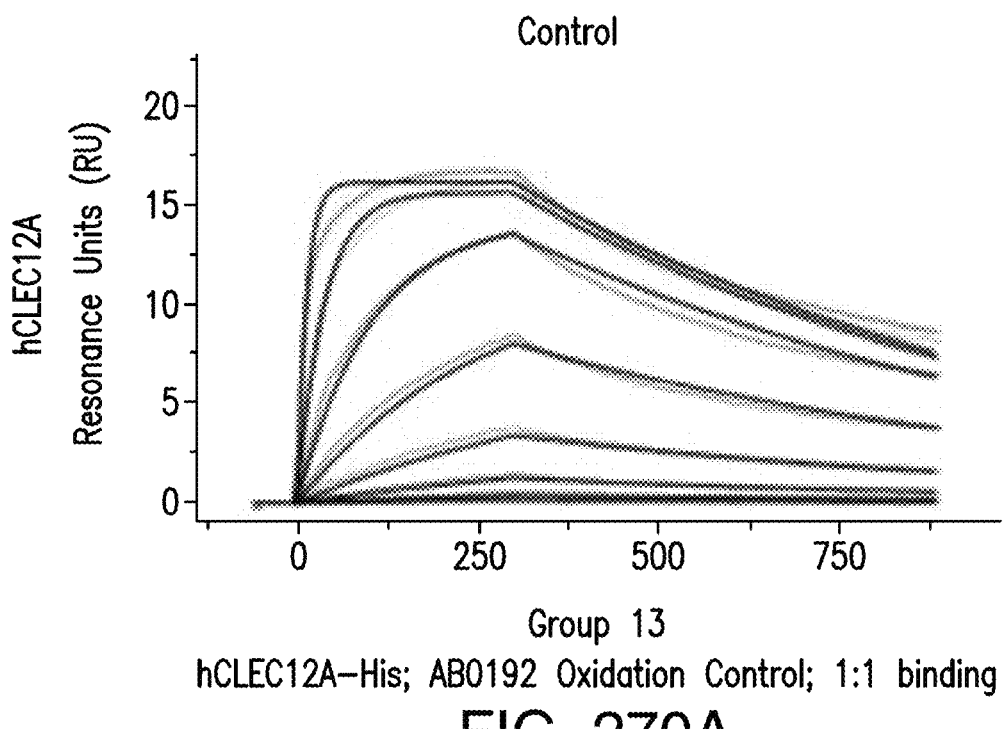
Figure 270B:
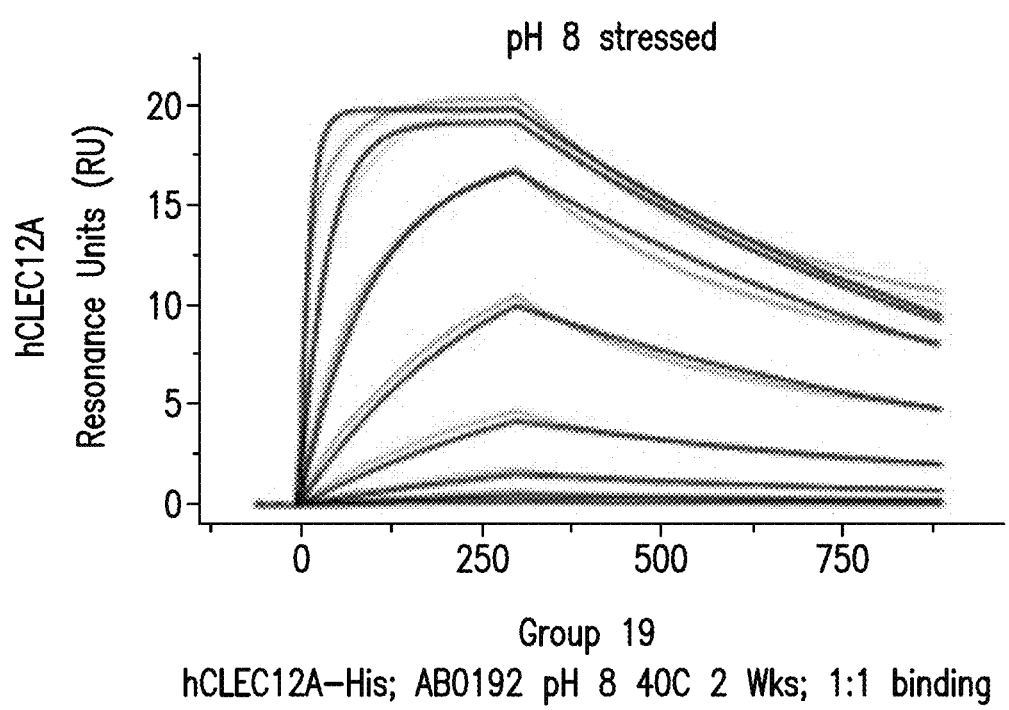
Figure 270C:
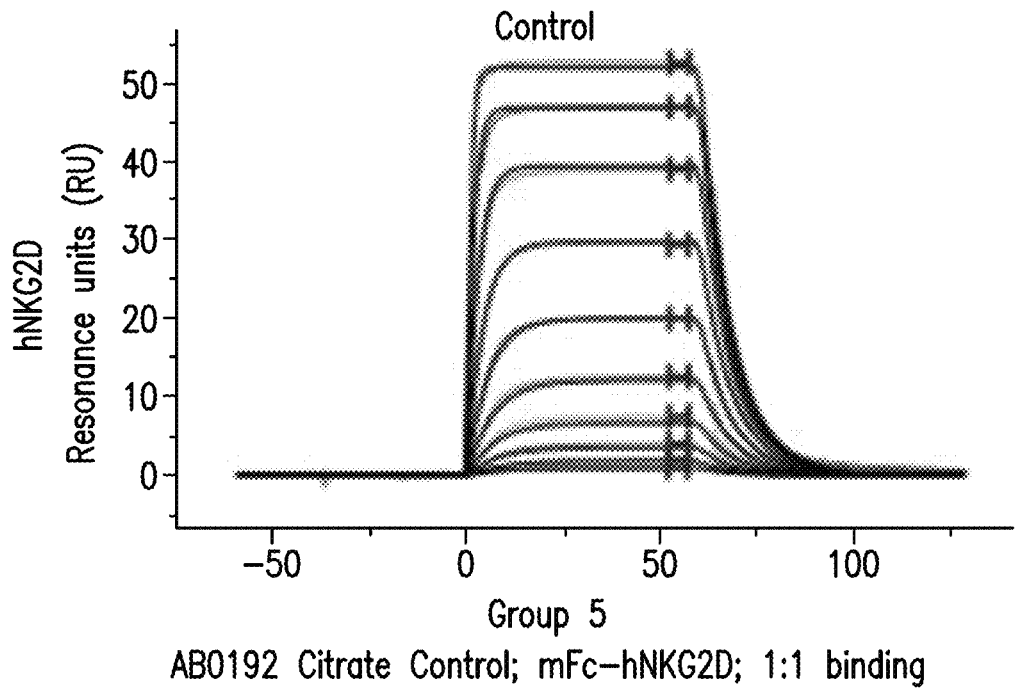
Figure 270D:
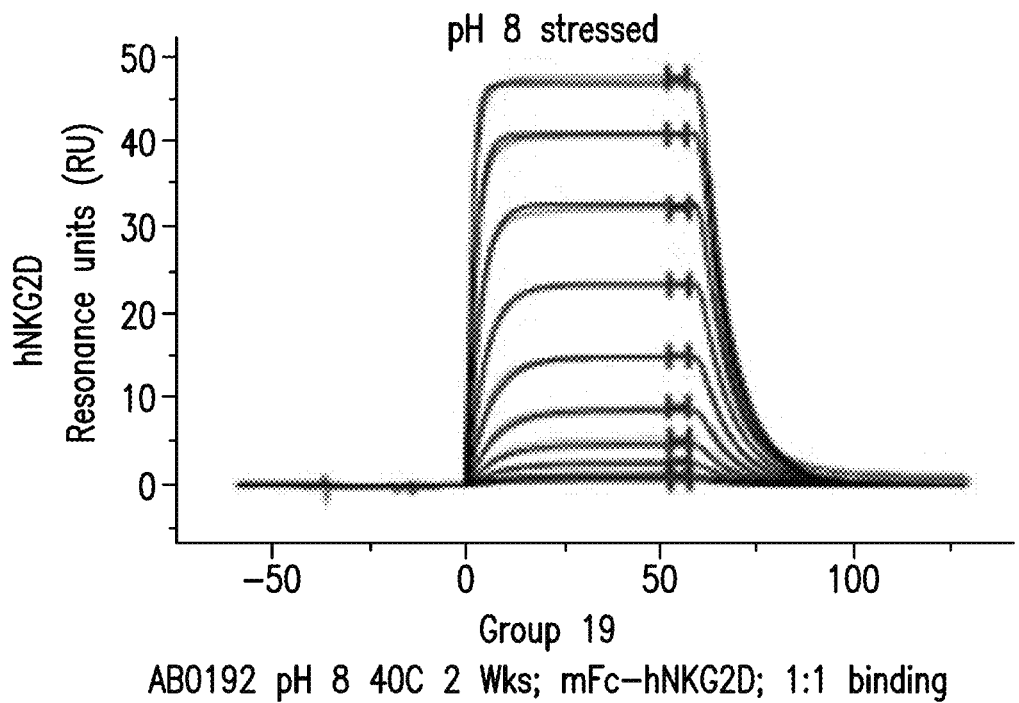
Figure 270E:
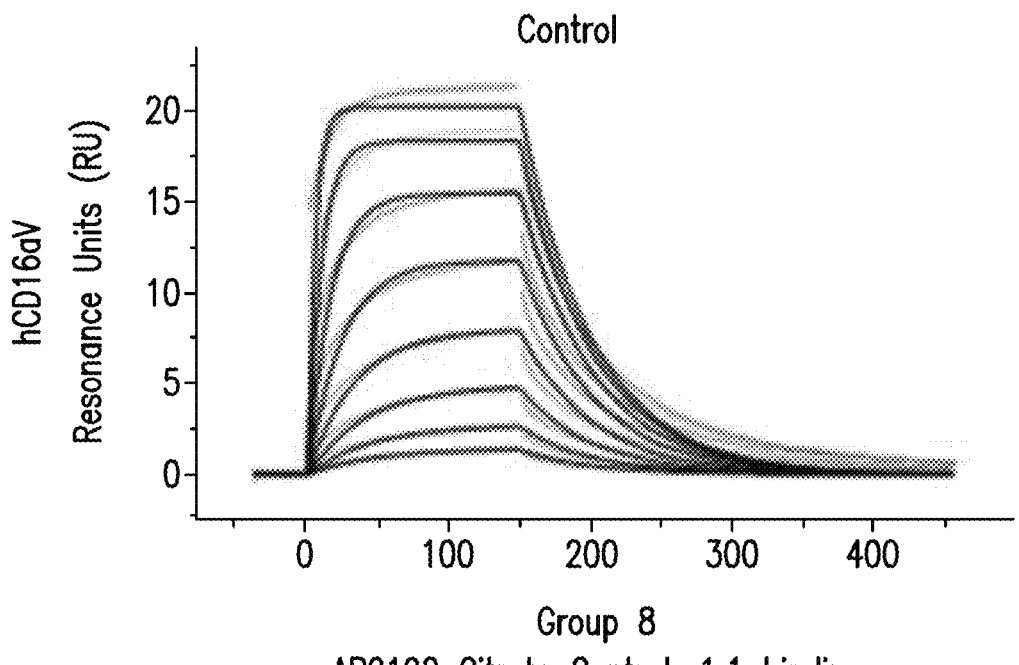
Figure 270F:
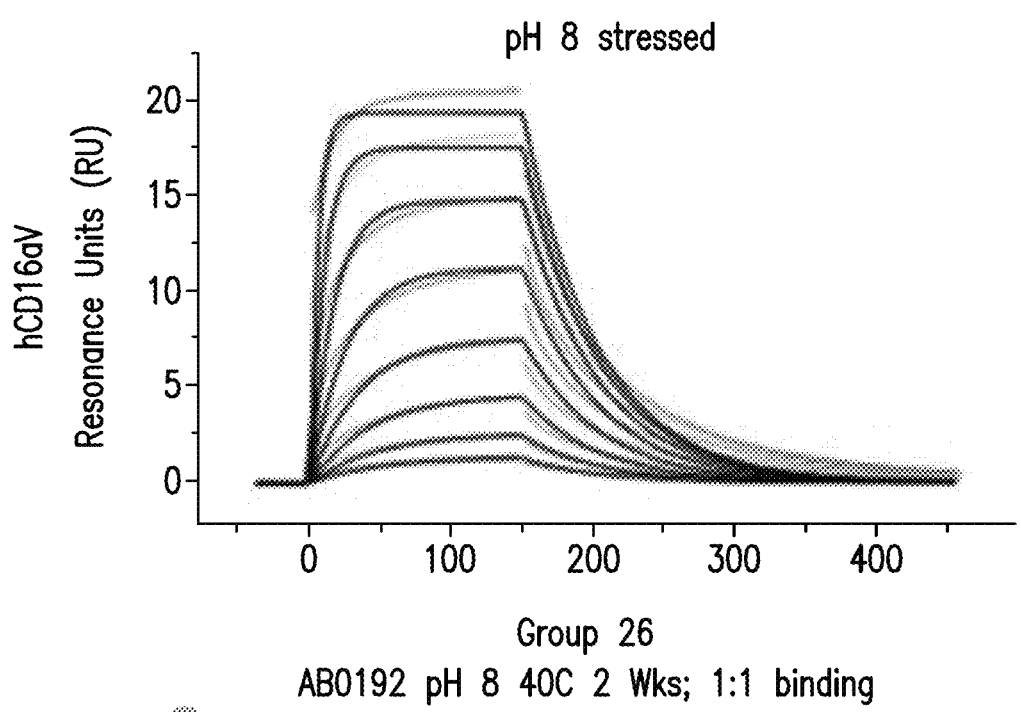

FIG. 269A-FIG. 269B show a CE-SDS analysis of AB0192 after long term high pH stress (pH 8.0, 40° C., 14 days). Minor differences in purity were detected by non-reduced (FIG. 269A) and reduced (FIG. 269B) conditions.

FIG. 270A-FIG. 270F show that AB0192 is stable after high pH stress: no effect on CLEC12A, NKG2D or CD16a binding.

Figure 271:
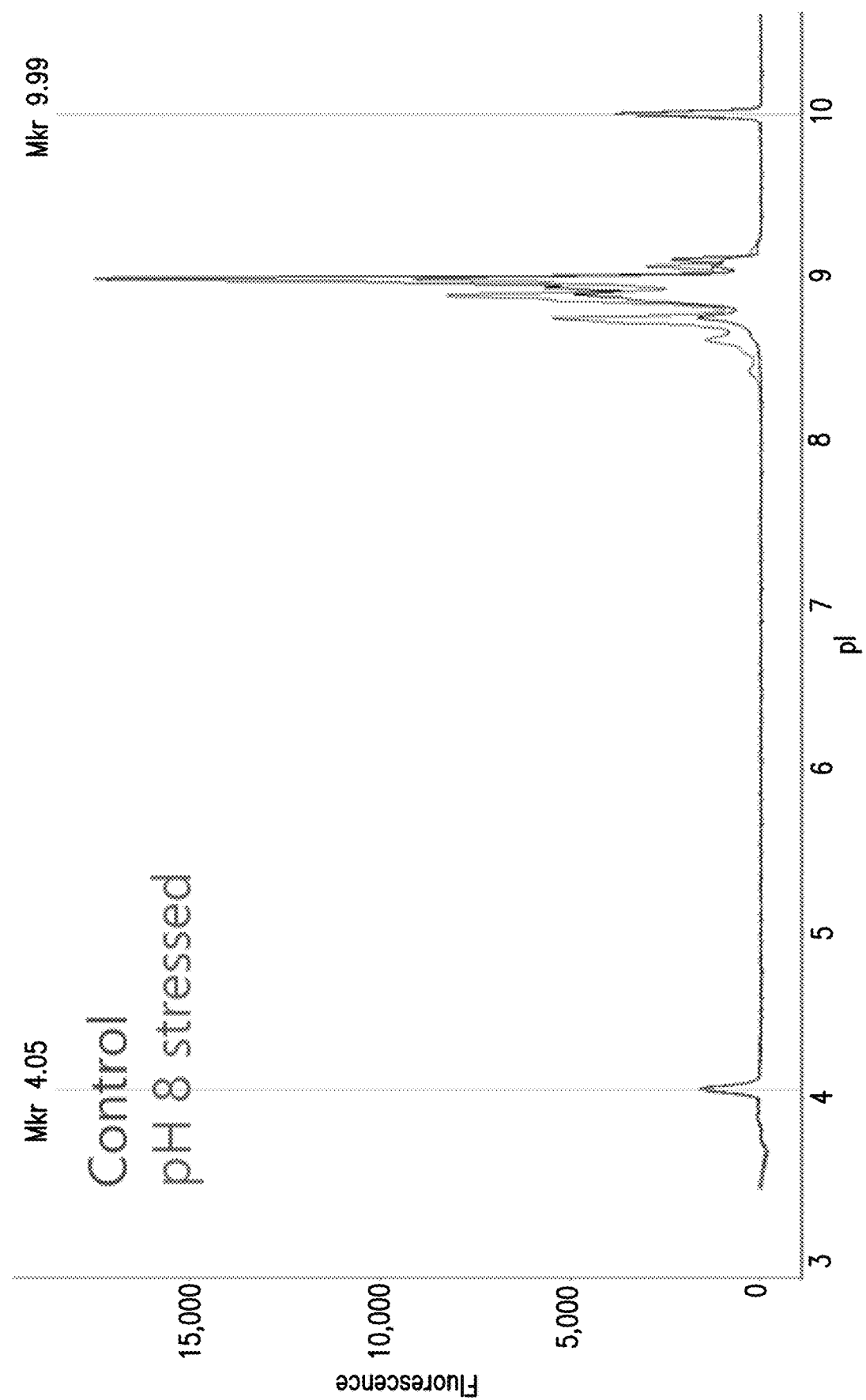

FIG. 271 shows a charge analysis of AB0192 after long term high pH stress (pH 8.0, 40° C., 14 days) by cIEF, with an acidic shift in the pH 8 stressed sample relative to the control sample.

Figure 272:
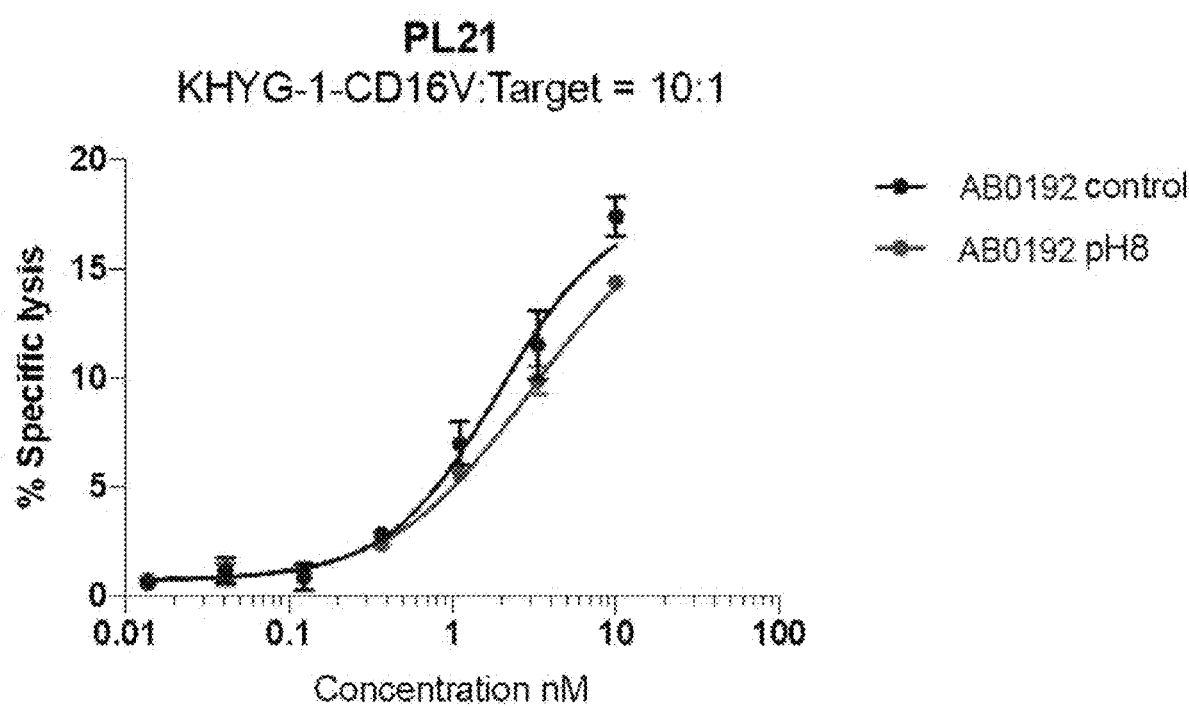

FIG. 272 shows the potency of AB0192 after long term exposure to high pH 8.0 stress was not significantly affected, as assessed by KHYG-1-CD16aV cytotoxicity assay.

Figure 273A:
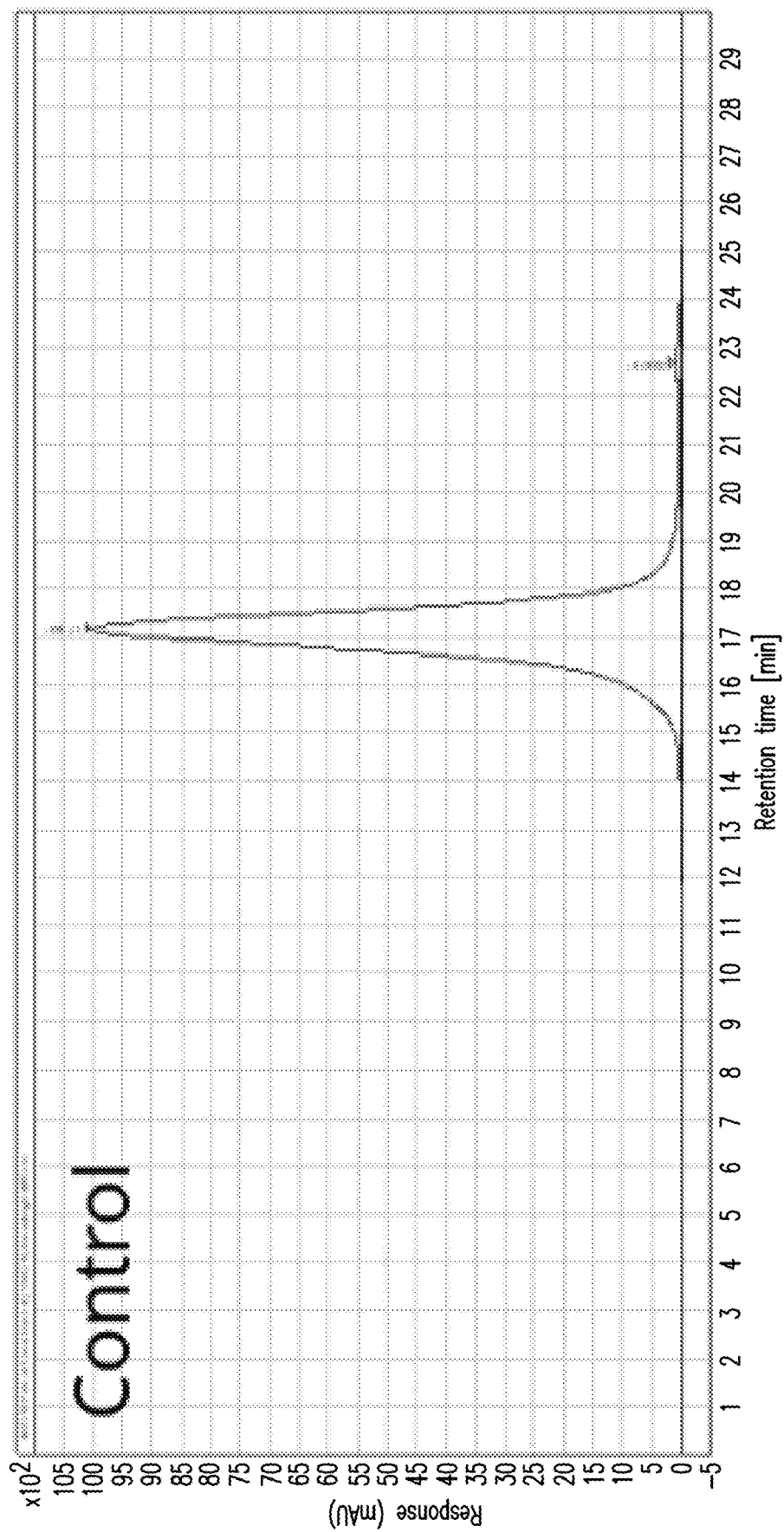
Figure 273B:
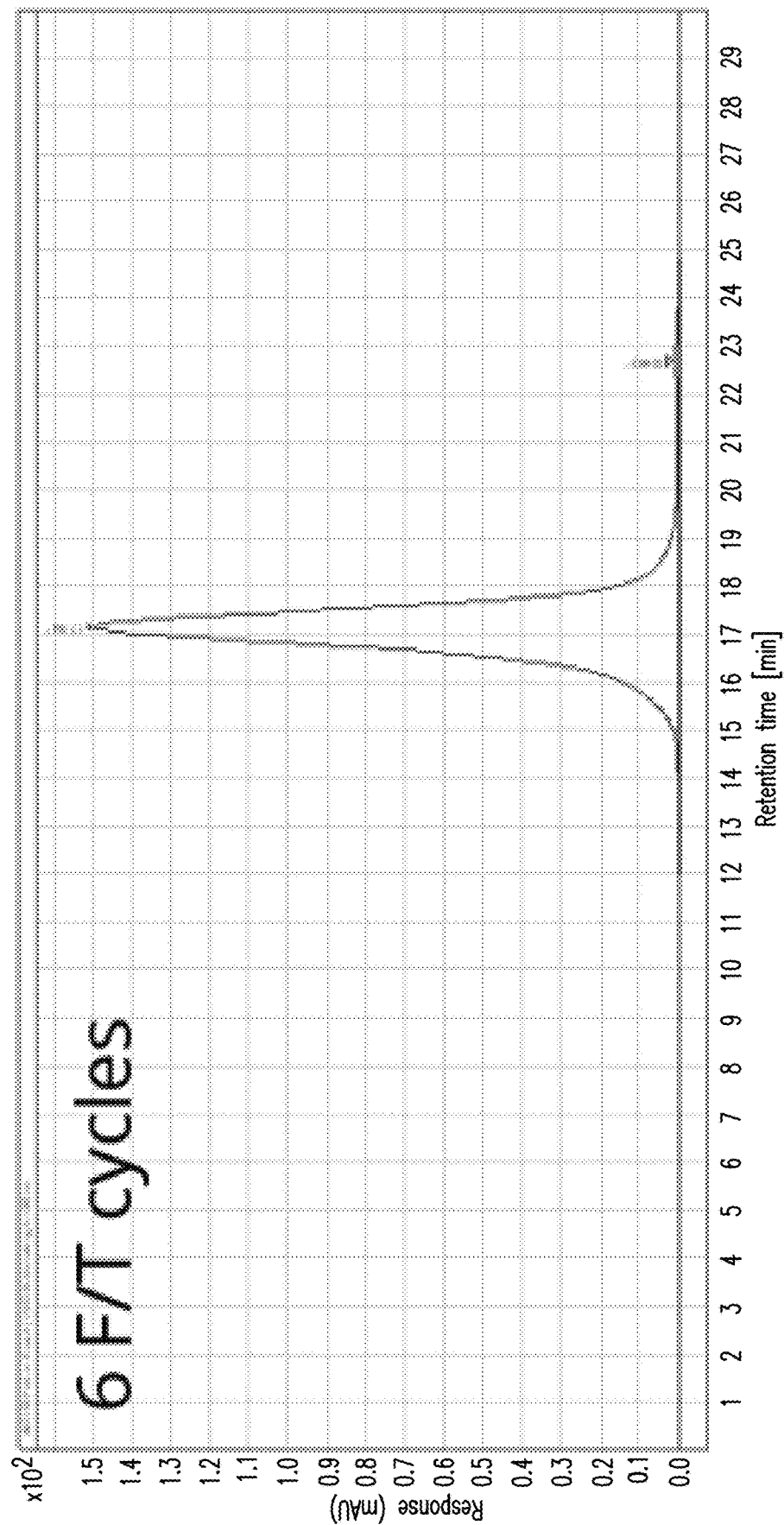

FIG. 273A-FIG. 273B show an SEC analysis of AB0192 after 6 cycles of freeze/thaw compared to control, which indicated no loss in monomer.

Figure 274A:
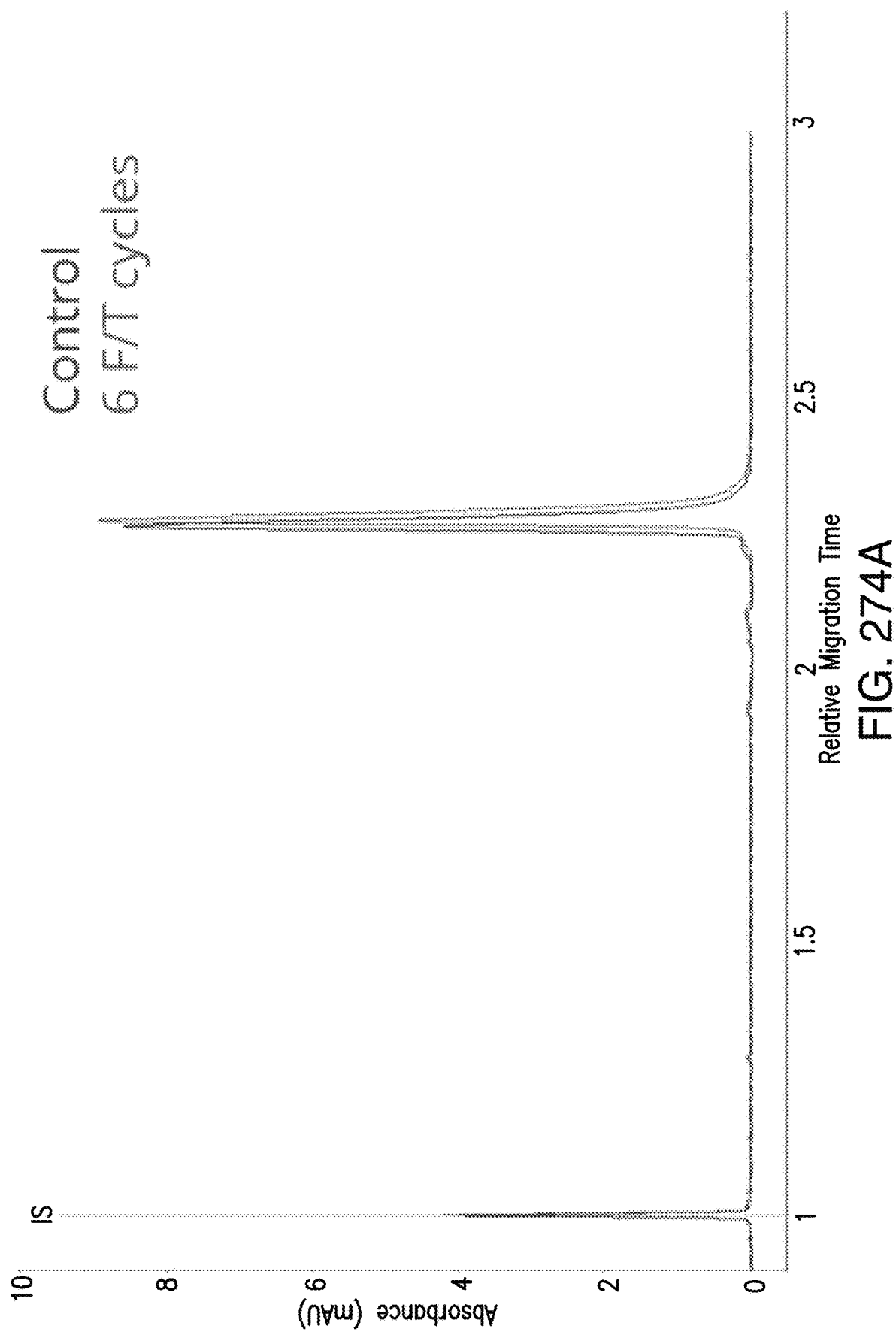
Figure 274B:
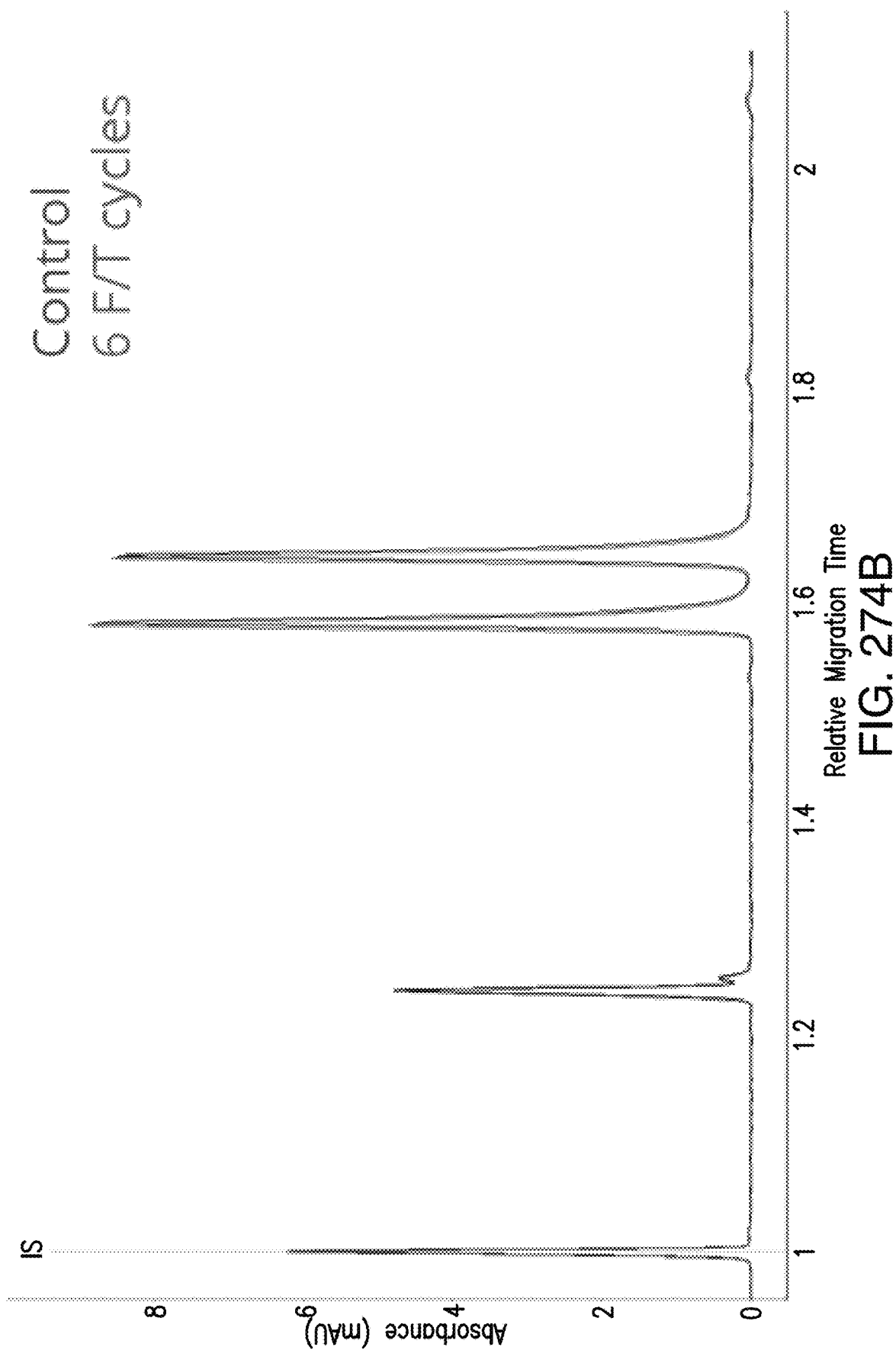

FIG. 274A-FIG. 274B show a CE-SDS analysis of AB0192 after freeze thaw stress, which indicated no loss of purity by either reduced (FIG. 274A) or non-reduced (FIG. 274B) conditions.

Figure 275A:
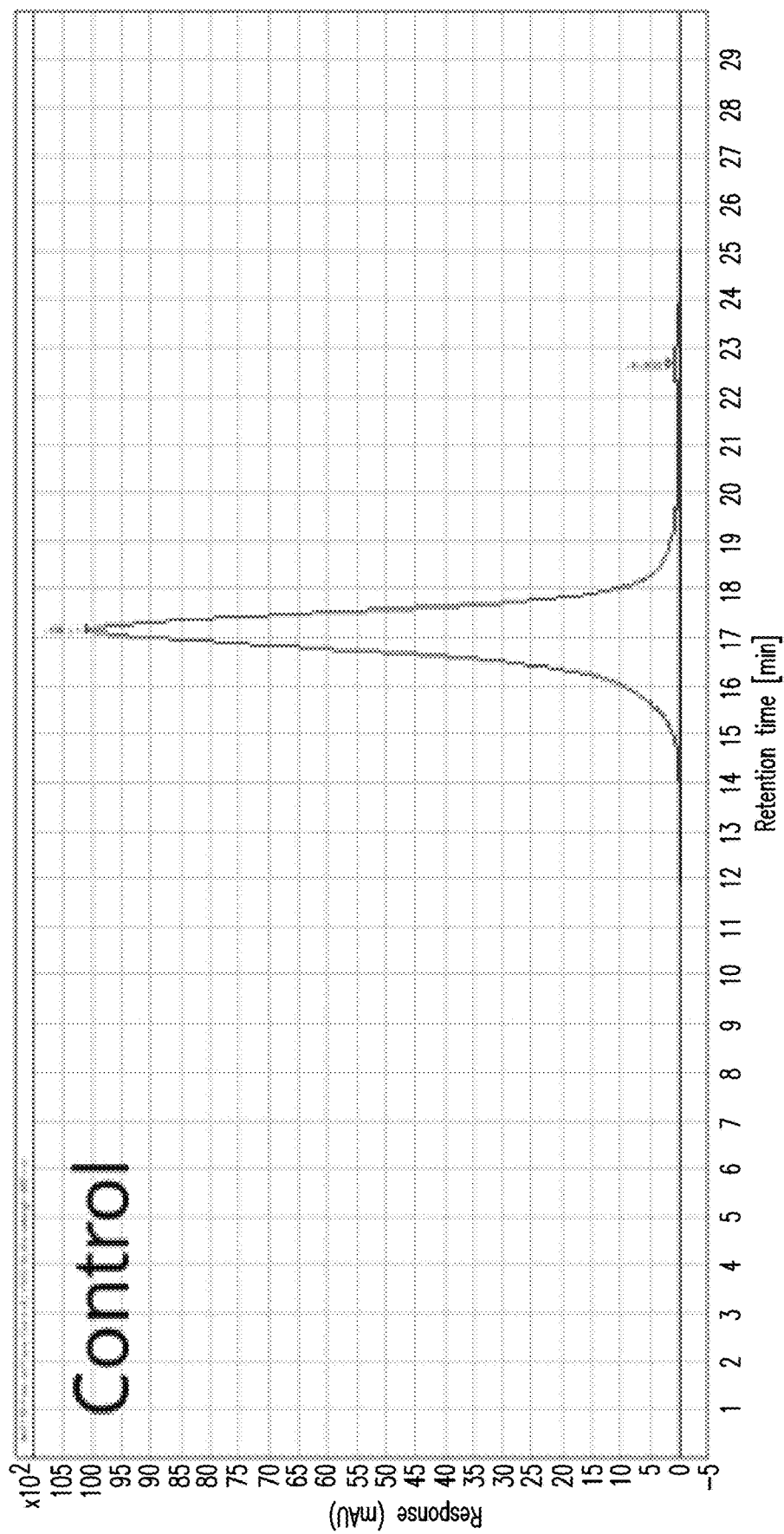
Figure 275B:
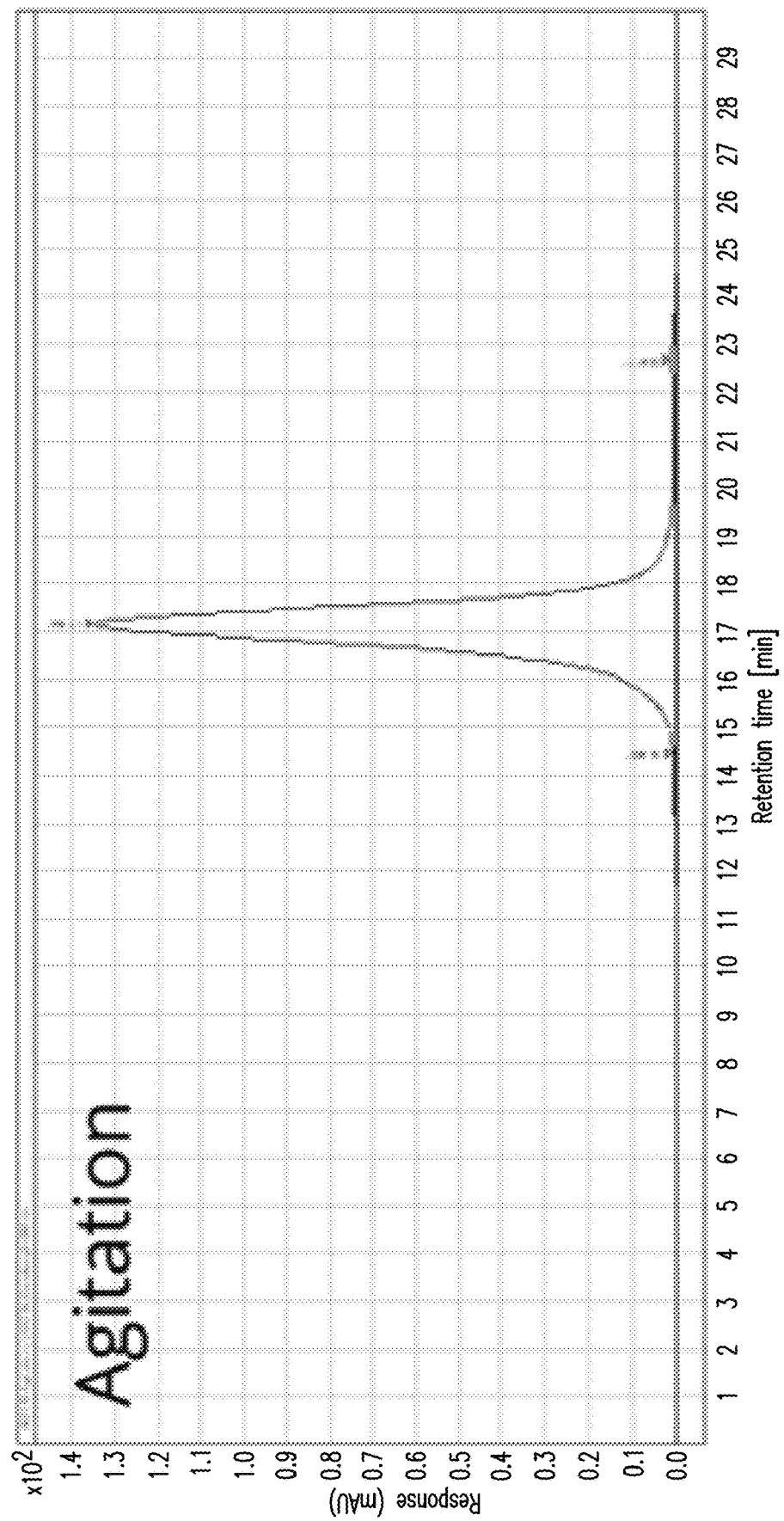

FIG. 275A-FIG. 275B show an SEC analysis of AB0192 after agitation stress compared to control, which indicated no loss of monomer.

Figure 276A:
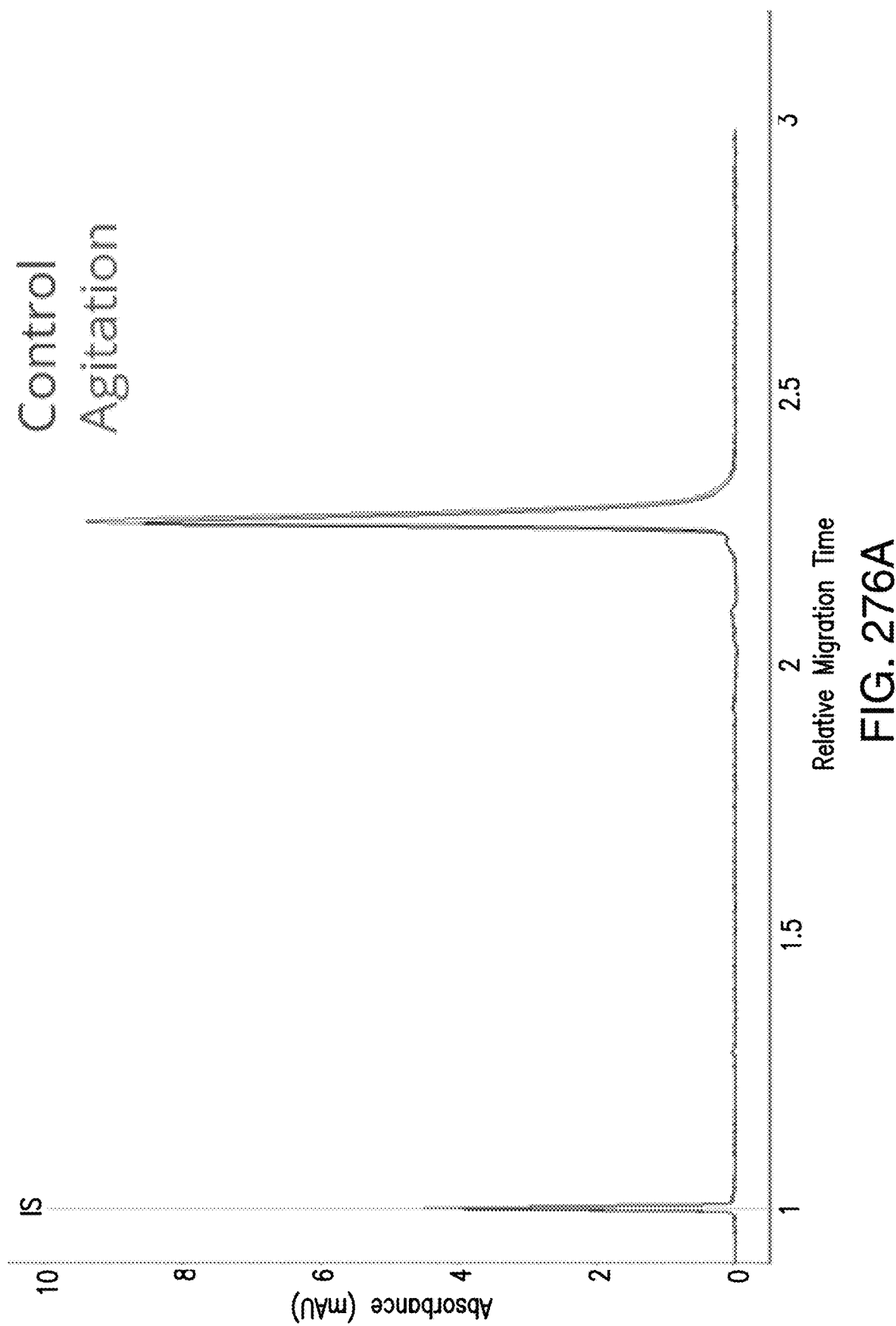
Figure 276B:
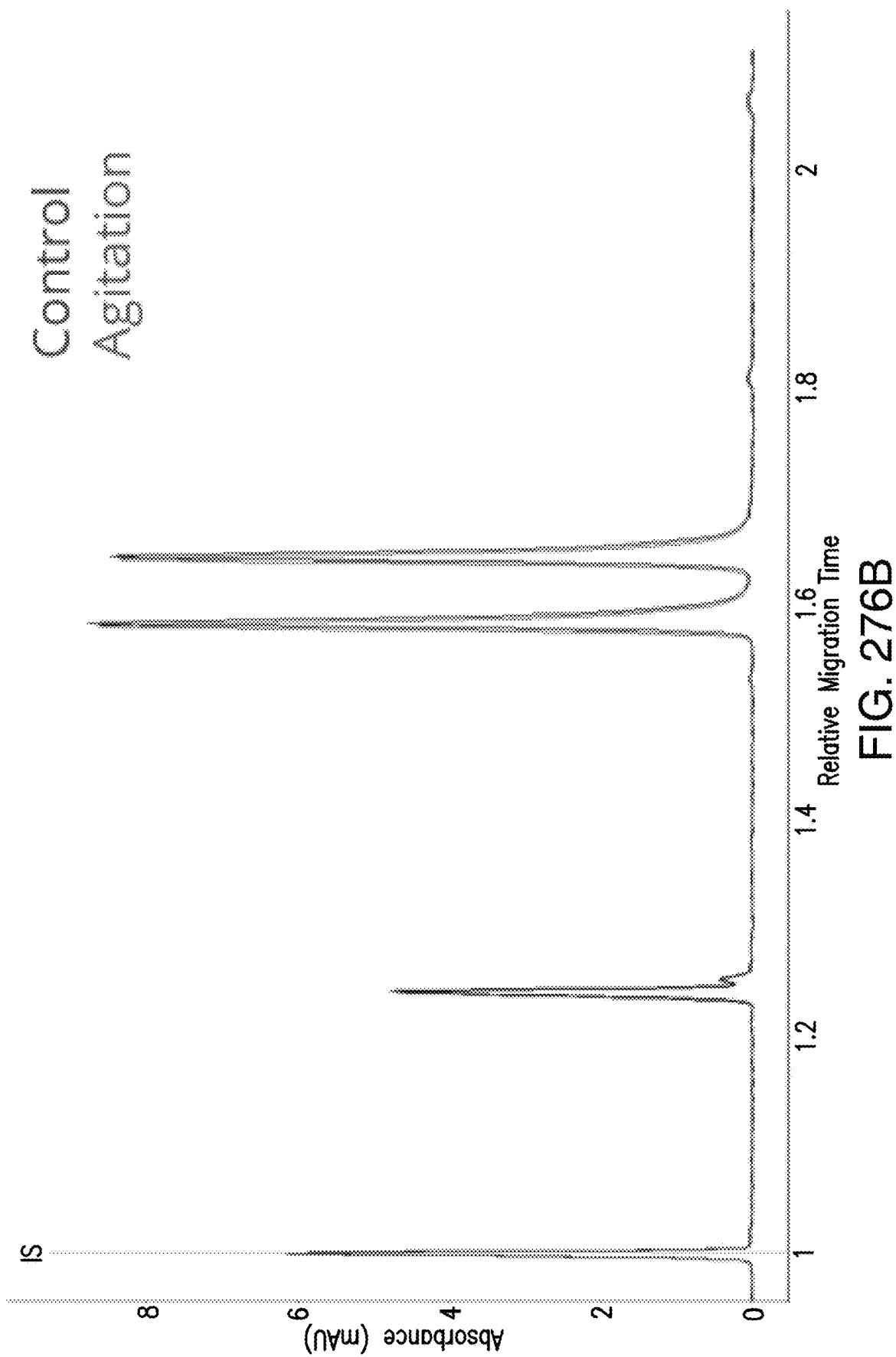

FIG. 276A-FIG. 276B show a CE-SDS analysis of AB0192 after agitation stress compared to control, which indicated no increase in fragmentation detected by reduced (FIG. 276A) or non-reduced (FIG. 276B).

Figure 277A:
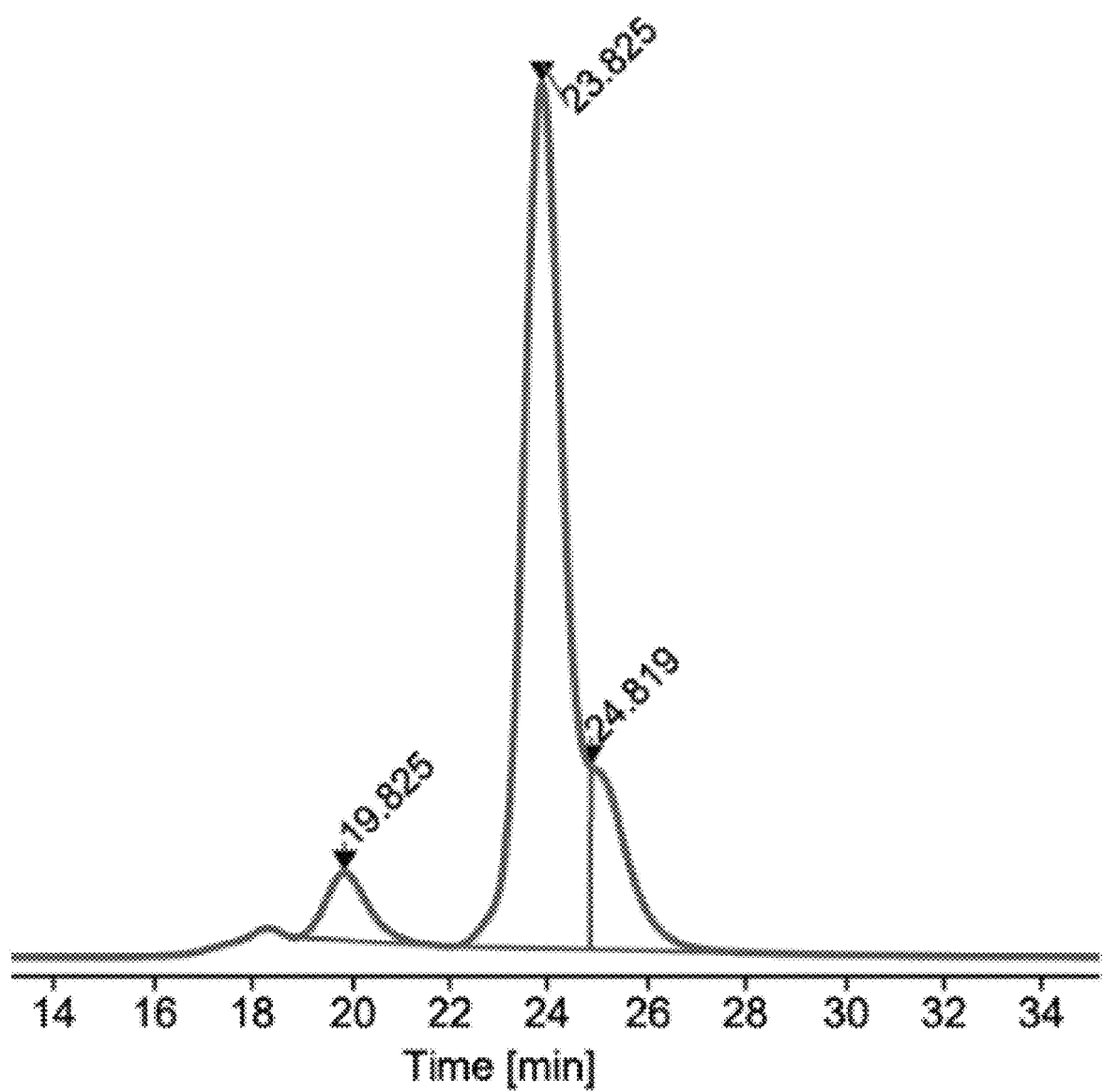
Figure 277B:
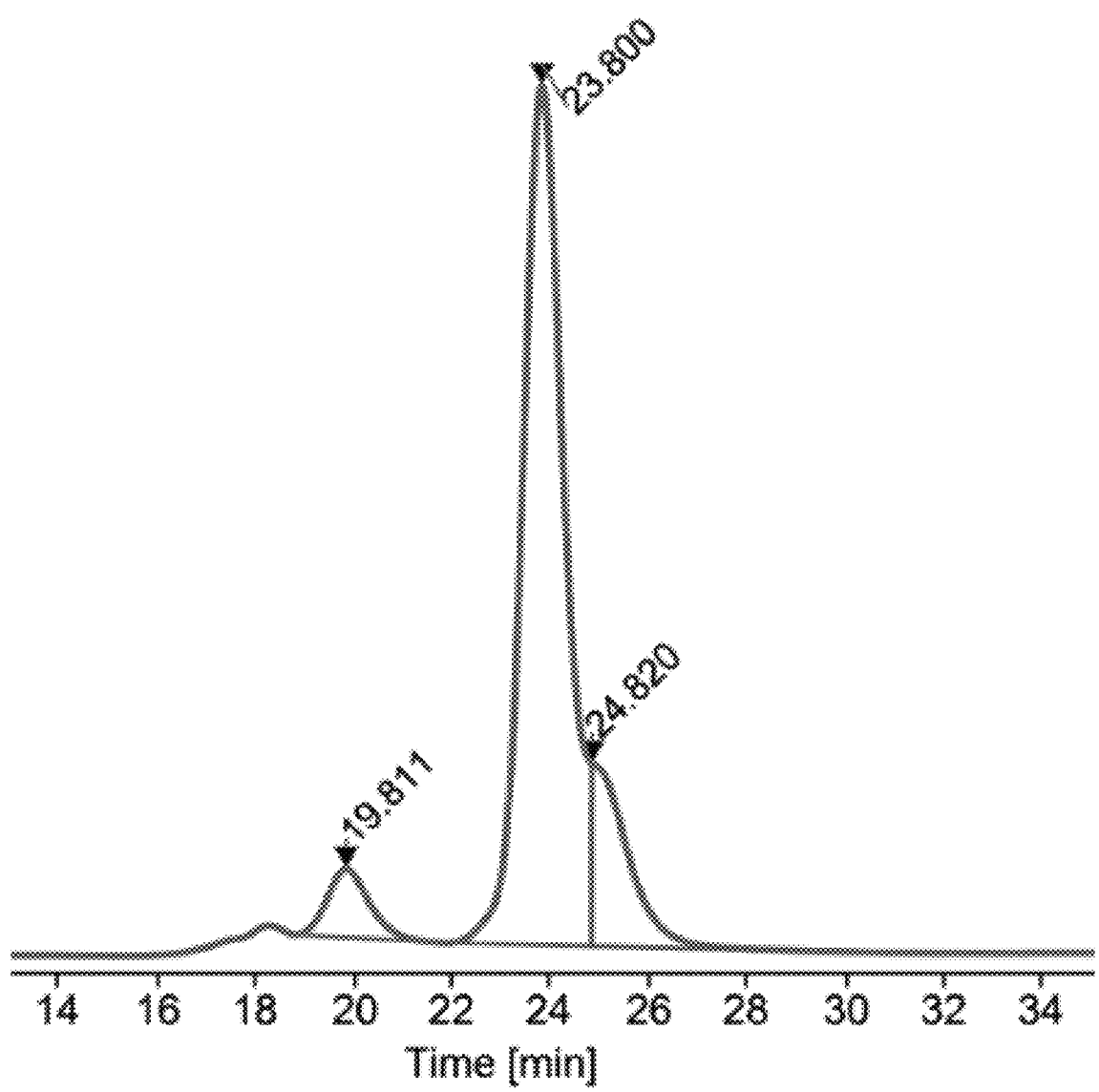

FIG. 277A-FIG. 277B show an SEC analysis of pH hold sample vs control, which indicated that no change in profile was observed after low pH hold.

Figure 278:
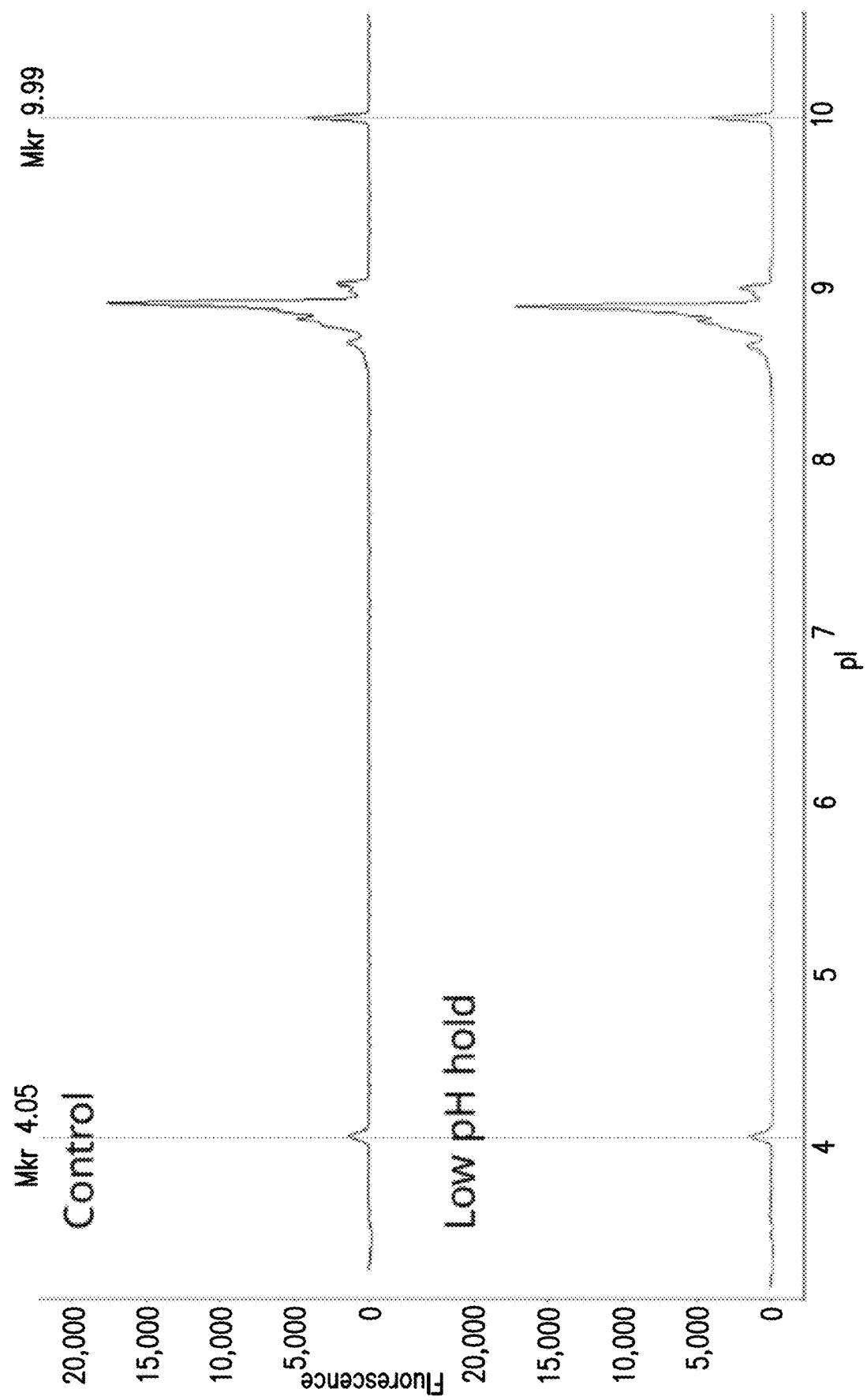
Figure 279A:
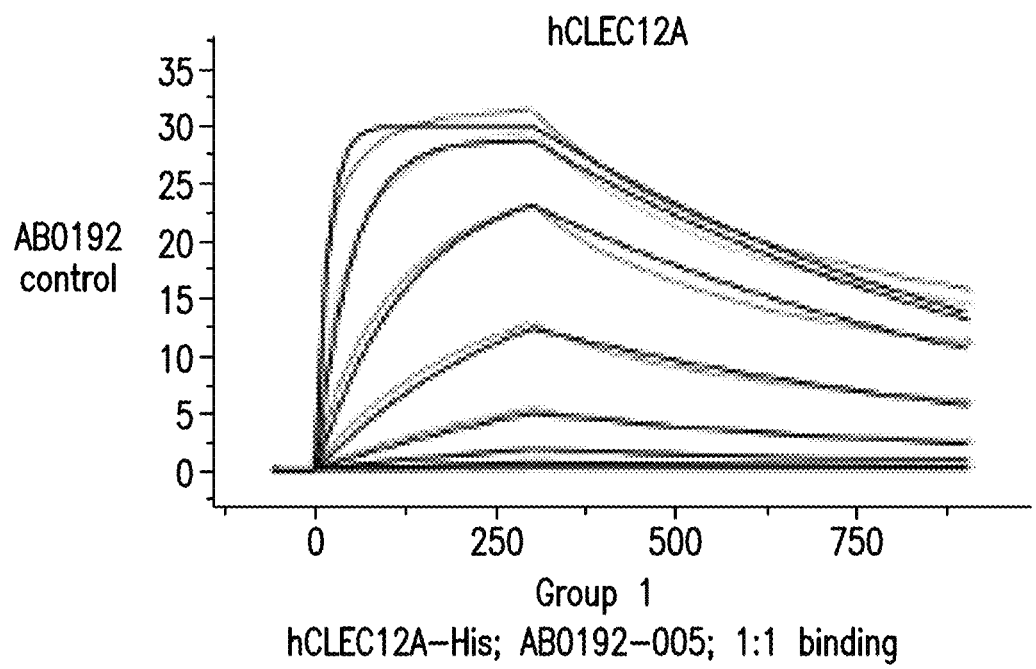
Figure 279B:
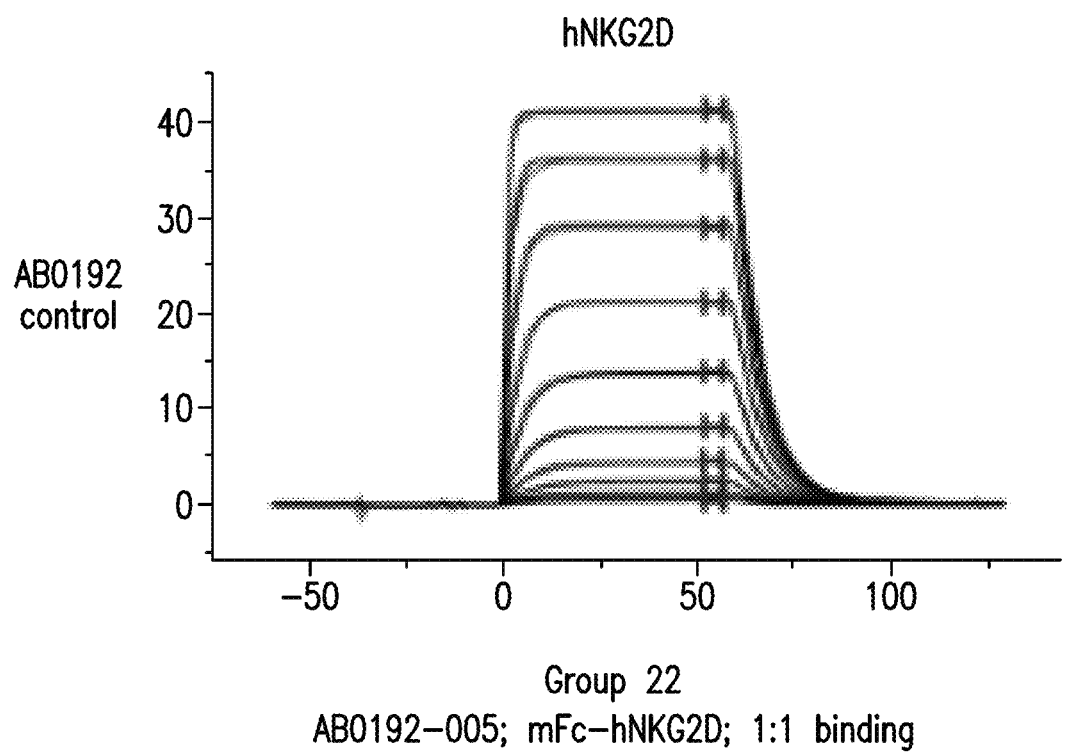
Figure 279C:
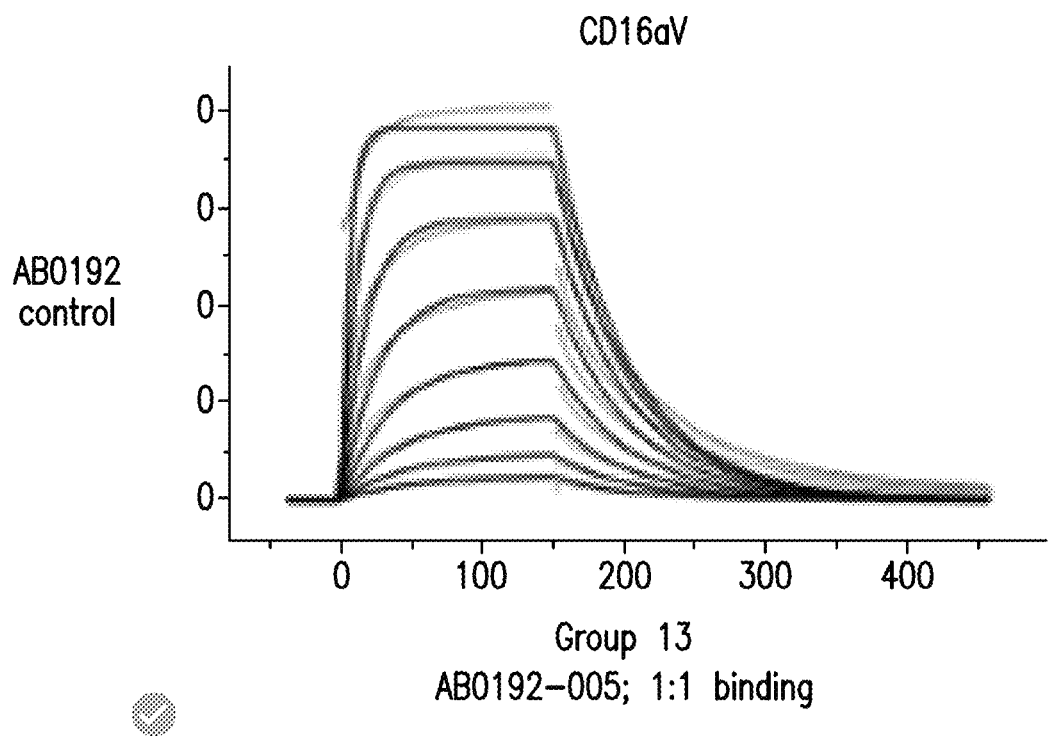
Figure 279D:
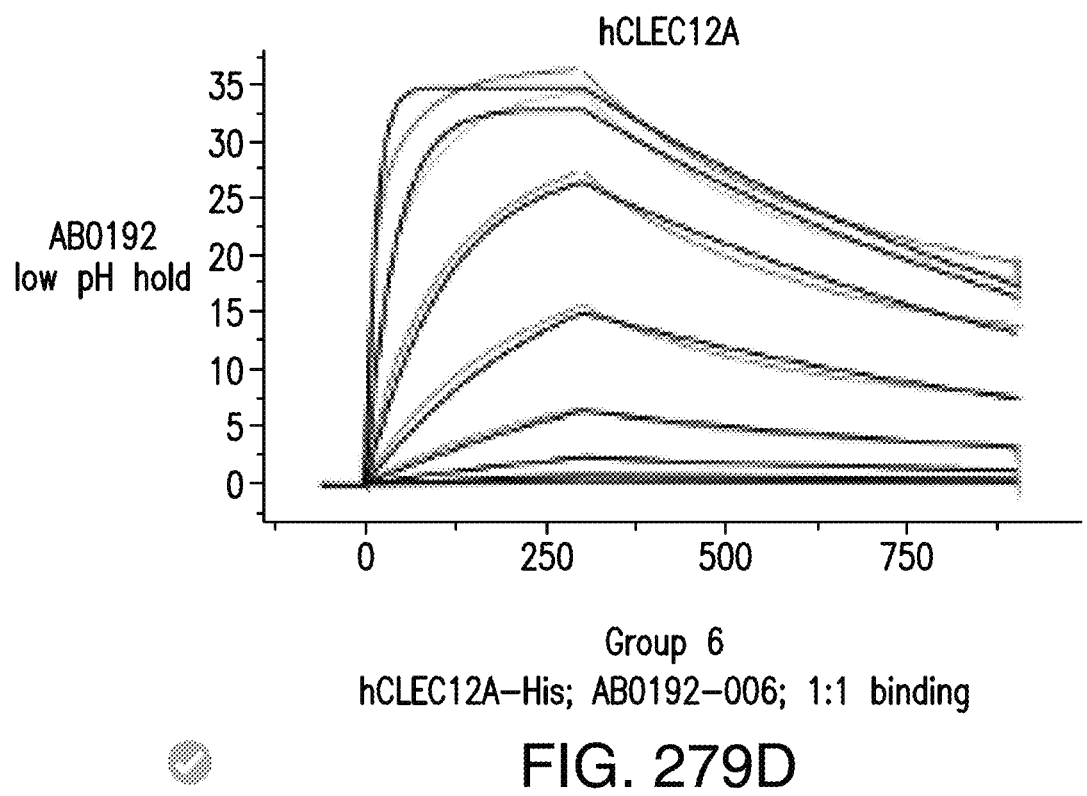
Figure 279E:
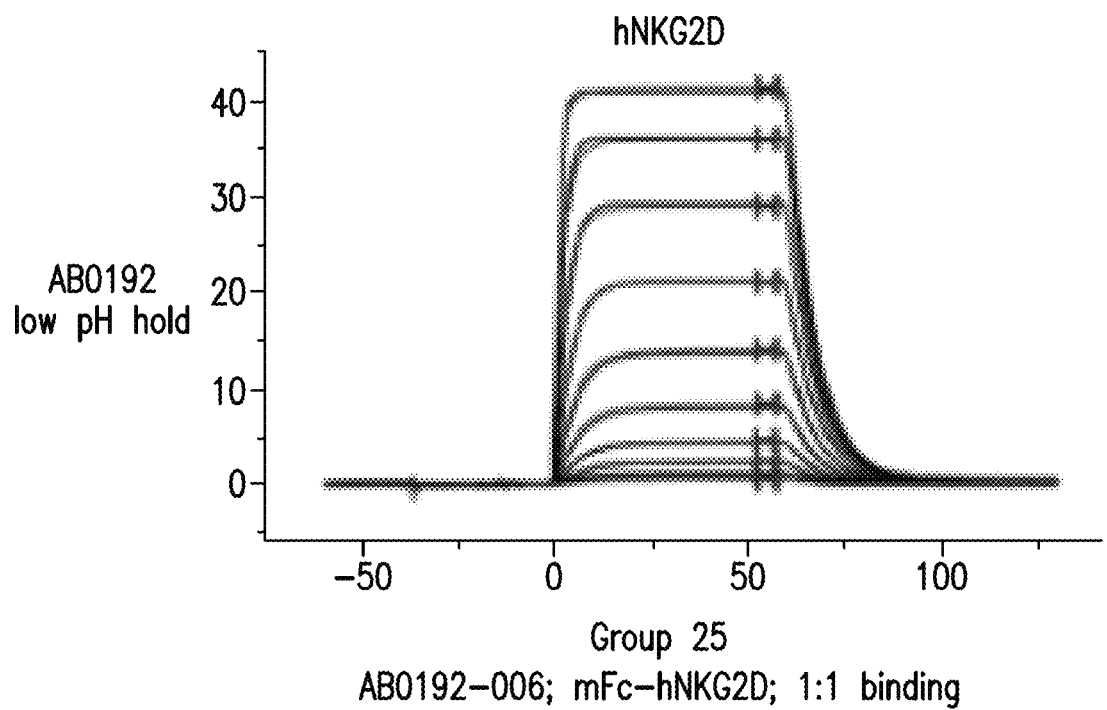
Figure 279F:
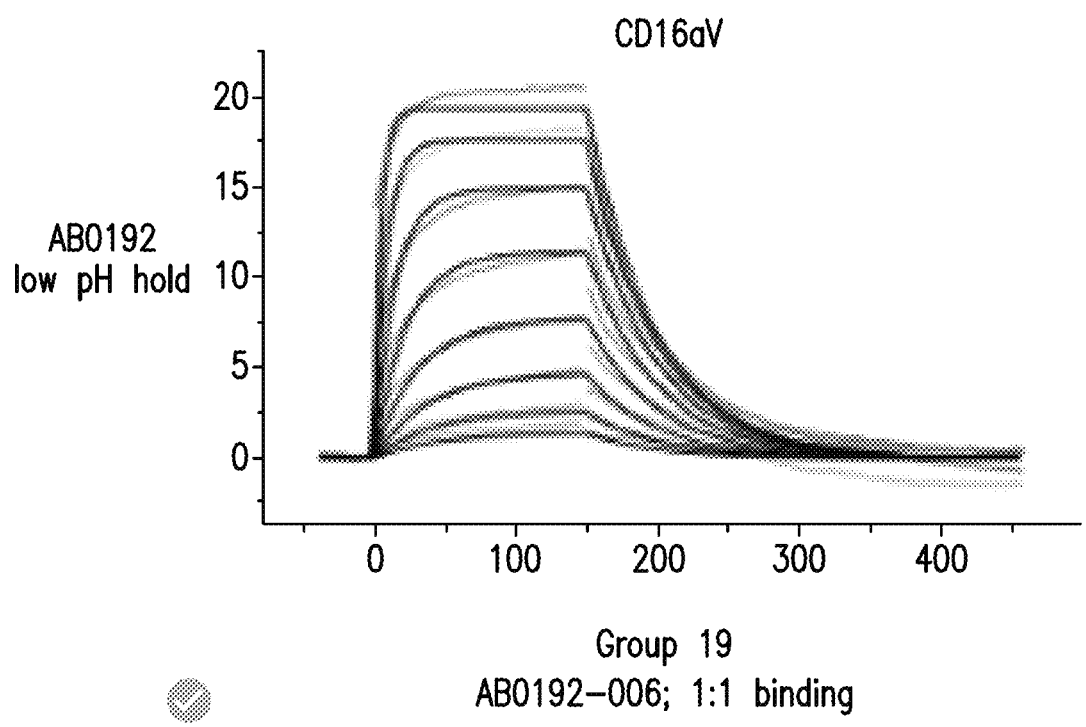

FIG. 278 shows a cIEF analysis of AB0192 after low pH hold compared to control, which indicated that the low pH hold did not have a measurable effect on the charge profile of AB0192.

FIG. 279A-FIG. 279F show that AB0192 is stable after low pH hold: no effect on CLEC12A, NKG2D or CD16a binding. Slight differences in the maximum binding signal reflect differences in capture levels.

Figure 280:
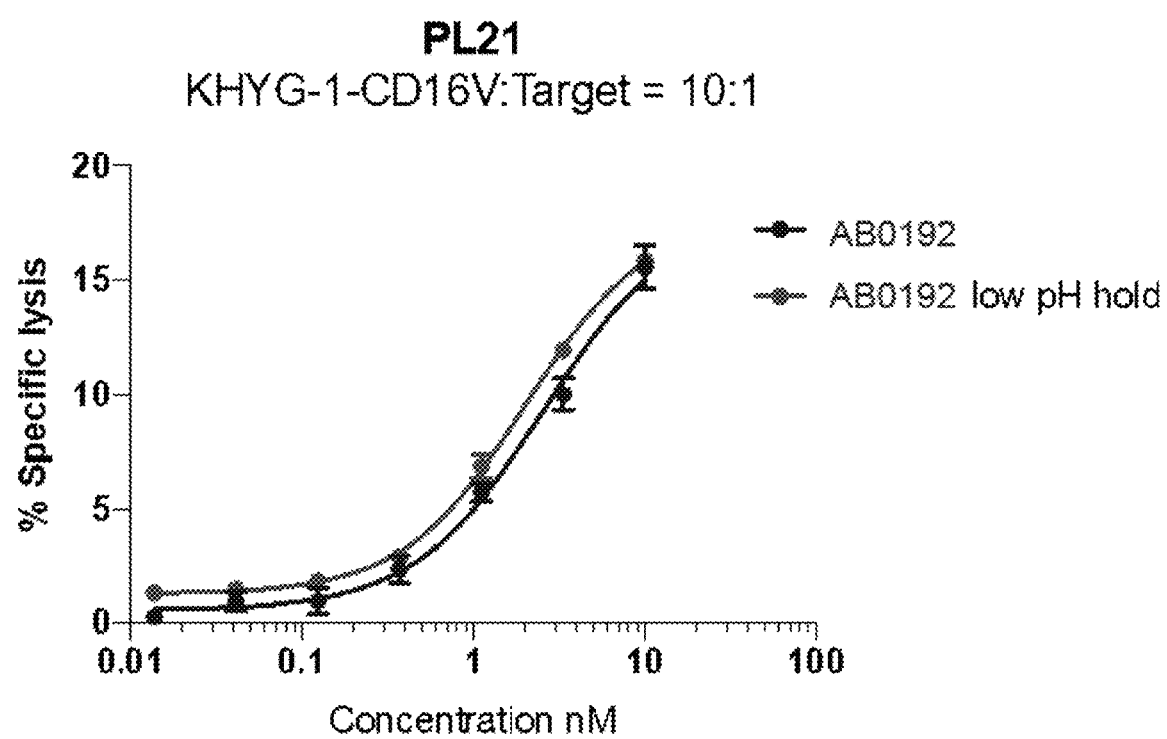

FIG. 280 shows the potency of AB0192 after low pH hold in KHYG1-CD16a mediated cytotoxicity assay, which indicated that the potency of AB0192 was unaltered after the low pH hold step.

Figure 281A:
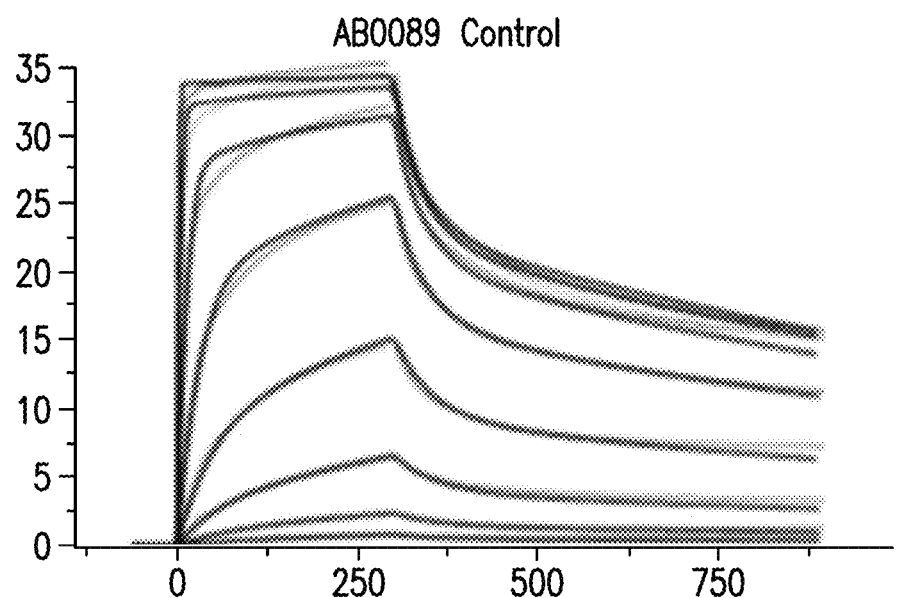
Figure 281B:
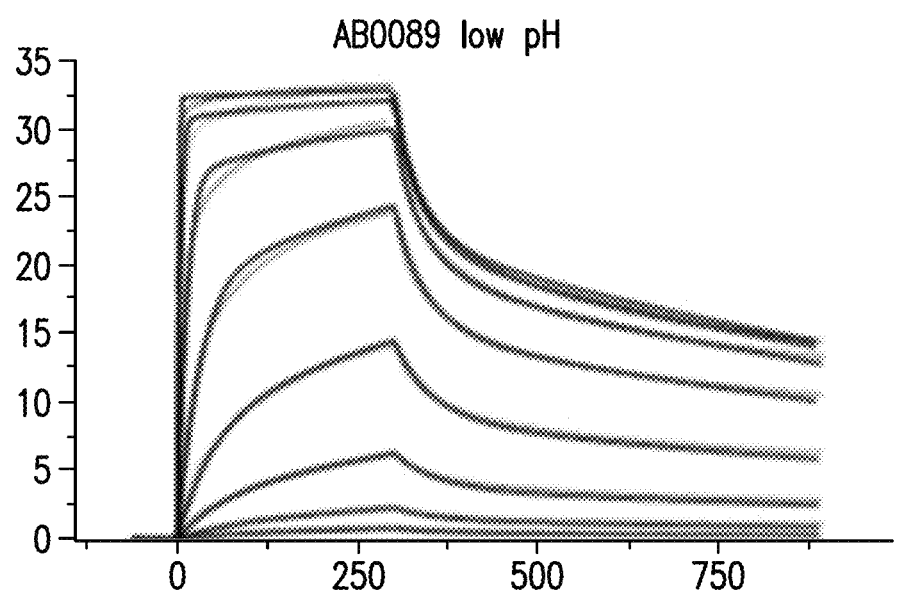

FIG. 281A-FIG. 281B show binding of AB0089 to hCLEC12A pre and post low pH hold. Slight differences in absolute maximal signals reflect difference in capture levels of AB0089.

Figure 282:
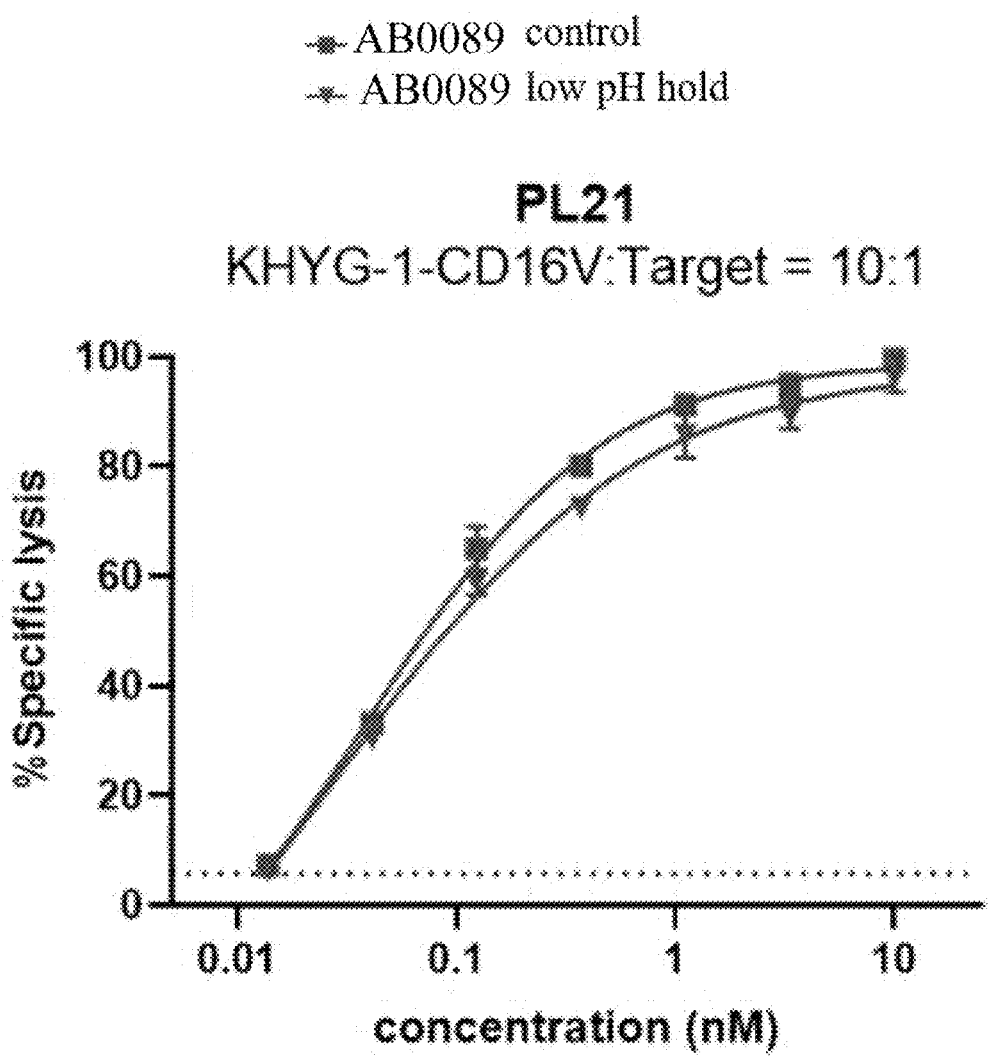

FIG. 282 shows AB0089 is stable after low pH hold. No difference between potencies of low pH hold and control samples was observed.

DETAILED DESCRIPTION

The present application provides multispecific binding proteins that bind the NKG2D receptor and CD16 receptor on natural killer cells, and the tumor-associated antigen. In some embodiments, the multispecific proteins further include an additional antigen-binding site that binds the tumor-associated antigen. The application also provides pharmaceutical compositions comprising such multispecific binding proteins, and therapeutic methods using such multispecific proteins and pharmaceutical compositions, for purposes such as treating autoimmune diseases and cancer. Various aspects of the multispecific binding proteins described in the present application are set forth below in sections; however, aspects of the multispecific binding proteins described in one particular section are not to be limited to any particular section.

To facilitate an understanding of the present application, a number of terms and phrases are defined below.

The terms "a" and "an" as used herein mean "one or more" and include the plural unless the context is inappropriate.

As used herein, the term "antigen-binding site" refers to the part of the immunoglobulin molecule that participates in antigen binding. In human antibodies, the antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FR." Thus the term "FR" refers to amino acid sequences which are naturally found between and adjacent to hypervariable regions in immunoglobulins. In a human antibody molecule, the three hypervariable regions of a light chain and the three hypervariable regions of a heavy chain are disposed relative to each other in three-dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." In certain animals, such as camels and cartilaginous fish, the antigen-binding site is formed by a single antibody chain providing a "single domain antibody." Antigen-binding sites can exist in an intact antibody, in an antigen-binding fragment of an antibody that retains the antigen-binding surface, or in a recombinant polypeptide such as an scFv, using a peptide linker to connect the heavy chain variable domain to the light chain variable domain in a single polypeptide.

The term "tumor-associated antigen" as used herein means any antigen including but not limited to a protein, glycoprotein, ganglioside, carbohydrate, lipid that is associated with cancer. Such antigen can be expressed on malignant cells or in the tumor microenvironment such as on tumor-associated blood vessels, extracellular matrix, mesenchymal stroma, or immune infiltrates. In preferred embodiments of the present disclosure, the terms "tumor-associated antigen" refers to CLEC12A.

As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably include humans.

As used herein, the term "effective amount" refers to the amount of a compound (e.g., a compound of the present application) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

As used herein, the term "pharmaceutically acceptable salt" refers to any pharmaceutically acceptable salt (e.g., acid or base) of a compound described in the present application which, upon administration to a subject, is capable of providing a compound described in this application or an active metabolite or residue thereof. As is known to those of skill in the art, "salts" of the compounds described in the present application may be derived from inorganic or organic acids and bases. Exemplary acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, though not in themselves pharmaceutically acceptable, may be employed in the preparation of salts useful as intermediates in obtaining the compounds described in the application and their pharmaceutically acceptable acid addition salts.

Exemplary bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Exemplary salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds described in the present application compounded with a suitable cation such as $Na^+$, $NH_4^+$, and $NW_4^+$ (wherein W is a $C_{1-4}$ alkyl group), and the like.

For therapeutic use, salts of the compounds described in the present application are contemplated as being pharmaceutically acceptable. However, salts of acids and bases that are non-pharmaceutically acceptable may also find use, for example, in the preparation or purification of a pharmaceutically acceptable compound.

As used herein, CLEC12A (also known as CLL-1, DCAL-2, MICL, and CD371) refers to the protein of Uniprot Accession No. Q5QGZ9 and related isoforms and orthologs.

Throughout the description, where compositions are described as having, including, or comprising specific components, or where processes and methods are described as having, including, or comprising specific steps, it is contemplated that, additionally, there are compositions described in the present application that consist essentially of, or consist of, the recited components, and that there are processes and methods according to the present application that consist essentially of, or consist of, the recited processing steps.

As a general matter, compositions specifying a percentage are by weight unless otherwise specified. Further, if a variable is not accompanied by a definition, then the previous definition of the variable controls.

| Abbreviation | Convention |
| --- | --- |
| A49M-I | Human anti-NKG2D antibody clone A49M-I |
| ADCC | Antibody dependent cellular cytotoxicity |
| ADCP | Antibody dependent cellular phagocytosis |
| AML | Acute myeloid leukemia |
| BM | Back mutation (murine residues introduced to human mAb sequence) |
| cCLEC12A | Cynomolgus monkey CLEC12A |
| CD16 | Low affinity immunoglobulin gamma Fc region receptor III-A |
| CD16a | Fc gamma receptor III |
| CDC | Complement dependent cytotoxicity |
| CDR | complementarity determining region |
| CF SE | Carboxyfluorescein succinimidyl ester |
| CHO | Chinese Hamster Ovary |
| cIEF | capillary isoelectric focusing |
| CIEX | Cation Ion Exchange Chromatography |
| CLEC12A | C-type lectin domain family 12 member A |
| CLEC12A | C-type lectin domain family 12 member A, major variant with K244, also known as CLEC12A (K244) or CLEC12A WT |
| CLEC12AL | CLEC12A-Ligand |
| CMP | Common myeloid precursor |
| ConA | Concanavalin A |
| CST | 20 mM sodium citrate, 250 mM sucrose, 0.01% Tween-80, pH 7.0 |
| DI water | Distilled water |
| DSC | Differential Scanning Calorimetry |
| EC50 | effective concentration that gives half-maximal response |
| Fab | fragment antigen-binding |
| FACS | Fluorescence activated cell sorting |
| Fc | fragment crystallizable region |
| FcγR | Fc-gamma receptor |
| GMP | Granulocyte monocyte precursor |
| FIBS | Hepes buffered saline |
| hcFAE-A49.CLL1-Merus | Duobody TriNKET based on CLL1 antibody from Merus |
| hcFAE-49.h6E7 | Duobody TriNKET based on h6E7 antibody from Genentech |
| hcFAE-A49.tepoditamab | Duobody TriNKET based on CLEC12A binding arm of tepoditamab from Merus |
| hCLEC12A | Human CLEC12A |
| HCT | Hematopoietic cell transfer |

-continued

| Abbreviation | Convention |
| --- | --- |
| HI-FBS | Heat inactivated fetal bovine serum |
| BMWS | high molecular weight species |
| HPLC | high performance liquid chromatography |
| HST | 20 mM histidine, 250 mM sucrose, 0.01% polysorbate 80 |
| HTFR | Homogenous time resolved fluorescence |
| IgG1 | immunoglobulin G1 |
| ITIM | Immunoreceptor tyrosine-based inhibitory motif |
| $k_a$ | association rate constant |
| $K_D$ | equilibrium dissociation constant |
| $k_d$ | dissociation rate constant |
| LC | liquid chromatography |
| LMWS | low molecular weight species |
| LSC | Leukemic stem cells |
| mAb | Monoclonal antibody |
| MEP | Megakaryocyte erythroid precursor |
| MFI | Median Fluorescence Intensity |
| MHC | Major histocompatibility complex |
| MIC-A | MHC class I chain-related protein A |
| MS | mass spectrometry |
| MS/MS | tandem mass spectrometry |
| MSU | Monosodium urate |
| NK cell | Natural killer cell |
| NKG2D | NKG2-D type II integral membrane protein |
| PBS | phosphate buffered saline |
| PBSF | Phosphate Buffered Saline (0.1% Bovine Serum Albumin (BSA)) |
| pI | isoelectric point |
| PI3K | phosphatidylinositol 3' kinase |
| PMT | Photomultiplier tube |
| PS-80 | polysorbate-80, Tween-80 |
| PSR | Poly Specific Reagent |
| RU | resonance units, a measure of mass reported by SPR |
| ScFv | single-chain variable fragment |
| SDS-CE | sodium dodecyl sulfate capillary electrophoresis |
| SEC | size exclusion chromatography |
| SH2 | Src homology 2 domain |
| SHP1 | Src homology region 2 domain-containing phosphatase-1 |
| SHP2 | Src homology region 2 domain-containing phosphatase-2 |
| SPR | surface plasmon resonance |
| TAA | Tumor associated antigen |
| TriNKET | Trispecific Natural Killer cell Engaging Therapy |
| UHPLC | ultra-high performance liquid chromatography |
| WT | Wild-type |

I. Proteins

The present application provides multispecific binding proteins that bind to the NKG2D receptor and CD16 receptor on natural killer cells, and CLEC12A. The multispecific binding proteins are useful in the pharmaceutical compositions and therapeutic methods described herein. Binding of the multispecific binding proteins to the NKG2D receptor and CD16 receptor on a natural killer cell enhances the activity of the natural killer cell toward destruction of tumor cells expressing the tumor antigen. Binding of the multispecific binding proteins to tumor antigen expressing tumor cells brings these cells into proximity with the natural killer cell, which facilitates direct and indirect destruction of the tumor cells by the natural killer cell. Multispecific binding proteins that bind NKG2D, CD16, and another target are disclosed in International Application Publication Nos. WO2018148445 and WO2019157366, which are not incorporated herein by reference. Further description of some exemplary multispecific binding proteins is provided below.

The first component of the multispecific binding protein is an antigen-binding site that binds to NKG2D receptor-expressing cells, which can include but are not limited to NK cells, γδ T cells and CD8$^+$ αβ T cells. Upon NKG2D binding, the multispecific binding proteins may block natural ligands, such as ULBP6 and MICA, from binding to NKG2D and activating NK cells.

The second component of the multispecific binding proteins is an antigen-binding site that binds CLEC12A, a tumor-associated antigen. The tumor-associated antigen expressing cells may be found, for example, in solid tumor indications such as gastric cancer, esophageal cancer, lung cancer, breast cancer (e.g., triple-negative breast cancer), colorectal cancer, ovarian cancer, esophageal cancer, uterine cancer, cervical cancer, head and neck cancer, glioma, and pancreatic cancer, or in certain hematological malignancies such as acute myeloid leukemia.

The third component of the multispecific binding proteins is an antibody Fc domain or a portion thereof or an antigen-binding site that binds to cells expressing CD16, an Fc receptor on the surface of leukocytes including natural killer cells, macrophages, neutrophils, eosinophils, mast cells, and follicular dendritic cells.

An additional antigen-binding site of the multispecific binding proteins may bind the same tumor-associated antigen. In certain embodiments, the first antigen-binding site that binds NKG2D is an scFv, and the second and the additional antigen-binding sites that bind the tumor-associated antigen are each a Fab fragment. In certain embodiments, the first antigen-binding site that binds NKG2D is an scFv, and the second and the additional antigen-binding sites that bind the tumor-associated antigen are each an scFv. In certain embodiments, the first antigen-binding site that binds NKG2D is a Fab fragment, and the second and the additional antigen-binding sites that bind the tumor-associated antigen are each an scFv. In certain embodiments, the first antigen-binding site that binds NKG2D is a Fab, and the second and the additional antigen-binding sites that bind the tumor-associated antigen are each a Fab fragment.

The antigen-binding sites may each incorporate an antibody heavy chain variable domain and an antibody light chain variable domain (e.g., arranged as in an antibody, or fused together to form an scFv), or one or more of the antigen-binding sites may be a single domain antibody, such as a $V_HH$ antibody like a camelid antibody or a $V_{NAR}$ antibody like those found in cartilaginous fish.

In some embodiments, the second antigen-binding site incorporates a light chain variable domain having an amino acid sequence identical to the amino acid sequence of the light chain variable domain present in the first antigen-binding site.

Figure 1:
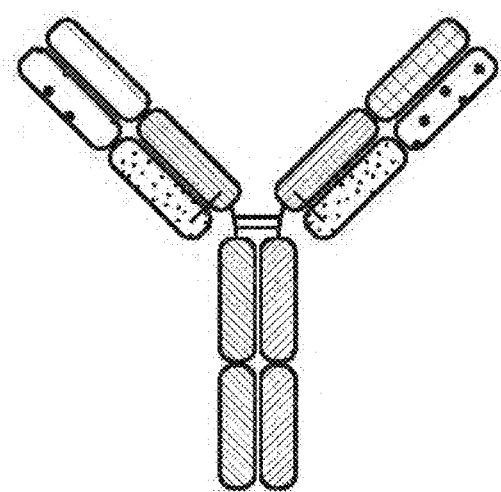
FIG. 1 is a representation of a heterodimeric, multispecific antibody, e.g., a trispecific binding protein (TriNKET). Each arm can represent either the NKG2D-binding domain, or the binding domain corresponding to a tumor-associated antigen. In some embodiments, the NKG2D binding domain and the tumor-associated antigen binding domains can share a common light chain.

The multispecific binding proteins described herein can take various formats. For example, one format is a heterodimeric, multispecific antibody including a first immunoglobulin heavy chain, a first immunoglobulin light chain, a second immunoglobulin heavy chain and a second immunoglobulin light chain (FIG. 1). The first immunoglobulin heavy chain includes a first Fc (hinge-CH2-CH3) domain, a first heavy chain variable domain and optionally a first CH1 heavy chain domain. The first immunoglobulin light chain includes a first light chain variable domain and optionally a first light chain constant domain. The first immunoglobulin light chain, together with the first immunoglobulin heavy chain, forms an antigen-binding site that binds NKG2D. The second immunoglobulin heavy chain comprises a second Fc (hinge-CH2-CH3) domain, a second heavy chain variable domain and optionally a second CH1 heavy chain domain. The second immunoglobulin light chain includes a second light chain variable domain and optionally a second light chain constant domain. The second immunoglobulin light chain, together with the second immunoglobulin heavy chain, forms an antigen-binding site that binds CLEC12A.

In some embodiments, the first Fc domain and second Fc domain together are able to bind to CD16 (FIG. 1). In some embodiments, the first immunoglobulin light chain is identical to the second immunoglobulin light chain.

Figure 2A:
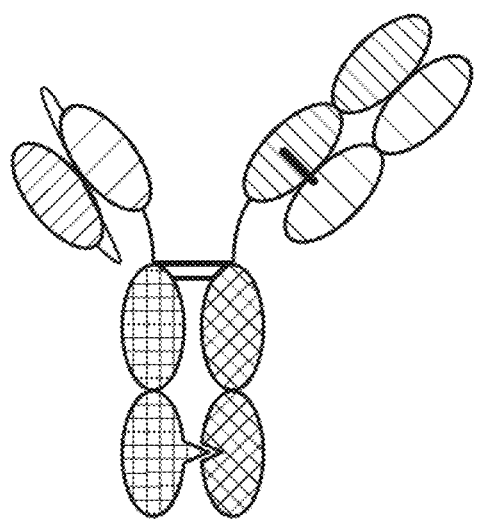
FIG. 2A-FIG. 2E illustrate five exemplary formats of a multispecific binding protein, e.g., a trispecific binding protein (TriNKET).

Another exemplary format involves a heterodimeric, multispecific antibody including a first immunoglobulin heavy chain, a second immunoglobulin heavy chain and an immunoglobulin light chain (e.g., FIG. 2A). In some embodiments, the first immunoglobulin heavy chain includes a first Fc (hinge-CH2-CH3) domain fused via either a linker or an antibody hinge to a single-chain variable fragment (scFv) composed of a heavy chain variable domain and light chain variable domain, which pair and bind NKG2D or bind CLEC12A. The second immunoglobulin heavy chain includes a second Fc (hinge-CH2-CH3) domain, a second heavy chain variable domain and a CH1 heavy chain domain. The immunoglobulin light chain includes a light chain variable domain and a light chain constant domain. In some embodiments, the second immunoglobulin heavy chain pairs with the immunoglobulin light chain and binds to NKG2D or binds the tumor-associated antigen, with the proviso that when the first Fc domain is fused to an scFv that binds NKG2D, the second immunoglobulin heavy chain paired with the immunoglobulin light chain binds the tumor-associated antigen, but not NKG2D, and vice versa. In some embodiments, the scFv in the first immunoglobulin heavy chain binds CLEC12A; and the heavy chain variable domain in the second immunoglobulin heavy chain and the light chain variable domain in the immunoglobulin light chain, when paired, bind NKG2D (e.g., FIG. 2E). In some embodiments, the scFv in the first immunoglobulin heavy chain binds NKG2D; and the heavy chain variable domain in the second immunoglobulin heavy chain and the light chain variable domain in the immunoglobulin light chain, when paired, bind CLEC12A. In some embodiments, the first Fc domain and the second Fc domain together are able to bind to CD16 (e.g., FIG. 2A).

Figure 2B:
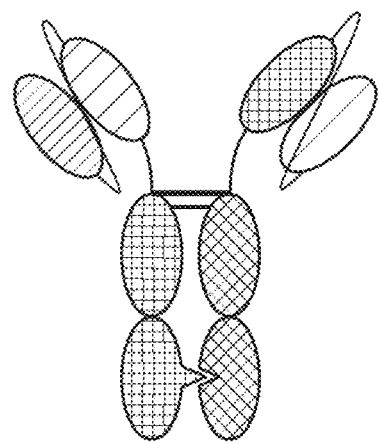

Another exemplary format involves a heterodimeric, multispecific antibody including a first immunoglobulin heavy chain, and a second immunoglobulin heavy chain (e.g., FIG. 2B). In some embodiments, the first immunoglobulin heavy chain includes a first Fc (hinge-CH2-CH3) domain fused via either a linker or an antibody hinge to a single-chain variable fragment (scFv) composed of a heavy chain variable domain and light chain variable domain, which pair and bind NKG2D, or bind CLEC12A. In some embodiments, the second immunoglobulin heavy chain includes a second Fc (hinge-CH2-CH3) domain fused via either a linker or an antibody hinge to a single-chain variable fragment (scFv) composed of a heavy chain variable domain and light chain variable domain which pair and bind NKG2D, or bind the tumor-associated antigen, with the proviso that when the first Fc domain is fused to an scFv that binds NKG2D, the second Fc domain fused to an scFv binds the tumor-associated antigen, but not NKG2D, and vice versa. In some embodiments, the first Fc domain and the second Fc domain together are able to bind to CD16 (e.g., FIG. 2B).

In some embodiments, the single-chain variable fragment (scFv) described above is linked to the antibody constant domain via a hinge sequence. In some embodiments, the hinge comprises amino acids Ala-Ser or Gly-Ser. In some embodiments, the hinge connects an scFv that binds NKG2D and the antibody heavy chain constant domain comprises amino acids Ala-Ser. In some embodiments, the hinge connects an scFv that binds the tumor-associated antigen and the antibody heavy chain constant domain comprises amino acids Gly-Ser. In some other embodiments, the hinge comprises amino acids Ala-Ser and Thr-Lys-Gly. The hinge sequence can provide flexibility of binding to the target antigen, and balance between flexibility and optimal geometry.

In some embodiments, the single-chain variable fragment (scFv) described above includes a heavy chain variable domain and a light chain variable domain. In some embodiments, the heavy chain variable domain forms a disulfide bridge with the light chain variable domain to enhance stability of the scFv. For example, a disulfide bridge can be formed between the C44 residue of the heavy chain variable domain and the C100 residue of the light chain variable domain, the amino acid positions numbered under Kabat. In some embodiments, the heavy chain variable domain is linked to the light chain variable domain via a flexible linker. Any suitable linker can be used, for example, the $(G_4S)_4$ linker (($GlyGlyGlyGlySer)_4$ (SEQ ID NO:119)). In some embodiments of the scFv, the heavy chain variable domain is positioned at the N-terminus of the light chain variable domain. In some embodiments of the scFv, the heavy chain variable domain is positioned at the C terminus of the light chain variable domain.

The multispecific binding proteins described herein can further include one or more additional antigen-binding sites. The additional antigen-binding site(s) may be fused to the N-terminus of the constant region CH2 domain or to the C-terminus of the constant region CH3 domain, optionally via a linker sequence. In certain embodiments, the additional antigen-binding site(s) takes the form of a single-chain variable region (scFv) that is optionally disulfide-stabilized, resulting in a tetravalent or trivalent multispecific binding protein. For example, a multispecific binding protein includes a first antigen-binding site that binds NKG2D, a second antigen-binding site that binds CLEC12A, an additional antigen-binding site that binds the tumor-associated antigen, and an antibody constant region or a portion thereof sufficient to bind CD16 or a fourth antigen-binding site that binds CD16. Any one of these antigen binding sites can either take the form of a Fab fragment or an scFv, such as an scFv described above.

Figure 2C:
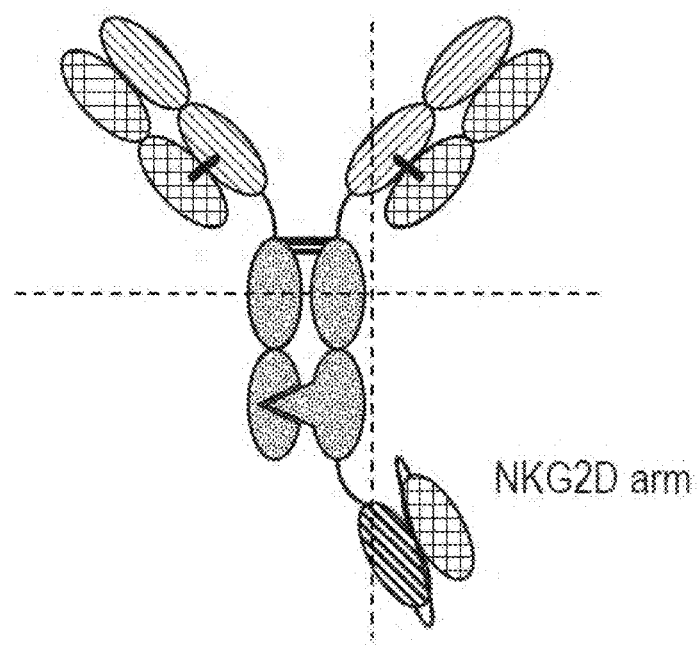
Figure 2D:
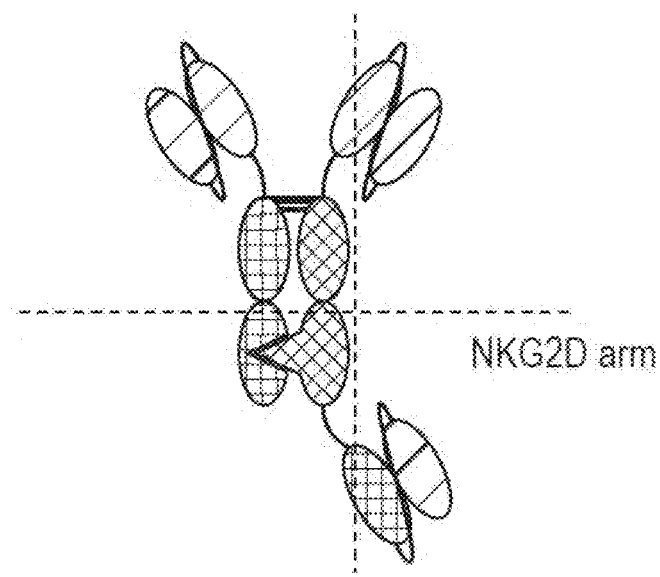
Figure 2E:
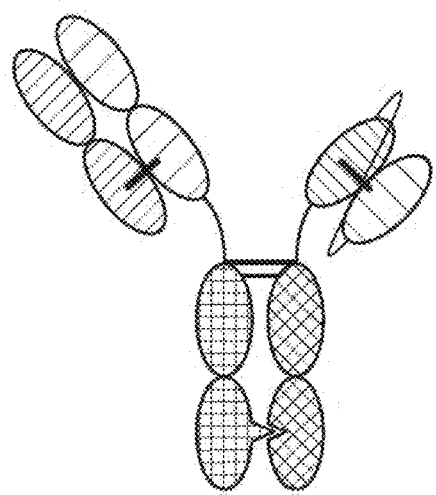
Figure 3:
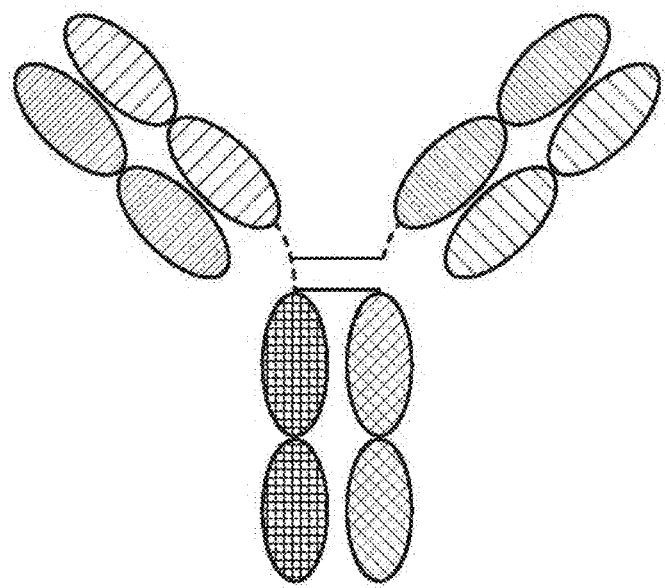
FIG. 3 is a representation of a TriNKET in the Triomab form, which is a trifunctional, bispecific antibody that maintains an IgG-like shape. This chimera consists of two half antibodies, each with one light and one heavy chain, that originate from two parental antibodies. Triomab form may be a heterodimeric construct containing ½ of rat antibody and ½ of mouse antibody.
Figure 4:
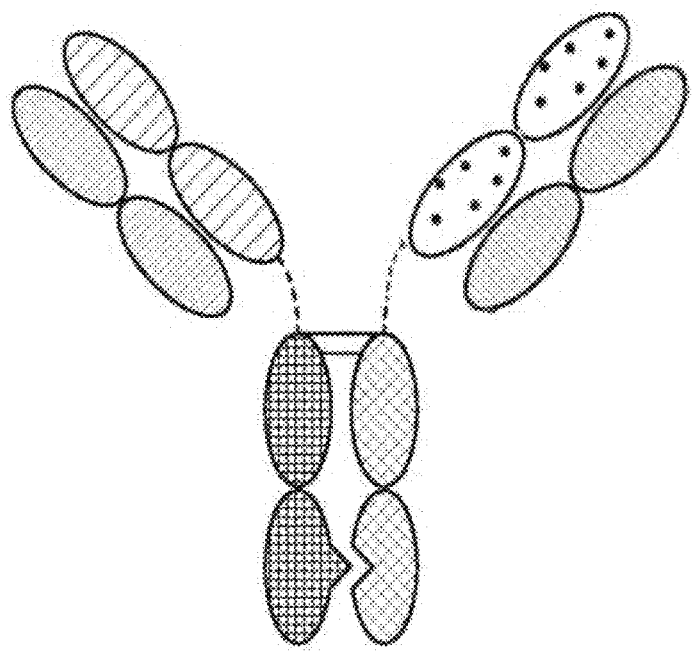
FIG. 4 is a representation of a TriNKET in the KiH Common Light Chain form, which involves the knobs-into-holes (KIHs) technology. KiH is a heterodimer containing 2 Fab fragments binding to target 1 and 2, and an Fc stabilized by heterodimerization mutations. TriNKET in the KiH format may be a heterodimeric construct with 2 Fab fragments binding to target 1 and target 2, containing two different heavy chains and a common light chain that pairs with both heavy chains.
Figure 5:
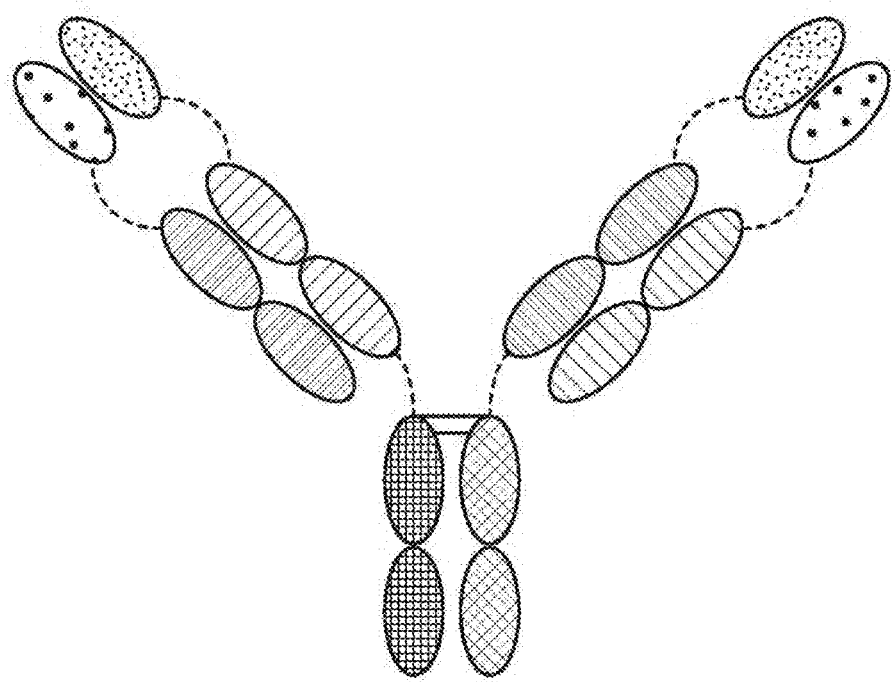
FIG. 5 is a representation of a TriNKET in the dual-variable domain immunoglobulin (DVD-Ig™) form, which combines the target-binding domains of two monoclonal antibodies via flexible naturally occurring linkers, and yields a tetravalent IgG-like molecule. DVD-Ig™ is a homodimeric construct where variable domain targeting antigen 2 is fused to the N-terminus of a variable domain of Fab fragment targeting antigen 1. DVD-Ig™ form contains normal Fc.
Figure 6:
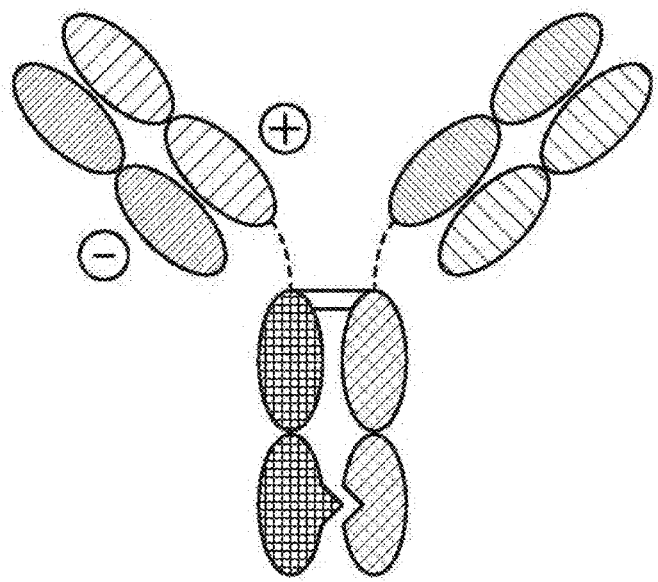
FIG. 6 is a representation of a TriNKET in the Orthogonal Fab fragment interface (Ortho-Fab) form, which is a heterodimeric construct that contains 2 Fab fragments binding to target 1 and target 2 fused to Fc. Light chain (LC)-heavy chain (HC) pairing is ensured by orthogonal interface. Heterodimerization is ensured by mutations in the Fc.
Figure 7:
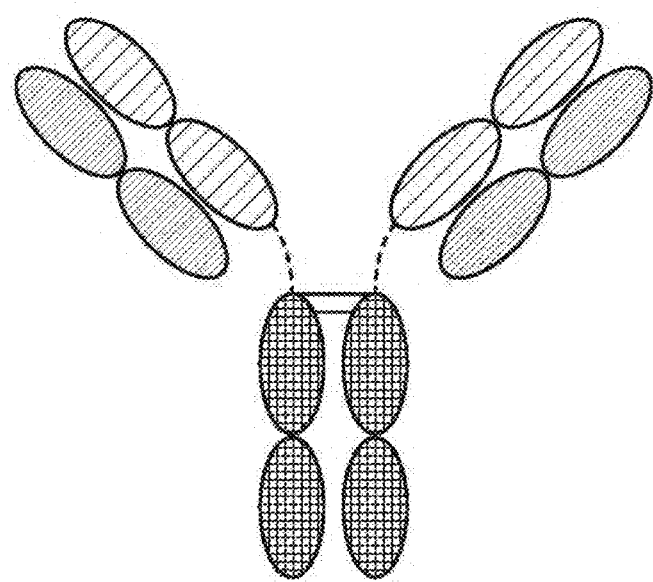
FIG. 7 is a representation of a TriNKET in the 2-in-1 Ig format.
Figure 8:
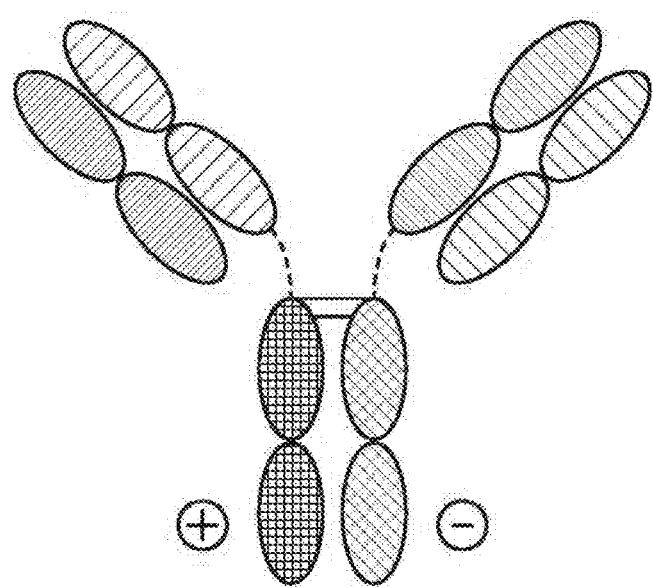
FIG. 8 is a representation of a TriNKET in the ES form, which is a heterodimeric construct containing two different Fab fragments binding to target 1 and target 2 fused to the Fc. Heterodimerization is ensured by electrostatic steering mutations in the Fc.
Figure 9:
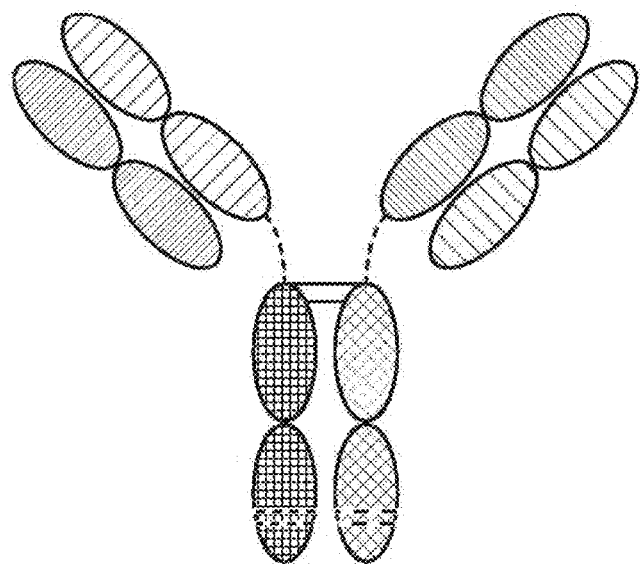
FIG. 9 is a representation of a TriNKET in the Fab Arm Exchange form: antibodies that exchange Fab fragment arms by swapping a heavy chain and attached light chain (half-molecule) with a heavy-light chain pair from another molecule, resulting in bispecific antibodies. Fab Arm Exchange form (cFae) is a heterodimer containing 2 Fab fragments binding to target 1 and 2, and an Fc stabilized by heterodimerization mutations.
Figure 10:
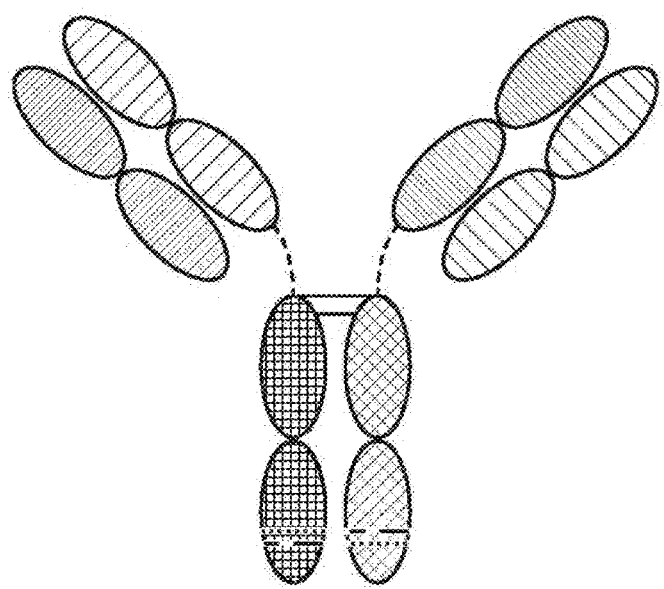
FIG. 10 is a representation of a TriNKET in the SEED Body form, which is a heterodimer containing 2 Fab fragments binding to target 1 and 2, and an Fc stabilized by heterodimerization mutations.
Figure 11:
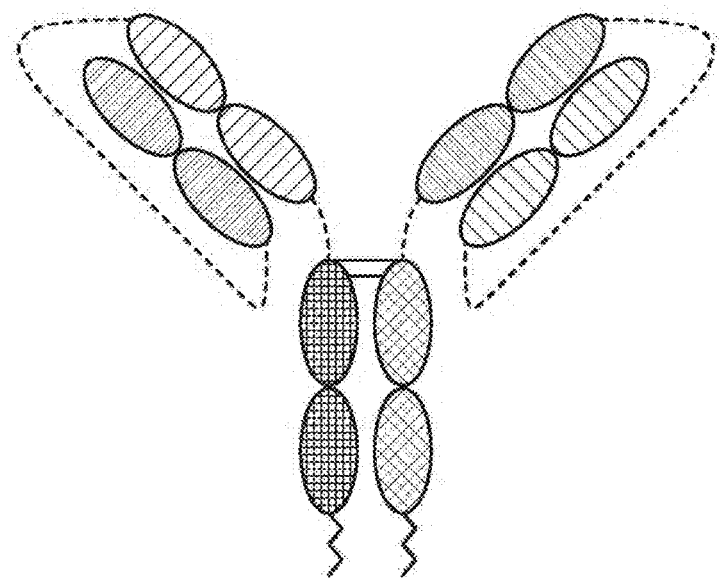
FIG. 11 is a representation of a TriNKET in the LuZ-Y form, in which a leucine zipper is used to induce heterodimerization of two different HCs. The LuZ-Y form is a heterodimer containing two different scFabs binding to target 1 and 2, fused to Fc. Heterodimerization is ensured through leucine zipper motifs fused to C-terminus of Fc.
Figure 12:
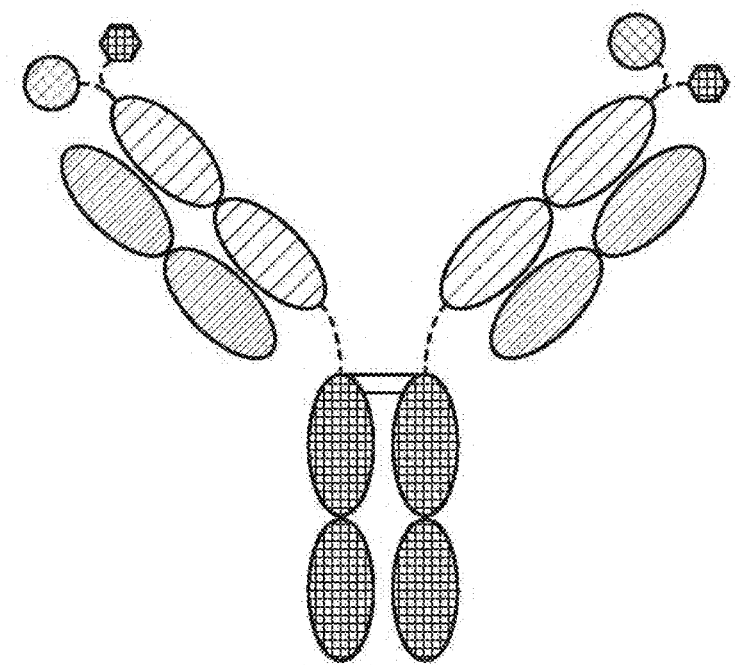
FIG. 12 is a representation of a TriNKET in the Cov-X-Body form.

In some embodiments, the additional antigen-binding site binds a different epitope of the tumor-associated antigen from the second antigen-binding site. In some embodiments, the additional antigen-binding site binds the same epitope as the second antigen-binding site. In some embodiments, the additional antigen-binding site comprises the same heavy chain and light chain CDR sequences as the second antigen-binding site. In some embodiments, the additional antigen-binding site comprises the same heavy chain and light chain variable domain sequences as the second antigen-binding site. In some embodiments, the additional antigen-binding site has the same amino acid sequence(s) as the second antigen-binding site. In some embodiments, the additional antigen-binding site comprises heavy chain and light chain variable domain sequences that are different from the heavy chain and light chain variable domain sequences of the second antigen-binding site. In some embodiments, the additional antigen-binding site has an amino acid sequence that is different from the sequence of the second antigen-binding site. In some embodiments, the second antigen-binding site and the additional antigen-binding site bind different tumor-associated antigens. In some embodiments, the second antigen-binding site and the additional antigen-binding site binds different antigens. Exemplary formats are shown in FIG. 2C and FIG. 2D. Accordingly, the multispecific binding proteins can provide bivalent engagement of the tumor-associated antigen. Bivalent engagement of the tumor-associated antigen by the multispecific proteins can stabilize the tumor-associated antigen on the tumor cell surface and enhance cytotoxicity of NK cells towards the tumor cells. Bivalent engagement of the tumor-associated antigen by the multispecific proteins can confer stronger binding of the multispecific proteins to the tumor cells, thereby facilitating stronger cytotoxic response of NK cells towards the tumor cells, especially towards tumor cells expressing a low level of the tumor-associated antigen.

The multispecific binding proteins can take additional formats. In some embodiments, the multispecific binding protein is in the Triomab form, which is a trifunctional, bispecific antibody that maintains an IgG-like shape. This chimera consists of two half antibodies, each with one light and one heavy chain, that originate from two parental antibodies.

In some embodiments, the multispecific binding protein is the KiH form, which involves the knobs-into-holes (KiHs) technology. The KiH involves engineering $C_H3$ domains to create either a "knob" or a "hole" in each heavy chain to promote heterodimerization. The concept behind the "Knobs-into-Holes (KiH)" Fc technology was to introduce a "knob" in one CH3 domain (CH3A) by substitution of a small residue with a bulky one (e.g., $T366W_{CH3A}$ in EU numbering). To accommodate the "knob," a complementary "hole" surface was created on the other CH3 domain (CH3B) by replacing the closest neighboring residues to the knob with smaller ones (e.g., $T366S/L368A/Y407V_{CH3B}$). The "hole" mutation was optimized by structured-guided phage library screening (Atwell S, Ridgway J B, Wells J A, Carter P., Stable heterodimers from remodeling the domain interface of a homodimer using a phage display library, *J. Mol. Biol.* (1997) 270(1):26-35). X-ray crystal structures of KiH Fc variants (Elliott J M, Ultsch M, Lee J, Tong R, Takeda K, Spiess C, et al., Antiparallel conformation of knob and hole aglycosylated half-antibody homodimers is mediated by a CH2-CH3 hydrophobic interaction. *J. Mol. Biol.* (2014) 426(9):1947-57; Mimoto F, Kadono S, Katada H, Igawa T, Kamikawa T, Hattori K. Crystal structure of a novel asymmetrically engineered Fc variant with improved affinity for FcγRs. *Mol. Immunol.* (2014) 58(1):132-8) demonstrated that heterodimerization is thermodynamically favored by hydrophobic interactions driven by steric complementarity at the inter-CH3 domain core interface, whereas the knob-knob and the hole-hole interfaces do not favor homodimerization owing to steric hindrance and disruption of the favorable interactions, respectively.

In some embodiments, the multispecific binding protein is in the dual-variable domain immunoglobulin (DVD-Ig™) form, which combines the target binding domains of two monoclonal antibodies via flexible naturally occurring linkers, and yields a tetravalent IgG-like molecule.

In some embodiments, the multispecific binding protein is in the Orthogonal Fab interface (Ortho-Fab) form. In the ortho-Fab IgG approach (Lewis S M, Wu X, Pustilnik A, Sereno A, Huang F, Rick H L, et al., Generation of bispecific IgG antibodies by structure-based design of an orthogonal Fab interface. *Nat. Biotechnol.* (2014) 32(2):191-8), structure-based regional design introduces complementary mutations at the LC and $HC_{VH-CH1}$ interface in only one Fab fragment, without any changes being made to the other Fab fragment.

In some embodiments, the multispecific binding protein is in the 2-in-1 Ig format. In some embodiments, the multispecific binding protein is in the ES form, which is a heterodimeric construct containing two different Fab fragments binding to targets 1 and target 2 fused to the Fc. Heterodimerization is ensured by electrostatic steering mutations in the Fc.

Figure 13A:
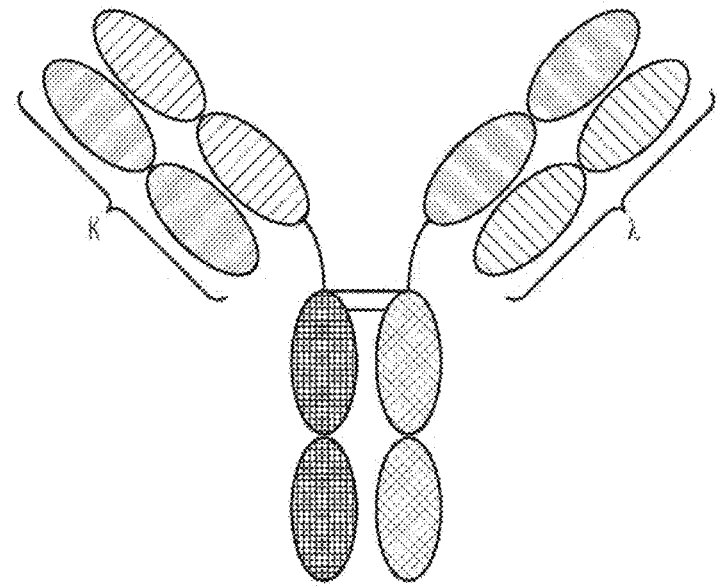
FIG. 13A-FIG. 13B are representations of TriNKETs in the κλ-Body forms, which are heterodimeric constructs with two different Fab fragments fused to Fc stabilized by heterodimerization mutations: one Fab fragment targeting antigen 1 contains kappa LC, and the second Fab fragment targeting antigen 2 contains lambda LC.
Figure 13B:
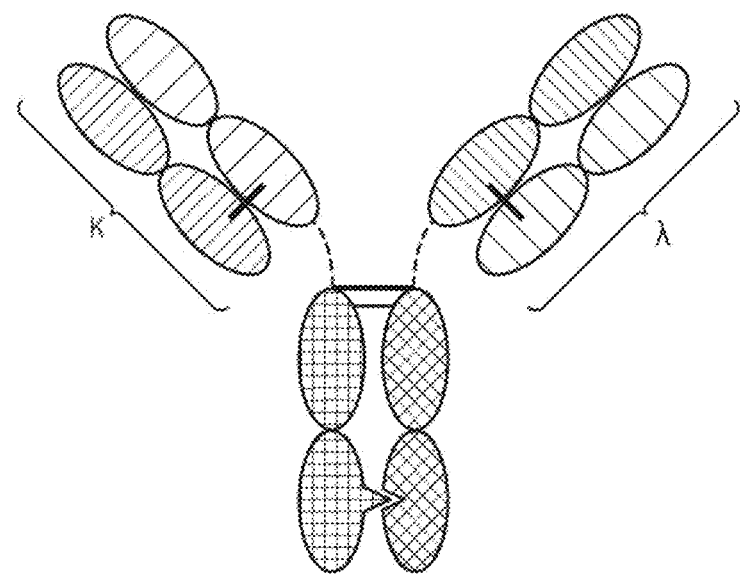
Figure 14:
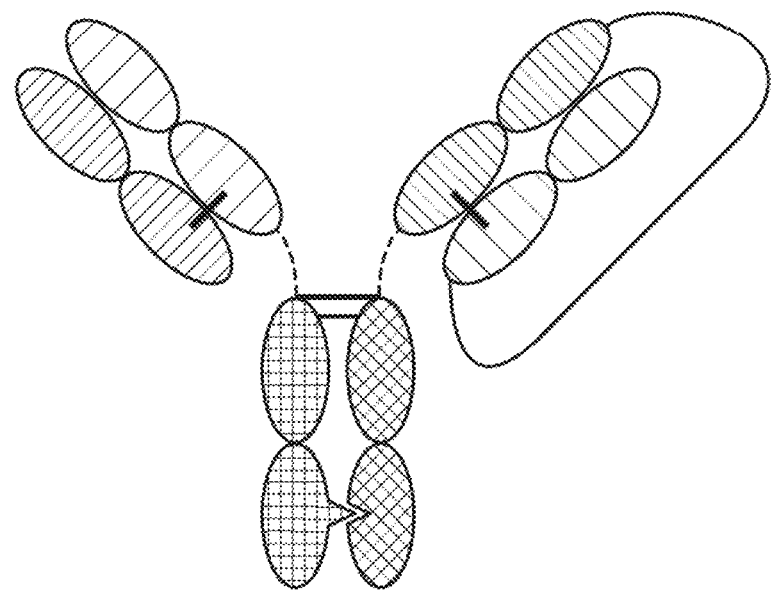
FIG. 14 is an Oasc-Fab heterodimeric construct that includes Fab fragment binding to target 1 and scFab binding to target 2, both of which are fused to the Fc domain. Heterodimerization is ensured by mutations in the Fc domain.
Figure 15:
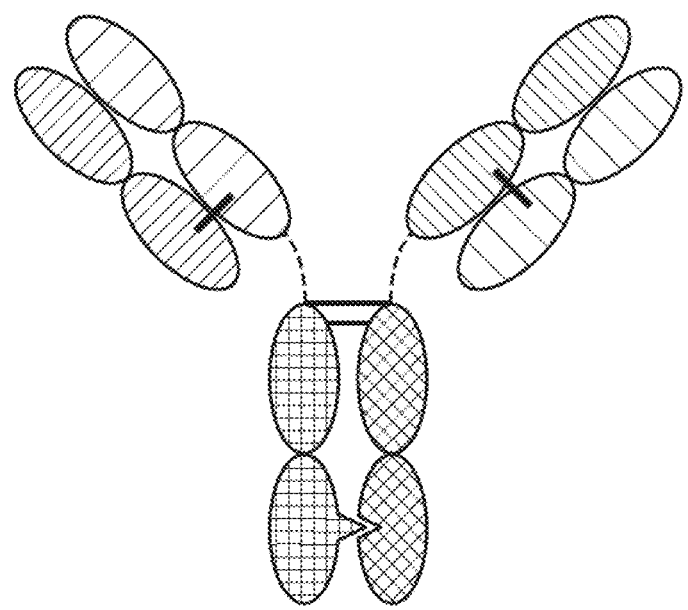
FIG. 15 is a DuetMab, which is a heterodimeric construct containing two different Fab fragments binding to antigens 1 and 2, and an Fc that is stabilized by heterodimerization mutations. Fab fragments 1 and 2 contain differential S—S bridges that ensure correct light chain and heavy chain pairing.
Figure 16:
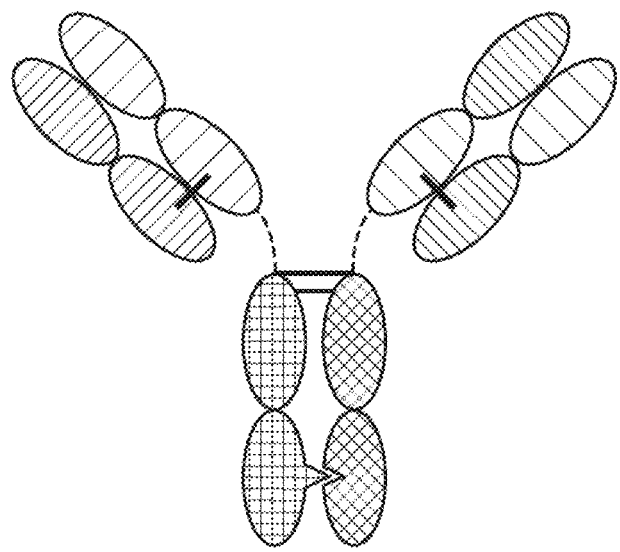
FIG. 16 is a CrossmAb, which is a heterodimeric construct with two different Fab fragments binding to targets 1 and 2, and an Fc stabilized by heterodimerization mutations. CL and CH1 domains, and VH and VL domains are switched, e.g., CH1 is fused in-line with VL, and CL is fused in-line with VH.
Figure 17:
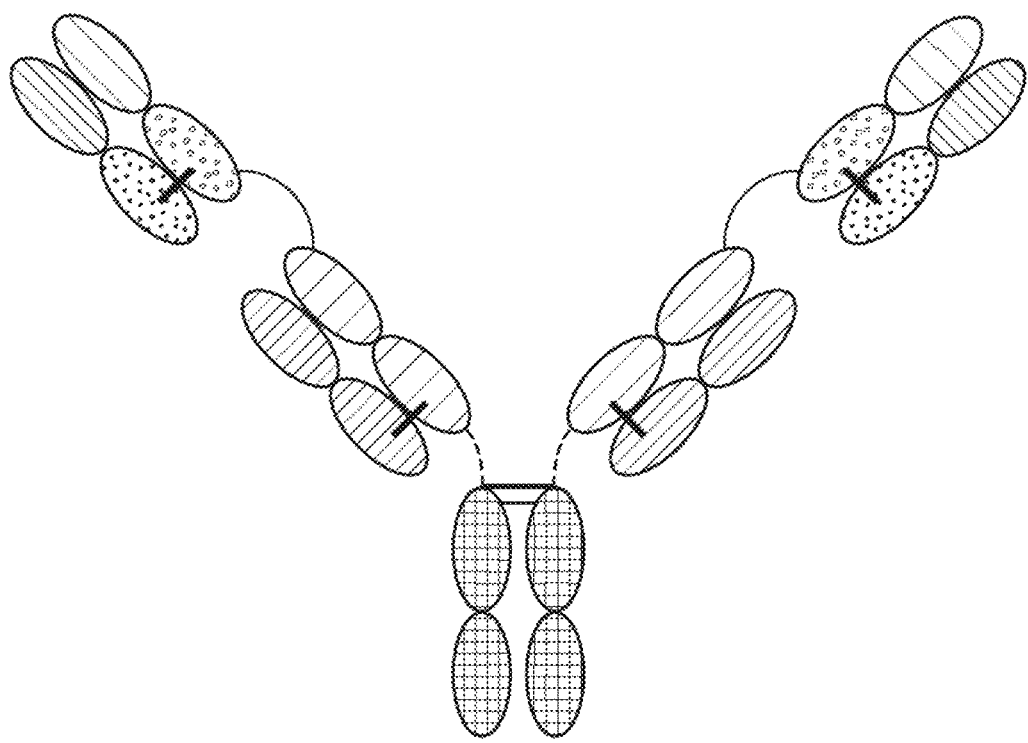
FIG. 17 is a Fit-Ig, which is a homodimeric construct where Fab fragment binding to antigen 2 is fused to the N-terminus of HC of Fab fragment that binds to antigen 1. The construct contains wild-type Fc.

In some embodiments, the multispecific binding protein is in the κλ-Body form, which is a heterodimeric construct with two different Fab fragments fused to Fc stabilized by heterodimerization mutations: Fab fragment 1 targeting antigen 1 contains kappa LC, and Fab fragment 2 targeting antigen 2 contains lambda LC. FIG. 13A is an exemplary representation of one form of a κλ-Body; FIG. 13B is an exemplary representation of another κλ-Body.

In some embodiments, the multispecific binding protein is in Fab Arm Exchange form (antibodies that exchange Fab fragment arms by swapping a heavy chain and attached light chain (half-molecule) with a heavy-light chain pair from another molecule, which results in bispecific antibodies).

In some embodiments, the multispecific binding protein is in the SEED Body form. The strand-exchange engineered domain (SEED) platform was designed to generate asymmetric and bispecific antibody-like molecules, a capability that expands therapeutic applications of natural antibodies. This protein engineering platform is based on exchanging structurally related sequences of immunoglobulin within the conserved CH3 domains. The SEED design allows efficient generation of AG/GA heterodimers, whereas disfavoring homodimerization of AG and GA SEED CH3 domains. (Muda M. et al., *Protein Eng. Des. Sel.* (2011, 24(5):447-54)).

In some embodiments, the multispecific binding protein is in the LuZ-Y form, in which a leucine zipper is used to induce heterodimerization of two different HCs. (Wranik, B J. et al., *J. Biol. Chem.* (2012), 287:43331-9).

In some embodiments, the multispecific binding protein is in the Cov-X-Body form. In bispecific CovX-Bodies, two different peptides are joined together using a branched azetidinone linker and fused to the scaffold antibody under mild conditions in a site-specific manner. Whereas the pharmacophores are responsible for functional activities, the antibody scaffold imparts long half-life and Ig-like distribution. The pharmacophores can be chemically optimized or replaced with other pharmacophores to generate optimized or unique bispecific antibodies. (Doppalapudi V R et al., *PNAS* (2010), 107(52); 22611-22616).

In some embodiments, the multispecific binding protein is in an Oasc-Fab heterodimeric form that includes Fab fragment binding to target 1, and scFab binding to target 2 fused to Fc. Heterodimerization is ensured by mutations in the Fc.

In some embodiments, the multispecific binding protein is in a DuetMab form, which is a heterodimeric construct containing two different Fab fragments binding to antigens 1 and 2, and Fc stabilized by heterodimerization mutations. Fab fragments 1 and 2 contain differential S—S bridges that ensure correct LC and HC pairing.

In some embodiments, the multispecific binding protein is in a CrossmAb form, which is a heterodimeric construct with two different Fab fragments binding to targets 1 and 2, fused to Fc stabilized by heterodimerization. CL and CH1 domains and VH and VL domains are switched, e.g., CH1 is fused in-frame with VL, and CL is fused in-frame with VH.

In some embodiments, the multispecific binding protein is in a Fit-Ig form, which is a homodimeric construct where Fab fragment binding to antigen 2 is fused to the N terminus of HC of Fab fragment that binds to antigen 1. The construct contains wild-type Fc.

Individual components of the multispecific binding proteins are described in more detail below.

NKG2D-Binding Site

Upon binding to the NKG2D receptor and CD16 receptor on natural killer cells, and CLEC12A, the multispecific binding proteins can engage more than one kind of NK-activating receptor, and may block the binding of natural ligands to NKG2D. In certain embodiments, the proteins can agonize NK cells in humans. In some embodiments, the proteins can agonize NK cells in humans and in other species such as rodents and cynomolgus monkeys. In some embodiments, the proteins can agonize NK cells in humans and in other species such as cynomolgus monkeys.

Table 1 lists peptide sequences of heavy chain variable domains and light chain variable domains that, in combination, can bind to NKG2D. In some embodiments, the heavy chain variable domain and the light chain variable domain are arranged in Fab format. In some embodiments, the heavy chain variable domain and the light chain variable domain are fused together to form an scFv.

The NKG2D binding sites listed in Table 1 can vary in their binding affinity to NKG2D, nevertheless, they all activate human NK cells.

Unless indicated otherwise, the CDR sequences provided in Table 1 are determined under Kabat numbering.

TABLE 1

| Clones | Heavy chain variable region amino acid sequence | Light chain variable region amino acid sequence |
| --- | --- | --- |
| ADI-27705 | QVQLQQWGAGLLKPSETLSLTCAVYGG SFSGYYWSWIRQPPGKGLEWIGEIDHSG STNYNPSLKSRVTISVDTSKNQFSLKLSS VTAADTAVYYCARARGPWSFDPWGQG TLVTVSS (SEQ ID NO: 1) CDR1 (SEQ ID NO: 2) - GSFSGYYWS CDR2 (SEQ ID NO: 3) - EIDHSGSTNYNPSLKS CDR3 (SEQ ID NO: 4) - ARARGPWSFDP | DIQMTQSPSTLSASVGDRVTITCRAS QSISSWLAWYQQKPGKAPKLLIYKA SSLESGVPSRFSGSGSGTEFTLTISSL QPDDFATYYCQQYNSYPITFGGGTK VEIK (SEQ ID NO: 5) |
| ADI-27724 | QVQLQQWGAGLLKPSETLSLTCAVYGG SFSGYYWSWIRQPPGKGLEWIGEIDHSG STNYNPSLKSRVTISVDTSKNQFSLKLSS VTAADTAVYYCARARGPWSFDPWGQG TLVTVSS (SEQ ID NO: 1) | EIVLTQSPGTLSLSPGERATLSCRASQ SVSSSYLAWYQQKPGQAPRLLIYGA SSRATGIPDRFSGSGSGTDFTLTISRL EPEDFAVYYCQQYGSSPITFGGGTK VEIK (SEQ ID NO: 6) |
| ADI-27740 (A40) | QVQLQQWGAGLLKPSETLSLTCAVYGG SFSGYYWSWIRQPPGKGLEWIGEIDHSG STNYNPSLKSRVTISVDTSKNQFSLKLSS VTAADTAVYYCARARGPWSFDPWGQG TLVTVSS (SEQ ID NO: 1) | DIQMTQSPSTLSASVGDRVTITCRAS QSIGSWLAWYQQKPGKAPKLLIYKA SSLESGVPSRFSGSGSGTEFTLTISSL QPDDFATYYCQQYHSFYTFGGGTK VEIK (SEQ ID NO: 7) |
| ADI-27741 | QVQLQQWGAGLLKPSETLSLTCAVYGG SFSGYYWSWIRQPPGKGLEWIGEIDHSG STNYNPSLKSRVTISVDTSKNQFSLKLSS VTAADTAVYYCARARGPWSFDPWGQG TLVTVSS (SEQ ID NO: 1) | DIQMTQSPSTLSASVGDRVTITCRAS QSIGSWLAWYQQKPGKAPKLLIYKA SSLESGVPSRFSGSGSGTEFTLTISSL QPDDFATYYCQQSNSYYTFGGGTK VEIK (SEQ ID NO: 8) |
| ADI-27743 | QVQLQQWGAGLLKPSETLSLTCAVYGG SFSGYYWSWIRQPPGKGLEWIGEIDHSG STNYNPSLKSRVTISVDTSKNQFSLKLSS VTAADTAVYYCARARGPWSFDPWGQG TLVTVSS (SEQ ID NO: 1) | DIQMTQSPSTLSASVGDRVTITCRAS QSISSWLAWYQQKPGKAPKLLIYKA SSLESGVPSRFSGSGSGTEFTLTISSL QPDDFATYYCQQYNSYPTFGGGTK VEIK (SEQ ID NO: 9) |
| ADI-28153 | QVQLQQWGAGLLKPSETLSLTCAVYGG SFSGYYWSWIRQPPGKGLEWIGEIDHSG STNYNPSLKSRVTISVDTSKNQFSLKLSS VTAADTAVYYCARARGPWGFDPWGQG TLVTVSS (SEQ ID NO: 10) | ELQMTQSPSSLSASVGDRVTITCRTS QSISSYLNWYQQKPGQPPKLLIYWA STRESGVPDRFSGSGSGTDFTLTISSL QPEDSATYYCQQSYDIPYTFGQGTK LEIK (SEQ ID NO: 11) |
| ADI-28226 (C26) | QVQLQQWGAGLLKPSETLSLTCAVYGG SFSGYYWSWIRQPPGKGLEWIGEIDHSG STNYNPSLKSRVTISVDTSKNQFSLKLSS VTAADTAVYYCARARGPWSFDPWGQG TLVTVSS (SEQ ID NO: 1) | DIQMTQSPSTLSASVGDRVTITCRAS QSISSWLAWYQQKPGKAPKLLIYKA SSLESGVPSRFSGSGSGTEFTLTISSL QPDDFATYYCQQYGSFPITFGGGTK VEIK (SEQ ID NO: 12) |
| ADI-28154 | QVQLQQWGAGLLKPSETLSLTCAVYGG SFSGYYWSWIRQPPGKGLEWIGEIDHSG STNYNPSLKSRVTISVDTSKNQFSLKLSS VTAADTAVYYCARARGPWSFDPWGQG TLVTVSS (SEQ ID NO: 1) | DIQMTQSPSTLSASVGDRVTITCRAS QSISSWLAWYQQKPGKAPKLLIYKA SSLESGVPSRFSGSGSGTDFTLTISSL QPDDFATYYCQQSKEVPWTFGQGT KVEIK (SEQ ID NO: 13) |

TABLE 1-continued

| Clones | Heavy chain variable region amino acid sequence | Light chain variable region amino acid sequence |
|---|---|---|
| ADI-29399 | QVQLQQWGAGLLKPSETLSLTCAVYGG SFSGYYWSWIRQPPGKGLEWIGEIDHSG STNYNPSLKSRVTISVDTSKNQFSLKLSS VTAADTAVYYCARARGPWSFDPWGQG TLVTVSS (SEQ ID NO: 1) | DIQMTQSPSTLSASVGDRVTITCRAS QSISSWLAWYQQKPGKAPKLLIYKA SSLESGVPSRFSGSGSGTEFTLTISSL QPDDFATYYCQQYNSFPTFGGGTKV EIK (SEQ ID NO: 14) |
| ADI-29401 | QVQLQQWGAGLLKPSETLSLTCAVYGG SFSGYYWSWIRQPPGKGLEWIGEIDHSG STNYNPSLKSRVTISVDTSKNQFSLKLSS VTAADTAVYYCARARGPWSFDPWGQG TLVTVSS (SEQ ID NO: 1) | DIQMTQSPSTLSASVGDRVTITCRAS QSIGSWLAWYQQKPGKAPKLLIYKA SSLESGVPSRFSGSGSGTEFTLTISSL QPDDFATYYCQQYDIYPTFGGGTKV EIK (SEQ ID NO: 15) |
| ADI-29403 | QVQLQQWGAGLLKPSETLSLTCAVYGG SFSGYYWSWIRQPPGKGLEWIGEIDHSG STNYNPSLKSRVTISVDTSKNQFSLKLSS VTAADTAVYYCARARGPWSFDPWGQG TLVTVSS (SEQ ID NO: 1) | DIQMTQSPSTLSASVGDRVTITCRAS QSISSWLAWYQQKPGKAPKLLIYKA SSLESGVPSRFSGSGSGTEFTLTISSL QPDDFATYYCQQYDSYPTFGGGTK VEIK (SEQ ID NO: 16) |
| ADI-29405 | QVQLQQWGAGLLKPSETLSLTCAVYGG SFSGYYWSWIRQPPGKGLEWIGEIDHSG STNYNPSLKSRVTISVDTSKNQFSLKLSS VTAADTAVYYCARARGPWSFDPWGQG TLVTVSS (SEQ ID NO: 1) | DIQMTQSPSTLSASVGDRVTITCRAS QSISSWLAWYQQKPGKAPKLLIYKA SSLESGVPSRFSGSGSGTEFTLTISSL QPDDFATYYCQQYGSFPTFGGGTKV EIK (SEQ ID NO: 17) |
| ADI-29407 | QVQLQQWGAGLLKPSETLSLTCAVYGG SFSGYYWSWIRQPPGKGLEWIGEIDHSG STNYNPSLKSRVTISVDTSKNQFSLKLSS VTAADTAVYYCARARGPWSFDPWGQG TLVTVSS (SEQ ID NO: 1) | DIQMTQSPSTLSASVGDRVTITCRAS QSISSWLAWYQQKPGKAPKLLIYKA SSLESGVPSRFSGSGSGTEFTLTISSL QPDDFATYYCQQYQSFPTFGGGTKV EIK (SEQ ID NO: 18) |
| ADI-29419 | QVQLQQWGAGLLKPSETLSLTCAVYGG SFSGYYWSWIRQPPGKGLEWIGEIDHSG STNYNPSLKSRVTISVDTSKNQFSLKLSS VTAADTAVYYCARARGPWSFDPWGQG TLVTVSS (SEQ ID NO: 1) | DIQMTQSPSTLSASVGDRVTITCRAS QSISSWLAWYQQKPGKAPKLLIYKA SSLESGVPSRFSGSGSGTEFTLTISSL QPDDFATYYCQQYSSFSTFGGGTKV EIK (SEQ ID NO: 19) |
| ADI-29421 | QVQLQQWGAGLLKPSETLSLTCAVYGG SFSGYYWSWIRQPPGKGLEWIGEIDHSG STNYNPSLKSRVTISVDTSKNQFSLKLSS VTAADTAVYYCARARGPWSFDPWGQG TLVTVSS (SEQ ID NO: 1) | DIQMTQSPSTLSASVGDRVTITCRAS QSISSWLAWYQQKPGKAPKLLIYKA SSLESGVPSRFSGSGSGTEFTLTISSL QPDDFATYYCQQYESYSTFGGGTKV EIK (SEQ ID NO: 20) |
| ADI-29424 | QVQLQQWGAGLLKPSETLSLTCAVYGG SFSGYYWSWIRQPPGKGLEWIGEIDHSG STNYNPSLKSRVTISVDTSKNQFSLKLSS VTAADTAVYYCARARGPWSFDPWGQG TLVTVSS (SEQ ID NO: 1) | DIQMTQSPSTLSASVGDRVTITCRAS QSISSWLAWYQQKPGKAPKLLIYKA SSLESGVPSRFSGSGSGTEFTLTISSL QPDDFATYYCQQYDSFITFGGGTKV EIK (SEQ ID NO: 21) |
| ADI-29425 | QVQLQQWGAGLLKPSETLSLTCAVYGG SFSGYYWSWIRQPPGKGLEWIGEIDHSG STNYNPSLKSRVTISVDTSKNQFSLKLSS VTAADTAVYYCARARGPWSFDPWGQG TLVTVSS (SEQ ID NO: 1) | DIQMTQSPSTLSASVGDRVTITCRAS QSISSWLAWYQQKPGKAPKLLIYKA SSLESGVPSRFSGSGSGTEFTLTISSL QPDDFATYYCQQYQSYPTFGGGTK VEIK (SEQ ID NO: 22) |
| ADI-29426 | QVQLQQWGAGLLKPSETLSLTCAVYGG SFSGYYWSWIRQPPGKGLEWIGEIDHSG STNYNPSLKSRVTISVDTSKNQFSLKLSS VTAADTAVYYCARARGPWSFDPWGQG TLVTVSS (SEQ ID NO: 1) | DIQMTQSPSTLSASVGDRVTITCRAS QSIGSWLAWYQQKPGKAPKLLIYKA SSLESGVPSRFSGSGSGTEFTLTISSL QPDDFATYYCQQHSFPTFGGGTKV EIK (SEQ ID NO: 23) |
| ADI-29429 | QVQLQQWGAGLLKPSETLSLTCAVYGG SFSGYYWSWIRQPPGKGLEWIGEIDHSG STNYNPSLKSRVTISVDTSKNQFSLKLSS VTAADTAVYYCARARGPWSFDPWGQG TLVTVSS (SEQ ID NO: 1) | DIQMTQSPSTLSASVGDRVTITCRAS QSIGSWLAWYQQKPGKAPKLLIYKA SSLESGVPSRFSGSGSGTEFTLTISSL QPDDFATYYCQQYELYSYTFGGGTK VEIK (SEQ ID NO: 24) |

TABLE 1-continued

| Clones | Heavy chain variable region amino acid sequence | Light chain variable region amino acid sequence |
|---|---|---|
| ADI-29447 (F47) | QVQLQQWGAGLLKPSETLSLTCAVYGG SFSGYYWSWIRQPPGKGLEWIGEIDHSG STNYNPSLKSRVTISVDTSKNQFSLKLSS VTAADTAVYYCARARGPWSFDPWGQG TLVTVSS (SEQ ID NO: 1) | DIQMTQSPSTLSASVGDRVTITCRAS QSISSWLAWYQQKPGKAPKLLIYKA SSLESGVPSRFSGSGSGTEFTLTISSL QPDDFATYYCQQYDTFITFGGGTKV EIK (SEQ ID NO: 25) |
| ADI-27727 | QVQLVQSGAEVKKPGSSVKVSCKASGG TFSSYAISWVRQAPGQGLEWMGGIIPIFG TANYAQKFQGRVTITADESTSTAYMELS SLRSEDTAVYYCARGDSSIRHAYYYYG MDVWGQGTTVTVSS (SEQ ID NO: 26) CDR1- GTFSSYAIS (non-Kabat)(SEQ ID NO: 27) or SYAIS (SEQ ID NO: 28) CDR2 (SEQ ID NO: 29) - GIIPIFGTANYAQKFQG CDR3 - ARGDSSIRHAYYYYGMDV (non-Kabat)(SEQ ID NO: 30) or GDSSIRHAYYYYGMDV (SEQ ID NO: 31) | DIVMTQSPDSLAVSLGERATINCKSS QSVLYSSNNKNYLAWYQQKPGQPP KLLIYWASTRESGVPDRFSGSGSGTD FTLTISSLQAEDVAVYYCQQYYSTPI TFGGGTKVEIK (SEQ ID NO: 32) CDR1 (SEQ ID NO: 33) - KSSQSVLYSSNNKNYLA CDR2 (SEQ ID NO: 34) - WASTRES CDR3 (SEQ ID NO: 35) - QQYYSTPIT |
| ADI-29443 (F43) | QLQLQESGPGLVKPSETLSLTCTVSGGSI SSSSYYWGWIRQPPGKGLEWIGSIYYSGS TYYNPSLKSRVTISVDTSKNQFSLKLSSV TAADTAVYYCARGSDRFHPYFDYWGQG TLVTVSS (SEQ ID NO: 36) CDR1- GSISSSSYYWG (non-Kabat)(SEQ ID NO: 37) or SSSYYWG (SEQ ID NO: 38) CDR2 (SEQ ID NO: 39) - SIYYSGSTYYNPSLKS CDR3 - ARGSDRFHPYFDY (non-Kabat) (SEQ ID NO: 40) or GSDRFHPYFDY (SEQ ID NO: 41) | EIVLTQSPATLSLSPGERATLSCRASQ SVSRYLAWYQQKPGQAPRLLIYDAS NRATGIPARFSGSGSGTDFTLTISSLE PEDFAVYYCQQFDTWPPTFGGGTKV EIK (SEQ ID NO: 42) CDR1 (SEQ ID NO: 43) - RASQSVSRYLA CDR2 (SEQ ID NO: 44) - DASNRAT CDR3 (SEQ ID NO: 45) - QQFDTWPPT |
| ADI-29404 (F04) | QVQLQQWGAGLLKPSETLSLTCAVYGG SFSGYYWSWIRQPPGKGLEWIGEIDHSG STNYNPSLKSRVTISVDTSKNQFSLKLSS VTAADTAVYYCARARGPWSFDPWGQG TLVTVSS (SEQ ID NO: 1) | DIQMTQSPSTLSASVGDRVTITCRAS QSISSWLAWYQQKPGKAPKLLIYKA SSLESGVPSRFSGSGSGTEFTLTISSL QPDDFATYYCEQYDSYPTFGGGTKV EIK (SEQ ID NO: 46) |
| ADI-28200 | QVQLVQSGAEVKKPGSSVKVSCKASGG TFSSYAISWVRQAPGQGLEWMGGIIPIFG TANYAQKFQGRVTITADESTSTAYMELS SLRSEDTAVYYCARRGRKASGSFYYY GMDVWGQGTTVTVSS (SEQ ID NO: 47) CDR1 (SEQ ID NO: 27) - GTFSSYAIS CDR2 (SEQ ID NO: 29) - GIIPIFGTANYAQKFQG CDR3 (SEQ ID NO: 48) - ARRGRKASGSFYYYGMDV | DIVMTQSPDSLAVSLGERATINCESS QSLLNSGNQKNYLTWYQQKPGQPP KPLIYWASTRESGVPDRFSGSGSGTD FTLTISSLQAEDVAVYYCQNDYSYP YTFGQGTKLEIK (SEQ ID NO: 49) CDR1 (SEQ ID NO: 50) - ESSQSLLNSGNQKNYLT CDR2 (SEQ ID NO: 34) - WASTRES CDR3 (SEQ ID NO: 51) - QNDYSYPYT |
| ADI-29379 (E79) | QVQLVQSGAEVKKPGASVKVSCKASGY TFTSYYMHWVRQAPGQGLEWMGIINPS GGSTSYAQKFQGRVTMTRDTSTSTVYM ELSSLRSEDTAVYYCARGAPNYGDTTHD YYYMDVWGKGTTVTVSS (SEQ ID NO: 52) CDR1 (SEQ ID NO: 53) - YTFTSYYMH (non-Kabat) or SYYMH (SEQ ID NO: 54) CDR2 (SEQ ID NO: 55) - IINPSGGSTSYAQKFQG CDR3 - ARGAPNYGDTTHDYYYMDV (non-Kabat)(SEQ ID NO: 56) or GAPNYGDTTHDYYYMDV (SEQ ID NO: 57) | EIVMTQSPATLSVSPGERATLSCRAS QSVSSNLAWYQQKPGQAPRLLIYGA STRATGIPARFSGSGSGTEFTLTISSL QSEDFAVYYCQQYDDWPFTFGGGT KVEIK (SEQ ID NO: 58) CDR1 (SEQ ID NO: 59) - RASQSVSSNLA CDR2 (SEQ ID NO: 60) - GASTRAT CDR3 (SEQ ID NO: 61) - QQYDDWPFT |
| ADI-29463 (F63) | QVQLVQSGAEVKKPGASVKVSCKASGY TFTGYYMHWVRQAPGQGLEWMGWINP NSGGTNYAQKFQGRVTMTRDTSISTAY MELSRLRSDDTAVYYCARDTGEYYDTD DHGMDVWGQGTTVTVSS (SEQ ID NO: 62) CDR1 - YTFTGYYMH (non-Kabat)(SEQ ID NO: 63) or GYYMH (SEQ ID NO: 64) | EIVLTQSPGTLSLSPGERATLSCRASQ SVSSNLAWYQQKPGQAPRLLIYGAS TRATGIPARFSGSGSGTEFTLTISSLQ SEDFAVYYCQQDDYWPPTFGGGTK VEIK (SEQ ID NO: 68) CDR1 (SEQ ID NO: 59) - RASQSVSSNLA |

TABLE 1-continued

| Clones | Heavy chain variable region amino acid sequence | Light chain variable region amino acid sequence |
| --- | --- | --- |
|  | CDR2 (SEQ ID NO: 65) - WINPNSGGTNYAQKFQG<br>CDR3 - ARDTGEYYDTDDHGMDV (non-Kabat)(SEQ ID NO: 66) or DTGEYYDTDDHGMDV (SEQ ID NO: 67) | CDR2 (SEQ ID NO: 60) - GASTRAT<br>CDR3 (SEQ ID NO: 69) - QQDDYWPPT |
| ADI-27744 (A44) | EVQLLESGGGLVQPGGSLRLSCAASGFT FSSYAMSWVRQAPGKGLEWVSAISGSG GSTYYADSVKGRFTISRDNSKNTLYLQM NSLRAEDTAVYYCAKDGGYYDSGAGD YWGQGTLVTVSS (SEQ ID NO: 70)<br>CDR1 - FTFSSYAMS (non-Kabat)(SEQ ID NO: 71) or SYAMS (SEQ ID NO: 115)<br>CDR2 (SEQ ID NO: 72) - AISGSGGSTYYADSVKG<br>CDR3 - AKDGGYYDSGAGDY (non-Kabat) (SEQ ID NO: 73) or DGGYYDSGAGDY (SEQ ID NO: 74) | DIQMTQSPSSVSASVGDRVTITCRAS QGIDSWLAWYQQKPGKAPKLLIYA ASSLQSGVPSRFSGSGSGTDFTLTISS LQPEDFATYYCQQGVSYPRTFGGGT KVEIK (SEQ ID NO: 75)<br>CDR1 (SEQ ID NO: 76) - RASQGIDSWLA<br>CDR2 (SEQ ID NO: 77) - AASSLQS<br>CDR3 (SEQ ID NO: 78) - QQGVSYPRT |
| ADI-27749 (A49) | EVQLVESGGGLVKPGGSLRLSCAASGFT FSSYSMNWVRQAPGKGLEWVSSISSSSS YIYYADSVKGRFTISRDNAKNSLYLQMN SLRAEDTAVYYCARGAPMGAAAGWFD PWGQGTLVTVSS (SEQ ID NO: 79)<br>CDR1 - FTFSSYSMN (SEQ ID NO: 80)(non-Kabat) or SYSMN (SEQ ID NO: 81)<br>CDR2 (SEQ ID NO: 82) - SISSSSSYIYYADSVKG<br>CDR3- ARGAPMGAAAGWFDP (SEQ ID NO: 83)(non-Kabat) or GAPMGAAAGWFDP (SEQ ID NO: 84)<br><br>scFv (VL-VH) with Q44C in VH and G100C in VL, linker italicized:<br>DIQMTQSPSSVSASVGDRVTITCRASQGISSWLAWYQQKPGKAPKLLIYAASSLQS GVPSRFSGSGSGTDFTLTISSLQPEDFATYYCQQGVSFPRTFGCGTKVEIK*GGGGSG GGGSGGGGSGGGGS*EVQLVESGGGLVKPGGSLRLSCAASGFTFSSYSMNWVRQA PGKCLEWVSSISSSSSYIYYADSVKGRFTISRDNAKNSLYLQMNSLRAEDTAVYYC ARGAPMGAAAGWFDPWGQGTLVTVSS (SEQ ID NO: 88) | DIQMTQSPSSVSASVGDRVTITCRAS QGISSWLAWYQQKPGKAPKLLIYAA SSLQSGVPSRFSGSGSGTDFTLTISSL QPEDFATYYCQQGVSFPRTFGGGTK VEIK (SEQ ID NO: 85)<br>CDR1 (SEQ ID NO: 86) - RASQGISSWLA<br>CDR2 (SEQ ID NO: 77) - AASSLQS<br>CDR3 (SEQ ID NO: 87) - QQGVSFPRT |
| ADI-29378 (E78) | QVQLVQSGAEVKKPGASVKVSCKASGY TFTSYYMHWVRQAPGQGLEWMGIINPS GGSTSYAQKFQGRVTMTRDTSTSTVYM ELSSLRSEDTAVYYCAREGAGFAYGMD YYYMDVWGKGTTVTVSS (SEQ ID NO: 89)<br>CDR1 - YTFTSYYMH (SEQ ID NO: 53) (non-Kabat) or SYYMH (SEQ ID NO: 54)<br>CDR2 (SEQ ID NO: 55) - IINPSGGSTSYAQKFQG<br>CDR3 - AREGAGFAYGMDYYYMDV (SEQ ID NO: 90)(non-Kabat) or EGAGFAYGMDYYYMDV (SEQ ID NO: 91) | EIVLTQSPATLSLSPGERATLSCRASQ SVSSYLAWYQQKPGQAPRLLIYDAS NRATGIPARFSGSGSGTDFTLTISSLE PEDFAVYYCQQSDNWPFTFGGGTK VEIK (SEQ ID NO: 92)<br>CDR1 (SEQ ID NO: 93) - RASQSVSSYLA<br>CDR2 (SEQ ID NO: 44) - DASNRAT<br>CDR3 (SEQ ID NO: 94) - QQSDNWPFT |
| A49MI | EVQLVESGGGLVKPGGSLRLSCAASGFT FSSYSMNWVRQAPGKGLEWVSSISSSSS YIYYADSVKGRFTISRDNAKNSLYLQMN SLRAEDTAVYYCARGAP<u>I</u>GAAAGWFDP WGQGTLVTVSS (SEQ ID NO: 95)<br>CDR1: FTFSSYSMN (SEQ ID NO: 80)(non-Kabat) or SYSMN (SEQ ID NO: 81)<br>CDR2: SISSSSSYIYYADSVKG (SEQ ID NO: 82)<br>CDR3: ARGAP<u>I</u>GAAAGWFDP (SEQ ID NO: 96)(non-Kabat) or GAP<u>I</u>GAAAGWFDP (SEQ ID NO: 97) | DIQMTQSPSSVSASVGDRVTITCRAS QGISSWLAWYQQKPGKAPKLLIYAA SSLQSGVPSRFSGSGSGTDFTLTISSL QPEDFATYYCQQGVSFPRTFGGGTK VEIK (SEQ ID NO: 85)<br>CDR1 (SEQ ID NO: 86) - RASQGISSWLA<br>CDR2 (SEQ ID NO: 77) - AASSLQS<br>CDR3 (SEQ ID NO: 87) - QQGVSFPRT |
| A49MQ | EVQLVESGGGLVKPGGSLRLSCAASGFT FSSYSMNWVRQAPGKGLEWVSSISSSSS YIYYADSVKGRFTISRDNAKNSLYLQMN SLRAEDTAVYYCARGAP<u>Q</u>GAAAGWFDP WGQGTLVTVSS (SEQ ID NO: 98)<br>CDR1: FTFSSYSMN (SEQ ID NO: 80)(non-Kabat) or SYSMN (SEQ ID NO: 81)<br>CDR2: SISSSSSYIYYADSVKG | DIQMTQSPSSVSASVGDRVTITCRAS QGISSWLAWYQQKPGKAPKLLIYAA SSLQSGVPSRFSGSGSGTDFTLTISSL QPEDFATYYCQQGVSFPRTFGGGTK VEIK (SEQ ID NO: 85)<br>CDR1 (SEQ ID NO: 86) - RASQGISSWLA<br>CDR2 (SEQ ID NO: 77) - AASSLQS |

TABLE 1-continued

| Clones | Heavy chain variable region amino acid sequence | Light chain variable region amino acid sequence |
| --- | --- | --- |
| | (SEQ ID NO: 82)<br>CDR3 - ARGAPQGAAAGWFDP (SEQ ID NO: 99)(non-Kabat) or GAPQGAAAGWFDP (SEQ ID NO: 100) | CDR3 (SEQ ID NO: 87) - QQGVSFPRT |
| A49ML | EVQLVESGGGLVKPGGSLRLSCAASGFT<br>FSSYSMNWVRQAPGKGLEWVSSISSSSS<br>YIYYADSVKGRFTISRDNAKNSLYLQMN<br>SLRAEDTAVYYCARGAPLGAAAGWFDP<br>WGQGTLVTVSS<br>(SEQ ID NO: 101)<br>CDR1: FTFSSYSMN (SEQ ID NO: 80)(non-Kabat) or SYSMN (SEQ ID NO: 81)<br>CDR2: SISSSSSYIYYADSVKG (SEQ ID NO: 82)<br>CDR3 - ARGAPLGAAAGWFDP (SEQ ID NO: 102)(non-Kabat) or GAPLGAAAGWFDP (SEQ ID NO: 103) | DIQMTQSPSSVSASVGDRVTITCRAS<br>QGISSWLAWYQQKPGKAPKLLIYAA<br>SSLQSGVPSRFSGSGSGTDFTLTISSL<br>QPEDFATYYCQQGVSFPRTFGGGTK<br>VEIK<br>(SEQ ID NO: 85)<br>CDR1 (SEQ ID NO: 86) - RASQGISSWLA<br>CDR2 (SEQ ID NO: 77) - AASSLQS<br>CDR3 (SEQ ID NO: 87) - QQGVSFPRT |
| A49MF | EVQLVESGGGLVKPGGSLRLSCAASGFT<br>FSSYSMNWVRQAPGKGLEWVSSISSSSS<br>YIYYADSVKGRFTISRDNAKNSLYLQMN<br>SLRAEDTAVYYCARGAPFGAAAGWFDP<br>WGQGTLVTVSS<br>(SEQ ID NO: 104)<br>CDR1: FTFSSYSMN (SEQ ID NO: 80)(non-Kabat) or SYSMN (SEQ ID NO: 81)<br>CDR2: SISSSSSYIYYADSVKG (SEQ ID NO: 82)<br>CDR3 - ARGAPFGAAAGWFDP (SEQ ID NO: 105)(non-Kabat) or GAPFGAAAGWFDP (SEQ ID NO: 106) | DIQMTQSPSSVSASVGDRVTITCRAS<br>QGISSWLAWYQQKPGKAPKLLIYAA<br>SSLQSGVPSRFSGSGSGTDFTLTISSL<br>QPEDFATYYCQQGVSFPRTFGGGTK<br>VEIK<br>(SEQ ID NO: 85)<br>CDR1 (SEQ ID NO: 86) - RASQGISSWLA<br>CDR2 (SEQ ID NO: 77) - AASSLQS<br>CDR3 (SEQ ID NO: 87) - QQGVSFPRT |
| A49MV | EVQLVESGGGLVKPGGSLRLSCAASGFT<br>FSSYSMNWVRQAPGKGLEWVSSISSSSS<br>YIYYADSVKGRFTISRDNAKNSLYLQMN<br>SLRAEDTAVYYCARGAPVGAAAGWFDP<br>WGQGTLVTVSS<br>(SEQ ID NO: 107)<br>CDR1: FTFSSYSMN (SEQ ID NO: 80)(non-Kabat) or SYSMN (SEQ ID NO: 81)<br>CDR2: SISSSSSYIYYADSVKG (SEQ ID NO: 82)<br>CDR3- ARGAPVGAAAGWFDP (SEQ ID NO: 108)(non-Kabat) or GAPVGAAAGWFDP (SEQ ID NO: 109) | DIQMTQSPSSVSASVGDRVTITCRAS<br>QGISSWLAWYQQKPGKAPKLLIYAA<br>SSLQSGVPSRFSGSGSGTDFTLTISSL<br>QPEDFATYYCQQGVSFPRTFGGGTK<br>VEIK<br>(SEQ ID NO: 85)<br>CDR1 (SEQ ID NO: 86) - RASQGISSWLA<br>CDR2 (SEQ ID NO: 77) - AASSLQS<br>CDR3 (SEQ ID NO: 87) - QQGVSFPRT |
| A49-consensus | EVQLVESGGGLVKPGGSLRLSCAASGFT<br>FSSYSMNWVRQAPGKGLEWVSSISSSSS<br>YIYYADSVKGRFTISRDNAKNSLYLQMN<br>SLRAEDTAVYYCARGAPXGAAAGWFDP<br>WGQGTLVTVSS, wherein X is M, L, I, V, Q, or F<br>(SEQ ID NO: 110)<br>CDR1: FTFSSYSMN (SEQ ID NO: 80)(non-Kabat) or SYSMN (SEQ ID NO: 81)<br>CDR2: SISSSSSYIYYADSVKG (SEQ ID NO: 82)<br>CDR3- ARGAPXGAAAGWFDP (SEQ ID NO: 111)(non-Kabat) or GAPXGAAAGWFDP (SEQ ID NO: 112), wherein X is M, L, I, V, Q, or F | DIQMTQSPSSVSASVGDRVTITCRAS<br>QGISSWLAWYQQKPGKAPKLLIYAA<br>SSLQSGVPSRFSGSGSGTDFTLTISSL<br>QPEDFATYYCQQGVSFPRTFGGGTK<br>VEIK<br>(SEQ ID NO: 85)<br>CDR1 (SEQ ID NO: 86) - RASQGISSWLA<br>CDR2 (SEQ ID NO: 77) - AASSLQS<br>CDR3 (SEQ ID NO: 87) - QQGVSFPRT |
| NKG2D binder in U.S. Pat. No. 9,273,136 | QVQLVESGGGLVKPGGSLRLSCAASGFT<br>FSSYGMHWVRQAPGKGLEWVAFIRYDG<br>SNKYYADSVKGRFTISRDNSKNTLYLQM<br>NSLRAEDTAVYYCAKDRGLGDGTYFDY<br>WGQGTTVTVSS (SEQ ID NO: 113) | QSALTQPASVSGSPGQSITISCSGSSS<br>NIGNNAVNWYQQLPGKAPKLLIYY<br>DDLLPSGVSDRFSGSKSGTSAFLAIS<br>GLQSEDEADYYCAAWDDSLNGPVF<br>GGGTKLTVL (SEQ ID NO: 114) |
| NKG2D binder in U.S. Pat. No. 7,879,985 | QVHLQESGPGLVKPSETLSLTCTVSDDSI<br>SSYYWSWIRQPPGKGLEWIGHISYSGSA<br>NYNPSLKSRVTISVDTSKNQFSLKLS<br>AADTAVYYCANWDDAFNIWGQGTMVT<br>VSS (SEQ ID NO: 116) | EIVLTQSPGTLSLSPGERATLSCRASQ<br>SVSSSYLAWYQQKPGQAPRLLIYGA<br>SVTSSRATGIPDRFSGSGSGTDFTLTISRL<br>EPEDFAVYYCQQYGSSPWTFGQGTK<br>VEIK (SEQ ID NO: 117) |

In certain embodiments, the first antigen-binding site that binds NKG2D (e.g., human NKG2D) comprises an antibody heavy chain variable domain (VH) that comprises an amino acid sequence at least 90% (e.g., at least 91%, at least 92%, at least 93%, at least 94%, at least 95%, at least 96%, at least 97%, at least 98%, at least 99%, or 100%) identical to the VH of an antibody disclosed in Table 1, and an antibody light chain variable domain (VL) that comprises an amino acid sequence at least 90% (e.g., at least 91%, at least 92%, at least 93%, at least 94%, at least 95%, at least 96%, at least 97%, at least 98%, at least 99%, or 100%) identical to the VL of the same antibody disclosed in Table 1. In certain embodiments, the first antigen-binding site comprises the heavy chain CDR1, CDR2, and CDR3 and the light chain CDR1, CDR2, and CDR3, determined under Kabat (see Kabat et al., (1991) Sequences of Proteins of Immunological Interest, NIH Publication No. 91-3242, Bethesda), Chothia (see, e.g., Chothia C & Lesk A M, (1987), J. Mol. Biol. 196: 901-917), MacCallum (see MacCallum R M et al., (1996) J. Mol. Biol. 262: 732-745), or any other CDR determination method known in the art, of the VH and VL sequences of an antibody discloses in Table 1. In certain embodiments, the first antigen-binding site comprises the heavy chain CDR1, CDR2, and CDR3 and the light chain CDR1, CDR2, and CDR3 of an antibody disclosed in Table 1.

In certain embodiments, the first antigen-binding site that binds to NKG2D comprises a heavy chain variable domain derived from SEQ ID NO:1, such as by having an amino acid sequence at least 90% (e.g., at least 90%, at least 91%, at least 92%, at least 93%, at least 94%, at least 95%, at least 96%, at least 97%, at least 98%, at least 99%, or 100%) identical to SEQ ID NO:1, and/or incorporating amino acid sequences identical to the CDR1 (SEQ ID NO:2), CDR2 (SEQ ID NO:3), and CDR3 (SEQ ID NO:4) sequences of SEQ ID NO:1. The heavy chain variable domain related to SEQ ID NO:1 can be coupled with a variety of light chain variable domains to form an NKG2D binding site. For example, the first antigen-binding site that incorporates a heavy chain variable domain related to SEQ ID NO:1 can further incorporate a light chain variable domain selected from the sequences derived from SEQ ID NOs: 5, 6, 7, 8, 9, 12, 13, 14, 15, 16, 17, 18, 19, 20, 21, 22, 23, 24, 25, and 46. For example, the first antigen-binding site incorporates a heavy chain variable domain with amino acid sequences at least 90% (e.g., at least 90%, at least 91%, at least 92%, at least 93%, at least 94%, at least 95%, at least 96%, at least 97%, at least 98%, at least 99%, or 100%) identical to SEQ ID NO:1 and a light chain variable domain with amino acid sequences at least 90% (e.g., at least 90%, at least 91%, at least 92%, at least 93%, at least 94%, at least 95%, at least 96%, at least 97%, at least 98%, at least 99%, or 100%) identical to any one of the sequences selected from SEQ ID NOs: 5, 6, 7, 8, 9, 12, 13, 14, 15, 16, 17, 18, 19, 20, 21, 22, 23, 24, 25, and 46.

In certain embodiments, the first antigen-binding site that binds NKG2D comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:26, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:32. In certain embodiments, the VH comprises CDR1, CDR2, and CDR3 comprising the amino acid sequences of SEQ ID NOs: 27 or 28, 29, and 30 or 31, respectively (e.g., SEQ ID NOs: 27, 29, and 30, respectively, or SEQ ID NOs: 28, 29, and 31, respectively). In certain embodiments, the VL comprises CDR1, CDR2, and CDR3 comprising the amino acid sequences of SEQ ID NOs: 33, 34, and 35, respectively. In certain embodiments, the first antigen-binding site comprises (a) a VH that comprises CDR1, CDR2, and CDR3 comprising the amino acid sequences of SEQ ID NOs: 27 or 28, 29, and 30 or 31, respectively (e.g., SEQ ID NOs: 27, 29, and 30, respectively, or SEQ ID NOs: 28, 29, and 31, respectively); and (b) a VL that comprises CDR1, CDR2, and CDR3 comprising the amino acid sequences of SEQ ID NOs: 33, 34, and 35, respectively.

In certain embodiments, the first antigen-binding site that binds NKG2D comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:36, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:42. In certain embodiments, the VH comprises CDR1, CDR2, and CDR3 comprising the amino acid sequences of SEQ ID NOs: 37 or 38, 39, and 40 or 41, respectively (e.g., SEQ ID NOs: 37, 39, and 40, respectively, or SEQ ID NOs: 38, 39, and 41, respectively). In certain embodiments, the VL comprises CDR1, CDR2, and CDR3 comprising the amino acid sequences of SEQ ID NOs: 43, 44, and 45, respectively. In certain embodiments, the first antigen-binding site comprises (a) a VH that comprises CDR1, CDR2, and CDR3 comprising the amino acid sequences of SEQ ID NOs: 37 or 38, 39, and 40 or 41, respectively (e.g., SEQ ID NOs: 37, 39, and 40, respectively, or SEQ ID NOs: 38, 39, and 41, respectively); and (b) a VL that comprises CDR1, CDR2, and CDR3 comprising the amino acid sequences of SEQ ID NOs: 43, 44, and 45, respectively.

In certain embodiments, the first antigen-binding site that binds NKG2D comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:47, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:49. In certain embodiments, the VH comprises CDR1, CDR2, and CDR3 comprising the amino acid sequences of SEQ ID NOs: 27, 29, and 48, respectively. In certain embodiments, the VL comprises CDR1, CDR2, and CDR3 comprising the amino acid sequences of SEQ ID NOs: 50, 34, and 51, respectively. In certain embodiments, the first antigen-binding site comprises (a) a VH that comprises CDR1, CDR2, and CDR3 comprising the amino acid sequences of SEQ ID NOs: 27, 29, and 48, respectively; and (b) a VL that comprises CDR1, CDR2, and CDR3 comprising the amino acid sequences of SEQ ID NOs: 50, 34, and 51, respectively.

In certain embodiments, the first antigen-binding site that binds NKG2D comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:52, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:58. In certain embodiments, the VH comprises CDR1, CDR2, and CDR3 comprising the amino acid sequences of SEQ ID NOs: 53 or 54, 55, and 56 or 57, respectively (e.g., SEQ ID NOs: 53, 55, and 56, respectively, or SEQ ID NOs: 54, 55, and 57, respectively). In certain embodiments, the VL comprises CDR1, CDR2, and CDR3 comprising the amino acid sequences of SEQ ID NOs: 59, 60, and 61, respectively. In certain embodiments, the first antigen-binding site comprises (a) a VH that comprises CDR1, CDR2, and CDR3 comprising the amino acid sequences of SEQ ID NOs: 53 or 54, 55, and 56 or 57, respectively (e.g., SEQ ID NOs: 53, 55, and 56, respectively, or SEQ ID NOs: 54, 55, and 57, respectively); and (b) a VL that comprises CDR1, CDR2, and CDR3 comprising the amino acid sequences of SEQ ID NOs: 59, 60, and 61, respectively.

In certain embodiments, the first antigen-binding site that binds NKG2D comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:62, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:68. In certain embodiments, the VH comprises CDR1, CDR2, and CDR3 comprising the amino acid sequences of SEQ ID NOs: 63 or 64, 65, and 66 or 67, respectively (e.g., SEQ ID NOs: 63, 65, and 66, respectively, or SEQ ID NOs: 64, 65, and 67, respectively). In certain embodiments, the VL comprises CDR1, CDR2, and CDR3 comprising the amino acid sequences of SEQ ID NOs: 59, 60, and 69, respectively. In certain embodiments, the first antigen-binding site comprises (a) a VH that comprises CDR1, CDR2, and CDR3 comprising the amino acid sequences of SEQ ID NOs: 63 or 64, 65, and 66 or 67, respectively (e.g., SEQ ID NOs: 63, 65, and 66, respectively, or SEQ ID NOs: 64, 65, and 67, respectively); and (b) a VL that comprises CDR1, CDR2, and CDR3 comprising the amino acid sequences of SEQ ID NOs: 59, 60, and 69, respectively.

In certain embodiments, the first antigen-binding site that binds NKG2D comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:89, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:92. In certain embodiments, the VH comprises CDR1, CDR2, and CDR3 comprising the amino acid sequences of SEQ ID NOs: 53 or 54, 55, and 90 or 91, respectively (e.g., SEQ ID NOs: 53, 55, and 90, respectively, or SEQ ID NOs: 54, 55, and 91, respectively). In certain embodiments, the VL comprises CDR1, CDR2, and CDR3 comprising the amino acid sequences of SEQ ID NOs: 93, 44, and 94, respectively. In certain embodiments, the first antigen-binding site comprises (a) a VH that comprises CDR1, CDR2, and CDR3 comprising the amino acid sequences of SEQ ID NOs: 53 or 54, 55, and 90 or 91, respectively (e.g., SEQ ID NOs: 53, 55, and 90, respectively, or SEQ ID NOs: 54, 55, and 91, respectively); and (b) a VL that comprises CDR1, CDR2, and CDR3 comprising the amino acid sequences of SEQ ID NOs: 93, 44, and 94, respectively.

In certain embodiments, the first antigen-binding site that binds NKG2D comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:70, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:75. In certain embodiments, the VH comprises CDR1, CDR2, and CDR3 comprising the amino acid sequences of SEQ ID NOs: 71 or 115, 72, and 73 or 74, respectively (e.g., SEQ ID NOs: 71, 72, and 73, respectively, or SEQ ID NOs: 115, 72, and 74, respectively). In certain embodiments, the VL comprises CDR1, CDR2, and CDR3 comprising the amino acid sequences of SEQ ID NOs: 76, 77, and 78, respectively. In certain embodiments, the first antigen-binding site comprises (a) a VH that comprises CDR1, CDR2, and CDR3 comprising the amino acid sequences of SEQ ID NOs: 71 or 115, 72, and 73 or 74, respectively (e.g., SEQ ID NOs: 71, 72, and 73, respectively, or SEQ ID NOs: 115, 72, and 74, respectively); and (b) a VL that comprises CDR1, CDR2, and CDR3 comprising the amino acid sequences of SEQ ID NOs: 76, 77, and 78, respectively.

In certain embodiments, the first antigen-binding site that binds NKG2D comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:79, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:85. In certain embodiments, the VH comprises CDR1, CDR2, and CDR3 comprising the amino acid sequences of SEQ ID NOs: 80 or 81, 82, and 83 or 84, respectively (e.g., SEQ ID NOs: 80, 82, and 83, respectively, or SEQ ID NOs: 81, 82, and 84, respectively). In certain embodiments, the VL comprises CDR1, CDR2, and CDR3 comprising the amino acid sequences of SEQ ID NOs: 86, 77, and 87, respectively. In certain embodiments, the first antigen-binding site comprises (a) a VH that comprises CDR1, CDR2, and CDR3 comprising the amino acid sequences of SEQ ID NOs: 80 or 81, 82, and 83 or 84 respectively (e.g., SEQ ID NOs: 80, 82, and 83, respectively, or SEQ ID NOs: 81, 82, and 84, respectively); and (b) a VL that comprises CDR1, CDR2, and CDR3 comprising the amino acid sequences of SEQ ID NOs: 86, 77, and 87, respectively.

In certain embodiments, the first antigen-binding site that binds NKG2D comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:95, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:85. In certain embodiments, the VH comprises CDR1, CDR2, and CDR3 comprising the amino acid sequences of SEQ ID NOs: 80 or 81, 82, and 96 or 97, respectively (e.g., SEQ ID NOs: 80, 82, and 96, respectively, or SEQ ID NOs: 81, 82, and 97, respectively). In certain embodiments, the VL comprises CDR1, CDR2, and CDR3 comprising the amino acid sequences of SEQ ID NOs: 86, 77, and 87, respectively. In certain embodiments, the first antigen-binding site comprises (a) a VH that comprises CDR1, CDR2, and CDR3 comprising the amino acid sequences of SEQ ID NOs: 80 or 81, 82, and 96 or 97, respectively (e.g., SEQ ID NOs: 80, 82, and 96, respectively, or SEQ ID NOs: 81, 82, and 97, respectively); and (b) a VL that comprises CDR1, CDR2, and CDR3 comprising the amino acid sequences of SEQ ID NOs: 86, 77, and 87, respectively.

In certain embodiments, the first antigen-binding site that binds NKG2D comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:98, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:85. In certain embodiments, the VH comprises CDR1, CDR2, and CDR3 comprising the amino acid sequences of SEQ ID NOs: 80 or 81, 82, and 99 or 100, respectively (e.g., SEQ ID NOs: 80, 82, and 99, respectively, or SEQ ID NOs: 81, 82, and 100, respectively). In certain embodiments, the VL comprises CDR1, CDR2, and CDR3 comprising the amino acid sequences of SEQ ID NOs: 86, 77, and 87, respectively. In certain embodiments, the first antigen-binding site comprises (a) a VH that comprises CDR1, CDR2, and CDR3 comprising the amino acid sequences of SEQ ID NOs: 80 or 81, 82, and 99 or 100, respectively (e.g., SEQ ID NOs: 80, 82, and 99, respectively, or SEQ ID NOs: 81, 82, and 100, respectively); and (b) a VL that comprises CDR1, CDR2, and CDR3 comprising the amino acid sequences of SEQ ID NOs: 86, 77, and 87, respectively.

In certain embodiments, the first antigen-binding site that binds NKG2D comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:101, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:85. In certain embodiments, the VH comprises CDR1, CDR2, and CDR3 comprising the amino acid sequences of SEQ ID NOs: 80 or 81, 82, and 102 or 103, respectively (e.g., SEQ ID NOs: 80, 82, and 102, respectively, or SEQ ID NOs: 81, 82, and 103, respectively). In certain embodiments, the VL comprises CDR1, CDR2, and CDR3 comprising the amino acid sequences of SEQ ID NOs: 86, 77, and 87, respectively. In certain embodiments, the first antigen-binding site comprises (a) a VH that comprises CDR1, CDR2, and CDR3 comprising the amino acid sequences of SEQ ID NOs: 80 or 81, 82, and 102 or 103, respectively (e.g., SEQ ID NOs: 80, 82, and 102, respectively, or SEQ ID NOs: 81, 82, and 103, respectively); and (b) a VL that comprises CDR1, CDR2, and CDR3 comprising the amino acid sequences of SEQ ID NOs: 86, 77, and 87, respectively.

In certain embodiments, the first antigen-binding site that binds NKG2D comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:104, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:85. In certain embodiments, the VH comprises CDR1, CDR2, and CDR3 comprising the amino acid sequences of SEQ ID NOs: 80 or 81, 82, and 105 or 106, respectively (e.g., SEQ ID NOs: 80, 82, and 105, respectively, or SEQ ID NOs: 81, 82, and 106, respectively). In certain embodiments, the VL comprises CDR1, CDR2, and CDR3 comprising the amino acid sequences of SEQ ID NOs: 86, 77, and 87, respectively. In certain embodiments, the first antigen-binding site comprises (a) a VH that comprises CDR1, CDR2, and CDR3 comprising the amino acid sequences of SEQ ID NOs: 80 or 81, 82, and 105 or 106, respectively (e.g., SEQ ID NOs: 80, 82, and 105, respectively, or SEQ ID NOs: 81, 82, and 106, respectively); and (b) a VL that comprises CDR1, CDR2, and CDR3 comprising the amino acid sequences of SEQ ID NOs: 86, 77, and 87, respectively.

In certain embodiments, the first antigen-binding site that binds NKG2D comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:107, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:85. In certain embodiments, the VH comprises CDR1, CDR2, and CDR3 comprising the amino acid sequences of SEQ ID NOs: 80 or 81, 82, and 108 or 109, respectively (e.g., SEQ ID NOs: 80, 82, and 108, respectively, or SEQ ID NOs: 81, 82, and 109, respectively). In certain embodiments, the VL comprises CDR1, CDR2, and CDR3 comprising the amino acid sequences of SEQ ID NOs: 86, 77, and 87, respectively. In certain embodiments, the first antigen-binding site comprises (a) a VH that comprises CDR1, CDR2, and CDR3 comprising the amino acid sequences of SEQ ID NOs: 80 or 81, 82, and 108 or 109, respectively (e.g., SEQ ID NOs: 80, 82, and 108, respectively, or SEQ ID NOs: 81, 82, and 109, respectively); and (b) a VL that comprises CDR1, CDR2, and CDR3 comprising the amino acid sequences of SEQ ID NOs: 86, 77, and 87, respectively.

In certain embodiments, the first antigen-binding site that binds NKG2D comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:110, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:85. In certain embodiments, the VH comprises CDR1, CDR2, and CDR3 comprising the amino acid sequences of SEQ ID NOs: 80 or 81, 82, and 111 or 112, respectively (e.g., SEQ ID NOs: 80, 82, and 111, respectively, or SEQ ID NOs: 81, 82, and 112, respectively). In certain embodiments, the VL comprises CDR1, CDR2, and CDR3 comprising the amino acid sequences of SEQ ID NOs: 86, 77, and 87, respectively. In certain embodiments, the first antigen-binding site comprises (a) a VH that comprises CDR1, CDR2, and CDR3 comprising the amino acid sequences of SEQ ID NOs: 80 or 81, 82, and 111 or 112, respectively (e.g., SEQ ID NOs: 80, 82, and 111, respectively, or SEQ ID NOs: 81, 82, and 112, respectively); and (b) a VL that comprises CDR1, CDR2, and CDR3 comprising the amino acid sequences of SEQ ID NOs: 86, 77, and 87, respectively.

In certain embodiments, the first antigen-binding site that binds NKG2D comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:113, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:114.

In certain embodiments, the first antigen-binding site that binds NKG2D comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:116, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:117.

The multispecific binding proteins can bind to NKG2D-expressing cells, which include but are not limited to NK cells, γδ T cells and CD8$^+$ αβ T cells. Upon NKG2D binding, the multispecific binding proteins may block natural ligands, such as ULBP6 and MICA, from binding to NKG2D and activating NK cells.

The multispecific binding proteins binds to cells expressing CD16, an Fc receptor on the surface of leukocytes including natural killer cells, macrophages, neutrophils, eosinophils, mast cells, and follicular dendritic cells. A protein of the present disclosure binds to NKG2D with an affinity of $K_D$ of 2 nM to 120 nM, e.g., 2 nM to 110 nM, 2 nM to 100 nM, 2 nM to 90 nM, 2 nM to 80 nM, 2 nM to 70 nM, 2 nM to 60 nM, 2 nM to 50 nM, 2 nM to 40 nM, 2 nM to 30 nM, 2 nM to 20 nM, 2 nM to 10 nM, about 15 nM, about 14 nM, about 13 nM, about 12 nM, about 11 nM, about 10 nM, about 9 nM, about 8 nM, about 7 nM, about 6 nM, about 5 nM, about 4.5 nM, about 4 nM, about 3.5 nM, about 3 nM, about 2.5 nM, about 2 nM, about 1.5 nM, about 1 nM, between about 0.5 nM to about 1 nM, about 1 nM to about 2 nM, about 2 nM to 3 nM, about 3 nM to 4 nM, about 4 nM to about 5 nM, about 5 nM to about 6 nM, about 6 nM to about 7 nM, about 7 nM to about 8 nM, about 8 nM to about 9 nM, about 9 nM to about 10 nM, about 1 nM to about 10 nM, about 2 nM to about 10 nM, about 3 nM to about 10 nM, about 4 nM to about 10 nM, about 5 nM to about 10 nM, about 6 nM to about 10 nM, about 7 nM to about 10 nM, or about 8 nM to about 10 nM. In some embodiments, NKG2D-binding sites bind to NKG2D with a $K_D$ of 10 to 62 nM.

CLEC12A Binding Site

The tumor associated antigen-binding site of the multispecific binding protein disclosed herein comprises a heavy chain variable domain and a light chain variable domain. Table 2 lists some exemplary sequences of heavy chain variable domains and light chain variable domains that, in combination, can bind to these tumor associated antigens.

In one aspect, the present disclosure provides multispecific binding proteins that bind to the NKG2D receptor and CD16 receptor on natural killer cells, and CLEC12A. Table 2 lists some exemplary sequences of heavy chain variable domains and light chain variable domains that, in combination, can bind to CLEC12A. CDR sequences are identified under Kabat numbering as indicated.

TABLE 2

Sequences of Exemplary Antigen-Binding Sites that Bind CLEC12A.

| Clone | VH | VL |
|---|---|---|
| 16B8.C8 | EVQLQESGPGLVQPSQSLSITCT VSGFSLTNYGLHWVRQSPGKG LEWLGVIWSGGKTDYNTPFKS RLSISKDISKNQVFFKMNSLQP NDTAIYFCAKYDYDDSLDYWG QGTSVTVSS [SEQ ID NO: 135] CDR1: GFSLTNY [SEQ ID NO: 137] CDR2: WSGGK [SEQ ID NO: 138] CDR3: YDYDDSLDY [SEQ ID NO: 139] | DIQMNQSPSSLSASLGDTIAITCHA SQNINFWLSWYQQKPGNIPKLLIY EASNLHTGVPSRFSGSGSGTRFTLT ISSLQPEDIATYYCQQSHSYPLTFG QGTKLEIK [SEQ ID NO: 136] CDR1: HASQNINFWLS [SEQ ID NO: 140] CDR2: EASNLHT [SEQ ID NO: 141] CDR3: QQSHSYPLT [SEQ ID NO: 142] |
| Humanized 16B8.C8 in scFv-1292 / scFv-1301 (back mutations in VH and VL underlined) | QLQLQESGPGLVKPSETLSLTCT VSGFSLTNYGLHWIRQPPGKGL EWIGVIWSGGKTDYNPSLKSRV TISKDTSKNQFSLKLSSVQAND TAVYYCAKYDYDDSLDYWGQ GTLVTVSS [SEQ ID NO: 143] CDR1: GFSLTNY [SEQ ID NO: 137] CDR2: WSGGK [SEQ ID NO: 138] CDR3: YDYDDSLDY [SEQ ID NO: 139] | DIQMTQSPSSLSASVGDRVTITCHA SQNINFWLSWYQQKPGKIPKLLIY EASNLHTGVPSRFSGSGSGTRFTLT ISSLQPEDIATYYCQQSHSYPLTFG QGTKLEIK [SEQ ID NO: 144] CDR1: HASQNINFWLS [SEQ ID NO: 140] CDR2: EASNLHT [SEQ ID NO: 141] CDR3: QQSHSYPLT [SEQ ID NO: 142] |
| scFv of humanized 16B8.C8 scFv-1292 / scFv-1301 | scFv -1292 (VH-VL): QLQLQESGPGLVKPSETLSLTCTVSGFSLTNYGLHWIRQPPGKCLEWIG VIWSGGKTDYNPSLKSRVTISKDTSKNQFSLKLSSVQANDTAVYYCAK YDYDDSLDYWGQGTLVTVSSGGGGSGGGGSGGGGSGGGGSDIQMT QSPSSLSASVGDRVTITCHASQNINFWLSWYQQKPGKIPKLLIYEASNL HTGVPSRFSGSGSGTRFTLTISSLQPEDIATYYCQQSHSYPLTFGCGTKL EIK [SEQ ID NO: 145] scFv -1301 (VL-VH): DIQMTQSPSSLSASVGDRVTITCHASQNINFWLSWYQQKPGKIPKLLIY | |

TABLE 2-continued

Sequences of Exemplary Antigen-Binding Sites that Bind CLEC12A.

| Clone | VH | VL |
| --- | --- | --- |
| | EASNLHTGVPSRFSGSGSGTRFTLTISSLQPEDIATYYCQQSHSYPLTFG<br>CGTKLEIKGGGGSGGGGSGGGGSGGGGSQLQLQESGPGLVKPSETLS<br>LTCTVSGFSLTNYGLHWIRQPPGKCLEWIGVIWSGGKTDYNPSLKSRV<br>TISKDTSKNQFSLKLSSVQANDTAVYYCAKYDYDDSLDYWGQGTLVT<br>VSS<br>[SEQ ID NO: 146] | |
| Humanized<br>16B8.C8<br>in scFv-1293/<br>scFv-1302<br>(back<br>mutations in<br>VH and VL<br>underlined) | QLQLQESGPGLVKPSETLSLTCT<br>VSGFSLTNYGLHWIRQPPGKGL<br>EWIGVIWSGGKTDYNPSLKSRV<br>TISVDTSKNQFSLKLSSVQAND<br>TAVYYCAKYDYDDSLDYWGQ<br>GTLVTVSS<br>[SEQ ID NO: 147]<br>CDR1: GFSLTNY [SEQ ID<br>NO: 137]<br>CDR2: WSGGK [SEQ ID NO: 138]<br>CDR3: YDYDDSLDY [SEQ ID<br>NO: 139] | DIQMTQSPSSLSASVGDRVTITCHA<br>SQNINFWLSWYQQKPGKIPKLLIY<br>EASNLHTGVPSRFSGSGSGTRFTLT<br>ISSLQPEDIATYYCQQSHSYPLTFG<br>QGTKLEIK<br>[SEQ ID NO: 144]<br>CDR1: HASQNINFWLS [SEQ ID<br>NO: 140]<br>CDR2: EASNLHT [SEQ ID NO: 141]<br>CDR3: QQSHSYPLT [SEQ ID<br>NO: 142] |
| scFv of<br>humanized<br>16B8.C8<br>scFv-1293/<br>scFv-1302 | scFv -1293 (VH-VL):<br>QLQLQESGPGLVKPSETLSLTCTVSGFSLTNYGLHWIRQPPGKCLEWIG<br>VIWSGGKTDYNPSLKSRVTISVDTSKNQFSLKLSSVQANDTAVYYCAK<br>YDYDDSLDYWGQGTLVTVSSGGGGSGGGGSGGGGSGGGGSDIQMT<br>QSPSSLSASVGDRVTITCHASQNINFWLSWYQQKPGKIPKLLIYEASNL<br>HTGVPSRFSGSGSGTRFTLTISSLQPEDIATYYCQQSHSYPLTFGCGTKL<br>EIK<br>[SEQ ID NO: 149]<br>scFv -1302 (VL-VH):<br>DIQMTQSPSSLSASVGDRVTITCHASQNINFWLSWYQQKPGKIPKLLIY<br>EASNLHTGVPSRFSGSGSGTRFTLTISSLQPEDIATYYCQQSHSYPLTFG<br>CGTKLEIKGGGGSGGGGSGGGGSGGGGSQLQLQESGPGLVKPSETLS<br>LTCTVSGFSLTNYGLHWIRQPPGKCLEWIGVIWSGGKTDYNPSLKSRV<br>TISKDTSKNQFSLKLSSVQANDTAVYYCAKYDYDDSLDYWGQGTLVT<br>VSS<br>[SEQ ID NO: 150] | |
| Humanized<br>16B8.C8<br>in scFv-1294 /<br>scFv-1303<br>(back<br>mutations in<br>VH and VL<br>underlined) | QLQLQESGPGLVKPSETLSLTCT<br>VSGFSLTNYGLHWIRQPPGKGL<br>EWIGVIWSGGKTDYNPSLKSRV<br>TISKDTSKNQFSLKLSSVTANDT<br>AVYYCAKYDYDDSLDYWGQG<br>TLVTVSS<br>[SEQ ID NO: 244]<br>CDR1: GFSLTNY [SEQ ID<br>NO: 137]<br>CDR2: WSGGK [SEQ ID NO: 138]<br>CDR3: YDYDDSLDY [SEQ ID<br>NO: 139] | DIQMTQSPSSLSASVGDRVTITCHA<br>SQNINFWLSWYQQKPGKIPKLLIY<br>EASNLHTGVPSRFSGSGSGTRFTLT<br>ISSLQPEDIATYYCQQSHSYPLTFG<br>QGTKLEIK<br>[SEQ ID NO: 144]<br>CDR1: HASQNINFWLS [SEQ ID<br>NO: 140]<br>CDR2: EASNLHT [SEQ ID NO: 141]<br>CDR3: QQSHSYPLT [SEQ ID<br>NO: 142] |
| scFv of<br>humanized<br>16B8.C8<br>scFv-1294 /<br>scFv-1303 | scFv -1294 (VH-VL):<br>QLQLQESGPGLVKPSETLSLTCTVSGFSLTNYGLHWIRQPPGKCLEWIG<br>VIWSGGKTDYNPSLKSRVTISKDTSKNQFSLKLSSVTANDTAVYYCAK<br>YDYDDSLDYWGQGTLVTVSSGGGGSGGGGSGGGGSGGGGSDIQMT<br>QSPSSLSASVGDRVTITCHASQNINFWLSWYQQKPGKIPKLLIYEASNL<br>HTGVPSRFSGSGSGTRFTLTISSLQPEDIATYYCQQSHSYPLTFGCGTKL<br>EIK<br>[SEQ ID NO: 153]<br>scFv -1303 (VL-VH):<br>DIQMTQSPSSLSASVGDRVTITCHASQNINFWLSWYQQKPGKIPKLLIY<br>EASNLHTGVPSRFSGSGSGTRFTLTISSLQPEDIATYYCQQSHSYPLTFG<br>CGTKLEIKGGGGSGGGGSGGGGSGGGGSQLQLQESGPGLVKPSETLS<br>LTCTVSGFSLTNYGLHWIRQPPGKCLEWIGVIWSGGKTDYNPSLKSRV<br>TISKDTSKNQFSLKLSSVTANDTAVYYCAKYDYDDSLDYWGQGTLVT<br>VSS<br>[SEQ ID NO: 154] | |
| Humanized<br>16B8.C8<br>in scFv-1295 /<br>scFv-1304<br>(back<br>mutations in<br>VH and VL<br>underlined) | QLQLQESGPGLVKPSETLSLTCT<br>VSGFSLTNYGLHWIRQPPGKGL<br>EWIGVIWSGGKTDYNPSLKSRV<br>TISKDTSKNQFSLKLSSVQAAD<br>TAVYYCAKYDYDDSLDYWGQ<br>GTLVTVSS<br>[SEQ ID NO: 178]<br>CDR1: GFSLTNY [SEQ ID<br>NO: 137] | DIQMTQSPSSLSASVGDRVTITCHA<br>SQNINFWLSWYQQKPGKIPKLLIY<br>EASNLHTGVPSRFSGSGSGTRFTLT<br>ISSLQPEDIATYYCQQSHSYPLTFG<br>QGTKLEIK<br>[SEQ ID NO: 144]<br>CDR1: HASQNINFWLS [SEQ ID<br>NO: 140]<br>CDR2: EASNLHT [SEQ ID NO: 141] |

TABLE 2-continued

Sequences of Exemplary Antigen-Binding Sites that Bind CLEC12A.

| Clone | VH | VL |
|---|---|---|
| | CDR2: WSGGK [SEQ ID NO: 138]<br>CDR3: YDYDDSLDY [SEQ ID NO: 139] | CDR3: QQSHSYPLT [SEQ ID NO: 142] |
| scFv of humanized 16B8.C8 scFv- 1295 / scFv-1304 | scFv -1295 (VH-VL):<br>QLQLQESGPGLVKPSETLSLTCTVSGFSLTNYGLHWIRQPPGKCLEWIG<br>VIWSGGKTDYNPSLKSRVTISKDTSKNQFSLKLSSVQAADTAVYYCAK<br>YDYDDSLDYWGQGTLVTVSSGGGGSGGGGSGGGGSGGGGSDIQMT<br>QSPSSLSASVGDRVTITCHASQNINFWLSWYQQKPGKIPKLLIYEASNL<br>HTGVPSRFSGSGSGTRFTLTISSLQPEDIATYYCQQSHSYPLTFGCGTKL<br>EIK<br>[SEQ ID NO: 156]<br>scFv -1304 (VL-VH):<br>DIQMTQSPSSLSASVGDRVTITCHASQNINFWLSWYQQKPGKIPKLLIY<br>EASNLHTGVPSRFSGSGSGTRFTLTISSLQPEDIATYYCQQSHSYPLTFG<br>CGTKLEIKGGGGSGGGGSGGGGSGGGGSQLQLQESGPGLVKPSETLS<br>LTCTVSGFSLTNYGLHWIRQPPGKCLEWIGVIWSGGKTDYNPSLKSRV<br>TISKDTSKNQFSLKLSSVQAADTAVYYCAKYDYDDSLDYWGQGTLVT<br>VSS<br>[SEQ ID NO: 157] | |
| Humanized 16B8.C8 in scFv-1296 / scFv-1305 (back mutations in VH and VL underlined) | QLQLQESGPGLVKPSETLSLTCT<br>VSGFSLTNYGLHWIRQPPGKGL<br>EWIGVIWSGGKTDYNPSLKSRV<br>TISKDTSKNQFSLKLSSVQAND<br>TAVYYCARYDYDDSLDYWGQ<br>GTLVTVSS<br>[SEQ ID NO: 256]<br>CDR1: GFSLTNY [SEQ ID NO: 137]<br>CDR2: WSGGK [SEQ ID NO: 138]<br>CDR3: YDYDDSLDY [SEQ ID NO: 139] | DIQMTQSPSSLSASVGDRVTITCHA<br>SQNINFWLSWYQQKPGKIPKLLIY<br>EASNLHTGVPSRFSGSGSGTRFTLT<br>ISSLQPEDIATYYCQQSHSYPLTFG<br>QGTKLEIK<br>[SEQ ID NO: 144]<br>CDR1: HASQNINFWLS [SEQ ID NO: 140]<br>CDR2: EASNLHT [SEQ ID NO: 141]<br>CDR3: QQSHSYPLT [SEQ ID NO: 142] |
| scFv of humanized 16B8.C8 scFv-1296 / scFv-1305 | scFv -1296 (VH-VL):<br>QLQLQESGPGLVKPSETLSLTCTVSGFSLTNYGLHWIRQPPGKCLEWIG<br>VIWSGGKTDYNPSLKSRVTISKDTSKNQFSLKLSSVQANDTAVYYCAR<br>YDYDDSLDYWGQGTLVTVSSGGGGSGGGGSGGGGSGGGGSDIQMT<br>QSPSSLSASVGDRVTITCHASQNINFWLSWYQQKPGKIPKLLIYEASNL<br>HTGVPSRFSGSGSGTRFTLTISSLQPEDIATYYCQQSHSYPLTFGCGTKL<br>EIK<br>[SEQ ID NO: 160]<br>scFv -1305 (VL-VH):<br>DIQMTQSPSSLSASVGDRVTITCHASQNINFWLSWYQQKPGKIPKLLIY<br>EASNLHTGVPSRFSGSGSGTRFTLTISSLQPEDIATYYCQQSHSYPLTFG<br>CGTKLEIKGGGGSGGGGSGGGGSGGGGSQLQLQESGPGLVKPSETLS<br>LTCTVSGFSLTNYGLHWIRQPPGKCLEWIGVIWSGGKTDYNPSLKSRV<br>TISKDTSKNQFSLKLSSVQANDTAVYYCARYDYDDSLDYWGQGTLVT<br>VSS<br>[SEQ ID NO: 161] | |
| Humanized 16B8.C8 in scFv-1297 / scFv-1306 (back mutations in VH and VL underlined) | QLQLQESGPGLVKPSETLSLTCT<br>VSGFSLTNYGLHWIRQPPGKGL<br>EWIGVIWSGGKTDYNPSLKSRV<br>TISKDTSKNQFSLKLSSVQAND<br>TAVYYCAKYDYDDSLDYWGQ<br>GTLVTVSS<br>[SEQ ID NO: 143]<br>CDR1: GFSLTNY [SEQ ID NO: 137]<br>CDR2: WSGGK [SEQ ID NO: 138]<br>CDR3: YDYDDSLDY [SEQ ID NO: 139] | DIQMTQSPSSLSASVGDRVTITCHA<br>SQNINFWLSWYQQKPGKAPKLLIY<br>EASNLHTGVPSRFSGSGSGTRFTLT<br>ISSLQPEDIATYYCQQSHSYPLTFG<br>QGTKLEIK<br>[SEQ ID NO: 163]<br>CDR1: HASQNINFWLS [SEQ ID NO: 140]<br>CDR2: EASNLHT [SEQ ID NO: 141]<br>CDR3: QQSHSYPLT [SEQ ID NO: 142] |
| scFv of humanized 16B8.C8 scFv-1297 / scFv-1306 | scFv -1297 (VH-VL):<br>QLQLQESGPGLVKPSETLSLTCTVSGFSLTNYGLHWIRQPPGKCLEWIG<br>VIWSGGKTDYNPSLKSRVTISKDTSKNQFSLKLSSVQANDTAVYYCAK<br>YDYDDSLDYWGQGTLVTVSSGGGGSGGGGSGGGGSGGGGSDIQMT<br>QSPSSLSASVGDRVTITCHASQNINFWLSWYQQKPGKAPKLLIYEASN<br>LHTGVPSRFSGSGSGTRFTLTISSLQPEDIATYYCQQSHSYPLTFGCGTK<br>LEIK<br>[SEQ ID NO: 164]<br>scFv -1306 (VL-VH):<br>DIQMTQSPSSLSASVGDRVTITCHASQNINFWLSWYQQKPGKAPKLLI<br>YEASNLHTGVPSRFSGSGSGTRFTLTISSLQPEDIATYYCQQSHSYPLTF<br>GCGTKLEIKGGGGSGGGGSGGGGSGGGGSQLQLQESGPGLVKPSETL | |

TABLE 2-continued

Sequences of Exemplary Antigen-Binding Sites that Bind CLEC12A.

| Clone | VH | VL |
|---|---|---|
| | SLTCTVSGFSLTNYGLHWIRQPPGKCLEWIGVIWSGGKTDYNPSLKSR<br>VTISKDTSKNQFSLKLSSVQANDTAVYYCAKYDYDDSLDYWGQGTLV<br>TVSS<br>[SEQ ID NO: 165] | |
| Humanized 16B8.C8 in scFv-1298 / scFv-1307 (back mutations in VH and VL underlined) | QLQLQESGPGLVKPSETLSLTCT<br>VSGFSLTNYGLHWIRQPPGKGL<br>EWIGVIWSGGKTDYNPSLKSRV<br>TISKDTSKNQFSLKLSSVQAND<br>TAVYYCAKYDYDDSLDYWGQ<br>GTLVTVSS<br>[SEQ ID NO: 143]<br>CDR1: GFSLTNY [SEQ ID NO: 137]<br>CDR2: WSGGK [SEQ ID NO: 138]<br>CDR3: YDYDDSLDY [SEQ ID NO: 139] | DIQMTQSPSSLSASVGDRVTITCHA<br>SQNINFWLSWYQQKPGKIPKLLIY<br>EASNLHTGVPSRFSGSGSGTDFTLT<br>ISSLQPEDIATYYCQQSHSYPLTFG<br>QGTKLEIK<br>[SEQ ID NO: 167]<br>CDR1: HASQNINFWLS [SEQ ID NO: 140]<br>CDR2: EASNLHT [SEQ ID NO: 141]<br>CDR3: QQSHSYPLT [SEQ ID NO: 142] |
| scFv of humanized 16B8.C8 scFv-1298 / scFv-1307 | scFv -1298 (VH-VL):<br>QLQLQESGPGLVKPSETLSLTCTVSGFSLTNYGLHWIRQPPGKCLEWIG<br>VIWSGGKTDYNPSLKSRVTISKDTSKNQFSLKLSSVQANDTAVYYCAK<br>YDYDDSLDYWGQGTLVTVSSGGGGSGGGGSGGGGSGGGGSDIQMT<br>QSPSSLSASVGDRVTITCHASQNINFWLSWYQQKPGKIPKLLIYEASNL<br>HTGVPSRFSGSGSGTDFTLTISSLQPEDIATYYCQQSHSYPLTFGCGTKL<br>EIK<br>[SEQ ID NO: 168]<br>scFv -1307 (VL-VH):<br>DIQMTQSPSSLSASVGDRVTITCHASQNINFWLSWYQQKPGKIPKLLIY<br>EASNLHTGVPSRFSGSGSGTDFTLTISSLQPEDIATYYCQQSHSYPLTFG<br>CGTKLEIKGGGGSGGGGSGGGGSGGGGSQLQLQESGPGLVKPSETLS<br>LTCTVSGFSLTNYGLHWIRQPPGKCLEWIGVIWSGGKTDYNPSLKSRV<br>TISKDTSKNQFSLKLSSVQANDTAVYYCAKYDYDDSLDYWGQGTLVT<br>VSS<br>[SEQ ID NO: 169] | |
| Humanized 16B8.C8 in scFv-1299 / scFv-1308 | QLQLQESGPGLVKPSETLSLTCT<br>VSGFSLTNYGLHWIRQPPGKGL<br>EWIGVIWSGGKTDYNPSLKSRV<br>TISKDTSKNQFSLKLSSVQAND<br>TAVYYCAKYDYDDSLDYWGQ<br>GTLVTVSS<br>[SEQ ID NO: 143]<br>CDR1: GFSLTNY [SEQ ID NO: 137]<br>CDR2: WSGGK [SEQ ID NO: 138]<br>CDR3: YDYDDSLDY [SEQ ID NO: 139] | DIQMTQSPSSLSASVGDRVTITCHA<br>SQNINFWLSWYQQKPGKIPKLLIY<br>EASNLHTGVPSRFSGSGSGTRFTLT<br>ISSLQPEDFATYYCQQSHSYPLTFG<br>QGTKLEIK<br>[SEQ ID NO: 171]<br>CDR1: HASQNINFWLS [SEQ ID NO: 140]<br>CDR2: EASNLHT [SEQ ID NO: 141]<br>CDR3: QQSHSYPLT [SEQ ID NO: 142] |
| scFv of humanized 16B8.C8 scFv-1299 / scFv-1308 | scFv -1299 (VH-VL):<br>QLQLQESGPGLVKPSETLSLTCTVSGFSLTNYGLHWIRQPPGKCLEWIG<br>VIWSGGKTDYNPSLKSRVTISKDTSKNQFSLKLSSVQANDTAVYYCAK<br>YDYDDSLDYWGQGTLVTVSSGGGGSGGGGSGGGGSGGGGSDIQMT<br>QSPSSLSASVGDRVTITCHASQNINFWLSWYQQKPGKIPKLLIYEASNL<br>HTGVPSRFSGSGSGTRFTLTISSLQPEDFATYYCQQSHSYPLTFGCGTKL<br>EIK<br>[SEQ ID NO: 172]<br>scFv -1308 (VL-VH):<br>DIQMTQSPSSLSASVGDRVTITCHASQNINFWLSWYQQKPGKIPKLLIY<br>EASNLHTGVPSRFSGSGSGTRFTLTISSLQPEDFATYYCQQSHSYPLTFG<br>CGTKLEIKGGGGSGGGGSGGGGSGGGGSQLQLQESGPGLVKPSETLS<br>LTCTVSGFSLTNYGLHWIRQPPGKCLEWIGVIWSGGKTDYNPSLKSRV<br>TISKDTSKNQFSLKLSSVQANDTAVYYCAKYDYDDSLDYWGQGTLVT<br>VSS<br>[SEQ ID NO: 173] | |
| Humanized 16B8.C8 in scFv-1300/ scFv-1309 | QLQLQESGPGLVKPSETLSLTCT<br>VSGFSLTNYGLHWIRQPPGKGL<br>EWIGVIWSGGKTDYNPSLKSRV<br>TISVDTSKNQFSLKLSSVTAADT<br>AVYYCARYDYDDSLDYWGQG<br>TLVTVSS<br>[SEQ ID NO: 174]<br>CDR1: GFSLTNY [SEQ ID | DIQMTQSPSSLSASVGDRVTITCHA<br>SQNINFWLSWYQQKPGKAPKLLIY<br>EASNLHTGVPSRFSGSGSGTDFTLT<br>ISSLQPEDFATYYCQQSHSYPLTFG<br>QGTKLEIK<br>[SEQ ID NO: 175]<br>CDR1: HASQNINFWLS [SEQ ID NO: 140] |

TABLE 2-continued

Sequences of Exemplary Antigen-Binding Sites that Bind CLEC12A.

| Clone | VH | VL |
|---|---|---|
| | NO: 137]<br>CDR2: WSGGK [SEQ ID NO: 138]<br>CDR3: YDYDDSLDY [SEQ ID NO: 139] | CDR2: EASNLHT [SEQ ID NO: 141]<br>CDR3: QQSHSYPLT [SEQ ID NO: 142] |
| scFv of humanized 16B8.C8 scFv-1300/ scFv-1309 | scFv -1300 (VH-VL):<br>QLQLQESGPGLVKPSETLSLTCTVSGFSLTNYGLHWIRQPPGKCLEWIG<br>VIWSGGKTDYNPSLKSRVTISVDTSKNQFSLKLSSVTAADTAVYYCAR<br>YDYDDSLDYWGQGTLVTVSSGGGGSGGGGSGGGGSGGGGSDIQMT<br>QSPSSLSASVGDRVTITCHASQNINFWLSWYQQKPGKAPKLLIYEASN<br>LHTGVPSRFSGSGSGTDFTLTISSLQPEDFATYYCQQSHSYPLTFGCGTK<br>LEIK<br>[SEQ ID NO: 176]<br>scFv -1309 (VL-VH):<br>DIQMTQSPSSLSASVGDRVTITCHASQNINFWLSWYQQKPGKAPKLLI<br>YEASNLHTGVPSRFSGSGSGTDFTLTISSLQPEDFATYYCQQSHSYPLTF<br>GCGTKLEIKGGGGSGGGGSGGGGSGGGGSQLQLQESGPGLVKPSETL<br>SLTCTVSGFSLTNYGLHWIRQPPGKCLEWIGVIWSGGKTDYNPSLKSR<br>VTISVDTSKNQFSLKLSSVTAADTAVYYCARYDYDDSLDYWGQGTLV<br>TVSS<br>[SEQ ID NO: 177] | |
| Humanized 16B8.C8 in scFv-1602/ scFv-2061 | QLQLQESGPGLVKPSETLSLTCT<br>VSGFSLTNYGLHWIRQPPGKGL<br>EWIGVIWSGGKTDYNPSLKSRV<br>TISKDTSKNQFSLKLSSVQAAD<br>TAVYYCAKYDYDDSLDYWGQ<br>GTLVTVSS [SEQ ID NO: 178]<br>CDR1: GFSLTNY [SEQ ID NO: 137]<br>CDR2: WSGGK [SEQ ID NO: 138]<br>CDR3: YDYDDSLDY [SEQ ID NO: 139] | DIQMTQSPSSLSASVGDRVTITCHA<br>SQNINFWLSWYQQKPGKAPKLLIY<br>EASNLHTGVPSRFSGSGSGTRFTLT<br>ISSLQPEDIATYYCQQSHSYPLTFG<br>GGTKLEIK<br>[SEQ ID NO: 289]<br>CDR1: HASQNINFWLS [SEQ ID NO: 140]<br>CDR2: EASNLHT [SEQ ID NO: 141]<br>CDR3: QQSHSYPLT [SEQ ID NO: 142] |
| scFv of humanized 16B8.C8 scFv-1602/ scFv-2061 | scFv -1602 (VH-VL):<br>QLQLQESGPGLVKPSETLSLTCTVSGFSLTNYGLHWIRQPPGKCLEWIG<br>VIWSGGKTDYNPSLKSRVTISKDTSKNQFSLKLSSVQAADTAVYYCAK<br>YDYDDSLDYWGQGTLVTVSSGGGGSGGGGSGGGGSGGGGSDIQMT<br>QSPSSLSASVGDRVTITCHASQNINFWLSWYQQKPGKAPKLLIYEASN<br>LHTGVPSRFSGSGSGTRFTLTISSLQPEDIATYYCQQSHSYPLTFGCGTK<br>LEIK<br>[SEQ ID NO: 180]<br>scFv-2061 (VL-VH):<br>DIQMTQSPSSLSASVGDRVTITCHASQNINFWLSWYQQKPGKAPKLLI<br>YEASNLHTGVPSRFSGSGSGTRFTLTISSLQPEDIATYYCQQSHSYPLTF<br>GCGTKLEIKGGGGSGGGGSGGGGSGGGGSQLQLQESGPGLVKPSETL<br>SLTCTVSGFSLTNYGLHWIRQPPGKCLEWIGVIWSGGKTDYNPSLKSR<br>VTISKDTSKNQFSLKLSSVQAADTAVYYCAKYDYDDSLDYWGQGTLV<br>TVSS<br>[SEQ ID NO: 181] | |
| Humanized 16B8.C8 consensus | QLQLQESGPGLVKPSETLSLTCT<br>VSGFSLTNYGLHWIRQPPGKGL<br>EWIGVIWSGGKTDYNPSLKSRV<br>TISX$_1$DTSKNQFSLKLSSVX$_2$AX$_3$<br>DTAVYYCAX$_4$YDYDDSLDYWG<br>QGTLVTVSS<br>where X$_1$ is V or K, X$_2$ is T or Q,<br>X$_3$ is A or N, and X$_4$ is R or K<br>[SEQ ID NO: 182]<br>CDR1: GFSLTNY [SEQ ID NO: 137]<br>CDR2: WSGGK [SEQ ID NO: 138]<br>CDR3: YDYDDSLDY [SEQ ID NO: 139] | DIQMTQSPSSLSASVGDRVTITCHA<br>SQNINFWLSWYQQKPGKX$_1$PKLLI<br>YEASNLHTGVPSRFSGSGSGTX$_2$FT<br>LTISSLQPEDX$_3$ATYYCQQSHSYPLT<br>FGX$_4$GTKLEIK<br>where X$_1$ is A or I, X$_2$ is D or R, X$_3$ is F or I, and X$_4$ is Q or G<br>[SEQ ID NO: 151]<br>CDR1: HASQNINFWLS [SEQ ID NO: 140]<br>CDR2: EASNLHT [SEQ ID NO: 141]<br>CDR3: QQSHSYPLT [SEQ ID NO: 142] |
| Humanized 16B8.C8 in AB0305/ AB5030 (Cysteine heterodimeri-zation mutations are underlined. Such | QLQLQESGPGLVKPSETLSLTC<br>TVSGFSLTNYGLHWIRQPPGKG<br>LEWIGVIWVGGATDYNPSLKS<br>RVTISVDTSKNQFSLKLSSVQA<br>ADTAVYYCAKGDYGDTLDYW<br>GQGTLVTVSS<br>[SEQ ID NO: 270]<br>QLQLQESGPGLVKPSETLSLTCT<br>VSGFSLTNYGLHWIRQPPGKCL<br>EWIGVIWVGGATDYNPSLKSRV | DIQMTQSPSSLSASVGDRVTITCHA<br>SQNINFWLSWYQQKPGKAPKLLIY<br>EASNLHTGVPSRFSGSGSGTDFTLT<br>ISSLQPEDFATYYCQQSHSYPLTFG<br>SGTKLEIK<br>[SEQ ID NO: 271]<br>DIQMTQSPSSLSASVGDRVTITCHA<br>SQNINFWLSWYQQKPGKAPKLLIY<br>EASNLHTGVPSRFSGSGSGTDFTLT<br>ISSLQPEDFATYYCQQSHSYPLTFG |

TABLE 2-continued

Sequences of Exemplary Antigen-Binding Sites that Bind CLEC12A.

| Clone | VH | VL |
|---|---|---|
| mutations can facilitate formation of a disulfide bridge between the VH and VL of the scFv.) | TISVDTSKNQFSLKLSSVQAAD TAVYYCAKGDYGDTLDYWGQ GTLVTVSS [SEQ ID NO: 335] CDR1: GFSLTNY [SEQ ID NO: 137] CDR2: WVGGA [SEQ ID NO: 272] CDR3: GDYGDTLDY [SEQ ID NO: 273] | CGTKLEIK [SEQ ID NO: 336] CDR1: HASQNINFWLS [SEQ ID NO: 140] CDR2: EASNLHT [SEQ ID NO: 141] CDR3: QQSHSYPLT [SEQ ID NO: 142] |
| scFv of humanized 16B8.C8 AB0305/ AB5030 | AB0305 (VH-VL): QLQLQESGPGLVKPSETLSLTCTVSGFSLTNYGLHWIRQPPGKCLEWI GVIWVGGATDYNPSLKSRVTISVDTSKNQFSLKLSSVQAADTAVYYC AKGDYGDTLDYWGQGTLVTVSSGGGGSGGGGSGGGGSGGGGSSDIQ MTQSPSSLSASVGDRVTITCHASQNINFWLSWYQQKPGKAPKLLIYEA SNLHTGVPSRFSGSGSGTDFTLTISSLQPEDFATYYCQQSHSYPLTFGCG TKLEIK [SEQ ID NO: 274] AB5030 (VL-VH): DIQMTQSPSSLSASVGDRVTITCHASQNINFWLSWYQQKPGKAPKLLI YEASNLHTGVPSRFSGSGSGTDFTLTISSLQPEDFATYYCQQSHSYPLTF GCGTKLEIKGGGGSGGGGSGGGGSGGGGSQLQLQESGPGLVKPSETL SLTCTVSGFSLTNYGLHWIRQPPGKCLEWIGVIWVGGATDYNPSLKSR VTISVDTSKNQFSLKLSSVQAADTAVYYCAKGDYGDTLDYWGQGTL VTVSS [SEQ ID NO: 275] | |
| Humanized 16B8.C8 in AB0147/ AB7410 | QLQLQESGPGLVKPSETLSLTC TVSGFSLTNYGLHWIRQPPGKG LEWIGVILSGGWTDYNPSLKSR VTISKDTSKNQFSLKLSSVQAA DTAVYYCAKGDYGDALDYWG QGTLVTVSS [SEQ ID NO: 294] CDR1: GFSLTNY [SEQ ID NO: 137] CDR2: LSGGW [SEQ ID NO: 296] CDR3: GDYGDALDY [SEQ ID NO: 279] | DIQMTQSPSSLSASVGDRVTITCHA SQNINFWLSWYQQKPGKAPKLLIY EASNLHTGVPSRFSGSGSGTRFTLT ISSLQPEDIATYYCQQSHSYPLTFGS GTKLEIK [SEQ ID NO: 295] CDR1: HASQNINFWLS [SEQ ID NO: 140] CDR2: EASNLHT [SEQ ID NO: 141] CDR3: QQSHSYPLT [SEQ ID NO: 142] |
| scFv of humanized 16B8.C8 AB0147/ AB7410 | AB0147(VH-VL) QLQLQESGPGLVKPSETLSLTCTVSGFSLTNYGLHWIRQPPGKCLEWI GVILSGGWTDYNPSLKSRVTISKDTSKNQFSLKLSSVQAADTAVYYC AKGDYGDALDYWGQGTLVTVSSGGGGSGGGGSGGGGSGGGGSSDIQ MTQSPSSLSASVGDRVTITCHASQNINFWLSWYQQKPGKAPKLLIYEA SNLHTGVPSRFSGSGSGTRFTLTISSLQPEDIATYYCQQSHSYPLTFGCG TKLEIK [SEQ ID NO: 280] AB7410 (VL-VH) DIQMTQSPSSLSASVGDRVTITCHASQNINFWLSWYQQKPGKAPKLLI YEASNLHTGVPSRFSGSGSGTRFTLTISSLQPEDIATYYCQQSHSYPLTF GCGTKLEIKGGGGSGGGGSGGGGSGGGGSQLQLQESGPGLVKPSETL SLTCTVSGFSLTNYGLHWIRQPPGKCLEWIGVILSGGWTDYNPSLKSR VTISKDTSKNQFSLKLSSVQAADTAVYYCAKGDYGDALDYWGQGTL VTVSS [SEQ ID NO: 200] | |
| 9F11.B7 | EVQLQESGGGLVQPGGSRKLS CAASGFTFNSFGMHWVRQAPE KGLEWVAFISSGSTSIYYANTV KGRFTISRDNPKNTLFLQMTSL RSEDTAMYYCARDGYPTGGA MDYWGQGTSVTVSS [SEQ ID NO: 193] CDR1: GFTFNSF [SEQ ID NO: 192] CDR2: SSGSTS [SEQ ID NO: 196] CDR3: DGYPTGGAMDY [SEQ ID NO: 187] | DIKMTQSPSSMYASLGERVTITCK ASQDIYNYLSWFQLKPGKSPRPLIY RANILVSGVPSKFSGSGSGQDYSLT INSLEYEDLGIYYCLQFDAFPFTFG SGTKLEIK [SEQ ID NO: 194] CDR1: KASQDIYNYLS [SEQ ID NO: 198] CDR2: RANILVS [SEQ ID NO: 199] CDR3: LQFDAFPFT [SEQ ID NO: 201] |
| Humanized 9F11.B7 in AB0191 / AB0185 (back mutations in | EVQLVESGGGVVQPGGSLRLSC AASGFTFNSFGMHWVRQAPGK GLEWVAFISSGSTSIYYANTVK GRFTISRDNSKNTLYLQMNSLR AEDTAVYYCARDGYPTGGAMD YWGQGTSVTVSS | DIQMTQSPSSLSASVGDRVTITCKA SQDIYNYLSWFQQKPGKAPKPLIY RANILVSGVPSRFSGSGSGQDYTFT ISSLQPEDIATYYCLQFDAFPFTFGS GTKLEIK [SEQ ID NO: 203] |

TABLE 2-continued

Sequences of Exemplary Antigen-Binding Sites that Bind CLEC12A.

| Clone | VH | VL |
|---|---|---|
| VH and VL underlined) | [SEQ ID NO: 162]<br>CDR1: GFTFNSF [SEQ ID NO: 192]<br>CDR2: SSGSTS [SEQ ID NO: 196]<br>CDR3: DGYPTGGAMDY [SEQ ID NO: 187] | CDR1: KASQDIYNYLS [SEQ ID NO: 198]<br>CDR2: RANILVS [SEQ ID NO: 199]<br>CDR3: LQFDAFPFT [SEQ ID NO: 201] |
| scFv of humanized 9F11.B7 AB0191 / AB0185 | AB0191 (VH-VL):<br>EVQLVESGGGVVQPGGSLRLSCAASGFTFNSFGMHWVRQAPGKCLE<br>WVAFISSGSTSIYYANTVKGRFTISRDNSKNTLYLQMNSLRAEDTAVY<br>YCARDGYPTGGAMDYWGQGTSVTVSSGGGGSGGGGSGGGGSGGGG<br>SDIQMTQSPSSLSASVGDRVTITCKASQDIYNYLSWFQQKPGKAPKPLI<br>YRANILVSGVPSRFSGSGSGQDYTFTISSLQPEDIATYYCLQFDAFPFTF<br>GCGTKLEIK<br>[SEQ ID NO: 184]<br>AB0185 (VL-VH):<br>DIQMTQSPSSLSASVGDRVTITCKASQDIYNYLSWFQQKPGKAPKPLIY<br>RANILVSGVPSRFSGSGSGQDYTFTISSLQPEDIATYYCLQFDAFPFTFG<br>CGTKLEIKGGGGSGGGGSGGGGSGGGGSEVQLVESGGGVVQPGGSL<br>RLSCAASGFTFNSFGMHWVRQAPGKCLEWVAFISSGSTSIYYANTVKG<br>RFTISRDNSKNTLYLQMNSLRAEDTAVYYCARDGYPTGGAMDYWGQ<br>GTSVTVSS<br>[SEQ ID NO: 185] | |
| Humanized 9F11.B7 in AB0192/ AB0186 (back mutations in VH and VL underlined) | EVQLVESGGGVVQPGGSLRLSC<br>AASGFTFNAFGMHWVRQAPG<br>KGLEWVAFISSGSTSIYYANTV<br>KGRFTISRDNSKNTLYLQMNSL<br>RAEDTAVYYCARDGYPTGGAM<br>DYWGQGTSVTVSS<br>[SEQ ID NO: 148]<br>CDR1: GFTFNAF [SEQ ID NO: 195]<br>CDR2: SSGSTS [SEQ ID NO: 196]<br>CDR3: DGYPTGGAMDY [SEQ ID NO: 187] | DIQMTQSPSSLSASVGDRVTITCKA<br>SQDIYNYLSWFQQKPGKAPKPLIY<br>RANILVSGVPSRFSGSGSGQDYTFT<br>ISSLQPEDIATYYCLQFDAFPFTFGS<br>GTKLEIK<br>[SEQ ID NO: 203]<br>CDR1: KASQDIYNYLS [SEQ ID NO: 198]<br>CDR2: RANILVS [SEQ ID NO: 199]<br>CDR3: LQFDAFPFT [SEQ ID NO: 201] |
| scFv of humanized 9F11.B7 AB0192/ AB0186 | AB0192 (VH-VL):<br>EVQLVESGGGVVQPGGSLRLSCAASGFTFNAFGMHWVRQAPGKCLE<br>WVAFISSGSTSIYYANTVKGRFTISRDNSKNTLYLQMNSLRAEDTAVY<br>YCARDGYPTGGAMDYWGQGTSVTVSSGGGGSGGGGSGGGGSGGGG<br>SDIQMTQSPSSLSASVGDRVTITCKASQDIYNYLSWFQQKPGKAPKPLI<br>YRANILVSGVPSRFSGSGSGQDYTFTISSLQPEDIATYYCLQFDAFPFTF<br>GCGTKLEIK<br>[SEQ ID NO: 204]<br>AB0186 (VL-VH):<br>DIQMTQSPSSLSASVGDRVTITCKASQDIYNYLSWFQQKPGKAPKPLIY<br>RANILVSGVPSRFSGSGSGQDYTFTISSLQPEDIATYYCLQFDAFPFTFG<br>CGTKLEIKGGGGSGGGGSGGGGSGGGGSEVQLVESGGGVVQPGGSL<br>RLSCAASGFTFNAFGMHWVRQAPGKCLEWVAFISSGSTSIYYANTVK<br>GRFTISRDNSKNTLYLQMNSLRAEDTAVYYCARDGYPTGGAMDYWG<br>QGTSVTVSS<br>[SEQ ID NO: 205] | |
| Humanized 9F11.B7 in AB0193/ AB0187 (back mutations in VH and VL underlined) | EVQLVESGGGVVQPGGSLRLSC<br>AASGFTFNSFGMHWVRQAPGK<br>GLEWVAFISSGSTSIYYANTVK<br>GRFTISRDNSKNTLYLQMNSLR<br>AEDTAVYYCARSGYPTGGAMD<br>YWGQGTSVTVSS<br>[SEQ ID NO: 210]<br>CDR1: GFTFNSF [SEQ ID NO: 192]<br>CDR2: SSGSTS [SEQ ID NO: 196]<br>CDR3: SGYPTGGAMDY [SEQ ID NO: 213] | DIQMTQSPSSLSASVGDRVTITCKA<br>SQDIYNYLSWFQQKPGKAPKPLIY<br>RANILVSGVPSRFSGSGSGQDYTFT<br>ISSLQPEDIATYYCLQFDAFPFTFGS<br>GTKLEIK<br>[SEQ ID NO: 203]<br>CDR1: KASQDIYNYLS [SEQ ID NO: 198]<br>CDR2: RANILVS [SEQ ID NO: 199]<br>CDR3: LQFDAFPFT [SEQ ID NO: 201] |
| scFv of humanized 9F11.B7 AB0193/ AB0187 | AB0193 (VH-VL):<br>EVQLVESGGGVVQPGGSLRLSCAASGFTFNSFGMHWVRQAPGKCLE<br>WVAFISSGSTSIYYANTVKGRFTISRDNSKNTLYLQMNSLRAEDTAVY<br>YCARSGYPTGGAMDYWGQGTSVTVSSGGGGSGGGGSGGGGSGGGG<br>SDIQMTQSPSSLSASVGDRVTITCKASQDIYNYLSWFQQKPGKAPKPLI<br>YRANILVSGVPSRFSGSGSGQDYTFTISSLQPEDIATYYCLQFDAFPFTF<br>GCGTKLEIK<br>[SEQ ID NO: 208]<br>AB0187 (VL-VH): | |

TABLE 2-continued

Sequences of Exemplary Antigen-Binding Sites that Bind CLEC12A.

| Clone | VH | VL |
|---|---|---|
| | DIQMTQSPSSLSASVGDRVTITCKASQDIYNYLSWFQQKPGKAPKPLIY<br>RANILVSGVPSRFSGSGSGQDYTFTISSLQPEDIATYYCLQFDAFPFTFG<br>CGTKLEIKGGGGSGGGGSGGGGSGGGGSEVQLVESGGGVVQPGGSL<br>RLSCAASGFTFNSFGMHWVRQAPGKCLEWVAFISSGSTSIYYANTVKG<br>RFTISRDNSKNTLYLQMNSLRAEDTAVYYCARSGYPTGGAMDYWGQ<br>GTSVTVSS<br>[SEQ ID NO: 209] | |
| Humanized<br>9F11.B7 in<br>AB0194/<br>AB0188<br>(back<br>mutations in<br>VH and VL<br>underlined) | EVQLVESGGGVVQPGGSLRLSC<br>AASGFTFNSFGMHWVRQAPGK<br>GLEWVAFISSGSTSIYYANTVK<br>GRFTISRDNSKNTLYLQMNSLR<br>AEDTAVYYCARDGYPTGGAMD<br>YWGQGTSVTVSS<br>[SEQ ID NO: 162]<br>CDR1: GFTFNSF [SEQ ID<br>NO: 192]<br>CDR2: SSGSTS [SEQ ID NO: 196]<br>CDR3: DGYPTGGAMDY [SEQ<br>ID NO: 187] | DIKMTQSPSSLSASVGDRVTITCKA<br>SQDIYNYLSWFQQKPGKAPKPLIY<br>RANILVSGVPSRFSGSGSGQDYTLT<br>ISSLQPEDIATYYCLQFDAFPFTFGS<br>GTKLEIK<br>[SEQ ID NO: 218]<br>CDR1: KASQDIYNYLS [SEQ ID<br>NO: 198]<br>CDR2: RANILVS [SEQ ID NO: 199]<br>CDR3: LQFDAFPFT [SEQ ID<br>NO: 201] |
| scFv of<br>humanized<br>9F11.B7<br>AB0194/<br>AB0188 | AB0194 (VH-VL):<br>EVQLVESGGGVVQPGGSLRLSCAASGFTFNSFGMHWVRQAPGKCLE<br>WVAFISSGSTSIYYANTVKGRFTISRDNSKNTLYLQMNSLRAEDTAVY<br>YCARDGYPTGGAMDYWGQGTSVTVSSGGGGSGGGGSGGGGSGGGG<br>SDIKMTQSPSSLSASVGDRVTITCKASQDIYNYLSWFQQKPGKAPKPLI<br>YRANILVSGVPSRFSGSGSGQDYTLTISSLQPEDIATYYCLQFDAFPFTF<br>GCGTKLEIK<br>[SEQ ID NO: 215]<br>AB0188 (VL-VH):<br>DIKMTQSPSSLSASVGDRVTITCKASQDIYNYLSWFQQKPGKAPKPLIY<br>RANILVSGVPSRFSGSGSGQDYTLTISSLQPEDIATYYCLQFDAFPFTFG<br>CGTKLEIKGGGGSGGGGSGGGGSGGGGSEVQLVESGGGVVQPGGSL<br>RLSCAASGFTFNSFGMHWVRQAPGKCLEWVAFISSGSTSIYYANTVKG<br>RFTISRDNSKNTLYLQMNSLRAEDTAVYYCARDGYPTGGAMDYWGQ<br>GTSVTVSS<br>[SEQ ID NO: 216] | |
| Humanized<br>9F11.B7 in<br>AB0195/<br>AB0189<br>(back<br>mutations in<br>VH and VL<br>underlined) | EVQLVESGGGVVQPGGSLRLSC<br>AASGFTFNAFGMHWVRQAPG<br>KGLEWVAFISSGSTSIYYANTV<br>KGRFTISRDNSKNTLYLQMNSL<br>RAEDTAVYYCARDGYPTGGAM<br>DYWGQGTSVTVSS [SEQ ID<br>NO: 148]<br>CDR1: GFTFNAF [SEQ ID<br>NO: 195]<br>CDR2: SSGSTS [SEQ ID NO: 196]<br>CDR3: DGYPTGGAMDY [SEQ<br>ID NO: 187] | DIKMTQSPSSLSASVGDRVTITCKA<br>SQDIYNYLSWFQQKPGKAPKPLIY<br>RANILVSGVPSRFSGSGSGQDYTLT<br>ISSLQPEDIATYYCLQFDAFPFTFGS<br>GTKLEIK<br>[SEQ ID NO: 218]<br>CDR1: KASQDIYNYLS [SEQ ID<br>NO: 198]<br>CDR2: RANILVS [SEQ ID NO: 199]<br>CDR3: LQFDAFPFT [SEQ ID<br>NO: 201] |
| scFv of<br>humanized<br>9F11.B7<br>AB0195/<br>AB0189 | AB0195 (VH-VL):<br>EVQLVESGGGVVQPGGSLRLSCAASGFTFNAFGMHWVRQAPGKCLE<br>WVAFISSGSTSIYYANTVKGRFTISRDNSKNTLYLQMNSLRAEDTAVY<br>YCARDGYPTGGAMDYWGQGTSVTVSSGGGGSGGGGSGGGGSGGGG<br>SDIKMTQSPSSLSASVGDRVTITCKASQDIYNYLSWFQQKPGKAPKPLI<br>YRANILVSGVPSRFSGSGSGQDYTLTISSLQPEDIATYYCLQFDAFPFTF<br>GCGTKLEIK<br>[SEQ ID NO: 252]<br>AB0189 (VL-VH):<br>DIKMTQSPSSLSASVGDRVTITCKASQDIYNYLSWFQQKPGKAPKPLIY<br>RANILVSGVPSRFSGSGSGQDYTLTISSLQPEDIATYYCLQFDAFPFTFG<br>CGTKLEIKGGGGSGGGGSGGGGSGGGGSEVQLVESGGGVVQPGGSL<br>RLSCAASGFTFNAFGMHWVRQAPGKCLEWVAFISSGSTSIYYANTVK<br>GRFTISRDNSKNTLYLQMNSLRAEDTAVYYCARDGYPTGGAMDYWG<br>QGTSVTVSS<br>[SEQ ID NO: 253] | |
| Humanized<br>9F11.B7 in<br>AB0196/<br>AB0190<br>(back<br>mutations in<br>VH and VL<br>underlined) | EVQLVESGGGVVQPGGSLRLSC<br>AASGFTFNSFGMHWVRQAPGK<br>GLEWVAFISSGSTSIYYANTVK<br>GRFTISRDNSKNTLYLQMNSLR<br>AEDTAVYYCARSGYPTGGAMD<br>YWGQGTSVTVSS<br>[SEQ ID NO: 210]<br>CDR1: GFTFNSF [SEQ ID | DIKMTQSPSSLSASVGDRVTITCKA<br>SQDIYNYLSWFQQKPGKAPKPLIY<br>RANILVSGVPSRFSGSGSGQDYTLT<br>ISSLQPEDIATYYCLQFDAFPFTFGS<br>GTKLEIK<br>[SEQ ID NO: 218]<br>CDR1: KASQDIYNYLS [SEQ ID<br>NO: 198] |

TABLE 2-continued

Sequences of Exemplary Antigen-Binding Sites that Bind CLEC12A.

| Clone | VH | VL |
|---|---|---|
| | NO: 192]<br>CDR2: SSGSTS [SEQ ID NO: 196]<br>CDR3: SGYPTGGAMDY [SEQ ID NO: 213] | CDR2: RANILVS [SEQ ID NO: 199]<br>CDR3: LQFDAFPFT [SEQ ID NO: 201] |
| scFv of humanized 9F11.B7 AB0196/ AB0190 | AB0196 (VH-VL):<br>EVQLVESGGGVVQPGGSLRLSCAASGFTFNSFGMHWVRQAPGKCLE<br>WVAFISSGSTSIYYANTVKGRFTISRDNSKNTLYLQMNSLRAEDTAVY<br>YCARSGYPTGGAMDYWGQGTSVTVSSGGGGSGGGGSGGGGSGGGG<br>SDIKMTQSPSSLSASVGDRVTITCKASQDIYNYLSWFQQKPGKAPKPLI<br>YRANILVSGVPSRFSGSGSGQDYTLTISSLQPEDIATYYCLQFDAFPFTF<br>GCGTKLEIK<br>[SEQ ID NO: 254]<br>AB0190 (VL-VH):<br>DIKMTQSPSSLSASVGDRVTITCKASQDIYNYLSWFQQKPGKAPKPLIY<br>RANILVSGVPSRFSGSGSGQDYTLTISSLQPEDIATYYCLQFDAFPFTFG<br>CGTKLEIKGGGGSGGGGSGGGGSGGGGSEVQLVESGGGVVQPGGSL<br>RLSCAASGFTFNSFGMHWVRQAPGKCLEWVAFISSGSTSIYYANTVKG<br>RFTISRDNSKNTLYLQMNSLRAEDTAVYYCARSGYPTGGAMDYWGQ<br>GTSVTVSS<br>[SEQ ID NO: 255] | |
| Humanized 9F11.B7 consensus | EVQLVESGGGVVQPGGSLRLSC<br>AASGFTFNX$_1$FGMHWVRQAPG<br>KGLEWVAFISSGSTSIYYANTV<br>KGRFTISRDNSKNTLYLQMNSL<br>RAEDTAVYYCARX$_2$GYPTGGA<br>MDYWGQGTSVTVSS<br>where X$_1$ is S or A and X$_2$ is D or S<br>[SEQ ID NO: 249]<br>CDR1: GFTFNXF where X is S or A [SEQ ID NO: 251]<br>CDR2: SSGSTS [SEQ ID NO: 196]<br>CDR3: XGYPTGGAMDY where X is D or S [SEQ ID NO: 246] | DIX$_1$MTQSPSSLSASVGDRVTITCK<br>ASQDIYNYLSWFQQKPGKAPKPLI<br>YRANILVSGVPSRFSGSGSGQDYT<br>X$_2$TISSLQPEDIATYYCLQFDAFPFT<br>FGSGTKLEIK<br>where X$_1$ is Q or K and X$_2$ is F or L<br>[SEQ ID NO: 250]<br>CDR1: KASQDIYNYLS [SEQ ID NO: 198]<br>CDR2: RANILVS [SEQ ID NO: 199]<br>CDR3: LQFDAFPFT [SEQ ID NO: 201] |
| 30A9.E9 | EVQLQESGPGLVQPSQSLSITCT<br>VSGFSLTSFGVHWVRQSPGKG<br>LEWLGVIWSGGSTDSNAAFISR<br>LTITKDNSKSQVFFKMNSLQAT<br>DTAIYYCARSYFAMDYWGQGT<br>SVSVSS<br>[SEQ ID NO: 247]<br>CDR1: GFSLTSF [SEQ ID NO: 221]<br>CDR2: WSGGS [SEQ ID NO: 166]<br>CDR3: SYFAMDY [SEQ ID NO: 223] | DIVMTQSPSSLAVTAGEKVTMRCK<br>SSQSLLWNVNQNNYLLWYQQKQ<br>GQPPKLLIYGASIRESWVPDRFTGS<br>GSGTDFTLTISNVHVEDLAVYYCQ<br>HNHGSFLPYTFGGGTKLEIK<br>[SEQ ID NO: 248]<br>CDR1: KSSQSLLWNVNQNNYLL [SEQ ID NO: 240]<br>CDR2: GASIRES [SEQ ID NO: 226]<br>CDR3: QHNHGSFLPYT [SEQ ID NO: 179] |
| 23A5.H8 | QVQLRQSGPGLVQPSQSLSITC<br>TVSGFSLTSYGVHWVRQSPGK<br>GLEWLGVMWSGGSTDYNAAF<br>MSRLSISKDNSKSQVFFTMNSL<br>QADDTAIYYCARTHFGMDYW<br>GQGTPVTVSS<br>[SEQ ID NO: 242]<br>CDR1: GFSLTSY [SEQ ID NO: 206]<br>CDR2: WSGGS [SEQ ID NO: 166]<br>CDR3: THFGMDY [SEQ ID NO: 241] | GIVMTQSPSSLAVTAGEKVTMRCK<br>SSQSLLWSVNQNNYLLWYQQKQG<br>QPPKLLIYGASIRQSWVPDRFTGSG<br>SGTDFTLSISNVHAEDLAVYYCQH<br>NHGSFLPYTFGGGTKLEIK<br>[SEQ ID NO: 243]<br>CDR1: KSSQSLLWSVNQNNYLL [SEQ ID NO: 245]<br>CDR2: GASIRQS [SEQ ID NO: 239]<br>CDR3: QHNHGSFLPYT [SEQ ID NO: 179] |
| 20D6.H8 | EVQLQESGPGLVQPSQSLSITCT<br>VSGFSLTSFGIHWVRQSPGKGL<br>EWLGVIWSGGNTDSNAAFISRL<br>SITKDISKSQVFFKMNSLQVTD<br>TAIYYCARSYFAMDYWGQGTS<br>VTVSS<br>[SEQ ID NO: 238]<br>CDR1: GFSLTSF [SEQ ID NO: 221]<br>CDR2: WSGGN [SEQ ID NO: 236]<br>CDR3: SYFAMDY [SEQ ID NO: 223] | GIVMTQSPSSLAVTAGEKVTMRCK<br>SSQSLLWNVNQNNYLVWYQQKQ<br>GQPPKLLIYGASIRESWVPDRFTGS<br>GSGTDFTLTISNVHAEDLAVYYCQ<br>HNHGSFLPYTFGGGTKLEIK<br>[SEQ ID NO: 237]<br>CDR1: KSSQSLLWNVNQNNYLV [SEQ ID NO: 152]<br>CDR2: GASIRES [SEQ ID NO: 226]<br>CDR3: QHNHGSFLPYT [SEQ ID NO: 179] |

TABLE 2-continued

Sequences of Exemplary Antigen-Binding Sites that Bind CLEC12A.

| Clone | VH | VL |
|---|---|---|
| 15A10.G8 | EVQLQESGAELVRSGASIKLSC AASAFNIKDYFIHWVRQRPDQ GLEWIGWIDPENDDTEYAPKFQ DKATMTADTSSNTAYLQLSSLT SADTAVYYCNALWSRGGYFD YWGQGTTLTVSS [SEQ ID NO: 155] CDR1: AFNIKDY [SEQ ID NO: 159] CDR2: DPENDD [SEQ ID NO: 170] CDR3: LWSRGGYFDY [SEQ ID NO: 183] | EVLLTQSPAIIAASPGEKVTITCSAR SSVSYMSWYQQKPGSSPKIWIYGI SKLASGVPARFSGSGSGTYFSFTIN NLEAEDVATYYCQQRSYYPFTFGS GTKLEIK [SEQ ID NO: 158] CDR1: SARSSVSYMS [SEQ ID NO: 186] CDR2: GISKLAS [SEQ ID NO: 188] CDR3: QQRSYYPFT [SEQ ID NO: 189] |
| 13E1.A4 | EVQLQESGPELEKPGASVRISC KASGYSFTAYNMNWVKQSNG KSLEWIGNIDPSYGDATYNQKF KGKATLTVDKSSSTAYMQLKS LTSEDSAVYYCARDNYYGSGY FDYWGQGTTLTVSS [SEQ ID NO: 190] CDR1: GYSFTAY [SEQ ID NO: 197] CDR2: DPSYGD [SEQ ID NO: 202] CDR3: DNYYGSGYFDY [SEQ ID NO: 207] | SVLMTQTPLSLPVSLGDRASISCRS SQGIVHINGNTYLEWYLQKPGQSP KLLIYKVSNRFSGVPDRFSGSGSGT DFTLKISRVEAEDLGVYYCFQGSH VPWTFGGGTKLEIK [SEQ ID NO: 191] CDR1: RSSQGIVHINGNTYLE [SEQ ID NO: 211] CDR2: KVSNRFS [SEQ ID NO: 212] CDR3: FQGSHVPWT [SEQ ID NO: 214] |
| 12F8.H7 | EVQLQESGAELVRSGASVKLSC TVSGFNIKDYYMHWVKQRPEQ GLEWIGWIDPENGDTENVPKFQ GKATMTADTSSNTAYLQLRSL TSEDTAVYYCKSYYYDSSSRY VDVWGAGTTVTVSS [SEQ ID NO: 217] CDR1: GFNIKDY [SEQ ID NO: 220] CDR2: DPENGD [SEQ ID NO: 222] CDR3: YYYDSSSRYVDV [SEQ ID NO: 257] | GIVMTQAPLTLSVTIGQPASISCKS SQSLLDSDGKTFLNWFLQRPGQSP KRLISLVSKLDSGVPDRFTGSGSGT DFTLKLSRVEPEDLGVYYCWQGT HFPYTFGGGTKLEIK [SEQ ID NO: 219] CDR1: KSSQSLLDSDGKTFLN [SEQ ID NO: 224] CDR2: LVSKLDS [SEQ ID NO: 225] CDR3: WQGTHFPYT [SEQ ID NO: 227] |
| 9E4.B7 | EVQLQESGAELMKPGASVKISC RTTGYTFSTYWIEWVKQRPGR GPEWIGELFPGNSDTTLNEKFT GKATFTADSSSNTAYMQLSSLT SEDSAVYYCARSGYYGSSLDY WGQGTTLTVSS [SEQ ID NO: 228] CDR1: GYTFSTY [SEQ ID NO: 230] CDR2: FPGNSD [SEQ ID NO: 231] CDR3: SGYYGSSLDY [SEQ ID NO: 232] | GIVMTQSPASLSASVGETVTITCRA GENIHSYLAWYQQKQGKSPQLLV YNAKTLAEGVPSRFSGSGSGTQFS LKINSLQPEDFGSYYCQHHYGTPR TFGGGTKLEIK [SEQ ID NO: 229] CDR1: RAGENIHSYLA [SEQ ID NO: 233] CDR2: NAKTLAE [SEQ ID NO: 234] CDR3: QHHYGTPRT [SEQ ID NO: 235] |

In certain embodiments, the second antigen-binding site that binds CLEC12A (e.g., human CLEC12A) comprises an antibody heavy chain variable domain (VH) that comprises an amino acid sequence at least 90% (e.g., at least 91%, at least 92%, at least 93%, at least 94%, at least 95%, at least 96%, at least 97%, at least 98%, at least 99%, or 100%) identical to the VH of an antibody disclosed in Table 2, and an antibody light chain variable domain (VL) that comprises an amino acid sequence at least 90% (e.g., at least 91%, at least 92%, at least 93%, at least 94%, at least 95%, at least 96%, at least 97%, at least 98%, at least 99%, or 100%) identical to the VL of the same antibody disclosed in Table 2. In certain embodiments, the second antigen-binding site comprises the heavy chain CDR1, CDR2, and CDR3 and the light chain CDR1, CDR2, and CDR3, determined under Kabat (see Kabat et al., (1991) Sequences of Proteins of Immunological Interest, NIH Publication No. 91-3242, Bethesda), Chothia (see, e.g., Chothia C & Lesk A M, (1987), *J Mol Biol* 196: 901-917), MacCallum (see MacCallum R M et al., (1996) *J Mol Biol* 262: 732-745), or any other CDR determination method known in the art, of the VH and VL sequences of an antigen-binding site disclosed in Table 2. In certain embodiments, the second antigen-binding site comprises the heavy chain CDR1, CDR2, and CDR3 and the light chain CDR1, CDR2, and CDR3 of an antibody disclosed in Table 2.

In certain embodiments, the second antigen-binding site is derived from 16B8.C8. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:135, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:136. In certain embodiments, the VH comprises CDR1, CDR2, and CDR3 comprising the amino acid sequences of SEQ ID NOs: 137, 138, and 139, respectively. In certain embodiments, the VL comprises CDR1, CDR2, and CDR3 comprising the amino acid sequences of SEQ ID NOs: 140, 141, and 142, respectively. In certain embodiments, the second antigen-binding site comprises (a) a VH that comprises CDR1, CDR2, and CDR3 comprising the amino acid sequences of SEQ ID NOs: 137, 138, and 139, respectively; and (b) a VL that comprises CDR1, CDR2, and CDR3 comprising the amino acid sequences of SEQ ID NOs: 140, 141, and 142, respectively.

In certain embodiments, the second antigen-binding site is derived from scFv-1292 or scFv-1301. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:143, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:144. In certain embodiments, the VH comprises CDR1, CDR2, and CDR3 comprising the amino acid sequences of SEQ ID NOs: 137, 138, and 139, respectively. In certain embodiments, the VL comprises CDR1, CDR2, and CDR3 comprising the amino acid sequences of SEQ ID NOs: 140, 141, and 142, respectively. In certain embodiments, the second antigen-binding site comprises (a) a VH that comprises CDR1, CDR2, and CDR3 comprising the amino acid sequences of SEQ ID NOs: 137, 138, and 139, respectively; and (b) a VL that comprises CDR1, CDR2, and CDR3 comprising the amino acid sequences of SEQ ID NOs: 140, 141, and 142, respectively. In certain embodiments, the second antigen-binding site is present as an scFv, wherein the scFv comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:145 or 146.

In certain embodiments, the second antigen-binding site is derived from scFv-1293 or scFv-1302. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:147, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:144. In certain embodiments, the VH comprises CDR1, CDR2, and CDR3 comprising the amino acid sequences of SEQ ID NOs: 137, 138, and 139, respectively. In certain embodiments, the VL comprises CDR1, CDR2, and CDR3 comprising the amino acid sequences of SEQ ID NOs: 140, 141, and 142, respectively. In certain embodiments, the second antigen-binding site comprises (a) a VH that comprises CDR1, CDR2, and CDR3 comprising the amino acid sequences of SEQ ID NOs: 137, 138, and 139, respectively; and (b) a VL that comprises CDR1, CDR2, and CDR3 comprising the amino acid sequences of SEQ ID NOs: 140, 141, and 142, respectively. In certain embodiments, the second antigen-binding site is present as an scFv, wherein the scFv comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:149 or 150.

In certain embodiments, the second antigen-binding site is derived from scFv-1294 or scFv-1303. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:244, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:144. In certain embodiments, the VH comprises CDR1, CDR2, and CDR3 comprising the amino acid sequences of SEQ ID NOs: 137, 138, and 139, respectively. In certain embodiments, the VL comprises CDR1, CDR2, and CDR3 comprising the amino acid sequences of SEQ ID NOs: 140, 141, and 142, respectively. In certain embodiments, the second antigen-binding site comprises (a) a VH that comprises CDR1, CDR2, and CDR3 comprising the amino acid sequences of SEQ ID NOs: 137, 138, and 139, respectively; and (b) a VL that comprises CDR1, CDR2, and CDR3 comprising the amino acid sequences of SEQ ID NOs: 140, 141, and 142, respectively. In certain embodiments, the second antigen-binding site is present as an scFv, wherein the scFv comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:153 or 154.

In certain embodiments, the second antigen-binding site is derived from scFv-1295 or scFv-1304. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:178, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:144. In certain embodiments, the VH comprises CDR1, CDR2, and CDR3 comprising the amino acid sequences of SEQ ID NOs: 137, 138, and 139, respectively. In certain embodiments, the VL comprises CDR1, CDR2, and CDR3 comprising the amino acid sequences of SEQ ID NOs: 140, 141, and 142, respectively. In certain embodiments, the second antigen-binding site comprises (a) a VH that comprises CDR1, CDR2, and CDR3 comprising the amino acid sequences of SEQ ID NOs: 137, 138, and 139, respectively; and (b) a VL that comprises CDR1, CDR2, and CDR3 comprising the amino acid sequences of SEQ ID NOs: 140, 141, and 142, respectively. In certain embodiments, the second antigen-binding site is present as an scFv, wherein the scFv comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:156 or 157.

In certain embodiments, the second antigen-binding site is derived from scFv-1296 or scFv-1305. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:256, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:144. In certain embodiments, the VH comprises CDR1, CDR2, and CDR3 comprising the amino acid sequences of SEQ ID NOs: 137, 138, and 139, respectively. In certain embodiments, the VL comprises CDR1, CDR2, and CDR3 comprising the amino acid sequences of SEQ ID NOs: 140, 141, and 142, respectively. In certain embodiments, the second antigen-binding site comprises (a) a VH that comprises CDR1, CDR2, and CDR3 comprising the amino acid sequences of SEQ ID NOs: 137, 138, and 139, respectively; and (b) a VL that comprises CDR1, CDR2, and CDR3 comprising the amino acid sequences of SEQ ID NOs: 140, 141, and 142, respectively. In certain embodiments, the second antigen-binding site is present as an scFv, wherein the scFv comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:160 or 161.

In certain embodiments, the second antigen-binding site is derived from scFv-1297 or scFv-1306. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:143, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:163. In certain embodiments, the VH comprises CDR1, CDR2, and CDR3 comprising the amino acid sequences of SEQ ID NOs: 137, 138, and 139, respectively. In certain embodiments, the VL comprises CDR1, CDR2, and CDR3 comprising the amino acid sequences of SEQ ID NOs: 140, 141, and 142, respectively. In certain embodiments, the second antigen-binding site comprises (a) a VH that comprises CDR1, CDR2, and CDR3 comprising the amino acid sequences of SEQ ID NOs: 137, 138, and 139, respectively; and (b) a VL that comprises CDR1, CDR2, and CDR3 comprising the amino acid sequences of SEQ ID NOs: 140, 141, and 142, respectively. In certain embodiments, the second antigen-binding site is present as an scFv, wherein the scFv comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:164 or 165.

In certain embodiments, the second antigen-binding site is derived from scFv-1298 or scFv-1307. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:143, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:167. In certain embodiments, the VH comprises CDR1, CDR2, and CDR3 comprising the amino acid sequences of SEQ ID NOs: 137, 138, and 139, respectively. In certain embodiments, the VL comprises CDR1, CDR2, and CDR3 comprising the amino acid sequences of SEQ ID NOs: 140, 141, and 142, respectively. In certain embodiments, the second antigen-binding site comprises (a) a VH that comprises CDR1, CDR2, and CDR3 comprising the amino acid sequences of SEQ ID NOs: 137, 138, and 139, respectively; and (b) a VL that comprises CDR1, CDR2, and CDR3 comprising the amino acid sequences of SEQ ID NOs: 140, 141, and 142, respectively. In certain embodiments, the second antigen-binding site is present as an scFv, wherein the scFv comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:168 or 169.

In certain embodiments, the second antigen-binding site is derived from scFv-1299 or scFv-1308. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:143, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:171. In certain embodiments, the VH comprises CDR1, CDR2, and CDR3 comprising the amino acid sequences of SEQ ID NOs: 137, 138, and 139, respectively. In certain embodiments, the VL comprises CDR1, CDR2, and CDR3 comprising the amino acid sequences of SEQ ID NOs: 140, 141, and 142, respectively. In certain embodiments, the second antigen-binding site comprises (a) a VH that comprises CDR1, CDR2, and CDR3 comprising the amino acid sequences of SEQ ID NOs: 137, 138, and 139, respectively; and (b) a VL that comprises CDR1, CDR2, and CDR3 comprising the amino acid sequences of SEQ ID NOs: 140, 141, and 142, respectively. In certain embodiments, the second antigen-binding site is present as an scFv, wherein the scFv comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:172 or 173.

In certain embodiments, the second antigen-binding site is derived from scFv-1300 or scFv-1309. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:174, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:175. In certain embodiments, the VH comprises CDR1, CDR2, and CDR3 comprising the amino acid sequences of SEQ ID NOs: 137, 138, and 139, respectively. In certain embodiments, the VL comprises CDR1, CDR2, and CDR3 comprising the amino acid sequences of SEQ ID NOs: 140, 141, and 142, respectively. In certain embodiments, the second antigen-binding site comprises (a) a VH that comprises CDR1, CDR2, and CDR3 comprising the amino acid sequences of SEQ ID NOs: 137, 138, and 139, respectively; and (b) a VL that comprises CDR1, CDR2, and CDR3 comprising the amino acid sequences of SEQ ID NOs: 140, 141, and 142, respectively. In certain embodiments, the second antigen-binding site is present as an scFv, wherein the scFv comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:176 or 177.

In certain embodiments, the second antigen-binding site is derived from scFv-1602 or scFv-2061. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:178, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:289. In certain embodiments, the VH comprises CDR1, CDR2, and CDR3 comprising the amino acid sequences of SEQ ID NOs: 137, 138, and 139, respectively. In certain embodiments, the VL comprises CDR1, CDR2, and CDR3 comprising the amino acid sequences of SEQ ID NOs: 140, 141, and 142, respectively. In certain embodiments, the second antigen-binding site comprises (a) a VH that comprises CDR1, CDR2, and CDR3 comprising the amino acid sequences of SEQ ID NOs: 137, 138, and 139, respectively; and (b) a VL that comprises CDR1, CDR2, and CDR3 comprising the amino acid sequences of SEQ ID NOs: 140, 141, and 142, respectively. In certain embodiments, the second antigen-binding site is present as an scFv, wherein the scFv comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:180 or 181.

In certain embodiments, the second antigen-binding site is derived from humanized 16B.C8. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:182, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:151. In certain embodiments, the VH comprises CDR1, CDR2, and CDR3 comprising the amino acid sequences of SEQ ID NOs: 137, 138, and 139, respectively. In certain embodiments, the VL comprises CDR1, CDR2, and CDR3 comprising the amino acid sequences of SEQ ID NOs: 140, 141, and 142, respectively. In certain embodiments, the second antigen-binding site comprises (a) a VH that comprises CDR1, CDR2, and CDR3 comprising the amino acid sequences of SEQ ID NOs: 137, 138, and 139, respectively; and (b) a VL that comprises CDR1, CDR2, and CDR3 comprising the amino acid sequences of SEQ ID NOs: 140, 141, and 142, respectively.

In certain embodiments, the second antigen-binding site is derived from AB0305 or AB5030. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:270, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:271. In certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:335, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:336. In certain embodiments, the second antigen-binding site comprises a VH and a VL each comprises a cysteine heterodimerization mutation. Such heterodimerization mutation can facilitate formation of a disulfide bridge between the VH and VL of the scFv. In certain embodiments, the VH comprises CDR1, CDR2, and CDR3 comprising the amino acid sequences of SEQ ID NOs: 137, 272, and 273, respectively. In certain embodiments, the VL comprises CDR1, CDR2, and CDR3 comprising the amino acid sequences of SEQ ID NOs: 140, 141, and 142, respectively. In certain embodiments, the second antigen-binding site comprises (a) a VH that comprises CDR1, CDR2, and CDR3 comprising the amino acid sequences of SEQ ID NOs: 137, 272, and 273, respectively; and (b) a VL that comprises CDR1, CDR2, and CDR3 comprising the amino acid sequences of SEQ ID NOs: 140, 141, and 142, respectively. In certain embodiments, the second antigen-binding site is present as an scFv, wherein the scFv comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:274 or 275.

In certain embodiments, the second antigen-binding site is derived from AB0147 or AB7410. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:294, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:295. In certain embodiments, the VH comprises CDR1, CDR2, and CDR3 comprising the amino acid sequences of SEQ ID NOs: 137, 296, and 279, respectively. In certain embodiments, the VL comprises CDR1, CDR2, and CDR3 comprising the amino acid sequences of SEQ ID NOs: 140, 141, and 142, respectively. In certain embodiments, the second antigen-binding site comprises (a) a VH that comprises CDR1, CDR2, and CDR3 comprising the amino acid sequences of SEQ ID NOs: 137, 296, and 279, respectively; and (b) a VL that comprises CDR1, CDR2, and CDR3 comprising the amino acid sequences of SEQ ID NOs: 140, 141, and 142, respectively. In certain embodiments, the second antigen-binding site is present as an scFv, wherein the scFv comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:280 or 200.

In certain embodiments, the second antigen-binding site is derived from 9F11.B7. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:193, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:194. In certain embodiments, the VH comprises CDR1, CDR2, and CDR3 comprising the amino acid sequences of SEQ ID NOs: 192, 196, and 187, respectively. In certain embodiments, the VL comprises CDR1, CDR2, and CDR3 comprising the amino acid sequences of SEQ ID NOs: 198, 199, and 201, respectively. In certain embodiments, the second antigen-binding site comprises (a) a VH that comprises CDR1, CDR2, and CDR3 comprising the amino acid sequences of SEQ ID NOs: 192, 196, and 187, respectively; and (b) a VL that comprises CDR1, CDR2, and CDR3 comprising the amino acid sequences of SEQ ID NOs: 198, 199, and 201, respectively.

In certain embodiments, the second antigen-binding site is derived from AB0191 or AB0185. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:162, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:203. In certain embodiments, the VH comprises CDR1, CDR2, and CDR3 comprising the amino acid sequences of SEQ ID NOs: 192, 196, and 187, respectively. In certain embodiments, the VL comprises CDR1, CDR2, and CDR3 comprising the amino acid sequences of SEQ ID NOs: 198, 199, and 201, respectively. In certain embodiments, the second antigen-binding site comprises (a) a VH that comprises CDR1, CDR2, and CDR3 comprising the amino acid sequences of SEQ ID NOs: 192, 196, and 187, respectively; and (b) a VL that comprises CDR1, CDR2, and CDR3 comprising the amino acid sequences of SEQ ID NOs: 198, 199, and 201, respectively. In certain embodiments, the second antigen-binding site is present as an scFv, wherein the scFv comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:184 or 185.

In certain embodiments, the second antigen-binding site is derived from AB0192 or AB0186. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:148, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:203. In certain embodiments, the VH comprises CDR1, CDR2, and CDR3 comprising the amino acid sequences of SEQ ID NOs: 195, 196, and 187, respectively. In certain embodiments, the VL comprises CDR1, CDR2, and CDR3 comprising the amino acid sequences of SEQ ID NOs: 198, 199, and 201, respectively. In certain embodiments, the second antigen-binding site comprises (a) a VH that comprises CDR1, CDR2, and CDR3 comprising the amino acid sequences of SEQ ID NOs: 195, 196, and 187, respectively; and (b) a VL that comprises CDR1, CDR2, and CDR3 comprising the amino acid sequences of SEQ ID NOs: 198, 199, and 201, respectively. In certain embodiments, the second antigen-binding site is present as an scFv, wherein the scFv comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:204 or 205.

In certain embodiments, the second antigen-binding site is derived from AB0193 or AB0187. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:210, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:203. In certain embodiments, the VH comprises CDR1, CDR2, and CDR3 comprising the amino acid sequences of SEQ ID NOs: 192, 196, and 213, respectively. In certain embodiments, the VL comprises CDR1, CDR2, and CDR3 comprising the amino acid sequences of SEQ ID NOs: 198, 199, and 201, respectively. In certain embodiments, the second antigen-binding site comprises (a) a VH that comprises CDR1, CDR2, and CDR3 comprising the amino acid sequences of SEQ ID NOs: 192, 196, and 213, respectively; and (b) a VL that comprises CDR1, CDR2, and CDR3 comprising the amino acid sequences of SEQ ID NOs: 198, 199, and 201, respectively. In certain embodiments, the second antigen-binding site is present as an scFv, wherein the scFv comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:208 or 209.

In certain embodiments, the second antigen-binding site is derived from AB0194 or AB0188. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:162, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:218. In certain embodiments, the VH comprises CDR1, CDR2, and CDR3 comprising the amino acid sequences of SEQ ID NOs: 192, 196, and 187, respectively. In certain embodiments, the VL comprises CDR1, CDR2, and CDR3 comprising the amino acid sequences of SEQ ID NOs: 198, 199, and 201, respectively. In certain embodiments, the second antigen-binding site comprises (a) a VH that comprises CDR1, CDR2, and CDR3 comprising the amino acid sequences of SEQ ID NOs: 192, 196, and 187, respectively; and (b) a VL that comprises CDR1, CDR2, and CDR3 comprising the amino acid sequences of SEQ ID NOs: 198, 199, and 201, respectively. In certain embodiments, the second antigen-binding site is present as an scFv, wherein the scFv comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:215 or 216.

In certain embodiments, the second antigen-binding site is derived from AB0195 or AB0189. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:148, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:218. In certain embodiments, the VH comprises CDR1, CDR2, and CDR3 comprising the amino acid sequences of SEQ ID NOs: 195, 196, and 187, respectively. In certain embodiments, the VL comprises CDR1, CDR2, and CDR3 comprising the amino acid sequences of SEQ ID NOs: 198, 199, and 201, respectively. In certain embodiments, the second antigen-binding site comprises (a) a VH that comprises CDR1, CDR2, and CDR3 comprising the amino acid sequences of SEQ ID NOs: 195, 196, and 187, respectively; and (b) a VL that comprises CDR1, CDR2, and CDR3 comprising the amino acid sequences of SEQ ID NOs: 198, 199, and 201, respectively. In certain embodiments, the second antigen-binding site is present as an scFv, wherein the scFv comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:252 or 253.

In certain embodiments, the second antigen-binding site is derived from AB0196 or AB0190. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:210, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:218. In certain embodiments, the VH comprises CDR1, CDR2, and CDR3 comprising the amino acid sequences of SEQ ID NOs: 192, 196, and 213, respectively. In certain embodiments, the VL comprises CDR1, CDR2, and CDR3 comprising the amino acid sequences of SEQ ID NOs: 198, 199, and 201, respectively. In certain embodiments, the second antigen-binding site comprises (a) a VH that comprises CDR1, CDR2, and CDR3 comprising the amino acid sequences of SEQ ID NOs: 192, 196, and 213, respectively; and (b) a VL that comprises CDR1, CDR2, and CDR3 comprising the amino acid sequences of SEQ ID NOs: 198, 199, and 201, respectively. In certain embodiments, the second antigen-binding site is present as an scFv, wherein the scFv comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:254 or 255.

In certain embodiments, the second antigen-binding site is derived from humanized 9F11.B7. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:249, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:250. In certain embodiments, the VH comprises CDR1, CDR2, and CDR3 comprising the amino acid sequences of SEQ ID NOs: 251, 196, and 246, respectively. In certain embodiments, the VL comprises CDR1, CDR2, and CDR3 comprising the amino acid sequences of SEQ ID NOs: 198, 199, and 201, respectively. In certain embodiments, the second antigen-binding site comprises (a) a VH that comprises CDR1, CDR2, and CDR3 comprising the amino acid sequences of SEQ ID NOs: 251, 196, and 246, respectively; and (b) a VL that comprises CDR1, CDR2, and CDR3 comprising the amino acid sequences of SEQ ID NOs: 198, 199, and 201, respectively.

In certain embodiments, the second antigen-binding site is derived from 30A9.E9. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:247, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:248. In certain embodiments, the VH comprises CDR1, CDR2, and CDR3 comprising the amino acid sequences of SEQ ID NOs: 221, 166, and 223, respectively. In certain embodiments, the VL comprises CDR1, CDR2, and CDR3 comprising the amino acid sequences of SEQ ID NOs: 240, 226, and 179, respectively. In certain embodiments, the second antigen-binding site comprises (a) a VH that comprises CDR1, CDR2, and CDR3 comprising the amino acid sequences of SEQ ID NOs: 221, 166, and 223, respectively; and (b) a VL that comprises CDR1, CDR2, and CDR3 comprising the amino acid sequences of SEQ ID NOs: 240, 226, and 179, respectively.

In certain embodiments, the second antigen-binding site is derived from 23A5.H8. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:242, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:243. In certain embodiments, the VH comprises CDR1, CDR2, and CDR3 comprising the amino acid sequences of SEQ ID NOs: 206, 166, and 241, respectively. In certain embodiments, the VL comprises CDR1, CDR2, and CDR3 comprising the amino acid sequences of SEQ ID NOs: 245, 239, and 179, respectively. In certain embodiments, the second antigen-binding site comprises (a) a VH that comprises CDR1, CDR2, and CDR3 comprising the amino acid sequences of SEQ ID NOs: 206, 166, and 241, respectively; and (b) a VL that comprises CDR1, CDR2, and CDR3 comprising the amino acid sequences of SEQ ID NOs: 245, 239, and 179, respectively.

In certain embodiments, the second antigen-binding site is derived from 20D6.H8. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:238, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:237. In certain embodiments, the VH comprises CDR1, CDR2, and CDR3 comprising the amino acid sequences of SEQ ID NOs: 221, 236, and 223, respectively. In certain embodiments, the VL comprises CDR1, CDR2, and CDR3 comprising the amino acid sequences of SEQ ID NOs: 152, 226, and 179, respectively. In certain embodiments, the second antigen-binding site comprises (a) a VH that comprises CDR1, CDR2, and CDR3 comprising the amino acid sequences of SEQ ID NOs: 221, 236, and 223, respectively; and (b) a VL that comprises CDR1, CDR2, and CDR3 comprising the amino acid sequences of SEQ ID NOs: 152, 226, and 179, respectively.

In certain embodiments, the second antigen-binding site is derived from 15A10.G8. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:155, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:158. In certain embodiments, the VH comprises CDR1, CDR2, and CDR3 comprising the amino acid sequences of SEQ ID NOs: 159, 170, and 183, respectively. In certain embodiments, the VL comprises CDR1, CDR2, and CDR3 comprising the amino acid sequences of SEQ ID NOs: 186, 188, and 189, and respectively. In certain embodiments, the second antigen-binding site comprises (a) a VH that comprises CDR1, CDR2, and CDR3 comprising the amino acid sequences of SEQ ID NOs: 159, 170, and 183, respectively; and (b) a VL that comprises CDR1, CDR2, and CDR3 comprising the amino acid sequences of SEQ ID NOs: 186, 188, and 189, respectively.

In certain embodiments, the second antigen-binding site is derived from 13E1.A4. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:190, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:191. In certain embodiments, the VH comprises CDR1, CDR2, and CDR3 comprising the amino acid sequences of SEQ ID NOs: 197, 202, and 207, respectively. In certain embodiments, the VL comprises CDR1, CDR2, and CDR3 comprising the amino acid sequences of SEQ ID NOs: 211, 212, and 214, and respectively. In certain embodiments, the second antigen-binding site comprises (a) a VH that comprises CDR1, CDR2, and CDR3 comprising the amino acid sequences of SEQ ID NOs: 197, 202, and 207, respectively; and (b) a VL that comprises CDR1, CDR2, and CDR3 comprising the amino acid sequences of SEQ ID NOs: 211, 212, and 214, respectively.

In certain embodiments, the second antigen-binding site is derived from 12F8.H7. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:217, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:219. In certain embodiments, the VH comprises CDR1, CDR2, and CDR3 comprising the amino acid sequences of SEQ ID NOs: 220, 222, and 257, respectively. In certain embodiments, the VL comprises CDR1, CDR2, and CDR3 comprising the amino acid sequences of SEQ ID NOs: 224, 225, and 227, and respectively. In certain embodiments, the second antigen-binding site comprises (a) a VH that comprises CDR1, CDR2, and CDR3 comprising the amino acid sequences of SEQ ID NOs: 220, 222, and 257, respectively; and (b) a VL that comprises CDR1, CDR2, and CDR3 comprising the amino acid sequences of SEQ ID NOs: 224, 225, and 227, respectively.

In certain embodiments, the second antigen-binding site is derived from 9E4.B7. For example, in certain embodiments, the second antigen-binding site comprises a VH that comprises an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:228, and a VL that comprises an amino acid sequence at least 90% (e.g., at least 91%, at least 92%, at least 93%, at least 94%, at least 95%, at least 96%, at least 97%, at least 98%, at least 99%, or 100%) identical to SEQ ID NO:229. In certain embodiments, the VH comprises CDR1, CDR2, and CDR3 comprising the amino acid sequences of SEQ ID NOs: 230, 231, and 232, respectively. In certain embodiments, the VL comprises CDR1, CDR2, and CDR3 comprising the amino acid sequences of SEQ ID NOs: 233, 234, and 235, and respectively. In certain embodiments, the second antigen-binding site comprises (a) a VH that comprises CDR1, CDR2, and CDR3 comprising the amino acid sequences of SEQ ID NOs: 230, 231, and 232, respectively; and (b) a VL that comprises CDR1, CDR2, and CDR3 comprising the amino acid sequences of SEQ ID NOs: 233, 234, and 235, respectively.

In certain embodiments, the second antigen-binding site that binds CLEC12A is an scFv. For example, in certain embodiments, the second antigen-binding site comprises the amino acid sequence of SEQ ID NO:145, 146, 149, 150, 153, 154, 156, 157, 160, 161, 164, 165, 168, 169, 172, 173, 176, 177, 180, 181, 184, 185, 204, 205, 208, 209, 215, 216, 252, 253, 254, 255, 274, 275, 280, or 281. In specific embodiments, the second antigen-binding site comprises the amino acid sequence of SEQ ID NO:180.

Alternatively, novel antigen-binding sites that can bind to CLEC12A can be identified by screening for binding to the amino acid sequence defined by SEQ ID NO:258, a variant thereof, a mature extracellular fragment thereof or a fragment containing a domain of CLEC12A.

```
                                            SEQ ID NO: 258
MSEEVTYADLQFQNSSEMEKIPEIGKFGEKAPPAPSHVWRPAALFLTLLC

LLLLIGLGVLASMFHVTLKIEMKKMNKLQNISEELQRNISLQLMSNMNIS

NKIRNLSTTLQTIATKLCRELYSKEQEHKCKPCPRRWIWHKDSCYFLSDD

VQTWQESKMACAAQNASLLKINNKNALEFIKSQSRSYDYWLGLSPEEDST

RGMRVDNIINSSAWVIRNAPDLNNMYCGYINRLYVQYYHCTYKKRMICEK

MANPVQLGSTYFREA (Uniprot ID No. Q5QGZ9)
```

It is contemplated that in an scFv, a VH and a VL can be connected by a linker, e.g., (GlyGlyGlyGlySer)$_4$ i.e. (G$_4$S)$_4$ linker (SEQ ID NO:119). A skilled person in the art would appreciate that any of the other disclosed linkers (see, e.g., Table 10) may be used in an scFv having a VH and VL sequences disclosed herein (e.g., in Table 2).

In each of the foregoing embodiments, it is contemplated herein that the scFv, VH and/or VL sequences that bind CLEC12A may contain amino acid alterations (e.g., at least 1, 2, 3, 4, 5, or 10 amino acid substitutions, deletions, or additions) in the framework regions of the VH and/or VL without affecting their ability to CLEC12A. For example, it is contemplated herein that scFv, VH and/or VL sequences that bind CLEC12A may contain cysteine heterodimerization mutations, facilitating formation of a disulfide bridge between the VH and VL of the scFv.

In certain embodiments, the second antigen-binding site disclosed herein binds human CLEC12A with a $K_D$ (i.e., dissociation constant) of 1 nM or lower, 5 nM or lower, 10 nM or lower, 15 nM or lower, or 20 nM or lower, as measured by surface plasmon resonance (SPR) (e.g., using the method described in Example 12) or by bio-layer interferometry (BLI), and/or binds CLEC12A from a body fluid, tissue, and/or cell of a subject. In certain embodiments, a second antigen-binding site disclosed herein has a $K_d$ (i.e., off-rate, also called $K_{off}$) equal to or lower than $1\times10^{-5}$, $1\times10^{-4}$, $1\times10^{-3}$, $5\times10^{-3}$, 0.01, 0.02, or 0.05 l/s, as measured by SPR (e.g., using the method described in Example 12) or by BLI.

In certain embodiments, the second antigen-binding site derived from 15A10.G8 or 20D6.A8 binds cynomolgus CLEC12A with a $K_D$ (i.e., dissociation constant) of 5 nM or lower, 10 nM or lower, 15 nM or lower, 20 nM or lower, or 30 nM or lower, as measured by surface plasmon resonance (SPR) (e.g., using the method described in Example 12) or by bio-layer interferometry (BLI), and/or binds CLEC12A from a body fluid, tissue, and/or cell of a subject. In certain embodiments, a second antigen-binding site disclosed herein has a $K_d$ (i.e., off-rate, also called $K_{off}$) equal to or lower than $1\times10^{-3}$, $5\times10^{-3}$, 0.01, 0.02, or 0.03 l/s, as measured by SPR (e.g., using the method described in Example 12) or by BLI.

Variations in the glycosylation status of CLEC12A on the surface of different cell types has been reported (Marshall et al., (2006) *Eur J Immunol.* 36(8):2159-69). CLEC12A expressed on the surface of AML cells from different patients may have different glycosylation patterns as well. Moreover, branched glycans can restrict accessibility to the protein component of CLEC12A, limiting diversity of available epitopes. Certain antigen-binding sites or the present application can overcome the glycosylation variations. In certain embodiments, a second antigen-binding site disclosed herein, e.g., an antigen-binding site derived from 16B8.C8, a humanized 16B8.C8, 9F11.B7, or a humanized 9F11.B7, binds CLEC12A (e.g., human CLEC12A) in a glycosylation independent manner, i.e., binds both a glycosylated CLEC12A and a de-glycosylated CLEC12A. In certain embodiments, the ratio of the $K_D$ at which the second antigen-binding site binds deglycosylated CLEC12A to the $K_D$ at which the second antigen-binding site binds glycosylated CLEC12A is within the range of 1:10 to 10:1 (e.g., within the range of 1:5 to 5:1, 1:3 to 3:1, or 1:2 to 2:1). In certain embodiments, the ratio is about 1:5, about 1:3, about 1:2, about 1:1.5, about 1:1, about 1.5:1, about 2:1, about 3:1, or about 5:1. In certain embodiments, the ratio is about 1:1. In another aspect, the instant disclosure provides a multispecific binding protein comprising (a) a first antigen-binding site that binds NKG2D; (b) a second antigen-binding site that binds CLEC12A; and (c) an antibody Fc domain or a portion thereof sufficient to bind CD16, or a third antigen-binding site that binds CD16; wherein the second antigen-binding site binds CLEC12A in a glycosylation independent manner.

CLEC12A containing a K244Q substitution is a polymorphic variant prevalent in about 30% of the human population. In some embodiments, the second antigen-binding site of a multispecific binding protein disclosed herein binds CLEC12A-K244Q. In certain embodiments, the ratio of the $K_D$ at which the second antigen-binding site binds CLEC12A-K244Q to the $K_D$ at which the second antigen-binding site binds wild-type CLEC12A is within the range of 1:2 to 2:1. In certain embodiments, the ratio is about 1:2, about 1:1.5, about 1:1, about 1.5:1, or about 2:1. In certain embodiments, the ratio is about 1:1.

In some embodiments, the multispecific binding proteins described herein bind to CLEC12A with an isoelectric point (pI) of about 8 to about 9. In some embodiments, the multispecific binding proteins described herein bind to CLEC12A with a pI of about 8.5 to about 8.9. In certain embodiments, the multispecific binding proteins described herein bind to CLEC12A with a pI of about 8.7.

In some embodiments, the F3' format of a CLEC12A TriNKET described herein (e.g., hF3'-1602 TriNKET), has EC50 about 2-fold lower (e.g., about 1-fold lower, about 2-fold lower, about 3-fold lower, about 4 fold lower, about 5-fold lower, about 6-fold lower) than that of the corresponding F3 format TriNKET, e.g., AB0010, in binding to human CLEC12A on the surface of a cell, e.g., a cancer cell. In some embodiments, the F3' format of a CLEC12A TriNKET described herein (e.g., hF3'-1602 TriNKET), has EC50 about 50% lower (e.g., about 25% lower, about 30% lower, about 40% lower, about 50% lower, about 55% lower, about 60% lower, about 70% lower, about 75% lower) than that of the corresponding F3 format TriNKET, e.g., AB0010, in binding to human CLEC12A on the surface of a cell, e.g., a cancer cell.

In certain embodiments, the second antigen-binding site competes for binding to CLEC12A with a corresponding antigen-binding site described above. In one aspect, the instant disclosure provides a multispecific binding protein comprising (a) a first antigen-binding site that binds NKG2D; (b) a second antigen-binding site that binds CLEC12A; and (c) an antibody Fc domain or a portion thereof sufficient to bind CD16, or a third antigen-binding site that binds CD16; wherein the second antigen-binding site competes with an antigen-binding site that binds CLEC12A as disclosed herein. In certain embodiments, the second antigen-binding site competes with an antigen-binding site derived from 16B8.C8 disclosed above for binding to CLEC12A. In one embodiment, the second antigen-binding site competes with 16B8.C8 for binding to CLEC12A. In certain embodiments, the second antigen-binding site competes with an antigen-binding site derived from a humanized 16B8.C8 disclosed above for binding to CLEC12A. In one embodiment, the second antigen-binding site competes with a humanized 16B8.C8 for binding to CLEC12A. In certain embodiments, the second antigen-binding site competes with an antigen-binding site derived from 9F11.B7 disclosed above for binding to CLEC12A. In one embodiment, the second antigen-binding site competes with 9F11.B7 for binding to CLEC12A. In certain embodiments, the second antigen-binding site competes with an antigen-binding site derived from a humanized 9F11.B7 disclosed above for binding to CLEC12A. In one embodiment, the second antigen-binding site competes with a humanized 9F11.B7 for binding to CLEC12A. In certain embodiments, the second antigen-binding site competes with an antigen-binding site derived from 12F8.H7, 13E1.A4, 15A10.E8, 20D6.H8, or 23A5.H8 disclosed above for binding to CLEC12A. In some embodiments, the second antigen-binding site competes with 12F8.H7, 13E1.A4, 15A10.E8, 20D6.H8, or 23A5.H8 for binding to CLEC12A.

Fc Domain

Within the Fc domain, CD16 binding is mediated by the hinge region and the CH2 domain. For example, within human IgG1, the interaction with CD16 is primarily focused on amino acid residues Asp 265-Glu 269, Asn 297-Thr 299, Ala 327-Ile 332, Leu 234-Ser 239, and carbohydrate residue N-acetyl-D-glucosamine in the CH2 domain (see, Sondermann et al., Nature, 406 (6793):267-273). Based on the known domains, mutations can be selected to enhance or reduce the binding affinity to CD16, such as by using phage-displayed libraries or yeast surface-displayed cDNA libraries, or can be designed based on the known three-dimensional structure of the interaction. Accordingly, in certain embodiment, the antibody Fc domain or the portion thereof comprises a hinge and a CH2 domain.

The assembly of heterodimeric antibody heavy chains can be accomplished by expressing two different antibody heavy chain sequences in the same cell, which may lead to the assembly of homodimers of each antibody heavy chain as well as assembly of heterodimers. Promoting the preferential assembly of heterodimers can be accomplished by incorporating different mutations in the CH3 domain of each antibody heavy chain constant region as shown in U.S. Ser. Nos. 13/494,870, 16/028,850, 11/533,709, 12/875,015, 13/289,934, 14/773,418, 12/811,207, 13/866,756, 14/647,480, and 14/830,336. For example, mutations can be made in the CH3 domain based on human IgG1 and incorporating distinct pairs of amino acid substitutions within a first polypeptide and a second polypeptide that allow these two chains to selectively heterodimerize with each other. The positions of amino acid substitutions illustrated below are all numbered according to the EU index as in Kabat.

In one scenario, an amino acid substitution in the first polypeptide replaces the original amino acid with a larger amino acid, selected from arginine (R), phenylalanine (F), tyrosine (Y) or tryptophan (W), and at least one amino acid substitution in the second polypeptide replaces the original amino acid(s) with a smaller amino acid(s), chosen from alanine (A), serine (S), threonine (T), or valine (V), such that the larger amino acid substitution (a protuberance) fits into the surface of the smaller amino acid substitutions (a cavity). For example, one polypeptide can incorporate a T366W substitution, and the other can incorporate three substitutions including T366S, L368A, and Y407V.

An antibody heavy chain variable domain described in the application can optionally be coupled to an amino acid sequence at least 90% identical to an antibody constant region, such as an IgG constant region including hinge, CH2 and CH3 domains with or without CH1 domain. In some embodiments, the amino acid sequence of the constant region is at least 90% identical to a human antibody constant region, such as a human IgG1 constant region, an IgG2 constant region, IgG3 constant region, or IgG4 constant region. In one embodiment, the antibody Fc domain or a portion thereof sufficient to bind CD16 comprises an amino acid sequence at least 90% (e.g., at least 91%, at least 92%, at least 93%, at least 94%, at least 95%, at least 96%, at least 97%, at least 98%, at least 99%, or 100%) identical to wild-type human IgG1 Fc sequence DKTHTCPPCPA-PELLGGPSVFLFPPKPKDTLMISRTPE-VTCVVVDVSHEDPEVKFNWYV DGVEVHNAKTKPREEQYN-STYRVVSVLTVLHQDWLNGKEYKCKVSNKALPA-PIEKTIS KAKGQPREPQVYTLPPSRDELTKNQVSLT-CLVKGFYPSDIAVEWESNGQPENNYKTTPP VLDSDGSFFLYSK-LTVDKSRWQQGNVFSCSVMHEALHNHYTQKSLSL-SPG (SEQ ID NO:118). In some other embodiments, the amino acid sequence of the constant region is at least 90% identical to an antibody constant region from another mammal, such as rabbit, dog, cat, mouse, or horse.

In some embodiments, the antibody constant domain linked to the scFv or the Fab fragment is able to bind to CD16. In some embodiments, the protein incorporates a portion of an antibody Fc domain (for example, a portion of an antibody Fc domain sufficient to bind CD16), wherein the antibody Fc domain comprises a hinge and a CH2 domain (for example, a hinge and a CH2 domain of a human IgG1 antibody), and/or amino acid sequences at least 90% identical to amino acid sequence 234-332 of a human IgG antibody.

One or more mutations can be incorporated into the constant region as compared to human IgG1 constant region, for example at Q347, Y349, L351, S354, E356, E357, K360, Q362, S364, T366, L368, K370, N390, K392, T394, D399, S400, D401, F405, Y407, K409, T411 and/or K439. Exemplary substitutions include, for example, Q347E, Q347R, Y349S, Y349K, Y349T, Y349D, Y349E, Y349C, T350V, L351K, L351D, L351Y, S354C, E356K, E357Q, E357L, E357W, K360E, K360W, Q362E, S364K, S364E, S364H, S364D, T366V, T366I, T366L, T366M, T366K, T366W, T366S, L368E, L368A, L368D, K370S, N390D, N390E, K392L, K392M, K392V, K392F, K392D, K392E, T394F, T394W, D399R, D399K, D399V, S400K, S400R, D401K, F405A, F405T, Y407A, Y407I, Y407V, K409F, K409W, K409D, K409R, T411D, T411E, K439D, and K439E.

In certain embodiments, mutations that can be incorporated into the CH1 of a human IgG1 constant region may be at amino acid V125, F126, P127, T135, T139, A140, F170, P171, and/or V173. In certain embodiments, mutations that can be incorporated into the Cκ of a human IgG1 constant region may be at amino acid E123, F116, S176, V163, S174, and/or T164.

Alternatively, amino acid substitutions could be selected from the following sets of substitutions shown in Table 3.

TABLE 3

|  | First Polypeptide | Second Polypeptide |
| --- | --- | --- |
| Set 1 | S364E/F405A | Y349K/T394F |
| Set 2 | S364H/D401K | Y349T/T411E |
| Set 3 | S364H/T394F | Y349T/F405A |
| Set 4 | S364E/T394F | Y349K/F405A |
| Set 5 | S364E/T411E | Y349K/D401K |
| Set 6 | S364D/T394F | Y349K/F405A |
| Set 7 | S364H/F405A | Y349T/T394F |
| Set 8 | S364K/E357Q | L368D/K370S |
| Set 9 | L368D/K370S | S364K |
| Set 10 | L368E/K370S | S364K |
| Set 11 | K360E/Q362E | D401K |
| Set 12 | L368D/K370S | S364K/E357L |
| Set 13 | K370S | S364K/E357Q |
| Set 14 | F405L | K409R |
| Set 15 | K409R | F405L |

Alternatively, amino acid substitutions could be selected from the following sets of substitutions shown in Table 4.

TABLE 4

|  | First Polypeptide | Second Polypeptide |
| --- | --- | --- |
| Set 1 | K409W | D399V/F405T |
| Set 2 | Y349S | E357W |
| Set 3 | K360E | Q347R |
| Set 4 | K360E/K409W | Q347R/D399V/F405T |
| Set 5 | Q347E/K360E/K409W | Q347R/D399V/F405T |
| Set 6 | Y349S/K409W | E357W/D399V/F405T |

Alternatively, amino acid substitutions could be selected from the following sets of substitutions shown in Table 5.

TABLE 5

|  | First Polypeptide | Second Polypeptide |
|---|---|---|
| Set 1 | T366K/L351K | L351D/L368E |
| Set 2 | T366K/L351K | L351D/Y349E |
| Set 3 | T366K/L351K | L351D/Y349D |
| Set 4 | T366K/L351K | L351D/Y349E/L368E |
| Set 5 | T366K/L351K | L351D/Y349D/L368E |
| Set 6 | E356K/D399K | K392D/K409D |

Alternatively, at least one amino acid substitution in each polypeptide chain could be selected from Table 6.

TABLE 6

| First Polypeptide | Second Polypeptide |
|---|---|
| L351Y, D399R, D399K, S400K, S400R, Y407A, Y407I, Y407V | T366V, T366I, T366L, T366M, N390D, N390E, K392L, K392M, K392V, K392F K392D, K392E, K409F, K409W, T411D and T411E |

Alternatively, at least one amino acid substitution could be selected from the following sets of substitutions in Table 7, where the position(s) indicated in the First Polypeptide column is replaced by any known negatively-charged amino acid, and the position(s) indicated in the Second Polypeptide Column is replaced by any known positively-charged amino acid.

TABLE 7

| First Polypeptide | Second Polypeptide |
|---|---|
| K392, K370, K409, or K439 | D399, E356, or E357 |

Alternatively, at least one amino acid substitution could be selected from the following set in Table 8, where the position(s) indicated in the First Polypeptide column is replaced by any known positively-charged amino acid, and the position(s) indicated in the Second Polypeptide Column is replaced by any known negatively-charged amino acid.

TABLE 8

| First Polypeptide | Second Polypeptide |
|---|---|
| D399, E356, or E357 | K409, K439, K370, or K392 |

Alternatively, amino acid substitutions could be selected from the following sets in Table 9.

TABLE 9

| First Polypeptide | Second Polypeptide |
|---|---|
| T350V, L351Y, F405A, and Y407V | T350V, T366L, K392L, and T394W |

Alternatively, or in addition, the structural stability of a hetero-multimeric protein may be increased by introducing S354C on either of the first or second polypeptide chain, and Y349C on the opposing polypeptide chain, which forms an artificial disulfide bridge within the interface of the two polypeptides.

In some embodiments, the amino acid sequence of one polypeptide chain of the antibody constant region differs from the amino acid sequence of an IgG1 constant region at position T366, and wherein the amino acid sequence of the other polypeptide chain of the antibody constant region differs from the amino acid sequence of an IgG1 constant region at one or more positions selected from the group consisting of T366, L368 and Y407.

In some embodiments, the amino acid sequence of one polypeptide chain of the antibody constant region differs from the amino acid sequence of an IgG1 constant region at one or more positions selected from the group consisting of T366, L368 and Y407, and wherein the amino acid sequence of the other polypeptide chain of the antibody constant region differs from the amino acid sequence of an IgG1 constant region at position T366.

In some embodiments, the amino acid sequence of one polypeptide chain of the antibody constant region differs from the amino acid sequence of an IgG1 constant region at one or more positions selected from the group consisting of E357, K360, Q362, S364, L368, K370, T394, D401, F405, and T411 and wherein the amino acid sequence of the other polypeptide chain of the antibody constant region differs from the amino acid sequence of an IgG1 constant region at one or more positions selected from the group consisting of Y349, E357, S364, L368, K370, T394, D401, F405 and T411.

In some embodiments, the amino acid sequence of one polypeptide chain of the antibody constant region differs from the amino acid sequence of an IgG1 constant region at one or more positions selected from the group consisting of Y349, E357, S364, L368, K370, T394, D401, F405 and T411 and wherein the amino acid sequence of the other polypeptide chain of the antibody constant region differs from the amino acid sequence of an IgG1 constant region at one or more positions selected from the group consisting of E357, K360, Q362, S364, L368, K370, T394, D401, F405, and T411.

In some embodiments, the amino acid sequence of one polypeptide chain of the antibody constant region differs from the amino acid sequence of an IgG1 constant region at one or more positions selected from the group consisting of L351, D399, S400 and Y407 and wherein the amino acid sequence of the other polypeptide chain of the antibody constant region differs from the amino acid sequence of an IgG1 constant region at one or more positions selected from the group consisting of T366, N390, K392, K409 and T411.

In some embodiments, the amino acid sequence of one polypeptide chain of the antibody constant region differs from the amino acid sequence of an IgG1 constant region at one or more positions selected from the group consisting of T366, N390, K392, K409 and T411 and wherein the amino acid sequence of the other polypeptide chain of the antibody constant region differs from the amino acid sequence of an IgG1 constant region at one or more positions selected from the group consisting of L351, D399, S400 and Y407.

In some embodiments, the amino acid sequence of one polypeptide chain of the antibody constant region differs from the amino acid sequence of an IgG1 constant region at one or more positions selected from the group consisting of Q347, Y349, K360, and K409, and wherein the amino acid sequence of the other polypeptide chain of the antibody constant region differs from the amino acid sequence of an IgG1 constant region at one or more positions selected from the group consisting of Q347, E357, D399 and F405.

In some embodiments, the amino acid sequence of one polypeptide chain of the antibody constant region differs from the amino acid sequence of an IgG1 constant region at one or more positions selected from the group consisting of Q347, E357, D399 and F405, and wherein the amino acid sequence of the other polypeptide chain of the antibody constant region differs from the amino acid sequence of an IgG1 constant region at one or more positions selected from the group consisting of Y349, K360, Q347 and K409.

In some embodiments, the amino acid sequence of one polypeptide chain of the antibody constant region differs from the amino acid sequence of an IgG1 constant region at one or more positions selected from the group consisting of K370, K392, K409 and K439, and wherein the amino acid sequence of the other polypeptide chain of the antibody constant region differs from the amino acid sequence of an IgG1 constant region at one or more positions selected from the group consisting of D356, E357 and D399.

In some embodiments, the amino acid sequence of one polypeptide chain of the antibody constant region differs from the amino acid sequence of an IgG1 constant region at one or more positions selected from the group consisting of D356, E357 and D399, and wherein the amino acid sequence of the other polypeptide chain of the antibody constant region differs from the amino acid sequence of an IgG1 constant region at one or more positions selected from the group consisting of K370, K392, K409 and K439.

In some embodiments, the amino acid sequence of one polypeptide chain of the antibody constant region differs from the amino acid sequence of an IgG1 constant region at one or more positions selected from the group consisting of L351, E356, T366 and D399, and wherein the amino acid sequence of the other polypeptide chain of the antibody constant region differs from the amino acid sequence of an IgG1 constant region at one or more positions selected from the group consisting of Y349, L351, L368, K392 and K409.

In some embodiments, the amino acid sequence of one polypeptide chain of the antibody constant region differs from the amino acid sequence of an IgG1 constant region at one or more positions selected from the group consisting of Y349, L351, L368, K392 and K409, and wherein the amino acid sequence of the other polypeptide chain of the antibody constant region differs from the amino acid sequence of an IgG1 constant region at one or more positions selected from the group consisting of L351, E356, T366 and D399.

In some embodiments, the amino acid sequence of one polypeptide chain of the antibody constant region differs from the amino acid sequence of an IgG1 constant region by an S354C substitution and wherein the amino acid sequence of the other polypeptide chain of the antibody constant region differs from the amino acid sequence of an IgG1 constant region by a Y349C substitution.

In some embodiments, the amino acid sequence of one polypeptide chain of the antibody constant region differs from the amino acid sequence of an IgG1 constant region by a Y349C substitution and wherein the amino acid sequence of the other polypeptide chain of the antibody constant region differs from the amino acid sequence of an IgG1 constant region by an S354C substitution.

In some embodiments, the amino acid sequence of one polypeptide chain of the antibody constant region differs from the amino acid sequence of an IgG1 constant region by K360E and K409W substitutions and wherein the amino acid sequence of the other polypeptide chain of the antibody constant region differs from the amino acid sequence of an IgG1 constant region by Q347R, D399V and F405T substitutions.

In some embodiments, the amino acid sequence of one polypeptide chain of the antibody constant region differs from the amino acid sequence of an IgG1 constant region by Q347R, D399V and F405T substitutions and wherein the amino acid sequence of the other polypeptide chain of the antibody constant region differs from the amino acid sequence of an IgG1 constant region by K360E and K409W substitutions.

In some embodiments, the amino acid sequence of one polypeptide chain of the antibody constant region differs from the amino acid sequence of an IgG1 constant region by a T366W substitutions and wherein the amino acid sequence of the other polypeptide chain of the antibody constant region differs from the amino acid sequence of an IgG1 constant region by T366S, T368A, and Y407V substitutions.

In some embodiments, the amino acid sequence of one polypeptide chain of the antibody constant region differs from the amino acid sequence of an IgG1 constant region by T366S, T368A, and Y407V substitutions and wherein the amino acid sequence of the other polypeptide chain of the antibody constant region differs from the amino acid sequence of an IgG1 constant region by a T366W substitution.

In some embodiments, the amino acid sequence of one polypeptide chain of the antibody constant region differs from the amino acid sequence of an IgG1 constant region by T350V, L351Y, F405A, and Y407V substitutions and wherein the amino acid sequence of the other polypeptide chain of the antibody constant region differs from the amino acid sequence of an IgG1 constant region by T350V, T366L, K392L, and T394W substitutions.

In some embodiments, the amino acid sequence of one polypeptide chain of the antibody constant region differs from the amino acid sequence of an IgG1 constant region by T350V, T366L, K392L, and T394W substitutions and wherein the amino acid sequence of the other polypeptide chain of the antibody constant region differs from the amino acid sequence of an IgG1 constant region by T350V, L351Y, F405A, and Y407V substitutions.

Exemplary Multispecific Binding Proteins

Listed below are examples of TriNKETs comprising an antigen-binding site that binds CLEC12A and an antigen-binding site that binds NKG2D each linked to an antibody constant region, wherein the antibody constant regions include mutations that enable heterodimerization of two Fc chains.

Exemplary CLEC12A-targeting TriNKETs are contemplated in the F3' and F3 formats. As described above, in the F3' format, the antigen-binding site that binds the tumor-associated antigen is an scFv and the antigen-binding site that binds NKG2D is a Fab. In the F3 format, the antigen-binding site that binds the tumor-associated antigen is a Fab, and the antigen-binding site that binds NKG2D is an scFv. In each TriNKET, the scFv may comprise substitution of Cys in the VH and VL regions, facilitating formation of a disulfide bridge between the VH and VL of the scFv.

The VH and VL of the scFv can be connected via a linker, e.g., a peptide linker. In certain embodiments, the peptide linker is a flexible linker. Regarding the amino acid composition of the linker, peptides are selected with properties that confer flexibility, do not interfere with the structure and function of the other domains of the proteins described in the present application, and resist cleavage from proteases. For example, glycine and serine residues generally provide protease resistance. In certain embodiments, the VL is linked N-terminal or C-terminal to the VH via a (GlyGlyGlyGly-Ser)$_4$ ((G$_4$S)$_4$) linker (SEQ ID NO:119).

The length of the linker (e.g., flexible linker) can be "short," e.g., 0, 1, 2, 3, 4, 5, 6, 7, 8, 9, 10, 11 or 12 amino acid residues, or "long," e.g., at least 13 amino acid residues. In certain embodiments, the linker is 10-50, 10-40, 10-30, 10-25, 10-20, 15-50, 15-40, 15-30, 15-25, 15-20, 20-50, 20-40, 20-30, or 20-25 amino acid residues in length.

In certain embodiments, the linker comprises or consists of a (GS)$_n$ (SEQ ID NO:120), (GGS)$_n$ (SEQ ID NO:121), (GGGS)$_n$ (SEQ ID NO:122), (GGSG)$_n$ (SEQ ID NO:123), (GGSGG)$_n$ (SEQ ID NO:124), and (GGGGS)$_n$ (SEQ ID NO:125) sequence, wherein n is 1, 2, 3, 4, 5, 6, 7, 8, 9, 10, 11, 12, 13, 14, 15, 16, 17, 18, 19, or 20. In certain embodiments, the linker comprises or consists of an amino acid sequence selected from SEQ ID NO:119 and SEQ ID NO:126-134, as listed in Table 10.

TABLE 10

| SEQ ID | Amino Acid Sequence |
|---|---|
| SEQ ID NO: 126 | GSGSGSGSGSGSGSGSGSGS |
| SEQ ID NO: 127 | GGSGGSGGSGGSGGSGGSGGSGGSGGSGGS |
| SEQ ID NO: 128 | GGGSGGGSGGGSGGGSGGGSGGGSGGGSGGGGSGGGGSGGGS |
| SEQ ID NO: 129 | GGSGGGSGGGSGGGSGGGSGGGSGGGSGGGSGGGSGGGSG |
| SEQ ID NO: 130 | GGSGGGGSGGGGSGGGGSGGGGSGGGGSGGGGSGGGGSGGGGSGGGGSGG |
| SEQ ID NO: 131 | GGGGSGGGGSGGGGSGGGGSGGGGSGGGGSGGGGSGGGGSGGGGSGGGGS |
| SEQ ID NO: 119 | GGGGSGGGGSGGGGSGGGGS |
| SEQ ID NO: 132 | GGGGSGGGGSGGGGS |
| SEQ ID NO: 133 | GGGGSGGGGSGGGGSGGGGSGGGGSGGGGSGGGGSGGGGSGGGGSGGGGSGGGGSGGGGSGGGGSGGGGSGGGGSGGGGSGGGGSGGGGSGGGGSGGGGS |
| SEQ ID NO: 134 | GGSGGGGSGGGGSGGGGSGGGGSGGGGSGGGGSGGSGGGGSGGGGSGGGGSGGGGSGGGGSGGGGSGGSGGGGSGGGGSGGGGSGGGGSGGGGSGGGGSGGSGGGGSGG |

In the F3'-TriNKETs, the tumor-associated antigen-binding scFv is linked to the N-terminus of an Fc via a Gly-Ser linker. The Ala-Ser or Gly-Ser linker is included at the elbow hinge region sequence to balance between flexibility and optimal geometry. In certain embodiments, an additional sequence Thr-Lys-Gly can be added N-terminal or C-terminal to the Ala-Ser or Gly-Ser sequence at the hinge.

As used herein to describe these exemplary TriNKETs, an Fc includes an antibody hinge, CH2, and CH3. In each exemplary TriNKET, the Fc domain linked to an scFv comprises the mutations of Q347R, D399V, and F405T, and the Fc domain linked to a Fab comprises matching mutations K360E and K409W for forming a heterodimer. The Fc domain linked to the scFv further includes an S354C substitution in the CH3 domain, which forms a disulfide bond with a Y349C substitution on the Fc linked to the Fab. These substitutions are bold in the sequences described in this subsection.

For example, a TriNKET of the present disclosure is F3'-1602 TriNKET, also referred to herein as "hF3'-1602 TriNKET" and "AB0237". F3'-1602 TriNKET includes (a) a CLEC12A-binding scFv sequence derived from scFv-1602 of Table 2, in the orientation of VH positioned N-terminal to VL, linked to an Fc domain and (b) an NKG2D-binding Fab fragment derived from A49MI including a heavy chain portion comprising a heavy chain variable domain and a CH1 domain, and a light chain portion comprising a light chain variable domain and a light chain constant domain, wherein the CH1 domain is connected to the Fc domain. F3'-1602 TriNKET includes three polypeptides scFv-1602-VH-VL-Fc, A49MI-VH-CH1-Fc, and A49MI-VL-CL.

scFv-1602-VH-VL-Fc ("Chain S")
(SEQ ID NO: 259)
QLQLQESGPGLVKPSETLSLTCTVSGFSLTNYGLHWIRQPPGKCLEWIGV

IWSGGKTDYNPSLKSRVTISKDTSKNQFSLKLSSVQAADTAVYYCAKYDY

DDSLDYWGQGTLVTVSSGGGGSGGGGSGGGGSGGGGS

DIQMTQSPSSLSASVGDRVTITCHASQNINFWLSWYQQKPGKAPKLLIYE

ASNLHTGVPSRFSGSGSGTRFTLTISSLQPEDIATYYCQQSHSYPLTFGC

GTKLEIK

GS

DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPRVYTLPPCRDELTKNQVSLTCLVK

GFYPSDIAVEWESNGQPENNYKTTPPVLVSDGSFTLYSKLTVDKSRWQQG

NVFSCSVMHEALHNHYTQKSLSLSPG

A49MI-VH-CH1-Fc ("Chain H")
(SEQ ID NO: 260)
EVQLVESGGGLVKPGGSLRLSCAASGFTFSSYSMNWVRQAPGKGLEWVSS

ISSSSSYIYYADSVKGRFTISRDNAKNSLYLQMNSLRAEDTAVYYCARGA

PIGAAAGWFDPWGQGTLVTVSS

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVCTLPPSRDELTENQVSLTC

LVKGFYPSDIAVEWESNGQPENNYKTTPPVLDSDGSFFLYSWLTVDKSRW

QQGNVFSCSVMHEALHNHYTQKSLSLSPG

A49MI-VL-CL ("Chain L")
(SEQ ID NO: 261)
DIQMTQSPSSVSASVGDRVTITCRASQGISSWLAWYQQKPGKAPKLLIYA

ASSLQSGVPSRFSGSGSGTDFTLTISSLQPEDFATYYCQQGVSFPRTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC scFv-1602-VH-VL-Fc represents the full sequence of a CLEC12A binding scFv linked to an Fc domain via a hinge comprising Gly-Ser. The Fc domain linked to the scFv includes Q347R, D399V, and F405T substitutions for heterodimerization and an S354C substitution for forming a disulfide bond with a Y349C substitution in A49MI-VH-CH1-Fc as described below. The scFv has the amino acid sequence of scFv-1602, which includes a heavy chain variable domain of scFv-1602 connected to the N-terminus of a light chain variable domain of scFv-1602 via a (G$_4$S)$_4$ linker. scFv-1602-VH-VL-Fc comprises substitution of Cys in the VH and VL regions at G44 and S100, facilitating formation of a disulfide bridge between the VH and VL of the scFv.

A49MI-VH-CH1-Fc represents the heavy chain portion of the Fab fragment, which comprises a heavy chain variable domain (SEQ ID NO:95) of NKG2D-binding A49MI and a CH1 domain, connected to an Fc domain. The Fc domain in A49MI-VH-CH1-Fc includes a Y349C substitution in the CH3 domain, which forms a disulfide bond with an S354C substitution on the Fc in scFv-1602-VH-VL-Fc. In A49MI-VH-CH1-Fc, the Fc domain also includes K360E and K409W substitutions for heterodimerization with the Fc in scFv-1602-VH-VL-Fc.

A49MI-VL-CL represents the light chain portion of the Fab fragment comprising a light chain variable domain of NKG2D-binding A49MI (SEQ ID NO:85) and a light chain constant domain.

The DNA sequences encoding the polypeptides scFv-1602-VH-VL-Fc, A49MI-VH-CH1-Fc, and A49MI-VL-CL are provided in Table 260.

TABLE 260

DNA Sequences of F3'-1602 TriNKET

| Polypeptide | DNA Sequence |
|---|---|
| scFv-1602-VH-VL-Fc | ATGGACATGAGGGTACCAGCTCAGCTGCTGGGCCTGCTGCTGC TTTGGCTTCCTGGCGCTAGATGCCAATTGCAGCTGCAAGAATC CGGACCAGGGCTCGTAAAACCTTCTGAAACCCTCTCCCTCACT TGCACTGTGTCTGGATTCTCTCTCACGAACTACGGGTTGCATT GGATCCGACAGCCGCCTGGCAAGTGTCTTGAGTGGATTGGCGT TATCTGGTCAGGAGGGAAGACGGATTATAATCCAAGTCTGAA ATCCAGAGTGACAATTTCTAAGGACACGTCCAAAAATCAGTTT AGCCTCAAACTTTCCTCAGTTCAGGCTGCTGATACAGCGGTGT ACTATTGCGCAAAGTACGACTATGATGACAGTTTGGACTACTG GGGACAGGGTACACTGGTAACAGTGAGTTCTGGAGGCGGCGG TAGTGGAGGCGGGGGAAGTGGTGGCGGAGGGAGTGGAGGAG GGGGCAGTGATATTCAAATGACGCAGAGCCCCAGTTCCCTTTC AGCTAGCGTTGGCGACAGAGTAACGATAACGTGTCACGCTTCC CAGAACATTAATTTTTGGCTTAGCTGGTATCAACAGAAACCGG GAAAAGCACCCAAGCTGCTTATCTATGAAGCGTCCAATCTCCA CACGGGTGTCCCATCAAGATTTTCTGGATCAGGCAGTGGCACA CGATTCACACTGACCATTAGTTCCTTGCAGCCCGAGGATATCG CAACTTACTACTGTCAGCAAAGTCACTCTTACCCGTTGACATT CGGATGTGGAACTAAACTGGAGATTAAGGGATCCGATAAGAC CCACACCTGTCCTCCATGTCCTGCTCCAGAACTGCTCGGCGGA CCTTCCGTGTTCCTGTTTCCTCCAAAGCCTAAGGACACCCTGAT GATCAGCAGGACCCCTGAAGTGACCTGCGTGGTGGTGGATGT GTCTCACGAGGACCCAGAAGTGAAGTTCAATTGGTACGTGGA CGGCGTGGAAGTGCACAACGCCAAGACCAAGCCTAGAGAGGA ACAGTACAACAGCACCTACAGAGTGGTGTCCGTGCTGACCGT GCTGCACCAGGATTGGCTGAACGGCAAAGAGTACAAGTGCAA GGTGTCCAACAAGGCCCTGCCTGCTCCTATCGAGAAAACCATC AGCAAGGCCAAGGGCCAGCCTCGCGAGCCTAGAGTGTATACC TTGCCTCCATGCCGGGACGAGCTGACCAAGAATCAGGTGTCCC TGACCTGCCTGGTCAAGGGCTTCTACCCTTCCGATATCGCCGT GGAATGGGAGAGCAATGGCCAGCCAGAGAACAACTACAAGA CCACACCTCCTGTGCTGGTGTCCGACGGCAGCTTTACCCTGTA CAGCAAGCTGACAGTGGACAAGAGCAGATGGCAGCAGGGCA ACGTGTTCTCCTGCAGCGTGATGCACGAGGCCCTGCACAACCA CTACACCCAGAAAAGCCTGAGCCTGTCTCCTGGCTAA [SEQ ID NO: 267] |
| A49MI-VH-CH1-Fc | ATGGGCTGGTCCTGCATCATCCTGTTTCTGGTGGCCACAGCCA CAGGCGTGCACTCTGAGGTGCAGCTGGTTGAATCTGGCGGCG GACTTGTGAAGCCTGGCGGATCTCTGAGACTGAGCTGTGCCGC CAGCGGCTTCACCTTTAGCAGCTACAGCATGAACTGGGTCCGA CAGGCCCCTGGCAAAGGCCTTGAATGGGTGTCCAGCATCAGC AGCAGTTCCAGCTACATCTACTACGCCGACAGCGTGAAGGGC AGATTCACCATCAGCCGGGACAACGCCAAGAACAGCCTGTAC CTGCAGATGAACTCCCTGAGAGCCGAGGACACCGCCGTGTAC TATTGTGCTAGAGGCGCCCCTATTGGAGCCGCCGCTGATGGT TCGATCCTTGGGGACAGGGAACCCTGGTCACCGTTTCTTCTGC CTCTACAAAGGGCCCAGCGTTTTCCCACTGGCTCCTAGCAGC AAGAGCACAAGCGGAGGAACAGCTGCCCTGGGCTGTCTGGTC AAGGACTACTTTCCTGAGCCTGTGACCGTGTCCTGGAACAGCG GAGCACTGACTAGCGGCGTGCACACATTTCCAGCCGTGCTGCA |

TABLE 260-continued

DNA Sequences of F3'-1602 TriNKET

| Polypeptide | DNA Sequence |
|---|---|
| | AAGCAGCGGCCTGTACTCTCTGAGCAGCGTCGTGACAGTGCCT AGCAGCTCTCTGGGCACCCAGACCTACATCTGCAATGTGAACC ACAAGCCTAGCAACACCAAGGTGGACAAGAAGGTGGAACCCA AGAGCTGCGACAAGACCCACACCTGTCCTCCATGTCCTGCTCC AGAACTGCTCGGCGGACCTTCCGTGTTCCTGTTTCCTCCAAAG CCTAAGGACACCCTGATGATCAGCAGAACCCCTGAAGTGACC TGCGTGGTGGTGGATGTGTCTCACGAGGACCCCGAAGTGAAG TTCAATTGGTACGTGGACGGCGTGGAAGTGCACAACGCCAAG ACCAAGCCTAGAGAGGAACAGTACAACAGCACCTACAGAGTG GTGTCCGTGCTGACAGTGCTGCACCAGGATTGGCTGAACGGCA AAGAGTACAAGTGCAAGGTGTCCAACAAGGCCCTGCCTGCTC CTATCGAGAAAACCATCAGCAAGGCCAAGGGCCAGCCTCGCG AACCTCAAGTCTGTACACTGCCTCCTAGCCGGGATGAGCTGAC CGAGAATCAGGTGTCCCTGACCTGTCTCGTGAAGGGCTTCTAC CCCTCCGATATCGCCGTGGAATGGGAGAGCAATGGCCAGCCA GAGAACAACTACAAGACAACCCCTCCTGTGCTGGACAGCGAC GGCTCATTCTTCCTGTACAGCTGGCTGACCGTGGACAAGTCCA GATGGCAGCAGGGCAACGTGTTCTCCTGCAGCGTGATGCACG AGGCCCTGCACAACCACTACACCCAGAAGTCCCTGTCTCTGAG CCCAGGCTAA [SEQ ID NO: 268] |
| A49MI-VL-CL | ATGGACATGAGAGTTCCAGCTCAGCTGCTGGGCCTGCTGCTGC TTTGGCTTCCTGGCGCTAGATGCGACATCCAGATGACACAGAG CCCCAGCTCCGTGTCTGCCTCTGTGGGAGACAGAGTGACCATC ACCTGTAGAGCCAGCCAGGGCATCTCTTCTTGGCTGGCCTGGT ATCAGCAGAAGCCTGGCAAGGCCCCTAAGCTGCTGATCTATGC CGCTAGCTCTCTGCAGTCTGGCGTGCCCTCTAGATTTTCTGGCA GCGGCTCTGGCACCGACTTCACCCTGACCATATCTAGCCTGCA GCCTGAGGACTTCGCCACCTACTATTGTCAGCAGGGCGTGTCC TTTCCACGGACCTTTGGCGGCGGAACAAAGGTGGAAATCAAG CGGACAGTGGCCGCTCCTAGCGTGTTCATCTTTCCACCTAGCG ACGAGCAGCTGAAGTCCGGCACAGCCTCTGTTGTGTGCCTGCT GAACAACTTCTACCCCAGAGAAGCCAAGGTGCAGTGGAAGGT GGACAATGCCCTGCAGAGCGGCAACAGCCAAGAGAGCGTGAC AGAGCAGGACAGCAAGGACTCCACCTACAGCCTGAGCAGCAC CCTGACACTGAGCAAGGCCGACTACGAAGCACAAAGTGTA CGCCTGCGAAGTGACCCACCAGGGCCTTTCTAGCCCTGTGACC AAGAGCTTCAACCGGGGCGAGTGTTGA [SEQ ID NO: 269] |

In another example, a TriNKET of the present disclosure is hF3'-2061 TriNKET, also referred to herein as F3'2061 TriNKET. F3'-2061 TriNKET includes (a) a CLEC12A-binding scFv sequence derived from scFv-2061 of Table 2, in the orientation of VH positioned C-terminal to VL, linked to an Fc domain and (b) an NKG2D-binding Fab fragment derived from A49MI including a heavy chain portion comprising a heavy chain variable domain and a CH1 domain, and a light chain portion comprising a light chain variable domain and a light chain constant domain, wherein the CH1 domain is connected to the Fc domain. F3'-2061 TriNKET includes three polypeptides: scFv-2061-VL-VH-Fc, A49MI-VH-CH1-Fc, and A49MI-VL-CL.

scFv-2061-VL-VH-Fc
(SEQ ID NO: 262)
DIQMTQSPSSLSASVGDRVTITCHASQNINFWLSWYQQKPGKAPKLLIYE

ASNLHTGVPSRFSGSGSGTRFTLTISSLQPEDIATYYCQQSHSYPLTFGC

GTKLEIK

GGGGSGGGGSGGGGSGGGGS

QLQLQESGPGLVKPSETLSLTCTVSGFSLTNYGLHWIRQPPGKCLEWIGV

IWSGGKTDYNPSLKSRVTISKDTSKNQFSLKLSSVQAADTAVYYCAKYDY

DDSLDYWGQGTLVTVSSGS

DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPRVYTLPPCRDELTKNQVSLTCLVK

GFYPSDIAVEWESNGQPENNYKTTPPVLVSDGSFTLYSKLTVDKSRWQQG

NVFSCSVMHEALHNHYTQKSLSLSPG scFv-2061-VL-VH-Fc represents the full sequence of a tumor-associated antigen binding scFv linked to an Fc domain via a hinge comprising Gly-Ser. The Fc domain linked to the scFv includes Q347R, D399V, and F405T substitutions for heterodimerization and an S354C substitution for forming a disulfide bond with a Y349C substitution in A49MI-VH-CH1-Fc as described below. The scFv has the amino acid sequence of scFv-2061, which includes a heavy chain variable domain of scFv-2061 connected to the C-terminus of a light chain variable domain of scFv-2061 via a $(G_4S)_4$ linker. It is contemplated that scFv-2061-VL-VH-Fc may comprise substitution of Cys in the VH and VL regions, facilitating formation of a disulfide bridge between the VH and VL of the scFv.

A49MI-VH-CH1-Fc represents the heavy chain portion of the Fab fragment, which comprises a heavy chain variable domain (SEQ ID NO:95) of NKG2D-binding A49MI and a CH1 domain, connected to an Fc domain. The Fc domain in A49MI-VH-CH1-Fc includes a Y349C substitution in the CH3 domain, which forms a disulfide bond with an S354C substitution on the Fc in scFv-2061-VL-VH-Fc. In A49MI-VH-CH1-Fc, the Fc domain also includes K360E and K409W substitutions for heterodimerization with the Fc in scFv-2061-VL-VH-Fc.

A49MI-VL-CL represents the light chain portion of the Fab fragment comprising a light chain variable domain of NKG2D-binding A49MI (SEQ ID NO:85) and a light chain constant domain.

In another example, a TriNKET of the present disclosure is AB0089 TriNKET. AB0089 TriNKET includes (a) a CLEC12A-binding scFv sequence derived from AB0305 of Table 2, in the orientation of VH positioned N-terminal to VL, linked to an Fc domain and (b) an NKG2D-binding Fab fragment derived from A49MI including a heavy chain portion comprising a heavy chain variable domain and a CH1 domain, and a light chain portion comprising a light chain variable domain and a light chain constant domain, wherein the CH1 domain is connected to the Fc domain. AB0089 TriNKET includes three polypeptides AB0305-VH-VL-Fc, A49MI-VH-CH1-Fc, and A49MI-VL-CL.

AB0305-VH-VL-Fc
(SEQ ID NO: 276)
QLQLQESGPGLVKPSETLSLTCTVSGFSLTNYGLHWIRQPPGKCLEWIGV

IWVGGATDYNPSLKSRVTISVDTSKNQFSLKLSSVQAADTAVYYCAKGDY

GDTLDYWGQGTLVTVSSGGGGSGGGGSGGGGSGGGGS

DIQMTQSPSSLSASVGDRVTITCHASQNINFWLSWYQQKPGKAPKLLIYE

ASNLHTGVPSRFSGSGSGTDFTLTISSLQPEDFATYYCQQSHSYPLTFGC

GTKLEIK

GS

DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPRVYTLPPCRDELTKNQVSLTCLVK

GFYPSDIAVEWESNGQPENNYKTTPPVLVSDGSFTLYSKLTVDKSRWQQG

NVFSCSVMHEALHNHYTQKSLSLSPG

AB0305-VH-VL-Fc represents the full sequence of a tumor-associated antigen binding scFv linked to an Fc domain via a hinge comprising Gly-Ser. The Fc domain linked to the scFv includes Q347R, D399V, and F405T substitutions for heterodimerization and an S354C substitution for forming a disulfide bond with a Y349C substitution in A49MI-VH-CH1-Fc as described below. The scFv includes a heavy chain variable domain of AB0305 connected to the N-terminus of a light chain variable domain of AB0305 via a $(G_4S)_4$ linker. AB0305-VH-VL-Fc comprises substitution of Cys in the VH and VL regions at G44 and S100, facilitating formation of a disulfide bridge between the VH and VL of the scFv.

A49MI-VH-CH1-Fc represents the heavy chain portion of the Fab fragment, which comprises a heavy chain variable domain (SEQ ID NO:95) of NKG2D-binding A49MI and a CH1 domain, connected to an Fc domain. The Fc domain in A49MI-VH-CH1-Fc includes a Y349C substitution in the CH3 domain, which forms a disulfide bond with an S354C substitution on the Fc in AB0305-VH-VL-Fc. In A49MI-VH-CH1-Fc, the Fc domain also includes K360E and K409W substitutions for heterodimerization with the Fc in AB0305-VH-VL-Fc.

A49MI-VL-CL represents the light chain portion of the Fab fragment comprising a light chain variable domain of NKG2D-binding A49MI (SEQ ID NO:85) and a light chain constant domain.

In another example, a TriNKET of the present disclosure is AB0147 TriNKET. AB0147 TriNKET includes (a) a CLEC12A-binding scFv sequence derived from AB0304 of Table 2, in the orientation of VH positioned N-terminal to VL, linked to an Fc domain and (b) an NKG2D-binding Fab fragment derived from A49MI including a heavy chain portion comprising a heavy chain variable domain and a CH1 domain, and a light chain portion comprising a light chain variable domain and a light chain constant domain, wherein the CH1 domain is connected to the Fc domain. AB0147 TriNKET includes three polypeptides AB0304-VH-VL-Fc, A49MI-VH-CH1-Fc, and A49MI-VL-CL.

AB0304-VH-VL-Fc
(SEQ ID NO: 277)
QLQLQESGPGLVKPSETLSLTCTVSGFSLTNYGLHWIRQPPGKCLEWIGV

ILSGGWTDYNPSLKSRVTISKDTSKNQFSLKLSSVQAADTAVYYCAKGDY

GDALDYWGQGTLVTVSSGGGGSGGGGSGGGGSGGGGS

DIQMTQSPSSLSASVGDRVTITCHASQNINFWLSWYQQKPGKAPKLLIYE

ASNLHTGVPSRFSGSGSGTRFTLTISSLQPEDIATYYCQQSHSYPLTFGC

GTKLEIK

GS

DKTHTCPPCPAPELLGGPSVFLFPPKPKDTLMISRTPEVTCVVVDVSHED

```
PEVKFNWYVDGVEVHNAKTKPREEQYNSTYRVVSVLTVLHQDWLNGKEYK

CKVSNKALPAPIEKTISKAKGQPREPRVYTLPPCRDELTKNQVSLTCLVK

GFYPSDIAVEWESNGQPENNYKTTPPVLVSDGSFTLYSKLTVDKSRWQQG

NVFSCSVMHEALHNHYTQKSLSLSPG
```

AB0304-VH-VL-Fc represents the full sequence of a tumor-associated antigen binding scFv linked to an Fc domain via a hinge comprising Gly-Ser. The Fc domain linked to the scFv includes Q347R, D399V, and F405T substitutions for heterodimerization and an S354C substitution for forming a disulfide bond with a Y349C substitution in A49MI-VH-CH1-Fc as described below. The scFv includes a heavy chain variable domain of AB0304 connected to the N-terminus of a light chain variable domain of AB0304 via a $(G_4S)_4$ linker. AB0304-VH-VL-Fc comprises substitution of Cys in the VH and VL regions at G44 and S100, facilitating formation of a disulfide bridge between the VH and VL of the scFv.

A49MI-VH-CH1-Fc represents the heavy chain portion of the Fab fragment, which comprises a heavy chain variable domain (SEQ ID NO:95) of NKG2D-binding A49MI and a CH1 domain, connected to an Fc domain. The Fc domain in A49MI-VH-CH1-Fc includes a Y349C substitution in the CH3 domain, which forms a disulfide bond with an S354C substitution on the Fc in AB0037-VH-VL-Fc. In A49MI-VH-CH1-Fc, the Fc domain also includes K360E and K409W substitutions for heterodimerization with the Fc in AB0304-VH-VL-Fc.

A49MI-VL-CL represents the light chain portion of the Fab fragment comprising a light chain variable domain of NKG2D-binding A49MI (SEQ ID NO:85) and a light chain constant domain.

In another example, a TriNKET of the present disclosure is AB0192 TriNKET. AB0192 TriNKET includes (a) a CLEC12A-binding scFv sequence derived from AB0192 of Table 2, in the orientation of VH positioned N-terminal to VL, linked to an Fc domain and (b) an NKG2D-binding Fab fragment derived from A49MI including a heavy chain portion comprising a heavy chain variable domain and a CH1 domain, and a light chain portion comprising a light chain variable domain and a light chain constant domain, wherein the CH1 domain is connected to the Fc domain. AB0192 TriNKET includes three polypeptides AB0192-VH-VL-Fc, A49MI-VH-CH1-Fc, and A49MI-VL-CL.

```
AB0192-VH-VL-Fc
                                    (SEQ ID NO: 278)
EVQLVESGGGVVQPGGSLRLSCAASGFTFNAFGMHWVRQAPGKCLEWVAF

ISSGSTSIYYANTVKGRFTISRDNSKNTLYLQMNSLRAEDTAVYYCARDG

YPTGGAMDYWGQGTSVTVSS

GGGGSGGGGSGGGGSGGGGS

DIQMTQSPSSLSASVGDRVTITCKASQDIYNYLSWFQQKPGKAPKPLIYR

ANILVSGVPSRFSGSGSGQDYTFTISSLQPEDIATYYCLQFDAFPFTFGC

GTKLEIK

GS

DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPRVYTLPPCRDELTKNQVSLTCLVK

GFYPSDIAVEWESNGQPENNYKTTPPVLVSDGSFTLYSKLTVDKSRWQQG

NVFSCSVMHEALHNHYTQKSLSLSPG
```

AB0192-VH-VL-Fc represents the full sequence of a tumor-associated antigen binding scFv linked to an Fc domain via a hinge comprising Gly-Ser. The Fc domain linked to the scFv includes Q347R, D399V, and F405T substitutions for heterodimerization and an S354C substitution for forming a disulfide bond with a Y349C substitution in A49MI-VH-CH1-Fc as described below. The scFv includes a heavy chain variable domain of AB0192 connected to the N-terminus of a light chain variable domain of AB0192 via a $(G_4S)_4$ linker. AB0192-VH-VL-Fc comprises substitution of Cys in the VH and VL regions at G44 and S100, facilitating formation of a disulfide bridge between the VH and VL of the scFv.

A49MI-VH-CH1-Fc represents the heavy chain portion of the Fab fragment, which comprises a heavy chain variable domain (SEQ ID NO:95) of NKG2D-binding A49MI and a CH1 domain, connected to an Fc domain. The Fc domain in A49MI-VH-CH1-Fc includes a Y349C substitution in the CH3 domain, which forms a disulfide bond with an S354C substitution on the Fc in AB0192-VH-VL-Fc. In A49MI-VH-CH1-Fc, the Fc domain also includes K360E and K409W substitutions for heterodimerization with the Fc in AB0192-VH-VL-Fc.

A49MI-VL-CL represents the light chain portion of the Fab fragment comprising a light chain variable domain of NKG2D-binding A49MI (SEQ ID NO:85) and a light chain constant domain.

In another example, a TriNKET of the present disclosure is hF3'-1295 TriNKET, also referred to herein as F3'-1295 TriNKET. F3'-1295 TriNKET includes (a) a CLEC12A-binding scFv sequence derived from scFv-1295 of Table 2, in the orientation of VH positioned N-terminal to VL, linked to an Fc domain and (b) an NKG2D-binding Fab fragment derived from A49MI including a heavy chain portion comprising a heavy chain variable domain and a CH1 domain, and a light chain portion comprising a light chain variable domain and a light chain constant domain, wherein the CH1 domain is connected to the Fc domain. F3'-1295 TriNKET includes three polypeptides scFv-1295-VH-VL-Fc, A49MI-VH-CH1-Fc, and A49MI-VL-CL.

```
scFv-1295-VH-VL-Fc
                                    (SEQ ID NO: 281)
QLQLQESGPGLVKPSETLSLTCTVSGFSLTNYGLHWIRQPPGKCLEWIGV

IWSGGKTDYNPSLKSRVTISKDTSKNQFSLKLSSVQAADTAVYYCAKYDY

DDSLDYWGQGTLVTVSS

GGGGSGGGGSGGGGSGGGGS

DIQMTQSPSSLSASVGDRVTITCHASQNINFWLSWYQQKPGKIPKLLIYE

ASNLHTGVPSRFSGSGSGTRFTLTISSLQPEDIATYYCQQSHSYPLTFGC

GTKLEIK

GS

DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK
```

```
CKVSNKALPAPIEKTISKAKGQPREPRVYTLPPCRDELTKNQVSLTCLVK

GFYPSDIAVEWESNGQPENNYKTTPPVLVSDGSFTLYSKLTVDKSRWQQG

NVFSCSVMHEALHNHYTQKSLSLSPG
``` scFv-1295-VH-VL-Fc represents the full sequence of a tumor-associated antigen binding scFv linked to an Fc domain via a hinge comprising Gly-Ser. The Fc domain linked to the scFv includes Q347R, D399V, and F405T substitutions for heterodimerization and an S354C substitution for forming a disulfide bond with a Y349C substitution in A49MI-VH-CH1-Fc as described below. The scFv includes a heavy chain variable domain of scFv-1295 connected to the N-terminus of a light chain variable domain of scFv-1295 via a (G₄S)₄ linker. scFv-1295-VH-VL-Fc comprises substitution of Cys in the VH and VL regions at G44 and S100, facilitating formation of a disulfide bridge between the VH and VL of the scFv.

A49MI-VH-CH1-Fc represents the heavy chain portion of the Fab fragment, which comprises a heavy chain variable domain (SEQ ID NO:95) of NKG2D-binding A49MI and a CH1 domain, connected to an Fc domain. The Fc domain in A49MI-VH-CH1-Fc includes a Y349C substitution in the CH3 domain, which forms a disulfide bond with an S354C substitution on the Fc in AB0192-VH-VL-Fc. In A49MI-VH-CH1-Fc, the Fc domain also includes K360E and K409W substitutions for heterodimerization with the Fc in scFv-1295-VH-VL-Fc.

A49MI-VL-CL represents the light chain portion of the Fab fragment comprising a light chain variable domain of NKG2D-binding A49MI (SEQ ID NO:85) and a light chain constant domain.

In another example, a TriNKET of the present disclosure is F3 1602 TriNKET, also referred to herein as AB0010. F3 1602 TriNKET includes (a) an NKG2D-binding scFv sequence derived from scFv-A49MI of Table 1, in the orientation of VH positioned N-terminal to VL, linked to an Fc domain and (b) a CLEC12A-binding Fab fragment derived from scFv-1602 including a heavy chain portion comprising a heavy chain variable domain and a CH1 domain, and a light chain portion comprising a light chain variable domain and a light chain constant domain, wherein the CH1 domain is connected to the Fc domain. F3 1602 TriNKET includes three polypeptides scFv-A49MI-VH-VL-Fc, 1602-VH-CH1-Fc, and 1602-VL-CL.

```
scFv-A49MI-VH-VL-Fc
                                        (SEQ ID NO: 286)
DIQMTQSPSSVSASVGDRVTITCRASQGISSWLAWYQQKPGKAPKLLIYA

ASSLQSGVPSRFSGSGSGTDFTLTISSLQPEDFATYYCQQGVSFPRTFGG

GTKVEIKGGGGSGGGGSGGGGSGGGGS

EVQLVESGGGLVKPGGSLRLSCAASGFTFSSYSMNWVRQAPGKGLEWVSS

ISSSSSYIYYADSVKGRFTISRDNAKNSLYLQMNSLRAEDTAVYYCARGA

PIGAAAGWFDPWGQGTLVTVSS

GS

DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPRVYTLPPCRDELTKNQVSLTCLVK

GFYPSDIAVEWESNGQPENNYKTTPPVLVSDGSFTLYSKLTVDKSRWQQG

NVFSCSVMHEALHNHYTQKSLSLSPG

1602-VH-CH1-Fc
                                        (SEQ ID NO: 287)
QLQLQESGPGLVKPSETLSLTCTVSGFSLTNYGLHWIRQPPGKGLEWIGV

IWSGGKTDYNPSLKSRVTISKDTSKNQFSLKLSSVQAADTAVYYCAKYDY

DDSLDYWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKVEPKSCDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVCT

LPPSRDELTENQVSLTCLVKGFYPSDIAVEWESNGQPENNYKTTPPVLDS

DGSFFLYSWLTVDKSRWQQGNVFSCSVMHEALHNHYTQKSLSLSPG

1602-VL-CL
                                        (SEQ ID NO: 288)
DIQMTQSPSSLSASVGDRVTITCHASQNINFWLSWYQQKPGKAPKLLIYE

ASNLHTGVPSRFSGSGSGTRFTLTISSLQPEDIATYYCQQSHSYPLTFGG

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
``` scFv-A49MI-VH-VL-Fc represents the full sequence of NKG2D binding scFv A49MI linked to an Fc domain via a hinge comprising Gly-Ser. The Fc domain linked to the scFv includes Q347R, D399V, and F405T substitutions for heterodimerization and an S354C substitution for forming a disulfide bond with a Y349C substitution in A49MI-VH-CH1-Fc as described below. The scFv includes a heavy chain variable domain of scFv-1295 connected to the N-terminus of a light chain variable domain of scFv-A49MI via a (G₄S)₄ linker. scFv-A49MI-VH-VL-Fc comprises substitution of Cys in the VH and VL regions at G44 and S100, facilitating formation of a disulfide bridge between the VH and VL of the scFv.

1602-VH-CH1-Fc represents the heavy chain portion of the Fab fragment, which comprises a heavy chain variable domain of CLEC12A-binding 1602 and a CH1 domain, connected to an Fc domain. The Fc domain in 1602-VH-CH1-Fc includes a Y349C substitution in the CH3 domain, which forms a disulfide bond with an S354C substitution on the Fc in scFv-A49MI-VH-VL-Fc. In 1602-VH-CH1-Fc, the Fc domain also includes K360E and K409W substitutions for heterodimerization with the Fc in scFv-A49MI-VH-VL-Fc.

1602-VL-CL represents the light chain portion of the Fab fragment comprising a light chain variable domain of CLEC12A-binding 1602 and a light chain constant domain.

In certain embodiments, a TriNKET of the present disclosure is identical to one of the exemplary TriNKETs described above that includes the EW-RVT Fc mutations, except that the Fc domain linked to the NKG2D-binding Fab fragment comprises the substitutions of Q347R, D399V, and F405T, and the Fc domain linked to the tumor-associated antigen binding scFv comprises matching substitutions K360E and K409W for forming a heterodimer. In certain embodiments, a TriNKET of the present disclosure is identical to one of the exemplary TriNKETs described above that includes the KiH Fc mutations, except that the Fc domain linked to the NKG2D-binding Fab fragment comprises the "hole" substitutions of T366S, L368A, and Y407V, and the Fc domain linked to the tumor-associated antigen-binding scFv comprises the "knob" substitution of T366W for forming a heterodimer.

In certain embodiments, a TriNKET of the present disclosure is identical to one of the exemplary TriNKETs described above, except that the Fc domain linked to the NKG2D-binding Fab fragment includes an S354C substitution in the CH3 domain, and the Fc domain linked to the tumor-associated antigen-binding scFv includes a matching Y349C substitution in the CH3 domain for forming a disulfide bond.

A skilled person in the art would appreciate that during production and/or storage of proteins, N-terminal glutamate (E) or glutamine (Q) can be cyclized to form a lactam (e.g., spontaneously or catalyzed by an enzyme present during production and/or storage). Accordingly, in some embodiments where the N-terminal residue of an amino acid sequence of a polypeptide is E or Q, a corresponding amino acid sequence with the E or Q replaced with pyroglutamate is also contemplated herein.

A skilled person in the art would also appreciate that during protein production and/or storage, the C-terminal lysine (K) of a protein can be removed (e.g., spontaneously or catalyzed by an enzyme present during production and/or storage). Such removal of K is often observed with proteins that comprise an Fc domain at its C-terminus. Accordingly, in some embodiments where the C-terminal residue of an amino acid sequence of a polypeptide (e.g., an Fc domain sequence) is K, a corresponding amino acid sequence with the K removed is also contemplated herein.

The multispecific proteins described above can be made using recombinant DNA technology well known to a skilled person in the art. For example, a first nucleic acid sequence encoding the first immunoglobulin heavy chain can be cloned into a first expression vector; a second nucleic acid sequence encoding the second immunoglobulin heavy chain can be cloned into a second expression vector; a third nucleic acid sequence encoding the immunoglobulin light chain can be cloned into a third expression vector; and the first, second, and third expression vectors can be stably transfected together into host cells to produce the multimeric proteins.

To achieve the highest yield of the multispecific protein, different ratios of the first, second, and third expression vector can be explored to determine the optimal ratio for transfection into the host cells. After transfection, single clones can be isolated for cell bank generation using methods known in the art, such as limited dilution, ELISA, FACS, microscopy, or Clonepix.

The present application also provides a nucleic acid encoding a polypeptide that is a part of a multispecific protein provided herein. In some embodiments, a multispecific protein comprises three polypeptides. In some embodiments, a multispecific protein comprises (a) a first polypeptide comprising the amino acid sequence of SEQ ID NO:276; (b) a second polypeptide comprising the amino acid sequence of SEQ ID NO:260; and (c) a third polypeptide comprising the amino acid sequence of SEQ ID NO:261. In certain embodiments, the present application provides a nucleic acid encoding each of the three polypeptides that are part of the multispecific protein. In certain embodiments, provided herein is a nucleic acid that encodes a first polypeptide comprising the amino acid sequence of SEQ ID NO:276. In certain embodiments, provided herein is a nucleic acid that encodes a second polypeptide comprising the amino acid sequence of SEQ ID NO:260. In certain embodiments, provided herein is a nucleic acid that encodes a third polypeptide comprising the amino acid sequence of SEQ ID NO:261.

In another aspect, the present application provides a cell comprising one or more nucleic acids encoding a polypeptide that is part of a multispecific protein provided herein. In some embodiments, a cell comprises one or more nucleic acids each encoding one or more of the three polypeptides that are part of the multispecific protein. In certain embodiments, provided herein is a cell comprising a nucleic acid that encodes a first polypeptide comprising the amino acid sequence of SEQ ID NO:276. In certain embodiments, provided herein is a cell comprising a nucleic acid that encodes a second polypeptide comprising the amino acid sequence of SEQ ID NO:260. In certain embodiments, provided herein is a cell comprising a nucleic acid that encodes a third polypeptide comprising the amino acid sequence of SEQ ID NO:261.

Also provided herein are methods of producing or making a multispecific protein provided herein. In some embodiments, the method comprises: (a) culturing a host cell under conditions suitable for expression of the protein, wherein the host cell comprises one or more nucleic acids each encoding one or more polypeptides that is part of the multispecific protein; and (b) isolating and purifying the protein. In some embodiments, the method comprises: (a) culturing a host cell under conditions suitable for expression of the protein, wherein the host cell comprises a first nucleic acid encoding a first polypeptide comprising the amino acid sequence of SEQ ID NO:276, a second nucleic acid encoding a second polypeptide comprising the amino acid sequence of SEQ ID NO:260, and a third nucleic acid encoding a third polypeptide comprising the amino acid sequence of SEQ ID NO:261; and (b) isolating and purifying the protein.

Clones can be cultured under conditions suitable for bio-reactor scale-up and maintained expression of the multispecific protein. The multispecific proteins can be isolated and purified using methods known in the art including centrifugation, depth filtration, cell lysis, homogenization, freeze-thawing, affinity purification, gel filtration, ion exchange chromatography, hydrophobic interaction exchange chromatography, and mixed-mode chromatography.

II. Characteristics of the Multispecific Proteins

The multispecific proteins described herein include an NKG2D-binding site, a tumor-associated antigen binding site that binds CLEC12A, and an antibody Fc domain or a portion thereof sufficient to bind CD16, or an antigen-binding site that binds CD16. In some embodiments, the multispecific proteins contains an additional antigen-binding site that binds to the same tumor-associated antigen (CLEC12A), as exemplified in the F4-TriNKET format (e.g., FIGS. 2C and 2D).

In some embodiments, the multispecific proteins display similar thermal stability to the corresponding monoclonal antibody, i.e., a monoclonal antibody containing the same tumor-associated antigen binding site as the one incorporated in the multispecific proteins.

In some embodiments, the multispecific proteins simultaneously bind to cells expressing NKG2D and/or CD16, such as NK cells, and cells expressing CLEC12A, such as certain tumor cells. Binding of the multispecific proteins to NK cells can enhance the activity of the NK cells toward destruction of the tumor-associated antigen expressing tumor cells. It has been reported that NK cells exhibit more potent cytotoxicity against target cells that are stressed (see Chan et al., (2014) Cell Death Differ. 21(1):5-14). Without wishing to be bound by theory, it is hypothesized that when NK cells are engaged to a population of cells by a TriNKET, the NK cells may selectively kill the target cells that are stressed (e.g., malignant cells and cells in a tumor microenvironment). This mechanism could contribute to increased specificity and reduced toxicity of TriNKETs, making it possible to selectively clear the stressed cells even if expression of the tumor-associated antigen is not limited to the desired target cells.

In some embodiments, the multispecific proteins induce antibody dependent cellular phagocytosis (ADCP). In some embodiments, the multispecific proteins induce antibody dependent cellular cytotoxicity (ADCC)-like activity. In some embodiments, the multispecific proteins induce ADCC activity. In some embodiments, the multispecific proteins do not induce complement dependent cytotoxicity (CDC).

In some embodiments, the multispecific proteins bind to the tumor-associated antigen with a similar affinity to the corresponding the anti-tumor-associated antigen monoclonal antibody (i.e., a monoclonal antibody containing the same tumor-associated antigen binding site as the one incorporated in the multispecific proteins). In some embodiments, the multispecific proteins are more effective in killing the tumor cells expressing the tumor-associated antigen than the corresponding monoclonal antibodies.

In certain embodiments, the multispecific proteins described herein, which include a binding site for a tumor-associated antigen, activate primary human NK cells when co-culturing with cells expressing that tumor-associated antigen. NK cell activation is marked by the increase in CD107a degranulation and IFN-γ cytokine production. Furthermore, compared to a corresponding anti-tumor-associated antigen monoclonal antibody, the multispecific proteins can show superior activation of human NK cells in the presence of cells expressing the tumor-associated antigen.

In some embodiments, the multispecific proteins described herein, which include a binding site for the tumor-associated antigen, enhance the activity of rested and IL-2-activated human NK cells when co-culturing with cells expressing the tumor-associated antigen.

In some embodiments, compared to the corresponding monoclonal antibody that binds to the tumor-associated antigen, the multispecific proteins offer an advantage in targeting tumor cells that express medium and low levels of the tumor-associated antigen.

In some embodiments, the bivalent F4 format of the TriNKETs (i.e., TriNKETs include an additional antigen-binding site that binds to the tumor-associated antigen) improve the avidity with which the TriNKETs bind to the tumor-associated antigen, which in effect stabilize expression and maintenance of high levels of the tumor-associated antigen on the surface of the tumor cells. In some embodiments, the F4-TriNKETs mediate more potent killing of tumor cells than the corresponding F3-TriNKETs or F3'-TriNKETs.

III. Pharmaceutical Formulations

The present disclosure also provides pharmaceutical formulations that contain a therapeutically effective amount of a multispecific binding protein disclosed herein (e.g., F3'-1602). The pharmaceutical formulation comprises one or more excipients and is maintained at a certain pH. The term "excipient," as used herein, means any non-therapeutic agent added to the formulation to provide a desired physical or chemical property, for example, pH, osmolarity, viscosity, clarity, color, isotonicity, odor, sterility, stability, rate of dissolution or release, adsorption, or penetration.

Excipients and pH

The one or more excipients in the pharmaceutical formulation of the multispecific binding proteins described in the present application comprises a buffering agent. The term "buffering agent," as used herein, refers to one or more components that when added to an aqueous solution is able to protect the solution against variations in pH when adding acid or alkali, or upon dilution with a solvent. In addition to phosphate buffers, glycinate, carbonate, citrate, histidine buffers and the like can be used, in which case, sodium, potassium or ammonium ions can serve as counterion.

In certain embodiments, the buffer or buffer system comprises at least one buffer that has a buffering range that overlaps fully or in part with the range of pH 7.0-9.0. In certain embodiments, the buffer has a pKa of about 7.0±0.5. In certain embodiments, the buffer has a pKa of about 7.5±0.5.

In certain embodiments, the buffer comprises a citrate buffer. In certain embodiments, the citrate is present at a concentration of 5 to 100 mM, 10 to 100 mM, 15 to 100 mM, 20 to 100 mM, 5 to 50 mM, 10 to 50 mM, 15 to 100 mM, 20 to 100 mM, 5 to 25 mM, 10 to 25 mM, 15 to 25 mM, 20 to 25 mM, 5 to 20 mM, 10 to 20 mM, or 15 to 20 mM. In certain embodiments, the citrate is present at a concentration of 5 mM, 10 mM, 15 mM, 20 mM, 25 mM, or 50 mM. In certain embodiments, the citrate is present at a concentration of 20 mM.

In certain embodiments, the buffer comprises or further comprise a phosphate buffer. In certain embodiments, the phosphate is present at a concentration of 5 to 100 mM, 10 to 100 mM, 15 to 100 mM, 20 to 100 mM, 5 to 50 mM, 10 to 50 mM, 15 to 100 mM, 20 to 100 mM, 5 to 25 mM, 10 to 25 mM, 15 to 25 mM, 20 to 25 mM, 5 to 20 mM, 10 to 20 mM, or 15 to 20 mM. In certain embodiments, the phosphate is present at a concentration of 5 mM, 10 mM, 15 mM, 20 mM, 25 mM, or 50 mM. In certain embodiments, the phosphate is present at a concentration of 10 mM. It is understood that phosphate is not readily compatible with a lyophilized presentation. Accordingly, in certain embodiments, the concentration of phosphate in the pharmaceutical formulation, if any, is equal to or lower than 5 mM, 4 mM, 3 mM, 2 mM, 1 mM, 0.5 mM, 0.1 mM, 50 μM, 10 μM, 5 μM, or 1 μM. In certain embodiments, the concentration of phosphate in the pharmaceutical formulation is below the detection limit. In certain embodiments, no phosphate is added when preparing the pharmaceutical formulation.

The pharmaceutical formulation of the multispecific binding proteins described in the present application may have a pH above 7.0. For example, in certain embodiments, the pharmaceutical formulation has a pH of 7.0 to 8.0 (i.e., 7.5±0.5), 7.0 to 7.8 (i.e., 7.4±0.4), 7.0 to 7.6 (i.e., 7.3±0.3), 7.0 to 7.4 (i.e., 7.2±0.2), 7.0 to 7.2 (i.e., 7.1±0.1), 7.1 to 7.3 (i.e., 7.2±0.1), 7.2 to 7.4 (i.e., 7.3±0.1), 7.3 to 7.5 (i.e., 7.4±0.1), 7.4 to 7.6 (i.e., 7.5±0.1), 7.5 to 7.7 (i.e., 7.6±0.1), 7.6 to 7.8 (i.e., 7.7±0.1), 7.7 to 7.9 (i.e., 7.8±0.1), or 7.8 to 8.0 (i.e., 7.9±0.1). In certain embodiments, the pharmaceutical formulation has a pH of 7.0, 7.1, 7.2, 7.3, 7.4, 7.5, 7.6, 7.7, 7.8, 7.9, or 8.0. In certain embodiments, the pharmaceutical formulation has a pH of 7.0. Under the rules of scientific rounding, a pH greater than or equal to 6.95 and smaller than or equal to 7.05 is rounded as 7.0.

The one or more excipients in the pharmaceutical formulation of the multispecific binding proteins described in the present application further comprises a sugar or sugar alcohol. Sugars and sugar alcohols are useful in pharmaceutical formulations as a thermal stabilizer. In certain embodiments, the pharmaceutical formulation comprises a sugar, for example, a monosaccharide (glucose, xylose, or erythritol), a disaccharide (e.g., sucrose, trehalose, maltose, or galactose), or an oligosaccharide (e.g., stachyose). In specific embodiments, the pharmaceutical formulation comprises sucrose. In certain embodiments, the pharmaceutical composition comprises a sugar alcohol, for example, a sugar alcohol derived from a monosaccharide (e.g., mannitol, sorbitol, or xylitol), a sugar alcohol derived from a disaccharide (e.g., lactitol or maltitol), or a sugar alcohol derived from an oligosaccharide. In specific embodiments, the pharmaceutical formulation comprises sorbitol.

The amount of the sugar or sugar alcohol contained within the formulation can vary depending on the specific circumstances and intended purposes for which the formulation is used. In certain embodiments, the pharmaceutical formulation comprises 50 to 300 mM, 50 to 250 mM, 100 to 300 mM, 100 to 250 mM, 150 to 300 mM, 150 to 250 mM, 200 to 300 mM, 200 to 250 mM, or 250 to 300 mM of the sugar or sugar alcohol. In certain embodiments, the pharmaceutical formulation comprises 50 mM, 75 mM, 100 mM, 125 mM, 150 mM, 200 mM, 250 mM, or 300 mM of the sugar or sugar alcohol. In specific embodiments, the pharmaceutical formulation comprises 250 mM of the sugar or sugar alcohol (e.g., sucrose or sorbitol).

The one or more excipients in the pharmaceutical formulation disclosed herein further comprises a surfactant. The term "surfactant," as used herein, refers to a surface active molecule containing both a hydrophobic portion (e.g., alkyl chain) and a hydrophilic portion (e.g., carboxyl and carboxylate groups). Surfactants are useful in pharmaceutical formulations for reducing aggregation of a therapeutic protein. Surfactants suitable for use in the pharmaceutical formulations are generally non-ionic surfactants and include, but are not limited to, polysorbates (e.g. polysorbates 20 or 80); poloxamers (e.g. poloxamer 188); sorbitan esters and derivatives; Triton; sodium laurel sulfate; sodium octyl glycoside; lauryl-, myristyl-, linoleyl-, or stearyl-sulfobetadine; lauryl-, myristyl-, linoleyl- or stearyl-sarcosine; linoleyl-, myristyl-, or cetyl-betaine; lauramidopropyl-cocamidopropyl-, linoleamidopropyl-, myristamidopropyl-, palmidopropyl-, or isostearamidopropylbetaine (e.g., lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), polyethylene glycol, polypropyl glycol, and copolymers of ethylene and propylene glycol (e.g., Pluronics, PF68 etc.). In certain embodiments, the surfactant is a polysorbate. In certain embodiments, the surfactant is polysorbate 80.

The amount of a non-ionic surfactant contained within the pharmaceutical formulation of the multispecific binding proteins described in the present application may vary depending on the specific properties desired of the formulation, as well as the particular circumstances and purposes for which the formulations are intended to be used. In certain embodiments, the pharmaceutical formulation comprises 0.005% to 0.5%, 0.005% to 0.2%, 0.005% to 0.1%, 0.005% to 0.05%, 0.005% to 0.02%, 0.005% to 0.01%, 0.01% to 0.5%, 0.01% to 0.2%, 0.01% to 0.1%, 0.01% to 0.05%, or 0.01% to 0.02% of the non-ionic surfactant (e.g., polysorbate 80). In certain embodiments, the pharmaceutical formulation comprises 0.005%, 0.01%, 0.02%, 0.03%, 0.04%, 0.05%, 0.06%, 0.07%, 0.08%, 0.09%, 0.1%, 0.15%, 0.2%, 0.25%, 0.3%, 0.35%, 0.4%, 0.45%, or 0.5% of the non-ionic surfactant (e.g., polysorbate 80).

In certain embodiments, the pharmaceutical formulation is isotonic. An "isotonic" formulation is one which has essentially the same osmotic pressure as human blood. Isotonic formulations generally have an osmotic pressure from about 250 to 350 mOsmol/kgH$_2$O. Isotonicity can be measured using a vapor pressure or ice-freezing type osmometer. In certain embodiments, the osmolarity of the pharmaceutical formulation is 250 to 350 mOsmol/kgH$_2$O. In certain embodiments, the osmolarity of the pharmaceutical formulation is 300 to 350 mOsmol/kgH$_2$O.

Substances such as sugar, sugar alcohol, and NaCl can be included in the pharmaceutical formulation for desired osmolarity. It is understood that NaCl is not readily compatible with a lyophilized presentation. Accordingly, in certain embodiments, the concentration of NaCl in the pharmaceutical formulation, if any, is equal to or lower than 10 mM, 9 mM, 8 mM, 7 mM, 6 mM, 5 mM, 4 mM, 3 mM, 2 mM, 1 mM, 0.5 mM, 0.1 mM, 50 µM, 10 µM, 5 µM, or 1 µM. In certain embodiments, the concentration of NaCl in the pharmaceutical formulation is below the detection limit. In certain embodiments, no NaCl salt is added when preparing the pharmaceutical formulation.

The pharmaceutical formulation of the multispecific binding proteins described in the present application may further comprise one or more other substances, such as a bulking agent or a preservative. A "bulking agent" is a compound which adds mass to a lyophilized mixture and contributes to the physical structure of the lyophilized cake (e.g., facilitates the production of an essentially uniform lyophilized cake which maintains an open pore structure). Illustrative bulking agents include mannitol, glycine, polyethylene glycol and sorbitol. The lyophilized formulations of the multispecific binding proteins described in the present application may contain such bulking agents. A preservative reduces bacterial action and may, for example, facilitate the production of a multi-use (multiple-dose) formulation.

Exemplary Formulations

In certain embodiments, the pharmaceutical formulation of the multispecific binding proteins described in the present application comprises the multispecific binding protein in a buffer at pH 7.0 or higher (e.g., at pH 7.0 to 8.0).

In certain embodiments, the pharmaceutical formulation comprises 10 to 200 mg/mL of the multispecific binding protein, 10 to 25 mM of citrate, 200 to 300 mM of a sugar or sugar alcohol (e.g., sucrose), and 0.005% to 0.05% of a polysorbate (e.g., polysorbate 80), at pH 7.0 to 8.0. In certain embodiments, the pharmaceutical formulation comprises 10 to 200 mg/mL of the multispecific binding protein, 20 mM of citrate, 250 mM of a sugar or sugar alcohol (e.g., sucrose), and 0.01% of a polysorbate (e.g., polysorbate 80), at pH 7.0 to 8.0. In certain embodiments, the pharmaceutical formulation comprises 10 to 200 mg/mL of the multispecific binding protein, 20 mM of citrate, 250 mM of a sugar or sugar alcohol (e.g., sucrose), and 0.01% of a polysorbate (e.g., polysorbate 80), at pH 7.0 to 7.5 (e.g., pH 7.0).

In certain embodiments, the pharmaceutical formulation comprises 10 to 50 mg/mL of the multispecific binding protein, 10 to 25 mM of citrate, 200 to 300 mM of a sugar or sugar alcohol (e.g., sucrose), and 0.005% to 0.05% of a polysorbate (e.g., polysorbate 80), at pH 7.0 to 8.0. In certain embodiments, the pharmaceutical formulation comprises 10 to 50 mg/mL of the multispecific binding protein, 20 mM of citrate, 250 mM of a sugar or sugar alcohol (e.g., sucrose), and 0.01% of a polysorbate (e.g., polysorbate 80), at pH 7.0 to 8.0. In certain embodiments, the pharmaceutical formulation comprises 10 to 50 mg/mL of the multispecific binding protein, 20 mM of citrate, 250 mM of a sugar or sugar alcohol (e.g., sucrose), and 0.01% of a polysorbate (e.g., polysorbate 80), at pH 7.0 to 7.5 (e.g., pH 7.0).

In certain embodiments, the pharmaceutical formulation comprises 10 to 200 mg/mL of the multispecific binding protein, 5 to 20 mM of citrate, 5 to 20 mM of phosphate, and 100 to 150 mM of NaCl, at pH 7.0 to 8.0. In certain embodiments, the pharmaceutical formulation comprises 10 to 200 mg/mL of the multispecific binding protein, 10 mM of citrate, 10 mM of phosphate, and 125 mM of NaCl, at pH 7.0 to 8.0. In certain embodiments, the pharmaceutical formulation comprises 10 to 200 mg/mL of the multispecific binding protein, 10 mM of citrate, 10 mM of phosphate, and 125 mM of NaCl, at pH 7.5 to 8.0 (e.g., pH 7.8).

In certain embodiments, the pharmaceutical formulation comprises 10 to 50 mg/mL of the multispecific binding protein, 5 to 20 mM of citrate, 5 to 20 mM of phosphate, and 100 to 150 mM of NaCl, at pH 7.0 to 8.0. In certain embodiments, the pharmaceutical formulation comprises 10 to 50 mg/mL of the multispecific binding protein, 10 mM of citrate, 10 mM of phosphate, and 125 mM of NaCl, at pH 7.0 to 8.0. In certain embodiments, the pharmaceutical formulation comprises 10 to 50 mg/mL of the multispecific binding protein, 10 mM of citrate, 10 mM of phosphate, and 125 mM of NaCl, at pH 7.5 to 8.0 (e.g., pH 7.8).

Stability of the Multispecific Binding Protein

The pharmaceutical formulations of the multispecific binding proteins described in the present application exhibit high levels of stability. A pharmaceutical formulation is stable when the multispecific binding protein within the formulation retains an acceptable degree of physical property, chemical structure, and/or biological function after storage under defined conditions.

Stresses during manufacture, storage, and use of the pharmaceutical formulation include but are not limited to heat stress (e.g., incubation at 40° C. for 4 weeks), freeze/thaw stress (e.g., after 6 freeze/thaw cycles), agitation stress (e.g., stirring at 60 rpm at 4° C. for 18 hours), low pH stress (e.g., incubation at pH 5.0 at 40° C. for 2 weeks), high pH stress (e.g., incubation at pH 8.0 at 40° C. for 2 weeks), oxidative stress (e.g., forced oxidation in 0.02% hydrogen peroxide at room temperature for 24 hours), or low pH hold (e.g., incubation at pH 3.3 at room temperature for 1.5 hours). In certain embodiments, the multispecific binding protein is stable after exposure to one or more of these stresses.

Stability can be measured by determining the percentage of the multispecific binding protein in the formulation that remains in a native conformation after storage for a defined amount of time at a defined temperature. The percentage of a protein in a native conformation can be determined by, for example, size exclusion chromatography (e.g., size exclusion high performance liquid chromatography), where a protein in the native conformation is not aggregated (eluted in a high molecular weight fraction) or degraded (eluted in a low molecular weight fraction). In certain embodiments, less than 0.5%, 0.6%, 0.7%, 0.8%, 0.9%, or 1% of the multispecific binding protein forms a high molecular weight complex (i.e., having a higher molecular weight than the native protein), as determined by size-exclusion chromatography, after one or more of the stresses disclosed herein. In certain embodiments, less than 0.5%, 0.6%, 0.7%, 0.8%, 0.9%, or 1% of the multispecific binding protein is degraded (i.e., having a lower molecular weight than the native protein), as determined by size-exclusion chromatography, after one or more of the stresses disclosed herein.

Stability can also be measured by determining the percentage of multispecific binding protein present in a more acidic fraction ("acidic form") relative to the main fraction of protein ("main charge form"). Though not wishing to be bound by theory, deamidation of a protein may cause it to become more negatively charged and thus more acidic relative to the non-deamidated protein (see, e.g., Robinson, Protein Deamidation, (2002) PNAS 99(8):5283-88). The percentage of the acidic form of a protein can be determined by ion exchange chromatography (e.g., cation exchange high performance liquid chromatography) or imaged capillary isoelectric focusing (icIEF). In certain embodiments, at least 30%, 40%, 50%, 60%, 70%, 80%, or 90% of the multispecific binding protein in the pharmaceutical formulation is in the main charge form, after one or more of the stresses disclosed herein. In certain embodiments, no more than 10%, 20%, 30%, 40%, or 50% of the multispecific binding protein in the pharmaceutical formulation is in an acidic form, after one or more of the stresses disclosed herein.

Stability can also be measured by determining the purity of the multispecific binding protein by electrophoresis after denaturing the protein with sodium dodecyl sulfate (SDS). The protein sample can be denatured in the presence or absence of an agent that reduces protein disulfide bonds (e.g., β-mercaptoethanol). In certain embodiments, the purity of the multispecific binding protein in the pharmaceutical formulation, as measured by capillary electrophoresis after denaturing the protein sample under reducing conditions (e.g., in the presence of β-mercaptoethanol), is at least 95%, 96%, 97%, 98%, or 99%, after one or more of the stresses disclosed herein. In certain embodiments, the purity of the multispecific binding protein in the pharmaceutical formulation, as measured by capillary electrophoresis after denaturing the protein sample under reducing conditions (e.g., in the presence of β-mercaptoethanol), is at least 90%, 91%, 92%, 93%, 94%, 95%, 96%, 97%, 98%, or 99%, after one or more of the stresses disclosed herein. In certain embodiments, the purity of the multispecific binding protein in the pharmaceutical formulation, as measured by capillary electrophoresis after denaturing the protein sample under non-reducing conditions, is at least 95%, 96%, 97%, 98%, or 99%, after one or more of the stresses disclosed herein. In certain embodiments, the purity of the multispecific binding protein in the pharmaceutical formulation, as measured by capillary electrophoresis after denaturing the protein sample under non-reducing conditions, is at least 85%, 86%, 87%, 88%, 89%, 90%, 91%, 92%, 93%, 94%, 95%, 96%, 97%, 98%, or 99%, after one or more of the stresses disclosed herein.

Stability can also be measured by determining the parameters of a protein solution by dynamic light scattering. The Z-average and polydispersity index (PDI) values indicate the average diameter of particles in a solution and these measures increase when aggregates are present in the solution. The monomer % Pd value indicates the spread of different monomers detected, where lower values indicate a monodispere solution, which is preferred. The monomer size detected by DLS is useful in confirming that the main population is monomer and to characterize any higher order aggregates that may be present. In certain embodiments, the Z-average value of the pharmaceutical formulation does not increase by more than 5%, 10%, or 15%, after one or more of the stresses disclosed herein. In certain embodiments, the PDI value of the pharmaceutical formulation does not increase by more than 10%, 20%, 30%, 40%, or 50%, after one or more of the stresses disclosed herein.

In addition to the assessment of the parameters above, stability can also be measured by determining the protein's functional characters. The multispecific binding proteins disclosed herein bind CLEC12A, NKG2D, and CD16. According, in certain embodiments, the binding affinity of the multispecific binding protein to CLEC12A (e.g., human CLEC12A) after one or more of the stresses disclosed herein, as measured by dissociation constant ($K_D$) or maximal binding response (capture level), is not lower than that in the control sample (not exposed to the stress) by more than 1%, 2%, 3%, 4%, 5%, 10%, 20%, or 30%. In certain embodiments, the binding affinity of the multispecific binding protein to NKG2D (e.g., human NKG2D) after one or more of the stresses disclosed herein, as measured by dissociation constant ($K_D$) or maximal binding response (capture level), is not lower than that in the control sample (not exposed to the stress) by more than 1%, 2%, 3%, 4%, 5%, 10%, 20%, or 30%. In certain embodiments, the binding affinity of the multispecific binding protein to CD16 (e.g., human CD16a V158) after one or more of the stresses disclosed herein, as measured by dissociation constant ($K_D$) or maximal binding response (capture level), is not lower than that in the control sample (not exposed to the stress) by more than 1%, 2%, 3%, 4%, 5%, 10%, 20%, or 30%.

The multispecific binding protein disclosed herein has the ability to mediate cytotoxicity against a CLEC12A-expressing tumor cell by an NK cell. In certain embodiments, the ability of the multispecific binding protein to mediate such cytotoxicity after one or more of the stresses disclosed herein, as measured by EC50 of the multispecific binding protein in a mixed culture cytotoxicity assay, is not greater than that in the control sample (not exposed to the stress) by more than 1%, 2%, 3%, 4%, 5%, 10%, 20%, or 30%. In certain embodiments, the ability of the multispecific binding protein to mediate such cytotoxicity after one or more of the stresses disclosed herein, as measured by the maximum lysis of the target cells in a mixed culture cytotoxicity assay, is not greater than that in the control sample (not exposed to the stress) by more than 1%, 2%, 3%, 4%, 5%, 10%, 20%, or 30%.

Exemplary methods to determine stability of the multispecific binding protein in the pharmaceutical formulation are described in Examples 13 and 14 of the present disclosure. Additionally, stability of the protein can be assessed by measuring the binding affinity of the multispecific binding protein to its targets or the biological activity of the multispecific binding protein in certain in vitro assays, such as the NK cell activation assays and cytotoxicity assays described in WO 2018/152518.

Dosage Forms

The pharmaceutical formulation can be prepared and stored as a liquid formulation or a lyophilized form. In certain embodiments, the pharmaceutical formulation is a liquid formulation for storage at 2-8° C. (e.g., 4° C.) or a frozen formulation for storage at −20° C. or lower. The sugar or sugar alcohol in the formulation is used as a lyoprotectant.

Prior to pharmaceutical use, the pharmaceutical formulation can be diluted or reconstituted in an aqueous carrier is suitable for the route of administration. Other exemplary carriers include sterile water for injection (SWFI), bacteriostatic water for injection (BWFI), a pH buffered solution (e.g., phosphate-buffered saline), sterile saline solution, Ringer's solution, or dextrose solution. For example, when the pharmaceutical formulation is prepared for intravenous administration, the pharmaceutical formulation can be diluted in a 0.9% sodium chloride (NaCl) solution. In certain embodiments, the diluted pharmaceutical formulation is isotonic and suitable for administration by intravenous infusion.

The pharmaceutical formulation comprises the multispecific binding protein at a concentration suitable for storage. In certain embodiments, the pharmaceutical formulation comprises the multispecific binding protein at a concentration of 10-200 mg/mL, 10-150 mg/mL, 10-100 mg/mL, 10-50 mg/mL, 10-40 mg/mL, 10-30 mg/mL, 10-25 mg/mL, 10-20 mg/mL, 10-15 mg/mL, 20-200 mg/mL, 20-150 mg/mL, 20-100 mg/mL, 20-50 mg/mL, 20-40 mg/mL, 20-30 mg/mL, 20-25 mg/mL, 50-200 mg/mL, 50-150 mg/mL, 50-100 mg/mL, 100-200 mg/mL, 100-150 mg/mL, or 150-200 mg/mL. In certain embodiments, the pharmaceutical formulation comprises the multispecific binding protein at a concentration of 10 mg/mL, 15 mg/mL, 20 mg/mL, 25 mg/mL, 30 mg/mL, 40 mg/mL, 50 mg/mL, 60 mg/mL, 70 mg/mL, 80 mg/mL, 90 mg/mL, 100 mg/mL, 150 mg/mL, or 200 mg/mL.

In certain embodiments, the pharmaceutical formulation is packaged in a container (e.g., a vial, bag, pen, or syringe). In certain embodiments, the formulation may be a lyophilized formulation or a liquid formulation. In certain embodiments, the amount of multispecific binding protein in the container is suitable for administration as a single dose. In certain embodiments, the amount of multispecific binding protein in the container is suitable for administration in multiple doses. In certain embodiments, the pharmaceutical formulation comprises the multispecific binding protein at an amount of 0.1 to 2000 mg. In certain embodiments, the pharmaceutical formulation comprises the multispecific binding protein at an amount of 1 to 2000 mg, 10 to 2000 mg, 20 to 2000 mg, 50 to 2000 mg, 100 to 2000 mg, 200 to 2000 mg, 500 to 2000 mg, 1000 to 2000 mg, 0.1 to 1000 mg, 1 to 1000 mg, 10 to 1000 mg, 20 to 1000 mg, 50 to 1000 mg, 100 to 1000 mg, 200 to 1000 mg, 500 to 1000 mg, 0.1 to 500 mg, 1 to 500 mg, 10 to 500 mg, 20 to 500 mg, 50 to 500 mg, 100 to 500 mg, 200 to 500 mg, 0.1 to 200 mg, 1 to 200 mg, 10 to 200 mg, 20 to 200 mg, 50 to 200 mg, 100 to 200 mg, 0.1 to 100 mg, 1 to 100 mg, 10 to 100 mg, 20 to 100 mg, 50 to 100 mg, 0.1 to 50 mg, 1 to 50 mg, 10 to 50 mg, 20 to 50 mg, 0.1 to 20 mg, 1 to 20 mg, 10 to 20 mg, 0.1 to 10 mg, 1 to 10 mg, or 0.1 to 1 mg. In certain embodiments, the pharmaceutical formulation comprises the multispecific binding protein at an amount of 0.1 mg, 1 mg, 2 mg, 5 mg, 10 mg, 20 mg, 30 mg, 40 mg, 50 mg, 60 mg, 70 mg, 80 mg, 90 mg, 100 mg, 150 mg, 200 mg, 250 mg, 300 mg, 400 mg, 500 mg, 600 mg, 700 mg, 800 mg, 900 mg, 1000 mg, 1500 mg, or 2000 mg.

IV. Therapeutic Applications

The present application provides methods for treating autoimmune disease or cancer using a multispecific binding protein described herein and/or a pharmaceutical composition (e.g., pharmaceutical formulation) described herein. The methods may be used to treat a variety of cancers expressing CLEC12A.

The therapeutic method can be characterized according to the cancer to be treated. The cancer to be treated can be characterized according to the presence of a particular antigen expressed on the surface of the cancer cell.

Cancers characterized by the expression of CLEC12A, include, without limitation, solid tumor indications such as gastric cancer, esophageal cancer, lung cancer, triple-negative breast cancer, colorectal cancer, and head and neck cancer.

It is contemplated that the protein, conjugate, cells, and/or pharmaceutical compositions of the present disclosure can be used to treat a variety of cancers, not limited to cancers in which the cancer cells or the cells in the cancer microenvironment express CLEC12A.

The therapeutic method can be characterized according to the cancer to be treated. For example, in certain embodiments, the cancer is acute myeloid leukemia, multiple myeloma, diffuse large B cell lymphoma, thymoma, adenoid cystic carcinoma, gastrointestinal cancer, renal cancer, breast cancer, glioblastoma, lung cancer, ovarian cancer, brain cancer, prostate cancer, pancreatic cancer, or melanoma. In some embodiments, the cancer is a hematologic malignancy or leukemia. In certain embodiments, the cancer is acute myeloid leukemia (AML), acute lymphoblastic leukemia (ALL), myelodysplasia, myelodysplastic syndromes, acute T-lymphoblastic leukemia, or acute promyelocytic leukemia, chronic myelomonocytic leukemia, or myeloid blast crisis of chronic myeloid leukemia.

In certain embodiments, the AML is a minimal residual disease (MRD). In certain embodiments, the MRD is characterized by the presence or absence of a mutation selected from CLEC12A-ITD ((Fms-like tyrosine kinase 3)-internal tandem duplications (ITD)), NPM1 (Nucleophosmin 1), DNMT3A (DNA methyltransferase gene DNMT3A), and IDH (Isocitrate dehydrogenase 1 and 2 (IDH1 and IDH2)). In certain embodiments, the MDS is selected from MDS with multilineage dysplasia (MDS-MLD), MDS with single lineage dysplasia (MDS-SLD), MDS with ring sideroblasts (MDS-RS), MDS with excess blasts (MDS-EB), MDS with isolated del(5q), and MDS, unclassified (MDS-U). In certain embodiments, the MDS is a primary MDS or a secondary MDS.

In certain embodiments, the ALL is selected from B-cell acute lymphoblastic leukemia (B-ALL) and T-cell acute lymphoblastic leukemia (T-ALL). In certain embodiments, the MPN is selected from polycythaemia vera, essential thrombocythemia (ET), and myelofibrosis. In certain embodiments, the non-Hodgkin lymphoma is selected from B-cell lymphoma and T-cell lymphoma. In certain embodiments, the lymphoma is selected from chronic lymphocytic leukemia (CLL), lymphoblastic lymphoma (LPL), diffuse large B-cell lymphoma (DLBCL), Burkitt lymphoma (BL), primary mediastinal large B-cell lymphoma (PMBL), follicular lymphoma, mantle cell lymphoma, hairy cell leukemia, plasma cell myeloma (PCM) or multiple myeloma (MM), mature T/NK neoplasms, and histiocytic neoplasms.

In certain embodiments, the cancer is a solid tumor. In certain other embodiments, the cancer is brain cancer, bladder cancer, breast cancer, cervical cancer, colon cancer, colorectal cancer, endometrial cancer, esophageal cancer, leukemia, lung cancer, liver cancer, melanoma, ovarian cancer, pancreatic cancer, prostate cancer, rectal cancer, renal cancer, stomach cancer, testicular cancer, or uterine cancer. In yet other embodiments, the cancer is a vascularized tumor, squamous cell carcinoma, adenocarcinoma, small cell carcinoma, melanoma, glioma, neuroblastoma, sarcoma (e.g., an angiosarcoma or chondrosarcoma), larynx cancer, parotid cancer, biliary tract cancer, thyroid cancer, acral lentiginous melanoma, actinic keratoses, acute lymphocytic leukemia, acute myeloid leukemia, adenoid cystic carcinoma, adenomas, adenosarcoma, adenosquamous carcinoma, anal canal cancer, anal cancer, anorectum cancer, astrocytic tumor, Bartholin gland carcinoma, basal cell carcinoma, biliary cancer, bone cancer, bone marrow cancer, bronchial cancer, bronchial gland carcinoma, carcinoid, cholangiocarcinoma, chondrosarcoma, choroid plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangioblastomas, hemangioendothelioma, hemangiomas, hepatic adenoma, hepatic adenomatosis, hepatobiliary cancer, hepatocellular carcinoma, Hodgkin's disease, ileum cancer, insulinoma, intraepithelial neoplasia, intraepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanomas, lymphoma, male genital cancer, malignant melanoma, malignant mesothelial tumors, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma nodular melanoma, non-epithelial skin cancer, non-Hodgkin's lymphoma, oat cell carcinoma, oligodendroglial cancer, oral cavity cancer, osteosarcoma, papillary serous adenocarcinoma, penile cancer, pharynx cancer, pituitary tumors, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T cell leukemia, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, VIPoma, vulva cancer, well differentiated carcinoma, or Wilms tumor.

In certain other embodiments, the cancer is non-Hodgkin's lymphoma, such as a B-cell lymphoma or a T-cell lymphoma. In certain embodiments, the non-Hodgkin's lymphoma is a B-cell lymphoma, such as a diffuse large B-cell lymphoma, primary mediastinal B-cell lymphoma, follicular lymphoma, small lymphocytic lymphoma, mantle cell lymphoma, marginal zone B-cell lymphoma, extranodal marginal zone B-cell lymphoma, nodal marginal zone B-cell lymphoma, splenic marginal zone B-cell lymphoma, Burkitt lymphoma, lymphoplasmacytic lymphoma, hairy cell leukemia, or primary central nervous system (CNS) lymphoma. In certain other embodiments, the non-Hodgkin's lymphoma is a T-cell lymphoma, such as a precursor T-lymphoblastic lymphoma, peripheral T-cell lymphoma, cutaneous T-cell lymphoma, angioimmunoblastic T-cell lymphoma, extranodal natural killer/T-cell lymphoma, enteropathy type T-cell lymphoma, subcutaneous panniculitis-like T-cell lymphoma, anaplastic large cell lymphoma, or peripheral T-cell lymphoma.

IV. Combination Therapy

Another aspect of the present application provides for combination therapy. A multispecific binding protein described herein can be used in combination with additional therapeutic agents to treat autoimmune disease or to treat cancer.

Exemplary therapeutic agents that may be used as part of a combination therapy in treating autoimmune inflammatory diseases are described in Li et al. (2017) Front. Pharmacol., 8:460, and include, for example, non-steroidal anti-inflammatory drugs (NSAIDs) (e.g., COX-2 inhibitors), glucocorticoids (e.g., prednisone/prednisolone, methylprednisolone, and the fluorinated glucocorticoids such as dexamethasone and betamethasone), disease-modifying antirheumatic drugs (DMARDs) (e.g., methotrexate, leflunomide, gold compounds, sulfasalazine, azathioprine, cyclophosphamide, antimalarials, D-penicillamine, and cyclosporine), anti-TNF biologics (e.g., infliximab, etanercept, adalimumab, golimumab, Certolizumab pegol, and their biosimilars), and other biologics targeting CTLA-4 (e.g., abatacept), IL-6 receptor (e.g., tocilizumab), IL-1 (e.g., anakinra), Th1 immune responses (IL-12/IL-23) (e.g., ustekinumab), Th17 immune responses (IL-17) (e.g., secukinumab) and CD20 (e.g., rituximab).

Exemplary therapeutic agents that may be used as part of a combination therapy in treating cancer include, for example, radiation, mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma (IFN-γ), colony stimulating factor-1, colony stimulating factor-2, denileukin diftitox, interleukin-2, luteinizing hormone releasing factor and variations of the aforementioned agents that may exhibit differential binding to its cognate receptor, or increased or decreased serum half-life.

An additional class of agents that may be used as part of a combination therapy in treating cancer is immune checkpoint inhibitors. Exemplary immune checkpoint inhibitors include agents that inhibit one or more of (i) cytotoxic T lymphocyte-associated antigen 4 (CTLA4), (ii) programmed cell death protein 1 (PD1), (iii) PDL1, (iv) LAG3, (v) B7-H3, (vi) B7-H4, and (vii) TIM3. The CTLA4 inhibitor ipilimumab has been approved by the United States Food and Drug Administration for treating melanoma.

Yet other agents that may be used as part of a combination therapy in treating cancer are monoclonal antibody agents that target non-checkpoint targets (e.g., herceptin) and non-cytotoxic agents (e.g., tyrosine-kinase inhibitors).

Yet other categories of anti-cancer agents include, for example: (i) an inhibitor selected from an ALK Inhibitor, an ATR Inhibitor, an A2A Antagonist, a Base Excision Repair Inhibitor, a Bcr-Abl Tyrosine Kinase Inhibitor, a Bruton's Tyrosine Kinase Inhibitor, a CDC7 Inhibitor, a CHK1 Inhibitor, a Cyclin-Dependent Kinase Inhibitor, a DNA-PK Inhibitor, an Inhibitor of both DNA-PK and mTOR, a DNMT1 Inhibitor, a DNMT1 Inhibitor plus 2-chloro-deoxyadenosine, an HDAC Inhibitor, a Hedgehog Signaling Pathway Inhibitor, an IDO Inhibitor, a JAK Inhibitor, a mTOR Inhibitor, a MEK Inhibitor, a MELK Inhibitor, a MTH1 Inhibitor, a PARP Inhibitor, a Phosphoinositide 3-Kinase Inhibitor, an Inhibitor of both PARP1 and DHODH, a Proteasome Inhibitor, a Topoisomerase-II Inhibitor, a Tyrosine Kinase Inhibitor, a VEGFR Inhibitor, and a WEE1 Inhibitor; (ii) an agonist of OX40, CD137, CD40, GITR, CD27, HVEM, TNFRSF25, or ICOS; and (iii) a cytokine selected from IL-12, IL-15, GM-CSF, and G-CSF.

Proteins of the present application can also be used as an adjunct to surgical removal of the primary lesion.

The amount of multispecific binding protein and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a multispecific binding protein may be administered during a time when the additional therapeutic agent(s) exerts its prophylactic or therapeutic effect, or vice versa.

V. Pharmaceutical Compositions

The present disclosure also features pharmaceutical compositions that contain a therapeutically effective amount of a protein described herein. The composition can be formulated for use in a variety of drug delivery systems. One or more physiologically acceptable excipients or carriers can also be included in the composition for proper formulation. Suitable formulations for use in the present disclosure are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990).

The intravenous drug delivery formulation of the present disclosure may be contained in a bag, a pen, or a syringe. In certain embodiments, the bag may be connected to a channel comprising a tube and/or a needle. In certain embodiments, the formulation may be a lyophilized formulation or a liquid formulation. In certain embodiments, the formulation may be freeze-dried (lyophilized) and contained in about 12-60 vials. In certain embodiments, the formulation may be freeze-dried and 45 mg of the freeze-dried formulation may be contained in one vial. In certain embodiments, the about 40 mg to about 100 mg of freeze-dried formulation may be contained in one vial. In certain embodiments, freeze-dried formulation from 12, 27, or 45 vials are combined to obtain a therapeutic dose of the protein in the intravenous drug formulation. In certain embodiments, the formulation may be a liquid formulation and stored as about 250 mg/vial to about 1000 mg/vial. In certain embodiments, the formulation may be a liquid formulation and stored as about 600 mg/vial. In certain embodiments, the formulation may be a liquid formulation and stored as about 250 mg/vial.

The protein could exist in a liquid aqueous pharmaceutical formulation including a therapeutically effective amount of the protein in a buffered solution forming a formulation.

These compositions may be sterilized by conventional sterilization techniques, or may be sterile filtered. The resulting aqueous solutions may be packaged for use as-is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents. The composition in solid form can also be packaged in a container for a flexible quantity.

In certain embodiments, the present disclosure provides a formulation with an extended shelf life including a protein of the present disclosure, in combination with mannitol, citric acid monohydrate, sodium citrate, disodium phosphate dihydrate, sodium dihydrogen phosphate dihydrate, sodium chloride, polysorbate 80, water, and sodium hydroxide.

In certain embodiments, an aqueous formulation is prepared including a protein of the present disclosure in a pH-buffered solution. The buffer may have a pH ranging from about 4 to about 8, e.g., from about 4.5 to about 6.0, or from about 4.8 to about 5.5, or may have a pH of about 5.0 to about 5.2. Ranges intermediate to the above recited pH's are also intended to be part of this disclosure. For example, ranges of values using a combination of any of the above recited values as upper and/or lower limits are intended to be included. Examples of buffers that will control the pH within this range include acetate (e.g., sodium acetate), succinate (such as sodium succinate), gluconate, histidine, citrate and other organic acid buffers.

In certain embodiments, the formulation includes a buffer system which contains citrate and phosphate to maintain the pH in a range of about 4 to about 8. In certain embodiments the pH range may be from about 4.5 to about 6.0, or from about pH 4.8 to about 5.5, or in a pH range of about 5.0 to about 5.2. In certain embodiments, the buffer system includes citric acid monohydrate, sodium citrate, disodium phosphate dihydrate, and/or sodium dihydrogen phosphate dihydrate. In certain embodiments, the buffer system includes about 1.3 mg/mL of citric acid (e.g., 1.305 mg/mL), about 0.3 mg/mL of sodium citrate (e.g., 0.305 mg/mL), about 1.5 mg/mL of disodium phosphate dihydrate (e.g., 1.53 mg/mL), about 0.9 mg/mL of sodium dihydrogen phosphate dihydrate (e.g., 0.86 mg/mL), and about 6.2 mg/mL of sodium chloride (e.g., 6.165 mg/mL). In certain embodiments, the buffer system includes about 1 to about 1.5 mg/mL of citric acid, about 0.25 to about 0.5 mg/mL of sodium citrate, about 1.25 to about 1.75 mg/mL of disodium phosphate dihydrate, about 0.7 to about 1.1 mg/mL of sodium dihydrogen phosphate dihydrate, and about 6.0 to about 6.4 mg/mL of sodium chloride. In certain embodiments, the pH of the formulation is adjusted with sodium hydroxide.

A polyol, which acts as a tonicifier and may stabilize the antibody, may also be included in the formulation. The polyol is added to the formulation in an amount which may vary with respect to the desired isotonicity of the formulation. In certain embodiments, the aqueous formulation may be isotonic. The amount of polyol added may also be altered with respect to the molecular weight of the polyol. For example, a lower amount of a monosaccharide (e.g., mannitol) may be added, compared to a disaccharide (such as trehalose). In certain embodiments, the polyol which may be used in the formulation as a tonicity agent is mannitol. In certain embodiments, the mannitol concentration may be about 5 to about 20 mg/mL. In certain embodiments, the concentration of mannitol may be about 7.5 to about 15 mg/mL. In certain embodiments, the concentration of mannitol may be about 10 to about 14 mg/mL. In certain embodiments, the concentration of mannitol may be about 12 mg/mL. In certain embodiments, the polyol sorbitol may be included in the formulation.

A detergent or surfactant may also be added to the formulation. Exemplary detergents include nonionic detergents such as polysorbates (e.g., polysorbates 20, 80 etc.) or poloxamers (e.g., poloxamer 188). The amount of detergent added is such that it reduces aggregation of the formulated antibody and/or minimizes the formation of particulates in the formulation and/or reduces adsorption. In certain embodiments, the formulation may include a surfactant which is a polysorbate. In certain embodiments, the formulation may contain the detergent polysorbate 80 or Tween 80. Tween 80 is a term used to describe polyoxyethylene (20) sorbitanmonooleate (see Fiedler, Lexikon der Hifsstoffe, Editio Cantor Verlag Aulendorf, 4th ed., 1996). In certain embodiments, the formulation may contain between about 0.1 mg/mL and about 10 mg/mL of polysorbate 80, or between about 0.5 mg/mL and about 5 mg/mL. In certain embodiments, about 0.1% polysorbate 80 may be added in the formulation.

In embodiments, the protein product of the present disclosure is formulated as a liquid formulation. The liquid formulation may be presented at a 10 mg/mL concentration in either a USP/Ph Eur type I 50R vial closed with a rubber stopper and sealed with an aluminum crimp seal closure. The stopper may be made of elastomer complying with USP and Ph Eur. In certain embodiments vials may be filled with 61.2 mL of the protein product solution in order to allow an extractable volume of 60 mL. In certain embodiments, the liquid formulation may be diluted with 0.9% saline solution.

In certain embodiments, the liquid formulation of the disclosure may be prepared as a 10 mg/mL concentration solution in combination with a sugar at stabilizing levels. In certain embodiments the liquid formulation may be prepared in an aqueous carrier. In certain embodiments, a stabilizer may be added in an amount no greater than that which may result in a viscosity undesirable or unsuitable for intravenous administration. In certain embodiments, the sugar may be disaccharides, e.g., sucrose. In certain embodiments, the liquid formulation may also include one or more of a buffering agent, a surfactant, and a preservative.

In certain embodiments, the pH of the liquid formulation may be set by addition of a pharmaceutically acceptable acid and/or base. In certain embodiments, the pharmaceutically acceptable acid may be hydrochloric acid. In certain embodiments, the base may be sodium hydroxide.

In addition to aggregation, deamidation is a common product variant of peptides and proteins that may occur during fermentation, harvest/cell clarification, purification, drug substance/drug product storage and during sample analysis. Deamidation is the loss of $NH_3$ from a protein forming a succinimide intermediate that can undergo hydrolysis. The succinimide intermediate results in a 17 dalton mass decrease of the parent peptide. The subsequent hydrolysis results in an 18 dalton mass increase. Isolation of the succinimide intermediate is difficult due to instability under aqueous conditions. As such, deamidation is typically detectable as 1 dalton mass increase. Deamidation of an asparagine results in either aspartic or isoaspartic acid. The parameters affecting the rate of deamidation include pH, temperature, solvent dielectric constant, ionic strength, primary sequence, local polypeptide conformation and tertiary structure. The amino acid residues adjacent to Asn in the peptide chain affect deamidation rates. Gly and Ser following an Asn in protein sequences results in a higher susceptibility to deamidation.

In certain embodiments, the liquid formulation of the present disclosure may be preserved under conditions of pH and humidity to prevent deamination of the protein product.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution, Ringer's solution or dextrose solution.

A preservative may be optionally added to the formulations herein to reduce bacterial action. The addition of a preservative may, for example, facilitate the production of a multi-use (multiple-dose) formulation.

Intravenous (IV) formulations may be the preferred administration route in particular instances, such as when a patient is in the hospital after transplantation receiving all drugs via the IV route. In certain embodiments, the liquid formulation is diluted with 0.9% Sodium Chloride solution before administration. In certain embodiments, the diluted drug product for injection is isotonic and suitable for administration by intravenous infusion.

In certain embodiments, a salt or buffer components may be added in an amount of 10 mM-200 mM. The salts and/or buffers are pharmaceutically acceptable and are derived from various known acids (inorganic and organic) with "base forming" metals or amines. In certain embodiments, the buffer may be phosphate buffer. In certain embodiments, the buffer may be glycinate, carbonate, citrate buffers, in which case, sodium, potassium or ammonium ions can serve as counterion.

A preservative may be optionally added to the formulations herein to reduce bacterial action. The addition of a preservative may, for example, facilitate the production of a multi-use (multiple-dose) formulation.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution, Ringer's solution or dextrose solution.

A protein of the present disclosure could exist in a lyophilized formulation including the proteins and a lyoprotectant. The lyoprotectant may be sugar, e.g., disaccharides. In certain embodiments, the lyoprotectant may be sucrose or maltose. The lyophilized formulation may also include one or more of a buffering agent, a surfactant, a bulking agent, and/or a preservative.

The amount of sucrose or maltose useful for stabilization of the lyophilized drug product may be in a weight ratio of at least 1:2 protein to sucrose or maltose. In certain embodiments, the protein to sucrose or maltose weight ratio may be of from 1:2 to 1:5.

In certain embodiments, the pH of the formulation, prior to lyophilization, may be set by addition of a pharmaceutically acceptable acid and/or base. In certain embodiments the pharmaceutically acceptable acid may be hydrochloric acid. In certain embodiments, the pharmaceutically acceptable base may be sodium hydroxide.

Before lyophilization, the pH of the solution containing a protein of the present disclosure may be adjusted between 6 to 8. In certain embodiments, the pH range for the lyophilized drug product may be from 7 to 8.

In certain embodiments, a salt or buffer components may be added in an amount of 10 mM-200 mM. The salts and/or buffers are pharmaceutically acceptable and are derived from various known acids (inorganic and organic) with "base forming" metals or amines. In certain embodiments, the buffer may be phosphate buffer. In certain embodiments, the buffer may be glycinate, carbonate, citrate buffers, in which case, sodium, potassium or ammonium ions can serve as counterion.

In certain embodiments, a "bulking agent" may be added. A "bulking agent" is a compound which adds mass to a lyophilized mixture and contributes to the physical structure of the lyophilized cake (e.g., facilitates the production of an essentially uniform lyophilized cake which maintains an open pore structure). Illustrative bulking agents include mannitol, glycine, polyethylene glycol and sorbitol. The lyophilized formulations of the multispecific binding proteins described in the present application may contain such bulking agents.

A preservative may be optionally added to the formulations herein to reduce bacterial action. The addition of a preservative may, for example, facilitate the production of a multi-use (multiple-dose) formulation.

In certain embodiments, the lyophilized drug product may be constituted with an aqueous carrier. The aqueous carrier of interest herein is one which is pharmaceutically acceptable (e.g., safe and non-toxic for administration to a human) and is useful for the preparation of a liquid formulation, after lyophilization. Illustrative diluents include sterile water for injection (SWFI), bacteriostatic water for injection (BWFI), a pH buffered solution (e.g., phosphate-buffered saline), sterile saline solution, Ringer's solution or dextrose solution.

In certain embodiments, the lyophilized drug product of the current disclosure is reconstituted with either Sterile Water for Injection, USP (SWFI) or 0.9% Sodium Chloride Injection, USP. During reconstitution, the lyophilized powder dissolves into a solution.

In certain embodiments, the lyophilized protein product of the instant disclosure is constituted to about 4.5 mL water for injection and diluted with 0.9% saline solution (sodium chloride solution).

Actual dosage levels of the active ingredients in the pharmaceutical compositions of multispecific binding proteins described in this application may be varied so as to obtain an amount of the active ingredient which is effective to achieve the desired therapeutic response for a particular patient, composition, and mode of administration, without being toxic to the patient.

The specific dose can be a uniform dose for each patient, for example, 50-5000 mg of protein. Alternatively, a patient's dose can be tailored to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data. An individual patient's dosage can be adjusted as the progress of the disease is monitored. Blood levels of the targetable construct or complex in a patient can be measured to see if the dosage needs to be adjusted to reach or maintain an effective concentration. Pharmacogenomics may be used to determine which targetable constructs and/or complexes, and dosages thereof, are most likely to be effective for a given individual (Schmitz et al., *Clinica Chimica Acta* 308: 43-53, 2001; Steimer et al., *Clinica Chimica Acta* 308: 33-41, 2001).

In general, dosages based on body weight are from about 0.01 µg to about 100 mg per kg of body weight, such as about 0.01 µg to about 100 mg/kg of body weight, about 0.01 µg to about 50 mg/kg of body weight, about 0.01 µg to about 10 mg/kg of body weight, about 0.01 µg to about 1 mg/kg of body weight, about 0.01 µg to about 100 µg/kg of body weight, about 0.01 µg to about 50 µg/kg of body weight, about 0.01 µg to about 10 µg/kg of body weight, about 0.01 µg to about 1 µg/kg of body weight, about 0.01 µg to about 0.1 μg/kg of body weight, about 0.1 μg to about 100 mg/kg of body weight, about 0.1 μg to about 50 mg/kg of body weight, about 0.1 μg to about 10 mg/kg of body weight, about 0.1 μg to about 1 mg/kg of body weight, about 0.1 μg to about 100 μg/kg of body weight, about 0.1 μg to about 10 μg/kg of body weight, about 0.1 μg to about 1 μg/kg of body weight, about 1 μg to about 100 mg/kg of body weight, about 1 μg to about 50 mg/kg of body weight, about 1 μg to about 10 mg/kg of body weight, about 1 μg to about 1 mg/kg of body weight, about 1 μg to about 100 μg/kg of body weight, about 1 μg to about 50 μg/kg of body weight, about 1 μg to about 10 μg/kg of body weight, about 10 μg to about 100 mg/kg of body weight, about 10 μg to about 50 mg/kg of body weight, about 10 μg to about 10 mg/kg of body weight, about 10 μg to about 1 mg/kg of body weight, about 10 μg to about 100 μg/kg of body weight, about 10 μg to about 50 μg/kg of body weight, about 50 μg to about 100 mg/kg of body weight, about 50 μg to about 50 mg/kg of body weight, about 50 μg to about 10 mg/kg of body weight, about 50 μg to about 1 mg/kg of body weight, about 50 μg to about 100 μg/kg of body weight, about 100 μg to about 100 mg/kg of body weight, about 100 μg to about 50 mg/kg of body weight, about 100 μg to about 10 mg/kg of body weight, about 100 μg to about 1 mg/kg of body weight, about 1 mg to about 100 mg/kg of body weight, about 1 mg to about 50 mg/kg of body weight, about 1 mg to about 10 mg/kg of body weight, about 10 mg to about 100 mg/kg of body weight, about 10 mg to about 50 mg/kg of body weight, about 50 mg to about 100 mg/kg of body weight.

Doses may be given once or more times daily, weekly, monthly or yearly, or even once every 2 to 20 years. Persons of ordinary skill in the art can easily estimate repetition rates for dosing based on measured residence times and concentrations of the targetable construct or complex in bodily fluids or tissues. Administration of the multispecific binding proteins described in the present application could be intravenous, intraarterial, intraperitoneal, intramuscular, subcutaneous, intrapleural, intrathecal, intracavitary, by perfusion through a catheter or by direct intralesional injection. This may be administered once or more times daily, once or more times weekly, once or more times monthly, and once or more times annually.

The description above provides multiple aspects and embodiments of the multispecific binding proteins described in the application. The patent application specifically contemplates all combinations and permutations of the aspects and embodiments. The use of any and all examples, or exemplary language herein, for example, "such as" or "including," is intended merely to illustrate better the multispecific binding proteins described in the present application, and does not pose a limitation on the scope of the disclosure, unless so expressly stated. No language in the specification should be construed as indicating any non-claimed element as essential to the practice of the multispecific binding proteins described in the present application.

EXAMPLES

The following examples are merely illustrative and are not intended to limit the scope or content of the multispecific binding proteins described in the present application in any way.

Example 1. Characterization of Supernatants of Selected Hybridoma Clones

Figure 18P:
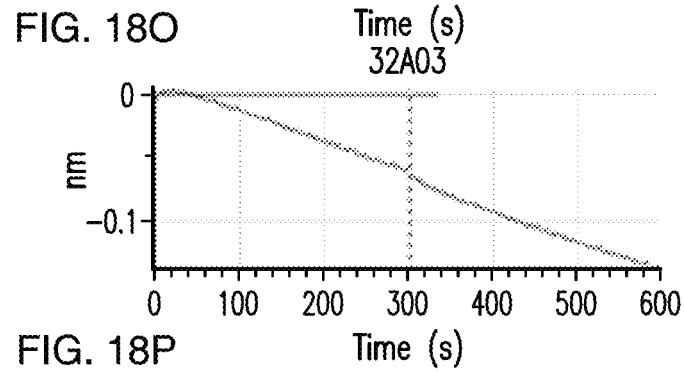

CLEC12A-specific antibodies were generated by immunizing BALB/c mice with hCLEC12A-His fusion protein. Supernatants of 16 hybridomas were assessed for CLEC12A binding by Bio-layer Interferometry (BLI) binding using an OctetRed384 (ForteBio). These 16 hybridomas were further analyzed for binding to human and cynomolgus CLEC12A expressed on the cell surface of isogenic RMA cells; binding to cynomolgus CLEC12A was not observed. Estimated kinetic parameters are presented in Table 11 and binding traces are shown in FIGS. 18A-18P. Nine clones were selected for further study. The ability of these nine clones to bind hCLEC12A-His RMA and CLEC12A-expressing cancer cell lines U937 and PL21 was further analyzed by high resolution surface plasmon resonance (SPR). The experiment was performed at 37° C. to mimic physiological temperature using a Biacore 8K instrument.

TABLE 11

Kinetic parameters and affinities of CLEC12A-His binding to the antibodies produced from candidate hybridomas

| Test articles | Binning profile | SPR at 37° C. | | | Cell Binding MFI | | |
|---|---|---|---|---|---|---|---|
| | | $k_a$ (1/Ms) | $k_d$ (1/s) | $K_D$ (nM) | RMA-hCLEC12A | $k_a$ (1/Ms) | $k_d$ (1/s) |
| 9E04 | competitor | 247.0 | $3.51 \times 10^{-2}$ | 9E04 | competitor | 247.0 | $3.51 \times 10^{-2}$ |
| 9F11 | competitor | 549.0 | $5.57 \times 10^{-3}$ | 9F11 | competitor | 549.0 | $5.57 \times 10^{-3}$ |
| 11E02 | — | 779.0 | $7.28 \times 10^{-3}$ | 11E02 | — | 779.0 | $7.28 \times 10^{-3}$ |
| 12F08 | unique | 76.7 | $6.23 \times 10^{-3}$ | 12F08 | unique | 76.7 | $6.23 \times 10^{-3}$ |
| 13E01 | unique | 178.0 | $7.50 \times 10^{-3}$ | 13E01 | unique | 178.0 | $7.50 \times 10^{-3}$ |
| 15A10 | unique | 79.5 | $2.23 \times 10^{-3}$ | 15A10 | unique | 79.5 | $2.23 \times 10^{-3}$ |
| 15D11 | — | 372.0 | $6.64 \times 10^{-3}$ | 15D11 | — | 372.0 | $6.64 \times 10^{-3}$ |
| 16B08 | competitor | Heterogeneous binding | | | 819.0 | 16B08 | competitor |
| 20D06 | unique | 819.0 | $5.25 \times 10^{-2}$ | 20D06 | unique | 819.0 | $5.25 \times 10^{-2}$ |
| 23A05 | unique | 90.2 | $4.49 \times 10^{-2}$ | 23A05 | unique | 90.2 | $4.49 \times 10^{-2}$ |
| 30A09 | — | Heterogeneous binding | | | 74.7 | 30A09 | — |
| 6D07 | — | Non binder | | | 247.0 | 6D07 | — |
| 12B06 | — | Non binder | | | 178.0 | 12B06 | — |
| 20G10 | — | Non binder | | | 82.2 | 20G10 | — |
| 30H07 | — | Non binder | | | 76.3 | 30H07 | — |
| 32A03 | — | Non binder | | | 71.4 | 32A03 | — |

Binning of hybridoma fusions compared to reference mAbs was performed by BLI using OctetRed384 (ForteBio). Briefly, hybridoma supernatants were loaded onto anti-mouse IgG capture sensor tips for 15 minutes and equilibrated for 5 minutes in PBSF. Sensors were dipped into 200 nM hCLEC12A-His and allowed to associate for 180 seconds followed by dipping into 100 nM reference CLEC12A mAb. The increase in response units indicated that the hybridoma was a non-competitor to the reference mAb, whereas no increase in signal indicated that the hybridoma did compete with the reference mAb. The VH and VL sequences of these reference antibodies are provided in Table 12.

TABLE 12

Reference antibodies

| Anti-CLEC12A mAbs | Source | Sequence ID | Epitope |
|---|---|---|---|
| Merus-CLL1 | Merus US 2014/0120096A1 | VH [SEQ ID NO: 263] EVQLVQSGAEVKKPGASVKVSCKASGY TFTSYYMHWVRQAPGQGLEWMGIINPS GGSTSYAQKFQGRVTMTRDTSTSTVYM ELSSLRSEDTAVYYCARGNYGDEFDYW GQGTLVTVSS VL[SEQ ID NO: 264] DIQMTQSPSSLSASVGDRVTITCRASQSIS SYLNWYQQKPGKAPKLLIYAASSLQSGV PSRFSGSGSGTDFTLTISSLQPEDFATYYC QQSYSTPPTFGQGTKVEIK | unknown |
| Genentech-h6E7 | Genentech US 2016/0075787A1 | VH [SEQ ID NO: 265] DIQMTQSPSSLSASVGDRVTITCRASQSV STSSYNYMHWYQQKPGKPPKLLIKYASN LESGVPSRFSGSGSGTDFTLTISSLQPEDF ATYYCQHSWEIPLTFGQGTKVEIK VL [SEQ ID NO: 266] EVQLVQSGAEVKKPGASVKVSCKASGY SFTDYYMHWVRQAPGQGLEWIGRINPY NGAAFYSQNFKDRVTLTVDTSTSTAYLE LSSLRSEDTAVYYCAIERGADLEGYAMD YWGQGTLVTVSS | C-type lectin-like domain, residues 142-158 |

Binning analysis demonstrated that antibodies produced from five of the hybridomas, namely 12F8.G3, 13E01, 15A10.G8, 20D6.A8, and 23A5.D4, did not compete with the reference antibodies for binding to hCLEC12A-His. Binding of hybridomas to isogenic human CLEC12A (hCLEC12A) and cross-reactivity with cynomolgus monkey CLEC12A (cCLEC12A) were also evaluated by measuring the binding of the antibodies to isogenic RMA cells expressing CLEC12A and the U937 AML cancer cell line.

Briefly, RMA cells were transducted with a retroviral vector encoding cCLEC12A or hCLEC12A. Binding of the α-CLEC12A mAbs from crude hybridoma harvests to the hCLEC12A or cCLEC12A isogenic cell lines, as well as CLEC12A+ U937 (ATCC catalog number CRL-1593.2) cancer cell lines, was performed as follows. 100,000 RMA, REH or SEM cells were added per well of a 96 well round bottom plate. Cells were spun down and the pellet was gently dissociated by vortexing. 100 μL of Zombie live/dead dye (PBS+1:2000 dye) were added per well and incubated in the dark at room temperature for 20 minutes. Cells were washed with 200 μL of FACS buffer (PBS+2% FBS). 50 μL of hybridoma supernatants were added to the washed cells and the mixtures were incubated for 30 minutes on ice in the dark. Cells were washed twice with FACS buffer and then 50 μL of anti-mouse Fc-PE secondary reagent (1:200 dilution) were added and incubated for 20 minutes on ice in the dark. After the incubation, the cells were washed and then fixed with 50 μL of 4% paraformaldehyde for 15 minutes on ice. The fixed cells were washed with FACS buffer, resuspended in 200 μL FACS buffer, and stored at 4° C. until ready for acquisition. The samples of cells resuspended in FACS buffer were run on BD FACSCelesta equipped with an HTS (high throughput sampler) to determine the binding affinities of the antibodies to isogenic RMA cells expressing CLEC12A and the U937 AML cancer cell line.

The binding affinities of the hybridoma supernatants to PL21 AML cancer cells (DSMZ catalog number ACC536), a human AML cell line reported to express CLEC12A, were also measured. As shown in Table 11, nine of the clones displayed binding affinity to cancer cells expressing hCLEC12A. Binding to cCLEC12A was not observed.

Example 2. Analysis of Purified Anti-CLEC12A Murine Antibodies

In this Example, kinetic parameters and binding affinities of the purified anti-CLEC12A murine antibodies were analyzed. Based on the analysis described in Example 1, eight hybridomas (9F11.B7, 12F8.G3, 16B8.C8, 15A10.G8, 20D6.A8, 9E4.B7, 13E1.A4, and 23A5.D4) were selected for subcloning and sequencing. Each subclone was purified from the hybridoma culture, and binding to hCLEC12A-His and cCLEC12A-His was assessed by SPR as shown in FIG. 19. The data from these experiments are shown in FIG. 19A. Antibodies 9E4.B7, 9F11.B7, 12F8.G3, and 16B8.C8 bound to hCLEC12A only (FIG. 19A); whereas antibodies 13E1.A4, 15A10.G8, 20D6.A8, and 23A5.D4 bound to both hCLEC12A and cCLEC12A (FIG. 19B). Kinetic constants and binding affinities of hCLEC12A and cCLEC12A to purified murine subcloned mAbs are provided in Table 13.

TABLE 13

Kinetic parameters and affinities of hCLEC12A binding to purified murine subclones

| Test Article | Human CLEC12A-His | | | Cyno CLEC12A-His | | |
|---|---|---|---|---|---|---|
| | $k_a$ (M$^{-1}$s$^{-1}$) | $k_d$ (s$^{-1}$) | $K_D$ (nM) | $k_a$ (M$^{-1}$s$^{-1}$) | $k_d$ (s$^{-1}$) | $K_D$ (nM) |
| 9E4.B7 | Low affinity heterogenous interaction | | | No binding | | |
| 9F11.B7 | $1.14 \times 10^6$ | $1.57 \times 10^{-3}$ | 1.4 | No binding | | |
| 12F8.G3 | $3.97 \times 10^5$ | $1.39 \times 10^{-3}$ | 3.5 | No binding | | |
| 16B8.C8* | $4.05 \times 10^6$ | $4.44 \times 10^{-5}$ | 0.01 | No binding | | |
| 13E1.A4 | Low affinity heterogenous interaction | | | Low affinity heterogenous interaction | | |
| 15A10.G8 | $3.01 \times 10^5$ | $4.94 \times 10^{-4}$ | 1.6 | $1.96 \times 10^5$ | $6.59 \times 10^{-4}$ | 3.3 |
| 20D6.A8 | $1.31 \times 10^7$ | $9.50 \times 10^{-2}$ | 7.2 | $9.16 \times 10^5$ | $2.46 \times 10^{-2}$ | 26 |
| 23A5.D4 | Low affinity heterogenous interaction | | | Low affinity heterogenous interaction | | |

Figure 20:
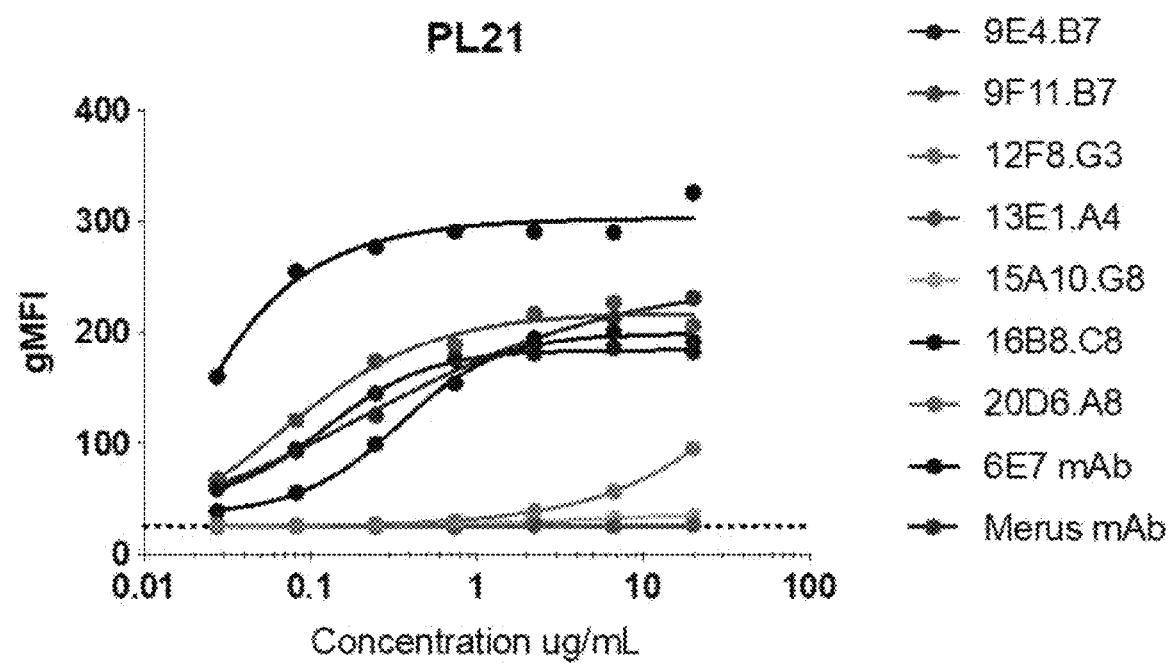
FIG. 20 is a line graph showing binding of purified CLEC12A subclones to PL21 AML cell line.

The ability of the eight purified subcloned mAbs to bind to CLEC12A expressing cells was assessed by FACS analysis with human CLEC12A-positive PL21 cancer cell line. As shown in FIG. 20, 9E4.B7, 9F11.B7 and 16B8.C8 all bound to the PL21 cell line with sub-nanomolar EC50 values; however, only 9F11.B7 and 16B8.C8 satisfied both recombinant protein binding and cell binding criteria, as 9E4.B7 demonstrated low affinity heterogenous binding to recombinant hCLEC12A-His (Table 14). Although 15A10.G8, 13E1.A4, 20D6.A8 and 23A5.D4 showed binding to recombinant human and cyno CLEC12A in the SPR assay, these mAbs failed to recognize cancer cells, suggesting conformational differences in the binding epitope between recombinant and cell surface expressed CLEC12A. As demonstrated, both Merus-CLL1 and Genentech-h6E7 mAbs bound to PL21 with significantly inferior EC50 values as compared to the novel CLEC12A hybridoma clones.

TABLE 14

Cell binding confirmation of purified mouse mAbs to human PL21 cell line

| Test article | $EC_{50}$ (nM) | Max MFI |
|---|---|---|
| 9E4.B7 | 0.64 | 186 |
| 9F11.B7 | 0.56 | 217 |
| 12F8.G3 | Non binder | n/a* |
| 16B8.C8 | 0.18 | 300 |
| 13E1.A4 | Non binder | n/a |
| 15A10.G8 | Non binder | n/a |
| 20D6.A8 | Non binder | n/a |
| 23A5.D4 | Non binder | n/a |
| Merus-CLL1# | 2.02 | 201 |
| Genentech-h6E7# | 5 | 265 |

Figure 21A:
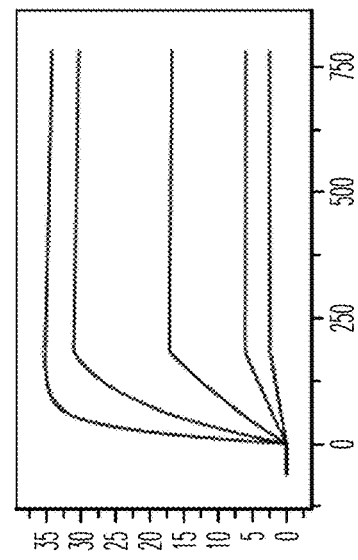
FIG. 21A-FIG. 21F are a set of sensorgrams showing SPR profiles of antibodies 16B8.C8 and 9F11.B7 binding to glycosylated (FIG. 21A and FIG. 21D), de-glycosylated (FIG. 21B and FIG. 21E), and de-sialylated (FIG. 21C and FIG. 21F) hCLEC12A.
Figure 21B:
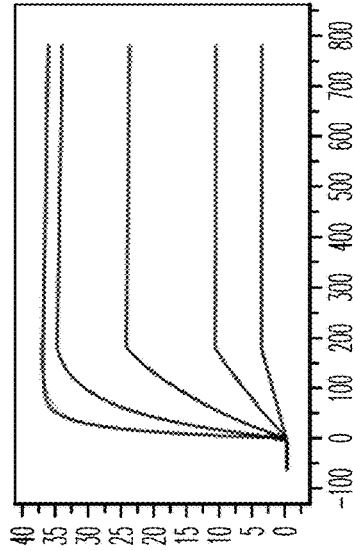
Figure 21C:
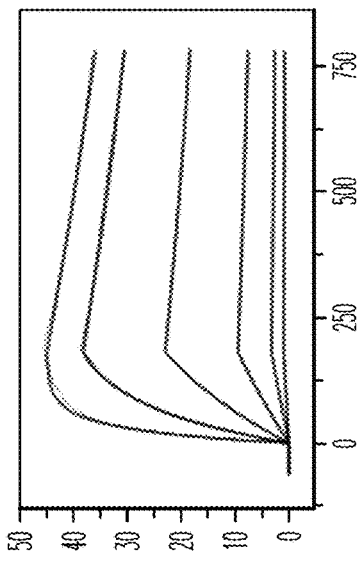
Figure 21D:
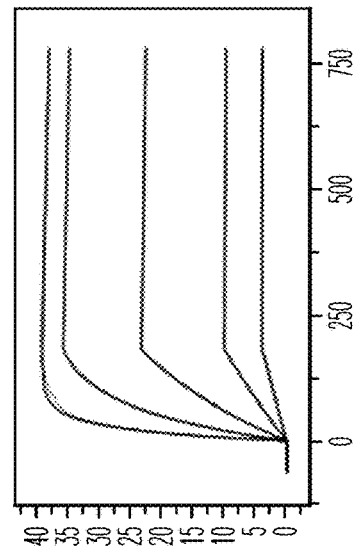
Figure 21E:
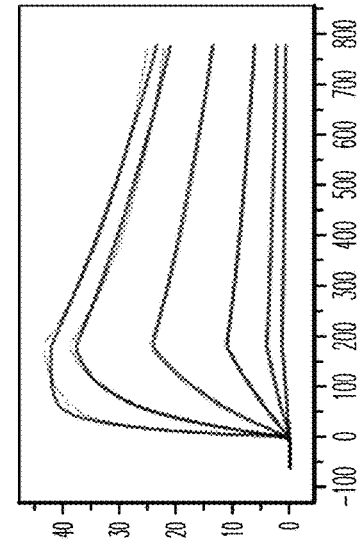
Figure 21F:
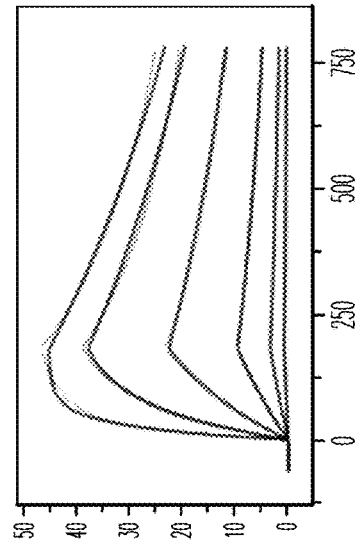

To assess if mAbs bind to CLEC12A in a glycosylation independent manner, binding of clones 16B8.C8 and 9F11.B7 to glycosylated (FIGS. 21A and 21D), de-sialylated (FIGS. 21C and 21F) and PNGase-treated hCLEC12A (FIGS. 21B and 21E) was assessed by SPR. As demonstrated by the sensorgrams and in Table 15, both 16B8.C8 and 9F11.B7 bound to de-sialylated and deglycosylated versions of hCLEC12A without loss of affinity, suggesting that the antibody interactions with hCLEC12A are not affected by glycosylation status of the target.

TABLE 15

Kinetic parameters and affinities of 16B8.C8 and 9F11.B7 to differentially glycosylated hCLEC12A by SPR.

| Test article | Analyte | $k_a$ (M$^{-1}$s$^{-1}$) | $k_d$ (s$^{-1}$) | $K_D$ (nM) |
|---|---|---|---|---|
| Murine 16B8. mAb | Glycosylated hCLEC12A | $4.05 \times 10^6$ | $4.70 \times 10^{-5}$ | 0.012 |
| Murine 16B8 mAb | De-sialylated hCLEC12A | $5.25 \times 10^6$ | $3.62 \times 10^{-5}$ | 0.007 |
| Murine 16B8 mAb | De-glycosylated hCLEC12A | $4.26 \times 10^6$ | $4.45 \times 10^{-5}$ | 0.011 |
| Murine F3'-9F11 | Glycosylated hCLEC12A | $1.15 \times 10^6$ | $1.11 \times 10^{-3}$ | 0.96 |
| Murine F3'-9F11 | De-sialylated hCLEC12A | $1.58 \times 10^6$ | $9.80 \times 10^{-4}$ | 0.62 |
| Murine F3'-9F11 | De-glycosylated hCLEC12A | $1.11 \times 10^6$ | $3.74 \times 10^{-4}$ | 0.34 |

Example 3. Putative Sequence Liability Analysis

Potential sequence liabilities in CDRs (identified under Chothia) of the 16B8.C8 and 9F11.B7 antibodies were examined. The following potential liabilities were considered: M (potential oxidation site); NG, NS and NT sequence motif (potential deamidation site); DG, DS and DT sequence motif (potential isomerization site); DP sequence motif (potential site for chemical hydrolysis). The results are summarized in Table 16.

TABLE 16

Putative sequence liabilities in the CDRs of selected murine mAbs

| Clone ID | Potential sequence liability motif | Location |
|---|---|---|
| 16B8.C8 | DS (Isomerization site) | CDRH3 |
| 9F11.B7 | M (Oxidation site) | CDRH3 |
| | DG (Isomerization site) | CDRH3 |
| | NS (Deamidation site) | CDRH1 |

Variants of these antibodies were designed to remove the putative sequence liability motifs.

Example 4. Humanization of Subclones

Based on the data collected regarding kinetics and affinity for recombinant hCLEC12A protein, binding to cell surface expressed hCLEC12A, and binding to AML cancer cell lines, two mouse hybridoma subclones, namely 16B8.C8 and 9F11.B7, were selected for humanization.

The 16B8.C8 antibody was humanized. Back mutations were introduced in the framework regions to create variants having the VH and VL sequences of scFv-1292 to scFv-1309, and scFv-1602 and scFv-2061.

The 9F11.B7 antibody was humanized. Back mutations were introduced in the framework regions to create variants AB0186 to AB0196.

Example 5. CLEC12A TriNKET Selection

Figure 22A:
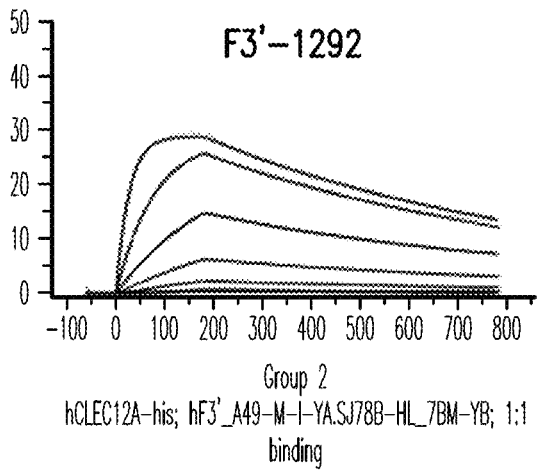
FIG. 22A-FIG. 22S are a set of sensorgrams showing SPR profiles of TriNKETs derived from antibody 16B8.C8.
Figure 22B:
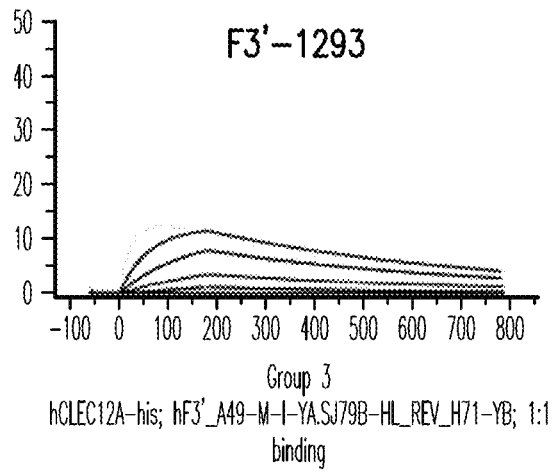
Figure 22C:
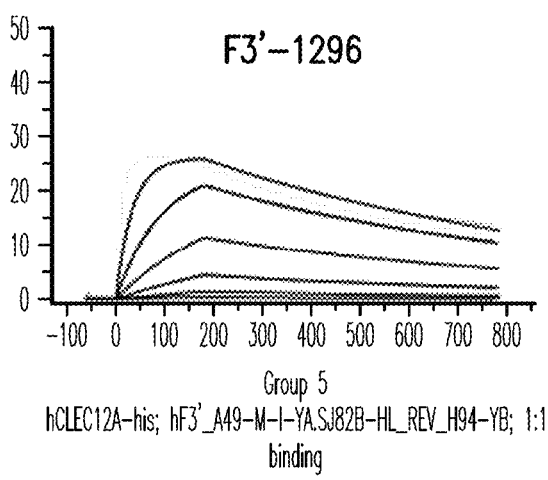
Figure 22D:
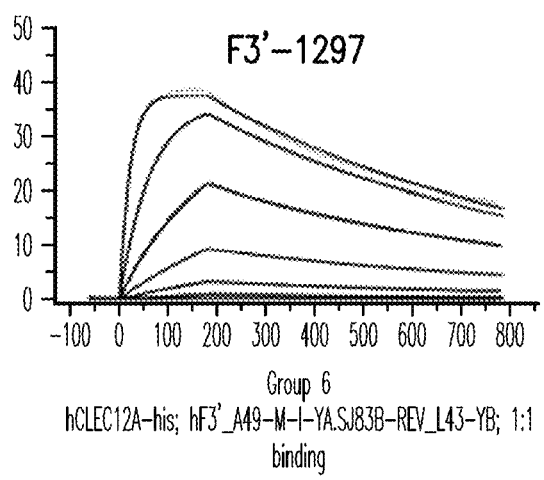
Figure 22E:
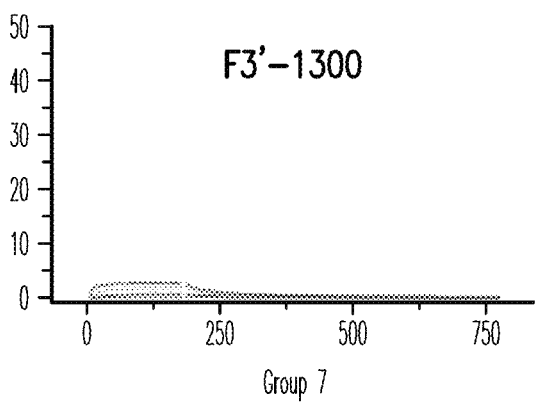
Figure 22F:
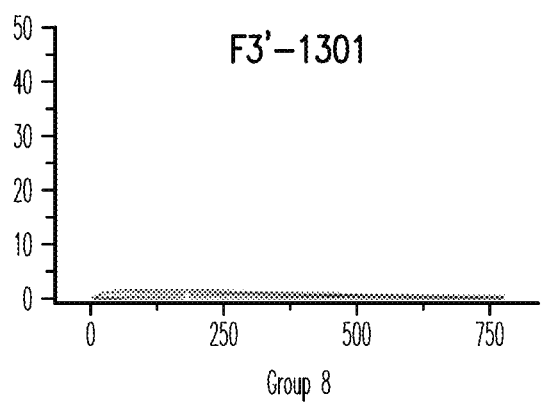
Figure 22G:
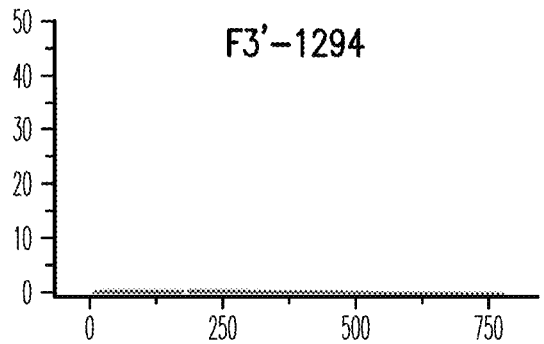
Figure 22H:
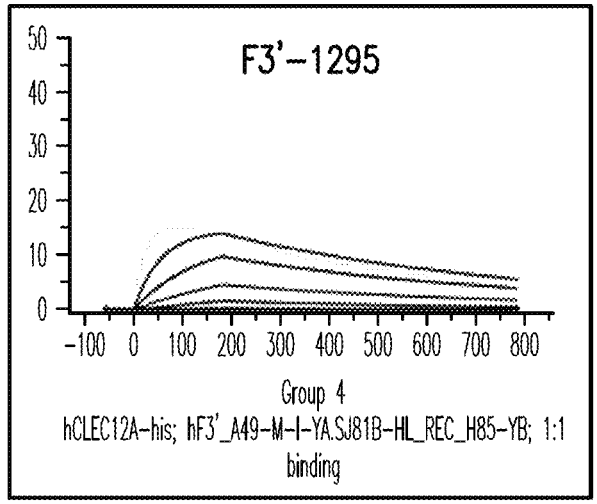
Figure 22I:
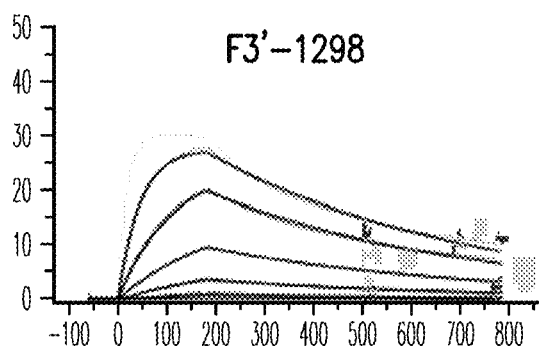
Figure 22J:
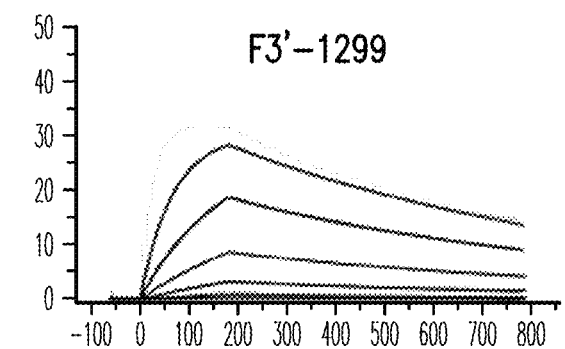
Figure 22K:
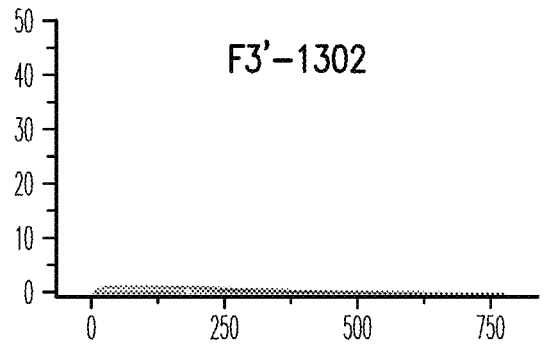
Figure 22L:
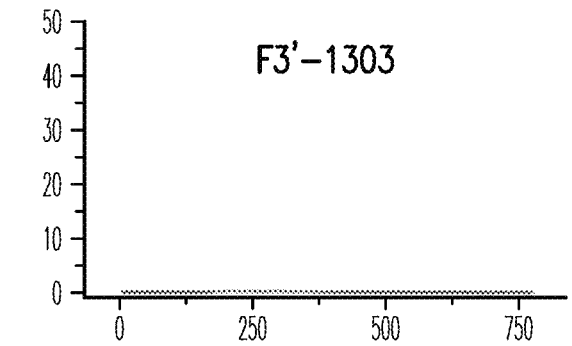
Figure 22Q:
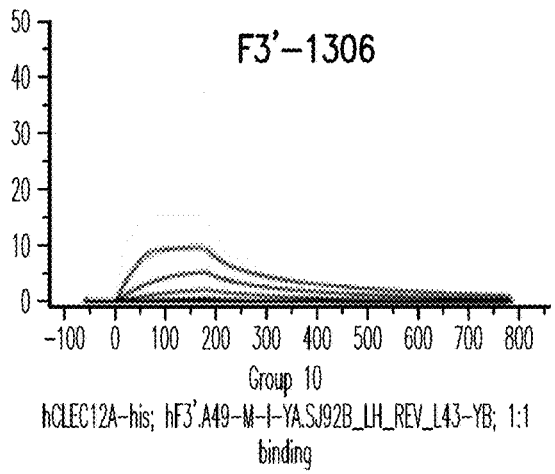
Figure 22R:
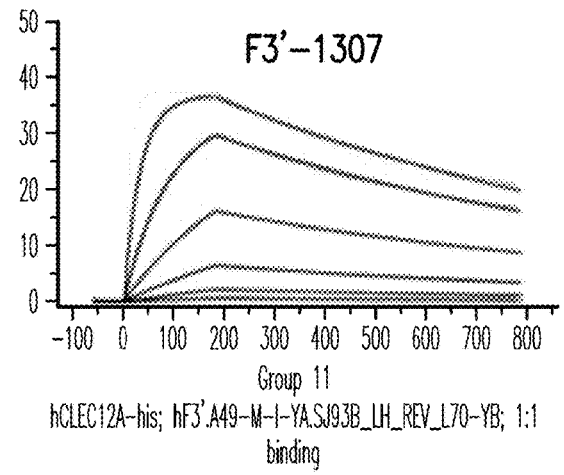
Figure 22S:
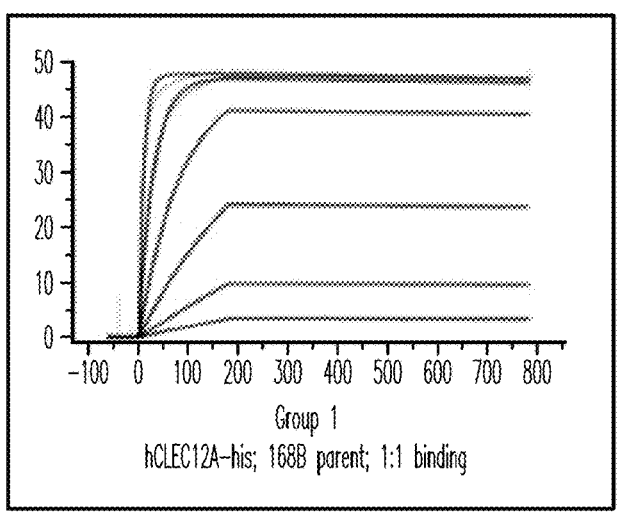

The following criteria were applied in choosing the optimal TriNKET candidate, which led to selection of F3'-1602 TriNKET as the lead candidate:
Potent enhancement of NK activity against AML cancer cells
Potency greater than the corresponding monoclonal antibody
Binding to multiple AML cell lines
High affinity for recombinant hCLEC12A
Low affinity for human NKG2D
Cross-reactivity with cynomolgus monkey (cyno) targets
Good developability profile:
Thermostability of scFv≥65° C.
isoelectric point (pI) between 8-9
Hydrophobicity Interaction Chromatography (HIC) retention time similar to well behaved therapeutic mAbs
High specificity for human CLEC12A
Clean polyspecific reagent (PSR) profile
Transient expression titers similar to mAb All 18 humanized scFv variants of clone 16B8.C8 were combined with an A49MI NKG2D Fab arm to produce humanized F3' CLEC12A TriNKETs. Binding affinities of the 18 semi-purified TriNKETs for hCLEC12A were assessed by SPR in screening. Binding signals for eight F3'-TriNKETs were less than 5 RU (approximately 15% of the expected signal ran in this assay) and, therefore, these TriNKETs were considered as nonbinders to hCLEC12A. The remaining ten F3'-TriNKETs bound to hCLEC12A with <10 nM affinity, as shown in FIGS. 22A-22S and Table 17. However, a potential N-glycosylation site was involuntarily introduced in eight out of the ten F3'-TriNKETs by introducing murine back mutation N in position H85. Only constructs F3'-1295 and F3'-1304 (containing A in position H85) did not present the N-glycosylation sequence liability; therefore, only these two constructs were carried forward for further characterization.

TABLE 17

Kinetics and affinities of hCLEC12A binding to semi-purified humanized F3' TriNKETs.

| Test article | scFv orientations | Number of back mutations and residues reverted to human | N-glycosylation sequence liability site | $k_a$ ($M^{-1}s^{-1}$) | $k_d$ ($s^{-1}$) | $K_D$ (nM) |
| --- | --- | --- | --- | --- | --- | --- |
| F3'-1292 | VH-VL | 7 BM | Yes | $4.02 \times 10^5$ | $1.30 \times 10^{-3}$ | 3.22 |
| F3'-1293 | VH-VL | 6 BM, K(H71)V* | Yes | $4.58 \times 10^5$ | $1.75 \times 10^{-3}$ | 3.81 |
| F3'-1294 | VH-VL | 6 BM, Q(H83)T | Yes | Binding signal < 5 RU | | |
| F3'-1295 | VH-VL | 6 BM, N(H85)A | No | $5.20 \times 10^5$ | $1.53 \times 10^{-3}$ | 2.94 |
| F3'-1296 | VH-VL | 6 BM, K(H94)R | Yes | $8.74 \times 10^5$ | $1.17 \times 10^{-3}$ | 1.34 |
| F3'-1297 | VH-VL | 6 BM, I(L43)A | Yes | $5.04 \times 10^5$ | $1.41 \times 10^{-3}$ | 2.79 |
| F3'-1298 | VH-VL | 6 BM, R(L70)D | Yes | $6.44 \times 10^5$ | $1.85 \times 10^{-3}$ | 2.87 |
| F3'-1299 | VH-VL | 6 BM, I(L83)F | Yes | $4.26 \times 10^5$ | $1.21 \times 10^{-3}$ | 2.83 |
| F3'-1300 | VH-VL | No BM | No | Binding signal < 5 RU | | |
| F3'-1301 | VL-VH | 7 BM | Yes | Binding signal < 5 RU | | |
| F3'-1302 | VL-VH | 6 BM, K(H71)V | Yes | Binding signal < 5 RU | | |
| F3'-1303 | VL-VH | 6 BM, Q(H83)T | Yes | Binding signal < 5 RU | | |
| F3'-1304 | VL-VH | 6 BM, N(H85)A | No | $4.80 \times 10^5$ | $1.30 \times 10^{-3}$ | 2.70 |
| F3'-1305 | VL-VH | 6 BM, K(H94)R | Yes | Binding signal < 5 RU | | |
| F3'-1306 | VL-VH | 6 BM, I(L43)A | Yes | $9.48 \times 10^6$ | $4.89 \times 10^{-2}$ | 5.16 |
| F3'-1307 | VL-VH | 6 BM, R(L70)D | Yes | $9.14 \times 10^5$ | $1.00 \times 10^{-3}$ | 1.10 |
| F3'-1308 | VL-VH | 6 BM, I(L83)F | Yes | Binding signal < 5 RU | | |
| F3'-1309 | VL-VH | No BM | No | Binding signal < 5 RU | | |
| m16B8.C8** | Mouse mAb | | Yes | $3.03 \times 10^6$ | $2.35 \times 10^{-5}$ | 0.008 |

*In the "residues reverted to human," the first letter is a murine residue, and the letter and number in the parentheses indicate positions of reverted residues in the heavy chain and light chain, and the last letter is the human residue, e.g., in K(H71)V, murine K in position 71 of the heavy chain is replaced by human residue V.
**murine parental mAb 16B8.C8 was fully purified.

Figure 23:
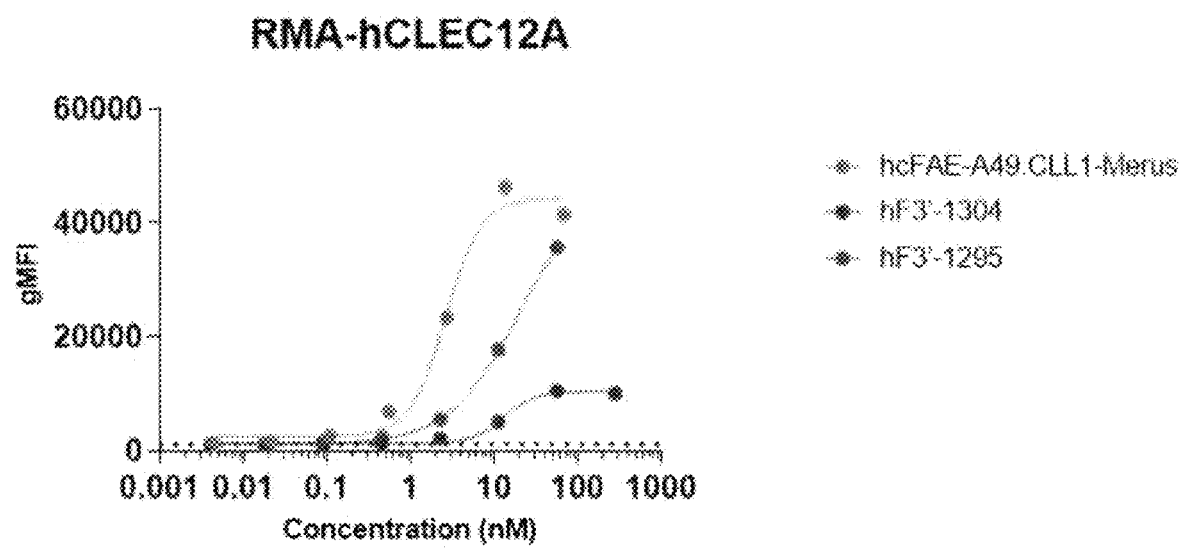
FIG. 23 is a line graph showing binding of hCLEC12A-targeting TriNKETs F3'-1304, F3'-1295 and a control CLEC12A-TriNKET to hCLEC12A-expressing cell line RMA-hCLEC12A.

F3'-1295 and F3'-1304 TriNKETs were tested for binding isogenic to hCLEC12A+RMA cells, as shown in FIG. 23, and using the methods as described in Example 5 or 6. Binding of F3'-1295 to cell-surface expressed hCLEC12A was comparable to hcFAE-A49.CLL1-Merus control TriN-KET, derived from the Merus antibody described above in Example 1, whereas binding of F3'-1304 to cell-surface expressed hCLEC12A was poorer compared to the hcFAE-A49.CLL1-Merus control multispecific binding protein.

Figure 24:
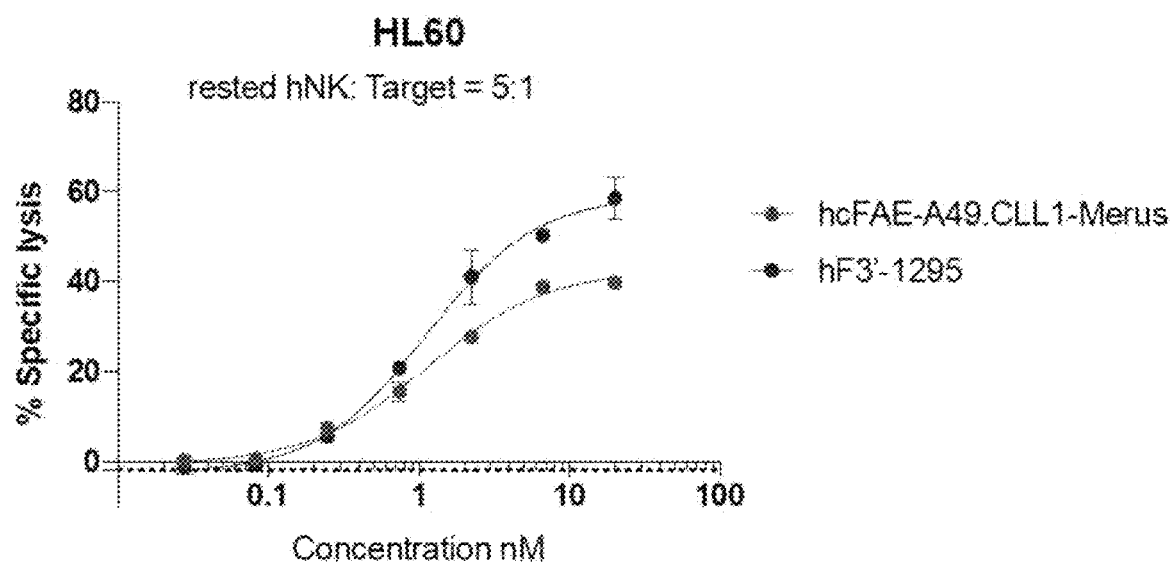
FIG. 24 is a line graph showing NK cell-mediated lysis of CLEC12A-expressing cancer cell line HL60 in the presence of F3'-1295 and a control CLEC12A-TriNKET.
Figure 26E:
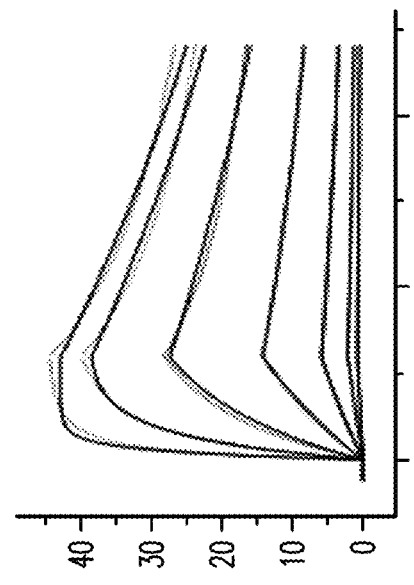
Figure 26F:
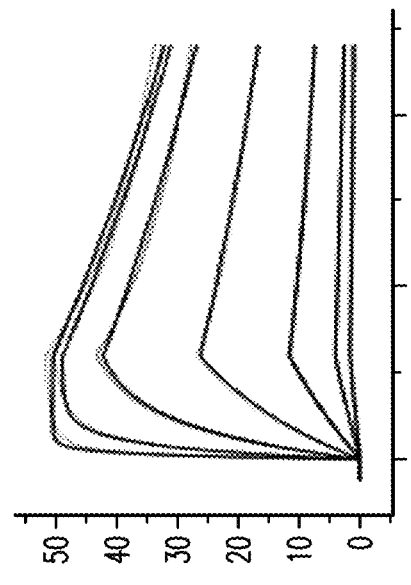
Figure 26G:
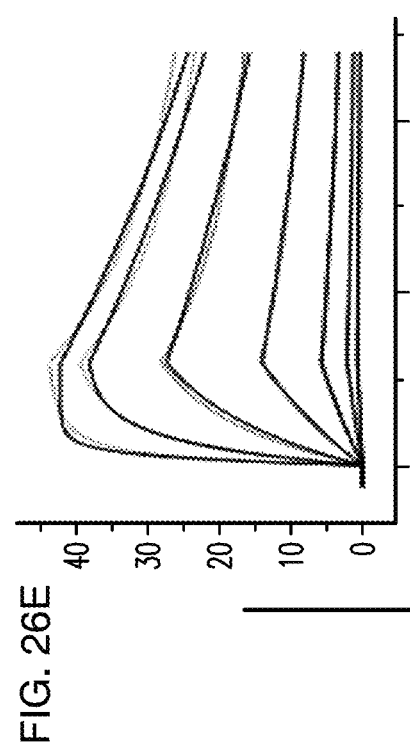
Figure 26H:
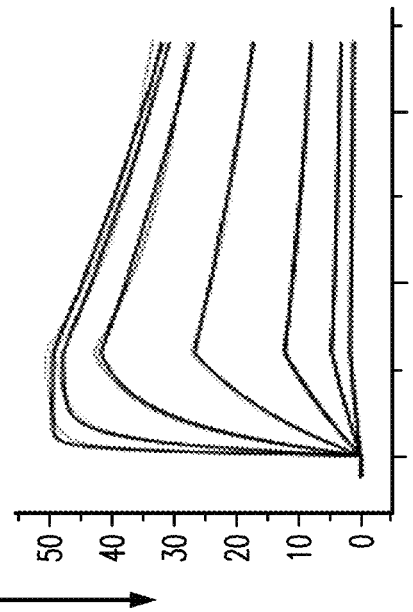

Potency of F3'-1295 was assessed in the primary NK cell mediated cytotoxicity assay with HL-60 AML cells, as shown in FIG. 24, and using the methods as described in Example 8. F3'-1295 induced potent lysis of HL60 AML cells. Cell killing EC50 was similar, and maximum percentage of cell lysis was higher than control hcFAE-A49.CLL1-Merus TriNKET (Table 18).

TABLE 18

Potency of F3'-1295 in primary NK cells mediated cytotoxicity assay.

| Test articles | EC50 (nM) | Max lysis (%) |
|---|---|---|
| F3'-1295 | 1.1 | 59 |
| hcFAE-A49.CLL1-Merus | 1.1 | 43 |

Thermostability of F3'-1295 was evaluated by differential scanning calorimetry (DSC). To perform DSC, briefly, TriN-KETs were diluted to 0.5 mg/mL with PBS. 325 μL were added to a 96-well deep well plate along with a matching buffer blank. Thermograms were generated using a Micro-Cal PEAQ DSC (Malvern, PA). Temperature was ramped from 20-100° C. at 90° C./hour. Raw thermograms were background subtracted, the baseline model was splined, and data were fitted using a non-two state model.

The melting temperature of the first transition ($T_{m1}$) for F3'-1295 was 60.9° C., which is 4° C. lower than pre-defined criteria of ≥65° C. for the $T_m$ of the first TriNKET transition. In the process of humanization, it is possible that the introduction of the murine residue to human framework (back mutation) may have had an impact on the thermal stability. Therefore, by reverting the back mutations to human residues thermal stability of F3'-1295 may improve. Therefore, the thermal stability of the ten F3' variants was assessed by DSC regardless of the presence or absence of the N-glycosylation sequence liability, as shown in Table 19. The first transition $T_m$ (attributed to the scFv domain) of F3'-1297 and F3'-1306 TriNKETs was significantly higher (66.5° C. to 67.5° C.) than the other F3' TriNKETs. Moreover, the $T_{onset}$ of these two molecules was significantly better compared to other F3' TriNKETs tested. The sole difference between these two F3'-TriNKETs is the orientation of scFv; F3'-1297 (VH-VL orientation) and F3'-1306 (VL-VH orientation).

To determine if the human residue in position (L43) was responsible for an increase in thermostability, in both F3'-1306 and F3'-1297, the mouse residue I(L43) was reverted back to the original human framework residue A(L43). Moreover, the murine Ile in position L43 of F3'-1295 was replaced with human Ala, and then was produced recombinantly. The new second generation humanized TriNKET derived from F3'-1295 was named F3'-1602, or F3'-1602 TriNKET.

TABLE 19

DSC analysis of purified F3'-TriNKETs in PBS.

| Test articles | scFv orientation | Mouse residues changed to human | $T_{onset}$ (° C.) | $T_{m1}$ (° C.) | $T_{m2}$ (° C.) | $T_{m3}$ (° C.) | $T_{m4}$ (° C.) | $T_{m5}$ (° C.) |
|---|---|---|---|---|---|---|---|---|
| F3'-1292 | VH-VL | none | 51.4 | 60.0 | 67.6 | 76.4 | 81.6 | 83.7 |
| F3'-1293 | VH-VL | K(H71)V [#] | 51.2 | 59.8 | 66.9 | 76.5 | 81.6 | 83.7 |
| F3'-1295 | VH-VL | N(H85)A | 52.5 | 60.9 | 67.1 | 76.6 | 81.6 | 83.4 |
| F3'-1296 | VH-VL | K(H94)R | 50.5 | 59.7 | 67.1 | 76.3 | 81.6 | 83.7 |
| F3'-1297 | VH-VL | I(L43)A | 56.4 | 66.5* | | 76.0 | 81.5 | 83.6 |
| F3'-1298 | VH-VL | R(L70)D | 48.7 | 59.2 | 66.5 | 76.0 | 81.7 | 83.8 |
| F3'-1299 | VH-VL | I(L83)F | 49.6 | 59.8 | 66.1 | 76.0 | 81.8 | 83.8 |
| F3'-1304 | VL-VH | N(H85)A | 50.5 | 60.1 | 65.5 | 76.3 | 81.7 | 83.5 |
| F3'-1306 | VL-VH | I(L43)A | 58.5 | 67.5 | | 76.2 | 81.6 | 83.7 |
| F3'-1307 | VL-VH | R(L70)D | 50.5 | 60.2 | 66.0 | 76.0 | 81.8 | 83.9 |

[#] Chothia position (mouse residue to human residue)

*Overlaps with $T_{m2}$

Thermostability of F3'-1295 and second generation F3'-1602 TriNKETs was evaluated by DSC in PBS (FIGS. 25A-25B). Based on the $T_m$ of the first transition, the scFv of F3'-1602 was thermally stabilized by 7.5° C. compared to F3'-1295, shown in Table 20. This stabilization is attributed to the Ile/Ala mutations. Thus, F3'-1602 met the $T_{m1}$ cut-off at ≥65° C.

TABLE 20

DSC analysis of F3'-1295 and F3'-1602 TriNKETs in PBS.

| Test article | $T_{onset}$ (° C.) | $T_{m1}$ (° C.) | $T_{m2}$ (° C.) | $T_{m3}$ (° C.) | $T_{m4}$ (° C.) |
|---|---|---|---|---|---|
| F3'-1295 | 52.5 | 60.9 | 67.1 | 76.6 | 81.6 |
| F3'-1602 | 58.5 | 66.8 | 76.0 | 81.5 | 83.3 |

To understand if the I(L43)A substitution had an effect on the TriNKET affinity for hCLEC12A, binding of hCLEC12A to F3'-1295 and F3'-1602 was determined by SPR (Biacore) at 37° C. (FIGS. 26A-26H), and using the methods as described in Example 1. The kinetic constants and equilibrium binding affinities are listed in Table 21. Both TriNKETs have very similar off rates, but F3'-1602 displays about 2-fold lower $K_D$ due to its faster on rate. Therefore, the I(L43)A substitution had an effect on the $K_D$.

TABLE 21

Kinetic parameters and affinities of F3'-1295 and F3'-1602 binding to hCLEC12A by SPR.

| Test article | Target | $k_a$ (M$^{-1}$s$^{-1}$) | $k_d$ (s$^{-1}$) | $K_D$ (nM) |
|---|---|---|---|---|
| F3'1295 | hCLEC12A-His | 4.11 × 10$^5$ | 5.87 × 10$^{-4}$ | 1.43 |
|  | hCLEC12A-His | 4.15 × 10$^5$ | 5.89 × 10$^{-4}$ | 1.42 |
|  | hCLEC12A-His | 4.19 × 10$^5$ | 6.05 × 10$^{-4}$ | 1.44 |
|  | hCLEC12A-His | 4.16 × 10$^5$ | 5.96 × 10$^{-4}$ | 1.43 |
| Average ± StDev |  | (4.15 ± 0.03) × 10$^5$ | (5.94 ± 0.09) × 10$^{-4}$ | 1.43 ± 0.01 |
| F3'1602 | hCLEC12A-His | 8.54 × 10$^5$ | 4.94 × 10$^{-4}$ | 0.58 |
|  | hCLEC12A-His | 8.33 × 10$^5$ | 4.94 × 10$^{-4}$ | 0.59 |
|  | hCLEC12A-His | 8.63 × 10$^5$ | 4.89 × 10$^{-4}$ | 0.57 |
|  | hCLEC12A-His | 8.26 × 10$^5$ | 4.99 × 10$^{-4}$ | 0.60 |
| Average ± StDev |  | (8.44 ± 0.17) × 10$^5$ | (4.94 ± 0.04) × 10$^{-4}$ | 0.57 ± 0.01 |

Figures 27C, 27D:
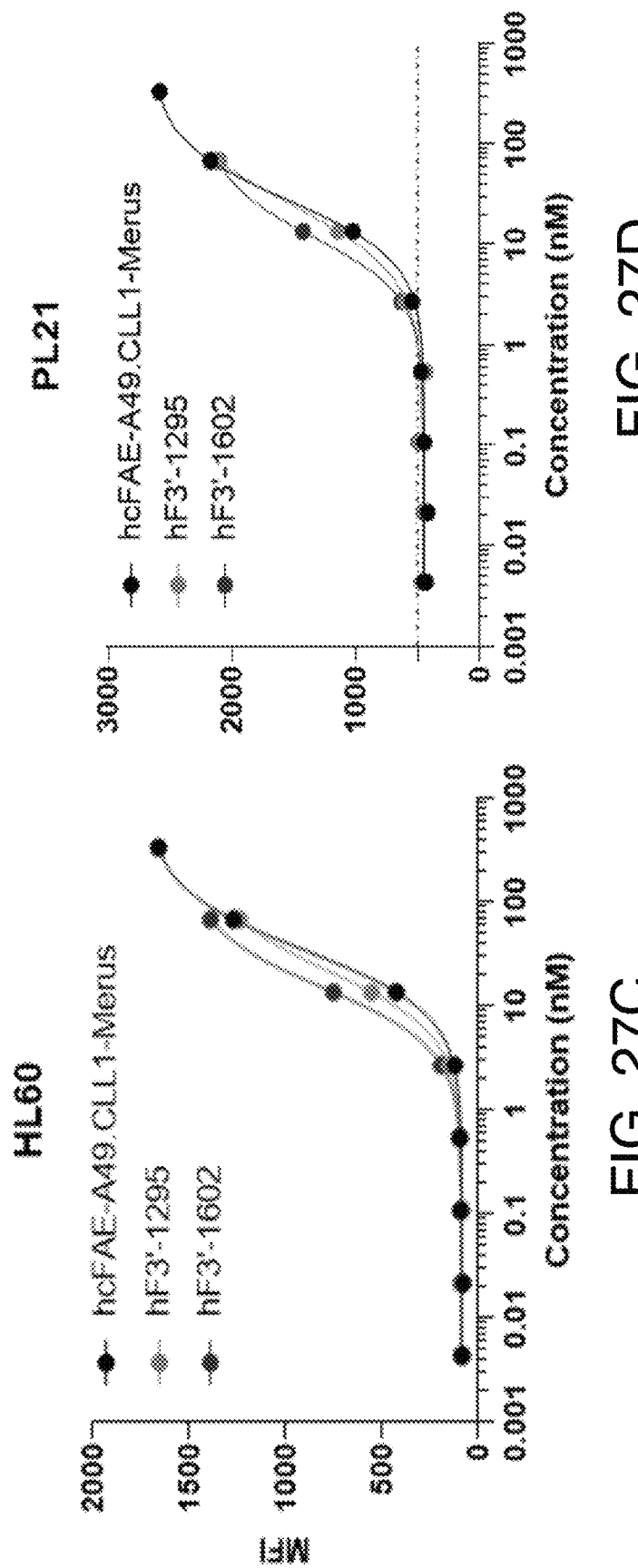

F3'-1295 and F3'-1602 were tested for their ability to bind isogenic Ba/F3 cells expressing human CLEC12A, in comparison to the parental Ba/F3 cells (as shown in FIG. 27A, and the data listed in Table 22) using the methods as described in Example 5 or 6. F3'-1602 was able to bind hCLEC12A+Ba/F3 with about 2-fold lower EC50 value but with similar maximum binding MFI compared to F3'-1295. No binding to the parental Ba/F3 cell lacking expression of CLEC12A was detected by either F3'-1295 or F3'-1602 (FIG. 27B), suggesting high specificity of TriNKET binding to hCLEC12A.

TABLE 22

EC50 and max MFI of F3'-TriNKETs binding to hCLEC12A + Ba/F3 isogenic cell line.

| Test article | hCLEC12A + Ba/F3 cell line | | Ba/F3 parental cell line | |
|---|---|---|---|---|
|  | EC50 (nM) | Max MFI | EC50 (nM) | Max MFI |
| F3'-1295 | 26.1 | 48040 | No binding | |
| F3'-1602 | 14.4 | 50160 | No binding | |
| hcFAE-A49.CLL-Merus | 14.3 | 39740 | No binding | |

F3'-1295 and F3'-1602 were further tested for their ability to bind HL60 (FIG. 27C) and PL21 (FIG. 27D) AML cancer cell lines, and using the methods as described in Example 5 or 6. F3'-1602 was able to bind to both cell lines with lower EC50 values but with similar maximum binding MFI as compared to F3'-1295, as shown in Table 23.

Figure 28B:
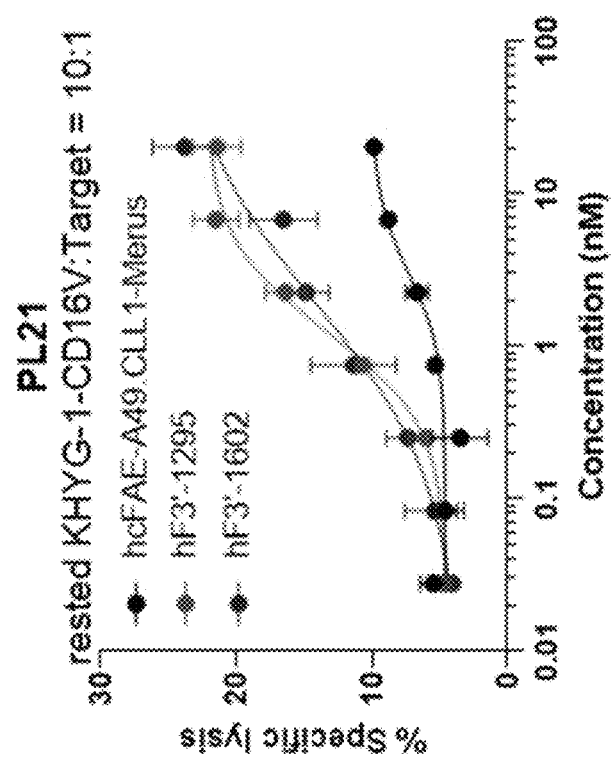
FIG. 28A-FIG. 28B are line graphs showing NK cell-mediated lysis of CLEC12A-expressing cancer cell lines PL21 (FIG. 28A) and HL60 (FIG. 28B) in the presence of F3'-1295, F3'-1602, and a control CLEC12A-TriNKET.
Figure 28A:
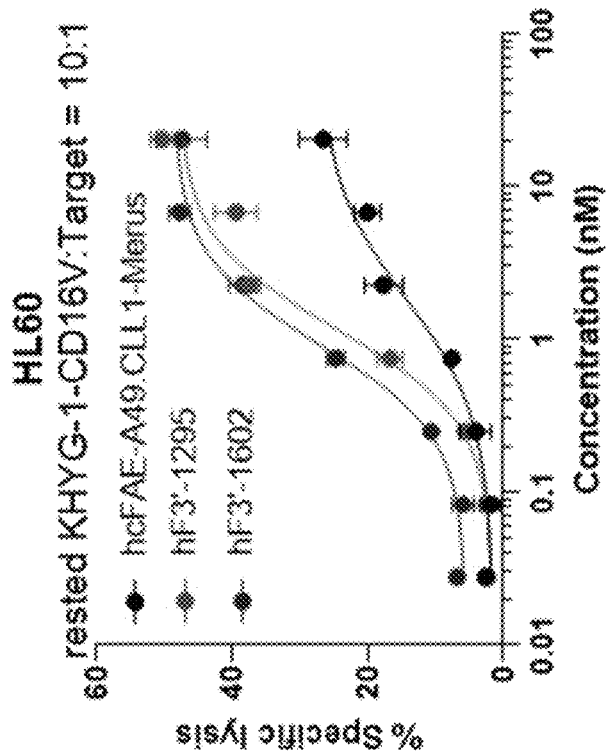
Figure 30A:
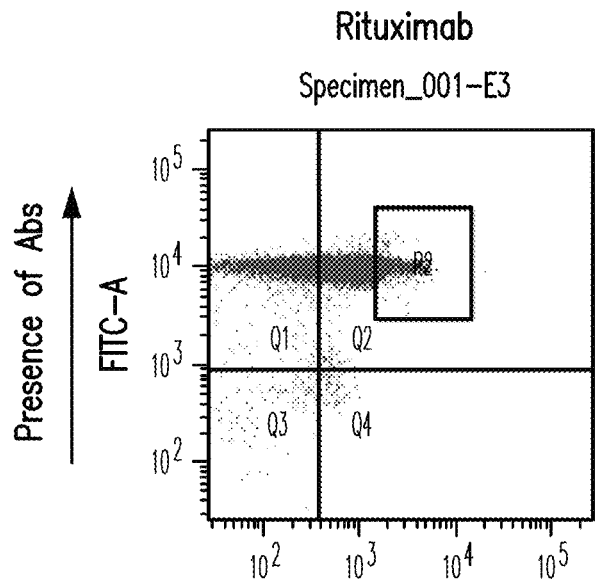
FIG. 30A-FIG. 30D show flow cytometry based polyspecificity reagent (PSR) analysis of Rituximab (FIG. 30A), Trastuzumab (FIG. 30B), F3'-1602 TriNKET (FIG. 30C) and F3'-1295 TriNKET (FIG. 30D).
Figure 30B:
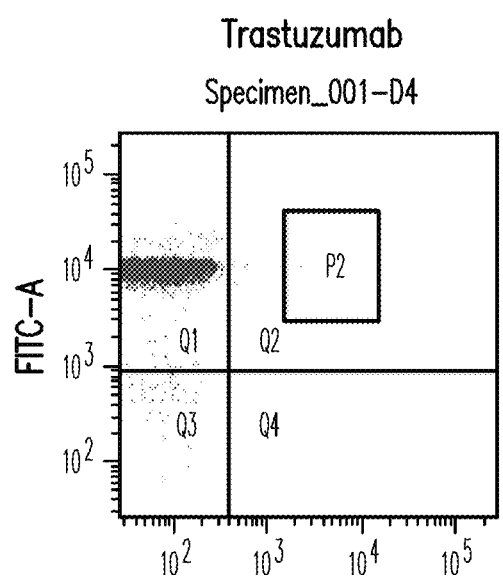
Figure 30C:
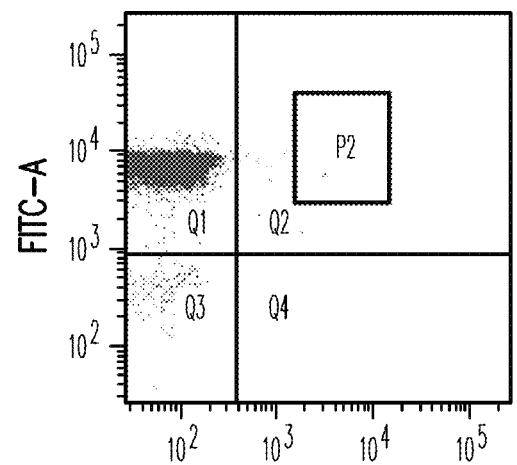
Figure 30D:
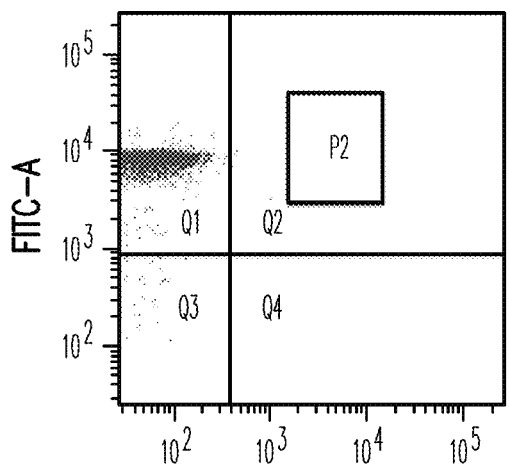
Figure 31A:
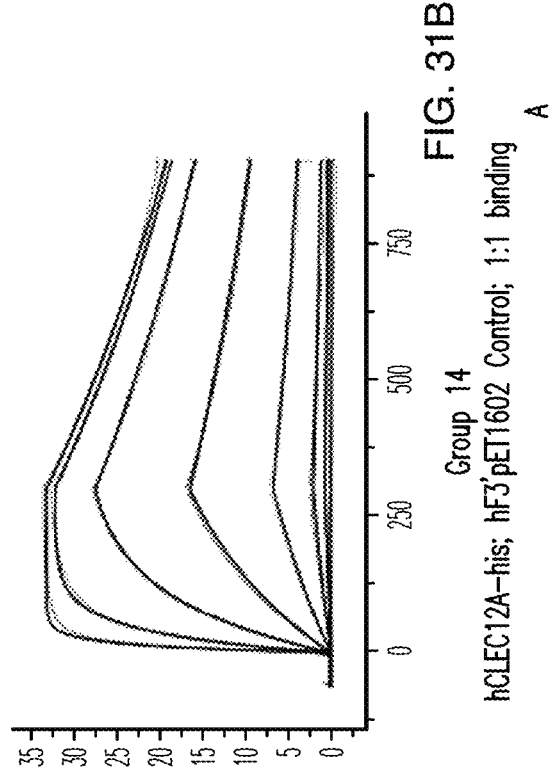
FIG. 31A-FIG. 31D is a set of sensorgrams showing SPR profiles of hF3'-1602 TriNKET (FIG. 31A and FIG. 31B) and F3-TriNKET AB0010 (FIG. 31C and FIG. 31D-).
Figure 31B:

Figure 31C:
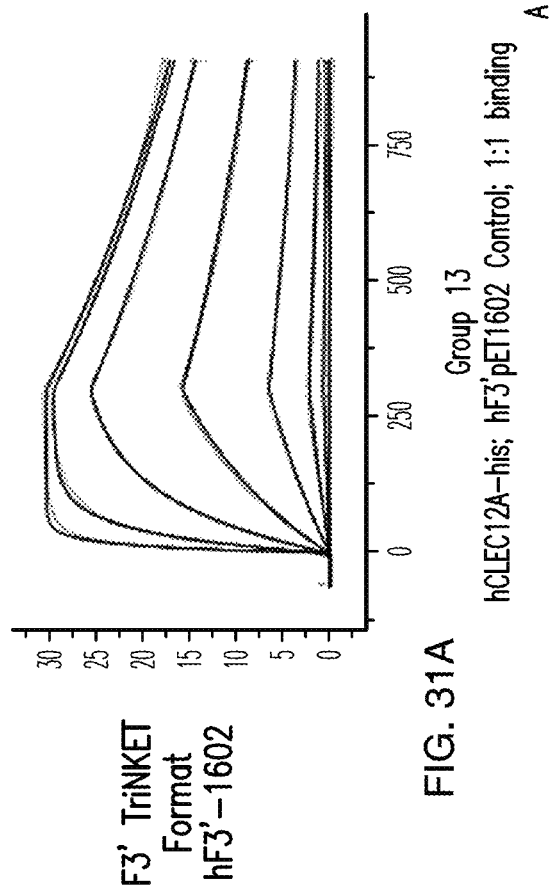
Figure 31D:
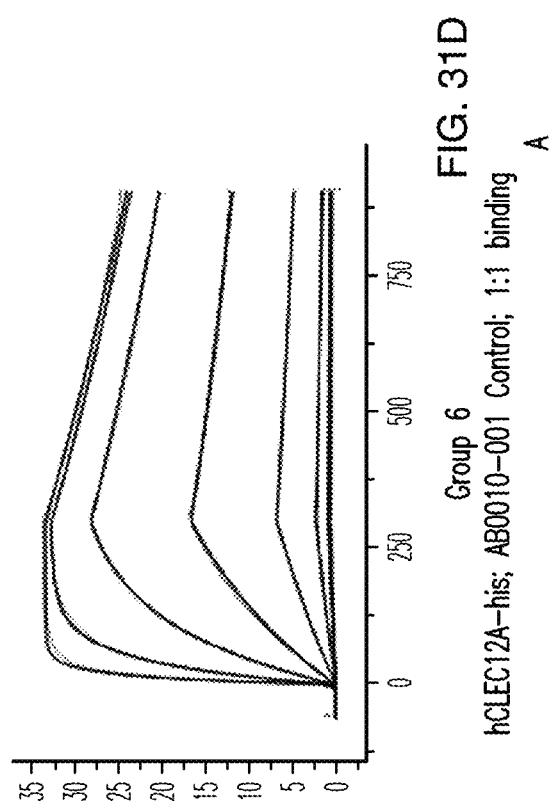

Potency of F3'-1295 and F3'-1602 TriNKETs was assessed in a KHYG-1-CD16aV mediated cytotoxicity assay, the results of which are shown in FIG. 28. Both F3'-1602 and F3'-1295 induced potent lysis of PL21 (FIG. 28A) and HL60 (FIG. 28B) AML cancer cells, and both display similar EC50 values and % max lysis, shown in Table 23.

TABLE 23

Potency of F3'-1294 and F3'1602 in KHYG-1CD16aV mediated cytotoxicity assay.

| Test articles | PL21 cancer cell line | | HL60 cancer cell line | |
|---|---|---|---|---|
|  | EC50 (nM) | Max cell lysis (%) | EC50 (nM) | Max cell lysis (%) |
| F3'-1295 | 1.23 | 22 | 1.15 | 48 |
| F3'-1602 | 1.87 | 25 | 0.90 | 49 |
| hcFAE-A49.CLL-Merus | 2.97 | 10 | 1.83 | 27 |

Hydrophobic properties of F3'-1295 and F3'-1602 TriNKETs were evaluated by analytical hydrophobic interaction chromatography (HIC), the results of which are shown in Table 24. Trastuzumab (Roche) was used as a representative control of a therapeutic antibody. The retention times (RT) for both TriNKETs were similar to the RT of Trastuzumab, suggesting that predicted aggregation propensity of both TriNKETs is low.

TABLE 24

HIC retention times for F3'-1295 and F3'-1602 TriNKETs compared to Trastuzumab.

| Test article | Absolute retention time (min) | ΔRT relative to Trastuzumab (min) |
|---|---|---|
| F3'-1295 | 9.7 | +0.6 |
| F3'-1602 | 9.4 | +0.3 |
| Trastuzumab | 9.1 | 0.0 |

The experimental isoelectric point (pI) of F3'-1295 (FIG. 29A) and F3'-1602 (FIG. 29B) was assessed by capillary isoelectric focusing (cIEF), as described in Example 15. Both constructs showed nearly identical pIs. The major peak of F3'-1295 has a pI of 8.73 and that of F3'-1602 has a pI of 8.81 (Table 25).

TABLE 25 pI of F3'-1295 and F3'-1602 determined by cIEF.

| Test article | pI (main peak) |
|---|---|
| F3'-1295 | 8.73 |
| F3'-1602 | 8.81 |

Off-target effects of a drug need to be evaluated when developing protein therapeutics. A flow cytometry based polyspecificity reagent (PSR) assay allows for determination of antibodies that have a higher probability to bind non-specifically. F3'-1295 and F3'-1602 were tested for non-specific binding to a preparation of detergent solubilized CHO cell membrane proteins in the PSR assay, using the methods as described in Example 12. Both humanized F3'-1602 and F3'-1295 did not bind to PSR (no signal shift to the right) and showed very similar profiles as the PSR control Trastuzumab, demonstrated in FIGS. 30A-30D, suggesting high specificity of the TriNKETs. Rituximab was used as a positive control in this assay. F3'-1602 was selected for further comparison with additional TriNKETs described.

The effect of different TriNKET formats was tested experimentally for alterations in efficacy. To obtain CLEC12A TriNKET in the F3 format, humanized 16B8.C8 was converted using the same humanization variant that was used F3'-1602, into Chains VH-CH1-Fc and VL-CL, whereas NKG2D A49M-I mAb was converted into VH-VL-Fc. The protein received the designation AB0010 or F3-1602.

Binding affinities of human CLEC12A-His for AB0010 (F3 TriNKET format) and F3'-1602 (F3' TriNKET format) were assessed by SPR (Biacore) at 37° C. The kinetic constants and equilibrium binding affinities are shown in Table 26, and the raw data and fits are shown in FIGS. 31A-31D. Overall binding affinities of both constructs were within 2-fold difference, with AB0010 forming slightly a stronger complex with CLEC12A compared to F3'-1602, as evidenced by the $K_D$.

TABLE 26

Kinetic parameters and affinities of CLEC12A binding to F3' (F3'-1602) and F3 (AB0010) TriNKETs.

| Format | Test article | Target | $k_a$ (M$^{-1}$s$^{-1}$) | $k_d$ (s$^{-1}$) | $K_D$ (nM) |
|---|---|---|---|---|---|
| F3' | F3'1602 | hCLEC12A-His | 7.91 × 10$^5$ | 9.52 × 10$^{-4}$ | 1.20 |
| F3' | F3'1602 | hCLEC12A-His | 7.68 × 10$^5$ | 9.13 × 10$^{-4}$ | 1.19 |
| F3' | | Average | 7.79 × 10$^5$ | 9.33 × 10$^{-4}$ | 1.20 |
| F3 | AB0010 | hCLEC12A-His | 7.15 × 10$^5$ | 5.08 × 10$^{-4}$ | 0.71 |
| F3 | AB0010 | hCLEC12A-His | 7.04 × 10$^5$ | 5.41 × 10$^{-4}$ | 0.77 |
| F3 | | Average | 7.10 × 10$^5$ | 5.25 × 10$^{-4}$ | 0.74 |

TriNKETs of different formats, F3'-1602 (F3') and AB0010 (F3), were tested for their abilities to bind Ba/F3 cells expressing human CLEC12A (FIG. 32A) and AML cancer cell line (FIG. 32B). The EC50 value for F3'-1602 was superior over AB0010 in HL-60 cells, about 2-fold decreased (Table 27). Neither AB0010 nor F3'-1602 showed any binding to the parental Ba/F3 cells, demonstrating high specificity of binding to CLEC12A (FIG. 32C).

TABLE 27

Binding EC50 and max MFI of F3'-1602 and AB0010 to hCLEC12A+ Ba/F3 and HL60 AML cells.

| | | hCLEC12A+ Ba/F3 cell line | | HL60 | | Ba/F3 parent cell line | |
|---|---|---|---|---|---|---|---|
| Format | Test article | Max MFI | EC50 (nM) | Max MFI | EC50 (nM) | Max MFI | EC50 (nM) |
| F3' | F3'-1602 | 36920 | 3.20 | 3820 | 1.1 | No binding | |
| F3 | AB0010 | 54827 | 6.13 | 6064 | 4.2 | No binding | |

Figure 33A:
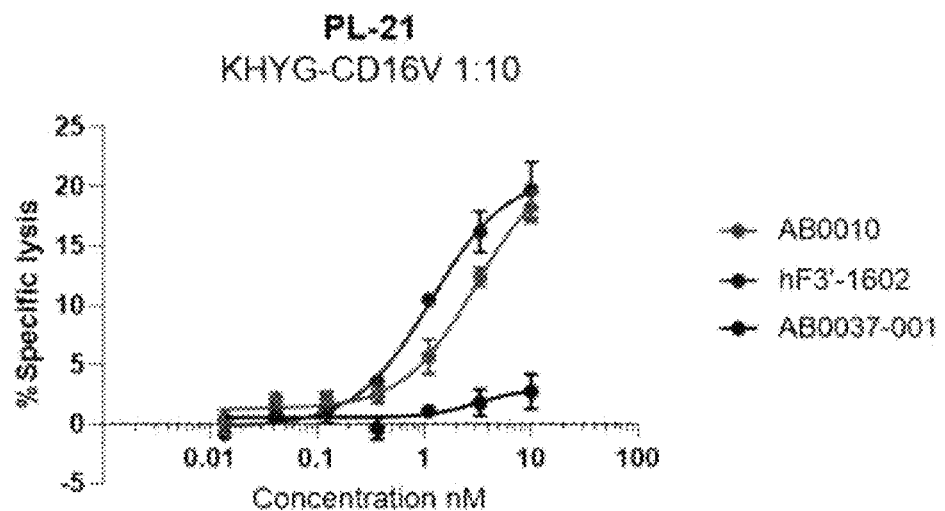
FIG. 33A-FIG. 33B are line graphs showing NK cell-mediated lysis of CLEC12A-expressing cancer cell line PL21 using KHYG-CD16V cells (FIG. 33A) and primary NK cells (FIG. 33B) in the presence of hF3'-1602 TriNKET and F3-TriNKET AB0010.

The potency of AB0010 and F3'-1602 TriNKETs was assessed in KHYG-1-CD16aV mediated cytotoxicity assay, shown in FIG. 33A. F3'-1602 induced lysis of HL60 and PL21 AML cancer cells with a 2-fold better EC50 value than AB0010 (Table 28). Both F3 (AB0010) and F3' (F3'-1602) TriNKETs showed superiority over corresponding humanized parental mAb (AB0037-001).

TABLE 28

Potency of F3'-1602 and AB0010 in KHYG-1-CD16aV mediated cytotoxicity assay.

| | | PL21 AML cancer cell line | |
|---|---|---|---|
| Format | Test articles | EC50 (nM) | Max cell lysis (%) |
| F3 | AB0010 | 2.99 | 21.75 |
| F3' | F3'-1602 | 1.16 | 20.97 |
| mAb | AB0037-001 | N/A | N/A |

Figure 33B:
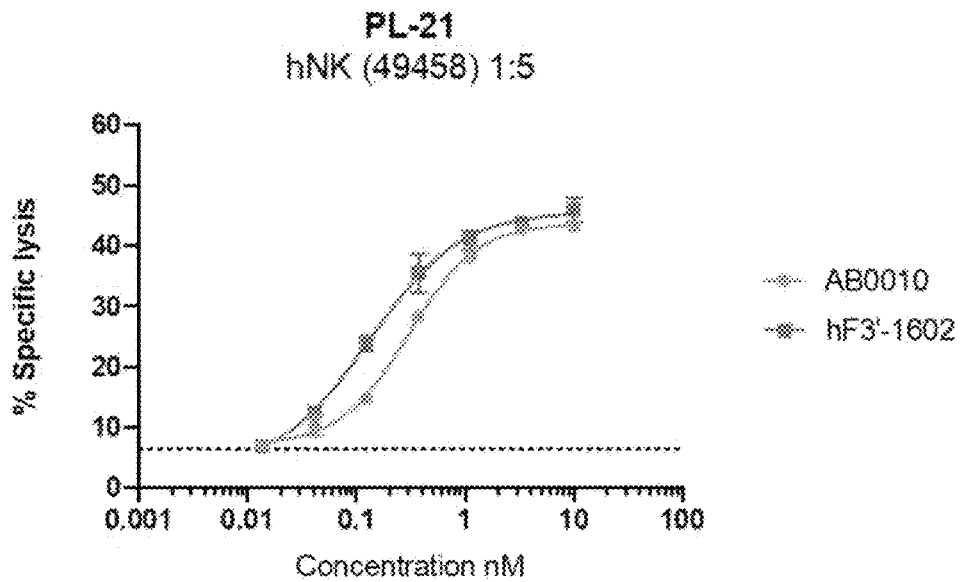

The potencies of AB0010 and F3'-1602 TriNKETs were assessed in a human primary NK cell mediated cytotoxicity assay (FIG. 33B). F3'-1602 (F3' format) induced lysis of PL21 AML cancer cells with a 2-fold lower EC50 value than AB0010 (F3 format) (Table 29).

TABLE 29

Potency of F3'1602 and AB0010 in primary NK cell mediated cytotoxicity assay.

| | | PL21 cancer cell lines | |
|---|---|---|---|
| Format | Test article | EC50 (nM) | Max cell lysis (%) |
| F3' | F3'-1602 | 0.13 | 45.85 |
| F3 | AB0010 | 0.30 | 43.82 |

It was observed in both KHYG-1 mediated and primary NK cell mediated cytotoxic assays that F3'-1602 (F3'-format) demonstrated about 2-fold better EC50 than AB0010 (F3-format), whereas the overall maximum percentage of killing was not affected. In accelerated stability and forced degradation studies AB0010 was less structurally stable compared to F3'-1602 (F3'-1602) (see Example 16). Therefore, the CLEC12A TriNKET in the F3' format (F3'-1602) was chosen to move forward for further study.

For generation of 9F11.B7 TriNKETs, all 12 scFv variants of 9F11.B7 were combined with A49M-I NKG2D Fab arm to produce humanized F3' TriNKETs. Affinities of the 10 semi-purified (Protein A) TriNKETs for hCLEC12A were assessed by SPR in the screening mode shown in Table 30. Three (AB0190, AB0193 and AB0196) 9F11.B7 based F3'-TriNKETs showed heterogenous binding and could not be fitted to a 1:1 kinetic model with high confidence. The binding kinetics of the remaining 7 TriNKETs were similar to the chimeric parent mouse 9F11.B7 mAb, suggesting that neither humanization nor conversion of Fab to scFv affected the affinity for hCLEC12A.

TABLE 30

Kinetics and affinities of hCLEC12A binding to semi-purified, humanized F3' TriNKETs.

| Test article | $k_a$ ($M^{-1}s^{-1}$) | $k_d$ ($s^{-1}$) | $K_D$ (nM) | Comments |
|---|---|---|---|---|
| AB0185 | $7.26 \times 10^5$ | $1.01 \times 10^{-3}$ | 1.40 | |
| AB0186 | $1.12 \times 10^6$ | $1.17 \times 10^{-3}$ | 1.04 | |
| AB0188 | $5.69 \times 10^5$ | $9.01 \times 10^{-4}$ | 1.58 | Low heterodimer yield |
| AB0189 | $1.04 \times 10^6$ | $1.27 \times 10^{-3}$ | 1.21 | |
| AB0190 | $1.55 \times 10^7$ | $1.77 \times 10^{-2}$ | 1.14 | Estimated/heterogeneous binding |
| AB0191 | $7.28 \times 10^5$ | $1.26 \times 10^{-3}$ | 1.73 | |
| AB0192 | $1.09 \times 10^6$ | $1.38 \times 10^{-3}$ | 1.26 | |
| AB0193 | $1.97 \times 10^7$ | $2.07 \times 10^{-2}$ | 1.04 | Estimated/heterogeneous binding |
| AB0195 | $7.66 \times 10^5$ | $1.29 \times 10^{-3}$ | 1.68 | |
| AB0196 | | | | Heterogenous weak binding; data insufficient for estimation |
| m9F11-hIgG1 | $9.50 \times 10^5$ | $1.02 \times 10^{-3}$ | 1.07 | |

Figure 34A:
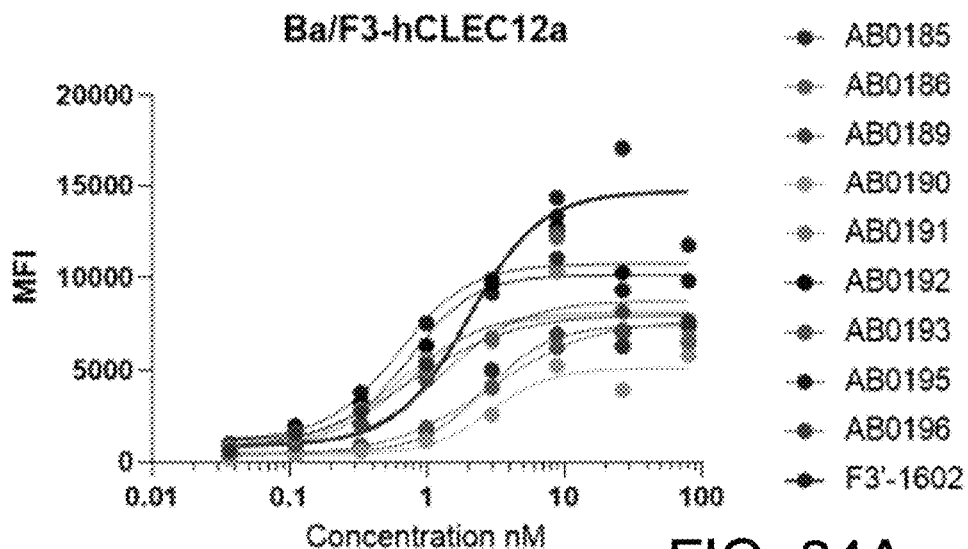
FIG. 34A-FIG. 34B are line graphs showing binding of TriNKETs derived from 9F11.B7 and hF3'-1602 TriNKET and F3-TriNKET AB0010 to Ba/F3 expressing hCLEC12A (FIG. 34A) and cancer line HL60 (FIG. 34B).
Figure 34B:
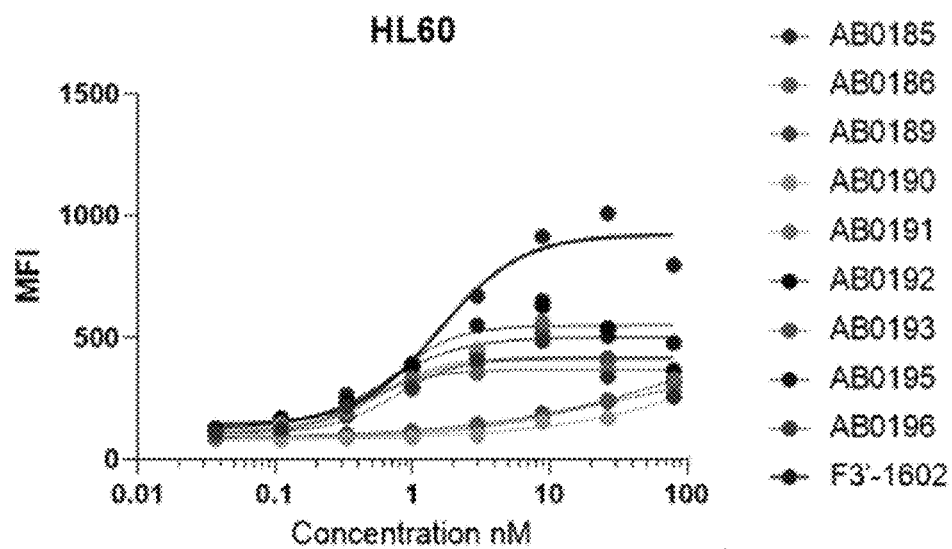

Binding of 9 fully purified humanized 9F11.B7 TriNKETs to hCLEC12A+Ba/F3 and HL60 AML cancer cell lines, shown in FIG. 34A and FIG. 34B, was tested by FACS. AB0190, AB0193 and AB0196 showed inferior binding EC50 values for both cell lines (Table 31), which correlates with poor behavior in SPR described in Table 30. EC50 values for the remaining 6 clones were similar, showing correlation with the SPR data.

TABLE 31

Binding EC50 and max MFI of 9F11.B7 based F3'-TriNKETs to hCLEC12A + Ba/F3 isogenic and HL60 AML cell lines

| Test Article | hCLEC12A + Ba/F3 isogenic cell line | | HL60 cancer cell line | |
|---|---|---|---|---|
| | EC50 (nM) | Max binding MFI | EC50 (nM) | Max binding MFI |
| AB0185 | 0.7 | 8025 | 0.4 | 372 |
| AB0186 | 0.7 | 8160 | 0.5 | 412 |
| AB0189 | 1.3 | 8760 | 0.7 | 420 |
| AB0190 | 2.9 | 5139 | N/A | n/a |
| AB0191 | 0.6 | 7941 | 0.6 | 420 |
| AB0192 | 0.7 | 10158 | 0.6 | 503 |
| AB0193 | 2.9 | 7732 | 19 | 345 |
| AB0195 | 0.6 | 10775 | 0.7 | 551 |
| AB0196 | 2.7 | 7427 | 135 | 650 |
| F3'-1602 | 2.0 | 14712 | 1.6 | 924 |

Figure 35:
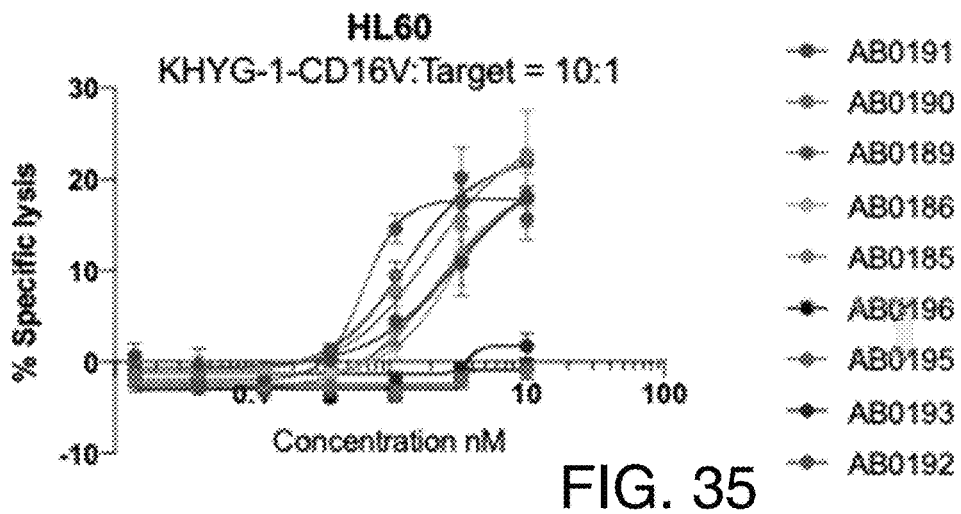
FIG. 35 are line graphs showing NK cell-mediated lysis of CLEC12A-expressing cancer cell line HL60 in the presence of TriNKETs derived from 9F11.B7.

Potencies of 9F11.B7-based TriNKETs were assessed in KHYG-1-CD16aV cell mediated cytotoxicity assay (FIG. 35 and Table 32). AB0190, AB0193 and AB0196 displayed minimal activity. AB0189 and AB0192 showed the highest potency among other TriNKET candidates. AB0192 TriNKET emerged as the lead TriNKET from 9F11.B7 humanization efforts.

TABLE 32

Potency of humanized 9F11.B7 F3'-TriNKETs in KHYG-1CD16aV mediated cytotoxicity assay.

| | HL60 AML cancer cell line | |
|---|---|---|
| Test article | EC50 (nM) | Max cell lysis (%) |
| AB0185 | 2.0 | 25 |
| AB0186 | 2.7 | 19 |
| AB0189 | 0.6 | 18 |
| AB0190 | n/a | n/a |
| AB0191 | 3.1 | 22 |
| AB0192 | 1.3 | 22 |
| AB0193 | n/a | n/a |
| AB0195 | 2.2 | 20 |
| AB0196 | n/a | n/a |

Figure 36A:
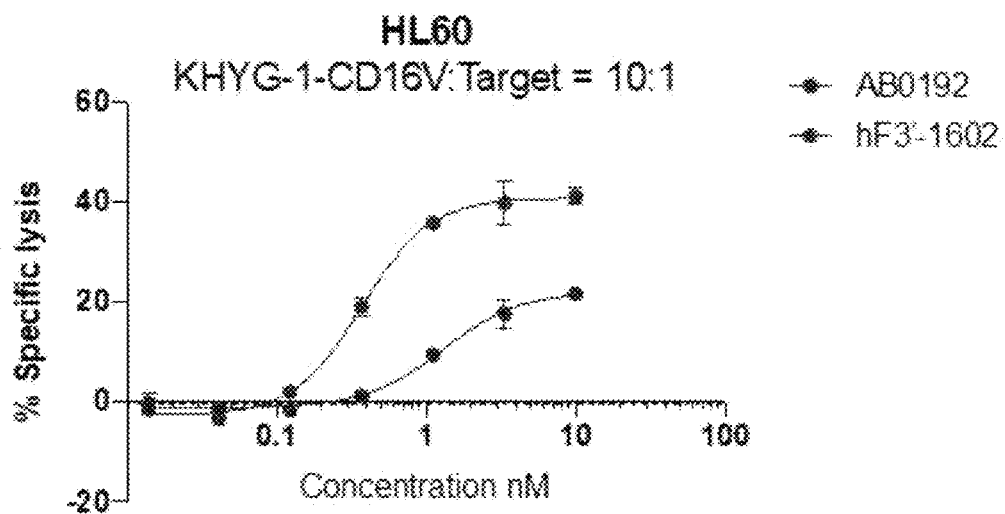
FIG. 36A-FIG. 36B are line graphs showing NK cell-mediated lysis of CLEC12A-expressing cancer cell line HL60 using KHYG-CD16V cells (FIG. 36A) and primary NK cells (FIG. 36B) in the presence of hF3'-1602 TriNKET and AB0192.

The potency of AB0192 was assessed in a KHYG-1-CD16aV cell mediated cytotoxicity assay in comparison with the F3'-1602 (FIG. 36A). F3'-1602 showed improved efficacy over AB0192 both in EC50 (0.4 nM and 1.3 nM, respectively) and percentage maximum HL-60 cell lysis (41% and 22%, respectively).

Figure 36B:
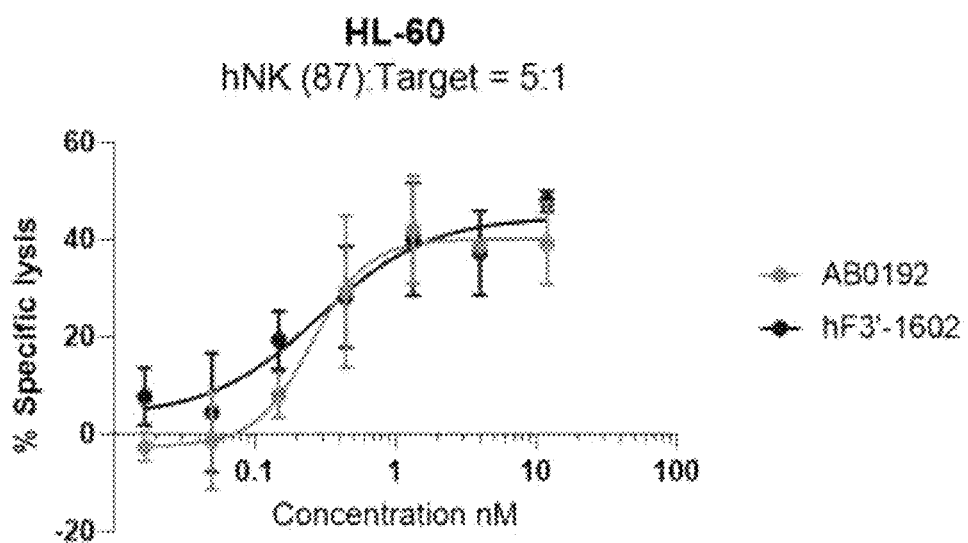

The potencies of AB0192 and F3'-1602 TriNKETs were further assessed in a human primary NK cell mediated cytotoxicity assay (FIG. 36B). F3'-1602 and AB0192 induced lysis of HL60 AML cancer with similar EC50 and % max cell killing (Table 33).

AB0192 satisfies TriNKET pre-developability criteria: high affinity for hCLEC12A, efficient binding to AML cells, high potency in killing AML cells in primary NK cells mediated cytotoxicity assay, high thermostability, $T_{m1} \geq 65°$ C., low hydrophobicity, $8.0 < PI < 9.0$, expression level in transient transfection similar to monoclonal antibody, clean PSR (Table 33).

F3'-1602 demonstrated better potency, higher humanness, and fewer potential sequence liabilities compared to AB0192. Structural stability of F3'-1602 was confirmed in an extensive panel of accelerated stability and forced degradation studies, described in Example 15. Therefore, F3'-1602 was chosen for further development.

TABLE 33

Summary of biochemical characterization of F3'-1602 (F3'-1602) and AB0192.

| Properties | F3'-1602 | AB0192 |
|---|---|---|
| Number of back mutations | 5 | 7 |
| % humanness T20 score | 80.09 (VH), 84.67(VK) | 82.3 (VH), 81.2 (VK) |
| Potential seq liabilities | DS (isomerization site) in CDRH3 | M (oxidation site) in CDRH3 DG (isomerization site) in CDRH3 NS (deamidation site) in CDRH1 |
| HIC retention time relative to Humira (min) | +0.91 | +0.97 |
| pI (cIEF, major peak) | 8.81 | N/A |
| Thermal stability by DSC (Tm1° C.) in PBS | 66.8 | 65.0 |
| Expression Titer (ExpiCHO, mg/L) | 73.3 50.2 | 64.4 |
| EC50 (nM): Potency (KHYG-CD16a mediated, HL60 cell line) | 0.4 | 1.3 |

TABLE 33-continued

Summary of biochemical characterization of F3'-1602 (F3'-1602) and AB0192.

| Properties | F3'-1602 | AB0192 |
|---|---|---|
| EC50 (nM): Potency (Primary NK cell mediated, HL60 cell line) | 0.29 | 0.25 |
| Affinity to hCLEC12A by SPR ($K_D$ in nM) | 0.80 | 1.2 |
| PSR specificity | Clean | Clean |

Figure 37B:
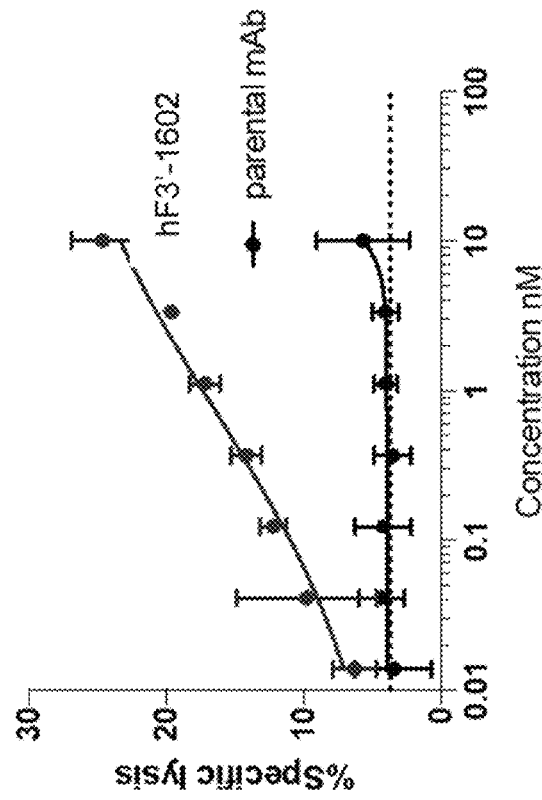
FIG. 37A-FIG. 37B are line graphs showing NK cell-mediated lysis of CLEC12A-expressing cancer cell line PL21 (FIG. 37A) and THP-1 (FIG. 37B) in the presence of hF3'-1602 TriNKET and parental mAb.
Figure 37A:
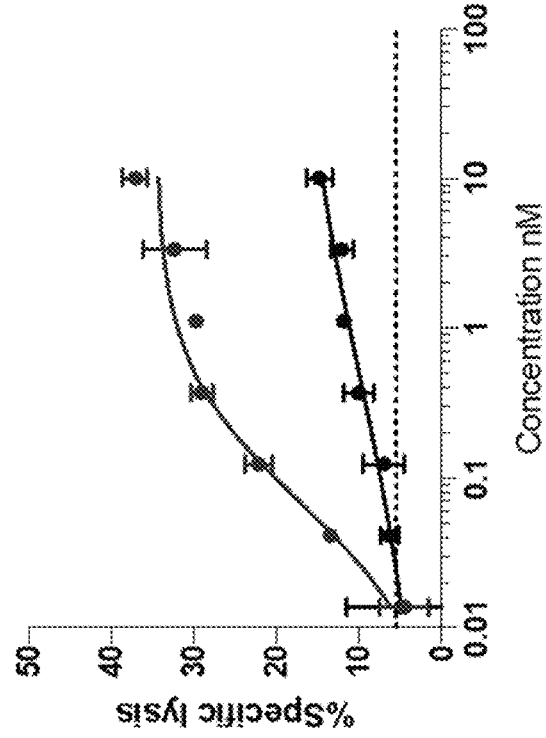

F3'-1602 and its corresponding humanized mAb (h16B8.C8) were assessed for cell killing by primary NK cell mediated cytotoxicity. F3'-1602 demonstrated potent killing of PL21 (FIG. 37A) and THP-1 (FIG. 37B) AML cancer cell lines, whereas the corresponding monoclonal antibody markedly reduced potency (Table 34).

TABLE 34

Potency of F3'-1602 in comparison with parental mAb in primary NK mediated cytotoxicity assay.

| | F3'-1602 | | Parent mAb | |
|---|---|---|---|---|
| Cell line | EC50 (nM) | Max lysis (%) | EC50 (nM) | Max lysis (%) |
| PL21 | 0.07 | 35 | 0.5 | 18 |
| THP-1 | 0.7 | 30 | NA | NA |

Example 6. Assessment of TriNKET Binding to Cell Expressed Human Cancer Antigens Isogenic Ba/F3 cells expressing hCLEC12A, and human cancer cell lines HL60 and PL21 expressing human CLEC12A were used to assess tumor antigen binding of CLEC12A targeted TriNKETs and mAbs.

AB0089 is an F3' TriNKET derived from the same binding domain as parental mAb AB0305. AB0192 is an F3' TriNKET derived from the same binding domain as parental mAb AB0192. AB0237 is an F3' TriNKET, also referred to herein as hF3'-1602 or F3'-1602 TriNKET, and is derived from scFv-1602. AB0300 (also referred to as F3'-1602si or AB0237si) is also an F3' TriNKET from the same sequence as AB0237 but bears mutations in the CH2 domain to eliminate Fc-gamma receptor binding. F3' TriNKETs generally showed weaker binding compared to parental mAb.

To assess whether the antigen-binding site that binds NKG2D and the effector function of the Fc contributed to the cytotoxicity of AB0237, two TriNKET variants were constructed. The first variant contains mutations in the light chain variable domain of the A49 antigen-binding site that binds NKG2D. As a result, this variant does not bind human NKG2D. The amino acid sequence of the mutant light chain variable domain is DIQMTQSPSTLSASVGDRVTITCRASNSIS SWLAWYQQKPGKAPKLLIYEAS STKSGVPS RFSGSGSGTEFTLTISSLQPDDFA-TYYCQQYDDLPTFGGGTKVEIK (SEQ ID NO:282). The amino acid sequences of this first variant are otherwise identical to those of AB0237. The second variant contains mutations in the Fc domain. Specifically, each polypeptide chain of the Fc domain contains L234A/L235A/P329G substitutions (numbered under EU numbering system), which was reported to reduce the binding of the Fc to Fcγ receptors. The amino acid sequences of this second variant are otherwise identical to those of AB0237. F3'-palivizumab contains the same NKG2D and CD16 binder sequences as in F3'-1602 and an scFv that binds an irrelevant target not expressed in either of the two cancer cell lines tested. EC50 values are provided in Table 35.

TABLE 35

EC50 values and % max cell lysis in KHYG-1-CD16aV-mediated potency assay.

| | PL-21 | | HL-60 | |
|---|---|---|---|---|
| Test article | EC50 nM | % Max lysis | EC50 nM | % Max lysis |
| F3'-1602 | 0.7 | 33 | 0.27 | 87 |
| F3'-1602-Dead-2D | NA | 2 | 2.5 | 33 |
| F3'-1602 si | NA | NA | NA | 12 |
| F3'-Palivizumab | NA | NA | NA | NA |

The cells were then incubated with a fluorophore conjugated anti-human IgG secondary antibody and were analyzed by flow cytometry. The mean fluorescence intensity (MFI) values were normalized to secondary antibody only controls to obtain fold over background (FOB) values.

AB0237 demonstrates high affinity binding to the two AML cell lines tested, namely, HL60 (FIG. 38A) and PL21 (FIG. 38B). The EC50 for HL60 was 2.2 nM and the EC50 for PL21 was 1.2 nM.

Figure 39A:
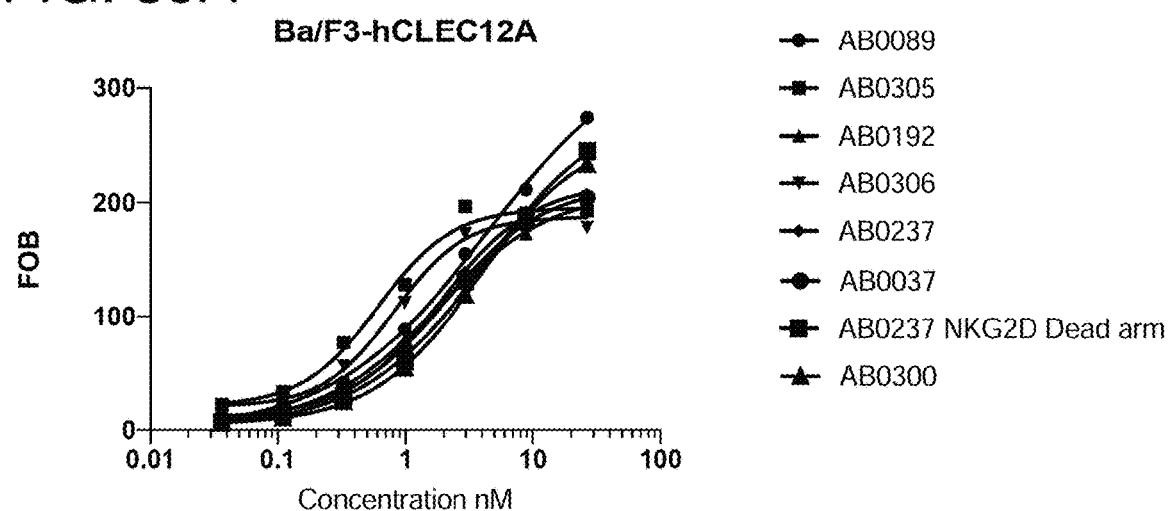
FIG. 39A-FIG. 39C are line graphs showing binding of CLEC12A-targeting TriNKETs, parental mAbs, and AB0237 NKG2D dead arm variant TriNKET to Ba/F3 expressing hCLEC12A (FIG. 39A), and cancer cell lines HL60 (FIG. 39B) and PL21 (FIG. 39C).
Figure 39B:
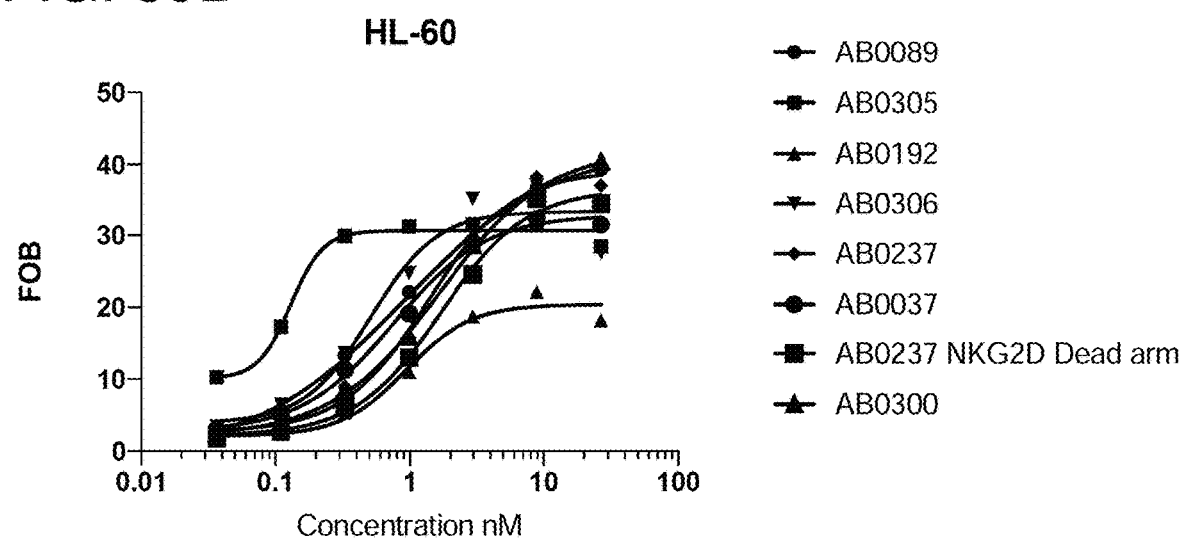
Figure 39C:
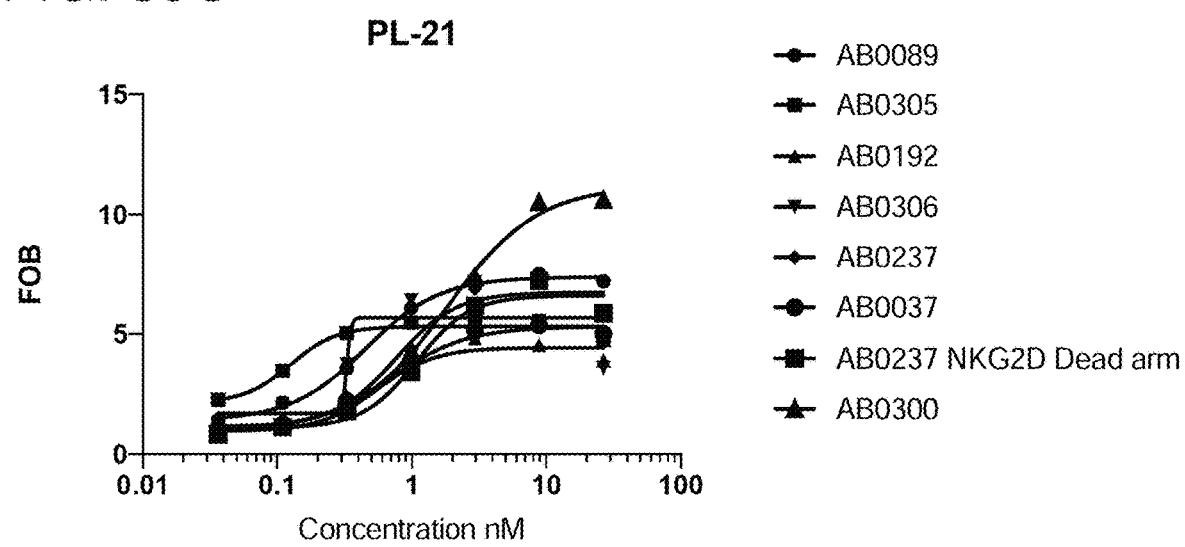

For two of the three binders F3' TriNKETs showed higher loading onto target cells compared to its parental mAb. Mutated variants of AB0237, AB0300 and AB0237 NKG2D dead arm, showed similar binding as their parental TriNKET AB0237 to Ba/F3-hCLEC12A (FIG. 39A), HL-60 (FIG. 39B), and PL-21 (FIG. 39C).

Example 7. Assessment of TriNKET Surface Retention to Cell Expressed Human Cancer Antigens Human cancer cell lines HL60 and PL21 expressing human CLEC12A were used to assess surface retention of CLEC12A-TriNKETs after incubation with cells. PL21 or HL60 cells in duplicate plates were incubated with TriNKETs or mAbs as indicated. The first plate was moved to 37° C. for two hours, whereas the second plate was incubated on ice for 20 minutes. After the respective incubation times, cells were washed. Surface bound TriNKET or mAb was detected using a fluorescent secondary antibody for flow cytometry.

Surface retention was calculated as follows:

% surface retention=(sample MFI 2 hrs/sample MFI 20 min))*100%

Figure 40A:
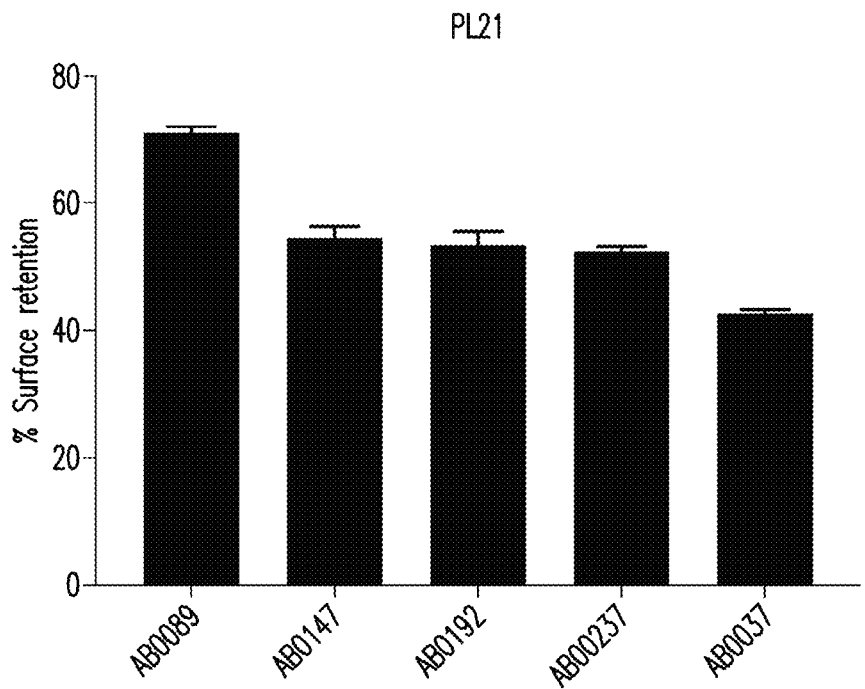
FIG. 40A-FIG. 40B are bar graphs showing surface retention of CLEC12A-targeting TriNKETs and parental mAbs to cell lines PL21 (FIG. 40A) and HL60 (FIG. 40B).
Figure 40B:
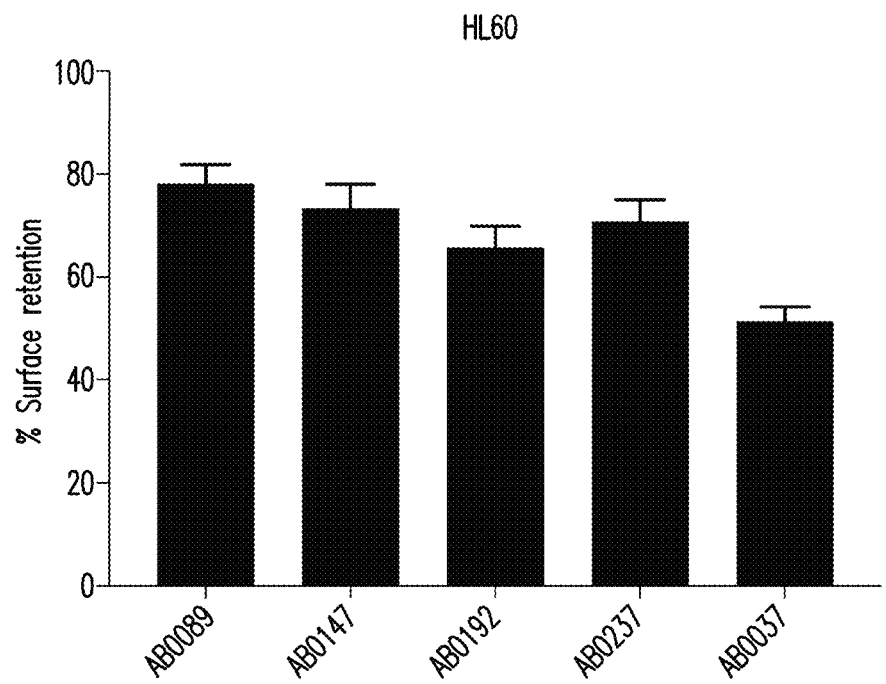

FIG. 40A and FIG. 40B show cell surface retention of TriNKETs bound to CLEC12A+ cell lines, PL21 and HL60, respectively. Monovalent binding TriNKETs, AB0089, AB0147, AB0192 and AB0237 showed high surface retention at two hours on both PL21 and HL60 cells lines. For both PL21 and HL60, bivalent binding mAb AB0037 showed lower surface retention at two hours compared to TriNKETs.

Example 8. Human NK Cell Cytotoxicity Assay

Lysis of target cells was measured by the DELFIA cytotoxicity assay. Briefly, human cancer cell lines expressing CLEC12A were harvested from culture, washed with HBS, and resuspended in growth media at $10^6$/mL for labeling with BATDA reagent (Perkin Elmer AD0116). Manufacturer instructions were followed for labeling of the target cells. After labeling, cells were washed three times with HBS, and were resuspended at 0.5-1.0×10⁵/mL in culture media. 100 µl of BATDA labeled cells were added to each well of the 96-well plate. Monoclonal antibodies or TriNKETs against CLEC12A were diluted in culture media, and 50 µl of diluted mAb or TriNKET were added to each well.

To prepare NK cells, PBMCs were isolated from human peripheral blood buffy coats using density gradient centrifugation, washed, and prepared for NK cell isolation. NK cells were isolated using a negative selection technique with magnetic beads. Purity of isolated NK cells was typically >90% CD3−CD56+. Isolated NK cells were rested overnight and harvested from culture. The cells were then washed and resuspended at concentrations of $10^5$-$2.0 \times 10^6$/mL in culture media for an effector-to-target (E:T) ratio of 5:1. 50 µl of NK cells were added to each well of the plate for a total of 200 µl culture volume. The plate was incubated at 37° C. with 5% $CO_2$ for 2-3 hours.

After the incubation, the plate was removed from the incubator and the cells were pelleted by centrifugation at 200×g for 5 minutes. 20 µl of culture supernatant were transferred to a clean microplate and 200 µl of room temperature europium solution (Perkin Elmer C135-100) were added to each well. The plate was protected from light and incubated on a plate shaker at 250 rpm for 15 minutes, then read using SpectraMax i3X instruments.

Spontaneous release of a substance that can form a fluorescent chelate with europium was measured in target cells incubated in the absence of NK cells. Maximum release of such a substance was measured in target cells lysed with 1% Triton-X. % Specific lysis was calculated as follows:

% Specific lysis=((Experimental release−Spontaneous release)/(Maximum release−Spontaneous release))*100%.

Figure 41A:
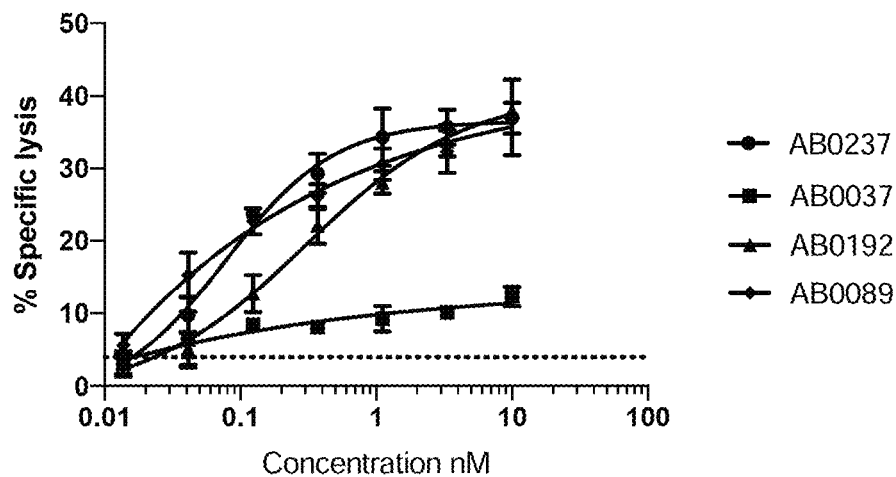
FIG. 41A-FIG. 41B are line graphs showing NK cell-mediated lysis of CLEC12A-expressing cancer cell line PL21 (FIG. 41A) and HL60 (FIG. 41B) in the presence of hF3'-1602 TriNKET, AB0192, and parental mAbs.
Figure 41B:
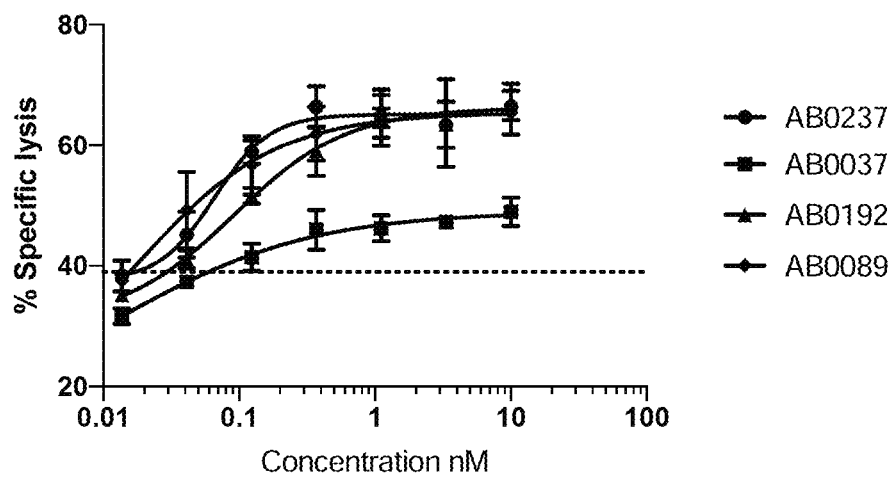

FIG. 41A and FIG. 41B show CLEC12A-TriNKET mediated killing of PL21 and HL60 target cells by rested human NK cells, respectively. AB0037 a CLEC12A targeted monoclonal antibody showed little enhancement of NK cell mediated lysis of PL21 and HL60 target cells. All three CLEC12A targeted TriNKETs (AB0237, AB0192 and AB0089) showed superior lysis of target cells compared to the CLEC12A targeted monoclonal antibody. EC50 values are shown in Table 36.

TABLE 36

Potency of F3'-1602 in comparison with parental mAb in primary NK mediated cytotoxicity assay.

| | F3'-1602 | | Parent mAb | |
|---|---|---|---|---|
| Cell line | EC50 (nM) | Max lysis (%) | EC50 (nM) | Max lysis (%) |
| PL-21 | 0.07 | 35 | 0.5 | 18 |
| THP-1 | 0.7 | 30 | NA | NA |

Figure 42A:
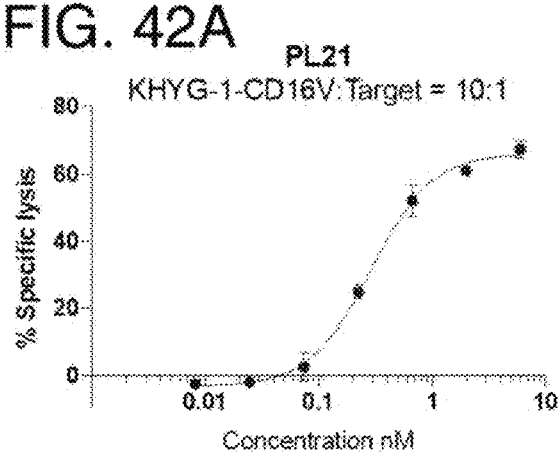
FIG. 42A-FIG. 42B are line graphs showing NK cell-mediated lysis of CLEC12A-expressing cancer cell line PL21 (FIG. 42A) and HL60 (FIG. 42B) in the presence of hF3'-1602 TriNKET.
Figure 42B:
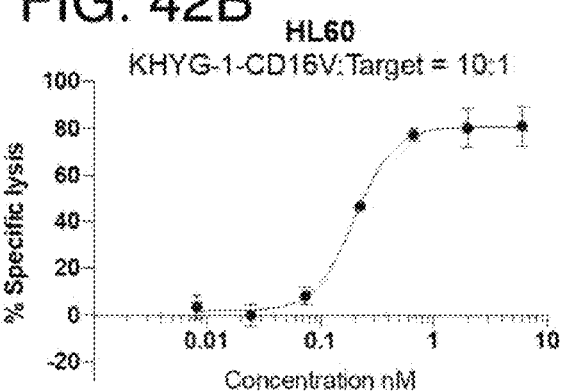

To confirm the cytoxicity findings, a second NK cell line, KHYG-1-CD16aV was engineered to stably express CD16aV and NKG2D, and the assay was conducted as described above. Cytotoxicity of PL21 is shown in FIG. 42A; Cytotoxicity of HL60 is shown in FIG. 42B. The EC50 values and maximum lysis values were derived from the cell lysis curves by the GraphPad Prism software using four parameter logistic non-linear regression curve fitting model (Table 37). F3'-1602 shows subnanomolar EC50 and high efficiency maximum lysis in the KHYG-1 CD16A mediated cytotoxicity assay.

TABLE 37

Potency of F3'-1602 in KHYG-1-CD16aV mediated cytotoxicity assay.

| Test articles | Cell line | EC50 | % Max lysis |
|---|---|---|---|
| F3'-1602 #1 | PL21 | 0.3 | 66 |
| F3'-1602 #2 | HL60 | 0.2 | 77 |

Example 9. Primary Human CD8+ T Cell Cytotoxicity Assay

Lysis of target cells was measured by the DELFIA cytotoxicity assay as described in Example 8, except that CD8+ T cells were used as immune effector cells. CD8+ T cells were prepared as follows: Human PBMCs were isolated from human peripheral blood buffy coats using density gradient centrifugation with Lymphoprep and SepMate 50, according to the manufacturer's instructions. Isolated PBMCs were stimulated with 1 µg/mL ConA (an IL-2 culture supplement) in culture media at 37° C. for 18 hours. ConA was then removed and PBMCs were cultured with 25 units/mL IL-2 at 37° C. for 4 days. CD8+ T cells were purified using a negative selection technique with magnetic beads (EasySep™ Human CD8+ T Cell Isolation Kit), according to the manufacturer's instructions. CD8+ T cells were cultured in media containing 10 ng/mL IL-15 at 37° C. for 6-13 days before using in the cytolysis assay.

Figure 43:
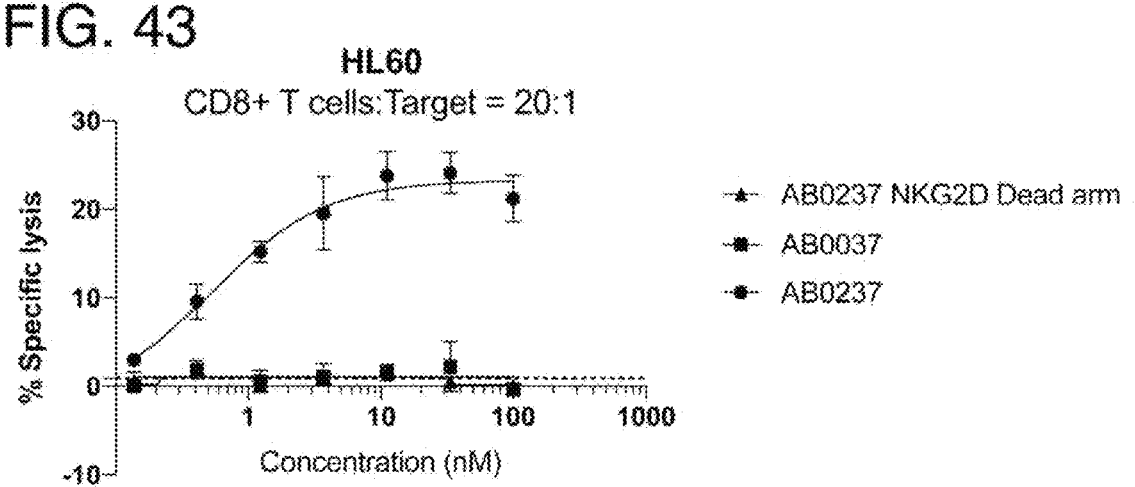
FIG. 43 are line graphs showing CD8-T cell-mediated lysis of CLEC12A-expressing cancer cell line PL21 in the presence of hF3'-1602 TriNKET, parental mAb, or an NKG2D-dead variant thereof.
Figure 44A:
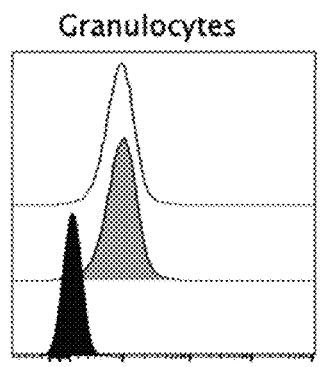
FIG. 44A-FIG. 44I are a set of histograms showing binding of hF3'-1602 TriNKET (grey), parental mAb (white), and control IgG (black) to blood cells. Blood cells include granulocytes (FIG. 44A), monocytes (FIG. 44B), B cells (FIG. 44C), NK cells (FIG. 44D), NKT cells (FIG. 44E), Dendritic cells (FIG. 44F), CD4+ cells (FIG. 44G), CD8+ cells (FIG. 44H), and Lin-CD34+ cells (FIG. 44I).
Figure 44B:
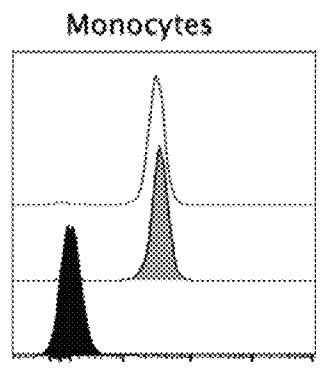
Figure 44C:
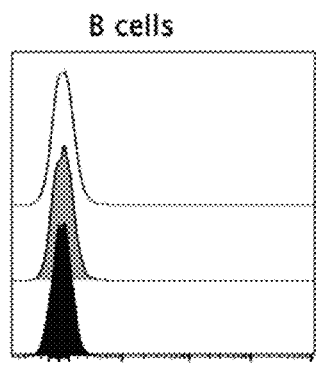
Figure 44D:
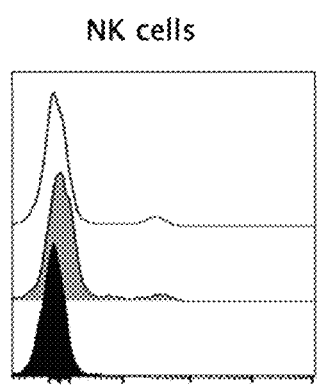
Figure 44E:
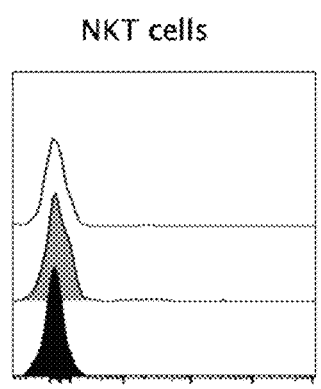
Figure 44F:
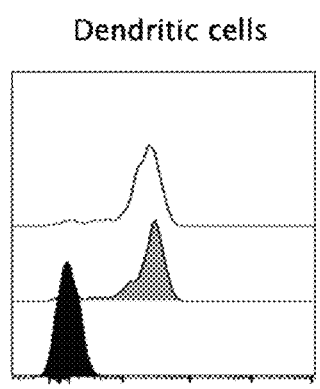
Figure 44G:
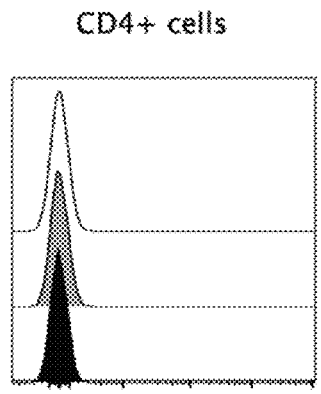
Figure 44H:
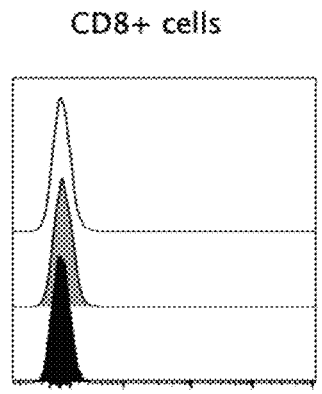
Figure 44I:
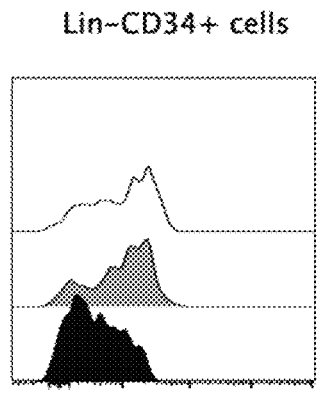

As shown in FIG. 43, AB0237 TriNKET, but not parental AB0037 mAb, significantly enhanced the ability of CD8 T cell to lyse target cells. AB0237 TriNKET increased CD8+ T cell-mediated lysis of cells in a dose-dependent manner.

To assess whether the antigen-binding site that binds NKG2D and the effector function of the Fc contributed to the cytotoxicity of AB0237 TriNKET, a TriNKET variant was constructed. The variant contains mutations in the light chain variable domain of the A49 antigen-binding site that binds NKG2D. As a result, this variant does not bind human NKG2D. The amino acid sequence of the mutant light chain variable domain is DIQMTQSPSTLSASVGDRVTIT-CRASNSISSWLAWYQQKPGKAPKLLIYEAS-STKSGVPS RFSGSGSGTEFTLTISSLQPDDFA-TYYCQQYDDLPTFGGGTKVEIK (SEQ ID NO:282). The amino acid sequences of this first variant are otherwise identical to those of AB0237 TriNKET.

The ability of the variant to induce NK cell-mediated lysis of target cells was assessed using the DELFIA cytotoxicity assay described above. As shown in FIG. 43, the mutations in the NKG2D-targeting domain substantially reduced cytotoxicity. This result suggested that binding to NKG2D and binding to Fcγ receptors both contributed to the cytotoxic activity of AB0237 TriNKET.

Example 10. Assessment of TriNKET or mAb Binding to Whole Human Blood

The ability of AB0237 and mAb AB0037 to bind different types of blood cells was assessed. Briefly, human whole blood was incubated with AB0237 (grey), mAb AB0037 (white), or a human IgG1 isotype control antibody (black). The blood cells were analyzed by flow cytometry and binding of AB0237, mAb AB0037, or the isotype control antibody was detected using a fluorophore conjugated anti-human IgG secondary antibody.

As shown in FIGS. 44A-44I, staining was observed on monocytes, granulocytes, and a proportion of dendritic cells in whole blood for AB0237 and its parental mAb AB0037.

Example 11. Binding of F3'-1602 TriNKET to Fc Receptors: Label Free Surface Plasmon Resonance Characterization The binding affinities of F3'-1602 TriNKET for recombinant human and cynomolgus Fcγ Receptors was determined and compared the binding affinities of an IgG1 isotype control, trastuzumab. Binding affinity of F3'-1602 TriNKET to human and cynomolgus monkey (cyno) FcRn at pH 6.0 and pH 7.4 was also determined.

FcγR Binding

Human and cyno CD64, high and low affinity alleles of CD16a (V158 and F158, respectively), two alleles of CD32a (H131 and R131), CD16b, CD32b and cynomolgus CD16 were captured via biotin on a primed Biacore chip, prepared according to the manufacturer's instructions. Prior to FcγR binding experiment requiring a high starting concentration, F3'-1602 TriNKET and trastuzumab, samples were buffer exchanged into 1×HBS-EP+ SPR running buffer by three consecutive dilution and concentration cycles with the use of a 0.5 mL concentrator unit, resulting in >300-fold dilution of original buffer components while maintaining a high concentration of protein. Protein concentration was measured at absorbance of A280 on a NanoDrop instrument with the use of sample appropriate theoretical molar extinction coefficients (198405 $M^{-1}cm^{-1}$ for F3'-1602 TriNKET and standard IgG setting for trastuzumab).

Each FcγR binding experiment was performed with multiple cycles utilizing 2-fold serially diluted F3'-1602 TriNKET or trastuzumab. For no-signal reference, a 0 nM blank cycle at the start of each concentration series and receptor free chip surface were used. Each experimental cycle included association, dissociation and regeneration steps. All steps were executed at a flow rate of 30 μL/min and at 25° C. Analyte (F3'-1602 TriNKET or trastuzumab) concentrations, association and dissociation times, and regeneration parameters were FcγR-specific (Table 38).

TABLE 38

Parameters used in Biacore FcγR binding experiments

| Parameter | hCD64, cyno CD64 | hCD16a V158 | hCD16a F158 | cyno CD16 | hCD32a H131, R131 | hCD16b | hCD32b |
|---|---|---|---|---|---|---|---|
| Type of chip | CAP chip | | | | Type S SA chip | | |
| FcγR capture level, RU | 35-50 | 34-37 | 24-27 | | 5-15 | 10-15 | |
| Concentration range, nM | 400-1.56 | 1500-0.023 | 6000-0.023 | | 16000-125 | 24000-188 | |
| Association time, sec | 240 | 150 | | | 60 | 60 | |
| Dissociation time, sec | 600 | 300 | | | 60 | 150 | |
| Surface regeneration | CAPture kit regeneration | 5 sec pulse of 1-2 mM NaOH | | | 5 sec of 10 mM Gly, pH 3.0 | | |

The shape of the raw sensorgrams representing F3'-1602 TriNKET and trastuzumab binding recombinant human CD64 enabled fitting the data with a 1:1 kinetic fit model. The black traces representing the 1:1 kinetic fit closely follow the actual sensorgrams depicted in color in FIGS. 45A-45D.

The $\chi^2$ error value calculated by the Biacore Insight evaluation software was ≤1.9% of calculated $R_{max}$, representing a good fit. Table 39 summarizes kinetic rates and human CD64 affinity values for F3'-1602 TriNKET and trastuzumab.

TABLE 39

Kinetic parameters and affinity values of F3'-1602 TriNKET binding to human CD64.

| Sample | $k_a$ (1/Ms) | $k_d$ (1/s) | $K_D$ (nM) |
|---|---|---|---|
| F3'-1602 TriNKET | $5.3 \times 10^4$ | $2.7 \times 10^{-4}$ | 5.2 |
| | $5.2 \times 10^4$ | $2.8 \times 10^{-4}$ | 5.3 |
| | $5.1 \times 10^4$ | $2.6 \times 10^{-4}$ | 5.2 |
| | $5.2 \times 10^4$ | $2.7 \times 10^{-4}$ | 5.3 |
| Average ± SD | $(5.2 \pm 0.1) \times 10^4$ | $(2.7 \pm 0.1) \times 10^{-4}$ | 5.2 ± 0.1 |
| trastuzumab | $9.6 \times 10^4$ | $2.3 \times 10^{-4}$ | 2.4 |
| | $9.6 \times 10^4$ | $2.3 \times 10^{-4}$ | 2.5 |
| | $9.6 \times 10^4$ | $2.3 \times 10^{-4}$ | 2.5 |
| | $9.2 \times 10^4$ | $2.3 \times 10^{-4}$ | 2.5 |
| Average ± SD | $(9.3 \pm 0.1) \times 10^4$ | $(2.3 \pm 0.0) \times 10^{-4}$ | 2.5 ± 0.1 |

Figure 46A:
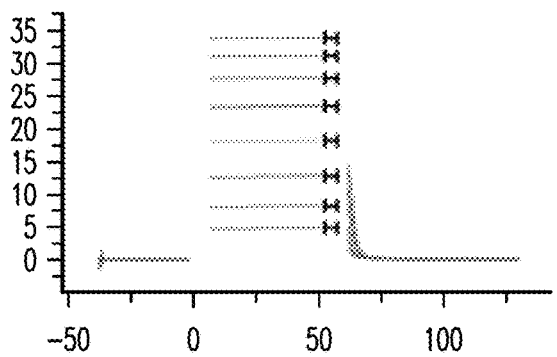
FIG. 46A-FIG. 46P are a set of sensorgrams showing SPR profiles of hF3'-1602 TriNKET (FIG. 46A-FIG. 45H) and trastuzumab control (FIG. 46I-FIG. 46P) binding to CD32a H131.
Figure 46B:
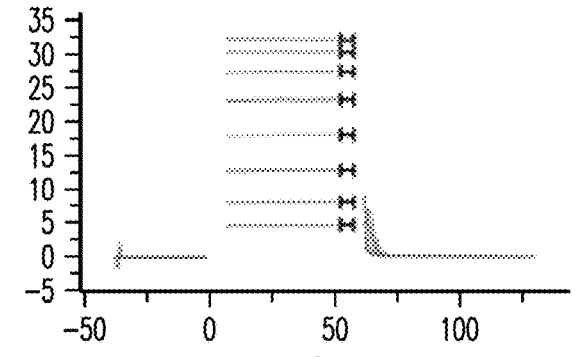
Figure 46C:
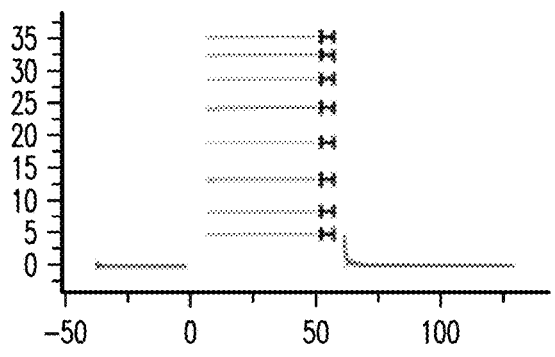
Figure 46D:
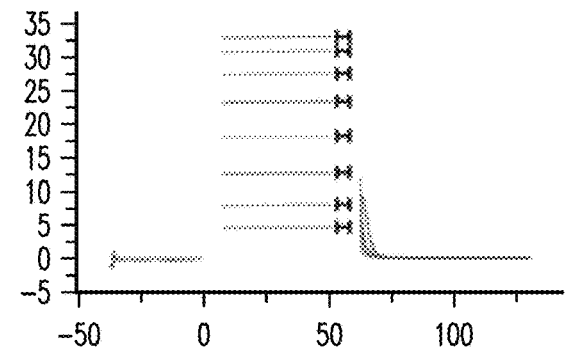
Figure 46E:
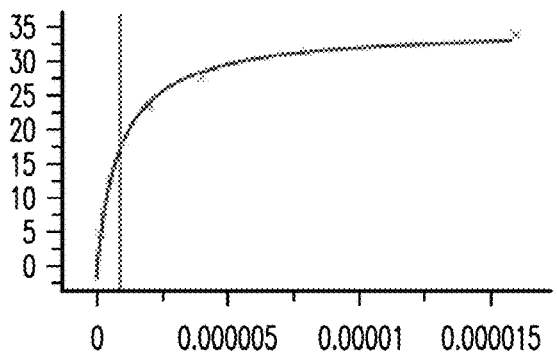
Figure 46F:
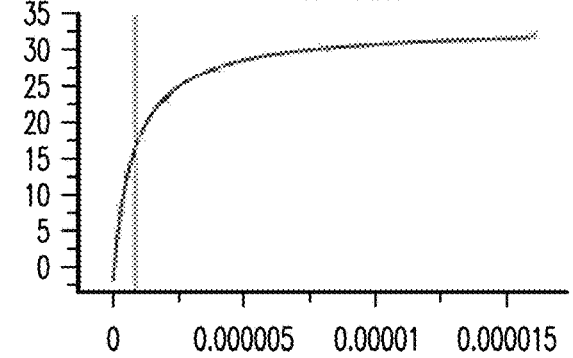
Figure 46G:
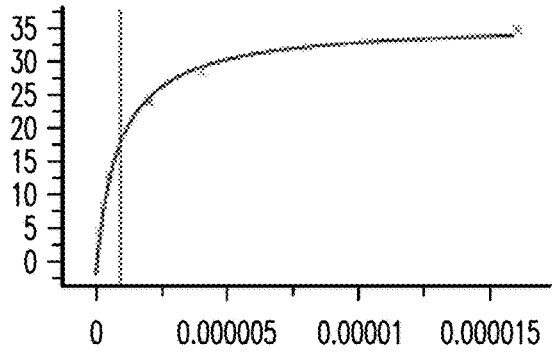
Figure 46H:
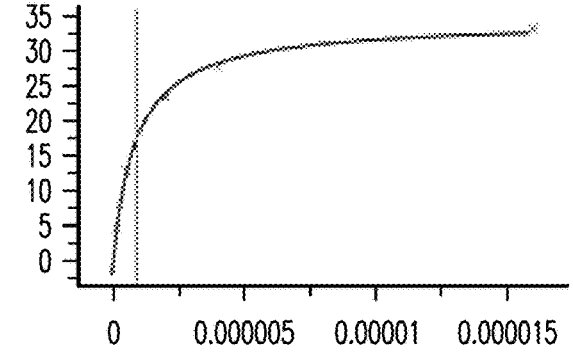
Figure 46I:
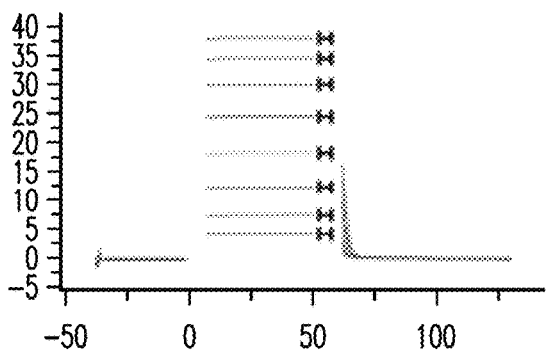
Figure 46J:
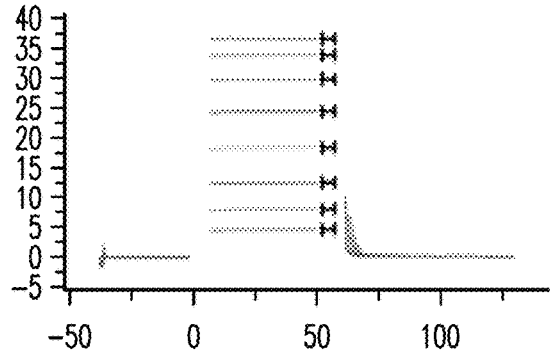
Figure 46K:

Figure 46L:
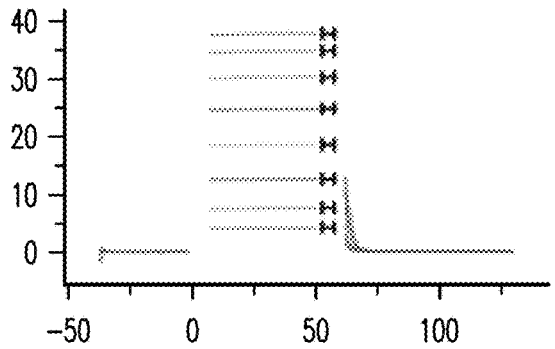
Figure 46M:
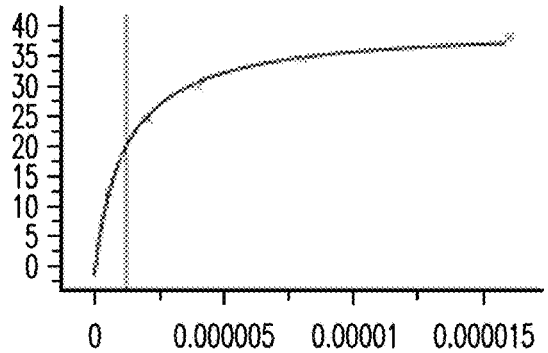
Figure 46N:
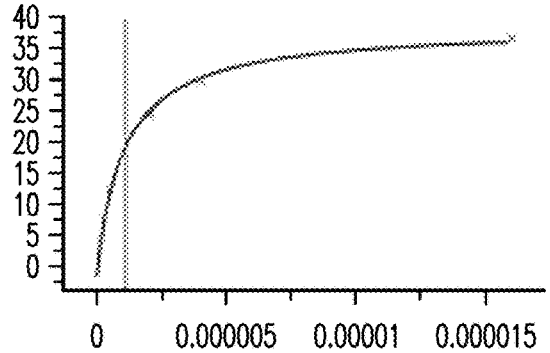
Figure 46O:
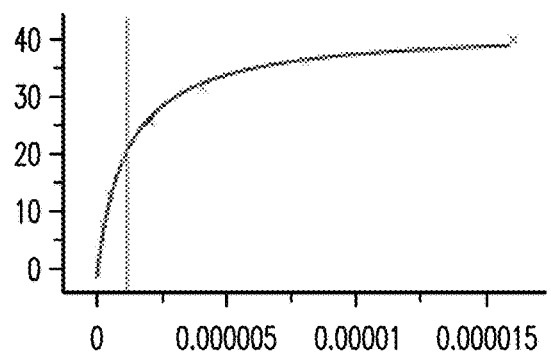
Figure 46P:
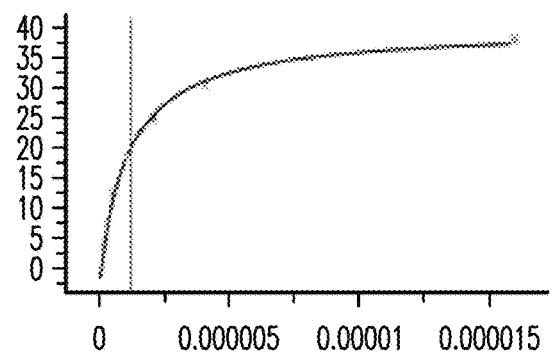

Binding of F3'-1602 TriNKET to CD32a H131 was determined as described above and is shown in FIGS. 46A-46P. The data were fit with a steady state affinity fit model; affinity values are summarized in Table 40.

TABLE 40

Affinity values of F3'-1602 TriNKET and trastuzumab for human CD32a H131.

| Sample | Replicate $K_D$ (μM) | Replicate $K_D$ (μM) | Replicate $K_D$ (μM) | Replicate $K_D$ (μM) | $K_D$ (μM) Average ± SD |
|---|---|---|---|---|---|
| F3'-1602 TriNKET | 0.9 | 0.8 | 0.9 | 0.9 | 0.9 ± 0.0 |
| trastuzumab | 1.2 | 1.1 | 1.2 | 1.1 | 1.1 ± 0.1 |

Figure 47A:
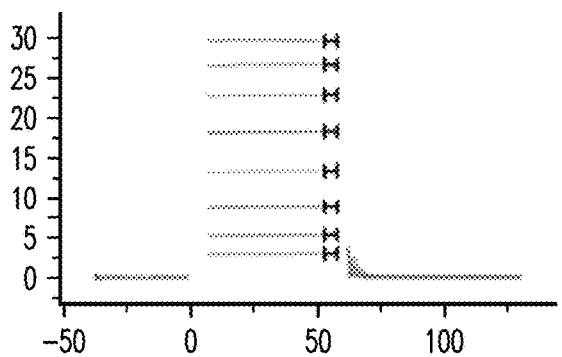
FIG. 47A-FIG. 47P are a set of sensorgrams showing SPR profiles of hF3'-1602 TriNKET (FIG. 47A-FIG. 47H) and trastuzumab control (FIG. 47I-FIG. 47P) binding to human CD32a R131 allele (FcγRIIa R131).
Figure 47B:
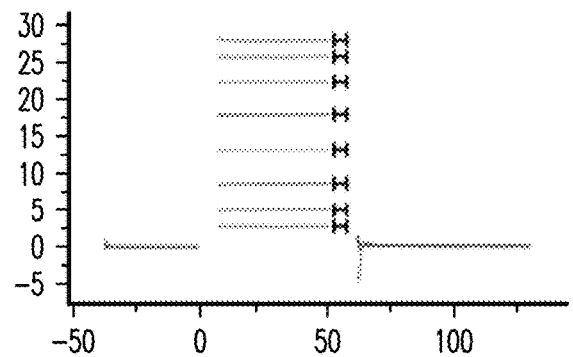
Figure 47C:
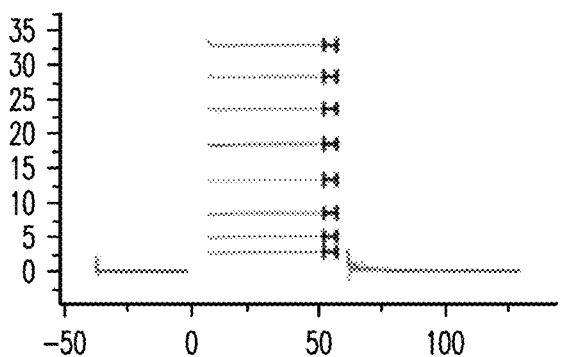
Figure 47D:
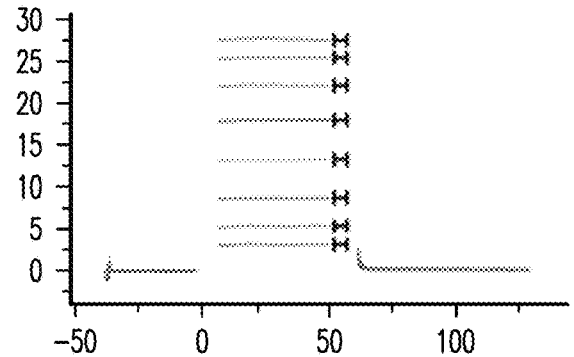
Figure 47E:
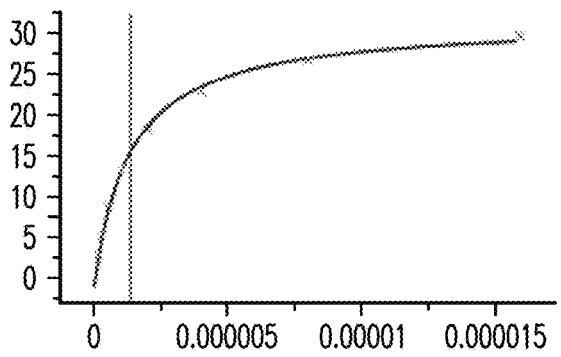
Figure 47F:
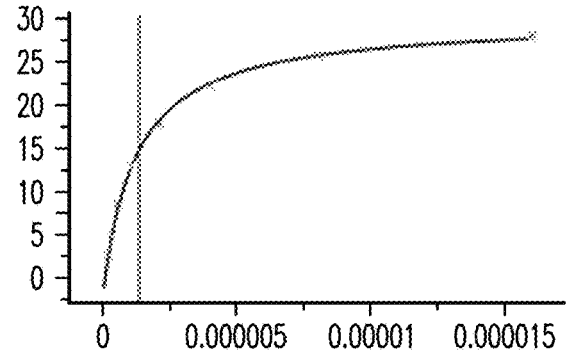
Figure 47G:
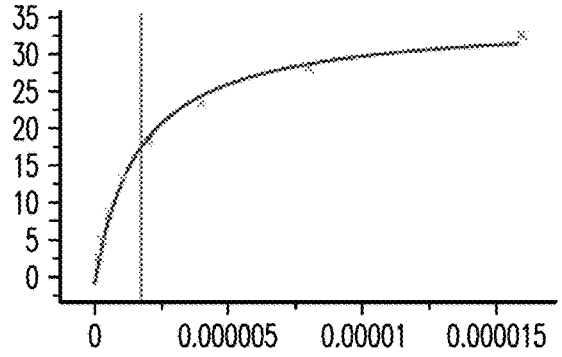
Figure 47H:
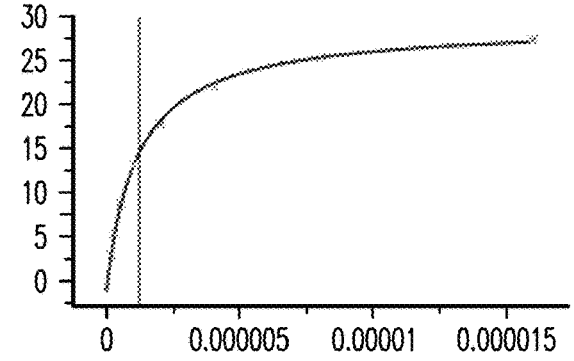
Figure 47I:
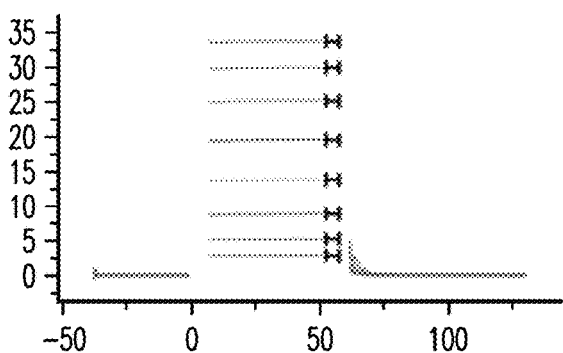
Figure 47J:
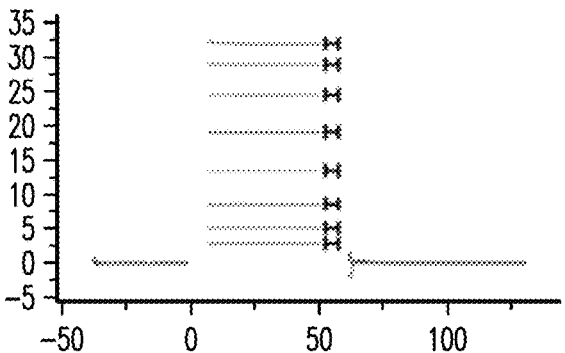
Figure 47K:
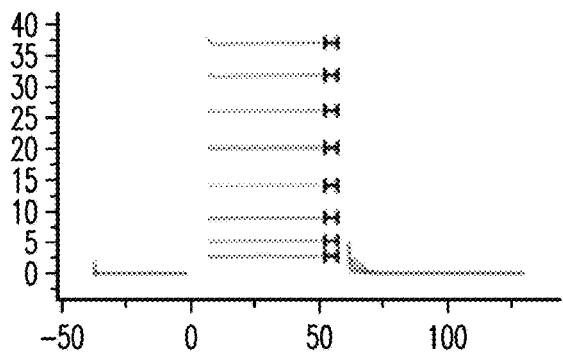
Figure 47L:
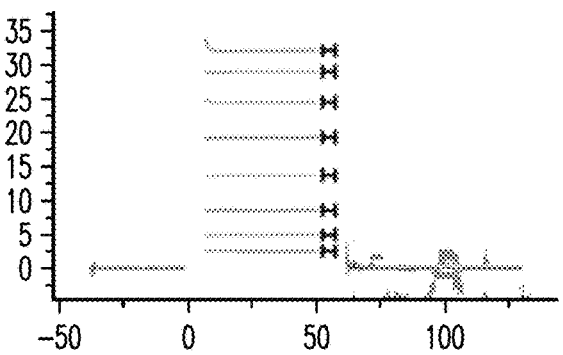
Figure 47M:
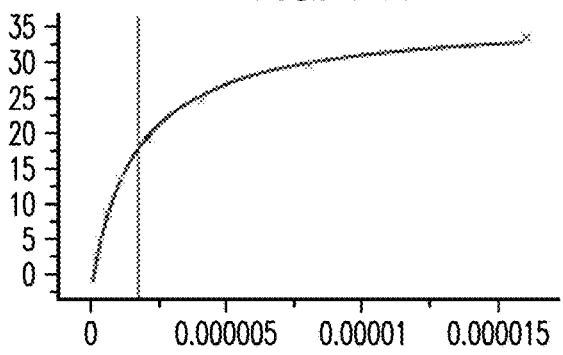
Figure 47N:
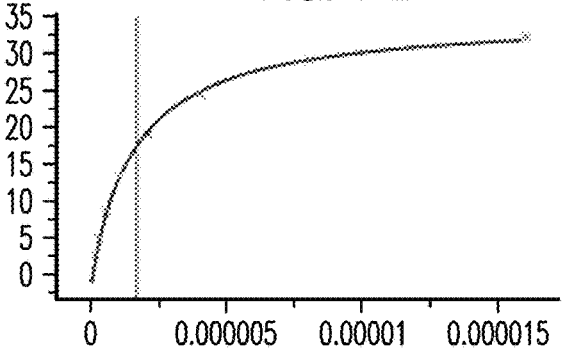
Figure 47O:
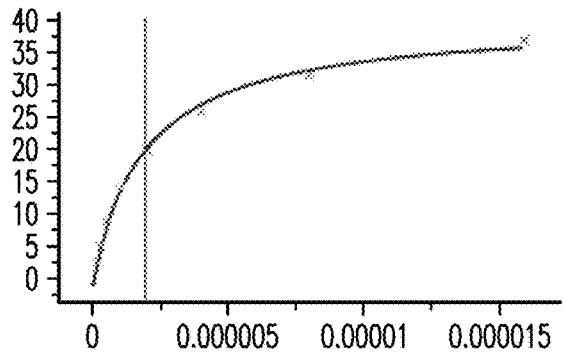
Figure 47P:
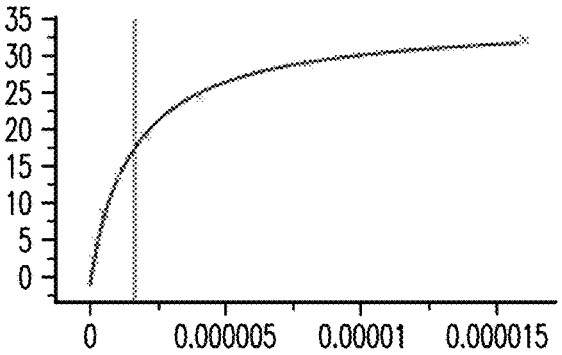

Binding of F3'-1602 TriNKET to human CD32a R131 allele (FcγRIIa R131) was determined as described above and is shown in FIGS. 47A-47P. The data were fit with a steady state affinity fit model; affinity values are summarized in Table 41.

TABLE 41

Affinity values of F3'-1602 TriNKET and trastuzumab for human CD32a R131.

| Sample | Replicate $K_D$ (nM) | Replicate $K_D$ (nM) | Replicate $K_D$ (nM) | Replicate $K_D$ (nM) | $K_D$ (nM) Average ± SD |
|---|---|---|---|---|---|
| F3'-1602 TriNKET | 1.4 | 1.3 | 1.7 | 1.2 | 1.4 ± 0.2 |
| trastuzumab | 1.7 | 1.6 | 1.9 | 1.6 | 1.7 ± 0.2 |

Binding of F3'-1602 TriNKET to human CD16a high affinity allele V158 (FcγRIIIa V158) was determined as described above and is shown in FIGS. 48A-48H. The data were fit with a 1:1 kinetic fit model; kinetic parameters and affinity values are summarized in Table 42. The affinity of F3'-1602 TriNKET for both alleles is comparable (three-fold or less difference) to trastuzumab's affinity for the same receptors.

TABLE 42

Kinetic parameters and affinity values of human CD16a V158 for F3'-1602 TriNKET and trastuzumab.

| Sample | $k_a$ (1/Ms) | $k_d$ (1/s) | Kinetic Fit $K_D$ (nM) |
|---|---|---|---|
| F3'-1602 TriNKET | $9.6 \times 10^4$ | $2.2 \times 10^{-2}$ | 234.0 |
|  | $9.5 \times 10^4$ | $2.2 \times 10^{-2}$ | 235.0 |
|  | $9.3 \times 10^4$ | $2.3 \times 10^{-2}$ | 243.0 |
|  | $9.3 \times 10^4$ | $2.2 \times 10^{-2}$ | 241.0 |
| Average ± SD | $(9.4 \pm 0.2) \times 10^4$ | $(2.2 \pm 0.0) \times 10^{-2}$ | 238.3 ± 4.4 |
| trastuzumab | $1.7 \times 10^5$ | $1.3 \times 10^{-2}$ | 76.5 |
|  | $1.7 \times 10^5$ | $1.3 \times 10^{-2}$ | 76.0 |
|  | $1.3 \times 10^5$ | $1.0 \times 10^{-2}$ | 80.3 |
|  | $1.3 \times 10^5$ | $1.0 \times 10^{-2}$ | 77.7 |
| Average ± SD | $(1.5 \pm 0.2) \times 10^5$ | $(1.1 \pm 0.1) \times 10^{-2}$ | 77.6 ± 1.9 |

Figure 49A:
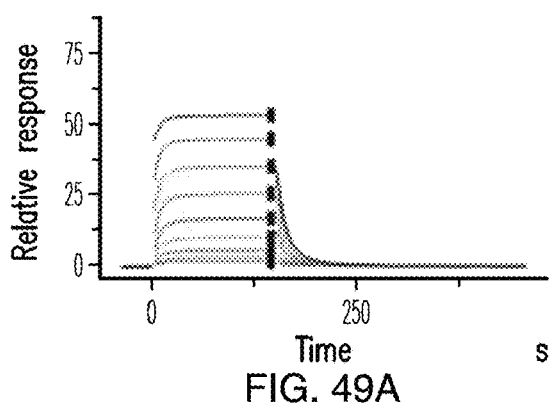
FIG. 49A-FIG. 49P are a set of sensorgrams showing SPR profiles of hF3'-1602 TriNKET (FIG. 49A-FIG. 49H) and trastuzumab control (FIG. 49I-FIG. 49P) binding to human CD16a low affinity allele F158 (FcγRIIIa F158).
Figure 49B:
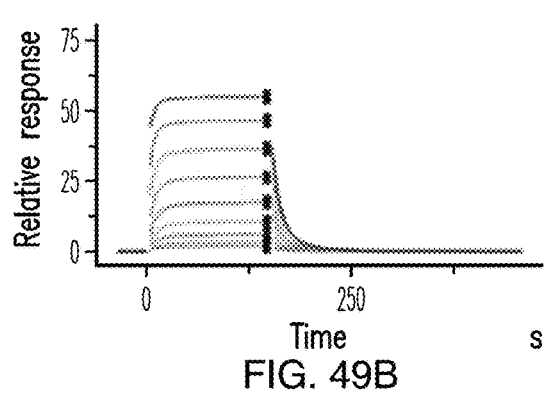
Figure 49C:
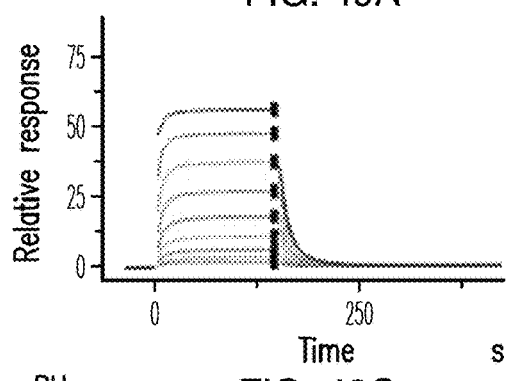
Figure 49D:
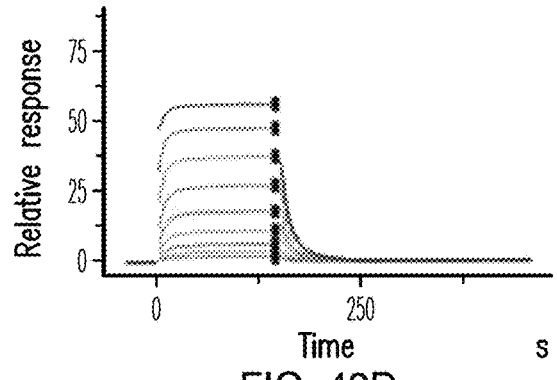
Figure 49E:
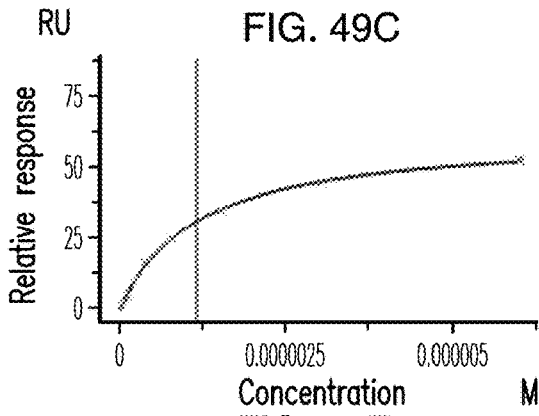
Figure 49F:
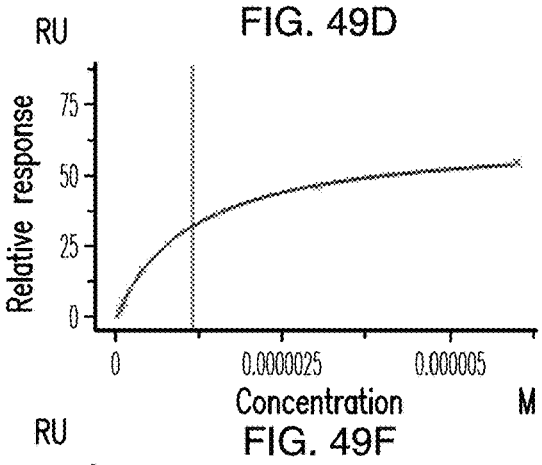
Figure 49G:
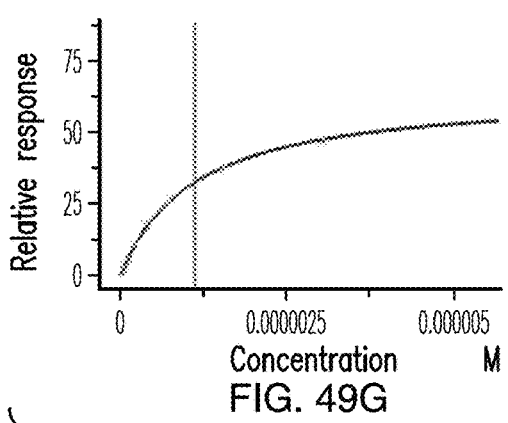
Figure 49H:
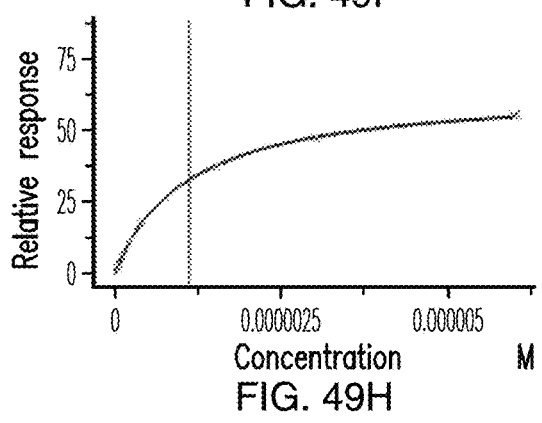
Figure 49I:
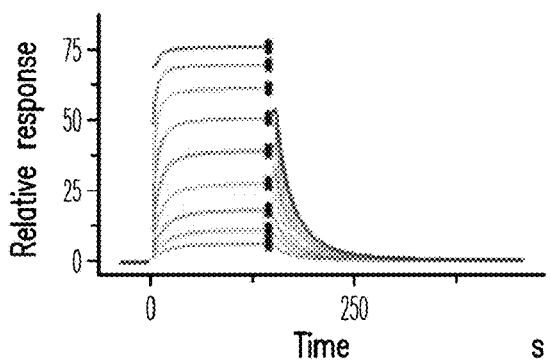
Figure 49J:
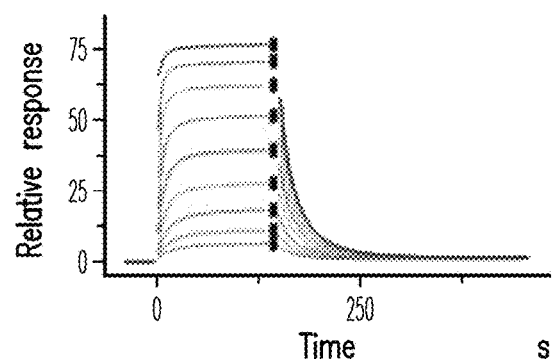
Figure 49K:
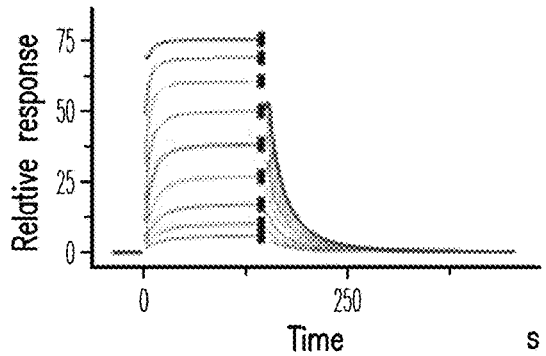
Figure 49L:
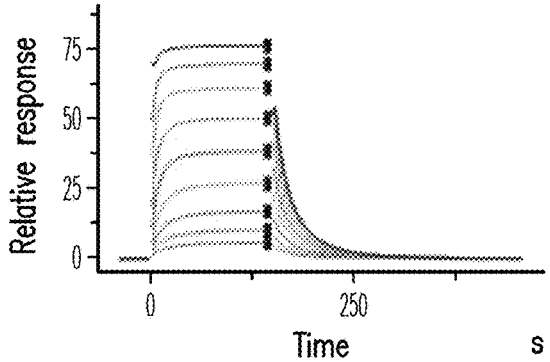
Figure 49M:
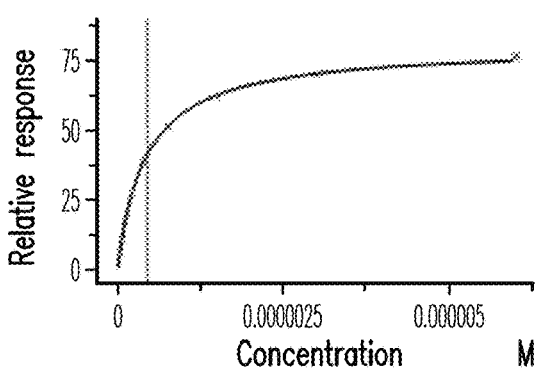
Figure 49N:
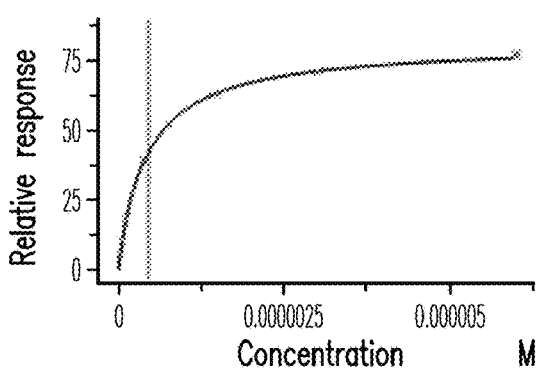
Figure 49O:
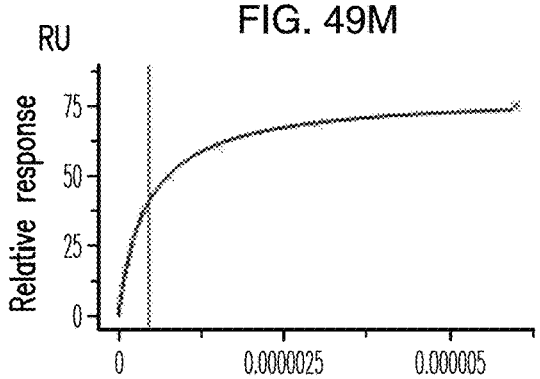
Figure 49P:
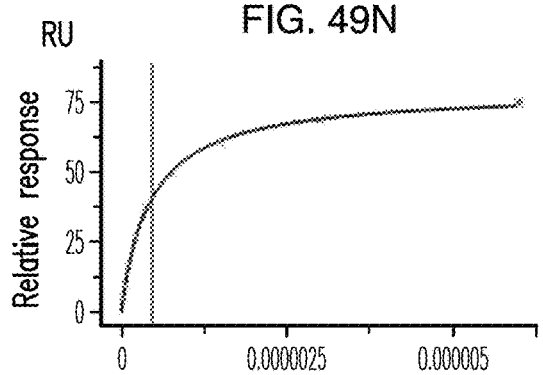

Binding of F3'-1602 TriNKET to human CD16a low affinity allele F158 (FcγRIIIa F158) was determined as described above and is shown in FIGS. 49A-49P. The data were fit with a steady state affinity fit model; affinity values are summarized in Table 43.

TABLE 43

Affinity of F3'-1602 TriNKET and trastuzumab for human CD16a F158.

| Sample | Replicate $K_D$ (nM) | Replicate $K_D$ (nM) | Replicate $K_D$ (nM) | Replicate $K_D$ (nM) | $K_D$ (nM) Average ± SD |
|---|---|---|---|---|---|
| F3'-1602 TriNKET | 1130.0 | 1120.0 | 1090.0 | 1090.0 | 1107.5 ± 20.6 |
| trastuzumab | 436.0 | 430.0 | 445.0 | 448.0 | 439.8 ± 8.3 |

Figure 50A:
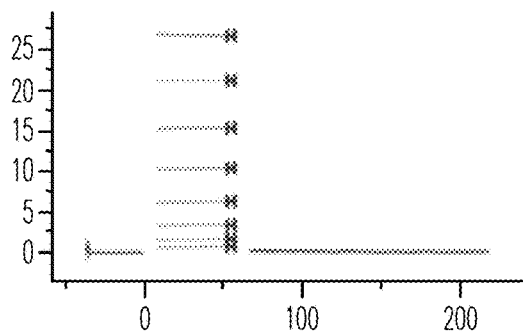
FIG. 50A-FIG. 50P are a set of sensorgrams showing SPR profiles of hF3'-1602 TriNKET (FIG. 50A-FIG. 50H) and trastuzumab control (FIG. 50I-FIG. 50P) binding to human CD32b (FcγRIIb).
Figure 50B:
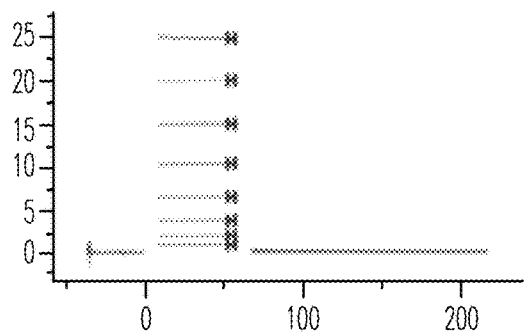
Figure 50C:
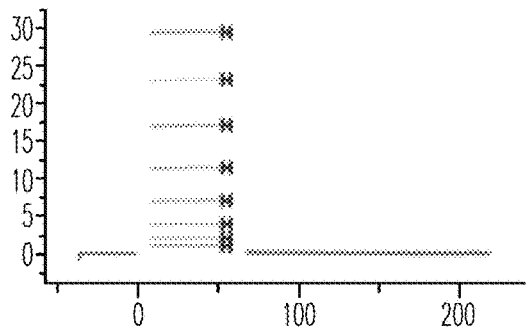
Figure 50D:
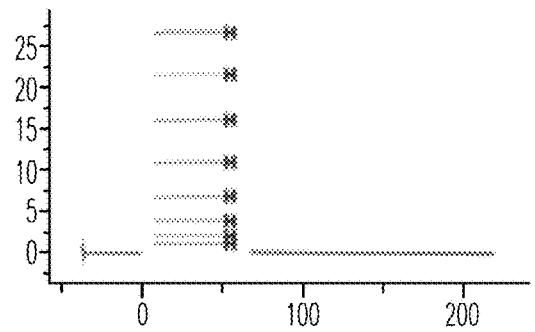
Figure 50E:
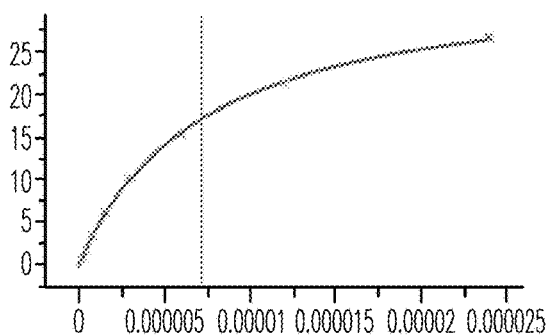
Figure 50F:
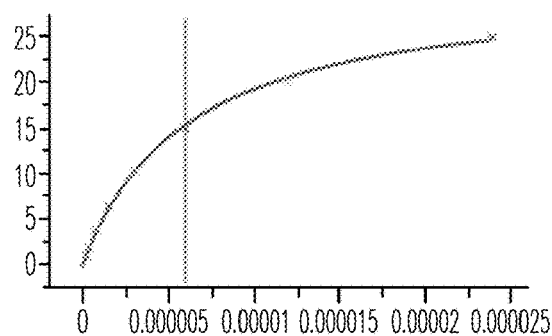
Figure 50G:
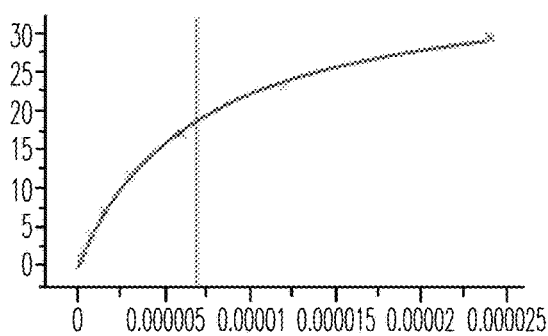
Figure 50H:
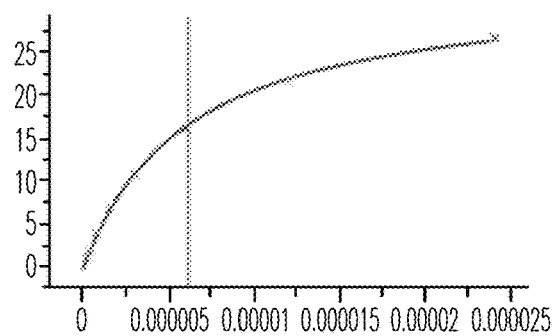
Figure 50I:
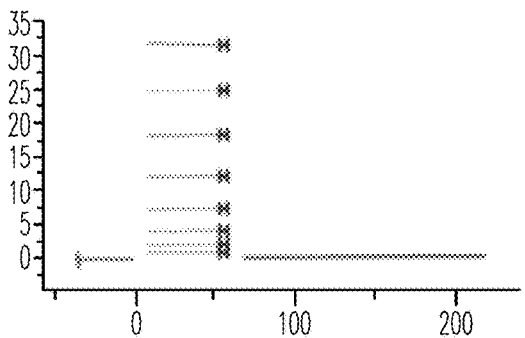
Figure 50J:
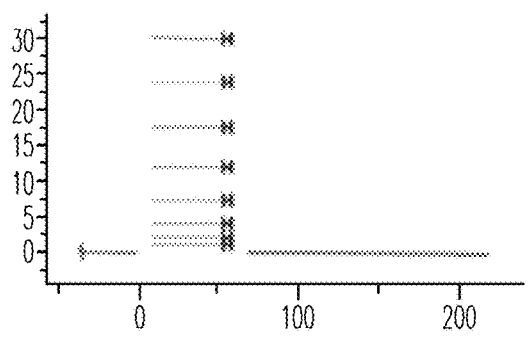
Figure 50K:
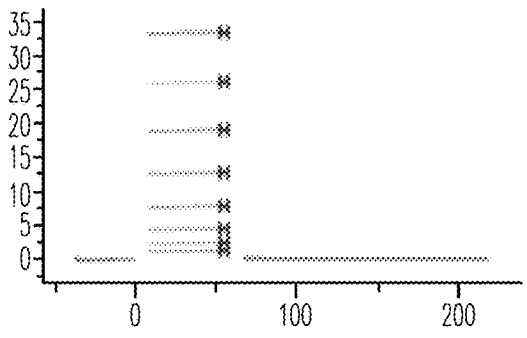
Figure 50L:
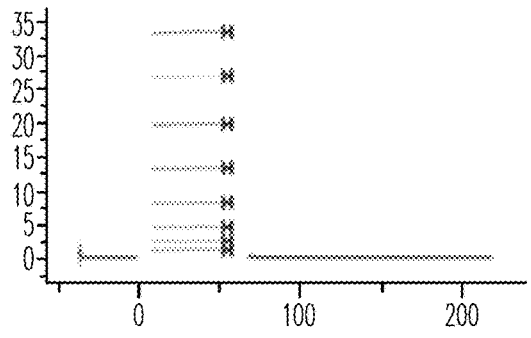
Figure 50M:
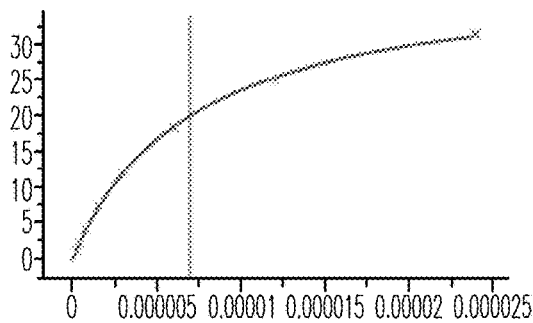
Figure 50N:
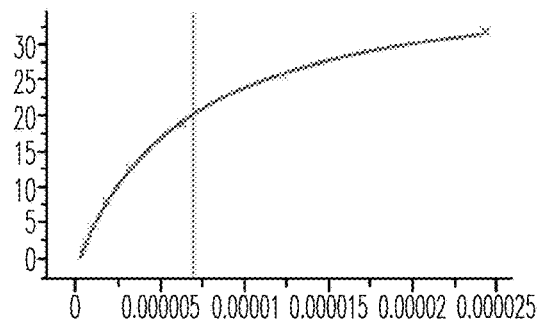
Figure 50O:
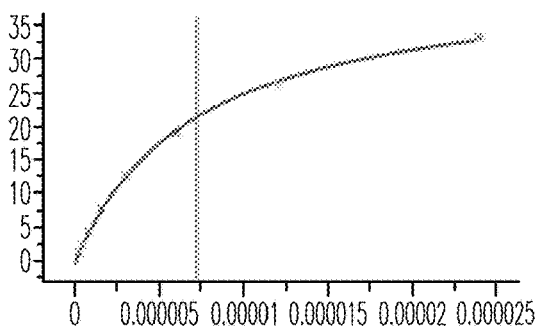
Figure 50P:
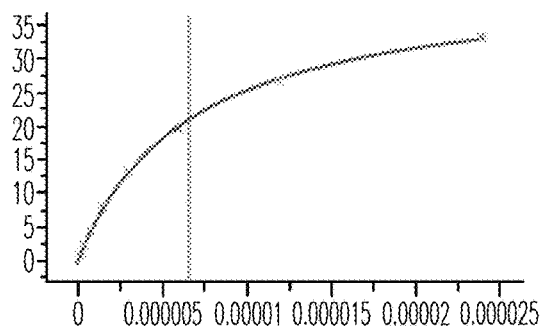

Binding of F3'-1602 TriNKET to human CD32b (FcγRIIb) was determined as described above and is shown in FIGS. 50A-50P. The data were fit with a steady state affinity fit model; affinity values are summarized in Table 44.

TABLE 44

Affinity of human CD32b for F3'-1602 TriNKET and trastuzumab.

| Sample | Replicate $K_D$ (μM) | Replicate $K_D$ (μM) | Replicate $K_D$ (μM) | Replicate $K_D$ (μM) | $K_D$ (μM) Average ± SD |
|---|---|---|---|---|---|
| F3'-1602 TriNKET | 7.2 | 6.1 | 6.9 | 6.1 | 6.6 ± 0.6 |
| trastuzumab | 7.0 | 6.7 | 7.2 | 6.6 | 6.9 ± 0.3 |

Figure 51A:
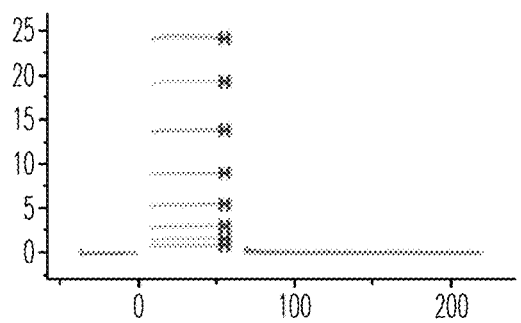
FIG. 51A-FIG. 51P are a set of sensorgrams showing SPR profiles of hF3'-1602 TriNKET (FIG. 51A-FIG. 51H) and trastuzumab control (FIG. 51I-FIG. 51P) binding to human CD16b (FcγRIIIb).
Figure 51B:
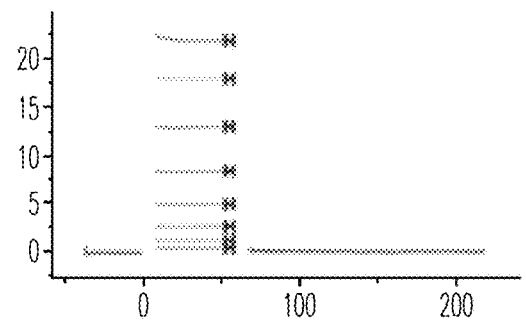
Figure 51C:
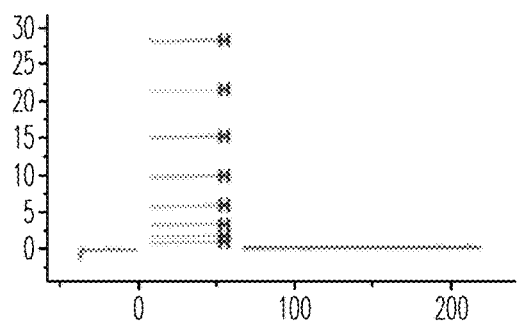
Figure 51D:
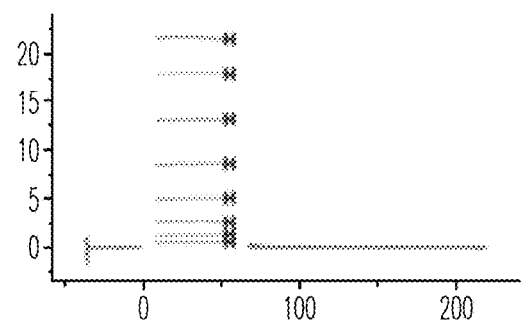
Figure 51E:
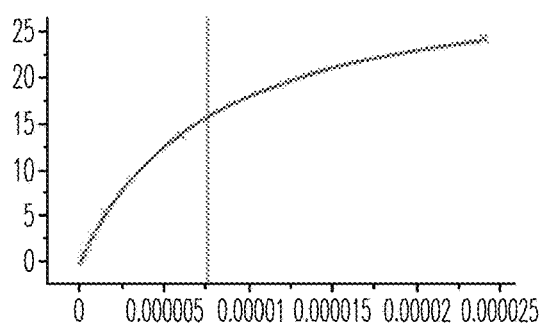
Figure 51F:
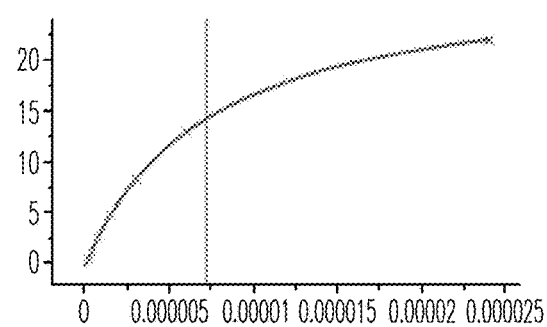
Figure 51G:
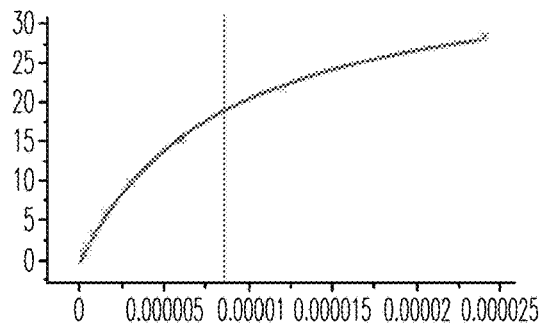
Figure 51H:
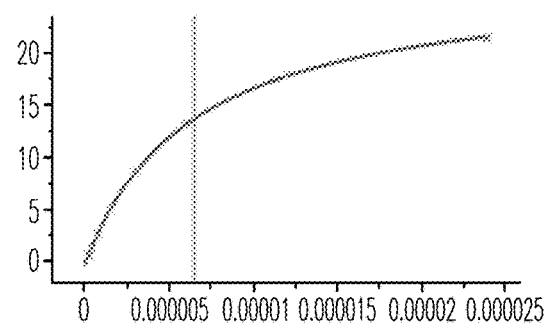
Figure 51I:
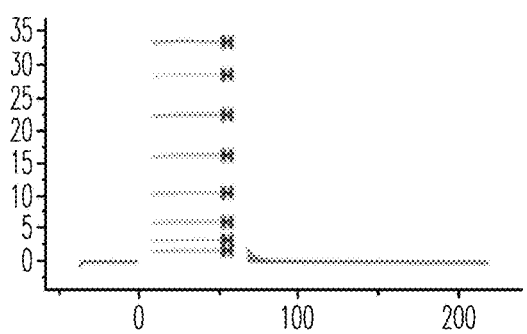
Figure 51J:
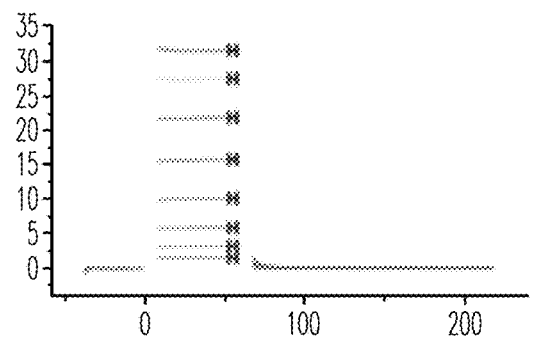
Figure 51K:
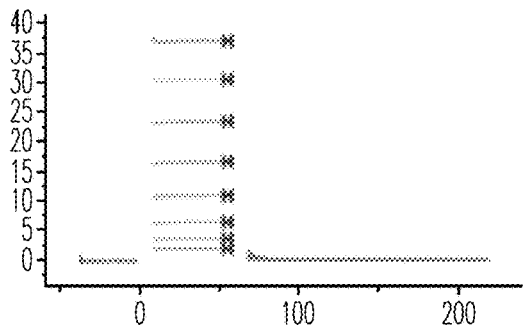
Figure 51L:
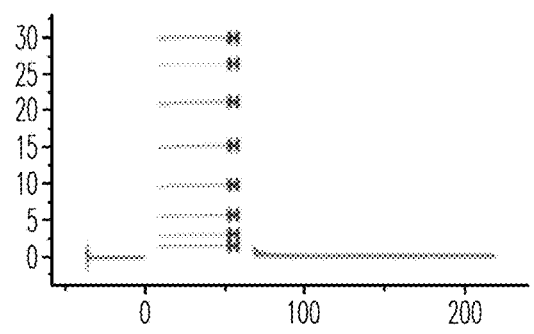
Figure 51M:
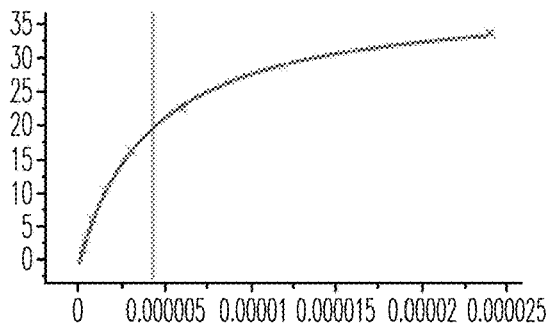
Figure 51N:
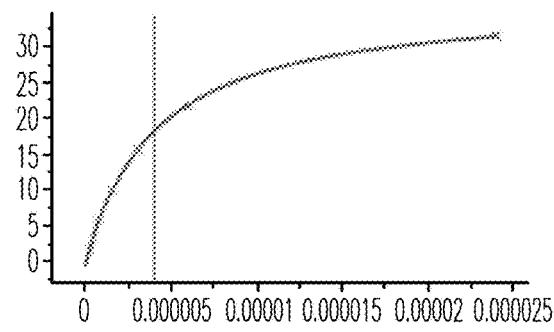
Figure 51O:
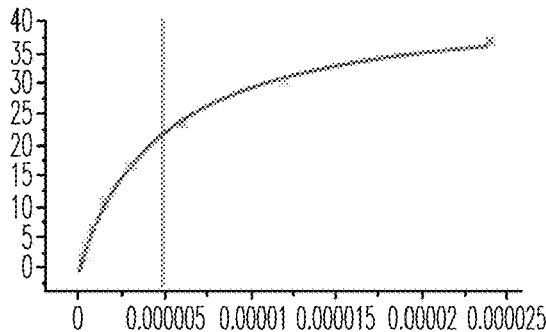
Figure 51P:
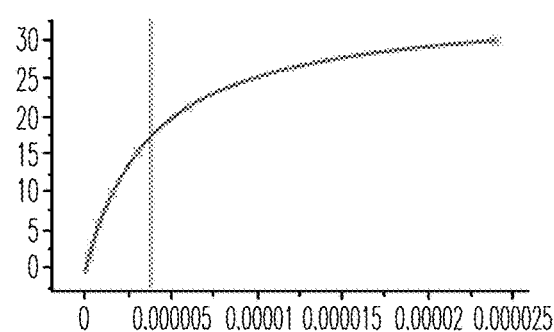
Figure 55A:
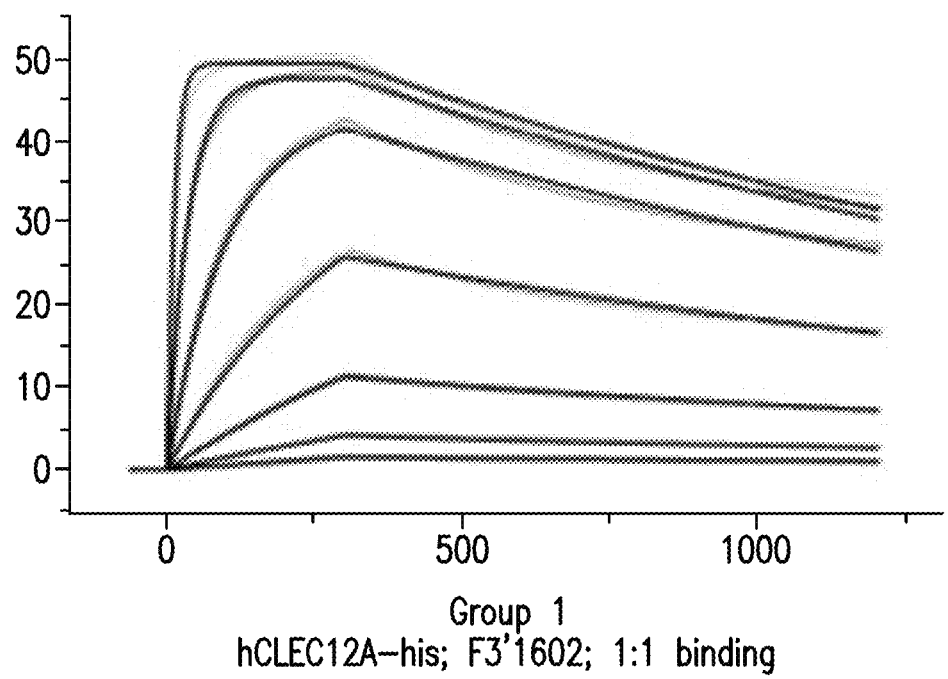
FIG. 55A-FIG. 55D are a set of sensorgrams showing SPR profiles of hF3'-1602 TriNKET binding to human CLEC12A.
Figure 55B:
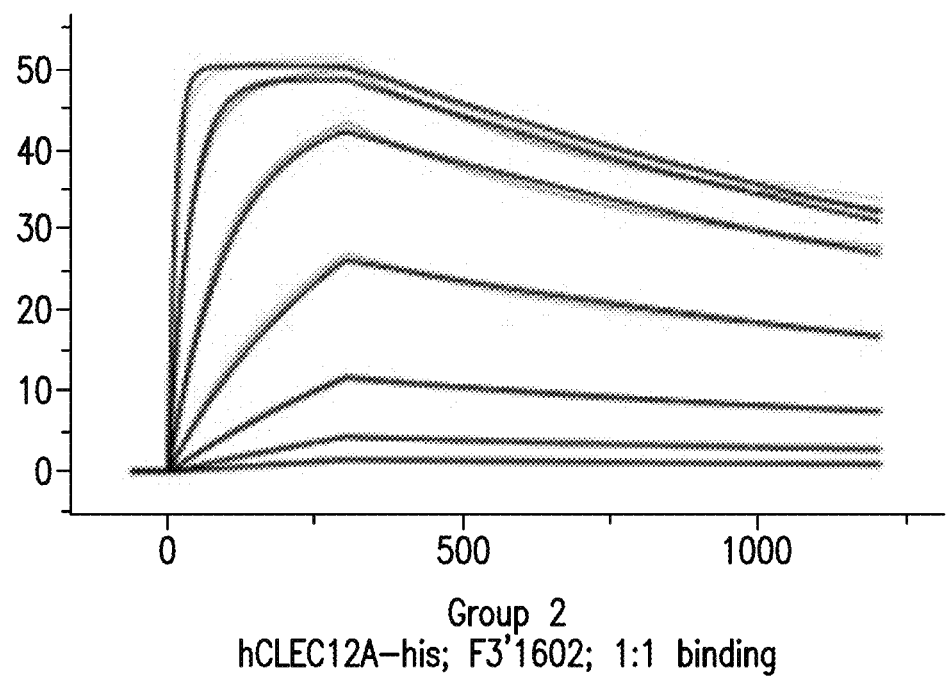
Figure 55C:
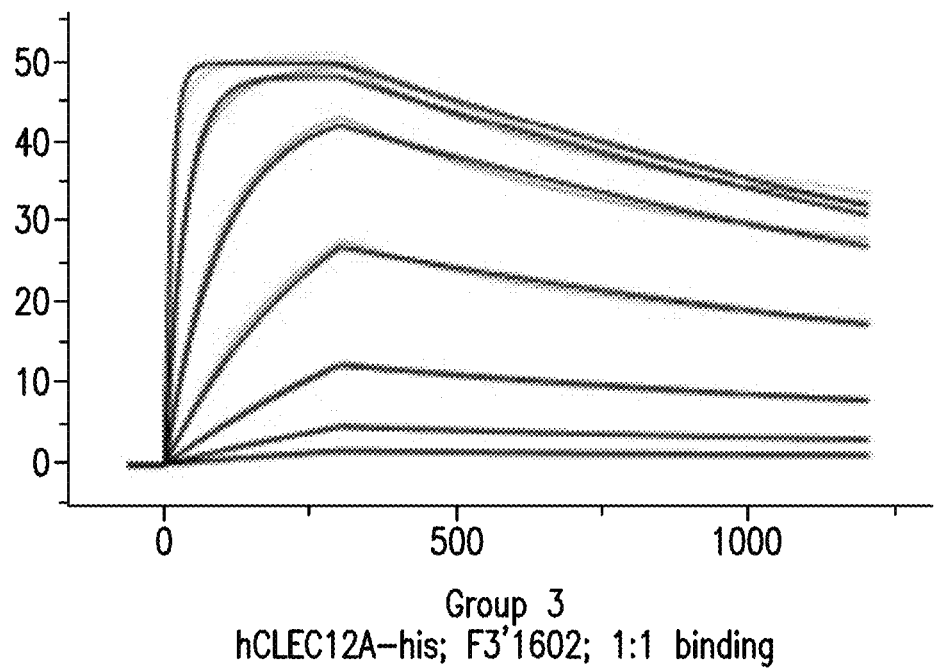
Figure 55D:
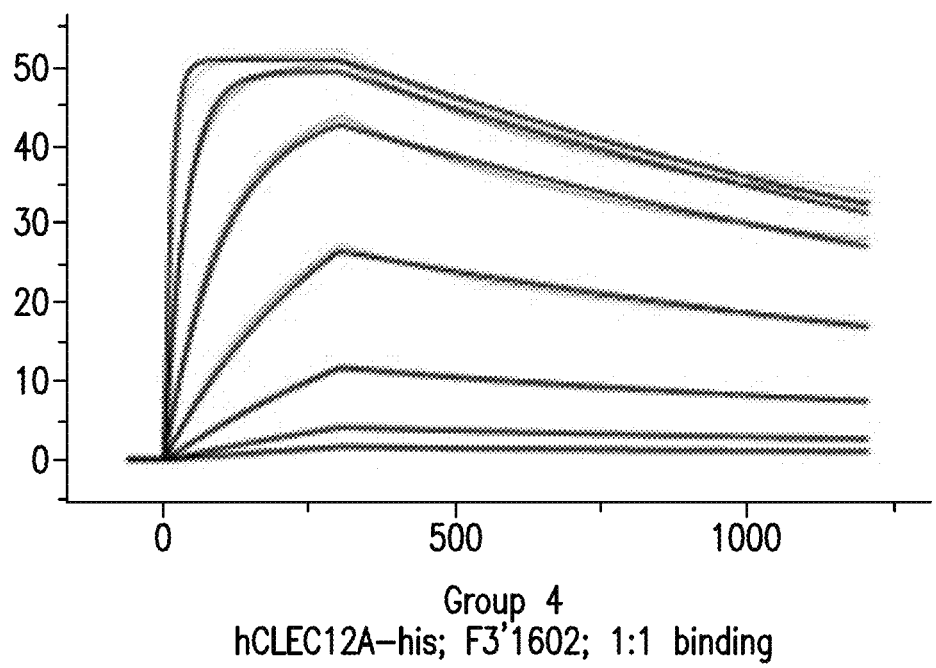
Figure 57A:
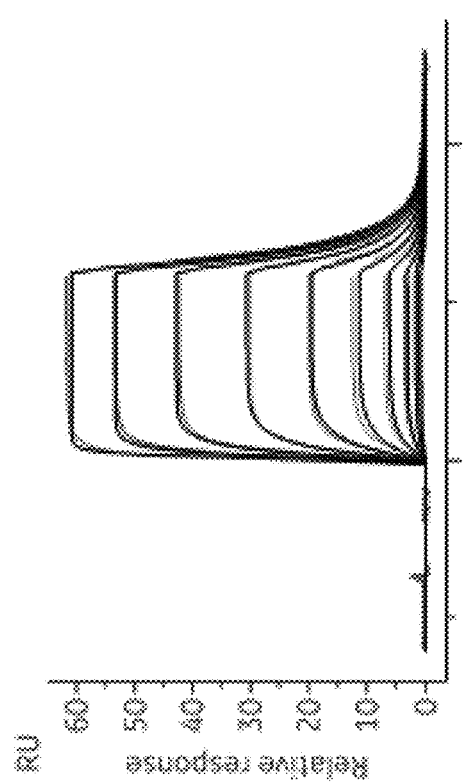
FIG. 57A-FIG. 57H are a set of sensorgrams showing SPR profiles of hF3'-1602 TriNKET binding to recombinant cyno NKG2D (cNKG2D) extracellular domain (ECD).
Figure 57B:
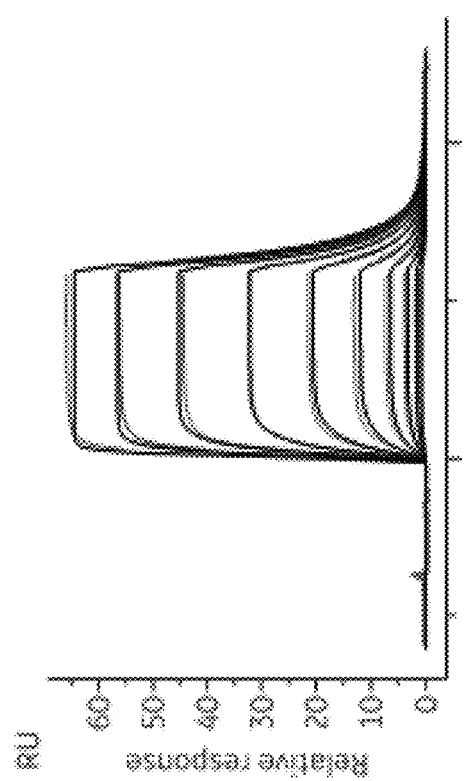
Figure 57C:
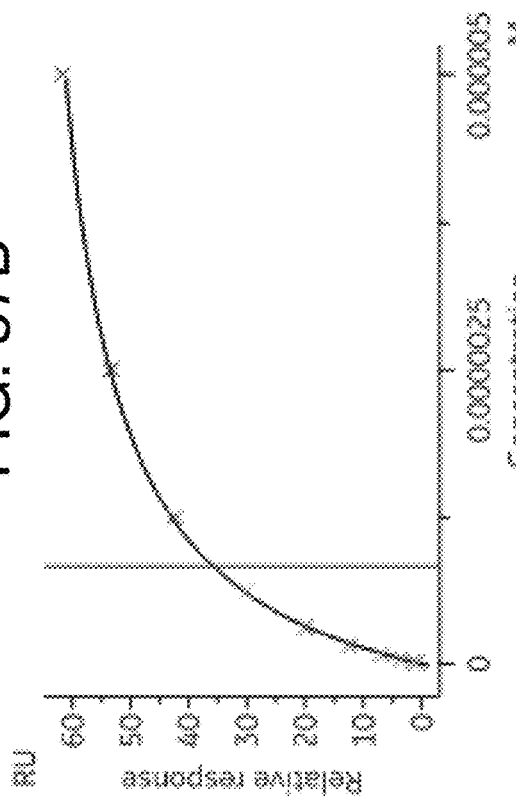
Figure 57D:
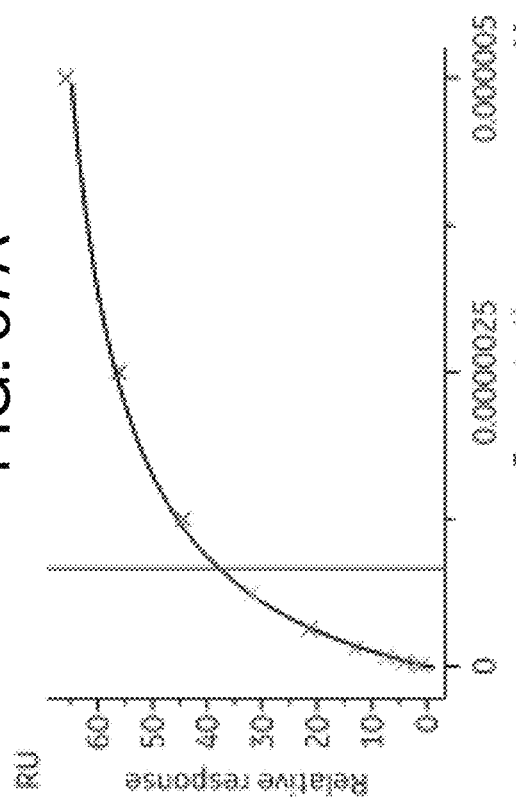
Figure 57E:
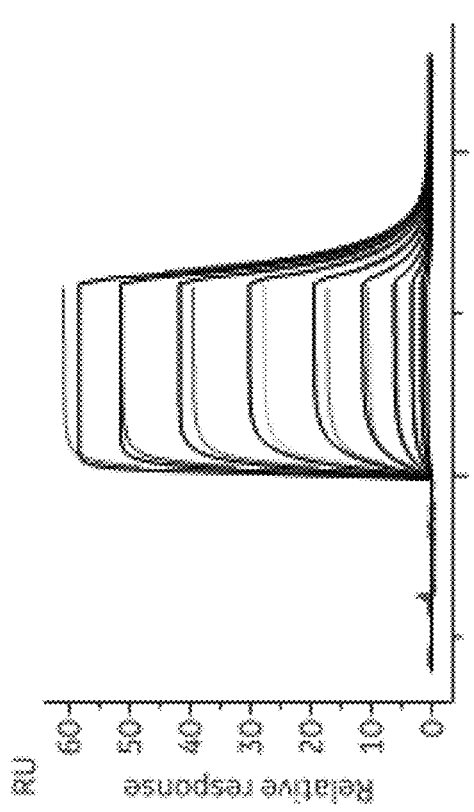
Figure 57F:
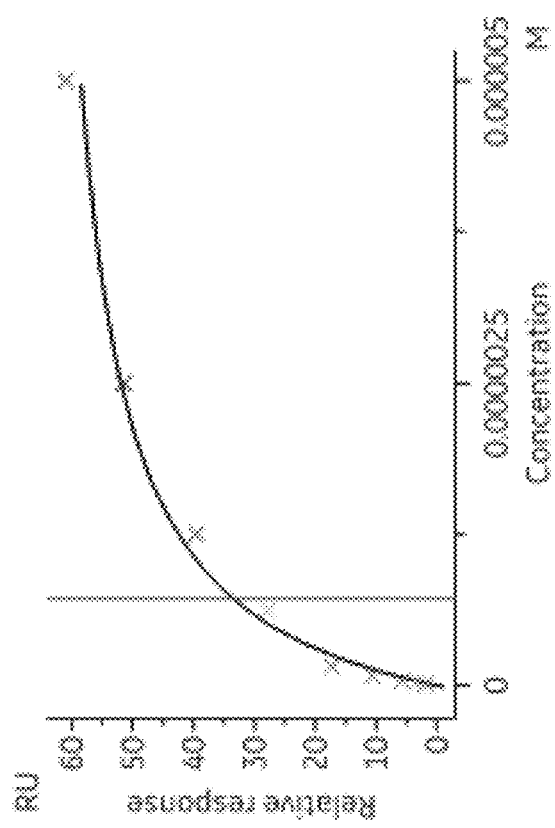
Figure 57G:
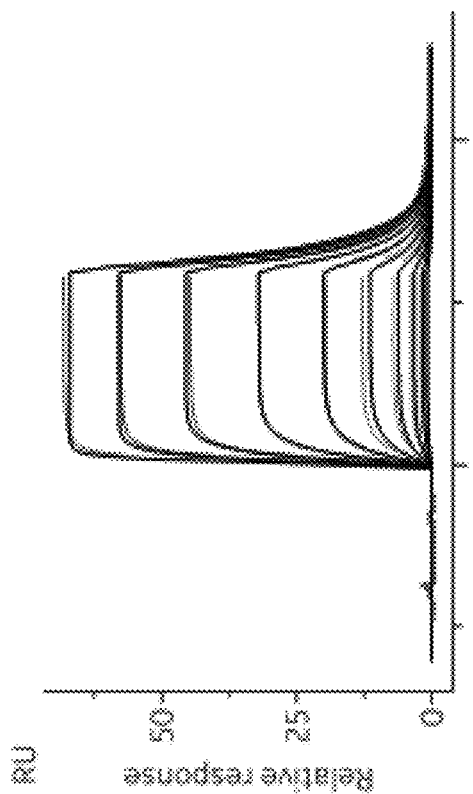
Figure 57H:
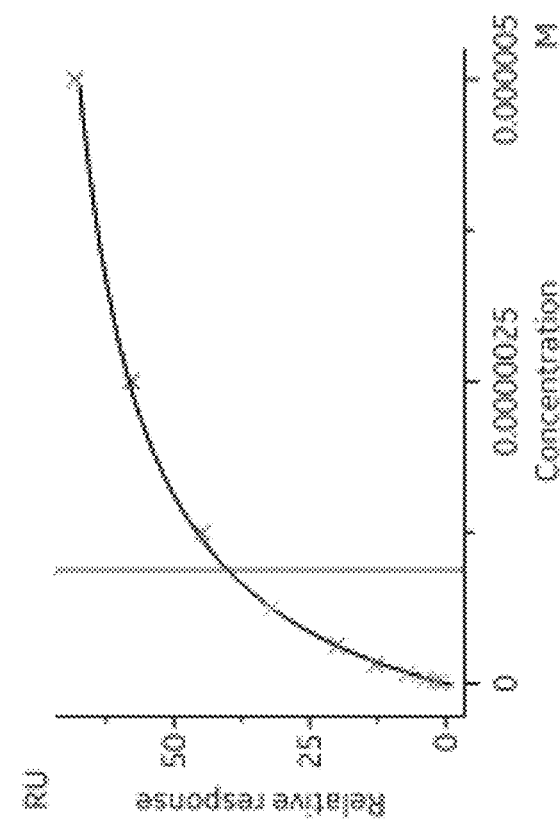

Binding of F3'-1602 TriNKET to human CD16b (FcγRIIIb) was determined as described above and is shown in FIGS. 51A-51P. The data were fit with a steady state affinity fit model; affinity values are summarized in Table 45.

TABLE 45

Affinity of human CD16b for F3'-1602 TriNKET and trastuzumab.

| Sample | Replicate $K_D$ (μM) | Replicate $K_D$ (μM) | Replicate $K_D$ (μM) | Replicate $K_d$ (μM) | $K_D$ (μM) Average ± SD |
|---|---|---|---|---|---|
| F3'-1602 TriNKET | 7.6 | 7.2 | 8.6 | 6.5 | 7.5 ± 0.8 |
| trastuzumab | 4.2 | 4.0 | 4.8 | 3.8 | 4.2 ± 0.4 |

Binding of F3'-1602 TriNKET to cyno CD16 was measured as described above and is shown in FIGS. 52A-52P. The data were fit with a steady state affinity fit model; affinity values are summarized in Table 46.

TABLE 46

Affinity values of F3'-1602 TriNKET and trastuzumab for cynomolgus CD16.

| Sample | Replicate $K_D$ (nM) | Replicate $K_D$ (nM) | Replicate $K_D$ (nM) | Replicate $K_D$ (nM) | $K_D$ (nM) Average ± SD |
|---|---|---|---|---|---|
| F3'-1602 TriNKET | 315.0 | 315.0 | 294.0 | 302.0 | 306.5 ± 10.3 |
| trastuzumab | 148.0 | 141.0 | 164.0 | 149.0 | 150.5 ± 9.7 |

Binding of F3'-1602 TriNKET to human FcRn was measured at pH 6.0 as described above and is shown in FIGS. 53A-53P. The data were fit with a steady state affinity fit model; affinity values are summarized in Table 47.

TABLE 47

Affinity values of F3'-1602 TriNKET and trastuzumab for human FcRn at pH 6.0.

| Sample | Replicate $K_D$ (μM) | Replicate $K_D$ (μM) | Replicate $K_D$ (μM) | Replicate $K_D$ (μM) | $K_D$ (μM) Average ± SD |
|---|---|---|---|---|---|
| F3'-1602 TriNKET | 1.3 | 1.1 | 1.5 | 1.6 | 1.4 ± 0.2 |
| trastuzumab | 1.8 | 1.3 | 1.3 | 1.2 | 1.4 ± 0.2 |

Binding of F3'-1602 TriNKET to cyno FcRn was measured at pH 6.0 as described above and is shown in FIGS. 54A-54P. The data were fit with a steady state affinity fit model; affinity values are summarized in Table 48.

TABLE 48

Affinity values of F3'-1602 TriNKET and trastuzumab for cyno FcRn at pH 6.0.

| Sample | Replicate $K_D$ (μM) | Replicate $K_D$ (μM) | Replicate $K_D$ (μM) | Replicate $K_D$ (μM) | $K_D$ (μM) Average ± SD |
|---|---|---|---|---|---|
| F3'-1602 TriNKET | 1.1 | 1.1 | 1.4 | 1.5 | 1.3 ± 0.2 |
| trastuzumab | 1.6 | 1.6 | 1.2 | 1.3 | 1.4 ± 0.2 |

Binding of F3'-1602 TriNKET to human and cyno FcRn was measured at pH 7.4 as described above. No quantifiable binding was observed.

F3'-1602 TriNKET and IgG1 isotype control trastuzumab do not demonstrate physiologically meaningful differences (less than 3-fold difference) and are comparable in their binding to human and cynomolgus CD64 (FcγRI), CD16

(FcγRIII) recombinant receptors tested (Table 49). F3'-1602 TriNKET and trastuzumab are similar (less than 1.2-fold difference) in their binding to human CD32 (FcγRII) receptors (Table 49). F3'-1602 TriNKET is similar to trastuzumab in its affinity for human and cynomolgus FcRn at pH 6.0. F3'-1602 TriNKET and trastuzumab did not demonstrate any detectable binding at the concentrations tested at pH 7.4 (Table 50).

TABLE 49

Summary of FcγRs affinities for F3'-1602 TriNKET and trastuzumab.

| Sample | Human CD64 $K_D$, nM | Cyno CD64 $K_D$, nM | Human CD32a $K_D$, µM | | Human CD16a $K_D$, nM | | Human CD32b $K_D$, µM | Human CD16b $K_D$, µM | Cyno CD16 $K_D$, nM |
|---|---|---|---|---|---|---|---|---|---|
| | | | H131 | R131 | V158 | F158 | | | |
| F3'-1602 TriNKET | 5.2 ± 0.1 | 2.0 ± 0.0 | 0.9 ± 0.0 | 1.4 ± 0.2 | 238.2 ± 4.4 | 1107.5 ± 20.6 | 6.6 ± 0.6 | 7.5 ± 0.8 | 306.5 ± 10.3 |
| trastuzumab | 2.5 ± 0.1 | 0.9 ± 0.0 | 1.1 ± 0.1 | 1.7 ± 0.2 | 77.6 ± 1.9 | 439.8 ± 8.3 | 6.9 ± 0.3 | 4.2 ± 0.4 | 150.5 ± 9.7 |

TABLE 50

Summary of F3'-1602 TriNKET and trastuzumab binding human and cynomolgus FcRn.

| Sample | Human FcRn, pH 6.0 $K_D$, µM | Human FcRn, pH 7.4 $K_D$, µM | Cyno FcRn, pH 6.0 $K_D$, µM | Cyno FcRn, pH 7.4 $K_D$, µM |
|---|---|---|---|---|
| F3'-1602 TriNKET | 1.4 ± 0.2 | No quantifiable binding | 1.3 ± 0.2 | No quantifiable binding |
| trastuzumab | 1.4 ± 0.2 | No quantifiable binding | 1.4 ± 0.2 | No quantifiable binding |

FcRn Binding

Recombinant human or cynomolgus monkey (cyno) FcRn was directly immobilized via amine coupling at a density of 169-216 RU. F3'-1602 TriNKET and commercial trastuzumab as an IgG1 assay control were buffer exchanged into MBS-EP+, pH 6.0 as described above before the SPR binding experiment. Each FcRn binding experiment consisted of multiple cycles utilizing varying concentrations of analytes. Two-fold dilution series (12 µM-0.023 µM) of F3'-1602 TriNKET and trastuzumab were used. As no-signal, negative controls, a 0 nM blank cycle was placed at the start of each concentration series, and a blank amine coupling modified chip surface lacking FcRn were used. Each experimental cycle included association, dissociation, and regeneration steps. The association step consisted of 60 sec analyte injection and was followed by a 60 sec dissociation step. Surface regeneration (60 sec injection of HBS-EP+ buffer, pH 7.4) completed each kinetic cycle. All steps were executed at a flow rate of 30 µL/min and at 25° C. MBS-EP+ buffer, pH 6.0 was used as a running buffer. The data were fitted to a steady state affinity model with Biacore Insight evaluation software. Chi$^2$ (calculated by the software) related to the calculated $R_{max}$ was used to assess goodness of the fit.

Example 12. Molecular Format and Design, Structure, Affinity, Potency, Specificity and Cross-Reactivity Analysis of F3'-1602 TriNKET Surface Plasmon Resonance (SPR)

Binding affinities of F3'-1602 TriNKET for recombinant human CLEC12A (hCLEC12A) or cyno CLEC12A (cCLEC12A) were measured by SPR using a Biacore 8K instrument at physiological temperature of 37° C. Briefly, human Fc specific antibodies were covalently immobilized at a density of about 8000-10000 resonance units (RU) on carboxy methyl dextran matrix of a CM5 biosensor chip to create an anti-hFc IgG chip. F3'-1602 TriNKET samples were injected on the anti-hFc IgG chip at a flow rate of 10 µL/min for 60 seconds to achieve an about 250 RU capture level. hCLEC12A-His or cCLEC12A-His was serially diluted (100 nM-0.14 nM) in three-fold dilutions with running buffer and injected at a flow rate of 30 µl/min over the captured test articles. Association was monitored for 300 seconds, and dissociation was monitored for 900 seconds. Surfaces were regenerated between cycles with three pulses of 10 mM glycine-HCl (pH 1.7) injected for 20 seconds at 100 µL/min.

The kinetic constants and equilibrium binding affinities are provided in Table 51, and raw data and fits are shown in FIGS. 55A-55D. The molecule binds strongly to CLEC12A and weakly to NKG2D and CD16a. The complex between F3'-1602 TriNKET and human CLEC12A is strong as evidenced from the slow rate dissociation constant 4.94±0.09× $10^{-4}$ s$^{-1}$. The equilibrium binding affinity $K_D$ for F3'-1602 TriNKET was 0.59±0.01 nM.

TABLE 51

Comparison of kinetic parameters of F3'-1602 TriNKET to human CLEC12A at pH 7.4 and pH 6.0.

| Test article | Target | $k_a$ (M$^{-1}$s$^{-1}$) | $k_d$ (s$^{-1}$) | $K_D$ (nM) |
|---|---|---|---|---|
| F3'-1602 TriNKET #1 | hCLEC12A-His | 8.54 × 10$^5$ | 4.94 × 10$^{-4}$ | 0.58 |
| F3'-1602 TriNKET #2 | hCLEC12A-His | 8.33 × 10$^5$ | 4.94 × 10$^{-4}$ | 0.59 |
| F3'-1602 TriNKET #3 | hCLEC12A-His | 8.63 × 10$^5$ | 4.89 × 10$^{-4}$ | 0.57 |
| F3'-1602 TriNKET #4 | hCLEC12A-His | 8.26 × 10$^5$ | 4.99 × 10$^{-4}$ | 0.60 |
| Average ± Std Dev | hCLEC12A-His | (8.44 ± 0.03) × 10$^5$ | (4.94 ± 0.09) × 10$^{-4}$ | 0.59 ± 0.01 |

Further, polymorphic variant CLEC12A-K244Q is prevalent in about 30% of the population. Binding of F3'-1602 TriNKET to CLEC12A-K244Q was examined by SPR and compared its affinity to wild-type CLEC12A. As shown in Table 52, binding kinetics of F3'-1602 TriNKET for wild-type and the K244Q variant of CLEC12A are similar.

TABLE 52

Kinetic parameters and affinities of F3'-1602 TriNKET for human CLEC12A-K244Q.

| Test article | Target | $k_a$ (M$^{-1}$s$^{-1}$) | $k_d$ (s$^{-1}$) | $K_D$ (nM) |
|---|---|---|---|---|
| F3'-1602 TriNKET | hCLEC12A WT | $8.26 \times 10^5$ | $4.96 \times 10^{-4}$ | 0.60 |
| F3'-1602 TriNKET | hCLEC12A-K244Q | $5.65 \times 10^5$ | $4.36 \times 10^{-4}$ | 0.77 |

Binding affinities of F3'-1602 TriNKET for recombinant human NKG2D were measured by SPR using a Biacore 8K instrument at physiological temperature of 37° C. Briefly, mouse (mFc) specific antibodies were covalently immobilized at a density of about 8000-10000 RU on carboxy methyl dextran matrix of a CM5 biosensor chip to create an anti-mFc IgG chip. mFc-tagged human NKG2D was captured on the anti-mFc IgG chip at a flow rate of 10 μL/min for 60 seconds to achieve an about 35 RU capture level. F3'-1602 TriNKET was buffer exchanged into running buffer and serially diluted (5000 nM-9.78 nM) in two-fold dilutions with 1×HBS-EP+. F3'-1602 TriNKET was injected at a flow rate of 30 μl/min over the captured test articles. Association was monitored for 60 seconds, and dissociation was monitored for 60 seconds. Surfaces were regenerated between cycles with three pulses of 10 mM glycine-HCl (pH 1.7) injected for 20 seconds at 100 μL/min.

FIGS. 56A-56H show F3'-1602 TriNKET binding sensorgrams to human NKG2D. Two different fits were utilized to obtain the equilibrium affinity data: steady state affinity fit and kinetic fit. The kinetic constants and equilibrium affinity constants are shown in Table 54. The dissociation rate constant was $(1.30 \pm 0.03) \times 10^{-1}$ s$^{-1}$. Equilibrium affinity constants ($K_D$) obtained by kinetics fit and steady state affinity fit were, 721±21 nM and 727±22 nM respectively.

TABLE 54

Kinetic parameters and affinities of F3'-1602 TriNKET for human NKG2D measured by SPR.

| Test articles | Target | $k_a$ (M$^{-1}$s$^{-1}$) | $k_d$ (s$^{-1}$) | Kinetics fit $K_D$ (nM) | Steady State Affinity fit $K_D$ (nM) |
|---|---|---|---|---|---|
| F3'-1602 TriNKET #1 | hNKG2D | $1.80 \times 10^5$ | $1.26 \times 10^{-1}$ | 703 | 709 |
| F3'-1602 TriNKET #2 | hNKG2D | $1.84 \times 10^5$ | $1.30 \times 10^{-1}$ | 705 | 709 |
| F3'-1602 TriNKET #3 | hNKG2D | $1.75 \times 10^5$ | $1.31 \times 10^{-1}$ | 745 | 751 |
| F3'-1602 TriNKET #4 | hNKG2D | $1.80 \times 10^5$ | $1.32. \times 10^{-1}$ | 732 | 740 |
| Average ± St Dev | hNKG2D | $(1.80 \pm 0.04) \times 10^5$ | $(1.30 \pm 0.03) \times 10^{-1}$ | 721 ± 21 | 727 ± 22 |

Cross-reactivity of F3'-1602 TriNKET with cyno NKG2D was further investigated by SPR as described in Example 5 or 6. F3'-1602 TriNKET was tested for binding to recombinant cyno NKG2D (cNKG2D) extracellular domain (ECD) by SPR (Biacore) at 37° C. (FIGS. 57A-57H). NKG2D is a dimer in nature, therefore recombinant mFc-tagged cyno NKG2D dimer was used for this experiment. The binding affinities are shown in Table 55. Binding affinities were obtained from kinetic fit ($K_D$ 839±67 nM) and steady fit ($K_D$ 828±88 nM), and were similar to the binding affinity observed with hCLEC12A ($K_D$ 721±21 nM obtained with kinetic fit).

TABLE 55

Kinetic parameters and affinities of F3'-1602 TriNKET for cyno NKG2D measured by SPR.

| Test articles | Target | $k_a$ (M$^{-1}$s$^{-1}$) | $k_d$ (s$^{-1}$) | Kinetics fit $K_D$ (nM) | Steady State Affinity fit $K_D$ (nM) |
|---|---|---|---|---|---|
| F3'-1602 TriNKET #1 | cNKG2D | $1.77 \times 10^5$ | $1.47 \times 10^{-1}$ | 831 | 829 |
| F3'-1602 TriNKET #2 | cNKG2D | $1.64 \times 10^5$ | $1.36 \times 10^{-1}$ | 825 | 828 |
| F3'-1602 TriNKET #3 | cNKG2D | $1.56 \times 10^5$ | $1.45 \times 10^{-1}$ | 931 | 935 |
| F3'-1602 TriNKET #4 | cNKG2D | $1.76 \times 10^5$ | $1.35 \times 10^{-1}$ | 769 | 719 |
| Average ± St Dev | cNKG2D | $(1.68 \pm 0.1) \times 10^5$ | $(1.41 \pm 0.06) \times 10^{-1}$ | 839 ± 67 | 828 ± 88 |

Simultaneous Engagement of CLEC12A and NKG2D

F3'-1602 TriNKET was diluted in 1×HBS-EP+ buffer containing 0.1 mg/mL BSA and was captured on an anti-human Fc surface of CM5 chip at a flow rate 5 µL/min for 60 sec to achieve capture level of 150-250 RU. The net difference between baseline signal and the signal after completion of F3'-1602 TriNKET injection representing the amount of F3'-1602 captured was recorded. hCLEC12A-His (100 nM) or mFc-hNKG2D (7 µM) was injected over captured F3'-1602 TriNKET at 30 µL/min for 90 sec to reach saturation. This injection was immediately followed by an injection of a pre-incubated mixture of hCLEC12A-His (100 nM) and mFc-hNKG2D (7 µM) at a flow rate of 30 µL/min for 90 sec with the use of the A-B-A injection command in the Biacore 8K control software (the second target was pre-mixed with the first target to assure all binding sites for the first target are occupied). The chip was regenerated by two 20 second pulses of 10 mM Glycine (pH 1.7) at 100 µL/min. The experiment was conducted at 37° C. to mimic physiological temperature. An average relative binding stoichiometry of each target bound to captured F3'-1602 TriNKET that is already saturated with the other target (injected second) was expressed as a fraction of the full capacity binding to unoccupied F3'-1602 TriNKET.

Figure 58A:
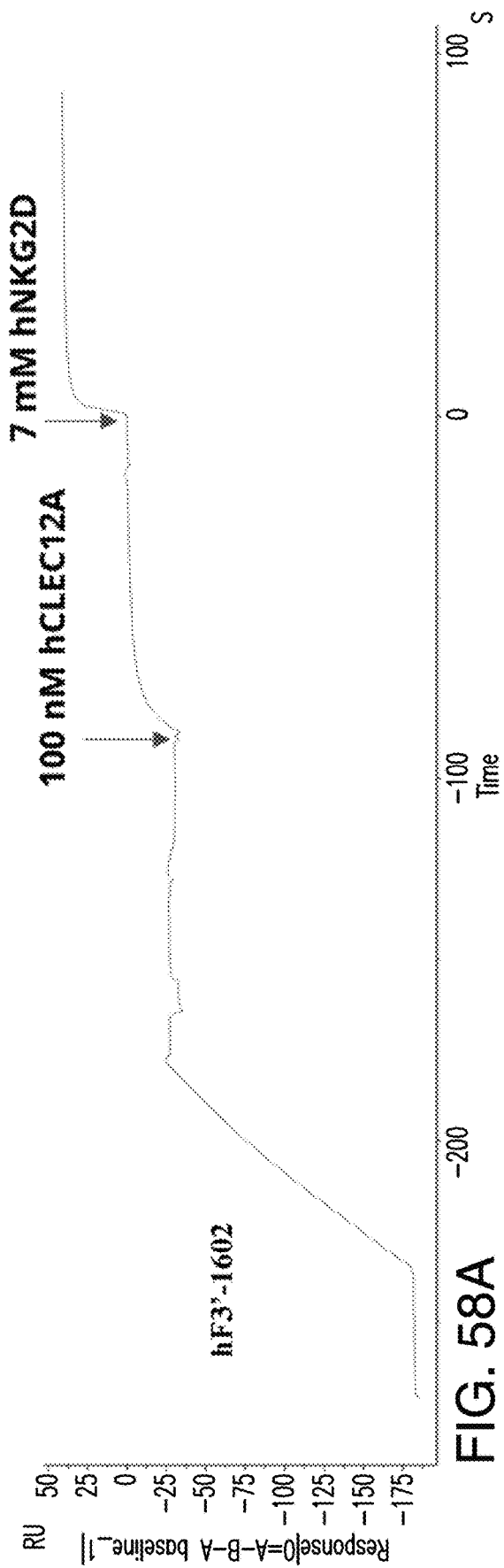
FIG. 58A-FIG. 58B are line graphs showing target binding as determined by SPR for occupancy of one TriNKET arm on binding of the other TriNKET arm.
Figure 58B:
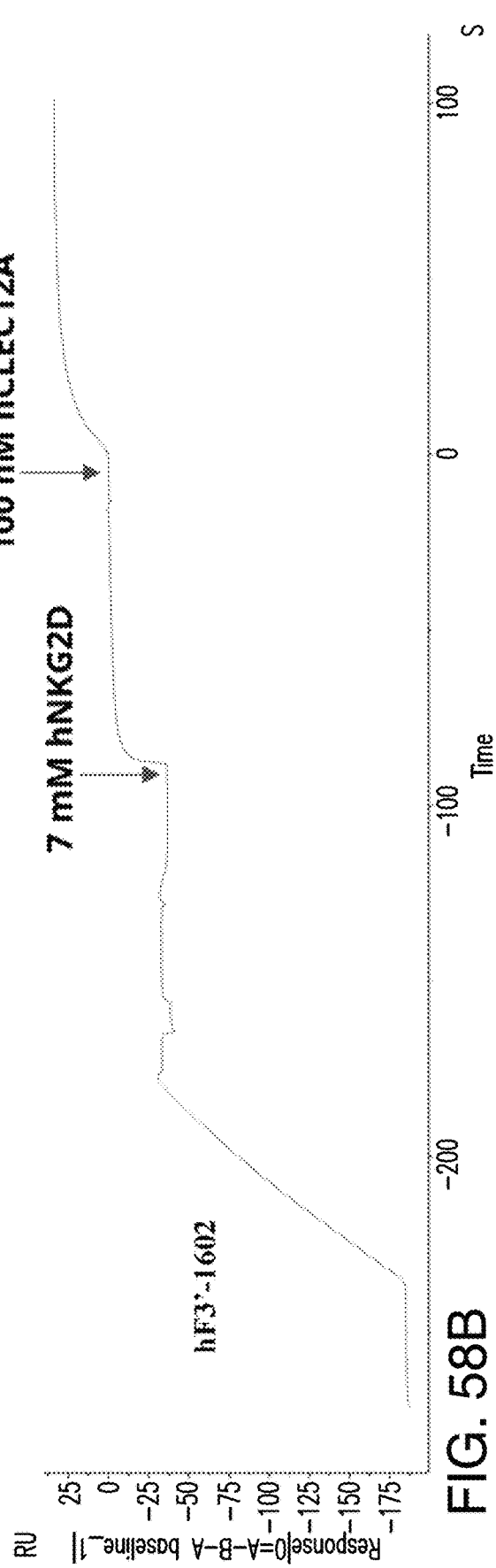

Target binding sensorgrams as shown in FIGS. 58A-58B demonstrate that the occupancy status of the CLEC12A domain does not interfere with NKG2D binding and occupancy status of the NKG2D domain does not interfere with CLEC12A binding. Similarity in shapes of the respective sensorgram segments depicting binding of each target to free F3'-1602 TriNKET and F3'-1602 TriNKET that has been saturated with the other target suggests that the kinetic parameters are not meaningfully affected by the target occupancy status of the F3'-1602 TriNKET molecule. For instance, the shape of the CLEC12A binding segment of the sensorgrams is similar in both panels. Saturating concentration of the NKG2D was maintained throughout the entire experiment, represented in the lower panel due to the fast dissociation rate of the target. Additionally, the lack of any impact on relative stoichiometry of each target binding (when compared to binding to unoccupied F3'-1602) signifies full independence of NKG2D and CLEC12A binding sites on F3'-1602 TriNKET (Table 56).

TABLE 56

Relative binding stoichiometries of F3'-1602 TriNKET for CLEC12A and NKG2D, expressed relative to binding of each target to unoccupied captured F3'-1602 TriNKET.

|  | CLEC12A, relative binding stoichiometry | NKG2D, relative binding stoichiometry |
| --- | --- | --- |
| Target Bound to F3'-1602 TriNKET unoccupied with another target (injected first) | 1.00 | 1.00 |
| Target Bound to F3'-1602 TriNKET saturated with another target (injected second) | 1.21 ± 0.06 | 1.19 ± 0.04 |

NKG2D-CD16a Synergy

Synergistic NKG2D and CD16a binding was evaluated by SPR. 233 RU of hNKG2D alone, 618 RU of CD16a F158 allele alone, and 797 RU of the mixture of hNKG2D and CD16a(F158) were amino-coupled to the surface of the CM5 Series S Biacore chip. 2.8 µM F3'-1602 TriNKET or trastuzumab were injected for 150 sec at 10 µL/min. Dissociation phase was observed for 180 seconds when regeneration was not needed and 1500 second when natural regeneration of the surface (almost complete dissociation of analyte) was needed between the cycles at the same flow rate.

Figure 59A:
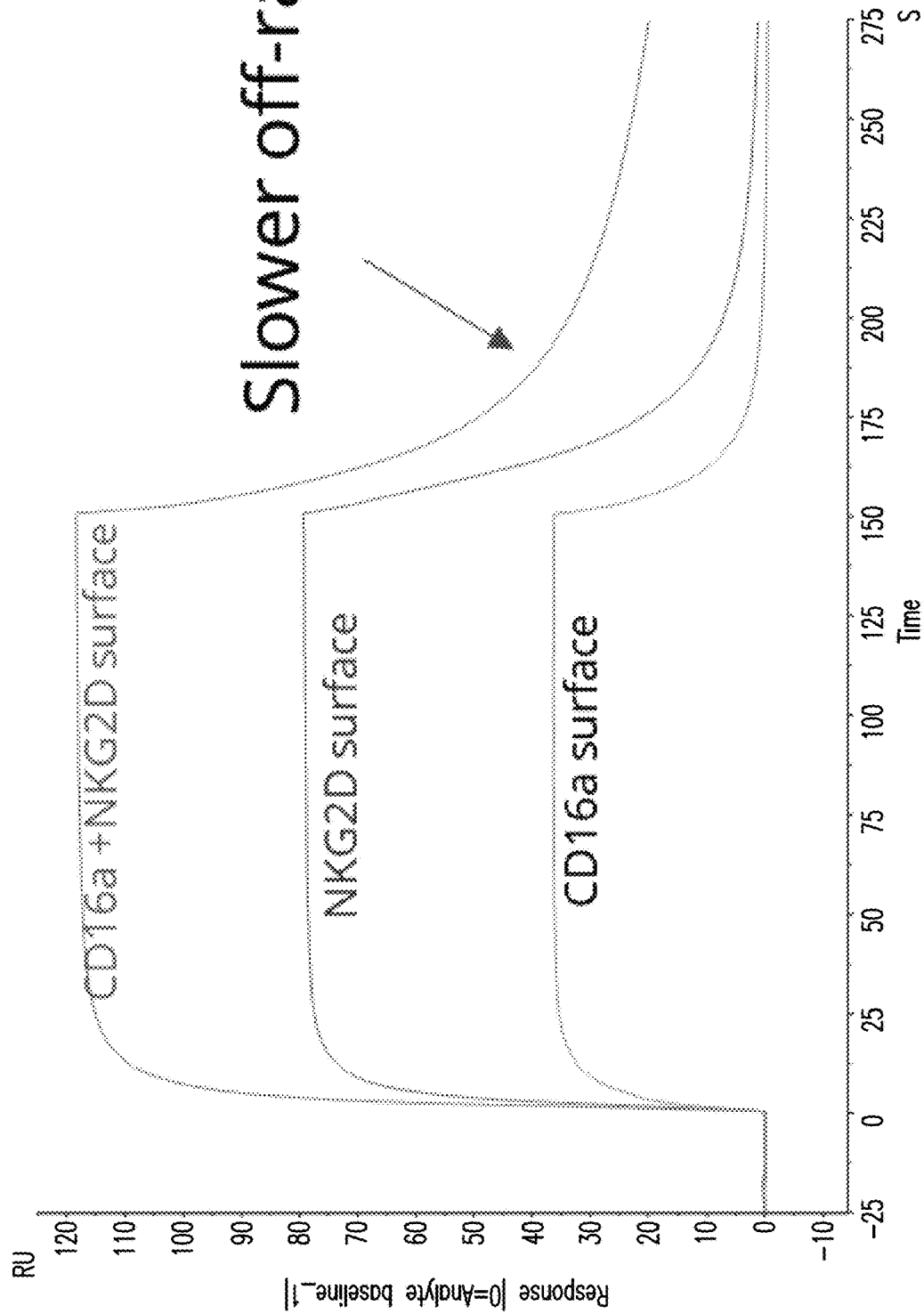
FIG. 59A-FIG. 59B are line graphs showing target binding as determined by SPR for synergy of NKG2D TriNKET (FIG. 59A) arm and CD16a (FIG. 59B).
Figure 59B:
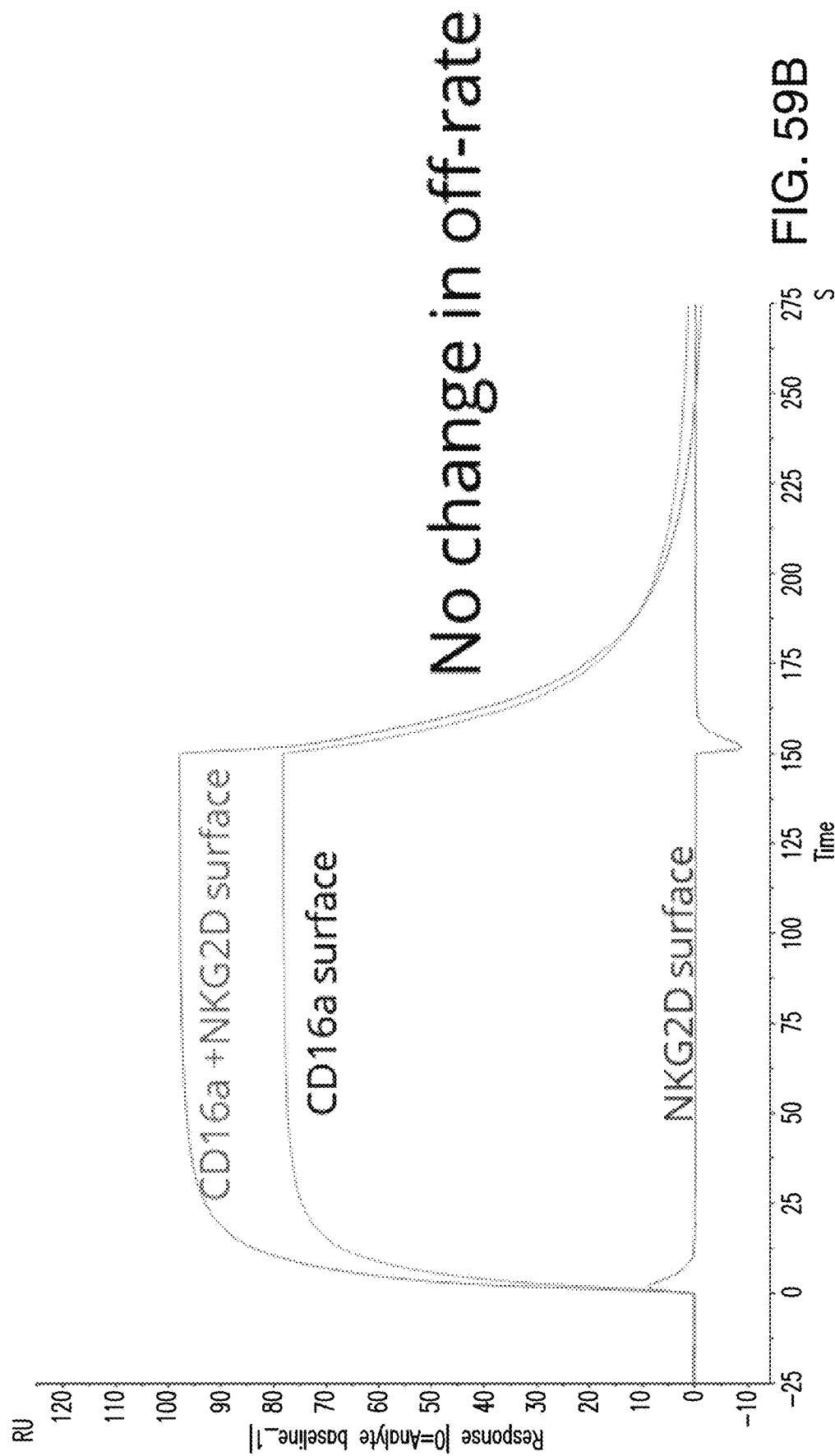
Figure 60A:
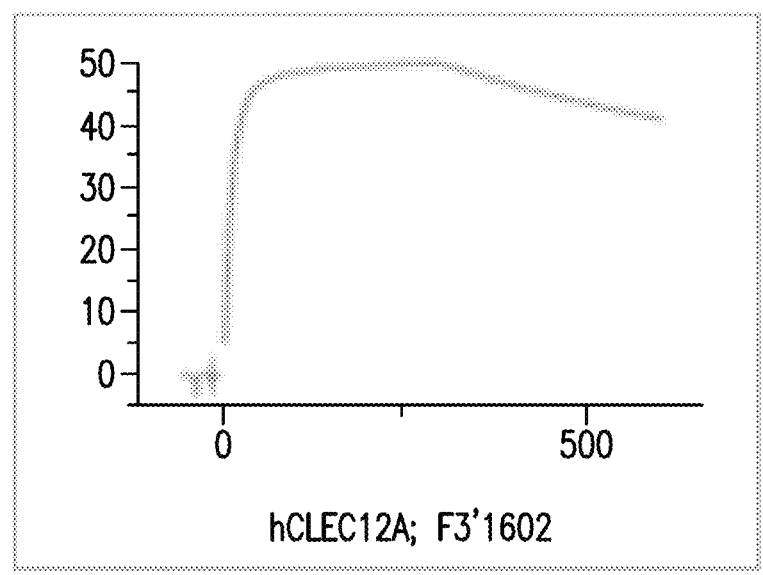
FIG. 60A-FIG. 60E show that no non-specific binding was observed in any of the unrelated recombinant targets (FIG. 60B, FIG. 60C), whereas positive control (CLEC12A) showed binding of 50 RU at 100 nM concentration (FIG. 60A). Specificity was also tested against proteins expressed on the surface of the Ba/F3 cell line. No non-nonspecific binding of F3'-1602 at a concentration of 333 nM to the Ba/F3 parental cell line was observed (FIG. 60E), whereas Ba/F3 cell lines engineered to express CLEC12A, used as a positive control, showed a significant shift by flow cytometry (FIG. 60D).
Figure 60B:
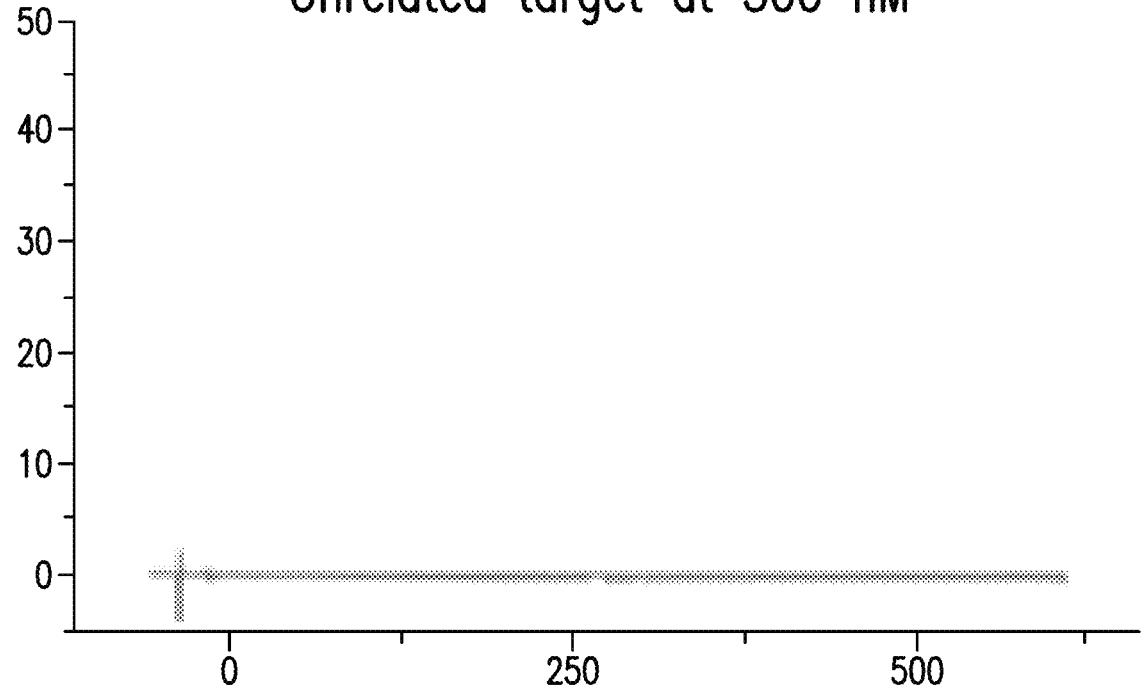
Figure 60C:
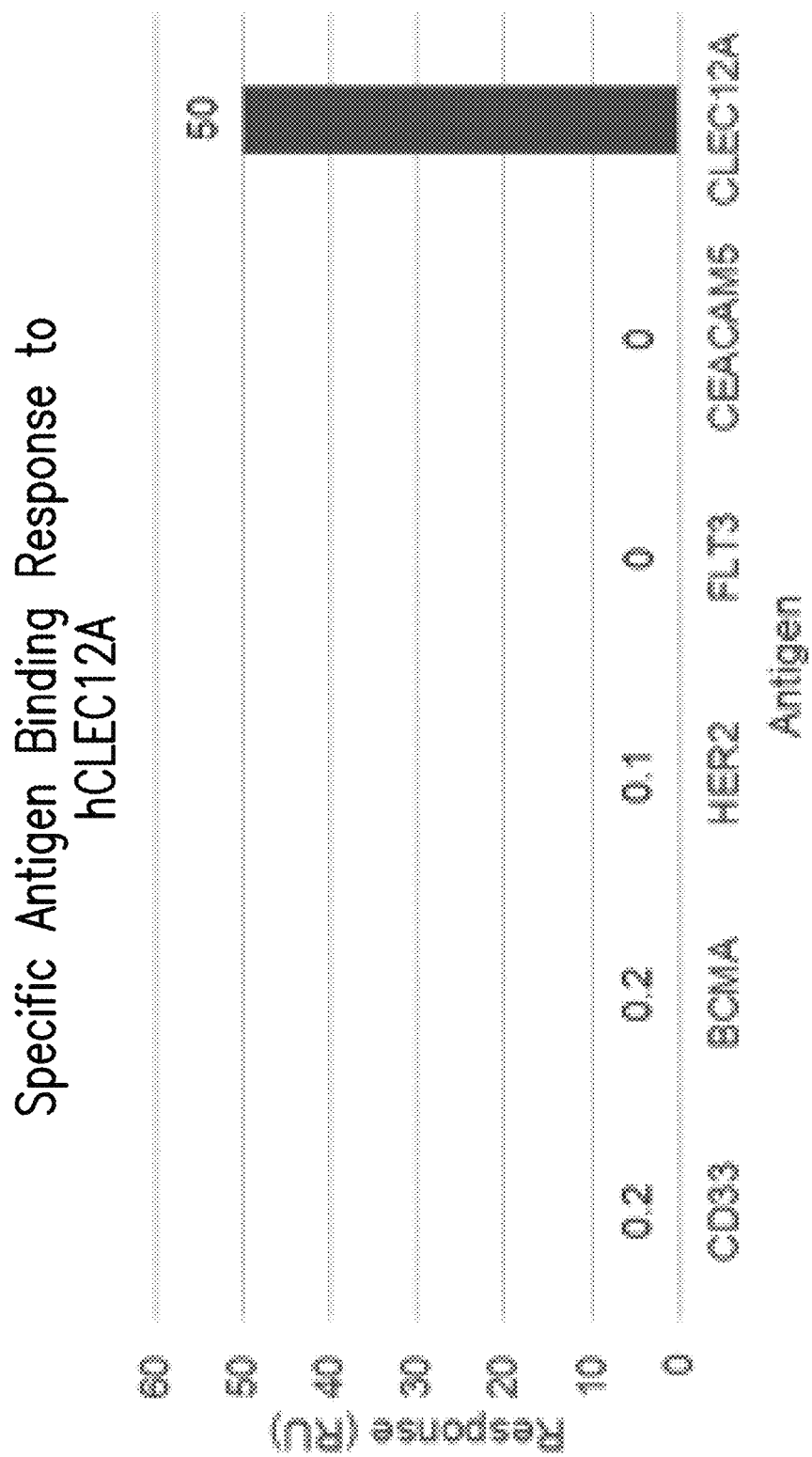
Figures 60D, 60E:
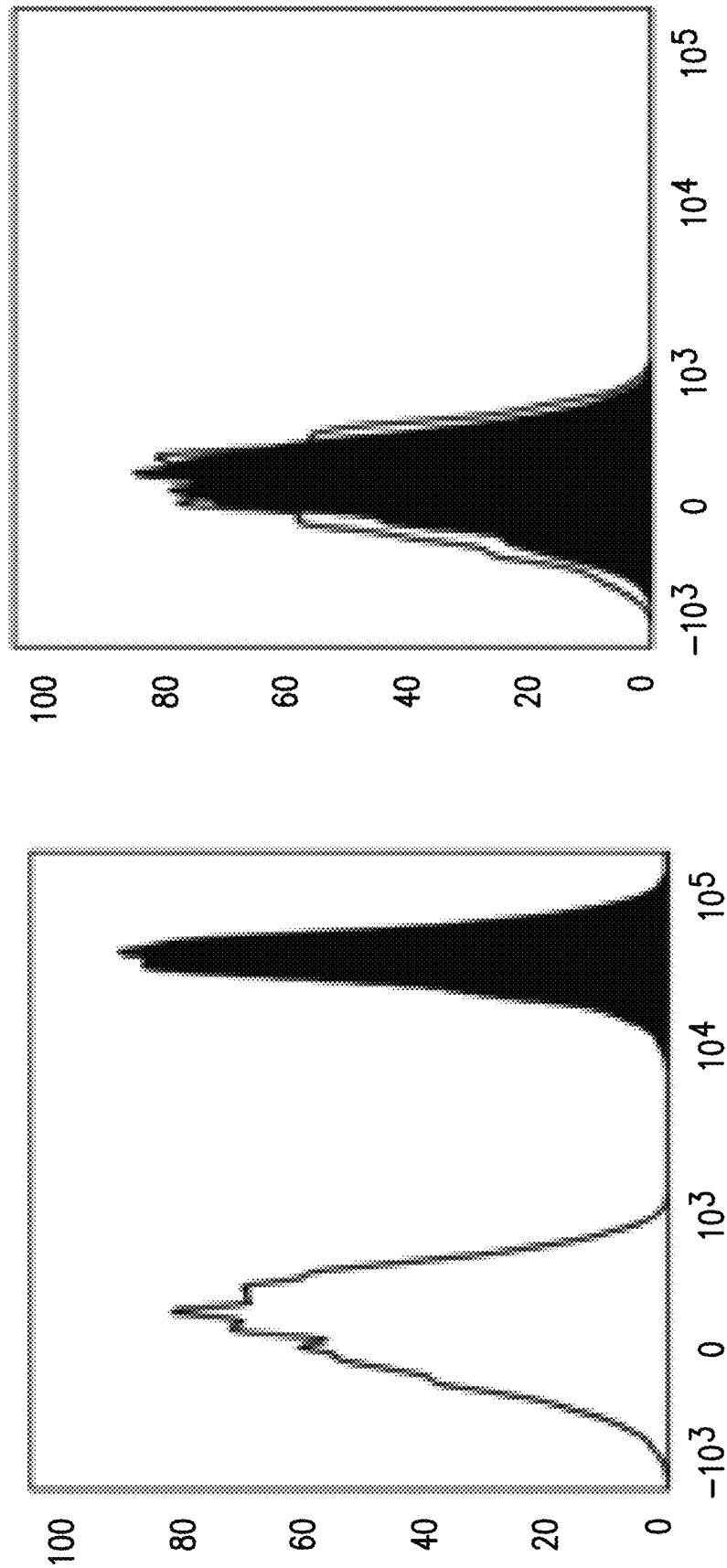

As shown in FIG. 59, while F3'-1602 TriNKET binds with low affinity to CD16a or NKG2D alone, F3'-1602 TriNKET injected over the mixed surface manifests in avidity of simultaneous CD16a and NKG2D binding through much slower off-rate (FIG. 59A). Experimental control trastuzumab does not bind immobilized NKG2D and exhibits the same apparent off-rate when injected over both mixed (CD16a+NKG2D) and CD16a-only surfaces (FIG. 59B). The data indicate that F3'-1602 TriNKET avidly engages both CD16a and NKG2D.

Binding Unrelated Recombinant Proteins and Cell Binding Specificity

Specificity for CLEC12A was tested by SPR against five different unrelated proteins at concentrations as high as 500 nM and is shown in FIG. 60. No non-specific binding was observed to any of the unrelated recombinant targets (FIG. 60B, FIG. 60C), whereas positive control (CLEC12A) showed binding of 50 RU at 100 nM concentration (FIG. 60A). Specificity was also tested against proteins expressed on the surface of the Ba/F3 cell line. No non-nonspecific binding of F3'-1602 at a concentration of 333 nM to the Ba/F3 parental cell line was observed (FIG. 60E), whereas Ba/F3 cell lines engineered to express CLEC12A, used as a positive control, showed a significant shift by flow cytometry (FIG. 60D).

Non-Specific Binding to Polyspecific Reagent (PSR)

Figure 61B:
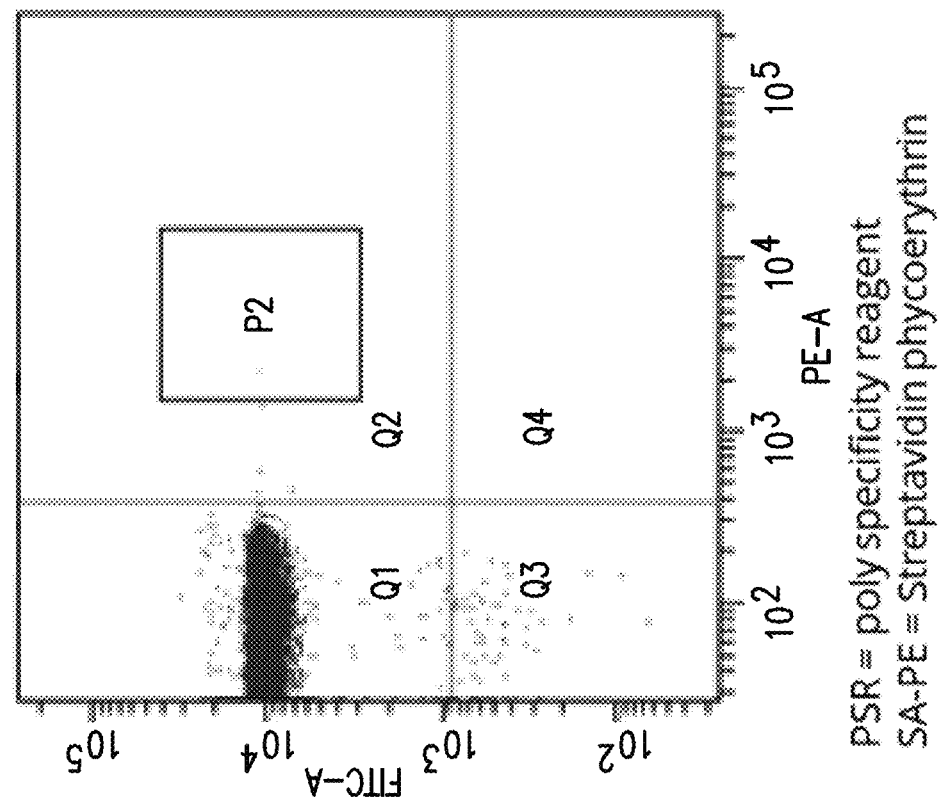
Figure 61A:
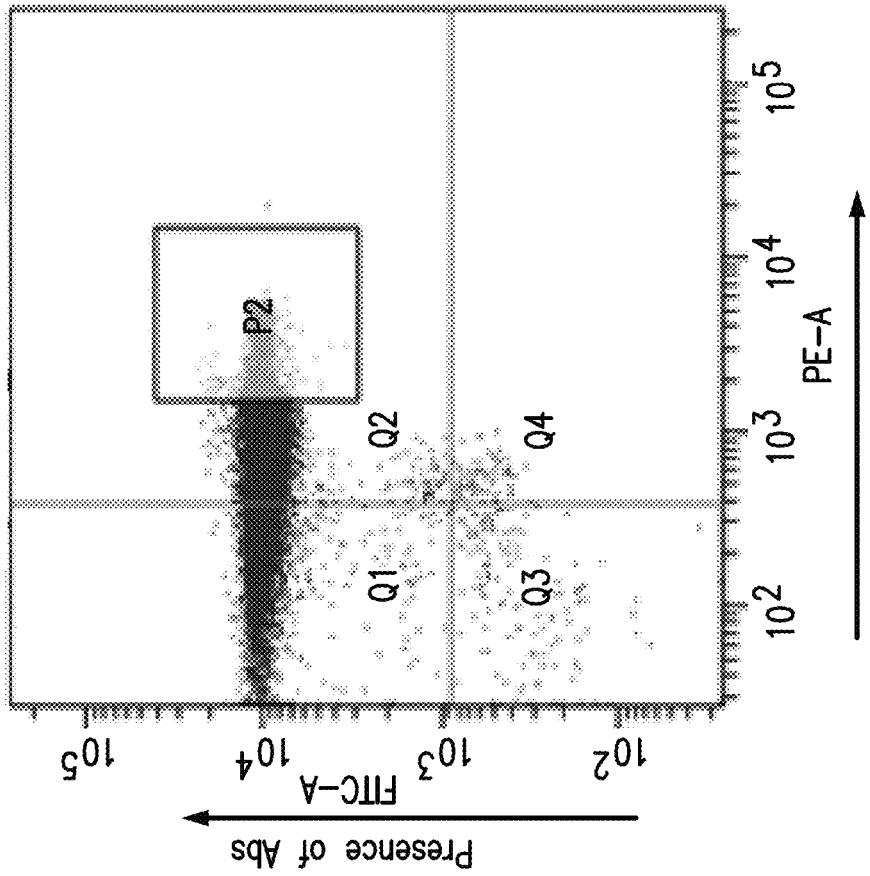

A flow cytometry based PSR assay allows the filtering out of antibodies that have a higher probability to bind non-specifically to unrelated proteins. As part of the developability assessment, F3'-1602 was tested for non-specific binding to a preparation of detergent solubilized membrane proteins in a PSR assay (FIGS. 61A-61C). PSR assay correlates well with cross-interaction chromatography, a surrogate for antibody solubility, as well as with baculovirus particle enzyme-linked immunosorbent assay, a surrogate for in vivo clearance (Xu et. al (2013). Addressing polyspecificity of antibodies selected from an in vitro yeast presentation system: a FACS-based, high-throughput selection and analytical tool. *Protein engineering design and selection*, 26, 663-670).

50 µL of 100 nM TriNKET or control mAb in PBSF were incubated with pre-washed 5 µL protein A dyna beads slurry (Invitrogen, catalog #10001D) for 30 minutes at room temperature. TriNKET or mAb bound magnetic beads were allowed to stand on a magnetic rack for 60 seconds and the supernatant was discarded. The bound beads were washed with 100 PBSF. Beads were incubated for 20 minutes on ice with 50 µL of biotinylated PSR reagent which was diluted 25-fold from the stock (Xu et. al., (2013) *Protein engineering design and selection*, 26, 663-670). Samples were put on the magnetic rack, supernatant discarded, and washed with 100 µL of PBSF. A secondary FACS reagent, to detect binding of biotinylated PSR reagent to TriNKETs or control mAbs, was made as follows: 1:250 µL of Streptavidin-PE (Biologend, catalog #405204) and 1:100 donkey anti-human Fc were combined in PBSF. To each sample, 100 µL of the secondary reagents were added and allowed to incubate for 20 minutes on ice. The beads were washed twice with 100 µL PBSF, and samples were analyzed on a FACS Celesta (BD). Two PSR controls, Rituximab (PSR positive) and Trastuzumab (PSR clean), were used in the assay.

High-Spec® Cross Reactivity Assay on HuProt™ Human Proteome Assays

To examine specificity of F3'-1602 TriNKET, a protein array technology was used. The HuProt™ human proteome microarray provides the largest database of individually purified human full length proteins on a single microscopic slide. An array consisting of 22,000 full-length human proteins are expressed in yeast *S. cerevisiae*, purified, and subsequently printed in duplicate on a mircoarray glass slide that allows thousands of interactions to be profiled in a high-throughput manner.

Specificity of F3'-1602 TriNKET was tested at 0.1 µg/mL and 1 µg/mL concentration against native Huprot human proteome array embedded on microslides at CDI laboratories (Baltimore, MD), according to their standard procedure.

Figure 62:
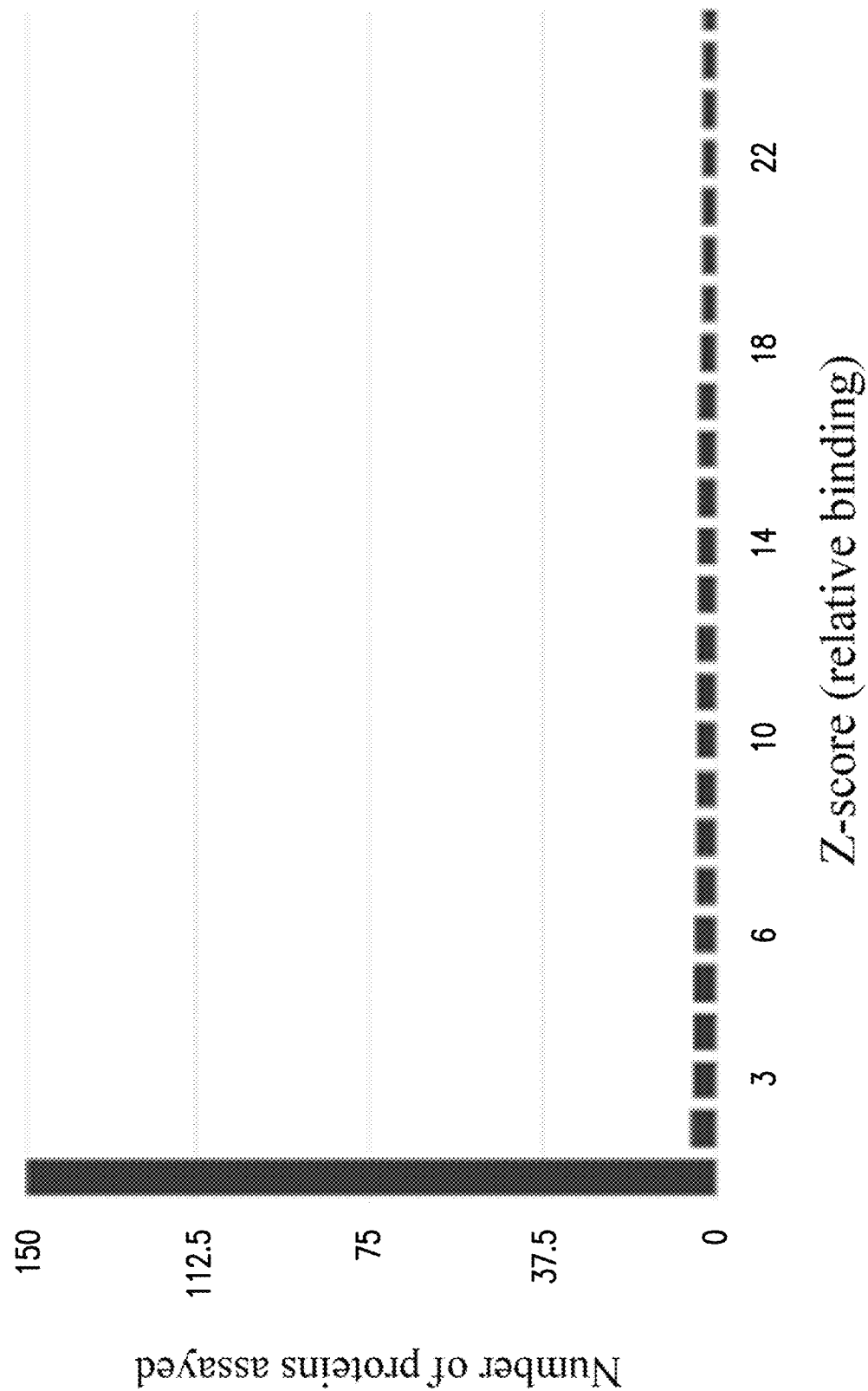
FIG. 62 are bar graphs showing relative binding (Z score) of F3'-1602 TriNKET at 1 to human CLEC12A in comparison to the entire human proteome microarray
Figures 64C, 64D:
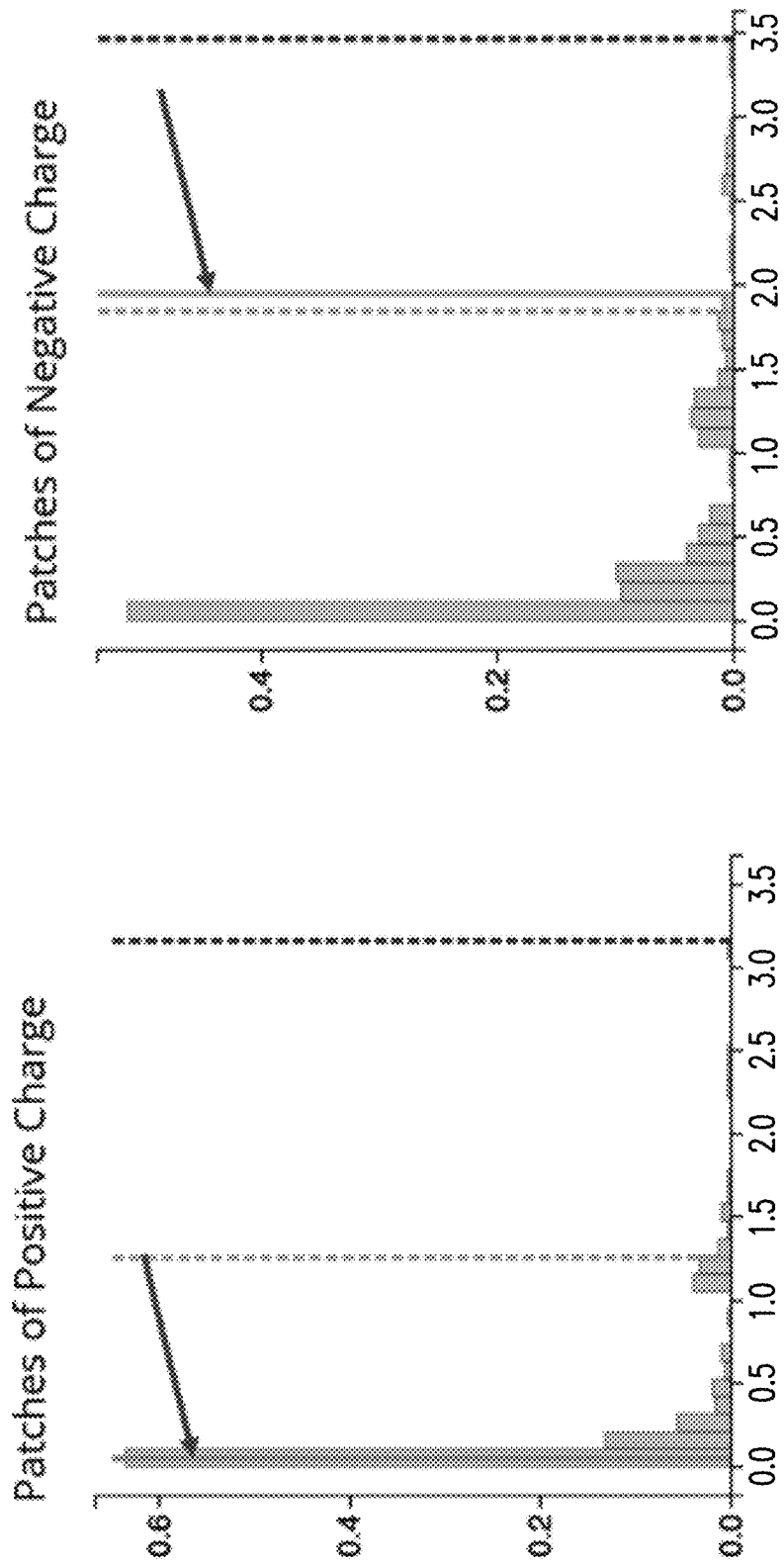
Figure 64E:
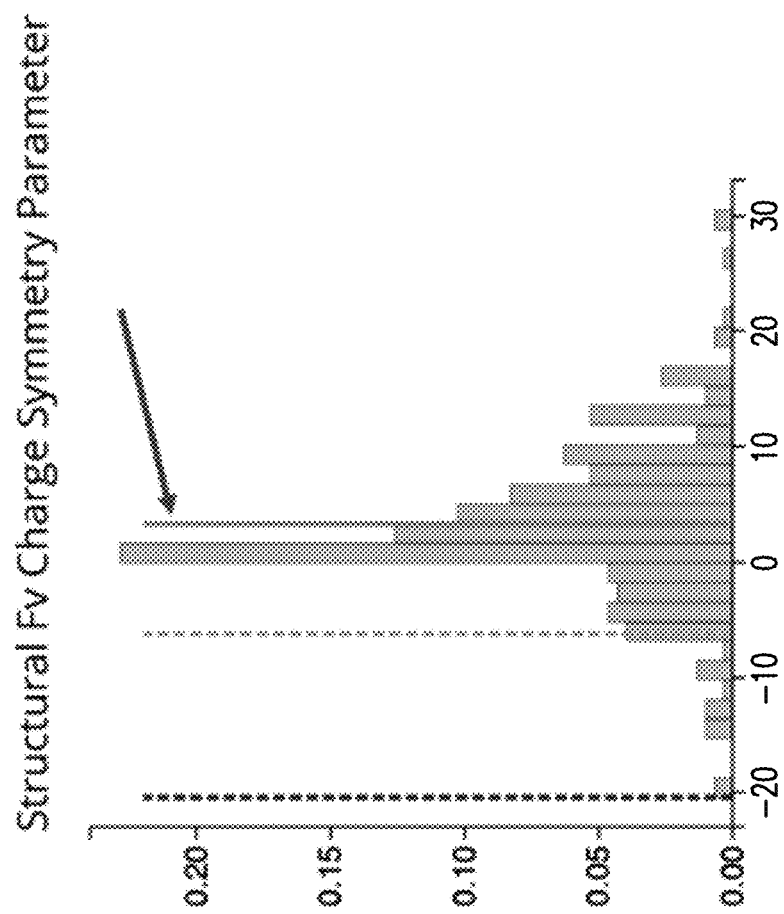
Figures 66A, 66B:
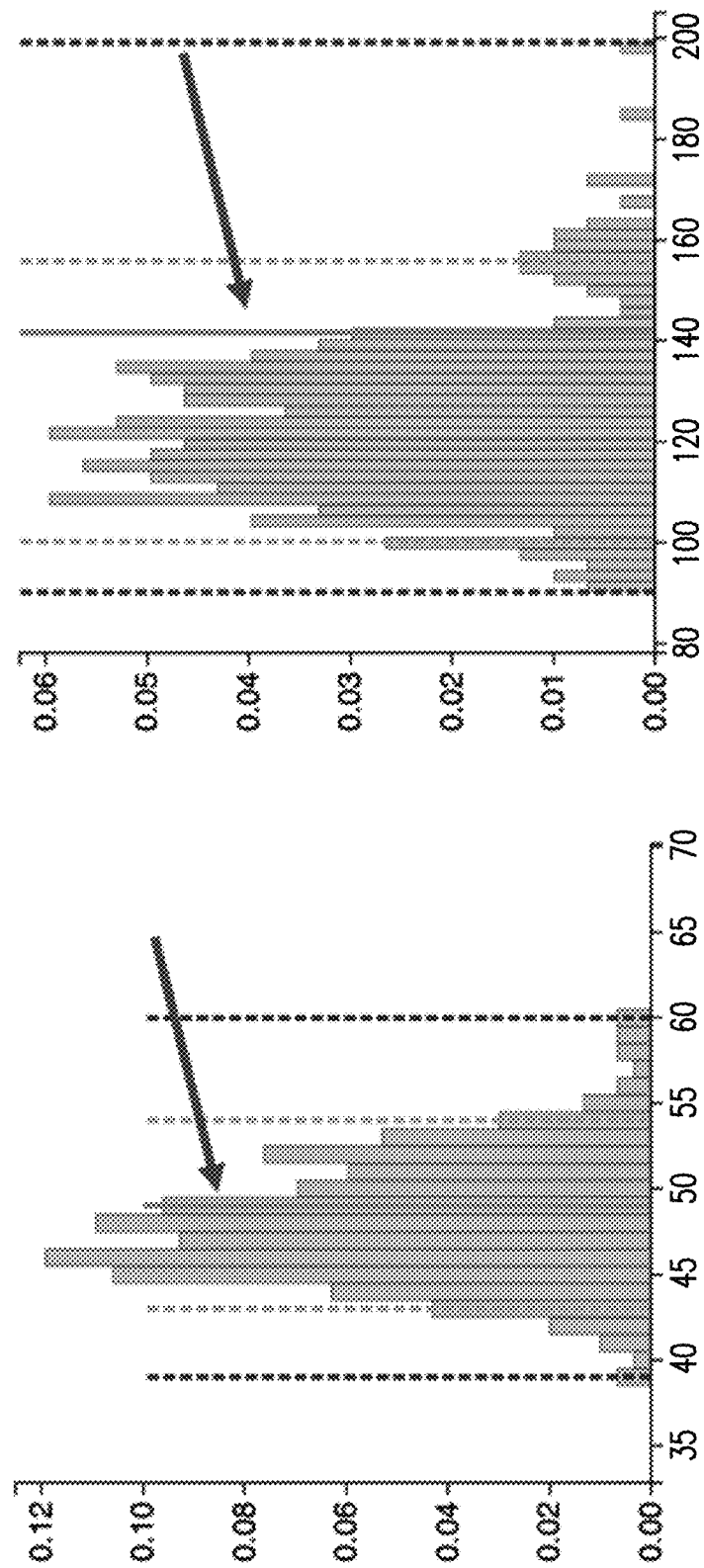
FIG. 66A-FIG. 66E are bar graphs based on models of CDR-length (FIG. 66A), surface hydrophobicity (FIG. 66B), and surface charge (FIG. 66C-FIG. 66E) in hF3'-1602 TriNKET NKG2D-binding arm.
Figure 66C:
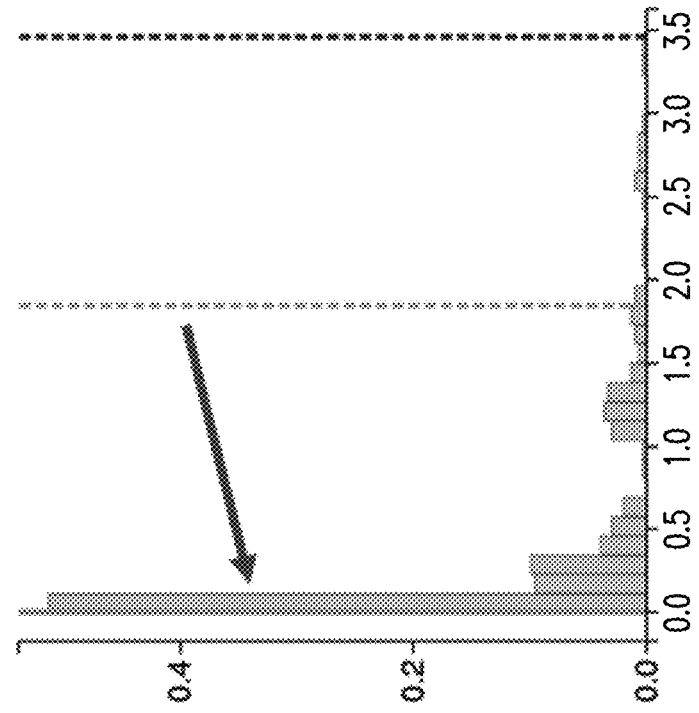
Figure 66D:
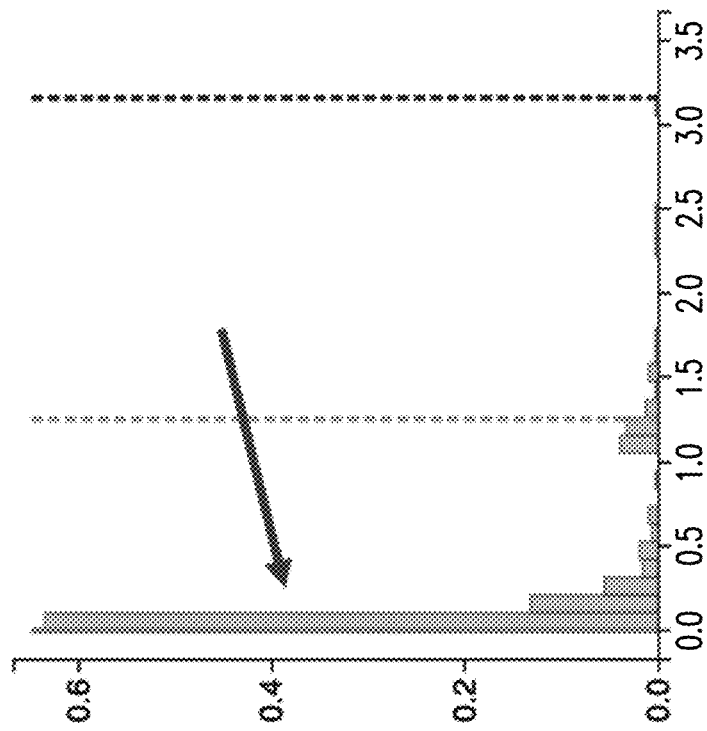
Figure 66E:
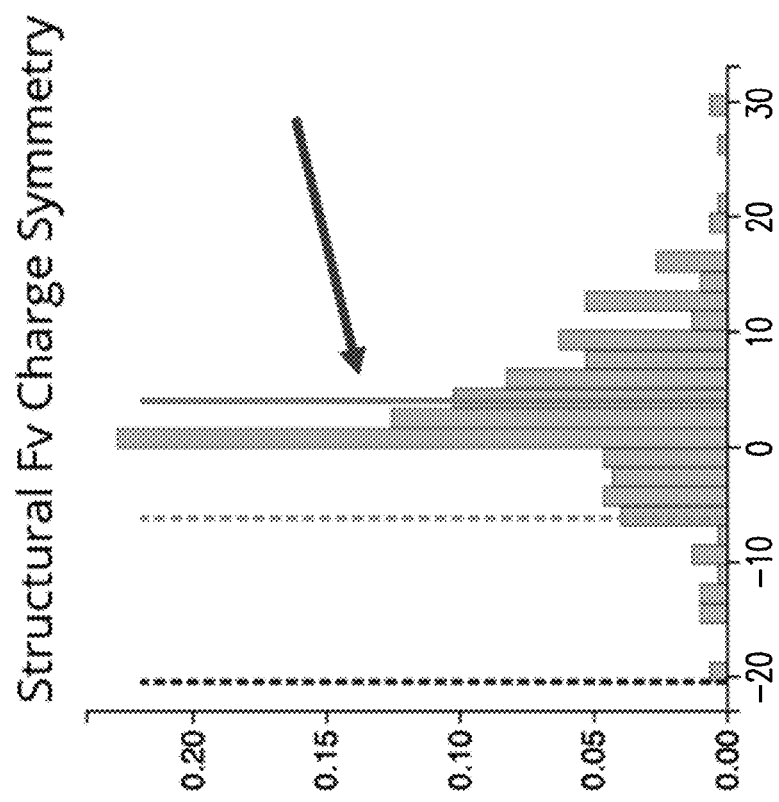

FIG. 62 shows the relative binding (Z score) of F3'-1602 TriNKET at 1 µg/mL to human CLEC12A in comparison to the entire human proteome microarray. Z score is the average binding score of two duplicates of a given protein. For comparison purpose, the top 24 proteins with residual background binding to F3'-1602 TriNKET were also provided in FIG. 62. Table 57 shows the Z and S scores of F3'-1602 TriNKET to human CLEC12A and the top 6 proteins from the microarray. S score is the difference of Z score of a given protein and the one rank next to it. If the S score of the top hit is >3 an antibody is considered to be highly specific to its target. Based on the Z and S score criteria, F3'-1602 TriNKET showed high specificity to human and lack of off-target binding in the HuProt™ human proteome assay.

TABLE 57

Z and S scores of F3'-1602 TriNKET in HuProt ™ human proteome microarray assay.

| Name | Rank | Protein-ID | Z score | S score |
| --- | --- | --- | --- | --- |
| hCLEC12A | 1 | | 150.21 | 144.62 |
| MFF | 2 | JHU15965.P1168B06 | 5.60 | 0.59 |
| RPLP0 | 3 | JHU16464.P173H05 | 5.01 | 0.12 |
| PARS2 | 4 | JHU06781.P071H01 | 4.89 | 0.062 |
| HMGA1_frag | 5 | JHU16418.P173B08 | 4.83 | 0.27 |
| THEMIS2_frag | 6 | JHU15201.P160B01 | 4.56 | 0.37 |
| HAGHL | 7 | JHU08774.P092D12 | 4.19 | 0.01 |

Molecular Modeling

Anti-CLEC12A and anti-NKG2D binding arms of F3'-1602 TriNKET were compared with 377 post Phase I biotherapeutic molecules using Therapeutic Antibody Profiler (TAP) available at the SAbPred website. TAP used ABodyBuilder to generate a model for F3'-1602 TriNKET with side chains by PEARS. The CDRH3 was built by MODELLER due to its diversity.

Five different parameters were evaluated:
Total CDR length
Patches of surface hydrophobicity (PSH) across the CDR vicinity
Patches of positive charge (PPC) across the CDR vicinity
Patches of negative charge (PNC) across the CDR vicinity
Structural Fv charge symmetry parameter (sFvCSP)

These parameters of F3'-1602 TriNKET were then compared with the profile distributions of therapeutic antibodies to predict the developability and any potential issues that might cause downstream challenges.

FIGS. 63A-63C illustrate a ribbon diagram model of the CLEC12A binding scFv in three different orientations (upper panel) and their corresponding surface charge distribution of the same orientation (lower panel). The charge distribution of anti-CLEC12A scFv is polarized ("top view", lower panel), with negatively-charged residues populated predominately within CDRH3 and CDRL2. The uneven distribution of electrostatic patches on the paratope is likely to be target-related and reflects the complementarity of charge distribution on its cognate epitope, which may likely contribute to the high affinity interaction between CLEC12A and the scFv of F3'-1602 TriNKET.

FIGS. 64A-64E show the CDR length and surface hydrophobicity analyses of scFv CLEC12A targeting arm of F3'-1602 TriNKET. The length of CDRs for the CLEC12A binding arm of F3'-1602 TriNKET are typical for late stage therapeutic antibodies.

The hydrophobicity of a monoclonal antibody is an important biophysical property relevant for its developability into a therapeutic. Hydrophobic patch analysis of the CDRs of an antibody is predictive of its behavior. The CLEC12A arm of F3'-1602 TriNKET has much lower hydrophobicity comparing to other reference molecules. Based on the modeling, there is no hydrophobic patch of significant size on the surface of CLEC12A-binding arm of F3'-1602 TriNKET.

The charge distribution of anti-CLEC12A scFv is polarized, with negatively-charged residues populated predominately within CDRH3 and CDRL2 (as shown in FIGS. 63A-63C). Although the positively charged patches and charge symmetry are within the norm, without wishing to be bound by theory, it is hypothesized that the distinct negatively charged patches on the paratope is target-related and reflects the complementarity of charge distribution on its cognate epitope, which may contribute to its high affinity interaction with CLEC12A.

The NKG2D-binding Fab arm of F3'-1602 TriNKET is shown in ribbon diagrams with three different orientations (FIGS. 65A-65C) and their corresponding surface charge distribution of the same orientation are provided in FIGS. 65A-65C (lower panel). In contrast to CLEC12A binding arm, the surface charge distribution on NKG2D A49M-I arm is more evenly distributed.

FIGS. 66A-66E show the CDR length and patches of surface hydrophobicity analyses of NKG2D-targeting arm of F3'-1602 TriNKET. Analysis was performed using TAP and was benchmarked 377 late-stage therapeutic antibodies. It appears that the CDR length, the hydrophobic properties, the positive/negative charge distributions, and the Fc charge symmetry of the NKG2D-targeting arm of F3'-1602 TriNKET are well within the norm of existing therapeutic antibodies. The modelling suggests that F3'-1602 TriNKET will not have developability complications during the manufacturing processes.

Hydrophobic Interactions Chromatography

Figure 67:
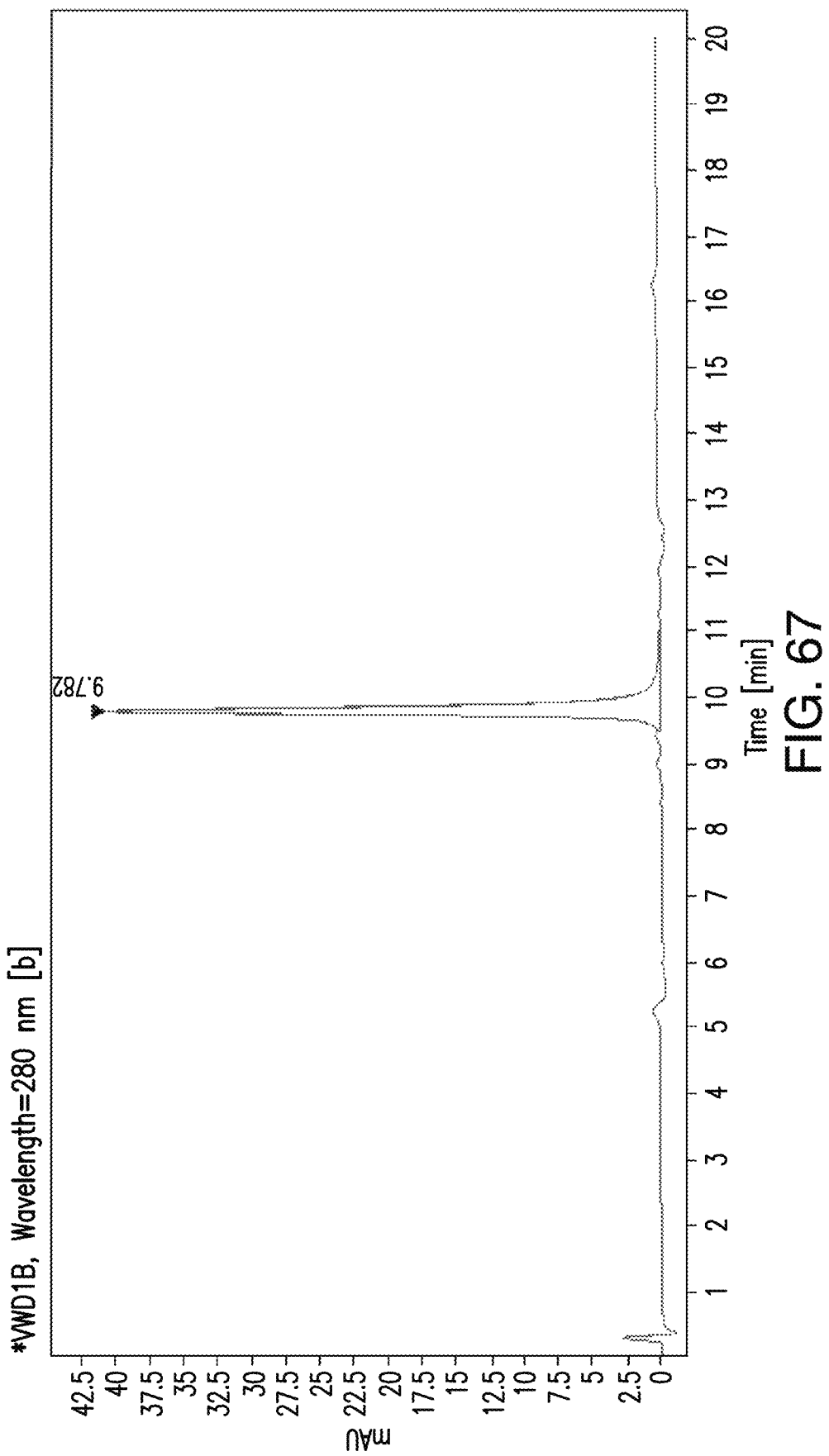
FIG. 67 is a line graph showing Hydrophobic Interactions Chromatography (HIC) analysis of hF3'-1602 TriNKET.

The hydrophobicity prediction data was confirmed by investigating F3'-1602 TriNKET behavior with analytical Hydrophobic Interactions Chromatography (HIC), a technique that relies upon proteins with significant patches of exposed hydrophobic patches being more prone to aggregation. To perform HIC, briefly, injections of TriNKETs (5 µg of protein) were prepared in a 5:4 ratio of high salt buffer (100 mM sodium phosphate, 1.8 M ammonium sulfate, pH 6.5) to sample. Samples were analyzed using an Agilent 1260 Infinity II HPLC equipped with a Sepax Proteomix HIC Butyl-NP5 5 uM column held at 25° C. The gradient was run from 0% low salt buffer (100 mM sodium phosphate, pH 6.5) to 100% low salt buffer over 6.5 minutes at a flow rate of 1.0 mL/minute. Chromatograms were monitored at 280 nm. Retention times of F3'-1602 TriNKET on the analytical HIC column is shown in Table 58 and HIC profile in FIG. 67. Commercial trastuzumab (Roche) was used as an example of a well-behaved biologic and functioned as an internal control for the assay. F3'-1602 TriNKET has a retention time of 9.8 minutes, compared to 9.6 minutes for trastuzumab. Thus, experimental hydrophobicity analysis suggests that the hydrophobic properties of F3'-1602 TriNKET are acceptable for further development.

TABLE 58

HIC retention time of F3'-1602 TriNKET in comparison with trastuzumab.

| Test article | HIC retention time (min) |
| --- | --- |
| F3-1602 TriNKET | 9.8 |
| Trastuzumab | 9.6 |

Capillary Isoelectric Focusing (cIEF)

Figure 68:
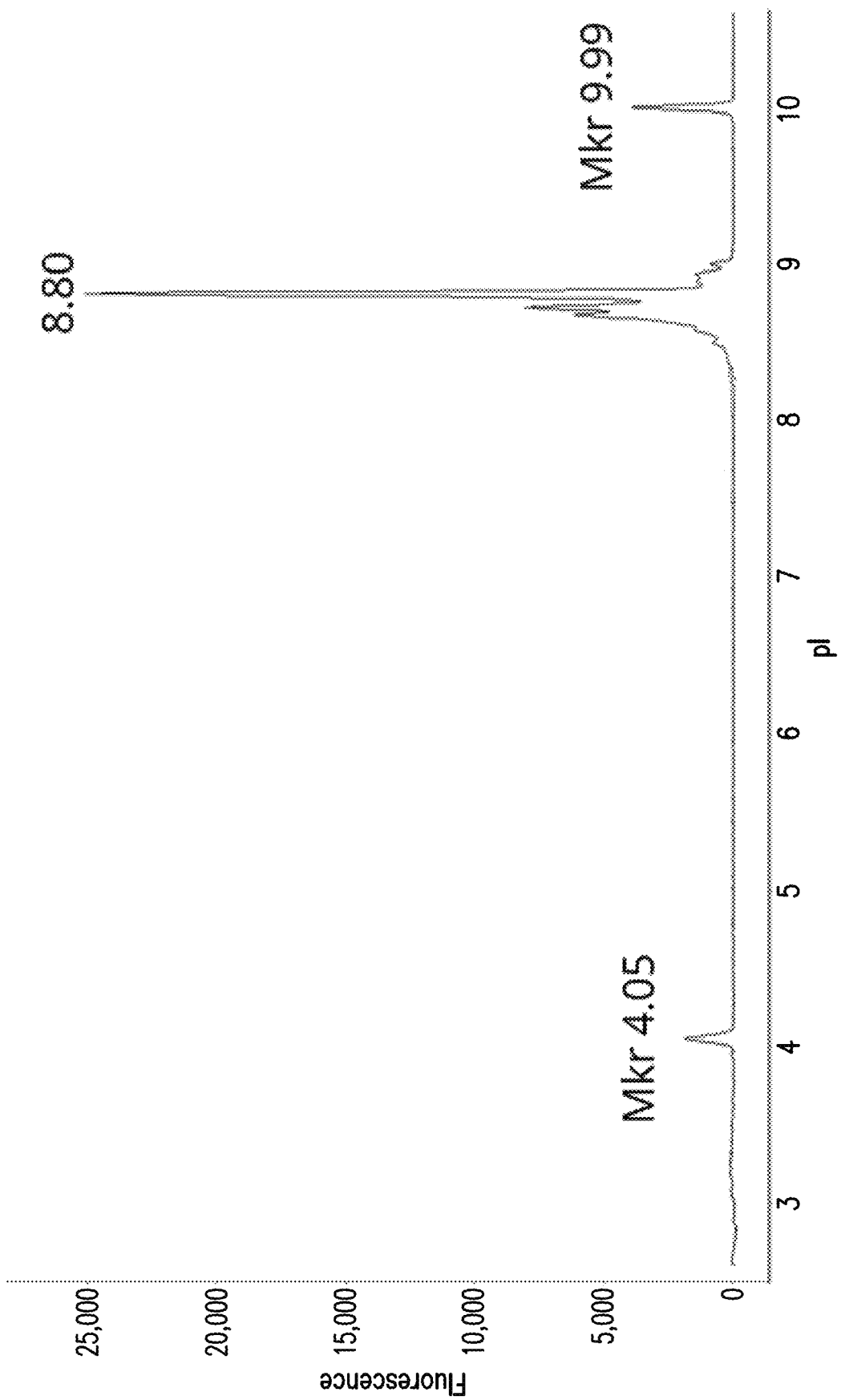
FIG. 68 is a line graph showing pI as determined by cIEF for hF3'-1602 TriNKET.
Figure 69A:
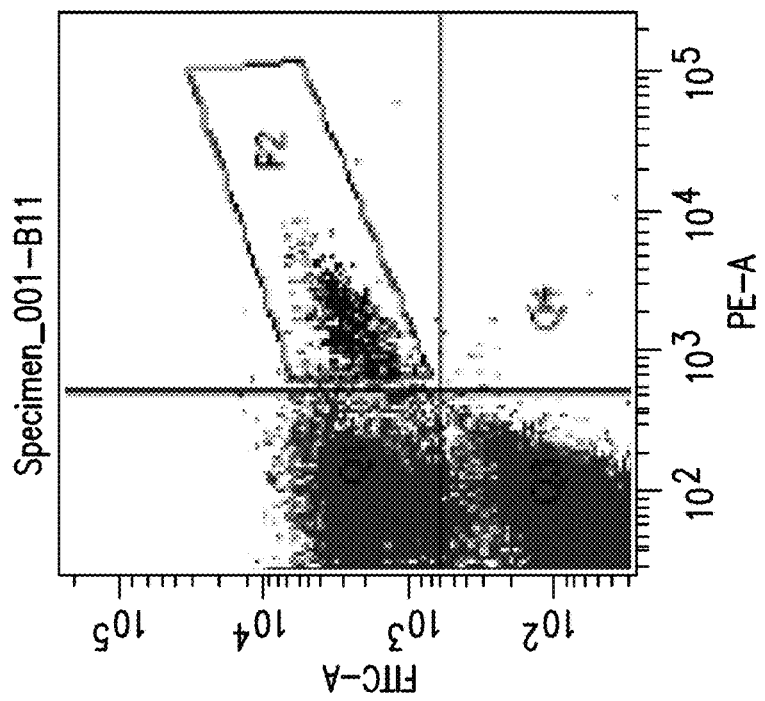
Figure 69B:
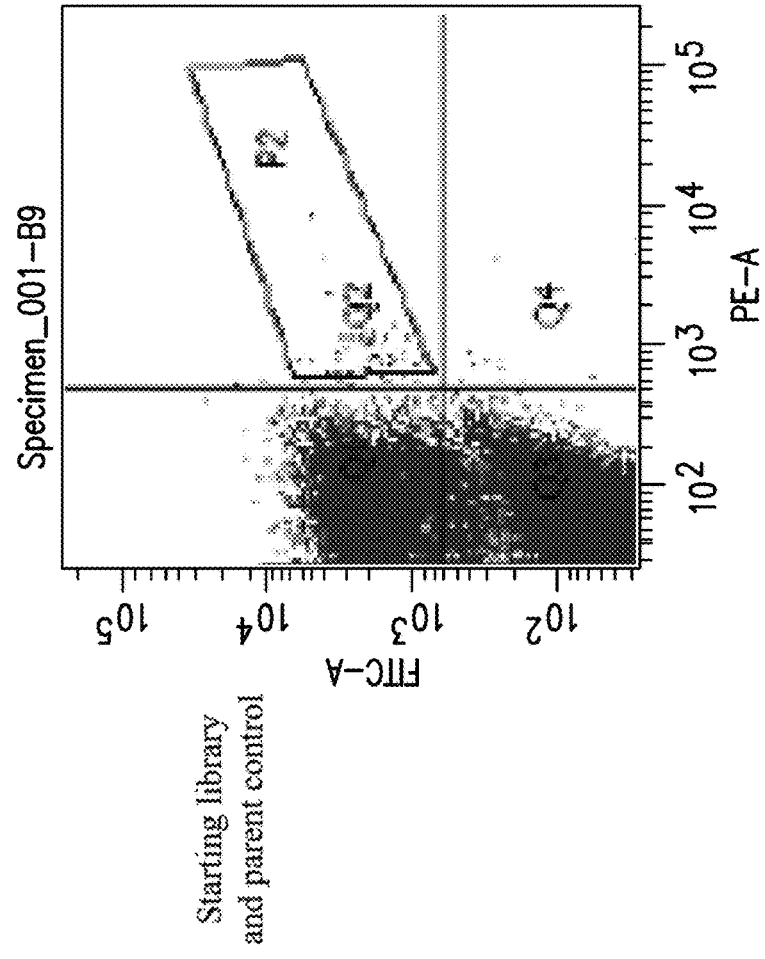
Figure 69F:
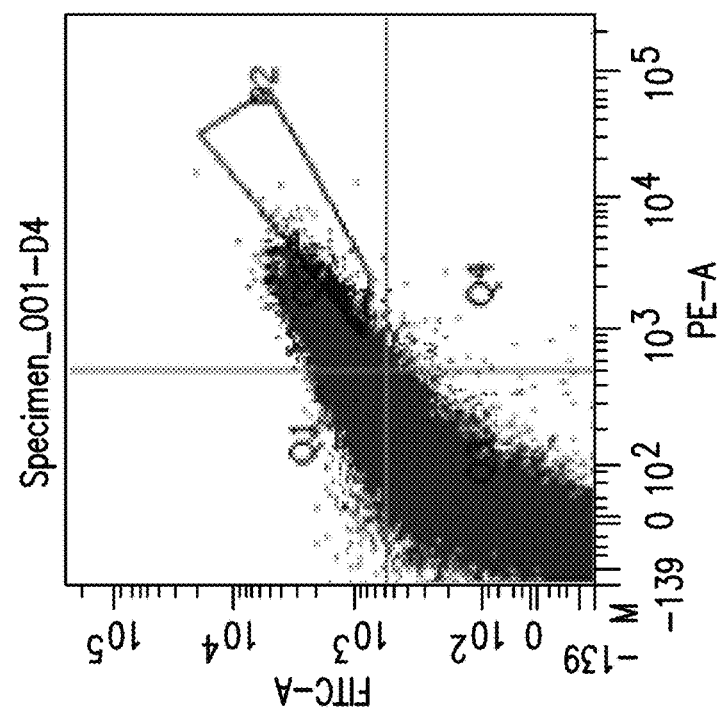
Figure 69E:
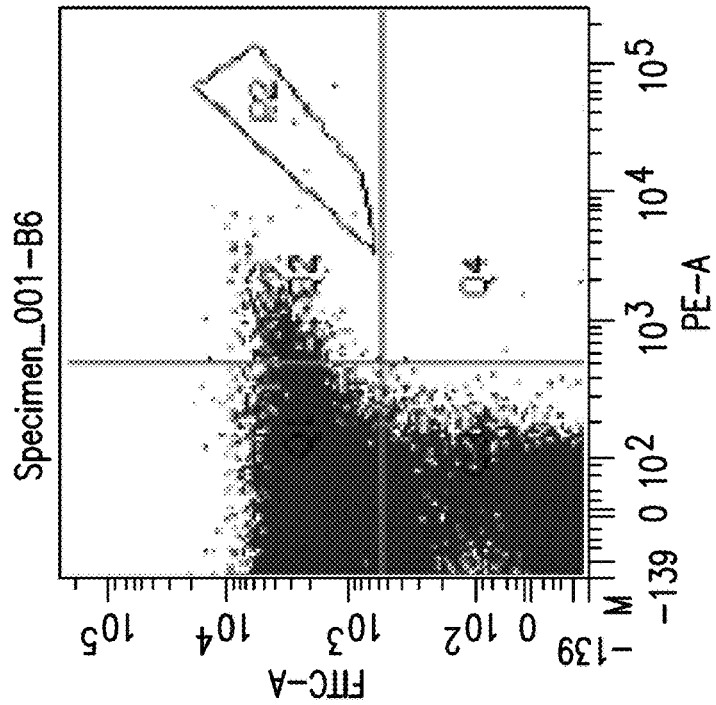
Figure 69I:
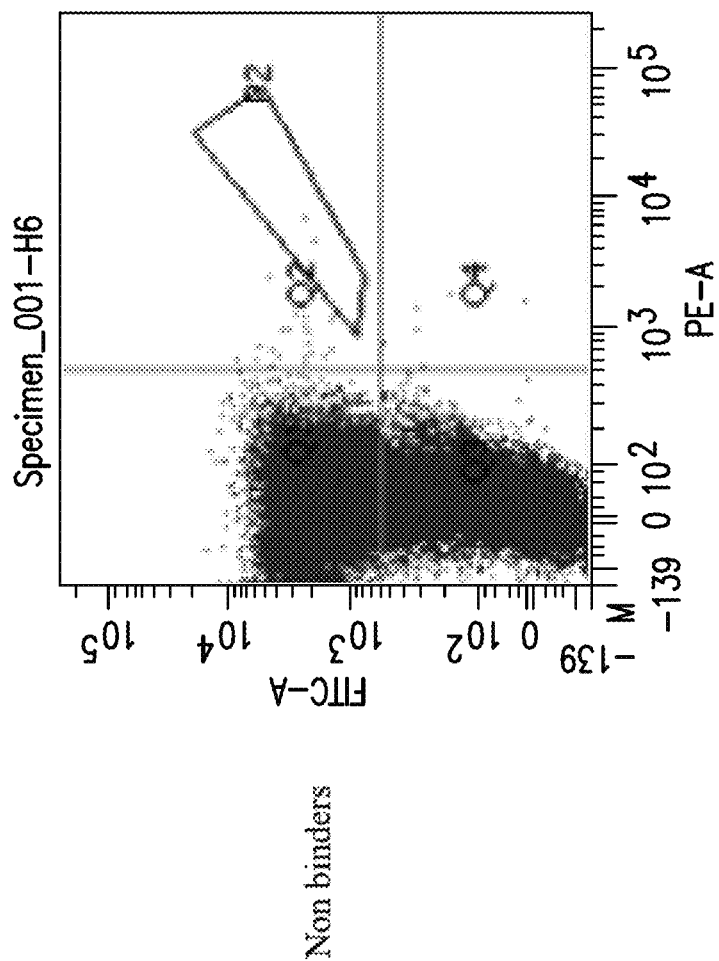

Experimental pI of F3'-1602 was obtained by cIEF, as described in Example 15 (FIG. 68). Commercial grade Trastuzumab was included in the assay as an internal control. The cIEF profile of F3'-1602 TriNKET was typical for a monoclonal antibody, with a main peak at pI 8.80 (Table 59). The presence of minor amounts of acidic and basic species were also observed.

TABLE 59 pI of scFv-1602 F3' by cIEF compared to trastuzumab.

| Test article | pI (major peak) |
| --- | --- |
| scFv-1602 F3' | 8.80 |
| Trastuzumab | 8.91 |

Immunogenicity Assessment

Immunogenicity assessment was performed using the EpiMatrix algorithm from EpiVax was used as described in Cohen et al. (2010) A method for individualizing the prediction of immunogenicity of protein vaccines and biologic therapeutics: individualized T cell epitope measure (iTEM). *J. Biomed. Biotechnol.* 961752. The $T_{reg}$ adjusted Epimatrix Protein Score, which ranges from −80 (no immunogenicity) to 80 (highly immunogenic), for the sequences of the three chains of scFv-1602 F3' are VH-CH1-Fc: −33.39, VH-VL-Fc: −26.4 and VL-CL: −27.4. Thus, the predicted risk of immunogenicity for the scFv-1602 F3' appears to be low.

Example 13. F3'-1602 TriNKET Analysis of Putative Sequence Liabilities

The amino acid sequences of the three polypeptide chains of F3'-1602 TriNKET was analyzed for putative sequence liabilities as described in Example 3. Putative sequence liabilities are shown in Table 60.

TABLE 60

Putative sequence liabilities in F3'-1602 TriNKET. CDRs are under Chothia numbering.

| VL-CL | VH-CH1-Fc | VH-VL-Fc |
| --- | --- | --- |
| None | DP in CDRH3 (potential chemical instability) | DS in CDRH3 (potential aspartate isomerization) |

To examine the liabilities, accelerated stability (4 weeks at 40° C.) and forced degradation studies were performed. The DP in the CDRH3 of VH-CH1-Fc was not modified in accelerated stability studies or forced degradation studies, and therefore, no further analysis was necessary. However, it was observed that modification of the DS in the CDRH3 in the scFv led to a reduction in CLEC12A binding and decreased potency of F3'-1602 TriNKET in accelerated stability studies, as described in Example 14.

Figure 70:
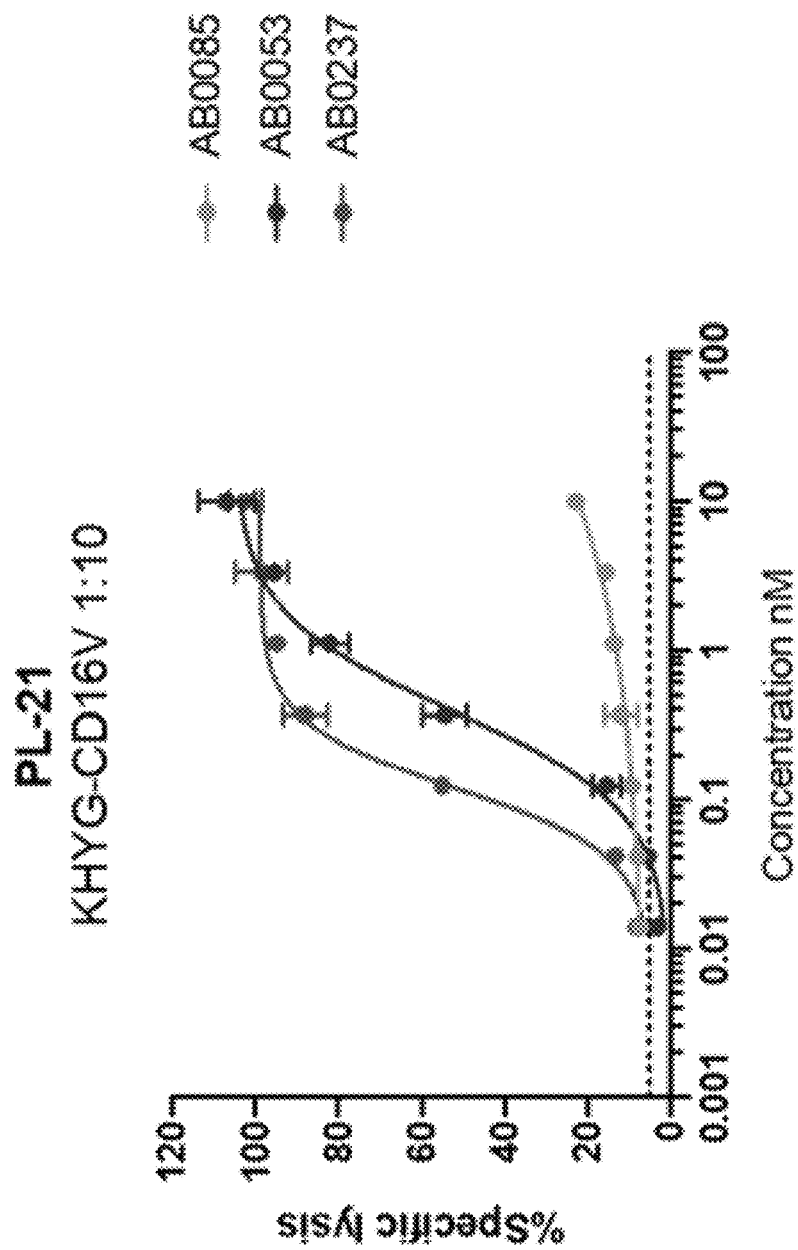
FIG. 70 are line graphs showing NK cell-mediated lysis of CLEC12A-expressing cancer cell line PL21 in the presence of hF3'-1602 TriNKET and liability-remediated variants.
Figure 71A:
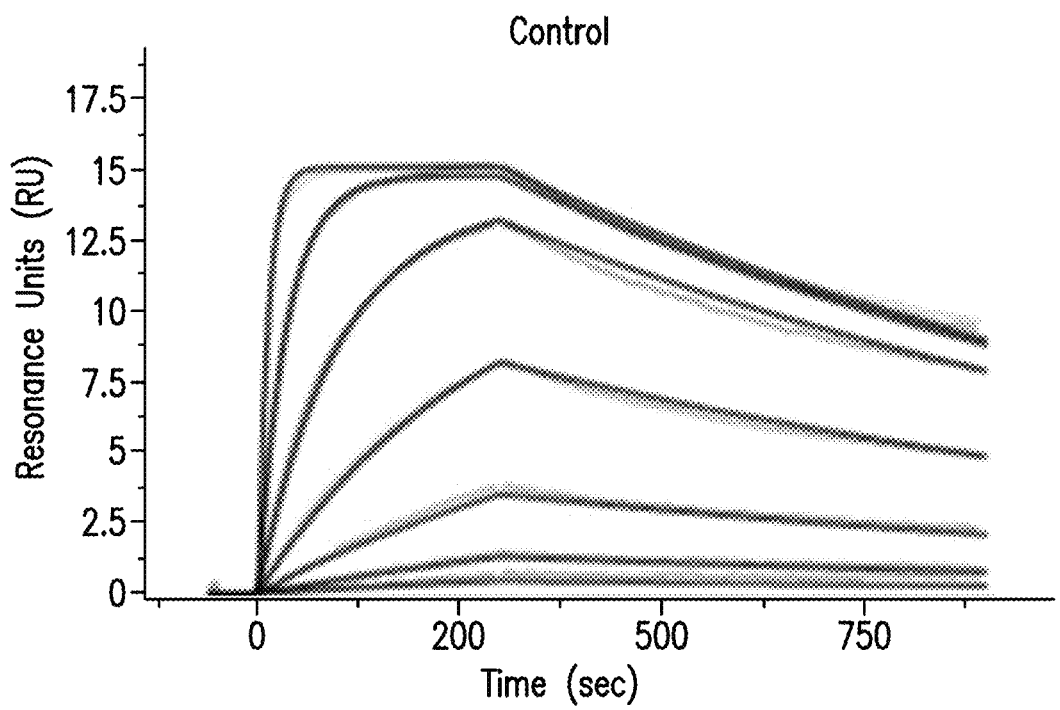
FIG. 71A-FIG. 71B are a set of sensorgrams showing the binding of hCLEC12A at three-fold serial dilution (300 nM to 0.41 nM) to F3'-1602 in the HST formulation. The black overlays represent the 1:1 kinetic fit of the raw data.
Figure 71B:
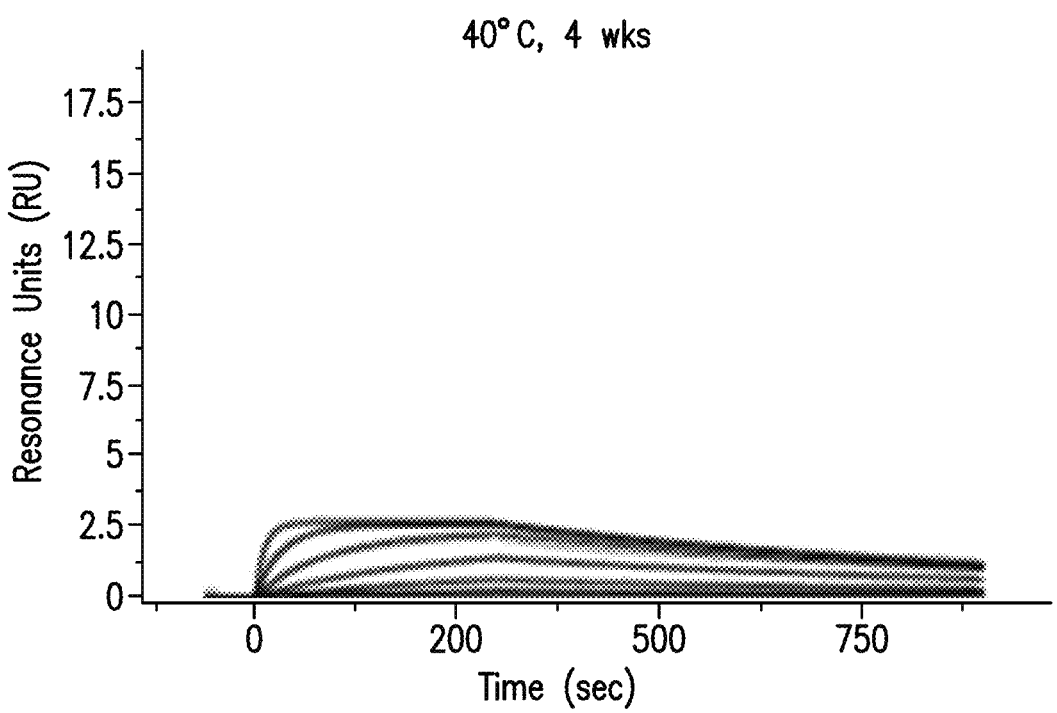

To replace the DS in CDRH3, yeast display was performed to identify alternative sequence motifs without the DS site. Three variants, namely YDYDDALDY (SEQ ID NO:283) YDYDDILDY (SEQ ID NO:284) and YDYDD-LLDY (SEQ ID NO:285), were identified that showed binding to hCLEC12A albeit with weaker binding signal compared to the parent scFv (YDYDDSLDY) (SEQ ID NO:139), while variants YDYDDVLDY (SEQ ID NO:290), YDYDDTLDY (SEQ ID NO:291), and YDYDESLDY (SEQ ID NO:292) were identified as non-binders. Based on the binding analysis only variants YDYDDALDY ((SEQ ID NO:283), AB0053) and YDYDDILDY ((SEQ ID NO:284), AB0085) were considered for mammalian production and further characterization. Binding of AB0053 and AB0085 to hCLEC12A-His was characterized using Surface Plasmon Resonance (SPR) at 37° C. Both mutations introduced to remove DS sequence liability had an effect on the binding to hCLEC12A-His (Table 61). FIGS. 69A-69I demonstrate FACS analysis of binding to hCLEC12A-his using yeast libraries generated to remove the sequence liability in CDRH3. The data showed complete loss of binding in the DS to DI engineered variant (AB0085). Introduction of DA in place of DS (AB0053) did not eliminate binding completely but lead to apparent heterogeneity in binding sensorgram. Following SPR analysis, potency of the liability-remediated variants (AB0053 and AB0085) were tested in KHYG-1-CD16aV mediated cytotoxicity assay (FIG. 70, Table 62). AB0085 lost ability to kill AML cells as determined by significantly reduced percentage of maximum killing. EC50 for AB0053 construct increased ~3-fold compared to F3'-1602 TriNKET (AB0237) control, whereas percentage of maximum killing was not affected. This finding is in line with the 3-fold change in overall affinity for hCLEC12A established in the SPR experiment (Table 61).

Binding affinities of F3'-1602 TriNKET to recombinant human CLEC12A were measured by SPR at 37° C. using a Biacore 8K instrument. Briefly, human Fc specific antibodies were covalently immobilized at a density ~8000-10000 resonance units (RU) on carboxy methyl dextran matrix of a CM5 biosensor chip via amine-coupling chemistry to create an anti-hFc IgG chip. F3'-1602 TriNKET samples were captured on the anti-hFc IgG chip at a concentration of 1.5 μg/mL at a flow rate of 10 μL/min for 60 seconds to achieve ~150-250 RU capture level. hCLEC12A-His was serially diluted (100 nM-0.046 nM) in three-fold dilutions with HBS-EP+ buffer (1×; 10 mM HEPES, 150 mM NaCl, 3 mM EDTA, 0.05% P20 pH 7.4) with 0.1 mg/mL bovine serum albumin (BSA) and injected at a flow rate of 30 μl/min over the captured test articles. Association was monitored for 300 seconds and dissociation was monitored for 600 seconds. Surfaces were regenerated between cycles with three pulses of 10 mM glycine-HCl, pH 1.7 injected for 20 seconds at 100 μL/min. HBS-EP+ (1×) with 0.1 mg/mL BSA buffer was used throughout the experiment. Data were analyzed using Biacore 8K Insight Evaluation software (GE Healthcare).

TABLE 61

Kinetic parameters and affinities of DS engineered clones for hCLEC12A for CLEC12A.

| Test Article | $k_a$ (M$^{-1}$s$^{-1}$) | $k_d$ (s$^{-1}$) | $K_D$ (nM) | Notes |
|---|---|---|---|---|
| AB0053 | 1.63 × 10$^6$* | $k_{d1}$ = 1.57 × 10$^{-2}$ and $k_{d2}$ = 9.49 × 10$^{-4}$ | 2.41 | Two-state fit |
| AB0085 | | No Binding | | |
| F3'-1602 (AB0237) | 1.11 × 10$^6$ | 8.95 × 10$^{-4}$ | 0.80 | Classical 1:1 fit |

*$k_{a2}$ value was insignificant compared to the $k_{a1}$ value. Therefore, only $k_{a1}$ value is shown.

TABLE 62

Comparison of potency of DS engineered TriNKETs in KHYG-1-CD16aV cytotoxicity assay.

| | PL-21 cells | |
|---|---|---|
| Test Article | EC50 (nM) | Max lysis (%) |
| F3'-1602 TriNKET (AB0237) | 0.12 | 98.96 |
| AB0053 | 0.39 | 105.10 |
| AB0085 | N/D* | N/D |

*N/D not determined

As the library approach produced AB0053 as the only hit, and that hit demonstrated kinetics of binding to hCLEC12A significantly different from F3'-1602 TriNKET and inferior potency in the cytotoxicity assay, it was concluded that the DS motif is necessary for maintaining architecture of CDRH3 and therefore cannot be effectively removed. The DS liability was instead controlled with formulation, as described in Example 14.

Example 14. Formulations of F3'-1602

In Example 13, sequence liability sites were found to be critical for the ability of F3'-1602 to bind CLEC12A and therefore cannot be removed. This example was designed to assess the formulations that may maintain the stability of F3'-1602 despite the presence of the sequence liabilities.

Briefly, three formulations were tested for F3'-1602:

(1) 20 mM histidine, 250 mM sucrose, and 0.01% polysorbate 80, at pH of 6.0, referred to herein as the "HST formulation." F3'-1602 was diafiltered into the HST buffer and the recovered sample was passed through a 0.2 μm filter. The final concentration of F3'-1602 was 19.7 mg/mL, as measured by absorbance at 280 nm (A280).

(2) 20 mM potassium phosphate, 10 mM sodium citrate, and 125 mM sodium chloride, at pH 7.8, referred to herein as the "phosphate/citrate/NaCl formulation." F3'-1602 was buffer switched into the phosphate/citrate/NaCl formulation buffer using an Amicon Ultra 0.5 mL 30K device and Zeba Desalting Columns, and the recovered sample was passed through a 0.2 μm filter. The final concentration of F3'-1602 was 20.6 mg/mL, as measured by A280.

(3) 20 mM citrate, 250 mM sucrose, and 0.01% polysorbate 80, at pH 7.0, referred to herein as the "CST formulation." F3'-1602 was diafiltered into the CST formulation buffer and the recovered sample was passed through a 0.2 μm filter. The final concentration of F3'-1602 was 20 mg/mL, as measured by A280.

Stability of F3'-1602 in the HST Formulation

An accelerated stability study was carried out in the HST buffer at 40° C. for four weeks. Size exclusion chromatography (SEC) was used to monitor the formation of high molecular weight species (HMWS) and low molecular weight species (LMWS) as a function of storage conditions. Briefly, 50 μg of test material was injected onto an Agilent 1260 Infinity II high pressure liquid chromatography (HPLC) instrument with 1260 Quat Pump, 1260 Vialsampler, 1260 VWD. The sample was separated on a Tosoh TSKgel G3000SWxl, 7.8 mm I.D.×30 cm, 5 μm column. SEC running buffer was PBS, pH 7.0, flowing at 0.50 ml/min. Absorbance was monitored at both 214 and 280 nm, peak areas were manually integrated and the percent of HMWS, LMWS, and monomer were reported.

At the onset of the study, F3'-1602 was analyzed by SEC and was 99.6% monomer. After four weeks at 40° C., monomer decreased to 93.1%. LMWS were not detected in the control and increased to 5.4% after four weeks at 40° C. HMWS were present in the control at 0.4% and increased to 1.5% after four weeks at 40° C. (Table 63). These data suggest that F3'-1602 degrades primarily through the formation of LMW species (fragmentation).

TABLE 63

Summary of SEC % monomer, HMW, and LMW (accelerated stability in the HST formulation)

| Test article | Monomer (%) | HMW (%) | LMW (%) |
|---|---|---|---|
| Control | 99.6 | 0.4 | ND |
| 1 week | 99.0 | 0.7 | 0.3 |
| 2 weeks | 98.5 | 1.0 | 0.5 |
| 3 weeks | 97.8 | 1.5 | 0.8 |
| 4 weeks | 93.1 | 1.5 | 5.4 |

ND: none detected

The binding affinities of F3'-1602 samples to recombinant human CLEC12A were measured by SPR at 37° C. using a Biacore 8K instrument. Briefly, human Fc specific antibodies were covalently immobilized at a density ~8000-10000 resonance units (RU) on carboxy methyl dextran matrix of a CM5 biosensor chip via amine-coupling chemistry to create an anti-hFc IgG chip. F3'-1602 samples were captured on the anti-hFc IgG chip at a concentration of 1.5 μg/mL at a flow rate of 10 μL/min for 60 seconds to achieve ~150-250 RU capture level. hCLEC12A-His was serially diluted (100 nM-0.046 nM) in three-fold dilutions with HBS-EP+ (1×) with 0.1 mg/mL bovine serum albumin (BSA) buffer and injected at a flow rate of 30 μl/min over the captured test articles. Association was monitored for 300 seconds and dissociation was monitored for 600 seconds. Surfaces were regenerated between cycles with three pulses of 10 mM glycine-HCl, pH 1.7 injected for 20 seconds at 100 μL/min. HBS-EP+ (1×) with 0.1 mg/mL BSA buffer was used throughout the experiment. Data were analyzed using Biacore 8K Insight evaluation software (GE Healthcare). The kinetic rate constants and overall affinity were obtained using 1:1 kinetic fit binding model (FIGS. 71A-71B).

After four weeks of incubation at 40° C. in the HST formulation, binding of F3'-1602 to human CLEC12A was decreased (FIG. 71B). The difference in association and dissociation rate constants between the control and 40° C. stressed sample are within the experimental variability of the assay (Table 64); however, the maximal binding response expressed in resonance units (RU) decreased more than fivefold after the incubation at 40° C. (FIG. 71B). The nominal capture of F3'-1602 protein was the same for both, stressed and control, samples. Under such circumstances, $R_{max}$ is roughly proportional to the active concentration of F3'-1602 captured on the Biacore chip. This result in turn indicates that after thermal stress in the HST formulation, more than 80% of F3'-1602 molecules lost the ability to bind CLEC12A (Table 64).

TABLE 64

Summary of kinetic parameters and binding affinity of F3'-1602 for hCLEC12A (accelerated stability in the HST formulation)

| Test article | Target | $k_a$ (M$^{-1}$s$^{-1}$) | $k_d$ (s$^{-1}$) | $K_D$ (nM) | Capture level (RU) |
|---|---|---|---|---|---|
| F3'-1602 Control | hCLEC12A | $7.91 \times 10^5$ | $8.73 \times 10^{-4}$ | 1.11 | 83.8 |
| F3'-1602 in the HST formulation, 40° C. 4 wks | hCLEC12A | $1.24 \times 10^6$ | $2.14 \times 10^{-3}$ | 1.69 | 84.2 |

Results are an average of n = 2 replicates

The binding affinities of F3'-1602 samples to recombinant human NKG2D were measured by SPR at 37° C. using a Biacore 8K instrument. Briefly, mFc specific antibodies were covalently immobilized at a density of ~8000-10000 RU on carboxy methyl dextran matrix of a CM5 biosensor chips via amine coupling chemistry to create an anti-mFc IgG chip. mFc-tagged human NKG2D was captured on the anti-mFc IgG chip at a concentration of 0.2 µg/mL at a flow rate of 10 µL/min for 60 seconds to achieve ~35 RU capture level. F3'-1602 was buffer exchanged into HBS-EP+ (1×) buffer and serially diluted (5000 nM-9.78 nM) in two-fold dilutions with HBS-EP+. Analyte (F3'-1602) was injected at a flow rate of 30 µL/min over the captured test articles. Association was monitored for 60 seconds and dissociation was monitored for 60 seconds. Surfaces were regenerated between cycles with three pulses of 10 mM glycine-HCl, pH 1.7 injected for 20 seconds at 100 µL/min. HBS-EP+ (1×) buffer was used throughout the experiment. Data were analyzed using Biacore 8K Insight evaluation software (GE Healthcare). The binding affinity and kinetic rates were obtained with the use of both 1:1 kinetic and steady-state affinity model fits (FIGS. 72A-72D).

Figure 72A:
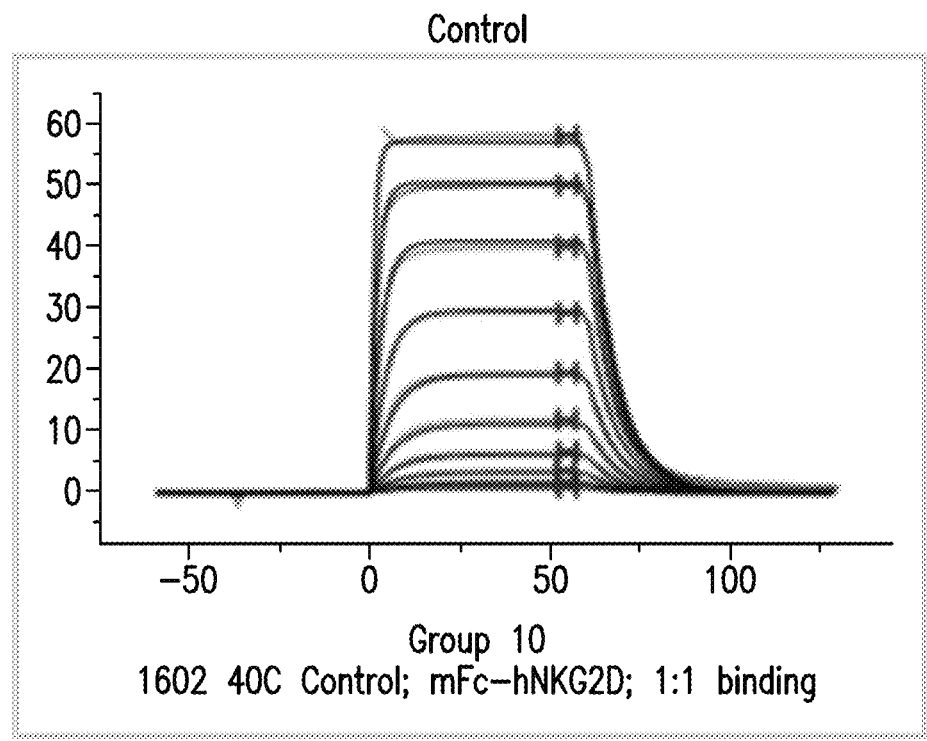
FIG. 72A-FIG. 72D is a set of graphs showing the binding of F3'-1602 in the HST formulation to hNKG2D.
Figure 72B:
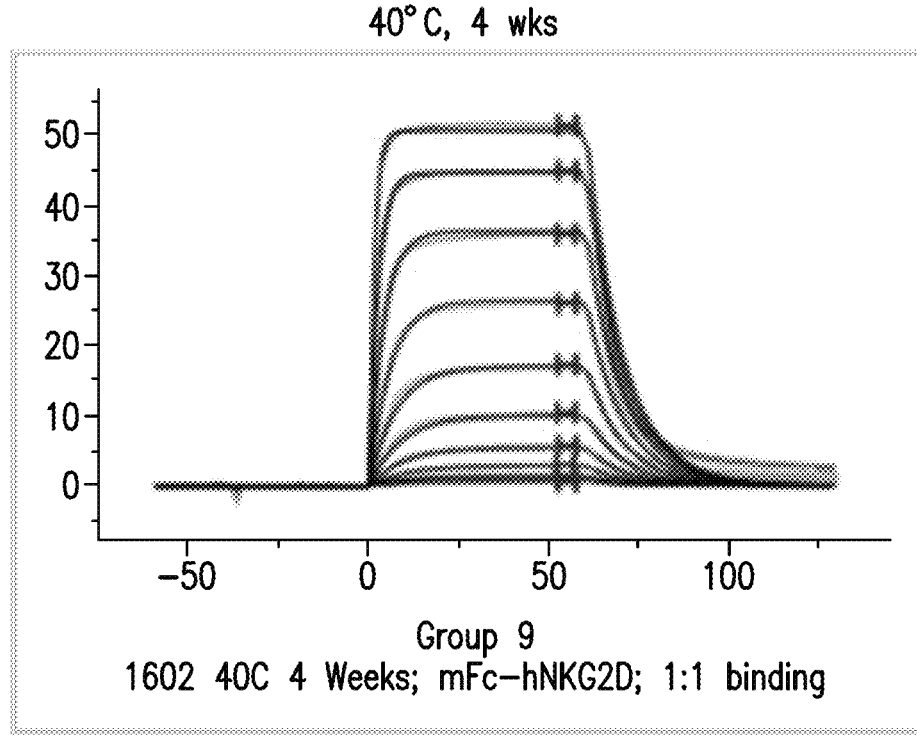
Figure 72C:
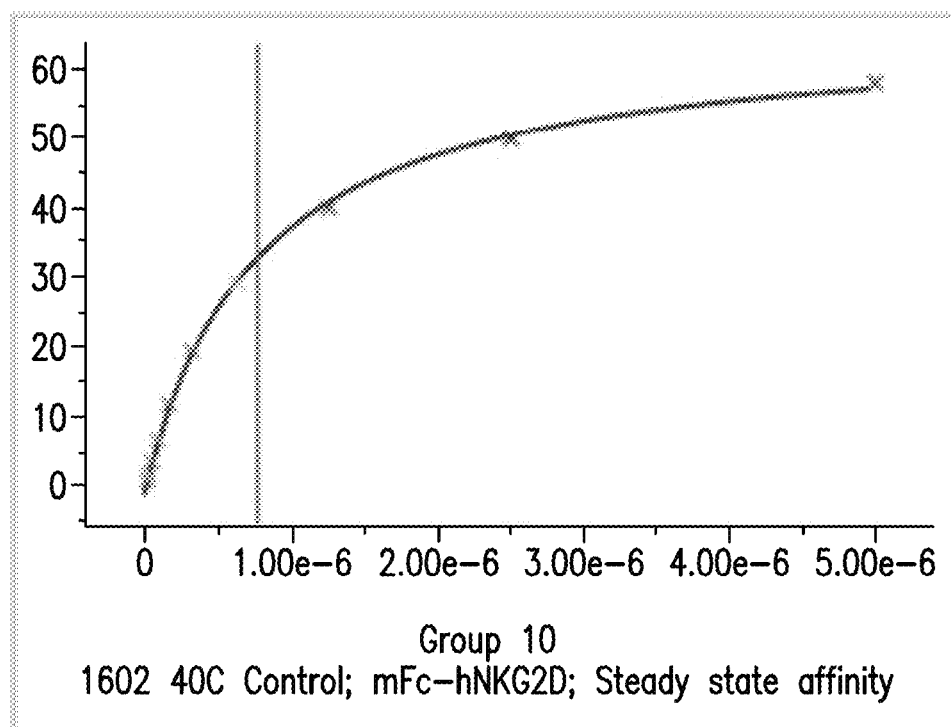
Figure 72D:
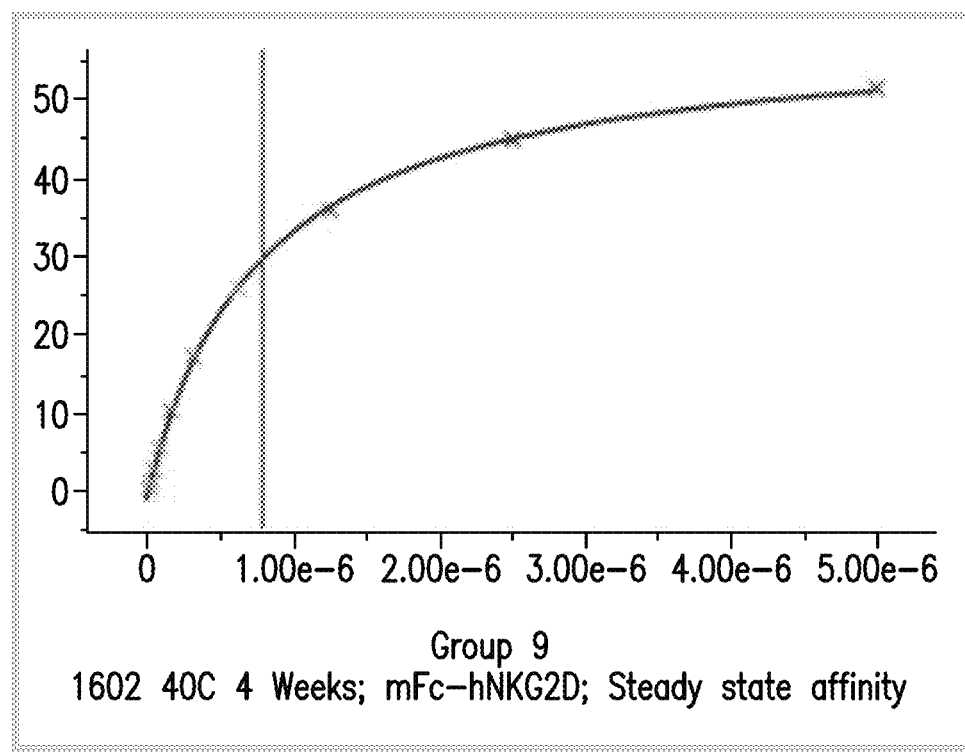

After four weeks of incubation at 40° C. in the HST formulation, binding of F3'-1602 to human NKG2D was unaltered (FIGS. 72B and 72D, Table 65). The difference in association and dissociation rate constants as well as overall affinity for NKG2D between the control and 40° C. stressed sample were within the experimental variability of the assay. Maximal binding response did not change significantly. The results indicate that F3'-1602 maintained the ability to bind NKG2D under these thermal stress conditions.

TABLE 65

Summary of kinetic parameters and binding affinity of F3'-1602 for hNKG2D (accelerated stability in the HST formulation)

| Test article | Target | $k_a$ (M$^{-1}$s$^{-1}$) | $k_d$ (s$^{-1}$) | 1:1 Kinetic Fit $K_D$ (nM) | Steady state $K_D$ (nM) | Capture level (RU) |
|---|---|---|---|---|---|---|
| F3'-1602 Control | hNKG2D | $1.70 \times 10^5$ | $1.29 \times 10^{-1}$ | 760 | 771 | 50.1 |
| F3'-1602 in the HST formulation, 40° C., 4 wks | hNKG2D | $1.29 \times 10^5$ | $9.86 \times 10^{-2}$ | 762 | 776 | 47.4 |

The binding affinities of F3'-1602 samples to biotinylated recombinant CD16a V158 (FcγRIIIa V158) receptor were measured by SPR. Briefly, FcγRIIIa V158 was captured on a SA Series S Biacore chip prior to the kinetic evaluation experiment to achieve capture ~10-25 RU. Trastuzumab, a well characterized IgG1 biologic drug, was used as an experimental control. The evaluation used injections of varying concentrations of ligand (F3'-1602 or trastuzumab) titrated over the captured receptor (1500 nM-11.7 nM in 1:1 serial dilution and 0 nM). Each injection cycle consisted of association, dissociation and regeneration steps. Association consisted of 150 seconds of ligand injection, dissociation was monitored for 300 seconds and then the surface was regenerated between cycles with 2 mM sodium hydroxide injected for 5 seconds. All steps were executed at a flow rate of 30 μL/min. 1×HBS-EP+ buffer solution was used as a running/sample dilution buffer. Data were analyzed using Biacore 8K Insight evaluation software (GE Healthcare). The data were fit with a 1:1 kinetic model (FIGS. 73A-73B).

Figure 73A:
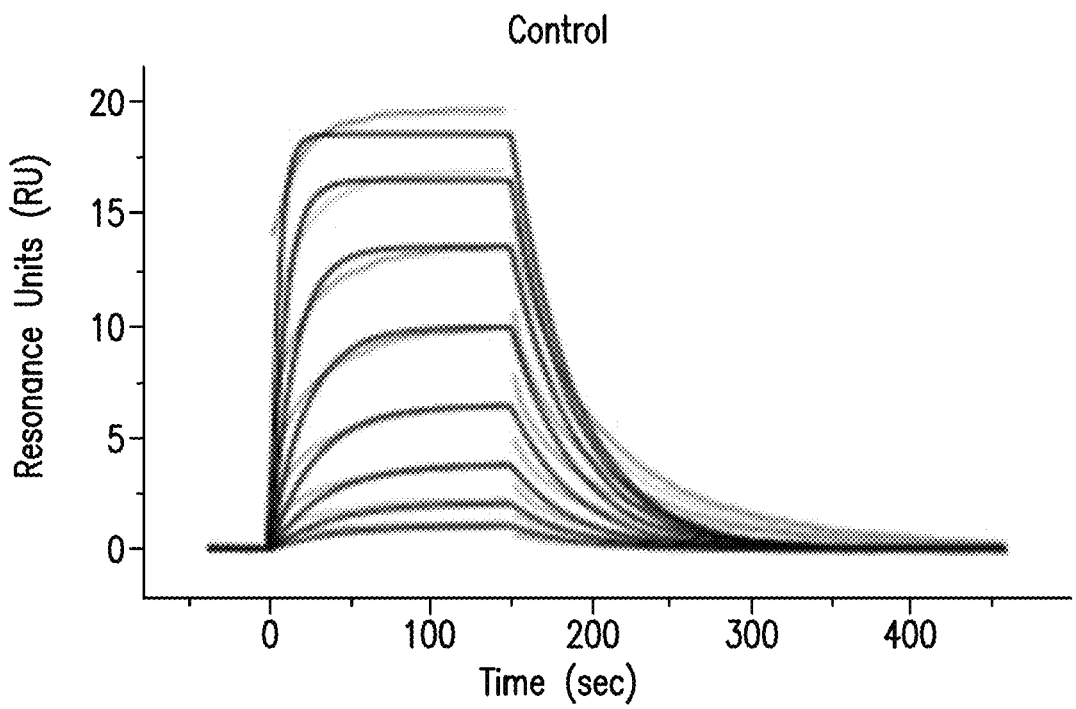
FIG. 73A-FIG. 73B are a set of sensorgrams showing the binding of F3'-1602 in the HST formulation to hCD16a V158.
Figure 73B:
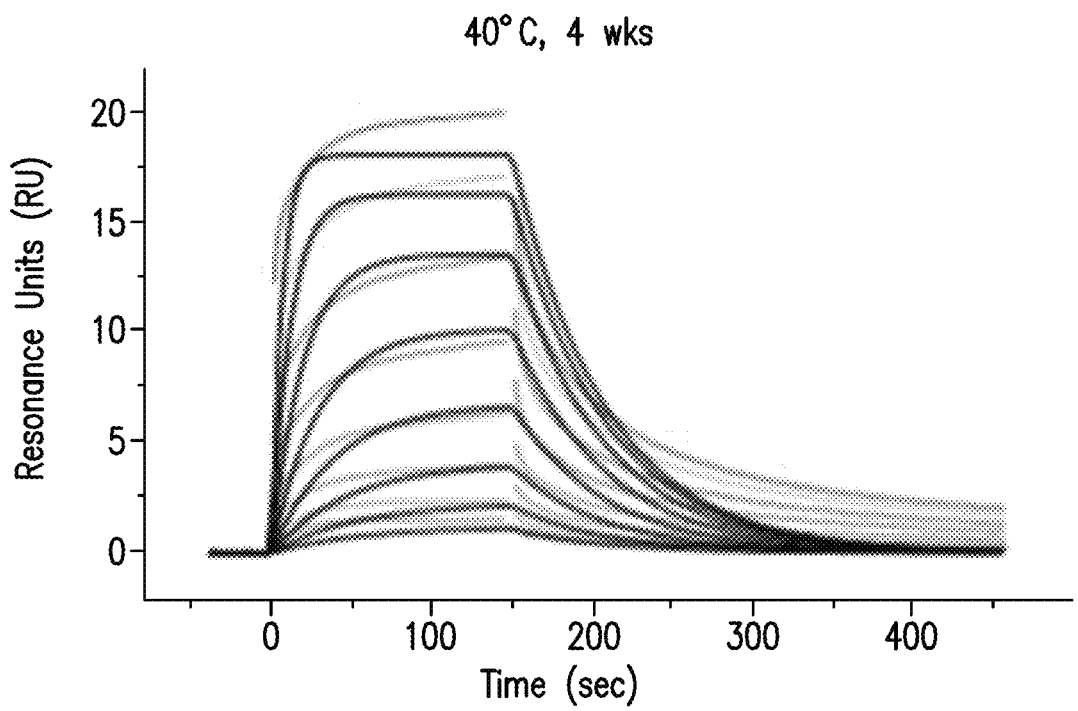

After four weeks of incubation at 20 mg/mL, 40° C. in the HST formulation, binding of F3'-1602 to human CD16a V158 was unaltered (FIG. 73A and Table 66). The difference in binding affinity between the control and 40° C. stressed sample as well as maximal binding response ($R_{max}$) were within the experimental variability of the assay. The results indicate that F3'-1602 retained affinity for human CD16a under these accelerated storage conditions.

TABLE 66

Summary of kinetic parameters and binding affinity of F3'-1602 for hNKG2D (accelerated stability in the HST formulation)

| Test article | Target | $k_a$ (M$^{-1}$s$^{-1}$) | $k_d$ (s$^{-1}$) | $K_D$ (nM) | Capture level (RU) |
|---|---|---|---|---|---|
| F3'-1602 Control | hCD16aV | (1.13 ± 0.04) × 10$^5$ | (2.40 ± 0.09) × 10$^{-2}$ | 212 ± 1 | 13.7 |
| F3'-1602 in the HST formulation, 40° C., 4 wks | hCD16aV | (8.24 ± 0.78) × 10$^4$ | (1.65 ± 0.06) × 10$^{-2}$ | 201 ± 12 | 14.2 |

Results are an average of n = 3 replicates

The effect of accelerated stability on F3'-1602 function was also assessed in a cytotoxicity assay using KHYG-1-CD16a cells engineered to express CD16a in addition to NKG2D. CLEC12A$^+$ human cancer cell lines (PL-21) were labeled with BATDA reagent. After labeling, cells were washed and resuspended in primary cell culture media. BATDA labeled cells, F3'-1602, and rested KHYG-1-CD16V cells were added to the wells of a 96-well plate. Additional wells were prepared for maximum lysis of target cells by addition of 1% Triton-X. Spontaneous release was monitored from wells with only BATDA-labeled cells. After three hours of culture, the cells were pelleted, the culture supernatant was transferred to a clean microplate, and room temperature europium solution was added to each well. The plate was protected from light and incubated on a plate-shaker at 250 rpm for 15 minutes. Plates were read using a SpectraMax i3X instrument. The % Specific lysis was calculated as follows:

% Specific lysis=((Experimental release−Spontaneous release)/(Maximum release−Spontaneous release))*100%

Figure 74:
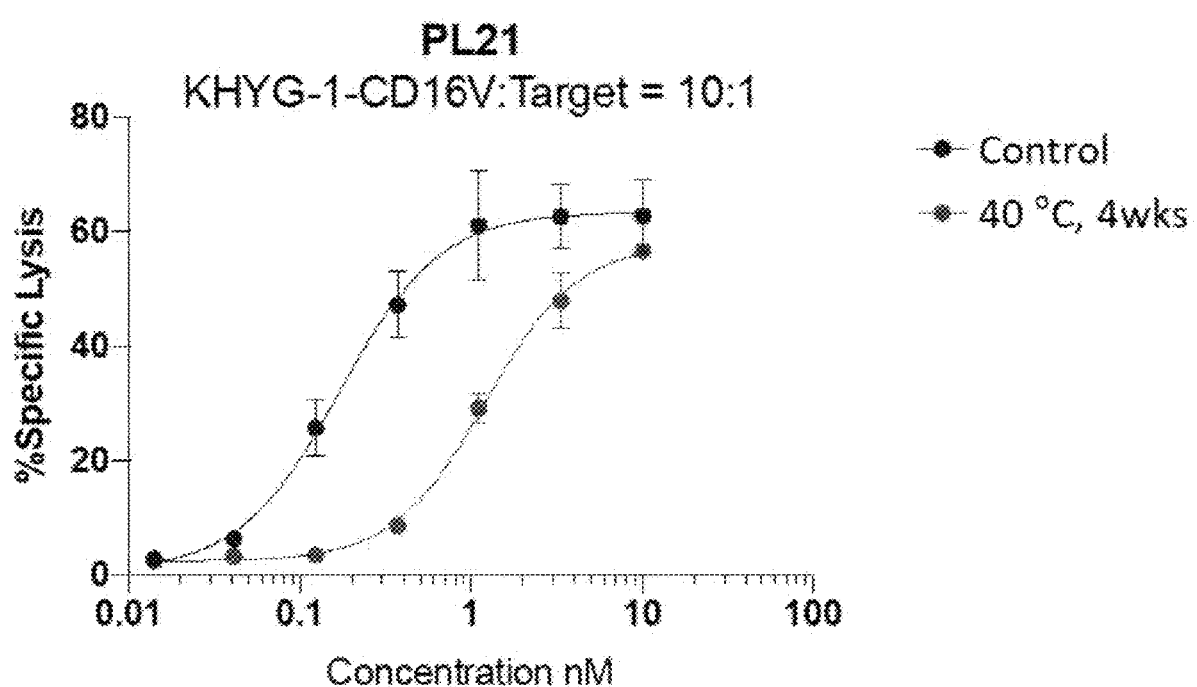
FIG. 74 is a graph showing the percentage lysis of PL21 cells by NKG2D- and CD16a-expressing KHYG-1-CD16a cells in the presence of stressed and control samples of F3'-1602 in the HST formulation.

As shown in FIG. 74 and Table 67, the ability of F3'-1602 to kill PL21 CLEC12A$^+$ cancer cells decreased by approximately 7-fold after 4 weeks at 40° C. in the HST formulation, whereas max % lysis decreased only slightly (5%).

TABLE 67

EC50 and maximum lysis of CLEC12A + PL21 cells by F3'-1602 (accelerated stability in the HST formulation)

| Test article | EC50 (nM) | Max. lysis (%) |
|---|---|---|
| F3'-1602 Control | 0.17 | 63 |
| F3'-1602 in the HST formulation, 40° C., 4 wks | 1.21 | 58 |

Figures 75A, 75B, 75C:
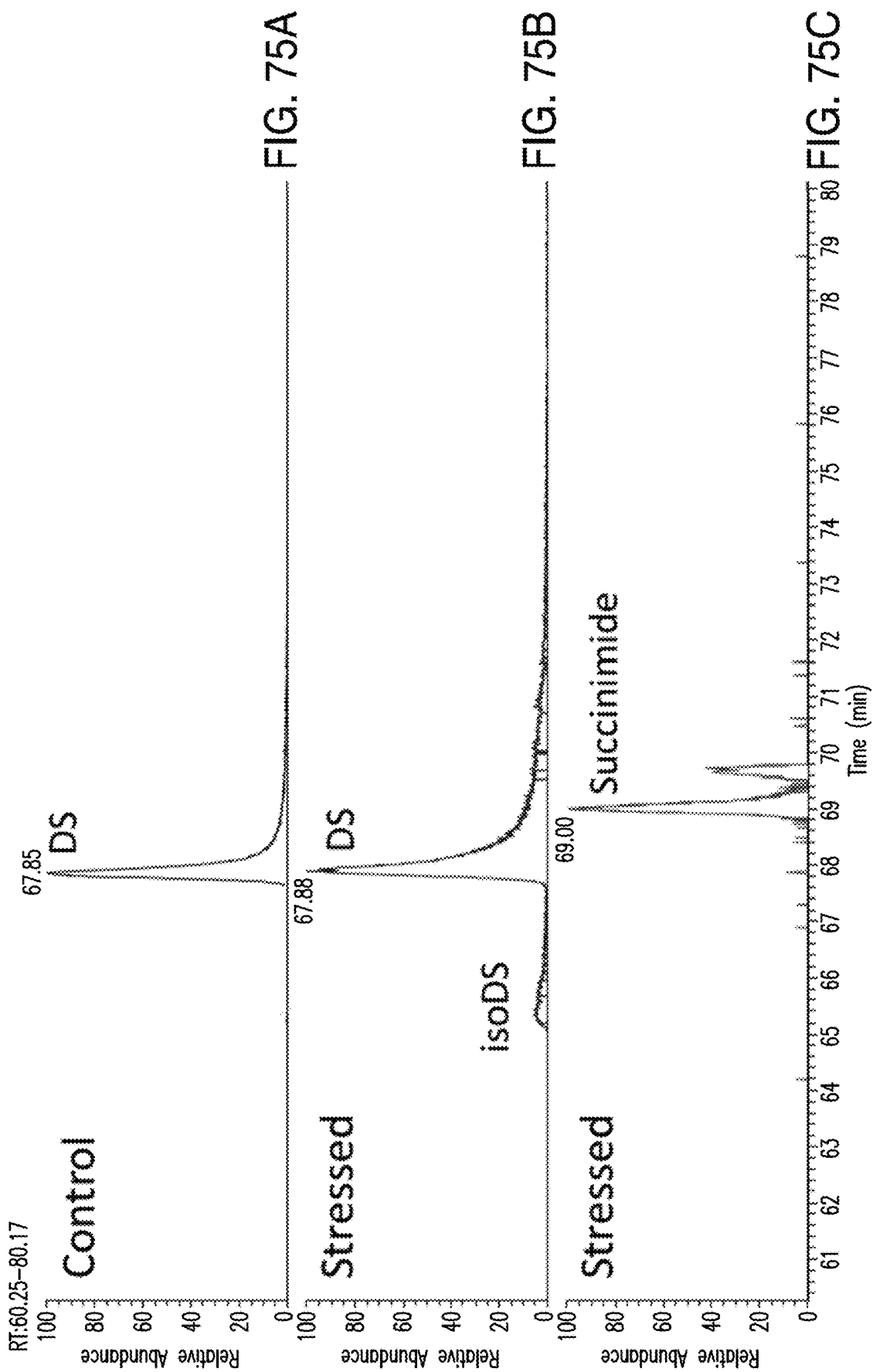
FIG. 75A-FIG. 75C are a set of extracted ion chromatograms of CDRH3 peptide in control (FIG. 75A) and stressed F3'-1602 (FIG. 75B and FIG. 75C).

The significant loss of binding to hCLEC12A after 40° C. incubation and the corresponding loss in potency led to an investigation into the root cause of this behavior. UHPLC-MS/MS peptide mapping revealed that an aspartic acid in the anti-CLEC12A scFv (CDR-H3) was undergoing isomerization (FIG. 75B).

F3'-1602 CDRH3, as defined under Chothia, contains four aspartic acids (DYDDSLDY [SEQ ID NO:293]). MS/MS was used to determine which of them was undergoing isomerization by monitoring the succinimide intermediate. Conversion to isoaspartic acid does not result in a mass difference, whereas the succinimide intermediate corresponds to a loss of water (approximately 18 Da). This mass shift can be used to identify the aspartic acid which is isomerizing. MS/MS spectra of the unmodified chymotryptic peptide and the corresponding succinimide variant showed that the aspartic acid at position H99 (Chothia) in the scFv VH (DYD<u>D</u>SLDY [SEQ ID NO:293]) was responsible for the isomerization.

Stability of F3'-1602 in the Phosphate/Citrate/NaCl Formulation

Attempts to remove the liability by mutagenesis revealed that the aspartic acid at position H99 of the CLEC12A-binding scFv is an important determinant of CDR structure and cannot be easily replaced without the loss of binding to the target. Therefore, limited pre-formulation development was performed to identify a formulation with a more basic pH since isomerization rate is pH dependent. The pH dependence was confirmed by stressing F3'-1602 in citrate and phosphate buffer covering pH 5.5-7.5. After 4 weeks at 40° C. in phosphate buffer (pH 6.5/7.0/7.5), F3'-1602 showed a pH-dependent loss of binding to CLEC12A. Interestingly, there was no trend observed in citrate buffer (pH 5.5/6.0/6.5). Additional formulations were designed based on these results, and common excipients (NaCl, sucrose, EDTA) were screened for their ability to stabilize CLEC12A binding (Table 68). This screening indicated that high pH and NaCl had a protective effect on CLEC12A binding.

TABLE 68

Phosphate/Citrate formulation buffers

| Buffer # | Citrate (mM) | Phosphate (mM) | EDTA (mM) | Sucrose (mM) | NaCl (mM) | pH |
|---|---|---|---|---|---|---|
| 1 | 50 | 0 | 0 | 0 | 0 | 7.0 |
| 2 | 20 | 50 | 0 | 0 | 0 | 7.0 |
| 3 | 20 | 50 | 0 | 0 | 0 | 7.5 |
| 4 | 20 | 50 | 0 | 0 | 0 | 8.0 |
| 5 | 0 | 50 | 10 | 0 | 0 | 7.0 |
| 6 | 0 | 50 | 10 | 0 | 0 | 7.5 |
| 7 | 0 | 50 | 10 | 0 | 0 | 8.0 |
| 8 | 50 | 0 | 0 | 250 | 0 | 7.0 |
| 9 | 50 | 0 | 0 | 0 | 250 | 7.0 |

Based on these results, F3'-1602 was formulated in 20 mM potassium phosphate, 10 mM sodium citrate, 125 mM sodium chloride, pH 7.8 (the phosphate/citrate/NaCl formulation).

The formation of HMWS and LMWS was assessed by SEC as described in the "Stability of F3'-1602 in the HST formulation" subsection. F3'-1602 was incubated at 40° C. for 4 weeks. At the onset of the study, F3'-1602 was analyzed by SEC and was 97.9% monomer. After four weeks at 40° C., monomer decreased to 91.4%. LMWS increased from 1.8 to 5.0% after four weeks at 40° C. HMWS were present in the control at 0.3% and increased to 3.6% after four weeks at 40° C. (Table 69). These data suggest that in the phosphate/citrate/NaCl formulation, F3'-1602 degraded through both aggregation (HMWS) and fragmentation (LMWS).

TABLE 69

Summary of SEC % monomer, HMW, and LMW
(accelerated stability in the phosphate/citrate/NaCl formulation)

| Test article | Monomer (%) | HMW (%) | LMW (%) |
|---|---|---|---|
| F3'-1602 control | 97.9 | 0.3 | 1.8 |
| F3'-1602, 4 weeks, 40° C. | 91.4 | 3.6 | 5.0 |

Fragmentation and aggregation of intact F3'-1602 was assessed in the accelerated stability study by non-reduced sodium dodecyl sulfate capillary electrophoresis (SDS-CE). Briefly, F3'-1602 was diluted to 0.5 mg/mL with 1× Sample Buffer to achieve a final sample volume of 50 μL. Internal standard and iodoacetamide were added to samples, which were then incubated at 70° C. for 10 minutes in a heat block, followed by an ice bath for 5 minutes. Samples were transferred to a 96-well plate, centrifuged, and loaded into the instrument. Individual samples were loaded into the capillary for 40 seconds at 4600 volts and separated for 35 minutes at 5750 volts on a Maurice (ProteinSimple, San Jose, CA).

The F3'-1602 main peak purity decreased from 97.0% to 91.2% by the end of the 4-week incubation. There was a corresponding increase in LMWS from 3.0% to 8.4% (Table 70). There was a slight increase in HMWS (none detected to 0.4%) throughout the duration of the study as determined by non-reduced SDS-CE. The difference in migration time of the main peak in the overlay was within the experimental variability of this assay.

TABLE 70

Summary of non-reduced SDS-CE purity
(accelerated stability in the phosphate/citrate/NaCl formulation)

| Test article | LMW (%) | Main (%) | HMW (%) |
|---|---|---|---|
| F3'-1602 control | 3.0 | 97.0 | ND |
| F3'-1602 4 weeks, 40° C. | 8.4 | 91.2 | 0.4 |

ND, none detected

Fragmentation of the three individual polypeptide chains of F3'-1602 was assessed at each timepoint in the accelerated stability study by reduced SDS-CE. In this assay, purity was determined by the sum of the three chains. Over the course of the study, purity decreased from 97.4% to 95.2% (Table 71). This decrease in purity was the result of increased LMWS, which agrees with the SEC and non-reduced SDS-CE results. The difference in migration times of the main peaks in the overlay was within the experimental variability of this assay.

TABLE 71

Summary of reduced SDS-CE purity
(accelerated stability in the phosphate/citrate/NaCl formulation)

| Test article | Light chain (%) | Heavy chain (%) | scFv-Fc chain (%) | Purity (%) |
|---|---|---|---|---|
| F3'-1602 control | 17.9 | 39.2 | 40.3 | 97.4 |
| F3'-1602 4 weeks, 40° C. | 20.3 | 39.4 | 35.5 | 95.2 |

Figure 76A:
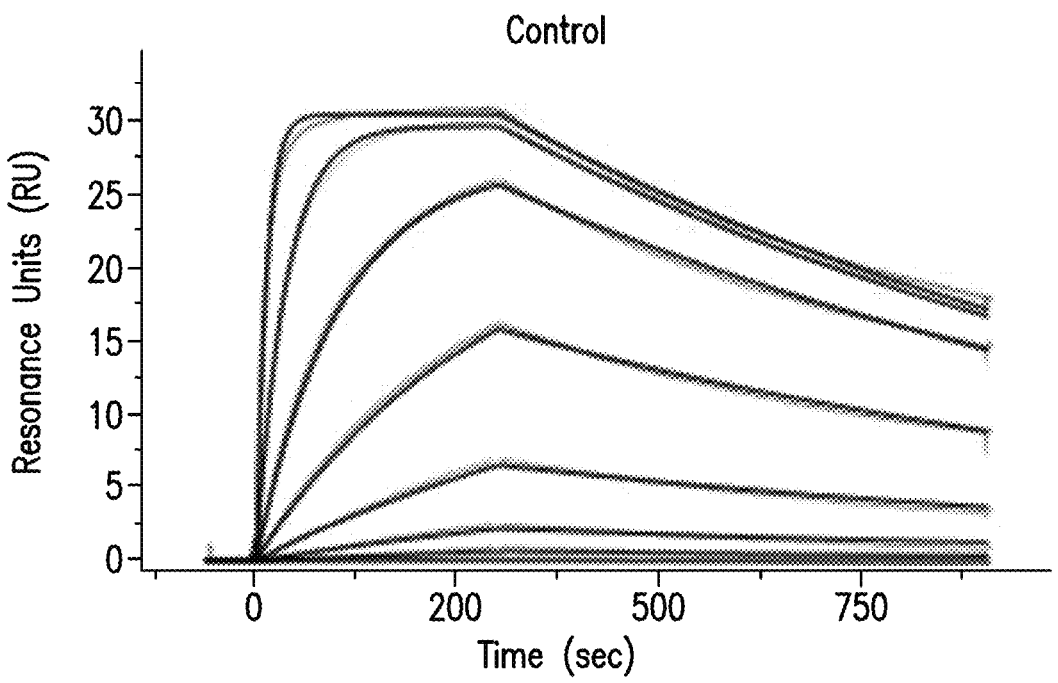
FIG. 76A-FIG. 76B are a set of sensorgrams showing the binding of hCLEC12A to F3'-1602 in the phosphate/citrate/NaCl formulation. The black overlays represent the 1:1 kinetic fit of the raw data.
Figure 76B:
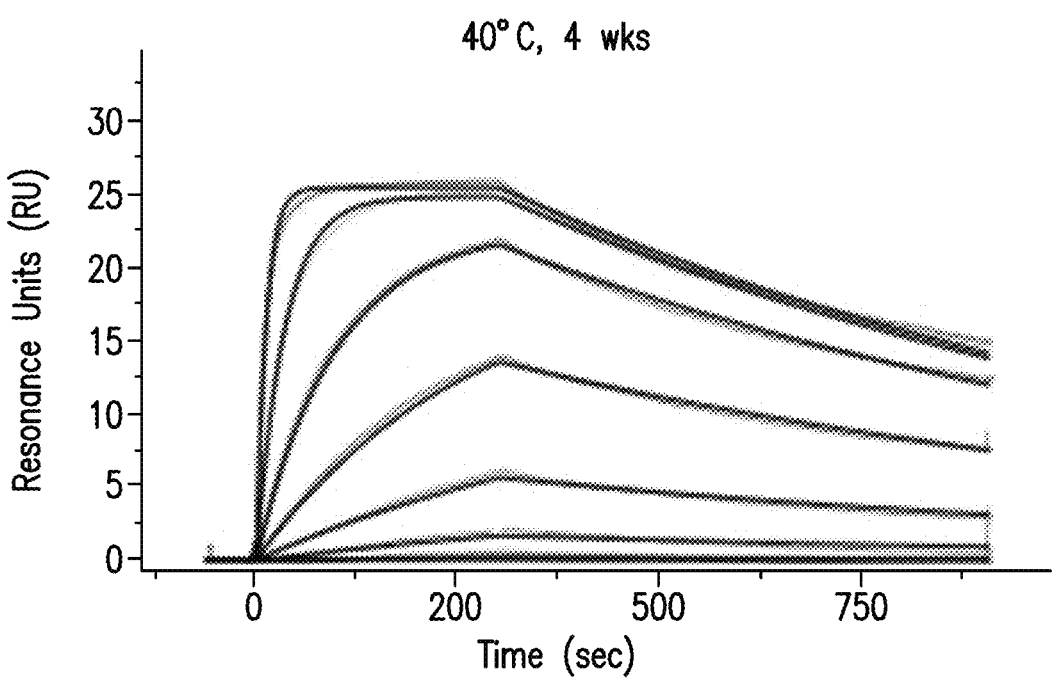

The binding affinities of F3'-1602 samples to recombinant human CLEC12A were measured by SPR as described in the "Stability of F3'-1602 in the HST formulation" subsection (FIGS. 76A-76B). After four weeks of incubation in the phosphate/citrate/NaCl formulation, human CLEC12A binding was reduced to some extent (FIG. 76B). The difference in association and dissociation rate constants between the control and 40° C. stressed sample were within the experimental variability of the assay (Table 72), whereas the maximal binding response (Rmax) adjusted for capture differences decreased approximately 10% after incubation at 40° C. Such a loss was significantly less than more than 80% that was observed after 4 weeks of incubation in the HST formulation, indicating that the phosphate/citrate/NaCl formulation was able to stabilize F3'-1602 under accelerated (40° C.) conditions. Therefore, the isomerization of H99, as described in the "stability of F3'-1602 in the HST formulation" subsection, was substantially reduced by formulation development.

TABLE 72

Summary of kinetic parameters and binding affinity of F3'-1602 for hCLEC12A
(accelerated stability in the phosphate/citrate/NaCl formulation)

| Test article | Target | $k_a$ (M$^{-1}$s$^{-1}$) | $k_d$ (s$^{-1}$) | $K_D$ (nM) | Capture level (RU) |
|---|---|---|---|---|---|
| F3'-1602 control | hCLEC12A | $7.79 \times 10^5$ | $9.33 \times 10^{-4}$ | 1.20 | 160.6 |
| F3'-1602 in the phosphate/Citrate/NaCl formulation, 40° C., 4 wks | hCLEC12A | $8.29 \times 10^5$ | $9.48 \times 10^{-4}$ | 1.14 | 146.7 |

Results are an average of n = 2 replicates

Figure 77A:
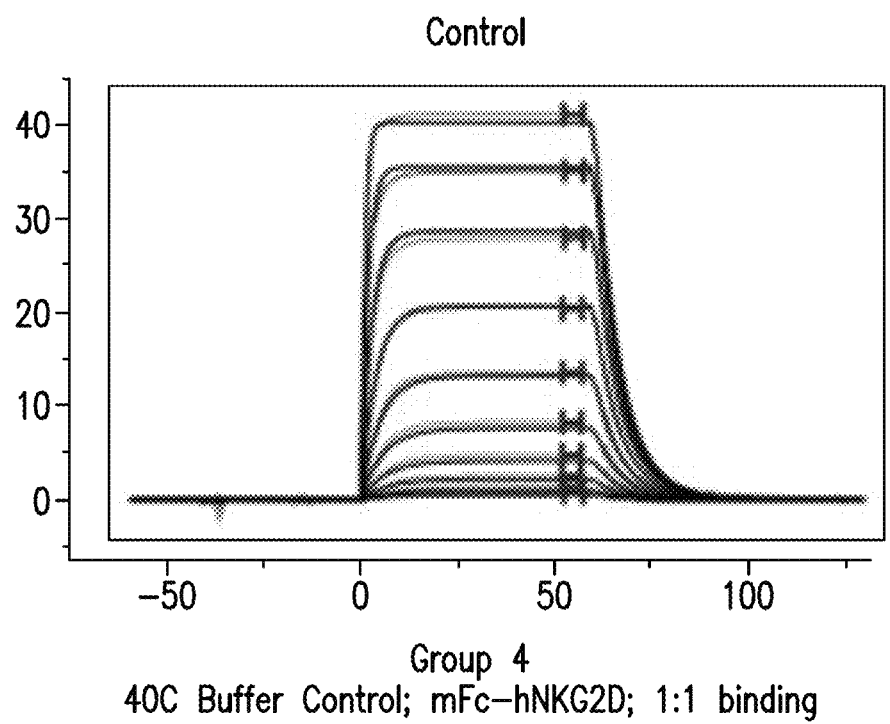
FIG. 77A-FIG. 77D are a set of graphs showing the binding of F3'-1602 in the phosphate/citrate/NaCl formulation to hNKG2D.
Figure 77B:
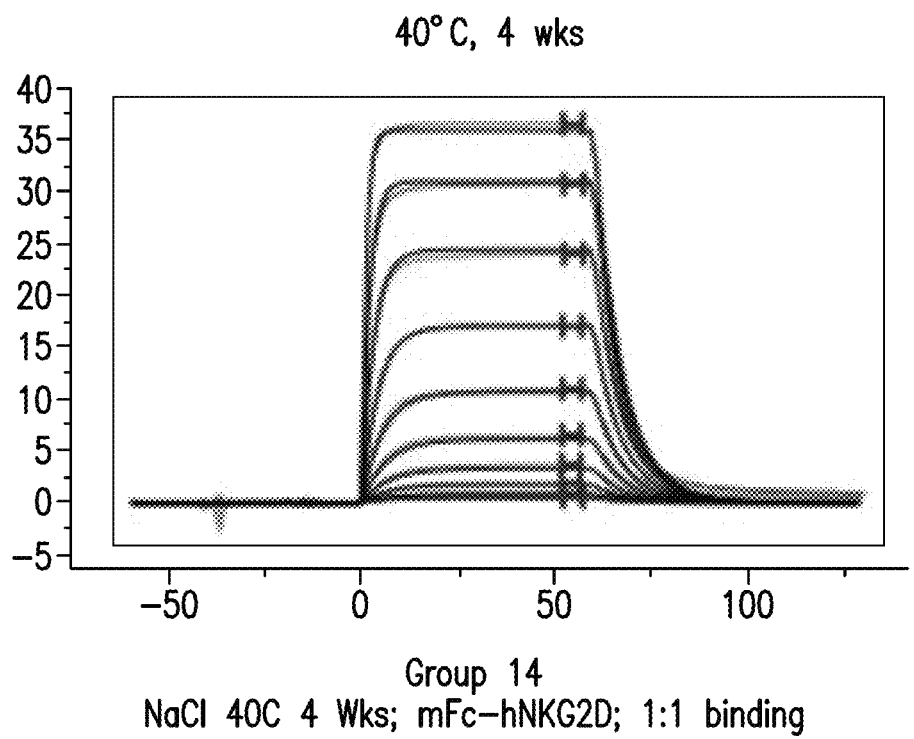
Figure 77C:
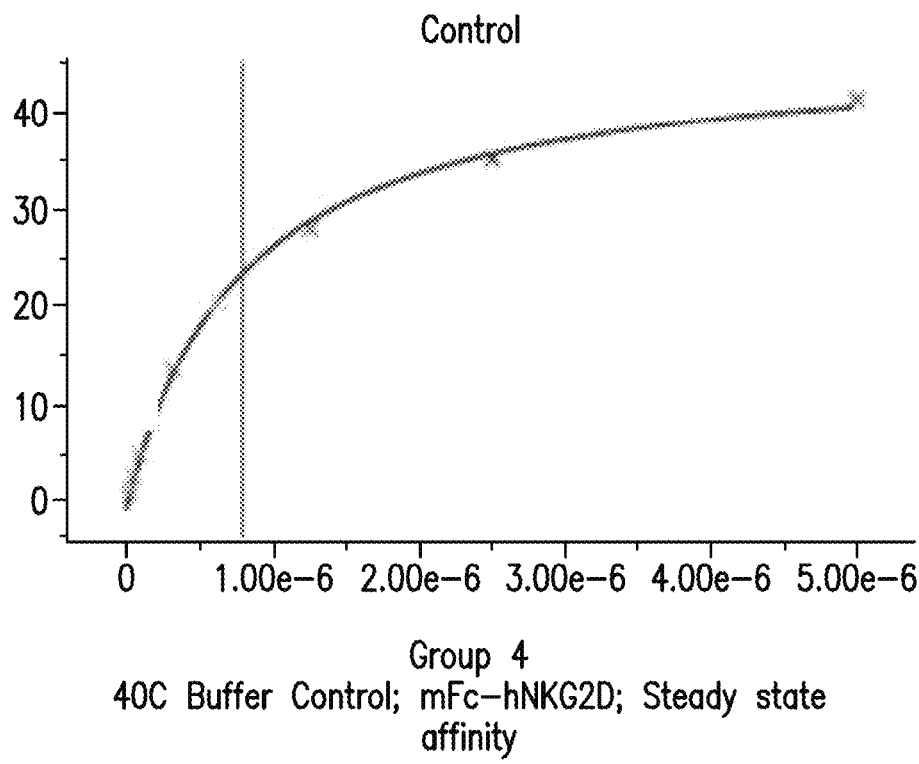
Figure 77D:
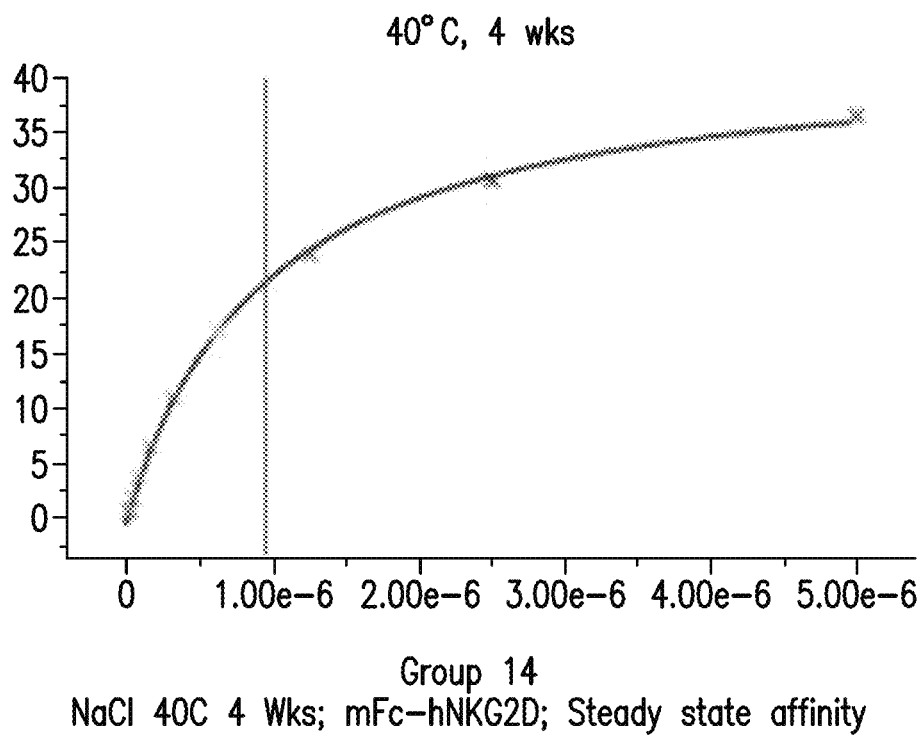

The binding affinities of F3'-1602 samples to recombinant human NKG2D were measured by SPR as described in the "Stability of F3'-1602 in the HST formulation" subsection (FIGS. 77A-77D). After four weeks of incubation at 20 mg/mL, 40° C. in the phosphate/citrate/NaCl formulation, binding of F3'-1602 to human NKG2D was unaltered (FIGS. 77B and 77D and Table 73). The difference in equilibrium binding affinity as well as Rmax between the control and 40° C. stressed sample were within the experimental variability of the assay. This indicates that F3'-1602 retained affinity for human NKG2D under these accelerated storage conditions.

TABLE 73

Summary of kinetic parameters and binding affinity of F3'-1602 for hNKG2D (accelerated stability in the phosphate/citrate/NaCl formulation)

| Test article | Target | $k_a$ (M$^{-1}$s$^{-1}$) | $k_d$ (s$^{-1}$) | 1:1 Kinetic Fit $K_D$ (nM) | Steady state $K_D$ (nM) | Capture level (RU) |
|---|---|---|---|---|---|---|
| F3'-1602 Control | hNKG2D | 1.93 × 10$^5$ | 1.53 × 10$^1$ | 790 | 791 | 34.5 |
| F3'-1602 in the phosphate/citrate/NaCl formulation, 40° C., 4 wks | hNKG2D | 1.53 × 10$^5$ | 1.33 × 10$^1$ | 869 | 872 | 31.4 |

Results are an average of n = 2 replicates

Figure 78A:
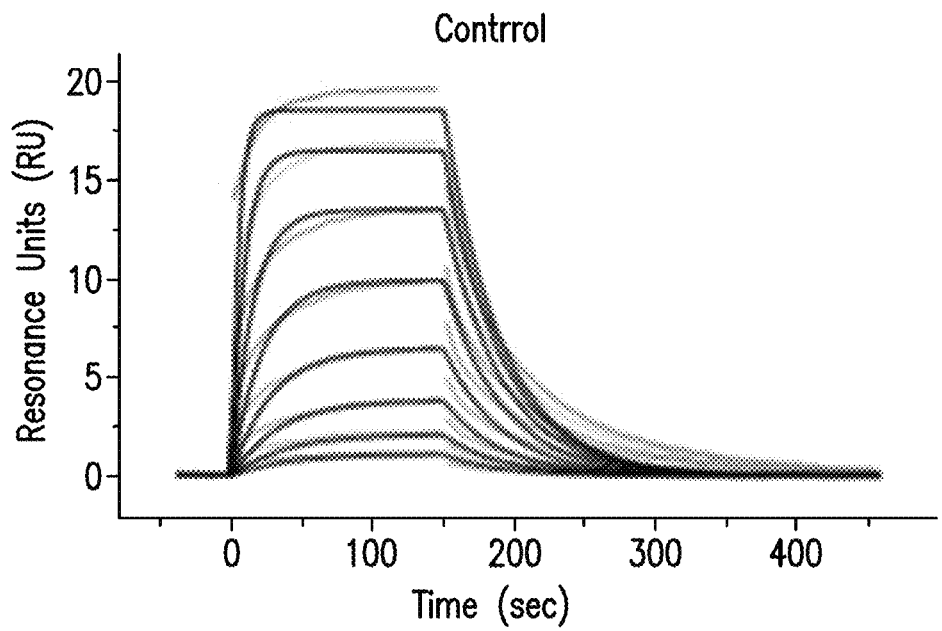
FIG. 78A-FIG. 78B are a set of sensorgrams showing the binding of F3'-1602 in the phosphate/citrate/NaCl formulation to hCD16a V158.
Figure 78B:
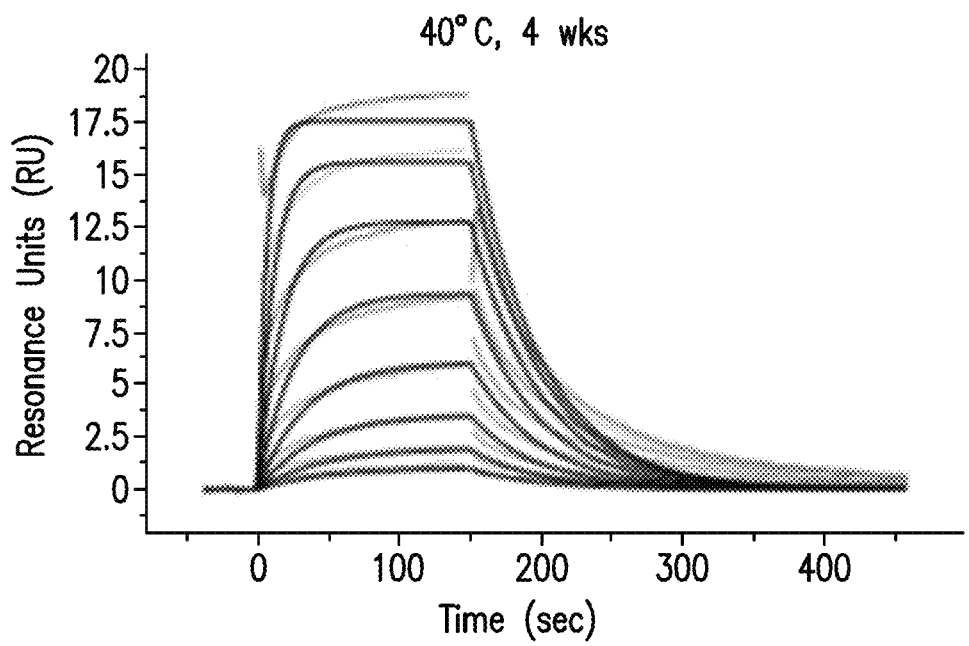

The binding affinities of F3'-1602 samples to biotinylated recombinant CD16a V158 (FcγRIIIa V158) receptor were measured by SPR as described in the "Stability of F3'-1602 in the HST formulation" subsection (FIGS. 78A-78B). After four weeks of incubation at 20 mg/mL, 40° C. in the phosphate/citrate/NaCl formulation, binding of F3'-1602 to human CD16a V158 was unaltered (FIG. 78B and Table 74). The difference in binding affinity as well as apparent maximal binding response between the control and 40° C. stressed sample are within the experimental variability of the assay. This indicates that F3'-1602 retains affinity for human CD16a under these accelerated storage conditions.

TABLE 74

Summary of kinetic parameters and binding affinity of F3'-1602 for hCD16a V158 (accelerated stability in the phosphate/citrate/NaCl formulation)

| Test article | Target | $k_a$ (M$^{-1}$s$^{-1}$) | $k_d$ (s$^{-1}$) | $K_D$ (nM) | Capture level (RU) |
|---|---|---|---|---|---|
| F3'-1602 Control[a] | hCD16aV | (1.13 ± 0.04) × 10$^5$ | (2.40 ± 0.09) × 10$^{-2}$ | 212 ± 1 | 13.7 |
| F3'-1602 in the phosphate/citrate/NaCl formulation, 40° C., 4 wks | hCD16aV | 9.67 × 10$^4$ | 2.09 × 10$^{-2}$ | 216 | 14.0 |

Figure 79:
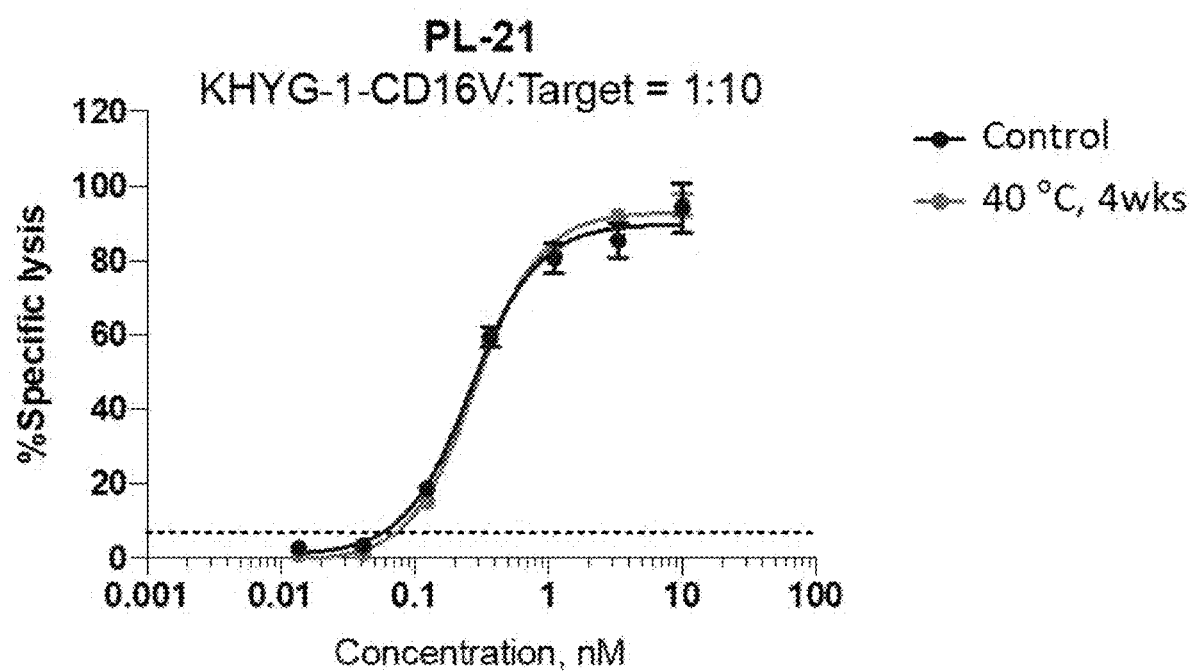
FIG. 79 is a graph showing the percentage lysis of PL21 cells by NKG2D- and CD16a-expressing KHYG-1-CD16a cells in the presence of stressed and control samples of F3'-1602 in the phosphate/citrate/NaCl formulation.

The effect of accelerated stability on F3'-1602 function was also assessed in a cytotoxicity assay using NKG2D- and CD16a-expressing KHYG-1-CD16a cells, as described in the "Stability of F3'-1602 in the HST formulation" subsection. The ability of F3'-1602 to kill PL-21 CLEC12A+ cancer cells was unaltered after 4 weeks incubation at 40° C. in the phosphate/citrate/NaCl formulation at a concentration of 20 mg/mL (FIG. 79 and Table 75). This result was in stark contrast to what was observed after incubation in the HST formulation, and indicates that F3'-1602 was stabilized in 20 mM phosphate, 10 mM citrate, 125 mM NaCl, pH 7.8.

TABLE 75

EC50 and maximum lysis of CLEC12A + PL-21 cells by F3'-1602 (accelerated stability in the phosphate/citrate/NaCl formulation)

| Test article | EC50 (nM) | Max. lysis (%) |
|---|---|---|
| F3'-1602 Control | 0.26 | 90 |
| F3'-1602 in the phosphate/citrate/NaCl formulation, 40° C., 4 wks | 0.29 | 93 |

Stability of F3'-1602 in the CST Formulation

Based on the stability data in the phosphate/citrate/NaCl formulation, it was concluded that the loss of activity at 40° C. could be minimized in a liquid formulation. Stability of F3'-1602 was further analyzed in a lyophilization-compatible liquid formulation containing sucrose as a lyoprotectant. An accelerated stability study at 20 mg/mL was carried out in 20 mM citrate, 250 mM sucrose, 0.01% Tween-80, pH 7.0 (the CST formulation) at refrigerated (2-8° C.) and accelerated (25 and 40° C.) conditions for four weeks. A full suite of analytics was carried out on the 40° C. stressed samples while only binding to CLEC12A (SPR) and potency were monitored for the 2-8° C. and 25° C. arms.

The formation of HMWS and LMWS was assessed by SEC as described in the "Stability of F3'-1602 in the HST formulation" subsection. At the onset of the study, F3'-1602 was analyzed by SEC and was 99.6% monomer. After four weeks at 40° C., monomer decreased to 98.6%. LMWS were not detected in the control and increased to 0.5% after four weeks at 40° C. HMWS were present in the control at 0.4% and increased to 1.0% after four weeks at 40° C. (Table 76). These data suggest that F3'-1602 was resistant to both aggregation and fragmentation under accelerated conditions in the CST formulation.

TABLE 76

Summary of SEC % monomer, HMW, and LMW (accelerated stability in the CST formulation)

| Test article | Monomer (%) | HMW (%) | LMW (%) |
|---|---|---|---|
| Control | 99.6 | 0.4 | ND |
| 1 week | 99.3 | 0.5 | 0.2 |
| 2 weeks | 99.0 | 0.7 | 0.3 |
| 3 weeks | 98.7 | 0.9 | 0.4 |
| 4 weeks | 98.6 | 1.0 | 0.5 |

ND, none detected

Fragmentation of intact F3'-1602 was assessed at each timepoint in the accelerated stability study by non-reduced SDS-CE, as described in the "Stability of F3'-1602 in the phosphate/citrate/NaCl formulation" subsection. The F3'-1602 main peak purity decreased from 96.1% to 91.0% by the end of the 4-week incubation. There was a corresponding increase in LMWS from 3.9% to 9.0% (Table 77). There was no increase in HMWS throughout the duration of the study as determined by non-reduced SDS-CE. The difference in migration time of the main peak in the overlay was within the experimental variability of this assay.

TABLE 77

Summary of non-reduced SDS-CE purity (accelerated stability in the CST formulation)

| Test article | LMW (%) | Main (%) | HMW (%) |
|---|---|---|---|
| Control | 3.9 | 96.1 | ND |
| 1 week | 4.8 | 95.2 | ND |
| 2 weeks | 6.6 | 93.4 | ND |
| 3 weeks | 5.3 | 94.7 | ND |
| 4 weeks | 9.0 | 91.0 | ND |

ND: none detected

Fragmentation of the three individual polypeptide chains of F3'-1602 was assessed at each timepoint in the accelerated stability study by reduced SDS-CE, as described in the "Stability of F3'-1602 in the phosphate/citrate/NaCl formulation" subsection. In this assay, purity was determined by the sum of the three chains. Over the course of the study, purity decreased from 98.3% to 97.7% (Table 78). The difference in migration times of the main peaks in the overlay was within the experimental variability of this assay.

TABLE 78

Summary of reduced SDS-CE purity (accelerated stability in the CST formulation)

| Test article | Purity (%) |
|---|---|
| Control | 98.3 |
| 1 week | 98.0 |
| 2 weeks | 98.0 |
| 3 weeks | 97.8 |
| 4 weeks | 97.7 |

Purity was the sum of chain L, H, and S % area

Figure 80A:
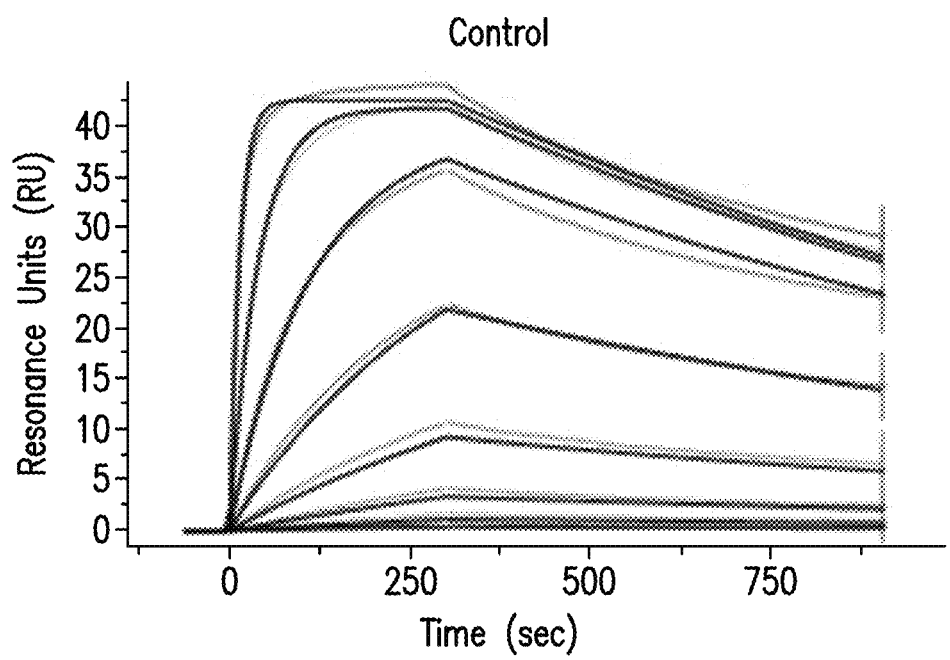
FIG. 80A-FIG. 80B are a set of sensorgrams showing the binding of hCLEC12A at three-fold serial dilution (300 nM to 0.41 nM) to F3'-1602 after incubation in the CST formulation at 40° C. for four weeks. The black overlays represent the 1:1 kinetic fit of the raw data.
Figure 80B:
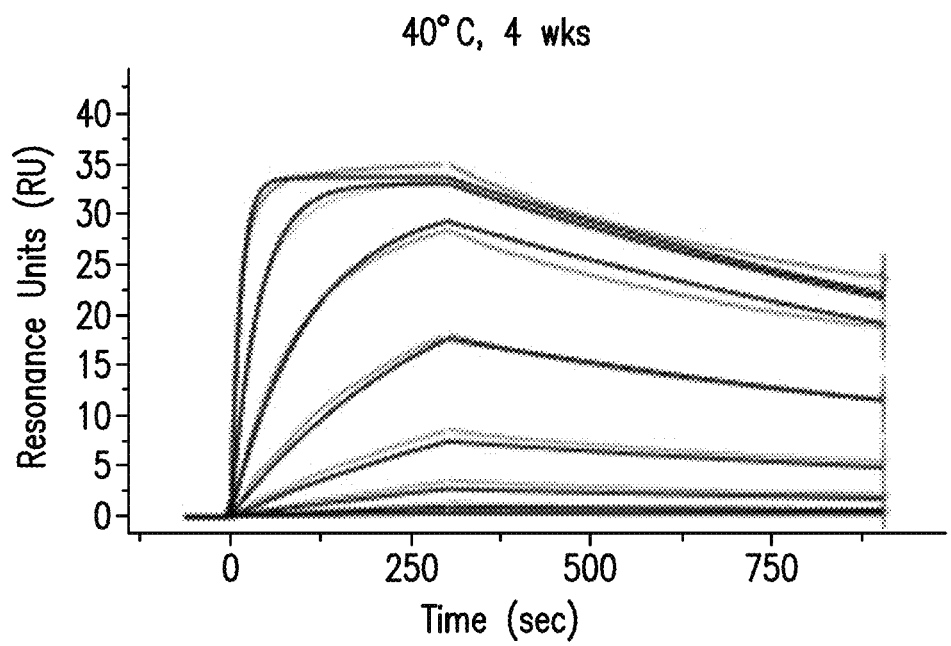

The binding affinities of F3'-1602 samples to recombinant human CLEC12A were measured by SPR as described in the "Stability of F3'-1602 in the HST formulation" subsection (FIG. 80A). After four weeks of incubation at 20 mg/mL, 40° C. in the CST formulation, human CLEC12A binding was reduced (FIG. 80B and Table 79). The difference in association and dissociation rate constants between the control and 40° C. stressed sample are within the experimental variability of the assay, however apparent binding response decreased about 15-17% after the stress at 40° C. This indicates that 15-17% of F3'-1602 lost the ability to bind CLEC12A after 4 weeks under these thermal stress conditions. While the classical SPR binding assay is a good indicator of potential loss of activity when it comes to stark differences in binding (20% or more), it is not reliable enough to address the impact of the smaller changes in activity of the sample (especially at the low replicate number); other analytical methods are used to elucidate the changes with more scientific certainty if needed.

TABLE 79

Summary of kinetic parameters and binding affinity of F3'-1602 for hCLEC12A (40° C. accelerated stability in the CST formulation)

| Test article | Target | $k_a$ (M$^{-1}$s$^{-1}$) | $k_d$ (s$^{-1}$) | $K_D$ (nM) | Capture level (RU) |
|---|---|---|---|---|---|
| F3'-1602 control | hCLEC12A | $7.50 \times 10^5$ | $7.35 \times 10^{-4}$ | 0.98 | 221.3 |
| F3'-1602 in the CST formulation, 40° C., 4 wks | hCLEC12A | $7.84 \times 10^5$ | $6.74 \times 10^{-4}$ | 0.86 | 211.5 |

Results are an average of n = 2 replicates

Figure 81A:
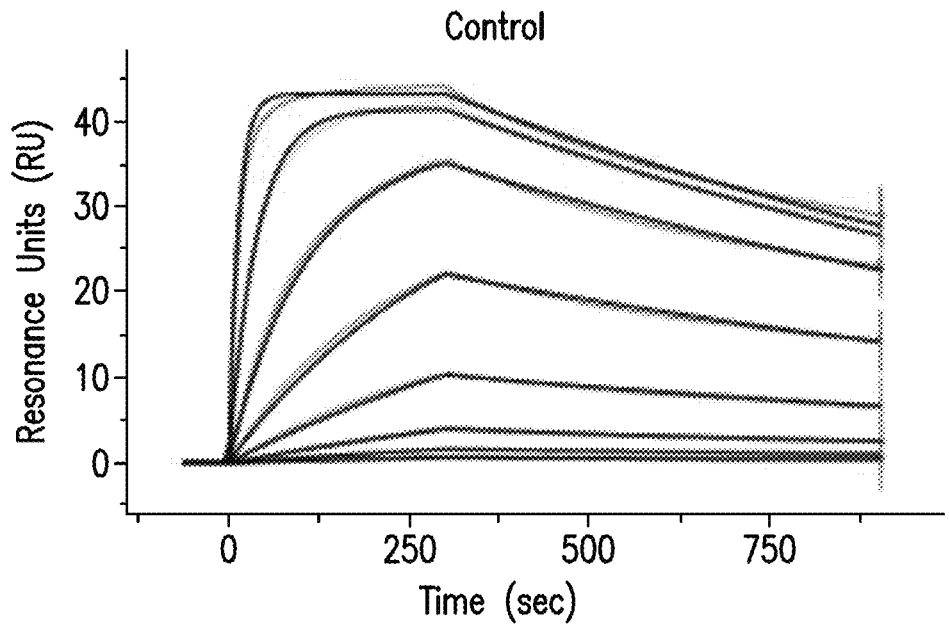
FIG. 81A-FIG. 81C are a set of sensorgrams showing the binding of hCLEC12A at three-fold serial dilution (300 nM to 0.41 nM) to F3'-1602 after incubation in the CST formulation at 2-8° C. and at 25° C. for four weeks. The black overlays represent the 1:1 kinetic fit of the raw data.
Figure 81B:
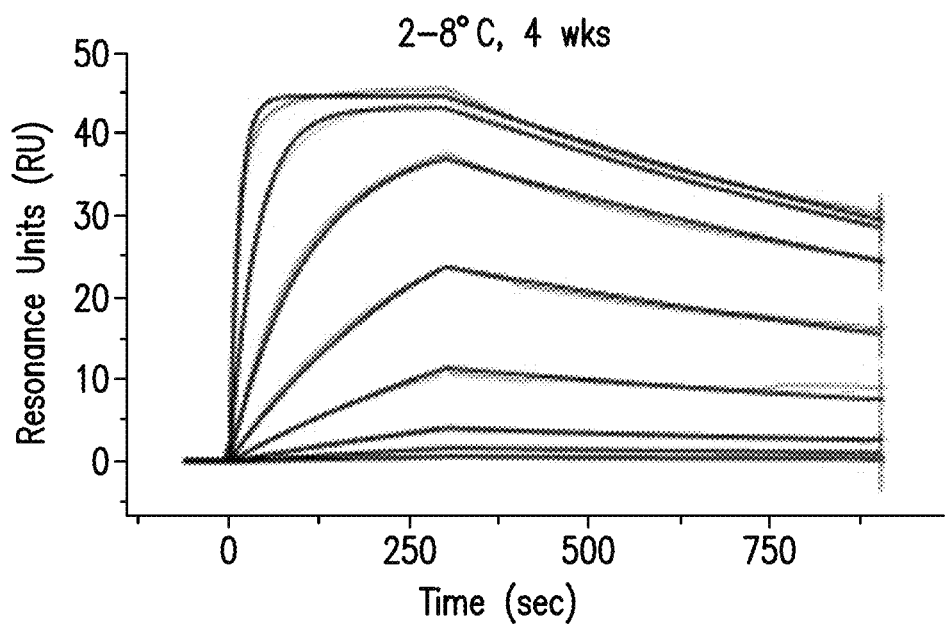
Figure 81C:
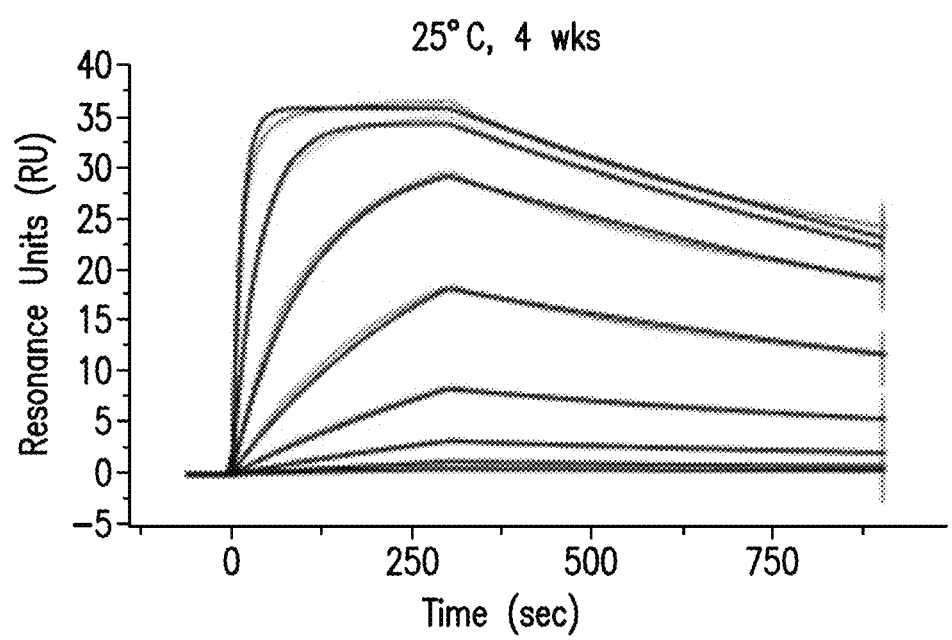

At the lower temperatures (refrigerated and 25° C.), no difference in affinity to hCLEC12A or apparent binding adjusted for differences in capture levels were observed after 4 weeks in the CST formulation (FIGS. 81A-81C, Table 80, and Table 81).

TABLE 80

Summary of kinetic parameters and binding affinity of F3'-1602 for hCLEC12A (2-8° C. stability in the CST formulation)

| Test article | Target | $k_a$ (M$^{-1}$s$^{-1}$) | $k_d$ (s$^{-1}$) | KD (nM) | Capture level (RU) |
|---|---|---|---|---|---|
| F3'-1602 control | hCLEC12A | $7.50 \times 10^5$ | $7.35 \times 10^{-4}$ | 0.98 | 221.3 |
| F3'-1602 in the CST formulation, 2-8° C., 2 wk | hCLEC12A | $6.72 \times 10^5$ | $6.00 \times 10^{-4}$ | 0.89 | 352.4 |
| F3'-1602 in the CST formulation, 2-8° C., 4 wk | hCLEC12A | $7.76 \times 10^5$ | $7.08 \times 10^{-4}$ | 0.91 | 222.8 |

Results are an average of n = 2 replicates

TABLE 81

Summary of kinetic parameters and binding affinity of F3'-1602 for hCLEC12A (25° C. stability in the CST formulation)

| Test article | Target | $k_a$ (M$^{-1}$s$^{-1}$) | $k_d$ (s$^{-1}$) | $K_D$ (nM) | Capture level (RU) |
|---|---|---|---|---|---|
| F3'-1602 control | hCLEC12A | $7.50 \times 10^5$ | $7.35 \times 10^{-4}$ | 0.98 | 221.3 |
| F3'-1602 in the CST formulation, 25° C., 2 wk | hCLEC12A | $8.24 \times 10^5$ | $7.65 \times 10^{-4}$ | 0.93 | 187.6 |
| F3'-1602 in the CST formulation, 25° C., 4 wk | hCLEC12A | $7.88 \times 10^5$ | $7.19 \times 10^{-4}$ | 0.91 | 179.9 |

Results are an average of n = 2 replicates

Figure 82A:
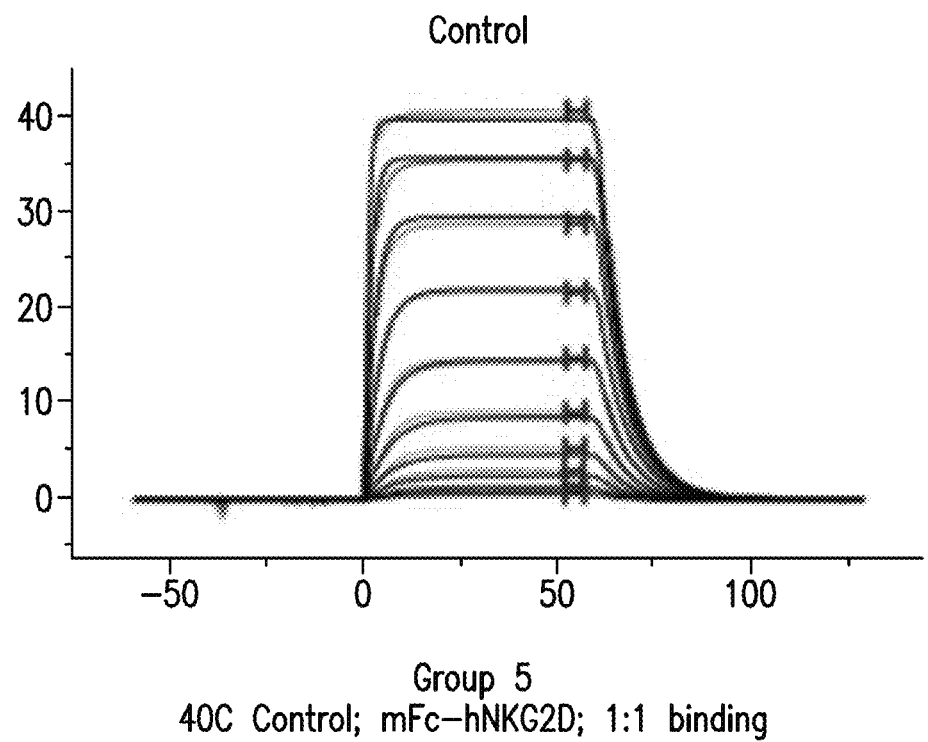
FIG. 82A-FIG. 82D are a set of graphs showing the binding of F3'-1602 in the CST formulation to hNKG2D.
Figure 82B:
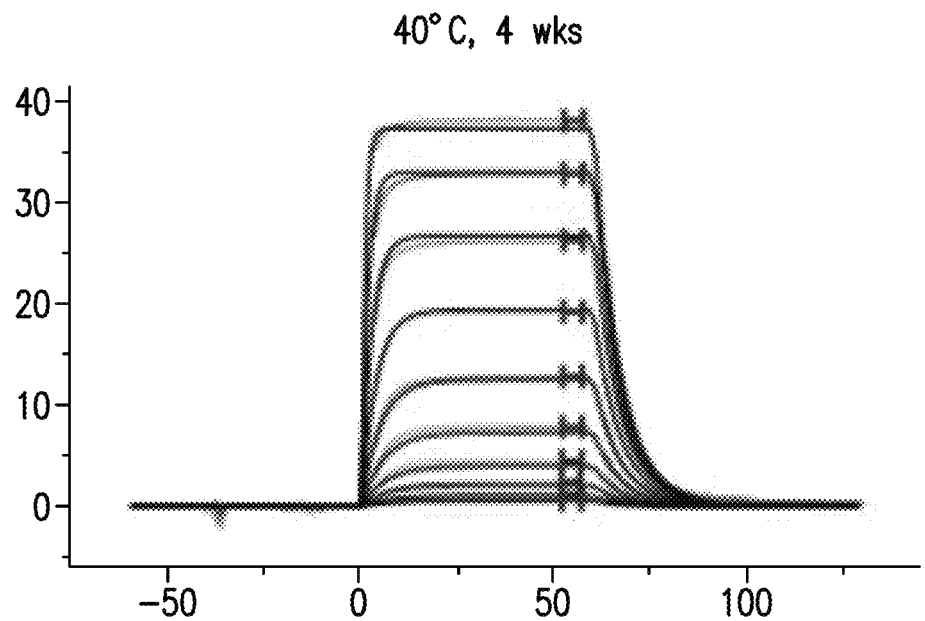
Figure 82C:
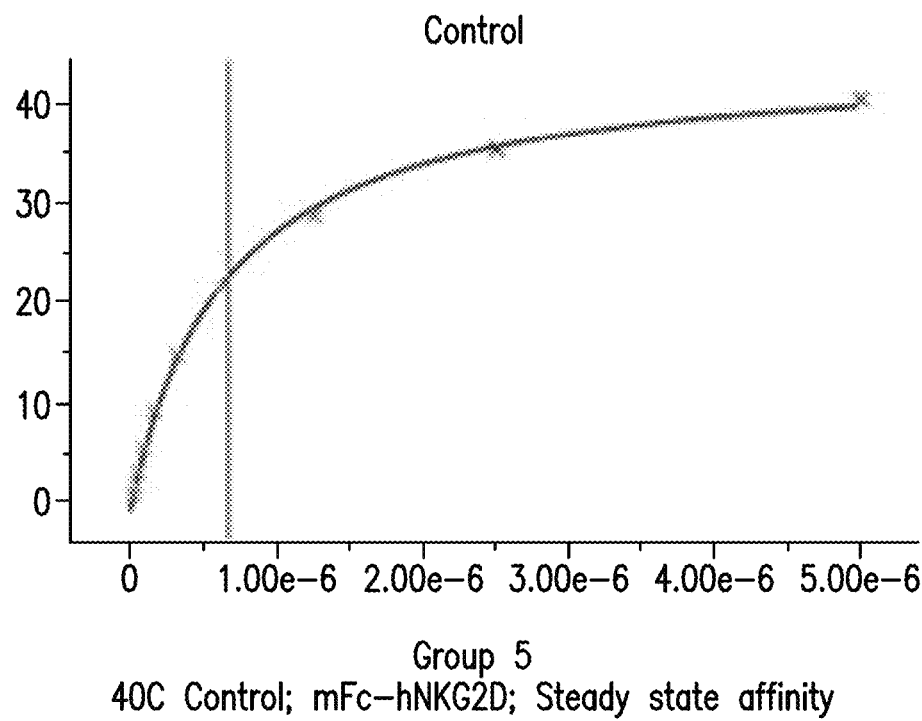
Figure 82D:
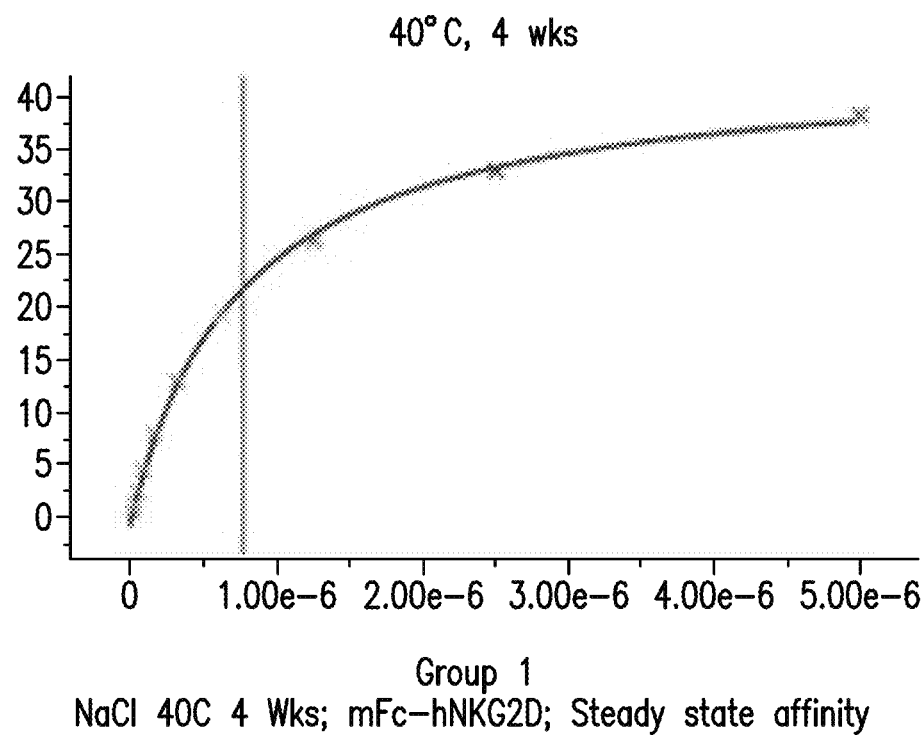

The binding affinities of F3'-1602 samples to recombinant human NKG2D were measured by SPR as described in the "Stability of F3'-1602 in the HST formulation" subsection (FIGS. 82A-82D). After four weeks of incubation at 20 mg/mL, 40° C. in the CST formulation, binding of F3'-1602 to human NKG2D was unaltered (FIGS. 82B and 82D and Table 82). The difference in equilibrium binding affinity as well as apparent Rmax between the control and 40° C. stressed sample were within the experimental variability of the assay. This indicates that F3'-1602 retained affinity for human NKG2D under these accelerated storage conditions.

TABLE 82

Summary of kinetic parameters and binding affinity of F3'-1602 for hNKG2D (accelerated stability in the CST formulation)

| Test article | Target | $k_a$ (M$^{-1}$s$^{-1}$) | $k_d$ (s$^{-1}$) | 1:1 Kinetic Fit $K_D$ (nM) | Steady state $K_D$ (nM) | Capture level (RU) |
|---|---|---|---|---|---|---|
| F3'-1602 Control | hNKG2D | $(2.11 \pm 0.06) \times 10^5$ | $(1.39 \pm 0.03) \times 10^1$ | 661 ± 9 | 664 ± 10 | 34.5 |
| F3'-1602 in the CST formulation, 40° C., 4 wks | hNKG2D | $(1.98 \pm 0.11) \times 10^5$ | $(1.40 \pm 0.08) \times 10^1$ | 708 ± 45 | 711 ± 45 | 33.2 |

Results are an average n = 3 measurements

Figure 83A:
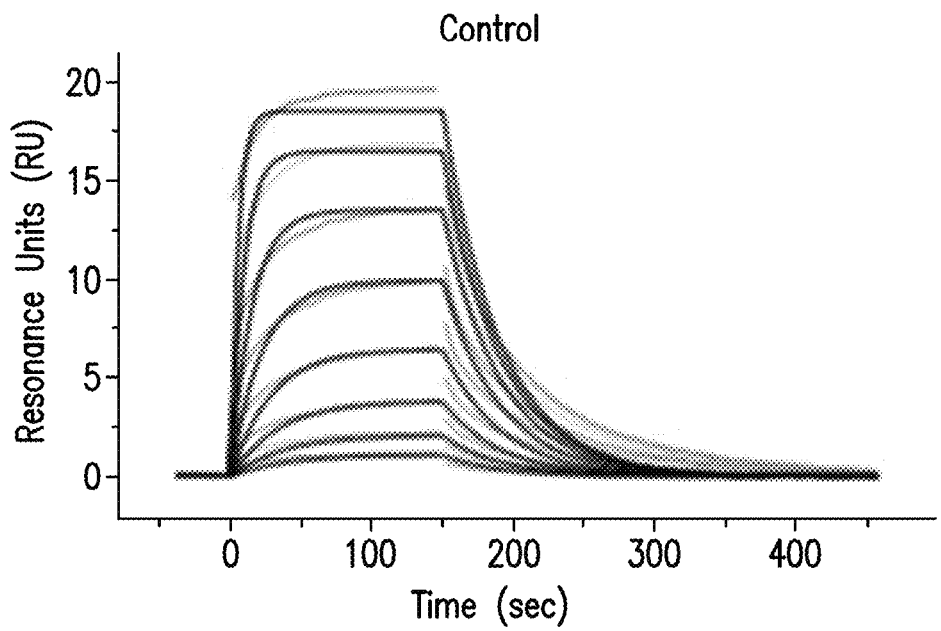
FIG. 83A-FIG. 83B are a set of sensorgrams showing the binding of F3'-1602 in the CST formulation to hCD16a V158.
Figure 83B:
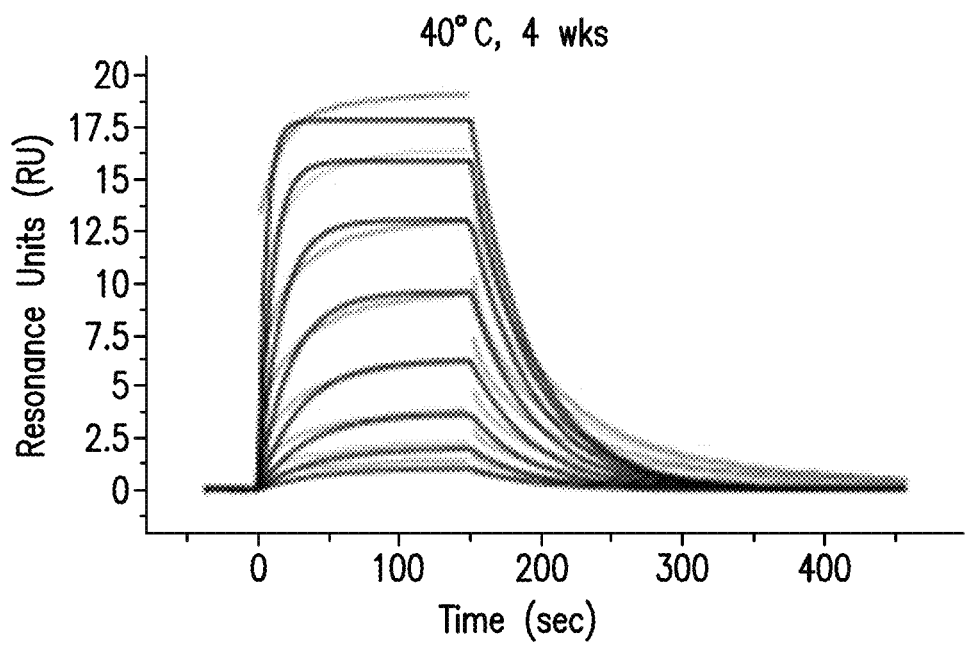

The binding affinities of F3'-1602 samples to biotinylated recombinant CD16a V158 (FcγRIIIa V158) receptor were measured by SPR as described in the "Stability of F3'-1602 in the HST formulation" subsection (FIGS. 83A-83B). After four weeks of incubation at 20 mg/mL, 40° C. in the CST formulation, binding of F3'-1602 to human CD16a V158 was unaltered (FIG. 83B and Table 83). The difference in binding affinity and apparent $R_{max}$ between the control and 40° C. stressed sample are within the experimental variability of the assay. This indicates that F3'-1602 retains affinity for human CD16a under these accelerated storage conditions.

TABLE 83

Summary of kinetic parameters and affinity of F3'-1602 for hCD16a V158 (accelerated stability in the CST formulation)

| Test article | Target | $k_a$ ($M^{-1}s^{-1}$) | $k_d$ ($s^{-1}$) | $K_D$ (nM) | Capture level (RU) |
|---|---|---|---|---|---|
| F3'-1602 Control | hCD16aV | (1.13 ± 0.04) × 10$^5$ | (2.40 ± 0.09) × 10$^{-2}$ | 212 ± 1 | 13.7 |
| F3'-1602, CST, pH 7.0, 40° C., 4 wks | hCD16aV | (1.05 ± 0.04) × 10$^5$ | (2.25 ± 0.09) × 10$^{-2}$ | 213 ± 3 | 13.6 |

Results are an average of n = 3 replicates

Figure 84:
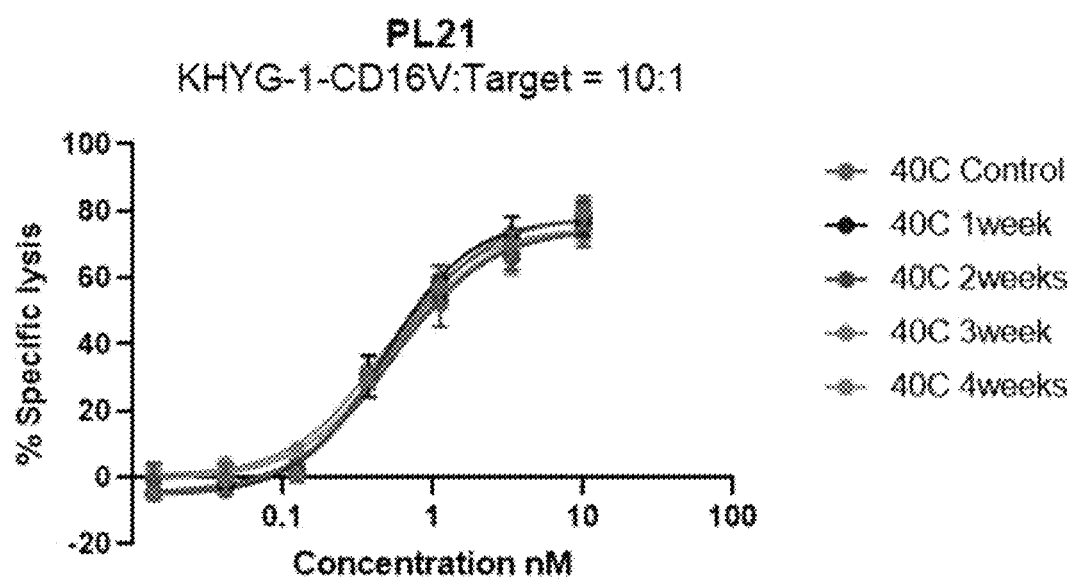
FIG. 84 is a graph showing the percentage lysis of PL21 cells by NKG2D- and CD16a-expressing KHYG-1-CD16a cells in the presence of stressed and control samples of F3'-1602 in the CST formulation.

The effect of accelerated stability on F3'-1602 function was also assessed in a cytotoxicity assay using NKG2D- and CD16a-expressing KHYG-1-CD16a cells, as described in the "Stability of F3'-1602 in the HST formulation" subsection. The ability of F3'-1602 to kill PL-21 CLEC12A+ cancer cells was unaltered after 4 weeks incubation at 40° C. in the CST formulation at a concentration of 20 mg/mL (FIG. 84 and Table 84).

TABLE 84

EC50 and maximum lysis of CLEC12A+ PL-21 cells by F3'-1602 (accelerated stability in CST pH 7.0)

| Test article | EC50 (nM) | Max. lysis (%) |
|---|---|---|
| F3'-1602 Control | 0.51 | 78.6 |
| F3'-1602 in the CST formulation, 40° C., 1 wk | 0.47 | 77.7 |
| F3'-1602 in the CST formulation, 40° C., 2 wk | 0.52 | 74.7 |
| F3'-1602 in the CST formulation, 40° C., 3 wk | 0.47 | 74.9 |
| F3'-1602 in the CST formulation, 40° C., 4 wk | 0.53 | 74.9 |

Example 15. Manufacturability of F3'-1602 in the CST Formulation

Various conditions throughout manufacturing of F3'-1602 could affect its stability. This example was designed to assess the stability of F3'-1602 in the CST formulation through freeze/thaw, agitation, low and high pH, forced oxidation, and low pH hold. The methods of measuring protein integrity and function, where provided in Example 14, are not repeated in this example.

Freeze/Thaw

Stability during freeze/thaw cycles is important for biotherapeutics as process intermediates and bulk drug substance may be frozen to ensure stability between process steps. To create freeze/thaw stress, 8.0 mg F3'-1602 was buffer switched into 20 mM sodium citrate, 250 mM sucrose, 0.01% Tween-80, pH 7.0 using Amicon Ultra 15 ml 30K devices and brought to 400 μL with the same buffer (~20 mg/mL F3'-1602, concentration was confirmed by A280 with a Nanodrop One spectrophotometer). The concentrated sample was divided into 4×100 μL aliquots. The control was immediately stored at −80° C. The remaining three aliquots were subjected to freeze/thaw cycles at −80° C. in a Styrofoam container to slow the freezing process. At cycles 2, 4, and 6, an aliquot was removed and transferred to −80° C. storage until analysis.

The freeze/thaw stability of F3'-1602 was assessed by measuring protein concentration by A280 at the completion of the study. F3'-1602 concentration was 20.4 mg/mL in the control and 20.2 mg/mL after 6 freeze/thaw cycles indicating that there was no loss of protein due to the freeze/thaw stress.

To assess whether F3'-1602 is stable through the freeze/thaw cycles, test article was frozen and thawed six times and analyzed by SEC after cycles 2, 4, and 6. F3'-1602 at time 0 was 99.5% monomer and the % monomer remained unchanged through all six freeze/thaw cycles (Table 85). This result indicates that F3'-1602 was resistant to both aggregation and fragmentation during freeze/thaw stress.

TABLE 85

Summary of SEC % monomer, HMW, and LMW (freeze/thaw stability)

| Test article | Monomer (%) | HMW (%) | LMW (%) |
|---|---|---|---|
| Control | 99.5 | 0.5 | ND |
| 2 F/T cycles | 99.8 | 0.2 | ND |
| 4 F/T cycles | 99.8 | 0.2 | ND |
| 6 F/T cycles | 99.8 | 0.2 | ND |

ND: none detected

Fragmentation of intact F3'-1602 was assessed in the freeze/thaw stability study by non-reduced SDS-CE. The F3'-1602 main peak purity decreased minimally (96.1% to 95.5%) after 6 freeze/thaw cycles. There was a corresponding increase in LMWS from 3.9% to 4.5% (Table 86). No HMWS was detected throughout the duration of the study. These results indicate that F3'-1602 was resistant to fragmentation in 20 mM citrate, 250 mM sucrose, 0.01% Tween-80, pH 7.0. The difference in migration time of the main peak in the overlay was within the experimental variability of this assay.

TABLE 86

Summary of non-reduced SDS-CE purity (freeze/thaw stability)

| Test article | LMW (%) | Main (%) | HMW (%) |
|---|---|---|---|
| Control | 3.9 | 96.1 | ND |
| 2 F/T cycles | 4.3 | 95.7 | ND |
| 4 F/T cycles | 4.4 | 95.6 | ND |
| 6 F/T cycles | 4.5 | 95.5 | ND |

ND: none detected

Fragmentation of the 3 individual polypeptide chains of F3'-1602 was assessed in the freeze/thaw stability study by reduced SDS-CE. In this assay, purity was determined by the sum of the three chains. F3'-1602 purity was unchanged after 6 freeze/thaw cycles (Table 87). These results indicate that F3'-1602 was resistant to fragmentation in 20 mM citrate, 250 mM sucrose, 0.01% Tween-80, pH 7.0. The difference in migration times of the main peaks in the overlay was within the experimental variability of this assay.

TABLE 87

Summary of reduced SDS-CE purity (freeze/thaw stability)

| Test article | Purity (%) |
|---|---|
| Control | 98.3 |
| 2 F/T cycles | 98.0 |
| 4 F/T cycles | 98.0 |
| 6 F/T cycles | 98.0 |

Purity was the sum of chain L, H, and S percent area

Agitation

Stability during agitation is important for biotherapeutics as process intermediates and bulk drug substance may experience shear stress during processing steps. To create agitation stress, 8.0 mg F3'-1602 was buffer switched into 20 mM sodium citrate, 250 mM sucrose, 0.01% Tween-80, pH 7.0 using Amicon Ultra 15 mL 30K devices and brought to 400 µL with the same buffer (~20 mg/mL F3'-1602, concentration was confirmed by A280 with a Nanodrop One spectrophotometer). The concentrated sample was transferred into glass vial with stir bar, placed on stir plate and stirred at 60 rpm at 4° C. for 18 hours. After the agitation, the sample was stored at −80° C. until analysis.

The agitation stability of F3'-1602 was assessed. After agitation, there was visible protein precipitation. The sample was spun down, and supernatant was used in all characterization assays. Protein concentration in the supernatant was assessed by A280. F3'-1602 concentration was 20.4 mg/mL in the control and 16.8 mg/mL after agitation stress.

To determine if F3'-1602 is stable during agitation stress, test article was analyzed by SEC before and after agitation. F3'-1602 control was 99.5% monomer and the % monomer remained unchanged after agitation (Table 88). This indicates that F3'-1602 was resistant to both aggregation and fragmentation during agitation.

TABLE 88

Summary of SEC % monomer, HMW, and LMW (agitation stability)

| Test article | HMW (%) | Monomer (%) | LMW (%) |
|---|---|---|---|
| Control | 0.5 | 99.5 | ND |
| Post-agitation | 0.7 | 99.3 | ND |

ND: none detected

Fragmentation of intact F3'-1602 was assessed after agitation by non-reduced SDS-CE. The F3'-1602 main peak purity decreased minimally (96.1% to 95.5%) after agitation. There was a corresponding increase in LMWS from 3.9% to 4.5% (Table 89). No BMWS was detected throughout the duration of the study. These results indicate that F3'-1602 was resistant to fragmentation in 20 mM citrate, 250 mM sucrose, 0.01% Tween-80, pH 7.0. The difference in migration time of the main peak in the overlay was within the experimental variability of this assay.

TABLE 89

Summary of SEC % monomer, HMW, and LMW (agitation stability)

| Test article | LMW (%) | Main (%) | HMW (%) |
|---|---|---|---|
| Control | 3.9 | 96.1 | ND |
| Post-agitation | 3.8 | 96.2 | ND |

ND: none detected

Fragmentation of the three individual polypeptide chains of F3'-1602 was assessed in the agitation study by reduced SDS-CE. In this assay, purity was determined by the sum of the three chains. F3'-1602 purity was unchanged after agitation stress (Table 90). These results indicate that F3'-1602 was resistant to fragmentation in 20 mM citrate, 250 mM sucrose, 0.01% Tween-80, pH 7.0. The difference in migration times of the main peaks in the overlay was within the experimental variability of this assay.

TABLE 90

Summary of reduced SDS-CE purity (agitation stability)

| Test article | Purity (%) |
|---|---|
| Control | 98.3 |
| Post-agitation | 98.2 |

Purity was the sum of chains L, H, and S percent area

Low and High pH

To create low pH stress, 1.0 mg of F3'-1602 was buffer switched into 20 mM sodium acetate, pH 5.0 using Amicon Ultra 0.5 mL 10K devices and brought to 1.0 mL with the same buffer (~1 mg/mL F3'-1602, concentration was confirmed by A280 with a Nanodrop One spectrophotometer). The sample was split. Half was stored at −80° C. as a control and the other half was incubated at 40° C. for 2 weeks. After the incubation, the sample was stored at −80° C. until analysis.

To create high pH stress, 1.0 mg of F3'-1602 was buffer switched into 20 mM Tris, pH 8.3 using Amicon Ultra 0.5 mL 10K devices and brought to 1.0 mL with the same buffer (~1 mg/mL F3'-1602, concentration was confirmed by A280 on the Nanodrop One). The sample was split. Half was stored at −80° C. as a control and the other half was incubated at 40° C. for 2 weeks. After the incubation, the sample was stored at −80° C. until analysis. The pKa of Tris will change as a result of temperature. At 40° C., the pH 8.3 buffer was ~pH 8.0.

To assess the chemical stability of F3'-1602, test article was held at pH 5.0 and pH 8.0 for two weeks at 40° C. At low pH, typical chemical modifications are aspartic acid isomerization and fragmentation, while at high pH, the primary degradation pathways are deamidation and oxidation. To confirm the integrity of F3'-1602 post-incubation, control and stressed samples were analyzed by SEC (Table 91). The results indicate that F3'-1602 remained largely intact with low levels of fragmentation as would be expected under these harsh conditions.

TABLE 91

Summary of SEC % monomer, HMW, and LMW (pH 5 and 8 stress)

| Test article | Monomer (%) | HMW (%) | LMW (%) |
|---|---|---|---|
| F3'-1602 pH 5 control | 99.8 | 0.2 | ND |
| F3'-1602 pH 5 stressed | 99.4 | 0.2 | 0.3 |
| F3'-1602 pH 8 control | 99.0 | 1.0 | ND |
| F3'-1602 pH 8 stressed | 95.2 | 0.9 | 3.9 |

ND: none detected

Chemical modification of amino acid side chains can typically be observed at a global scale with capillary isoelectric focusing (cIEF). To assess the modification of F3'-1602 samples held at low pH and high pH, F3'-1602 was diluted to 1 mg/mL with MilliQ water, 15 µL of sample was added to 60 µL of master mix (water, methyl cellulose, Pharmalyte 3-10, arginine, pI markers 4.05 and 9.99), vortexed, and centrifuged briefly. 60 µL of sample was aspirated from the top of the solution and added to a 96-well plate and centrifuged before testing. During the experiment, the sample was separated for one minute at 1500 volts followed by 8 minutes at 3000 volts on a Maurice (ProteinSimple, San Jose, CA).

Figure 85:
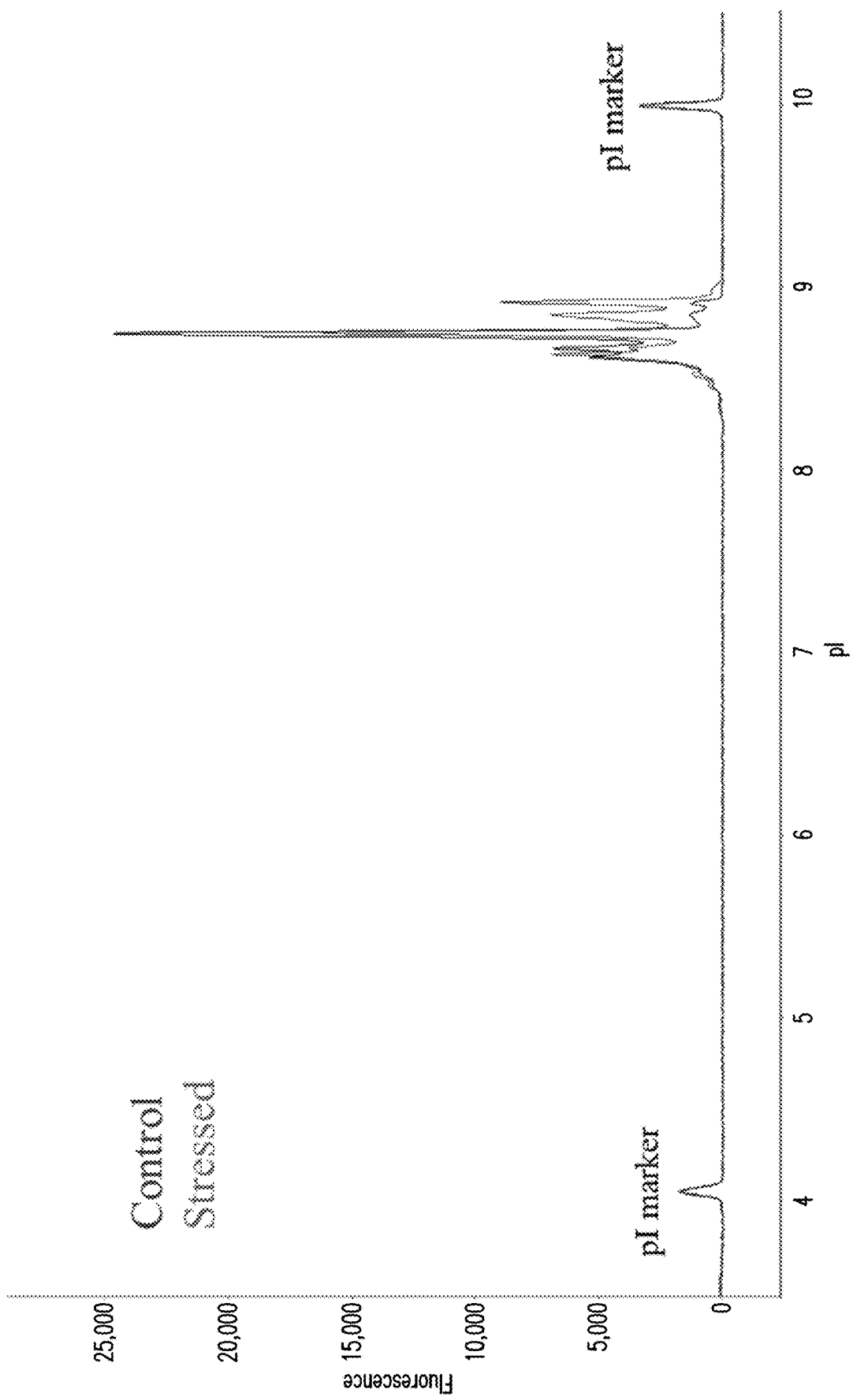
FIG. 85 is a cIEF profile of F3'-1602 after incubation under pH 5.0 stress.
Figure 86:
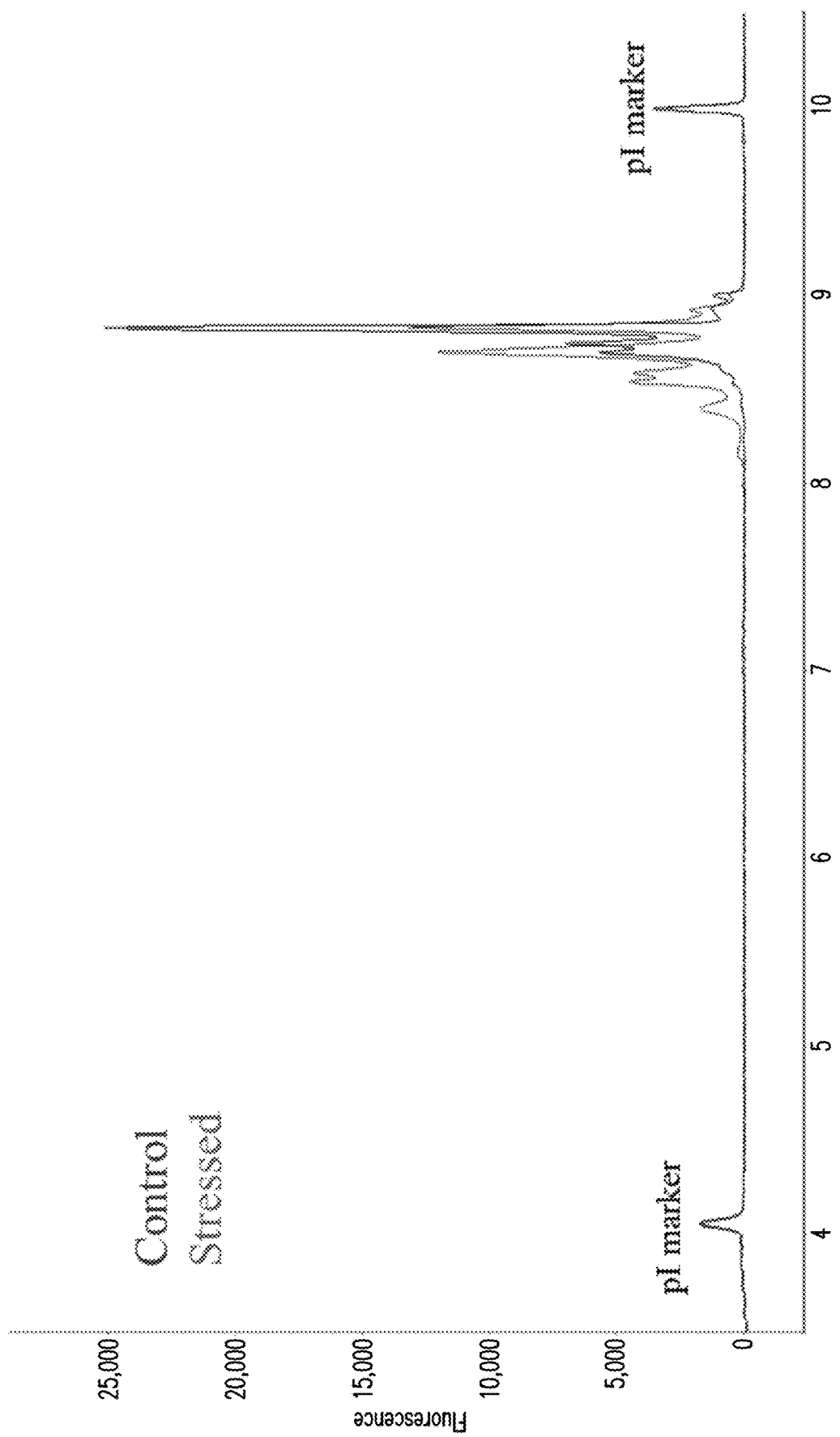
FIG. 86 is a cIEF profile of F3'-1602 after incubation under pH 8.0 stress.

The cIEF profile of F3'-1602 after being held at pH 5.0 for two weeks showed an increase in basic species from 8.9 to 39.1% (FIG. 85 and Table 92). A similar increase in acidic species was detected by cIEF after F3'-1602 was held at pH 8.0. A corresponding decrease in the main peak intensity (from 51.4 to 29.0%) was also observed (FIG. 86 and Table 92). Without wishing to be bound by theory, it is possible that deamidation throughout the F3'-1602 sequence lead to this acidic shift.

TABLE 92

Summary of F3'-1602 % acidic, main, and basic species (pH 5 and 8 stress)

| Test article | Acidic (%) | Main (%) | Basic (%) |
|---|---|---|---|
| pH 5.0, control | 39.8 | 51.4 | 8.9 |
| pH 5.0, 2 wks, 40° C. | 32.0 | 29.0 | 39.1 |
| pH 8.0, control | 39.6 | 52.2 | 8.4 |
| pH 8.0, 2 wks, 40° C. | 66.7 | 24.6 | 8.8 |

To determine whether the pH stress induced changes observed by cIEF was due to the modification in the complementarity determining regions (CDRs), the same pH 5 and pH 8 stressed samples were analyzed by LC-MS/MS peptide map. Briefly, 50 µg of F3'-1602 was diluted with 6 M guanidine hydrochloride in 250 mM Tris, pH 8.5, and disulfide bonds were reduced with 25 mM dithiothreitol for 30 minutes at 40° C. in a thermomixer. The reduced cysteines were then alkylated with 50 mM iodoacetamide for 60 minutes at room temperature in the dark. The reduced and alkylated protein was buffer-switched into 50 mM Tris, pH 8.0 and digested with trypsin (1:25 enzyme:substrate) for 1 hour at 37° C. LC-MS/MS was carried out on a Thermo Vanquish UHPLC coupled to a QExactive+ mass spectrometer. Briefly, 5 µg of protein digest was separated on a Waters UPLC BEH Peptide C18 column (2.1×150 mm) over 150 minutes using a 2% to 40% acetonitrile gradient at 0.3 mL/min. Mass spectra were acquired from 230-2000 m/z in positive mode at 35,000 resolution for the full MS scan and 17,500 resolution for the Top10 MS/MS scans. The UPLC-MS/MS files were analyzed using the Byos PTM workflow (Protein Metrics). Peptides were identified using accurate mass and MS/MS searching the F3'-1602 sequence.

Based on the peptide map data, all but one of the CDRs in F3'-1602 were resistant to modification during low and high pH stress. Only CDRH3 of the CLEC12A-binding scFv-Fc chain showed evidence of modification (isomerization) after the pH 5 stress (Table 93). This modification is the same one identified in the accelerated (40° C.) stability study.

TABLE 93

Post-translational modifications in F3'-1602 CDRs (pH 5.0 and pH 8.0)

| | | | | Relative abundance (%) | | | |
|---|---|---|---|---|---|---|---|
| | | | | pH 5 | | pH 8 | |
| Target | CDR | Sequence (Chothia) | Potential liability | control | stressed | control | stressed |
| CLEC 12A | H1 | GFSLTNY (SEQ ID NO: 137) | None | NA | NA | NA | NA |
| | H2 | WSGGK (SEQ ID NO: 138) | None | NA | NA | NA | NA |
| | H3 | YDYDDSLDY (SEQ ID NO: 139) | Isomerization | ND | Observed | ND | ND |
| | L1 | HASQNINFWLS (SEQ ID NO: 140) | None | NA | NA | NA | NA |
| | L2 | EASNLHT (SEQ ID NO: 141) | None | NA | NA | NA | NA |
| | L3 | QQSHSYPLT (SEQ ID NO: 142) | None | NA | NA | NA | NA |
| NKG2D | H1 | GFTFSSY (SEQ ID NO: 297) | None | NA | NA | NA | NA |
| | H2 | SSSSSY (SEQ ID NO: 298) | None | NA | NA | NA | NA |
| | H3 | GAPIGAAAGW FDP (SEQ ID NO: 97) | Truncation | ND | ND | ND | ND |
| | L1 | RASQGISSWLA (SEQ ID NO: 86) | None | NA | NA | NA | NA |
| | L2 | AASSLQS (SEQ ID NO: 77) | None | NA | NA | NA | NA |
| | L3 | QQGVSFPRT (SEQ ID NO: 87) | None | NA | NA | NA | NA |

ND: none detected; NA: not applicable

Figure 87A:
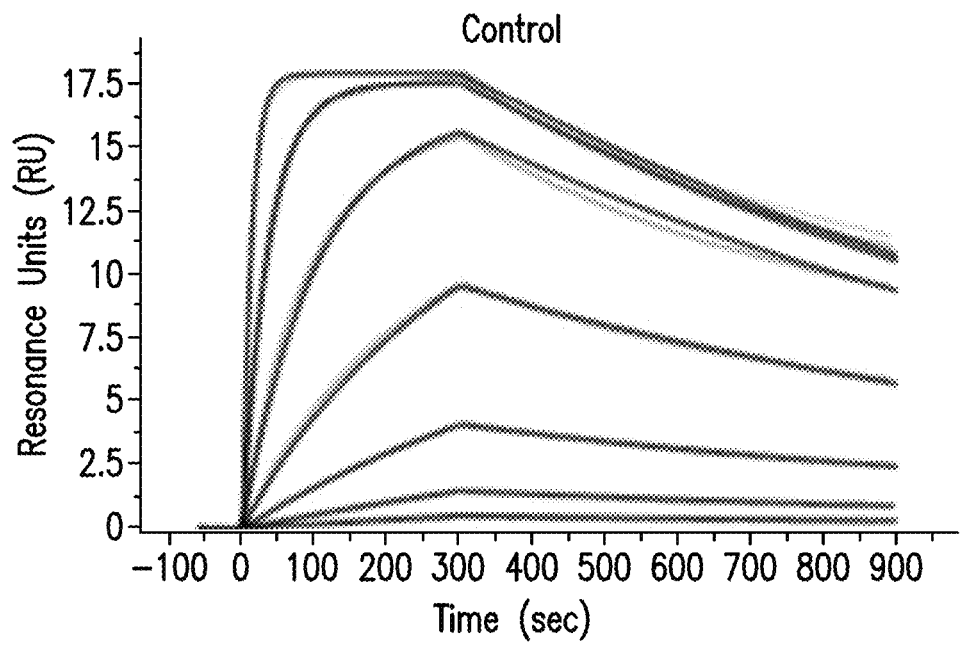
FIG. 87A-FIG. 87B are a set of sensorgrams showing the binding of hCLEC12A at three-fold serial dilution (300 nM to 0.41 nM) to F3'-1602 after pH 5 stress. The black overlays represent the 1:1 kinetic fit of the raw data.
Figure 87B:
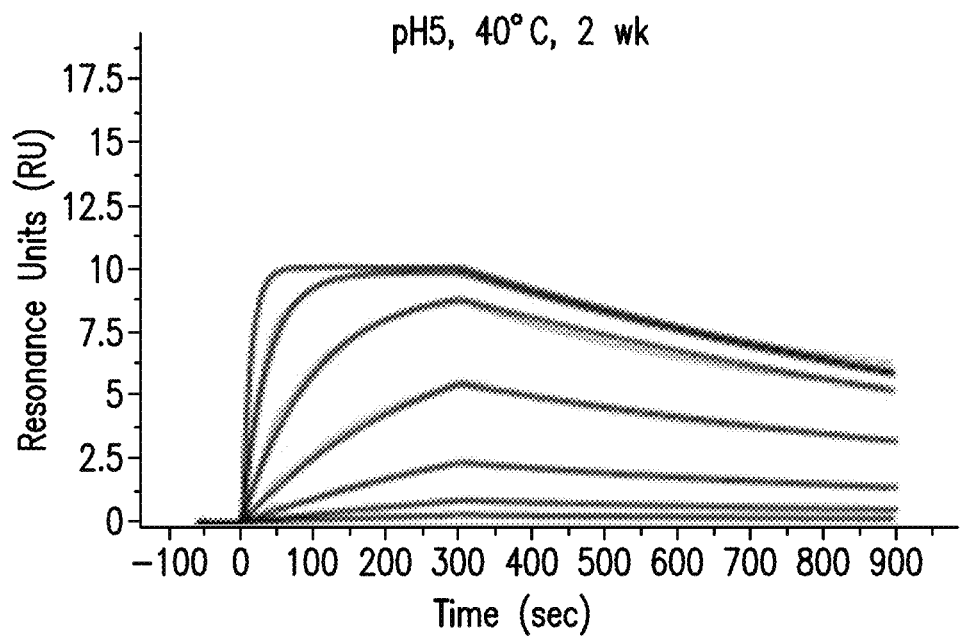
Figure 88A:
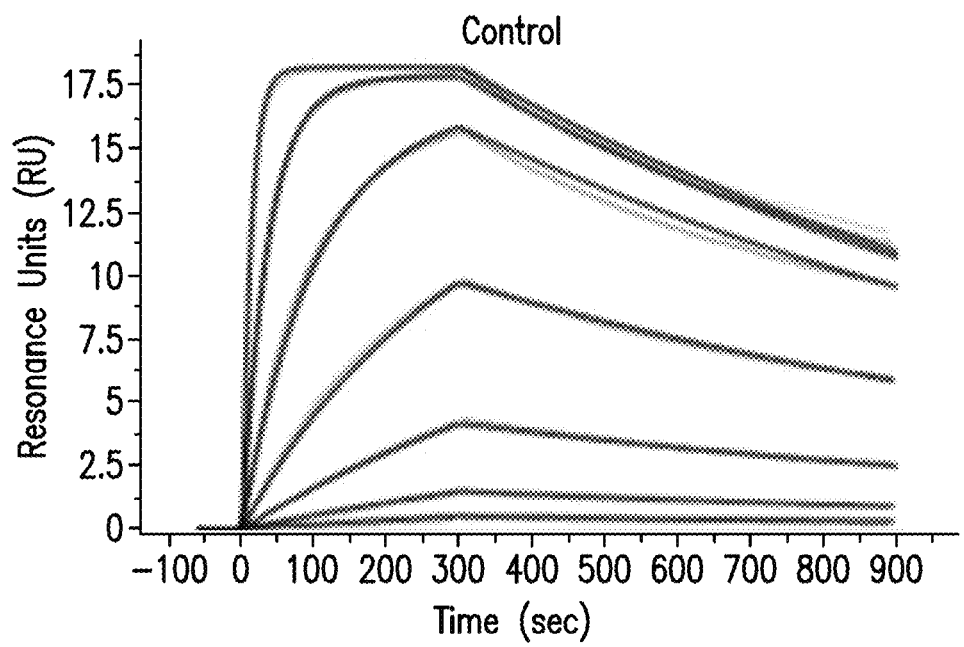
FIG. 88A-FIG. 88B are a set of sensorgrams showing the binding of hCLEC12A at three-fold serial dilution (300 nM to 0.41 nM) to F3'-1602 after pH 8 stress. The black overlays represent the 1:1 kinetic fit of the raw data.
Figure 88B:
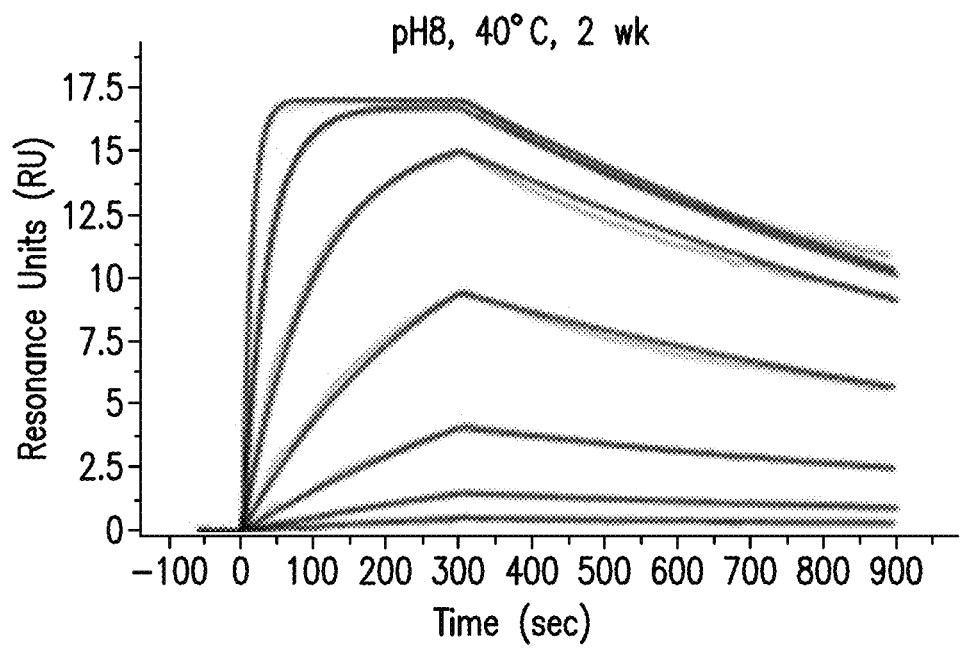

The binding affinities of F3'-1602 samples to recombinant human CLEC12A were measured by SPR as described in Example 14 (FIGS. 87A-87B). After two weeks of incubation at 40° C. in 20 mM sodium acetate, pH 5.0, binding of F3'-1602 to human CLEC12A was decreased (FIG. 87B and Table 94). The difference in association and dissociation rate constants between the control and low pH 40° C. stressed sample were within the experimental variability of the assay, however, apparent maximal binding response of the stressed sample was about half of the control after pH 5 stress. This indicates that F3'-1602 had a reduced ability to bind CLEC12A under these conditions (FIGS. 88A-88B). After two weeks of incubation at 40° C. in 20 mM Tris, pH 8.0, binding of F3'-1602 to human CLEC12A was unaltered (FIG. 88B and Table 94). This indicates that F3'-1602 retained affinity for CLEC12A under these accelerated pH stress conditions.

TABLE 94

Summary of kinetic parameters and binding affinity of F3'-1602 for hCLEC12A (pH 5.0 and pH 8.0 stress)

| Test article | Target | $k_a$ ($M^{-1}s^{-1}$) | $k_d$ ($s^{-1}$) | $K_D$ (nM) | Capture level (RU) |
|---|---|---|---|---|---|
| F3'-1602 Control | hCLEC12A | 7.99 × 10⁵ | 8.53 × 10⁻⁴ | 1.07 | 76.2 |
| F3'-1602, pH 5.0, 40° C., 2 wks | hCLEC12A | 8.65 × 10⁵ | 8.71 × 10⁻⁴ | 1.01 | 87.4 |
| F3'-1602 Control | hCLEC12A | 8.01 × 10⁵ | 8.40 × 10⁻⁴ | 1.1 | 86.9 |
| F3'-1602, pH 8.0, 40° C., 2 wks | hCLEC12A | 8.35 × 10⁵ | 8.45 × 10⁻⁴ | 1.0 | 82.8 |

Results are an average of n = 2 replicates

Figure 89A:
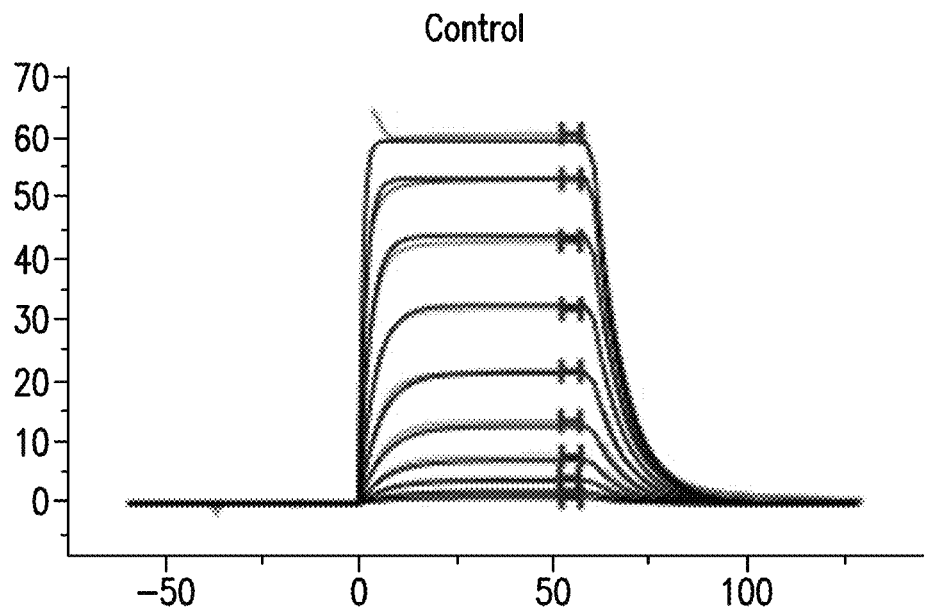
FIG. 89A-FIG. 89D are a set of graphs showing the binding of F3'-1602 to hNKG2D after pH 5 stress.
Figure 89B:
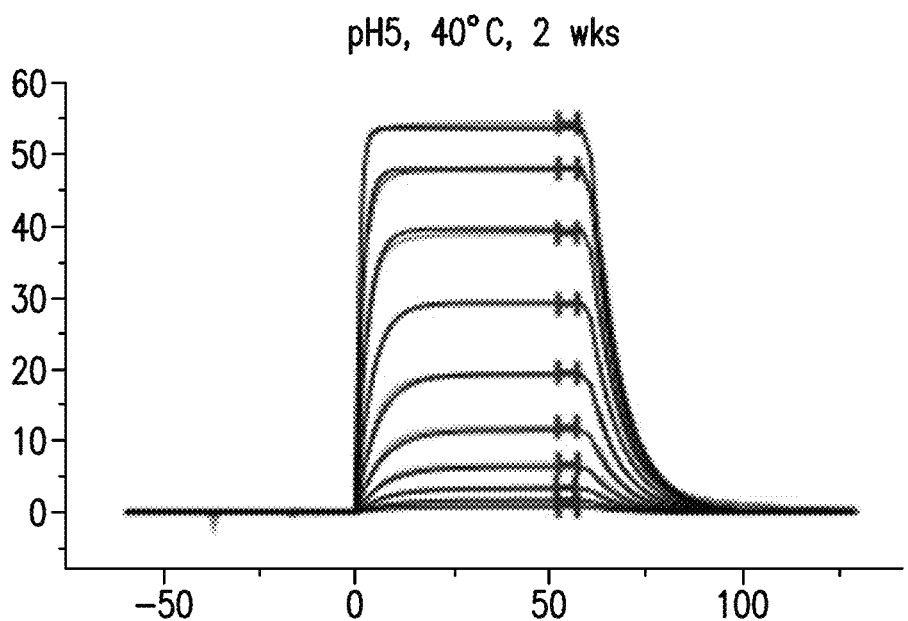
Figure 89C:
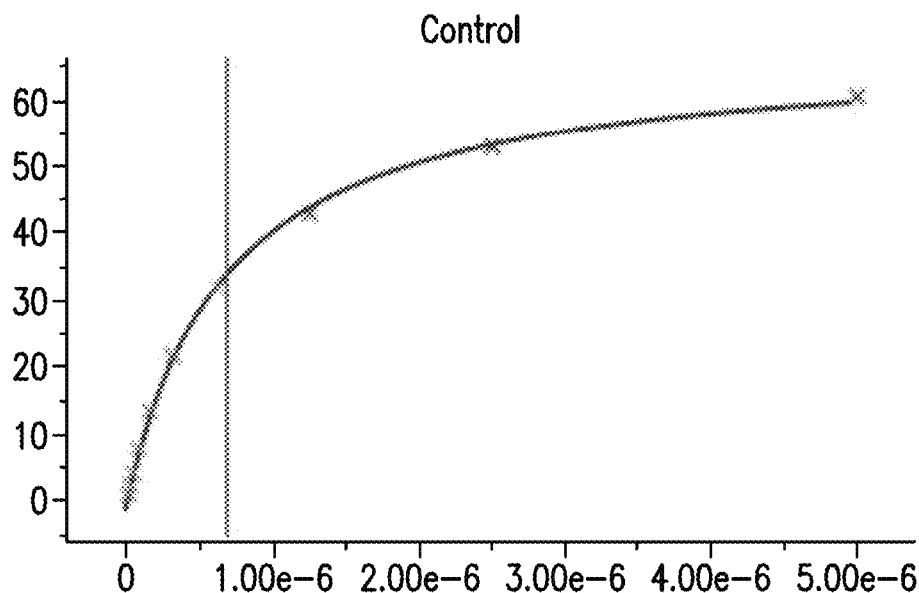
Figure 89D:
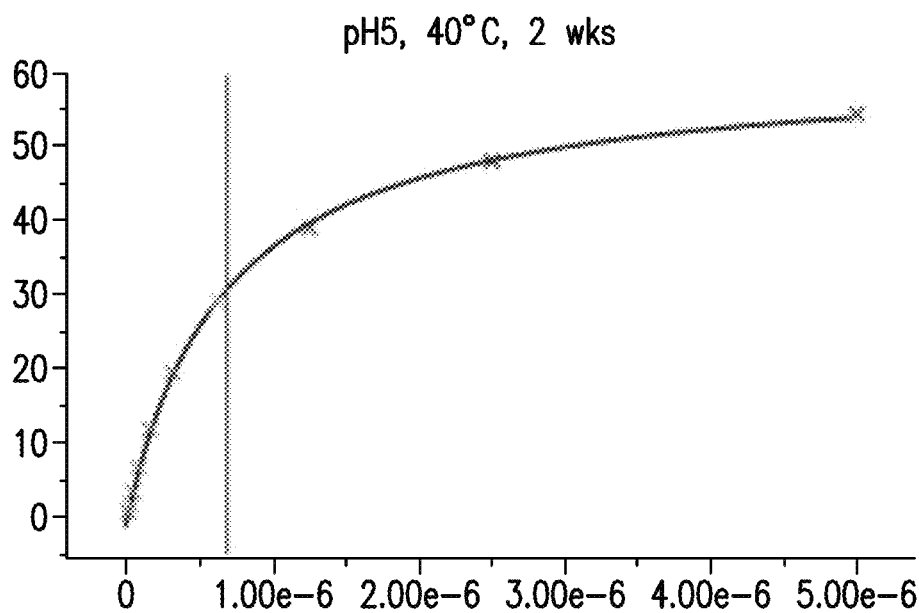
Figure 90A:
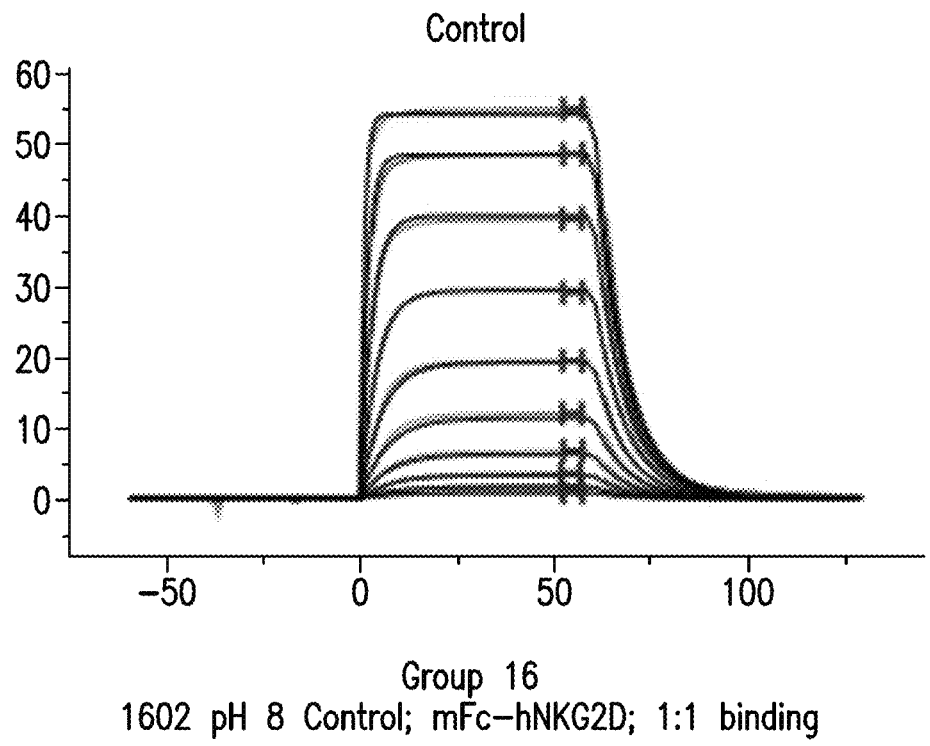
FIG. 90A-FIG. 90D are a set of graphs showing the binding of F3'-1602 to hNKG2D after pH 8 stress.
Figure 90B:
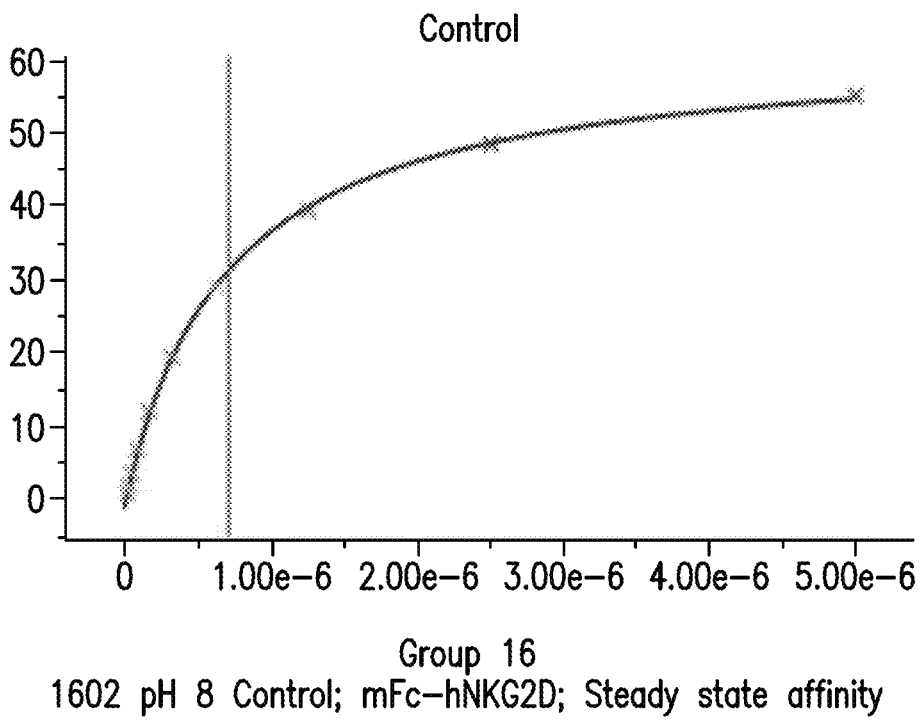
Figure 90C:
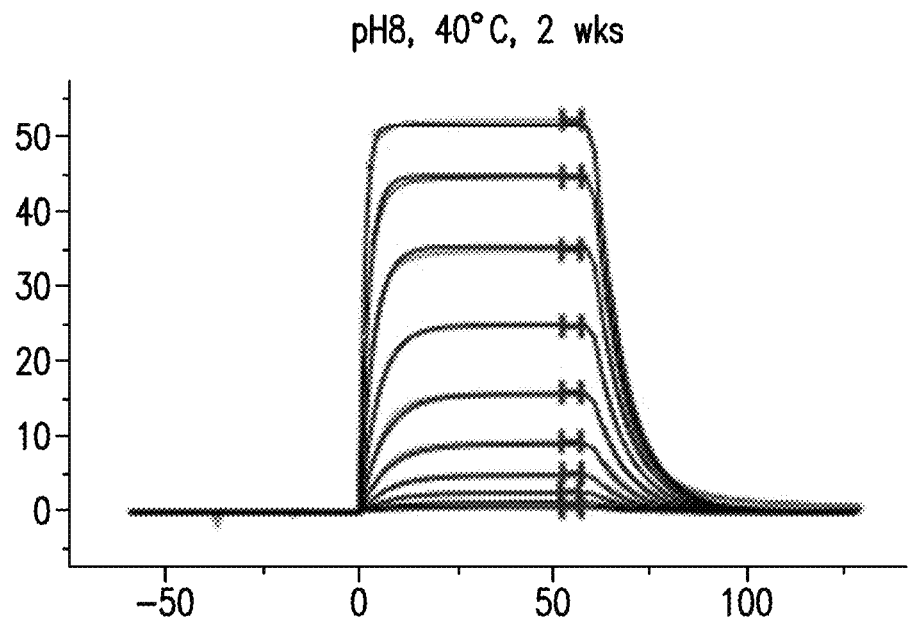
Figure 90D:
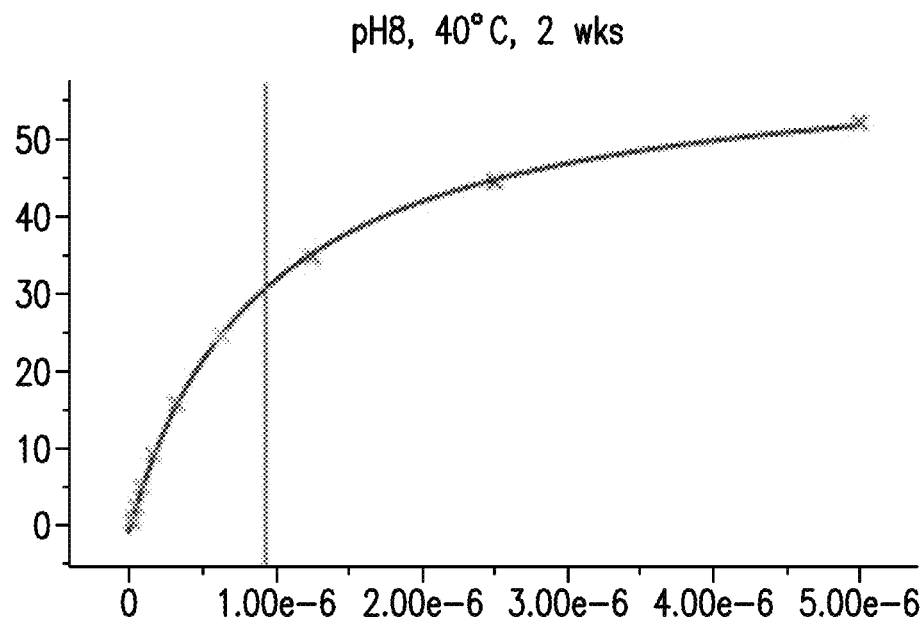

The binding affinities of F3'-1602 samples to recombinant human NKG2D were measured by SPR as described in Example 14 (FIGS. 89A-89D and FIGS. 90A-90D). After two weeks of incubation at 40° C. in 20 mM sodium acetate, pH 5.0, binding of F3'-1602 to human NKG2D was unaltered (FIGS. 89B and 89D and Table 95). This indicates that F3'-1602 retained affinity for NKG2D under these accelerated pH stress conditions. After two weeks of incubation at 40° C. in 20 mM tris, pH 8.0, binding of F3'-1602 to human NKG2D was unaltered (FIGS. 90B and 90D and Table 95). This indicates that F3'-1602 retained affinity for NKG2D under these accelerated pH stress conditions.

TABLE 95

Summary of kinetic parameters and binding affinity of F3'-1602 for hNKG2D (pH 5.0 and pH 8.0 stress)

| Test article | Target | $k_a$ ($M^{-1}s^{-1}$) | $k_d$ ($s^{-1}$) | 1:1 Kinetic Fit $K_D$ (nM) | Steady state $K_D$ (nM) | Capture level (RU) |
|---|---|---|---|---|---|---|
| F3'-1602 Control | hNKG2D | 1.89 × 10⁵ | 1.28 × 10⁻¹ | 678 | 684 | 51.9 |
| F3'-1602, pH 5.0, 40° C., 2 wks | hNKG2D | 1.88 × 10⁵ | 1.27 × 10⁻¹ | 675 | 677 | 46.2 |
| F3'-1602 Control | hNKG2D | 1.80 × 10⁵ | 1.25 × 10⁻¹ | 694 | 695 | 47.2 |
| F3'-1602, pH 8.0, 40° C., 2 wks | hNKG2D | 1.35 × 10⁵ | 1.22 × 10⁻¹ | 905 | 919 | 51.0 |

Figure 91:
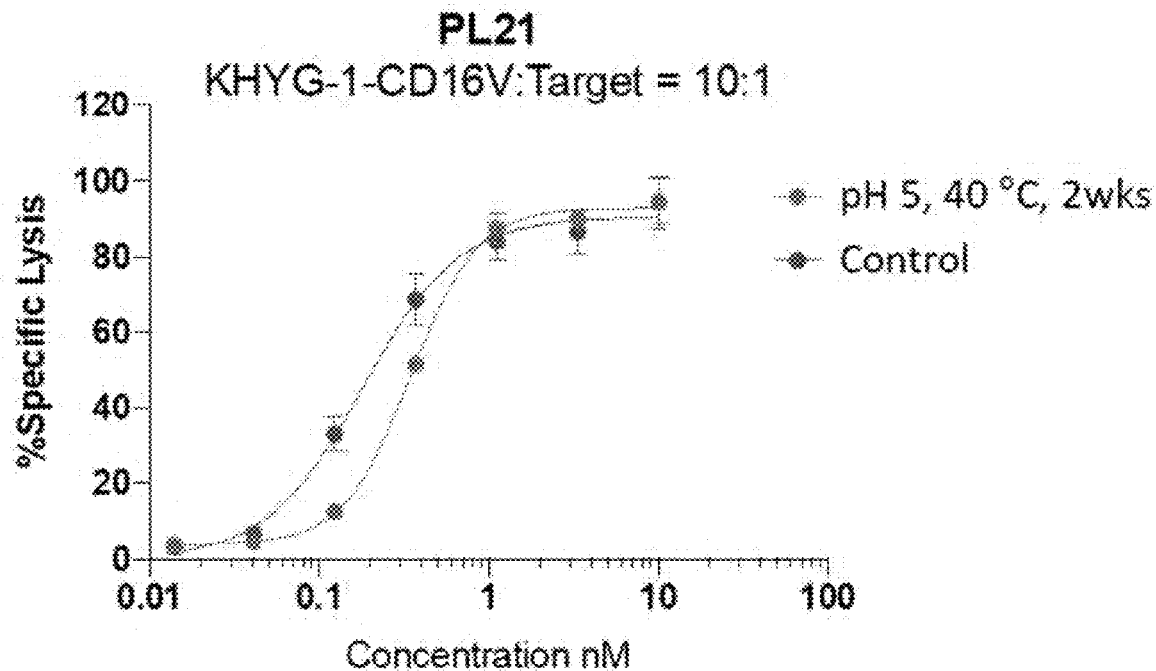
FIG. 91 is a graph showing the percentage lysis of PL21 cells by NKG2D- and CD16a-expressing KHYG-1-CD16a cells in the presence of F3'-1602 after pH 5 stress.
Figure 92:
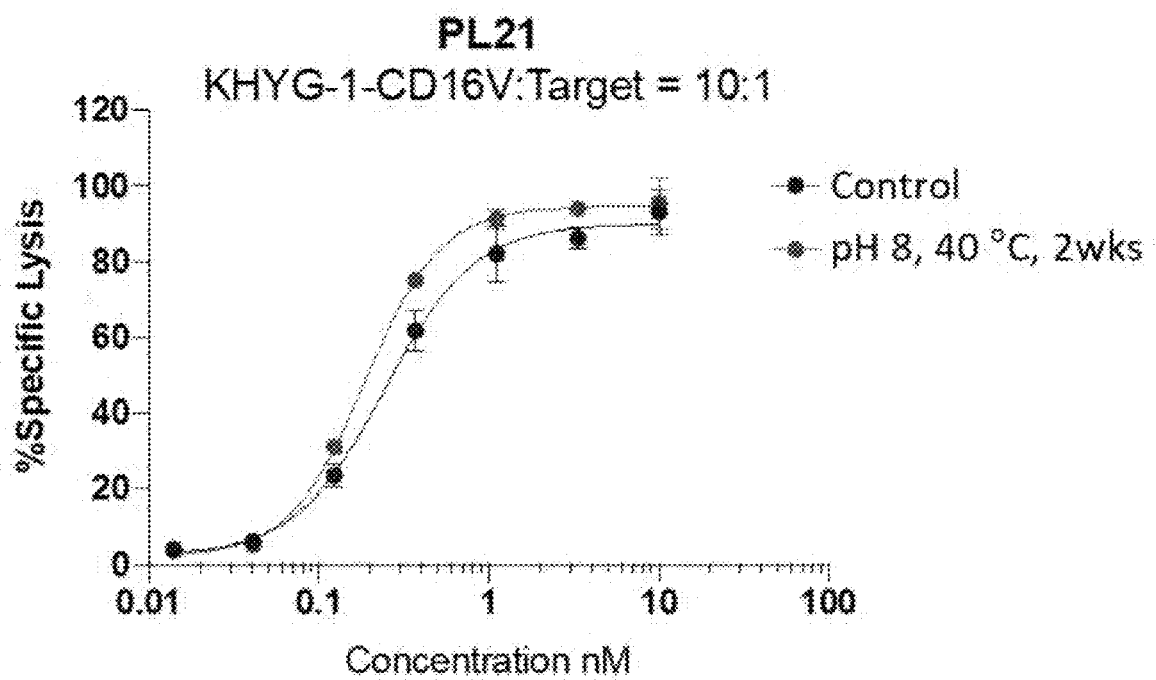
FIG. 92 is a graph showing the percentage lysis of PL21 cells by NKG2D- and CD16a-expressing KHYG-1-CD16a cells in the presence of F3'-1602 after pH 8 stress.

The effect of low and high pH stress on F3'-1602 function was assessed in a cytotoxicity assay using NKG2D- and CD16a-expressing KHYG-1-CD16a cells as described in Example 14. After pH 5.0 and 8.0 stress, F3'-1602 potency against PL-21 CLEC12A+ cancer cells reflected by EC50 and maximum lysis was reduced ~2-fold after pH 5 stress (FIG. 91 and Table 96) and was unchanged after pH 8 stress (FIG. 92 and Table 96). Without wishing to be bound by theory, it is possible that the loss of potency after pH 5 stress was due to the same isomerization of the scFv CDR-H3 aspartic acid identified in the initial accelerated stability study. The differences in the pH 5 and pH 8 results further demonstrates that F3'-1602 was more stable at elevated pH.

TABLE 96

EC50 and maximum lysis of CLEC12A+ PL-21 cells by F3'-1602 (pH 5.0 and pH 8.0 stress)

| Test article | EC50 (nM) | Maximum Lysis (%) |
|---|---|---|
| F3'-1602 Control | 0.18 | 91% |
| F3'-1602 pH 5.0, 2 wks, 40° C. | 0.34 | 93% |
| F3'-1602 Control | 0.19 | 95% |
| F3'-1602 pH 8.0, 2 wks, 40° C. | 0.24 | 90% |

Forced Oxidation

One of the most common stability indicating modifications of proteins is oxidation of methionine residues. To identify oxidation hot spots, 1.0 mg of F3'-1602 was diluted to 1 mg/mL with phosphate buffered saline (PBS). 3.3 µL of 3% hydrogen peroxide was added to a 0.5 mL aliquot of F3'-1602 (0.02% hydrogen peroxide). Oxidation of F3'-1602 proceeded for 24 hours at room temperature in the dark. After 24 hours, the sample was buffer switched into PBS, pH 7.4 using Amicon Ultra 0.5 mL 10K MWCO devices following the manufacturer's instructions. The un-oxidized control (0.5 mL) was stored at −80° C.

After forced oxidation, there were no significant differences in F3'-1602% monomer, BMWS or LMWS (Table 97).

TABLE 97

Summary of SEC % monomer, HMW, and LMW (forced oxidation)

| Test article | Monomer (%) | HMW (%) | LMW (%) |
|---|---|---|---|
| F3'-1602 Control | 99.9 | 0.1 | ND |
| F3'-1602 0.02% $H_2O_2$, 24 hrs | 99.9 | 0.1 | ND |

ND: none detected

After forced oxidation, the purity of F3'-1602 by non-reduced SDS-CE was decreased by less than 1% (Table 98). This indicates that F3'-1602 was resistant to fragmentation during forced oxidation. There were no new fragments detected after forced oxidation. The peak shape of the oxidized sample changed after the oxidative stress. Without wishing to be bound by theory, this may indicate that there was no longer a homogeneous population and that the high levels of oxidation resulted in a conformational change not present in the control sample of F3'-1602. The difference in migration times of the main peaks in the overlay was within the experimental variability of this assay.

TABLE 98

Summary of non-reduced SDS-CE purity (forced oxidation)

| Test article | LMW (%) | Main (%) | HMW (%) |
|---|---|---|---|
| F3'-1602, Control | 3.9 | 96.1 | ND |
| F3'-1602, 0.02% $H_2O_2$, 24 hrs | 4.7 | 95.2 | ND |

ND: none detected

After forced oxidation, the purity of F3'-1602 by reduced SDS-CE was unchanged (Table 99). This indicates that F3'-1602 was resistant to fragmentation during forced oxidation. There were no new fragments detected after forced oxidation. The difference in migration times of the main peaks in the overlay was within the experimental variability of this assay.

TABLE 99

Summary of reduced SDS-CE purity (forced oxidation)

| Test article | Chain L (%) | Chain H (%) | Chain S (%) | Purity (%) |
|---|---|---|---|---|
| F3'-1602, Control | 17.7 | 40.1 | 40.5 | 98.3 |
| F3'-1602, 0.02% $H_2O_2$, 24 hrs | 17.8 | 40.0 | 40.4 | 98.2 |

In addition to determining the biophysical effects of forced oxidation by SEC, it is important to understand which amino acids are most susceptible to oxidation. There are no methionine residues in the F3'-1602 CDRs, however, several methionines are found in the framework and constant domains. Levels of oxidation were low at all sites in the control and only two sites showed significant increases in oxidation after exposure to hydrogen peroxide (Table 100). Low levels of oxidation have been observed in other therapeutic mAbs.

TABLE 100

Summary of site-specific percent oxidation in F3'-1602 (forced oxidation)

| Peptide Sequence | SEQ ID NO | Chain | Position | Relative abundance (%) Control | Oxidized |
|---|---|---|---|---|---|
| LSCAASGFTFSSYSMNWVR | 299 | H | 34 | 0.6 | 0.8 |
| NSLYLQMNSLR | 300 | H | 83 | 0.2 | 0.3 |
| DTLMISR | 301 | H/S* | 257/283 | 2.3 | 71.3 |
| WQQGNVFSCSVMHEALHNHYTQK | 302 | H/S* | 433/454 | 1.5 | 47.4 |
| DIQMTQSPSSVSASVGDR | 303 | L | 4 | 0.3 | 0.4 |
| YDYDDSLDYWGQGTLVTVSSGGGGSGGGGSGGGGSGGGGSDIQMTQSPSSLSASVGDRVTITCHASFQNINWLSWYQQKPGKAPK | 304 | S | 141 | ND | ND |

*peptide is found in chain H and S;
ND, none detected

Figure 93A:
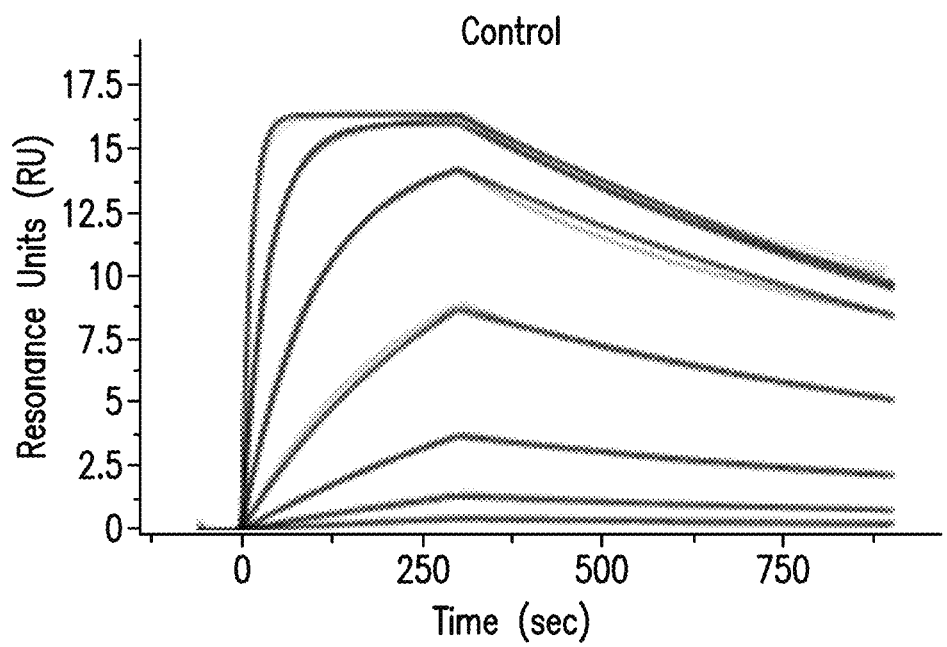
FIG. 93A-FIG. 93B are a set of sensorgrams showing the binding of hCLEC12A to F3'-1602 after forced oxidation stress. The black overlays represent the 1:1 kinetic fit of the raw data.
Figure 93B:
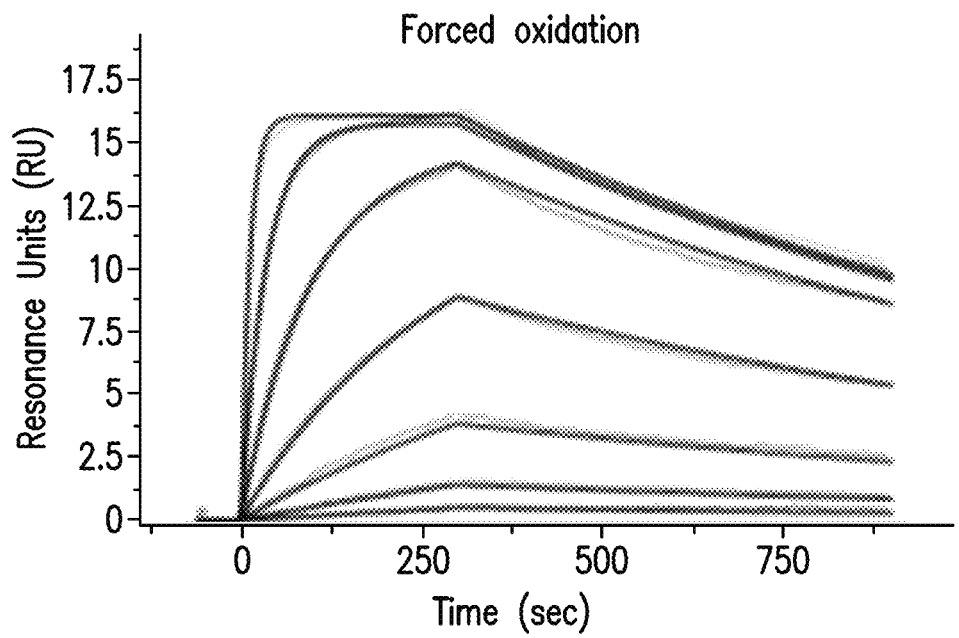

The binding affinities of forced oxidation stressed F3'-1602 samples to recombinant human CLEC12A were measured by SPR as described in Example 14 (FIGS. 93A-93B). After 24 hours of incubation at room temperature in presence of 0.02% hydrogen peroxide, kinetics and affinity of binding of F3'-1602 to human CLEC12A as well as apparent Rmax was unaltered (FIG. 93B and Table 101). This indicates that F3'-1602 retained binding to CLEC12A after forced oxidation and modifications of methionines in the constant regions and framework did not affect the affinity of the F3'-1602 for hCLEC12A.

TABLE 101

Summary of kinetic parameters and binding affinity of F3'-1602 for hCLEC12A (forced oxidation)

| Test article | Target | $k_a$ $(M^{-1}s^{-1})$ | $k_d$ $(s^{-1})$ | $K_D$ (nM) | Capture level (RU) |
|---|---|---|---|---|---|
| F3'-1602 Control | hCLEC12A | $7.99 \times 10^5$ | $8.58 \times 10^{-4}$ | 1.1 | 78.6 |
| F3'-1602 Forced Oxidized | hCLEC12A | $8.06 \times 10^5$ | $8.70 \times 10^{-4}$ | 1.1 | 76.8 |

Results are an average of n = 2 replicates

Figure 94A:
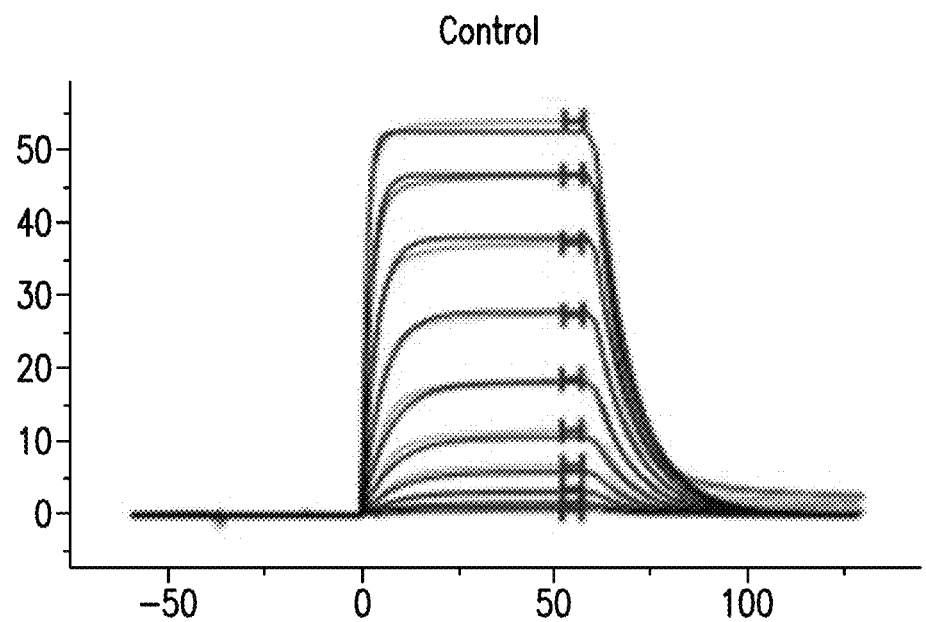
FIG. 94A-FIG. 94D are a set of graphs showing the binding of F3'-1602 to hNKG2D after forced oxidation stress.
Figure 94B:
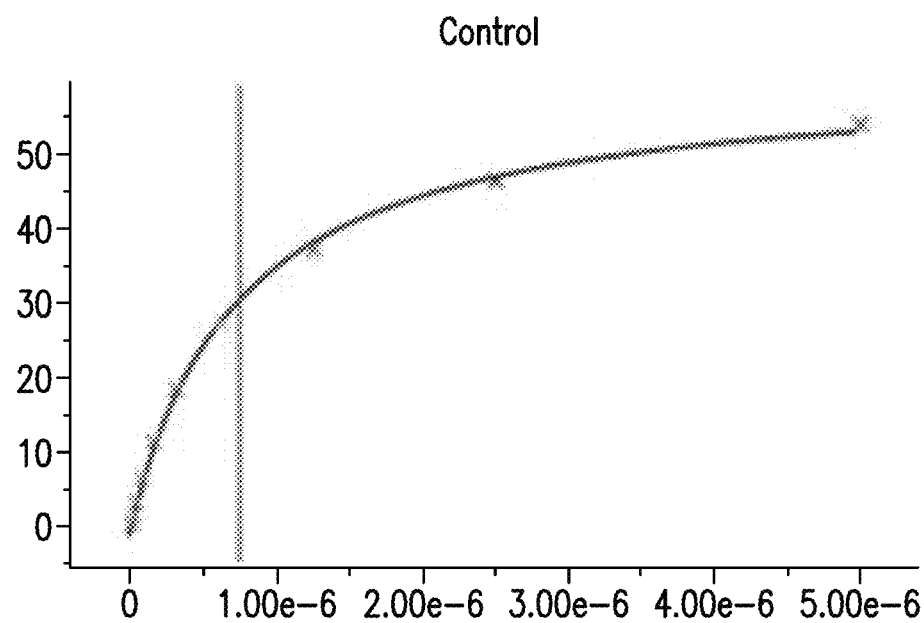
Figure 94C:
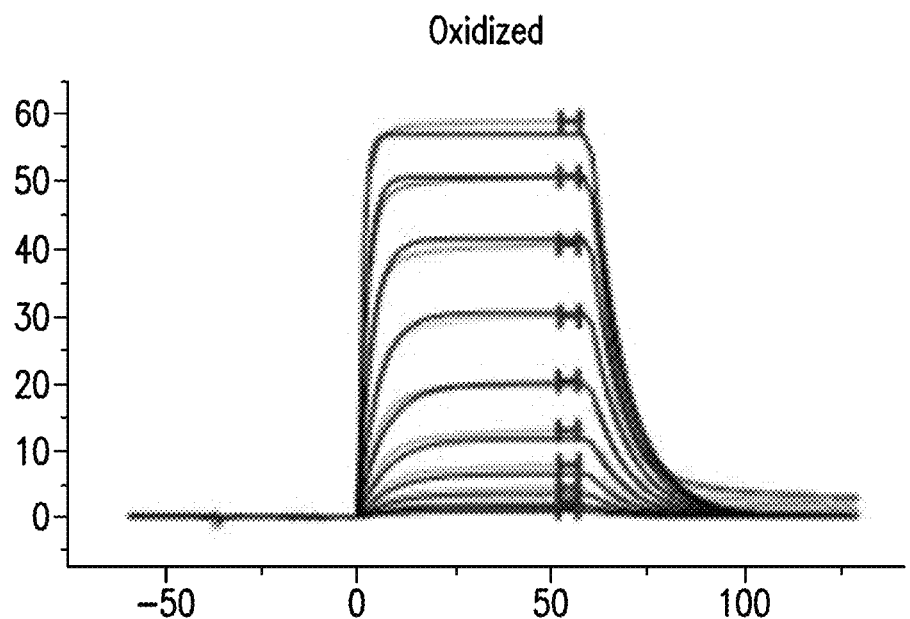
Figure 94D:
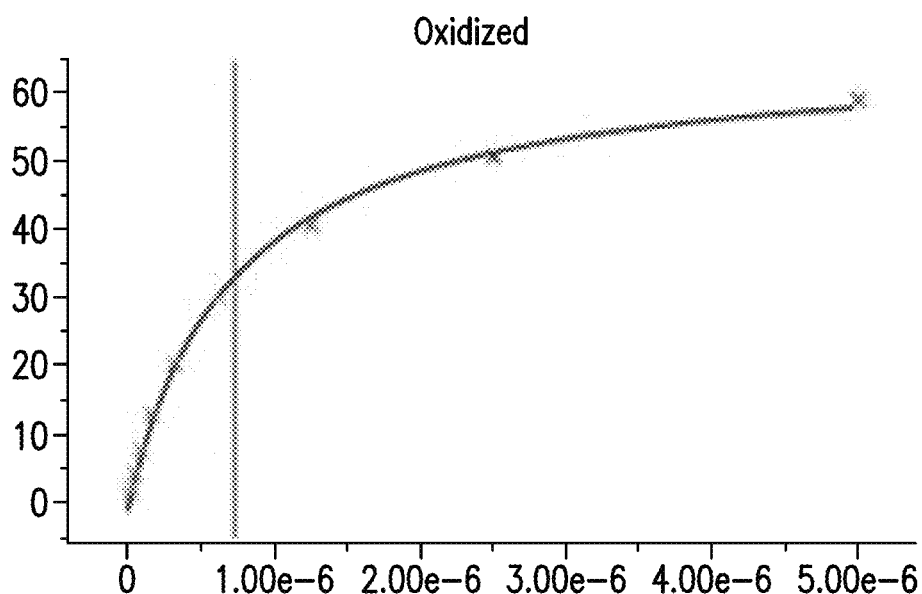

The binding affinities of forced oxidation stressed F3'-1602 samples to recombinant human NKG2D were measured by SPR as described in Example 14 (FIGS. 94A-94D). After 24 hours of incubation at room temperature in presence of 0.02% hydrogen peroxide, kinetics and affinity of binding of F3'-1602 to human NKG2D was unaltered (FIGS. 94B and 94D and Table 102). This indicates that F3'-1602 retains binding to NKG2D after forced oxidation and modifications of methionines in the constant regions and framework do not affect the affinity of the F3'-1602 for hNKG2D.

TABLE 102

Summary of kinetic parameters and binding affinity of F3'-1602 for hNKG2D (forced oxidation)

| Test article | Target | $k_a$ $(M^{-1}s^{-1})$ | $k_d$ $(s^{-1})$ | 1:1 Kinetic Fit $K_D$ (nM) | Steady state $K_D$ (nM) | Capture level (RU) |
|---|---|---|---|---|---|---|
| F3'-1602 Control | hNKG2D | $(1.43 \pm 0.03) \times 10^5$ | $(1.07 \pm 0.04) \times 10^{-1}$ | 750 ± 23 | 759 ± 23 | 44.1 |
| F3'-1602, 0.02% $H_2O_2$, 24 hrs | hNKG2D | $(1.48 \pm 0.06) \times 10^5$ | $(1.07 \pm 0.04) \times 10^{-1}$ | 722 ± 6 | 732 ± 7 | 48.2 |

The effect of forced oxidation stress on F3'-1602 function was assessed in a cytotoxicity assay using NKG2D- and CD16a-expressing KHYG-1-CD16a cells as described in Example 14. As shown in FIG. 95 and Table 103, after oxidative stress, F3'-1602 potency (EC50 and maximum lysis) was unchanged.

TABLE 103

EC50 and maximum lysis of CLEC12A+ PL-21 cells by F3'-1602 (forced oxidation)

| Test article | EC50 (nM) | Maximum Lysis (%) |
|---|---|---|
| F3'-1602 Control | 0.26 | 60% |
| F3'-1602 0.02% $H_2O_2$, 24 hrs | 0.28 | 63% |

Low pH Hold

Viral inactivation by low pH hold is an important step in biologics manufacturing. To assess the stability of F3'-1602 at low pH hold, F3'-1602 was captured on a MabSelect Sure Protein A column and eluted with 100 mM glycine, pH 3.0. Peak fractions were pooled, and the 12 mL of the protein A eluate was pH was adjusted to pH 3.3 with additional 100 mM glycine pH 3.0 buffer. The pH-adjusted eluate was held at room temperature. After 1.5 hours, the eluate was brought to neutral pH with 1.0 M Tris-HCl, pH 8.3. The pH-hold sample was further purified by cation exchange chromatography. The final product was buffer exchanged to PBS pH 7.4 for analysis.

After incubation at low pH, F3'-1602 was analyzed by SEC to determine if the hold caused aggregation. There was no increase in BMW and LMW content in F3'-1602 due to the low pH hold step (Table 104).

TABLE 104

Summary of SEC % monomer, HMW, and LMW (low pH hold)

| Test article | Monomer (%) | HMW (%) | LMW (%) |
|---|---|---|---|
| F3'-1602 Control, ProA eluate | 77.4 | 11.5 | 11.1 |
| F3'-1602 low pH hold, ProA eluate | 86.4 | 3.4 | 10.2 |

After low pH hold, the purity of F3'-1602 by non-reduced SDS-CE was unchanged (Table 105). This indicates that F3'-1602 was resistant to fragmentation during low pH hold. There were no new fragments detected after the low pH hold. The difference in migration times of the main peaks in the overlay was within the experimental variability of this assay.

TABLE 105

Summary of non-reduced SDS-CE purity (low pH hold)

| Test article | LMW (%) | Main (%) | HMW (%) |
|---|---|---|---|
| F3'-1602 Control | 1.3 | 98.7 | ND |
| F3'-1602 low pH hold | 1.1 | 98.9 | ND |

ND, none detected

After low pH hold, the purity of F3'-1602 by reduced SDS-CE was unchanged (Table 106). This indicates that F3'-1602 was resistant to fragmentation during low pH hold. There were no new fragments detected after the low pH hold.

TABLE 106

Summary of reduced SDS-CE purity (low pH hold)

| Test article | Light chain (%) | Heavy chain (%) | scFv-Fc chain (%) | Purity (%) |
|---|---|---|---|---|
| F3'-1602 Control | 18.1 | 39.9 | 40.4 | 98.4 |
| F3'-1602 low pH hold | 17.6 | 39.7 | 41.1 | 98.4 |

Chemical modification of amino acid side chains can typically be observed at a global scale with cIEF. The cIEF profiles of F3'-1602 control and low pH hold lot were visually very similar and the relative quantitation of acid, main, and basic species are all within 1% of each other, indicating that the low pH hold did not have a measurable effect on the charge profile of F3'-1602 (Table 107).

TABLE 107

Summary of F3'-1602 % acidic, main, and basic species (low pH hold)

| Test article | pI | Acidic species (%) | Main species (%) | Basic species (%) |
|---|---|---|---|---|
| F3'-1602 control | 8.75 | 42.4 | 48.5 | 9.1 |
| F3'-1602, low pH hold | 8.80 | 42.7 | 49.1 | 8.2 |

F3'-1602 samples were analyzed by intact mass to monitor modification and fragmentation as a result of the low pH hold. The observed mass for both the control and low pH hold sample matched each other and the theoretical F3'-1602 mass (G0F/G0F glycoform: 126,360.4 Da). Low pH hold did not affect the mass of F3'-1602 (Table 108) and fragmentation was not observed.

TABLE 108

F3'-1602 theoretical and observed masses (low pH hold)

| Test article | Theor. Mass (Da) | Obs. Mass (Da) | Delta mass (Da) | Mass accuracy (ppm) |
|---|---|---|---|---|
| F3'-1602 control | 126,360.4 | 126,360.8 | +0.4 | 3.2 |
| F3'-1602 low pH hold | 126,360.4 | 126,360.7 | +0.3 | 2.4 |

Figure 96A:
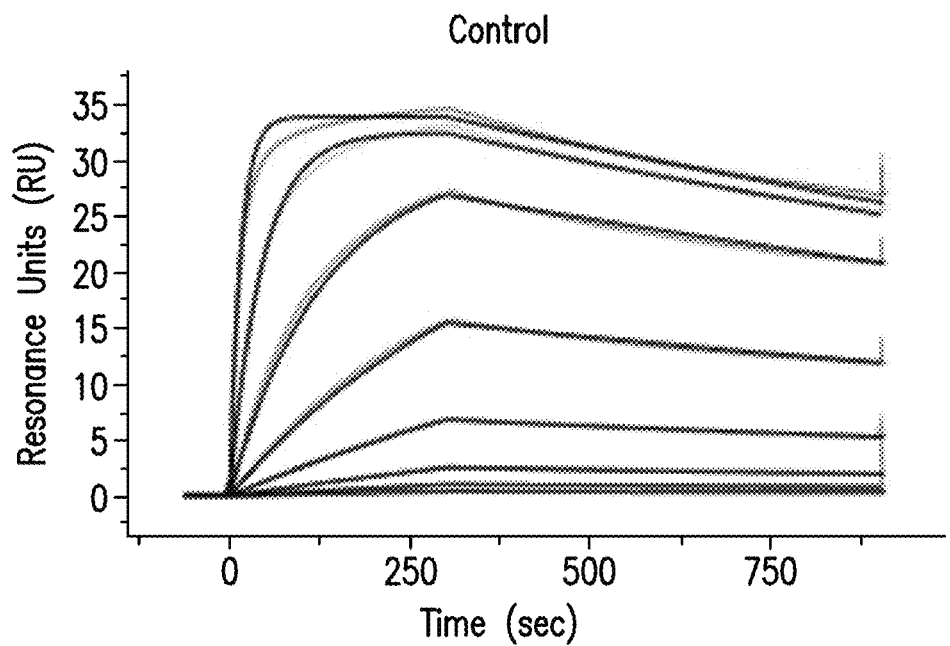
FIG. 96A-FIG. 96B are a set of sensorgrams showing the binding of hCLEC12A to F3'-1602 after low pH hold. The black overlays represent the 1:1 kinetic fit of the raw data.
Figure 96B:
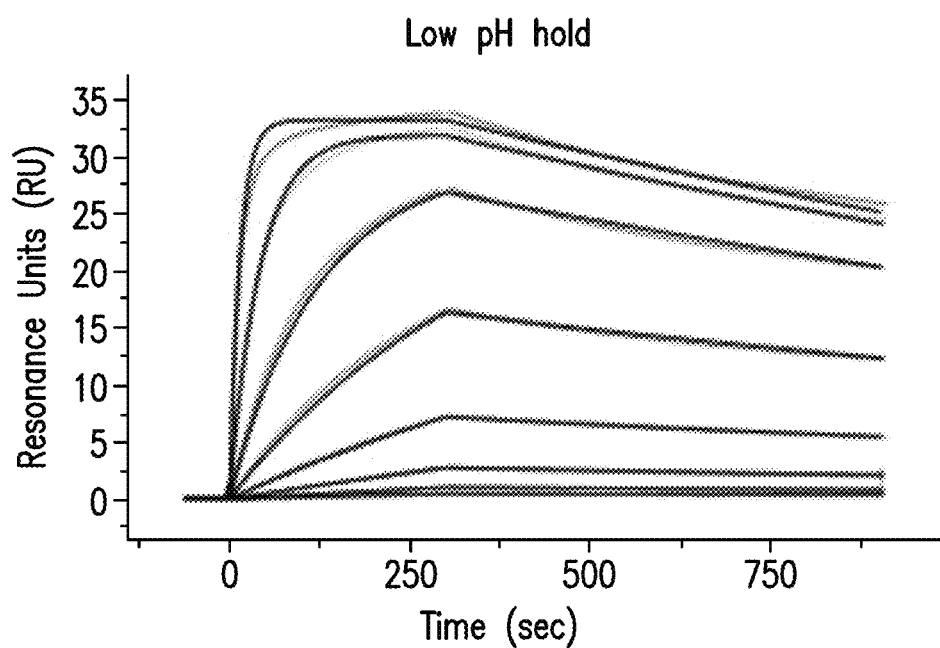

Low pH hold did not induce any change in kinetics or affinity of F3'-1602 binding to human CLEC12A (FIG. 96B and Table 109). The difference in association and dissociation rate constants as well as apparent maximal binding response (Rmax) between the control and low pH hold sample were within the experimental variability of the assay (FIGS. 96A-96B). This indicates that F3'-1602 retained affinity for CLEC12A after a low pH hold step of biotherapeutic manufacturing.

TABLE 109

Summary of kinetic parameters and binding affinity of F3'-1602 for hCLEC12A (low pH hold)

| Test article | Target | $k_a$ (M$^{-1}$s$^{-1}$) | $k_d$ (s$^{-1}$) | $K_D$ (nM) | Capture level (RU) |
|---|---|---|---|---|---|
| F3'-1602 Control | hCLEC12A | (6.78 ± 0.13) × 10$^5$ | (4.33 ± 0.20) × 10$^4$ | 0.638 ± 0.028 | 176 ± 19 |
| F3'-1602 Low pH hold | hCLEC12A | (7.15 ± 0.10) × 10$^5$ | (4.61 ± 0.03) × 10$^4$ | 0.644 ± 0.008 | 157 ± 7 |

Results are an average of n = 4 replicates

Figure 97A:
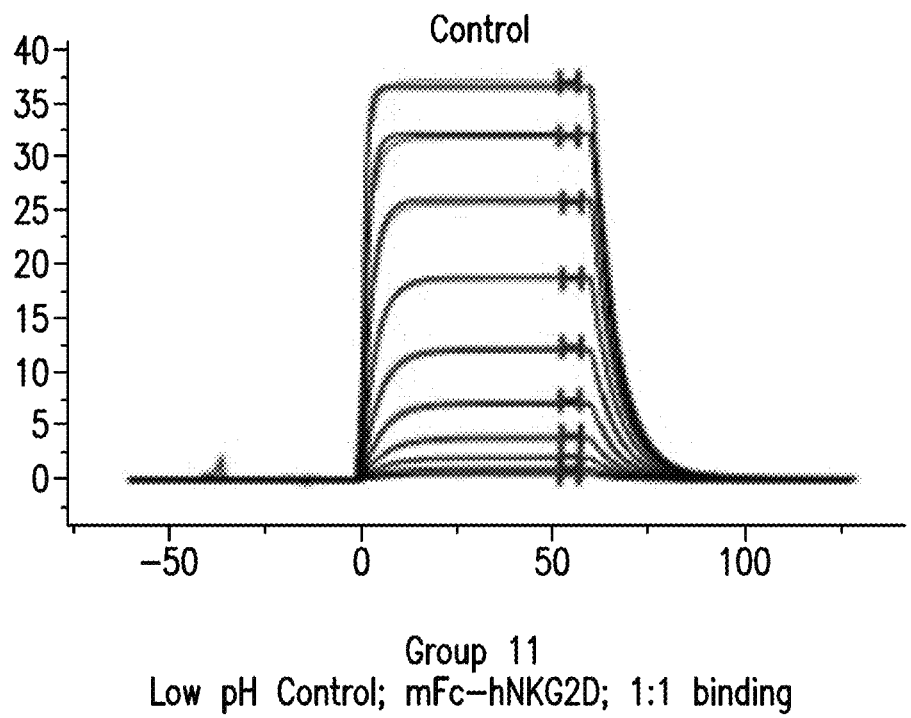
FIG. 97A-FIG. 97D are a set of graphs showing the binding of F3'-1602 to hNKG2D after low pH hold.
Figure 97B:
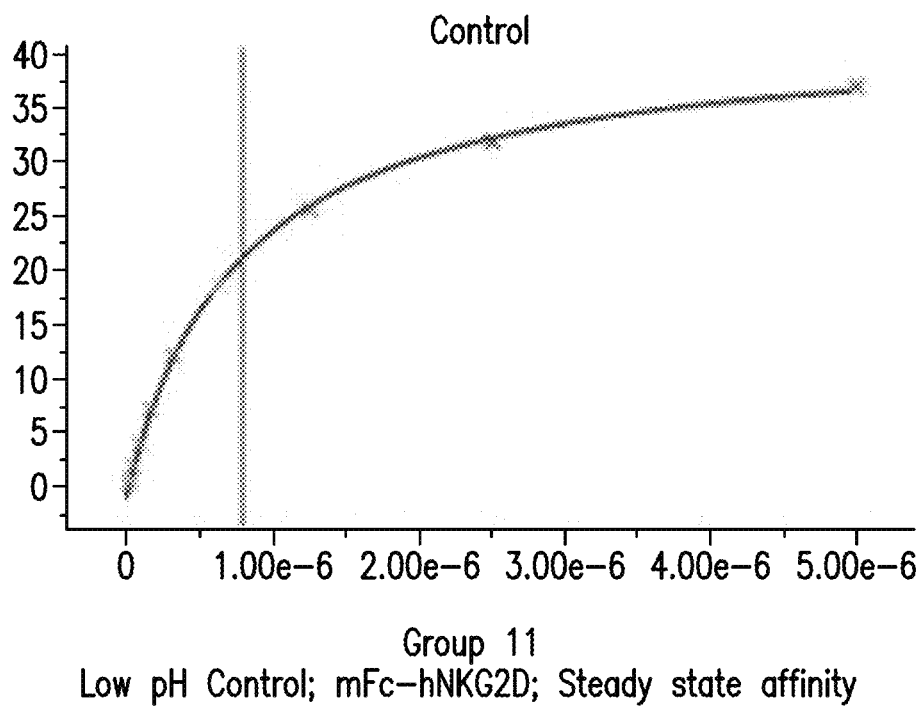
Figure 97C:
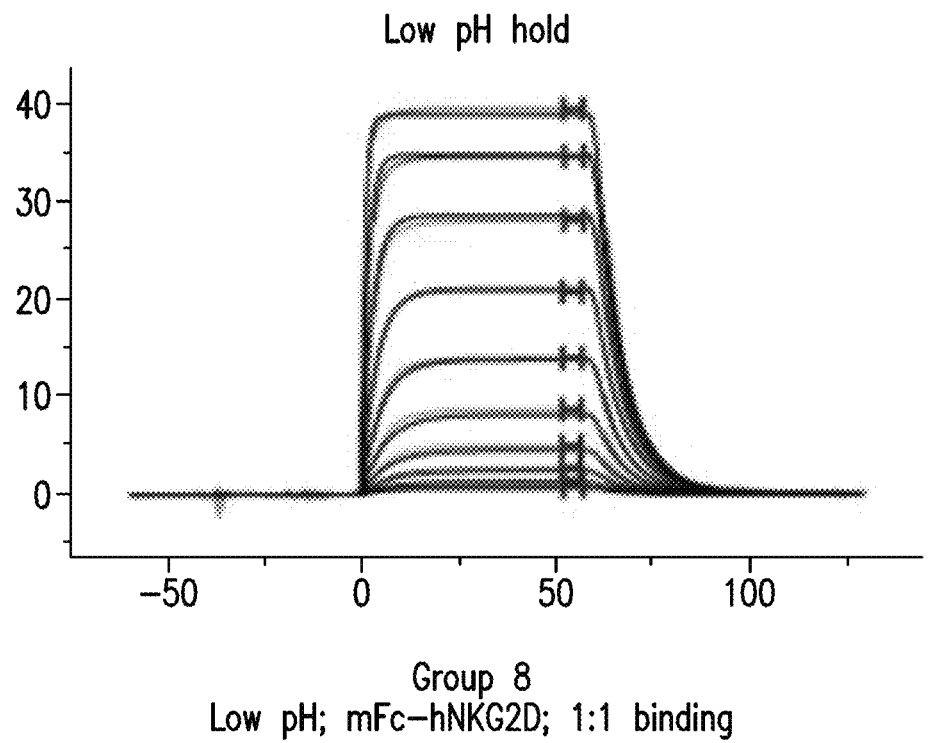
Figure 97D:
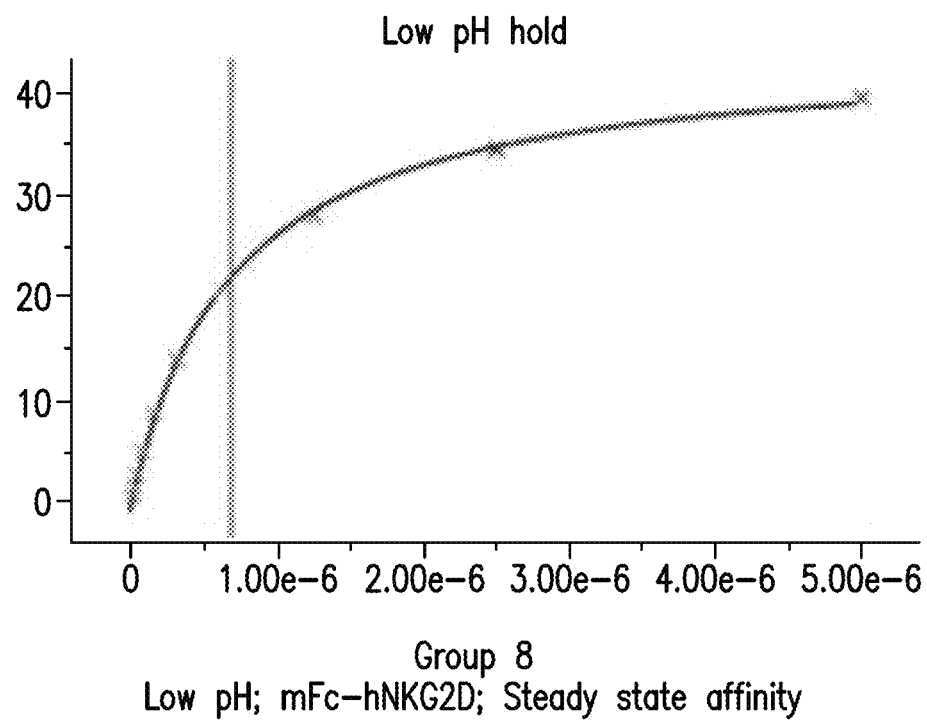

After low pH hold, human NKG2D binding was unaltered (FIGS. 97B and 97D and Table 110). The differences in steady state affinity and apparent maximal binding response affinity between the control and 40° C. stressed sample were within the experimental variability of the assay (FIGS. 97A-97D). This indicates that F3'-1602 retained affinity for human NKG2D after low pH hold.

TABLE 110

Summary of kinetic parameters and binding affinity of F3'-1602 for hNKG2D (low pH hold)

| Test article | Target | $k_a$ (M$^{-1}$s$^{-1}$) | $k_d$ (s$^{-1}$) | 1:1 Kinetic Fit $K_D$ (nM) | Steady state $K_D$ (nM) | Capture level (RU) |
|---|---|---|---|---|---|---|
| F3'-1602 Control | hNKG2D | (2.06 ± 0.09) × 10$^5$ | (1.46 ± 0.08) × 10$^{-1}$ | 714 ± 62 | 710 ± 63 | 34.0 |
| F3'-1602, low pH hold | hNKG2D | (2.07 ± 0.08) × 10$^5$ | (1.39 ± 0.02) × 10$^{-1}$ | 671 ± 20 | 672 ± 18 | 33.7 |

Results are an average of n = 3 measurements

Figure 98A:
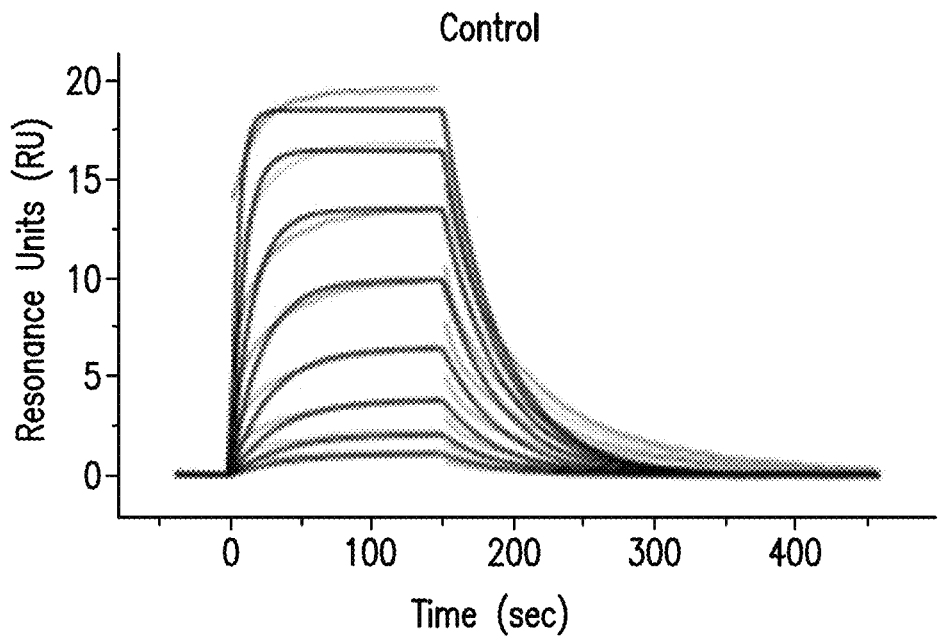
FIG. 98A-FIG. 98B are a set of sensorgrams showing the binding of F3'-1602 to hCD16a V158 after low pH hold.
Figure 98B:
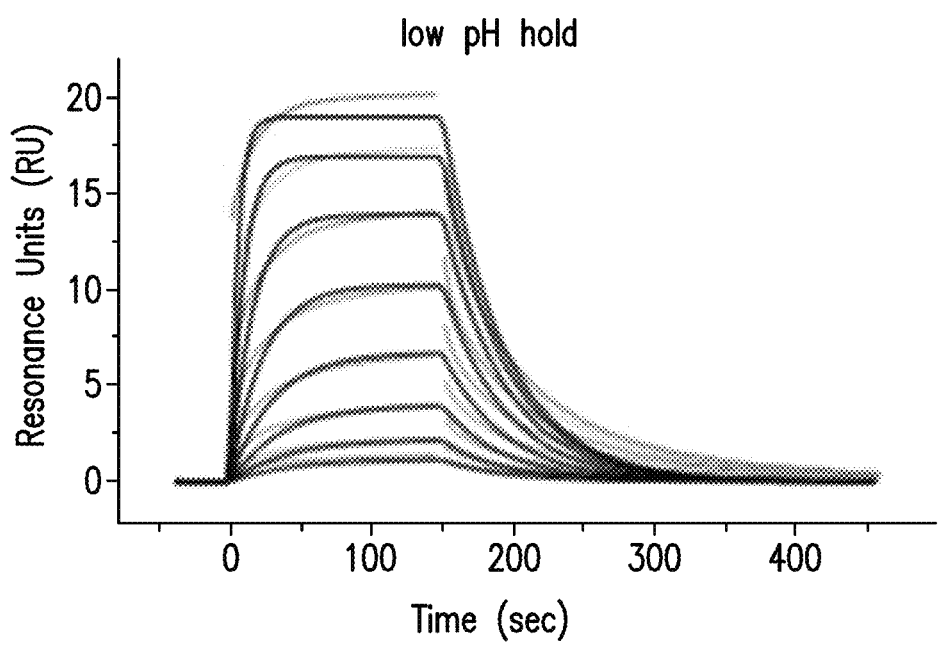

After low pH hold, binding of F3'-1602 to human CD16a V158 was unaltered (FIG. 98B and Table 111). The difference in binding affinity and maximal binding response between the control and low pH hold sample were within the experimental variability of the assay (FIGS. 98A-98B). This indicates that F3'-1602 retained affinity for human CD16a under these accelerated storage conditions.

TABLE 111

Summary of kinetic parameters and affinity of F3'-1602 for hCD16a V158 (low pH hold)

| Test article | Target | $k_a$ (M$^{-1}$s$^{-1}$) | $k_d$ (s$^{-1}$) | $K_D$ (nM) | Capture level (RU) |
|---|---|---|---|---|---|
| F3'-1602 Control | hCD16aV | (1.13 ± 0.04) × 10$^5$ | (2.40 ± 0.09) × 10$^{-2}$ | 212 ± 1 | 13.7 |
| F3'-1602, low pH hold | hCD16aV | (1.09 ± 0.04) × 10$^5$ | (2.29 ± 0.04) × 10$^{-2}$ | 210 ± 3 | 14.1 |

Results are an average of n = 3 replicates

Figure 99:
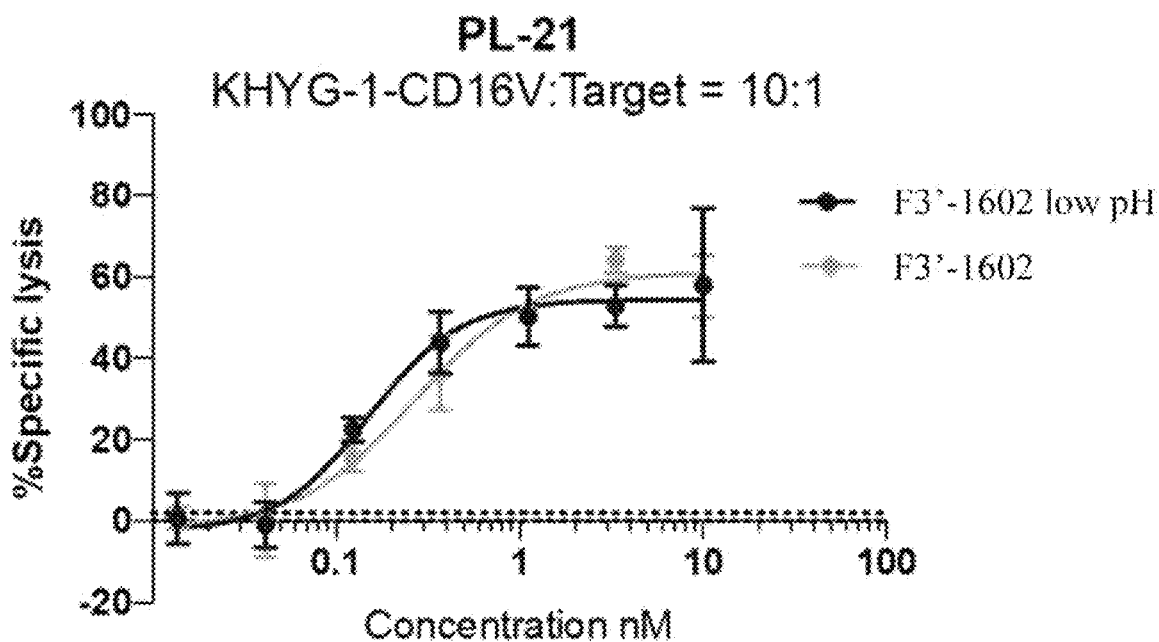
FIG. 99 is a graph showing the percentage lysis of PL21 cells by NKG2D- and CD16a-expressing KHYG-1-CD16a cells in the presence of F3'-1602 after low pH hold.

In addition to compromising biophysical stability and integrity, low pH could cause chemical degradation of amino acid side chains, in particular, aspartic acid isomerization. Chemical degradation of F3'-1602 in regions that are critical for function, if any, should manifest as reduced efficacy in a potency assay. Therefore, the potency of F3'-1602 against CLEC12A$^+$ PL-21 cancer cells were tested after low pH hold in the KHYG1-CD16V bioassay. The potency of F3'-1602 was unaltered by the low pH hold (FIG. 99 and Table 112).

TABLE 112

EC50 and maximum lysis of CLEC12A+ PL-21 cells by F3'-1602 (low pH hold)

| Test article | EC50 (nM) | Maximum Lysis (%) |
|---|---|---|
| F3'-1602 Control | 0.27 | 61 |
| F3'-1602 Low pH hold | 0.15 | 54 |

Colloidal Stability

PEG precipitation was used to assess the colloidal stability of F3'-1602. Briefly, concentrated F3'-1602 (~20 mg/mL) was diluted to 1 mg/mL in 100 μL aliquots (10 mM sodium acetate, pH 5.0) with final concentrations of PEG 6000 ranging from 0 to 30% (w/v). The aliquots were thoroughly mixed and placed at 2-8° C. overnight. The following day, the tubes were centrifuged to pellet any precipitation and the concentration of the supernatant was measured by A280 on a Lunatic (Unchained Labs).

Figure 100:
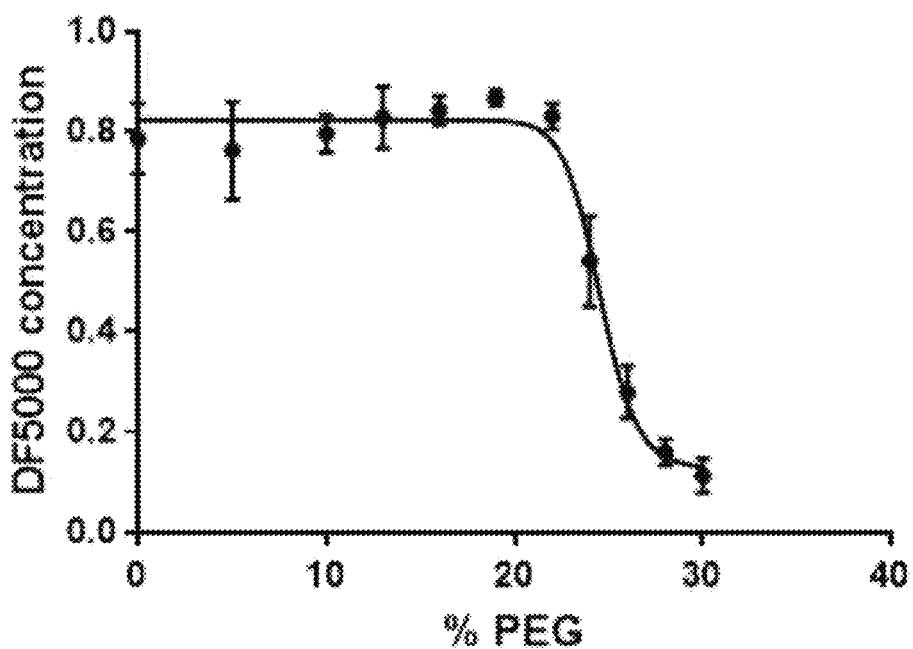
FIG. 100 is a graph showing the solubility of F3'-1602 in 10 mM sodium acetate buffer pH 5.0 in PEG-6000.

The solubility of F3'-1602 in acetate buffer pH 5.0 with increasing concentration of PEG 6000 (0%-30%) was monitored by A280. The midpoint transition (Cm) in 10 mM sodium acetate, pH 5.0 was 24.5%, indicating that F3'-1602 has high solubility in this buffer (FIG. 100). As comparators, trastuzumab and adalimumab were also assessed in the PEG precipitation assay in 10 mM sodium acetate, pH 5.0. The midpoint transitions of trastuzumab and adalimumab, used as assay controls, were >30% and 11.7% PEG-6000, respectively.

F3'-1602 was then concentrated using 30 kDa molecular weight cutoff devices in PBS, pH 7.4. Concentration was determined by A280 on a Nanodrop and product quality was monitored by SEC. Test material was injected onto an Agilent 1260 Infinity II high pressure liquid chromatography instrument with 1260 Quat Pump, 1260 Vialsampler, 1260 VWD. The sample was separated on a Superdex200 Increase 10/300 GL column. SEC running buffer was PBS, pH 7.4, flowing at 0.60 mL/min. Absorbance was monitored at both 214 and 280 nm, peak areas were manually integrated and the percent of BMWS, LMWS, and monomer were reported.

Figure 101:
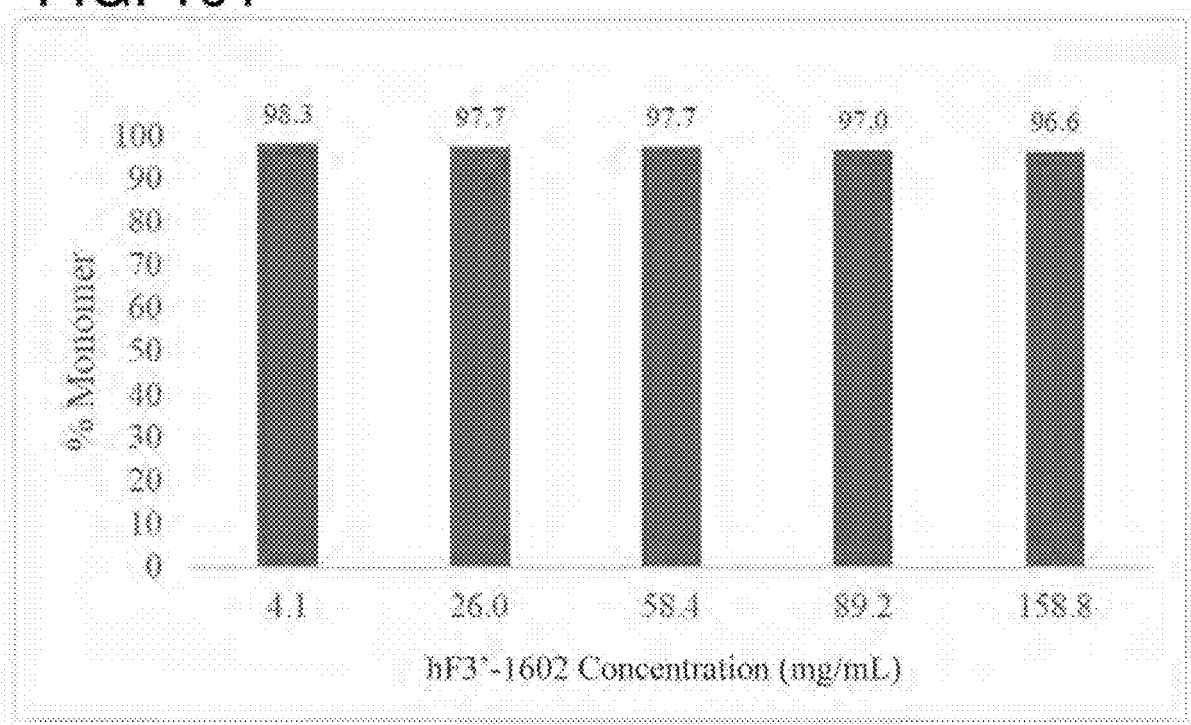
FIG. 101 is a graph showing the percentage of F3'-1602 monomer content as a function of concentration.

F3'-1602 was concentrated to approximately 25, 50, 100, and 150 mg/mL in PBS, pH 7.4 and recovery was monitored by visual inspection, concentration (A280), and SEC. F3'-1602 was able to be concentrated to >150 mg/mL in PBS, pH 7.4 with minimal loss in percent monomer and no visible precipitation (FIG. 101 and Table 113).

TABLE 113

F3'-1602 HMWS, Monomer, and LMWS content as a function of concentration

| Concentration (mg/mL) | HMWS (%) | Monomer (%) | LMWS (%) |
|---|---|---|---|
| 4.1 | ND | 98.3 | 1.7 |
| 26.0 | 0.1 | 97.7 | 2.3 |
| 58.4 | 0.1 | 97.7 | 2.2 |
| 89.2 | 0.2 | 97.0 | 2.9 |
| 158.8 | 0.2 | 96.6 | 3.2 |

Example 16. Stability and Manufacturability of F3'-1602 and AB0010

F3'-1602 and AB0010 are TriNKETs in the F3' and F3 formats, respectively, that have CLEC12A-binding sites derived from the same humanized anti-CLEC12A antibody. As described in Example 5 or 6, these two TriNKETs have similar binding affinity to CLEC12A. This example was designed to compare the stability and manufacturability of F3'-1602 and AB0010.

Briefly, F3'-1602 and AB0010 were formulated in 20 mM sodium phosphate, 10 mM sodium citrate, 125 mM NaCl, and 0.01% PS-80, at pH 7.8, as described in Example 14. The formulated proteins were subject to thermal stress at 40° C. for four weeks and their stabilities were assessed by the non-reduced SDS-CE, reduced SDS-CE, SEC, and cytotoxicity assays, as described in Example 14.

Data presented in Table 114 shows that the LMW fraction of the stressed AB0010 sample increased significantly more than that of the stressed F3'-1602 sample. Data presented in Table 115 shows that the purity of the stressed AB0010 sample decreased significantly more than that of the stressed F3'-1602 sample. These results indicate that AB0010 degraded significantly more than F3'-1602 under the thermal stress condition.

TABLE 114

Summary of non-reduced SDS-CE purity of F3'-1602 and AB0010

| Test article | LMW (%) | Main (%) | HMW (%) |
|---|---|---|---|
| F3'-1602 Control | 3.0 | 97.0 | ND |
| F3'-1602 40° C. 4 wks | 8.4 | 91.2 | 0.4 |
| AB0010 Control | 8.4 | 90.4 | 1.2 |
| AB0010 40° C. 4 wks | 27.8 | 71.4 | 0.9 |

ND, none detected

TABLE 115

Summary of reduced SDS-CE purity of F3'-1602 and AB0010

| Test article | Purity (%) |
| --- | --- |
| F3'-1602 Control | 97.4 |
| F3'-1602 40° C. 4 wks | 95.2 |
| AB0010 Control | 95.0 |
| AB0010 40° C. 4 wks | 89.3 |

As shown in Table 116, the amount of HMWS in the stressed AB0010 sample increased significantly more than that of the stressed F3'-1602 sample. This result suggests that AB0010 aggregated significantly more than F3'-1602 under the thermal stress conditions.

TABLE 116

Summary of SEC % monomer, HMW, and LMW of F3'-1602 and AB0010

| Test article | HMWS (%) | Monomer (%) | LMWS (%) |
| --- | --- | --- | --- |
| F3'-1602 Control | 0.3 | 97.9 | 1.8 |
| F3'-1602 40° C. 4 wks | 3.6 | 91.4 | 5.0 |
| AB0010 Control | 0.8 | 99.2 | 0.1 |
| AB0010 40° C. 4 wks | 13.8 | 81.7 | 4.5 |

Figure 102A:
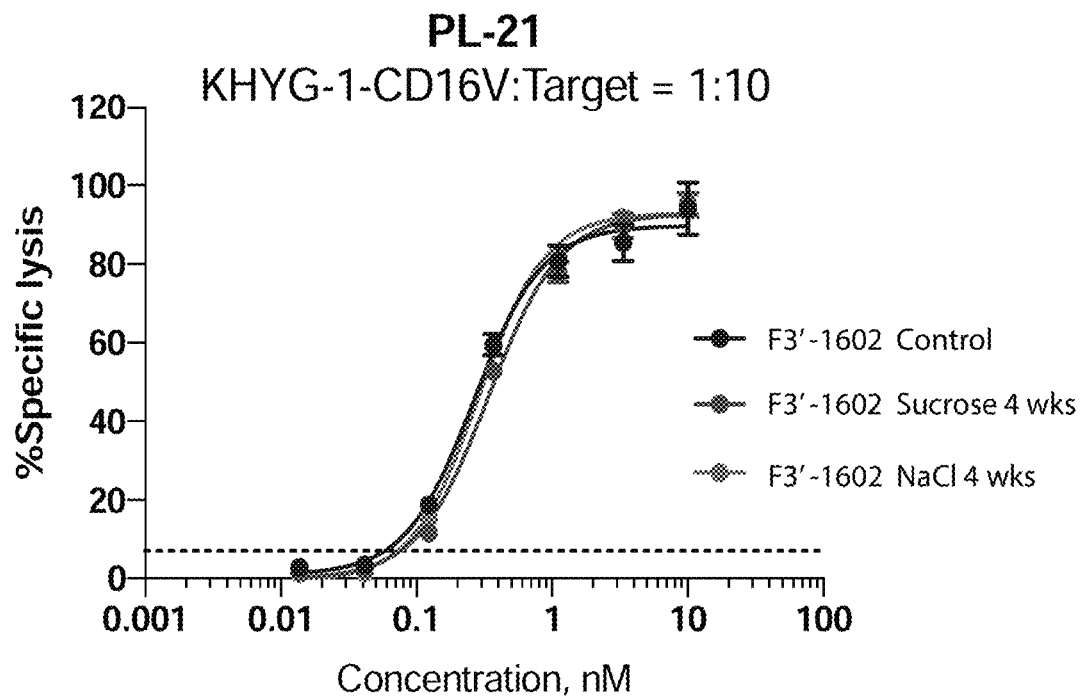
FIG. 102A-FIG. 102B are graphs showing the percentage lysis of PL-21 cells by NKG2D- and CD16a-expressing KHYG-1-CD16a cells in the presence of F3'-format TriNKET F3'-1602 (FIG. 102A) and F3-format TriNKET AB0010 (FIG. 102B) after thermal stress conditions.
Figure 102B:
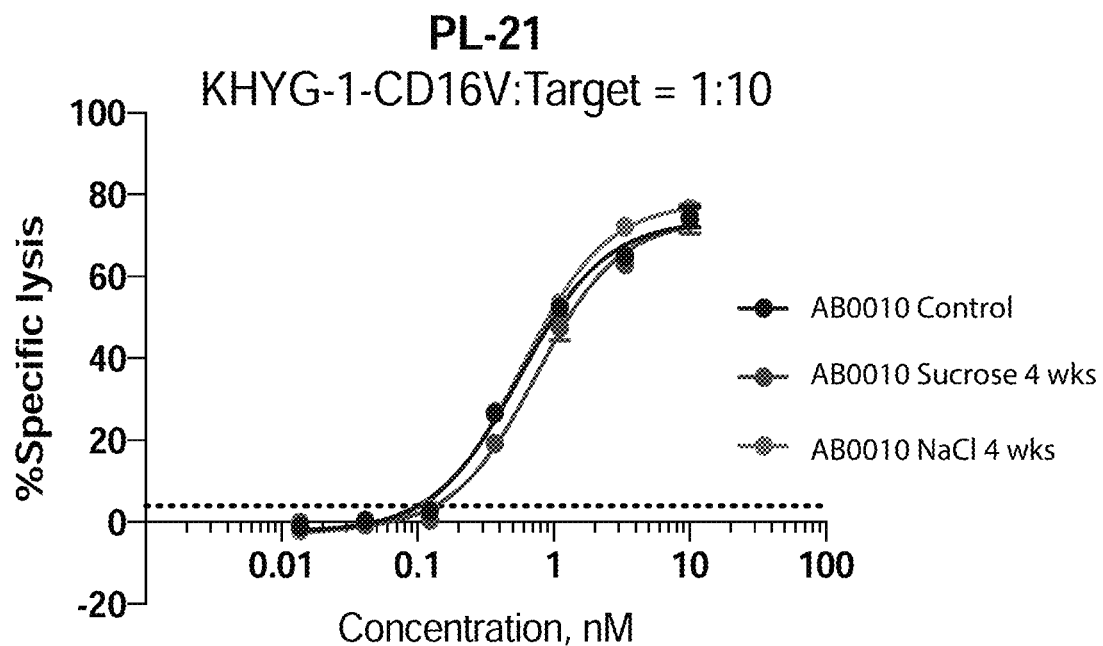

As described in Example 14, sucrose is more compatible with a lyophilized presentation than NaCl. Therefore, F3'-1602 and AB0010 were also formulated in 20 mM sodium phosphate, 10 mM sodium citrate, 250 mM sucrose, and 0.01% polysorbate 80, at pH 7.8. The TriNKET proteins in each formulation were then subject to thermal stress at 40° C. for four weeks, and their ability to mediate NK cell-mediated cytotoxicity were assessed by the cytotoxicity assay as described in Example 14. As shown in FIGS. 102A and 102B and Table 117, the ability of F3'-1602 and AB0010 to mediate killing of PL21 CLEC12A+ cancer cells by NKG2D- and CD16a-expressing KHYG-1-CD16a cells was not significantly affected by the thermal stress.

TABLE 117

EC50 and maximum lysis of CLEC12A+ PL21 cells by F3'-1602 or AB0010

| Test article | EC50 (nM) | Max. lysis (%) |
| --- | --- | --- |
| F3'-1602 Control | 0.26 | 90 |
| F3'-1602 40° C., 4 wks in 20 mM sodium phosphate, 10 mM sodium citrate, 250 mM sucrose, and 0.01% polysorbate 80, at pH 7.8 | 0.34 | 93 |
| F3'-1602 40° C., 4 wks in 20 mM sodium phosphate, 10 mM sodium citrate, 125 mM NaCl, and 0.01% polysorbate 80, at pH 7.8 | 0.29 | 93 |
| AB0010 Control | 0.57 | 74 |
| AB0010 40° C., 4 wks in 20 mM sodium phosphate, 10 mM sodium citrate, 250 mM sucrose, and 0.01% polysorbate 80, at pH 7.8 | 0.75 | 74 |
| AB0010 40° C., 4 wks in 20 mM sodium phosphate, 10 mM sodium citrate, 125 mM NaCl, and 0.01% polysorbate 80, at pH 7.8 | 0.58 | 78 |

Example 17. Molecular Format, Design, Structure, and Characteristics of CLEC12A TriNKET AB0089

Objective

The objectives of this study are to describe the molecular format, design, structure, and characteristics of CLEC12A TriNKET AB0089. AB0089 is an improved version of AB0237, in which the primary sequence of the CLEC12A binding VH was optimized to remove the isomerization sequence liability while retaining affinity for CLEC12A and potency in cytotoxic lysis of CLEC12A+ AML cells. In addition, we aimed at reduction of the number of murine backmutations in the framework regions which increased humanness of the molecule. In particular, in this report we a) describe molecular format and design of AB0089; b) outline protein engineering efforts to remove sequence liability in CDRH3; c) describe protein engineering efforts to reduce number of murine backmutations; d) provide information about expression and purification of AB0089; e) describe basic biochemical and biophysical characterization of the molecule; f) determine the affinity of AB0089 for recombinant human targets (CLEC12A, NKG2D and CD16a); g) demonstrate AB0089 binding to AML cancer cell lines expressing human CLEC12A; h) demonstrate selectivity of AB0089; i) determine potency of AB0089 in killing AML cancer cells; j) assess binding epitope; k) assess binding to FcγR and FcR and compare with IgG1 mAb control; and 1) describe behavior of AB0089 in developability studies including accelerated stability, forced degradation, and manufacturability.

Study Design

During the developability assessment of CLEC12A specific AB0237 TriNKET, an isomerization liability in the CDRH3 was identified, which led to a reduction in binding to CLEC12A and potency under harsh stresses. Yeast display was used to remove the sequence liability and optimize CMC properties of the molecule. In addition, the framework of the molecule was further optimized to remove murine backmutations and replace them with the corresponding human residues, thus improving the humanness of the molecule. Properties of AB0089 were assessed by binding to recombinant hCLEC12A, binding to isogenic and cancer cells expressing CLEC12A as well as potency of the molecule against CLEC12A+ AML cancer cells. The biophysical and biochemical characteristics of AB0089 including thermal stability (DSC), hydrophobicity (HIC), and pI (cIEF) were determined. Molecular modeling was used to assess charge and hydrophobic patch distribution on the surface of AB0089 and to benchmark with clinical stage monoclonal antibodies. Specificity of binding was assessed by PSR, binding to cells not expressing the target of interest, and by HuProt™ Array. AB0089 was expressed in two different mammalian cell lines (Expi293 and ExpiCHO) and purified using Dragonfly Tx 2-step platform purification method. The binding properties of AB0089, including CLEC12A, NKG2D, CD16a (V158 and F158), an extended panel of Fcγ receptors (CD32a (H131 and R131), CD16b, CD32b, cynomolgus CD16, human and cynomolgus CD64), and FcRn (human and cynomolgus) were fully characterized. Lastly, AB0089 was assessed in a full developability panel of assays, including accelerated (40° C.) stability in a platform formulation (20 mM histidine, 250 mM sucrose, 0.01% Tween-80, pH 6.0) and 20 mM citrate, 250 mM sucrose, 0.01% Tween-80, pH 7.0 buffers, forced degradation (long term pH 5, pH 8 stress, forced oxidation), and manufacturability (freeze/thaw, agitation, low pH hold).

Materials and Methods

Materials
Test Articles

TABLE 118

Summary of test articles.

| Name | Lot | Expression host |
|---|---|---|
| AB0237 | AB0237-002; 06Sep19AB | ExpiCHO |
| AB0089 | AB0089-001 | Expi293 |
| AB0089 | AB0089-002 (developability) | ExpiCHO |
| AB0089 | AB0089-003 (low pH hold) | ExpiCHO |
| AB0089 | AB0089-004 (low pH hold) | ExpiCHO |
| AB0192 | AB0192-005 | ExpiCHO |

Protein Reagents

TABLE 119

Summary of protein reagents.

| Name | Manufacturer | Lot |
|---|---|---|
| Human CLEC12A-His | Dragonfly Tx | 16Oct18GL |
| Human CLEC12A-K244Q-His | Dragonfly Tx | 30Apr18AC |
| Cyno CLEC12A-His | Dragonfly Tx | 30May18AC |
| Biotinylated CLEC12A-His | Dragonfly Tx | 17Apr19GL |
| mFc-hNKG2D | Dragonfly Tx | 01Dec17AB |
| mFc-cNKG2D | Dragonfly Tx | 28Sep18GL |
| humanized mAb 16B8.C8 | Dragonfly Tx | AB0037-001 |
| hcFAE-A49.CLL1-Merus (duobody TriNKET) | Dragonfly Tx | 10May18DF |
| hcFAE-A49.h6E7 (duobody TriNKET) | Dragonfly Tx | 05Feb19DF |
| hcFAE-A49.tepoditamab (duobody TriNKET) | Dragonfly Tx | 27Aug19XL |
| Trastuzumab | Roche | N3017H05 |
| Adalimumab | AbbVie | 83364XH07 |
| Rituximab | Dragonfly Tx | 19Apr19 MH |

TABLE 120

Summary of recombinant Fc receptor proteins.

| Reagent | Vendor | Catalog Number |
|---|---|---|
| Human CD64 | ACRO Biosystems | FCA-H82E8 |
| Cynomolgus CD64 | ACRO Biosystems | FCA-C82E8 |
| Human CD32a H131 | ACRO Biosystems | CDA-H82E6 |
| Human CD32a R131 | ACRO Biosystems | CDA-H82E7 |
| Human CD32b | ACRO Biosystems | CDB-H82E0 |
| Human CD16a V158 | Sino Biologicals | 10389-H27H1-B |
| Human CD16a F158 | Sino Biologicals | 10389-H27H-B |
| Human CD16b | ACRO Biosystems | CDB-H82E4 |
| Cynomolgus CD16 | ACRO Biosystems | FC6-C82E0 |
| Human FcRn | ACRO Biosystems | FCM-H5286 |
| Cynomolgus FcRn | ACRO Biosystems | FCM-C5284 |

Methods
Cell Binding by Flow Cytometry

Binding of AB0089 to isogenic CLEC12A expressing cells and to PL-21 cancer cells was performed as described in detail in Example 19. The EC50 values were derived from the cell binding curves using GraphPad Prism software (four parameter logistic non-linear regression curve fitting model).

Yeast Library Construction and Evaluation

Figure 103A:
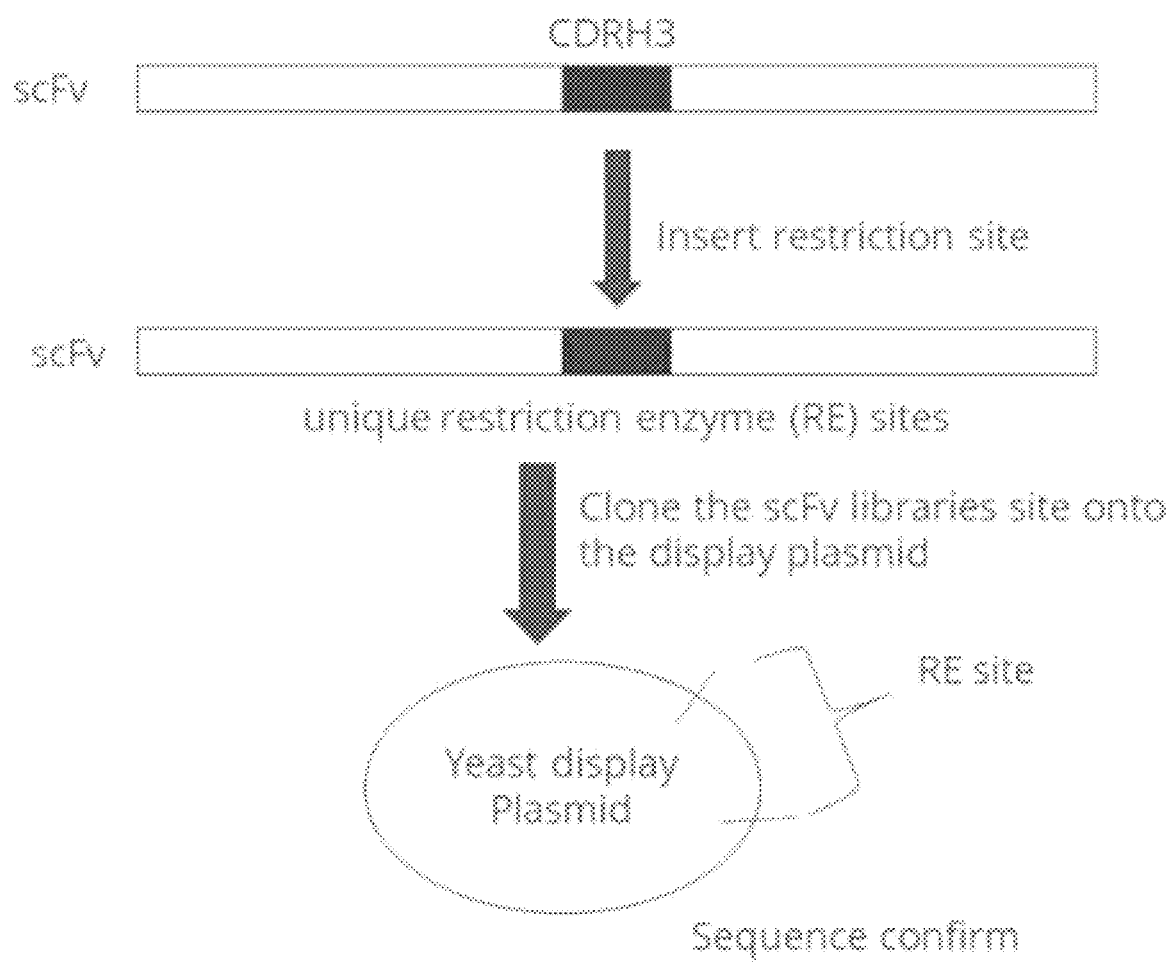
FIG. 103A-FIG. 103C shows an illustration of a yeast display affinity maturation library construction.
Figure 103B:
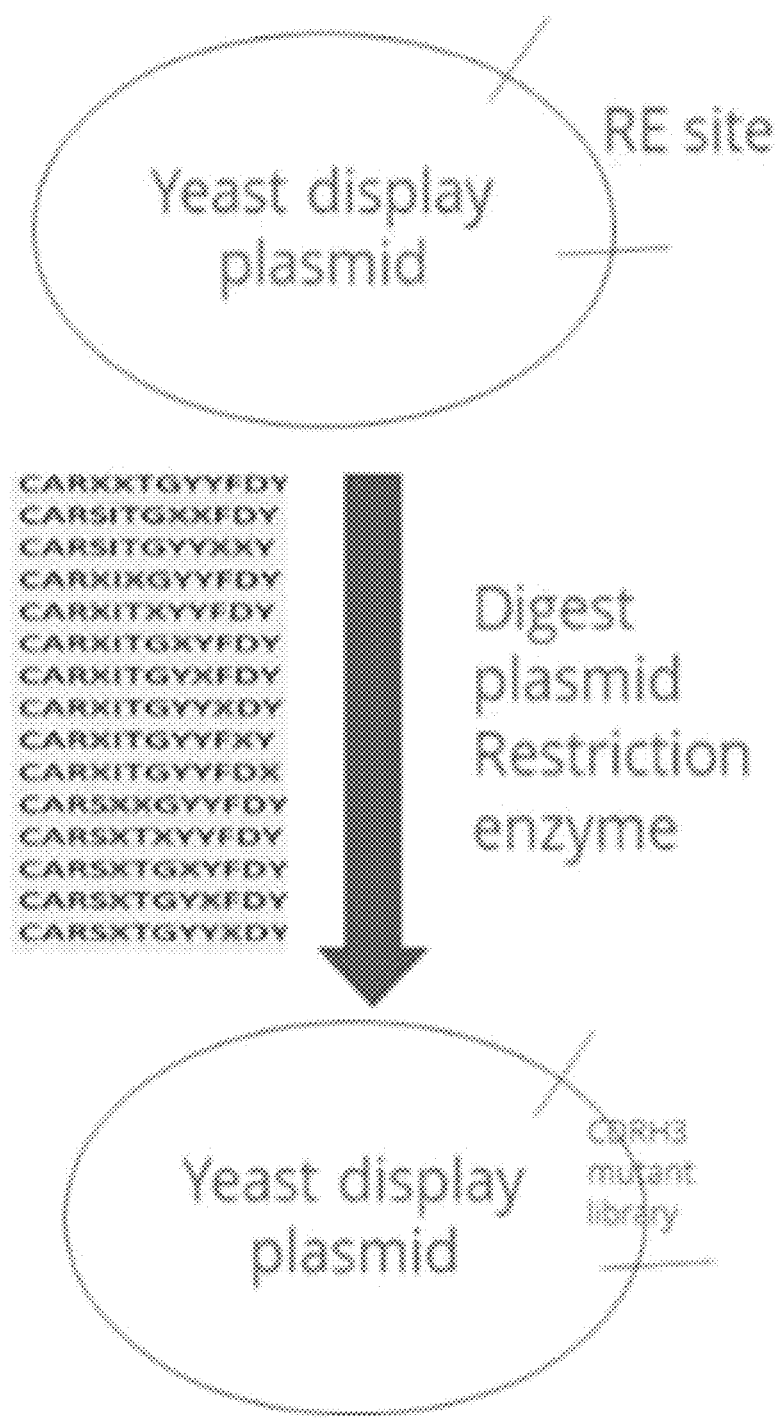
Figure 103C:
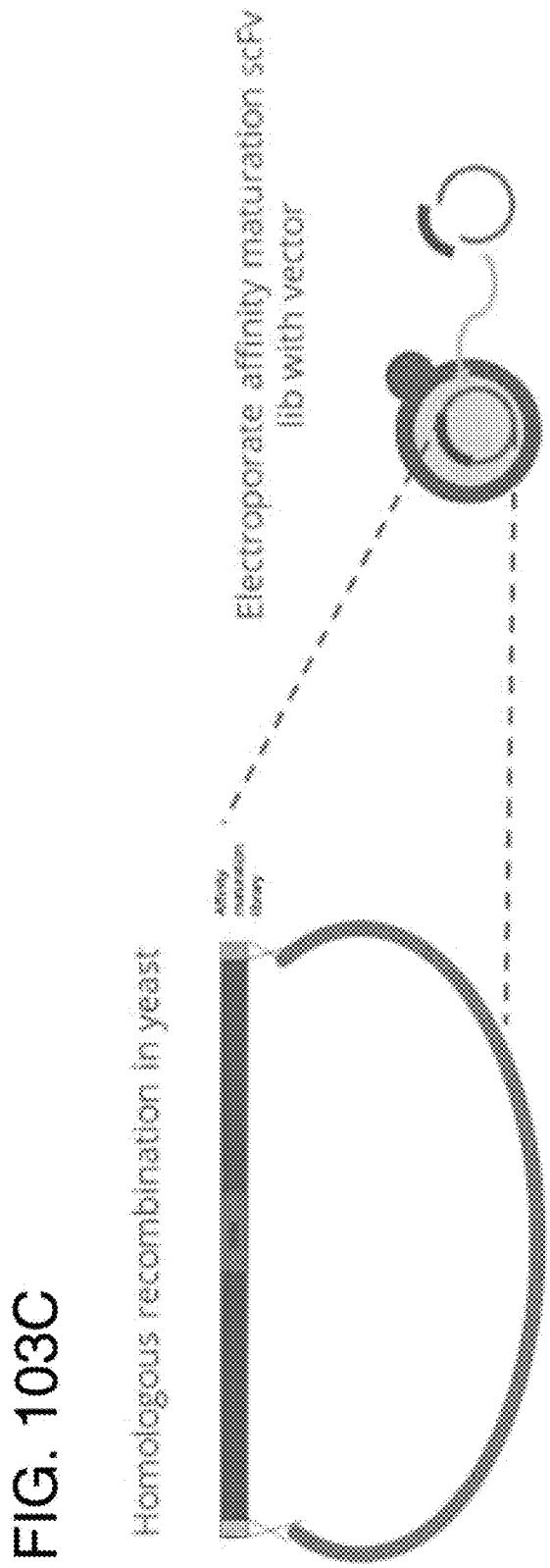
Figure 104A:
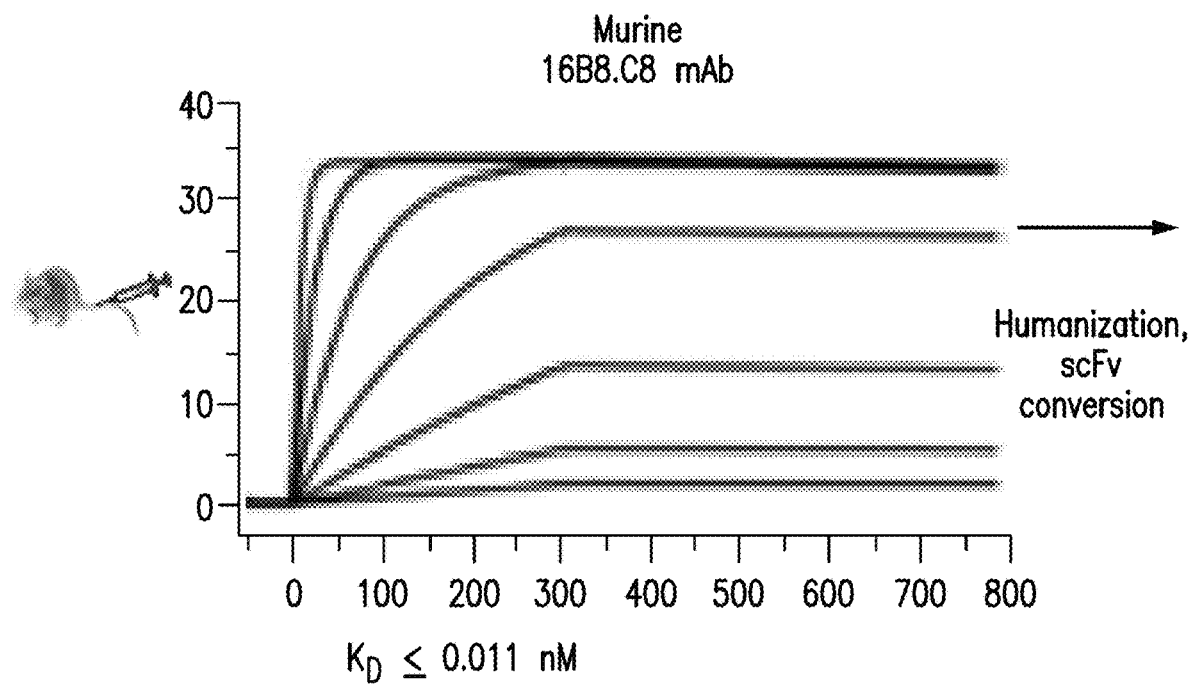
FIG. 104A-FIG. 104H show the discovery process from mouse immunization to AB0089.
Figure 104B:
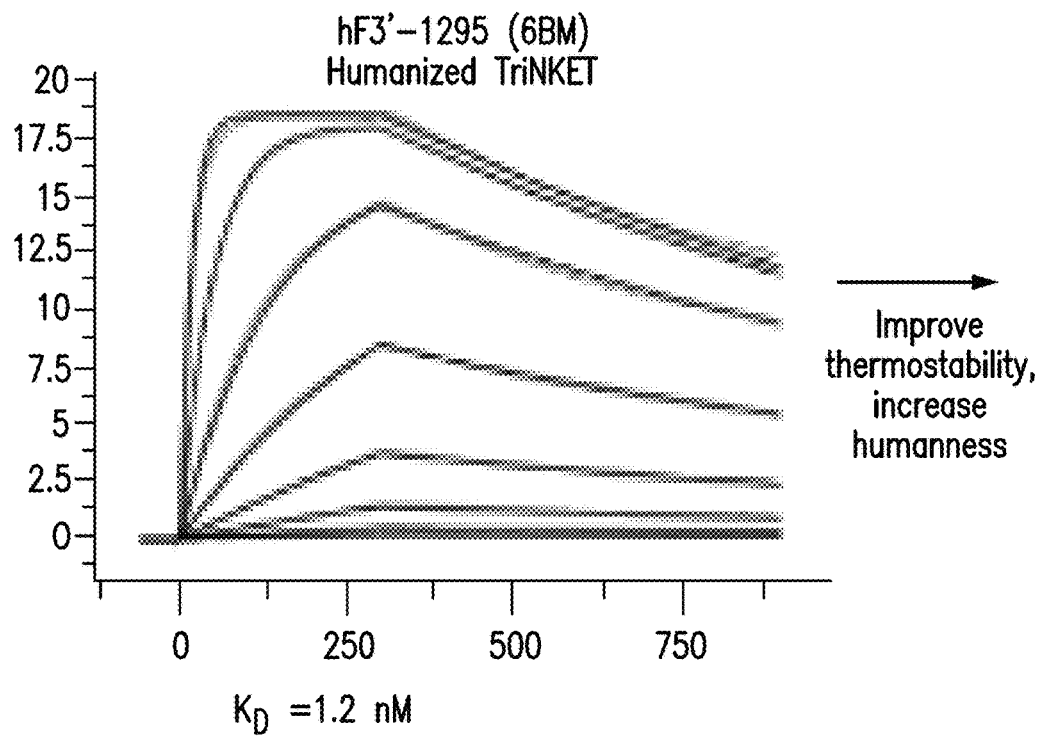
Figure 104C:
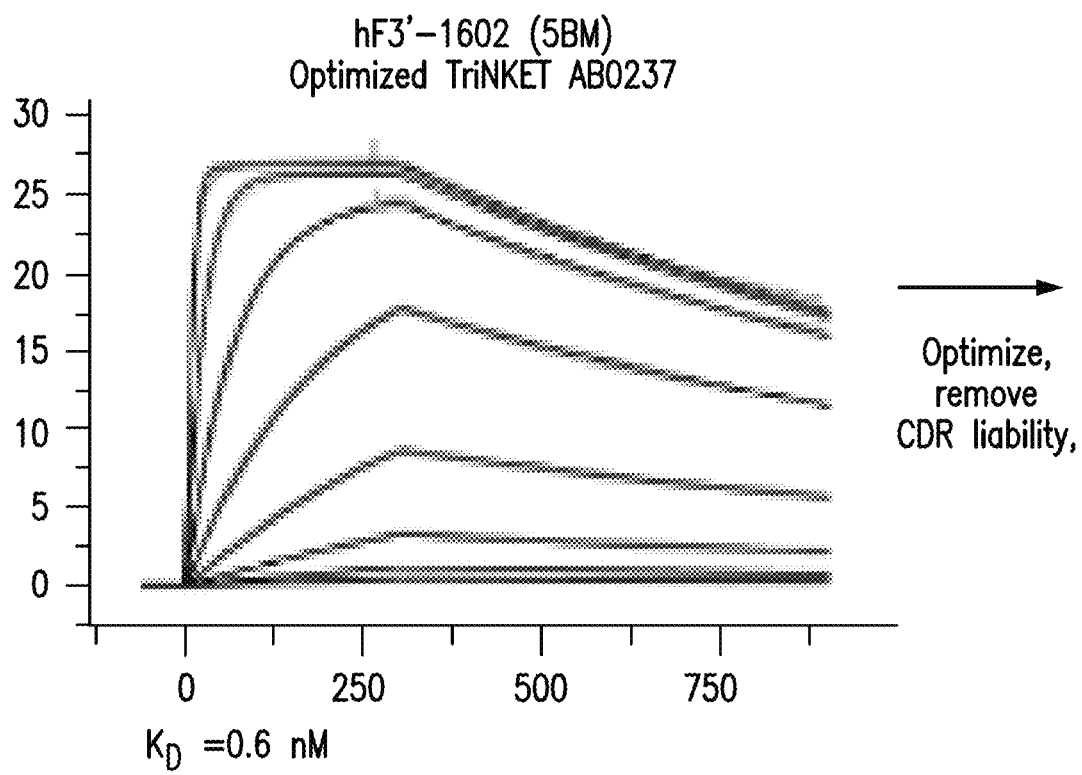
Figure 104D:
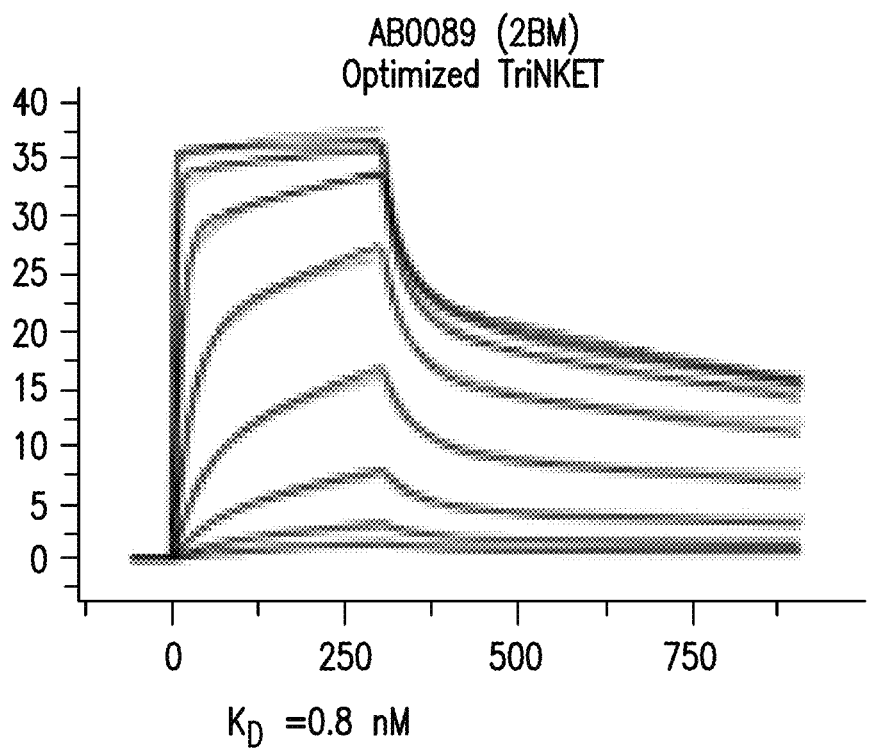
Figure 104E:
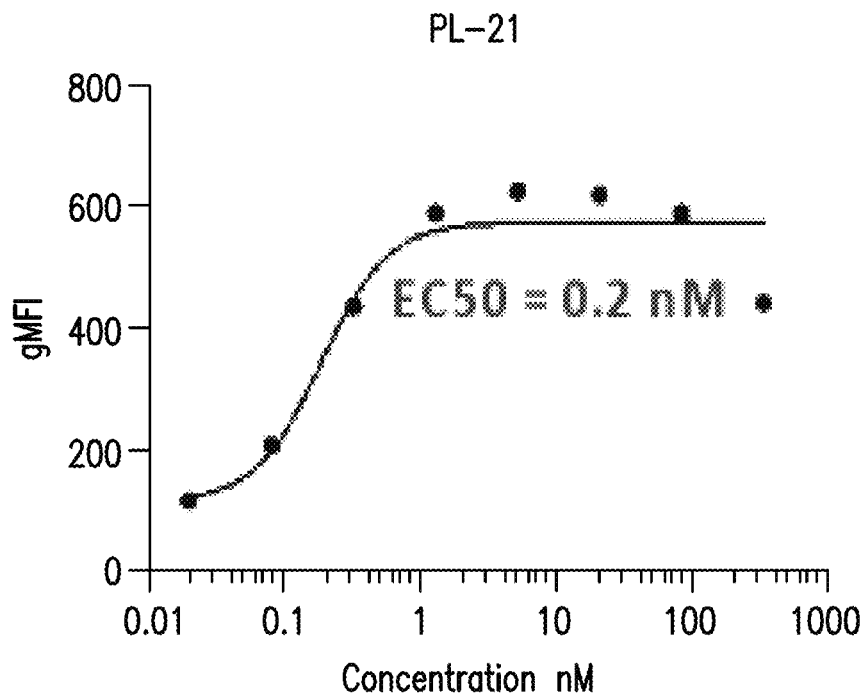
Figure 104F:
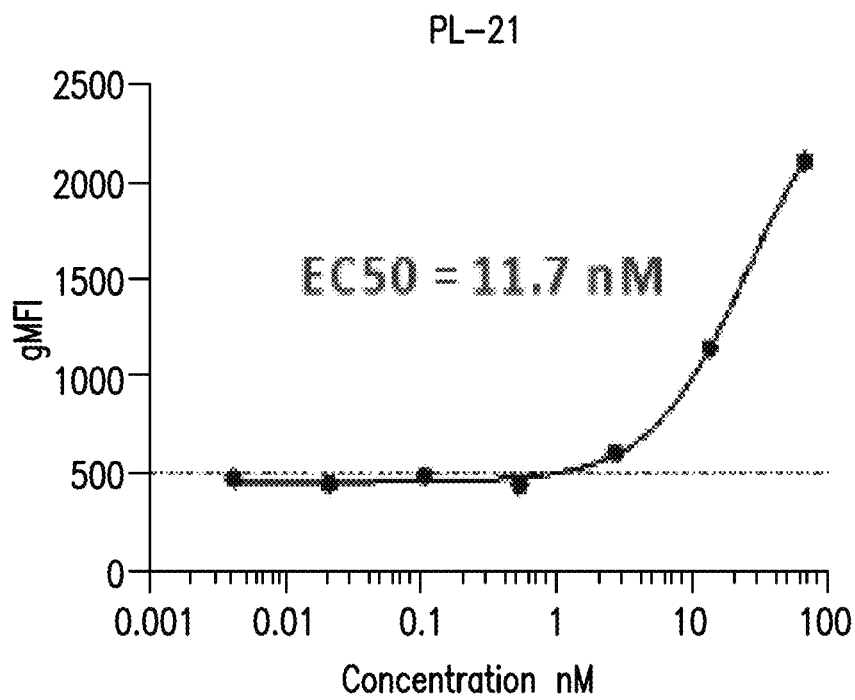
Figure 104G:
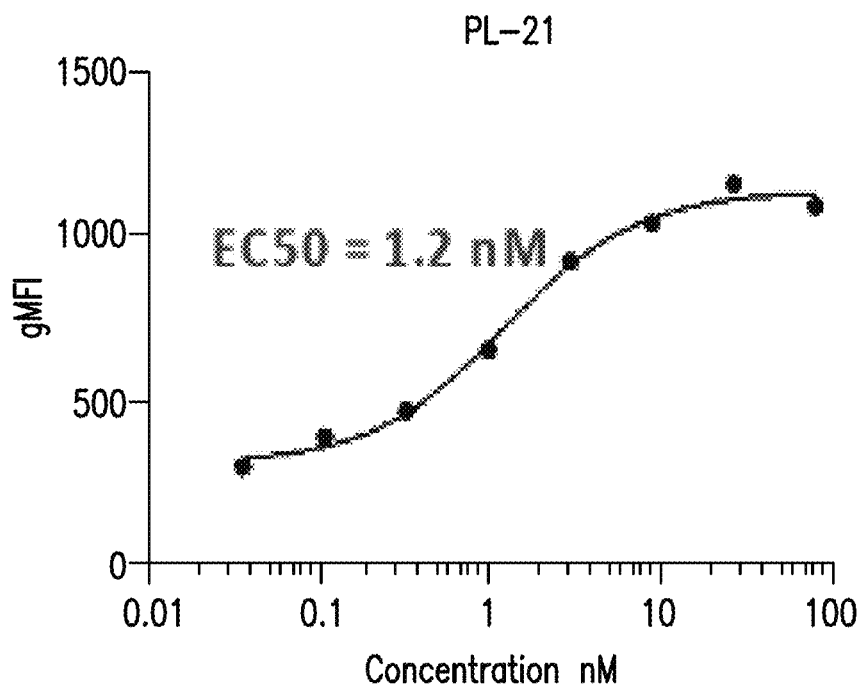
Figure 104H:
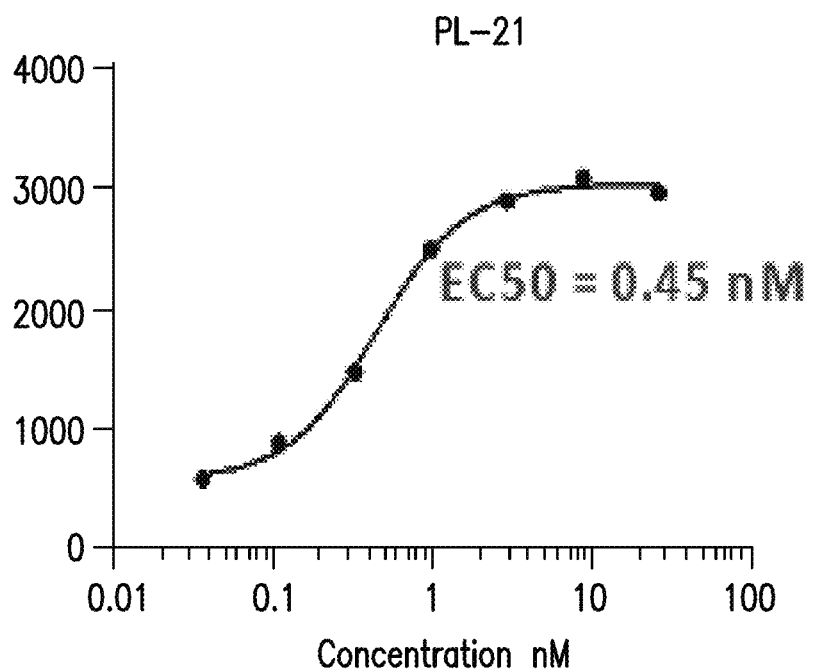

A walking mutagenesis strategy was employed using a synthetic CDRH3 oligonucleotide pool to construct a yeast display affinity library (referred to as Library 17) where each residue of the AB0237 CDRH3 (YDYDDSLDY, SEQ ID NO:139) was substituted with a randomization of all 20 amino acids, as a single site or in pairs (FIGS. 103A-103C).

First, a synthetic scFv double stranded DNA was designed by replacing the CDRH3 with a unique BamH1 restriction site. Then, the scFv was cloned into the yeast display plasmid (pYES-Aga2 vector) by Hifi cloning method, resulting in pYES-Aga2-scFv-BamH1 plasmid. DNA oligos with regions homologous to the vector were designed with the following randomizations introduced in the original CDRH3 (YDYDDSLDY, SEQ ID NO:139) to XDYDDSLDY (SEQ ID NO:305), YXYDDSLDY (SEQ ID NO:306), YDXDDSLDY (SEQ ID NO:307), YDYXDSLDY (SEQ ID NO:308), YDYDXSLDY (SEQ ID NO:309), YDYDDXLDY (SEQ ID NO:310), YDYDDSXDY (SEQ ID NO:311), YDYDDSLXY (SEQ ID NO:312), YDYDDSLDX (SEQ ID NO:313), XXYDDSLDY (SEQ ID NO:314), XDXDDSLDY (SEQ ID NO:315), XDYXDSLDY (SEQ ID NO:316), XDYDXSLDY (SEQ ID NO:317), XDYDDXLDY (SEQ ID NO:318), XDYDDSXDY (SEQ ID NO:319), XDYDDSLXY (SEQ ID NO:320), XDYDDSLDX (SEQ ID NO:321), where X=any amino acid) and pooled together. pYES-Aga2-scFv-BamHI vector was then digested with BamHI and this digested plasmid was electroporated with DNA oligo pools to yield the finalized yeast display Library 17. Through the process of homologous recombination, the yeast internally ligates the library oligos with the linearized plasmid, resulting in each yeast cell containing one plasmid with one CDRH3 mutated oligo. Following selection and characterization of Library 17 outputs, a similar affinity maturation strategy was employed targeting CDRH2 for walking mutagenesis in the background of a single optimized CDRH3. The library for this second round of affinity maturation is herein referred to as Library 30.

The library was assessed by FACS sorting after growing in D-UT media. 24 hours prior to sorting, the yeast were re-seeded to a final concentration of 0.5 O.D./ml (as measured by a visible light spectrophotometer), spun down, washed twice in GR-UT media, and then left to incubate overnight in the same media. On the day of the experiment, 3 O.D. of cells were taken be tested and placed in the well of a 96-well U-bottom plate. This was repeated up to the number of antigens desired to be tested. The cells were then washed twice with PBS-F (PBS+0.25% BSA), and then various concentrations of biotinylated CLEC12A-His were incubated for 30 min. Yeast cells were then stained with FITC labeled anti-Flag and streptavidin PE and sorted using the BD FACSAria for the highest affinity binders.

The final yeast libraries were analyzed by flow cytometry. The yeast library was initially seeded in D-UT media 24 hours prior to characterization. 24 hours prior to flow cytometry, the yeast were reseeded to a final concentration of 0.5 O.D./ml, spun down, washed twice in GR-UT media, and then left to incubate overnight in the same media. On the day of the experiment, 0.2 O.D. of cells were taken per antigen to be tested and placed in each well of a 96-well U-bottom plate. The cells were washed in PBS-F (PBS+ 0.25% BSA), and then biotinylated CLEC12A-His was added to a final concentration of 10 nM for 30 mins. The cells were washed again and non-biotinylated CLEC12A-His (final concentration 1 µM) was added for an additional 40 mins, with samples being pulled out every 20 minutes. Anti-Flag-FITC and streptavidin PE were added and incubated for 30 mins in the dark, on ice, washed twice, resuspended in PBS-F, and analyzed using the FACS Celesta.

Site-Directed Mutagenesis

The gBlock (double stranded DNA fragment) with DS to DT mutation encoding AB0089 scFv targeting CLEC12A arm was ordered from Integrated DNA Technologies (Coralville, IA). It was cloned into pcDNA3.4 vector following the protocol as described in below.

Codon Optimization

DNA codon optimization of the scFv portion of AB0089 Chain S was performed via Codon Optimization Tool from Integrated DNA Technologies (Coralville, IA), while the linker and Fc portion was codon optimized (as part of the vector backbone) using the Codon Optimization Tool from GeneArt Gene Synthesis (Thermo Fisher Scientific, Waltham, MA, USA). DNA codon optimization for the expression of AB0089 Chain H and Chain L were performed using the Codon Optimization Tool from GeneArt Gene Synthesis (Thermo Fisher Scientific, Waltham, MA, USA). The goal was to achieve high expression level in Expi293 cells (Thermo Fisher Scientific, Waltham, MA, USA).

Cloning into Vectors for Transient Expression

AB0089 Chain H and L were synthesized and cloned into pcDNA3.4 vector using Thermo Fisher Scientific's GeneArt gene synthesis platform. The vector backbone for cloning AB0089 Chain S was prepared internally using the pcDNA3.4 vector (Thermo Fisher Scientific, Waltham, MA, USA), by creating Kpnl and BamHI restriction sites for linearization and cloning using the NEBuilder HiFi Technology from New England Biolabs (Ipswich, MA). The general protocol for cloning using the NEBuilder HiFi Technology was followed. Briefly, the gBlocks (double stranded DNA fragments) expressing the gene of interest were cloned into the vector backbone, transformed using the TG-1 bacterial cells, DNA was harvested using the Zyppy Plasmid Miniprep Kit (Zymo Research, Irvine, CA) and the plasmid sequence was corroborated by Sanger sequencing (Genewiz, South Plainfield, NJ). Once sequence corroborated, maxi-preps were performed to isolate plasmid DNA using the Nucleo Bond Xtra Maxi EF Kit (Macherey-Nagel, Bethlehem, PA).

Expression

Transient Expression in Expi293 Cells

Transient transfection of Expi293 cells was performed according to the general protocol provided by manufacturer (Life Technologies, Thermo Fisher Scientific, Waltham, MA) with the exception that PEI reagent was used for transfection. Expi293 cells were transfected with the 3 DNA chains created for transient expression of the 3 polypeptides that make up AB0089: pETseq0854 (Chain H), pETseq0424 (Chain L) and pETseq1739 (Chain S) using the plasmid ratio 4:1:1 to achieve a high percentage of heterodimer. Briefly, DNA-PEI complexes were created by mixing DNA and PEIpro Reagent (Polyplus Transfection; Illkirch, France) separately first in OptiMEM media (Life Technologies, Thermo Fisher Scientific, Waltham, MA), followed by mixing and subsequent addition to the Expi293 cells (>95% viability; VCD of $2.5 \times 10^6$/mL). Following transfection, the cells were cultured in a humidified shaker-incubator at 37° C. and 8% $CO_2$. The cell supernatant was harvested 5 days later.

Transient Expression in ExpiCHO Cells

Transient transfections of ExpiCHO cells were performed according to the general protocol outlined by the manufacturer (Life Technologies, Thermo Fisher Scientific, Waltham, MA). ExpiCHO cells were transfected with the 3 DNA chains created for expression of the 3 polypeptides that make up AB0089: pETseq0854 (Chain H), pETseq0424 (Chain L) and pETseq1739 (Chain S) using the plasmid ratio 4:1:1 to achieve a high percentage of heterodimer. Briefly, DNA-Expifectamine complexes were created by mixing DNA and Expifectamine Reagent (Life Technologies) separately first in OptiPro media (Life Technologies), followed by mixing and subsequent addition to the ExpiCHO cells (>95% viability; VCD of $6 \times 10^6$/mL). Following transfection, the cells were cultured in a humidified shaker-incubator at 37° C. and 8% $CO_2$. ExpiCHO Feed and enhancer were added 18-20 hours later to boost protein expression, as per the protocol. The cell supernatant was harvested 9-11 days later, depending on cell viability (>70%).

Harvest

For harvest of AB0089, the cell culture supernatants were transferred to 500 mL or 1 L polycarbonate centrifuge bottles and spun at 7500 rpm for 35 mins at 4° C., followed by filtration using 0.2-micron filtration bottles. Below materials/reagents (vendor; catalog number) were used:

Vi-CELL XR Cell Counter (Beckman Coulter)

Vi-CELL 4 mL sample cups (Beckman Coulter; 08229NT2)

Vi-Cell Reagent Pack (Beckman Coulter; B94987)

1L Polycarbonate Centrifuge bottle (Beckman Coulter; 366751)

500 mL Polycarbonate Centrifuge bottle (Beckman Coulter; 355649)

Nalgene® Rapid-Flow™ Filter Units and Bottle Top Filters, PES Membrane, Sterile, Thermo Scientific, 1 L (VWR; 73520-986)

Nalgene® Rapid-Flow™ Filter Units and Bottle Top Filters, PES Membrane, Sterile, Thermo Scientific, 500 mL (VWR; 73520-984)

Purification

Protein A Capture Chromatography

A 5.0 cm diameter SNAP column was packed to a bed height of 5.6 cm with Protein A MabSelect SuRe gel for a column volume of approximately 110 ml. Protein A method steps and buffers are shown in Table 121. Elution fractions were neutralized to approximately pH 7.0 using 1.0 M Tris, pH 8.3 (5-10% of elution volume). Below materials/reagents (vendor; catalog number) were used:

SNAP Column (Essential Life Solutions; S-50/125-PASS-OE-FP10)

MabSelect SuRe Protein A Gel (GE Healthcare; 175-43-802)

5× Protein A Binding Buffer (500 mM Sodium Phosphate, 750 mM Sodium Chloride pH 7.2) (Boston Bioproducts; C-6332)

1× Protein A Binding Buffer (100 mM Sodium Phosphate, 150 mM Sodium Chloride, pH 7.2) (Diluted 5× stock)

100 mM Glycine pH 3.0 (Boston Bioproducts; BB-95-100 mM)

1.0 M Tris, pH 8.3 (Boston Bioproducts; LT-783)

10.0 N Sodium Hydroxide (VWR; BDH7247-4)

0.1 N Sodium Hydroxide (Diluted 10.0N stock)

TABLE 121

Protein A MabSelect Sure chromatography method steps.

| Step | Buffer/Material | Volume (CV) | Flow Rate (mL/min) |
|---|---|---|---|
| Equilibration | 1× Protein A Binding Buffer | 5 | 10 |
| Sample Application | Conditioned Media | | 10 |
| Wash | 1× Protein A Binding Buffer | 20 | 10 |
| Elution | 100 mM Glycine, pH 3.0 | 7 | 10 |
| Strip | 0.1 N Sodium Hydroxide | 4 | 10 |
| Re-Equilibration | 1× Protein A Binding Buffer | 5 | 10 |

Cation Exchange Chromatography

Cation Exchange chromatography (CIEX) was performed using Poros XS resin packed to a bed height of approximately 24.5 cm in a XK-26 column body for a final column volume of 130 ml. Equilibration and wash buffer (Buffer A) was 50 mM sodium acetate pH 5.0 with 10 mM sodium chloride. Elution buffer (Buffer B) was 50 mM sodium acetate pH 5.0 with 1.0 M sodium chloride.

The eluate from the Protein A column was pH- and conductivity-adjusted by diluting at least five-fold with Buffer A. After washing the loaded column, the protein was eluted with steps of increasing sodium chloride concentration. The IEX chromatography method steps are shown in Table 122.

TABLE 122

Cation exchange chromatography method steps.

| Step | Buffer | % B | Volume (CV) | Flow Rate (mL/min) |
|---|---|---|---|---|
| Equilibration | 50 mM Sodium Acetate, 10 mM NaCl, pH 5.0 | 0 | 7 | 15.0 |
| Sample Application | Neutralized ProA EL Buffer, Diluted ~10× with IEX EQ buffer | 0 | NA | 15.0 |
| Wash | 50 mM Sodium Acetate, 10 mM NaCl, pH 5.0 | 0 | 5 | 15.0 |
| Elution Step | Buffer A: 50 mM NaOAc, 10 mM NaCl, pH 5.0 | 10 | 4 | 15.0 |
| Elution Step | Buffer B: 50 mM NaOAc, 1 M NaCl, pH 5.0 | 15 | 15 | 15.0 |
| Elution Step | | 18 | 15 | 15.0 |
| Elution Step | | 20 | 15 | 15.0 |
| Elution Step | | 30 | 7 | 15.0 |
| Elution Step | | 100 | 7 | 15.0 |
| Strip/Sanitization | 0.1 N NaOH | 0 | 5 | 15.0 |

Buffer Exchange by G25 Chromatography and Diafiltration

The IEX product was buffer exchanged to PBS pH 7.4 (ThermoFisher Scientific, P/N 10010023) by gel filtration chromatography using Sephadex™ G25 Fine resin (GE Healthcare, P/N 17-0032-01) packed in a XK-26 column to a bed height of 30 cm (160 ml column volume). Alternatively, the product was buffer exchanged and concentrated by discontinuous diafiltration using Amicon Ultra 15 centrifugal filters (Millipore, P/N: UFC903024).

SDS-PAGE

NuPAGE 4-12% Bis-Tris gels were run with MES running buffer. Wells were loaded with 2-3 µg of sample for both non-reduced and reduced preparations. Reduced samples were treated with 20 mM DTT and heated at 70° C. for 10 minutes. Gel power supply settings were constant 200V for 50 minutes. Protein bands were visualized by staining with Novex SimplyBlue SafeStain according to manufacturer's instructions. Gels were scanned on an Azure Biosystems C600 imager. The below materials/reagents (vendor; catalog number) were used:

XCell SureLock Mini-Cell (Thermo Fisher; EI0001)
PowerEase™ 300 W Power Supply (Thermo Fisher; PS0301)
Isotemp Digital Heat Block (Fisher Scientific; 88-860-022)
NuPAGE MES SDS Running Buffer (20×) (Thermo Fisher; NP0002)
SimplyBlue SafeStain (Thermo Fisher; LC6065)
NuPAGE LDS Sample Buffer (4×) (Thermo Fisher; NP0007)
Novex Sharp Prestained Protein Standard (Thermo Fisher; LC5800)
2-MERCAPTOETHANOL (MP Biomedical; 194705)
Azure c600 imager (Azure Biosystems)

Analytical Size Exclusion Chromatography (Superdex 200)

Analytical size exclusion chromatography was performed with a Superdex 200 Increase 10/300 column installed on an Agilent 1260 HPLC system. Mobile phase was PBS pH 7.4 (ThermoFisher Scientific, P/N 10010023). Flow rate was 0.5 ml/min with run time of 45 minutes. Absorbance was measured at 214 nm and 280 nm. Peaks were integrated by the Open Lab CDS Data Analysis Software Version 2.3 using the GC/LC Area Percent Method. Peaks below the threshold of detection were integrated by manually defining the baseline.

Intact Mass

10 µg of AB0089 was diluted to 0.25 µg/µL with 0.1% formic acid and 1 µg was injected onto a MabPac 2.1×100 mM column and analyzed using a Thermo Vanquish UHPLC coupled to a QExactive+ mass spectrometer with the Biopharma option. Spectra were acquired in high-mass range mode at 17,500 resolution. Data was analyzed using the Sliding Window ReSpect algorithm in the BioPharma Finder data analysis software package. The below materials/reagents (vendor; catalog number) were used: 0.1% formic acid in water (Honeywell; LC452-2.5) and MAbPac RP 2.1×100 mm, 4 µm column (Thermo Scientific; 088647).

Endotoxin

Endotoxin readings were performed on an Endosafe® nexgen MCS cartridge reader (Charles River Laboratories) and cartridges (Charles River Laboratories P/N PTS2001F). Samples were prepared for assay by diluting in either endotoxin-free water or sterile PBS pH 7.4 (ThermoFisher Scientific, P/N 10010023). An assay was considered valid if all assay performance parameters and controls are within specification.

Hydrophobic Interaction Chromatography (HIC)

Injections of AB0089 (5 µg) were prepared in a 5:4 ratio of high salt buffer (100 mM sodium phosphate, 1.8 M ammonium sulfate, pH 6.5) to sample. Samples were analyzed using an Agilent 1260 Infinity II HPLC equipped with a Sepax Proteomix HIC Butyl-NP5 5 uM column held at 25° C. The gradient runs from 0% low salt buffer (100 mM sodium phosphate, pH 6.5) to 100% low salt buffer over 6.5 minutes at a flow rate of 1.0 mL/minute. Chromatograms were monitored at 280 nm. The below materials/reagents (vendor; catalog number) were used:

Proteomix HIC Butyl-NP5 5 uM Column, 4.6×35 mm (Sepax; 431NP5-4603)
Sodium Phosphate Monobasic (Sigma Aldrich; RES20906-A702X)
Sodium Phosphate Dibasic (Fisher Bioreagents; BB332-500)
Ammonium Sulfate, >99.0% (Sigma; A4418-500G)
Sodium Hydroxide, 10.0 N (Avantor Materials; 5000-03)
Hydrochloric Acid, 10.0 N (Ricca Chemical Company; 3770-32)

Non-Reduced CE-SDS

AB0089 was diluted to 0.5 mg/mL with 1× sample buffer to achieve a final sample volume of 50 µL. Internal standard and iodoacetamide were added to samples, which were then incubated at 70° C. for 10 minutes in a heat block, followed by an ice bath for 5 minutes. Samples were transferred to a 96-well plate, centrifuged, and loaded into the instrument. Individual samples were loaded into the capillary for 40 seconds at 4600 volts and separated for 35 minutes at 5750 volts on a Maurice instrument (ProteinSimple, San Jose, CA). The below materials/reagents (vendor; catalog number) were used:

25× Internal Standard (ProteinSimple; 046-016)
CE-SDS Plus Cartridge (ProteinSimple; 090-157)
Iodoacetamide (Sigma-Aldrich; 16125-5G)
Maurice CE-SDS PLUS Application Kit Reagents (Bottom Running Buffer, Separation Matrix, Wash Solution, Conditioning Solution 1 & 2, 1× Sample Buffer) (ProteinSimple; 046-571)
Top Running Buffer (ProteinSimple; 046-384)

Reduced CE-SDS

AB0089 was diluted to 0.5 mg/mL with 1× sample buffer to achieve a final sample volume of 50 µL. Internal standard and beta-mercaptoethanol (Bio-Rad, #161-0710) were added to samples, which were then incubated at 70° C. for 10 minutes in a heat block, followed by an ice bath for 5 minutes. Samples were transferred to a 96-well plate, centrifuged, and loaded into the instrument. Individual samples were loaded into the capillary for 40 seconds at 4600 volts and separated for 31.2 minutes at 5750 volts on a Maurice instrument (ProteinSimple, San Jose, CA).

Capillary Isoelectric Focusing (cIEF)

AB0089 was diluted to 1 mg/mL with MilliQ water, 15 µL of sample was added to 60 µL of master mix (water, methyl cellulose, Pharmalyte 3-10, arginine, pI markers 4.05 and 9.99), vortexed, and centrifuged briefly. 60 µL of sample was aspirated from the top of the solution and added to a 96-well plate and centrifuged before testing. The sample was separated for one minute at 1500 volts followed by 8 minutes at 3000 volts on a Maurice instrument (ProteinSimple, San Jose, CA). The below materials/reagents (vendor; catalog number) were used:

0.5% Methyl Cellulose (ProteinSimple; 102730)
1% Methyl Cellulose (ProteinSimple; 101876)
500 mM arginine (ProteinSimple; 042-691)
Anolyte (ProteinSimple; 102727)
Catholyte (ProteinSimple; 102728)
cIEF Cartridge (ProteinSimple; 090-101)
Fluorescence calibration standard (ProteinSimple; 046-025)
Pharmalytes 3-10 (Sigma Aldrich; P1522-25ML)
pI Marker 4.05 (ProteinSimple; 046-029)
pI Marker 9.99 (ProteinSimple; 046-034)
System suitability mix (ProteinSimple; 046-027)
System suitability peptide panel (ProteinSimple; 046-026)

Differential Scanning Calorimetry (DSC)

AB0089 was prepared at 0.5 mg/mL in 1×PBS (Gibco, #10010-031) or alternative formulations. 325 µL was added to a 96-well deep well plate along with a matching buffer blank. Thermograms were generated using a MicroCal PEAQ DSC (Malvern, PA). Temperature was ramped from 20-100° C. at 60° C./hour. Raw thermograms were background subtracted, the baseline model was spline, and data were fitted using a non-two state model.

SPR Instrument and Reagents

Biacore 8K (Instrument ID: 2222251, GE Healthcare Life Sciences) was used to run the kinetic measurements and Biacore 8K Insight Evaluation Software was used for analysis of experimental data. The below materials/reagents (vendor; catalog number) were used:

10 mM sodium acetate, pH 5.0 (Cytiva; BR100351)
10 mM Glycine, pH 1.7 (Boston BioProducts; BB-2413D)
10×HBS-EP+ (Cytiva; BR1006-69)
1×HBS-EP+ Prepared in house from 10× stock solution
1×MBS-EP+, pH6.0 (Prepared in house)
BSA Fraction V (7.5%) (Gibco; 15260-037)
NaCl (Fisher Scientific; S271-1)
NaOH (Cytiva; BR100358)
Amine coupling kit (Cytiva; BR-1000-50)
Mouse antibody capture kit (Cytiva; BR100838)
CM5 Chip (Cytiva; 29-1496-03)
Series S Sensor Chip SA (Cytiva; BR-1005-31)
SA Chip (Cytiva; BR100531)
Biotin CAPture kit (Cytiva; 28-9202-34)
Goat anti-human IgG Fc cross-absorbed secondary antibody (Invitrogen; 31125)
Micro Bio-Spin 30 columns (Bio-Rad; 732-6223)
Amicon Ultra 0.5 mL Centrifugal Filters 10,000 NMWL (Millipore Sigma; UFC501096)

CLEC12A Affinity by SPR

Binding affinities of AB0089 to recombinant human CLEC12A (Dragonfly Tx) were measured by SPR using a Biacore 8K instrument. Briefly, human Fc specific antibodies were covalently immobilized at a density ~8000-10000 resonance units (RU) on carboxy methyl dextran matrix of a CM5 biosensor chip via amine-coupling chemistry to create an anti-hFc IgG chip. AB0089 samples were captured on the anti-hFc IgG chip at a concentration of 1.5 µg/mL at a flow rate of 10 µL/min for 60 seconds to achieve approximately 150 RU capture level. hCLEC12A-His was serially diluted (100 nM-0.14 nM) in three-fold dilutions SPR running buffer and injected at a flow rate of 30 µl/min over the captured test articles. Association was monitored for 300 seconds and dissociation was monitored for 600 seconds. Surfaces were regenerated between cycles with three pulses of 10 mM glycine-HCl, pH 1.7 injected for 20 seconds at 100 µl/min. HBS-EP+ (1×) with 0.1 mg/ml BSA was used as running buffer throughout the experiment. Experiments were performed at physiological temperature of 37° C. To obtain kinetic rate constants and overall binding affinity, double-referenced data were fit to a two-state kinetic model using Biacore 8K Insight Evaluation software (Cytiva). Justification for the use of the two-state model is provided below. The goodness of the fit between the fitted curve and the experimental data were expressed by the evaluation software as $Chi^2$.

NKG2D Affinity by SPR

Binding affinity of AB0089 for recombinant human NKG2D (Dragonfly Tx) was measured by SPR using a Biacore 8K instrument. Briefly, mFc specific antibodies were covalently immobilized at a density of ~8000-10000 RU on carboxy methyl dextran matrix of a CM5 biosensor chip via amine coupling chemistry to create an anti-mFc IgG chip. mFc-tagged human NKG2D was captured on the anti-mFc IgG chip at a concentration of 0.2 μg/mL at a flow rate 10 μL/min for 60 seconds to achieve approximately 30 RU capture level. AB0089 was buffer exchanged into HBS-EP+ (1×) buffer and serially diluted (5000 nM-9.77 nM) in two-fold dilutions with HBS-EP+. Analyte (AB0089) was injected at a flow rate of 30 μl/min over the captured test articles. Association was monitored for 60 seconds and dissociation was monitored for 60 seconds. Surfaces were regenerated between cycles with three pulses of 10 mM glycine-HCl, pH 1.7 injected for 20 seconds at 100 μl/min. HBS-EP+ (1×) was used as running buffer throughout the experiment. Experiments were performed at physiological temperature of 37° C. Double-referenced data were fit to a 1:1 kinetic and a Steady State interaction models using Biacore 8K Insight Evaluation software (GE Healthcare) with global fit analysis in the 1:1 kinetic fit model. Since the samples had been buffer exchanged into the running buffer prior to each experiment, offset for a steady state fit was set to constant (0). The goodness of the fit was expressed by the evaluation software as $Chi^2$ that was considered in the context of $R_{max}$ value.

Synergy of Simultaneous Binding of CD16a and NKG2D

Synergistic NKG2D and CD16a binding was evaluated by SPR. hNKG2D alone (12.3 μg/mL), CD16a F158 allele alone (9 μg/mL) and the mixture of hNKG2D and CD16a F158 at the same concentration each were amine-coupled to the surface of the CM5 Series S Biacore chip for 1 minute. 1.8 μM AB0089 or trastuzumab were injected for 150 sec at 10 μL/min. Dissociation phase was observed for 180 sec when regeneration was not needed and 1800 sec when natural regeneration of the surface (almost complete dissociation of analyte) was needed between the cycles at the same flow rate. 1×HBS-EP+ buffer was used as running and sample dilution buffer.

Co-Engagement (CLEC12A and NKG2D)

AB0089 was diluted in 1×HBS-EP+ buffer containing 0.1 mg/ml BSA and was captured on an anti-human Fc surface of CM5 chip at a flow rate 5 μL/min for 60 sec to achieve capture level of 150-250 RU. The net difference between baseline signal and the signal after completion of AB0089 injection representing the amount of AB0089 captured was recorded. hCLEC12A-His (200 nM) or mFc-hNKG2D (7 μM) was injected over captured AB0089 at 20 μl/min for 90 sec to reach saturation. This injection was immediately followed by an injection of pre-incubated mixture of hCLEC12A-His (200 nM) and mFc-hNKG2D (7 μM) at a flow rate of 20 μl/min for 90 sec with the use of the A-B-A injection command in the Biacore 8K control software (second target was pre-mixed with the first target to assure all binding sites for the first target are occupied). The chip was regenerated by two 20 sec pulses of 10 mM Glycine (pH 1.7) at 100 μL/min. The experiment was conducted at 37° C. and 1×HBS-EP+ buffer containing 0.1 mg/ml BSA was used as a running buffer. Binding of each antigen, expressed in RU, was recorded as the net difference between the baseline signal prior and after the injection of individual antigen. An average relative binding ratio of each target bound to AB0089 unoccupied with another target (injected first) was assigned a value of 1.0. An average relative binding stoichiometry of each target bound to captured AB0089 that is already saturated with the other target (injected second) was expressed as a fraction of the full capacity binding to unoccupied AB0089.

Epitope Binning

Anti-CLEC12A antibody or TriNKET was directly immobilized to the active flow cell of a Series S CM5 sensor chip via amino coupling at 3 μg/mL concentration for a final density of 370-1070 RU. A classic sandwich assay run at 25° C. was used for epitope binning. The first injection was a 120 second association of 200 nM CLEC12A-His followed directly by 200 nM of the sandwiching antibody/TriNKET. The sandwiching antibody/TriNKET had a 120 seconds association time and 120 seconds dissociation time. Both analyte and sandwiching molecule injections were run at 30 μL/min. A 20 second pulse of 10 mM glycine pH 1.7 injected at 100 μL/min was used to regenerate the chip surface after dissociation. The first cycle included buffer injections for both the analyte and sandwiching molecule. The second cycle included 200 nM hCLEC12A-His analyte followed by a buffer injection for sandwiching molecule. Subsequent cycles included 200 nM hCLEC12A-His analyte injection followed by 200 nM sandwiching molecule. 1×HBS-EP+ running buffer was used throughout experiment. Sensorgrams were visualized using Biacore Insight Evaluation software.

FcγR Binding

Human and cynomolgus CD64, high and low affinity alleles of CD16a (V158 and F158, respectively), two alleles of CD32a (H131 and R131), CD16b, CD32b and cynomolgus CD16 were captured via biotin on a primed (according to the manufacturers instruction) Biacore chip. Table 123 summarizes respective capture levels and types of the Biacore chips used. Due to irreversibility of streptavidin-biotin interaction, the capture step for all receptors except FcγRI (CD64) was performed just once prior to the start of the binding experiment. hCD64 and cyno CD64 capture on the CAP chip surface was performed during each cycle in accordance with the manufacturer's instructions for the Biotin CAPture kit.

Prior to any FcγR binding experiment requiring a high starting concentration, AB0089 and trastuzumab, samples were buffer exchanged into 1×HBS-EP+ SPR running buffer by three consecutive dilution/concentration cycles with the use of a 0.5 mL concentrator unit resulting in >300-fold dilution of original buffer components while maintaining high concentration of protein. Protein concentration was measured at A280 on a NanoDrop instrument and with the use of sample appropriate theoretical molar extinction coefficients (196790 $M^{-1}cm^{-1}$ for AB0089 and standard IgG setting for trastuzumab).

Each FcγR binding experiment consisted of multiple cycles utilizing 2-fold serially diluted AB0089 or trastuzumab. 0 nM blank cycle placed at the start of each concentration series and receptor free chip surface were used for referencing. Each experimental cycle included association, dissociation and regeneration steps. Analyte (AB0089 or trastuzumab) concentrations, association and dissociation times, and regeneration parameters were FcγR-specific (Table 123). All steps were executed at a flow rate of 30 μL/min and at 25° C.

TABLE 123

Parameters used in SPR FcγR binding experiments.

| Parameter | hCD64, cyno CD64 | hCD16a V158 | hCD16a F158 | cyno CD16 | hCD32a H131, R131 | hCD16b | hCD32b |
|---|---|---|---|---|---|---|---|
| Type of chip | CAP chip | Type S SA chip | | | | | |
| FcγR capture level, RU | 35-50 | 10-27 | 10-27 | | 7-25 | 10-23 | |
| Concentration range, nM | 400-1.56 | 1500-0.023 | 6000-0.023 | | 16000-125 | 24000-188 | |
| Association time, sec | 240 | 150 | | | 60 | 60 | |
| Dissociation time, sec | 600 | 300 | | | 60 | 150 | |
| Surface regeneration | CAPture kit regeneration | 5 sec pulse of 1-2 mM NaOH | | | | | |

A series of 2-5 blank experimental cycles with the use of experiment appropriate running buffer in place of analyte was performed prior to sample analysis to stabilize the chip surface. Raw data was fitted to either a 1:1 kinetic model or a steady state affinity model using Biacore Insight evaluation software. Chi$^2$ (calculated by the software) related to either calculated $R_{max}$ or apparent maximal binding response was used to assess goodness of the fit. All reported values were rounded to one decimal place after the calculation.

FcRn Binding

Recombinant human or cynomolgus monkey (cyno) FcRn was captured on a surface of an SA series S chip at a concentration of 0.25 µg/mL for 1 minute. AB0089 and commercial trastuzumab (IgG1 assay control) were buffer exchanged into MBS-EP+, pH 6.0 prior to the SPR binding experiment. Each FcRn binding experiment consisted of multiple cycles utilizing varying concentrations of analytes. Two-fold dilution series (12 µM-0.023 µM) of AB0089 and trastuzumab were used. 0 nM blank cycle placed at the start of each concentration series and a blank amine coupling modified chip surface lacking FcRn were used for referencing. Each experimental cycle included association, dissociation and regeneration steps. The association step consisted of 60 sec analyte injection and was followed by a 60 sec dissociation step. Surface regeneration (60 sec injection of HBS-EP+ buffer, pH 7.4) completed each kinetic cycle. All steps were executed at a flow rate of 30 µL/min and at 25° C. MBS-EP+ buffer, pH 6.0 was used as a running buffer. The data were fitted to a steady state affinity model with Biacore Insight evaluation software. Chi$^2$ (calculated by the software) related to the calculated $R_{max}$ was used to assess goodness of the fit. All reported values were rounded to one decimal place.

KHYG-1-CD16aV Mediated Cytotoxicity Assay

The potency of AB0089 was tested with KHYG-1-CD16aV cells. The EC50 and maximum lysis values were derived from the cell lysis curves using GraphPad Prism software (four parameter logistic non-linear regression curve fitting model).

Primary NK Cells Mediated Cytotoxicity Assay

The potency of AB0089 was tested with primary NK cells. The EC50 and maximum lysis values were derived from the cell lysis curves using GraphPad Prism software (four parameter logistic non-linear regression curve fitting model).

Non-Specific Binding to Polyspecific Reagent (PSR)

50 µL of 100 nM TriNKET or control mAb in PBSF were incubated with pre-washed 5 µL protein A dyna beads slurry for 30 mins at room temperature. TriNKETs or mAb bound magnetic beads were allowed to stand on a magnetic rack for 60 seconds and the supernatant was discarded. The bound beads were washed with 100 µL PBSF. Beads were incubated for 20 minutes on ice with 50 µL of biotinylated PSR reagent which was diluted 25-fold from the stock (Xu et al., (2013) *Protein engineering design and selection,* 26, 663-670). Samples were put on the magnetic rack, supernatant discarded, and washed with 100 µL of PBSF. A secondary FACS reagent, to detect binding of biotinylated PSR reagent to TriNKETs or control mAbs, was made as follows: 1:250 µL of Streptavidin-PE and 1:100 donkey anti-human Fc were combined in PBSF. To each sample, 100 µL of the secondary reagents were added and allowed to incubate for 20 minutes on ice. The beads were washed twice with 100 µL PBSF. Samples were analyzed on a BDFACS Celesta. Two PSR controls, Rituximab (PSR positive) and Trastuzumab (PSR negative), were used in the assay. The below materials/reagents (vendor; catalog number) were used: PBSF (1×PBS pH 7.4+0.25% BSA) (Dragonfly Tx), Dyna beads (Invitrogen; 10001D), Streptavidin-PE (Biolegend; 405204), and Donkey anti-human Fc Ab (Jackson ImmunoResearch; 709-096-149).

High-Spec® Cross Reactivity Assay Using HuProt™ Arrays

The specificity of AB0089 was tested at 0.1 µg/ml and 1 µg/ml concentration against native HuProt human proteome array immobilized on microslides. The assay was performed at CDI laboratories (Baltimore, MD).

Immunogenicity Assessment

EpiMatrix program from EpiVax was used for all calculations as described in Cohen et al. (2013) *Mol Cancer Ther,* 12, 2748-59.

Molecular Modeling

Molecular modelling was performed using the SAbPred website (opig.stats.ox.ac.uk/webapps/newsabdab/sabpred/). CLEC12A and NKG2D binding arms were compared with 377 post Phase I biotherapeutic molecules using Therapeutic Antibody Profiler (TAP). TAP used ABodyBuilder to generate a model for AB0089 with side chains by PEARS. The CDRH3 was built by MODELLER, since this loop is the most diverse of all CDRs.

Five Different Parameters were Evaluated:
1. Total CDR length
2. Patches of surface hydrophobicity (PSH) across the CDR vicinity
3. Patches of positive charge (PPC) across the CDR vicinity
4. Patches of negative charge (PNC) across the CDR vicinity
5. Structural Fv charge symmetry parameter (sFvCSP) for CLEC12A binding scFv and NKG2D binding Fab Developability Accelerated (40° C.) Stability in HST, pH 6.0

AB0089 lot AB0089-002 was concentrated and diafiltered into 20 mM histidine, 250 mM sucrose, 0.01% Tween-80, pH 6.0 (HST, pH 6.0) using an Amicon Ultra15 30K device. The concentration of the recovered sample was determined by A280 and the sample was diluted to 20 mg/ml with HST buffer. A 0.2 ml aliquot was immediately frozen at −80° C. as the control and two 0.15 ml aliquots were stored at 40° C. in the dark. An aliquot was removed after 2 and 4 weeks and immediately frozen at −80° C. until analysis. The below materials/reagents were used:
- Amicon Ultra15 Centrifugal Filters (30K MWCO) (Millipore; UFC903024)
- Hydrochloric acid, 10N (RICCA; 3770-32)
- L-Histidine (MP Biomedicals; 101954)
- Sodium hydroxide, 10N (JT Baker; 5000-03)
- Sucrose (VWR; M117-500G)
- Tween-80 (VWR; 0442-1L)

Accelerated (40° C.) Stability in CST, pH 7.0

AB0089 lot AB0089-002 was concentrated and diafiltered into 20 mM sodium citrate, 250 mM sucrose, 0.01% Tween-80, pH 7.0 using an Amicon Ultra15 30K device. The concentration of the recovered sample was determined by A280 and the sample was diluted to 20 mg/ml with CST buffer. A 0.4 ml aliquot was immediately frozen at −80° C. as the control and four 0.15 ml aliquots were stored at 40° C. in the dark. An aliquot was removed weekly and immediately frozen at −80° C. until analysis. The below materials/reagents were used:
- Amicon Ultra15 Centrifugal Filters (30K MWCO) (Millipore; UFC903024)
- Hydrochloric acid, 10N (RICCA; 3770-32)
- Sodium Citrate Dihydrate (Fisher Chemical; 5466)
- Sodium hydroxide, 10N (JT Baker; 5000-03)
- Sucrose (VWR; M117-500G)
- Tween-80 Solution (10%) (Sigma: PB192-10ML)

Forced Oxidation

AB0089 lot AB0089-002 was diluted to 1 mg/ml with phosphate buffered saline (PBS). 6.7 µL of 3% hydrogen peroxide was added to a 1.0 ml aliquot of AB0089 to obtain a final concentration of 0.02% hydrogen peroxide. Oxidation of AB0089 proceeded for 24 hours at room temperature in the dark. After 24 hours, the sample was buffer switched into PBS, pH 7.4 using Amicon Ultra 0.5 ml 10K MWCO devices following the manufacturer's instructions. The unoxidized control (0.5 ml) was stored at −80° C. The below materials/reagents were used: 30% hydrogen peroxide (VWR; BDH7690-1), Gibco PBS pH 7.4 (1×) (ThermoFisher; 10010-031), and Zeba Desalting Columns (Thermo Scientifc; 89890).

pH 5 Stress

Concentrated AB0089 lot AB0089-002 was diluted to 1.0 mg/ml with 20 mM sodium acetate, pH 5.0. Concentration was corroborated by A280 with a Nanodrop One spectrophotometer. The sample was split. Half was stored at −80° C. as a control and the other half was incubated at 40° C. for 2 weeks. After the incubation, the sample was stored at −80° C. until analysis. Sodium acetate buffer (1 M, pH 5.0) (Boston Bioproducts; BB-60) was used.

pH 8 Stress

Concentrated AB0089 lot AB0089-002 was diluted to 1.0 mg/ml with 20 mM Tris, pH 8.3. Concentration was corroborated by A280 on the Nanodrop One spectrophotometer. The sample was split. Half was stored at −80° C. as a control and the other half was incubated at 40° C. for 2 weeks. After the incubation, the sample was stored at −80° C. until analysis. The pKa of Tris is temperature dependent. Tris, pH 8.3 measured at 25° C. is expected to have a pH of ~8.0 at 40° C. Tris buffer (1 M, pH 8.3) (Boston Bioproducts; LT-783) was used.

Freeze/Thaw

Three 0.1 ml aliquots of 20 mg/ml AB0089 lot AB0089-002 in CST, pH 7.0 buffer were subjected to freeze/thaw cycles at −80° C. in a Styrofoam container to slow the freezing process. At cycles 2, 4, and 6, an aliquot was removed and transferred to −80° C. storage until analysis.

Agitation 0.5 ml aliquots of 10 mg/ml AB0089 lot AB0089-002 in 20 mM sodium citrate, 250 mM sucrose, pH 7.0 or 20 mM sodium citrate, 250 mM sucrose, 0.01% Tween-80, pH 7.0 were added to a deep well plate (Thermo, #278752), the place was sealed, covered with foil and shaken at room temperature at 300 rpm for 3 days. After 3 days the plate was spun down and analyzed by A280 (concentration), A340 (turbidity), and SEC (aggregation).

Low pH Hold

AB0089 was captured on a Mab Select Sure Protein A column and eluted with 100 mM glycine, pH 3.0. Peak fractions were pooled, and 12 ml of the protein A eluate was pH was adjusted to pH 3.3 with 100 mM glycine pH 3.0 buffer. The pH-adjusted eluate was held at room temperature. After 1.5 hours, the eluate was brought to neutral pH with 1.0 M Tris-HCl, pH 8.3. The pH-hold sample was further purified by cation exchange chromatography. The final product was buffer exchanged to PBS pH 7.4 for analysis and received designation AB0089 lot AB0089-003.

High Concentration

AB0089 Lot AB0089-002 was concentrated using 30 kDa molecular weight cutoff devices in PBS, pH 7.4. Concentration was determined by A280 on a Nanodrop and product quality was monitored by SEC as described above.

Size Exclusion Chromatography (TSKgel G3000SWxl)

The following method was used for assessment of developability samples. 50 µg of test material was injected onto an Agilent 1260 Infinity II high pressure liquid chromatography (HPLC) instrument with 1260 Quat Pump, 1260 Vialsampler, 1260 VWD. The sample was separated on a Tosoh TSKgel G3000SWxl, 7.8 mm I.D.×30 cm, 5 µm column. SEC running buffer was PBS, pH 7.0, flowing at 0.50 ml/min. Absorbance was monitored at both 214 and 280 nm, peak areas were manually integrated and the percent of high molecular weight species (HMWS), low molecular weight species (LMWS), and monomer were reported. The below materials/reagents (vendor; catalog number) were used: gel filtration standards (Bio-Rad; 1511901), SEC buffer (20 mM Sodium Phosphate Monobasic Monohydrate/Sodium Phosphate Dibasic Heptahydrate, 0.3 M Sodium Chloride, pH 7.0) (Boston BioProducts; C-5194D), and TSKgel G3000SWxl, 7.8 mm×30 cm, 5 μm column (Tosoh; 08541).

LC-MS/MS Tryptic Peptide Mapping

50 μg of AB0089 was diluted with 6 M guanidine hydrochloride in 250 mM Tris, pH 8.5 and disulfide bonds were reduced with 25 mM dithiothreitol for 30 minutes at 40° C. in a thermomixer. The reduced cysteines were then alkylated with 50 mM iodoacetamide for 60 minutes at room temperature in the dark. The reduced and alkylated protein was buffer-switched into 50 mM Tris, pH 8.0 and digested with trypsin (1:25 enzyme:substrate) for 1 hour at 37° C. LC-MS/MS was carried out on a Thermo Vanquish UHPLC coupled to a QExactive+ mass spectrometer. Briefly, 5 μg of protein digest was separated on a Waters UPLC BEH Peptide C18 column (2.1×150 mm) over 150 minutes using a 2% to 40% acetonitrile gradient at 0.3 ml/min. Mass spectra were acquired from 230-2000 m/z in positive mode at 35,000 resolution for the full MS scan and 17,500 resolution for the Top10 MS/MS scans. The UPLC-MS/MS files were analyzed using the Byos PTM workflow (Protein Metrics). Peptides were identified using accurate mass and MS/MS searching the AB0089 sequence. Settings for peptide identification were as follows:
Precursor Mass Tolerance 6.00 ppm
Fragment Mass Tolerance 20.00 ppm
Cleavage Site(s) RK, C-terminal
Digestion Specificity Fully specific
Missed Cleavages 2
Modifications Carbamidomethyl/+57.021464 @ C, fixed
DTT/+151.994915 @ C
Oxidation/15.994915 @ M, W
Dethiomethyl/−48.003371 @ M
Deamidated/+0.984016 @ N, Q
pyro-Glu/−17.026549 @ NTerm Q
pyro-Glu/−18.010565 @ NTerm E
Carbamyl/+43.005814 @ NTerm, K, R
Acetyl/+42.010565 @ Protein NTerm
Ammonia-loss/−17.026549 @ N
Dioxidation/+31.989829 @ W
Kynurenine/+3.994915 @ W
N-glycan 50 common
The following materials/reagents (vendor; catalog number) were used:
0.1% formic acid in acetonitrile (JT Baker; LC441-2.5)
0.1% formic acid in water (JT Baker; LC452-2.5)
Formic acid (Thermo Scientific; 28905)
Guanidine HCl (Alfa Aesar; A13543)
Hydrochloric acid, 6 N (Avantor; 4103-01)
No-weigh dithiothreitol (Thermo Scientific; 20291)
No-weigh iodoacetamide (Thermo Scientific; 90034)
Sodium hydroxide, 6 N (Avantor; 5672-02)
Tris Base (Avantor; 4109-01)
Trypsin (Thermo Scientific; 90057)
UPLC BEH Peptide C18 column (2.1×150 mm) (Waters; 186003556)
Zeba spin desalting columns (Thermo Scientific; 89882)
Results
Discovery Hybridoma subclone 16B8.C8 (from which sequence optimized AB0089 and its predecessor AB0237 were derived) was discovered through immunization of BALB/c mice with recombinant human CLEC12A-His protein (FIGS. 104A-104H). A detailed description of the immunization process, antibody screening, assessment of recombinant and cell surface expressed CLEC12A binding, and epitope binning are described.

Figure 105E:
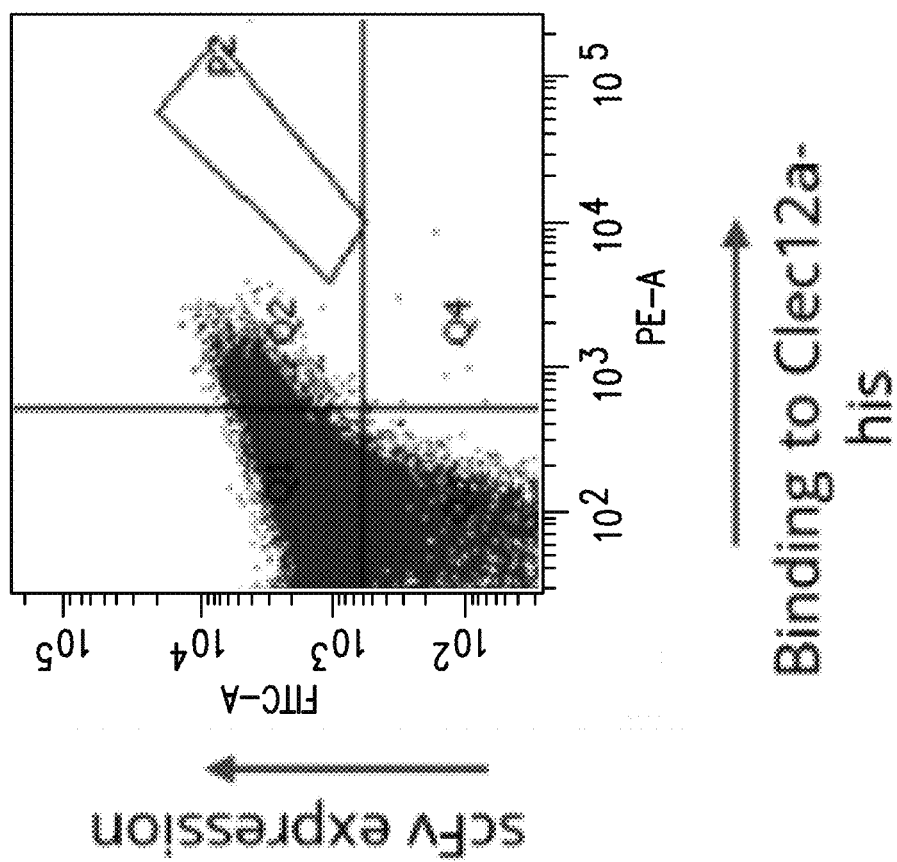
Figure 106B:
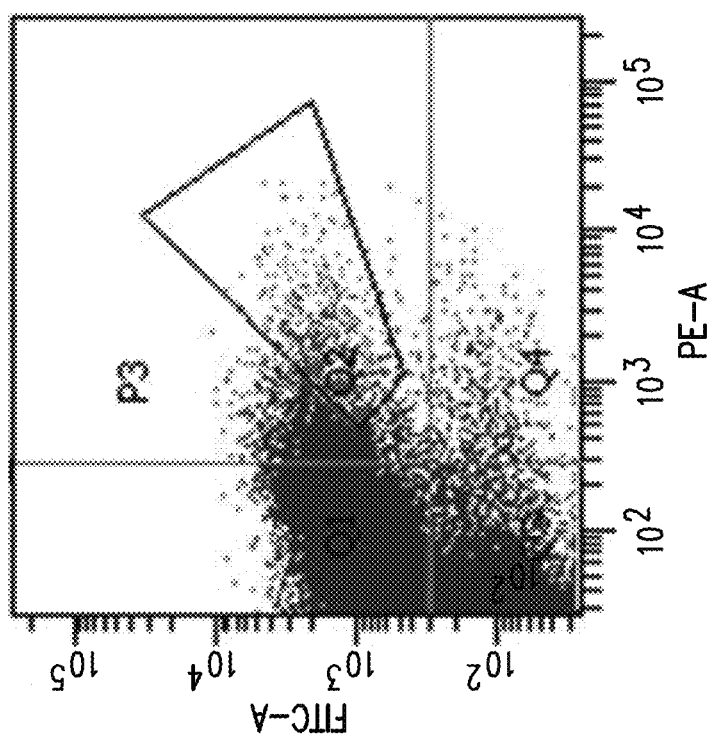
FIG. 106A-FIG. 106D shows FACS analysis of CDRH2 yeast library 30. Starting yeast display library which was generated by randomizing CDRH2 built on the background of the best clone identified from library 17 (GDYGDSLDY (SEQ ID NO:322) CDRH3) (FIG. 106A). Sorting was performed at 1 nM CLEC12A-His for both rounds. Flow cytometry analysis after round 1 (FIG. 106B), and round 2 (FIG. 106C) selection with CLEC12A-His, respectively. Binding of pET1596 displayed on yeast cells at 10 nM CLEC12A-His (FIG. 106D).
Figure 106A:
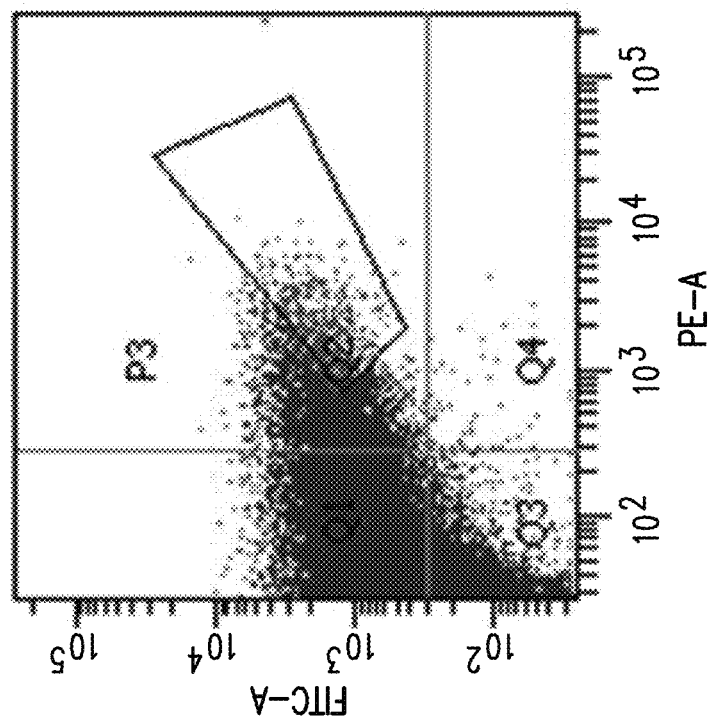
Figure 106D:
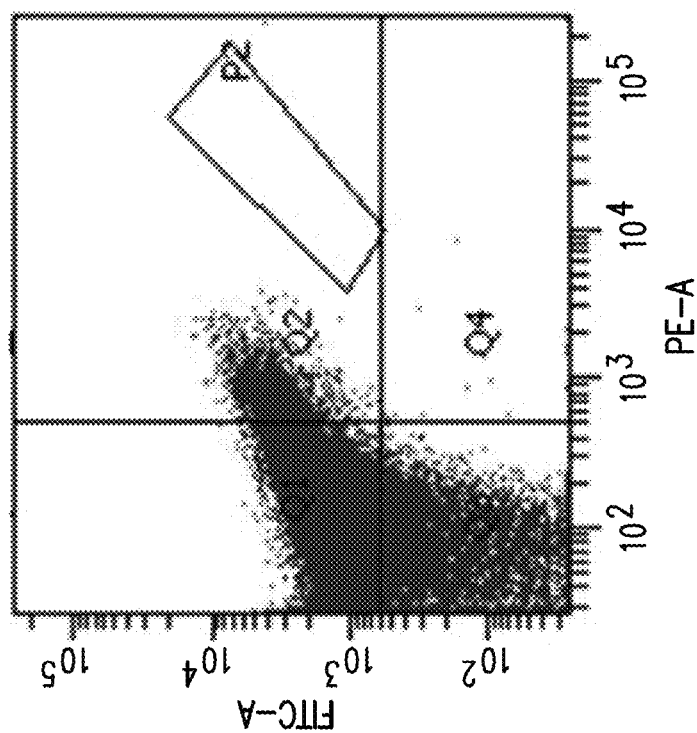
Figure 106C:
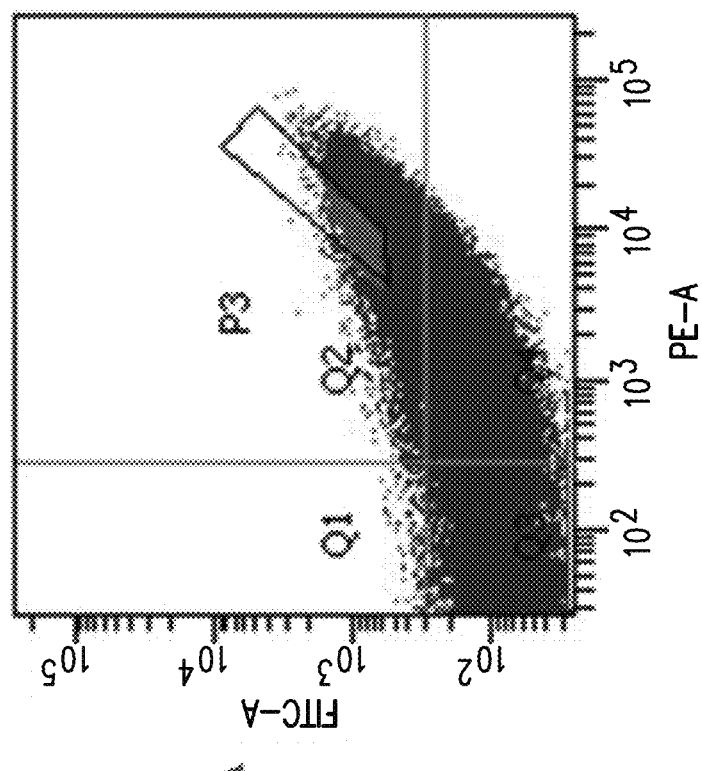
Figure 107B:
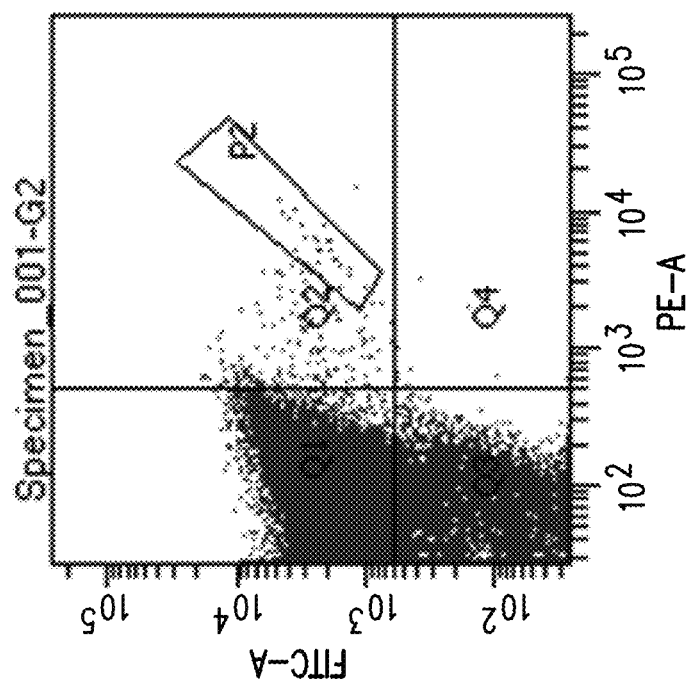
Figure 107A:
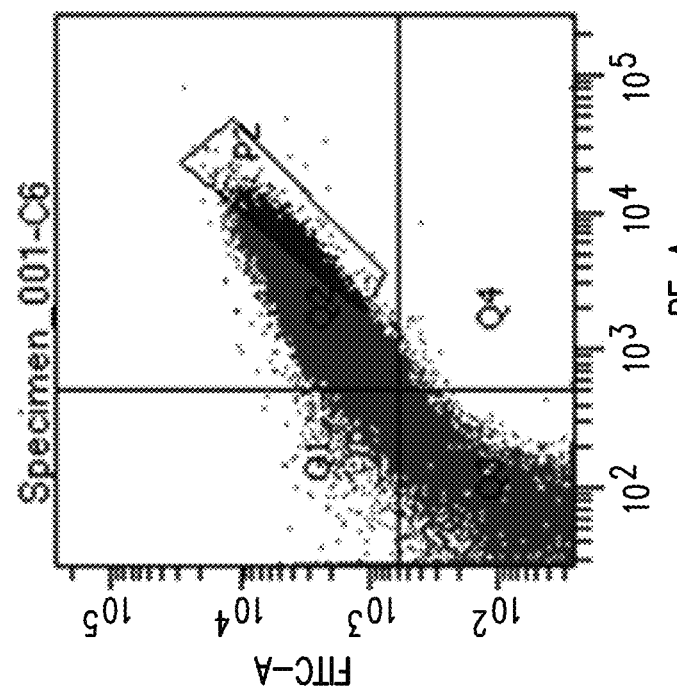
Figure 107C:
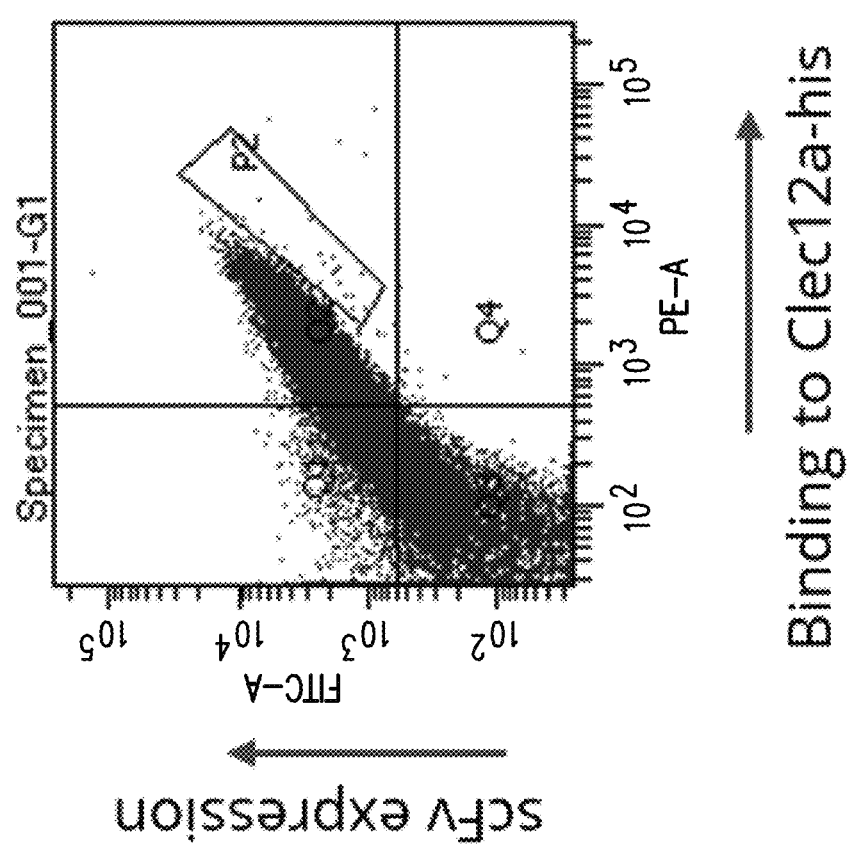

During the developability assessment of AB0237, an aspartic acid isomerization liability was identified in CDRH3 of the CLEC12A binding scFv. Attempts to remove this liability by single amino acid substitution or by targeted yeast display approaches (randomization of "DS" or "S") resulted in low expression yield and significant loss of binding to CLEC12A, suggesting that this motif may be important for maintaining CDR architecture. Therefore, an affinity maturation effort focusing on optimization of CDRH3 and CDRH2 was undertaken to further improve affinity for CLEC12A, and then the DS sequence was replaced by DT on the background of the optimized CDRH3. In addition, we sought to improve the humanness of the molecule by reducing the number of murine backmutations in the framework. We hypothesized that only one backmutation in position H83 was required, while other backmutations were not obligatory for maintaining CDRs architecture. The optimized scFv framework that contained a single backmutation was named pET1596 and was used as the background for all additional engineering. Later, the (H94)K backmutation was brought back to provide additional stabilization of the molecule. These engineering efforts resulted in the discovery of the AB0089 molecule, which retained high affinity for human CLEC12A and potency towards AML cancer cell lines, while both removing the isomerization liability and improving humanness.
Sequence Optimization
CDRH3 Focused Randomized Affinity Maturation Library A yeast display affinity maturation library (referred to as Library 17) was created successfully by mutating CDRH3 residues (YDYDDSLDY, SEQ ID NO:139) of pET1596 at each position one at a time or by changing two amino acid residues to all 20 amino acids as described above. To enrich for scFvs that have higher affinity towards hCLEC12A in library 17, three rounds of selections were carried out with biotinylated CLEC12A-His at 1 nM (1$^{st}$ and 2$^{nd}$ round of selection; FIGS. 105A-105B) and 0.1 nM (3$^{rd}$ round of selection; FIG. 105C). The affinities between the parental clone pET1596 and the library clones were compared and could be accurately discriminated, allowing a quantitative selection in real time (FIGS. 105B-105D). After 3 rounds of FACS sorting to isolate clones, one clone that contained 2 amino acid differences compared to the parental clone (GDYGDSLDY) (SEQ ID NO:322) exhibited higher binding affinity for CLEC12A than the parental clone (FIGS. 105D-105E).
CDRH3 Focused Combinatory Affinity Maturation Library Outcomes from the CDRH3 focused library demonstrated an improvement in affinity, however further improvement was highly desirable. Thus, Library 30 was created by incorporating the CDRH2 combinatory library (WSGGK (SEQ ID NO:138) to XSGGK (SEQ ID NO:323), WXGGK (SEQ ID NO:324), WSXGK (SEQ ID NO:325), WSGXK (SEQ ID NO:326), WSGGX (SEQ ID NO:327), XXGGK (SEQ ID NO:328), XSXGK (SEQ ID NO:329), XSGXK (SEQ ID NO:330), XSGGX (SEQ ID NO:331), WXXGK (SEQ ID NO:332), WXGXK (SEQ ID NO:333), WXGGX (SEQ ID NO:334), where X=any amino acid) into the optimized CDRH3 backbone. The goal was to engineer and select binders with better affinity than the parental clone (pET1596) or CDRH3 optimized variant. This created a library with a randomized CDRH2 while retaining a fixed CDRH3. Two rounds of FACS sorting were performed on this affinity maturation yeast display library (Library 30) to enrich for high affinity binders (FIGS. 106A-106D).

After 2 rounds of FACS sorting, one clone with changes in CDRH2 from WSGGK (SEQ ID NO:138) to WVGGA (SEQ ID NO:272) on the GDYGDSLDY (SEQ ID NO:322) CDRH3 background had the highest affinity for CLEC12A (FIGS. 107A-107D). This clone showed a significant improvement in CLEC12A affinity compared to parental pET1596 and AB0237.

Remediation of DS Sequence Liability

Once the affinity matured clone was identified, site-directed mutagenesis was used to produce a rational variant (CDRH3: GDYGDSLDY (SEQ ID NO:322) to GDYGDTLDY (SEQ ID NO:273)), resulting in a CLEC12A targeting scFv that does not contain the isomerization liability, while maintaining high affinity binding to the target. The comparison of the CDRs of the optimized AB0089 molecule and AB0237 is shown in Table 124.

TABLE 124

Comparison of CLEC12A binding CDRs in AB0089 and AB0237.

| TriNKETs | CDRH1 | CDRH2 | CDRH3 |
|---|---|---|---|
| AB0237 | GFSLTNY (SEQ ID NO: 137) | WSGGK (SEQ ID NO: 138) | YDYDDSLDY (SEQ ID NO: 139) |
| AB0089 | GFSLTNY (SEQ ID NO: 137) | WVGGA (SEQ ID NO: 272) | GDYGDTLDY (SEQ ID NO: 273) |

Sequence differences obtained as a result of affinity maturation are underlined. Isomerization liability correction obtained by site-directed mutagenesis (DS to DT) is shown in green.

Based on the structural modeling, we decided to re-introduce a murine residue in position H94 to provide additional support for the CDR architecture. AB0089 contains only 2 murine residues in position H83 and H94 in the VH of the CLEC12A binding scFv, while there are 5 murine backmutations in AB0237. The rest of the backmutations were reverted to human germline, thus improving the humanness of AB0089 (Table 125).

TABLE 125

Murine backmutations in the frameworks of AB0089 and AB0237.

| Chain | AB0089 | AB0237 |
|---|---|---|
| VH |  | (H71)K |
| VH | (H83)Q | (H83)Q |
| VH | (H94)K | (H94)K |
| VL |  | (L70)R |
| VL |  | (L83)I |

Molecular Format and Design

Figure 108:
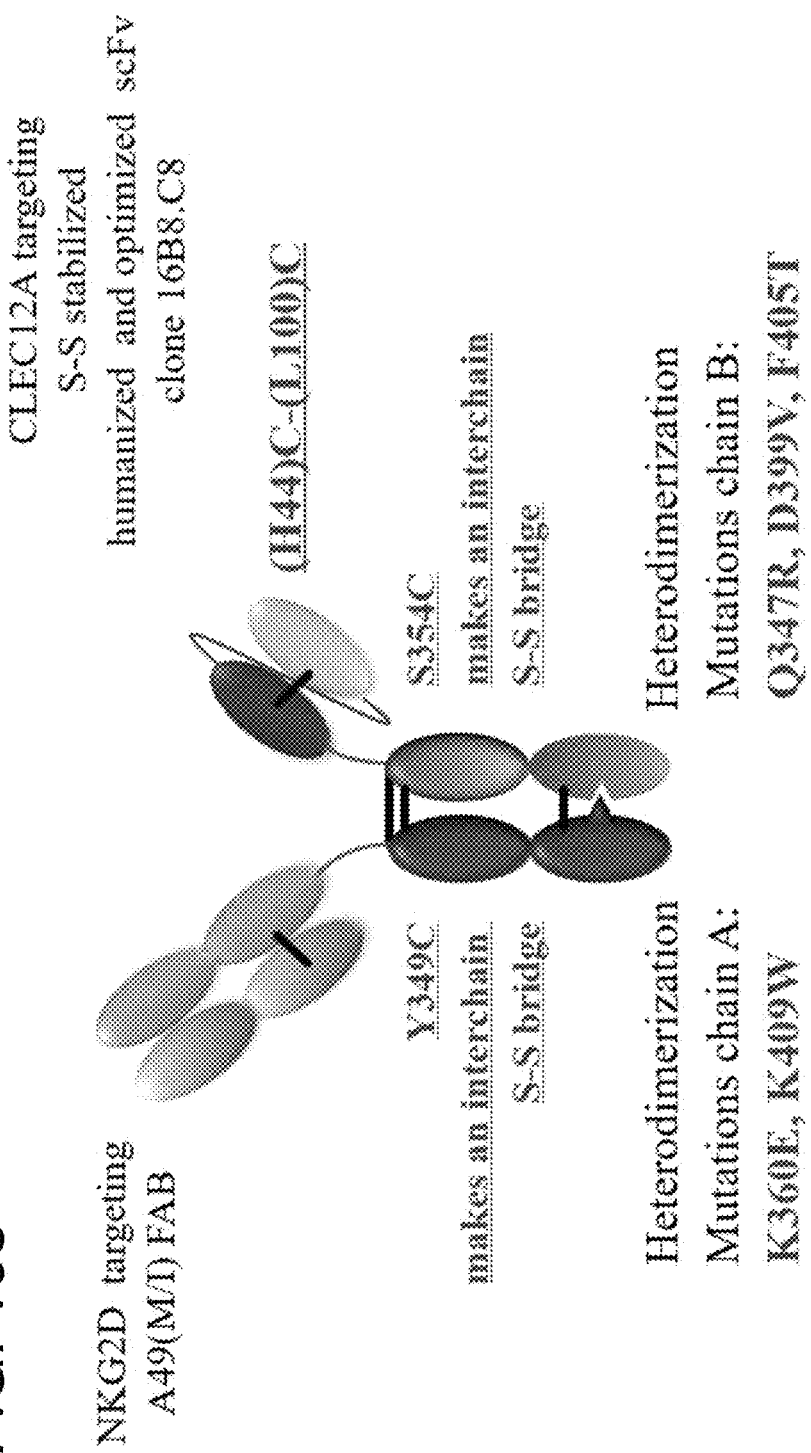
FIG. 108 is a schematic representation of AB0089. Heterodimerization mutations and an engineered interchain disulfide bridge ensure efficient chain pairing of the IgG1 Fc. The scFv is derived from the humanized and sequence liability corrected CLEC12A mAb 16B8.C8. The scFv is stabilized by an engineered disulfide bridge between VH and VL.

AB0089 is a heterodimeric tri-functional antibody that redirects NK and T cell activity against CLEC12A-expressing cancer cells. AB0089 contains three chains: Chain H, Chain L and Chain S. The schematic representation of the AB0089 molecule is provided in FIG. 108. Chain H is the heavy chain of A49M-I NKG2D-targeting antibody that was selected for having low affinity while being a potent agonist of NKG2D receptors on NK and cytotoxic T cells. The M-I mutation was introduced to eliminate Met102 residue in the CDRH3 that is sensitive to oxidation and therefore may present a potential liability. Chain L is the light chain of the NKG2D-targeting antibody A49M-I. Chain S contains a scFv that binds with high affinity to CLEC12A on AML cancer cells. Both scFv and Fab domains are fused to a human IgG1 Fc. Both chains bear several mutations in the CH3 domain introduced to ensure stable heterodimerization of two Fc monomers. There are seven such mutations in the IgG1 Fc of the AB0089: three mutations in Chain H and four mutations in Chain S. Two of these mutations are involved in the formation of a stabilizing S—S bridge (Y349C and S354C) between Chains H and Chain S (EU nomenclature). The scFv (VH-VL orientation) in Chain S is stabilized by two mutations introducing a S—S bridge ((H44)C and (L100)C, Chothia nomenclature). Chain S also contains a (G4S)4 non-immunogenic linker between VH and VL of the scFv. The amino acid sequence of the CLEC12A-targeting scFv is based on the sequence of humanized 16B8.C8 antibody, obtained from hybridoma (Green Mountain Antibodies). The amino acid sequence of the NKG2D Fab is based on the fully human antibody A49M-I, obtained using human yeast display technology (Adimab).

Amino Acid Sequence

The amino acid sequences of the three polypeptide chains that make up AB0089 are shown below. CDRs are defined using Chothia nomenclature and are represented in Table 126. The C-terminal K, commonly processed and cleaved in IgG1, is deleted in Chain S and Chain H to prevent heterogeneity.

Chain S: CLEC12A targeting scFv-CH2-CH3 (humanized sequence, CDRs are italicized, back mutations are double underlined, engineered scFv disulfide in lower case letters, and Fc mutations for heterodimerization and the engineered CH3 disulfide are single underlined).

(SEQ ID NO: 276)
QLQLQESGPGLVKPSETLSLTCTVS*GFSLTNY*GLHWIRQPPGKcLE

WIGVI*WVGGA*TDYNPSLKSRVTISVDTSKNQFSLKLSSVQAADTAV

YYCAKGDYGDTLDYWGQGTLVTVSSGGGGSGGGGSGGGGSGGGGSD

IQMTQSPSSLSASVGDRVTITC*HASQNINFWIS*WYQQKPGKAPKLL

IY*EASNLHT*GVPSRFSGSGSGTDFTLTISSLQPEDFATYYCQQSHS

*YPLT*FGcGTKLEIKGSDKTHTCPPCPAPELLGGPSVFLFPPKPKDT

LMISRTPEVTCVVVDVSHEDPEVKFNWYVDGVEVHNAKTKPREEQY

NSTYRVVSVLTVLHQDWLNGKEYKCKVSNKALPAPIEKTISKAKGQ

PREPRVYTLPPCRDELTKNQVSLTCLVKGFYPSDIAVEWESNGQPE

NNYKTTPPVLVSDGSFTLYSKLTVDKSRWQQGNVFSCSVMHEALHN

HYTQKSLSLSPG

Chain H: NKG2D targeting VH-CH1-CH2-CH3 (fully human, CDRs are italicized, Fc mutations for heterodimerization and the engineered CH3 disulfide are underlined).

(SEQ ID NO: 260)
EVQLVESGGGLVKPGGSLRLSCAAS*GFTFSSY*SMNWVRQAPGKGLEWVS

SI*SSSSSY*IYYADSVKGRFTISRDNAKNSLYLQMNSLRAEDTAVYYCAR

*GAPIGAAAGWFDP*WGQGTLVTVSSASTKGPSVFPLAPSSKSTSGGTAAL

GCLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPSV

-continued

```
FLEPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISK

AKGQPREPQVCTLPPSRDELTENQVSLTCLVKGFYPSDIAVEWESNGQP

ENNYKTTPPVLDSDGSFFLYSWLTVDKSRWQQGNVFSCSV

MHEALHNHYTQKSLSLSPG

Chain L: NKG2D targeting VL-CL (fully human,
CDRs are italicized).
                                         (SEQ ID NO: 261)
DIQMTQSPSSVSASVGDRVTITCRASQGISSWLAWYQQKPGKAPKLLIY

AASSLQSGVPSRFSGSGSGTDFTLTISSLQPEDFATYYCQQGVSFPRTF

GGGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC
```

TABLE 126

AB0089 CDRs sequences.

| AB0089 | Variable region | Framework | CDR1 | CDR2 | CDR3 |
|---|---|---|---|---|---|
| Chain S | VH | VH4-59 | GFSLTNY (SEQ ID NO: 137) | WVGGA (SEQ ID NO: 272) | GDYGDTLDY (SEQ ID NO: 273) |
| Chain S | VL | VK1-12 | HASQNIN FWLS (SEQ ID NO: 140) | EASNLHT (SEQ ID NO: 141) | QQSHSYPLT (SEQ ID NO: 142) |
| Chain H | VH | VH3-21 | GFTFSSY (SEQ ID NO: 297) | SSSSY (SEQ ID NO: 298) | GAPIGAAAG WFDP (SEQ ID NO: 97) |
| Chain L | VL | VK1-2 | RASQGIS SWLA (SEQ ID NO: 86) | AASSLQS (SEQ ID NO: 77) | QQGVSFPRT (SEQ ID NO: 87) |

CDRs are identified by Chothia

Analysis of Potential Sequence Liabilities in CDRs

Chain L (NKG2D binding light chain) has no predicted liabilities. Chain H (NKG2D binding heavy chain) has a DP in CDRH3. This motif is not affected by forced degradation (as in other constructs, data not shown). As such, this sequence was not altered in AB0089. Chain S (CLEC12A binding scFv-Fc chain) has no predicted liabilities.

Description of Heterodimerization Mutations

EU-numbering convention was used to annotate the amino acid residues in the Fc. Chain H contains the following mutations:

K360E—Heterodimerization mutation in the CH3 domain of the Fc region.

K409W—Heterodimerization mutation in the CH3 domain of the Fc region.

Y349C—Inter-subunit disulfide stabilization mutation in the CH3 domain of the Fc region.

The K360E/K409W mutations in the Fc region of Chain H are designed to render heterodimer-favoring interactions with Chain S due to hydrophobic/steric complementarity plus long-range electrostatic interactions (Choi et al., (2013) *Mol Cancer Ther*, 12, 2748-59; Choi et al., (2015) *Mol Immunol*, 65, 377-83). The mutation Y349C was introduced to generate an additional inter-chain disulfide bond Y349C-(CH3-ChainH)-S354C(CH3-ChainS) pair (Choi et al., (2015) *Mol Immunol*, 65, 377-83).

Chain S contains the following mutations:

G44C—Disulfide stabilization mutation in VH region of the scFv.

S100C—Disulfide stabilization mutation in VL region of the scFv.

Q347R—Heterodimerization mutation in the CH3 domain of the Fc region.

D399V—Heterodimerization mutation in the CH3 domain of the Fc region.

F405T—Heterodimerization mutation in the CH3 domain of the Fc region.

S354C—Inter-subunit disulfide stabilization mutation in the CH3 domain of the Fc region.

The mutations G44C and S100C were introduced to stabilize the scFv by an engineered disulfide bond between the VH and the VL. The disulfide stabilization improves structural and thermal stability of scFv. The Q347R/D399V/F405T mutations in the Fc region of Chain S were designed to render heterodimer-favoring interactions with Chain H due to hydrophobic/steric complementarity plus long-range electrostatic interactions (Choi et al, (2013) *Mol Cancer Ther*, 12, 2748-59). The mutation S354C was introduced to generate an additional inter-CH3 disulfide bond with a Y349C(CH3-ChainH)-S354C(CH3-ChainS) pair (Choi et al, (2015) *Mol Immunol*, 65, 377-83).

The heterodimerization of the Chain H and Chain S is based on five mutations, so called, EW-RVT, with the interaction pairs K409W(CH3A)-D399V/F405T(CH3B) (dubbed the W-VT pair) and K360E(CH3A)-Q347R(CH3B) (dubbed the E-R pair), which were designed to replace the conserved electrostatic interactions with asymmetric hydrophobic interactions and to add asymmetric long-range electrostatic interactions at the rim of the heterodimeric CH3 interface, respectively (Choi et al., (2013) *Mol Cancer Ther*, 12, 2748-59). Detailed analysis of the heterodimeric CH3A-CH3B inter-face revealed very few structural perturbations resulting from mutations at the interface compared to the native IgG1 Fc (FIGS. 109A-109C). Backbone and side-chain conformations of the residues adjacent to the interfacial mutations in Fc-EW-RVT are almost the same as those in Fc-WT, except for the side-chain substitutions of the mutated residues (FIG. 109A). The residues of W-VT mutation pairs, i.e., K409W(CH3A)-D399V(CH3B)/F405T (CH3B), were in close proximity to form complementary contacts in mostly buried CH3A-CH3B interfaces (FIG. 109B), suggesting that W-VT pairs strengthen the hydrophobic interface between CH3A-CH3B by forming optimal hydrophobic interactions. The residues of the E-R mutation pair, K360ECH3A-Q347RCH3B, were located sufficiently close at 3.45 Å to form a salt bridge unlike the wild-type K-Q pair (4.61 Å) (FIG. 109C), contributing to the preferential formation of the heterodimer by strong electrostatic interactions. Thus, the mutated residues introduced to Fc-EW-RVT form non-covalent interactions in the CH3A-CH3B interface favoring heterodimer formation without significant structural perturbations to the overall CH3 domain structure.

Figure 110:
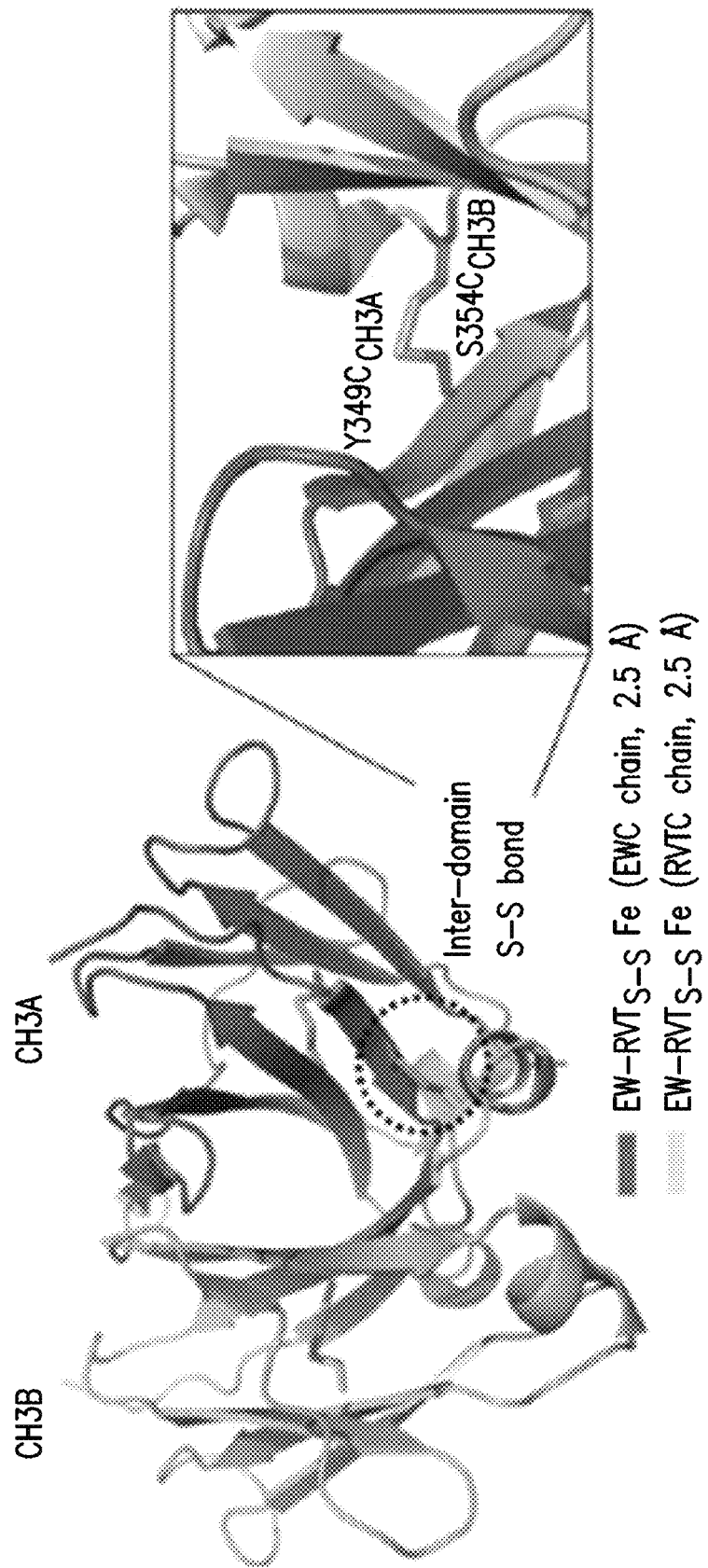
FIG. 110 shows the crystal structure of EW-RVTS-S heterodimeric Fc with a close-up view of the asymmetric disulfide bond formed between 349C(CH3A) and 354C (CH3B) residues.

By design the W-VT pair residues (K409W(CH3A)-D399V(CH3B)/F405T(CH3B)) and E-R pair residues (K360E(CH3A)-Q347R(CH3B)) are in the heterodimeric CH3 interface to form asymmetric, complementary hydrophobic interactions and electrostatic interactions at 3.45 Å, respectively, which preferentially favor the heterodimer. On the other hand, the respective homodimer formation was thermodynamically dis-favored due to the steric clash between 409WCH3A and F405CH3A residues as well as the repulsive electrostatic interactions between the 347R (CH3B) and K360(CH3B) residues. The loss of the wild-type electrostatic interaction residues of K409WT-D39WT also discourages homodimer formation. Additional stabilization of heterodimer is brought by the inter-CH3 disulfide-bonded EW-RVT(S—S) variant with Y349C(CH3A) and S354C(CH3B) mutations (FIG. 110). The X-ray structure of Fc-EW-RVT(S—S) has been described at 2.5 Å resolution (Choi et al., (2015) *Mol Immunol*, 65, 377-83) and was very similar to the known IgG1 structures.

Structural Modeling

In the absence of a crystal structure, structural models of the variable segments of CLEC12A and NKG2D binding arms were generated for comparison. Model building was performed using the SAbPred web site (opig.stats.ox.ac.uk/webapps/newsabdab/sabpred/).

Surface Charge Distribution and Hydrophobic Patch Analysis of CLEC12A Binding Arm of AB0089

FIGS. 111A-111C illustrate a ribbon diagram model of the CLEC12A binding scFv in three different orientations (upper panel) and their corresponding surface charge distribution of the same orientation (lower panel). The charge distribution of the anti-CLEC12A scFv is polarized ("top view", lower panel), with negatively charged residues populated predominately within CDRH3 and CDRL2. The uneven distribution of electrostatic patches on the paratope is likely to be target-related and reflects the complementarity of charge distribution on its cognate epitope, which may contribute to the high affinity interaction between CLEC12A and the scFv of AB0089.

FIGS. 112A-112B show the analysis of CDR length and surface hydrophobicity patches of the CLEC12A-targeting arm of AB0089. Analyses were performed using therapeutic antibody profiles (TAP): opig.stats.ox.ac.uk/webapps/newsabdab/sabpred/tap. It compares the candidate in reference to 377 late-stage therapeutic antibodies. The length of CDRs for the CLEC12A-binding arm of AB0089 are within the normal range for late stage therapeutic antibodies. Hydrophobic patch analysis of the CDRs of an antibody is predictive of its developability. The theoretical hydrophobic properties of the CLEC12A binding arm of AB0089 are well within the norm of commercialized biotherapeutics and late-stage therapeutic antibody candidates.

Figures 113A, 113B:
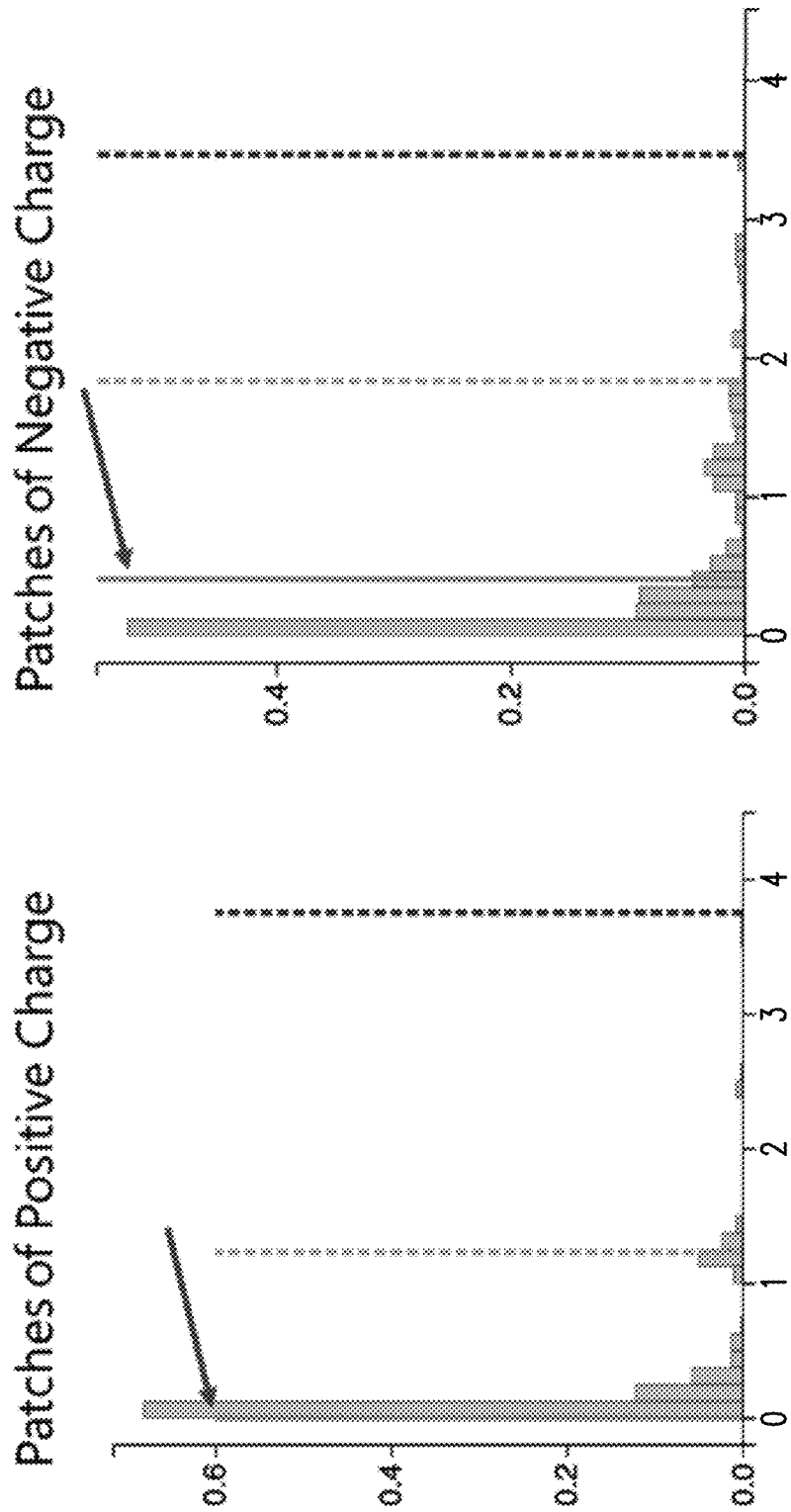
FIG. 113A-FIG. 113C show the analyses of patches containing positive (FIG. 113A) and negative charges (FIG. 113B), as well as the symmetry (FIG. 113C) of these charges around the CDR regions. Surface charge and charge symmetry analysis of CLEC12A targeting arm of AB0089. The arrow points to the line where CLEC12A targeting scFv of AB0089 stands in reference to advanced clinical stage mAbs. In each plot, there are two dashed lines—one closer and the other further to the solid line. The dashed line closer to the solid line indicates 2 SD (>95% of reference molecules within this region), whereas the dashed line further to the solid line indicates 3 SD (>99.7% of reference molecules within this region).
Figure 113C:
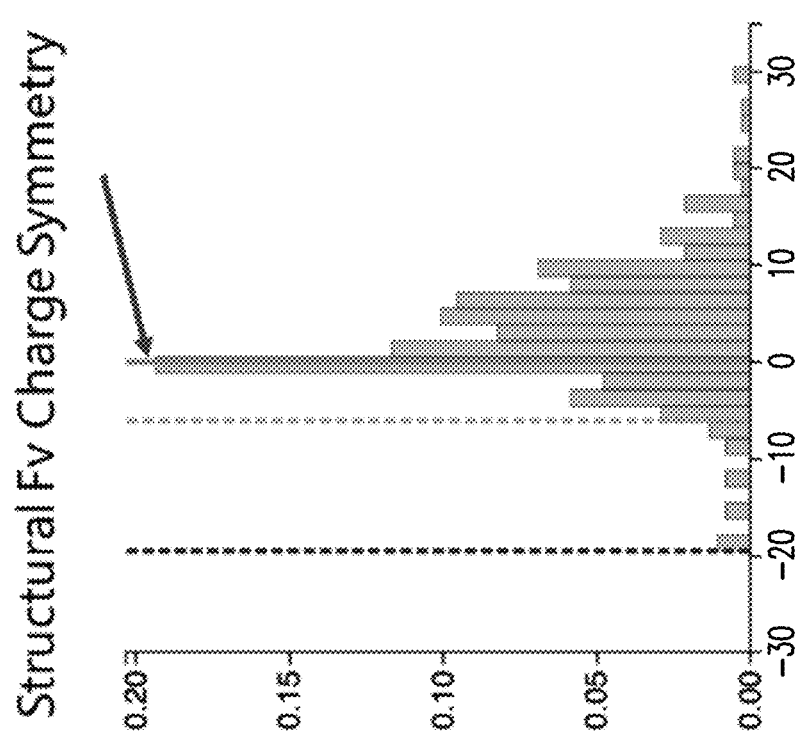

FIGS. 113A-113C show the analyses of patches containing positive and negative charges, as well as the symmetry of these charges around the CDR regions. All three charts indicate that the charge distributions are within the norm compared with the population of therapeutic antibodies.

Surface Charge Distribution and Hydrophobic Patch Analysis of NKG2D Binding Arm of AB0089

The NKG2D-binding Fab is shown in ribbon diagrams with three different orientations (FIGS. 114A-114C, upper panel) and the corresponding surface charge distribution in the same orientation are provided (FIGS. 114A-114C, lower panel). The surface charge on the NKG2D binding arm is more evenly distributed than charges on the CLEC12A targeting arm.

Figure 115B:
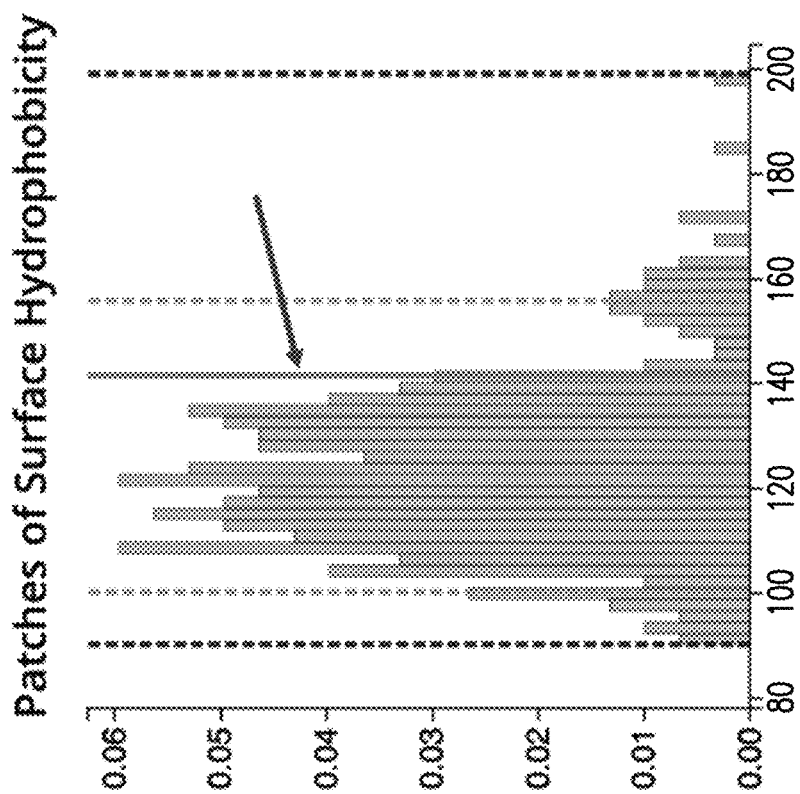
FIG. 115A-FIG. 115B show the CDR length (FIG. 115A) and patches of surface hydrophobicity (FIG. 115B) analyses of the NKG2D-targeting arm of AB0089. The arrow points to the line where NKG2D targeting arm of AB0089 stands in reference to advanced clinical stage mAbs. The two inner dotted lines indicate 2 SD (>95% of reference molecules within this region). The two outer most dotted lines indicate 3 SD (>99.7% of reference molecules within this region).
Figure 115A:
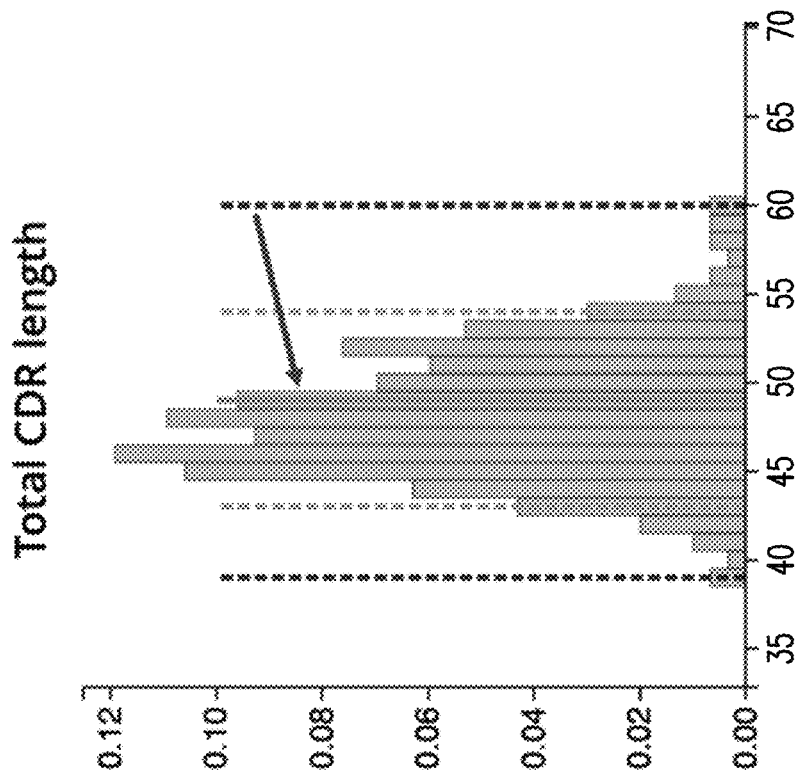

FIGS. 115A-115B show the CDR length and patches of surface hydrophobicity analyses of the NKG2D-targeting arm of AB0089. It appears that the CDR length, hydrophobic properties, and positive/negative charge distribution are well within the norm of existing therapeutic antibodies.

Figure 116B:
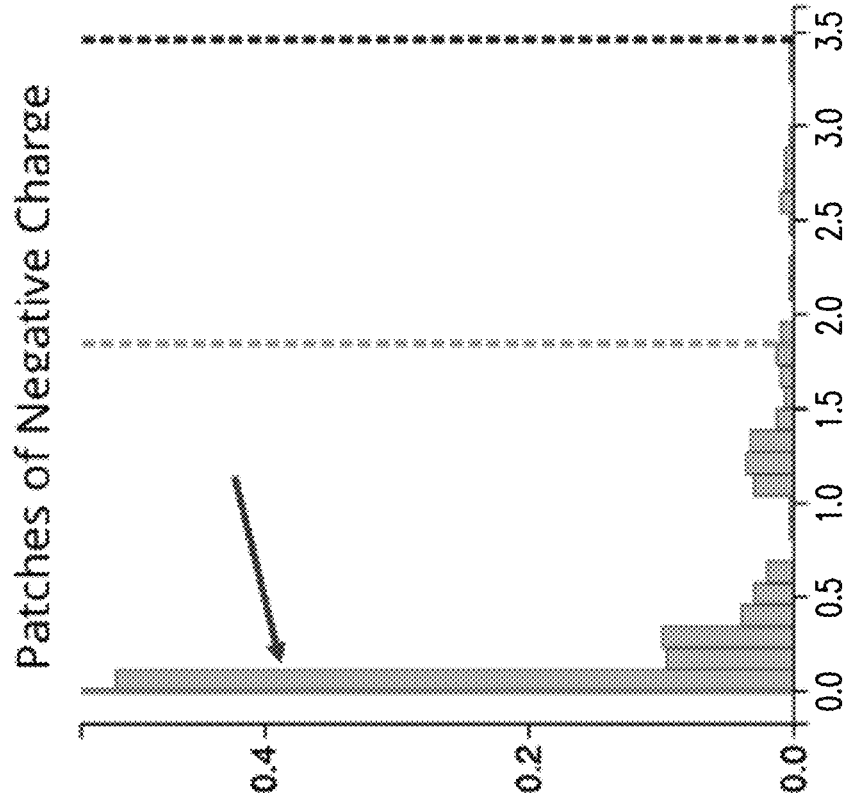
Figure 116A:
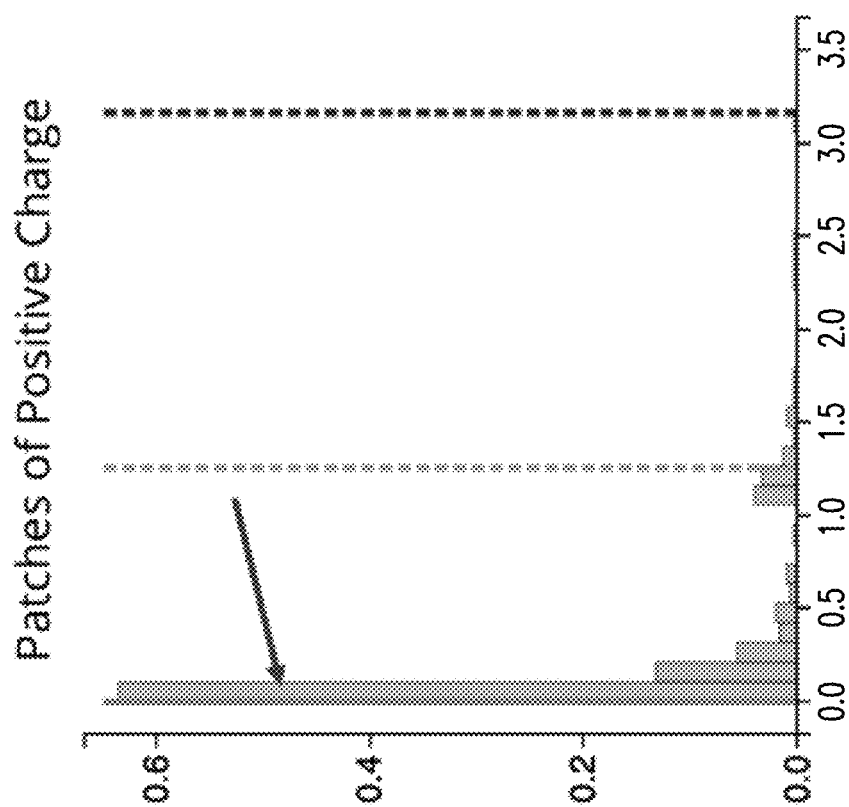
Figure 117A:
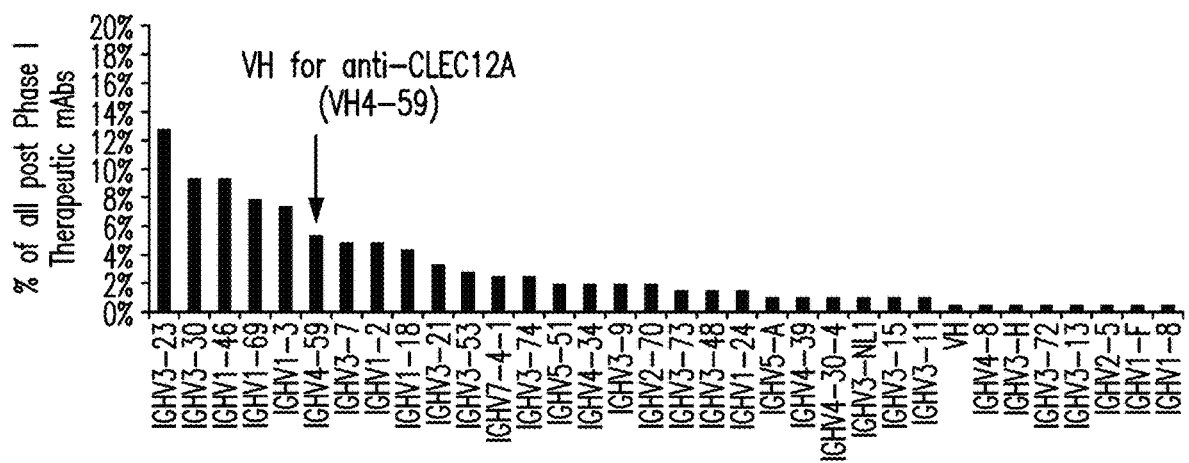
FIG. 117A-FIG. 117D show human acceptor frameworks used in AB0089 compared to other clinical stage therapeutic mAbs. Benchmarking of frameworks used in AB0089 against human germlines frequently used in clinical stage antibodies database containing 400+ mAbs from phase I+.
Figure 117B:
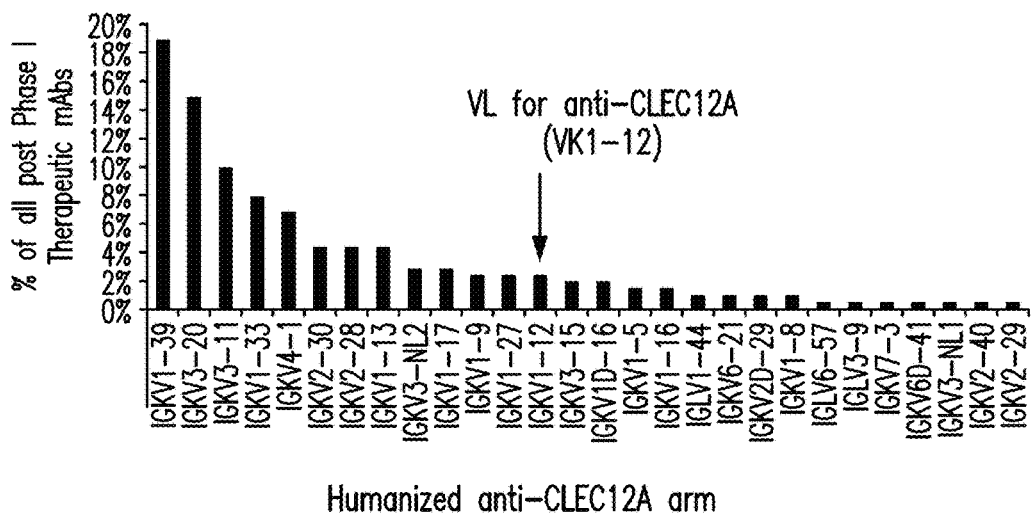
Figure 117C:
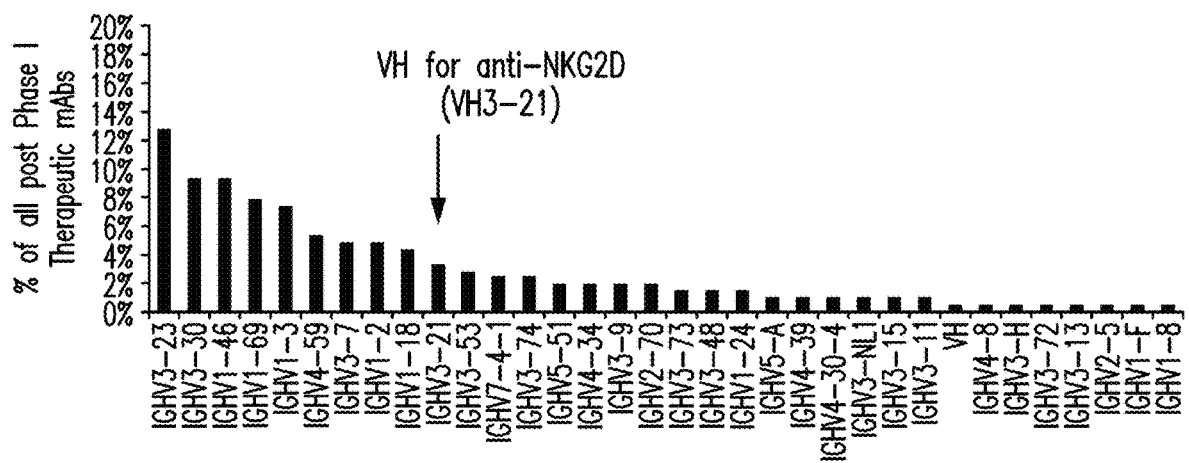
Figure 117D:
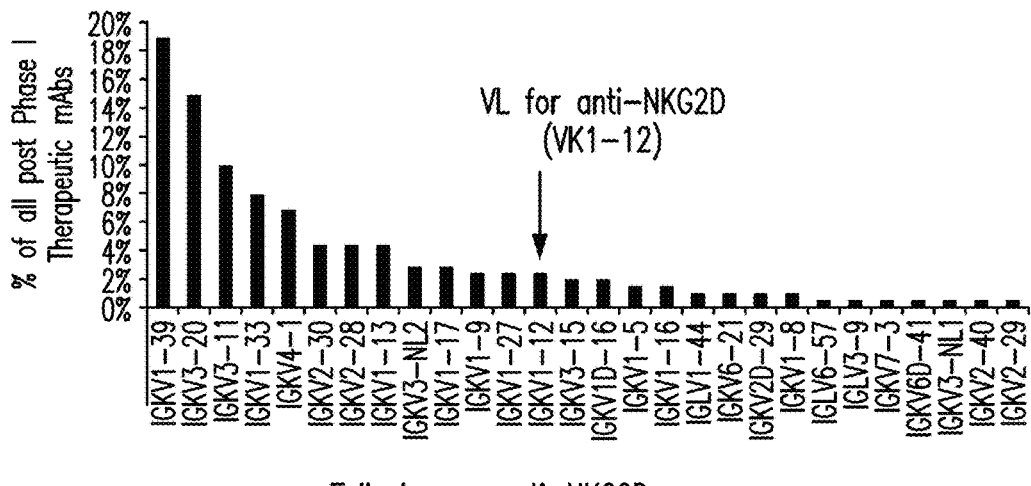

FIGS. 116A-116C show the analyses of patches containing positive and negative charges, as well as the symmetry of these charges around the CDR regions. All three charts indicate that the charge distributions are within the norm comparing with the population of therapeutic antibodies.

Framework Assessment

The CLEC12A binding arm of AB0089 was discovered through mouse immunization. The frameworks chosen for CDR grafting are frequently used in clinical stage therapeutic monoclonal antibodies (FIGS. 117A-117D). The NKG2D binding arm is fully human, is based on a framework frequently used in advanced stage mAbs and does not contain any unusual residues or deviations from the germline.

Immunogenicity Prediction

Figure 118A:
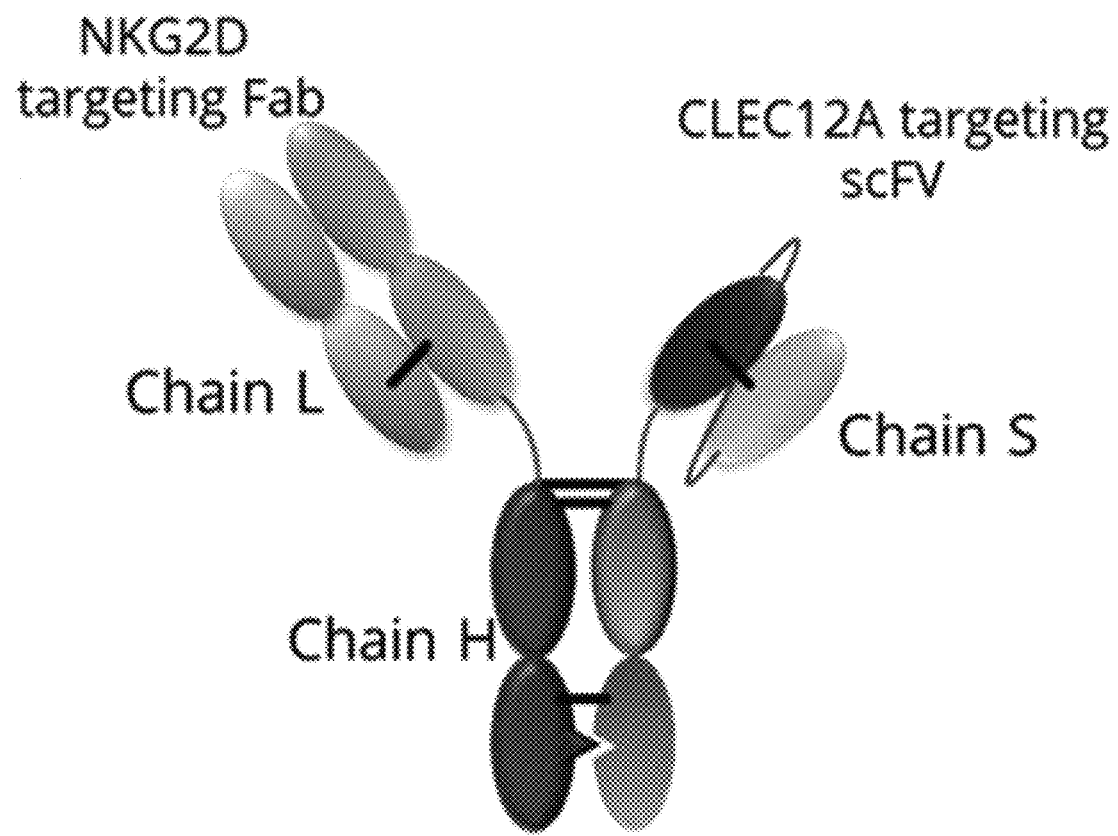
FIG. 118A-FIG. 118B show a cartoon representation of AB0089 indicating chain composition of the molecule (FIG. 118A) and the positions of chain H, S, and L of AB0089 on the Treg-adjusted EpiMatrix protein immunogenicity scale (FIG. 118B).
Figure 118B:
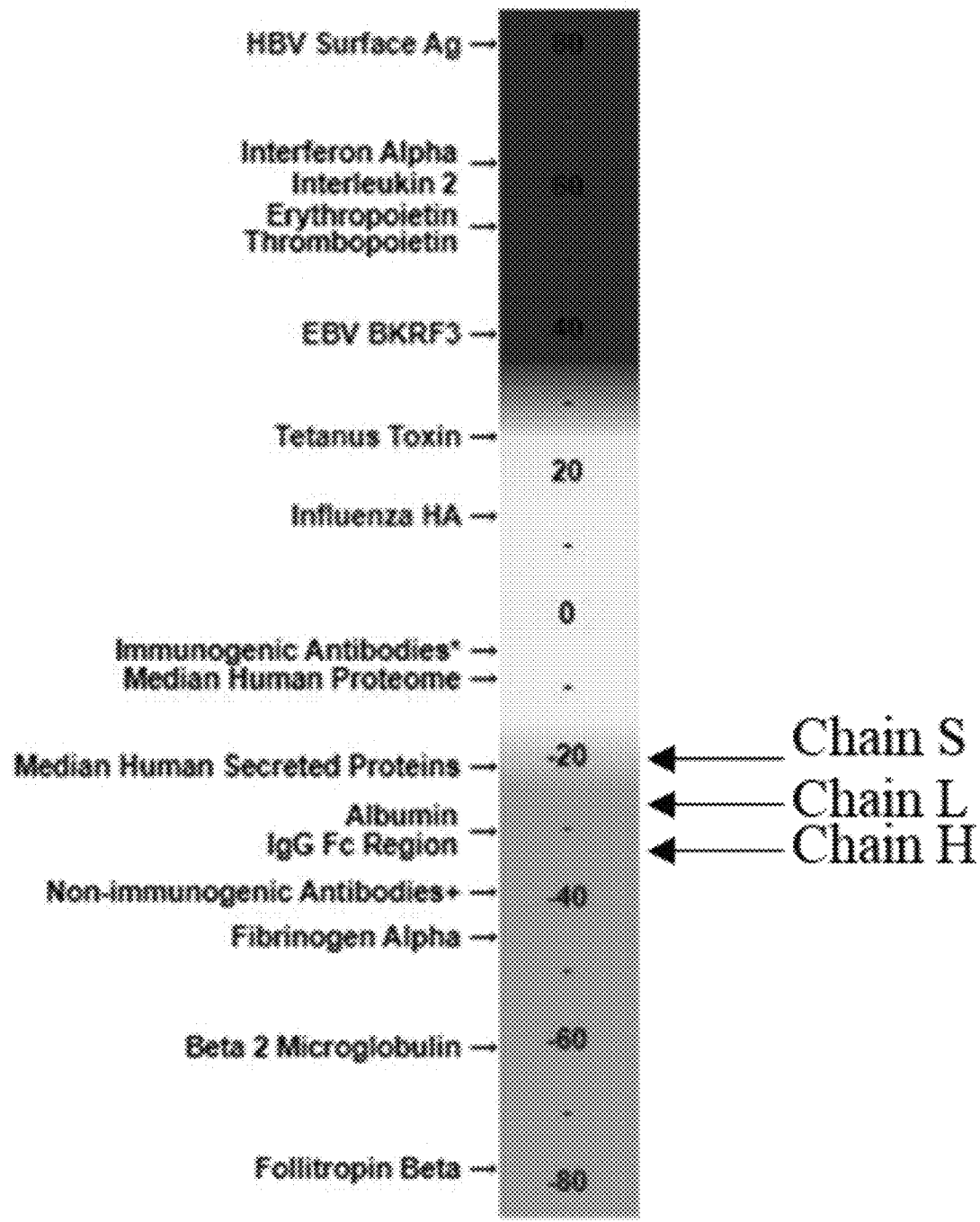

Protein sequences of the three chains of AB0089 were examined for the presence of potentially immunogenic T cell epitopes and to rank the immunogenicity potential using the EpiMatrix algorithm (FIGS. 118A-118B). AB0089 scores favorably on the Treg adjusted Immunogenicity Protein Scale. The Treg adjusted EpiMatrix Protein Score for the sequences of the three chains of AB0089 are −33.39 (chain H), −27.13 (chain S), and −23.49 (chain L) (Table 127). The predicted risk of immunogenicity for the AB0089 appears to be low.

TABLE 127

EpiVax immunogenicity analysis of AB0089.

| Protein Sequence | Length | EpiMatrix Hits | EpiMatrix Score | Treg adjusted Epx Score |
|---|---|---|---|---|
| AB0089_CHAIN_H | 451 | 207 | 5.99 | −33.39 |
| AB0089_CHAIN_L | 214 | 98 | 11.17 | −23.49 |
| AB0089_CHAIN_S | 472 | 202 | −2.96 | −27.13 |

Expression

Expression of AB0089 was achieved using Dragonfly Tx F3' TriNKET platform purification method. Briefly, AB0089 was expressed by transient transfection of Expi293 and ExpiCHO cells with three plasmids encoding the NKG2D targeting light chain (chain L), the NKG2D targeting IgG heavy chain (chain H), and the CLEC12A targeting scFv-Fc fusion (chain S). For both Expi293 and ExpiCHO expression, Chain S:Chain H:Chain L were transfected at the plasmid ratio 4:1:1 to maximize the percentage of desired heterodimer product. This ratio was empirically obtained based on previous humanized TriNKETs and was not specifically optimized for AB0089.

Purification

Figure 119:
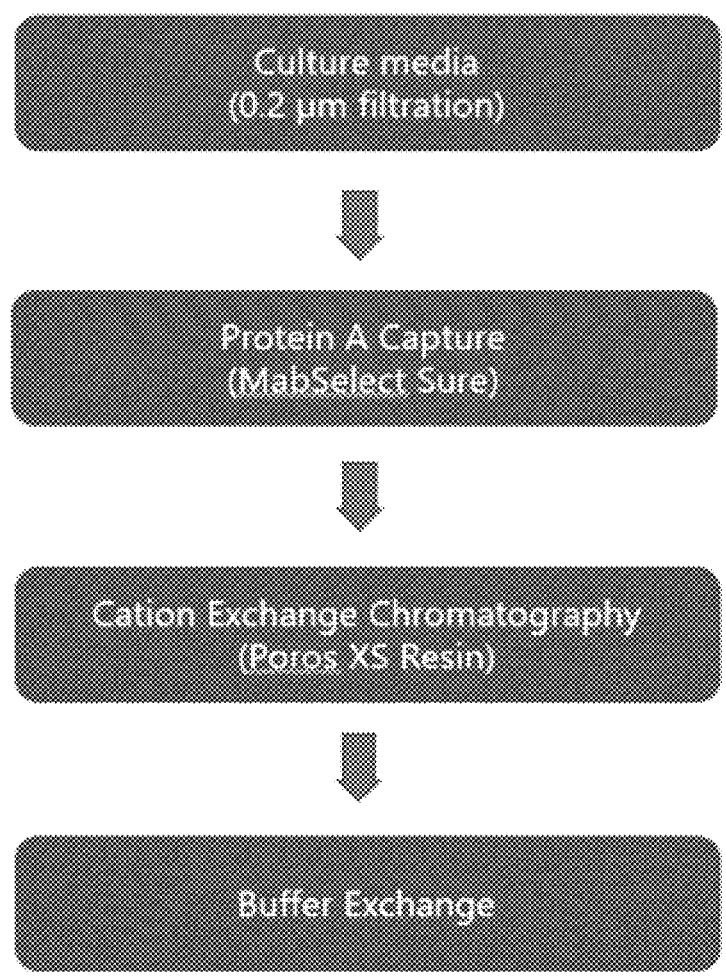
FIG. 119 shows a TriNKET purification process flow diagram.

Purification of AB0089 was performed using F3' TriNKET platform purification methods developed by Dragonfly Therapeutics (FIG. 119). This purification process has been applied before to material expressed in Expi293, ExpiCHO and CHO-M cell cultures for many different TriNKETs. No optimization or extensive process development for AB0089 purification was performed. Two-step purification process was employed.

Two lots of AB0089 were produced in transiently transfected ExpiCHO and Expi293 cells. Table 128 summarizes the titer and final product purity for both lots. Purification of the AB0089 lot AB0089-002 expressed in ExpiCHO is described in detail below.

TABLE 128

Summary of AB0089 purification.

| Lot | Expression host | Titer mg/L | Purity, % Monomer |
|---|---|---|---|
| AB0089-001 | Expi293 | 16.8 | >99 |
| AB0089-002 | ExpiCHO | 68.3 | >99 |

Protein A Capture

Figure 120:
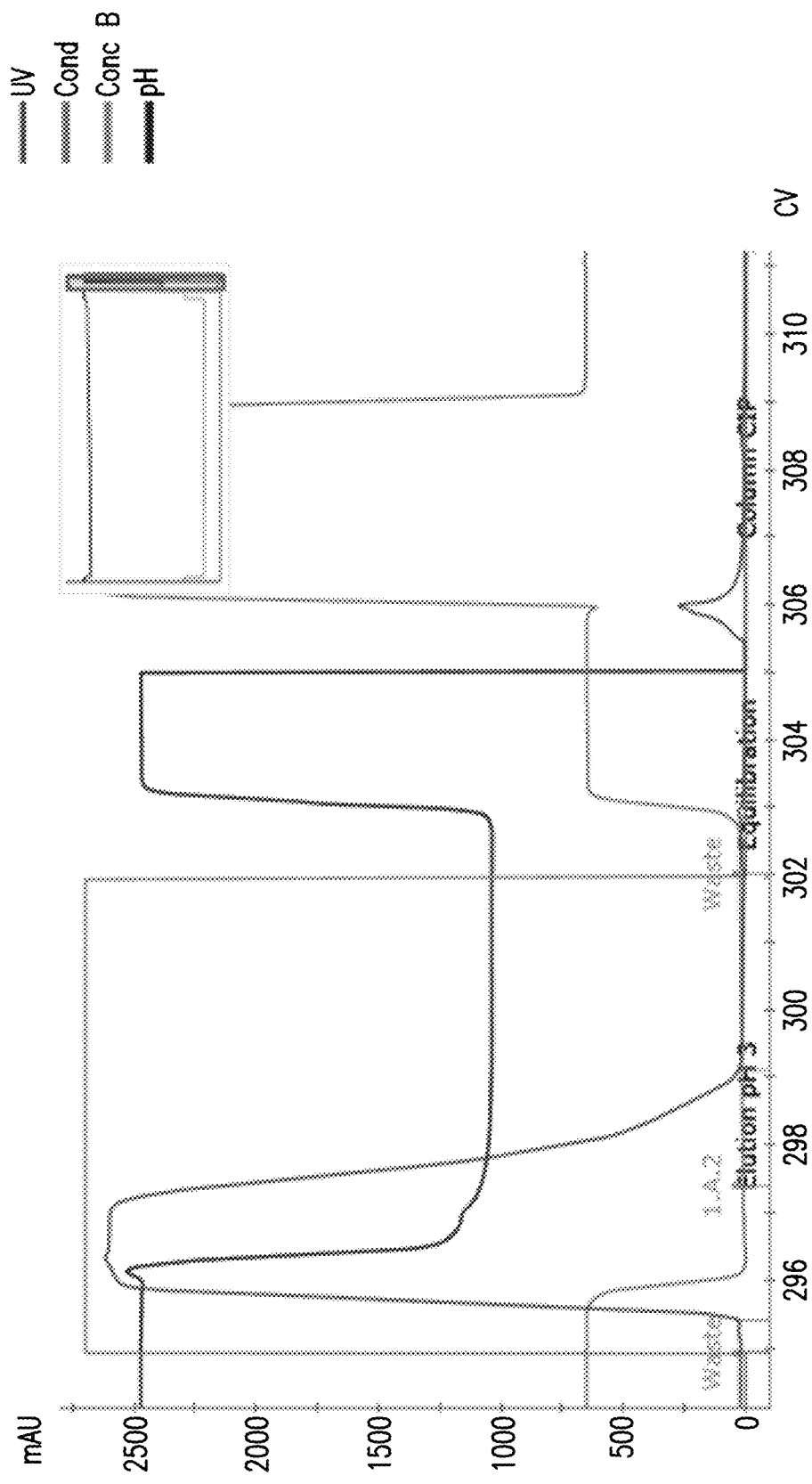
FIG. 120 shows a Mab Select Protein A capture elution chromatogram.

AB0089 was expressed in ExpiCHO cell line as described above. Approximately 5.7 liters of filtered supernatant was loaded on a Protein A column. Load flow rate was 10 ml/min (298 cm/h; 3.3 minute residence time). The capture step yield was approximately 752 mg. FIG. 120 shows the capture step chromatogram.

Figure 121:
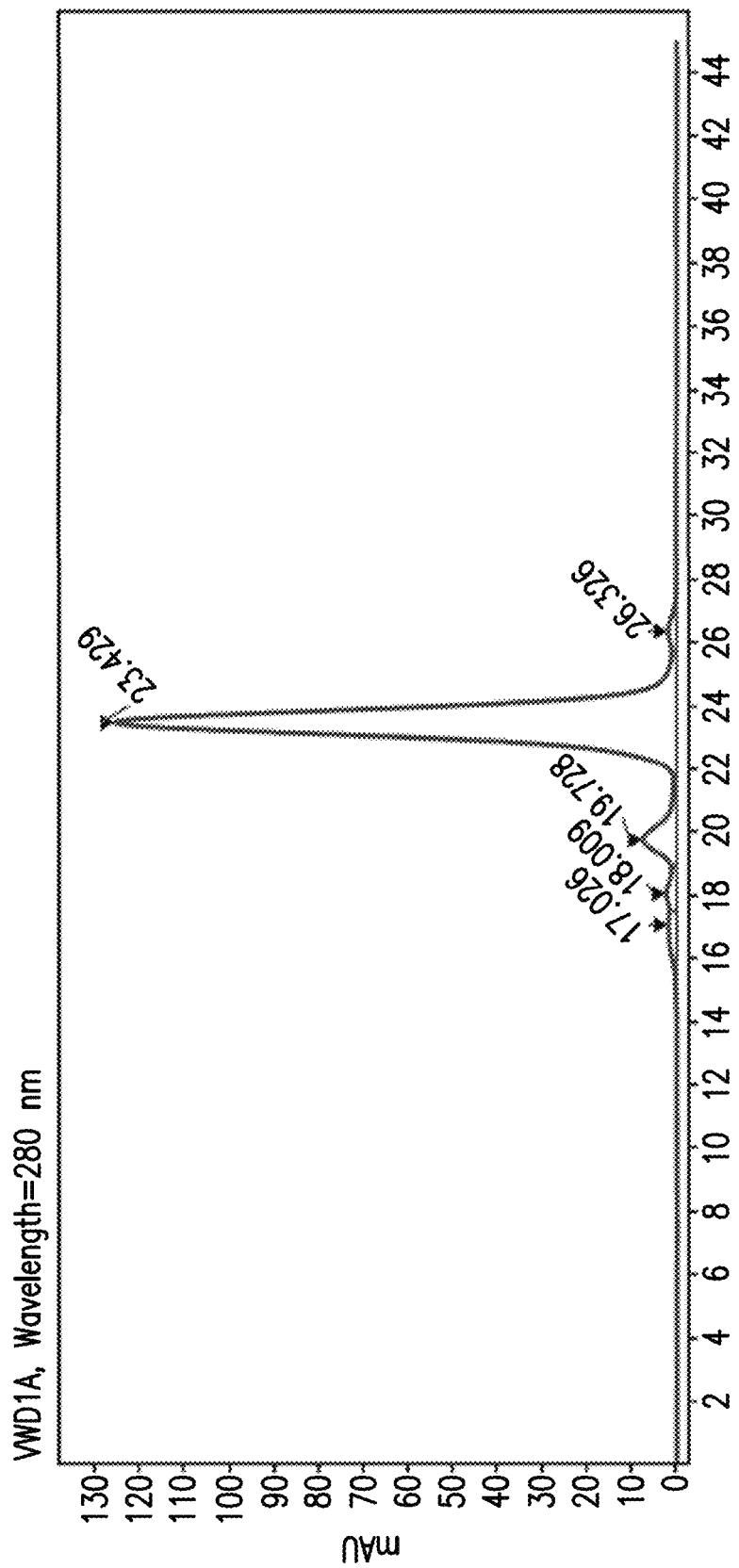

By SEC analysis, the Protein A eluate contains mainly desired heterodimeric AB0089 species (approximately 88.8%) eluting at 23.4 min (FIG. 121). Impurities include UMW aggregates and very little amount of LMW.

SDS-PAGE analysis of the Protein A load, flow-though and eluate demonstrate that capture of AB0089 was complete, based on absence of a AB0089 band in the flow through sample. The protein A eluate lane shows primarily TriNKET with additional bands corresponding to the HMW and LMW peaks observed by SEC (FIG. 122).

Cation Exchange Chromatography

The Protein A eluate was further purified by cation exchange chromatography using a Poros XS column (1.2 cm D×20 cm H) operated at a flow rate of 7 ml/min (371 cm/h; 3.2-minute residence time). The product began to elute with the 15% B elution step, when conductivity reached approximately 20 mS/cm (FIG. 123). SDS-PAGE analysis of the elution fractions shows highly pure product in the first five fractions (FIG. 124). Peak tail fractions were excluded from the IEX product pool as SDS-PAGE indicates the presence of contaminating product-related proteins.

The IEX fractions were concentrated resulting in approximately 401 mg of purified AB0089. The pooled fractions were buffer exchanged to PBS pH 7.4 by dialysis. The AB0089 yield after buffer exchange was approximately 391 mg at a final concentration of 9.66 mg/ml (AB0089 lot AB0089-002). Yields and recoveries for AB0089 lot AB0089-002 production are summarized in Table 129.

TABLE 129

Yields and recoveries of AB0089 purification and buffer exchange process.

| Step | Total Protein (mg) | Step Recovery (%) | Total Recovery (%) |
|---|---|---|---|
| MabSelect SuRe Capture | 752 | NA | NA |
| POROS XS Polish | 401 | 53 | 53 |
| Post Buffer Exchange | 391 | 98 | 52 |

NA, not applicable

Characterization of AB0089 Lot AB0089-002 Used in Cyno Study

AB0089 lot AB0089-002 intended for use in cyno study was extensively characterized for purity, identity, binding to the targets and potency. All tested criteria met specification.

Purity by SDS-PAGE

SDS-PAGE of the final sample showed major bands were consistent with expected molecular weight for both reduced and non-reduced AB0089 (FIG. 125).

Purity by Analytical SEC (Superdex 200)

SEC analysis of purified AB0089 lot AB0089-002 showed 100% monomer as determined by integrated peak area (FIG. 126).

Identity by Intact Mass Analysis

The identity of AB0089 (lot AB0089-002) was corroborated by mass spectrometry (FIG. 127). LC-MS analysis of the intact AB0089 showed an observed mass (126,130.0 Da) that agrees well with the theoretical mass of 126,129.1 Da. The major observed glycosylation pattern (G0F/G0F) is typical for an Fc-containing molecule expressed in CHO cells.

Endotoxin

The endotoxin level of the final AB0089 lot AB0089-002 was 0.259 EU/mg. All assay parameters met specification.

Biochemical and Biophysical Properties

AB0089 was characterized by SEC, CE, cIEF, HIC, and DSC to corroborate that is has the proper purity and pre-developability characteristics of a good biological therapeutic.

Purity

Purify of AB0089 was determined by CE-SDS (FIGS. 128A-128B). Under non-reduced conditions the major impurities are method induced (free light chain and TriNKET—LC). Under reduced conditions the 3 expected chains (LC, HC, and scFv-Fc chain) are observed. The purity of AB0089 lot AB0089-002 determined by SEC, NR and R CE-SDS is summarized in Table 130.

TABLE 130

Purity of AB0089 by SEC and CE-SDS analysis.

| Test article | SEC | | | NR CE-SDS | R CE-SDS |
|---|---|---|---|---|---|
| | HMW (%) | Monomer (%) | LMW (%) | Purity (%) | Purity (%) |
| AB0089 | ND | 100 | ND | 98.9 | 98.0 |

ND, none detected

Experimental pI and Charge Profile by cIEF

Charge profile of AB0089 was analyzed by cIEF (FIG. 129). AB0089 showed a major peak at a pI of 8.52±0.0. Several lesser abundant, overlapping acidic peaks and minor basic peaks are also observed.

Hydrophobicity Assessed by HIC.

The hydrophobic properties of AB0089 were assessed by HIC (FIG. 130, Table 131). The chromatogram revealed a single narrow peak, indicating that the molecule is highly pure and homogeneous. The HIC retention time was 10.2 minutes, which is within the range of well behaving marketed monoclonal antibodies (8.9-13.5 minutes, data not shown).

TABLE 131

Hydrophobicity assessment of AB0089 by HIC. Humira is used as an internal control of well-behaved IgG1 mAb.

| Test article | HIC retention time (min) |
|---|---|
| AB0089 | 10.2 |
| Humira | 8.9 |

Thermal Stability by DSC

The thermal stability of AB0089 was assessed by DSC in several buffers (PBS pH 7.4, HST pH 6.0, CST pH 7.0). AB0089 demonstrated high thermal stability in all buffers tested (FIGS. 131A-131C). $T_m1$ corresponding to the unfolding of scFv satisfied the ≥65° C. criteria utilized in thermostability assessment (Table 132).

TABLE 132

Thermal stability of AB0089 by DSC.

| Test Article | Buffer | $T_{onset}$ (° C.) | $T_{m1}$ (° C.) | $T_{m2}$ (° C.) | $T_{m3}$ (° C.) | $T_{m4}$ (° C.) |
|---|---|---|---|---|---|---|
| AB0089 | PBS, pH 7.4 | 64.0 | 71.8 | 76.7 | 81.3 | 83.4 |
| AB0089 | HST, pH 6.0 | 61.2 | 69.0 | 78.7 | 84.3 | 86.3 |
| AB0089 | CST, pH 7.0 | 64.7 | 72.4 | 77.1 | 82.2 | 84.2 |

Disulfide Bond Assignment

AB0089 is an engineered molecule based on the backbone of a monoclonal IgG1 antibody. While a typical IgG1 contains 16 disulfide bonds, AB0089's F3' format has only 15 disulfide bonds. Half of AB0089 is an anti-NKG2D half antibody, as such it contains the expected seven disulfide bonds (one in each IgG domain and the intermolecular disulfide connecting the LC to the HC). The other half of AB0089 is an anti-CLEC12A scFv-Fc fusion. The scFv contains three disulfide bonds (one in each anti-CLEC12A VH and VL domains and an engineered, stabilizing disulfide bridging the variable domains) and the Fc contains the two expected disulfides in the IgG domains. The heterodimer is covalently associated with two native IgG1 hinge disulfides and one additional intermolecular engineered disulfide connecting the Fab-Fc to the scFv-Fc in the CH3 domain. Together this results in 15 expected disulfide bonds in AB0089. The predicted disulfide map for AB0089 is shown in FIG. 132.

The disulfide bond connectivity of AB0089 was corroborated by LC-MS/MS peptide mapping analysis of a non-reduced digest. Disulfide bonded peptides were identified by MS/MS database searching and corroborated by comparing their intensities in the native and reduced digests. In the tryptic digestion, the VL and engineered disulfide pairs are connected by a long peptide that contains 2 cysteines (three peptides connected by two disulfide bonds, S7:S36:S22) that is not observed in the LC-MSMS data. To detect the engineered scFv stabilizing disulfide, AB0089 was digested with both trypsin and chymotrypsin. FIGS. 133A-133B show the extracted ion chromatogram (XICs) for the engineered disulfide pair in the scFv (non-reduced and reduced) and the most intense charge state for that peptide pair. The VL disulfide pair was not observed in the trypsin/chymotrypsin double digest, presumably because it is too small and hydrophilic to be retained on the column. All other disulfides were identified after digestion with only trypsin, including the engineered S—S bridge introduced to stabilize the Fc heterodimerization (FIGS. 134A-134B).

A summary of the observed disulfide linked peptides in AB0089 is shown in Table 133. All observed disulfide linked peptides were had high mass accuracy (<4 ppm), were reducible, and were sequence corroborated by MS/MS fragmentation.

TABLE 133

Disulfide linked peptides theoretical and experimental masses.

| Domain | Tryptic peptide | Theoretical mass (Da) | Experimental mass (Da) | Mass accuracy (ppm) |
|---|---|---|---|---|
| VL | L2:L7 | 4482.0784 | 4482.0786 | 0.4 |
| CL | L12:L19 | 3555.749 | 3555.755 | 1.8 |
| CL-CH1 intermolecular | L20-21:H19 | 1260.4863 | 1260.4861 | −0.3 |
| VH | H3:H10 | 3371.4686 | 3371.4666 | 2.5 |
| CH1 | H13:H14-15 | 7916.9194 | 7916.9282 | 1.5 |
| Hinge | H20-21:S17-18 | 5454.7834 | 5454.7905 | 1.5 |
| CH2 | H23:H30 | 2328.0977 | 2328.1018 | 1.8 |
| CH3-CH3 intermolecular[a] | H36:S34-35 | 2757.383 | 2757.3855 | 1.6 |
| CH3 | H37:H41 | 4432.0675 | 4432.0687 | 0.3 |
| scFv VH | S1-2:S8 | 5828.907 | 5828.9052 | −0.1 |
| scFv stabilizing[a] | S7:S36[b] | 1011.4154 | 1011.4188 | 3.4 |
| scFv VL | S10-11:S14 | | Not detected | |
| CH2 | S20:S27 | | non-unique, see H23:H30 | |
| CH3 | S36:S41 | 3844.8236 | 3844.8284 | 1.2 |

[a]Engineered disulfide, [b]Trypsin/chymotrypsin double digest

Binding Characteristics
Binding Affinity for Human CLEC12A

The affinity of AB0089 for human CLEC12A was determined by SPR at 37° C. AB0089 binds with high affinity to human CLEC12A (FIGS. 135A-135D and Table 134). However, the binding demonstrates heterogeneity and does not follow typical 1:1 binding kinetics. An experiment described below and in FIG. 136 established a two-state binding mechanism and justified the use of a two-state model for fitting the data. Similar two-state reaction kinetics was observed for CLEC12A binding arm of tepoditamab (Merus).

TABLE 134

Kinetic parameters and binding affinity of AB0089 for hCLEC12A.

| Test article | $k_{a1}$ (M$^{-1}$s$^{-1}$) | $k_{d1}$ (s$^{-1}$) | $k_{a2}$ (s$^{-1}$) | $k_{d2}$ (s$^{-1}$) | $K_D$ (nM) |
|---|---|---|---|---|---|
| AB0089 | $1.09 \times 10^7$ | $4.26 \times 10^{-2}$ | $3.41 \times 10^{-3}$ | $7.28 \times 10^{-4}$ | 0.69 |
| AB0089 | $1.06 \times 10^7$ | $4.49 \times 10^{-2}$ | $3.49 \times 10^{-3}$ | $7.48 \times 10^{-4}$ | 0.75 |
| AB0089 | $1.02 \times 10^7$ | $4.32 \times 10^{-2}$ | $3.45 \times 10^{-3}$ | $7.41 \times 10^{-4}$ | 0.75 |

TABLE 134-continued

Kinetic parameters and binding affinity of AB0089 for hCLEC12A.

| Test article | $k_{a1}$ (M$^{-1}$s$^{-1}$) | $k_{d1}$ (s$^{-1}$) | $k_{a2}$ (s$^{-1}$) | $k_{d2}$ (s$^{-1}$) | $K_D$ (nM) |
|---|---|---|---|---|---|
| AB0089 | $9.99 \times 10^6$ | $4.32 \times 10^{-2}$ | $3.39 \times 10^{-3}$ | $7.49 \times 10^{-4}$ | 0.78 |
| Average ± Std Dev. | $(1.04 \pm 0.03) \times 10^7$ | $(4.35 \pm 0.12) \times 10^{-2}$ | $(3.43 \pm 0.04) \times 10^{-3}$ | $(7.41 \pm 0.10) \times 10^{-4}$ | $0.74 \pm 0.04$ |

A two-state binding model assumes two binding stages that are defined by two sets of kinetic constants:

1. formation of an initial CLEC12A-AB0089 complex
2. transition of the initial complex into a more stable, final complex

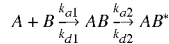

$$A + B \underset{k_{d1}}{\overset{k_{a1}}{\rightarrow}} AB \underset{k_{d2}}{\overset{k_{a2}}{\rightarrow}} AB^*$$

This mechanism implies that longer association times in an SPR experiment would lead to a higher ratio of the more stable complex on the surface and a slower apparent dissociation rate. Both AB0089 and a tepoditamab based molecule have an association time dependent apparent dissociation rate, thus corroborating the two-state interaction model (FIG. 136).

Binding to CLEC12A+Isogenic and Cancer Cell Lines

Assessment of AB0089 binding to isogenic cell lines expressing CLEC12A and AML cancer cells was monitored by FACS (FIGS. 137A-137D, Table 135). AB0089 showed high affinity for cell surface expressed CLEC12A and binds AML cell lines PL-21 and HL-60 with EC50 less than 1 nM.

Specificity of AB0089 for CLEC12A was demonstrated by lack of binding to the parental Ba/F3 cells that do not express the target.

TABLE 135

Binding of AB0089 to isogenic and cancer cell lines expressing CLEC12A.

| Cell line | EC50 (nM) |
|---|---|
| Ba/F3-hCLEC12A | 4.02 |
| Ba/F3 parental | No binding |
| PL21 | 0.45 |
| HL-60 | 0.74 |

Binding Affinity for Polymorphic Variant of Human CLEC12A (Q244)

Polymorphic variant CLEC12A (Q244) is prevalent in 30% of population. We tested binding of AB0089 to this genetic variant by SPR and compared its affinity to the major form of CLEC12A (K244) (FIGS. 138A-138C). Binding affinities of AB0089 for WT and Q244 variant of CLEC12A were similar (Table 136). Binding of AB0089 to cynomolgus monkey CLEC12A (cCLEC12A) was also tested. No binding was observed at 100 nM concentration, demonstrating that AB0089 is not cross-reactive to cynomolgus CLEC12A.

TABLE 136

Kinetic parameters and binding affinity of AB0089 for (K244) and (Q244) variants of human CLEC12A.

| Test article | Target | $k_{a1}$ (M$^{-1}$s$^{-1}$) | $k_{d1}$ (s$^{-1}$) | $k_{a2}$ (s$^{-1}$) | $k_{d2}$ (s$^{-1}$) | $K_D$ (nM) |
|---|---|---|---|---|---|---|
| AB0089 | hCLEC12A (K244) WT | $(1.63 \pm 0.51) \times 10^7$ | $(3.98 \pm 0.14) \times 10^{-2}$ | $(2.95 \pm 0.06) \times 10^{-3}$ | $(9.62 \pm 0.00) \times 10^{-4}$ | $0.60 \pm 0.26$ |
| AB0089 | hCLEC12A (Q244) | $(9.70 \pm 0.45) \times 10^{-6}$ | $(3.53 \pm 0.13) \times 10^{-3}$ | $(2.67 \pm 0.06) \times 10^{-3}$ | $(1.25 \pm 0.02) \times 10^{-3}$ | $1.17 \pm 0.00$ |

Binding to Differentially Glycosylated CLEC12A

Human CLEC12A is a heavily glycosylated protein (6 potential N-glycosylation sites with an extracellular domain (ECD) compromising of 201 amino acids). Variations in the glycosylation status of CLEC12A on the surface of different cell types is documented in the literature (Marshall et al., (2006) *Eur. J. Immunol.*, 36: 2159-2169). CLEC12A expressed on the surface of AML cells from different patients may have different glycosylation patterns as well. To determine if AB0089 binds to different glyco-variants of human CLEC12A, the antigen was treated with neuraminidase (to remove terminal sialic acids) or PNGaseF (to remove N-linked glycans) and affinity was compared to untreated CLEC12A by SPR (FIGS. 139A-139C and Table 137). AB0089 bound to both fully glycosylated and de-glycosylated CLEC12A and is expected to be unaffected by heterogeneity in target glycan composition.

TABLE 137

Kinetic parameters and binding affinity of AB0089 for differentially glycosylated CLEC12A.

| Test article | Target | $k_{a1}$ (M$^{-1}$s$^{-1}$) | $k_{d1}$ (s$^{-1}$) | $k_{a2}$(s$^{-1}$) | $k_{d2}$ (s$^{-1}$) | $K_D$ (nM) |
|---|---|---|---|---|---|---|
| AB0089 | Untreated CLEC12A | $(1.63 \pm 0.05) \times 10^7$ | $(3.98 \pm 0.01) \times 10^{-2}$ | $(2.95 \pm 0.06) \times 10^{-3}$ | $(9.62 \pm 0.00) \times 10^{-4}$ | $0.60 \pm 0.26$ |
| AB0089 | De-sialylated CLEC12A | $(2.09 \pm 0.21) \times 10^7$ | $(3.29 \pm 0.18) \times 10^{-2}$ | $(3.04 \pm 0.06) \times 10^{-3}$ | $(8.63 \pm 0.24) \times 10^{-4}$ | $0.35 \pm 0.47$ |
| AB0089 | De-glycosylated CLEC12A | $(8.96 \pm 0.86) \times 10^6$ | $(6.33 \pm 0.28) \times 10^{-3}$ | $(4.09 \pm 0.13) \times 10^{-3}$ | $(5.67 \pm 0.10) \times 10^{-4}$ | $0.09 \pm 0.01$ |

Average of 3 replicates

Binding Affinity for Human NKG2D

AB0089 was tested for binding to human NKG2D ECD by SPR (Biacore) at 37° C. (FIGS. 140A-140F). NKG2D is a dimer in nature, therefore recombinant mFc-tagged NKG2D dimer was used for this experiment. The shape of the binding sensorgrams depicted in FIGS. 140A-140F enabled two different fitting models to calculate affinity and kinetic rates data: steady state affinity fit and 1:1 kinetic fit. The kinetic constants and equilibrium affinity values are shown in Table 138. AB0089 was designed to bind to human NKG2D with low affinity, most importantly with the fast rate of dissociation. The dissociation rate constant was $1.43 \pm 0.03 \times 10^{-1}$ s$^{-1}$. Affinity values ($K_D$) obtained by fitting the data to a 1:1 kinetic and steady state affinity models were very similar, $881 \pm 10$ nM and $884 \pm 11$ nM respectively, which suggests high confidence in the measured parameters.

TABLE 138

Kinetic parameters and binding affinity of AB0089 for human NKG2D.

| Test article | $k_a$ (M$^{-1}$s$^{-1}$) | $k_d$ (s$^{-1}$) | Kinetics Fit $K_D$ (nM) | Steady State Fit $K_D$ (nM) |
|---|---|---|---|---|
| AB0089 | $1.61 \times 10^5$ | $1.41 \times 10^{-1}$ | 872 | 873 |
| AB0089 | $1.59 \times 10^5$ | $1.42 \times 10^{-1}$ | 892 | 894 |
| AB0089 | $1.66 \times 10^5$ | $1.46 \times 10^{-1}$ | 880 | 885 |
| Average ± Std Dev. | $(1.62 \pm 0.03) \times 10^5$ | $(1.43 \pm 0.03) \times 10^{-1}$ | $881 \pm 10$ | $884 \pm 11$ |

Binding Affinity for CD16a (FcγRIIIa)

One of the modalities of AB0089 mechanism of action is through engaging human CD16a (FcγRIIIa) that is expressed on NK cells via its Fc. Binding of AB0089 to CD16a (V158 allele) was evaluated by SPR and compared to the CD16a (V158) affinity for trastuzumab, an approved and marketed monoclonal antibody therapeutics of the same IgG1 isotype (FIGS. 141A-141F, Table 139). Binding of AB0089 to CD16a is comparable to the one of trastuzumab. A 3.8-fold difference in affinity is unlikely to be of physiological consequence and is also unlikely to impact AB0089 therapeutic effect since the latter relies on synergy of simultaneous engagement of two targets on the NK cells, CD16 and NKG2D. Additionally, a slightly weaker binding to CD16a may also be of benefit for the drug's safety.

TABLE 139

Kinetic parameters and binding affinity of AB0089 for hCD16a (V158).

| Test article | $k_a$ (M$^{-1}$s$^{-1}$) | $k_d$ (s$^{-1}$) | $K_D$ (nM) |
|---|---|---|---|
| AB0089 | $8.76 \times 10^4$ | $2.94 \times 10^{-2}$ | 336 |
| AB0089 | $7.70 \times 10^4$ | $2.64 \times 10^{-2}$ | 343 |
| AB0089 | $8.46 \times 10^4$ | $2.72 \times 10^{-2}$ | 321 |
| Average ± StDev | $(8.31 \pm 0.55) \times 10^4$ | $(2.77 \pm 0.16) \times 10^{-2}$ | $333 \pm 11$ |
| trastuzumab | $1.31 \times 10^5$ | $1.12 \times 10^{-2}$ | 86 |
| trastuzumab | $1.22 \times 10^5$ | $1.08 \times 10^{-2}$ | 89 |
| trastuzumab | $1.30 \times 10^5$ | $1.13 \times 10^{-2}$ | 87 |
| Average ± StDev | $(1.28 \pm 0.05) \times 10^5$ | $(1.11 \pm 0.03) \times 10^{-2}$ | $87 \pm 1$ |

Binding to Fcγ Receptors

Since AB0089 is an IgG1 derived biologic drug candidate it is important that it maintains appropriate Fc receptor binding properties. SPR data suggest that AB0089 binds human and cynomolgus Fcγ receptors with affinities comparable to trastuzumab, a marketed IgG1 biologic that served an experimental control (Table 140). Detailed description of each individual receptor binding is presented below.

TABLE 140

Summary of affinities of AB0089 and trastuzumab for human and cynomolgus FcγRs.

| Fcγ receptor | AB0089, $K_D$ (nM) | trastuzumab, $K_D$ (nM) |
|---|---|---|
| hFcγRI | 5.1 ± 1.0 | 2.9 ± 0.4 |
| cFcγRI | 1.5 ± 0.3[a] | 1.0 ± 0.1 |
| hFcγRIIa H131 | 900.4 ± 57.1 | 1045.1 ± 62.2 |
| hFcγRIIa R131 | 1253.3 ± 269.2 | 1493.2 ± 265.9 |
| hFcγRIIIa V158 | 333.4 ± 11.1 | 87.1 ± 1.4 |
| hFcγRIIIa F158 | 1271.0 ± 24.6 | 331.4 ± 3.3 |
| cFcγRIII[a] | 348.8 ± 2.4 | 128.8 ± 2.1 |
| hFcγRIIb | 6270.3 ± 1164.4 | 6270.3 ± 1031.7 |
| hFcγRIIIb[a] | 8851.3 ± 1454.4 | 3872.4 ± 486.3 |

[a] n = 3, otherwise n = 4

Binding of AB0089 to Recombinant Human and Cynomolgus CD64 (FcγRI)

FIGS. 142A-142H and FIGS. 143A-143G depict binding of AB0089 to human and cynomolgus CD64, respectively. Table 141 demonstrates that AB0089 binds recombinant human and cynomolgus CD64 with affinities comparable (less than two-fold different) to trastuzumab.

TABLE 141

Binding of AB0089 and trastuzumab to human and cynomolgus CD64.

| Human FcγRI | $k_a$ (M$^{-1}$s$^{-1}$) | $k_d$ (s$^{-1}$) | $K_D$ (nM) |
|---|---|---|---|
| AB0089 Lot AB0089-002 | 4.4 × 10$^4$ | 1.8 × 10$^{-4}$ | 6.4 |
| AB0089 Lot AB0089-002 | 4.6 × 10$^4$ | 2.2 × 10$^{-4}$ | 4.7 |
| AB0089 Lot AB0089-002 | 4.6 × 10$^4$ | 1.9 × 10$^{-4}$ | 4.1 |
| AB0089 Lot AB0089-002 | 4.6 × 10$^4$ | 2.4 × 10$^{-4}$ | 5.2 |
| Average ± StDev | (4.6 ± 0.1) × 10$^4$ | (2.3 ± 0.4) × 10$^{-4}$ | 5.1 ± 1.0 |
| trastuzumab | 9.0 × 10$^4$ | 2.3 × 10$^{-4}$ | 2.5 |
| trastuzumab | 8.6 × 10$^4$ | 2.1 × 10$^{-4}$ | 2.5 |
| trastuzumab | 8.3 × 10$^4$ | 2.7 × 10$^{-4}$ | 3.2 |
| trastuzumab | 8.8 × 10$^4$ | 2.8 × 10$^{-4}$ | 3.2 |
| Average ± StDev | (8.1 ± 0.0) × 10$^4$ | (2.5 ± 0.3) × 10$^{-4}$ | 2.9 ± 0.4 |
| Cynomolgus FcγRI | $k_a$ (M$^{-1}$s$^{-1}$) | $k_d$ (s$^{-1}$) | $K_D$ (nM) |
| AB0089 Lot AB0089-002 | 5.5 × 10$^4$ | 8.1 × 10$^{-5}$ | 1.5 |
| AB0089 Lot AB0089-002 | 5.4 × 10$^4$ | 9.5 × 10$^{-5}$ | 1.8 |
| AB0089 Lot AB0089-002 | 5.5 × 10$^4$ | 6.6 × 10$^{-5}$ | 1.2 |
| Average ± StDev | (5.5 ± 0.0) × 10$^4$ | (8.1 ± 1.5) × 10$^{-5}$ | 1.5 ± 0.3 |
| trastuzumab | 1.3 × 10$^5$ | 1.4 × 10$^{-4}$ | 1.1 |
| trastuzumab | 1.3 × 10$^5$ | 1.2 × 10$^{-4}$ | 0.9 |
| trastuzumab | 1.3 × 10$^5$ | 1.1 × 10$^{-4}$ | 0.8 |
| trastuzumab | 1.3 × 10$^5$ | 1.3 × 10$^{-4}$ | 1.0 |
| Average ± StDev | (1.3 ± 0.1) × 10$^5$ | (1.2 ± 0.2) × 10$^{-4}$ | 1.0 ± 0.1 |

Binding of AB0089 to Recombinant Human CD32a (FcγRIIa)

FIGS. 144A-144P and FIGS. 145A-145P depict binding of AB0089 and trastuzumab to CD32a (H131 and R131 alleles), respectively, tested by SPR. There is no meaningful difference between affinities of both alleles for AB0089 and trastuzumab (Table 142).

TABLE 142

Binding of AB0089 and trastuzumab to recombinant human CD32a (FcγRIIa).

| | $K_D$ (nM) | |
|---|---|---|
| Test article | FcgRIIa H131 | FcgRIIa R131 |
| AB0089 (lot AB0089-002) | 953.6 | 1335.7 |
| AB0089 (lot AB0089-002) | 822.8 | 1024.1 |
| AB0089 (lot AB0089-002) | 930.1 | 1598.0 |
| AB0089 (lot AB0089-002) | 895.0 | 1055.3 |
| Average ± StDev | 900.4 ± 57.1 | 1253.3 ± 269.2 |
| trastuzumab | 1069.2 | 1488.2 |
| trastuzumab | 953.1 | 1381.0 |
| trastuzumab | 1090.2 | 1862.1 |
| trastuzumab | 1068.0 | 1241.4 |
| Average ± StDev | 1045.1 ± 62.2 | 1493.2 ± 265.9 |

Binding of AB0089 to Human CD16a (FcγR3a) and Cynomolgus CD16 (FcγR3)

Detailed description of AB0089 binding to high affinity CD16a (V158) is provided herein. Binding of AB0089 to the F158 allele of human CD16a and cynomolgus CD16 are presented in Table 143, FIGS. 146A-146P, and FIGS. 147A-147L. Binding of AB0089 to recombinant human CD16a (V158 and F158 alleles) and cynomolgus CD16 is comparable to a marketed IgG1 biologic drug trastuzumab. A 2.3-3.8 difference in affinity for CD16 proteins between AB0089 and trastuzumab is unlikely to be of physiological consequence and also unlikely to impact the therapeutic effect since the latter relies on the synergy of engagement of two targets on the NK cells (CD16a and NKG2D). Small difference in apparent maximum binding responses between trastuzumab and AB0089 is attributed to a difference in molecular weight. Additionally, some replicates may display slight variability in apparent maximum binding responses caused by slight variation of receptor capture levels. Note that while the shape of the sensorgrams representing binding to human CD16a F158 allele affords fitting the interactions to both, steady-state and 1:1 kinetic, models, affinity fit (steady-state) model was used for historic reasons.

TABLE 143

Binding of AB0089 and trastuzumab to recombinant human CD16a F158 allele and cynomolgus CD16a.

| Test article | Human FcγIIIa F158 $K_D$ (nM) | Cyno FcγRIII $K_D$ (nM) |
|---|---|---|
| AB0089 (AB0089-002) | 1250.9 | 351.3 |
| AB0089 (AB0089-002) | 1250.6 | 346.7 |
| AB0089 (AB0089-002) | 1282.2 | 348.3 |
| AB0089 (AB0089-002) | 1300.4 | |
| Average ± StDev | 1271.0 ± 24.6 | 348.8 ± 2.4 |
| trastuzumab | 332.3 | 127.1 |
| trastuzumab | 326.6 | 128.1 |
| trastuzumab | 333.8 | 131.1 |
| trastuzumab | 333.1 | |
| Average ± StDev | 331.4 ± 3.3 | 128.8 ± 2.1 |

Binding of AB0089 to Human CD32b (FcγR2b)

FIGS. 148A-148P depict binding to AB0089 and trastuzumab to CD32b tested by SPR. There is no meaningful difference between affinities of CD32b for AB0089 and trastuzumab (Table 144).

TABLE 144

Binding of AB0089 and trastuzumab to
CD32b (FcγR2b).

| Test article | $K_D$ (μM) |
|---|---|
| AB0089 (lot AB0089-002) | 7.1 |
| AB0089 (lot AB0089-002) | 5.3 |
| AB0089 (lot AB0089-002) | 5.3 |
| AB0089 (lot AB0089-002) | 7.4 |
| Average ± StDev | 6.3 ± 1.2 |
| trastuzumab | 7.1 |
| trastuzumab | 5.6 |
| trastuzumab | 5.2 |
| trastuzumab | 7.2 |
| Average ± StDev | 6.3 ± 1.0 |

Binding of AB0089 to Human CD16b (FcγR3b)

FIGS. 149A-149L depict binding of AB0089 and trastuzumab to CD16b tested by SPR. AB0089 binds human CD16b (FcγR3b) comparably to trastuzumab (Table 145). 2.3-fold difference in affinity for the receptor is unlikely to be of physiological significance.

TABLE 145

Binding of AB0089 and trastuzumab to
recombinant human CD16b (FcγR3b).

| Test Article | $K_D$ (μM) |
|---|---|
| AB0089 (lot AB0089-002) | 10.3 |
| AB0089 (lot AB0089-002) | 8.8 |
| AB0089 (lot AB0089-002) | 7.4 |
| Average ± StDev | 8.9 ± 1.5 |
| trastuzumab | 4.3 |
| trastuzumab | 3.9 |
| trastuzumab | 3.4 |
| Average ± StDev | 3.9 ± 0.5 |

Binding to FcRn

FIGS. 150A-150P and FIGS. 151A-151L depict AB0089 binding to human and cyno FcRn, respectively, tested by SPR. Affinities of AB0089 for human and cynomolgus FcRn are similar to those of trastuzumab, a marketed IgG1 biologic that served as an experimental control (Table 146).

TABLE 146

Summary of affinities of AB0089 and
trastuzumab for human and cyno FcRn.

| FcRn | AB0089, $K_D$ (μM) | trastuzumab, $K_D$ (μM) |
|---|---|---|
| hFcRn, pH 6.0 | 1.1 ± 0.1 | 1.7 ± 0.2 |
| cFcRn, pH 6.0[a] | 1.0 ± 0.1 | 1.5 ± 0.1 |

[a] n = 3, otherwise n = 4

Simultaneous Engagement of AB0089 to CD16a and NKG2D

AB0089 is a tri-functional IgG-based biologic with two binding modalities on the NK cells: CD16a binding is achieved through the Fc and NKG2D binding is achieved through A49M-I Fab. Both interactions are important for the optimal cytotoxic activity of AB0089. To demonstrate synergy of co-engagement of human CD16a and human NKG2D binding, we performed an SPR experiment where we qualitatively compared binding of AB0089 to NKG2D, CD16a and mixed NKG2D-CD16a Biacore chip surfaces. The affinity of AB0089 for human NKG2D and human CD16a are both low, however, binding to both targets simultaneously results in an avidity effect that manifests as a slower off-rate. Thus, AB0089 can avidly engage CD16a and NKG2D (FIG. 152).

Co-Engagement of CLEC12A and NKG2D

To determine if binding of one target interferes with binding of the other target to AB0089, the CLEC12A and NKG2D were sequentially injected over AB0089 captured on an anti-hFc IgG SPR chip (FIGS. 153A-153B). Target binding sensorgrams demonstrate that the occupancy status of the CLEC12A domain does not interfere with NKG2D binding (FIG. 153A) and vice versa (FIG. 153B). Similarity in shapes of the respective sensorgram segments depicting binding of each target to free AB0089 and AB0089 that has been saturated with the other target suggests that the kinetic parameters are not meaningfully affected by the target occupancy status of the AB0089 molecule. For instance, the shape of the CLEC12A binding segment of the sensorgrams is similar in both panels. Note that saturating concentration of the NKG2D had to be maintained throughout the entire experiment represented in lower panel due to fast dissociation rate of this target. Additionally, the lack of any impact on relative stoichiometry of each target binding (when compared to binding to unoccupied AB0089) signifies full independence of NKG2D and CLEC12A binding sites on AB0089 (Table 147). Therefore, AB0089 may successfully achieve simultaneous co-engagement of the tumor antigen and the NKG2D targeting arm.

TABLE 147

Relative binding stoichiometry of AB0089 for
CLEC12A and NKG2D.
Binding stoichiometries are expressed relative to
binding of each target to unoccupied captured AB0089.

| | CLEC12A, relative binding stoichiometry | NKG2D, relative binding stoichiometry |
|---|---|---|
| Target bound to AB0089 unoccupied with another target (injected first) | 1.00 | 1.00 |
| Target bound to AB0089 saturated with another target (injected second) | 1.16 ± 0.02 | 1.16 ± 0.06 |

Epitope Binning

We compared binding epitope of AB0089 in relation to AB0237, AB0192 and three CLEC12A binding reference TriNKETs by SPR. cFAE-A49. Tepoditamab is based on CLEC12A binding arm of a molecule from Merus (WO_2014_051433_A1), cFAE-A49. CLL1-Merus is based on the clone 4331 from Merus (WO_2014_051433_A1) and cFAE-A49. h6E7 is based on h6E7 mAb from Genentech (h6E7) (US_2016_0075787_A1). AB0089 interaction with hCLEC12A was blocked by AB0237, and two control molecules, cFAE-A49. CLL1-Merus and cFAE-A49. Tepoditamab, but not by not Genentech-h6E7 based molecule (FIG. 154) suggesting that the binding epitope of AB0089 overlaps with the epitope of tepoditamab. The results indicated that both AB0089 and AB0237 share the same epitope. This footprint is different from AB0192 which additionally cross-blocks with cFAE-A49.h6E7.

Potency

Potency of AB0089 was tested using the KHYG-1-CD16aV cytotoxicity assay with a NK cell line engineered to stably express CD16aV and NKG2D (FIGS. 155A-155B and Table 148). AB0089 demonstrated sub-nanomolar potency in driving the lysis of HL60 and PL-21 AML cells. In addition AB0089 potently enhances cytotoxic lysis of PL21 AML cells mediated by purified human primary NK cells vastly outperforming the corresponding monoclonal antibody (FIG. 156 and Table 149). Additional cytotoxicity assessment of AB0089 is described in detail in Example 18.

TABLE 148

Potency of AB0089 in KHYG-1-CD16aV mediated cytotoxicity assay with HL60 and PL21 cells.

| Cancer cell | EC50 (nM) | Max killing (%) |
|---|---|---|
| HL60 | 0.27 | 111 |
| PL21 | 0.16 | 83 |

TABLE 149

Potency of AB0089 in primary NK mediated cytotoxic killing of PL21 cells.

| Test article | EC50 (nM) | Max killing (%) |
|---|---|---|
| AB0089 | 0.35 | 20 |
| AB0305 - parental mAb | 1.85 | 5 |

Specificity

Non-Specific Binding Assessed by PSR

To assess the specificity of AB0089, a flow cytometry based PSR assay that measures binding to a preparation of detergent solubilized CHO cell membrane proteins was performed (FIGS. 157A-157D). The PSR assay has been demonstrated to correlate with orthogonal specificity assays such as cross-interaction chromatography, and the baculovirus particle enzyme-linked immunosorbent assay. Behavior in these assays strongly associates with antibody solubility and in vivo clearance and therefore serves as a good developability predictive factor (Xu et al., (2013) *Protein engineering design and selection,* 26, 663-670). AB0089 showed very similar profile to the low PSR control (Trastuzumab), suggesting high specificity and lack of non-specific binding to unrelated proteins (FIG. 157B). Rituximab was used as a positive control for PSR binding.

Specificity Assessment of AB0089 in HuProt™ Array

To directly examine the specificity of AB0089 we have explored a protein array technology. The HuProt™ human proteome microarray provides the largest database of individually purified human full-length proteins on a single microscopic slide. An array consisting of 22,000 full-length human proteins are expressed in *S. cerevisiae* yeast, purified, and are subsequently printed in duplicate on a microarray glass slide that allows thousands of interactions to be profiled in a high-throughput manner. FIG. 158 shows the relative binding (Z score) of AB0089 at 1 µg/ml to human CLEC12A in comparison to the entire human proteome microarray. For comparison purpose, the top 24 proteins with residual background binding to AB0089 were also provided. Table 150 shows the Z and S scores of AB0089 to human CLEC12A and the top 6 proteins from the microarray. S score is the difference of Z score of a given protein and the one rank next to it. Based on the Z and S score criteria, AB0089 showed high specificity to human CLEC12A and lack of off-target binding in the HuProt™ human proteome assay.

TABLE 150

Summary of the top hits by HuProt™ array

| Name | Rank | Protein-ID | Z score | S score |
|---|---|---|---|---|
| hCLEC12A | 1 | hCLEC12A | 150.61 | 146.120 |
| RPLP0 | 2 | JHU16464.P173H05 | 4.49 | 0.051 |
| POLR2E | 3 | JHU02080.P189F02 | 4.44 | 0.57 |
| RPRD1A | 4 | JHU16457.P173E09 | 3.86 | 0.01 |
| ZNF608 | 5 | JHU13018.P136G04 | 3.85 | 0.10 |
| ECDHDC1 | 6 | JHU25034.P240F11 | 3.75 | 0.06 |
| BC089418 | 7 | JHU16002.P168E09 | 3.70 | 0.12 |

Developability Assessment

The stability and forced degradation of AB0089 was assessed under the following conditions:
  Accelerated (40° C.) Stability
    20 mg/ml AB0089 in a formulation HST, pH 6.0 (20 mM histidine, 250 mM sucrose, 0.01% Tween-80, pH 6.0), 40° C., 4 weeks (SEC, SPR, potency, CE-SDS, peptide map).
    20 mg/ml AB0089 in CST, pH 7.0 (20 mM sodium citrate, 250 mM sucrose, 0.01% Tween-80, pH 7.0), 40° C., 4 weeks (SEC, SPR, potency, CE-SDS, peptide map).
  Chemical Stability
    Oxidation: 1 mg/ml AB0089 in PBS with 0.02% hydrogen peroxide, room temperature, 24 hours (SEC, CE-SDS, SPR, potency, peptide map).
    pH 8.0: 1 mg/ml AB0089 in 20 mM Tris, 40° C., 2 weeks (cIEF, SPR, potency, peptide map).
    pH 5.0: 1 mg/ml AB0089 in 20 mM sodium acetate, 40° C., 2 weeks (cIEF, SPR, potency, peptide map).
  Manufacturability
    Freeze/thaw: 20 mg/ml AB0089 in 20 mM sodium citrate, 250 mM sucrose, 0.01% Tween-80, pH 7.0 (SEC, SDS-CE)
    Agitation: 10 mg/ml AB0089 in 20 mM sodium citrate, 250 mM sucrose, 0.01% Tween-80, pH 7.0 (SEC, SDS-CE)
    High concentration: >150 mg/ml, PBS (SEC, A280)
    Low pH hold (mimicking conditions of viral clearance step of manufacturing process): pH 3.3, 1.5 hours, ProA eluate (SEC); fully purified AB0089 (cIEF, CE-SDS, SPR, potency)
    Low pH hold (to investigate isomerization): fully purified AB0089 was diluted with ProA elution buffer and pH adjusted to 3.5. The sample was held for 1 hour at room temperature, neutralized with Tris buffer and buffer exchanged into PBS, pH 7.4. before additional analysis (SEC, cIEF, CE-SDS, SPR, potency, peptide map).
Accelerated (40° C.) Stability
  To assess the stability of AB0089, the molecule was staged at protein concentration of 20 mg/ml at 40° C. for 4 weeks under two different buffer conditions (1) in 20 mM histidine, 250 mM sucrose, 0.01% PS-80, pH 6.0 (HST), and (2) in 20 mM citrate, 250 mM sucrose, 0.01% PS-80, pH 7.0 (CST). Stability in both buffers was assessed by SEC, CE, SPR and potency.

Stability in HST, pH 6.0

AB0089 demonstrated high stability after 4 weeks of incubation in HST, pH 6.0, at 40° C. No aggregation and minimal loss of monomer (1.6%) was observed by SEC (FIG. 159 and Table 151). Minimal fragmentation was detected by R CE-SDS (FIGS. 160A-160B and Table 152). Additionally, there was no meaningful difference observed in the amount of active species, binding kinetics or affinities for hCLEC12A, hNKG2D and hCD16a between control and stressed samples (FIGS. 161A-161F and Table 153). Finally, no difference in potency between the control and stressed samples was detected (FIG. 162 and Table 154).

TABLE 151

SEC analysis of AB0089 after 2 and 4 weeks incubation at 40° C. in HST, pH 6.0.

| Test Article | Monomer (%) | LMWS (%) | HMWS (%) |
|---|---|---|---|
| AB0089 control | 99.5 | 0.5 | 0.0 |
| AB0089, HST, pH6.0, 40° C., 2 wks | 99.1 | 0.9 | ND |
| AB0089, HST, pH6.0, 40° C., 4 wks | 98.4 | 1.3 | 0.4 |

TABLE 152

NR and R CE-SDS analysis of AB0089 after 4 weeks at 40° C. in HST, pH 6.0.

| Test article | NR CE Purity (%) | R CE Purity (%) |
|---|---|---|
| AB0089 control | 98.2 | 94.3 |
| AB0089, HST, pH6.0, 40° C., 4 wks | 98.3 | 97.2 |

TABLE 153

Kinetic parameters and binding affinities of AB0089 for CLEC12A, NKG2D and CD16a after 4 weeks at 40° C. in HST, pH 6.0.

| Test article | Target | $k_a$ ($M^{-1}s^{-1}$) | | $k_d$ ($s^{-1}$) | | $K_D$ (nM) |
|---|---|---|---|---|---|---|
| AB0089 Control | hCLEC12A | $k_{a1}$ ($M^{-1}s^{-1}$) $(8.87 \pm 0.53) \times 10^6$ | $k_{a2}$ ($s^{-1}$) $(3.49 \pm 0.04) \times 10^{-3}$ | $k_{d1}$ ($s^{-1}$) $(4.20 \pm 0.07) \times 10^{-2}$ | $k_{d2}$ ($s^{-1}$) $(9.37 \pm 0.32) \times 10^{-4}$ | $1.0 \pm 0.0$ |
| AB0089 Stressed | hCLEC12A | $k_{a1}$ ($M^{-1}S^{-1}$) $(7.91 \pm 0.42) \times 10^6$ | $k_{a2}$ ($s^{-1}$) $(3.69 \pm 0.04) \times 10^{-3}$ | $k_{d1}$ ($s^{-1}$) $(4.24 \pm 0.17) \times 10^{-2}$ | $k_{d2}$ ($s^{-1}$) $(8.56 \pm 0.45) \times 10^{-4}$ | $1.0 \pm 0.1$ |
| AB0089 Control | hNKG2D | $(1.75 \pm 0.12) \times 10^5$ | | $(1.35 \pm 0.08) \times 10^{-1}$ | | $772 \pm 13$ |
| AB0089 Stressed | hNKG2D | $(1.66 \pm 0.03) \times 10^5$ | | $(1.32 \pm 0.02) \times 10^{-1}$ | | $796 \pm 5$ |
| AB0089 Control | CD16aV | $(8.53 \pm 0.05) \times 10^4$ | | $(2.76 \pm 0.02) \times 10^{-2}$ | | $323 \pm 3$ |
| AB0089 Stressed | CD16aV | $(7.93 \pm 0.27) \times 10^4$ | | $(2.84 \pm 0.07) \times 10^{-2}$ | | $359 \pm 6$ |

Average of 3 replicates

TABLE 154

AB0089 potency after 4 weeks at 40° C. in HST, pH 6.0, in KHYG-1-CD16aV cytotoxicity assay.

| Test article | EC50 (nM) | Max killing (%) |
|---|---|---|
| AB0089 control | 0.16 | 83 |
| AB0089, HST, pH 6.0, 40° C., 4 wks | 0.17 | 84 |

Stability in CST pH 7.0

AB0089 demonstrated high stability after 4 weeks of incubation in CST, pH 7.0, at 40° C. A minimal loss monomer content (1.6%) was observed by SEC (FIG. 163 and Table 155). No fragmentation of AB0089 was observed by CE-SDS (FIGS. 164A-164B and Table 156). Additionally, there was no meaningful difference in active protein content or in binding affinities for hCLEC12A, hNKG2D and hCD16a between control and stressed samples (FIGS. 165A-165F and Table 157). Finally, long term thermal stress did not affect potency of AB0089 (FIG. 166 and Table 158).

TABLE 155

SEC analysis of AB0089 during weeks 1-4 at 40° C. in CST, pH 7.0.

| Test Article | Conc. (mg/ml) | Monomer (%) | LMWS (%) | HMWS (%) |
|---|---|---|---|---|
| AB0089 control | 22.0 | 99.1 | 0.5 | 0.5 |
| AB0089, CST, pH7.0, 40° C., 1 wk | ND | 98.2 | 1.2 | 0.6 |
| AB0089, CST, pH 7.0, 40° C., 2 wks | | 97.9 | 1.3 | 0.7 |
| AB0089, CST, pH 7.0, 40° C., 3 wks | | 97.7 | 1.5 | 0.8 |
| AB0089, CST, pH 7.0, 40° C., 4 wks | 22.6 | 97.5 | 1.7 | 1.0 |

ND, none detected

TABLE 156

NR and R CE-SDS analysis of AB0089 after 4 weeks at 40° C. in CST, pH 7.0.

| Test article | NR CE Purity (%) | R CE Purity (%) |
|---|---|---|
| AB0089 control | 98.6 | 92.7 |
| AB0089, CST, pH 7.0, 40° C., 4 wks | 96.2 | 96.0 |

TABLE 157

Kinetic parameters and binding affinities of AB0089 for CLEC12A, NKG2D and CD16a after 4 weeks at 40° C. in CST, pH 7.0

| Test article | Target | $k_a$ (M$^{-1}$s$^{-1}$) | | $k_d$ (s$^{-1}$) | | $K_D$ (nM) |
|---|---|---|---|---|---|---|
| AB0089 Control | hCLEC12A | $k_{a1}$ (M$^{-1}$s$^{-1}$) $(8.87 \pm 0.53) \times 10^6$ | $k_{a2}$ (s$^{-1}$) $(3.49 \pm 0.04) \times 10^{-3}$ | $k_{d1}$ (s$^{-1}$) $(4.20 \pm 0.07) \times 10^{-2}$ | $k_{d2}$ (s$^{-1}$) $(9.37 \pm 0.32) \times 10^{-4}$ | $1.0 \pm 0.0$ |
| AB0089 Stressed | hCLEC12A | $k_{a1}$ (M$^{-1}$s$^{-1}$) $(6.31 \pm 0.32) \times 10^6$ | $k_{a2}$ (s$^{-1}$) $(3.93 \pm 0.12) \times 10^{-3}$ | $k_{d1}$ (s$^{-1}$) $(3.73 \pm 0.15) \times 10^{-2}$ | $k_{d2}$ (s$^{-1}$) $(8.00 \pm 0.05) \times 10^{-4}$ | $1.0 \pm 0.0$ |
| AB0089 Control | hNKG 2D | $(1.75 \pm 0.12) \times 10^5$ | | $(1.35 \pm 0.08) \times 10^{-1}$ | | $772 \pm 13$ |
| AB0089 Stressed | hNKG2D | $(1.60 \pm 0.04) \times 10^5$ | | $(1.26 \pm 0.06) \times 10^{-4}$ | | $791 \pm 13$ |
| AB0089 Control | CD16aV | $(8.53 \pm 0.05) \times 10^4$ | | $(2.76 \pm 0.02) \times 10^{-2}$ | | $323 \pm 3$ |
| AB0089 Stressed | CD16aV | $(8.31 \pm 0.43) \times 10^4$ | | $(2.84 \pm 0.07) \times 10^{-2}$ | | $342 \pm 9$ |

Average of 3 replicates

TABLE 158

Potency of AB0089 after 4 weeks at 40° C. in CST, pH 7.0 in KHYG1-CD16aV cytotoxicity assay.

| Test article | Buffer | EC50 (nM) | Max killing (%) |
|---|---|---|---|
| AB0089 control | CST, pH 7.0 | 0.13 | 87 |
| AB0089 stressed | CST, pH 7.0 | 0.16 | 88 |

Peptide Map Analysis of Accelerated Stability Samples

To determine if the 40° C. stress induced modifications in the complementarity determining regions (CDRs), the control and 4-week stressed samples were analyzed by LC-MS/MS peptide mapping. Based on the peptide map data, all of the CDRs in AB0089 are resistant to modification during elevated temperature stress (Table 159). No evidence of aspartic acid isomerization in the peptide encompassing the CLEC12A binding CDRH3 was observed, based on manual inspection of peak shape (FIGS. 167A-167C).

TABLE 159

Post-translational modifications in AB0089 CDRs after elevated temperature stress.

| Chain | CDR | Sequence (Chothia) | Modification | Relative Abundance (%) Control | Stressed (CST) | Stressed (HST) |
|---|---|---|---|---|---|---|
| S | H1 | GFSLTNY (SEQ ID NO: 137) | Deamidation | 0.7 | 1.7 | 0.9 |
| S | H2 | WVGGA (SEQ ID NO: 272) | None | | NA | |
| S | H3 | GDYGDTLDY (SEQ ID NO: 273) | Isomerization | | None detected | |
| S | L1 | HASQNINFWLS (SEQ ID NO: 140) | Deamidation | 0.3 | 1.0 | 0.4 |
| S | L2 | EASNLHT (SEQ ID NO: 141) | Deamidation | | None detected | |
| S | L3 | QQSHSYPLT (SEQ ID NO: 142) | None | | NA | |
| H | H1 | GFTFSSY (SEQ ID NO: 297) | None | | NA | |
| H | H2 | SSSSSY (SEQ ID NO: 298) | None | | NA | |
| H | H3 | GAPIGAAAGWFDP (SEQ ID NO: 97) | Truncation | | None detected | |
| L | L1 | RASQGISSWLA (SEQ ID NO: 86) | None | | NA | |

TABLE 159-continued

Post-translational modifications in AB0089 CDRs after elevated temperature stress.

| Chain | CDR (Chothia) | Sequence | Modification | Relative Abundance (%) Control | Relative Abundance (%) Stressed (CST) | Relative Abundance (%) Stressed (HST) |
|---|---|---|---|---|---|---|
| L | L2 | AASSLQS (SEQ ID NO: 77) | None | | NA | |
| L | L3 | QQGVSFPRT (SEQ ID NO: 87) | None | | NA | |

NA: not applicable

Chemical Stability

Forced Oxidation

To assess stability of AB0089 under oxidative stress, AB0089 was incubated with 0.02% hydrogen peroxide for 24 hours at room temperature in PBS. SEC analysis showed no difference in monomer content between oxidized AB0089 and control sample (FIG. 168 and Table 160). No increase in fragmentation was detected in AB0089 by both reduced and non-reduced CE-SDS (FIGS. 169A-169B and Table 161).

TABLE 160

SEC analysis of AB0089 after forced oxidation compared to control.

| Test article | Concentration (mg/ml) | Monomer (%) | LMWS (%) | HMWS (%) |
|---|---|---|---|---|
| AB0089 control | 1.1 | 99.3 | 0.4 | 0.3 |
| AB0089 forced oxidation | 1.0 | 99.1 | 0.5 | 0.4 |

TABLE 161

NR and R CE-SDS analysis of AB0089 after forced oxidation.

| Test article | NR CE Purity (%) | R CE Purity (%) |
|---|---|---|
| AB0089 control | 98.9 | 98.0 |
| AB0089 forced oxidization | 97.4 | 98.1 |

Site-specific oxidation of methionine was monitored by tryptic peptide mapping following forced oxidation. Significant levels of oxidation were only detected at two methionines in the Fc (Table 162). Our historic data show that the same residues are modified in trastuzumab at 61.6% and 39.1% under the same conditions.

TABLE 162

Summary of methionine oxidation in AB0089 before and after oxidative stress.

| Sequence | Chain | Position | Relative Abundance (%) Control | Relative Abundance (%) Oxidized |
|---|---|---|---|---|
| LSCAASGFTFSSYSMNWVR (SEQ ID NO: 300) | H | 34 | 0.6 | 0.9 |
| NSLYLQMNSLR (SEQ ID NO: 301) | H | 83 | 0.4 | 0.9 |
| DTLMISR (SEQ ID NO: 302) | H/S | 257/278 | 2.1 | 66.7 |
| WQQGNVFSCSVMHEALHNHYTQK (SEQ ID NO: 303) | H/S | 433/454 | 1.3 | 37.8 |
| DIQMTQSPSSVSASVGDR (SEQ ID NO: 304) | L | 4 | 0.5 | 1.1 |
| GDYGDTLDYWGQGTLVTVSSGGGGSGGGGSGGGGSGGGGSDIQMTQSPSSLSASVGDR (SEQ ID NO: 339) | S | 141 | 3.1 | 3.5 |

Oxidation of tryptophan residues in AB0089 CDRs was also monitored in the same experiment. None of the tryptophan residues had a significant increase in oxidation after stress (Table 163).

TABLE 163

Summary of tryptophan oxidation in AB0089 CDRs before and after oxidative stress.

| Sequence | Chain | CDR | Mass shift (Da)[a] | Relative Abundance (%) Control | Relative Abundance (%) Oxidized |
|---|---|---|---|---|---|
| WVGGA (SEQ ID NO: 272) | S | H2 | +16/+32/+4 | ND/0.1/0.2 | ND/0.2/0.3 |
| HASQNINFWLS (SEQ ID NO: 140) | S | L1 | +16/+32/+4 | ND/0.2/0.2 | ND/0.3/0.3 |

TABLE 163-continued

Summary of tryptophan oxidation in AB0089 CDRs before and after oxidative stress.

| Sequence | Chain | CDR | Mass shift (Da)[a] | Relative Abundance (%) | |
|---|---|---|---|---|---|
| | | | | Control | Oxidized |
| GAPIGAAAGWFDP (SEQ ID NO: 97) | H | H3 | +16/+32/+4 | 0.0/0.2/0.4 | 0.0/0.3/0.7 |
| RASQGISSWLA (SEQ ID NO: 86) | L | L1 | +16/+32/+4 | 0.2/0.1/0.2 | 0.2/0.2/0.3 |

[a] single oxidation (+16 Da), double oxidation (+32 Da), and kynurenine (+4 Da), ND, none detected.

Oxidative stress had no significant effect on the active protein content or on the affinities for hCLEC12A, hNKG2D, and hCD16aV (FIGS. 170A-170F and Table 164). No significant effect of oxidation on the potency of AB0089 was observed (FIG. 171 and Table 165).

TABLE 164

Kinetic parameters and binding affinities of AB0089 for CLEC12A, NKG2D and CD16A after forced oxidation compared to control.

| Test article | Target | $k_a$ (M$^{-1}$s$^{-1}$) | | $k_d$ (s$^{-1}$) | | $K_D$ (nM) |
|---|---|---|---|---|---|---|
| AB0089 Control | hCLEC12A | $k_{a1}$ (M$^{-1}$s$^{-1}$) $(1.01 \pm 0.04) \times 10^7$ | $k_{a2}$ (s$^{-1}$) $(3.46 \pm 0.01) \times 10^{-3}$ | $k_{d1}$ (s$^{-1}$) $(4.76 \pm 0.22) \times 10^{-2}$ | $k_{d2}$ (s$^{-1}$) $(8.37 \pm 0.29) \times 10^{-4}$ | $0.9 \pm 0.0$ |
| AB0089 Oxidized | hCLEC12A | $k_{a1}$ (M$^{-1}$s$^{-1}$) $(9.93 \pm 0.11) \times 10^6$ | $k_{a2}$ (s$^{-1}$) $(3.47 \pm 0.04) \times 10^{-3}$ | $k_{d1}$ (s$^{-1}$) $(4.81 \pm 0.10) \times 10^{-2}$ | $k_{d2}$ (s$^{-1}$) $(8.37 \pm 0.22) \times 10^{-4}$ | $0.9 \pm 0.0$ |
| AB0089 Control | hNKG2D | $(1.69 \pm 0.04) \times 10^5$ | | $(1.35 \pm 0.01) \times 10^{-1}$ | | $797 \pm 19$ |
| AB0089 Oxidized | hNKG2D | $(1.71 \pm 0.13) \times 10^5$ | | $(1.30 \pm 0.07) \times 10^{-1}$ | | $762 \pm 13$ |
| AB0089 Control | hCD16aV | $(8.64 \pm 0.22) \times 10^4$ | | $(2.78 \pm 0.05) \times 10^{-2}$ | | $322 \pm 7$ |
| AB0089 Oxidized | hCD16aV | $(8.65 \pm 0.43) \times 10^4$ | | $(2.77 \pm 0.05) \times 10^{-2}$ | | $320 \pm 10$ |

Average of 3 replicates

TABLE 165

AB0089 potency before and after forced oxidation in KHYG1-CD16aV cytotoxicity assay.

| Test article | EC50 (nM) | Max Killing (%) |
|---|---|---|
| AB0089 Control | 0.11 | 84 |
| AB0089 Oxidized | 0.16 | 87 | pH 8 Stress

Chemical stability of AB0089 was assessed by long term incubation at elevated pH (20 mM Tris, pH 8.0, 40° C., 2 weeks). AB0089 appears to be highly stable: only 1.2% loss of monomer was detected by SEC (FIG. 172 and Table 166).

TABLE 166

SEC analysis of AB0089 after long term high pH stress (pH 8.0, 40° C., 2 wks).

| Test article | Monomer (%) | LMWS (%) | HMWS (%) |
|---|---|---|---|
| AB0089 control | 99.4 | 0.4 | 0.2 |
| AB0089 pH 8 stressed | 98.2 | 1.1 | 0.7 |

Reduced and non-reduced CE-SDS showed low levels of degradation, 1.7% and 3.9%, respectively (FIGS. 173A-173B and Table 167).

TABLE 167

NR and R CE-SDS analysis of AB0089 after long term high pH stress (pH 8, 40° C., 2 wks).

| Test article | NR CE Purity (%) | R CE Purity (%) |
|---|---|---|
| AB0089 control | 98.6 | 98.2 |
| AB0089 pH 8 stressed | 96.9 | 94.3 |

After long term high pH stress, there was an acidic shift in the global charge profile detected by cIEF (FIG. 174 and Table 168). This acidic shift can be attributed to deamidation throughout the AB0089 sequence. A similar acidic shift was observed for trastuzumab after the same stress conditions (data not shown).

TABLE 168

AB0089 charge profile after long term high pH exposure (pH 8, 40° C., 2 wks).

| Test article | % acidic | % main | % basic |
|---|---|---|---|
| AB0089 control | 43.1 | 51.4 | 5.5 |
| AB0089 pH 8 stressed | 66.6 | 29.0 | 4.4 |

There was no meaningful difference in the amount of active protein or in the affinities for hCLEC12A, hNKG2D, or hCD16aV between stressed and control samples (FIGS. 175A-175F and Table 169).

TABLE 169

Kinetic parameters and binding affinities of AB0089 for CLEC12A, NKG2D, and CD16aV after long term high pH stress (pH 8, 40° C., 2 wks).

| Test article | Target | $k_a$ (M$^{-1}$s$^{-1}$) | | $k_d$ (s$^{-1}$) | | $K_D$ (nM) |
|---|---|---|---|---|---|---|
| AB0089 Control | hCLEC12A | $k_{a1}$ (M$^{-1}$s$^{-1}$) $(1.01 \pm 0.04) \times 10^7$ | $k_{a2}$ (s$^{-1}$) $(3.46 \pm 0.01) \times 10^{-3}$ | $k_{d1}$ (s$^{-1}$) $(4.76 \pm 0.22) \times 10^{-2}$ | $k_{d2}$ (s$^{-1}$) $(8.37 \pm 0.29) \times 10^{-4}$ | $0.9 \pm 0.0$ |
| AB0089 pH 8 Stressed | hCLEC12A | $k_{a1}$ (M$^{-1}$s$^{-1}$) $(9.93 \pm 0.05) \times 10^7$ | $k_{a2}$ (s$^{-1}$) $(3.36 \pm 0.09) \times 10^{-3}$ | $k_{d1}$ (s$^{-1}$) $(4.90 \pm 0.24) \times 10^{-2}$ | $k_{d2}$ (s$^{-1}$) $(8.63 \pm 0.33) \times 10^{-4}$ | $0.9 \pm 0.1$ |
| AB0089 Control | hNKG2D | $(1.69 \pm 0.04) \times 10^5$ | | $(1.35 \pm 0.01) \times 10^{-1}$ | | $797 \pm 19$ |
| AB0089 pH 8 Stressed | hNKG2D | $1.30 \times 10^5$ | | $1.27 \times 10^{-1}$ | | 983 |
| AB0089 Control | hCD16aV | $(8.64 \pm 0.22) \times 10^4$ | | $(2.78 \pm 0.05) \times 10^{-2}$ | | $322 \pm 7$ |
| AB0089 pH 8 Stressed | hCD16aV | $(7.94 \pm 0.28) \times 10^4$ | | $(2.79 \pm 0.15) \times 10^{-2}$ | | $350 \pm 11$ |

Average of 3 replicates for all samples, except pH 8 stressed binding to hNKG2D (n = 2)

After long term high pH exposure, the potency of AB0089 was reduced approximately 2-fold (FIG. 176 and Table 170). Considering that orthogonal methods of analysis did not show any difference in binding or in the factive species content (FIGS. 175A-175F), it appears that these differences may be due to potency assay variability.

TABLE 170

AB0089 potency after long term high pH exposure (pH 8, 40° C., 2 wks).

| Test article | EC50 (nM) | Max killing (%) |
|---|---|---|
| AB0089 control | 0.11 | 84 |
| AB0089 pH 8 stressed | 0.23 | 83 | pH 5 Stress

Chemical stability of AB0089 was also assessed by long term incubation at low pH (20 mM sodium acetate, pH 5.0, 40° C., 2 weeks). DF appears to be highly stable: only 0.3% loss of monomer was detected by SEC (FIG. 177 and Table 171).

TABLE 171

SEC analysis of AB0089 after long term low pH stress (pH 5.0, 40° C., 2 wks).

| Test article | Monomer (%) | LMWS (%) | HMWS (%) |
|---|---|---|---|
| AB0089 control | 99.3 | 0.4 | 0.2 |
| AB0089 pH 5 stressed | 99.0 | 0.8 | 0.2 |

After long term pH 5 stress, low levels of AB0089 degradation were detected by non-reduced and reduced CE-SDS: 1.0% and 0.3% loss of monomer content, respectively (FIGS. 178A-178B and Table 172).

TABLE 172

NR and R CE-SDS analysis of AB0089 after long term low pH stress (pH 5.0, 40° C., 2 wks).

| Test article | NR CE Purity (%) | R CE Purity (%) |
|---|---|---|
| AB0089 control | 98.6 | 97.7 |
| AB0089 pH 5 stressed | 97.6 | 97.4 |

After long term pH 5 stress, there was a small acidic shift in the global charge profile detected by cIEF (FIG. 178A-178B and Table 173), with one acidic variant in particular increasing significantly.

TABLE 173

Charge profile of AB0089 after long term low pH stress (pH 5.0 40° C., 2 wks).

| Test article | % acidic | % main | % basic |
|---|---|---|---|
| AB0089 control | 37.8 | 56.4 | 5.8 |
| AB0089 pH 5 stressed | 47.3 | 45.9 | 6.8 |

After long term low pH exposure, there was no meaningful difference in active protein content or in AB0089 affinities for hCLEC12A, hNKG2D, or hCD16aV (FIGS. 180A-180F and Table 174).

TABLE 174

Kinetic parameters and binding affinity of AB0089 for CLEC12A, NKG2D, and CD16aV after high pH stress (pH 5.0, 40° C., 2 wks).

| Test article | Target | $k_a$ (M$^{-1}$s$^{-1}$) | | $k_d$ (s$^{-1}$) | | $K_D$ (nM) |
|---|---|---|---|---|---|---|
| AB0089 Control | hCLEC12A | $k_{a1}$ (M$^{-1}$s$^{-1}$) $(1.01 \pm 0.04) \times 10^7$ | $k_{a2}$ (s$^{-1}$) $(3.46 \pm 0.01) \times 10^{-3}$ | $k_{d1}$ (s$^{-1}$) $(4.76 \pm 0.22) \times 10^{-2}$ | $k_{d2}$ (s$^{-1}$) $(8.37 \pm 0.29) \times 10^{-4}$ | $0.9 \pm 0.0$ |
| AB0089 pH 5 stressed | hCLEC12A | $k_{a1}$ (M$^{-1}$s$^{-1}$) $(8.62 \pm 0.02) \times 10^6$ | $k_{a2}$ (s$^{-1}$) $(3.47 \pm 0.04) \times 10^{-3}$ | $k_{d1}$ (s$^{-1}$) $(4.27 \pm 0.22) \times 10^{-2}$ | $k_{d2}$ (s$^{-1}$) $(8.40 \pm 0.09) \times 10^{-4}$ | $1.0 \pm 0.0$ |
| AB0089 Control | hNKG2D | $(1.69 \pm 0.04) \times 10^5$ | | $(1.35 \pm 0.01) \times 10^{-1}$ | | $797 \pm 19$ |
| AB0089 pH 5 Stressed | hNKG2D | $1.87 \times 10^5$ | | $1.31 \times 10^{-1}$ | | 703 |
| AB0089 Control | CD16aV | $(8.64 \pm 0.22) \times 10^4$ | | $(2.78 \pm 0.05) \times 10^{-2}$ | | $322 \pm 7$ |
| AB0089 pH 5 Stressed | CD16aV | $(7.54 \pm 0.36) \times 10^4$ | | $(2.89 \pm 0.05) \times 10^{-2}$ | | $383 \pm 12$ |

Average of 3 replicates for all samples, except pH 5 stressed sample binding to hNKG2D (n = 2)

Potency of AB0089 after long term pH 5 exposure remained similar to potency of the control sample (FIG. 18I and Table 175).

TABLE 175

AB0089 potency after long term low pH stress (pH 5.0 40° C., 2 wks) in KHYG-1-CD16aV cytotoxicity assay.

| Test article | EC50 (nM) | Max killing (%) |
|---|---|---|
| AB0089 control | 0.11 | 84 |
| AB0089 pH 5 stressed | 0.16 | 86 |

Peptide Mapping Analysis of the pH 5 and pH 8 Stressed Material

To determine if the pH stress induced changes observed by cIEF are due to the modification in the complementarity determining regions (CDRs), pH 5 and pH 8 stressed samples were analyzed by LC-MS/MS peptide mapping. Based on the peptide map data, all of the CDRs in AB0089 are resistant to modification during low and high pH stress (Table 176). No evidence of aspartic acid isomerization in the peptide encompassing the CDRH3 of the CLEC12A targeting arm of AB0089 was observed, based on manual inspection of peak shape (FIGS. 182A-182B).

TABLE 176

Post-translational modifications in AB0089 CDRs after long term exposure to low and high pH (pH 5.0 and pH 8.0).

| | | | | Relative abundance (%) | | | |
|---|---|---|---|---|---|---|---|
| | | | | pH 5 | | pH 8 | |
| Chain | CDR | Sequence (Chothia) | Modification | control | stressed | control | stressed |
| S | H1 | GFSLTNY (SEQ ID NO: 137) | Deamidation | 0.2 | 0.6 | 0.4 | 1.4 |
| S | H2 | WVGGA (SEQ ID NO: 272) | None | NA | | | |
| S | H3 | GDYGDTLDY (SEQ ID NO: 273) | Isomerization | None detected | | | |
| S | L1 | HASQNINFWLS (SEQ ID NO: 140) | Deamidation | 0.1 | 0.1 | 0.2 | 0.4 |
| S | L2 | EASNLHT (SEQ ID NO: 141) | Deamidation | None detected | | | |
| S | L3 | QQSHSYPLT (SEQ ID NO: 142) | None | NA | | | |
| H | H1 | GFTFSSY (SEQ ID NO: 297) | None | NA | | | |
| H | H2 | SSSSSY (SEQ ID NO: 298) | None | NA | | | |
| H | H3 | GAPIGAAAGWFDP (SEQ ID NO: 97) | Truncation | None detected | | | |
| L | L1 | RASQGISSWLA (SEQ ID NO: 86) | None | NA | | | |
| L | L2 | AASSLQS (SEQ ID NO: 77) | None | NA | | | |
| L | L3 | QQGVSFPRT (SEQ ID NO: 87) | None | NA | | | |

NA: not applicable

Manufacturability

Freeze/Thaw Stability

Aliquots of AB0089 (20 mg/ml in CST pH 7.0) were frozen and thawed 6 times by placing the vials in Styrofoam container (to slow the freezing rate) and placing the container at −80° C. After 6 cycles of freeze/thaw AB0089 showed no loss in monomer by SEC. Protein concentration measured by A280 remained the same (FIG. 183 and Table 177).

TABLE 177

SEC analysis of AB0089 after freeze/thaw stress.

| Test article | Conc. (mg/ml) | Monomer (%) | LMWS (%) | HMWS (%) |
|---|---|---|---|---|
| AB0089 control | 22.3 | 99.0 | 0.7 | 0.3 |
| AB0089 after 6 F/T cycles | 22.1 | 98.9 | 0.8 | 0.3 |

After 6 freeze/thaw cycles no loss of purity was detected by reduced or non-reduced CE-SDS (FIGS. 184A-184B and Table 178).

TABLE 178

Purity by NR and R CE-SDS analysis of AB0089 after freeze/thaw stress.

| Test article | NR CE Purity (%) | R CE Purity (%) |
|---|---|---|
| AB0089 control | 98.4 | 93.2 |
| AB0089 after 6 F/T cycles | 98.3 | 93.7 |

Agitation

AB0089 (at 10 mg/ml in 20 mM sodium citrate, 250 mM sucrose, pH 7.0, with or without 0.01% Tween-80) was shaken at 300 rpm at room temperature in a deep well plate for 3 days. After agitation stress, there was no loss of monomer detected by SEC (FIGS. 185A-185B and Table 179), no loss of protein concentration (A280), and no increase in turbidity (A340) was observed.

TABLE 179

SEC analysis of AB0089 after agitation stress.

| Test article | 0.01% Tween-80 | Conc. (mg/ml) | Monomer (%) |
|---|---|---|---|
| AB0089 control | + | 9.86 | 99.5 |
| AB0089 agitation | + | 9.97 | 99.7 |
| AB0089 control | − | 9.81 | 99.4 |
| AB0089 agitation | − | 9.93 | 99.1 |

High Concentration

AB0089 was concentrated to approximately 10, 15, 25, 50, 100, 150 and 175 mg/ml in PBS, pH 7.4 and recovery was monitored by visual inspection, concentration (A280), and SEC. For SEC analysis, samples were injected undiluted (injection volume was normalized to the concentration). AB0089 was able to be concentrated to >175 mg/ml with minimal loss in percent monomer (FIGS. 186A-186B, FIG. 187, Table 180) and no visible precipitation.

TABLE 180

SEC analysis of AB0089 at different concentrations.

| Concentration (mg/ml) | % Monomer | % HMW |
|---|---|---|
| 9.7 | 99.7 | 0.3 |
| 14.7 | 99.7 | 0.3 |
| 26.2 | 99.7 | 0.3 |
| 53.4 | 99.6 | 0.4 |
| 94.2 | 99.6 | 0.4 |
| 143.5 | 99.6 | 0.4 |
| 178.4 | 99.5 | 0.5 |

Low pH Hold

Two different methods were used to assess the behavior of AB0089 during low pH hold (mock viral inactivation). The first method mimicked the manufacturing process, where the eluate from the first chromatography step (Protein A) was held at low pH before additional purification. The second method incubated fully purified AB0089 under low pH conditions. This method was used to assess potential low pH induced chemical modifications of the CDRs.

Low pH Hold Exposure of Protein A Eluate

To determine if AB0089 is resistant to low pH hold, AB0089 Protein A eluate was adjusted to pH 3.5 and held for 2 hours at room temperature. After the hold period, the Protein A eluate was neutralized with 1.0 M Tris, pH 8.3 to achieve neutral pH. Analytical SEC was performed to determine if there were any changes in profile or aggregate content pre- and post-low pH exposure (FIGS. 188A-188B). No change in the SEC profile of AB0089 was observed after low pH hold compared to "no-hold" control sample, suggesting that AB0089 is highly stable during low pH hold/viral inactivation conditions used in biologics manufacturing.

Protein was further processed through the second step of DF platform purification method and analyzed using a panel of additional assays in comparison with purified protein that was not subjected to low pH hold. Chemical modification of amino acid side chains can typically be observed at a global scale with cIEF. The cIEF profiles of AB0089 control and low pH hold lot are visually very similar and the relative quantitation of acidic, main, and basic species are all within 5% of each other. This indicates that the low pH hold did not have a measurable effect on the charge profile of AB0089 (FIG. 189 and Table 181).

TABLE 181

AB0089 charge profile after low pH hold.

| Test article | pI | % acidic | % main | % basic |
|---|---|---|---|---|
| AB0089 control | 8.5 | 43.7 | 50.8 | 5.5 |
| AB0089 low pH hold | 8.6 | 39.5 | 54.3 | 6.2 |

The affinities of AB0089 for hCLEC12a, hNKG2D, and CD16aV were not affected by low pH hold (FIGS. 190A-190F and Table 182). No difference in active protein content was observed. The difference in binding affinity and maximal binding response between the control and low pH hold sample were within the experimental variability of the assay. This indicates that AB0089 retains affinity for all three targets after low pH hold.

TABLE 182

Kinetic parameters and binding affinities of AB0089 for
CLEC12A, NKG2D, and CD16aV after low pH hold.

| Test article | Target | $k_a$ (M$^{-1}$s$^{-1}$) | $k_d$ (s$^{-1}$) | $K_D$ (nM) |
|---|---|---|---|---|
| AB0089 Control | hCLEC12A | $k_{a1}$ (M$^{-1}$s$^{-1}$) $k_{a2}$ (s$^{-1}$) $(1.04 \pm 0.03) \times 10^7$ $(3.43 \pm 0.04) \times 10^{-3}$ | $k_{d1}$ (s$^{-1}$) $k_{d2}$ (s$^{-1}$) $(4.35 \pm 0.12) \times 10^{-2}$ $(7.41 \pm 0.10) \times 10^{-4}$ | $0.7 \pm 0.0$ |
| AB0089 low pH hold | hCLEC12A | $k_{a1}$ (M$^{-1}$s$^{-1}$) $k_{a2}$ (s$^{-1}$) $(1.11 \pm 0.07) \times 10^7$ $(3.50 \pm 0.03) \times 10^{-3}$ | $k_{d1}$ (s$^{-1}$) $k_{d2}$ (s$^{-1}$) $(4.65 \pm 0.05) \times 10^{-2}$ $(7.49 \pm 0.03) \times 10^{-4}$ | $0.7 \pm 0.0$ |
| AB0089 Control | hNKG2D | $(1.62 \pm 0.03) \times 10^5$ | $(1.43 \pm 0.03) \times 10^{-1}$ | $881 \pm 10$ |
| AB0089 low pH hold | hNKG2D | $(1.59 \pm 0.07) \times 10^5$ | $(1.50 \pm 0.05) \times 10^{-4}$ | $941 \pm 45$ |
| AB0089 Control | CD16aV | $(8.31 \pm 0.55) \times 10^4$ | $(2.77 \pm 0.16) \times 10^{-2}$ | $333 \pm 11$ |
| AB0089 low pH hold | CD16aV | $(8.73 \pm 0.22) \times 10^4$ | $(2.74 \pm 0.05) \times 10^{-2}$ | $314 \pm 8$ |

Results are an average of 3 replicates

Potency of AB0089 subjected to low pH hold and potency of control sample were tested against CLEC12A+ HL-60 cancer cells in the KHYG1-CD16aV bioassay. The potency of AB0089 was unaltered after the low pH hold step (FIG. 19I and Table 183).

TABLE 183

Potency of AB0089 after low pH hold in
KHYG-1-CD16aV cytotoxicity assay.

| Test article | EC50 (nM) | Max killing (%) |
|---|---|---|
| AB0089 control | 0.11 | 95 |
| AB0089 low pH hold | 0.11 | 89 |

Low pH Hold Exposure of Fully Purified Protein

An additional low pH hold study was carried out to investigate if the DT motif in the CDRH3 (KGDYGDTLDY) of the CLEC12A targeting scFv would isomerize during a viral inactivation step. Low pH hold material was prepared from fully purified AB0089 material using the following steps:
1. AB0089 was diluted 1:1 with 0.1 M glycine, pH 3.0 to mimic ProA elution
2. The pH was adjusted to 3.5±0.1 with 2 M acetic acid (to mimic low pH hold conditions)
3. The low pH hold was carried out for 60 min at room temperature
4. The pH was neutralized to ~7.5 with 1 M Tris, pH 8.0
5. AB0089 was buffer exchanged into PBS, pH 7.4

The final low pH hold material (AB0089 lot AB0089-004) was compared to control (AB0089 lot AB0089-002) using a panel of biological assays: SEC, cIEF, SPR binding to CLEC12A, peptide map, and potency. Analytical SEC was performed to determine if there were any changes in profile or aggregate content pre- and post-low pH exposure (FIGS. 192A-192B and Table 184). No change in profile of % monomer was observed after the low pH hold.

TABLE 184

SEC analysis of AB0089 after low pH hold
compared to control.

| Test article | Monomer (%) | LMWS (%) | HMWS (%) |
|---|---|---|---|
| AB0089 control | 99.7 | ND | 0.3 |
| AB0089 low pH hold | 99.7 | ND | 0.3 |

ND, none detected

As was seen in the first low pH hold study, the cIEF profiles of AB0089 control and low pH hold lot are visually very similar and the relative quantitation of acidic, main, and basic species are all within 6% of each other. Hence, low pH hold did not have a significant effect on the charge profile of AB0089 (FIG. 193 and Table 185).

TABLE 185

Charge profile of AB0089 after low pH hold.

| Test article | pI | % acidic | % main | % basic |
|---|---|---|---|---|
| AB0089 control | 8.6 | 42.5 | 51.1 | 6.5 |
| AB0089 low pH hold | 8.6 | 38.0 | 56.8 | 5.4 |

The affinity of AB0089 for hCLEC12a was unaltered compared to control (FIGS. 281A-281B and Table 186). The difference in binding affinity and maximal binding response between the control and low pH hold sample are within the experimental variability of the assay. This indicates that there was no impact of low pH incubation on the binding of the CLEC12A binding arm with target antigen.

TABLE 186

Summary of kinetic parameters and binding affinities of AB0089 for hCLEC12A
after low pH hold compared to control.

| Test article | $k_{a1}$ (M$^{-1}$ s$^{-1}$) | $k_{d1}$ (s$^{-1}$) | $k_{a2}$ (s$^{-1}$) | $k_{d2}$ (s$^{-1}$) | $K_D$ (nM) |
|---|---|---|---|---|---|
| AB0089 control | $(1.03 \pm 0.03) \times 10^7$ | $(2.72 \pm 0.11) \times 10^{-2}$ | $(3.59 \pm 0.05) \times 10^{-3}$ | $(8.56 \pm 0.32) \times 10^{-4}$ | $0.51 \pm 0.02$ |
| AB0089 low pH hold | $(1.02 \pm 0.06) \times 10^7$ | $(2.76 \pm 0.10) \times 10^{-2}$ | $(3.60 \pm 0.04) \times 10^{-3}$ | $(8.62 \pm 0.11) \times 10^{-4}$ | $0.53 \pm 0.02$ |

Results are an average of 3 replicates

The potency of AB0089 after low pH hold against CLEC12A+ HL-60 cancer cells was assessed in the KHYG1-CD16V bioassay. No difference between potencies of low pH hold and control samples was observed (FIG. 282 and Table 187).

TABLE 187

Potency AB0089 after low pH hold in the KHYG1-CD16aV cytotoxicity assay.

| Test article | EC50 (nM) | Maximum Lysis (%) |
|---|---|---|
| AB0089 control (AB0089-002) | 0.04 | 99 |
| AB0089 low pH hold (AB0089-004) | 0.03 | 98 |

To determine if the low pH hold induced changes in the modification in the CDRs, the control and low pH hold samples were analyzed by LC-MS/MS peptide mapping. Based on the peptide map data, all of the CDRs in AB0089 are resistant to modification during low pH hold (Table 188). No evidence of aspartic acid isomerization was observed, based on manual inspection of peak shape.

TABLE 188

AB0089 are resistant to post-translational modifications after low pH hold.

| Chain | CDR | Sequence (Chothia) | Potential liability | Relative abundance (%) control | Relative abundance (%) low pH hold |
|---|---|---|---|---|---|
| S | H1 | GFSLTNY (SEQ ID NO: 137) | Deamidation | 0.7 | 1.1 |
| S | H2 | WVGGA (SEQ ID NO: 272) | None | NA | |
| S | H3 | GDYGDTLDY (SEQ ID NO: 273) | Isomerization | ND | ND |
| S | L1 | HASQNINFWLS (SEQ ID NO: 140) | Deamidation | 0.2 | 0.1 |
| S | L2 | EASNLHT (SEQ ID NO: 141) | Deamidation | ND | ND |
| S | L3 | QQSHSYPLT (SEQ ID NO: 142) | None | NA | |
| H | H1 | GFTFSSY (SEQ ID NO: 297) | None | NA | |
| H | H2 | SSSSSY (SEQ ID NO: 298) | None | NA | |
| H | H3 | GAPIGAAAGWFDP (SEQ ID NO: 97) | Truncation | ND | ND |
| L | L1 | RASQGISSWLA (SEQ ID NO: 86) | None | NA | |
| L | L2 | AASSLQS (SEQ ID NO: 77) | None | NA | |
| L | L3 | QQGVSFPRT (SEQ ID NO: 87) | None | NA | |

NA, not applicable

Taken together, these results demonstrate that AB0089 is an improved version of AB0192 with an optimized CMC profile. The molecular format and structure of AB0089 meets the conceptual requirements for a new multi-specific therapeutic modality that simultaneously engages CLEC12A, NKG2D and CD16a to treat AML. AB0089 is potent and has a favorable developability profile with no sequence liabilities or significant post-translational modifications observed under any stresses. AB0089 binds to an epitope on CLEC12a similar to tepoditamab (Merus).

Example 18. AB0089 Cytotoxicity and Mechanism of Action

Objectives

Measure the activity of AB0089 in cell-based assays in vitro using physiologically relevant conditions to characterize AB0089's modes of action.

Study Design

The primary mechanism of action for AB0089 was tested using in vitro assays systems with human NK cells and CLEC12A+ cancer cells. Other effector functions aside from NK cell-mediated cytolysis were also paired with CLEC12A+ cancer cells to test additional mechanisms of action for AB0089. Macrophages were effector cells for ADCP assays and human serum was used as a source of complement to test CDC activity.

Materials and Methods

Primary Cells and Cell Lines

Human cancer cell lines were obtained from research cell banks. Below cell lines (item number; vendor) were used: PL21 (ACC-536; DSMZ) and HL60 (CCL-240; ATCC).

Human blood was obtained from Biological Specialty Corporation (225-11-04). PBMCs were isolated by density gradient centrifugation, and NK cells were purified using negative depletion with magnetic beads (StemCell CAT #17955). The manufacturer's instructions were followed for purification of NK cells from PBMCs. Frozen NK cells were purchased from BioIVTHUMAN-HL65-U-200429 CD14+ monocytes were obtained from BioIVT (HMN370652, HMN370653, HMN370654) Frozen PBMC were purified in-house (see above) and frozen for later use.

Cell Culture Materials

Below items (vendor; item number) were used: RPMI-1640 (Corning; 10040CV), DMEM (Corning; 10031CV), Heat inactivated FBS (ThermoFisher; 16140-071), GlutaMax I (ThermoFisher; 35050-061), Penn/Strep (ThermoFisher; 151450-122), 2-Mercaptoethanol (MP Biomedicals; 02194705), IL-2 (PeproTech; 200-02), CFSE (ThermoFisher; C34554), Cell Trace Violet (ThermoFisher; C34557), rhM-CSF (R&D Systems; 216-MC/CF), TrypLE (ThermoFisher; 12604-013), BFA (Biolegend; 420601), Monensin (BioLegend; 420701), and Human serum (Sigma Aldrich; 51764-5X1ML).

Assay Materials

Below items (vendor; item number) were used: Hepes buffered saline (Alfa Aesar; J67502), BATDA reagent (Perkin Elmer; C136-100), TC round bottom 96-well plate (Corning; 3799), Europium solution (Perkin Elmer; C135-100), DELFIA yellow microplates 96-well (Perkin Elmer; AAAND-0001), Fixation buffer (BioLegend; 420801), Zombie NIR (BioLegend; 77184), and Anti-WIC class I clone W6/32 (Invitrogen; HLA-C1).

Below test articles (description) were used: AB0237 (CLEC12A-Targeted TriNKET with Fab NKG2D binding (A49), and scFv CLEC12A binding domain (1602)), AB0300 (AB0237 with LALAPG mutation in CH2 domain), AB0037 mAb (Humanized 1602 anti-CLEC12A mAb), AB0089 (CLEC12A-Targeted TriNKET with Fab NKG2D binding (A49) and scFv CLEC12A binding domain (1739)), AB0305 mAb (Humanized 1739 anti-CLEC12A mAb), AB0192 (CLEC12A-Targeted TriNKET with Fab NKG2D binding (A49), and scFv CLEC12A binding domain (1797)), AB0306 mAb (Humanized 1797 anti-CLEC12A mAb), and F3'-palivizumab (Non-Targeting TriNKET with Fab NKG2D binding (A49), and scFv binding domain from palivizumab).

Below instruments (serial number) were used: Attune NxT (2AFC228271119), BD Celesta (H66034400085), BD Celesta (H66034400160), Spectramax i3x (363704226) and Spectramax i3x (363703638).

Preparation of Reagents

RPMI primary cell culture media was prepared starting with RPMI-1640. 10% HI-FBS, 1× GlutaMax, 1× penn/strep, and 50 μM 2-mercaptoethanol were added for complete media. RPMI cell culture media was prepared starting with RPMI-1640. 10% HI-FBS, 1× GlutaMax, and 1× penn/strep, were added for complete media. 1×HBS was prepared by diluting 1 part of 5×HBS into 4 parts of DI water. Solution was sterile filtered before use.

DELFIA Cytotoxicity Assay

Labeling Target Cells:

Briefly, CLEC12A+ target cells were pelleted, and washed with 1×HBS. Target cells were resuspended in pre-warmed RPMI primary cell culture media at $10^6$ cells/mL. BATDA reagent (bis(acetoxymethyl) 2,2':6',2"-terpyridine-6,6"-dicarboxylate) was diluted 1:400 into the cell suspension. Cells were mixed and incubated at 37° C. with 5% $CO_2$ for 15 minutes. The labeled target cells were washed 3× with 1×HBS and resuspended at $5\times10^4$ cells/mL in RPMI primary cell culture media.

Preparing the Assay Plate:

Rested human NK cells were removed from culture and pelleted, the cells were resuspended in RPMI primary cell culture media at $0.5\times10^6$ cells/mL. 4× test articles were prepared in RPMI primary cell culture media. In a round bottom TC 96-well plate, 100 μl of labeled target cells, 50 μl of 4× TriNKET/mAb, and 50 μl of effector cells were added. Control wells for background were prepared by pelleting labeled target cells, and 100 μl of the supernatant was added to background wells, containing 100 μl of RPMI primary cell culture media. Spontaneous release wells were prepared by adding 100 μl of labeled target cells to wells containing 100 μl of RPMI primary cell culture media. Maximum release wells were prepared by adding 100 μl of labeled target cells to wells containing 80 μl of RPMI primary cell culture media and 20 μl of 10% TritonX-100 solution. The assay plate was incubated at 37° C. with 5% $CO_2$ for 2-3 hours.

Reading the Assay Plate:

The assay plate was removed from the incubator and the plate was centrifuged to pellet cells. 20 μl of supernatant was removed from each well and transferred to a clean 96-well yellow DELFIA assay plate. 200 μl of room temperature Europium solution was added to each well and the plate was placed on a plate shaker 15 minutes at 250 RPM. The plate was read using an HTRF cartridge in a SpectraMax i3x with the following PMT and optics settings:

Integration time 0.4 ms
  Excitation time 0.05 ms
  Number of pulses 100
  Measurement delay 0.25 ms
  Read height 2.36 mm Data Analysis:

The mean of the background samples was calculated and subtracted from all samples. Specific lysis was calculated as follows:

% Specific lysis=(sample−spontaneous)/(max−spontaneous)*100%

Data were fit to a four-parameter non-linear regression model using Prism GraphPad 7.0 or 8.0.

IFNγ and CD107a Activation Assays

Plate Setup:

Human cancer cell lines expressing CLEC12A were harvested from culture, and cells were adjusted to $2 \times 10^6$ cells/mL. Test articles were diluted in culture media. Rested NK cells or PBMCs were harvested from culture, cells were washed, and were resuspended at $2$-$4 \times 10^6$ cells/mL in culture media. IL-2 and fluorophore conjugated anti-CD107a were added to the NK cells or PBMCs for the activation culture. Brefeldin-A (BFA) and monensin were diluted into culture media to block protein transport out of the cell for intracellular cytokine staining. Into a 96-well plate, 50 µl of tumor targets, mAbs/TriNKETs, BFA/monensin, and NK cells were added for a total culture volume of 200 µl. Plate was cultured for 4 hours before samples were prepared for FACS analysis.

Preparation of Samples for FACS:

Following the 4-hour activation culture, cells were prepared for analysis by flow cytometry using fluorophore conjugated antibodies listed in Table 189. CD107a and IFNγ staining was analyzed in CD3-CD56+ populations to assess NK cell activation.

TABLE 18

FACS NK activation panel

| Fluorophore | Target | Dilution factor |
|---|---|---|
| BV421 | IFNγ | 50 |
| BV510 | CD8 | 100 |
| BV605 | dump | |
| BV785 | CD3 | 100 |
| PE-D594 | CD56 | 100 |
| PE-Cy7 | CD4 | 100 |
| APC | CD107a | 50 |
| A700 | CD45 | 50 |
| NIR | live-dead | 1000 |
| | TruStain FcX | 50 |
| | BV buffer | 50 |
| | mono block | 50 |

Cells of interest were identified using FSC vs. SSC plot, and an appropriately shaped gate was drawn around the cells. Within the gated cells, doublet cells were removed by viewing FSC-H vs FSC-A plot. Within the single cell population, live cells were gated. Within live cells, NK cells were identified as CD56+CD3−. CD107a degranulation and intracellular (IC) IFNγ were analyzed within the NK cell population.

ADCP Assays

Primary human CD14+ monocytes are obtained from BioIVT. Monocytes were isolated from peripheral blood via negative selection yielding >93% purity. Monocytes were cultured for 6 days in 50 ng/ml rhM-CSF (R&D systems), replenishing rhM-CSF every two days. After 6 days, macrophages were detached from the culture flask(s) with TrypLE Express (Gibco) and labeled with Celltrace Violet (2 µM, ThermoFisher). Target cells were labeled with CFSE (2 µM, ThermoFisher). In round-bottom 96-well plates, target cells ($1 \times 10^4$ cells/well) are first incubated with the indicated concentrations of each test article for 30 minutes. Labeled macrophages ($8 \times 10^4$ cells/well) are then added to the appropriate wells and plates were incubated for an additional 2 hours. Cells were stained with Zombie NIR Dye (Biolegend) for live dead discrimination and fixed. Phagocytosis is quantified by Celesta HTS (BD Biosciences), with data analysis in FlowJo 10.5.3. Data were gated on single, live cells, and % phagocytosis was calculated as follows: % phagocytosis=100×(count CFSE+, Celltrace Violet+ cells)/(total count CFSE+ cells). Data were graphed and analyzed using GraphPad Prism.

CDC Assays

CDC was measured in a DELFIA cytotoxicity assay. PL21 cancer cell targets were labeled with BATDA labeling reagent. Labeled target cells were then incubated with the indicated concentrations of TriNKETs or mAbs for 30 min, to allow for opsonization. Human serum was added to a 5% final concentration. The plate was then incubated for 60 minutes before termination of assay. 20 µl of culture supernatant was transferred to DELFIA yellow plate. 200 µl europium solution was added per well and incubated at room temperature for 15 minutes with shaking in the dark. Fluorescence was then measured on the Spectramax plate reader.

Results and Discussion

Rested Human NK Cell Lysis of CLEC12A+ Target Cells

The activities of AB0089 and AB0192 was characterized using rested primary human NK cells from healthy donors in co-culture with either human CLEC12A+ AML line PL21 or HL60. AB0089 and AB0192 were compared to their parental hIgG1 mAbs AB0305 and AB0306, respectively. FIG. 194 shows a representative plot of PL21 leukemia target cell lysis by rested human NK cells in the presence of AB0089. AB0089 showed dose-dependent cell lysis enhancement activity that was more potent and reached a higher maximum lysis than its parental mAb AB0305. The results of similar cytotoxicity assays using NK cells derived from a total of six donors are summarized in Table 190. Across the assays, the potency AB0089 in enhancing NK cell lysis of PL21 target cells had mean EC50 value 0.25±0.24 nM.

TABLE 190

AB0089 EC50 and % Max lysis values for rested NK cell lysis of PL21 cells
(Values represent the mean of assays with a total of six donors standard deviation)

| Molecule | EC50 (nM) | % Max lysis |
|---|---|---|
| AB0089 | 0.25 ± 0.24 | 17 ± 10 |
| AB0305 | ND | ND |

ND = Not determined

FIG. 195 shows a representative plot of HL60 leukemia target cell lysis by rested primary human NK cells in the presence of AB0089. Again, AB0089 showed more potent dose-dependent lysis and higher specific lysis overall than its parental mAb AB0305. The results of assays using NK cells derived from four healthy donors yielded a mean EC50 of 0.09±0.05 nM as summarized in Table 191.

TABLE 191

AB0089 EC50 and % Max lysis values for
rested NK cells lysis of HL60 cells
(Values represent the mean of assays with a
total of four donors ± the standard deviation)

| Molecule | EC50 (nM) | % Max lysis |
|---|---|---|
| AB0089 | 0.09 ± 0.05 | 47 ± 14 |
| AB0305 | ND | ND |

ND = Not determined

FIG. 196 shows a representative plot of PL21 leukemia target cell lysis by rested human NK cells in the presence of AB0192. AB0192 showed dose-dependent cell lysis enhancement activity that was more potent and reached a higher maximum lysis than its parental mAb AB0306. The results of similar cytotoxicity assays using NK cells derived from a total of six healthy donors are summarized in Table 192. Across the assays, the potency AB0192 in enhancing NK cell lysis of PL21 target cells had mean EC50 value 0.61±0.60 nM.

TABLE 192

AB0192 EC50 and % Max lysis values for
rested NK cell lysis of PL21 cells
(Values represent the mean of assays with a
total of six donors ± the standard deviation)

| Molecule | EC50 (nM) | % Max lysis |
|---|---|---|
| AB0192 | 0.61 ± 0.60 | 18 ± 13 |
| AB0306 | ND | ND |

ND = Not determined

FIG. 197 shows a representative plot of HL60 leukemia target cell lysis by rested primary human NK cells in the presence of AB0192. Again, AB0192 showed more potent dose-dependent lysis and higher specific lysis overall than its parental mAb. The results of assays using NK cells derived from four healthy donors yielded a mean EC50 of 0.30±0.27 nM as summarized in Table 193.

TABLE 193

AB0192 EC50 and % Max lysis values for
rested NK cells lysis of HL60 cells
(Values represent the mean of assays with
a total of four donors ± the standard deviation)

| Molecule | EC50 (nM) | % Max lysis |
|---|---|---|
| AB0192 | 0.30 ± 0.27 | 50 ± 14 |
| AB0306 | ND | ND |

ND = Not determined

AB0089 Activity in the Presence of Soluble MIC-A

We also tested the activity of AB0089 in the presence of soluble NKG2D ligand. For these assays, we selected to use a recombinant version of the NKG2D ligand MIC-A. MIC-A has broad expression across cancer indications and is known to shed from the cell surface resulting in accumulation in patient serum. Soluble MIC-A-Fc was added to a NK cell cytolysis assay system at 20 ng/mL, a physiologically relevant serum concentration found in cancer patients. FIG. 198 shows the dose-response curves of AB0089 and its parental mAb AB0305 in a primary NK cell cytolysis assay against PL21 target cells in the absence and presence of soluble MIC-A. The addition of MIC-A had no effect on the potency or maximum lysis achieved by AB0089 (see Table 194 for EC50 and max lysis values).

TABLE 194

AB0089 EC50 and % Max lysis values for lysis
of PL21 cells by NK cells with sMIC-A-Fc

| Molecule | EC50 (nM) | % Max lysis |
|---|---|---|
| AB0089 | 0.32 | 15 |
| AB0089 + sMIC-A-Fc | 0.26 | 13 |
| AB0305 | ND | ND |
| AB0305 + sMIC-A-Fc | ND | ND |

ND = Not determined

AB0089 Stimulation of NK Cell IFNγ Production and Degranulation

In addition to direct lysis of target cells, NK cells also produce cytokines upon activation. Thus, we wanted to examine alternative readouts of NK activation in addition to target cell lysis. We chose to analyze IFNγ production and CD107a degranulation from NK cells co-cultured with CLEC12A+ AML cells in the presence of AB0089. Rested NK cells within PBMCs in co-culture with PL21 and HL60 target cells showed little basal induction of CD107a degranulation or intracellular IFNγ accumulation after four hours (FIG. 199 and FIG. 200, respectively). Addition of AB0089 to the co-cultures resulted in robust induction of degranulation and IFNγ production in a dose-responsive manner. In contrast, neither parental mAb AB0305 nor non-CLEC12A-targeting TriNKET F3'-palivizumab showed a robust increase in CD107a+IFNγ+ NK cells. Assays were performed with three independent PBMC donors in co-cultures with PL21 or HL60 target cells; the results are summarized in Tables 195 and 196, respectively.

TABLE 195

Summary of NK cell induction of IFNγ and
CD107a in co-culture with PL21 cells
(Values represent the mean of assays with a
total of three donors ± the standard deviation)

| Molecule | EC50 (nM) | % Max |
|---|---|---|
| AB0089 | 0.08 ± 0.05 | 15.3 ± 4.0 |
| AB0305 | ND | ND |
| F3'-palivizumab | ND | ND |

ND = Not determined

TABLE 196

Summary of NK cell induction of IFNγ and
CD107a in co-culture with HL60 cells
(Values represent the mean of assays with a
total of three donors ± the standard deviation)

| Molecule | EC50 (nM) | % Max |
|---|---|---|
| AB0089 | 0.05 ± 0.03 | 15.0 ± 4.6 |
| AB0305 | ND | ND |
| F3'-palivizumab | ND | ND |

ND = Not determined

AB0089 Induces ADCP Activity

The Fc domain of a human IgG1 antibody can mediate three different types of effector functions.

One type of Fc-mediated effector function is ADCC, which is carried out by engagement of CD16 on NK cells;

NK cell stimulation has been extensively characterized for AB0089. A second Fc-mediated effector function is ADCP, where macrophages attack and engulf cells coated with antibody. For AB0089 and alternative CLEC12A TriNKETs, we wanted to assess their ability to induce ADCP of opsonized target cells. We utilized an in vitro assay system with M0 macrophages, derived from culturing purified CD14+ monocytes with M-CSF, as effector cells. CLEC12A+ target cells were labeled with Cell Trace CFSE dye, opsonized with test articles and co-cultured with Cell Trace Violet-labeled M0 macrophages. Phagocytosis was analyzed by flow cytometry as Cell Trace Violet+ Cell Trace CFSE+ (double-positive) events.

AB0089 and other CLEC12A TriNKETs AB0237 and AB0192 all enhanced phagocytosis of PL21 AML cells by M0 macrophages. Parental mAbs for each TriNKET also all showed an ability to induce M0 macrophage phagocytosis of opsonized target cells, but to a lower maximum level compared to their respective corresponding TriNKET (FIG. 201). AB0237si, which bears mutations in the CH2 domain to silence Fcγ-receptor binding, served as a negative control. As expected, AB0237si failed to mediate ADCP of opsonized target cells. Results using M0 macrophages derived from three different donors are summarized in Table 197.

TABLE 197

Summary of EC50 and % Max values for ADCP activity
(Values represent the mean of assays with a total
of three donors ± the standard deviation.)

| Molecule | EC50 (nM) | % Max |
|---|---|---|
| AB0237si | ND | ND |
| AB0037 | 0.05 ± 0.06 | 11 ± 9 |
| AB0237 | 0.08 ± 0.07 | 12 ± 8 |
| AB0305 | 0.02 ± 0.01 | 10 ± 7 |
| AB0089 | 0.03 ± 0.02 | 15 ± 10 |
| AB0306 | ND | ND |
| AB0192 | 0.03 ± 0.02 | 15 ± 7 |

ND = Not determined

AB0089 does not have CDC Activity

A third effector function of human IgG1 isotype antibodies is initiation of the complement cascade, leading to complement dependent cytotoxicity (CDC). AB0089 is constructed using a human IgG1 Fc domain; therefore, we wanted to understand the ability of AB0089 to stimulate CDC activity. We used PL21 cells as targets and 5% human serum as a source of complement factors. Neither AB0089 nor its parental mAb AB0305 stimulated complement-mediated killing of PL21 AML cells (FIG. 202). In contrast, a positive control antibody against MHC class I (clone W6/32) showed dose-dependent lysis of PL21 target cells in the presence of human serum, corroborating that the serum has active complement factors. Cell characterization analysis indicated similar expression levels of CLEC12A and MHC class I on PL21 target cells.

AB0089 demonstrated potent activity in a variety of physiologically relevant contexts. AB0089 was first tested in CLEC12A+ target cell killing assays using rested primary human NK cells. We chose to test killing of CLEC12A+ target cells derived from AML, being the indication that overexpresses CLEC12A in the clinic. For these experiments, we selected HL60 and PL21 as representative AML cell lines.

AB0089 enhanced primary NK cell cytolysis of both target cell lines and outperformed its parental hIgG1 antibody in enhancing cytolysis. We also examined the impact of soluble NKG2D ligand on the activity of AB0089 and found that physiological levels of soluble MIC-A-Fc did not alter the activity of AB0089 in cell lysis.

In addition to cell lysis, AB0089 also stimulated cytokine production from NK cells co-cultured with CLEC12A+ target cells. AB0089 enhanced intracellular accumulation of IFNγ as well as NK cell degranulation in co-cultures of human PBMCs with PL21 and HL60 AML cells. EC50 values for IFNγ and CD107a induction by AB0089 were consistent with EC50 values generated in cell lysis assays.

Finally, we investigated additional mechanisms of action for AB0089. AB0089 was demonstrated to engage macrophages to mediate ADCP of AB0089-opsonized target cells. In contrast, AB0089 does not mediate CDC of AB0089-opsonized target cells.

AB0089 was demonstrated to have potent activity against CLEC12A+ cancer cells through various effectors, including NK cells and macrophages. Moreover, the activity of AB0089 was maintained in the presence of a physiologically-relevant concentration of soluble NKG2D ligand MIC-A.

Example 19. AB0089 Binding to CLEC12A+ Cell Lines and Primary AML

Objectives

Measure the binding of AB0089 to human CLEC12A-expressing cells. Quantify CLEC12A surface retention following incubation with AB0089. Demonstrate binding of AB0089 to primary AML patient samples and compare to CLEC12A expression pattern.

Study Design

Representative cell lines with positive CLEC12A surface expression were used for characterization of AB0089 cell binding. Primary AML patient samples were obtained from Creative Bioarray and BioIVT. Binding of AB0089 and parental mAb AB0305 were compared to a commercially available CLEC12A antibody.

Materials and Methods

Primary Cells and Cell Lines

Human cancer cell lines were obtained from research cell banks. Below cell lines (item number; vendor) were used: PL21 (ACC-536; DSMZ), HL60 (CCL-240; ATCC), Ba/F3-hCLEC12A (made in-house) and Ba/F3 (available from DSMZ ACC-300).

Human CLEC12A was introduced into Ba/F3 parental cells by retroviral transduction.

Cell Culture Materials

Below items (vendor; item number) were used: RPMI-1640 (Corning; 10040CV), DMEM (Corning; 10031CV), Heat inactivated FBS (ThermoFisher; 16140-071), GlutaMax I (ThermoFisher; 35050-061), Penn/Strep (ThermoFisher; 151450-122), and 2-Mercaptoethanol (MP Biomedicals; 02194705).

Assay Materials

Below items (vendor; item number) were used: Hepes buffered saline (Alfa Aesar; J67502), BATDA reagent (Perkin Elmer; C136-100), TC round bottom 96-well plate (Corning; 3799), Europium solution (Perkin Elmer; C135-100), and DELFIA yellow microplates 96-well (Perkin Elmer; AAAND-0001).

Below test articles (description) were used: AB0237 (CLEC12A-Targeted TriNKET with Fab NKG2D binding (A49), and scFv CLEC12A binding domain (1602)), AB0300 (AB0237 with LALAPG mutation in CH2 domain), AB0237-Dead-2D (AB0237, NKG2D binding domain mutated to ablate binding), AB0037 mAb (Humanized 1602 anti-CLEC12A mAb), AB0089 (CLEC12A-Targeted TriNKET with Fab NKG2D binding (A49) and scFv CLEC12A binding domain (1739)), AB0305 mAb (Humanized 1739 anti-CLEC12A mAb), AB0192 (CLEC12A-Targeted TriNKET with Fab NKG2D binding (A49), and scFv CLEC12A binding domain (1797)), AB0306 mAb (Humanized 1797 anti-CLEC12A mAb), hcFAE-A49.h6E7 (CLEC12A-Targeted TriNKET with Fab NKG2D binding (A49), and Fab CLEC12A binding domain (Genentech 6E7)) and hcFAE-A49.CLL1-Merus (CLEC12A-Targeted TriNKET with Fab NKG2D binding (A49), and Fab CLEC12A binding domain (Merus CLL-1 binder)).

Below instruments (serial number) were used: Attune NxT (2AFC228271119), BD Celesta (H66034400085), and BD Celesta (H66034400160).

Preparation of Reagents

RPMI primary cell culture media was prepared starting with RPMI-1640. 10% HI-FBS, 1× GlutaMax, 1× penn/strep, and 50 μM 2-mercaptoethanol were added for complete media. RPMI cell culture media was prepared starting with RPMI-1640. 10% HI-FBS, 1× GlutaMax, and 1× penn/strep, were added for complete media. 1×HBS was prepared by diluting 1 part of 5×HBS into 4 parts of DI water. Solution was sterile filtered before use.

Binding and Detection of Surface Bound mAb/TriNKET 100,000 cells were seeded per well into a 96-well plate for FACS staining. Cells were washed with PBS. Cells were incubated in a 1:2000 dilution of live/dead dye in PBS for 15 minutes, then washed with FACS buffer. TriNKETs or mAbs were diluted into FACS buffer, and 50 μl containing diluted TriNKET or mAb was added to cells. Cells were incubated on ice for 20 minutes. After the incubation, cells were washed with FACS buffer. Anti-human IgG-Fc secondary antibody was diluted into FACS buffer, and 50 μl was added per well for detection of the bound TriNKETs or mAbs. Cells were incubated for 20 minutes on ice, then washed with FACS buffer. 50 μl of fixation buffer was added to each well, and cells were incubated for 10 minutes at room temperature. Cells were washed with FACS buffer and resuspended in FACS buffer for analysis with BD FACS Celesta SN #H66034400085, or BD FACS Celesta SN #H66034400160. Cells of interest were identified using FSC vs. SSC plot, and an appropriately shaped gate was drawn around the cells. Within the gated cells, doublet cells were removed by viewing FSC-H vs FSC-A plot. Within the single cell population, live cells were gated. Within the live gate, the mean fluorescence intensity (MFI) of each sample and the secondary-only control was calculated. Fold-over-background (FOB) was calculated as the ratio of test article MFI over secondary-only background MFI. Data were fit to a four-parameter non-linear regression curve using GraphPad Prism 7.0.

Surface Retention Assays 100,000 cells were seeded per well into duplicate 96-well plates for FACS staining. Cells were washed with FACS buffer. Test articles were diluted to 40 nM and were added to each of the duplicate plates. The first plate was incubated on ice for 2 hours, while the second plate was moved to 37° C. for two hours. After the incubation, cells were washed with PBS and cells were incubated in a 1:2000 dilution of live/dead dye in PBS for 15 minutes, then washed with FACS buffer. Anti-human IgG-Fc secondary antibody was diluted into FACS buffer, and 50 μl was added per well for detection of the bound TriNKETs or mAbs. Cells were incubated for 20 minutes on ice, then washed with FACS buffer. 50 μl of fixation buffer was added to each well, and cells were incubated for 10 minutes at room temperature. Cells were washed with FACS buffer and resuspended in FACS buffer for analysis with BD FACS Celesta SN #H66034400085, or BD FACS Celesta SN #H66034400160. Cells of interest were identified using FSC vs. SSC plot, and an appropriately shaped gate was drawn around the cells. Within the gated cells, doublet cells were removed by viewing FSC-H vs FSC-A plot. Within the single cell population, live cells were gated. Within the live gate, the MFI of each sample was calculated. hIgG1 isotype control MFI was subtracted from all test article MFIs. Surface retention was then calculated as follows:

% surface retention=(2-hour 37° C. MFI/2-hour ice MFI)*100

Analysis of AB0089 Binding in Primary AML Samples

Frozen AML patient samples were thawed at 37° C. and used immediately in binding assays. Test articles, hIgG1 isotype control and commercial reagent anti-CLEC12A antibody clone 50C1 were labeled using the Biotium Mix-n-Stain CF568 labeling kit; manufacturer's instructions were followed. AML samples were stained with a cocktail of antibodies as described in Tables 198 and 199. Samples were analyzed using an Attune NxT cytometer equipped with CytKick Max autosampler. Raw data was analyzed using FlowJo X software.

TABLE 198

AML patient sample flow cytometry panel

| Fluorophore | Antigen | Dilution factor | Vendor | Cat # |
| --- | --- | --- | --- | --- |
| BV421 | CD38 | 100 | BioLegend | 368514 |
| BV510 | CD33 | 100 | BioLegend | 366610 |
| BV605 | CD15 | 100 | BioLegend | 323032 |
| BV650 | CD14 | 100 | BioLegend | 301836 |
| BV785 | CD45 | 50 | BioLegend | 368528 |
| FITC | CD34 | 50 | StemCell | 60013F1 |
| PE or CF568 | CLEC12A | | See Table 200 | |
| PE-Cy7 | CD117 | 100 | BioLegend | 313212 |
| APC | CD13 | 100 | BioLegend | 301706 |
| NIR | live-dead | 1000 | BioLegend | 423105 |
| | TruStain FcX | 25 | BioLegend | 422302 |
| | BV buffer | 25 | BD | 566349 |
| | mono block | 25 | BioLegend | 426103 |

TABLE 199

CLEC12A antibodies and labeled test articles

| Molecule | lot # |
| --- | --- |
| hIgG1 | EXP20000921-RMR 18 Mar. 2020 |
| AB0305 | EXP200001542-RMR 22 May 2020 |
| AB0089 | EXP200001542-RMR 22 May 2020 |
| AB0306 | EXP200001542-RMR 22 May 2020 |
| AB0192 | EXP200001542-RMR 22 May 2020 |
| 50C1 | EXP200001542-RMR 22 May 2020 |

TABLE 200

Primary AML patient samples

| Sample ID | Tissue | AML subtype | Vendor |
|---|---|---|---|
| 19217S | PBMC | M3 | Creative Bioarray |
| 19224S | PBMC | M1 | Creative Bioarray |
| 19233S | PBMC | M1 | Creative Bioarray |
| 19246S | PBMC | M5a | Creative Bioarray |
| 19258S | Bone marrow | M5b | Creative Bioarray |
| Y1724 | PBMC | M4 | Creative Bioarray |
| W5299 | PBMC | M2 | Creative Bioarray |
| W5300 | PBMC | M3 | Creative Bioarray |
| W5313 | Bone marrow | M1 | Creative Bioarray |
| W5294 | PBMC | M0 | Creative Bioarray |

Results and Discussion

CLEC12A TriNKETs Bind Cell Lines Expressing Human CLEC12A

Binding of CLEC12A TriNKETs and their parental mAbs were tested using three cell lines expressing human CLEC12A (FIGS. 203A-203C). Mouse Ba/F3 cells were engineered to express human CLEC12A, while PL21 and HL60 are human AML cell lines with endogenous CLEC12A expression.

As comparators, two tool TriNKETs were generated using CLEC12A binding domains from Genentech (h6E7) and Merus (CLL1-Merus) known in the public domain. Duobody TriNKETs with Fab CLEC12A binding domains were paired with Fab NKG2D binder A49. Duobody TriNKET hcFAE-A49.h6E7 is derived from the Genentech binder, while hcFAE-A49.CLL1-Merus is derived from the Merus binder.

Lead TriNKET AB0089 and alternative CLEC12A TriNKETs AB0237 and AB0192 all bound CLEC12A expressing cells with nanomolar potency (Table 4). AB0089 had reduced potency but reached a higher maximum FOB compared to its parental mAb AB0305 on the three cell lines tested. AB0237 demonstrated comparable binding to its parental mAb AB0037, yielding potency values within 2-fold of each other for all three cell lines. Variants of AB0237 AB0237-Dead 2D and AB0300 bearing mutations in the NKG2D and CD16 binding domains, respectively, showed similar cell binding compared to AB0237. In contrast, AB0192 showed decreased potency and maximum FOB compared to its parental mAb AB0306.

In comparison to tool TriNKETs, AB0089 showed comparable cell loading to hcFAE-A49.CLL1-Merus and higher cell loading than hcFAE-A40.h6E7. In addition, AB0237 binding CLEC12A cell lines was more potent than hcFAE-A49.CLL1-Merus and comparable in potency to hcFAE-h6E7. All EC50 binding potencies and maximum FOB binding are summarized in Table 201.

TABLE 201

Summary of cell binding values

Average EC50 values in nM and mean FOB with ± standard deviation from three independent experiments.

| | HL60 | | PL21 | | Ba/F3-hCLEC12A | |
|---|---|---|---|---|---|---|
| | EC50 nM | FOB | EC50 nM | FOB | EC50 nM | FOB |
| AB0089 | 1.08 ± 0.24 | 70 ± 28 | 0.34 ± 0.13 | 16 ± 8 | 2.28 ± 0.59 | 434 ± 258 |
| AB0305 | 0.12 ± 0.01 | 53 ± 16 | 0.12 ± 0.01 | 15 ± 9 | 0.67 ± 0.20 | 279 ± 182 |
| AB0192 | 0.61 ± 0.15 | 42 ± 14 | 0.37 ± 0.08 | 12 ± 5 | 1.33 ± 0.41 | 325 ± 242 |
| AB0306 | 0.26 ± 0.08 | 47 ± 10 | 0.18 ± 0.05 | 12 ± 5 | 0.68 ± 0.09 | 303 ± 205 |
| AB0237 | 1.01 ± 0.14 | 66 ± 18 | 0.52 ± 0.09 | 15 ± 6 | 1.54 ± 0.35 | 341 ± 249 |
| AB0037 | 0.52 ± 0.12 | 51 ± 14 | 0.52 ± 0.09 | 13 ± 7 | 1.40 ± 0.24 | 301 ± 173 |
| AB0237 Dead-2D | 1.19 ± 0.15 | 59 ± 14 | 0.63 ± 0.14 | 14 ± 6 | 2.35 ± 0.62 | 357 ± 233 |
| AB0300 | 1.50 ± 0.19 | 65 ± 20 | 1.58 ± 0.14 | 18 ± 6 | 2.92 ± 0.57 | 368 ± 249 |
| hcFAE-A49.h6E7 | 1.33 ± 0.22 | 31 ± 10 | 0.55 ± N/A | 10 ± 5 | 2.87 ± 0.56 | 318 ± 212 |
| hcFAE-A49.CLL1-Merus | 2.79 ± 1.04 | 59 ± 24 | 1.13 ± 0.14 | 15 ± 10 | 4.45 ± 0.78 | 369 ± 186 |

CLEC12A-TriNKET Surface Retention

Internalization of CLEC12A following antibody ligation has been described in the literature. Leveraging on this phenomenon, antibody-drug conjugates targeting CLEC12A have been developed that depend on internalization of conjugated drugs to kill target cells. TriNKET activity, however, requires cell surface retention of CLEC12A in complex with TriNKETs to allow for NK cell engagement and effector activity against CLEC12A+ cancer cells. To better understand CLEC12A retention on cell surfaces in the presence of CLEC12A TriNKETs, we examined the binding of saturating concentrations of each TriNKET and parental mAb to CLEC12A+ cell lines after a two-hour incubation at 37° C. compared to incubations on ice.

When bound to cells for 2 hours at 37° C., 90% or more of cell surface CLEC12A was retained with each of the TriNKETs. FIGS. 204A-204B show examples of surface retention for AB0089, AB0192, AB0237 and their parental antibodies on HL60 and PL21 AML lines. The data from three independent experiments are summarized in Table 202. AB0089 appeared to demonstrate superior surface retention compared to other CLEC12A TriNKETs and their parental mAbs.

However, AB0089 showed a lower binding signal after incubation on ice compared to AB0237 but had a similar signal after incubation at 37° C. for two hours, which may have led to inflated surface retention values for AB0089 (FIG. 205). Nevertheless, these data suggest temperature-dependent binding of AB0089 to reach equilibrium, which could result from two-step binding mechanism suggested by kinetic binding data (Example 17).

By contrast, AB0192 and its parental mAb AB0306, which originates from a different parental murine mAb, showed similar surface retention on HL60 and PL21 cells. These data indicate that surface retention of CLEC12A may be dependent upon whether bound monovalently (as is the case for F3' TriNKETs) versus bivalently (as mAbs do) as well as the epitope of the specific binder.

TABLE 202

Summary of CLEC12A cell surface retention Values indicate the average percent surface retention for a given test article after two hours at 37° C. relative to the same test article after two hours on ice in three experiments ± standard deviation.

|  | HL60 | PL21 |
| --- | --- | --- |
| AB0089 | 147 ± 13 | 124 ± 12 |
| AB0305 | 90 ± 7 | 92 ± 2 |
| AB0192 | 103 ± 8 | 101 ± 10 |
| AB0306 | 114 ± 4 | 106 ± 9 |
| AB0237 | 106 ± 4 | 91 ± 9 |
| AB0037 | 74 ± 1 | 79 ± 3 |

AB0089 Binds CLEC12A on Human AML Patient Samples

Primary bone marrow and PBMC samples from a total of 10 AML patients were obtained (see Table 200 for sample information) to examine binding of AB0089 and its parental mAb AB0305 on primary AML cells. We compared binding patterns of fluorophore-labeled test articles AB0089 and AB0305 to a commercially available anti-CLEC12A antibody clone 50C1 (Lahoud et al, The Journal of Immunology. 2009; 182:7587-7594). Among the 10 donors, the percentage of CLEC12A+ cells in the AML blast gate varied widely from ~40-95%. We analyzed AML patient samples from different FAB subtypes, which might contribute to the variation in CLEC12A expression and proportion observed.

AB0089 and AB0305 demonstrate a comparable binding pattern to anti-CLEC12A clone 50C1 across the 10 AML patient samples tested (FIGS. 206A-206J). We further gated blasts to examine the CD34+CD38– subpopulation, which is enriched for leukemic stem cells, from each sample. Again, AB0089 and AB0305 had similar staining on CD34+CD38– blasts as clone 50C1 (FIGS. 207A-207J). Overall, these data corroborated that AB0089 is able to bind CLEC12A on primary AML blasts as well as on the CD34+CD38– subset that is enriched for LSCs.

AB0089 and other CLEC12A TriNKETs bound to Ba/F3 cells ectopically expressing human CLEC12A as well as PL21 and HL60 AML cells expressing endogenous CLEC12A in a dose-responsive manner with similar nanomolar potencies across the lines. Despite reports in the literature of CLEC12A internalization following antibody ligation, AB0089 and both alternative CLEC12A TriNKETs AB0237 and AB0192 showed high cell surface retention of CLEC12A after two hours of incubation with HL60 and PL21 CLEC12A+ cell lines. Finally, AB0089 and its parental mAb AB0305 bound similarly to a commercial reagent anti-CLEC12A antibody clone 50C1 on bulk and CD34+CD38– blasts across primary AML patient samples from 10 donors. Together, these data support potent binding of AB0089 to cells expressing CLEC12A and indicates that AB0089 binds to primary AML blasts.

Example 20. AB0089 CLEC12A TrinKET

Objectives

The objectives of this study are to describe the molecular format, design, structure, and characteristics of CLEC12A TriNKET AB0192. In particular, in this report we a) describe the molecular format and design of AB0192, b) provide information about expression and purification of AB0192, c) describe basic biochemical and biophysical characterization of the molecule, d) determine the affinity of AB0192 for recombinant human targets (CLEC12A, NKG2D and CD16a), e) demonstrate AB0192 binding to isogenic and AML cancer cell lines expressing human CLEC12A, f) demonstrate selectivity of AB0192, g) determine potency of AB0192 in killing AML cancer cells, h) assess binding epitope, i) assess binding to FcγR and FcRn and compare with IgG1 mAb control, j) describe behavior of AB0192 in developability studies including accelerated stability, forced degradation, and manufacturability.

Study Design

Murine anti-human CLEC12A mAb (9F11.B7) was discovered by mouse immunization. 9F11.B7 was humanized, converted to a scFv and combined with A49M-I NKG2D Fab binding arm to produce an F3'-TriNKET (AB0192). AB0192 was assessed by binding to recombinant human and cyno CLEC12A, binding to isogenic and cancer cells expressing CLEC12A as well as potency of the molecule against CLEC12A+ AML cancer cells. The biophysical and biochemical characteristics of AB0192 including thermal stability (DSC), hydrophobicity (HIC), and pI (cIEF) were determined. Specificity of binding was assessed by PSR, binding to cells not expressing the target of interest and by HuProt™ Array. AB0192 was expressed in two different mammalian cell lines (Expi293 and ExpiCHO) and purified using DragonflyTx 2-step platform purification method. Binding properties of AB0192, including CLEC12A, NKG2D, CD16a (V158 and F158), an extended panel of Fcγ receptors (CD32a (H131 and R131), CD16b, CD32b, cynomolgus CD16, human and cynomolgus CD64), and FcRn (human and cynomolgus) was fully characterized. Binding epitope was characterized in binning experiment with CLEC12A binding molecules from Merus and Genentech. Lastly, AB0192 was assessed in a full developability panel, including accelerated (40° C.) stability in the Dragonfly Tx platform formulation (20 mM histidine, 250 mM sucrose, 0.01% Tween-80, pH 6.0) and 20 mM citrate, 250 mM sucrose, 0.01% Tween-80, pH 7.0 buffer, forced degradation (long term pH 5, pH 8 stress, forced oxidation), and manufacturability (freeze/thaw, agitation, low pH hold).

Materials and Methods

Methods used to produce and characterize AB0192 are similar to the ones used in Example 17.

Test Articles

AB0192-002, (Benchling record name AB0192), humanized TriNKET expressed in Expi293 (lot AB0192-002).

AB0192-005, (Benchling record name AB0192), humanized TriNKET expressed in ExpiCHO (lot AB0192-005).

Protein Reagents

TABLE 203

Summary of protein reagents.

| Name | Manufacturer | Lot |
| --- | --- | --- |
| Human CLEC12A-His | Dragonfly Tx | 16 Oct. 2018 GL |
| Human CLEC12A-K244Q-His | Dragonfly Tx | 30 Apr. 2018 AC |
| Cyno CLEC12A-His | Dragonfly Tx | 30 May 2018 AC |
| mFc-hNKG2D | Dragonfly Tx | 1 Dec. 2017 AB |
| mFc-cNKG2D | Dragonfly Tx | 28 Sep. 2018 GL |
| humanized mAb 16B8.C8 | Dragonfly Tx | AB0037-001 |
| hcFAE-A49.CLL1-Merus (Duobody TriNKET) | Dragonfly Tx | 10 May 2018 DF |
| hcFAE-A49.h6E7 (Duobody TriNKET) | Dragonfly Tx | 5 Feb. 2019 DF |
| hcFAE-A49.tepoditamab (Duobody TriNKET) | Dragonfly Tx | 27 Aug. 2019 XL |
| Trastuzumab | Roche | N3017H05 |
| Adalimumab | AbbVie | 83364XH07 |
| Rituximab | Dragonfly Tx | 19 Apr. 2019 MH |

Results

Discovery of AB0192 TriNKET

Hybridoma subclone 9F11.B7 was discovered through immunization of BALB/c mouse strain with recombinant human CLEC12A-his preformed at Green Mountain Antibodies (Burlington, VT).

Murine 9F11.B7 was humanized by grafting murine CDRs to the appropriate human framework (VH3-30*02 and VK1-33) without loss of affinity for recombinant CLEC12A or cell surface expressed target (FIGS. 208A-208F). 7 murine backmutations were introduced to maintain CDRs architecture. Humanized 9F11.B7 mAb was converted to a scFv and paired with NKG2D targeting A49 M-I Fab to produce F3' TriNKET (AB00192). This TriNKET was extensively characterized and designated as a candidate for CLEC12A program AB0192.

Molecular Format and Design

AB0192 is a heterodimeric tri-functional antibody that redirects NK and T cell activity against CLEC12A-expressing cancer cells. AB0192 contains three chains: Chain H, Chain L and Chain S. The schematic representation of the AB0192 molecule is provided in FIG. 209. Chain H is the heavy chain of A49M-I that was selected for having low affinity while being a potent agonist of NKG2D receptors on NK and cytotoxic T cells. The M-I mutation was introduced to replace the Met102 residue in the CDRH3 that is sensitive to oxidation and therefore may present a liability. Chain L is the light chain of the anti-NKG2D-targeting antibody A49M-I. Chain S contains a scFv that binds with high affinity to CLEC12A on AML cancer cells. Both scFv and Fab domains are fused to a human IgG1 Fc that has native, unmodified sequence in the CH2 domain, where antibodies bind to Fc receptors. Both chains bear several mutations in the CH3 domain introduced to ensure stable heterodimerization of two Fc monomers. There are seven such mutations in the IgG1 Fc of the AB0192: three mutations in Chain H (K360E, K409W, Y349C) and four mutations in Chain S (Q347R, D399V, F405T and S354C). Two of these mutations are involved in the formation of a stabilizing S—S bridge (Y349C and S354C) between Chains H and Chain S (EU nomenclature). scFv (VH-VL orientation) in Chain S is stabilized by two mutations introducing a S—S bridge ((H44)C and (L100)C, Chothia nomenclature). Chain S also contains a (G4S)4 non-immunogenic linker between VH and VL of scFv. The amino acid sequence of the CLEC12A-targeting scFv is based on the sequence of humanized 9F11.B7 antibody, obtained from hybridoma (Green Mountain Antibodies, Burlington, VT). The amino acid sequence of NKG2D Fab is based on the fully human antibody A49M-I, obtained using human yeast display technology (Adimab, Lebanon, NH).

Description of Heterodimerization Mutants

EU-numbering convention was used to annotate the amino acid residues in the Fc.

Chain H contains the following mutations:
  K360E—Heterodimerization mutation in the CH3 domain of the Fc region.
  K409W—Heterodimerization mutation in the CH3 domain of the Fc region.
  Y349C—Inter-subunit disulfide stabilization mutation in the CH3 domain of the Fc region.

The K360E/K409W mutations in the Fc region of Chain H are designed to render heterodimer-favoring interactions with Chain S due to hydrophobic/steric complementarity plus long-range electrostatic interactions (Choi et al., (2013) Mol Cancer Ther 12(12):2748-59; Choi et al., (2015) Mol Immunol 65(2):377-83). The mutation Y349C was introduced to generate an additional inter-chain disulfide bond Y349C-(CH3-ChainH)-S354C(CH3-ChainS) pair (Choi et al., (2015) Mol Immunol 65(2):377-83).

Chain S Contains the Following Mutations:
  G44C—Disulfide stabilization mutation in VH region of the scFv.
  Q100C—Disulfide stabilization mutation in VL region of the scFv.
  Q347R—Heterodimerization mutation in the CH3 domain of the Fc region.
  D399V—Heterodimerization mutation in the CH3 domain of the Fc region.
  F405T—Heterodimerization mutation in the CH3 domain of the Fc region.
  S354C—Inter-subunit disulfide stabilization mutation in the CH3 domain of the Fc region.

The mutations G(H44)C and Q(L100)C were introduced to stabilize the scFv by an engineered disulfide bond between the VH and the VL. The disulfide stabilization improves structural and thermal stability of scFv. The Q347R/D399V/F405T mutations in the Fc region of Chain S were designed to render heterodimer-favoring interactions with Chain H due to hydrophobic/steric complementarity plus long-range electrostatic interactions (Choi et al, (2013) Mol Cancer Ther 12(12):2748-59). The mutation S354C was introduced to generate an additional inter-CH3 disulfide bond with a Y349C(CH3-ChainH)-S354C(CH3-ChainS) pair (Choi et al., (2015) *Mol Immunol* 65(2):377-83).

Amino Acid Sequence

The amino acid sequences of the three polypeptide chains that make up AB0192 are shown in FIG. 210. CDRs are outlined in Table 204.

TABLE 204

Sequences of AB0192 CDRs*.

| AB0192 | Variable region | Frame- work | CDR1 | CDR2 | CDR3 |
|---|---|---|---|---|---|
| Chain S | VH | VH3-30 | GFTFNAF (SEQ ID NO: 195) | SSGSTS (SEQ ID NO: 196) | DGYPTGGA MDY (SEQ ID NO: 187) |
| Chain S | VL | VK1-33 | KASQDIYN YLS (SEQ ID NO: 198) | RAN1LVS (SEQ ID NO: 199) | LQFDAFPF T (SEQ ID NO: 201) |
| Chain H | VH | VH3-21 | GFTFSSY (SEQ ID NO: 297) | SSSSY (SEQ ID NO: 338) | GAPMIGAA AGWFDP (SEQ ID NO: 339) |
| Chain L | VL | VK1-12 | RASQGISS WA (SEQ ID NO: 337) | AASSLQS (SEQ ID NO: 77) | QQGVSFPR T (SEQ ID NO: 87) |

*CDRs are identified by Chothia

Analysis of Potential Sequence Liabilities

Chain L (NKG2D binding light chain) has no predicted liabilities. Chain H (NKG2D binding heavy chain) has a DP in CDRH3. This motif is not affected by forced degradation. As such, this sequence was not altered in AB0089. Chain S contains a Met (potential oxidation site) and DG (potential isomerization site) in CDRH3. No preemptive removal of M or DG in CDRH3 was attempted. We have carefully monitored modification of these residues during accelerated stability and forced degradation studies. No modification of Met or DG was observed under any stresses tested, as shown below.

Framework Assessment

The CLEC12A binding arm of AB0192 was discovered through mouse immunization. The frameworks chosen for humanization are frequently used in clinical stage therapeutic monoclonal antibodies (FIGS. 211A-211D). The NKG2D binding arm is fully human, is based on a framework frequently used in advanced stage mAbs and does not contain any unusual residues or deviations from the germline.

Backmutations

Molecular modelling was used to choose murine backmutations that help maintaining CDRs architecture (Table 205). Seven backmutations: 3 in the HC and 4 in the LC were introduced.

TABLE 205

Summary of murine backmutations introduced in the human framework in AB0192.

| Framework | Number of back mutations | Murine framework residues (Chothia) |
|---|---|---|
| VH | 3 | E(H1), R(H94), S(H108) |
| VL | 4 | F(L36), P(L46), Q(L69), Y(L71) |

Structure Modeling

In the absence of a crystal structure, structural models of the variable segments of CLEC12A and NKG2D binding arm were generated for comparison. Model building was performed using the SAbPred website (opig.stats.ox.ac.uk/webapps/newsabdab/sabpred/).

Surface Charge Distribution and Hydrophobic Patch Analysis of CLEC12A Binding Arm of AB0192

FIGS. 212A-212C illustrate a ribbon diagram model of the CLEC12A binding scFv in three different orientations (upper panel) and their corresponding surface charge distribution of the same orientation (lower panel). The charge distribution of anti-CLEC12A scFv is polarized ("top view", lower panel), with negatively-charged residues populated predominately within CDRH3 and CDRL2. The uneven distribution of electrostatic patches on the paratope is likely to be target-related and reflects the complementarity of charge distribution on its cognate epitope, which may likely contribute to the high affinity interaction between CLEC12A and the scFv of AB0192.

FIGS. 213A-213B show the analysis of CDR length and surface hydrophobicity patches of the CLEC12A-targeting arm of AB0192. Analyses were performed using therapeutic antibody profiles (TAP): opig.stats.ox.ac.uk/webapps/newsabdab/sabpred/tap. It compares the candidate in reference to 377 late-stage therapeutic antibodies. The length of CDRs for the CLEC12A-binding arm of AB0192 are within typical for late stage therapeutic antibodies. Hydrophobic patch analysis of the CDRs of an antibody is predictive of its developability. The theoretical hydrophobic properties of the TAA arm of AB0192 are well within the norm of commercialized biotherapeutics and late-stage therapeutic antibody candidates.

FIGS. 214A-214C shows the analysis of patches containing positive and negative charges, as well as the symmetry of these charges around the CDR regions. All three charts indicate that the charge distributions are within the norm compared to advanced stage therapeutic antibodies.

Surface Charge Distribution and Hydrophobic Patch Analysis of NKG2D Binding Arm of AB0192

The NKG2D-binding Fab arm is shown in ribbon diagrams with three different orientations (FIGS. 215A-215C, upper panel) and their corresponding surface charge distribution of the same orientation are provided in FIGS. 215A-215C, lower panel). The surface charge distribution on NKG2D A49M-I arm is more evenly distributed than charges on CLEC12A targeting arm of the molecule.

FIGS. 216A-216B show the CDR length and patches of surface hydrophobicity analyses of NKG2D-targeting arm of AB0192. It appears that the CDR length, the hydrophobic properties, the positive/negative charge distributions of the NKG2D-targeting arm of AB0192 are well within the norm of existing therapeutic antibodies.

FIGS. 217A-217C show the analyses of patches containing positive and negative charges, as well as the symmetry of these charges around the CDR regions. All three charts indicate that the charge distributions are within the norm comparing with the population of therapeutic antibodies.

Immunogenicity Prediction

The protein sequences of three chains of AB0192 were examined for the presence of potentially immunogenic T cell epitopes using the EpiMatrix algorithm and to rank the immunogenicity potential (FIGS. 218A-218B). AB0192 scores favorably on the Treg adjusted Immunogenicity Protein Scale. The Treg adjusted Epimatrix Protein Score for the sequences of the three chains of AB0192 are chain H: −33.39, chain S: −19.94 and chain L: −23.49 (Table 206). The predicted risk of immunogenicity for the AB0192 appears to be low.

TABLE 206

EpiVax immunogenicity analysis of AB0192.

| Protein Sequence | Length | EpiMatrix Hits | EpiMatrix Score | Treg adjusted Score |
|---|---|---|---|---|
| AB0192_CHAIN_H | 451 | 207 | 5.99 | −33.39 |
| AB0192_CHAIN_L | 214 | 98 | 11.17 | −23.49 |
| AB0192_CHAIN_S | 475 | 227 | 12.13 | −19.94 |

Expression

Expression of AB0192 was achieved using Dragonfly Tx F3' TriNKET platform purification method. Briefly, AB0192 was expressed by transient transfection of Expi293 and ExpiCHO cells with three plasmids encoding the NKG2D targeting light chain (chain L), the NKG2D targeting IgG heavy chain (chain H), and the CLEC12A targeting scFv-Fc fusion (chain S). For both Expi293 and ExpiCHO expression, Chain S:Chain H:Chain L were transfected at the plasmid ratio 4:1:1 to maximize the percentage of desired heterodimer product. This ratio was empirically obtained based on previous humanized TriNKETs developed and was not specifically optimized for AB0192.

Purification

Purification of AB0192 was performed using 2 step F3' TriNKET platform purification method. No optimization or extensive process development for AB0192 purification was performed. The schematic representation of AB0192 purification (lot AB0192-005) expressed in ExpiCHO is shown on FIGS. 219A-219D.

Two lots of AB0192 were produced in transiently transfected ExpiCHO and Expi293 cells. Table 207 summarizes the titer and final product purity for both lots.

TABLE 207

Summary of expression titers and final purity of two AB0192 lots.

| AB0192 Lot | Expression host | Titer (mg/L) | Purity, % Monomer |
|---|---|---|---|
| AB0192-002 | Expi293 | 16 | 99.5 |
| AB0192-005 | ExpiCHO | 26 | 100.0 |

The identity of AB0192 was corroborated by mass spectrometry. LC-MS analysis of the intact AB0192 (lot AB0192-005) showed an observed mass (126,429.9 Da) (FIG. 220) that agrees well with the theoretical mass of 126,429.5 Da. The major observed glycosylation pattern (G0F/G0F) is typical for an Fc-containing molecule expressed in CHO cells.

Biochemical and Biophysical Properties

AB0192 was characterized by SEC, CE, cIEF, HIC, and DSC to corroborate that is has the proper purity and pre-developability characteristics of a good biological therapeutic.

Purity

Purity of AB0192 (lot AB0192-005) assessed by SEC, non-reduced and reduced CE-SDS is summarized Table 208.

TABLE 208

Purity of AB0192 by SEC and CE-SDS analysis.

| | SEC | | | NR CE-SDS | R CE-SDS |
|---|---|---|---|---|---|
| Test article | HMW (%) | Monomer (%) | LMW (%) | Purity (%) | Purity (%) |
| AB0192 (lot AB0192-005) | ND | 100 | ND | 95 | 98.8 |

Size Excluscion Chromatography

SEC analysis of purified AB0192 (lot AB0192-005) showed >99% monomer as determined by integrated peak area (FIG. 221).

Non-Reduced and Reduced CE-SDS

AB0192 has high purify by CE-SDS (FIGS. 222A-222B). Under non-reduced conditions (left panel) the major impurities are method induced (free light chain and TriNKET—LC). Under reduced conditions (right panel) three expected chains (light chain (L), heavy chain (H), and scFv-Fc chain (S)) are observed.

Experimental pI and Charge Profile by cIEF cIEF profile of AB0192 (lot AB0192-005) is shown on (FIG. 223). AB0192 has a major peak at a pI of 8.9±0.0. Several lesser abundant, overlapping acidic peaks and minor basic peaks are also observed.

Hydrophobicity Assessed by HIC

Hydrophobicity of AB0192 was assessed using hydrophobic interactions chromatography (HIC) (FIG. 224 and Table 209). The chromatogram reveals a single narrow peak, indicating that the molecule is highly pure and homogeneous. Retention time for AB0192 is comparable with retention time of Humira (a well behaved therapeutic monoclonal antibody).

TABLE 209

Hydrophobicity assessment of AB0192 by HIC. Humira is used as an internal control of well-behaved IgG1 mAb.

| Test article | Retention time (min) |
|---|---|
| AB0192 | 9.9 |
| Humira | 8.9 |

Thermal Stability by DSC

The thermal stability of AB0192 was assessed by DSC in several buffers (PBS, pH 7.4, HST, pH 6.0, CST, pH 7.0). AB0192 demonstrated high thermal stability in all buffers tested (FIGS. 225A-225C, Table 210). Tm1 corresponding to the unfolding of scFv satisfied ≥65° C. criteria postulated in thermostability assessment.

TABLE 210

Thermal stability analysis of AB0192 in three different buffer systems by DSC.

| Test Article | Buffer | $T_{onset}$ (° C.) | $T_{m1}$ (° C.) | $T_{m2}$ (° C.) | $T_{m3}$ (° C.) | $T_{m4}$ (° C.) |
|---|---|---|---|---|---|---|
| AB0192 | PBS, pH 7.4 | 60.0 | 67.3 | 76.5 | 81.4 | 83.3 |
| AB0192 | HST, pH 6.0 | 60.8 | 69.0 | 78.8 | 84.0 | 86.1 |
| AB0192 | CST, pH 7.0 | 61.2 | 68.0 | 77.4 | 82.0 | 83.9 |

Disulfide Bond Assignment

AB0192 is an engineered molecule based on the backbone of a monoclonal IgG1 antibody. While a typical IgG1 contains 16 disulfide bonds, AB0192's F3' format has only 15 disulfide bonds. Half of AB0192 is an anti-NKG2D half antibody, as such it contains the expected seven disulfide bonds (one in each IgG domain and the intermolecular disulfide connecting the LC to the HC). The other half of AB0192 is an anti-CLEC12A scFv-Fc fusion. The scFv contains three disulfide bonds (one in each anti-CLEC12A VH and VL domains and an engineered, stabilizing disulfide bridging the variable domains) and the Fc contains the two expected disulfides in the IgG domains. The heterodimer is held together with two hinge disulfides and one additional intermolecular engineered disulfide connecting the Fab-Fc to the scFv-Fc in the CH3 domain. Together this results in 15 expected disulfide bonds in AB0192. The predicted disulfide map for AB0192 is shown in FIG. 226.

The disulfide bond connectivity of AB0192 was corroborated by LC-MS/MS peptide mapping analysis of a non-reduced digest. Disulfide bonded peptides were identified by MS/MS database searching and corroborated by comparing their intensities in the native and reduced digests. To observe the engineered scFv stabilizing disulfide, AB0192 was digested with both trypsin and chymotrypsin. FIGS. 227A-227B show the extracted ion chromatogram (XICs) for the engineered disulfide pair in the scFv (non-reduced and reduced) and the most intense charge state for that peptide pair. All other disulfides were identified after digestion with only trypsin. XICs in FIGS. 228A-228B corroborate the existence of the engineered S—S bridge introduced to stabilize the Fc heterodimerization. A summary of the observed disulfide linked peptides in AB0192 is shown in Table 211. All theoretical disulfide linked peptides were observed with high mass accuracy (<5 ppm), were reducible, and were sequence corroborated by MS/MS fragmentation.

TABLE 211

Disulfide linked peptides theoretical and experimental masses.

| Domain | Peptide | Theoretical mass (Da) | Experimental mass (Da) | Mass accuracy (ppm) |
|---|---|---|---|---|
| VL | L2:L7 | 4482.0784 | 4482.0791 | 0.5 |
| CL | L12:L19 | 3555.7490 | 3555.7527 | 1.4 |
| CL-CH1 intermolecular | L20-21:H19 | 1260.4863 | 1260.4862 | 0.2 |
| VH | H3:H10 | 3371.4686 | 3371.4728 | 1.3 |
| CH1 | H13:H14-15 | 7916.9194 | 7916.9162 | 0.2 |
| Hinge | H20-21:S20-21 | 5454.7834 | 5454.7899 | 1.6 |
| CH2 | H23:H30 | 2328.0977 | 2328.1015 | 1.5 |
| CH3-CH3 intermolecular[a] | H36:S37-38 | 2757.3830 | 2757.3866 | 1.7 |
| CH3 | H37:H41 | 4432.0675 | 4432.073 | 1.3 |
| scFv VL | S26:S42-44[b] | 1747.8314 | 1747.8381 | 3.8 |
| scFv VH | S2:S9 | 3359.4951 | 3359.4993 | 1.3 |
| scFv stabilizing[a] | S8:S46[b] | 1011.4154 | 1011.4198 | 4.4 |
| CH2 | S23:S30 | non-unique, see H23:H30 | | |
| CH3 | S39:S44 | 3844.8236 | 3844.8287 | 1.2 |

[a]Engineered disulfide
[b]Trypsin/chymotrypsin double digest

Binding Characteristics
Binding to Human CLEC12A

The affinity of AB0089 for human CLEC12A was determined by SPR at 37° C. AB0089 binds with high affinity to human CLEC12A (FIGS. 229A-229C, Table 212). Per TriNKET MOA, the molecule is designed to bind strongly to TAA and weakly to NKG2D and CD16a. The complex between AB0192 and human CLEC12A is strong as evidenced from the slow rate dissociation constant $1.40\pm0.09\times 10^{-3}$ $s^{-1}$. The equilibrium binding affinity $K_D$ for AB0192 is $1.81\pm0.16$ nM.

TABLE 212

Kinetic parameters and binding affinity of AB0192 for hCLEC12A measured by SPR.

| Test article | Target | $k_a$ ($M^{-1}s^{-1}$) | $k_d$ ($s^{-1}$) | $K_D$ (nM) |
|---|---|---|---|---|
| AB0192 | hCLEC12A-His | $7.87 \times 10^5$ | $1.36 \times 10^{-3}$ | 1.72 |
| AB0192 | hCLEC12A-His | $7.57 \times 10^5$ | $1.51 \times 10^{-3}$ | 1.99 |
| AB0192 | hCLEC12A-His | $7.85 \times 10^5$ | $1.34 \times 10^{-3}$ | 1.71 |
| Average ± Std Dev. | hCLEC12A-His | $(7.76 \pm 0.17) \times 10^5$ | $(1.40 \pm 0.09) \times 10^{-3}$ | $1.81 \pm 0.16$ |

Average of 3 replicates

Binding to Polymorphic Variant of Human CLEC12A (Q244)

Polymorphic variant CLEC12A (Q244) is prevalent in 30% of population. We tested binding of AB0192 to this genetic variant by SPR and compared its affinity to CLEC12A (K244) WT (FIGS. 230A-230C). Binding affinities of AB0192 for WT and (K244Q) variant of CLEC12A are within 2.5-fold (Table 213). Binding of AB0192 to cynomolgus monkey CLEC12A (cCLEC12A) was also tested. No quantifiable binding was observed at 100 nM concentration.

TABLE 213

Kinetic parameters and binding affinities for (K244) and (Q244) variants of human CLEC12A.

| Test article | Target | $k_a$ (M$^{-1}$s$^{-1}$) | $k_d$ (s$^{-1}$) | $K_D$ (nM) |
|---|---|---|---|---|
| AB0192 | hCLEC12A (K244) WT | $(6.98 \pm 0.09) \times 10^5$ | $(1.15 \pm 0.01) \times 10^{-3}$ | $1.65 \pm 0.04$ |
| AB0192 | hCLEC12A (Q244) | $(8.24 \pm 1.33) \times 10^5$ | $(3.70 \pm 0.38) \times 10^{-3}$ | $4.51 \pm 0.26$ |

Binding to Differentially Glycosylated CLEC12A

Human CLEC12A is a heavily glycosylated protein (6 potential N-glycosylation sites with an ECD compromising of 201 amino acids). Variations in the glycosylation status of CLEC12A on the surface of different cell types is documented in the literature (Marshall et al., 2006) *Eur. J. Immunol.*, 36: 2159-2169). CLEC12A expressed on the surface of AML cells from different patients may have different glycosylation pattern as well. To determine AB0089 binds to different glyco-variants of human CLEC12A, the antigen was treated with neuraminidase (to remove terminal sialic acids) or PNGase F (to remove N-linked glycans) and affinity was compared to untreated CLEC12A by SPR. AB0192 bound to both glycosylated and de-glycosylated variants of CLEC12A (FIGS. 231A-231C and Table 214) and is expected to be unaffected by heterogeneity in target glycan composition.

TABLE 214

Kinetic parameters and binding affinity of AB0192 for differentially glycosylated CLEC12A.

| Test article | Target | $k_a$ (M$^{-1}$s$^{-1}$) | $k_d$ (s$^{-1}$) | $K_D$ (nM) |
|---|---|---|---|---|
| AB0192 | untreated CLEC12A | $(6.98 \pm 0.09) \times 10^5$ | $(1.15 \pm 0.01) \times 10^{-3}$ | $1.65 \pm 0.04$ |
| AB0192 | De-sialylated CLEC12A | $(1.01 \pm 0.03) \times 10^6$ | $(1.04 \pm 0.00) \times 10^{-3}$ | $1.04 \pm 0.03$ |
| AB0192 | De-glycosylated CLEC12A | $(1.31 \pm 0.02) \times 10^6$ | $(3.48 \pm 0.11) \times 10^{-4}$ | $0.27 \pm 0.01$ |

Average of 3 replicates

Binding to CLEC12A+ Isogenic and Cancer Cell Lines

Assessment of AB0192 binding to both isogenic cell lines expressing CLEC12A and AML cancer cells was monitored by FACS (FIGS. 232-232D and Table 215). AB0192 showed high affinity for cell surface expressed CLEC12A on the isogenic Ba/F3-CLEC12A cells and binds AML cell lines PL-21 and HL-60 with EC50 of less than 1 nM. Specificity of AB0089 for CLEC12A was demonstrated by lack of binding to the parental Ba/F3 cells that do not express the target.

TABLE 215

Binding of AB0192 to isogenic Ba/F3-CLEC12A and cancer cell lines expressing CLEC12A.

| Cell line | EC50 (nM) |
|---|---|
| Ba/F3-hCLEC12A | 0.91 |
| Ba/F3 parental | No binding |
| PL21 | 0.43 |
| HL-60 | 0.6 |

Binding to Human NKG2D

Binding of AB0192 to human NKG2D ECD by SPR at 37° C. (Biacore) (FIGS. 233A-233F). NKG2D is a dimer in nature, therefore recombinant mFc-tagged NKG2D dimer was used for this experiment. Affinity was determined using AB0192. FIGS. 233A-233F shows AB0192 binding sensorgrams to human NKG2D. Two different fits were utilized to obtain the equilibrium affinity data: steady state affinity fit and kinetic fit. The kinetic constants and equilibrium affinity constants are shown in Table 216. AB0192 was designed to bind to human NKG2D with low affinity, most importantly with the fast rate of dissociation. The dissociation rate constant was $(1.46 \pm 0.06 \times 10^{-1}$ s$^{-1}$). Equilibrium affinity constants (KD) obtained by kinetics fit and steady state affinity fit were very similar, $779 \pm 10$ nM and $781 \pm 9$ nM, respectively, which suggests high confidence in the measured parameters.

TABLE 216

Kinetic parameters and affinities of AB0192 for human NKG2D measured by SPR.

| Test article | Target | $k_a$ (M$^{-1}$s$^{-1}$) | $k_d$ (s$^{-1}$) | Kinetics Fit $K_D$ (nM) | Steady State Fit $K_D$ (nM) |
|---|---|---|---|---|---|
| AB0192 | hNKG2D | $1.86 \times 10^5$ | $1.43 \times 10^{-1}$ | 770 | 770 |
| AB0192 | hNKG2D | $1.96 \times 10^5$ | $1.53 \times 10^{-1}$ | 778 | 783 |
| AB0192 | hNKG2D | $1.81 \times 10^5$ | $1.43 \times 10^{-1}$ | 790 | 788 |
| Average ± Std Dev. | hNKG2D | $(1.88 \pm 0.08) \times 10^5$ | $(1.46 \pm 0.06) \times 10^{-1}$ | $779 \pm 10$ | $781 \pm 9$ |

Binding to Human CD16a (V158 Allele)

One of the modalities of AB0192 mechanism of action is through engaging human CD16a (FcγRIIIa) that is expressed on NK cells via its Fc. AB0192 binding to human CD16a was tested by SPR (FIGS. 234A-234F, Table 217). CD16a high affinity V158 allele was used for this experiment. Since the literature reported Fc receptor affinity values for IgG1 vary depending on the experimental design and sourcing of the receptors, trastuzumab (Herceptin) was included as a human IgG1 control. The affinity of AB0192 for both alleles is comparable (around two-fold different) to trastuzumab's affinity for the same receptor. We do not expect this difference to have any meaningful physiological significance.

TABLE 217

Kinetics and affinities of AB0192 for hCD16a (V158) and trastuzumab measured by SPR.

| Test article | $k_a$ (M$^{-1}$s$^{-1}$) | $k_d$ (s$^{-1}$) | $K_D$ (nM) |
|---|---|---|---|
| AB0192 | $1.03 \times 10^5$ | $1.90 \times 10^{-2}$ | 184 |
| AB0192 | $1.16 \times 10^5$ | $2.01 \times 10^{-2}$ | 173 |
| AB0192 | $1.16 \times 10^5$ | $2.06 \times 10^{-2}$ | 177 |
| Average ± StDev | $(1.12 \pm 0.08) \times 10^5$ | $(1.99 \pm 0.08) \times 10^{-2}$ | 178 ± 6 |
| Trastuzumab | $1.31 \times 10^5$ | $1.12 \times 10^{-2}$ | 86 |
| Trastuzumab | $1.22 \times 10^5$ | $1.08 \times 10^{-2}$ | 89 |
| Trastuzumab | $1.30 \times 10^5$ | $1.13 \times 10^{-2}$ | 87 |
| Average ± StDev | $(1.28 \pm 0.05) \times 10^5$ | $(1.11 \pm 0.03) \times 10^{-2}$ | 87 ± 1 |

Testing CD16a-NKG2D Synergy

AB0192 is a tri-functional IgG-based biologic with two binding modalities on the NK cells: CD16a binding is achieved through the Fc and NKG2D binding is achieved through A49M-I Fab. Both interactions are important for the optimal cytotoxic activity of AB0192. To demonstrate synergy of co-engagement of human CD16a and human NKG2D binding, we performed an SPR experiment where we qualitatively compared binding of AB0192 to NKG2D, CD16a and mixed NKG2D-CD16a Biacore chip surfaces. The affinity of AB0192 for human NKG2D and human CD16a are both low, however, binding to both targets simultaneously results in an avidity effect that manifests as a slower off-rate (FIG. 235). Thus, AB0192 can avidly engage CD16a and NKG2D.

Co-Engagement of CLEC12A and NKG2D

To determine if binding of one target interferes with binding of the other target to AB0192, CLEC12A and NKG2D were sequentially injected over AB0192 captured on an anti-hFc IgG SPR chip (FIGS. 236A-236B). Target binding sensorgrams demonstrate that the occupancy status of CLEC12A does not interfere with NKG2D binding (FIG. 236A) and vice versa (FIG. 236B). Similarity in the shapes of the respective sensorgrams segments depicting binding of each target to free AB0192 and AB0192 that has been saturated with the other target suggest that the kinetic parameters are not meaningfully affected by the target occupancy status of the AB0192 molecule. For instance, the shape of the CLEC12A binding segment of the sensorgrams is similar in both panels. Additionally, the lack of any impact on relative stoichiometry of each target binding (when compared to binding to unoccupied AB0192) signifies full independence of NKG2D and CLEC12A binding sites on AB0192 (Table 218). Therefore, AB0192 successfully achieves simultaneous co-engagement of the tumor antigen and the NKG2D targeting arm.

TABLE 218

Relative binding stoichiometries of AB0192 for CLEC12A and NKG2D. Binding stoichiometries are expressed relative to binding of each target to unoccupied captured AB0192.

| | CLEC12A, relative binding stoichiometry | NKG2D, relative binding stoichiometry |
|---|---|---|
| Target bound to AB0192 unoccupied with another target (injected first) | 1.00 | 1.00 |
| Target bound to AB0192 saturated with another target (injected second) | 1.03 ± 0.07 | 1.15 ± 0.20 |

Binding to Fcγ Receptors

Since AB0192 is an IgG1 derived biologic drug candidate it is important that it maintains appropriate Fc receptor binding properties. SPR data suggest that AB0089 binds human and cynomolgus Fcγ receptors with affinities comparable to trastuzumab, a marketed IgG1 biologic that served an experimental control (Table 219). Detailed description of each individual receptor binding is presented below.

TABLE 219

Binding of AB0192 and trastuzumab binding recombinant human and cynomolgus FcγRs.

| Fcγ receptor | AB0192 $K_D$ (nM) | Trastuzumab, hIgG1 control $K_D$ (nM) |
|---|---|---|
| hFcγRI | 5.2 ± 1.2 | 2.9 ± 0.4 |
| cFcγRI | 1.9 ± 0.3 | 1.0 ± 0.1 |
| hFcγRIIa H131 | 1011.3 ± 63.3 | 1045.1 ± 62.2 |
| hFcγRIIa R131 | 1398.8 ± 286.1 | 1493.2 ± 265.9 |
| hFcγRIIIa V158[a] | 178.3 ± 5.5 | 87.1 ± 1.4 |
| hFcγRIIIa F158 | 680.0 ± 69.6 | 331.4 ± 3.3 |
| cFcγRIII[a] | 203.8 ± 1.0 | 128.8 ± 2.1 |
| hFcγRIIb | 6062.3 ± 827.0 | 6270.3 ± 1031.7 |
| hFcγRIIIb[a] | 6014.8 ± 735.5 | 3872.4 ± 486.3 |

[a] n = 3, otherwise n = 4.

Binding to Human and Cynomolgus CD64 (FcγRI)

Table 220 demonstrates that AB0089 binds recombinant human and cynomolgus CD64 (FcγRI) with affinities comparable (less than two-fold different) to trastuzumab. FIGS. 237A-237H and FIGS. 238A-238H depict binding of AB0089 to human and cynomolgus CD64, respectively.

TABLE 220

Binding of AB0192 and trastuzumab to recombinant human and cynomolgus CD64 (FcγRI)

| Test article | $k_a$ (M$^{-1}$s$^{-1}$) | $k_d$ (s$^{-1}$) | $K_D$ (nM) |
|---|---|---|---|
| Human CD64 (FcγRI) | | | |
| AB0192 Lot AB0192-005 | $4.7 \times 10^4$ | $2.9 \times 10^{-4}$ | 6.1 |
| AB0192 Lot AB0192-005 | $4.7 \times 10^4$ | $2.6 \times 10^{-4}$ | 5.5 |
| AB0192 Lot AB0192-005 | $4.7 \times 10^4$ | $2.6 \times 10^{-4}$ | 5.5 |
| AB0192 Lot AB0192-005 | $5.2 \times 10^4$ | $1.8 \times 10^{-4}$ | 3.5 |
| Average ± StDev | $(4.8 \pm 0.3) \, 10^4$ | $(2.5 \pm 0.5) \times 10^{-4}$ | 5.2 ± 1.2 |
| trastuzumab | $9.0 \times 10^4$ | $2.3 \times 10^{-4}$ | 2.5 |
| trastuzumab | $8.6 \times 10^4$ | $2.1 \times 10^{-4}$ | 2.5 |
| trastuzumab | $8.3 \times 10^4$ | $2.7 \times 10^{-4}$ | 3.2 |
| trastuzumab | $8.8 \times 10^4$ | $2.8 \times 10^{-4}$ | 3.2 |
| Average ± StDev | $(8.1 \pm 0.0) \times 10^4$ | $(2.5 \pm 0.3) \times 10^{-4}$ | 2.9 ± 0.4 |

TABLE 220-continued

Binding of AB0192 and trastuzumab to recombinant human and cynomolgus CD64 (FcγRI)

| Test article | $k_a$ (M$^{-1}$s$^{-1}$) | $k_d$ (s$^{-1}$) | $K_D$ (nM) |
|---|---|---|---|
| Cynomolgus CD64 (FcγRI) | | | |
| AB0192 Lot AB0192-005 | $5.4 \times 10^4$ | $1.2 \times 10^{-4}$ | 2.2 |
| AB0192 Lot AB0192-005 | $8.0 \times 10^4$ | $1.2 \times 10^{-4}$ | 1.5 |
| AB0192 Lot AB0192-005 | $5.7 \times 10^4$ | $1.1 \times 10^{-4}$ | 1.9 |
| AB0192 Lot AB0192-005 | $5.5 \times 10^4$ | $1.2 \times 10^{-4}$ | 2.1 |
| Average ± StDev | $(6.2 \pm 1.3) \times 10^4$ | $(1.2 \pm 0.1) \times 10^{-4}$ | $1.9 \pm 0.3$ |
| trastuzumab | $1.3 \times 10^5$ | $1.4 \times 10^{-4}$ | 1.1 |
| trastuzumab | $1.3 \times 10^5$ | $1.2 \times 10^{-4}$ | 0.9 |
| trastuzumab | $1.3 \times 10^5$ | $1.1 \times 10^{-4}$ | 0.8 |
| trastuzumab | $1.3 \times 10^5$ | $1.3 \times 10^{-4}$ | 1.0 |
| Average ± StDev | $(1.3 \pm 0.1) \times 10^5$ | $(1.2 \pm 0.2) \times 10^{-4}$ | $1.0 \pm 0.1$ |

Binding to Human CD32a (FcγRIIa)

There is no meaningful difference between affinities of both alleles of human CD32a for AB0089 and trastuzumab (Table 221). FIGS. 239A-239P and FIGS. 240A-240P depict binding of AB0089 and trastuzumab to CD32a (H131 and R131 alleles), respectively, tested by SPR.

TABLE 221

Binding of AB0192 and trastuzumab to recombinant human CD32a (FcγRIIa) H131 and R131 alleles.

| | $K_D$ (nM) | |
|---|---|---|
| Test article | FcγRIIa H131 | FcγRIIa R131 |
| AB0192 Lot AB0192-005 | 1035.5 | 1376.1 |
| AB0192 Lot AB0192-005 | 921.1 | 1286.2 |
| AB0192 Lot AB0192-005 | 1068.0 | 1800.6 |
| AB0192 Lot AB0192-005 | 1020.6 | 1132.4 |
| Average ± StDev | 1011.3 ± 63.3 | 1398.8 ± 286.1 |
| trastuzumab | 1069.2 | 1488.2 |
| trastuzumab | 953.1 | 1381.0 |
| trastuzumab | 1090.2 | 1862.1 |
| trastuzumab | 1068.0 | 1241.4 |
| Average ± StDev | 1045.1 ± 62.2 | 1493.2 ± 265.9 |

Binding to Human CD16a F158 (FcγRIIIa F158) and Cyno CD16

Detailed description of AB0192 binding CD16a V158 is provided in Section 6.9.6. Binding of AB0192 to the low affinity F158 allele of human FcγRIIIa and cynomolgus FcγRIII are presented in Table 222, FIG. 241A-241P and FIG. 242A-242L. The AB0192 binding affinity values for recombinant human CD16a (F158 allele) and cynomolgus CD16 are comparable, less than two-fold different in affinity, to the ones of trastuzumab (Table 222).

TABLE 222

Binding of AB0192 and trastuzumab to recombinant human CD16a (FcγRIIIa) F158 allele and cynomolgus CD16 (FcγRIII).

| Test article | Human FcγRIIIa F158 $K_D$ (nM) | Cynomolgus FcγRIII $K_D$ (nM) |
|---|---|---|
| AB0192 Lot AB0192-005 | 772.9 | 202.7 |
| AB0192 Lot AB0192-005 | 633.7 | 204.6 |
| AB0192 Lot AB0192-005 | 693.3 | 204.1 |
| AB0192 Lot AB0192-005 | 620.0 | n/a |
| Average ± StDev | 680.0 ± 69.6 | 203.8 ± 1.0 |
| trastuzumab | 332.3 | 127.1 |

TABLE 222-continued

Binding of AB0192 and trastuzumab to recombinant human CD16a (FcγRIIIa) F158 allele and cynomolgus CD16 (FcγRIII).

| Test article | Human FcγRIIIa F158 $K_D$ (nM) | Cynomolgus FcγRIII $K_D$ (nM) |
|---|---|---|
| trastuzumab | 326.6 | 128.1 |
| trastuzumab | 333.8 | 131.1 |
| trastuzumab | 333.1 | n/a |
| Average ± StDev | 331.4 ± 3.3 | 128.8 ± 2.1 |

Binding to Human CD32b (FcγRIIb)

There is no meaningful difference between affinities of CD32b for AB0089 and trastuzumab (Table 223). FIGS. 243A-243P depict binding to AB0089 and trastuzumab to CD32b tested by SPR.

TABLE 223

Binding of AB0192 and trastuzumab to recombinant human CD32b (FcγRIIb).

| Test article | $K_D$ (μM) |
|---|---|
| AB0192 Lot AB0192-005 | 6.5 |
| AB0192 Lot AB0192-005 | 5.6 |
| AB0192 Lot AB0192-005 | 5.2 |
| AB0192 Lot AB0192-005 | 7.0 |
| Average ± StDev | 6.1 ± 0.8 |
| trastuzumab | 7.1 |
| trastuzumab | 5.6 |
| trastuzumab | 5.2 |
| trastuzumab | 7.2 |
| Average ± StDev | 6.3 ± 1.0 |

Binding to Human CD16b (FcγRIIIb)

AB0089 binds human CD16b (FcγR3b) with affinity comparable (less than two-fold different) to the one of trastuzumab (Table 224). FIGS. 244A-244P depict binding of AB0089 and trastuzumab to CD16b tested by SPR.

TABLE 224

Binding of AB0192 and trastuzumab to recombinant human CD16b (FcγRIIIb).

| | $K_D$ (μM) |
|---|---|
| AB0192 Lot AB0192-005 | 6.8 |
| AB0192 Lot AB0192-005 | 6.0 |
| AB0192 Lot AB0192-005 | 5.3 |
| Average ± StDev | 6.0 ± 0.7 |
| trastuzumab | 4.3 |
| trastuzumab | 3.9 |
| trastuzumab | 3.4 |
| Average ± StDev | 3.9 ± 0.5 |

Binding to Human and Cynomolgus FcRn

FIGS. 245A-245P and FIGS. 246A-246L depict AB0192 binding to human and cynomolgus FcRn, respectively, tested by SPR. Affinities of AB0192 for human and cynomolgus FcRn are similar to those of trastuzumab, a marketed IgG1 biologic that served as an experimental control (Table 225).

TABLE 225

Binding of AB0192 and trastuzumab to human and cynomolgus FcRn.

| | Human FcRn $K_D$ (µM) | Cyno FcRn $K_D$ (µM) |
|---|---|---|
| AB0192 Lot AB0192-005 | 1.5 | 1.5 |
| AB0192 Lot AB0192-005 | 1.3 | 1.4 |
| AB0192 Lot AB0192-005 | 1.5 | 1.2 |
| AB0192 Lot AB0192-005 | 1.5 | n/a |
| Average ± StDev | 1.5 ± 0.1 | 1.4 ± 0.1 |
| trastuzumab | 1.8 | 1.6 |
| trastuzumab | 1.5 | 1.6 |
| trastuzumab | 2.0 | 1.5 |
| trastuzumab | 1.7 | n/a |
| Average ± StDev | 1.7 ± 0.2 | 1.5 ± 0.1 |

Epitope Binning

We compared binding epitope of AB0192 in relation to AB0237, AB0089 and three reference controls TriNKETs by SPR (FIG. 247). cFAE-A49. Tepoditamab is based on CLEC12A binding arm of tepoditamab from Merus (WO_2014_051433_A1), cFAE-A49.CLL1-Merus is based on the clone 4331 from Merus (WO_2014_051433_A1) and cFAE-A49.h6E7 is based on h6E7 mAb from Genentech (h6E7) (US_2016_0075787_A1) AB0192 interaction with hCLEC12A was blocked by all three control molecules cFAE-A49.Tepoditamab, cFAE.A49.h6E7 and cFAE-A49.CLL1-Merus suggesting the AB0192 binding epitope is broad and overlaps with both Merus and Genentech molecules. This footprint is different from AB0237 and AB0089 which cross-block only with Merus molecules. Thus, binding epitope for AB0192 is different from AB0089 and AB0237.

Potency

The ability of AB0192 to lyse human cancer cells expressing CLEC12A was determined in the human NK cells mediated cytotoxicity assay. AB0192 demonstrated high potency in killing PL21 AML cells and vastly outperformed corresponding monoclonal antibody (FIG. 248 and Table 226).

TABLE 226

Potency of AB0192 in primary NK mediated cytotoxicity assay compared to corresponding mAb control.

| Test article | EC50 (nM) | Max killing (%) |
|---|---|---|
| AB0192 | 1.72 | 24 |
| Parental mAb (AB0306) | ND | ND |

Specificity
Non-Specific Binding Assessed by PSR Assay

Non-specific binding of AB0192 was assessed by flow cytometry based PSR assay that measures binding to a preparation of detergent solubilized CHO cell membrane proteins (FIGS. 249A-249B). PSR assay is known to correlate well with cross-interaction chromatography, a surrogate for antibody solubility, as well as with baculovirus particle enzyme-linked immunosorbent assay, a surrogate for in vivo clearance and therefore serves as a good developability predictive factor. AB0192 showed no non-specific binding, similar to low PSR control (Trastuzumab), suggesting high specificity and lack on non-specific binding to unrelated proteins.

Specificity Assessment of AB0192 in HuProt™ Microarray Assay

To examine specificity of AB0192 we have explored a protein array technology. The HuProt™ human proteome microarray provides the largest database of individually purified human full-length proteins on a single microscopic slide. An array consisting of 22,000 full-length human proteins are expressed in yeast Cerevisiae, purified, and are subsequently printed in duplicate on a microarray glass slide that allows thousands of interactions to be profiled in a high-throughput manner. FIG. 250 and shows the relative binding (Z score) of AB0192 at 1 µg/ml to human CLEC12A in comparison to the entire human proteome microarray. Z score is the average binding score of two duplicates of a given protein. For comparison purpose, the top 24 proteins with residual background binding to AB0192 were also provided in FIG. 250. Table 227 shows the Z and S scores of AB0192 to human CLEC12A and the top 6 proteins from the microarray. S score is the difference of Z score of a given protein and the one rank next to it. Based on the Z and S score criteria, AB0192 showed high specificity to human and lack of off-target binding in the HuProt™ human proteome assay.

TABLE 227

Summary of the top hits by HuProt™ array.

| Name | Rank | Protein-ID | Z score | S score |
|---|---|---|---|---|
| hCLEC12A | 1 | hCLEC12A | 150.06 | 144.04 |
| MFF | 2 | JHU15965.P168B06 | 6.05 | 0.81 |
| POLR2E | 3 | JHU02080.P189F02 | 5.24 | 0.22 |
| HMGA1_frag | 4 | JHU16418.P173B08 | 5.02 | 0.12 |
| PARS2 | 5 | JHU06781.P071H01 | 4.90 | 0.24 |
| THEMIS_frag | 6 | JHU15201.P160B01 | 4.66 | 0.23 |
| ZNF608 | 7 | JHU13018.P136G04 | 4.43 | 0.006 |

Developability Assessment

The stability and forced degradation of AB0192 was assessed under the following conditions:
Accelerated (40° C.) Stability
 20 mg/ml in 20 mM histidine, 250 mM sucrose, 0.01% Tween-80, pH 6.0, 40° C., 4 weeks (SEC, SPR, potency, SDS-CE)
 20 mg/ml in 20 mM sodium citrate, 250 mM sucrose, 0.01% Tween-80, pH 7.0, 40° C., 4 weeks (SEC, SPR, potency, SDS-CE)
Chemical Stability
 Oxidation: 1 mg/ml in 0.02% hydrogen peroxide, PBS, room temp., 24 hours (SEC, CE-SDS, SPR, potency, peptide map)
 pH 8.0: 1 mg/ml 20 mM Tris, 40° C., 2 weeks (cIEF, SPR, potency, peptide map)
 pH 5.0: 1 mg/ml 20 mM sodium acetate, 40° C., 2 weeks (cIEF, SPR, potency, peptide map)
Manufacturability
 Freeze/thaw: 20 mg/ml 6 cycles, 20 mM sodium citrate, 250 mM sucrose, 0.01% Tween-80, pH 7.0 (SEC, SDS-CE)
 Agitation: 20 mg/ml in 20 mM sodium citrate, 250 mM sucrose, 0.01% Tween-80, pH 7.0 (SEC, SDS-CE)
 High concentration: >150 mg/ml, PBS (SEC, A280)
 Low pH hold: pH 3.3, 1.0 hours, ProA elution buffer (SEC, cIEF, SDS-CE, intact mass, SPR, potency)
Accelerated (40° C.) Stability To assess the stability of AB0192, the molecule was staged at 40° C. for 4 weeks under two different buffer conditions (1) 20 mg/ml in 20 mM histidine, 250 mM sucrose, 0.01% PS-80, pH 6.0 (HST), and (2) 20 mg/ml in 20 mM citrate, 250 mM sucrose, 0.01% PS-80, pH 7.0 (CST). Stability in both buffers was assessed by SEC, CE, SPR and potency.

Stability in HST, pH 6.0

After 4 weeks at 40° C., AB0192 in HST, pH 6.0 showed minimal aggregation or fragmentation by SEC (FIGS. 251A-251B, Table 228) or CE-SDS (FIGS. 252A-252B, Table 229). Loss of monomer was 1.6% by SEC and 1% by non-reduced CE. There is no meaningful difference in the active species content or the affinities for hCLEC12A, hNKG2D and hCD16a between control and stressed samples (FIGS. 253A-253F and Table 230). Finally, there was no difference in potency between the control and stressed samples tested in KHYG-1-CD16aV cytotoxicity assay (FIG. 254 and Table 231).

TABLE 228

SEC analysis of AB0192 after 2 and 4 weeks at 40° C. in HST, pH 6.0.

| Test article | Conc. (mg/ml) | Monomer (%) | LMWS (%) | HMWS (%) |
|---|---|---|---|---|
| AB0192 control | 20.1 | 98.9 | 1.2 | 0.0 |
| AB0192 2 wks., 40° C. | 20.2 | 98.0 | 2.0 | 0.0 |
| AB0192, 4 wks., 40° C. | 21.3 | 97.3 | 2.8 | 0.0 |

TABLE 229

NR and R CE-SDS analysis of AB0192 after 4 weeks at 40° C. in HST pH 6.0.

| Test article | NR CE purity (%) | R CE purity (%) |
|---|---|---|
| AB0192 control | 99.1 | 97.5 |
| AB0192, 4 wks., 40° C. | 98.1 | 97.4 |

TABLE 230

Kinetic parameters and binding affinities of AB0089 for CLEC12A, NKG2D and CD16a after 4 weeks at 40° C. in HST, pH 6.0, measured by SPR.

| Test article | Target | $k_a$ (M$^{-1}$ s$^{-1}$) | $k_d$ (s$^{-1}$) | $K_D$ (nM) |
|---|---|---|---|---|
| AB0192 control | hCLEC12A | $(7.76 \pm 0.17) \times 10^5$ | $(1.40 \pm 0.09) \times 10^{-3}$ | $1.81 \pm 0.2$ |
| AB0192, 4 wks., 40° C. | hCLEC12A | $(7.76 \pm 0.40) \times 10^5$ | $(1.40 \pm 0.07) \times 10^{-3}$ | $1.81 \pm 0.2$ |
| AB0192 control | hNKG2D | $(2.08 \pm 0.03) \times 10^5$ | $(1.22 \pm 0.01) \times 10^{-1}$ | $588 \pm 6$ |
| AB0192, 4 wks., 40° C. | hNKG2D | $(2.11 \pm 0.35) \times 10^5$ | $(1.27 \pm 0.19) \times 10^{-1}$ | $602 \pm 9$ |
| AB0192 control | CD16aV | $(1.17 \pm 0.02) \times 10^5$ | $(1.99 \pm 0.05) \times 10^{-2}$ | $171 \pm 2$ |
| AB0192, 4 wks., 40° C. | CD16aV | $(1.03 \pm 0.03) \times 10^5$ | $(2.01 \pm 0.03) \times 10^{-2}$ | $194 \pm 4$ |

Average of n = 3 replicates

TABLE 231

Potency of AB0192 after 4 weeks at 40° C. in HST, pH 6.0 in KHYG-1-CD16aV mediated cytotoxicity assay.

| Test article | Buffer | EC50 (nM) | Max killing (%) |
|---|---|---|---|
| AB0192 control | HST | 3.3 | 21 |
| AB0192, 40° C. 4 wks. | HST | 1.6 | 17 |

Stability in CST, pH 7.0

After 4 weeks at 40° C., AB0192 in CST, pH 7.0, showed minimal aggregation (FIG. 255A-255B and Table 232) and fragmentation (FIG. 256A-256B and Table 233). 1.6% and 0.8% loss of monomer was observed by SEC and non-reduced CE-SDS, respectively. There was no meaningful difference in the active species content or in the affinities for hCLEC12A, hNKG2D and hCD16a between control and stressed samples (FIG. 257A-257F and Table 234). Finally, there was no difference in potency between the control and stressed samples in KHYG-1-CD16aV cytotoxicity assay (FIG. 258 and Table 235).

TABLE 232

SEC analysis of AB0192 after 1-4 weeks at 40° C. in CST, pH 7.0.

| Test article | Conc. (mg/ml) | Monomer (%) | LMWS (%) | HMWS (%) |
|---|---|---|---|---|
| AB0192 control | 21.3 | 99.0 | 1.1 | ND |
| AB0192, 1 wk., 40° C. | 21.4 | 98.1 | 1.5 | 0.4 |
| AB0192, 2 wks., 40° C. | 21.4 | 97.9 | 1.6 | 0.5 |
| AB0192, 3 wks., 40° C. | 21.7 | 97.8 | 1.7 | 0.5 |
| AB0192, 4 wks., 40° C. | 22.2 | 97.4 | 1.8 | 0.8 |

TABLE 233

NR and R CE-SDS analysis of AB0192 after 4 weeks at 40° C. in CST, pH 7.0.

| Test article | Conc. (mg/ml) | NR CE purity (%) | R CE purity (%) |
|---|---|---|---|
| AB0192 control | 21.3 | 98.8 | 97.8 |
| AB0192, 40° C. 4 wks. | 22.4 | 98.0 | 97.0 |

TABLE 234

Kinetic parameters and binding affinities of AB0089 for CLEC12A, NKG2D and CD16a after 4 weeks at 40° C. in CST, pH 7.0, measured by SPR.

| Test article | Target | $k_a$ (M$^{-1}$ s$^{-1}$) | $k_d$ (s$^{-1}$) | $K_D$ (nM) |
|---|---|---|---|---|
| AB0192 control | hCLEC12A | $(7.76 \pm 0.17) \times 10^5$ | $(1.40 \pm 0.09) \times 10^{-3}$ | $1.81 \pm 0.2$ |
| AB0192, 4 wks. 40° C. | hCLEC12A | $(7.49 \pm 0.22) \times 10^5$ | $(1.47 \pm 0.12) \times 10^{-3}$ | $1.96 \pm 0.2$ |
| AB0192 control | hNKG2D | $(2.08 \pm 0.03) \times 10^5$ | $(1.22 \pm 0.01) \times 10^{-1}$ | $588 \pm 6$ |
| AB0192, 4 wks. 40° C. | hNKG2D | $(1.85 \pm 0.06) \times 10^5$ | $(1.21 \pm 0.04) \times 10^{-1}$ | $653 \pm 10$ |
| AB0192 control | CD16aV | $(1.17 \pm 0.02) \times 10^5$ | $(1.99 \pm 0.05) \times 10^{-2}$ | $171 \pm 2$ |
| AB0192, 4 wks. 40° C. | CD16aV | $(1.11 \pm 0.07) \times 10^5$ | $(1.94 \pm 0.01) \times 10^{-2}$ | $174 \pm 10$ |

Average of 3 replicates

TABLE 235

Potency of AB0192 after 4 weeks at 40° C. in CST, pH 7.0, in KHYG-1-CD16aV mediated cytotoxicity assay.

| Test article | EC50 (nM) | Max killing (%) |
|---|---|---|
| AB0192 control | 3.3 | 21 |
| AB0192 40° C. 4 wks | 1.4 | 19 |

Chemical Stability

Forced Oxidation

After 24 h of oxidative stress in 0.02% hydrogen peroxide AB0192 showed no significant decrease in monomer content (FIGS. 259A-259B and Table 236). Purity assessed by CE remained high (FIGS. 260A-260B and Table 237). Amount of active species and affinities for CLEC12A, NKG2D, and CD16aV were unaltered (FIGS. 261A-261F and Table 238), and potency was similar to the control sample (FIG. 262 and Table 239).

TABLE 236

SEC analysis of AB0192 after forced oxidation compared to control.

| Test article | Conc. (mg/ml) | % Monomer | LMWS (%) | HMWS (%) |
|---|---|---|---|---|
| AB0192 control | 1.1 | 99.4 | 0.7 | ND |
| AB0192 oxidized | 0.9 | 99.7 | 0.3 | ND |

TABLE 237

NR and R CE-SDS analysis of AB0192 after forced oxidation.

| Test article | Conc. (mg/ml) | NR CE Purity (%) | R CE Purity (%) |
|---|---|---|---|
| AB0192 control | 1.1 | 99.1 | 97.8 |
| AB0192 oxidized | 0.9 | 98.9 | 97.7 |

TABLE 238

Kinetic parameters and binding affinities of AB0089 for CLEC12A, NKG2D and CD16a after forced oxidation measured by SPR.

| Test article | Target | $k_a$ (M$^{-1}$ s$^{-1}$) | $k_d$ (s$^{-1}$) | $K_D$ (nM) |
|---|---|---|---|---|
| AB0192 control | hCLEC12A | $(7.71 \pm 0.04) \times 10^5$ | $(1.29 \pm 0.02) \times 10^{-3}$ | $1.68 \pm 0.0$ |
| AB0192 | hCLEC12A | $(7.75 \pm 0.07) \times 10^5$ | $(1.32 \pm 0.05) \times 10^{-3}$ | $1.71 \pm 0.1$ |
| AB0192 control | hNKG2D | $(2.08 \pm 0.05) \times 10^5$ | $(1.24 \pm 0.03) \times 10^{-1}$ | $598 \pm 9$ |
| AB0192 oxidized | hNKG2D | $(1.95 \pm 0.02) \times 10^5$ | $(1.19 \pm 0.03) \times 10^{-1}$ | $612 \pm 11$ |
| AB0192 control | CD16aV | $(1.15 \pm 0.07) \times 10^5$ | $(2.02 \pm 0.05) \times 10^{-2}$ | $177 \pm 7$ |
| AB0192 oxidized | CD16aV | $(1.19 \pm 0.04) \times 10^5$ | $(1.92 \pm 0.04) \times 10^{-2}$ | $162 \pm 3$ |

Average of n = 3 replicates

TABLE 239

Potency of AB0192 after forced oxidation stress assessed by KHYG-1-CD16aV mediated cytotoxicity assay.

| Test article | EC50 (nM) | Max killing (%) |
|---|---|---|
| AB0192 control | 1.9 | 18 |
| AB0192 oxidized | 2.6 | 18 |

Site-specific oxidation of methionine was monitored after forced oxidation by tryptic peptide mapping. Significant levels of oxidation were only detected at two methionines in the Fc, as expected (Table 240) as expected for an IgG1. Our historic data show that the same residues are modified in trastuzumab at 61.6% and 39.1% under the same conditions.

TABLE 240

Summary of methionine oxidation in AB0192 after oxidative stress.

| SEQ ID NO | Sequence | Chain | Position | Relative Abundance (%) Control | Relative Abundance (%) Oxidized |
|---|---|---|---|---|---|
| 299 | LSCAASGFTFSSYSMNWVR | H | 34 | 0.5 | 0.8 |
| 300 | NSLYLQMNSLR | H | 83 | 0.1 | 0.3 |
| 301 | DTLMISR | H/S | 257/281 | 1.4 | 64.7 |
| 302 | WQQGNVFSCSVMHEALHNHYTQK | H/S | 433/457 | 1.2 | 35.9 |
| 303 | DIQMTQSPSSVSASVGDR | L | 4 | 0.1 | 0.3 |
| 340 | LSCAASGFTFNAFGMHWVR | S | 34 | 0.8 | 0.9 |
| 341 | NTLYLQMNSLR | S | 83 | 0.1 | 0.2 |
| 342 | DGYPTGGAMDYWGQGTSVTVSSGGGGSGGGGSGGGGSGGGGSDIQMTQSPSSLSASVGDR[a] | S | 107/110/144 | 0.2 | 0.9 |

[a] % oxidation reported as the sum of oxidation on M107, W110, and M144

Oxidation of tryptophan residues in AB0192 CDRs was also monitored in the same experiment. None of the tryptophan residues had a significant increase in oxidation after stress (Table 241).

TABLE 241

Summary of tryptophan oxidation in AB0192 CDRs after oxidative stress.

| Sequence | Chain | CDR | Mass shift (Da)[a] | Relative Abundance (%) Control | Relative Abundance (%) Oxidized |
|---|---|---|---|---|---|
| GAPIGAAAGWFDP (SEQ ID NO: 97) | H | H3 | +16/+32/+4 | ND/0.2/0.2 | ND/0.1/0.0 |
| RASQGISSWLA (SEQ ID NO: 86) | L | L1 | +16/+32/+4 | 0.1/0.2/0.0 | 0.2/0.1/0.0 |

[a] single oxidation (+16 Da), double oxidation (+32 Da), and kyneurenine (+4 Da)
ND, none detected.

pH 5 Stress

The chemical stability of AB0192 was assessed at low pH (20 mM sodium acetate, pH 5.0, 40° C., 2 weeks). After 2 weeks at pH 5, no loss of monomer (FIGS. 263A-263B and Table 242) was observed by SEC. Differences in purity detected by non-reduced and reduced CE-SDS were less than 1% (FIGS. 264A-264B and Table 243). There were no meaningful differences in CLEC12A, NKG2D, or CD16aV affinity of the amount of active species observed (FIGS. 265A-265F and Table 242). A small acidic shift in the global charge profile was detected by cIEF (FIG. 266 and Table 245), however, this acidic shift did not affect AB0192 potency (FIG. 267 and Table 246).

TABLE 242

SEC analysis of AB0192 after long term low pH stress (pH 5.0, 40° C., 14 days).

| Test article | Conc, (mg/ml) | Monomer (%) | LMWS (%) | HMWS (%) |
|---|---|---|---|---|
| AB0192 control | 1.2 | 99.3 | 0.7 | ND |
| AB0192, pH 5 40° C., 2 wks. | 1.2 | 99.4 | 0.6 | ND |

TABLE 244

Kinetic parameters and binding affinities of AB0089 for CLEC12A, NKG2D and CD16a after long term low pH stress (pH 5.0, 40° C., 14 days) measured by SPR.

| Test article | Target | $k_a$ (M$^{-1}$s$^{-1}$) | $k_d$ (s$^{-1}$) | $K_D$ (nM) |
|---|---|---|---|---|
| AB0192 control | hCLEC12A | $(7.71 \pm 0.04) \times 10^5$ | $(1.29 \pm 0.02) \times 10^{-3}$ | $1.68 \pm 0.0$ |
| AB0192, pH 5 40° C., 2 wks. | hCLEC12A | $(7.87 \pm 0.12) \times 10^5$ | $(1.30 \pm 0.03) \times 10^{-3}$ | $1.65 \pm 0.0$ |
| AB0192 control | hNKG2D | $(2.08 \pm 0.03) \times 10^5$ | $(1.22 \pm 0.01) \times 10^{-1}$ | $588 \pm 6$ |
| AB0192, pH 5 40° C., 2 wks. | hNKG2D | $(2.10 \pm 0.06) \times 10^5$ | $(1.20 \pm 0.01) \times 10^{-1}$ | $574 \pm 12$ |
| AB0192 control | CD16aV | $(1.17 \pm 0.02) \times 10^5$ | $(1.99 \pm 0.05) \times 10^{-2}$ | $171 \pm 2$ |
| AB0192, pH 5 40° C., 2 wks. | CD16aV | $(1.08 \pm 0.02) \times 10^5$ | $(2.08 \pm 0.04) \times 10^{-2}$ | $192 \pm 2$ |

Average of 3 replicates

TABLE 245

Charge profile of AB0192 after long term low pH stress (pH 5.0, 40° C., 14 days).

| Test article | % acidic | % main | % basic |
|---|---|---|---|
| AB0192 control | 41.9 | 49.4 | 8.7 |
| AB0192, pH 5 40° C., 2 wks. | 49.8 | 41.4 | 8.8 |

TABLE 246

Potency of AB0192 after long term low pH stress (pH 5.0, 40° C., 14 days) in KHYG-1-CD16aV cytotoxicity assay.

| Test article | EC50 (nM) | Max killing (%) |
|---|---|---|
| AB0192 control | 1.9 | 18 |
| AB0192, pH 5 40° C., 2 wks. | 2.0 | 18 | pH 8 Stress

Chemical stability of AB0192 was also assessed by incubation at elevated pH (20 mM Tris, pH 8.0, 40° C., 2 weeks). After 2 weeks at pH 8, there was a 1.6% loss of monomer by SEC (FIGS. 268A-268B and Table 247). Minor differences in purity were detected by non-reduced and reduced CE-SDS (FIGS. 269A-269B and Table 248). There were no meaningful differences in CLEC12A, NKG2D, or CD16aV affinities or amount of active species observed (FIGS. 270A-270F and Table 249). A significant acidic shift in the global charge profile detected by cIEF was detected (FIG. 271 and Table 250), which can be attributed to deamidation throughout the molecule. However, this acidic shift did not have any significant effect on AB0192 potency (FIG. 272 and Table 251).

TABLE 247

SEC analysis of AB0192 after long term high pH stress (pH 8.0, 40 C., 14 days)

| Test article | Conc. (mg/ml) | Monomer (%) | LMWS (%) | HMWS (%) |
|---|---|---|---|---|
| AB0192 control | 1.1 | 99.3 | 0.7 | 0.0 |
| AB0192, pH 8 40° C., 2 wks. | 1.2 | 97.7 | 1.6 | 0.7 |

TABLE 248

NR and R CE-SDS analysis of AB0192 after long term high pH stress (pH 8.0, 40° C., 14 days).

| Test article | NR CE Purity (%) | R CE Purity (%) |
|---|---|---|
| AB0192 control | 97.4 | 98.3 |
| AB0192, pH 8 40° C., 2 wks. | 95.7 | 94.7 |

TABLE 249

Kinetic parameters and binding affinity of AB0089 for CLEC12A, NKG2D and CD16a after long term high pH stress (pH 8.0, 40° C., 14 days) measured by SPR.

| Test article | Target | $k_a$ (M$^{-1}$s$^{-1}$) | $k_d$ (s$^{-1}$) | $K_D$ (nM) |
|---|---|---|---|---|
| AB0192 control | hCLEC12A | $(7.71 \pm 0.04) \times 10^5$ | $(1.29 \pm 0.02) \times 10^{-3}$ | $1.68 \pm 0.00$ |
| AB0192, pH 8 40° C., 2 wks. | hCLEC12A | $(7.68 \pm 0.17) \times 10^5$ | $(1.28 \pm 0.04) \times 10^{-3}$ | $1.66 \pm 0.10$ |
| AB0192 control | hNKG2D | $(2.08 \pm 0.03) \times 10^5$ | $(1.22 \pm 0.01) \times 10^{-1}$ | $588 \pm 6$ |
| AB0192, pH 8 40° C., 2 wks. | hNKG2D | $(1.56 \pm 0.09) \times 10^5$ | $(1.21 \pm 0.04) \times 10^{-1}$ | $779 \pm 45$ |
| AB0192 control | CD16aV | $(1.17 \pm 0.02) \times 10^5$ | $(1.99 \pm 0.05) \times 10^{-2}$ | $171 \pm 2$ |
| AB0192, pH 8 40° C., 2 wks. | CD16aV | $(1.10 \pm 0.04) \times 10^5$ | $(1.91 \pm 0.04) \times 10^{-2}$ | $173 \pm 2$ |

Average of 3 replicates

TABLE 250

AB0192 charge profile after long term high pH stress (pH 8.0, 40° C., 14 days).

| Test article | % acidic | % main | % basic |
|---|---|---|---|
| AB0192 control | 42.7 | 48.6 | 8.7 |
| AB0192, pH 8 40° C., 2 wks. | 60.3 | 30.5 | 9.1 |

TABLE 251

Potency of AB0192 after long term high pH stress (pH 8.0, 40 C., 14 days) assessed by KHYG-1-CD16aV cytotoxicity assay.

| Test article | EC50 (nM) | Max killing (%) |
|---|---|---|
| AB0192 control | 1.9 | 18 |
| AB0192, pH 8 40° C., 2 wks. | 3.0 | 18 |

Peptide Mapping Analysis of the pH 5 and pH 8 Stressed Material

To determine if the pH stress induced changes observed by cIEF are due to the modification in the complementarity determining regions (CDRs), the same pH 5 and pH 8 stressed samples were analyzed by LC-MS/MS peptide mapping. Based on the peptide map data, all of the CDRs in AB0192 are resistant to modification during low and high pH stress (Table 252). No evidence of aspartic acid isomerization was observed, based on manual inspection of peak shape.

TABLE 252

Post-translational modifications in AB0192 CDRs after low and high pH stresses.

| Chain | CDR | Sequence (Chothia) | Potential liability | pH 5 control | pH 5 stressed | pH 8 control | pH 8 stressed |
|---|---|---|---|---|---|---|---|
| S | H1 | GFTFNAF (SEQ ID NO: 195) | Deamidation | | NA | | |
| S | H2 | SSGSTS (SEQ ID NO: 196) | None | | NA | | |
| S | H3 | DGYPTGGAMDY (SEQ ID NO: 187) | Isomerization | | None detected | | |
| S | L1 | KASQDIYNYLS (SEQ ID NO: 198) | Deamidation | | NA | | |
| S | L2 | RANILVS (SEQ ID NO: 199) | Deamidation | | None detected | | |
| S | L3 | LQFDAFPFT (SEQ ID NO: 201) | None | | NA | | |
| H | H1 | GFTFSSY (SEQ ID NO: 297) | None | | NA | | |
| H | H2 | SSSSSY (SEQ ID NO: 298) | None | | NA | | |
| H | H3 | GAPIGAAAGWFDP (SEQ ID NO: 97) | Truncation | | None detected | | |
| L | L1 | RASQGISSWLA (SEQ ID NO: 86) | None | | NA | | |
| L | L2 | AASSLQS (SEQ ID NO: 77) | None | | NA | | |
| L | L3 | QQGVSFPRT (SEQ ID NO: 87) | None | | NA | | |

NA, not applicable

Manufacturability

Freeze/Thaw Stability

Aliquots of AB0192 (20 mg/ml in CST pH 7.0) were frozen and thawed 6 times by placing the vials in Styrofoam container (to slow the freezing rate) and placing the container at −80° C. Once frozen, the container was placed on a lab bench and the aliquots were allowed to thaw. After 6 cycles of freeze/thaw AB0192 showed no loss in monomer by SEC and protein concentration remained the same (FIGS. 273A-273B and Table 253).

TABLE 253

SEC analysis of AB0192 after freeze/thaw stress.

| Test article | Conc. (mg/ml) | Monomer (%) | LMWS (%) | HMWS (%) |
|---|---|---|---|---|
| AB0192 control | 21.2 | 98.9 | 1.1 | ND |
| AB0192 6 F/T | 20.8 | 98.9 | 1.1 | ND |

After 6 freeze/thaw cycles no loss of purity was detected by either reduced or non-reduced CE-SDS (FIGS. 274A-274B and Table 254).

TABLE 254

NR and R CE-SDS analysis of AB0192 after freeze/thaw stress.

| Test article | NR CE Purity (%) | R CE Purity (%) |
|---|---|---|
| AB0192 control | 99.0 | 97.3 |
| AB0192 6 F/T | 99.1 | 97.7 |

Agitation

Agitation study was performed in CST, pH 7.0 buffer. AB0192 was incubated for 24 h at constant steering (60 rpm) in a glass vial with a micro steer bar. No loss of monomer was detected by SEC compared to the control sample (FIGS. 275A-275B and Table 255).

TABLE 255

SEC analysis of AB0192 after agitation stress.

| Test article | Conc. (mg/ml) | Monomer (%) | LMWS (%) | BMWS (%) |
|---|---|---|---|---|
| AB0192 control | 21.2 | 98.9 | 1.1 | ND |
| AB0192 agitation | 21.4 | 98.7 | 1.0 | 0.3 |

ND, none detected

After 24 hours of stirring, there was no increase in fragmentation detected by reduced or non-reduced CE-SDS (FIGS. 276A-276B and Table 256).

TABLE 256

NR and R CE-SDS analysis of AB0192 after agitation stress.

| Test article | NR CE Purity (%) | R CE Purity (%) |
|---|---|---|
| AB0192 control | 99.0 | 97.3 |
| AB0192 agitation | 99.2 | 97.1 |

Low pH Hold

To determine if AB0192 is amendable to commonly used low pH hold protocol used for viral inactivation in biologics manufacturing, we performed low pH hold study. Incubation at low pH can potentially compromise biophysical stability and integrity of the molecule and could cause chemical degradation of amino acid side chains, in particular, aspartic acid isomerization. There is a potential sequence liability DS in CDRH3 of Chain S. Therefore, we have applied a wide range of assays to assess protein quality after low pH hold. The bulk of the AB0192 Protein A eluate was immediately adjusted to neutral pH, while a smaller sample was adjusted to pH 3.7 and held at room temperature for 1 hour to mimic a typical viral inactivation step. After the hold period, Protein A eluate was neutralized with 1.0 M Tris, pH 8.3 to achieve neutral pH. Analytical size exclusion chromatography was performed to determine if there were any changes in profile or aggregate content pre- and post-low pH exposure (FIGS. 277A-277B). No change in profile was observed after low pH hold. Both aliquots were further purified by second ion exchange chromatography and subjected to a panel of characterization assays.

Chemical modification of amino acid side chains can typically be observed at a global scale with cIEF. The cIEF profiles of AB0192 control and low pH hold lot are visually very similar and the relative quantitation of acid, main, and basic species are all within 2% of each other. Indicating that the low pH hold did not have a measurable effect on the charge profile of AB0192 (FIG. 278 and Table 257).

TABLE 257

Charge profile of AB0192 after low pH hold.

| Test article | pI | % acidic | % main | % basic |
|---|---|---|---|---|
| AB0192 control | 8.9 | 41.4 | 49.8 | 8.8 |
| AB0192 low pH hold | 8.9 | 43.1 | 48.2 | 8.7 |

After the low pH hold step, affinities for hCLEC12a, hNKG2D, and CD16aV were unaltered (FIGS. 279A-279F and Table 258). This indicates that AB0192 retains affinity for all three targets under low pH hold conditions used as viral inactivation step in biologics manufacturing

TABLE 258

Kinetic parameters and binding affinities of AB0192 for CLEC12A, NKG2D and CD16a after low pH hold measured by SPR.

| Test article | Target | $k_a$ (M$^{-1}$s$^{-1}$) | $k_d$ (s$^{-1}$) | $K_D$ (nM) |
|---|---|---|---|---|
| AB0192 Control | hCLEC12A | $6.85 \times 10^5$ | $1.25 \times 10^{-3}$ | 1.83 |
| AB0192 low pH hold | hCLEC12A | $(6.90 \pm 0.17) \times 10^5$ | $(1.15 \pm 0.01) \times 10^{-3}$ | $1.66 \pm 0.05$ |
| AB0192 Control | hNKG2D | $(1.88 \pm 0.08) \times 10^5$ | $(1.46 \pm 0.060) \times 10^{-1}$ | $779 \pm 10$ |
| AB0192 low pH hold | hNKG2D | $(1.78 \pm 0.08) \times 10^5$ | $(1.42 \pm 0.03) \times 10^{-1}$ | $796 \pm 47$ |
| AB0192 Control | CD16aV | $(1.12 \pm 0.08) \times 10^5$ | $(1.99 \pm 0.08) \times 10^{-2}$ | $178 \pm 6$ |
| AB0192 low pH hold | CD16aV | $(1.18 \pm 0.06) \times 10^5$ | $(2.12 \pm 0.09) \times 10^{-2}$ | $180 \pm 15$ |

Potency of low pH hold sample was further tested against CLEC12A+ PL-21 cancer cells in the KHYG1-CD16aV cytotoxicity bioassay. The potency of AB0192 was unaltered after the low pH hold step (FIG. 280 and Table 259).

TABLE 259

Potency of AB0192 after low pH hold in
KHYG1-CD16a mediated cytotoxicity assay.

| Test article | EC50 (nM) | Max killing (%) |
|---|---|---|
| AB0192 control | 2.5 | 18 |
| AB0192 low pH hold | 2.0 | 18 |

Taken together, these results demonstrate that the molecular format and structure of AB0192 meets the conceptual requirements for a new multi-specific therapeutic modality that simultaneously engages CLEC12A, NKG2D and CD16a to treat AML. AB0192 is potent and has a favorable developability profile with no sequence liabilities or significant post-translational modifications observed under any stresses. AB0192 binds to an epitope different from AB0237 and AB0089 TriNKETs.

INCORPORATION BY REFERENCE

Unless stated to the contrary, the entire disclosure of each of the patent documents and scientific articles referred to herein is incorporated by reference for all purposes.

Equivalents

The application may be embodied in other specific forms without departing from the spirit or essential characteristics thereof. The foregoing embodiments are therefore to be considered in all respects illustrative rather than limiting the application described herein. Scope of the application is thus indicated by the appended claims rather than by the foregoing description, and all changes that come within the meaning and range of equivalency of the claims are intended to be embraced therein.

SEQUENCES

| SEQ ID NO | Sequence |
|---|---|
| 1 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS |
| 2 | GSFSGYYWS |
| 3 | EIDHSGSTNYNPSLKS |
| 4 | ARARGPWSFDP |
| 5 | DIQMTQSPSTLSASVGDRVTITCRASQSISSWLAWYQQKPGKAPKLLIYKASSLESGVPSRFSGSGSGTEFTLTISSLQPDDFATYYCQQYNSYPITFGGGTKVEIK |
| 6 | EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPITFGGGTKVEIK |
| 7 | DIQMTQSPSTLSASVGDRVTITCRASQSIGSWLAWYQQKPGKAPKLLIYKASSLESGVPSRFSGSGSGTEFTLTISSLQPDDFATYYCQQYHSFYTFGGGTKVEIK |
| 8 | DIQMTQSPSTLSASVGDRVTITCRASQSIGSWLAWYQQKPGKAPKLLIYKASSLESGVPSRFSGSGSGTEFTLTISSLQPDDFATYYCQQSNSYYTFGGGTKVEIK |
| 9 | DIQMTQSPSTLSASVGDRVTITCRASQSISSWLAWYQQKPGKAPKLLIYKASSLESGVPSRFSGSGSGTEFTLTISSLQPDDFATYYCQQYNSYPTFGGGTKVEIK |
| 10 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWGFDPWGQGTLVTVSS |
| 11 | ELQMTQSPSSLSASVGDRVTITCRTSQSISSYLNWYQQKPGQPPKLLIYWASTRESGVPDRFSGSGSGTDFTLTISSLQPEDSATYYCQQSYDIPYTFGQGTKLEIK |
| 12 | DIQMTQSPSTLSASVGDRVTITCRASQSISSWLAWYQQKPGKAPKLLIYKASSLESGVPSRFSGSGSGTEFTLTISSLQPDDFATYYCQQYGSFPITFGGGTKVEIK |
| 13 | DIQMTQSPSTLSASVGDRVTITCRASQSISSWLAWYQQKPGKAPKLLIYKASSLESGVPSRFSGSGSGTDFTLTISSLQPDDFATYYCQQSKEVPWTFGQGTKVEIK |
| 14 | DIQMTQSPSTLSASVGDRVTITCRASQSISSWLAWYQQKPGKAPKLLIYKASSLESGVPSRFSGSGSGTEFTLTISSLQPDDFATYYCQQYNSFPTFGGGTKVEIK |
| 15 | DIQMTQSPSTLSASVGDRVTITCRASQSIGSWLAWYQQKPGKAPKLLIYKASSLESGVPSRFSGSGSGTEFTLTISSLQPDDFATYYCQQYDIYPTFGGGTKVEIK |
| 16 | DIQMTQSPSTLSASVGDRVTITCRASQSISSWLAWYQQKPGKAPKLLIYKASSLESGVPSRFSGSGSGTEFTLTISSLQPDDFATYYCQQYDSYPTFGGGTKVEIK |
| 17 | DIQMTQSPSTLSASVGDRVTITCRASQSISSWLAWYQQKPGKAPKLLIYKASSLESGVPSRFSGSGSGTEFTLTISSLQPDDFATYYCQQYGSFPTFGGGTKVEIK |
| 18 | DIQMTQSPSTLSASVGDRVTITCRASQSISSWLAWYQQKPGKAPKLLIYKASSLESGVPSRFSGSGSGTEFTLTISSLQPDDFATYYCQQYQSFPTFGGGTKVEIK |
| 19 | DIQMTQSPSTLSASVGDRVTITCRASQSISSWLAWYQQKPGKAPKLLIYKASSLESGVPSRFSGSGSGTEFTLTISSLQPDDFATYYCQQYSSFSTFGGGTKVEIK |

| SEQUENCES |
|---|

| SEQ ID NO | Sequence |
|---|---|
| 20 | DIQMTQSPSTLSASVGDRVTITCRASQSISSWLAWYQQKPGKAPKLLIYKASSLESGVPSRFSGSGSG TEFTLTISSLQPDDFATYYCQQYESYSTFGGGTKVEIK |
| 21 | DIQMTQSPSTLSASVGDRVTITCRASQSISSWLAWYQQKPGKAPKLLIYKASSLESGVPSRFSGSGSG TEFTLTISSLQPDDFATYYCQQYDSFITFGGGTKVEIK |
| 22 | DIQMTQSPSTLSASVGDRVTITCRASQSISSWLAWYQQKPGKAPKLLIYKASSLESGVPSRFSGSGSG TEFTLTISSLQPDDFATYYCQQYQSYPTFGGGTKVEIK |
| 23 | DIQMTQSPSTLSASVGDRVTITCRASQSIGSWLAWYQQKPGKAPKLLIYKASSLESGVPSRFSGSGSG TEFTLTISSLQPDDFATYYCQQYHSFPTFGGGTKVEIK |
| 24 | DIQMTQSPSTLSASVGDRVTITCRASQSIGSWLAWYQQKPGKAPKLLIYKASSLESGVPSRFSGSGSG TEFTLTISSLQPDDFATYYCQQYELYSYTFGGGTKVEIK |
| 25 | DIQMTQSPSTLSASVGDRVTITCRASQSISSWLAWYQQKPGKAPKLLIYKASSLESGVPSRFSGSGSG TEFTLTISSLQPDDFATYYCQQYDTFITFGGGTKVEIK |
| 26 | QVQLVQSGAEVKKPGSSVKVSCKASGGTFSSYAISWVRQAPGQGLEWMGGIIPIFGTANYAQKFQGRV TITADESTSTAYMELSSLRSEDTAVYYCARGDSSIRHAYYYYGMDVWGQGTTVTVSS |
| 27 | GTFSSYAIS |
| 28 | SYAIS |
| 29 | GIIPIFGTANYAQKFQG |
| 30 | ARGDSSIRHAYYYYGMDV |
| 31 | GDSSIRHAYYYYGMDV |
| 32 | DIVMTQSPDSLAVSLGERATINCKSSQSVLYSSNNKNYLAWYQQKPGQPPKLLIYWASTRESGVPDRF SGSGSGTDFTLTISSLQAEDVAVYYCQQYYSTPITFGGGTKVEIK |
| 33 | KSSQSVLYSSNNKNYLA |
| 34 | WASTRES |
| 35 | QQYYSTPIT |
| 36 | QLQLQESGPGLVKPSETLSLTCTVSGGSISSSSYYWGWIRQPPGKGLEWIGSIYYSGSTYYNPSLKSR VTISVDTSKNQFSLKLSSVTAADTAVYYCARGSDRFHPYFDYWGQGTLVTVSS |
| 37 | GSISSSSYYWG |
| 38 | SSSYYWG |
| 39 | SIYYSGSTYYNPSLKS |
| 40 | ARGSDRFHPYFDY |
| 41 | GSDRFHPYFDY |
| 42 | EIVLTQSPATLSLSPGERATLSCRASQSVSRYLAWYQQKPGQAPRLLIYDASNRATGIPARFSGSGSG TDFTLTISSLEPEDFAVYYCQQFDTWPPTFGGGTKVEIK |
| 43 | RASQSVSRYLA |
| 44 | DASNRAT |
| 45 | QQFDTWPPT |
| 46 | DIQMTQSPSTLSASVGDRVTITCRASQSISSWLAWYQQKPGKAPKLLIYKASSLESGVPSRFSGSGSG TEFTLTISSLQPDDFATYYCEQYDSYPTFGGGTKVEIK |
| 47 | QVQLVQSGAEVKKPGSSVKVSCKASGGTFSSYAISWVRQAPGQGLEWMGGIIPIFGTANYAQKFQGRV TITADESTSTAYMELSSLRSEDTAVYYCARRGRKASGSFYYYYGMDVWGQGTTVTVSS |
| 48 | ARRGRKASGSFYYYYGMDV |
| 49 | DIVMTQSPDSLAVSLGERATINCESSQSLLNSGNQKNYLTWYQQKPGQPPKPLIYWASTRESGVPDRF SGSGSGTDFTLTISSLQAEDVAVYYCQNDYSYPYTFGQGTKLEIK |

SEQUENCES

| SEQ ID NO | Sequence |
|---|---|
| 50 | ESSQSLLNSGNQKNYLT |
| 51 | QNDYSYPYT |
| 52 | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARGAPNYGDTTHDYYYMDVWGKGTTVTVSS |
| 53 | YTFTSYYMH |
| 54 | SYYMH |
| 55 | IINPSGGSTSYAQKFQG |
| 56 | ARGAPNYGDTTHDYYYMDV |
| 57 | GAPNYGDTTHDYYYMDV |
| 58 | EIVMTQSPATLSVSPGERATLSCRASQSVSSNLAWYQQKPGQAPRLLIYGASTRATGIPARESGSGSGTEFTLTISSLQSEDFAVYYCQQYDDWPFTFGGGTKVEIK |
| 59 | RASQSVSSNLA |
| 60 | GASTRAT |
| 61 | QQYDDWPFT |
| 62 | QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCARDTGEYYDTDDHGMDVWGQGTTVTVSS |
| 63 | YTFTGYYMH |
| 64 | GYYMH |
| 65 | WINPNSGGTNYAQKFQG |
| 66 | ARDTGEYYDTDDHGMDV |
| 67 | DTGEYYDTDDHGMDV |
| 68 | EIVLTQSPGTLSLSPGERATLSCRASQSVSSNLAWYQQKPGQAPRLLIYGASTRATGIPARESGSGSGTEFTLTISSLQSEDFAVYYCQQDDYWPPTFGGGTKVEIK |
| 69 | QQDDYWPPT |
| 70 | EVQLLESGGGLVQPGGSLRLSCAASGETFSSYAMSWVRQAPGKGLEWVSAISGSGGSTYYADSVKGRFTISRDNSKNTLYLQMNSLRAEDTAVYYCAKDGGYYDSGAGDYWGQGTLVTVSS |
| 71 | FTFSSYAMS |
| 72 | AISGSGGSTYYADSVKG |
| 73 | AKDGGYYDSGAGDY |
| 74 | DGGYYDSGAGDY |
| 75 | DIQMTQSPSSVSASVGDRVTITCRASQGIDSWLAWYQQKPGKAPKLLIYAASSLQSGVPSRFSGSGSGTDFTLTISSLQPEDFATYYCQQGVSYPRTFGGGTKVEIK |
| 76 | RASQGIDSWLA |
| 77 | AASSLQS |
| 78 | QQGVSYPRT |
| 79 | EVQLVESGGGLVKPGGSLRLSCAASGETFSSYSMNWVRQAPGKGLEWVSSISSSSSYIYYADSVKGRFTISRDNAKNSLYLQMNSLRAEDTAVYYCARGAPMGAAAGWFDPWGQGTLVTVSS |
| 80 | FTFSSYSMN |
| 81 | SYSMN |
| 82 | SISSSSSYIYYADSVKG |
| 83 | ARGAPMGAAAGWFDP |

-continued

SEQUENCES

| SEQ ID NO | Sequence |
|---|---|
| 84 | GAPMGAAAGWFDP |
| 85 | DIQMTQSPSSVSASVGDRVTITCRASQGISSWLAWYQQKPGKAPKLLIYAASSLQSGVPSRFSGSGSG<br>TDFTLTISSLQPEDFATYYCQQGVSFPRTFGGGTKVEIK |
| 86 | RASQGISSWLA |
| 87 | QQGVSFPRT |
| 88 | DIQMTQSPSSVSASVGDRVTITCRASQGISSWLAWYQQKPGKAPKLLIYAASSLQSGVPSRFSGSGSG<br>TDFTLTISSLQPEDFATYYCQQGVSFPRTFGCGTKVEIKGGGGSGGGGSGGGGSGGGGSEVQLVESGG<br>GLVKPGGSLRLSCAASGFTFSSYSMNWVRQAPGKCLEWVSSISSSSSYTYYADSVKGRFTISRDNAKN<br>SLYLQMNSLRAEDTAVYYCARGAPMGAAAGWFDPWGQGTLVTVSS |
| 89 | QVQLVQSGAEVKKPGASVKVSCKASGYTFTSYYMHWVRQAPGQGLEWMGIINPSGGSTSYAQKFQGRV<br>TMTRDTSTSTVYMELSSLRSEDTAVYYCAREGAGFAYGMDYYYMDVWGKGTTVTVSS |
| 90 | AREGAGFAYGMDYYYMDV |
| 91 | EGAGFAYGMDYYYMDV |
| 92 | EIVLTQSPATLSLSPGERATLSCRASQSVSSYLAWYQQKPGQAPRLLIYDASNRATGIPARFSGSGSG<br>TDFTLTISSLEPEDFAVYYCQQSDNWPFTFGGGTKVEIK |
| 93 | RASQSVSSYLA |
| 94 | QQSDNWPFT |
| 95 | EVQLVESGGGLVKPGGSLRLSCAASGFTFSSYSMNWVRQAPGKGLEWVSSISSSSSYTYYADSVKGRF<br>TISRDNAKNSLYLQMNSLRAEDTAVYYCARGAPIGAAAGWFDPWGQGTLVTVSS |
| 96 | ARGAPIGAAAGWFDP |
| 97 | GAPIGAAAGWFDP |
| 98 | EVQLVESGGGLVKPGGSLRLSCAASGFTFSSYSMNWVRQAPGKGLEWVSSISSSSSYTYYADSVKGRF<br>TISRDNAKNSLYLQMNSLRAEDTAVYYCARGAPQGAAAGWFDPWGQGTLVTVSS |
| 99 | ARGAPQGAAAGWFDP |
| 100 | GAPQGAAAGWFDP |
| 101 | EVQLVESGGGLVKPGGSLRLSCAASGFTFSSYSMNWVRQAPGKGLEWVSSISSSSSYTYYADSVKGRF<br>TISRDNAKNSLYLQMNSLRAEDTAVYYCARGAPLGAAAGWFDPWGQGTLVTVSS |
| 102 | ARGAPLGAAAGWFDP |
| 103 | GAPLGAAAGWFDP |
| 104 | EVQLVESGGGLVKPGGSLRLSCAASGFTFSSYSMNWVRQAPGKGLEWVSSISSSSSYTYYADSVKGRF<br>TISRDNAKNSLYLQMNSLRAEDTAVYYCARGAPFGAAAGWFDPWGQGTLVTVSS |
| 105 | ARGAPFGAAAGWFDP |
| 106 | GAPFGAAAGWFDP |
| 107 | EVQLVESGGGLVKPGGSLRLSCAASGFTFSSYSMNWVRQAPGKGLEWVSSISSSSSYTYYADSVKGRF<br>TISRDNAKNSLYLQMNSLRAEDTAVYYCARGAPVGAAAGWFDPWGQGTLVTVSS |
| 108 | ARGAPVGAAAGWFDP |
| 109 | GAPVGAAAGWFDP |
| 110 | EVQLVESGGGLVKPGGSLRLSCAASGFTFSSYSMNWVRQAPGKGLEWVSSISSSSSYTYYADSVKGRF<br>TISRDNAKNSLYLQMNSLRAEDTAVYYCARGAPXGAAAGWFDPWGQGTLVTVSS, wherein X is M, L, I, V, Q, or F |
| 111 | ARGAPXGAAAGWFDP wherein X is M, L, I, V, Q, or F |
| 112 | GAPXGAAAGWFDP wherein X is M, L, I, V, Q, or F |
| 113 | QVQLVESGGGLVKPGGSLRLSCAASGFTFSSYGMHWVRQAPGKGLEWVAFIRYDGSNKYYADSVKGRF<br>TISRDNSKNTLYLQMNSLRAEDTAVYYCAKDRGLGDGTYFDYWGQGTTVTVSS |

| SEQUENCES | |
|---|---|
| SEQ ID NO | Sequence |
| 114 | QSALTQPASVSGSPGQSITISCSGSSSNIGNNAVNWYQQLPGKAPKLLIYYDDLLPSGVSDRFSGSKS GTSAFLAISGLQSEDEADYYCAAWDDSLNGPVFGGGTKLTVL |
| 115 | SYAMS |
| 116 | QVHLQESGPGLVKPSETLSLTCTVSDDSISSYYWSWIRQPPGKGLEWIGHISYSGSANYNPSLKSRVT ISVDTSKNQFSLKLSSVTAADTAVYYCANWDDAFNIWGQGTMVTVSS |
| 117 | EIVLTQSPGTLSLSPGERATLSCRASQSVSSSYLAWYQQKPGQAPRLLIYGASSRATGIPDRFSGSGS GTDFTLTISRLEPEDFAVYYCQQYGSSPWTFGQGTKVEIK |
| 118 | DKTHTCPPCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFFLYSKLTVDKSRWQQGNVFS CSVMHEALHNHYTQKSLSLSPG |
| 119 | (GlyGlyGlyGlySer)$_4$ ((G$_4$S)$_4$) |
| 120 | (GS)$_n$ wherein n is 1, 2, 3, 4, 5, 6, 7, 8, 9, 10, 11, 12, 13, 14, 15, 16, 17, 18, 19, or 20 |
| 121 | (GGS)$_n$ wherein n is 1, 2, 3, 4, 5, 6, 7, 8, 9, 10, 11, 12, 13, 14, 15, 16, 17, 18, 19, or 20 |
| 122 | (GGGS)$_n$ wherein n is 1, 2, 3, 4, 5, 6, 7, 8, 9, 10, 11, 12, 13, 14, 15, 16, 17, 18, 19, or 20 |
| 123 | (GGSG)$_n$ wherein n is 1, 2, 3, 4, 5, 6, 7, 8, 9, 10, 11, 12, 13, 14, 15, 16, 17, 18, 19, or 20 |
| 124 | (GGSGG)$_n$ wherein n is 1, 2, 3, 4, 5, 6, 7, 8, 9, 10, 11, 12, 13, 14, 15, 16, 17, 18, 19, or 20 |
| 125 | (GGGGS)$_n$ wherein n is 1, 2, 3, 4, 5, 6, 7, 8, 9, 10, 11, 12, 13, 14, 15, 16, 17, 18, 19, or 20 |
| 126 | GSGSGSGSGSGSGSGSGSGS |
| 127 | GGSGGSGGSGGSGGSGGSGGSGGSGGS |
| 128 | GGGSGGGSGGGSGGGSGGGSGGGSGGGSGGGSGGGSGGGS |
| 129 | GGSGGGSGGGSGGGSGGGSGGGSGGGSGGGSGGGSGGGSG |
| 130 | GGSGGGGSGGGGSGGGGSGGGGSGGGGSGGGGSGGGGSGGGGSGGGGSGG |
| 131 | GGGGSGGGGSGGGGSGGGGSGGGGSGGGGSGGGGSGGGGSGGGGSGGGGS |
| 132 | GGGGSGGGGSGGGGS |
| 133 | GGGGSGGGGSGGGGSGGGGSGGGGSGGGGSGGGGSGGGGSGGGGSGGGGSGGGGSGGGGSGGGGSGGG GSGGGGSGGGGSGGGGSGGGGSGGGGSGGGGS |
| 134 | GGSGGGGSGGGGSGGGGSGGGGSGGGGSGGGGSGGGGSGGGGSGGGGSGGGGSGGGGSGGGGSGGGGS GGGGSGGGGSGGGGSGGGGSGGGGSGGGGSGG |
| 135 | EVQLQESGPGLVQPSQSLSITCTVSGFSLTNYGLHWVRQSPGKGLEWLGVIWSGGKTDYNTPFKSRLS ISKDISKNQVFFKMNSLQPNDTAIYFCAKYDYDDSLDYWGQGTSVTVSS |
| 136 | DIQMNQSPSSLSASLGDTIAITCHASQNINFWLSWYQQKPGNIPKLLIYEASNLHTGVPSRFSGSGSG TRFTLTISSLQPEDIATYYCQQSHSYPLTFGQGTKLEIK |
| 137 | GFSLTNY |
| 138 | WSGGK |
| 139 | YDYDDSLDY |
| 140 | HASQNINFWLS |
| 141 | EASNLHT |
| 142 | QQSHSYPLT |

| SEQ ID NO | Sequence |
|---|---|
| 143 | QLQLQESGPGLVKPSETLSLTCTVSGFSLTNYGLHWIRQPPGKGLEWIGVIWSGGKTDYNPSLKSRVT ISKDTSKNQFSLKLSSVQANDTAVYYCAKYDYDDSLDYWGQGTLVTVSS |
| 144 | DIQMTQSPSSLSASVGDRVTITCHASQNINFWLSWYQQKPGKIPKLLIYEASNLHTGVPSRFSGSGSG TRFTLTISSLQPEDIATYYCQQSHSYPLTFGQGTKLEIK |
| 145 | QLQLQESGPGLVKPSETLSLTCTVSGFSLTNYGLHWIRQPPGKCLEWIGVIWSGGKTDYNPSLKSRVT ISKDTSKNQFSLKLSSVQANDTAVYYCAKYDYDDSLDYWGQGTLVTVSSGGGGSGGGGSGGGGSGGGG SDIQMTQSPSSLSASVGDRVTITCHASQNINFWLSWYQQKPGKIPKLLIYEASNLHTGVPSRFSGSGS GTRFTLTISSLQPEDIATYYCQQSHSYPLTFGCGTKLEIK |
| 146 | DIQMTQSPSSLSASVGDRVTITCHASQNINFWLSWYQQKPGKIPKLLIYEASNLHTGVPSRFSGSGSG TRFTLTISSLQPEDIATYYCQQSHSYPLTFGCGTKLEIKGGGGSGGGGSGGGGSGGGGSQLQLQESGP GLVKPSETLSLTCTVSGFSLTNYGLHWIRQPPGKCLEWIGVIWSGGKTDYNPSLKSRVTISKDTSKNQ FSLKLSSVQANDTAVYYCAKYDYDDSLDYWGQGTLVTVSS |
| 147 | QLQLQESGPGLVKPSETLSLTCTVSGFSLTNYGLHWIRQPPGKGLEWIGVIWSGGKTDYNPSLKSRVT ISVDTSKNQFSLKLSSVQANDTAVYYCAKYDYDDSLDYWGQGTLVTVSS |
| 148 | EVQLVESGGGVVQPGGSLRLSCAASGFTENAFGMHWVRQAPGKGLEWVAFISSGSTSIYYANTVKGRF TISRDNSKNTLYLQMNSLRAEDTAVYYCARDGYPTGGAMDYWGQGTSVTVSS |
| 149 | QLQLQESGPGLVKPSETLSLTCTVSGFSLTNYGLHWIRQPPGKCLEWIGVIWSGGKTDYNPSLKSRVT ISVDTSKNQFSLKLSSVQANDTAVYYCAKYDYDDSLDYWGQGTLVTVSSGGGGSGGGGSGGGGSGGGG SDIQMTQSPSSLSASVGDRVTITCHASQNINFWLSWYQQKPGKIPKLLIYEASNLHTGVPSRFSGSGS GTRFTLTISSLQPEDIATYYCQQSHSYPLTFGCGTKLEIK |
| 150 | DIQMTQSPSSLSASVGDRVTITCHASQNINFWLSWYQQKPGKIPKLLIYEASNLHTGVPSRFSGSGSG TRFTLTISSLQPEDIATYYCQQSHSYPLTFGCGTKLEIKGGGGSGGGGSGGGGSGGGGSQLQLQESGP GLVKPSETLSLTCTVSGFSLTNYGLHWIRQPPGKCLEWIGVIWSGGKTDYNPSLKSRVTISVDTSKNQ FSLKLSSVQANDTAVYYCAKYDYDDSLDYWGQGTLVTVSS |
| 151 | DIQMTQSPSSLSASVGDRVTITCHASQNINEWLSWYQQKPGKX$_1$PKLLIYEASNLHTGVPSRFSGSGS GTX$_2$FTLTISSLQPEDX$_3$ATYYCQQSHSYPLTFGX$_4$GTKLEIK wherein X$_1$ is A or I, X$_2$ is D or R, X$_3$ is F or I, and X$_4$ is Q or G |
| 152 | KSSQSLLWNVNQNNYLV |
| 153 | QLQLQESGPGLVKPSETLSLTCTVSGFSLTNYGLHWIRQPPGKCLEWIGVIWSGGKTDYNPSLKSRVT ISKDTSKNQFSLKLSSVTANDTAVYYCAKYDYDDSLDYWGQGTLVTVSSGGGGSGGGGSGGGGSGGGG SDIQMTQSPSSLSASVGDRVTITCHASQNINFWLSWYQQKPGKIPKLLIYEASNLHTGVPSRFSGSGS GTRFTLTISSLQPEDIATYYCQQSHSYPLTFGCGTKLEIK |
| 154 | DIQMTQSPSSLSASVGDRVTITCHASQNINFWLSWYQQKPGKIPKLLIYEASNLHTGVPSRFSGSGSG TRFTLTISSLQPEDIATYYCQQSHSYPLTFGCGTKLEIKGGGGSGGGGSGGGGSGGGGSQLQLQESGP GLVKPSETLSLTCTVSGFSLTNYGLHWIRQPPGKCLEWIGVIWSGGKTDYNPSLKSRVTISKDTSKNQ FSLKLSSVTANDTAVYYCAKYDYDDSLDYWGQGTLVTVSS |
| 155 | EVQLQESGAELVRSGASIKLSCAASAFNIKDYFIHWVRQRPDQGLEWIGWIDPENDDTEYAPKFQDKA TMTADTSSNTAYLQLSSLTSADTAVYYCNALWSRGGYFDYWGQGTTLTVSS |
| 156 | QLQLQESGPGLVKPSETLSLTCTVSGFSLTNYGLHWIRQPPGKCLEWIGVIWSGGKTDYNPSLKSRVT ISKDTSKNQFSLKLSSVQAADTAVYYCAKYDYDDSLDYWGQGTLVTVSSGGGGSGGGGSGGGGSGGGG SDIQMTQSPSSLSASVGDRVTITCHASQNINFWLSWYQQKPGKIPKLLIYEASNLHTGVPSRFSGSGS GTRFTLTISSLQPEDIATYYCQQSHSYPLTFGCGTKLEIK |
| 157 | DIQMTQSPSSLSASVGDRVTITCHASQNINFWLSWYQQKPGKIPKLLIYEASNLHTGVPSRFSGSGSG TRFTLTISSLQPEDIATYYCQQSHSYPLTFGCGTKLEIKGGGGSGGGGSGGGGSGGGGSQLQLQESGP GLVKPSETLSLTCTVSGFSLTNYGLHWIRQPPGKCLEWIGVIWSGGKTDYNPSLKSRVTISKDTSKNQ FSLKLSSVQAADTAVYYCAKYDYDDSLDYWGQGTLVTVSS |
| 158 | EVLLTQSPAITAASPGEKVTITCSARSSVSYMSWYQQKPGSSPKIWIYGISKLASGVPARFSGSGSGT YFSFTINNLEAEDVATYYCQQRSYYPFTFGSGTKLEIK |
| 159 | AFNIKDY |
| 160 | QLQLQESGPGLVKPSETLSLTCTVSGFSLTNYGLHWIRQPPGKCLEWIGVIWSGGKTDYNPSLKSRVT ISKDTSKNQFSLKLSSVQANDTAVYYCARYDYDDSLDYWGQGTLVTVSSGGGGSGGGGSGGGGSGGGG SDIQMTQSPSSLSASVGDRVTITCHASQNINFWLSWYQQKPGKIPKLLIYEASNLHTGVPSRFSGSGS GTRFTLTISSLQPEDIATYYCQQSHSYPLTFGCGTKLEIK |
| 161 | DIQMTQSPSSLSASVGDRVTITCHASQNINFWLSWYQQKPGKIPKLLIYEASNLHTGVPSRFSGSGSG TRFTLTISSLQPEDIATYYCQQSHSYPLTFGCGTKLEIKGGGGSGGGGSGGGGSGGGGSQLQLQESGP |

| SEQ ID NO | Sequence |
|---|---|
| | GLVKPSETLSLTCTVSGFSLTNYGLHWIRQPPGKCLEWIGVIWSGGKTDYNPSLKSRVTISKDTSKNQFSLKLSSVQANDTAVYYCARYDYDDSLDYWGQGTLVTVSS |
| 162 | EVQLVESGGGVVQPGGSLRLSCAASGFTFNSFGMHWVRQAPGKGLEWVAFISSGSTSIYYANTVKGRFTISRDNSKNTLYLQMNSLRAEDTAVYYCARDGYPTGGAMDYWGQGTSVTVSS |
| 163 | DIQMTQSPSSLSASVGDRVTITCHASQNINFWLSWYQQKPGKAPKLLIYEASNLHTGVPSRFSGSGSGTRFTLTISSLQPEDIATYYCQQSHSYPLTFGQGTKLEIK |
| 164 | QLQLQESGPGLVKPSETLSLTCTVSGFSLTNYGLHWIRQPPGKCLEWIGVIWSGGKTDYNPSLKSRVTISKDTSKNQFSLKLSSVQANDTAVYYCAKYDYDDSLDYWGQGTLVTVSSGGGGSGGGGSGGGGSGGGGSDIQMTQSPSSLSASVGDRVTITCHASQNINFWLSWYQQKPGKAPKLLIYEASNLHTGVPSRFSGSGSGTRFTLTISSLQPEDIATYYCQQSHSYPLTFGCGTKLEIK |
| 165 | DIQMTQSPSSLSASVGDRVTITCHASQNINFWLSWYQQKPGKAPKLLIYEASNLHTGVPSRFSGSGSGTRFTLTISSLQPEDIATYYCQQSHSYPLTFGCGTKLEIKGGGGSGGGGSGGGGSGGGGSQLQLQESGPGLVKPSETLSLTCTVSGFSLTNYGLHWIRQPPGKCLEWIGVIWSGGKTDYNPSLKSRVTISKDTSKNQFSLKLSSVQANDTAVYYCAKYDYDDSLDYWGQGTLVTVSS |
| 166 | WSGGS |
| 167 | DIQMTQSPSSLSASVGDRVTITCHASQNINFWLSWYQQKPGKIPKLLIYEASNLHTGVPSRFSGSGSGTDFTLTISSLQPEDIATYYCQQSHSYPLTFGQGTKLEIK |
| 168 | QLQLQESGPGLVKPSETLSLTCTVSGFSLTNYGLHWIRQPPGKCLEWIGVIWSGGKTDYNPSLKSRVTISKDTSKNQFSLKLSSVQANDTAVYYCAKYDYDDSLDYWGQGTLVTVSSGGGGSGGGGSGGGGSGGGGSDIQMTQSPSSLSASVGDRVTITCHASQNINFWLSWYQQKPGKIPKLLIYEASNLHTGVPSRFSGSGSGTDFTLTISSLQPEDIATYYCQQSHSYPLTFGCGTKLEIK |
| 169 | DIQMTQSPSSLSASVGDRVTITCHASQNINFWLSWYQQKPGKIPKLLIYEASNLHTGVPSRFSGSGSGTDFTLTISSLQPEDIATYYCQQSHSYPLTFGCGTKLEIKGGGGSGGGGSGGGGSGGGGSQLQLQESGPGLVKPSETLSLTCTVSGFSLTNYGLHWIRQPPGKCLEWIGVIWSGGKTDYNPSLKSRVTISKDTSKNQFSLKLSSVQANDTAVYYCAKYDYDDSLDYWGQGTLVTVSS |
| 170 | DPENDD |
| 171 | DIQMTQSPSSLSASVGDRVTITCHASQNINFWLSWYQQKPGKIPKLLIYEASNLHTGVPSRFSGSGSGTRFTLTISSLQPEDFATYYCQQSHSYPLTFGQGTKLEIK |
| 172 | QLQLQESGPGLVKPSETLSLTCTVSGFSLTNYGLHWIRQPPGKCLEWIGVIWSGGKTDYNPSLKSRVTISKDTSKNQFSLKLSSVQANDTAVYYCAKYDYDDSLDYWGQGTLVTVSSGGGGSGGGGSGGGGSGGGGSDIQMTQSPSSLSASVGDRVTITCHASQNINFWLSWYQQKPGKIPKLLIYEASNLHTGVPSRFSGSGSGTRFTLTISSLQPEDFATYYCQQSHSYPLTFGCGTKLEIK |
| 173 | DIQMTQSPSSLSASVGDRVTITCHASQNINFWLSWYQQKPGKIPKLLIYEASNLHTGVPSRFSGSGSGTRFTLTISSLQPEDFATYYCQQSHSYPLTFGCGTKLEIKGGGGSGGGGSGGGGSGGGGSQLQLQESGPGLVKPSETLSLTCTVSGFSLTNYGLHWIRQPPGKCLEWIGVIWSGGKTDYNPSLKSRVTISKDTSKNQFSLKLSSVQANDTAVYYCAKYDYDDSLDYWGQGTLVTVSS |
| 174 | QLQLQESGPGLVKPSETLSLTCTVSGFSLTNYGLHWIRQPPGKGLEWIGVIWSGGKTDYNPSLKSRVTISVDTSKNQFSLKLSSVTAADTAVYYCARYDYDDSLDYWGQGTLVTVSS |
| 175 | DIQMTQSPSSLSASVGDRVTITCHASQNINFWLSWYQQKPGKAPKLLIYEASNLHTGVPSRFSGSGSGTDFTLTISSLQPEDFATYYCQQSHSYPLTFGQGTKLEIK |
| 176 | QLQLQESGPGLVKPSETLSLTCTVSGFSLTNYGLHWIRQPPGKCLEWIGVIWSGGKTDYNPSLKSRVTISVDTSKNQFSLKLSSVTAADTAVYYCARYDYDDSLDYWGQGTLVTVSSGGGGSGGGGSGGGGSGGGGSDIQMTQSPSSLSASVGDRVTITCHASQNINFWLSWYQQKPGKAPKLLIYEASNLHTGVPSRFSGSGSGTDFTLTISSLQPEDFATYYCQQSHSYPLTFGCGTKLEIK |
| 177 | DIQMTQSPSSLSASVGDRVTITCHASQNINFWLSWYQQKPGKAPKLLIYEASNLHTGVPSRFSGSGSGTDFTLTISSLQPEDFATYYCQQSHSYPLTFGCGTKLEIKGGGGSGGGGSGGGGSGGGGSQLQLQESGPGLVKPSETLSLTCTVSGFSLTNYGLHWIRQPPGKCLEWIGVIWSGGKTDYNPSLKSRVTISVDTSKNQFSLKLSSVTAADTAVYYCARYDYDDSLDYWGQGTLVTVSS |
| 178 | QLQLQESGPGLVKPSETLSLTCTVSGFSLTNYGLHWIRQPPGKGLEWIGVIWSGGKTDYNPSLKSRVTISKDTSKNQFSLKLSSVQAADTAVYYCAKYDYDDSLDYWGQGTLVTVSS |
| 179 | QHNHGSFLPYT |
| 180 | QLQLQESGPGLVKPSETLSLTCTVSGFSLTNYGLHWIRQPPGKCLEWIGVIWSGGKTDYNPSLKSRVTISKDTSKNQFSLKLSSVQAADTAVYYCAKYDYDDSLDYWGQGTLVTVSSGGGGSGGGGSGGGGSGGGGSDIQMTQSPSSLSASVGDRVTITCHASQNINFWLSWYQQKPGKAPKLLIYEASNLHTGVPSRFSGSGSGTRFTLTISSLQPEDIATYYCQQSHSYPLTFGCGTKLEIK |

| SEQUENCES |
|---|
| SEQ ID NO Sequence |

181 DIQMTQSPSSLSASVGDRVTITCHASQNINFWLSWYQQKPGKAPKLLIYEASNLHTGVPSRFSGSGSG
TRFTLTISSLQPEDIATYYCQQSHSYPLTFGCGTKLEIKGGGGSGGGGSGGGGSGGGGSQLQLQESGP
GLVKPSETLSLTCTVSGFSLTNYGLHWIRQPPGKCLEWIGVIWSGGKTDYNPSLKSRVTISKDTSKNQ
FSLKLSSVQAADTAVYYCAKYDYDDSLDYWGQGTLVTVSS

182 QLQLQESGPGLVKPSETLSLTCTVSGFSLTNYGLHWIRQPPGKGLEWIGVIWSGGKTDYNPSLKSRVT
ISX₁DTSKNQFSLKLSSVX₂AX₃DTAVYYCAX₄YDYDDSLDYWGQGTLVTVSS; wherein X₁ is
V or K, X₂ is T or Q, X₃ is A or N, and X₄ is R or K

183 LWSRGGYFDY

184 EVQLVESGGGVVQPGGSLRLSCAASGFTFNSFGMHWVRQAPGKCLEWVAFISSGSTSIYYANTVKGRF
TISRDNSKNTLYLQMNSLRAEDTAVYYCARDGYPTGGAMDYWGQGTSVTVSSGGGGSGGGGSGGGGSG
GGGSDIQMTQSPSSLSASVGDRVTITCKASQDIYNYLSWFQQKPGKAPKPLIYRANILVSGVPSRFSG
SGSGQDYTFTISSLQPEDIATYYCLQFDAFPFTFGCGTKLEIK

185 DIQMTQSPSSLSASVGDRVTITCKASQDIYNYLSWFQQKPGKAPKPLIYRANILVSGVPSRFSGSGSG
QDYTFTISSLQPEDIATYYCLQFDAFPFTFGCGTKLEIKGGGGSGGGGSGGGGSGGGGSEVQLVESGG
GVVQPGGSLRLSCAASGFTFNSFGMHWVRQAPGKCLEWVAFISSGSTSIYYANTVKGRFTISRDNSKN
TLYLQMNSLRAEDTAVYYCARDGYPTGGAMDYWGQGTSVTVSS

186 SARSSVSYMS

187 DGYPTGGAMDY

188 GISKLAS

189 QQRSYYPFT

190 EVQLQESGPELEKPGASVRISCKASGYSFTAYNMNWVKQSNGKSLEWIGNIDPSYGDATYNQKFKGKA
TLTVDKSSSTAYMQLKSLTSEDSAVYYCARDNYYGSGYFDYWGQGTTLTVSS

191 SVLMTQTPLSLPVSLGDRASISCRSSQGIVHINGNTYLEWYLQKPGQSPKLLIYKVSNRFSGVPDRFS
GSGSGTDFTLKISRVEAEDLGVYYCFQGSHVPWTFGGGTKLEIK

192 GFTFNSF

193 EVQLQESGGGLVQPGGSRKLSCAASGFTFNSFGMHWVRQAPEKGLEWVAFISSGSTSIYYANTVKGRF
TISRDNPKNTLFLQMTSLRSEDTAMYYCARDGYPTGGAMDYWGQGTSVTVSS

194 DIKMTQSPSSMYASLGERVTITCKASQDIYNYLSWFQLKPGKSPRPLIYRANILVSGVPSKFSGSGSG
QDYSLTINSLEYEDLGIYYCLQFDAFPFTFGSGTKLEIK

195 GFTFNAF

196 SSGSTS

197 GYSFTAY

198 KASQDIYNYLS

199 RANILVS

200 DIQMTQSPSSLSASVGDRVTITCHASQNINFWLSWYQQKPGKAPKLLIYEASNLHTGVPSRFSGSGSG
TRFTLTISSLQPEDIATYYCQQSHSYPLTFGCGTKLEIKGGGGSGGGGSGGGGSGGGGSQLQLQESGP
GLVKPSETLSLTCTVSGFSLTNYGLHWIRQPPGKCLEWIGVILSGGWTDYNPSLKSRVTISKDTSKNQ
FSLKLSSVQAADTAVYYCAKGDYGDALDYWGQGTLVTVSS

201 LQFDAFPFT

202 DPSYGD

203 DIQMTQSPSSLSASVGDRVTITCKASQDIYNYLSWFQQKPGKAPKPLIYRANILVSGVPSRFSGSGSG
QDYTFTISSLQPEDIATYYCLQFDAFPFTFGSGTKLEIK

204 EVQLVESGGGVVQPGGSLRLSCAASGFTFNAFGMHWVRQAPGKCLEWVAFISSGSTSTYYANTVKGRF
TISRDNSKNTLYLQMNSLRAEDTAVYYCARDGYPTGGAMDYWGQGTSVTVSSGGGGSGGGGSGGGGSG
GGGSDIQMTQSPSSLSASVGDRVTITCKASQDIYNYLSWFQQKPGKAPKPLIYRANILVSGVPSRFSG
SGSGQDYTFTISSLQPEDIATYYCLQFDAFPFTFGCGTKLEIK

| SEQUENCES | |
|---|---|
| SEQ ID NO | Sequence |
| 205 | DIQMTQSPSSLSASVGDRVTITCKASQDIYNYLSWFQQKPGKAPKPLIYRANILVSGVPSRFSGSGSG QDYTFTISSLQPEDIATYYCLQFDAFPFTFGCGTKLEIKGGGGSGGGGSGGGGSGGGGSEVQLVESGG GVVQPGGSLRLSCAASGFTFNAFGMHWVRQAPGKCLEWVAFISSGSTSTYYANTVKGRFTISRDNSKN TLYLQMNSLRAEDTAVYYCARDGYPTGGAMDYWGQGTSVTVSS |
| 206 | GFSLTSY |
| 207 | DNYYGSGYFDY |
| 208 | EVQLVESGGGVVQPGGSLRLSCAASGFTFNSFGMHWVRQAPGKCLEWVAFISSGSTSTYYANTVKGRF TISRDNSKNTLYLQMNSLRAEDTAVYYCARSGYPTGGAMDYWGQGTSVTVSSGGGGSGGGGSGGGGSG GGGSDIQMTQSPSSLSASVGDRVTITCKASQDIYNYLSWFQQKPGKAPKPLIYRANILVSGVPSRFSG SGSGQDYTFTISSLQPEDIATYYCLQFDAFPFTFGCGTKLEIK |
| 209 | DIQMTQSPSSLSASVGDRVTITCKASQDIYNYLSWFQQKPGKAPKPLIYRANILVSGVPSRFSGSGSG QDYTFTISSLQPEDIATYYCLQFDAFPFTFGCGTKLEIKGGGGSGGGGSGGGGSGGGGSEVQLVESGG GVVQPGGSLRLSCAASGFTFNSFGMHWVRQAPGKCLEWVAFISSGSTSTYYANTVKGRFTISRDNSKN TLYLQMNSLRAEDTAVYYCARSGYPTGGAMDYWGQGTSVTVSS |
| 210 | EVQLVESGGGVVQPGGSLRLSCAASGFTFNSFGMHWVRQAPGKGLEWVAFISSGSTSTYYANTVKGRF TISRDNSKNTLYLQMNSLRAEDTAVYYCARSGYPTGGAMDYWGQGTSVTVSS |
| 211 | RSSQGIVHINGNTYLE |
| 212 | KVSNRFS |
| 213 | SGYPTGGAMDY |
| 214 | FQGSHVPWT |
| 215 | EVQLVESGGGVVQPGGSLRLSCAASGFTFNSFGMHWVRQAPGKCLEWVAFISSGSTSTYYANTVKGRF TISRDNSKNTLYLQMNSLRAEDTAVYYCARDGYPTGGAMDYWGQGTSVTVSSGGGGSGGGGSGGGGSG GGGSDIKMTQSPSSLSASVGDRVTITCKASQDIYNYLSWFQQKPGKAPKPLIYRANILVSGVPSRFSG SGSGQDYTLTISSLQPEDIATYYCLQFDAFPFTFGCGTKLEIK |
| 216 | DIKMTQSPSSLSASVGDRVTITCKASQDIYNYLSWFQQKPGKAPKPLIYRANILVSGVPSRFSGSGSG QDYTLTISSLQPEDIATYYCLQFDAFPFTFGCGTKLEIKGGGGSGGGGSGGGGSGGGGSEVQLVESGG GVVQPGGSLRLSCAASGFTFNSFGMHWVRQAPGKCLEWVAFISSGSTSTYYANTVKGRFTISRDNSKN TLYLQMNSLRAEDTAVYYCARDGYPTGGAMDYWGQGTSVTVSS |
| 217 | EVQLQESGAELVRSGASVKLSCTVSGFNIKDYYMHWVKQRPEQGLEWIGWIDPENGDTENVPKFQGKA TMTADTSSNTAYLQLRSLTSEDTAVYYCKSYYYDSSSRYVDVWGAGTTVTVSS |
| 218 | DIKMTQSPSSLSASVGDRVTITCKASQDIYNYLSWFQQKPGKAPKPLIYRANILVSGVPSRFSGSGSG QDYTLTISSLQPEDIATYYCLQFDAFPFTFGSGTKLEIK |
| 219 | GIVMTQAPLTLSVTIGQPASISCKSSQSLLDSDGKTFLNWFLQRPGQSPKRLISLVSKLDSGVPDRFT GSGSGTDFTLKLSRVEPEDLGVYYCWQGTHFPYTFGGGTKLEIK |
| 220 | GFNIKDY |
| 221 | GFSLTSF |
| 222 | DPENGD |
| 223 | SYFAMDY |
| 224 | KSSQSLLDSDGKTFLN |
| 225 | LVSKLDS |
| 226 | GASIRES |
| 227 | WQGTHFPYT |
| 228 | EVQLQESGAELMKPGASVKISCRTTGYTFSTYWIEWVKQRPGRGPEWIGELFPGNSDTTLNEKFTGKA TFTADSSSNTAYMQLSSLTSEDSAVYYCARSGYYGSSLDYWGQGTTLTVSS |
| 229 | GIVMTQSPASLSASVGETVTITCRAGENIHSYLAWYQQKQGKSPQLLVYNAKTLAEGVPSRFSGSGSG TQFSLKINSLQPEDFGSYYCQHHYGTPRTFGGGTKLEIK |
| 230 | GYTFSTY |

| SEQ ID NO | Sequence |
|---|---|
| 231 | FPGNSD |
| 232 | SGYYGSSLDY |
| 233 | RAGENIHSYLA |
| 234 | NAKTLAE |
| 235 | QHHYGTPRT |
| 236 | WSGGN |
| 237 | GIVMTQSPSSLAVTAGEKVTMRCKSSQSLLWNVNQNNYLVWYQQKQGQPPKLLIYGASIRESWVPDRF TGSGSGTDFTLTISNVHAEDLAVYYCQHNHGSFLPYTFGGGTKLEIK |
| 238 | EVQLQESGPGLVQPSQSLSITCTVSGFSLTSFGIHWVRQSPGKGLEWLGVIWSGGNTDSNAAFISRLS ITKDISKSQVFFKMNSLQVTDTAIYYCARSYFAMDYWGQGTSVTVSS |
| 239 | GASIRQS |
| 240 | KSSQSLLWNVNQNNYLL |
| 241 | THFGMDY |
| 242 | QVQLRQSGPGLVQPSQSLSITCTVSGFSLTSYGVHWVRQSPGKGLEWLGVMWSGGSTDYNAAFMSRLS ISKDNSKSQVFFTMNSLQADDTAIYYCARTHFGMDYWGQGTPVTVSS |
| 243 | GIVMTQSPSSLAVTAGEKVTMRCKSSQSLLWSVNQNNYLLWYQQKQGQPPKLLIYGASIRQSWVPDRF TGSGSGTDFTLSISNVHAEDLAVYYCQHNHGSFLPYTFGGGTKLEIK |
| 244 | QLQLQESGPGLVKPSETLSLTCTVSGFSLTNYGLHWIRQFPGKGLEWIGVIWSGGKTDYNPSLKSRVT ISKDTSKNQFSLKLSSVTANDTAVYYCAKYDYDDSLDYWGQGTLVTVSS |
| 245 | KSSQSLLWSVNQNNYLL |
| 246 | XGYPTGGAMDY wherein X is D or S |
| 247 | EVQLQESGPGLVQPSQSLSITCTVSGFSLTSFGVHWVRQSPGKGLEWLGVIWSGGSTDSNAAFISRLT ITKDNSKSQVFFKMNSLQATDTAIYYCARSYFAMDYWGQGTSVSVSS |
| 248 | DIVMTQSPSSLAVTAGEKVTMRCKSSQSLLWNVNQNNYLLWYQQKQGQPPKLLIYGASIRESWVPDRF TGSGSGTDFTLTISNVHVEDLAVYYCQHNHGSFLPYTFGGGTKLEIK |
| 249 | EVQLVESGGGVVQPGGSLRLSCAASGFTENX$_1$FGMHWVRQAPGKGLEWVAFISSGSTSIYYANTVKGR FTISRDNSKNTLYLQMNSLRAEDTAVYYCARX$_2$GYPTGGAMDYWGQGTSVTVSS wherein X$_1$ is S or A and X$_2$ is D or S |
| 250 | DIX$_1$MTQSPSSLSASVGDRVTITCKASQDIYNYLSWFQQKPGKAPKPLIYRANILVSGVPSRFSGSGS GQDYTX$_2$TISSLQPEDIATYYCLQFDAFPFTFGSGTKLEIK wherein X$_1$ is Q or K and X$_2$ is F or L |
| 251 | GFTFNXF wherein X is S or A |
| 252 | EVQLVESGGGVVQPGGSLRLSCAASGFTFNAFGMHWVRQAPGKCLEWVAFISSGSTSIYYANTVKGRF TISRDNSKNTLYLQMNSLRAEDTAVYYCARDGYPTGGAMDYWGQGTSVTVSSGGGGSGGGGSGGGGSG GGGSDIKMTQSPSSLSASVGDRVTITCKASQDIYNYLSWFQQKPGKAPKPLIYRANILVSGVPSRFSG SGSGQDYTLTISSLQPEDIATYYCLQFDAFPFTFGCGTKLEIK |
| 253 | DIKMTQSPSSLSASVGDRVTITCKASQDIYNYLSWFQQKPGKAPKPLIYRANILVSGVPSRFSGSGSG QDYTLTISSLQPEDIATYYCLQFDAFPFTFGCGTKLEIKGGGGSGGGGSGGGGSGGGGSEVQLVESGG GVVQPGGSLRLSCAASGFTFNAFGMHWVRQAPGKCLEWVAFISSGSTSIYYANTVKGRFTISRDNSKN TLYLQMNSLRAEDTAVYYCARDGYPTGGAMDYWGQGTSVTVSS |
| 254 | EVQLVESGGGVVQPGGSLRLSCAASGFTENSFGMHWVRQAPGKCLEWVAFISSGSTSIYYANTVKGRF TISRDNSKNTLYLQMNSLRAEDTAVYYCARSGYPTGGAMDYWGQGTSVTVSSGGGGSGGGGSGGGGSG GGGSDIKMTQSPSSLSASVGDRVTITCKASQDIYNYLSWFQQKPGKAPKPLIYRANILVSGVPSRFSG SGSGQDYTLTISSLQPEDIATYYCLQFDAFPFTFGCGTKLEIK |
| 255 | DIKMTQSPSSLSASVGDRVTITCKASQDIYNYLSWFQQKPGKAPKPLIYRANILVSGVPSRFSGSGSG QDYTLTISSLQPEDIATYYCLQFDAFPFTFGCGTKLEIKGGGGSGGGGSGGGGSGGGGSEVQLVESGG GVVQPGGSLRLSCAASGFTENSFGMHWVRQAPGKCLEWVAFISSGSTSIYYANTVKGRFTISRDNSKN TLYLQMNSLRAEDTAVYYCARSGYPTGGAMDYWGQGTSVTVSS |

-continued

| SEQUENCES | |
|---|---|
| SEQ ID NO | Sequence |
| 256 | QLQLQESGPGLVKPSETLSLTCTVSGFSLTNYGLHWIRQPPGKGLEWIGVIWSGGKTDYNPSLKSRVT<br>ISKDTSKNQFSLKLSSVQANDTAVYYCARYDYDDSLDYWGQGTLVTVSS |
| 257 | YYYDSSSRYVDV |
| 258 | MSEEVTYADLQFQNSSEMEKIPEIGKFGEKAPPAPSHVWRPAALFLTLLCLLLLIGLGVLASMFHVTL<br>KIEMKKMNKLQNISEELQRNISLQLMSNMNISNKIRNLSTTLQTIATKLCRELYSKEQEHKCKPCPRR<br>WIWHKDSCYFLSDDVQTWQESKMACAAQNASLLKINNKNALEFIKSQSRSYDYWLGLSPEEDSTRGMR<br>VDNIINSSAWVIRNAPDLNNMYCGYINRLYVQYYHCTYKKRMICEKMANPVQLGSTYFREA |
| 259 | QLQLQESGPGLVKPSETLSLTCTVSGFSLTNYGLHWIRQPPGKCLEWIGVIWSGGKTDYNPSLKSRVT<br>ISKDTSKNQFSLKLSSVQAADTAVYYCAKYDYDDSLDYWGQGTLVTVSSGGGGSGGGGSGGGGSGGGG<br>SDIQMTQSPSSLSASVGDRVTITCHASQNINFWLSWYQQKPGKAPKLLIYEASNLHTGVPSRFSGSGS<br>GTRFTLTISSLQPEDIATYYCQQSHSYPLTFGCGTKLEIKGSDKTHTCPPCPAPELLGGPSVFLFPPPK<br>PKDTLMISRTPEVTCVVVDVSHEDPEVKFNWYVDGVEVHNAKTKPREEQYNSTYRVVSVLTVLHQDWL<br>NGKEYKCKVSNKALPAPIEKTISKAKGQPREPRVYTLPPCRDELTKNQVSLTCLVKGFYPSDIAVEWE<br>SNGQPENNYKTTPPVLVSDGSFTLYSKLTVDKSRWQQGNVFSCSVMHEALHNHYTQKSLSLSPG |
| 260 | EVQLVESGGGLVKPGGSLRLSCAASGFTFSSYSMNWVRQAPGKGLEWVSSISSSSSYTYYADSVKGRF<br>TISRDNAKNSLYLQMNSLRAEDTAVYYCARGAPIGAAAGWFDPWGQGTLVTVSSASTKGPSVFPLAPS<br>SKSTSGGTAALGCLVKDYFPEPVTVSWNSGALTSGVHTFPAVLQSSGLYSLSSVVTVPSSSLGTQTYI<br>CNVNHKPSNTKVDKKVEPKSCDKTHTCPPCPAPELLGGPSVFLEPPKPKDTLMISRTPEVTCVVVDVS<br>HEDPEVKFNWYVDGVEVHNAKTKPREEQYNSTYRVVSVLTVLHQDWLNGKEYKCKVSNKALPAPIEKT<br>ISKAKGQPREPQVCTLPPSRDELTENQVSLTCLVKGFYPSDIAVEWESNGQPENNYKTTPPVLDSDGS<br>FFLYSWLTVDKSRWQQGNVFSCSVMHEALHNHYTQKSLSLSPG |
| 261 | DIQMTQSPSSVSASVGDRVTITCRASQGISSWLAWYQQKPGKAPKLLIYAASSLQSGVPSRFSGSGSG<br>TDFTLTISSLQPEDFATYYCQQGVSFPRTEGGGTKVEIKRTVAAPSVFIFPPSDEQLKSGTASVVCL1<br>NNFYPREAKVQWKVDNALQSGNSQESVTEQDSKDSTYSLSSTLTLSKADYEKHKVYACEVTHQGLSSP<br>VTKSFNRGEC |
| 262 | DIQMTQSPSSLSASVGDRVTITCHASQNINFWLSWYQQKPGKAPKLLIYEASNLHTGVPSRFSGSGSG<br>TRFTLTISSLQPEDIATYYCQQSHSYPLTFGCGTKLEIKGGGGSGGGGSGGGGSGGGGSQLQLQESGP<br>GLVKPSETLSLTCTVSGFSLTNYGLHWIRQPPGKCLEWIGVIWSGGKTDYNPSLKSRVTISKDTSKNQ<br>FSLKLSSVQAADTAVYYCAKYDYDDSLDYWGQGTLVTVSSGSDKTHTCPPCPAPELLGGPSVFLFPPPK<br>PKDTLMISRTPEVTCVVVDVSHEDPEVKFNWYVDGVEVHNAKTKPREEQYNSTYRVVSVLTVLHQDWL<br>NGKEYKCKVSNKALPAPIEKTISKAKGQPREPRVYTLPPCRDELTKNQVSLTCLVKGFYPSDIAVEWE<br>SNGQPENNYKTTPPVLVSDGSFTLYSKLTVDKSRWQQGNVFSCSVMHEALHNHYTQKSLSLSPG |
| 263 | EVQLVQSGAEVKKPGASVKVSCKASGYTFTSYYMHWVRQAPGQGLEWMGIINPSGGSTSYAQKFQGRV<br>TMTRDTSTSTVYMELSSLRSEDTAVYYCARGNYGDEFDYWGQGTLVTVSS |
| 264 | DIQMTQSPSSLSASVGDRVTITCRASQSISSYLNWYQQKPGKAPKLLIYAASSLQSGVPSRFSGSGSG<br>TDFTLTISSLQPEDFATYYCQQSYSTPPTFGQGTKVEIK |
| 265 | DIQMTQSPSSLSASVGDRVTITCRASQSVSTSSYNYMHWYQQKPGKPPKLLIKYASNLESGVPSRFSG<br>SGSGTDFTLTISSLQPEDFATYYCQHSWEIPLTFGQGTKVEIK |
| 266 | EVQLVQSGAEVKKPGASVKVSCKASGYSFTDYYMHWVRQAPGQGLEWIGRINPYNGAAFYSQNFKDRV<br>TLTVDTSTSTAYLELSSLRSEDTAVYYCAIERGADLEGYAMDYWGQGTLVTVSS |
| 267 | ATGGACATGAGGGTACCAGCTCAGCTGCTGGGCCTGCTGCTGCTTTGGCTTCCTGGCGCTAGATGCCA<br>ATTGCAGCTGCAAGAATCCGGACCAGGGCTCGTAAAACCTTCTGAACCCTCCCTCACTTGCACTG<br>TGTCTGGATTCTCTCTCACGAACTACGGGTTGCATTGGATCCGACAGCCGCCTGGCAAGTGTCTTGAG<br>TGGATTGCCGTTATCTGGTCAGGAGGGAAGACGGATTATAATCCAAGTCTGAAATCCAGAGTGACAAT<br>TTCTAAGGACACGTCCAAAAATCAGTTTAGCCTCAAACTTTCCTCAGTTCAGGCTGCTGATACAGCGG<br>TGTACTATTGCGCAAAGTACGACTATGATGACAGTTTGGACTACTGGGGACAGGGTACACTGGTAACA<br>GTGAGTTCTGGAGGCGGCGGTAGTGGAGGCGGGGGAAGTGGTGGCGGAGGGAGTGGAGGAGGGGGCAG<br>TGATATTCAAATGACGCAGAGCCCCAGTTCCCTTTCAGCTAGCGTTGGCGACAGAGTAACGATAACGT<br>GTCACGCTTCCCAGAACATTAATTTTTGGCTTAGCTGGTATCAACAGAAACCGGGAAAAGCACCCAAG<br>CTGCTTATCTATGAAGCGTCCAATCTCCACACGGGTGTCCCATCAAGATTTTCTGGATCAGGCAGTGG<br>CACACGATTCACACTGACCATTAGTTCCTTGCAGCCCGAGGATATCGCAACTTACTACTGTCAGCAAA<br>GTCACTCTTACCCGTTGACATTCGGATGTGGAACTAAACTGGAGATTAAGGGATCCGATAAGACCCAC<br>ACCTGTCCTCCATGTCCTGCTCCAGAACTGCTCGGCGGACCTTCCGTGTTCCTGTTTCCTCCAAAGCC<br>TAAGGACACCCTGATGATCAGCAGGACCCCTGAAGTGACCTGCGTGGTGGTGGATGTGTCTCACGAGG<br>ACCCAGAAGTGAAGTTCAATTGGTACGTGGACGGCGTGGAAGTGCACAACGCCAAGACCAAGCCTAGA<br>GAGGAACAGTACAACAGCACCTACAGAGTGGTGTCCGTGCTGACCGTGCTGCACCAGGATTGGCTGAA<br>CGGCAAAGAGTACAAGTGCAAGGTGTCCAACAAGGCCCTGCCTGCTCCTATCGAGAAAACCATCAGCA<br>AGGCCAAGGGCCAGCCTCGCGAGCCTAGAGTGTATACCTTGCCTCCATGCCGGGACGAGCTGACCAAG<br>AATCAGGTGTCCCTGACCTGCCTGGTCAAGGGCTTCTACCCTTCCGATATCGCCGTGGAATGGGAGAG<br>CAATGGCCAGCCAGAGAACAACTACAAGACCACACCTCCTGTGCTGGTGTCCGACGGCAGCTTTACCC<br>TGTACAGCAAGCTGACAGTGGACAAGAGCAGATGGCAGCAGGGCAACGTGTTCTCCTGCAGCGTGATG<br>CACGAGGCCCTGCACAACCACTACACCCAGAAAAGCCTGAGCCTGTCTCCTGGCTAA |

SEQUENCES

| SEQ ID NO | Sequence |
|---|---|
| 268 | ATGGGCTGGTCCTGCATCATCCTGTTTCTGGTGGCCACAGCCACAGGCGTGCACTCTGAGGTGCAGCT<br>GGTTGAATCTGGCGGCGGACTTGTGAAGCCTGGCGGATCTCTGAGACTGAGCTGTGCCGCCAGCGGCT<br>TCACCTTTAGCAGCTACAGCATGAACTGGGTCCGACAGGCCCCTGGCAAAGGCCTTGAATGGGTGTCC<br>AGCATCAGCAGCAGCTCCAGCTACATCTACTACGCCGACAGCGTGAAGGGCAGATTCACCATCAGCCG<br>GGACAACGCCAAGAACAGCCTGTACCTGCAGATGAACTCCCTGAGAGCCGAGGACACCGCCGTGTACT<br>ATTGTGCTAGAGGCGCCCCTATTGGAGCCGCCGCTGGATGGTTCGATCCTTGGGGACAGGGAACCCTG<br>GTCACCGTTTCTTCTGCCTCTACAAAGGGCCCCAGCGTTTCCCACTGGCTCCTAGCAGCAAGAGCAC<br>AAGCGGAGGAACAGCTGCCCTGGGCTGTCTGGTCAAGGACTACTTTCCTGAGCCTGTGACCGTGTCCT<br>GGAACAGCGGAGCACTGACTAGCGGCGTGCACACATTTCCAGCCGTGCTGCAAAGCAGCGGCCTGTAC<br>TCTCTGAGCAGCGTCGTGACAGTGCCTAGCAGCTCTCTGGGCACCCAGACCTACATCTGCAATGTGAA<br>CCACAAGCCTAGCAACACCAAGGTGGACAAGAAGGTGGAACCCAAGAGCTGCGACAAGACCCACACCT<br>GTCCTCCATGTCCTGCTCCAGAACTGCTCGGCGGACCTTCCGTGTTCCTGTTTCCTCCAAAGCCTAAG<br>GACACCCTGATGATCAGCAGAACCCCTGAAGTGACCTGCGTGGTGGTGGATGTGTCTCACGAGGACCC<br>CGAAGTGAAGTTCAATTGGTACGTGGACGGCGTGGAAGTGCACAACGCCAAGACCAAGCCTAGAGAGG<br>AACAGTACAACAGCACCTACAGAGTGGTGTCCGTGCTGACAGTGCTGCACCAGGATTGGCTGAACGGC<br>AAAGAGTACAAGTGCAAGGTGTCCAACAAGGCCCTGCCTGCTCCTATCGAGAAAACCATCAGCAAGGC<br>CAAGGGCCAGCCTCGCGAACCTCAAGTCTGTACACTGCCTCCTAGCCGGGATGAGCTGACCGAGAATC<br>AGGTGTCCCTGACCTGTCTCGTGAAGGGCTTCTACCCCTCCGATATCGCCGTGGAATGGGAGAGCAAT<br>GGCCAGCCAGAGAACAACTACAAGACAACCCCTCCTGTGCTGGACAGCGACGGCTCATTCTTCCTGTA<br>CAGCTGGCTGACCGTGGACAAGTCCAGATGGCAGCAGGGCAACGTGTTCTCCTGCAGCGTGATGCACG<br>AGGCCCTGCACAACCACTACACCCAGAAGTCCCTGTCTCTGAGCCCAGGCTAA |
| 269 | ATGGACATGAGAGTTCCAGCTCAGCTGCTGGGCCTGCTGCTGCTTTGGCTTCCTGGCGCTAGATGCGA<br>CATCCAGATGACACAGAGCCCCAGCTCCGTGTCTGCCTCTGTGGGAGACAGAGTGACCATCACCTGTA<br>GAGCCCAGCCAGGGCATCTCTTCTTGGCTGGCCTGGTATCAGCAGAAGCCTGGCAAGGCCCCTAAGCTG<br>CTGATCTATGCCGCTAGCTCTCTGCAGTCTGGCGTGCCCTCTAGATTTTCTGGCAGCGGCTCTGGCAC<br>CGACTTCACCCTGACCATATCTAGCCTGCAGCCTGAGGACTTCGCCACCTACTATTGTCAGCAGGGCG<br>TGTCCTTTCCACGGACCTTTGGCGGCGGAACAAAGGTGGAAATCAAGCGGACAGTGGCCGCTCCTAGC<br>GTGTTCATCTTTCCACCTAGCGACGAGCAGCTGAAGTCCGGCACAGCCTCTGTTGTGCCTGCTGAA<br>CAACTTCTACCCCAGAGAAGCCAAGGTGCAGTGGAAGGTGGACAATGCCCTGCAGAGCGGCAACAGCC<br>AAGAGAGCGTGACAGAGCAGGACAGCAAGGACTCCACCTACAGCCTGAGCAGCACCCTGACACTGAGC<br>AAGGCCGACTACGAGAAGCACAAAGTGTACGCCTGCGAAGTGACCCACCAGGGCCTTTCTAGCCCTGT<br>GACCAAGAGCTTCAACCGGGGCGAGTGTTGA |
| 270 | QLQLQESGPGLVKPSETLSLTCTVSGFSLTNYGLHWIRQPPGKGLEWIGVIWVGGATDYNPSLKSRVT<br>ISVDTSKNQFSLKLSSVQAADTAVYYCAKGDYGDTLDYWGQGTLVTVSS |
| 271 | DIQMTQSPSSLSASVGDRVTITCHASQNINFWLSWYQQKPGKAPKLLIYEASNLHTGVPSRFSGSGSG<br>TDFTLTISSLQPEDFATYYCQQSHSYPLTFGSGTKLEIK |
| 272 | WVGGA |
| 273 | GDYGDTLDY |
| 274 | QLQLQESGPGLVKPSETLSLTCTVSGFSLTNYGLHWIRQPPGKCLEWIGVIWVGGATDYNPSLKSRVT<br>ISVDTSKNQFSLKLSSVQAADTAVYYCAKGDYGDTLDYWGQGTLVTVSSGGGGSGGGGSGGGGSGGGG<br>SDIQMTQSPSSLSASVGDRVTITCHASQNINFWLSWYQQKPGKAPKLLIYEASNLHTGVPSRFSGSGS<br>GTDFTLTISSLQPEDFATYYCQQSHSYPLTFGCGTKLEIK |
| 275 | DIQMTQSPSSLSASVGDRVTITCHASQNINFWLSWYQQKPGKAPKLLIYEASNLHTGVPSRFSGSGSG<br>TDFTLTISSLQPEDFATYYCQQSHSYPLTFGCGTKLEIKGGGGSGGGGSGGGGSGGGGSQLQLQESGP<br>GLVKPSETLSLTCTVSGFSLTNYGLHWIRQPPGKCLEWIGVIWVGGATDYNPSLKSRVTISVDTSKNQ<br>FSLKLSSVQAADTAVYYCAKGDYGDTLDYWGQGTLVTVSS |
| 276 | QLQLQESGPGLVKPSETLSLTCTVSGFSLTNYGLHWIRQPPGKCLEWIGVIWVGGATDYNPSLKSRVT<br>ISVDTSKNQFSLKLSSVQAADTAVYYCAKGDYGDTLDYWGQGTLVTVSSGGGGSGGGGSGGGGSGGGG<br>SDIQMTQSPSSLSASVGDRVTITCHASQNINFWLSWYQQKPGKAPKLLIYEASNLHTGVPSRFSGSGS<br>GTDFTLTISSLQPEDFATYYCQQSHSYPLTFGCGTKLEIKGSDKTHTCPPCPAPELLGGPSVFLEPPK<br>PKDTLMISRTPEVTCVVVDVSHEDPEVKFNWYVDGVEVHNAKTKPREEQYNSTYRVVSVLTVLHQDWL<br>NGKEYKCKVSNKALPAPIEKTISKAKGQPREPRVYTLPPCRDELTKNQVSLTCLVKGFYPSDIAVEWE<br>SNGQPENNYKTTPPVLVSDGSFTLYSKLTVDKSRWQQGNVFSCSVMHEALHNHYTQKSLSLSPG |
| 277 | QLQLQESGPGLVKPSETLSLTCTVSGFSLTNYGLHWIRQPPGKCLEWIGVILSGGWTDYNPSLKSRVT<br>ISKDTSKNQFSLKLSSVQAADTAVYYCAKGDYGDALDYWGQGTLVTVSSGGGGSGGGGSGGGGSGGGG<br>SDIQMTQSPSSLSASVGDRVTITCHASQNINFWLSWYQQKPGKAPKLLIYEASNLHTGVPSRFSGSGS<br>GTRFTLTISSLQPEDIATYYCQQSHSYPLTFGCGTKLEIKGSDKTHTCPPCPAPELLGGPSVFLFPPK<br>PKDTLMISRTPEVTCVVVDVSHEDPEVKFNWYVDGVEVHNAKTKPREEQYNSTYRVVSVLTVLHQDWL<br>NGKEYKCKVSNKALPAPIEKTISKAKGQPREPRVYTLPPCRDELTKNQVSLTCLVKGFYPSDIAVEWE<br>SNGQPENNYKTTPPVLVSDGSFTLYSKLTVDKSRWQQGNVFSCSVMHEALHNHYTQKSLSLSPG |
| 278 | EVQLVESGGGVVQPGGSLRLSCAASGETFNAFGMHWVRQAPGKCLEWVAFISSGSTSIYYANTVKGRF<br>TISRDNSKNTLYLQMNSLRAEDTAVYYCARDGYPTGGAMDYWGQGTSVTVSSGGGGSGGGGSGGGGSG<br>GGGSDIQMTQSPSSLSASVGDRVTITCKASQDIYNYLSWFQQKPGKAPKPLIYRANILVSGVPSRFSG |

| SEQ ID NO | Sequence |
|---|---|
| | SGSGQDYTFTISSLQPEDIATYYCLQFDAFPFTFGCGTKLEIKGSDKTHTCPPCPAPELLGGPSVFLF PPKPKDTLMISRTPEVTCVVVDVSHEDPEVKFNWYVDGVEVHNAKTPREEQYNSTYRVVSVLTVLHQ DWLNGKEYKCKVSNKALPAPIEKTISKAKGQPREPRVYTLPPCRDELTKNQVSLTCLVKGFYPSDIAV EWESNGQPENNYKTTPPVLSDGSFTLYSKLTVDKSRWQQGNVFSCSVMHEALHNHYTQKSLSLSPG |
| 279 | GDYGDALDY |
| 280 | QLQLQESGPGLVKPSETLSLTCTVSGFSLTNYGLHWIRQPPGKCLEWIGVILSGGWTDYNPSLKSRVT ISKDTSKNQFSLKLSSVQAADTAVYYCAKGDYGDALDYWGQGTLVTVSSGGGGSGGGGSGGGGSGGGG SDIQMTQSPSSLSASVGDRVTITCHASQNINFWLSWYQQKPGKAPKLLIYEASNLHTGVPSRFSGSGS GTRFTLTISSLQPEDIATYYCQQSHSYPLTFGCGTKLEIK |
| 281 | QLQLQESGPGLVKPSETLSLTCTVSGFSLTNYGLHWIRQPPGKCLEWIGVIWSGGKTDYNPSLKSRVT ISKDTSKNQFSLKLSSVQAADTAVYYCAKYDYDDSLDYWGQGTLVTVSSGGGGSGGGGSGGGGSGGGG SDIQMTQSPSSLSASVGDRVTITCHASQNINFWLSWYQQKPGKIPKLLIYEASNLHTGVPSRFSGSGS GTRFTLTISSLQPEDIATYYCQQSHSYPLTFGCGTKLEIKGSDKTHTCPPCPAPELLGGPSVFLFPPK PKDTLMISRTPEVTCVVVDVSHEDPEVKFNWYVDGVEVHNAKTKPREEQYNSTYRVVSVLTVLHQDWL NGKEYKCKVSNKALPAPIEKTISKAKGQPREPRVYTLPPCRDELTKNQVSLTCLVKGFYPSDIAVEWE SNGQPENNYKTTPPVLSDGSFTLYSKLTVDKSRWQQGNVFSCSVMHEALHNHYTQKSLSLSPG |
| 282 | DIQMTQSPSTLSASVGDRVTITCRASNSISSWLAWYQQKPGKAPKLLIYEASSTKSGVPSRFSGSGSG TEFTLTISSLQPDDFATYYCQQYDDLPTFGGGTKVEIK |
| 283 | YDYDDALDY |
| 284 | YDYDDILDY |
| 285 | YDYDDLLDY |
| 286 | DIQMTQSPSSVSASVGDRVTITCRASQGISSWLAWYQQKPGKAPKLLIYAASSLQSGVPSRFSGSGSG TDFTLTISSLQPEDFATYYCQQGVSFPPRTFGGGTKVEIKGGGGSGGGGSGGGGSGGGGSEVQLVESGG GLVKPGGSLRLSCAASGETFSSYSMNWVRQAPGKGLEWVSSISSSSSYIYYADSVKGRFTISRDNAKN SLYLQMNSLRAEDTAVYYCARGAPIGAAAGWFDPWGQGTLVTVSSGGDKTHTCPPCPAPELLGGPSVF LFPPKPKDTLMISRTPEVTCVVVDVSHEDPEVKFNWYVDGVEVHNAKTPREEQYNSTYRVVSVLTVL HQDWLNGKEYKCKVSNKALPAPIEKTISKAKGQPREPRVYTLPPCRDELTKNQVSLTCLVKGFYPSDI AVEWESNGQPENNYKTTPPVLSDGSFTLYSKLTVDKSRWQQGNVFSCSVMHEALHNHYTQKSLSLSP G |
| 287 | QLQLQESGPGLVKPSETLSLTCTVSGFSLTNYGLHWIRQPPGKGLEWIGVIWSGGKTDYNPSLKSRVT ISKDTSKNQFSLKLSSVQAADTAVYYCAKYDYDDSLDYWGQGTLVTVSSASTKGPSVFPLAPSSKSTS GGTAALGCLVKDYFPEPVTVSWNSGALTSGVHTFPAVLQSSGLYSLSSVVTVPSSSLGTQTYICNVNH KPSNTKVDKKVEPKSCDKTHTCPPCPAPELLGGPSVFLFPPKPKDTLMISRTPEVTCVVVDVSHEDPE VKFNWYVDGVEVHNAKTKPREEQYNSTYRVVSVLTVLHQDWLNGKEYKCKVSNKALPAPIEKTISKAK GQPREPQVCTLPPSRDELTENQVSLTCLVKGFYPSDIAVEWESNGQPENNYKTTPPVLDSDGSFFLYS WLTVDKSRWQQGNVFSCSVMHEALHNHYTQKSLSLSPG |
| 288 | DIQMTQSPSSLSASVGDRVTITCHASQNINFWLSWYQQKPGKAPKLLIYEASNLHTGVPSRFSGSGSG TRFTLTISSLQPEDIATYYCQQSHSYPLTFGGGTKLEIKRTVAAPSVFIFPPSDEQLKSGTASVVCL1 NNFYPREAKVQWKVDNALQSGNSQESVTEQDSKDSTYSLSSTLTLSKADYEKHKVYACEVTHQGLSSP VTKSFNRGEC |
| 289 | DIQMTQSPSSLSASVGDRVTITCHASQNINFWLSWYQQKPGKAPKLLIYEASNLHTGVPSRFSGSGSG TRFTLTISSLQPEDIATYYCQQSHSYPLTFGGGTKLEIK |
| 290 | YDYDDVLDY |
| 291 | YDYDDTLDY |
| 292 | YDYDESLDY |
| 293 | DYDDSLDY |
| 294 | QLQLQESGPGLVKPSETLSLTCTVSGFSLTNYGLHWIRQPPGKGLEWIGVILSGGWTDYNPSLKSRVT ISKDTSKNQFSLKLSSVQAADTAVYYCAKGDYGDALDYWGQGTLVTVSS |
| 295 | DIQMTQSPSSLSASVGDRVTITCHASQNINFWLSWYQQKPGKAPKLLIYEASNLHTGVPSRFSGSGSG TRFTLTISSLQPEDIATYYCQQSHSYPLTFGSGTKLEIK |
| 296 | LSGGW |
| 297 | GFTFSSY |
| 298 | SSSSSY |

-continued

| SEQ ID NO | Sequence |
|---|---|
| 299 | LSCAASGFTFSSYSMNWVR |
| 300 | NSLYLQMNSLR |
| 301 | DTLMISR |
| 302 | WQQGNVFSCSVMHEALHNHYTQK |
| 303 | DIQMTQSPSSVSASVGDR |
| 304 | YDYDDSLDYWGQGTLVTVSSGGGGSGGGGSGGGGSGGGGSDIQMTQSPSSLSASVGDRVTITCHASQNINFWLSWYQQKPGKAPK |
| 305 | XDYDDSLDY, wherein X = any amino acid |
| 306 | YXYDDSLDY, wherein X = any amino acid |
| 307 | YDXDDSLDY, wherein X = any amino acid |
| 308 | YDYXDSLDY, wherein X = any amino acid |
| 309 | YDYDXSLDY, wherein X = any amino acid |
| 310 | YDYDDXLDY, wherein X = any amino acid |
| 311 | YDYDDSXDY, wherein X = any amino acid |
| 312 | YDYDDSLXY, wherein X = any amino acid |
| 313 | YDYDDSLDX, wherein X = any amino acid |
| 314 | XXYDDSLDY, wherein X = any amino acid |
| 315 | XDXDDSLDY, wherein X = any amino acid |
| 316 | XDYXDSLDY, wherein X = any amino acid |
| 317 | XDYDXSLDY, wherein X = any amino acid |
| 318 | XDYDDXLDY, wherein X = any amino acid |
| 319 | XDYDDSXDY, wherein X = any amino acid |
| 320 | XDYDDSLXY, wherein X = any amino acid |
| 321 | XDYDDSLDX, wherein X = any amino acid |
| 322 | GDYGDSLDY |
| 323 | XSGGK, wherein X = any amino acid |
| 324 | WXGGK, wherein X = any amino acid |
| 325 | WSXGK, wherein X = any amino acid |
| 326 | WSGXK, wherein X = any amino acid |
| 327 | WSGGX, wherein X = any amino acid |
| 328 | XXGGK, wherein X = any amino acid |
| 329 | XSXGK, wherein X = any amino acid |
| 330 | XSGXK, wherein X = any amino acid |
| 331 | XSGGX, wherein X = any amino acid |
| 332 | WXXGK, wherein X = any amino acid |
| 333 | WXGXK, wherein X = any amino acid |
| 334 | WXGGX, wherein X = any amino acid |

| SEQUENCES | |
|---|---|
| SEQ ID NO | Sequence |
| 335 | QLQLQESGPGLVKPSETLSLTCTVSGFSLTNYGLHWIRQPPGKCLEWIGVIWVGGATDYNPSLKSRVTISVDTSKNQFSLKLSSVQAADTAVYYCAKGDYGDTLDYWGQGTLVTVSS |
| 336 | DIQMTQSPSSLSASVGDRVTITCHASQNINFWLSWYQQKPGKAPKLLIYEASNLHTGVPSRFSGSGSGTDFTLTISSLQPEDFATYYCQQSHSYPLTFGCGTKLEIK |
| 337 | RASQGISSWA |
| 338 | SSSSY |
| 339 | GAPMIGAAAGWFDP |
| 340 | LSCAASGFTFNAFGMHWVR |
| 341 | NTLYLQMNSLR |
| 342 | DGYPTGGAMDYWGQGTSVTVSSGGGGSGGGGSGGGGSGGGGSDIQMTQSPSSLSASVGDR |

What is claimed is:

1. A protein comprising:
  (a) a first antigen-binding site that binds NKG2D;
  (b) a second antigen-binding site that binds CLEC12A; and
  (c) an antibody Fc domain or a portion thereof sufficient to bind CD16, or a third antigen-binding site that binds CD16,
  wherein the first antigen-binding site comprises a heavy chain variable domain (VH) comprising a VH-complementarity-determining region 1 (VH-CDR1) comprising the amino acid sequence of SEQ ID NO:81, a VH-complementarity-determining region 2 (VH-CDR2) comprising the amino acid sequence of SEQ ID NO:82, and a VH-complementarity-determining region 2 (VH-CDR3) comprising the amino acid sequence of SEQ ID NO:112, wherein amino acid X within SEQ ID NO: 112 is M, L, I, V, Q, or F; and a light chain variable domain (VL) comprising a VL-CDR1 comprising the amino acid sequence of SEQ ID NO:86, a VL-CDR2 comprising the amino acid sequence of SEQ ID NO:77, and a VL-CDR3 comprising the amino acid sequence of SEQ ID NO: 87; and
  wherein the second antigen-binding site comprises a VH comprising a VH-CDR1 comprising the amino acid sequence of SEQ ID NO:137, a VH-CDR2 comprising the amino acid sequence of SEQ ID NO:272, and a VH-CDR3 comprising the amino acid sequence of SEQ ID NO: 273; and a VL comprising a VL-CDR1 comprising the amino acid sequence of SEQ ID NO:140, a VL-CDR2 comprising the amino acid sequence of SEQ ID NO: 141, and a VL-CDR3 comprising the amino acid sequence of SEQ ID NO: 142.

2. The protein of claim 1, wherein the VH of the first antigen-binding site comprises an amino acid sequence at least 90% identical to SEQ ID NO:95, and the VL of the first antigen-binding site comprises an amino acid sequence at least 90% identical to SEQ ID NO:85.

3. The protein of claim 2, wherein the VH of the first antigen-binding site comprises the amino acid sequences of SEQ ID NO:95, and the VL of the first antigen-binding site comprises the amino acid sequences of SEQ ID NO:85.

4. A protein comprising:
  (a) a first antigen-binding site that binds NKG2D;
  (b) a second antigen-binding site that binds CLEC12A; and (c) an antibody Fc domain or a portion thereof sufficient to bind CD16, or a third antigen-binding site that binds CD16, wherein the first antigen-binding site comprises:
- (i) a VH comprising a VH-CDR1 comprising the amino acid sequence of SEQ ID NO:81, a VH-CDR2 comprising the amino acid sequence of SEQ ID NO:82, and a VH-CDR3 comprising the amino acid sequence of SEQ ID NO:97; and a VL comprising a VL-CDR1 comprising the amino acid sequence of SEQ ID NO:86, a VL-CDR2 comprising the amino acid sequence of SEQ ID NO:77, and a VL-CDR3 comprising the amino acid sequence of SEQ ID NO:87; or
- (ii) a VH comprising a VH-CDR1 comprising the amino acid sequence of SEQ ID NO:297, a VH-CDR2 comprising the amino acid sequence of SEQ ID NO:298, and a VH-CDR3 comprising the amino acid sequence of SEQ ID NO:97; and a VL comprising a VL-CDR1 comprising the amino acid sequence of SEQ ID NO:86, a VL-CDR2 comprising the amino acid sequence of SEQ ID NO:77, and a VL-CDR3 comprising the amino acid sequence of SEQ ID NO:87; and wherein the second antigen-binding site comprises a VH comprising a VH-CDR1 comprising the amino acid sequence of SEQ ID NO:137, a VH-CDR2 comprising the amino acid sequence of SEQ ID NO:272, and a VH-CDR3 comprising the amino acid sequence of SEQ ID NO: 273; and a VL comprising a VL-CDR1 comprising the amino acid sequence of SEQ ID NO:140, a VL-CDR2 comprising the amino acid sequence of SEQ ID NO:141, and a VL-CDR3 comprising the amino acid sequence of SEQ ID NO: 142.

5. The protein of claim 4, wherein the VH of the first antigen-binding site comprises the VH-CDR1 comprising the amino acid sequence of SEQ ID NO:81, the VH-CDR2 comprising the amino acid sequence of SEQ ID NO:82, and the VH-CDR3 comprising the amino acid sequence of SEQ ID NO:97; and the VL of the first antigen-binding site comprises the VL-CDR1 comprising the amino acid sequence of SEQ ID NO:86, the VL-CDR2 comprising the amino acid sequence of SEQ ID NO:77, and the VL-CDR3 comprising the amino acid sequence of SEQ ID NO:87.

6. The protein of claim 4, wherein the VH of the first antigen-binding site comprises the VH-CDR1 comprising the amino acid sequence of SEQ ID NO:297, the VH-CDR2 comprising the amino acid sequence of SEQ ID NO:298, and the VH-CDR3 comprising the amino acid sequence of SEQ ID NO:97; and the VL of the first antigen-binding site comprises the VL-CDR1 comprising the amino acid sequence of SEQ ID NO:86, the VL-CDR2 comprising the amino acid sequence of SEQ ID NO:77, and the VL-CDR3 comprising the amino acid sequence of SEQ ID NO:87.

7. The protein of claim 6, wherein the VH of the first antigen-binding site comprises an amino acid sequence at least 90% identical to SEQ ID NO:95, and the VL of the first antigen-binding site comprises an amino acid sequence at least 90% identical to SEQ ID NO:85.

8. The protein of claim 7, wherein the VH of the first antigen-binding site comprises the amino acid sequences of SEQ ID NO:95, and the VL of the first antigen-binding site comprises the amino acid sequences of SEQ ID NO:85.

9. The protein of claim 5, wherein the VH of the first antigen-binding site comprises an amino acid sequence at least 90% identical to SEQ ID NO:95, and the VL of the first antigen-binding site comprises an amino acid sequence at least 90% identical to SEQ ID NO:85.

10. The protein of claim 9, wherein the VH of the first antigen-binding site comprises the amino acid sequences of SEQ ID NO:95, and the VL of the first antigen-binding site comprises the amino acid sequences of SEQ ID NO:85.

11. A protein comprising:
- (a) a first antigen-binding site comprising a Fab fragment that binds NKG2D, wherein the Fab fragment that binds NKG2D comprises a VH comprising a VH-CDR1 comprising the amino acid sequence of SEQ ID NO:81, a VH-CDR2 comprising the amino acid sequence of SEQ ID NO:82, and a VH-CDR3 comprising the amino acid sequence of SEQ ID NO:97; and a VL comprising a VL-CDR1 comprising the amino acid sequence of SEQ ID NO:86, a VL-CDR2 comprising the amino acid sequence of SEQ ID NO:77, and a VL-CDR3 comprising the amino acid sequence of SEQ ID NO:87;
- (b) a second antigen-binding site comprising a scFv that binds CLEC12A, wherein the scFv that binds CLEC12A comprises a VH comprising a VH-CDR1 comprising the amino acid sequence of SEQ ID NO:137, a VH-CDR2 comprising the amino acid sequence of SEQ ID NO:272, and a VH-CDR3 comprising the amino acid sequence of SEQ ID NO:273; and a VL comprising a VL-CDR1 comprising the amino acid sequence of SEQ ID NO:140, a VL-CDR2 comprising the amino acid sequence of SEQ ID NO:141, and a VL-CDR3 comprising the amino acid sequence of SEQ ID NO:142; and
- (c) an antibody Fc domain or a portion thereof sufficient to bind CD16.

12. The protein of claim 11, wherein
- (i) the VH of the Fab fragment that binds NKG2D comprises an amino acid sequence at least 90% identical to SEQ ID NO:95, and the VL of the Fab fragment that binds NKG2D comprises an amino acid sequence at least 90% identical to SEQ ID NO:85; and
- (ii) the VH of the scFv that binds CLEC12A comprises an amino acid sequence at least 90% identical to SEQ ID NO:335, and the VL of the scFv that binds CLEC12A comprises an amino acid sequence at least 90% identical to SEQ ID NO:336.

13. The protein of claim 11, wherein the scFv that binds CLEC12A comprises an amino acid sequence of SEQ ID NO:274.

14. The protein of claim 11, wherein the antibody Fc domain or the portion thereof comprises an amino acid sequence at least 90% identical to SEQ ID NO:118, and a first polypeptide chain of the antibody Fc domain or the portion thereof comprises Y349C, K360E and K409W substitutions relative to SEQ ID NO:118; and a second polypeptide chain of the antibody Fc domain or the portion thereof comprises S354C, Q347R, D399V and F405T substitutions relative to SEQ ID NO:118, numbered according to the EU numbering system.

15. A protein comprising:
- (a) a first antigen-binding site comprising a Fab fragment that binds NKG2D, wherein the Fab fragment that binds NKG2D comprises a VH comprising a VH-CDR1 comprising the amino acid sequence of SEQ ID NO:297, a VH-CDR2 comprising the amino acid sequence of SEQ ID NO:298, and a VH-CDR3 comprising the amino acid sequence of SEQ ID NO:97; and a VL comprising a VL-CDR1 comprising the amino acid sequence of SEQ ID NO:86, a VL-CDR2 comprising the amino acid sequence of SEQ ID NO:77, and a VL-CDR3 comprising the amino acid sequence of SEQ ID NO:87;

(b) a second antigen-binding site comprising a scFv that binds CLEC12A, wherein the scFv that binds CLEC12A comprises a VH comprising a VH-CDR1 comprising the amino acid sequence of SEQ ID NO:137, a VH-CDR2 comprising the amino acid sequence of SEQ ID NO:272, and a VH-CDR3 comprising the amino acid sequence of SEQ ID NO:273; and a VL comprising a VL-CDR1 comprising the amino acid sequence of SEQ ID NO:140, a VL-CDR2 comprising the amino acid sequence of SEQ ID NO:141, and a VL-CDR3 comprising the amino acid sequence of SEQ ID NO: 142; and (c) an antibody Fc domain or a portion thereof sufficient to bind CD16.

16. The protein of claim 15, wherein
(i) the VH of the Fab fragment that binds NKG2D comprises an amino acid sequence at least 90% identical to SEQ ID NO:95, and the VL of the Fab fragment that binds NKG2D comprises an amino acid sequence at least 90% identical to SEQ ID NO:85; and
(ii) the VH of the scFv that binds CLEC12A comprises an amino acid sequence at least 90% identical to SEQ ID NO:335, and the VL of the scFv that binds CLEC12A comprises an amino acid sequence at least 90% identical to SEQ ID NO:336.

17. The protein of claim 15, wherein the scFv that binds CLEC12A comprises an amino acid sequence of SEQ ID NO:274.

18. The protein of claim 15, wherein the antibody Fc domain or the portion thereof comprises an amino acid sequence at least 90% identical to SEQ ID NO:118, and a first polypeptide chain of the antibody Fc domain or the portion thereof comprises Y349C, K360E and K409W substitutions relative to SEQ ID NO:118; and a second polypeptide chain of the antibody Fc domain or the portion thereof comprises S354C, Q347R, D399V and F405T substitutions relative to SEQ ID NO:118, numbered according to the EU numbering system.

19. A protein comprising:
(a) a first antigen-binding site comprising a Fab fragment that binds NKG2D, wherein the Fab fragment that binds NKG2D comprises a VH comprising the amino acid sequence SEQ ID NO:95, and a VL comprising the amino acid sequences of SEQ ID NO:85;
(b) a second antigen-binding site comprising a scFv that binds CLEC12A, wherein the scFv that binds CLEC12A comprises a VH comprising the amino acid sequence SEQ ID NO:335, and a VL comprising the amino acid sequences of SEQ ID NO:336; and
(c) an antibody Fc domain or a portion thereof sufficient to bind CD16.

20. The protein of claim 19, wherein the scFv that binds CLEC12A comprises an amino acid sequence of SEQ ID NO:274.

21. The protein of claim 19, wherein the antibody Fc domain or the portion thereof comprises an amino acid sequence at least 90% identical to SEQ ID NO:118, and a first polypeptide chain of the antibody Fc domain or the portion thereof comprises Y349C, K360E and K409W substitutions relative to SEQ ID NO:118; and a second polypeptide chain of the antibody Fc domain or the portion thereof comprises S354C, Q347R, D399V and F405T substitutions relative to SEQ ID NO:118, numbered according to the EU numbering system.

* * * * *